United States Patent
Gifford et al.

(10) Patent No.: US 12,064,475 B2
(45) Date of Patent: *Aug. 20, 2024

(54) COMPOSITIONS AND METHOD FOR OPTIMIZED PEPTIDE VACCINES USING RESIDUE OPTIMIZATION

(71) Applicant: Think Therapeutics, Inc., Newton, MA (US)

(72) Inventors: David Kenneth Gifford, Newton, MA (US); Brandon Carter, Cambridge, MA (US)

(73) Assignee: Think Therapeutics, Inc., Newton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/170,994

(22) Filed: Feb. 17, 2023

(65) Prior Publication Data

US 2023/0364212 A1 Nov. 16, 2023

Related U.S. Application Data

(63) Continuation of application No. 17/729,290, filed on Apr. 26, 2022, now Pat. No. 11,672,850, which is a continuation of application No. 17/243,096, filed on Apr. 28, 2021, now Pat. No. 11,464,842.

(51) Int. Cl.
| | | |
|---|---|---|
| *A61K 39/00* | (2006.01) | |
| *A61K 38/00* | (2006.01) | |
| *A61K 38/04* | (2006.01) | |
| *A61K 38/08* | (2019.01) | |
| *A61K 38/10* | (2006.01) | |
| *A61P 35/00* | (2006.01) | |
| *C07K 5/00* | (2006.01) | |
| *C07K 7/00* | (2006.01) | |
| *C07K 7/06* | (2006.01) | |
| *C07K 7/08* | (2006.01) | |
| *C07K 16/00* | (2006.01) | |
| *C07K 17/00* | (2006.01) | |
| *A61K 48/00* | (2006.01) | |

(52) U.S. Cl.
CPC ........ *A61K 39/00116* (2018.08); *A61K 38/08* (2013.01); *A61K 38/10* (2013.01); *A61K 39/001152* (2018.08); *A61K 39/001158* (2018.08); *A61P 35/00* (2018.01); *C07K 7/06* (2013.01); *C07K 7/08* (2013.01); *A61K 2039/812* (2018.08); *A61K 2039/82* (2018.08); *A61K 2039/86* (2018.08); *A61K 48/00* (2013.01)

(58) Field of Classification Search
None
See application file for complete search history.

(56) References Cited

U.S. PATENT DOCUMENTS

| | | |
|---|---|---|
| 5,443,956 A | 8/1995 | Carney |
| 5,961,978 A | 10/1999 | Gaudernack et al. |
| 6,602,510 B1 | 8/2003 | Fikes et al. |
| 7,488,718 B2 | 2/2009 | Scheinberg et al. |
| 7,756,644 B2 | 7/2010 | Fridman et al. |
| 7,973,128 B2 | 7/2011 | Kosmatopoulos et al. |
| 8,007,810 B2 | 8/2011 | Fikes et al. |
| 8,465,747 B2 | 6/2013 | Kosmatopoulos et al. |
| 8,653,237 B2 | 2/2014 | Liu et al. |
| 8,741,576 B2 | 6/2014 | Tangri et al. |
| 8,765,687 B2 | 7/2014 | Scheinberg et al. |
| 8,900,600 B2 | 12/2014 | Kosmatopoulos et al. |
| 9,340,577 B2 | 5/2016 | Grey et al. |
| 9,913,884 B2 | 3/2018 | Fikes et al. |
| 10,024,868 B2 | 7/2018 | Kosmatopoulos et al. |
| 10,238,741 B2 | 3/2019 | Creusot |
| 10,335,473 B2 | 7/2019 | Eriksen |
| 10,456,457 B2 | 10/2019 | Eriksen |
| 10,556,943 B2 | 2/2020 | Knutson et al. |
| 10,596,239 B2 | 3/2020 | Eriksen |

(Continued)

FOREIGN PATENT DOCUMENTS

| | | |
|---|---|---|
| WO | WO-97/33602 A1 | 9/1997 |
| WO | WO-99/63945 A2 | 12/1999 |

(Continued)

OTHER PUBLICATIONS

Betts et al., "Chap. 14: Amino Acid Properties and Consequences of Substitutions," Bioinformatics for Geneticists, Barnes et al., eds., John Wiley & Sons, Ltd., pp. 297-316 (2003) (Year: 2003).*

(Continued)

*Primary Examiner* — Thea D' Ambrosio
(74) *Attorney, Agent, or Firm* — Wilmer Cutler Pickering Hale and Dorr LLP

(57) ABSTRACT

Described herein is an immunogenic composition comprising nucleic acid sequences encoding two or more amino acid sequences selected from the group consisting of SEQ ID NOs: 19 to 50. Also described herein is an immunogenic composition comprising nucleic acid sequences encoding two or more amino acid sequences selected from the group consisting of SEQ ID NOs: 141 to 272. Also described herein is an immunogenic composition comprising nucleic acid sequences encoding two or more amino acid sequences selected from the group consisting of SEQ ID NOs: 273 to 322. Also described herein is an immunogenic composition comprising nucleic acid sequences encoding two or more amino acid sequences selected from the group consisting of SEQ ID NOs: 354 to 458.

30 Claims, 14 Drawing Sheets

Specification includes a Sequence Listing.

(56) References Cited

U.S. PATENT DOCUMENTS

| | | |
|---|---|---|
| 10,738,355 B2 | 8/2020 | Sahin et al. |
| 10,835,585 B2 | 11/2020 | Fritsch et al. |
| 11,058,751 B1 | 7/2021 | Gifford et al. |
| 11,161,892 B1 | 11/2021 | Gifford et al. |
| 11,222,711 B2 | 1/2022 | Sahin et al. |
| 11,235,039 B1 | 2/2022 | Gifford et al. |
| 11,464,842 B1* | 10/2022 | Gifford .......... A61K 39/001104 |
| 11,466,053 B2 | 10/2022 | Tang et al. |
| 11,672,850 B2* | 6/2023 | Gifford ............ A61K 39/00116 424/185.1 |
| 2002/0155093 A1 | 10/2002 | Houghton et al. |
| 2002/0164346 A1 | 11/2002 | Nicolette |
| 2003/0220239 A1 | 11/2003 | Simard et al. |
| 2003/0224036 A1 | 12/2003 | Fikes et al. |
| 2004/0037843 A1 | 2/2004 | Fikes et al. |
| 2004/0072240 A1 | 4/2004 | Kosmatopoulos et al. |
| 2006/0018915 A1 | 1/2006 | Ishioka et al. |
| 2006/0093617 A1 | 5/2006 | Buyse et al. |
| 2007/0054262 A1 | 3/2007 | Baker et al. |
| 2007/0098776 A1 | 5/2007 | Fikes et al. |
| 2007/0224201 A1 | 9/2007 | Wu et al. |
| 2011/0002963 A1 | 1/2011 | Weinschenk et al. |
| 2011/0182926 A1 | 7/2011 | La Monica et al. |
| 2011/0257890 A1 | 10/2011 | Weinschenk et al. |
| 2014/0178421 A1 | 6/2014 | Kosmatopoulos |
| 2016/0101170 A1 | 4/2016 | Hacohen et al. |
| 2016/0125129 A1 | 5/2016 | Sahin et al. |
| 2018/0066017 A1 | 3/2018 | Hunt et al. |
| 2018/0102585 A1 | 4/2018 | Forster |
| 2018/0117133 A1 | 5/2018 | Chaplin et al. |
| 2018/0134804 A1 | 5/2018 | Scheinberg et al. |
| 2018/0141998 A1 | 5/2018 | Nguyen et al. |
| 2019/0175727 A1 | 6/2019 | Huang et al. |
| 2019/0307868 A1 | 10/2019 | Rooney |
| 2019/0322714 A1 | 10/2019 | Petit et al. |
| 2020/0061166 A1 | 2/2020 | Sahin et al. |
| 2020/0069782 A1 | 3/2020 | Biskup et al. |
| 2020/0078454 A1 | 3/2020 | Kosmatopoulos et al. |
| 2020/0105378 A1 | 4/2020 | Abelin et al. |
| 2020/0237885 A1 | 7/2020 | Levey et al. |
| 2021/0154280 A1 | 5/2021 | Martin et al. |
| 2021/0177954 A1 | 6/2021 | Juneja |
| 2021/0177955 A1 | 6/2021 | Petit et al. |
| 2021/0196806 A1 | 7/2021 | Yelensky et al. |
| 2021/0196809 A1 | 7/2021 | Maianti et al. |
| 2021/0268086 A1 | 9/2021 | Zhong et al. |
| 2021/0268091 A1 | 9/2021 | Juneja |
| 2021/0275657 A1 | 9/2021 | Juneja et al. |
| 2021/0290746 A1 | 9/2021 | Sahin et al. |
| 2021/0389280 A1 | 12/2021 | Wang |
| 2022/0160848 A1 | 5/2022 | Gifford et al. |
| 2022/0194999 A1 | 6/2022 | Krishna et al. |

FOREIGN PATENT DOCUMENTS

| | | |
|---|---|---|
| WO | WO-2005/042698 A2 | 5/2005 |
| WO | WO-2009/002418 A2 | 12/2008 |
| WO | WO-2016/172722 A1 | 10/2016 |
| WO | WO-2016/187508 | 11/2016 |
| WO | WO-2017/075531 A1 | 5/2017 |
| WO | WO-2018/081480 A1 | 5/2018 |
| WO | WO-2018/102585 A1 | 6/2018 |
| WO | WO-2018/187356 A2 | 10/2018 |
| WO | WO-2019/246286 | 12/2019 |
| WO | WO-2020/037239 A1 | 2/2020 |
| WO | WO-2020/154617 A1 | 7/2020 |
| WO | WO-2020/252039 A1 | 12/2020 |
| WO | WO-2020/253643 A1 | 12/2020 |
| WO | WO-2021/055594 | 3/2021 |
| WO | WO-2021/087840 A1 | 5/2021 |
| WO | WO-2022/036142 A2 | 2/2022 |
| WO | WO-2022/132596 A2 | 6/2022 |
| WO | WO-2022/171032 A1 | 8/2022 |
| WO | WO-2022/180219 A1 | 9/2022 |
| WO | WO-2023/170535 A2 | 9/2023 |
| WO | WO-2023/230014 A1 | 11/2023 |

OTHER PUBLICATIONS

UniProt Accession No. A0A1M6V319, 5 pages (2017) (Year: 2017).*

NCBI Database, GenBank Accession No. AB051004, 73 pages (2016) (Year: 2016).*

UniProt Accession No. A4YTR3, 5 pages (2007) (Year: 2007).*

Accession No. CU234118, 1543 pages (2015) (Year: 2015).*

UniProt Accession No. A0A4S8INI8, 6 pages (2019) (Year: 2019).*

NCBI Database, GenBank Accession No. PYDT01000009, 983 pages (2019) (Year: 2019).*

U.S. Appl. No. 17/243,096, Gifford et al., filed Apr. 28, 2021.

U.S. Appl. No. 17/551,679, Gifford et al., filed Dec. 15, 2021.

U.S. Appl. No. 17/815,086, Gifford et al., filed Jul. 26, 2022.

Abelin et al., "Defining HLA-II Ligand Processing and Binding Rules with Mass Spectrometry Enhances Cancer Epitope Prediction," Immunity, Oct. 15, 2019, vol. 51(4), pp. 766-779; e1-e17, and Update (Feb. 9, 2021, 54(2):388). 34 pages.

Alhadj-Ali et al., "Metabolic and immune effects of immunotherapy with proinsulin peptide in human new-onset type 1 diabetes," Science Translation Medicine, Aug. 9, 2017, vol. 9;9(402):eaaf7779. 9 pages.

Alvarez, B. et al., "NNAlign_MA; MHC Peptidome Deconvolution for Accurate MHC Binding Motif Characterization and Improved T-cell Epitope Predictions", Molecular & Cellular Proteomics, Dec. 2019, vol. 18(12), pages: cover, 2459-2477 (20 pages).

Asahara et al., "Phase I/II clinical trial using HLA-A24-restricted peptide vaccine derived from KIF20A for patients with advanced pancreatic cancer," Journal of Translational Medicine, Nov. 16, 2013, vol. 11:291. 13 pages.

Bae et al., "Myeloma-Specific Multiple Peptides Able to Generate Cytotoxic T Lymphocytes: A Potential Therapeutic Application in Muliple Myeloma and other Plasma Cell Disorders," Clinical Cancer Research, published online Jul. 2, 2012, vol. 18(17), pp. 4850-4860.

Berzofsky et al., "Progress on new vaccine strategies for the immunotherapy and prevention of cancer," The Journal of Clinical Investigation, Jun. 2004, vol. 113(11), pp. 1515-1525.

Berzofsky et al., "Strategies for designing and optimizing new generation vaccines," Nature Reviews: Immunology, vol. 1(3), Dec. 2001, pp. 209-219.

Berzofsky, "Epitope selection and design of synthetic vaccines. Molecular approaches to enhancing immunogenicity and cross-reactivity of engineered vaccines," Annals of the New York Academy of Sciences, Aug. 12, 1993, vol. 690(1), pp. 256-264.

Bhasin, M. and Raghava, G.P.S., "Prediction of Promiscuous and High-Affinity Mutated MHC Binders", Hybridoma and Hybridomics, Nov. 4, 2003, vol. 22, 229-234, (8 pages).

Candia et al., "On Peptides and Altered Peptide Ligands: From Origin, Mode of Action and Design to Clinical Application (Immunotherapy)," International Archives of Allergy and Immunology, published online Sep. 20, 2016; vol. 170(4), pp. 211-233.

Chicz et al., "Predominant naturally processed peptides bound to HLA-DR1 are derived from MHC-related molecules and are heterogeneous in size," Nature, Aug. 27, 1992, vol. 358(6389), pp. 764-768.

Cleveland et al., "Routine large-scale production of monoclonal antibodies in a protein-free culture medium," Journal of Immunological Methods, Jan. 28, 1983, vol. 56, Issue 2, pp. 221-234.

Croft et al., "Most viral peptides displayed by class I MHC on infected cells are immunogenic," Proceedings of the National Academy of Sciences, Feb. 19, 2019, vol. 116(8), pp. 3112-3117.

Dai et al., "Machine learning optimization of peptides for presentation by class II MHCs," bioRxiv, posted Aug. 18, 2020 (https://doi.org/10.1101/2020.08.18.256081). 35 pages.

Dastagir et al., "Efficient Presentation of Multiple Endogenous Epitopes to Both CD4+ and CD8+ Diabetogenic T Cells for Tolerance," Molecular Therapy: Methods & Clinical Development, Mar. 2017, vol. 4, pp. 27-38.

(56) References Cited

OTHER PUBLICATIONS

Dey et al., "A Bioinformatics approach to designing a Zika virus vaccine," Computational Biology and Chemistry, available online Mar. 10, 2017, vol. 68, pp. 143-152.
Dyall et al., "Heteroclitic Immunization Induces Tumor Immunity," J. Exp. Med., Nov. 2, 1998, vol. 188(9), pp. 1553-1561.
Fikes et al., "Design of multi-epitope, analogue-based cancer vaccines," Expert Opinion on Biological Therapy, published online Mar. 3, 2005, vol. 3:6, pp. 985-993. 10 pages.
Fong et al., "Altered peptide ligand vaccination with Flt3 ligand expanded dendritic cells for tumor immunotherapy," PNAS, Jul. 17, 2001, vol. 98(15), pp. 8809-8814.
Gibson et al., "Proinsulin multi-peptide immunotherapy induces antigen-specific regulatory T cells and limits autoimmunity in a humanized model," Clinical and Experimental Immunology, Dec. 2015, vol. 182(3), pp. 251-260.
Guevara-Patino et al., "Optimization of a self antigen for presentation of multiple epitopes in cancer immunity," The Journal of Clinical Investigation, May 2006, vol. 116(5), pages: cover, 1382-1390.
Hollingsworth et al., "Turning the corner on therapeutic cancer vaccines," npj Vaccines, published online Feb. 8, 2019, vol. 4(7), pp. 1-10.
Hong et al., "Epitope-optimized alpha-fetoprotein genetic vaccines prevent carcinogen-induced murine autochthonous hepatocellular carcinoma," Hepatology, Apr. 2014, vol. 59(4), pp. 1448-1458.
Hoppes et al., "Altered Peptide Ligands Revisited: Vaccine Design through Chemically Modified HLA-A2-Restricted T Cell Epitopes," Journal of Immunology, published online Oct. 13, 2014, vol. 193, pp. 4803-4813. (12 pages).
Houghton et al., "Immunological validation of the EpitOptimizer program for streamlined design of heteroclitic epitopes," Vaccine, available online Jun. 4, 2007, vol. 25(29), pp. 5330-5342.
International Search Report and Written Opinion mailed Mar. 28, 2022, in the International Application No. PCT/US2021/060013. 14 pages.
International Search Report and Written Opinion mailed Oct. 14, 2022, in the International Application No. PCT/US22/26354. 21 pages.
Jain et al., "Synthetic Tumor-Specific Breakpoint Peptide Vaccine in Patients With Chronic Myeloid Leukemia and Minimal Residual Disease," Cancer, Sep. 1, 2009, vol. 115, pp. 3924-3934.
Jaravine et al., "Assessment of cancer and virus antigens for cross-reactivity in human tissues," Bioinformatics, Jan. 1, 2017, vol. 33, No. 1, pp. 104-111.
Jaravine et al., "Expitope 2.0: a tool to assess immunotherapeutic antigens for their potential cross-reactivity against naturally expressed proteins in human tissues," BMC Cancer, Dec. 28, 2017, vol. 17:892. 9 pages.
Jurtz, V. et al., "NetMHCpan-4.0: Improved Peptide-MHC Class I Interaction Predictions Integrating Eluted Ligand and Peptide Binding Affinity Data", The Journal of Immunology, prepublished online Oct. 4, 2017, vol. 199, pp. 3360-3368 (9 pages).
Keogh et al., "Identification of new epitopes from four different tumor-associated antigens: Recognition of naturally processed epitopes correlates with HLA-A*0201-binding affinity," The Journal of Immunology, Jul. 15, 2001, vol. 167(2), pp. 787-796. 11 pages.
Klinger et al., "Multiplex identification of antigen-specific T cell receptors using a combination of immune assays and immune receptor sequencing," PLOS One, Oct. 28, 2015, vol. 10(10), e0141561. 21 pages.
Kranz et al., "Systemic RNA delivery to dendritic cells exploits antiviral defence for cancer immunotherapy," Nature, Jun. 16, 2016, vol. 534(7607), pp. 396-401, and Methods. 16 pages.
Kreiter, et al., "Increased antigen presentation efficiency by coupling antigens to MHC class I trafficking signals," The Journal of Immunology, Jan. 2008, vol. 180(1), pp. 309-318, and Corrections. 12 pages.

Krienke, C. et al., "A noninflammatory mRNA vaccine for treatment of experimental autoimmune encephalomyelitis", Science, Jan. 8, 2021, vol. 371, pp. 145-153 (10 pages).
Liu et al. "Computationally Optimized SARS-CoV-2 MHC Class I and II Vaccine Formulations Predicted to Target Human Haplotype Distributions," Cell Systems, Aug. 26, 2020, vol. 11(2), pp. 131-144, e1-e6, Supplementary Table. 23 pages.
Liu et al., "Maximum n-times Coverage for CoVID-19 Vaccine Design," arXiv (arXiv:2101.10902v1), submitted Jan. 24, 2021. 13 pages.
Liu et al., "Predicted Cellular Immunity Population Coverage Gaps for SARS-CoV-2 Subunit Vaccines and their Augmentation by Compact Peptide Sets," bioRxiv, posted Oct. 21, 2020, 29 pages. (https://www.biorxiv.org/content/10.1101/2020.08.04.200691v2).
Liu et al., "Predicted Cellular Immunity Population Coverage Gaps for SARS-CoV-2 Subunit Vaccines and their Augmentation by Compact Peptide Sets," Cell Systems, Journal Pre-proof, Nov. 26, 2020. (https://doi.org/10.1016/j.cels.2020.11.010). 36 pages.
Longmate et al., "Population coverage by HLA class-I restricted cytotoxic T-lymphocyte epitopes," Immunogenetics (2001), published online Dec. 19, 2000, vol. 52, pp. 165-173.
Maa et al., "Biopharmaceutical Powders: Particle Formation and Formulation Considerations," Current Pharmaceutical Biotechnology, Nov. 2000, vol. 1, No. 3, pp. 283-302.
Mahanty et al., "Immunogenicity of infectious pathogens and vaccine antigens," BMC Immunology, published online May 29, 2015, vol. 16(31), pp. 1-6.
Mashiba et al., "Identification of CTL epitopes in hepatitis C virus by a genome-wide computational scanning and a rational design of peptide vaccine," Immunogenetics, published online Jan. 16, 2007, vol. 59, pp. 197-209.
Merriam-Webster, "Prevent", available online at https://www.merriam-webster.com/dictionary/prevent. 10 pages. Accessed on Sep. 24, 2021.
Mösch et al., "Machine Learning for Cancer Immunotherapies Based on Epitope Recognition by T Cell Receptors," Frontiers in Genetics, Nov. 19, 2019, vol. 10, Article 1141. 17 pages.
Nair et al., "A simple practice guide for dose conversion between animals and human," Journal of Basic and Clinical Pharmacy, Article Review, Mar.-May 2016, vol. 7, Issue 2, pp. 27-31.
Ng et al., "In silico-guided sequence modifications of K-ras epitopes improve immunological outcome against G12V and G13D mutant KRAS antigens," PeerJ, published Jul. 20, 2018, 6:e5056. doi: 10.7717/peerj.5056. 21 pages.
Nielsen et al., "NNAlign: a platform to construct and evaluate artificial neural network models of receptor-ligand interactions," Nucleic Acids Research, published online Apr. 12, 2017, vol. 45, pp. W344-W349.
Nielsen et al., "The role of the proteasome in generating cytotoxic T-cell epitopes: insights obtained from improved predictions of proteasomal cleavage," Immunogenetics, published online Mar. 3, 2005, vol. 57, pp. 33-41.
Nielsen, M. and Lund, O., "NN-align. An artificial neural network-based alignment algorithm for MHC class II peptide binding prediction", BMC Bioinformatics, Sep. 18, 2009, vol. 10:296, pp. 1-10 (10 pages).
Nielsen, M. et al., "Quantitative Predictions of Peptide Binding to Any HLA-DR Molecule of Known Sequence: NetMHCIIpan", PLOS Computational Biology, Jul. 4, 2008, vol. 4(7):e1000107, pp. 1-10 (10 pages).
O'Donnell, T.J. et al., "MHCflurry 2.0: Improved Pan-Allele Prediction of MHC Class I-Presented Peptides by Incorporating Antigen Processing", Cell Systems, Jul. 22, 2020, vol. 11, pages: cover, 42-48 (15 pages).
O'Donnell, T.J. et al., "MHCflurry: Open-Source Class I MHC Binding Affinity Prediction", Cell Systems, Jul. 25, 2018, vol. 7, pages: cover, 129-132 (9 pages).
Ogishi et al., "Quantitative Prediction of the Landscape of T Cell Epitope Immunogenicity in Sequence Space," Frontiers in Immunology, Apr. 16, 2019, vol. 10, Article 827. 20 pages.
Park et al., "Accurate structure prediction of peptide-MHC complexes for identifying highly immunogenic antigens," Mol. Immunol., Nov. 2013, vol. 56(0):81-90. NIH Author Manuscript. 25 pages.

(56) References Cited

OTHER PUBLICATIONS

Reynisson et al., "NetMHCpan-4.1 and NetMHCIIpan-4.0: improved predictions of MHC antigen presentation by concurrent motif deconvolution and integration of MS MHC eluted ligand data," Nucleic Acids Research, published online May 14, 2020; vol. 48(W1), pp. W449-W454.

Rist et al., "HLA peptide length preferences control CD8+ T cell responses," The Journal of Immunology, published online Jun. 7, 2013, vol. 191(2), pp. 561-571. 12 pages.

Rosenberg et al., "Immunologic and therapeutic evaluation of a synthetic peptide vaccine for the treatment of patients with metastatic melanoma," Nature Medicine, Mar. 1998, vol. 4(3), pp. 321-327.

Sahin et al., "Personalized RNA mutanome vaccines mobilize poly-specific therapeutic immunity against cancer," Nature, Jul. 13, 2017, vol. 547(7662), pp. 222-226, and Methods. 19 pages.

Schipper et al., "Minimal Phenotype Panels, A Method for Achieving Maximum Population Coverage with a Minimum of HLA Antigens," Human Immunology, vol. 51, Dec. 1996, pp. 95-98.

Sette et al., "Peptides and Methods for Creating Synthetic Peptides With Modulated Binding Affinity for HLA Molecules," Application for utility U.S. Appl. No. 09/226,775, filed Jan. 6, 1999—not published, abandoned. 133 pages.

Sette et al., "The Relationship Between Class I Binding Affinity and Immunogenicity of Potential Cytotoxic T Cell Epitopes," The Journal of Immunology, Dec. 15, 1994, vol. 153, pp. 5586-5592.

Shimokawa, C. et al., "CD8+ regulatory T cells are critical in prevention of autoimmune-mediated diabetes", Nature Communications, Apr. 22, 2020, vol. 11:1922, pp. 1-9 (9 pages).

Sim et al., "Correction—High-affinity oligoclonal TCRs define effective adoptive T cell therapy targeting mutant KRAS-G12D," Proc. Natl. Acad. Sci. USA, Nov. 3, 2020, vol. 117(44), pp. 27743-27744.

Sim et al., "High-affinity oligoclonal TCRs define effective adoptive T cell therapy targeting mutant KRAS-G12D," Proc. Natl. Acad. Sci. USA, first published May 27, 2020, vol. 117(23), pp. 12826-12835.

Slansky et al., "Enhanced antigen-specific antitumor immunity with altered peptide ligands that stabilize the MHC-peptide-TCR complex," Immunity, Oct. 2000, vol. 13(4), pp. 529-538.

Slota et al., "ELISpot for measuring human immune responses to vaccines," Expert Review of Vaccines, Mar. 2011, vol. 10(3), pp. 299-306. NIH Author Manuscript. 14 pages.

Soria-Guerra et al., "An overview of bioinformatics tools for epitope prediction: implications on vaccine development," Journal of Biomedical Informatics (2015), available online Nov. 10, 2014, vol. 53, pp. 405-414.

Takahashi et al., "Induction of Broadly Cross-Reactive Cytotoxic T Cells Recognizing an HIV-1 Envelope Determinant," Science, Jan. 17, 1992, vol. 255(5042), pp. 333-336.

Tangri et al., "Structural Features of Peptide Analogs of Human Histocompatibility Leukocyte Antigen Class I Epitopes That Are More Potent and Immunogenic than Wild-Type Peptide," Journal of Experimental Medicine, Sep. 17, 2001, vol. 194(6), pp. 833-846.

Tapia-Calle et al., "A PBMC-Based System to Assess Human T Cell Responses to Influenza Vaccine Candidates In Vitro," Vaccines, Nov. 13, 2019, vol. 7(4):181. 26 pages.

Toussaint, N.C. et al., "A Mathematical Framework for the Selection of an Optimal Set of Peptides for Epitope-Based Vaccines", PLoS Computational Biology, Dec. 26, 2008, vol. 4(12):e1000246, pp. 1-10 (10 pages).

Trolle et al., "The length distribution of class I-restricted T cell epitopes is determined by both peptide supply and MHC allele-specific binding preference," The Journal of Immunology, Feb. 15, 2016, vol. 196(4), 1480-1487. HSS Author Manuscript. 21 pages.

Vita et al., "The Immune Epitope Database (IEDB): 2018 update," Nucleic Acids Research (2019), published online Oct. 24, 2018, vol. 47, database issue D339-D343. 5 pages.

Woodham et al., "Nanobody-Antigen Conjugates Elicit HPV-Specific Antitumor Immune Responses," Cancer Immunology Research, Jul. 2018, vol. 6(7); pp. 870-880.

Zaremba et al., "Identification of an enhancer agonist cytotoxic T lymphocyte peptide from human carcinoembryonic antigen," Cancer Research, Oct. 15, 1997, vol. 57(20), pp. 4570-4577.

Zhang et al., "Cancer vaccines: Targeting KRAS-driven cancers," Expert Review of Vaccines, published online Mar. 14, 2020, vol. 19(2), pp. 163-173. 12 pages.

Zirlik et al., "Cytotoxic T cells generated against heteroclitic peptides kill primary tumor cells independent of the binding affinity of the native tumor antigen peptide," Blood, Dec. 1, 2006, Vo. 108, No. 12, pp. 3865-3870.

Antunes et al., "General Prediction of Peptide-MHC Binding Modes Using Incremental Docking: A Proof of Concept," Scientific Reports, published online Mar. 12, 2018, vol. 8(1):4327-4339. 13 pages.

Badrinath et al., "A vaccine targeting resistant tumours by dual T cell plus NK cell attack," Nature, Jun. 30, 2022, vol. 606, pp. 992-998 and Methods. 31 pages.

Bai et al., "Immune-based mutation classification enables neoantigen prioritization and immune feature discovery in cancer immunotherapy," Oncoimmunology, Jan. 15, 2021, vol. 10(1), e1868130. 13 pages.

Bear et al., "Biochemical and functional characterization of mutant KRAS epitopes validates this oncoprotein for immunological targeting," Nature Communications, published online Jul. 16, 2021, vol. 12(1):4365-4380. 16 pages.

Brito et al., "A cationic nanoemulsion for the delivery of next-generation RNA vaccines," Molecular Therapy, Dec. 2014, vol. 22(12), pp. 2118-2129.

Bulik-Sullivan et al., "Deep learning using tumor HLA peptide mass spectrometry datasets improves neoantigen identification," Nature Biotechnology (2019), published online Dec. 17, 2018, vol. 37, pp. 55-63 and Online Methods. 13 pages.

Dai et al., "Constrained Submodular Optimization for Vaccine Design," arXiv preprint, arXiv:2206.08336v2. https://arxiv.org/abs/2206.08336, version 2, Jan. 27, 2023. 24 pages.

Geall et al., "Nonviral delivery of self-amplifying RNA vaccines," Proc. Natl. Acad. Sci., Sep. 4, 2012, vol. 109(36), pp. 14604-14609.

Hie et al., "Learning the language of viral evolution and escape," Science, Jan. 15, 2021, vol. 371(6526):284-288. 5 pages.

Kreiner et al., "Current state of antigen-specific immunotherapy for type 1 diabetes," Curr. Opin. Endocrinol. Diabetes Obes., Aug. 2021, vol. 28(4), pp. 411-418.

Li et al., "Circular RNA cancer vaccines drive immunity in hard-to-treat malignancies," Theranostics, Aug. 29, 2022, vol. 12(14), pp. 6422-6436.

London et al., "Rosetta FlexPepDock web server—high resolution modeling of peptide-protein interactions," Nucleic Acids Research, published online May 27, 2011, vol. 39, Web Server issue: W249-253.

Parkhurst et al., "Improved induction of melanoma-reactive CTL with peptides from the melanoma antigen gp100 modified at HLA-A*0201-binding residues," The Journal of Immunology, Sep. 15, 1996, vol. 157(6), pp. 2539-2548.

Pishesha et al., "Induction of antigen-specific tolerance by nanobody-antigen adducts that target class-II major histocompatibility complexes," Nature Biomedical Engineering, Nov. 2021, vol. 5(11), pp. 1389-1401.

Postigo-Fernandez et al., "A multi-epitope DNA vaccine enables a broad engagement of diabetogenic T cells for tolerance in Type 1 diabetes," Journal of Autoimmunity (2019), available online Nov. 17, 2018, vol. 98, pp. 13-23.

Robinson et al., "Potential for Antigen-Specific Tolerizing Immunotherapy in Systematic Lupus Erythematosus," Frontiers in Immunology, Jul. 16, 2021, vol. 12:654701, pp. 1-13.

Slingluff et al., "Immunologic and clinical outcomes of a randomized phase II trial of two multipeptide vaccines for melanoma in the adjuvant setting," Clin. Cancer Res., Nov. 2007, vol. 13(21), pp. 6386-6395.

Wang et al., "A benchmark study of sequence alignment methods for protein clustering," BMC Bioinformatics, Dec. 31, 2018, vol. 19(Suppl 19):529, pp. 95-104.

(56) References Cited

OTHER PUBLICATIONS

Wang et al., "Direct Detection and Quantification of Neoantigens," Cancer Immunology Research, published online Sep. 16, 2019, vol. 7(11), pp. 1748-1754.

Aurisicchio et al., "A novel minigene scaffold for therapeutic cancer vaccines," OncoImmunology, published online Jan. 16, 2014, vol. 3, e27529, pp. 1-13. 14 pages.

Fridman et al., "An efficient T-cell epitope discovery strategy using in silico prediction and the iTopia assay platform," OncoImmunology, published online Nov. 30, 2012, vol. 1:8, pp. 1258-1270 and Supplemental Material. 21 pages.

Zhang et al., "Epitope-based minigene vaccine targeting fibroblast activation protein α induces specific immune responses and antitumor effects in 4 T1 murine breast cancer model," International Immunopharmacology, available online Sep. 21, 2022, vol. 112, 109237, pp. 1-10.

Carter et al., "A pan-variant mRNA-LNP T cell vaccine protects HLA transgenic mice from mortality after infection with SARS-CoV-2 Beta," bioRxiv. Sep. 26, 2022. 38 pages. (https://doi.org/10.1101/2022.09.23.509206).

Carter et al., "A pan-variant mRNA-LNP T cell vaccine protects HLA transgenic mice from mortality after infection with SARS-CoV-2 Beta," Frontiers in Immunology, Mar. 9, 2023, vol. 14:1135815, pp. 1-9.

Chu et al., "A transformer-based model to predict peptide—HLA class I binding and optimize mutated peptides for vaccine design," Nature Machine Intelligence, vol. 4(3), Mar. 23, 2022, pp. 300-311 and figures. 15 pages.

Chu et al., "TransMut: a program to predict HLA-I peptide binding and optimize mutated peptides for vaccine design by the Transformer-derived self-attention model," Research Square, Sep. 30, 2021. 47 pages. (https://doi.org/10.21203/rs.3.rs-785618/v1).

Racle et al., "Robust prediction of HLA class II epitopes by deep motif deconvolution of immunopeptidomes," Nature Biotechnology, Nov. 2019, vol. 37(11), pp. 1283-1286, Methods and Reporting Summary. 12 pages.

Bakker et al., "Analogues of CTL epitopes with improved MHC class-I binding capacity elicit anti-melanoma CTL recognizing the wild-type epitope," Int. J. Cancer, Jan. 27, 1997, vol. 70(3), pp. 302-309.

Gross et al., "High vaccination efficiency of low-affinity epitopes in antitumor immunotherapy," The Journal of Clinical Investigation, Feb. 2004, vol. 113(3), pp. 425-433.

International Search Report and Written Opinion mailed Apr. 2, 2024, in the International Application No. PCT/US23/74984. 11 pages.

Menez-Jamet et al., "Optimized tumor cryptic peptides: the basis for universal neo-antigen-like tumor vaccines," Ann. Transl. Med., Jul. 2016, 4(14):266, Review Article pp. 1-11.

Scardino et al., "HER-2/neu and hTERT cryptic epitopes as novel targets for broad spectrum tumor immunotherapy," The Journal of Immunology, Jun. 2002, 168(11):5900-6. 8 pages.

Tourdot et al., "A general strategy to enhance immunogenicity of low-affinity HLA-A2.1-associated peptides: implication in the identification of cryptic tumor epitopes," Eur. J. Immunol., Dec. 2000, vol. 30(12), pp. 3411-3421.

Valmori et al., "Enhanced generation of specific tumor-reactive CTL in vitro by selected Melan-A/MART-1 immunodominant peptide analogues," The Journal of Immunology, Feb. 15, 1998, 160(4):1750-8. 10 pages.

\* cited by examiner

Factoring of disease presentation type probabilities and for each presentation, probability of targets presented

|  | Brain Cancer | Bronchus and Lung Cancer | Colorectal Cancer | Pancreatic Cancer | Skin Cancer | Thyroid Cancer | Breast Cancer | Ovarian Cancer |
|---|---|---|---|---|---|---|---|---|
| BRAF_V600E | - | - | 0.1029 | - | 0.4392 | 0.5854 | - | - |
| BRAF_V600M | - | - | - | - | 0.0853 | - | - | - |
| EGFR_A289V | 0.0230 | - | - | - | - | - | - | - |
| EGFR_G598V | 0.0208 | - | - | - | - | - | - | - |
| EGFR_L858R | - | 0.0216 | - | - | - | - | - | - |
| HRAS_Q61K | - | - | - | - | - | 0.0061 | - | - |
| HRAS_Q61R | - | - | - | - | - | 0.0285 | - | - |
| IDH1_R132C | 0.0197 | - | - | - | - | - | - | - |
| IDH1_R132H | 0.4178 | - | - | - | - | - | - | - |
| KRAS_G12A | - | 0.0169 | - | - | - | - | - | - |
| KRAS_G12C | - | 0.0583 | - | - | - | - | - | - |
| KRAS_G12D | - | 0.0188 | 0.1235 | 0.3280 | - | - | - | - |
| KRAS_G12R | - | - | - | 0.1505 | - | - | - | - |
| KRAS_G12V | - | 0.0376 | 0.0947 | 0.2258 | - | - | - | 0.0092 |
| KRAS_G13D | - | - | 0.0700 | - | - | - | - | - |
| NRAS_Q61K | - | - | - | - | 0.0832 | 0.0163 | - | - |
| NRAS_Q61L | - | - | - | - | 0.0384 | - | - | - |
| NRAS_Q61R | - | - | - | - | 0.1215 | 0.0630 | - | 0.0069 |
| PIK3CA_E542K | - | 0.0169 | - | - | - | - | 0.0435 | - |
| PIK3CA_E545K | - | 0.0197 | 0.0700 | - | - | - | 0.0638 | - |
| PIK3CA_H1047R | - | - | - | - | - | - | 0.1225 | - |
| TP53_R158L | - | 0.0188 | - | - | - | - | - | - |
| TP53_R175H | 0.0186 | - | 0.0679 | - | - | - | 0.0202 | 0.0343 |
| TP53_R248Q | - | - | - | - | - | - | - | 0.0252 |
| TP53_R273C | 0.0581 | - | - | - | - | - | 0.0051 | 0.0137 |
| TP53_R273H | - | - | - | - | - | - | 0.0121 | 0.0206 |

FIG. 7

```
def merge_multi(lists):
    values = []

# While any list in lists has elements remaining
    while max(map(lambda l: len(l), lists)) > 0:
        # Find list with largest value at its head.
        cur_max = None
        cur_max_idx = None
        for idx, l in enumerate(lists):
            if not l:  # List is empty.
                continue
            if cur_max is None or l[0] > cur_max:
                cur_max = l[0]
                cur_max_idx = idx
        # Pop that value from list l.
        values.append((lists[cur_max_idx].pop(0), cur_max_idx))

return values
```

FIG. 13

COMPOSITIONS AND METHOD FOR OPTIMIZED PEPTIDE VACCINES USING RESIDUE OPTIMIZATION

This application is a continuation of U.S. patent application Ser. No. 17/729,290, filed Apr. 26, 2022, which is a continuation of U.S. patent application Ser. No. 17/243,096, filed Apr. 28, 2021, now U.S. Pat. No. 11,464,842, each of which is incorporated by reference herein in its entirety.

This patent disclosure contains material that is subject to copyright protection. The copyright owner has no objection to the facsimile reproduction of the patent document or the patent disclosure as it appears in the U.S. Patent and Trademark Office patent file or records, but otherwise reserves any and all copyright rights.

INCORPORATION BY REFERENCE

All documents cited herein are incorporated herein by reference in their entireties

SEQUENCE LISTING

The Sequence Listing is submitted on one compact disc (Copy 1), together with two duplicates thereof (Copies 2 and 3), each created on Jan. 15, 2023 and each containing one 586,016,000 byte file in XML format entitled "2215269_00125US3_SL.xml." Each compact disc was prepared in Macintosh machine format, is compatible with the Macintosh operating system. The material contained on the compact disc is specifically incorporated herein by reference.

TECHNICAL FIELD

The present invention relates generally to compositions, systems, and methods of peptide vaccines. More particularly, the present invention relates to compositions, systems, and methods of designing peptide vaccines to treat or prevent disease optimized based on predicted population immunogenicity.

BACKGROUND

The goal of a peptide vaccine is to train the immune system to recognize and expand its capacity to engage cells that display target peptides to improve the immune response to cancerous cells or pathogens. A peptide vaccine can also be administered to someone who is already diseased to increase their immune response to a causal cancer, other diseases, or pathogen. Alternatively, a peptide vaccine can be administered to induce the immune system to have therapeutic tolerance to one or more peptides. There exists a need for compositions, systems, and methods of peptide vaccines based on prediction of the target peptides that will be displayed to protect a host from cancer, other disease, or pathogen infection.

SUMMARY OF THE INVENTION

In one aspect, the invention provides for nucleic acid sequences encoding one or more amino acid sequences selected from the group consisting of SEQ ID NOs: 1 to 474.

In some embodiments, the nucleic acid sequences encode two or more amino acid sequences selected from the group consisting of SEQ ID NOs: 1 to 474.

In another aspect, the invention provides for an immunogenic composition comprising nucleic acid sequences encoding one or more amino acid sequences selected from the group consisting of SEQ ID NOs: 1 to 474.

In some embodiments, the immunogenic composition is administered to a subject. In some embodiments, the immunogenic composition comprises nucleic acid sequences encoding two or more amino acid sequences selected from the group consisting of SEQ ID NOs: 1 to 474. In some embodiments, the nucleic acid sequences are administered in a construct for expression in vivo. In some embodiments, the in vivo administration of the nucleic acid sequences is configured to produce one or more peptides that is displayed by an HLA class I molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic composition is administered in an effective amount to a subject to prevent cancer. In some embodiments, the immunogenic composition is administered in an effective amount to a subject to treat cancer. In some embodiments, the cancer is selected from the group consisting of pancreatic cancer, skin cancer, thyroid cancer, brain cancer, colorectal cancer, bronchus and lung cancer, breast cancer, and ovarian cancer. In some embodiments, the immunogenic composition comprises nucleic acid sequences encoding at least three amino acid sequences selected from the group consisting of SEQ ID NOs: 1 to 474.

In another aspect, the invention provides for an immunogenic peptide composition comprising one or more peptides selected from the group consisting of SEQ ID NOs: 1 to 474.

In some embodiments, the immunogenic peptide composition comprises two or more peptides selected from the group consisting of SEQ ID NOs: 1 to 474.

In another aspect, the invention provides for an immunogenic composition comprising nucleic acid sequences encoding one or more amino acid sequences selected from the group consisting of SEQ ID NOs: 1 to 18.

In some embodiments, the immunogenic composition comprises nucleic acid sequences encoding one or more amino acid sequences derived from a AKT1 protein mutation. In some embodiments, the immunogenic composition comprises nucleic acid sequences encoding two or more amino acid sequences selected from the group consisting of SEQ ID NOs: 1 to 18.

In another aspect, the invention provides for an immunogenic peptide composition comprising one or more peptides selected from the group consisting of SEQ ID NOs: 1 to 18.

In some embodiments, the immunogenic peptide composition comprises two or more peptides selected from the group consisting of SEQ ID NOs: 1 to 18. In some embodiments, the one or more peptides is a modified or unmodified fragment of a mutated AKT1 protein.

In another aspect, the invention provides for an immunogenic composition comprising nucleic acid sequences encoding one or more amino acid sequences selected from the group consisting of SEQ ID NOs: 19 to 50.

In some embodiments, the immunogenic composition comprises nucleic acid sequences encoding one or more amino acid sequences derived from a BRAF protein mutation. In some embodiments, the immunogenic composition comprises nucleic acid sequences encoding two or more amino acid sequences selected from the group consisting of SEQ ID NOs: 19 to 50.

In another aspect, the invention provides for an immunogenic peptide composition comprising one or more peptides selected from the group consisting of SEQ ID NOs: 19 to 50.

In some embodiments, the immunogenic peptide composition comprises two or more peptides selected from the group consisting of SEQ ID NOs: 19 to 50. In some embodiments, the one or more peptides is a modified or unmodified fragment of a mutated BRAF protein.

In another aspect, the invention provides for an immunogenic composition comprising nucleic acid sequences encoding one or more amino acid sequences selected from the group consisting of SEQ ID NOs: 51 to 98.

In some embodiments, the immunogenic composition comprises nucleic acid sequences encoding one or more amino acid sequences derived from a EGFR protein mutation. In some embodiments, the immunogenic composition comprises nucleic acid sequences encoding two or more amino acid sequences selected from the group consisting of SEQ ID NOs: 51 to 98.

In another aspect, the invention provides for an immunogenic peptide composition comprising one or more peptides selected from the group consisting of SEQ ID NOs: 51 to 98.

In some embodiments, the immunogenic peptide composition comprises two or more peptides selected from the group consisting of SEQ ID NOs: 51 to 98. In some embodiments, the one or more peptides is a modified or unmodified fragment of a mutated EGFR protein.

In another aspect, the invention provides for an immunogenic composition comprising nucleic acid sequences encoding one or more amino acid sequences selected from the group consisting of SEQ ID NOs: 99 to 118.

In some embodiments, the immunogenic composition comprises nucleic acid sequences encoding one or more amino acid sequences derived from a GTF2I protein mutation. In some embodiments, the immunogenic composition comprises nucleic acid sequences encoding two or more amino acid sequences selected from the group consisting of SEQ ID NOs: 99 to 118.

In another aspect, the invention provides for an immunogenic peptide composition comprising one or more peptides selected from the group consisting of SEQ ID NOs: 99 to 118.

In some embodiments, the immunogenic peptide composition comprises two or more peptides selected from the group consisting of SEQ ID NOs: 99 to 118. In some embodiments, the one or more peptides is a modified or unmodified fragment of a mutated GTF2I protein.

In another aspect, the invention provides for an immunogenic composition comprising nucleic acid sequences encoding one or more amino acid sequences selected from the group consisting of SEQ ID NOs: 119 to 140.

In some embodiments, the immunogenic composition comprises nucleic acid sequences encoding one or more amino acid sequences derived from a IDH1 protein mutation. In some embodiments, the immunogenic composition comprises nucleic acid sequences encoding two or more amino acid sequences selected from the group consisting of SEQ ID NOs: 119 to 140.

In another aspect, the invention provides for an immunogenic peptide composition comprising one or more peptides selected from the group consisting of SEQ ID NOs: 119 to 140.

In some embodiments, the immunogenic peptide composition comprises two or more peptides selected from the group consisting of SEQ ID NOs: 119 to 140. In some embodiments, the one or more peptides is a modified or unmodified fragment of a mutated IDH1 protein.

In another aspect, the invention provides for an immunogenic composition comprising nucleic acid sequences encoding one or more amino acid sequences selected from the group consisting of SEQ ID NOs: 141 to 229.

In some embodiments, the immunogenic composition comprises nucleic acid sequences encoding one or more amino acid sequences derived from a KRAS protein mutation. In some embodiments, the immunogenic composition comprises nucleic acid sequences encoding two or more amino acid sequences selected from the group consisting of SEQ ID NOs: 141 to 229.

In another aspect, the invention provides for an immunogenic peptide composition comprising one or more peptides selected from the group consisting of SEQ ID NOs: 141 to 229.

In some embodiments, the immunogenic peptide composition comprises two or more peptides selected from the group consisting of SEQ ID NOs: 141 to 229. In some embodiments, the one or more peptides is a modified or unmodified fragment of a mutated KRAS protein.

In another aspect, the invention provides for an immunogenic composition comprising nucleic acid sequences encoding one or more amino acid sequences selected from the group consisting of SEQ ID NOs: 230 to 272.

In some embodiments, the immunogenic composition comprises nucleic acid sequences encoding one or more amino acid sequences derived from a NRAS protein mutation. In some embodiments, the immunogenic composition comprises nucleic acid sequences encoding two or more amino acid sequences selected from the group consisting of SEQ ID NOs: 230 to 272.

In another aspect, the invention provides for an immunogenic peptide composition comprising one or more peptides selected from the group consisting of SEQ ID NOs: 230 to 272.

In some embodiments, the immunogenic peptide composition comprises two or more peptides selected from the group consisting of SEQ ID NOs: 230 to 272. In some embodiments, the one or more peptides is a modified or unmodified fragment of a mutated NRAS protein.

In another aspect, the invention provides for an immunogenic composition comprising nucleic acid sequences encoding one or more amino acid sequences selected from the group consisting of SEQ ID NOs: 273 to 322.

In some embodiments, the immunogenic composition comprises nucleic acid sequences encoding one or more amino acid sequences derived from a PIK3CA protein mutation. In some embodiments, the immunogenic composition comprises nucleic acid sequences encoding two or more amino acid sequences selected from the group consisting of SEQ ID NOs: 273 to 322.

In another aspect, the invention provides for an immunogenic peptide composition comprising one or more peptides selected from the group consisting of SEQ ID NOs: 273 to 322.

In some embodiments, the immunogenic peptide composition comprises two or more peptides selected from the group consisting of SEQ ID NOs: 273 to 322. In some embodiments, the one or more peptides is a modified or unmodified fragment of a mutated PIK3CA protein.

In another aspect, the invention provides for an immunogenic composition comprising nucleic acid sequences encoding one or more amino acid sequences selected from the group consisting of SEQ ID NOs: 323 to 353.

In some embodiments, the immunogenic composition comprises nucleic acid sequences encoding one or more amino acid sequences derived from a PTEN protein mutation. In some embodiments, the immunogenic composition comprises nucleic acid sequences encoding two or more amino acid sequences selected from the group consisting of SEQ ID NOs: 323 to 353.

In another aspect, the invention provides for an immunogenic peptide composition comprising one or more peptides selected from the group consisting of SEQ ID NOs: 323 to 353.

In some embodiments, the immunogenic peptide composition comprises two or more peptides selected from the group consisting of SEQ ID NOs: 323 to 353. In some embodiments, the one or more peptides is a modified or unmodified fragment of a mutated PTEN protein.

In another aspect, the invention provides for an immunogenic composition comprising nucleic acid sequences encoding one or more amino acid sequences selected from the group consisting of SEQ ID NOs: 354 to 458.

In some embodiments, the immunogenic composition comprises nucleic acid sequences encoding one or more amino acid sequences derived from a TP53 protein mutation. In some embodiments, the immunogenic composition comprises nucleic acid sequences encoding two or more amino acid sequences selected from the group consisting of SEQ ID NOs: 354 to 458.

In another aspect, the invention provides for an immunogenic peptide composition comprising one or more peptides selected from the group consisting of SEQ ID NOs: 354 to 458.

In some embodiments, the immunogenic peptide composition comprises two or more peptides selected from the group consisting of SEQ ID NOs: 354 to 458. In some embodiments, the one or more peptides is a modified or unmodified fragment of a mutated TP53 protein.

In another aspect, the invention provides for an immunogenic composition comprising nucleic acid sequences encoding one or more amino acid sequences selected from the group consisting of SEQ ID NOs: 141 to 272.

In some embodiments, the immunogenic composition comprises nucleic acid sequences encoding one or more amino acid sequences derived from a RAS protein mutation. In some embodiments, the immunogenic composition comprises nucleic acid sequences encoding two or more amino acid sequences selected from the group consisting of SEQ ID NOs: 141 to 272.

In another aspect, the invention provides for an immunogenic peptide composition comprising one or more peptides selected from the group consisting of SEQ ID NOs: 141 to 272.

In some embodiments, the immunogenic peptide composition comprises two or more peptides selected from the group consisting of SEQ ID NOs: 141 to 272. In some embodiments, the one or more peptides is a modified or unmodified fragment of a mutated RAS protein.

In another aspect, the invention provides for an immunogenic composition comprising nucleic acid sequences encoding one or more amino acid sequences selected from the group consisting of SEQ ID NOs: 19 to 33.

In some embodiments, the immunogenic composition comprises nucleic acid sequences encoding one or more amino acid sequences derived from a BRAF V600 protein mutation. In some embodiments, the immunogenic composition comprises nucleic acid sequences encoding two or more amino acid sequences selected from the group consisting of SEQ ID NOs: 19 to 33.

In another aspect, the invention provides for an immunogenic peptide composition comprising one or more peptides selected from the group consisting of SEQ ID NOs: 19 to 33.

In some embodiments, the immunogenic peptide composition comprises two or more peptides selected from the group consisting of SEQ ID NOs: 19 to 33. In some embodiments, the immunogenic peptide composition comprises a peptide derived from a BRAF V600 protein mutation.

In another aspect, the invention provides for an immunogenic composition comprising nucleic acid sequences encoding one or more amino acid sequences selected from the group consisting of SEQ ID NOs: 34 to 50.

In some embodiments, the immunogenic composition comprises nucleic acid sequences encoding one or more amino acid sequences derived from a BRAF V600M protein mutation. In some embodiments, the immunogenic composition comprises nucleic acid sequences encoding two or more amino acid sequences selected from the group consisting of SEQ ID NOs: 34 to 50.

In another aspect, the invention provides for an immunogenic peptide composition comprising one or more peptides selected from the group consisting of SEQ ID NOs: 34 to 50.

In some embodiments, the immunogenic peptide composition comprises two or more peptides selected from the group consisting of SEQ ID NOs: 34 to 50. In some embodiments, the immunogenic peptide composition comprises a peptide derived from a BRAF V600M protein mutation.

In another aspect, the invention provides for an immunogenic composition comprising nucleic acid sequences encoding one or more amino acid sequences selected from the group consisting of SEQ ID NOs: 51 to 66.

In some embodiments, the immunogenic composition comprises nucleic acid sequences encoding one or more amino acid sequences derived from a EGFR A289V protein mutation. In some embodiments, the immunogenic composition comprises nucleic acid sequences encoding two or more amino acid sequences selected from the group consisting of SEQ ID NOs: 51 to 66.

In another aspect, the invention provides for an immunogenic peptide composition comprising one or more peptides selected from the group consisting of SEQ ID NOs: 51 to 66.

In some embodiments, the immunogenic peptide composition comprises two or more peptides selected from the group consisting of SEQ ID NOs: 51 to 66. In some embodiments, the immunogenic peptide composition comprises a peptide derived from a EGFR A289V protein mutation.

In another aspect, the invention provides for an immunogenic composition comprising nucleic acid sequences encoding one or more amino acid sequences selected from the group consisting of SEQ ID NOs: 67 to 81.

In some embodiments, the immunogenic composition comprises nucleic acid sequences encoding one or more amino acid sequences derived from a EGFR G598V protein mutation. In some embodiments, the immunogenic composition comprises nucleic acid sequences encoding two or more amino acid sequences selected from the group consisting of SEQ ID NOs: 67 to 81.

In another aspect, the invention provides for an immunogenic peptide composition comprising one or more peptides selected from the group consisting of SEQ ID NOs: 67 to 81.

In some embodiments, the immunogenic peptide composition comprises two or more peptides selected from the group consisting of SEQ ID NOs: 67 to 81. In some embodiments, the immunogenic peptide composition comprises a peptide derived from a EGFR G598V protein mutation.

In another aspect, the invention provides for an immunogenic composition comprising nucleic acid sequences encoding one or more amino acid sequences selected from the group consisting of SEQ ID NOs: 82 to 98.

In some embodiments, the immunogenic composition comprises nucleic acid sequences encoding one or more amino acid sequences derived from a EGFR L858R protein mutation. In some embodiments, the immunogenic composition comprises nucleic acid sequences encoding two or more amino acid sequences selected from the group consisting of SEQ ID NOs: 82 to 98.

In another aspect, the invention provides for an immunogenic peptide composition comprising one or more peptides selected from the group consisting of SEQ ID NOs: 82 to 98.

In some embodiments, the immunogenic peptide composition comprises two or more peptides selected from the group consisting of SEQ ID NOs: 82 to 98. In some embodiments, the immunogenic peptide composition comprises a peptide derived from a EGFR L858R protein mutation.

In another aspect, the invention provides for an immunogenic composition comprising nucleic acid sequences encoding one or more amino acid sequences selected from the group consisting of SEQ ID NOs: 125 to 140.

In some embodiments, the immunogenic composition comprises nucleic acid sequences encoding one or more amino acid sequences derived from a IDH1 R132H protein mutation. In some embodiments, the immunogenic composition comprises nucleic acid sequences encoding two or more amino acid sequences selected from the group consisting of SEQ ID NOs: 125 to 140.

In another aspect, the invention provides for an immunogenic peptide composition comprising one or more peptides selected from the group consisting of SEQ ID NOs: 125 to 140.

In some embodiments, the immunogenic peptide composition comprises two or more peptides selected from the group consisting of SEQ ID NOs: 125 to 140. In some embodiments, the immunogenic peptide composition comprises a peptide derived from a IDH1 R132H protein mutation.

In another aspect, the invention provides for an immunogenic composition comprising nucleic acid sequences encoding one or more amino acid sequences selected from the group consisting of SEQ ID NOs: 119 to 124.

In some embodiments, the immunogenic composition comprises nucleic acid sequences encoding one or more amino acid sequences derived from a IDH1 R132C protein mutation. In some embodiments, the immunogenic composition comprises nucleic acid sequences encoding two or more amino acid sequences selected from the group consisting of SEQ ID NOs: 119 to 124.

In another aspect, the invention provides for an immunogenic peptide composition comprising one or more peptides selected from the group consisting of SEQ ID NOs: 119 to 124.

In some embodiments, the immunogenic peptide composition comprises two or more peptides selected from the group consisting of SEQ ID NOs: 119 to 124. In some embodiments, the immunogenic peptide composition comprises a peptide derived from a IDH1 R132C protein mutation.

In another aspect, the invention provides for an immunogenic composition comprising nucleic acid sequences encoding one or more amino acid sequences selected from the group consisting of SEQ ID NOs: 167 to 178.

In some embodiments, the immunogenic composition comprises nucleic acid sequences encoding one or more amino acid sequences derived from a KRAS G12D protein mutation. In some embodiments, the immunogenic composition comprises nucleic acid sequences encoding two or more amino acid sequences selected from the group consisting of SEQ ID NOs: 167 to 178.

In another aspect, the invention provides for an immunogenic peptide composition comprising one or more peptides selected from the group consisting of SEQ ID NOs: 167 to 178.

In some embodiments, the immunogenic peptide composition comprises two or more peptides selected from the group consisting of SEQ ID NOs: 167 to 178. In some embodiments, the immunogenic peptide composition comprises a peptide derived from a KRAS G12D protein mutation.

In another aspect, the invention provides for an immunogenic composition comprising nucleic acid sequences encoding one or more amino acid sequences selected from the group consisting of SEQ ID NOs: 203 to 213.

In some embodiments, the immunogenic composition comprises nucleic acid sequences encoding one or more amino acid sequences derived from a KRAS G12V protein mutation. In some embodiments, the immunogenic composition comprises nucleic acid sequences encoding two or more amino acid sequences selected from the group consisting of SEQ ID NOs: 203 to 213.

In another aspect, the invention provides for an immunogenic peptide composition comprising one or more peptides selected from the group consisting of SEQ ID NOs: 203 to 213.

In some embodiments, the immunogenic peptide composition comprises two or more peptides selected from the group consisting of SEQ ID NOs: 203 to 213. In some embodiments, the immunogenic peptide composition comprises a peptide derived from a KRAS G12V protein mutation.

In another aspect, the invention provides for an immunogenic composition comprising nucleic acid sequences encoding one or more amino acid sequences selected from the group consisting of SEQ ID NOs: 179 to 191.

In some embodiments, the immunogenic composition comprises nucleic acid sequences encoding one or more amino acid sequences derived from a KRAS G12R protein mutation. In some embodiments, the immunogenic composition comprises nucleic acid sequences encoding two or more amino acid sequences selected from the group consisting of SEQ ID NOs: 179 to 191.

In another aspect, the invention provides for an immunogenic peptide composition comprising one or more peptides selected from the group consisting of SEQ ID NOs: 179 to 191.

In some embodiments, the immunogenic peptide composition comprises two or more peptides selected from the group consisting of SEQ ID NOs: 179 to 191. In some embodiments, the immunogenic peptide composition comprises a peptide derived from a KRAS G12R protein mutation.

In another aspect, the invention provides for an immunogenic composition comprising nucleic acid sequences encoding one or more amino acid sequences selected from the group consisting of SEQ ID NOs: 154 to 166.

In some embodiments, the immunogenic composition comprises nucleic acid sequences encoding one or more amino acid sequences derived from a KRAS G12C protein mutation. In some embodiments, the immunogenic composition comprises nucleic acid sequences encoding two or more amino acid sequences selected from the group consisting of SEQ ID NOs: 154 to 166.

In another aspect, the invention provides for an immunogenic peptide composition comprising one or more peptides selected from the group consisting of SEQ ID NOs: 154 to 166.

In some embodiments, the immunogenic peptide composition comprises two or more peptides selected from the group consisting of SEQ ID NOs: 154 to 166. In some embodiments, the immunogenic peptide composition comprises a peptide derived from a KRAS G12C protein mutation.

In another aspect, the invention provides for an immunogenic composition comprising nucleic acid sequences encoding one or more amino acid sequences selected from the group consisting of SEQ ID NOs: 214 to 229.

In some embodiments, the immunogenic composition comprises nucleic acid sequences encoding one or more amino acid sequences derived from a KRAS G13D protein mutation. In some embodiments, the immunogenic composition comprises nucleic acid sequences encoding two or more amino acid sequences selected from the group consisting of SEQ ID NOs: 214 to 229.

In another aspect, the invention provides for an immunogenic peptide composition comprising one or more peptides selected from the group consisting of SEQ ID NOs: 214 to 229.

In some embodiments, the immunogenic peptide composition comprises two or more peptides selected from the group consisting of SEQ ID NOs: 214 to 229. In some embodiments, the immunogenic peptide composition comprises a peptide derived from a KRAS G13D protein mutation.

In another aspect, the invention provides for an immunogenic composition comprising nucleic acid sequences encoding one or more amino acid sequences selected from the group consisting of SEQ ID NOs: 141 to 153.

In some embodiments, the immunogenic composition comprises nucleic acid sequences encoding one or more amino acid sequences derived from a KRAS G12A protein mutation. In some embodiments, the immunogenic composition comprises nucleic acid sequences encoding two or more amino acid sequences selected from the group consisting of SEQ ID NOs: 141 to 153.

In another aspect, the invention provides for an immunogenic peptide composition comprising one or more peptides selected from the group consisting of SEQ ID NOs: 141 to 153.

In some embodiments, the immunogenic peptide composition comprises two or more peptides selected from the group consisting of SEQ ID NOs: 141 to 153. In some embodiments, the immunogenic peptide composition comprises a peptide derived from a KRAS G12A protein mutation.

In another aspect, the invention provides for an immunogenic composition comprising nucleic acid sequences encoding one or more amino acid sequences selected from the group consisting of SEQ ID NOs: 192 to 202.

In some embodiments, the immunogenic composition comprises nucleic acid sequences encoding one or more amino acid sequences derived from a KRAS G12S protein mutation. In some embodiments, the immunogenic composition comprises nucleic acid sequences encoding two or more amino acid sequences selected from the group consisting of SEQ ID NOs: 192 to 202.

In another aspect, the invention provides for an immunogenic peptide composition comprising one or more peptides selected from the group consisting of SEQ ID NOs: 192 to 202.

In some embodiments, the immunogenic peptide composition comprises two or more peptides selected from the group consisting of SEQ ID NOs: 192 to 202. In some embodiments, the immunogenic peptide composition comprises a peptide derived from a KRAS G12S protein mutation.

In another aspect, the invention provides for an immunogenic composition comprising nucleic acid sequences encoding one or more amino acid sequences selected from the group consisting of SEQ ID NOs: 256 to 272.

In some embodiments, the immunogenic composition comprises nucleic acid sequences encoding one or more amino acid sequences derived from a NRAS Q61R protein mutation. In some embodiments, the immunogenic composition comprises nucleic acid sequences encoding two or more amino acid sequences selected from the group consisting of SEQ ID NOs: 256 to 272.

In another aspect, the invention provides for an immunogenic peptide composition comprising one or more peptides selected from the group consisting of SEQ ID NOs: 256 to 272.

In some embodiments, the immunogenic peptide composition comprises two or more peptides selected from the group consisting of SEQ ID NOs: 256 to 272. In some embodiments, the immunogenic peptide composition comprises a peptide derived from a NRAS Q61R protein mutation.

In another aspect, the invention provides for an immunogenic composition comprising nucleic acid sequences encoding one or more amino acid sequences selected from the group consisting of SEQ ID NOs: 230 to 238.

In some embodiments, the immunogenic composition comprises nucleic acid sequences encoding one or more amino acid sequences derived from a NRAS Q61K protein mutation. In some embodiments, the immunogenic composition comprises nucleic acid sequences encoding two or more amino acid sequences selected from the group consisting of SEQ ID NOs: 230 to 238.

In another aspect, the invention provides for an immunogenic peptide composition comprising one or more peptides selected from the group consisting of SEQ ID NOs: 230 to 238.

In some embodiments, the immunogenic peptide composition comprises two or more peptides selected from the group consisting of SEQ ID NOs: 230 to 238. In some embodiments, the immunogenic peptide composition comprises a peptide derived from a NRAS Q61K protein mutation.

In another aspect, the invention provides for an immunogenic composition comprising nucleic acid sequences encoding one or more amino acid sequences selected from the group consisting of SEQ ID NOs: 239 to 255.

In some embodiments, the immunogenic composition comprises nucleic acid sequences encoding one or more amino acid sequences derived from a NRAS Q61L protein mutation. In some embodiments, the immunogenic composition comprises nucleic acid sequences encoding two or more amino acid sequences selected from the group consisting of SEQ ID NOs: 239 to 255.

In another aspect, the invention provides for an immunogenic peptide composition comprising one or more peptides selected from the group consisting of SEQ ID NOs: 239 to 255.

In some embodiments, the immunogenic peptide composition comprises two or more peptides selected from the group consisting of SEQ ID NOs: 239 to 255. In some embodiments, the immunogenic peptide composition comprises a peptide derived from a NRAS Q61L protein mutation.

In another aspect, the invention provides for an immunogenic composition comprising nucleic acid sequences encoding one or more amino acid sequences selected from the group consisting of SEQ ID NOs: 273 to 285.

In some embodiments, the immunogenic composition comprises nucleic acid sequences encoding one or more amino acid sequences derived from a PIK3CA E542K protein mutation. In some embodiments, the immunogenic composition comprises nucleic acid sequences encoding two or more amino acid sequences selected from the group consisting of SEQ ID NOs: 273 to 285.

In another aspect, the invention provides for an immunogenic peptide composition comprising one or more peptides selected from the group consisting of SEQ ID NOs: 273 to 285.

In some embodiments, the immunogenic peptide composition comprises two or more peptides selected from the group consisting of SEQ ID NOs: 273 to 285. In some embodiments, the immunogenic peptide composition comprises a peptide derived from a PIK3CA E542K protein mutation.

In another aspect, the invention provides for an immunogenic composition comprising nucleic acid sequences encoding one or more amino acid sequences selected from the group consisting of SEQ ID NOs: 286 to 293.

In some embodiments, the immunogenic composition comprises nucleic acid sequences encoding one or more amino acid sequences derived from a PIK3CA E545K protein mutation. In some embodiments, the immunogenic composition comprises nucleic acid sequences encoding two or more amino acid sequences selected from the group consisting of SEQ ID NOs: 286 to 293.

In another aspect, the invention provides for an immunogenic peptide composition comprising one or more peptides selected from the group consisting of SEQ ID NOs: 286 to 293.

In some embodiments, the immunogenic peptide composition comprises two or more peptides selected from the group consisting of SEQ ID NOs: 286 to 293. In some embodiments, the immunogenic peptide composition comprises a peptide derived from a PIK3CA E545K protein mutation.

In another aspect, the invention provides for an immunogenic composition comprising nucleic acid sequences encoding one or more amino acid sequences selected from the group consisting of SEQ ID NOs: 294 to 309.

In some embodiments, the immunogenic composition comprises nucleic acid sequences encoding one or more amino acid sequences derived from a PIK3CA H1047R protein mutation. In some embodiments, the immunogenic composition comprises nucleic acid sequences encoding two or more amino acid sequences selected from the group consisting of SEQ ID NOs: 294 to 309.

In another aspect, the invention provides for an immunogenic peptide composition comprising one or more peptides selected from the group consisting of SEQ ID NOs: 294 to 309.

In some embodiments, the immunogenic peptide composition comprises two or more peptides selected from the group consisting of SEQ ID NOs: 294 to 309. In some embodiments, the immunogenic peptide composition comprises a peptide derived from a PIK3CA H1047R protein mutation.

In another aspect, the invention provides for an immunogenic composition comprising nucleic acid sequences encoding one or more amino acid sequences selected from the group consisting of SEQ ID NOs: 359 to 374.

In some embodiments, the immunogenic composition comprises nucleic acid sequences encoding one or more amino acid sequences derived from a TP53 R158L protein mutation. In some embodiments, the immunogenic composition comprises nucleic acid sequences encoding two or more amino acid sequences selected from the group consisting of SEQ ID NOs: 359 to 374.

In another aspect, the invention provides for an immunogenic peptide composition comprising one or more peptides selected from the group consisting of SEQ ID NOs: 359 to 374.

In some embodiments, the immunogenic peptide composition comprises two or more peptides selected from the group consisting of SEQ ID NOs: 359 to 374. In some embodiments, the immunogenic peptide composition comprises a peptide derived from a TP53 R158L protein mutation.

In another aspect, the invention provides for an immunogenic composition comprising nucleic acid sequences encoding one or more amino acid sequences selected from the group consisting of SEQ ID NOs: 375 to 386.

In some embodiments, the immunogenic composition comprises nucleic acid sequences encoding one or more amino acid sequences derived from a TP53 R175H protein mutation. In some embodiments, the immunogenic composition comprises nucleic acid sequences encoding two or more amino acid sequences selected from the group consisting of SEQ ID NOs: 375 to 386.

In another aspect, the invention provides for an immunogenic peptide composition comprising one or more peptides selected from the group consisting of SEQ ID NOs: 375 to 386.

In some embodiments, the immunogenic peptide composition comprises two or more peptides selected from the group consisting of SEQ ID NOs: 375 to 386. In some embodiments, the immunogenic peptide composition comprises a peptide derived from a TP53 R175H protein mutation.

In another aspect, the invention provides for an immunogenic composition comprising nucleic acid sequences encoding one or more amino acid sequences selected from the group consisting of SEQ ID NOs: 387 to 401.

In some embodiments, the immunogenic composition comprises nucleic acid sequences encoding one or more amino acid sequences derived from a TP53 R248Q protein mutation. In some embodiments, the immunogenic composition comprises nucleic acid sequences encoding two or more amino acid sequences selected from the group consisting of SEQ ID NOs: 387 to 401.

In another aspect, the invention provides for an immunogenic peptide composition comprising one or more peptides selected from the group consisting of SEQ ID NOs: 387 to 401.

In some embodiments, the immunogenic peptide composition comprises two or more peptides selected from the group consisting of SEQ ID NOs: 387 to 401. In some embodiments, the immunogenic peptide composition comprises a peptide derived from a TP53 R248Q protein mutation.

In another aspect, the invention provides for an immunogenic composition comprising nucleic acid sequences encoding one or more amino acid sequences selected from the group consisting of SEQ ID NOs: 422 to 432.

In some embodiments, the immunogenic composition comprises nucleic acid sequences encoding one or more amino acid sequences derived from a TP53 R273C protein mutation. In some embodiments, the immunogenic composition comprises nucleic acid sequences encoding two or more amino acid sequences selected from the group consisting of SEQ ID NOs: 422 to 432.

In another aspect, the invention provides for an immunogenic peptide composition comprising one or more peptides selected from the group consisting of SEQ ID NOs: 422 to 432.

In some embodiments, the immunogenic peptide composition comprises two or more peptides selected from the group consisting of SEQ ID NOs: 422 to 432. In some embodiments, the immunogenic peptide composition comprises a peptide derived from a TP53 R273C protein mutation.

In another aspect, the invention provides for an immunogenic composition comprising nucleic acid sequences encoding one or more amino acid sequences selected from the group consisting of SEQ ID NOs: 433 to 446.

In some embodiments, the immunogenic composition comprises nucleic acid sequences encoding one or more amino acid sequences derived from a TP53 R273H protein mutation. In some embodiments, the immunogenic composition comprises nucleic acid sequences encoding two or more amino acid sequences selected from the group consisting of SEQ ID NOs: 433 to 446.

In another aspect, the invention provides for an immunogenic peptide composition comprising one or more peptides selected from the group consisting of SEQ ID NOs: 433 to 446.

In some embodiments, the immunogenic peptide composition comprises two or more peptides selected from the group consisting of SEQ ID NOs: 433 to 446. In some embodiments, the immunogenic peptide composition comprises a peptide derived from a TP53 R273H protein mutation.

In another aspect, the invention provides for an immunogenic composition comprising nucleic acid sequences encoding one or more amino acid sequences selected from the group consisting of SEQ ID NOs: 402 to 421.

In some embodiments, the immunogenic composition comprises nucleic acid sequences encoding one or more amino acid sequences derived from a TP53 R248W protein mutation. In some embodiments, the immunogenic composition comprises nucleic acid sequences encoding two or more amino acid sequences selected from the group consisting of SEQ ID NOs: 402 to 421.

In another aspect, the invention provides for an immunogenic peptide composition comprising one or more peptides selected from the group consisting of SEQ ID NOs: 402 to 421.

In some embodiments, the immunogenic peptide composition comprises two or more peptides selected from the group consisting of SEQ ID NOs: 402 to 421. In some embodiments, the immunogenic peptide composition comprises a peptide derived from a TP53 R248W protein mutation.

In another aspect, the invention provides for an immunogenic composition comprising nucleic acid sequences encoding one or more amino acid sequences selected from the group consisting of SEQ ID NOs: 447 to 449.

In some embodiments, the immunogenic composition comprises nucleic acid sequences encoding one or more amino acid sequences derived from a TP53 R282W protein mutation. In some embodiments, the immunogenic composition comprises nucleic acid sequences encoding two or more amino acid sequences selected from the group consisting of SEQ ID NOs: 447 to 449.

In another aspect, the invention provides for an immunogenic peptide composition comprising one or more peptides selected from the group consisting of SEQ ID NOs: 447 to 449.

In some embodiments, the immunogenic peptide composition comprises two or more peptides selected from the group consisting of SEQ ID NOs: 447 to 449. In some embodiments, the immunogenic peptide composition comprises a peptide derived from a TP53 R282W protein mutation.

In another aspect, the invention provides for an immunogenic composition comprising nucleic acid sequences encoding one or more amino acid sequences selected from the group consisting of SEQ ID NOs: 450 to 458.

In some embodiments, the immunogenic composition comprises nucleic acid sequences encoding one or more amino acid sequences derived from a TP53 Y220C protein mutation. In some embodiments, the immunogenic composition comprises nucleic acid sequences encoding two or more amino acid sequences selected from the group consisting of SEQ ID NOs: 450 to 458.

In another aspect, the invention provides for an immunogenic peptide composition comprising one or more peptides selected from the group consisting of SEQ ID NOs: 450 to 458.

In some embodiments, the immunogenic peptide composition comprises two or more peptides selected from the group consisting of SEQ ID NOs: 450 to 458. In some embodiments, the immunogenic peptide composition comprises a peptide derived from a TP53 Y220C protein mutation.

In another aspect, the invention provides for an immunogenic composition comprising nucleic acid sequences encoding one or more amino acid sequences selected from the group consisting of SEQ ID NOs: 310 to 322.

In some embodiments, the immunogenic composition comprises nucleic acid sequences encoding one or more amino acid sequences derived from a PIK3CA R88Q protein mutation. In some embodiments, the immunogenic composition comprises nucleic acid sequences encoding two or more amino acid sequences selected from the group consisting of SEQ ID NOs: 310 to 322.

In another aspect, the invention provides for an immunogenic peptide composition comprising one or more peptides selected from the group consisting of SEQ ID NOs: 310 to 322.

In some embodiments, the immunogenic peptide composition comprises two or more peptides selected from the group consisting of SEQ ID NOs: 310 to 322. In some embodiments, the immunogenic peptide composition comprises a peptide derived from a PIK3CA R88Q protein mutation.

In another aspect, the invention provides for an immunogenic composition comprising nucleic acid sequences encoding one or more amino acid sequences selected from the group consisting of SEQ ID NOs: 99 to 118.

In some embodiments, the immunogenic composition comprises nucleic acid sequences encoding one or more amino acid sequences derived from a GTF2I L424H protein mutation. In some embodiments, the immunogenic composition comprises nucleic acid sequences encoding two or more amino acid sequences selected from the group consisting of SEQ ID NOs: 99 to 118.

In another aspect, the invention provides for an immunogenic peptide composition comprising one or more peptides selected from the group consisting of SEQ ID NOs: 99 to 118.

In some embodiments, the immunogenic peptide composition comprises two or more peptides selected from the group consisting of SEQ ID NOs: 99 to 118. In some embodiments, the immunogenic peptide composition comprises a peptide derived from a GTF2I L424H protein mutation.

In another aspect, the invention provides for an immunogenic composition comprising nucleic acid sequences encoding one or more amino acid sequences selected from the group consisting of SEQ ID NOs: 338 to 353.

In some embodiments, the immunogenic composition comprises nucleic acid sequences encoding one or more amino acid sequences derived from a PTEN R130Q protein mutation. In some embodiments, the immunogenic composition comprises nucleic acid sequences encoding two or more amino acid sequences selected from the group consisting of SEQ ID NOs: 338 to 353.

In another aspect, the invention provides for an immunogenic peptide composition comprising one or more peptides selected from the group consisting of SEQ ID NOs: 338 to 353.

In some embodiments, the immunogenic peptide composition comprises two or more peptides selected from the group consisting of SEQ ID NOs: 338 to 353. In some embodiments, the immunogenic peptide composition comprises a peptide derived from a PTEN R130Q protein mutation.

In another aspect, the invention provides for an immunogenic composition comprising nucleic acid sequences encoding one or more amino acid sequences selected from the group consisting of SEQ ID NOs: 1 to 18.

In some embodiments, the immunogenic composition comprises nucleic acid sequences encoding one or more amino acid sequences derived from a AKT1 E17K protein mutation. In some embodiments, the immunogenic composition comprises nucleic acid sequences encoding two or more amino acid sequences selected from the group consisting of SEQ ID NOs: 1 to 18.

In another aspect, the invention provides for an immunogenic peptide composition comprising one or more peptides selected from the group consisting of SEQ ID NOs: 1 to 18.

In some embodiments, the immunogenic peptide composition comprises two or more peptides selected from the group consisting of SEQ ID NOs: 1 to 18. In some embodiments, the immunogenic peptide composition comprises a peptide derived from a AKT1 E17K protein mutation.

In another aspect, the invention provides for an immunogenic composition comprising nucleic acid sequences encoding one or more amino acid sequences selected from the group consisting of SEQ ID NOs: 323 to 337.

In some embodiments, the immunogenic composition comprises nucleic acid sequences encoding one or more amino acid sequences derived from a PTEN R130G protein mutation. In some embodiments, the immunogenic composition comprises nucleic acid sequences encoding two or more amino acid sequences selected from the group consisting of SEQ ID NOs: 323 to 337.

In another aspect, the invention provides for an immunogenic peptide composition comprising one or more peptides selected from the group consisting of SEQ ID NOs: 323 to 337.

In some embodiments, the immunogenic peptide composition comprises two or more peptides selected from the group consisting of SEQ ID NOs: 323 to 337. In some embodiments, the immunogenic peptide composition comprises a peptide derived from a PTEN R130G protein mutation.

In another aspect, the invention provides for an immunogenic composition comprising nucleic acid sequences encoding one or more amino acid sequences selected from the group consisting of SEQ ID NOs: 354 to 358.

In some embodiments, the immunogenic composition comprises nucleic acid sequences encoding one or more amino acid sequences derived from a TP53 H179R protein mutation. In some embodiments, the immunogenic composition comprises nucleic acid sequences encoding two or more amino acid sequences selected from the group consisting of SEQ ID NOs: 354 to 358.

In another aspect, the invention provides for an immunogenic peptide composition comprising one or more peptides selected from the group consisting of SEQ ID NOs: 354 to 358.

In some embodiments, the immunogenic peptide composition comprises two or more peptides selected from the group consisting of SEQ ID NOs: 354 to 358. In some embodiments, the immunogenic peptide composition comprises a peptide derived from a TP53 H179R protein mutation.

In another aspect, the invention provides for an immunogenic composition comprising nucleic acid sequences encoding one or more amino acid sequences selected from the group consisting of SEQ ID NOs: 168 to 169, SEQ ID NO: 171, SEQ ID NOs: 179 to 180, SEQ ID NOs: 182 to 183, SEQ ID NOs: 203 to 204, and SEQ ID NO: 207.

In some embodiments, the immunogenic composition comprises nucleic acid sequences encoding two or more amino acid sequences selected from the group consisting of SEQ ID NOs: 168 to 169, SEQ ID NO: 171, SEQ ID NOs: 179 to 180, SEQ ID NOs: 182 to 183, SEQ ID NOs: 203 to 204, and SEQ ID NO: 207. In some embodiments, the nucleic acid sequences are administered in a construct for expression in vivo. In some embodiments, the in vivo administration of the nucleic acid sequences is configured to produce one or more peptides that is displayed by an HLA class I molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is pancreatic cancer.

In another aspect, the invention provides for a method of treating or preventing pancreatic cancer by administering to a subject an immunogenic composition comprising nucleic acid sequences encoding one or more amino acid sequences selected from the group consisting of SEQ ID NOs: 168 to 169, SEQ ID NO: 171, SEQ ID NOs: 179 to 180, SEQ ID NOs: 182 to 183, SEQ ID NOs: 203 to 204, and SEQ ID NO: 207.

In some embodiments, the immunogenic composition comprises nucleic acid sequences encoding two or more amino acid sequences selected from the group consisting of SEQ ID NOs: 168 to 169, SEQ ID NO: 171, SEQ ID NOs: 179 to 180, SEQ ID NOs: 182 to 183, SEQ ID NOs: 203 to 204, and SEQ ID NO: 207.

In another aspect, the invention provides for an immunogenic peptide composition comprising one or more peptides selected from the group consisting of SEQ ID NOs: 168 to 169, SEQ ID NO: 171, SEQ ID NOs: 179 to 180, SEQ ID NOs: 182 to 183, SEQ ID NOs: 203 to 204, and SEQ ID NO: 207.

In some embodiments, the immunogenic peptide composition comprises two or more peptides selected from the group consisting of SEQ ID NOs: 168 to 169, SEQ ID NO: 171, SEQ ID NOs: 179 to 180, SEQ ID NOs: 182 to 183, SEQ ID NOs: 203 to 204, and SEQ ID NO: 207. In some embodiments, a peptide in the immunogenic peptide composition is displayed by an HLA class I molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is pancreatic cancer.

In another aspect, the invention provides for a method of treating or preventing pancreatic cancer in a subject comprising administering to the subject an immunogenic peptide composition comprising one or more peptides selected from the group consisting of SEQ ID NOs: 168 to 169, SEQ ID NO: 171, SEQ ID NOs: 179 to 180, SEQ ID NOs: 182 to 183, SEQ ID NOs: 203 to 204, and SEQ ID NO: 207.

In some embodiments, the immunogenic peptide composition comprises two or more peptides selected from the group consisting of SEQ ID NOs: 168 to 169, SEQ ID NO: 171, SEQ ID NOs: 179 to 180, SEQ ID NOs: 182 to 183, SEQ ID NOs: 203 to 204, and SEQ ID NO: 207.

In another aspect, the invention provides for an immunogenic composition comprising nucleic acid sequences encoding one or more amino acid sequences selected from the group consisting of SEQ ID NOs: 19 to 23, SEQ ID NOs: 34 to 40, SEQ ID NOs: 230 to 231, SEQ ID NO: 239, SEQ ID NOs: 241 to 242, and SEQ ID NOs: 260 to 262.

In some embodiments, the immunogenic composition comprises nucleic acid sequences encoding two or more amino acid sequences selected from the group consisting of SEQ ID NOs: 19 to 23, SEQ ID NOs: 34 to 40, SEQ ID NOs: 230 to 231, SEQ ID NO: 239, SEQ ID NOs: 241 to 242, and SEQ ID NOs: 260 to 262. In some embodiments, the nucleic acid sequences are administered in a construct for expression in vivo. In some embodiments, the in vivo administration of the nucleic acid sequences is configured to produce one or more peptides that is displayed by an HLA class I molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is skin cancer.

In another aspect, the invention provides for a method of treating or preventing skin cancer by administering to a subject an immunogenic composition comprising nucleic acid sequences encoding one or more amino acid sequences selected from the group consisting of SEQ ID NOs: 19 to 23, SEQ ID NOs: 34 to 40, SEQ ID NOs: 230 to 231, SEQ ID NO: 239, SEQ ID NOs: 241 to 242, and SEQ ID NOs: 260 to 262.

In some embodiments, the immunogenic composition comprises nucleic acid sequences encoding two or more amino acid sequences selected from the group consisting of SEQ ID NOs: 19 to 23, SEQ ID NOs: 34 to 40, SEQ ID NOs: 230 to 231, SEQ ID NO: 239, SEQ ID NOs: 241 to 242, and SEQ ID NOs: 260 to 262.

In another aspect, the invention provides for an immunogenic peptide composition comprising one or more peptides selected from the group consisting of SEQ ID NOs: 19 to 23, SEQ ID NOs: 34 to 40, SEQ ID NOs: 230 to 231, SEQ ID NO: 239, SEQ ID NOs: 241 to 242, and SEQ ID NOs: 260 to 262.

In some embodiments, the immunogenic peptide composition comprises two or more peptides selected from the group consisting of SEQ ID NOs: 19 to 23, SEQ ID NOs: 34 to 40, SEQ ID NOs: 230 to 231, SEQ ID NO: 239, SEQ ID NOs: 241 to 242, and SEQ ID NOs: 260 to 262. In some embodiments, a peptide in the immunogenic peptide composition is displayed by an HLA class I molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is skin cancer.

In another aspect, the invention provides for a method of treating or preventing skin cancer in a subject comprising administering to the subject an immunogenic peptide composition comprising one or more peptides selected from the group consisting of SEQ ID NOs: 19 to 23, SEQ ID NOs: 34 to 40, SEQ ID NOs: 230 to 231, SEQ ID NO: 239, SEQ ID NOs: 241 to 242, and SEQ ID NOs: 260 to 262.

In some embodiments, the immunogenic peptide composition comprises two or more peptides selected from the group consisting of SEQ ID NOs: 19 to 23, SEQ ID NOs: 34 to 40, SEQ ID NOs: 230 to 231, SEQ ID NO: 239, SEQ ID NOs: 241 to 242, and SEQ ID NOs: 260 to 262.

In another aspect, the invention provides for an immunogenic composition comprising nucleic acid sequences encoding one or more amino acid sequences selected from the group consisting of SEQ ID NOs: 19 to 23, SEQ ID NOs: 230 to 231, and SEQ ID NOs: 260 to 262.

In some embodiments, the immunogenic composition comprises nucleic acid sequences encoding two or more amino acid sequences selected from the group consisting of SEQ ID NOs: 19 to 23, SEQ ID NOs: 230 to 231, and SEQ ID NOs: 260 to 262. In some embodiments, the nucleic acid sequences are administered in a construct for expression in vivo. In some embodiments, the in vivo administration of the nucleic acid sequences is configured to produce one or more peptides that is displayed by an HLA class I molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is thyroid cancer.

In another aspect, the invention provides for a method of treating or preventing thyroid cancer by administering to a subject an immunogenic composition comprising nucleic acid sequences encoding one or more amino acid sequences selected from the group consisting of SEQ ID NOs: 19 to 23, SEQ ID NOs: 230 to 231, and SEQ ID NOs: 260 to 262.

In some embodiments, the immunogenic composition comprises nucleic acid sequences encoding two or more amino acid sequences selected from the group consisting of SEQ ID NOs: 19 to 23, SEQ ID NOs: 230 to 231, and SEQ ID NOs: 260 to 262.

In another aspect, the invention provides for an immunogenic peptide composition comprising one or more peptides selected from the group consisting of SEQ ID NOs: 19 to 23, SEQ ID NOs: 230 to 231, and SEQ ID NOs: 260 to 262.

In some embodiments, the immunogenic peptide composition comprises two or more peptides selected from the group consisting of SEQ ID NOs: 19 to 23, SEQ ID NOs: 230 to 231, and SEQ ID NOs: 260 to 262. In some embodiments, a peptide in the immunogenic peptide composition is displayed by an HLA class I molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is thyroid cancer.

In another aspect, the invention provides for a method of treating or preventing thyroid cancer in a subject comprising administering to the subject an immunogenic peptide composition comprising one or more peptides selected from the group consisting of SEQ ID NOs: 19 to 23, SEQ ID NOs: 230 to 231, and SEQ ID NOs: 260 to 262.

In some embodiments, the immunogenic peptide composition comprises two or more peptides selected from the group consisting of SEQ ID NOs: 19 to 23, SEQ ID NOs: 230 to 231, and SEQ ID NOs: 260 to 262.

In another aspect, the invention provides for an immunogenic composition comprising nucleic acid sequences encoding one or more amino acid sequences selected from the group consisting of SEQ ID NOs: 51 to 55, SEQ ID NOs: 67 to 70, SEQ ID NOs: 72 to 73, SEQ ID NOs: 119 to 120, SEQ ID NOs: 125 to 130, SEQ ID NO: 375, SEQ ID NO: 423, and SEQ ID NO: 425.

In some embodiments, the immunogenic composition comprises nucleic acid sequences encoding two or more amino acid sequences selected from the group consisting of SEQ ID NOs: 51 to 55, SEQ ID NOs: 67 to 70, SEQ ID NOs: 72 to 73, SEQ ID NOs: 119 to 120, SEQ ID NOs: 125 to 130, SEQ ID NO: 375, SEQ ID NO: 423, and SEQ ID NO: 425. In some embodiments, the nucleic acid sequences are administered in a construct for expression in vivo. In some embodiments, the in vivo administration of the nucleic acid sequences is configured to produce one or more peptides that is displayed by an HLA class I molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is brain cancer.

In another aspect, the invention provides for a method of treating or preventing brain cancer by administering to a subject an immunogenic composition comprising nucleic acid sequences encoding one or more amino acid sequences selected from the group consisting of SEQ ID NOs: 51 to 55, SEQ ID NOs: 67 to 70, SEQ ID NOs: 72 to 73, SEQ ID NOs: 119 to 120, SEQ ID NOs: 125 to 130, SEQ ID NO: 375, SEQ ID NO: 423, and SEQ ID NO: 425.

In some embodiments, the immunogenic composition comprises nucleic acid sequences encoding two or more amino acid sequences selected from the group consisting of SEQ ID NOs: 51 to 55, SEQ ID NOs: 67 to 70, SEQ ID NOs: 72 to 73, SEQ ID NOs: 119 to 120, SEQ ID NOs: 125 to 130, SEQ ID NO: 375, SEQ ID NO: 423, and SEQ ID NO: 425.

In another aspect, the invention provides for an immunogenic peptide composition comprising one or more peptides selected from the group consisting of SEQ ID NOs: 51 to 55, SEQ ID NOs: 67 to 70, SEQ ID NOs: 72 to 73, SEQ ID NOs: 119 to 120, SEQ ID NOs: 125 to 130, SEQ ID NO: 375, SEQ ID NO: 423, and SEQ ID NO: 425.

In some embodiments, the immunogenic peptide composition comprises two or more peptides selected from the group consisting of SEQ ID NOs: 51 to 55, SEQ ID NOs: 67 to 70, SEQ ID NOs: 72 to 73, SEQ ID NOs: 119 to 120, SEQ ID NOs: 125 to 130, SEQ ID NO: 375, SEQ ID NO: 423, and SEQ ID NO: 425. In some embodiments, a peptide in the immunogenic peptide composition is displayed by an HLA class I molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is brain cancer.

In another aspect, the invention provides for a method of treating or preventing brain cancer in a subject comprising administering to the subject an immunogenic peptide composition comprising one or more peptides selected from the group consisting of SEQ ID NOs: 51 to 55, SEQ ID NOs: 67 to 70, SEQ ID NOs: 72 to 73, SEQ ID NOs: 119 to 120, SEQ ID NOs: 125 to 130, SEQ ID NO: 375, SEQ ID NO: 423, and SEQ ID NO: 425.

In some embodiments, the immunogenic peptide composition comprises two or more peptides selected from the group consisting of SEQ ID NOs: 51 to 55, SEQ ID NOs: 67 to 70, SEQ ID NOs: 72 to 73, SEQ ID NOs: 119 to 120, SEQ ID NOs: 125 to 130, SEQ ID NO: 375, SEQ ID NO: 423, and SEQ ID NO: 425.

In another aspect, the invention provides for an immunogenic composition comprising nucleic acid sequences encoding one or more amino acid sequences selected from the group consisting of SEQ ID NOs: 20 to 23, SEQ ID NOs: 167 to 169, SEQ ID NO: 171, SEQ ID NOs: 203 to 207, SEQ ID NOs: 215 to 217, and SEQ ID NO: 288.

In some embodiments, the immunogenic composition comprises nucleic acid sequences encoding two or more amino acid sequences selected from the group consisting of SEQ ID NOs: 20 to 23, SEQ ID NOs: 167 to 169, SEQ ID NO: 171, SEQ ID NOs: 203 to 207, SEQ ID NOs: 215 to 217, and SEQ ID NO: 288. In some embodiments, the nucleic acid sequences are administered in a construct for expression in vivo. In some embodiments, the in vivo administration of the nucleic acid sequences is configured to produce one or more peptides that is displayed by an HLA class I molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is colorectal cancer.

In another aspect, the invention provides for a method of treating or preventing colorectal cancer by administering to a subject an immunogenic composition comprising nucleic acid sequences encoding one or more amino acid sequences selected from the group consisting of SEQ ID NOs: 20 to 23, SEQ ID NOs: 167 to 169, SEQ ID NO: 171, SEQ ID NOs: 203 to 207, SEQ ID NOs: 215 to 217, and SEQ ID NO: 288.

In some embodiments, the immunogenic composition comprises nucleic acid sequences encoding two or more amino acid sequences selected from the group consisting of SEQ ID NOs: 20 to 23, SEQ ID NOs: 167 to 169, SEQ ID NO: 171, SEQ ID NOs: 203 to 207, SEQ ID NOs: 215 to 217, and SEQ ID NO: 288.

In another aspect, the invention provides for an immunogenic peptide composition comprising one or more peptides selected from the group consisting of SEQ ID NOs: 20 to 23, SEQ ID NOs: 167 to 169, SEQ ID NO: 171, SEQ ID NOs: 203 to 207, SEQ ID NOs: 215 to 217, and SEQ ID NO: 288.

In some embodiments, the immunogenic peptide composition comprises two or more peptides selected from the group consisting of SEQ ID NOs: 20 to 23, SEQ ID NOs: 167 to 169, SEQ ID NO: 171, SEQ ID NOs: 203 to 207, SEQ ID NOs: 215 to 217, and SEQ ID NO: 288. In some embodiments, a peptide in the immunogenic peptide composition is displayed by an HLA class I molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is colorectal cancer.

In another aspect, the invention provides for a method of treating or preventing colorectal cancer in a subject comprising administering to the subject an immunogenic peptide composition comprising one or more peptides selected from the group consisting of SEQ ID NOs: 20 to 23, SEQ ID NOs: 167 to 169, SEQ ID NO: 171, SEQ ID NOs: 203 to 207, SEQ ID NOs: 215 to 217, and SEQ ID NO: 288.

In some embodiments, the immunogenic peptide composition comprises two or more peptides selected from the group consisting of SEQ ID NOs: 20 to 23, SEQ ID NOs: 167 to 169, SEQ ID NO: 171, SEQ ID NOs: 203 to 207, SEQ ID NOs: 215 to 217, and SEQ ID NO: 288.

In another aspect, the invention provides for an immunogenic composition comprising nucleic acid sequences encoding one or more amino acid sequences selected from the group consisting of SEQ ID NOs: 82 to 86, SEQ ID NOs: 141 to 144, SEQ ID NOs: 154 to 159, SEQ ID NOs: 168 to 169, SEQ ID NO: 171, SEQ ID NOs: 203 to 204, SEQ ID NO: 207, SEQ ID NOs: 274 to 276, SEQ ID NO: 288, SEQ ID NO: 359, and SEQ ID NOs: 362 to 364.

In some embodiments, the immunogenic composition comprises nucleic acid sequences encoding two or more amino acid sequences selected from the group consisting of SEQ ID NOs: 82 to 86, SEQ ID NOs: 141 to 144, SEQ ID NOs: 154 to 159, SEQ ID NOs: 168 to 169, SEQ ID NO: 171, SEQ ID NOs: 203 to 204, SEQ ID NO: 207, SEQ ID NOs: 274 to 276, SEQ ID NO: 288, SEQ ID NO: 359, and SEQ ID NOs: 362 to 364. In some embodiments, the nucleic acid sequences are administered in a construct for expression in vivo. In some embodiments, the in vivo administration of the nucleic acid sequences is configured to produce one or more peptides that is displayed by an HLA class I molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is bronchus and lung cancer.

In another aspect, the invention provides for a method of treating or preventing bronchus and lung cancer by administering to a subject an immunogenic composition comprising nucleic acid sequences encoding one or more amino acid sequences selected from the group consisting of SEQ ID NOs: 82 to 86, SEQ ID NOs: 141 to 144, SEQ ID NOs: 154 to 159, SEQ ID NOs: 168 to 169, SEQ ID NO: 171, SEQ ID NOs: 203 to 204, SEQ ID NO: 207, SEQ ID NOs: 274 to 276, SEQ ID NO: 288, SEQ ID NO: 359, and SEQ ID NOs: 362 to 364.

In some embodiments, the immunogenic composition comprises nucleic acid sequences encoding two or more amino acid sequences selected from the group consisting of SEQ ID NOs: 82 to 86, SEQ ID NOs: 141 to 144, SEQ ID NOs: 154 to 159, SEQ ID NOs: 168 to 169, SEQ ID NO: 171, SEQ ID NOs: 203 to 204, SEQ ID NO: 207, SEQ ID NOs: 274 to 276, SEQ ID NO: 288, SEQ ID NO: 359, and SEQ ID NOs: 362 to 364.

In another aspect, the invention provides for an immunogenic peptide composition comprising one or more peptides selected from the group consisting of SEQ ID NOs: 82 to 86, SEQ ID NOs: 141 to 144, SEQ ID NOs: 154 to 159, SEQ ID NOs: 168 to 169, SEQ ID NO: 171, SEQ ID NOs: 203 to 204, SEQ ID NO: 207, SEQ ID NOs: 274 to 276, SEQ ID NO: 288, SEQ ID NO: 359, and SEQ ID NOs: 362 to 364.

In some embodiments, the immunogenic peptide composition comprises two or more peptides selected from the group consisting of SEQ ID NOs: 82 to 86, SEQ ID NOs: 141 to 144, SEQ ID NOs: 154 to 159, SEQ ID NOs: 168 to 169, SEQ ID NO: 171, SEQ ID NOs: 203 to 204, SEQ ID NO: 207, SEQ ID NOs: 274 to 276, SEQ ID NO: 288, SEQ ID NO: 359, and SEQ ID NOs: 362 to 364. In some embodiments, a peptide in the immunogenic peptide composition is displayed by an HLA class I molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is bronchus and lung cancer.

In another aspect, the invention provides for a method of treating or preventing bronchus and lung cancer in a subject comprising administering to the subject an immunogenic peptide composition comprising one or more peptides selected from the group consisting of SEQ ID NOs: 82 to 86, SEQ ID NOs: 141 to 144, SEQ ID NOs: 154 to 159, SEQ ID NOs: 168 to 169, SEQ ID NO: 171, SEQ ID NOs: 203 to 204, SEQ ID NO: 207, SEQ ID NOs: 274 to 276, SEQ ID NO: 288, SEQ ID NO: 359, and SEQ ID NOs: 362 to 364.

In some embodiments, the immunogenic peptide composition comprises two or more peptides selected from the group consisting of SEQ ID NOs: 82 to 86, SEQ ID NOs: 141 to 144, SEQ ID NOs: 154 to 159, SEQ ID NOs: 168 to 169, SEQ ID NO: 171, SEQ ID NOs: 203 to 204, SEQ ID NO: 207, SEQ ID NOs: 274 to 276, SEQ ID NO: 288, SEQ ID NO: 359, and SEQ ID NOs: 362 to 364.

In another aspect, the invention provides for an immunogenic composition comprising nucleic acid sequences encoding one or more amino acid sequences selected from the group consisting of SEQ ID NOs: 273 to 309, SEQ ID NOs: 375 to 386, and SEQ ID NOs: 422 to 446.

In some embodiments, the immunogenic composition comprises nucleic acid sequences encoding two or more amino acid sequences selected from the group consisting of SEQ ID NOs: 273 to 309, SEQ ID NOs: 375 to 386, and SEQ ID NOs: 422 to 446. In some embodiments, the nucleic acid sequences are administered in a construct for expression in vivo. In some embodiments, the in vivo administration of the nucleic acid sequences is configured to produce one or more peptides that is displayed by an HLA class I molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is breast cancer.

In another aspect, the invention provides for a method of treating or preventing breast cancer by administering to a subject an immunogenic composition comprising nucleic acid sequences encoding one or more amino acid sequences selected from the group consisting of SEQ ID NOs: 273 to 309, SEQ ID NOs: 375 to 386, and SEQ ID NOs: 422 to 446.

In some embodiments, the immunogenic composition comprises nucleic acid sequences encoding two or more amino acid sequences selected from the group consisting of SEQ ID NOs: 273 to 309, SEQ ID NOs: 375 to 386, and SEQ ID NOs: 422 to 446.

In another aspect, the invention provides for an immunogenic peptide composition comprising one or more peptides selected from the group consisting of SEQ ID NOs: 273 to 309, SEQ ID NOs: 375 to 386, and SEQ ID NOs: 422 to 446.

In some embodiments, the immunogenic peptide composition comprises two or more peptides selected from the group consisting of SEQ ID NOs: 273 to 309, SEQ ID NOs: 375 to 386, and SEQ ID NOs: 422 to 446. In some embodiments, a peptide in the immunogenic peptide composition is displayed by an HLA class I molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is breast cancer.

In another aspect, the invention provides for a method of treating or preventing breast cancer in a subject comprising administering to the subject an immunogenic peptide composition comprising one or more peptides selected from the group consisting of SEQ ID NOs: 273 to 309, SEQ ID NOs: 375 to 386, and SEQ ID NOs: 422 to 446.

In some embodiments, the immunogenic peptide composition comprises two or more peptides selected from the group consisting of SEQ ID NOs: 273 to 309, SEQ ID NOs: 375 to 386, and SEQ ID NOs: 422 to 446.

In another aspect, the invention provides for an immunogenic composition comprising nucleic acid sequences encoding one or more amino acid sequences selected from the group consisting of SEQ ID NOs: 273 to 309, SEQ ID NOs: 375 to 386, and SEQ ID NOs: 422 to 446.

In some embodiments, the immunogenic composition comprises nucleic acid sequences encoding two or more amino acid sequences selected from the group consisting of SEQ ID NOs: 273 to 309, SEQ ID NOs: 375 to 386, and SEQ ID NOs: 422 to 446. In some embodiments, the nucleic acid sequences are administered in a construct for expression in vivo. In some embodiments, the in vivo administration of the nucleic acid sequences is configured to produce one or more peptides that is displayed by an HLA class I molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is ovarian cancer.

In another aspect, the invention provides for a method of treating or preventing ovarian cancer by administering to a subject an immunogenic composition comprising nucleic acid sequences encoding one or more amino acid sequences selected from the group consisting of SEQ ID NOs: 273 to 309, SEQ ID NOs: 375 to 386, and SEQ ID NOs: 422 to 446.

In some embodiments, the immunogenic composition comprises nucleic acid sequences encoding two or more amino acid sequences selected from the group consisting of SEQ ID NOs: 273 to 309, SEQ ID NOs: 375 to 386, and SEQ ID NOs: 422 to 446.

In another aspect, the invention provides for an immunogenic peptide composition comprising one or more peptides selected from the group consisting of SEQ ID NOs: 273 to 309, SEQ ID NOs: 375 to 386, and SEQ ID NOs: 422 to 446.

In some embodiments, the immunogenic peptide composition comprises two or more peptides selected from the group consisting of SEQ ID NOs: 273 to 309, SEQ ID NOs: 375 to 386, and SEQ ID NOs: 422 to 446. In some embodiments, a peptide in the immunogenic peptide composition is displayed by an HLA class I molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is ovarian cancer.

In another aspect, the invention provides for a method of treating or preventing ovarian cancer in a subject comprising administering to the subject an immunogenic peptide composition comprising one or more peptides selected from the group consisting of SEQ ID NOs: 273 to 309, SEQ ID NOs: 375 to 386, and SEQ ID NOs: 422 to 446.

In some embodiments, the immunogenic peptide composition comprises two or more peptides selected from the group consisting of SEQ ID NOs: 273 to 309, SEQ ID NOs: 375 to 386, and SEQ ID NOs: 422 to 446.

In one aspect, the invention provides for nucleic acid sequences encoding one or more amino acid sequences selected from the group consisting of SEQ ID NOs: 475 to 759.

In some embodiments, the nucleic acid sequences encode two or more amino acid sequences selected from the group consisting of SEQ ID NOs: 475 to 759.

In another aspect, the invention provides for an immunogenic composition comprising nucleic acid sequences encoding one or more amino acid sequences selected from the group consisting of SEQ ID NOs: 475 to 759.

In some embodiments, the immunogenic composition is administered to a subject. In some embodiments, the immunogenic composition comprises nucleic acid sequences encoding two or more amino acid sequences selected from the group consisting of SEQ ID NOs: 475 to 759. In some embodiments, the nucleic acid sequences are administered in a construct for expression in vivo. In some embodiments, the in vivo administration of the nucleic acid sequences is configured to produce one or more peptides that is displayed by an HLA class II molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic composition is administered in an effective amount to a subject to prevent cancer. In some embodiments, the immunogenic composition is administered in an effective amount to a subject to treat cancer. In some embodiments, the cancer is selected from the group consisting of pancreatic cancer, skin cancer, thyroid cancer, brain cancer, colorectal cancer, bronchus and lung cancer, breast cancer, and ovarian cancer. In some embodiments, the immunogenic composition comprises nucleic acid sequences encoding at least three amino acid sequences selected from the group consisting of SEQ ID NOs: 475 to 759.

In another aspect, the invention provides for an immunogenic peptide composition comprising one or more peptides selected from the group consisting of SEQ ID NOs: 475 to 759.

In some embodiments, the immunogenic peptide composition comprises two or more peptides selected from the group consisting of SEQ ID NOs: 475 to 759.

In another aspect, the invention provides for an immunogenic composition comprising nucleic acid sequences encoding one or more amino acid sequences selected from the group consisting of SEQ ID NOs: 475 to 483.

In some embodiments, the immunogenic composition comprises nucleic acid sequences encoding one or more amino acid sequences derived from a AKT1 protein mutation. In some embodiments, the immunogenic composition comprises nucleic acid sequences encoding two or more amino acid sequences selected from the group consisting of SEQ ID NOs: 475 to 483.

In another aspect, the invention provides for an immunogenic peptide composition comprising one or more peptides selected from the group consisting of SEQ ID NOs: 475 to 483.

In some embodiments, the immunogenic peptide composition comprises two or more peptides selected from the group consisting of SEQ ID NOs: 475 to 483. In some embodiments, the one or more peptides is a modified or unmodified fragment of a mutated AKT1 protein.

In another aspect, the invention provides for an immunogenic composition comprising nucleic acid sequences encoding one or more amino acid sequences selected from the group consisting of SEQ ID NOs: 484 to 502.

In some embodiments, the immunogenic composition comprises nucleic acid sequences encoding one or more amino acid sequences derived from a BRAF protein mutation. In some embodiments, the immunogenic composition comprises nucleic acid sequences encoding two or more amino acid sequences selected from the group consisting of SEQ ID NOs: 484 to 502.

In another aspect, the invention provides for an immunogenic peptide composition comprising one or more peptides selected from the group consisting of SEQ ID NOs: 484 to 502.

In some embodiments, the immunogenic peptide composition comprises two or more peptides selected from the group consisting of SEQ ID NOs: 484 to 502. In some embodiments, the one or more peptides is a modified or unmodified fragment of a mutated BRAF protein.

In another aspect, the invention provides for an immunogenic composition comprising nucleic acid sequences encoding one or more amino acid sequences selected from the group consisting of SEQ ID NOs: 503 to 527.

In some embodiments, the immunogenic composition comprises nucleic acid sequences encoding one or more amino acid sequences derived from a EGFR protein mutation. In some embodiments, the immunogenic composition comprises nucleic acid sequences encoding two or more amino acid sequences selected from the group consisting of SEQ ID NOs: 503 to 527.

In another aspect, the invention provides for an immunogenic peptide composition comprising one or more peptides selected from the group consisting of SEQ ID NOs: 503 to 527.

In some embodiments, the immunogenic peptide composition comprises two or more peptides selected from the group consisting of SEQ ID NOs: 503 to 527. In some embodiments, the one or more peptides is a modified or unmodified fragment of a mutated EGFR protein.

In another aspect, the invention provides for an immunogenic composition comprising nucleic acid sequences encoding one or more amino acid sequences selected from the group consisting of SEQ ID NOs: 528 to 534.

In some embodiments, the immunogenic composition comprises nucleic acid sequences encoding one or more amino acid sequences derived from a GTF2I protein mutation. In some embodiments, the immunogenic composition comprises nucleic acid sequences encoding two or more amino acid sequences selected from the group consisting of SEQ ID NOs: 528 to 534.

In another aspect, the invention provides for an immunogenic peptide composition comprising one or more peptides selected from the group consisting of SEQ ID NOs: 528 to 534.

In some embodiments, the immunogenic peptide composition comprises two or more peptides selected from the group consisting of SEQ ID NOs: 528 to 534. In some embodiments, the one or more peptides is a modified or unmodified fragment of a mutated GTF2I protein.

In another aspect, the invention provides for an immunogenic composition comprising nucleic acid sequences encoding one or more amino acid sequences selected from the group consisting of SEQ ID NOs: 535 to 553.

In some embodiments, the immunogenic composition comprises nucleic acid sequences encoding one or more amino acid sequences derived from a IDH1 protein mutation. In some embodiments, the immunogenic composition comprises nucleic acid sequences encoding two or more amino acid sequences selected from the group consisting of SEQ ID NOs: 535 to 553.

In another aspect, the invention provides for an immunogenic peptide composition comprising one or more peptides selected from the group consisting of SEQ ID NOs: 535 to 553.

In some embodiments, the immunogenic peptide composition comprises two or more peptides selected from the group consisting of SEQ ID NOs: 535 to 553. In some embodiments, the one or more peptides is a modified or unmodified fragment of a mutated IDH1 protein.

In another aspect, the invention provides for an immunogenic composition comprising nucleic acid sequences encoding one or more amino acid sequences selected from the group consisting of SEQ ID NOs: 554 to 615.

In some embodiments, the immunogenic composition comprises nucleic acid sequences encoding one or more amino acid sequences derived from a KRAS protein mutation. In some embodiments, the immunogenic composition comprises nucleic acid sequences encoding two or more amino acid sequences selected from the group consisting of SEQ ID NOs: 554 to 615.

In another aspect, the invention provides for an immunogenic peptide composition comprising one or more peptides selected from the group consisting of SEQ ID NOs: 554 to 615.

In some embodiments, the immunogenic peptide composition comprises two or more peptides selected from the group consisting of SEQ ID NOs: 554 to 615. In some embodiments, the one or more peptides is a modified or unmodified fragment of a mutated KRAS protein.

In another aspect, the invention provides for an immunogenic composition comprising nucleic acid sequences encoding one or more amino acid sequences selected from the group consisting of SEQ ID NOs: 616 to 645.

In some embodiments, the immunogenic composition comprises nucleic acid sequences encoding one or more amino acid sequences derived from a NRAS protein mutation. In some embodiments, the immunogenic composition comprises nucleic acid sequences encoding two or more amino acid sequences selected from the group consisting of SEQ ID NOs: 616 to 645.

In another aspect, the invention provides for an immunogenic peptide composition comprising one or more peptides selected from the group consisting of SEQ ID NOs: 616 to 645.

In some embodiments, the immunogenic peptide composition comprises two or more peptides selected from the group consisting of SEQ ID NOs: 616 to 645. In some embodiments, the one or more peptides is a modified or unmodified fragment of a mutated NRAS protein.

In another aspect, the invention provides for an immunogenic composition comprising nucleic acid sequences encoding one or more amino acid sequences selected from the group consisting of SEQ ID NOs: 646 to 675.

In some embodiments, the immunogenic composition comprises nucleic acid sequences encoding one or more amino acid sequences derived from a PIK3CA protein mutation. In some embodiments, the immunogenic composition comprises nucleic acid sequences encoding two or more amino acid sequences selected from the group consisting of SEQ ID NOs: 646 to 675.

In another aspect, the invention provides for an immunogenic peptide composition comprising one or more peptides selected from the group consisting of SEQ ID NOs: 646 to 675.

In some embodiments, the immunogenic peptide composition comprises two or more peptides selected from the group consisting of SEQ ID NOs: 646 to 675. In some embodiments, the one or more peptides is a modified or unmodified fragment of a mutated PIK3CA protein.

In another aspect, the invention provides for an immunogenic composition comprising nucleic acid sequences encoding one or more amino acid sequences selected from the group consisting of SEQ ID NOs: 676 to 690.

In some embodiments, the immunogenic composition comprises nucleic acid sequences encoding one or more amino acid sequences derived from a PTEN protein mutation. In some embodiments, the immunogenic composition comprises nucleic acid sequences encoding two or more amino acid sequences selected from the group consisting of SEQ ID NOs: 676 to 690.

In another aspect, the invention provides for an immunogenic peptide composition comprising one or more peptides selected from the group consisting of SEQ ID NOs: 676 to 690.

In some embodiments, the immunogenic peptide composition comprises two or more peptides selected from the group consisting of SEQ ID NOs: 676 to 690. In some embodiments, the one or more peptides is a modified or unmodified fragment of a mutated PTEN protein.

In another aspect, the invention provides for an immunogenic composition comprising nucleic acid sequences encoding one or more amino acid sequences selected from the group consisting of SEQ ID NOs: 691 to 758.

In some embodiments, the immunogenic composition comprises nucleic acid sequences encoding one or more amino acid sequences derived from a TP53 protein mutation. In some embodiments, the immunogenic composition comprises nucleic acid sequences encoding two or more amino acid sequences selected from the group consisting of SEQ ID NOs: 691 to 758.

In another aspect, the invention provides for an immunogenic peptide composition comprising one or more peptides selected from the group consisting of SEQ ID NOs: 691 to 758.

In some embodiments, the immunogenic peptide composition comprises two or more peptides selected from the group consisting of SEQ ID NOs: 691 to 758. In some embodiments, the one or more peptides is a modified or unmodified fragment of a mutated TP53 protein.

In another aspect, the invention provides for an immunogenic composition comprising nucleic acid sequences encoding one or more amino acid sequences selected from the group consisting of SEQ ID NOs: 554 to 645.

In some embodiments, the immunogenic composition comprises nucleic acid sequences encoding one or more amino acid sequences derived from a RAS protein mutation. In some embodiments, the immunogenic composition comprises nucleic acid sequences encoding two or more amino acid sequences selected from the group consisting of SEQ ID NOs: 554 to 645.

In another aspect, the invention provides for an immunogenic peptide composition comprising one or more peptides selected from the group consisting of SEQ ID NOs: 554 to 645.

In some embodiments, the immunogenic peptide composition comprises two or more peptides selected from the group consisting of SEQ ID NOs: 554 to 645. In some embodiments, the one or more peptides is a modified or unmodified fragment of a mutated RAS protein.

In another aspect, the invention provides for an immunogenic composition comprising nucleic acid sequences encoding one or more amino acid sequences selected from the group consisting of SEQ ID NOs: 484 to 494.

In some embodiments, the immunogenic composition comprises nucleic acid sequences encoding one or more amino acid sequences derived from a BRAF V600 protein mutation. In some embodiments, the immunogenic composition comprises nucleic acid sequences encoding two or more amino acid sequences selected from the group consisting of SEQ ID NOs: 484 to 494.

In another aspect, the invention provides for an immunogenic peptide composition comprising one or more peptides selected from the group consisting of SEQ ID NOs: 484 to 494.

In some embodiments, the immunogenic peptide composition comprises two or more peptides selected from the group consisting of SEQ ID NOs: 484 to 494. In some embodiments, the immunogenic peptide composition comprises a peptide derived from a BRAF V600 protein mutation.

In another aspect, the invention provides for an immunogenic composition comprising nucleic acid sequences encoding one or more amino acid sequences selected from the group consisting of SEQ ID NOs: 495 to 502.

In some embodiments, the immunogenic composition comprises nucleic acid sequences encoding one or more amino acid sequences derived from a BRAF V600M protein mutation. In some embodiments, the immunogenic composition comprises nucleic acid sequences encoding two or more amino acid sequences selected from the group consisting of SEQ ID NOs: 495 to 502.

In another aspect, the invention provides for an immunogenic peptide composition comprising one or more peptides selected from the group consisting of SEQ ID NOs: 495 to 502.

In some embodiments, the immunogenic peptide composition comprises two or more peptides selected from the group consisting of SEQ ID NOs: 495 to 502. In some embodiments, the immunogenic peptide composition comprises a peptide derived from a BRAF V600M protein mutation.

In another aspect, the invention provides for an immunogenic composition comprising nucleic acid sequences encoding one or more amino acid sequences selected from the group consisting of SEQ ID NOs: 503 to 509.

In some embodiments, the immunogenic composition comprises nucleic acid sequences encoding one or more amino acid sequences derived from a EGFR A289V protein mutation. In some embodiments, the immunogenic composition comprises nucleic acid sequences encoding two or more amino acid sequences selected from the group consisting of SEQ ID NOs: 503 to 509.

In another aspect, the invention provides for an immunogenic peptide composition comprising one or more peptides selected from the group consisting of SEQ ID NOs: 503 to 509.

In some embodiments, the immunogenic peptide composition comprises two or more peptides selected from the group consisting of SEQ ID NOs: 503 to 509. In some embodiments, the immunogenic peptide composition comprises a peptide derived from a EGFR A289V protein mutation.

In another aspect, the invention provides for an immunogenic composition comprising nucleic acid sequences encoding one or more amino acid sequences selected from the group consisting of SEQ ID NOs: 510 to 519.

In some embodiments, the immunogenic composition comprises nucleic acid sequences encoding one or more amino acid sequences derived from a EGFR G598V protein mutation. In some embodiments, the immunogenic composition comprises nucleic acid sequences encoding two or more amino acid sequences selected from the group consisting of SEQ ID NOs: 510 to 519.

In another aspect, the invention provides for an immunogenic peptide composition comprising one or more peptides selected from the group consisting of SEQ ID NOs: 510 to 519.

In some embodiments, the immunogenic peptide composition comprises two or more peptides selected from the group consisting of SEQ ID NOs: 510 to 519. In some embodiments, the immunogenic peptide composition comprises a peptide derived from a EGFR G598V protein mutation.

In another aspect, the invention provides for an immunogenic composition comprising nucleic acid sequences encoding one or more amino acid sequences selected from the group consisting of SEQ ID NOs: 520 to 527.

In some embodiments, the immunogenic composition comprises nucleic acid sequences encoding one or more amino acid sequences derived from a EGFR L858R protein mutation. In some embodiments, the immunogenic composition comprises nucleic acid sequences encoding two or more amino acid sequences selected from the group consisting of SEQ ID NOs: 520 to 527.

In another aspect, the invention provides for an immunogenic peptide composition comprising one or more peptides selected from the group consisting of SEQ ID NOs: 520 to 527.

In some embodiments, the immunogenic peptide composition comprises two or more peptides selected from the group consisting of SEQ ID NOs: 520 to 527. In some embodiments, the immunogenic peptide composition comprises a peptide derived from a EGFR L858R protein mutation.

In another aspect, the invention provides for an immunogenic composition comprising nucleic acid sequences encoding one or more amino acid sequences selected from the group consisting of SEQ ID NOs: 543 to 553.

In some embodiments, the immunogenic composition comprises nucleic acid sequences encoding one or more amino acid sequences derived from a IDH1 R132H protein mutation. In some embodiments, the immunogenic composition comprises nucleic acid sequences encoding two or more amino acid sequences selected from the group consisting of SEQ ID NOs: 543 to 553.

In another aspect, the invention provides for an immunogenic peptide composition comprising one or more peptides selected from the group consisting of SEQ ID NOs: 543 to 553.

In some embodiments, the immunogenic peptide composition comprises two or more peptides selected from the group consisting of SEQ ID NOs: 543 to 553. In some embodiments, the immunogenic peptide composition comprises a peptide derived from a IDH1 R132H protein mutation.

In another aspect, the invention provides for an immunogenic composition comprising nucleic acid sequences encoding one or more amino acid sequences selected from the group consisting of SEQ ID NOs: 535 to 542.

In some embodiments, the immunogenic composition comprises nucleic acid sequences encoding one or more amino acid sequences derived from a IDH1 R132C protein mutation. In some embodiments, the immunogenic composition comprises nucleic acid sequences encoding two or more amino acid sequences selected from the group consisting of SEQ ID NOs: 535 to 542.

In another aspect, the invention provides for an immunogenic peptide composition comprising one or more peptides selected from the group consisting of SEQ ID NOs: 535 to 542.

In some embodiments, the immunogenic peptide composition comprises two or more peptides selected from the group consisting of SEQ ID NOs: 535 to 542. In some embodiments, the immunogenic peptide composition comprises a peptide derived from a IDH1 R132C protein mutation.

In another aspect, the invention provides for an immunogenic composition comprising nucleic acid sequences encoding one or more amino acid sequences selected from the group consisting of SEQ ID NOs: 569 to 577.

In some embodiments, the immunogenic composition comprises nucleic acid sequences encoding one or more amino acid sequences derived from a KRAS G12D protein mutation. In some embodiments, the immunogenic composition comprises nucleic acid sequences encoding two or more amino acid sequences selected from the group consisting of SEQ ID NOs: 569 to 577.

In another aspect, the invention provides for an immunogenic peptide composition comprising one or more peptides selected from the group consisting of SEQ ID NOs: 569 to 577.

In some embodiments, the immunogenic peptide composition comprises two or more peptides selected from the group consisting of SEQ ID NOs: 569 to 577. In some embodiments, the immunogenic peptide composition comprises a peptide derived from a KRAS G12D protein mutation.

In another aspect, the invention provides for an immunogenic composition comprising nucleic acid sequences encoding one or more amino acid sequences selected from the group consisting of SEQ ID NOs: 596 to 605.

In some embodiments, the immunogenic composition comprises nucleic acid sequences encoding one or more amino acid sequences derived from a KRAS G12V protein mutation. In some embodiments, the immunogenic composition comprises nucleic acid sequences encoding two or more amino acid sequences selected from the group consisting of SEQ ID NOs: 596 to 605.

In another aspect, the invention provides for an immunogenic peptide composition comprising one or more peptides selected from the group consisting of SEQ ID NOs: 596 to 605.

In some embodiments, the immunogenic peptide composition comprises two or more peptides selected from the group consisting of SEQ ID NOs: 596 to 605. In some embodiments, the immunogenic peptide composition comprises a peptide derived from a KRAS G12V protein mutation.

In another aspect, the invention provides for an immunogenic composition comprising nucleic acid sequences encoding one or more amino acid sequences selected from the group consisting of SEQ ID NOs: 578 to 587.

In some embodiments, the immunogenic composition comprises nucleic acid sequences encoding one or more amino acid sequences derived from a KRAS G12R protein mutation. In some embodiments, the immunogenic composition comprises nucleic acid sequences encoding two or more amino acid sequences selected from the group consisting of SEQ ID NOs: 578 to 587.

In another aspect, the invention provides for an immunogenic peptide composition comprising one or more peptides selected from the group consisting of SEQ ID NOs: 578 to 587.

In some embodiments, the immunogenic peptide composition comprises two or more peptides selected from the group consisting of SEQ ID NOs: 578 to 587. In some embodiments, the immunogenic peptide composition comprises a peptide derived from a KRAS G12R protein mutation.

In another aspect, the invention provides for an immunogenic composition comprising nucleic acid sequences encoding one or more amino acid sequences selected from the group consisting of SEQ ID NOs: 561 to 568.

In some embodiments, the immunogenic composition comprises nucleic acid sequences encoding one or more amino acid sequences derived from a KRAS G12C protein mutation. In some embodiments, the immunogenic composition comprises nucleic acid sequences encoding two or more amino acid sequences selected from the group consisting of SEQ ID NOs: 561 to 568.

In another aspect, the invention provides for an immunogenic peptide composition comprising one or more peptides selected from the group consisting of SEQ ID NOs: 561 to 568.

In some embodiments, the immunogenic peptide composition comprises two or more peptides selected from the group consisting of SEQ ID NOs: 561 to 568. In some embodiments, the immunogenic peptide composition comprises a peptide derived from a KRAS G12C protein mutation.

In another aspect, the invention provides for an immunogenic composition comprising nucleic acid sequences encoding one or more amino acid sequences selected from the group consisting of SEQ ID NOs: 606 to 615.

In some embodiments, the immunogenic composition comprises nucleic acid sequences encoding one or more amino acid sequences derived from a KRAS G13D protein mutation. In some embodiments, the immunogenic composition comprises nucleic acid sequences encoding two or more amino acid sequences selected from the group consisting of SEQ ID NOs: 606 to 615.

In another aspect, the invention provides for an immunogenic peptide composition comprising one or more peptides selected from the group consisting of SEQ ID NOs: 606 to 615.

In some embodiments, the immunogenic peptide composition comprises two or more peptides selected from the group consisting of SEQ ID NOs: 606 to 615. In some embodiments, the immunogenic peptide composition comprises a peptide derived from a KRAS G13D protein mutation.

In another aspect, the invention provides for an immunogenic composition comprising nucleic acid sequences encoding one or more amino acid sequences selected from the group consisting of SEQ ID NOs: 554 to 560.

In some embodiments, the immunogenic composition comprises nucleic acid sequences encoding one or more amino acid sequences derived from a KRAS G12A protein mutation. In some embodiments, the immunogenic composition comprises nucleic acid sequences encoding two or more amino acid sequences selected from the group consisting of SEQ ID NOs: 554 to 560.

In another aspect, the invention provides for an immunogenic peptide composition comprising one or more peptides selected from the group consisting of SEQ ID NOs: 554 to 560.

In some embodiments, the immunogenic peptide composition comprises two or more peptides selected from the group consisting of SEQ ID NOs: 554 to 560. In some embodiments, the immunogenic peptide composition comprises a peptide derived from a KRAS G12A protein mutation.

In another aspect, the invention provides for an immunogenic composition comprising nucleic acid sequences encoding one or more amino acid sequences selected from the group consisting of SEQ ID NOs: 588 to 595.

In some embodiments, the immunogenic composition comprises nucleic acid sequences encoding one or more amino acid sequences derived from a KRAS G12S protein mutation. In some embodiments, the immunogenic composition comprises nucleic acid sequences encoding two or more amino acid sequences selected from the group consisting of SEQ ID NOs: 588 to 595.

In another aspect, the invention provides for an immunogenic peptide composition comprising one or more peptides selected from the group consisting of SEQ ID NOs: 588 to 595.

In some embodiments, the immunogenic peptide composition comprises two or more peptides selected from the group consisting of SEQ ID NOs: 588 to 595. In some embodiments, the immunogenic peptide composition comprises a peptide derived from a KRAS G12S protein mutation.

In another aspect, the invention provides for an immunogenic composition comprising nucleic acid sequences encoding one or more amino acid sequences selected from the group consisting of SEQ ID NOs: 634 to 645.

In some embodiments, the immunogenic composition comprises nucleic acid sequences encoding one or more amino acid sequences derived from a NRAS Q61R protein mutation. In some embodiments, the immunogenic composition comprises nucleic acid sequences encoding two or more amino acid sequences selected from the group consisting of SEQ ID NOs: 634 to 645.

In another aspect, the invention provides for an immunogenic peptide composition comprising one or more peptides selected from the group consisting of SEQ ID NOs: 634 to 645.

In some embodiments, the immunogenic peptide composition comprises two or more peptides selected from the group consisting of SEQ ID NOs: 634 to 645. In some embodiments, the immunogenic peptide composition comprises a peptide derived from a NRAS Q61R protein mutation.

In another aspect, the invention provides for an immunogenic composition comprising nucleic acid sequences encoding one or more amino acid sequences selected from the group consisting of SEQ ID NOs: 616 to 624.

In some embodiments, the immunogenic composition comprises nucleic acid sequences encoding one or more amino acid sequences derived from a NRAS Q61K protein mutation. In some embodiments, the immunogenic composition comprises nucleic acid sequences encoding two or more amino acid sequences selected from the group consisting of SEQ ID NOs: 616 to 624.

In another aspect, the invention provides for an immunogenic peptide composition comprising one or more peptides selected from the group consisting of SEQ ID NOs: 616 to 624.

In some embodiments, the immunogenic peptide composition comprises two or more peptides selected from the group consisting of SEQ ID NOs: 616 to 624. In some embodiments, the immunogenic peptide composition comprises a peptide derived from a NRAS Q61K protein mutation.

In another aspect, the invention provides for an immunogenic composition comprising nucleic acid sequences encoding one or more amino acid sequences selected from the group consisting of SEQ ID NOs: 625 to 633.

In some embodiments, the immunogenic composition comprises nucleic acid sequences encoding one or more amino acid sequences derived from a NRAS Q61L protein mutation. In some embodiments, the immunogenic composition comprises nucleic acid sequences encoding two or more amino acid sequences selected from the group consisting of SEQ ID NOs: 625 to 633.

In another aspect, the invention provides for an immunogenic peptide composition comprising one or more peptides selected from the group consisting of SEQ ID NOs: 625 to 633.

In some embodiments, the immunogenic peptide composition comprises two or more peptides selected from the group consisting of SEQ ID NOs: 625 to 633. In some embodiments, the immunogenic peptide composition comprises a peptide derived from a NRAS Q61L protein mutation.

In another aspect, the invention provides for an immunogenic composition comprising nucleic acid sequences encoding one or more amino acid sequences selected from the group consisting of SEQ ID NOs: 646 to 650.

In some embodiments, the immunogenic composition comprises nucleic acid sequences encoding one or more amino acid sequences derived from a PIK3CA E542K protein mutation. In some embodiments, the immunogenic composition comprises nucleic acid sequences encoding two or more amino acid sequences selected from the group consisting of SEQ ID NOs: 646 to 650.

In another aspect, the invention provides for an immunogenic peptide composition comprising one or more peptides selected from the group consisting of SEQ ID NOs: 646 to 650.

In some embodiments, the immunogenic peptide composition comprises two or more peptides selected from the group consisting of SEQ ID NOs: 646 to 650. In some embodiments, the immunogenic peptide composition comprises a peptide derived from a PIK3CA E542K protein mutation.

In another aspect, the invention provides for an immunogenic composition comprising nucleic acid sequences encoding one or more amino acid sequences selected from the group consisting of SEQ ID NOs: 651 to 657.

In some embodiments, the immunogenic composition comprises nucleic acid sequences encoding one or more amino acid sequences derived from a PIK3CA E545K protein mutation. In some embodiments, the immunogenic composition comprises nucleic acid sequences encoding two or more amino acid sequences selected from the group consisting of SEQ ID NOs: 651 to 657.

In another aspect, the invention provides for an immunogenic peptide composition comprising one or more peptides selected from the group consisting of SEQ ID NOs: 651 to 657.

In some embodiments, the immunogenic peptide composition comprises two or more peptides selected from the group consisting of SEQ ID NOs: 651 to 657. In some embodiments, the immunogenic peptide composition comprises a peptide derived from a PIK3CA E545K protein mutation.

In another aspect, the invention provides for an immunogenic composition comprising nucleic acid sequences encoding one or more amino acid sequences selected from the group consisting of SEQ ID NOs: 658 to 667.

In some embodiments, the immunogenic composition comprises nucleic acid sequences encoding one or more amino acid sequences derived from a PIK3CA H1047R protein mutation. In some embodiments, the immunogenic composition comprises nucleic acid sequences encoding two or more amino acid sequences selected from the group consisting of SEQ ID NOs: 658 to 667.

In another aspect, the invention provides for an immunogenic peptide composition comprising one or more peptides selected from the group consisting of SEQ ID NOs: 658 to 667.

In some embodiments, the immunogenic peptide composition comprises two or more peptides selected from the group consisting of SEQ ID NOs: 658 to 667. In some embodiments, the immunogenic peptide composition comprises a peptide derived from a PIK3CA H1047R protein mutation.

In another aspect, the invention provides for an immunogenic composition comprising nucleic acid sequences encoding one or more amino acid sequences selected from the group consisting of SEQ ID NOs: 700 to 707.

In some embodiments, the immunogenic composition comprises nucleic acid sequences encoding one or more amino acid sequences derived from a TP53 R158L protein mutation. In some embodiments, the immunogenic composition comprises nucleic acid sequences encoding two or more amino acid sequences selected from the group consisting of SEQ ID NOs: 700 to 707.

In another aspect, the invention provides for an immunogenic peptide composition comprising one or more peptides selected from the group consisting of SEQ ID NOs: 700 to 707.

In some embodiments, the immunogenic peptide composition comprises two or more peptides selected from the group consisting of SEQ ID NOs: 700 to 707. In some embodiments, the immunogenic peptide composition comprises a peptide derived from a TP53 R158L protein mutation.

In another aspect, the invention provides for an immunogenic composition comprising nucleic acid sequences encoding one or more amino acid sequences selected from the group consisting of SEQ ID NOs: 708 to 717.

In some embodiments, the immunogenic composition comprises nucleic acid sequences encoding one or more amino acid sequences derived from a TP53 R175H protein mutation. In some embodiments, the immunogenic composition comprises nucleic acid sequences encoding two or more amino acid sequences selected from the group consisting of SEQ ID NOs: 708 to 717.

In another aspect, the invention provides for an immunogenic peptide composition comprising one or more peptides selected from the group consisting of SEQ ID NOs: 708 to 717.

In some embodiments, the immunogenic peptide composition comprises two or more peptides selected from the group consisting of SEQ ID NOs: 708 to 717. In some embodiments, the immunogenic peptide composition comprises a peptide derived from a TP53 R175H protein mutation.

In another aspect, the invention provides for an immunogenic composition comprising nucleic acid sequences encoding one or more amino acid sequences selected from the group consisting of SEQ ID NOs: 718 to 723.

In some embodiments, the immunogenic composition comprises nucleic acid sequences encoding one or more amino acid sequences derived from a TP53 R248Q protein mutation. In some embodiments, the immunogenic composition comprises nucleic acid sequences encoding two or more amino acid sequences selected from the group consisting of SEQ ID NOs: 718 to 723.

In another aspect, the invention provides for an immunogenic peptide composition comprising one or more peptides selected from the group consisting of SEQ ID NOs: 718 to 723.

In some embodiments, the immunogenic peptide composition comprises two or more peptides selected from the group consisting of SEQ ID NOs: 718 to 723. In some embodiments, the immunogenic peptide composition comprises a peptide derived from a TP53 R248Q protein mutation.

In another aspect, the invention provides for an immunogenic composition comprising nucleic acid sequences encoding one or more amino acid sequences selected from the group consisting of SEQ ID NOs: 733 to 739.

In some embodiments, the immunogenic composition comprises nucleic acid sequences encoding one or more amino acid sequences derived from a TP53 R273C protein mutation. In some embodiments, the immunogenic composition comprises nucleic acid sequences encoding two or more amino acid sequences selected from the group consisting of SEQ ID NOs: 733 to 739.

In another aspect, the invention provides for an immunogenic peptide composition comprising one or more peptides selected from the group consisting of SEQ ID NOs: 733 to 739.

In some embodiments, the immunogenic peptide composition comprises two or more peptides selected from the group consisting of SEQ ID NOs: 733 to 739. In some embodiments, the immunogenic peptide composition comprises a peptide derived from a TP53 R273C protein mutation.

In another aspect, the invention provides for an immunogenic composition comprising nucleic acid sequences encoding one or more amino acid sequences selected from the group consisting of SEQ ID NOs: 740 to 748.

In some embodiments, the immunogenic composition comprises nucleic acid sequences encoding one or more amino acid sequences derived from a TP53 R273H protein mutation. In some embodiments, the immunogenic composition comprises nucleic acid sequences encoding two or more amino acid sequences selected from the group consisting of SEQ ID NOs: 740 to 748.

In another aspect, the invention provides for an immunogenic peptide composition comprising one or more peptides selected from the group consisting of SEQ ID NOs: 740 to 748.

In some embodiments, the immunogenic peptide composition comprises two or more peptides selected from the group consisting of SEQ ID NOs: 740 to 748. In some embodiments, the immunogenic peptide composition comprises a peptide derived from a TP53 R273H protein mutation.

In another aspect, the invention provides for an immunogenic composition comprising nucleic acid sequences encoding one or more amino acid sequences selected from the group consisting of SEQ ID NOs: 724 to 732.

In some embodiments, the immunogenic composition comprises nucleic acid sequences encoding one or more amino acid sequences derived from a TP53 R248W protein mutation. In some embodiments, the immunogenic composition comprises nucleic acid sequences encoding two or more amino acid sequences selected from the group consisting of SEQ ID NOs: 724 to 732.

In another aspect, the invention provides for an immunogenic peptide composition comprising one or more peptides selected from the group consisting of SEQ ID NOs: 724 to 732.

In some embodiments, the immunogenic peptide composition comprises two or more peptides selected from the group consisting of SEQ ID NOs: 724 to 732. In some embodiments, the immunogenic peptide composition comprises a peptide derived from a TP53 R248W protein mutation.

In another aspect, the invention provides for an immunogenic composition comprising nucleic acid sequences encoding one or more amino acid sequences selected from the group consisting of SEQ ID NOs: 749 to 750.

In some embodiments, the immunogenic composition comprises nucleic acid sequences encoding one or more amino acid sequences derived from a TP53 R282W protein mutation. In some embodiments, the immunogenic composition comprises nucleic acid sequences encoding two or more amino acid sequences selected from the group consisting of SEQ ID NOs: 749 to 750.

In another aspect, the invention provides for an immunogenic peptide composition comprising one or more peptides selected from the group consisting of SEQ ID NOs: 749 to 750.

In some embodiments, the immunogenic peptide composition comprises two or more peptides selected from the group consisting of SEQ ID NOs: 749 to 750. In some embodiments, the immunogenic peptide composition comprises a peptide derived from a TP53 R282W protein mutation.

In another aspect, the invention provides for an immunogenic composition comprising nucleic acid sequences encoding one or more amino acid sequences selected from the group consisting of SEQ ID NOs: 751 to 758.

In some embodiments, the immunogenic composition comprises nucleic acid sequences encoding one or more amino acid sequences derived from a TP53 Y220C protein mutation. In some embodiments, the immunogenic composition comprises nucleic acid sequences encoding two or more amino acid sequences selected from the group consisting of SEQ ID NOs: 751 to 758.

In another aspect, the invention provides for an immunogenic peptide composition comprising one or more peptides selected from the group consisting of SEQ ID NOs: 751 to 758.

In some embodiments, the immunogenic peptide composition comprises two or more peptides selected from the group consisting of SEQ ID NOs: 751 to 758. In some embodiments, the immunogenic peptide composition comprises a peptide derived from a TP53 Y220C protein mutation.

In another aspect, the invention provides for an immunogenic composition comprising nucleic acid sequences encoding one or more amino acid sequences selected from the group consisting of SEQ ID NOs: 668 to 675.

In some embodiments, the immunogenic composition comprises nucleic acid sequences encoding one or more amino acid sequences derived from a PIK3CA R88Q protein mutation. In some embodiments, the immunogenic composition comprises nucleic acid sequences encoding two or more amino acid sequences selected from the group consisting of SEQ ID NOs: 668 to 675.

In another aspect, the invention provides for an immunogenic peptide composition comprising one or more peptides selected from the group consisting of SEQ ID NOs: 668 to 675.

In some embodiments, the immunogenic peptide composition comprises two or more peptides selected from the group consisting of SEQ ID NOs: 668 to 675. In some embodiments, the immunogenic peptide composition comprises a peptide derived from a PIK3CA R88Q protein mutation.

In another aspect, the invention provides for an immunogenic composition comprising nucleic acid sequences encoding one or more amino acid sequences selected from the group consisting of SEQ ID NOs: 528 to 534.

In some embodiments, the immunogenic composition comprises nucleic acid sequences encoding one or more amino acid sequences derived from a GTF2I L424H protein mutation. In some embodiments, the immunogenic composition comprises nucleic acid sequences encoding two or more amino acid sequences selected from the group consisting of SEQ ID NOs: 528 to 534.

In another aspect, the invention provides for an immunogenic peptide composition comprising one or more peptides selected from the group consisting of SEQ ID NOs: 528 to 534.

In some embodiments, the immunogenic peptide composition comprises two or more peptides selected from the group consisting of SEQ ID NOs: 528 to 534. In some embodiments, the immunogenic peptide composition comprises a peptide derived from a GTF2I L424H protein mutation.

In another aspect, the invention provides for an immunogenic composition comprising nucleic acid sequences encoding one or more amino acid sequences selected from the group consisting of SEQ ID NOs: 681 to 690.

In some embodiments, the immunogenic composition comprises nucleic acid sequences encoding one or more amino acid sequences derived from a PTEN R130Q protein mutation. In some embodiments, the immunogenic composition comprises nucleic acid sequences encoding two or more amino acid sequences selected from the group consisting of SEQ ID NOs: 681 to 690.

In another aspect, the invention provides for an immunogenic peptide composition comprising one or more peptides selected from the group consisting of SEQ ID NOs: 681 to 690.

In some embodiments, the immunogenic peptide composition comprises two or more peptides selected from the group consisting of SEQ ID NOs: 681 to 690. In some embodiments, the immunogenic peptide composition comprises a peptide derived from a PTEN R130Q protein mutation.

In another aspect, the invention provides for an immunogenic composition comprising nucleic acid sequences encoding one or more amino acid sequences selected from the group consisting of SEQ ID NOs: 475 to 483.

In some embodiments, the immunogenic composition comprises nucleic acid sequences encoding one or more amino acid sequences derived from a AKT1 E17K protein mutation. In some embodiments, the immunogenic composition comprises nucleic acid sequences encoding two or more amino acid sequences selected from the group consisting of SEQ ID NOs: 475 to 483.

In another aspect, the invention provides for an immunogenic peptide composition comprising one or more peptides selected from the group consisting of SEQ ID NOs: 475 to 483.

In some embodiments, the immunogenic peptide composition comprises two or more peptides selected from the group consisting of SEQ ID NOs: 475 to 483. In some embodiments, the immunogenic peptide composition comprises a peptide derived from a AKT1 E17K protein mutation.

In another aspect, the invention provides for an immunogenic composition comprising nucleic acid sequences encoding one or more amino acid sequences selected from the group consisting of SEQ ID NOs: 676 to 680.

In some embodiments, the immunogenic composition comprises nucleic acid sequences encoding one or more amino acid sequences derived from a PTEN R130G protein mutation. In some embodiments, the immunogenic composition comprises nucleic acid sequences encoding two or more amino acid sequences selected from the group consisting of SEQ ID NOs: 676 to 680.

In another aspect, the invention provides for an immunogenic peptide composition comprising one or more peptides selected from the group consisting of SEQ ID NOs: 676 to 680.

In some embodiments, the immunogenic peptide composition comprises two or more peptides selected from the group consisting of SEQ ID NOs: 676 to 680. In some embodiments, the immunogenic peptide composition comprises a peptide derived from a PTEN R130G protein mutation.

In another aspect, the invention provides for an immunogenic composition comprising nucleic acid sequences encoding one or more amino acid sequences selected from the group consisting of SEQ ID NOs: 691 to 699.

In some embodiments, the immunogenic composition comprises nucleic acid sequences encoding one or more amino acid sequences derived from a TP53 H179R protein mutation. In some embodiments, the immunogenic composition comprises nucleic acid sequences encoding two or more amino acid sequences selected from the group consisting of SEQ ID NOs: 691 to 699.

In another aspect, the invention provides for an immunogenic peptide composition comprising one or more peptides selected from the group consisting of SEQ ID NOs: 691 to 699.

In some embodiments, the immunogenic peptide composition comprises two or more peptides selected from the group consisting of SEQ ID NOs: 691 to 699. In some embodiments, the immunogenic peptide composition comprises a peptide derived from a TP53 H179R protein mutation.

In another aspect, the invention provides for an immunogenic composition comprising nucleic acid sequences encoding one or more amino acid sequences selected from the group consisting of SEQ ID NOs: 569 to 574, SEQ ID NOs: 578 to 584, SEQ ID NOs: 596 to 599, and SEQ ID NOs: 601 to 603.

In some embodiments, the immunogenic composition comprises nucleic acid sequences encoding two or more amino acid sequences selected from the group consisting of SEQ ID NOs: 569 to 574, SEQ ID NOs: 578 to 584, SEQ ID NOs: 596 to 599, and SEQ ID NOs: 601 to 603. In some embodiments, the nucleic acid sequences are administered in a construct for expression in vivo. In some embodiments, the in vivo administration of the nucleic acid sequences is configured to produce one or more peptides that is displayed by an HLA class II molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is pancreatic cancer.

In another aspect, the invention provides for a method of treating or preventing pancreatic cancer by administering to a subject an immunogenic composition comprising nucleic acid sequences encoding one or more amino acid sequences selected from the group consisting of SEQ ID NOs: 569 to 574, SEQ ID NOs: 578 to 584, SEQ ID NOs: 596 to 599, and SEQ ID NOs: 601 to 603.

In some embodiments, the immunogenic composition comprises nucleic acid sequences encoding two or more amino acid sequences selected from the group consisting of SEQ ID NOs: 569 to 574, SEQ ID NOs: 578 to 584, SEQ ID NOs: 596 to 599, and SEQ ID NOs: 601 to 603.

In another aspect, the invention provides for an immunogenic peptide composition comprising one or more peptides selected from the group consisting of SEQ ID NOs: 569 to 574, SEQ ID NOs: 578 to 584, SEQ ID NOs: 596 to 599, and SEQ ID NOs: 601 to 603.

In some embodiments, the immunogenic peptide composition comprises two or more peptides selected from the group consisting of SEQ ID NOs: 569 to 574, SEQ ID NOs: 578 to 584, SEQ ID NOs: 596 to 599, and SEQ ID NOs: 601 to 603. In some embodiments, a peptide in the immunogenic peptide composition is displayed by an HLA class II molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is pancreatic cancer.

In another aspect, the invention provides for a method of treating or preventing pancreatic cancer in a subject comprising administering to the subject an immunogenic peptide composition comprising one or more peptides selected from the group consisting of SEQ ID NOs: 569 to 574, SEQ ID NOs: 578 to 584, SEQ ID NOs: 596 to 599, and SEQ ID NOs: 601 to 603.

In some embodiments, the immunogenic peptide composition comprises two or more peptides selected from the group consisting of SEQ ID NOs: 569 to 574, SEQ ID NOs: 578 to 584, SEQ ID NOs: 596 to 599, and SEQ ID NOs: 601 to 603.

In another aspect, the invention provides for an immunogenic composition comprising nucleic acid sequences encoding one or more amino acid sequences selected from the group consisting of SEQ ID NOs: 484 to 485, SEQ ID NOs: 488 to 489, SEQ ID NOs: 495 to 499, SEQ ID NO: 616, SEQ ID NOs: 619 to 620, SEQ ID NOs: 625 to 628, SEQ ID NO: 634, SEQ ID NO: 637, and SEQ ID NOs: 639 to 640.

In some embodiments, the immunogenic composition comprises nucleic acid sequences encoding two or more amino acid sequences selected from the group consisting of SEQ ID NOs: 484 to 485, SEQ ID NOs: 488 to 489, SEQ ID NOs: 495 to 499, SEQ ID NO: 616, SEQ ID NOs: 619 to 620, SEQ ID NOs: 625 to 628, SEQ ID NO: 634, SEQ ID NO: 637, and SEQ ID NOs: 639 to 640. In some embodiments, the nucleic acid sequences are administered in a construct for expression in vivo. In some embodiments, the in vivo administration of the nucleic acid sequences is configured to produce one or more peptides that is displayed by an HLA class II molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is skin cancer.

In another aspect, the invention provides for a method of treating or preventing skin cancer by administering to a subject an immunogenic composition comprising nucleic acid sequences encoding one or more amino acid sequences selected from the group consisting of SEQ ID NOs: 484 to 485, SEQ ID NOs: 488 to 489, SEQ ID NOs: 495 to 499, SEQ ID NO: 616, SEQ ID NOs: 619 to 620, SEQ ID NOs: 625 to 628, SEQ ID NO: 634, SEQ ID NO: 637, and SEQ ID NOs: 639 to 640.

In some embodiments, the immunogenic composition comprises nucleic acid sequences encoding two or more amino acid sequences selected from the group consisting of SEQ ID NOs: 484 to 485, SEQ ID NOs: 488 to 489, SEQ ID NOs: 495 to 499, SEQ ID NO: 616, SEQ ID NOs: 619 to 620, SEQ ID NOs: 625 to 628, SEQ ID NO: 634, SEQ ID NO: 637, and SEQ ID NOs: 639 to 640.

In another aspect, the invention provides for an immunogenic peptide composition comprising one or more peptides selected from the group consisting of SEQ ID NOs: 484 to 485, SEQ ID NOs: 488 to 489, SEQ ID NOs: 495 to 499, SEQ ID NO: 616, SEQ ID NOs: 619 to 620, SEQ ID NOs: 625 to 628, SEQ ID NO: 634, SEQ ID NO: 637, and SEQ ID NOs: 639 to 640.

In some embodiments, the immunogenic peptide composition comprises two or more peptides selected from the group consisting of SEQ ID NOs: 484 to 485, SEQ ID NOs: 488 to 489, SEQ ID NOs: 495 to 499, SEQ ID NO: 616, SEQ ID NOs: 619 to 620, SEQ ID NOs: 625 to 628, SEQ ID NO: 634, SEQ ID NO: 637, and SEQ ID NOs: 639 to 640. In some embodiments, a peptide in the immunogenic peptide composition is displayed by an HLA class II molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is skin cancer.

In another aspect, the invention provides for a method of treating or preventing skin cancer in a subject comprising administering to the subject an immunogenic peptide composition comprising one or more peptides selected from the group consisting of SEQ ID NOs: 484 to 485, SEQ ID NOs: 488 to 489, SEQ ID NOs: 495 to 499, SEQ ID NO: 616, SEQ ID NOs: 619 to 620, SEQ ID NOs: 625 to 628, SEQ ID NO: 634, SEQ ID NO: 637, and SEQ ID NOs: 639 to 640.

In some embodiments, the immunogenic peptide composition comprises two or more peptides selected from the group consisting of SEQ ID NOs: 484 to 485, SEQ ID NOs: 488 to 489, SEQ ID NOs: 495 to 499, SEQ ID NO: 616, SEQ ID NOs: 619 to 620, SEQ ID NOs: 625 to 628, SEQ ID NO: 634, SEQ ID NO: 637, and SEQ ID NOs: 639 to 640.

In another aspect, the invention provides for an immunogenic composition comprising nucleic acid sequences encoding one or more amino acid sequences selected from the group consisting of SEQ ID NOs: 484 to 485, SEQ ID NOs: 488 to 489, SEQ ID NO: 616, SEQ ID NOs: 619 to 620, SEQ ID NO: 634, SEQ ID NO: 637, and SEQ ID NO: 640.

In some embodiments, the immunogenic composition comprises nucleic acid sequences encoding two or more amino acid sequences selected from the group consisting of SEQ ID NOs: 484 to 485, SEQ ID NOs: 488 to 489, SEQ ID NO: 616, SEQ ID NOs: 619 to 620, SEQ ID NO: 634, SEQ ID NO: 637, and SEQ ID NO: 640. In some embodiments, the nucleic acid sequences are administered in a construct for expression in vivo. In some embodiments, the in vivo administration of the nucleic acid sequences is configured to produce one or more peptides that is displayed by an HLA class II molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is thyroid cancer.

In another aspect, the invention provides for a method of treating or preventing thyroid cancer by administering to a subject an immunogenic composition comprising nucleic acid sequences encoding one or more amino acid sequences selected from the group consisting of SEQ ID NOs: 484 to 485, SEQ ID NOs: 488 to 489, SEQ ID NO: 616, SEQ ID NOs: 619 to 620, SEQ ID NO: 634, SEQ ID NO: 637, and SEQ ID NO: 640.

In some embodiments, the immunogenic composition comprises nucleic acid sequences encoding two or more amino acid sequences selected from the group consisting of SEQ ID NOs: 484 to 485, SEQ ID NOs: 488 to 489, SEQ ID NO: 616, SEQ ID NOs: 619 to 620, SEQ ID NO: 634, SEQ ID NO: 637, and SEQ ID NO: 640.

In another aspect, the invention provides for an immunogenic peptide composition comprising one or more peptides selected from the group consisting of SEQ ID NOs: 484 to 485, SEQ ID NOs: 488 to 489, SEQ ID NO: 616, SEQ ID NOs: 619 to 620, SEQ ID NO: 634, SEQ ID NO: 637, and SEQ ID NO: 640.

In some embodiments, the immunogenic peptide composition comprises two or more peptides selected from the group consisting of SEQ ID NOs: 484 to 485, SEQ ID NOs: 488 to 489, SEQ ID NO: 616, SEQ ID NOs: 619 to 620, SEQ ID NO: 634, SEQ ID NO: 637, and SEQ ID NO: 640. In some embodiments, a peptide in the immunogenic peptide composition is displayed by an HLA class II molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is thyroid cancer.

In another aspect, the invention provides for a method of treating or preventing thyroid cancer in a subject comprising administering to the subject an immunogenic peptide composition comprising one or more peptides selected from the group consisting of SEQ ID NOs: 484 to 485, SEQ ID NOs: 488 to 489, SEQ ID NO: 616, SEQ ID NOs: 619 to 620, SEQ ID NO: 634, SEQ ID NO: 637, and SEQ ID NO: 640.

In some embodiments, the immunogenic peptide composition comprises two or more peptides selected from the group consisting of SEQ ID NOs: 484 to 485, SEQ ID NOs: 488 to 489, SEQ ID NO: 616, SEQ ID NOs: 619 to 620, SEQ ID NO: 634, SEQ ID NO: 637, and SEQ ID NO: 640.

In another aspect, the invention provides for an immunogenic composition comprising nucleic acid sequences encoding one or more amino acid sequences selected from the group consisting of SEQ ID NO: 508, SEQ ID NO: 510, SEQ ID NO: 512, SEQ ID NO: 514, SEQ ID NOs: 535 to 537, SEQ ID NO: 539, SEQ ID NOs: 543 to 551, SEQ ID NO: 708, SEQ ID NO: 712, and SEQ ID NO: 738.

In some embodiments, the immunogenic composition comprises nucleic acid sequences encoding two or more amino acid sequences selected from the group consisting of SEQ ID NO: 508, SEQ ID NO: 510, SEQ ID NO: 512, SEQ ID NO: 514, SEQ ID NOs: 535 to 537, SEQ ID NO: 539, SEQ ID NOs: 543 to 551, SEQ ID NO: 708, SEQ ID NO: 712, and SEQ ID NO: 738. In some embodiments, the nucleic acid sequences are administered in a construct for expression in vivo. In some embodiments, the in vivo administration of the nucleic acid sequences is configured to produce one or more peptides that is displayed by an HLA class II molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is brain cancer.

In another aspect, the invention provides for a method of treating or preventing brain cancer by administering to a subject an immunogenic composition comprising nucleic acid sequences encoding one or more amino acid sequences selected from the group consisting of SEQ ID NO: 508, SEQ ID NO: 510, SEQ ID NO: 512, SEQ ID NO: 514, SEQ ID NOs: 535 to 537, SEQ ID NO: 539, SEQ ID NOs: 543 to 551, SEQ ID NO: 708, SEQ ID NO: 712, and SEQ ID NO: 738.

In some embodiments, the immunogenic composition comprises nucleic acid sequences encoding two or more amino acid sequences selected from the group consisting of SEQ ID NO: 508, SEQ ID NO: 510, SEQ ID NO: 512, SEQ ID NO: 514, SEQ ID NOs: 535 to 537, SEQ ID NO: 539, SEQ ID NOs: 543 to 551, SEQ ID NO: 708, SEQ ID NO: 712, and SEQ ID NO: 738.

In another aspect, the invention provides for an immunogenic peptide composition comprising one or more peptides selected from the group consisting of SEQ ID NO: 508, SEQ ID NO: 510, SEQ ID NO: 512, SEQ ID NO: 514, SEQ ID NOs: 535 to 537, SEQ ID NO: 539, SEQ ID NOs: 543 to 551, SEQ ID NO: 708, SEQ ID NO: 712, and SEQ ID NO: 738.

In some embodiments, the immunogenic peptide composition comprises two or more peptides selected from the group consisting of SEQ ID NO: 508, SEQ ID NO: 510, SEQ ID NO: 512, SEQ ID NO: 514, SEQ ID NOs: 535 to 537, SEQ ID NO: 539, SEQ ID NOs: 543 to 551, SEQ ID NO: 708, SEQ ID NO: 712, and SEQ ID NO: 738. In some embodiments, a peptide in the immunogenic peptide composition is displayed by an HLA class II molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is brain cancer.

In another aspect, the invention provides for a method of treating or preventing brain cancer in a subject comprising administering to the subject an immunogenic peptide composition comprising one or more peptides selected from the group consisting of SEQ ID NO: 508, SEQ ID NO: 510, SEQ ID NO: 512, SEQ ID NO: 514, SEQ ID NOs: 535 to 537, SEQ ID NO: 539, SEQ ID NOs: 543 to 551, SEQ ID NO: 708, SEQ ID NO: 712, and SEQ ID NO: 738.

In some embodiments, the immunogenic peptide composition comprises two or more peptides selected from the group consisting of SEQ ID NO: 508, SEQ ID NO: 510, SEQ ID NO: 512, SEQ ID NO: 514, SEQ ID NOs: 535 to 537, SEQ ID NO: 539, SEQ ID NOs: 543 to 551, SEQ ID NO: 708, SEQ ID NO: 712, and SEQ ID NO: 738.

In another aspect, the invention provides for an immunogenic composition comprising nucleic acid sequences encoding one or more amino acid sequences selected from the group consisting of SEQ ID NOs: 484 to 485, SEQ ID NOs: 488 to 489, SEQ ID NOs: 569 to 575, SEQ ID NOs: 596 to 599, SEQ ID NOs: 601 to 604, SEQ ID NOs: 606 to 612, SEQ ID NO: 656, SEQ ID NO: 708, and SEQ ID NO: 712.

In some embodiments, the immunogenic composition comprises nucleic acid sequences encoding two or more amino acid sequences selected from the group consisting of SEQ ID NOs: 484 to 485, SEQ ID NOs: 488 to 489, SEQ ID NOs: 569 to 575, SEQ ID NOs: 596 to 599, SEQ ID NOs: 601 to 604, SEQ ID NOs: 606 to 612, SEQ ID NO: 656, SEQ ID NO: 708, and SEQ ID NO: 712. In some embodiments, the nucleic acid sequences are administered in a construct for expression in vivo. In some embodiments, the in vivo administration of the nucleic acid sequences is configured to produce one or more peptides that is displayed by an HLA class II molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is colorectal cancer.

In another aspect, the invention provides for a method of treating or preventing colorectal cancer by administering to a subject an immunogenic composition comprising nucleic acid sequences encoding one or more amino acid sequences selected from the group consisting of SEQ ID NOs: 484 to 485, SEQ ID NOs: 488 to 489, SEQ ID NOs: 569 to 575, SEQ ID NOs: 596 to 599, SEQ ID NOs: 601 to 604, SEQ ID NOs: 606 to 612, SEQ ID NO: 656, SEQ ID NO: 708, and SEQ ID NO: 712.

In some embodiments, the immunogenic composition comprises nucleic acid sequences encoding two or more amino acid sequences selected from the group consisting of SEQ ID NOs: 484 to 485, SEQ ID NOs: 488 to 489, SEQ ID NOs: 569 to 575, SEQ ID NOs: 596 to 599, SEQ ID NOs: 601 to 604, SEQ ID NOs: 606 to 612, SEQ ID NO: 656, SEQ ID NO: 708, and SEQ ID NO: 712.

In another aspect, the invention provides for an immunogenic peptide composition comprising one or more peptides selected from the group consisting of SEQ ID NOs: 484 to 485, SEQ ID NOs: 488 to 489, SEQ ID NOs: 569 to 575, SEQ ID NOs: 596 to 599, SEQ ID NOs: 601 to 604, SEQ ID NOs: 606 to 612, SEQ ID NO: 656, SEQ ID NO: 708, and SEQ ID NO: 712.

In some embodiments, the immunogenic peptide composition comprises two or more peptides selected from the group consisting of SEQ ID NOs: 484 to 485, SEQ ID NOs: 488 to 489, SEQ ID NOs: 569 to 575, SEQ ID NOs: 596 to 599, SEQ ID NOs: 601 to 604, SEQ ID NOs: 606 to 612, SEQ ID NO: 656, SEQ ID NO: 708, and SEQ ID NO: 712. In some embodiments, a peptide in the immunogenic peptide composition is displayed by an HLA class II molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is colorectal cancer.

In another aspect, the invention provides for a method of treating or preventing colorectal cancer in a subject comprising administering to the subject an immunogenic peptide composition comprising one or more peptides selected from the group consisting of SEQ ID NOs: 484 to 485, SEQ ID NOs: 488 to 489, SEQ ID NOs: 569 to 575, SEQ ID NOs: 596 to 599, SEQ ID NOs: 601 to 604, SEQ ID NOs: 606 to 612, SEQ ID NO: 656, SEQ ID NO: 708, and SEQ ID NO: 712.

In some embodiments, the immunogenic peptide composition comprises two or more peptides selected from the group consisting of SEQ ID NOs: 484 to 485, SEQ ID NOs: 488 to 489, SEQ ID NOs: 569 to 575, SEQ ID NOs: 596 to 599, SEQ ID NOs: 601 to 604, SEQ ID NOs: 606 to 612, SEQ ID NO: 656, SEQ ID NO: 708, and SEQ ID NO: 712.

In another aspect, the invention provides for an immunogenic composition comprising nucleic acid sequences encoding one or more amino acid sequences selected from the group consisting of SEQ ID NOs: 520 to 521, SEQ ID NOs: 523 to 524, SEQ ID NOs: 554 to 556, SEQ ID NO: 558, SEQ ID NO: 561, SEQ ID NOs: 563 to 565, SEQ ID NOs: 569 to 573, SEQ ID NOs: 596 to 600, SEQ ID NO: 650, SEQ ID NO: 656, and SEQ ID NOs: 700 to 705.

In some embodiments, the immunogenic composition comprises nucleic acid sequences encoding two or more amino acid sequences selected from the group consisting of SEQ ID NOs: 520 to 521, SEQ ID NOs: 523 to 524, SEQ ID NOs: 554 to 556, SEQ ID NO: 558, SEQ ID NO: 561, SEQ ID NOs: 563 to 565, SEQ ID NOs: 569 to 573, SEQ ID NOs: 596 to 600, SEQ ID NO: 650, SEQ ID NO: 656, and SEQ ID NOs: 700 to 705. In some embodiments, the nucleic acid sequences are administered in a construct for expression in vivo. In some embodiments, the in vivo administration of the nucleic acid sequences is configured to produce one or more peptides that is displayed by an HLA class II molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is bronchus and lung cancer.

In another aspect, the invention provides for a method of treating or preventing bronchus and lung cancer by administering to a subject an immunogenic composition comprising nucleic acid sequences encoding one or more amino acid sequences selected from the group consisting of SEQ ID NOs: 520 to 521, SEQ ID NOs: 523 to 524, SEQ ID NOs: 554 to 556, SEQ ID NO: 558, SEQ ID NO: 561, SEQ ID NOs: 563 to 565, SEQ ID NOs: 569 to 573, SEQ ID NOs: 596 to 600, SEQ ID NO: 650, SEQ ID NO: 656, and SEQ ID NOs: 700 to 705.

In some embodiments, the immunogenic composition comprises nucleic acid sequences encoding two or more amino acid sequences selected from the group consisting of SEQ ID NOs: 520 to 521, SEQ ID NOs: 523 to 524, SEQ ID NOs: 554 to 556, SEQ ID NO: 558, SEQ ID NO: 561, SEQ ID NOs: 563 to 565, SEQ ID NOs: 569 to 573, SEQ ID NOs: 596 to 600, SEQ ID NO: 650, SEQ ID NO: 656, and SEQ ID NOs: 700 to 705.

In another aspect, the invention provides for an immunogenic peptide composition comprising one or more peptides selected from the group consisting of SEQ ID NOs: 520 to 521, SEQ ID NOs: 523 to 524, SEQ ID NOs: 554 to 556, SEQ ID NO: 558, SEQ ID NO: 561, SEQ ID NOs: 563 to 565, SEQ ID NOs: 569 to 573, SEQ ID NOs: 596 to 600, SEQ ID NO: 650, SEQ ID NO: 656, and SEQ ID NOs: 700 to 705.

In some embodiments, the immunogenic peptide composition comprises two or more peptides selected from the group consisting of SEQ ID NOs: 520 to 521, SEQ ID NOs: 523 to 524, SEQ ID NOs: 554 to 556, SEQ ID NO: 558, SEQ ID NO: 561, SEQ ID NOs: 563 to 565, SEQ ID NOs: 569 to 573, SEQ ID NOs: 596 to 600, SEQ ID NO: 650, SEQ ID NO: 656, and SEQ ID NOs: 700 to 705. In some embodiments, a peptide in the immunogenic peptide composition is displayed by an HLA class II molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is bronchus and lung cancer.

In another aspect, the invention provides for a method of treating or preventing bronchus and lung cancer in a subject comprising administering to the subject an immunogenic peptide composition comprising one or more peptides selected from the group consisting of SEQ ID NOs: 520 to 521, SEQ ID NOs: 523 to 524, SEQ ID NOs: 554 to 556, SEQ ID NO: 558, SEQ ID NO: 561, SEQ ID NOs: 563 to 565, SEQ ID NOs: 569 to 573, SEQ ID NOs: 596 to 600, SEQ ID NO: 650, SEQ ID NO: 656, and SEQ ID NOs: 700 to 705.

In some embodiments, the immunogenic peptide composition comprises two or more peptides selected from the group consisting of SEQ ID NOs: 520 to 521, SEQ ID NOs: 523 to 524, SEQ ID NOs: 554 to 556, SEQ ID NO: 558, SEQ ID NO: 561, SEQ ID NOs: 563 to 565, SEQ ID NOs: 569 to 573, SEQ ID NOs: 596 to 600, SEQ ID NO: 650, SEQ ID NO: 656, and SEQ ID NOs: 700 to 705.

In another aspect, the invention provides for an immunogenic composition comprising nucleic acid sequences encoding one or more amino acid sequences selected from the group consisting of SEQ ID NOs: 646 to 667, SEQ ID NOs: 708 to 717, and SEQ ID NOs: 733 to 748.

In some embodiments, the immunogenic composition comprises nucleic acid sequences encoding two or more amino acid sequences selected from the group consisting of SEQ ID NOs: 646 to 667, SEQ ID NOs: 708 to 717, and SEQ ID NOs: 733 to 748. In some embodiments, the nucleic acid sequences are administered in a construct for expression in vivo. In some embodiments, the in vivo administration of the nucleic acid sequences is configured to produce one or more peptides that is displayed by an HLA class II molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is breast cancer.

In another aspect, the invention provides for a method of treating or preventing breast cancer by administering to a subject an immunogenic composition comprising nucleic acid sequences encoding one or more amino acid sequences selected from the group consisting of SEQ ID NOs: 646 to 667, SEQ ID NOs: 708 to 717, and SEQ ID NOs: 733 to 748.

In some embodiments, the immunogenic composition comprises nucleic acid sequences encoding two or more amino acid sequences selected from the group consisting of SEQ ID NOs: 646 to 667, SEQ ID NOs: 708 to 717, and SEQ ID NOs: 733 to 748.

In another aspect, the invention provides for an immunogenic peptide composition comprising one or more peptides selected from the group consisting of SEQ ID NOs: 646 to 667, SEQ ID NOs: 708 to 717, and SEQ ID NOs: 733 to 748.

In some embodiments, the immunogenic peptide composition comprises two or more peptides selected from the group consisting of SEQ ID NOs: 646 to 667, SEQ ID NOs: 708 to 717, and SEQ ID NOs: 733 to 748. In some embodiments, a peptide in the immunogenic peptide composition is displayed by an HLA class II molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is breast cancer.

In another aspect, the invention provides for a method of treating or preventing breast cancer in a subject comprising administering to the subject an immunogenic peptide composition comprising one or more peptides selected from the group consisting of SEQ ID NOs: 646 to 667, SEQ ID NOs: 708 to 717, and SEQ ID NOs: 733 to 748.

In some embodiments, the immunogenic peptide composition comprises two or more peptides selected from the group consisting of SEQ ID NOs: 646 to 667, SEQ ID NOs: 708 to 717, and SEQ ID NOs: 733 to 748.

In another aspect, the invention provides for an immunogenic composition comprising nucleic acid sequences encoding one or more amino acid sequences selected from the group consisting of SEQ ID NOs: 646 to 667, SEQ ID NOs: 708 to 717, and SEQ ID NOs: 733 to 748.

In some embodiments, the immunogenic composition comprises nucleic acid sequences encoding two or more amino acid sequences selected from the group consisting of SEQ ID NOs: 646 to 667, SEQ ID NOs: 708 to 717, and SEQ ID NOs: 733 to 748. In some embodiments, the nucleic acid sequences are administered in a construct for expression in vivo. In some embodiments, the in vivo administration of the nucleic acid sequences is configured to produce one or more peptides that is displayed by an HLA class II molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is ovarian cancer.

In another aspect, the invention provides for a method of treating or preventing ovarian cancer by administering to a subject an immunogenic composition comprising nucleic acid sequences encoding one or more amino acid sequences selected from the group consisting of SEQ ID NOs: 646 to 667, SEQ ID NOs: 708 to 717, and SEQ ID NOs: 733 to 748.

In some embodiments, the immunogenic composition comprises nucleic acid sequences encoding two or more amino acid sequences selected from the group consisting of SEQ ID NOs: 646 to 667, SEQ ID NOs: 708 to 717, and SEQ ID NOs: 733 to 748.

In another aspect, the invention provides for an immunogenic peptide composition comprising one or more peptides selected from the group consisting of SEQ ID NOs: 646 to 667, SEQ ID NOs: 708 to 717, and SEQ ID NOs: 733 to 748.

In some embodiments, the immunogenic peptide composition comprises two or more peptides selected from the group consisting of SEQ ID NOs: 646 to 667, SEQ ID NOs: 708 to 717, and SEQ ID NOs: 733 to 748. In some embodiments, a peptide in the immunogenic peptide composition is displayed by an HLA class II molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is ovarian cancer.

In another aspect, the invention provides for a method of treating or preventing ovarian cancer in a subject comprising administering to the subject an immunogenic peptide composition comprising one or more peptides selected from the group consisting of SEQ ID NOs: 646 to 667, SEQ ID NOs: 708 to 717, and SEQ ID NOs: 733 to 748.

In some embodiments, the immunogenic peptide composition comprises two or more peptides selected from the group consisting of SEQ ID NOs: 646 to 667, SEQ ID NOs: 708 to 717, and SEQ ID NOs: 733 to 748.

Vaccines for CT Antigens

In one aspect, the invention provides for nucleic acid sequences encoding one or more amino acid sequences selected from the group consisting of SEQ ID NOs: 28796 to 28864, SEQ ID NOs: 37110 to 37174, SEQ ID NOs: 41321 to 41397, SEQ ID NO: 41770, SEQ ID NO: 49004, SEQ ID NO: 49071, SEQ ID NO: 49395, SEQ ID NO: 50632, SEQ ID NO: 50729, SEQ ID NOs: 51434 to 51510, SEQ ID NO: 55758, SEQ ID NOs: 60456 to 60527, SEQ ID NOs: 68238 to 68321, SEQ ID NO: 77091, SEQ ID NO: 77210, SEQ ID NO: 84188, SEQ ID NO: 87951, SEQ ID NO: 88144, SEQ ID NOs: 95593 to 95664, SEQ ID NOs: 113808 to 113869, SEQ ID NOs: 125134 to 125218, SEQ ID NOs: 144109 to 144188, SEQ ID NOs: 162383 to 162453, SEQ ID NOs: 166444 to 166531, SEQ ID NO: 167118, SEQ ID NO: 169740, SEQ ID NO: 173412, SEQ ID NO: 179404, and SEQ ID NOs: 182574 to 182654.

In some embodiments, the nucleic acid sequences encode two or more amino acid sequences selected from the group consisting of SEQ ID NOs: 28796 to 28864, SEQ ID NOs: 37110 to 37174, SEQ ID NOs: 41321 to 41397, SEQ ID NO: 41770, SEQ ID NO: 49004, SEQ ID NO: 49071, SEQ ID NO: 49395, SEQ ID NO: 50632, SEQ ID NO: 50729, SEQ ID NOs: 51434 to 51510, SEQ ID NO: 55758, SEQ ID NOs: 60456 to 60527, SEQ ID NOs: 68238 to 68321, SEQ ID NO: 77091, SEQ ID NO: 77210, SEQ ID NO: 84188, SEQ ID NO: 87951, SEQ ID NO: 88144, SEQ ID NOs: 95593 to 95664, SEQ ID NOs: 113808 to 113869, SEQ ID NOs: 125134 to 125218, SEQ ID NOs: 144109 to 144188, SEQ ID NOs: 162383 to 162453, SEQ ID NOs: 166444 to 166531, SEQ ID NO: 167118, SEQ ID NO: 169740, SEQ ID NO: 173412, SEQ ID NO: 179404, and SEQ ID NOs: 182574 to 182654.

In another aspect, the invention provides for an immunogenic composition comprising nucleic acid sequences encoding one or more amino acid sequences selected from the group consisting of SEQ ID NOs: 28796 to 28864, SEQ ID NOs: 37110 to 37174, SEQ ID NOs: 41321 to 41397, SEQ ID NO: 41770, SEQ ID NO: 49004, SEQ ID NO: 49071, SEQ ID NO: 49395, SEQ ID NO: 50632, SEQ ID NO: 50729, SEQ ID NOs: 51434 to 51510, SEQ ID NO: 55758, SEQ ID NOs: 60456 to 60527, SEQ ID NOs: 68238 to 68321, SEQ ID NO: 77091, SEQ ID NO: 77210, SEQ ID NO: 84188, SEQ ID NO: 87951, SEQ ID NO: 88144, SEQ ID NOs: 95593 to 95664, SEQ ID NOs: 113808 to 113869, SEQ ID NOs: 125134 to 125218, SEQ ID NOs: 144109 to 144188, SEQ ID NOs: 162383 to 162453, SEQ ID NOs: 166444 to 166531, SEQ ID NO: 167118, SEQ ID NO: 169740, SEQ ID NO: 173412, SEQ ID NO: 179404, and SEQ ID NOs: 182574 to 182654.

In some embodiments, the immunogenic composition is administered to a subject. In some embodiments, the immunogenic composition comprises nucleic acid sequences encoding two or more amino acid sequences selected from the group consisting of SEQ ID NOs: 28796 to 28864, SEQ ID NOs: 37110 to 37174, SEQ ID NOs: 41321 to 41397, SEQ ID NO: 41770, SEQ ID NO: 49004, SEQ ID NO: 49071, SEQ ID NO: 49395, SEQ ID NO: 50632, SEQ ID NO: 50729, SEQ ID NOs: 51434 to 51510, SEQ ID NO: 55758, SEQ ID NOs: 60456 to 60527, SEQ ID NOs: 68238 to 68321, SEQ ID NO: 77091, SEQ ID NO: 77210, SEQ ID NO: 84188, SEQ ID NO: 87951, SEQ ID NO: 88144, SEQ ID NOs: 95593 to 95664, SEQ ID NOs: 113808 to 113869, SEQ ID NOs: 125134 to 125218, SEQ ID NOs: 144109 to 144188, SEQ ID NOs: 162383 to 162453, SEQ ID NOs: 166444 to 166531, SEQ ID NO: 167118, SEQ ID NO: 169740, SEQ ID NO: 173412, SEQ ID NO: 179404, and SEQ ID NOs: 182574 to 182654. In some embodiments, the nucleic acid sequences are administered in a construct for expression in vivo. In some embodiments, the in vivo administration of the nucleic acid sequences is configured to produce one or more peptides that is displayed by an HLA class I molecule. In some embodiments, the one or more peptides is a modified or unmodified fragment of a protein selected from the group consisting of CTG1B, KKLC1, MAGA1, MAGA3, MAGA4, MAGC1, MAGC3, MAR1, PMEL, PRAME, SSX2, TYRP1, and TYRP2. In some embodiments, the immunogenic composition is administered in an effective amount to a subject to prevent cancer. In some embodiments, the immunogenic composition is administered in an effective amount to a subject to treat cancer. In some embodiments, the cancer is selected from the group consisting of pancreatic cancer, skin cancer, thyroid cancer, brain cancer, colorectal cancer, bronchus and lung cancer, breast cancer, and ovarian cancer. In some embodiments, the immunogenic composition comprises nucleic acid sequences encoding at least three amino acid sequences selected from the group consisting of SEQ ID NOs: 28796 to 28864, SEQ ID NOs: 37110 to 37174, SEQ ID NOs: 41321 to 41397, SEQ ID NO: 41770, SEQ ID NO: 49004, SEQ ID NO: 49071, SEQ ID NO: 49395, SEQ ID NO: 50632, SEQ ID NO: 50729, SEQ ID NOs: 51434 to 51510, SEQ ID NO: 55758, SEQ ID NOs: 60456 to 60527, SEQ ID NOs: 68238 to 68321, SEQ ID NO: 77091, SEQ ID NO: 77210, SEQ ID NO: 84188, SEQ ID NO: 87951, SEQ ID NO: 88144, SEQ ID NOs: 95593 to 95664, SEQ ID NOs: 113808 to 113869, SEQ ID NOs: 125134 to 125218, SEQ ID NOs: 144109 to 144188, SEQ ID NOs: 162383 to 162453, SEQ ID NOs: 166444 to 166531, SEQ ID NO: 167118, SEQ ID NO: 169740, SEQ ID NO: 173412, SEQ ID NO: 179404, and SEQ ID NOs: 182574 to 182654.

In another aspect, the invention provides for an immunogenic peptide composition comprising one or more peptides selected from the group consisting of SEQ ID NOs: 28796 to 28864, SEQ ID NOs: 37110 to 37174, SEQ ID NOs: 41321 to 41397, SEQ ID NO: 41770, SEQ ID NO: 49004, SEQ ID NO: 49071, SEQ ID NO: 49395, SEQ ID NO: 50632, SEQ ID NO: 50729, SEQ ID NOs: 51434 to 51510, SEQ ID NO: 55758, SEQ ID NOs: 60456 to 60527, SEQ ID NOs: 68238 to 68321, SEQ ID NO: 77091, SEQ ID NO: 77210, SEQ ID NO: 84188, SEQ ID NO: 87951, SEQ ID NO: 88144, SEQ ID NOs: 95593 to 95664, SEQ ID NOs: 113808 to 113869, SEQ ID NOs: 125134 to 125218, SEQ ID NOs: 144109 to 144188, SEQ ID NOs: 162383 to 162453, SEQ ID NOs: 166444 to 166531, SEQ ID NO: 167118, SEQ ID NO: 169740, SEQ ID NO: 173412, SEQ ID NO: 179404, and SEQ ID NOs: 182574 to 182654.

In some embodiments, the immunogenic peptide composition comprises two or more peptides selected from the group consisting of SEQ ID NOs: 28796 to 28864, SEQ ID NOs: 37110 to 37174, SEQ ID NOs: 41321 to 41397, SEQ ID NO: 41770, SEQ ID NO: 49004, SEQ ID NO: 49071, SEQ ID NO: 49395, SEQ ID NO: 50632, SEQ ID NO: 50729, SEQ ID NOs: 51434 to 51510, SEQ ID NO: 55758, SEQ ID NOs: 60456 to 60527, SEQ ID NOs: 68238 to 68321, SEQ ID NO: 77091, SEQ ID NO: 77210, SEQ ID NO: 84188, SEQ ID NO: 87951, SEQ ID NO: 88144, SEQ ID NOs: 95593 to 95664, SEQ ID NOs: 113808 to 113869, SEQ ID NOs: 125134 to 125218, SEQ ID NOs: 144109 to 144188, SEQ ID NOs: 162383 to 162453, SEQ ID NOs: 166444 to 166531, SEQ ID NO: 167118, SEQ ID NO: 169740, SEQ ID NO: 173412, SEQ ID NO: 179404, and SEQ ID NOs: 182574 to 182654.

In another aspect, the invention provides for an immunogenic composition comprising nucleic acid sequences encoding one or more amino acid sequences selected from the group consisting of SEQ ID NOs: 28796 to 28830.

In some embodiments, the immunogenic composition comprises nucleic acid sequences encoding one or more amino acid sequences derived from a CTG1B protein. In some embodiments, the immunogenic composition comprises nucleic acid sequences encoding two or more amino acid sequences selected from the group consisting of SEQ ID NOs: 28796 to 28830.

In another aspect, the invention provides for an immunogenic peptide composition comprising one or more peptides selected from the group consisting of SEQ ID NOs: 28796 to 28830.

In some embodiments, the immunogenic peptide composition comprises two or more peptides selected from the group consisting of SEQ ID NOs: 28796 to 28830. In some embodiments, the one or more peptides is a modified or unmodified fragment of a CTG1B protein.

In another aspect, the invention provides for an immunogenic composition comprising nucleic acid sequences encoding one or more amino acid sequences selected from the group consisting of SEQ ID NOs: 41321 to 41354.

In some embodiments, the immunogenic composition comprises nucleic acid sequences encoding one or more amino acid sequences derived from a MAGA1 protein. In some embodiments, the immunogenic composition comprises nucleic acid sequences encoding two or more amino acid sequences selected from the group consisting of SEQ ID NOs: 41321 to 41354.

In another aspect, the invention provides for an immunogenic peptide composition comprising one or more peptides selected from the group consisting of SEQ ID NOs: 41321 to 41354.

In some embodiments, the immunogenic peptide composition comprises two or more peptides selected from the group consisting of SEQ ID NOs: 41321 to 41354. In some embodiments, the one or more peptides is a modified or unmodified fragment of a MAGA1 protein.

In another aspect, the invention provides for an immunogenic composition comprising nucleic acid sequences encoding one or more amino acid sequences selected from the group consisting of SEQ ID NO: 41770, SEQ ID NO: 49004, and SEQ ID NOs: 51434 to 51468.

In some embodiments, the immunogenic composition comprises nucleic acid sequences encoding one or more amino acid sequences derived from a MAGA3 protein. In some embodiments, the immunogenic composition comprises nucleic acid sequences encoding two or more amino acid sequences selected from the group consisting of SEQ ID NO: 41770, SEQ ID NO: 49004, and SEQ ID NOs: 51434 to 51468.

In another aspect, the invention provides for an immunogenic peptide composition comprising one or more peptides selected from the group consisting of SEQ ID NO: 41770, SEQ ID NO: 49004, and SEQ ID NOs: 51434 to 51468.

In some embodiments, the immunogenic peptide composition comprises two or more peptides selected from the group consisting of SEQ ID NO: 41770, SEQ ID NO: 49004, and SEQ ID NOs: 51434 to 51468. In some embodiments, the one or more peptides is a modified or unmodified fragment of a MAGA3 protein.

In another aspect, the invention provides for an immunogenic composition comprising nucleic acid sequences encoding one or more amino acid sequences selected from the group consisting of SEQ ID NO: 41352, SEQ ID NO: 41770, and SEQ ID NOs: 60456 to 60487.

In some embodiments, the immunogenic composition comprises nucleic acid sequences encoding one or more amino acid sequences derived from a MAGA4 protein. In some embodiments, the immunogenic composition comprises nucleic acid sequences encoding two or more amino acid sequences selected from the group consisting of SEQ ID NO: 41352, SEQ ID NO: 41770, and SEQ ID NOs: 60456 to 60487.

In another aspect, the invention provides for an immunogenic peptide composition comprising one or more peptides selected from the group consisting of SEQ ID NO: 41352, SEQ ID NO: 41770, and SEQ ID NOs: 60456 to 60487.

In some embodiments, the immunogenic peptide composition comprises two or more peptides selected from the group consisting of SEQ ID NO: 41352, SEQ ID NO: 41770, and SEQ ID NOs: 60456 to 60487. In some embodiments, the one or more peptides is a modified or unmodified fragment of a MAGA4 protein.

In another aspect, the invention provides for an immunogenic composition comprising nucleic acid sequences encoding one or more amino acid sequences selected from the group consisting of SEQ ID NO: 49395 and SEQ ID NOs: 68238 to 68272.

In some embodiments, the immunogenic composition comprises nucleic acid sequences encoding one or more amino acid sequences derived from a MAGC1 protein. In some embodiments, the immunogenic composition comprises nucleic acid sequences encoding two or more amino acid sequences selected from the group consisting of SEQ ID NO: 49395 and SEQ ID NOs: 68238 to 68272.

In another aspect, the invention provides for an immunogenic peptide composition comprising one or more peptides selected from the group consisting of SEQ ID NO: 49395 and SEQ ID NOs: 68238 to 68272.

In some embodiments, the immunogenic peptide composition comprises two or more peptides selected from the group consisting of SEQ ID NO: 49395 and SEQ ID NOs: 68238 to 68272. In some embodiments, the one or more peptides is a modified or unmodified fragment of a MAGC1 protein.

In another aspect, the invention provides for an immunogenic composition comprising nucleic acid sequences encoding one or more amino acid sequences selected from the group consisting of SEQ ID NO: 77091, SEQ ID NO: 77210, SEQ ID NO: 84188, SEQ ID NO: 88144, and SEQ ID NOs: 95593 to 95624.

In some embodiments, the immunogenic composition comprises nucleic acid sequences encoding one or more amino acid sequences derived from a MAGC3 protein. In some embodiments, the immunogenic composition comprises nucleic acid sequences encoding two or more amino acid sequences selected from the group consisting of SEQ ID NO: 77091, SEQ ID NO: 77210, SEQ ID NO: 84188, SEQ ID NO: 88144, and SEQ ID NOs: 95593 to 95624.

In another aspect, the invention provides for an immunogenic peptide composition comprising one or more peptides selected from the group consisting of SEQ ID NO: 77091, SEQ ID NO: 77210, SEQ ID NO: 84188, SEQ ID NO: 88144, and SEQ ID NOs: 95593 to 95624.

In some embodiments, the immunogenic peptide composition comprises two or more peptides selected from the group consisting of SEQ ID NO: 77091, SEQ ID NO: 77210, SEQ ID NO: 84188, SEQ ID NO: 88144, and SEQ ID NOs: 95593 to 95624. In some embodiments, the one or more peptides is a modified or unmodified fragment of a MAGC3 protein.

In another aspect, the invention provides for an immunogenic composition comprising nucleic acid sequences encoding one or more amino acid sequences selected from the group consisting of SEQ ID NOs: 162383 to 162420.

In some embodiments, the immunogenic composition comprises nucleic acid sequences encoding one or more amino acid sequences derived from a SSX2 protein. In some embodiments, the immunogenic composition comprises nucleic acid sequences encoding two or more amino acid sequences selected from the group consisting of SEQ ID NOs: 162383 to 162420.

In another aspect, the invention provides for an immunogenic peptide composition comprising one or more peptides selected from the group consisting of SEQ ID NOs: 162383 to 162420.

In some embodiments, the immunogenic peptide composition comprises two or more peptides selected from the group consisting of SEQ ID NOs: 162383 to 162420. In some embodiments, the one or more peptides is a modified or unmodified fragment of a SSX2 protein.

In another aspect, the invention provides for an immunogenic composition comprising nucleic acid sequences encoding one or more amino acid sequences selected from the group consisting of SEQ ID NOs: 144109 to 144142.

In some embodiments, the immunogenic composition comprises nucleic acid sequences encoding one or more amino acid sequences derived from a PRAME protein. In some embodiments, the immunogenic composition comprises nucleic acid sequences encoding two or more amino acid sequences selected from the group consisting of SEQ ID NOs: 144109 to 144142.

In another aspect, the invention provides for an immunogenic peptide composition comprising one or more peptides selected from the group consisting of SEQ ID NOs: 144109 to 144142.

In some embodiments, the immunogenic peptide composition comprises two or more peptides selected from the group consisting of SEQ ID NOs: 144109 to 144142. In some embodiments, the one or more peptides is a modified or unmodified fragment of a PRAME protein.

In another aspect, the invention provides for an immunogenic composition comprising nucleic acid sequences encoding one or more amino acid sequences selected from the group consisting of SEQ ID NOs: 37110 to 37145.

In some embodiments, the immunogenic composition comprises nucleic acid sequences encoding one or more amino acid sequences derived from a KKLC1 protein. In some embodiments, the immunogenic composition comprises nucleic acid sequences encoding two or more amino acid sequences selected from the group consisting of SEQ ID NOs: 37110 to 37145.

In another aspect, the invention provides for an immunogenic peptide composition comprising one or more peptides selected from the group consisting of SEQ ID NOs: 37110 to 37145.

In some embodiments, the immunogenic peptide composition comprises two or more peptides selected from the group consisting of SEQ ID NOs: 37110 to 37145. In some embodiments, the one or more peptides is a modified or unmodified fragment of a KKLC1 protein.

In another aspect, the invention provides for an immunogenic composition comprising nucleic acid sequences encoding one or more amino acid sequences selected from the group consisting of SEQ ID NOs: 125134 to 125167.

In some embodiments, the immunogenic composition comprises nucleic acid sequences encoding one or more amino acid sequences derived from a PMEL protein. In some embodiments, the immunogenic composition comprises nucleic acid sequences encoding two or more amino acid sequences selected from the group consisting of SEQ ID NOs: 125134 to 125167.

In another aspect, the invention provides for an immunogenic peptide composition comprising one or more peptides selected from the group consisting of SEQ ID NOs: 125134 to 125167.

In some embodiments, the immunogenic peptide composition comprises two or more peptides selected from the group consisting of SEQ ID NOs: 125134 to 125167. In some embodiments, the one or more peptides is a modified or unmodified fragment of a PMEL protein.

In another aspect, the invention provides for an immunogenic composition comprising nucleic acid sequences encoding one or more amino acid sequences selected from the group consisting of SEQ ID NOs: 166444 to 166480.

In some embodiments, the immunogenic composition comprises nucleic acid sequences encoding one or more amino acid sequences derived from a TYRP1 protein. In some embodiments, the immunogenic composition comprises nucleic acid sequences encoding two or more amino acid sequences selected from the group consisting of SEQ ID NOs: 166444 to 166480.

In another aspect, the invention provides for an immunogenic peptide composition comprising one or more peptides selected from the group consisting of SEQ ID NOs: 166444 to 166480.

In some embodiments, the immunogenic peptide composition comprises two or more peptides selected from the group consisting of SEQ ID NOs: 166444 to 166480. In some embodiments, the one or more peptides is a modified or unmodified fragment of a TYRP1 protein.

In another aspect, the invention provides for an immunogenic composition comprising nucleic acid sequences encoding one or more amino acid sequences selected from the group consisting of SEQ ID NO: 169740, SEQ ID NO: 173412, SEQ ID NO: 179404, and SEQ ID NOs: 182574 to 182606.

In some embodiments, the immunogenic composition comprises nucleic acid sequences encoding one or more amino acid sequences derived from a TYRP2 protein. In some embodiments, the immunogenic composition comprises nucleic acid sequences encoding two or more amino acid sequences selected from the group consisting of SEQ ID NO: 169740, SEQ ID NO: 173412, SEQ ID NO: 179404, and SEQ ID NOs: 182574 to 182606.

In another aspect, the invention provides for an immunogenic peptide composition comprising one or more peptides selected from the group consisting of SEQ ID NO: 169740, SEQ ID NO: 173412, SEQ ID NO: 179404, and SEQ ID NOs: 182574 to 182606.

In some embodiments, the immunogenic peptide composition comprises two or more peptides selected from the group consisting of SEQ ID NO: 169740, SEQ ID NO: 173412, SEQ ID NO: 179404, and SEQ ID NOs: 182574 to 182606. In some embodiments, the one or more peptides is a modified or unmodified fragment of a TYRP2 protein.

In another aspect, the invention provides for an immunogenic composition comprising nucleic acid sequences encoding one or more amino acid sequences selected from the group consisting of SEQ ID NOs: 113808 to 113843.

In some embodiments, the immunogenic composition comprises nucleic acid sequences encoding one or more amino acid sequences derived from a MAR1 protein. In some embodiments, the immunogenic composition comprises nucleic acid sequences encoding two or more amino acid sequences selected from the group consisting of SEQ ID NOs: 113808 to 113843.

In another aspect, the invention provides for an immunogenic peptide composition comprising one or more peptides selected from the group consisting of SEQ ID NOs: 113808 to 113843.

In some embodiments, the immunogenic peptide composition comprises two or more peptides selected from the group consisting of SEQ ID NOs: 113808 to 113843. In some embodiments, the one or more peptides is a modified or unmodified fragment of a MAR1 protein.

In one aspect, the invention provides for nucleic acid sequences encoding one or more amino acid sequences selected from the group consisting of SEQ ID NOs: 28796 to 28864, SEQ ID NOs: 37110 to 37174, SEQ ID NOs: 41321 to 41397, SEQ ID NO: 41770, SEQ ID NO: 49004, SEQ ID NO: 49071, SEQ ID NO: 49395, SEQ ID NO: 50632, SEQ ID NO: 50729, SEQ ID NOs: 51434 to 51510, SEQ ID NO: 55758, SEQ ID NOs: 60456 to 60527, SEQ ID NOs: 68238 to 68321, SEQ ID NO: 77091, SEQ ID NO: 77210, SEQ ID NO: 84188, SEQ ID NO: 87951, SEQ ID NO: 88144, SEQ ID NOs: 95593 to 95664, SEQ ID NOs: 113808 to 113869, SEQ ID NOs: 125134 to 125218, SEQ ID NOs: 144109 to 144188, SEQ ID NOs: 162383 to 162453, SEQ ID NOs: 166444 to 166531, SEQ ID NO: 167118, SEQ ID NO: 169740, SEQ ID NO: 173412, SEQ ID NO: 179404, and SEQ ID NOs: 182574 to 182654.

In some embodiments, the nucleic acid sequences encode two or more amino acid sequences selected from the group consisting of SEQ ID NOs: 28796 to 28864, SEQ ID NOs: 37110 to 37174, SEQ ID NOs: 41321 to 41397, SEQ ID NO: 41770, SEQ ID NO: 49004, SEQ ID NO: 49071, SEQ ID NO: 49395, SEQ ID NO: 50632, SEQ ID NO: 50729, SEQ ID NOs: 51434 to 51510, SEQ ID NO: 55758, SEQ ID NOs: 60456 to 60527, SEQ ID NOs: 68238 to 68321, SEQ ID NO: 77091, SEQ ID NO: 77210, SEQ ID NO: 84188, SEQ ID NO: 87951, SEQ ID NO: 88144, SEQ ID NOs: 95593 to 95664, SEQ ID NOs: 113808 to 113869, SEQ ID NOs: 125134 to 125218, SEQ ID NOs: 144109 to 144188, SEQ ID NOs: 162383 to 162453, SEQ ID NOs: 166444 to 166531, SEQ ID NO: 167118, SEQ ID NO: 169740, SEQ ID NO: 173412, SEQ ID NO: 179404, and SEQ ID NOs: 182574 to 182654.

In another aspect, the invention provides for an immunogenic composition comprising nucleic acid sequences encoding one or more amino acid sequences selected from the group consisting of SEQ ID NOs: 28796 to 28864, SEQ ID NOs: 37110 to 37174, SEQ ID NOs: 41321 to 41397, SEQ ID NO: 41770, SEQ ID NO: 49004, SEQ ID NO: 49071, SEQ ID NO: 49395, SEQ ID NO: 50632, SEQ ID NO: 50729, SEQ ID NOs: 51434 to 51510, SEQ ID NO: 55758, SEQ ID NOs: 60456 to 60527, SEQ ID NOs: 68238 to 68321, SEQ ID NO: 77091, SEQ ID NO: 77210, SEQ ID NO: 84188, SEQ ID NO: 87951, SEQ ID NO: 88144, SEQ ID NOs: 95593 to 95664, SEQ ID NOs: 113808 to 113869, SEQ ID NOs: 125134 to 125218, SEQ ID NOs: 144109 to 144188, SEQ ID NOs: 162383 to 162453, SEQ ID NOs: 166444 to 166531, SEQ ID NO: 167118, SEQ ID NO: 169740, SEQ ID NO: 173412, SEQ ID NO: 179404, and SEQ ID NOs: 182574 to 182654.

In some embodiments, the immunogenic composition is administered to a subject. In some embodiments, the immunogenic composition comprises nucleic acid sequences encoding two or more amino acid sequences selected from the group consisting of SEQ ID NOs: 28796 to 28864, SEQ ID NOs: 37110 to 37174, SEQ ID NOs: 41321 to 41397, SEQ ID NO: 41770, SEQ ID NO: 49004, SEQ ID NO: 49071, SEQ ID NO: 49395, SEQ ID NO: 50632, SEQ ID NO: 50729, SEQ ID NOs: 51434 to 51510, SEQ ID NO: 55758, SEQ ID NOs: 60456 to 60527, SEQ ID NOs: 68238 to 68321, SEQ ID NO: 77091, SEQ ID NO: 77210, SEQ ID NO: 84188, SEQ ID NO: 87951, SEQ ID NO: 88144, SEQ ID NOs: 95593 to 95664, SEQ ID NOs: 113808 to 113869, SEQ ID NOs: 125134 to 125218, SEQ ID NOs: 144109 to 144188, SEQ ID NOs: 162383 to 162453, SEQ ID NOs: 166444 to 166531, SEQ ID NO: 167118, SEQ ID NO: 169740, SEQ ID NO: 173412, SEQ ID NO: 179404, and SEQ ID NOs: 182574 to 182654. In some embodiments, the nucleic acid sequences are administered in a construct for expression in vivo. In some embodiments, the in vivo administration of the nucleic acid sequences is configured to produce one or more peptides that is displayed by an HLA class II molecule. In some embodiments, the one or more peptides is a modified or unmodified fragment of a protein selected from the group consisting of CTG1B, KKLC1, MAGA1, MAGA3, MAGA4, MAGC1, MAGC3, MAR1, PMEL, PRAME, SSX2, TYRP1, and TYRP2. In some embodiments, the immunogenic composition is administered in an effective amount to a subject to prevent cancer. In some embodiments, the immunogenic composition is administered in an effective amount to a subject to treat cancer. In some embodiments, the cancer is selected from the group consisting of pancreatic cancer, skin cancer, thyroid cancer, brain cancer, colorectal cancer, bronchus and lung cancer, breast cancer, and ovarian cancer. In some embodiments, the immunogenic composition comprises nucleic acid sequences encoding at least three amino acid sequences selected from the group consisting of SEQ ID NOs: 28796 to 28864, SEQ ID NOs: 37110 to 37174, SEQ ID NOs: 41321 to 41397, SEQ ID NO: 41770, SEQ ID NO: 49004, SEQ ID NO: 49071, SEQ ID NO: 49395, SEQ ID NO: 50632, SEQ ID NO: 50729, SEQ ID NOs: 51434 to 51510, SEQ ID NO: 55758, SEQ ID NOs: 60456 to 60527, SEQ ID NOs: 68238 to 68321, SEQ ID NO: 77091, SEQ ID NO: 77210, SEQ ID NO: 84188, SEQ ID NO: 87951, SEQ ID NO: 88144, SEQ ID NOs: 95593 to 95664, SEQ ID NOs:

113808 to 113869, SEQ ID NOs: 125134 to 125218, SEQ ID NOs: 144109 to 144188, SEQ ID NOs: 162383 to 162453, SEQ ID NOs: 166444 to 166531, SEQ ID NO: 167118, SEQ ID NO: 169740, SEQ ID NO: 173412, SEQ ID NO: 179404, and SEQ ID NOs: 182574 to 182654.

In another aspect, the invention provides for an immunogenic peptide composition comprising one or more peptides selected from the group consisting of SEQ ID NOs: 28796 to 28864, SEQ ID NOs: 37110 to 37174, SEQ ID NOs: 41321 to 41397, SEQ ID NO: 41770, SEQ ID NO: 49004, SEQ ID NO: 49071, SEQ ID NO: 49395, SEQ ID NO: 50632, SEQ ID NO: 50729, SEQ ID NOs: 51434 to 51510, SEQ ID NO: 55758, SEQ ID NOs: 60456 to 60527, SEQ ID NOs: 68238 to 68321, SEQ ID NO: 77091, SEQ ID NO: 77210, SEQ ID NO: 84188, SEQ ID NO: 87951, SEQ ID NO: 88144, SEQ ID NOs: 95593 to 95664, SEQ ID NOs: 113808 to 113869, SEQ ID NOs: 125134 to 125218, SEQ ID NOs: 144109 to 144188, SEQ ID NOs: 162383 to 162453, SEQ ID NOs: 166444 to 166531, SEQ ID NO: 167118, SEQ ID NO: 169740, SEQ ID NO: 173412, SEQ ID NO: 179404, and SEQ ID NOs: 182574 to 182654.

In some embodiments, the immunogenic peptide composition comprises two or more peptides selected from the group consisting of SEQ ID NOs: 28796 to 28864, SEQ ID NOs: 37110 to 37174, SEQ ID NOs: 41321 to 41397, SEQ ID NO: 41770, SEQ ID NO: 49004, SEQ ID NO: 49071, SEQ ID NO: 49395, SEQ ID NO: 50632, SEQ ID NO: 50729, SEQ ID NOs: 51434 to 51510, SEQ ID NO: 55758, SEQ ID NOs: 60456 to 60527, SEQ ID NOs: 68238 to 68321, SEQ ID NO: 77091, SEQ ID NO: 77210, SEQ ID NO: 84188, SEQ ID NO: 87951, SEQ ID NO: 88144, SEQ ID NOs: 95593 to 95664, SEQ ID NOs: 113808 to 113869, SEQ ID NOs: 125134 to 125218, SEQ ID NOs: 144109 to 144188, SEQ ID NOs: 162383 to 162453, SEQ ID NOs: 166444 to 166531, SEQ ID NO: 167118, SEQ ID NO: 169740, SEQ ID NO: 173412, SEQ ID NO: 179404, and SEQ ID NOs: 182574 to 182654.

In another aspect, the invention provides for an immunogenic composition comprising nucleic acid sequences encoding one or more amino acid sequences selected from the group consisting of SEQ ID NOs: 197897 to 197901.

In some embodiments, the immunogenic composition comprises nucleic acid sequences encoding one or more amino acid sequences derived from a CTG1B protein. In some embodiments, the immunogenic composition comprises nucleic acid sequences encoding two or more amino acid sequences selected from the group consisting of SEQ ID NOs: 197897 to 197901.

In another aspect, the invention provides for an immunogenic peptide composition comprising one or more peptides selected from the group consisting of SEQ ID NOs: 197897 to 197901.

In some embodiments, the immunogenic peptide composition comprises two or more peptides selected from the group consisting of SEQ ID NOs: 197897 to 197901. In some embodiments, the one or more peptides is a modified or unmodified fragment of a CTG1B protein.

In another aspect, the invention provides for an immunogenic composition comprising nucleic acid sequences encoding one or more amino acid sequences selected from the group consisting of SEQ ID NOs: 211901 to 211904.

In some embodiments, the immunogenic composition comprises nucleic acid sequences encoding one or more amino acid sequences derived from a MAGA1 protein. In some embodiments, the immunogenic composition comprises nucleic acid sequences encoding two or more amino acid sequences selected from the group consisting of SEQ ID NOs: 211901 to 211904.

In another aspect, the invention provides for an immunogenic peptide composition comprising one or more peptides selected from the group consisting of SEQ ID NOs: 211901 to 211904.

In some embodiments, the immunogenic peptide composition comprises two or more peptides selected from the group consisting of SEQ ID NOs: 211901 to 211904. In some embodiments, the one or more peptides is a modified or unmodified fragment of a MAGA1 protein.

In another aspect, the invention provides for an immunogenic composition comprising nucleic acid sequences encoding one or more amino acid sequences selected from the group consisting of SEQ ID NOs: 223623 to 223627.

In some embodiments, the immunogenic composition comprises nucleic acid sequences encoding one or more amino acid sequences derived from a MAGA3 protein. In some embodiments, the immunogenic composition comprises nucleic acid sequences encoding two or more amino acid sequences selected from the group consisting of SEQ ID NOs: 223623 to 223627.

In another aspect, the invention provides for an immunogenic peptide composition comprising one or more peptides selected from the group consisting of SEQ ID NOs: 223623 to 223627.

In some embodiments, the immunogenic peptide composition comprises two or more peptides selected from the group consisting of SEQ ID NOs: 223623 to 223627. In some embodiments, the one or more peptides is a modified or unmodified fragment of a MAGA3 protein.

In another aspect, the invention provides for an immunogenic composition comprising nucleic acid sequences encoding one or more amino acid sequences selected from the group consisting of SEQ ID NOs: 236016 to 236020.

In some embodiments, the immunogenic composition comprises nucleic acid sequences encoding one or more amino acid sequences derived from a MAGA4 protein. In some embodiments, the immunogenic composition comprises nucleic acid sequences encoding two or more amino acid sequences selected from the group consisting of SEQ ID NOs: 236016 to 236020.

In another aspect, the invention provides for an immunogenic peptide composition comprising one or more peptides selected from the group consisting of SEQ ID NOs: 236016 to 236020.

In some embodiments, the immunogenic peptide composition comprises two or more peptides selected from the group consisting of SEQ ID NOs: 236016 to 236020. In some embodiments, the one or more peptides is a modified or unmodified fragment of a MAGA4 protein.

In another aspect, the invention provides for an immunogenic composition comprising nucleic acid sequences encoding one or more amino acid sequences selected from the group consisting of SEQ ID NOs: 247059 to 247063.

In some embodiments, the immunogenic composition comprises nucleic acid sequences encoding one or more amino acid sequences derived from a MAGC1 protein. In some embodiments, the immunogenic composition comprises nucleic acid sequences encoding two or more amino acid sequences selected from the group consisting of SEQ ID NOs: 247059 to 247063.

In another aspect, the invention provides for an immunogenic peptide composition comprising one or more peptides selected from the group consisting of SEQ ID NOs: 247059 to 247063.

In some embodiments, the immunogenic peptide composition comprises two or more peptides selected from the group consisting of SEQ ID NOs: 247059 to 247063. In some embodiments, the one or more peptides is a modified or unmodified fragment of a MAGC1 protein.

In another aspect, the invention provides for an immunogenic composition comprising nucleic acid sequences encoding one or more amino acid sequences selected from the group consisting of SEQ ID NOs: 281350 to 281353.

In some embodiments, the immunogenic composition comprises nucleic acid sequences encoding one or more amino acid sequences derived from a MAGC3 protein. In some embodiments, the immunogenic composition comprises nucleic acid sequences encoding two or more amino acid sequences selected from the group consisting of SEQ ID NOs: 281350 to 281353.

In another aspect, the invention provides for an immunogenic peptide composition comprising one or more peptides selected from the group consisting of SEQ ID NOs: 281350 to 281353.

In some embodiments, the immunogenic peptide composition comprises two or more peptides selected from the group consisting of SEQ ID NOs: 281350 to 281353. In some embodiments, the one or more peptides is a modified or unmodified fragment of a MAGC3 protein.

In another aspect, the invention provides for an immunogenic composition comprising nucleic acid sequences encoding one or more amino acid sequences selected from the group consisting of SEQ ID NOs: 369027 to 369031.

In some embodiments, the immunogenic composition comprises nucleic acid sequences encoding one or more amino acid sequences derived from a SSX2 protein. In some embodiments, the immunogenic composition comprises nucleic acid sequences encoding two or more amino acid sequences selected from the group consisting of SEQ ID NOs: 369027 to 369031.

In another aspect, the invention provides for an immunogenic peptide composition comprising one or more peptides selected from the group consisting of SEQ ID NOs: 369027 to 369031.

In some embodiments, the immunogenic peptide composition comprises two or more peptides selected from the group consisting of SEQ ID NOs: 369027 to 369031. In some embodiments, the one or more peptides is a modified or unmodified fragment of a SSX2 protein.

In another aspect, the invention provides for an immunogenic composition comprising nucleic acid sequences encoding one or more amino acid sequences selected from the group consisting of SEQ ID NOs: 342521 to 342525.

In some embodiments, the immunogenic composition comprises nucleic acid sequences encoding one or more amino acid sequences derived from a PRAME protein. In some embodiments, the immunogenic composition comprises nucleic acid sequences encoding two or more amino acid sequences selected from the group consisting of SEQ ID NOs: 342521 to 342525.

In another aspect, the invention provides for an immunogenic peptide composition comprising one or more peptides selected from the group consisting of SEQ ID NOs: 342521 to 342525.

In some embodiments, the immunogenic peptide composition comprises two or more peptides selected from the group consisting of SEQ ID NOs: 342521 to 342525. In some embodiments, the one or more peptides is a modified or unmodified fragment of a PRAME protein.

In another aspect, the invention provides for an immunogenic composition comprising nucleic acid sequences encoding one or more amino acid sequences selected from the group consisting of SEQ ID NOs: 206663 to 206665.

In some embodiments, the immunogenic composition comprises nucleic acid sequences encoding one or more amino acid sequences derived from a KKLC1 protein. In some embodiments, the immunogenic composition comprises nucleic acid sequences encoding two or more amino acid sequences selected from the group consisting of SEQ ID NOs: 206663 to 206665.

In another aspect, the invention provides for an immunogenic peptide composition comprising one or more peptides selected from the group consisting of SEQ ID NOs: 206663 to 206665.

In some embodiments, the immunogenic peptide composition comprises two or more peptides selected from the group consisting of SEQ ID NOs: 206663 to 206665. In some embodiments, the one or more peptides is a modified or unmodified fragment of a KKLC1 protein.

In another aspect, the invention provides for an immunogenic composition comprising nucleic acid sequences encoding one or more amino acid sequences selected from the group consisting of SEQ ID NOs: 317360 to 317363.

In some embodiments, the immunogenic composition comprises nucleic acid sequences encoding one or more amino acid sequences derived from a PMEL protein. In some embodiments, the immunogenic composition comprises nucleic acid sequences encoding two or more amino acid sequences selected from the group consisting of SEQ ID NOs: 317360 to 317363.

In another aspect, the invention provides for an immunogenic peptide composition comprising one or more peptides selected from the group consisting of SEQ ID NOs: 317360 to 317363.

In some embodiments, the immunogenic peptide composition comprises two or more peptides selected from the group consisting of SEQ ID NOs: 317360 to 317363. In some embodiments, the one or more peptides is a modified or unmodified fragment of a PMEL protein.

In another aspect, the invention provides for an immunogenic composition comprising nucleic acid sequences encoding one or more amino acid sequences selected from the group consisting of SEQ ID NOs: 373348 to 373350.

In some embodiments, the immunogenic composition comprises nucleic acid sequences encoding one or more amino acid sequences derived from a TYRP1 protein. In some embodiments, the immunogenic composition comprises nucleic acid sequences encoding two or more amino acid sequences selected from the group consisting of SEQ ID NOs: 373348 to 373350.

In another aspect, the invention provides for an immunogenic peptide composition comprising one or more peptides selected from the group consisting of SEQ ID NOs: 373348 to 373350.

In some embodiments, the immunogenic peptide composition comprises two or more peptides selected from the group consisting of SEQ ID NOs: 373348 to 373350. In some embodiments, the one or more peptides is a modified or unmodified fragment of a TYRP1 protein.

In another aspect, the invention provides for an immunogenic composition comprising nucleic acid sequences encoding one or more amino acid sequences selected from the group consisting of SEQ ID NOs: 392434 to 392437.

In some embodiments, the immunogenic composition comprises nucleic acid sequences encoding one or more amino acid sequences derived from a TYRP2 protein. In some embodiments, the immunogenic composition comprises nucleic acid sequences encoding two or more amino acid sequences selected from the group consisting of SEQ ID NOs: 392434 to 392437.

In another aspect, the invention provides for an immunogenic peptide composition comprising one or more peptides selected from the group consisting of SEQ ID NOs: 392434 to 392437.

In some embodiments, the immunogenic peptide composition comprises two or more peptides selected from the group consisting of SEQ ID NOs: 392434 to 392437. In some embodiments, the one or more peptides is a modified or unmodified fragment of a TYRP2 protein.

In another aspect, the invention provides for an immunogenic composition comprising nucleic acid sequences encoding one or more amino acid sequences selected from the group consisting of SEQ ID NOs: 305566 to 305570.

In some embodiments, the immunogenic composition comprises nucleic acid sequences encoding one or more amino acid sequences derived from a MAR1 protein. In some embodiments, the immunogenic composition comprises nucleic acid sequences encoding two or more amino acid sequences selected from the group consisting of SEQ ID NOs: 305566 to 305570.

In another aspect, the invention provides for an immunogenic peptide composition comprising one or more peptides selected from the group consisting of SEQ ID NOs: 305566 to 305570.

In some embodiments, the immunogenic peptide composition comprises two or more peptides selected from the group consisting of SEQ ID NOs: 305566 to 305570. In some embodiments, the one or more peptides is a modified or unmodified fragment of a MAR1 protein.

Vaccines for Autoimmune Diseases

In another aspect, the invention provides for an immunogenic composition comprising nucleic acid sequences encoding one or more amino acid sequences selected from the group consisting of SEQ ID NOs: 34169 to 34204.

In some embodiments, the immunogenic composition comprises nucleic acid sequences encoding one or more amino acid sequences derived from an INS protein. In some embodiments, the immunogenic composition comprises nucleic acid sequences encoding two or more amino acid sequences selected from the group consisting of SEQ ID NOs: 34169 to 34204.

In another aspect, the invention provides for an immunogenic peptide composition comprising one or more peptides selected from the group consisting of SEQ ID NOs: 34169 to 34204.

In some embodiments, the immunogenic peptide composition comprises two or more peptides selected from the group consisting of SEQ ID NOs: 34169 to 34204. In some embodiments, the one or more peptides is a modified or unmodified fragment of a INS protein.

In another aspect, the invention provides for an immunogenic composition comprising nucleic acid sequences encoding one or more amino acid sequences selected from the group consisting of SEQ ID NOs: 116478 to 116515.

In some embodiments, the immunogenic composition comprises nucleic acid sequences encoding one or more amino acid sequences derived from a MOG protein. In some embodiments, the immunogenic composition comprises nucleic acid sequences encoding two or more amino acid sequences selected from the group consisting of SEQ ID NOs: 116478 to 116515.

In another aspect, the invention provides for an immunogenic peptide composition comprising one or more peptides selected from the group consisting of SEQ ID NOs: 116478 to 116515.

In some embodiments, the immunogenic peptide composition comprises two or more peptides selected from the group consisting of SEQ ID NOs: 116478 to 116515. In some embodiments, the one or more peptides is a modified or unmodified fragment of a MOG protein.

In another aspect, the invention provides for an immunogenic composition comprising nucleic acid sequences encoding one or more amino acid sequences selected from the group consisting of SEQ ID NOs: 203517 to 203521.

In some embodiments, the immunogenic composition comprises nucleic acid sequences encoding one or more amino acid sequences derived from a INS protein. In some embodiments, the immunogenic composition comprises nucleic acid sequences encoding two or more amino acid sequences selected from the group consisting of SEQ ID NOs: 203517 to 203521.

In another aspect, the invention provides for an immunogenic peptide composition comprising one or more peptides selected from the group consisting of SEQ ID NOs: 203517 to 203521.

In some embodiments, the immunogenic peptide composition comprises two or more peptides selected from the group consisting of SEQ ID NOs: 203517 to 203521. In some embodiments, the one or more peptides is a modified or unmodified fragment of a INS protein.

In another aspect, the invention provides for an immunogenic composition comprising nucleic acid sequences encoding one or more amino acid sequences selected from the group consisting of SEQ ID NOs: 307670 to 307674.

In some embodiments, the immunogenic composition comprises nucleic acid sequences encoding one or more amino acid sequences derived from a MOG protein. In some embodiments, the immunogenic composition comprises nucleic acid sequences encoding two or more amino acid sequences selected from the group consisting of SEQ ID NOs: 307670 to 307674.

In another aspect, the invention provides for an immunogenic peptide composition comprising one or more peptides selected from the group consisting of SEQ ID NOs: 307670 to 307674.

In some embodiments, the immunogenic peptide composition comprises two or more peptides selected from the group consisting of SEQ ID NOs: 307670 to 307674. In some embodiments, the one or more peptides is a modified or unmodified fragment of a MOG protein.

BRIEF DESCRIPTION OF THE DRAWINGS

The following figures depict illustrative embodiments of the invention.

FIG. 7 is a table showing the respective probabilities of target presentations for various mutated protein targets across different cancers.

FIG. 13 shows an example Python implementation of the MergeMulti function for combined vaccine design procedures.

DETAILED DESCRIPTION

Figure 1:
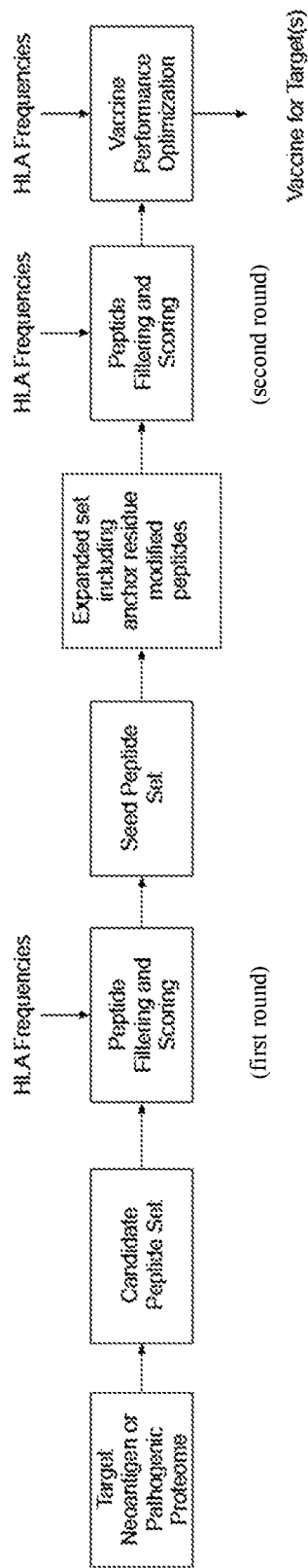
FIG. 1 is a flow chart of a vaccine optimization method.

In some embodiments, the disclosure provides for peptide vaccines that incorporate peptide sequences that will be displayed by Major Histocompatibility Complex (MHC) molecules on cells and train the immune system to recognize cancer or pathogen diseased cells. In some embodiments, the disclosure provides for peptide vaccines that that incorporate peptide sequences that will be displayed by Major Histocompatibility Complex (MHC) molecules on cells to induce therapeutic tolerance in antigen-specific immunotherapy for autoimmune diseases (Alhadj Ali et al., 2017, Gibson, et al., 2015). In some embodiments, a peptide vaccine is a composition that consists of one or more peptides. In some embodiments, a peptide vaccine is an mRNA or DNA construct administered for expression in vivo that encodes for one or more peptides.

Peptide display by an MHC molecule is necessary, but not sufficient, for a peptide to be immunogenic and cause the recognition of the resulting peptide-MHC complex by an individual's T cells to trigger T cell activation, expansion, and immune memory. In some embodiments, experimental data from assays such as the ELISPOT (Slota et al., 2011) or the Multiplex Identification of Antigen-Specific T Cell Receptors Using a Combination of Immune Assays and Immune Receptor Sequencing (MIRA) assay (Klinger et al., 2015) is used for scoring peptide display (e.g., peptide immunogenicity that requires peptide binding) by an MHC molecule (e.g., HLA allele) (e.g., measured as a peptide-HLA binding score). In some embodiments, experimental data from assays such as the ELISPOT (Slota et al., 2011) or the Multiplex Identification of Antigen-Specific T Cell Receptors Using a Combination of Immune Assays and Immune Receptor Sequencing (MIRA) assay (Klinger et al., 2015) can be used to score peptides for peptide-HLA immunogenicity. In some embodiments, experimental data from assays such as the ELISPOT (Slota et al., 2011) or the Multiplex Identification of Antigen-Specific T Cell Receptors Using a Combination of Immune Assays and Immune Receptor Sequencing (MIRA) assay (Klinger et al., 2015) can be combined with machine learning based predictions for scoring peptide display (e.g., binding affinity) by an MHC molecule (e.g., HLA allele) (e.g., measured as a peptide-HLA binding score) or for peptide-HLA immunogenicity. In some embodiments, the MHCflurry or NetMHCpan (Reynisson et al., 2020) computational methods (as known in the art) are used to predict MHC class I display of a peptide by an HLA allele (see Table 1). In some embodiments, the NetMHCIIpan computational method (Reynisson et al., 2020) is used to predict MHC class II display of a peptide by an HLA allele (see Table 2).

In some embodiments, computational methods such as MHCflurry (Odonnell et al., 2018, Odonnell et al., 2020, incorporated by reference in their entireties herein), NetMHCpan (Reynisson et al., 2020, incorporated by reference in its entirety herein), and NetMHCIIpan (Reynisson et al., 2020) are used to predict either MHC class I (MHCflurry, NetMHCpan) or class II (NetMHCIIpan) display of peptides by an HLA allele. In other embodiments, other methods of determining peptide-HLA binding are used as disclosed in International Publication No. WO 2005/042698, incorporated by reference in its entirety herein. NetMHCpan-4.1 and NetMHCIIpan-4.0 utilize the NNAlign_MA algorithm (Alvarez et al., 2019, incorporated by reference in its entirety herein) for predicting peptide-HLA binding. NNAlign_MA is in turn based upon the NNAlign (Nielsen et al., 2009, Nielsen et al., 2017, incorporated by reference in their entireties herein) neural network. NetMHCpan-4.1 (Reynisson et al., 2020) uses NNAlign_MA networks with at least 180 inputs that describe the peptide sequence (9×20=180 inputs). Networks with both 56 and 66 hidden neurons and two outputs are utilized (Alvarez et al., 2019). Each network architecture (56 or 66 hidden neurons) is trained with 5 different random parameter initializations and 5-fold cross-validation resulting in a total of 50 individual trained networks (2 architectures×5 initializations×5 cross-validation). These 50 trained networks are used as an ensemble with 25 networks having at least 10,800 parameters (180 inputs×56 neurons) and 25 networks consist of at least 11,880 parameters (180 inputs× 66 neurons). Thus, the ensemble of 50 networks in NetMHCpan-4.1 consists of at least 567,000 parameters that must be evaluated with at least 567,000 arithmetic operations for computing peptide-MHC binding. NetMHCIIpan-4.1 (Reynisson et al., 2020) uses NNAlign_MA networks with at least 180 inputs that describe the peptide sequence (9×20=180 inputs). Networks with 2, 10, 20, 40, and 60 hidden neurons and two outputs are utilized (Alvarez et al., 2019). Each network architecture (2, 10, 20, 40, or 60 hidden neurons) is trained with 10 different random parameter initializations and 5-fold cross-validation resulting in a total of 250 individual trained networks (5 architectures×10 initializations×5 cross-validation). These 250 trained networks are used as an ensemble with 50 networks having at least 360 parameters (180 inputs×2 neurons), 50 networks having at least 1800 parameters (180 inputs×10 neurons), 50 networks having at least 3600 parameters (180 inputs×20 neurons), 50 networks having at least 7200 parameters (180 inputs×40 neurons), and 50 networks having at least 10,800 parameters (180 inputs×60 neurons). Thus, the ensemble of 250 networks in NetMHCIIpan-4.0 consists of at least 1,188,000 parameters that must be evaluated with at least 1,188,000 arithmetic operations for computing peptide-WIC binding.

A peptide is displayed by an MHC molecule when it binds within the groove of the WIC molecule and is transported to the cell surface where it can be recognized by a T cell receptor. A target peptide refers to a foreign peptide or a self-peptide. In some embodiments, a peptide that is part of the normal proteome in a healthy individual is a self-peptide, and a peptide that is not part of the normal proteome is a foreign peptide. In some embodiments, target peptides can be part of the normal proteome that exhibit aberrant expression (e.g., cancer-testis antigens such as NY-ESO-1). Foreign peptides can be generated by mutations in normal self-proteins in tumor cells that create epitopes called neoantigens, or by pathogenic infections. In some embodiments, a neoantigen is any subsequence of a human protein, where the subsequence contains one or more altered amino acids or protein modifications that do not appear in a healthy individual. Therefore, in this disclosure, foreign peptide refers to an amino acid sequence encoding a fragment of a target protein/peptide (or a full-length protein/peptide), the target protein/peptide consisting of: a neoantigen protein, a pathogen proteome, or any other undesired protein that is non-self and is expected to be bound and displayed by an HLA allele.

Protein genes identified by their UniProt ID that are frequently mutated in cancer include AKT1_HUMAN, BRAF_HUMAN, EGFR_HUMAN, GTF2I_HUMAN, RASH_HUMAN (also called HRAS), IDHC_HUMAN (also called IDH1), RASK_HUMAN (also called KRAS), RASN_HUMAN (also called NRAS), PIK3CA_HUMAN, PTEN_HUMAN, and P53_HUMAN (also called TP53). We describe a missense mutation in a protein by the one letter amino acid code for the wild type amino acid, the amino acid position of the mutation, and the one letter amino acid code that is present in the mutated protein. For example, KRAS G12D is a mutation in the KRAS protein of position 12 from glycine to aspartic acid (G12D). Proteins may contain multiple mutations at different positions. Herein we may refer to a gene without the "HUMAN" suffix for conciseness KRAS gene mutations are the most frequently mutated oncogenes in cancer, but they have been very difficult to treat with small molecule therapeutics. The KRAS protein is part of a signaling pathway that controls cellular growth and point mutations in the protein can cause constitutive pathway activation and uncontrolled cell growth. Single amino acid KRAS mutations result in minor changes in protein structure, making it difficult to engineer small molecule drugs that recognize a mutant specific binding pocket and inactivate KRAS signaling. KRAS oncogenic mutations include the mutation of position 12 from glycine to aspartic acid (G12D), glycine to valine (G12V), glycine to arginine (G12R), or the mutation of glycine to cystine (G12C); or the mutation of position 13 from glycine to aspartic acid (G13D). The corresponding foreign peptides contain these mutations.

KRAS is a member of the RAS family of genes that also includes HRAS and NRAS. KRAS, HRAS, and NRAS have identical sequences from residue 1 to residue 86. Thus, all of the vaccines and peptide sequences described herein for a mutation in one RAS family member can be used for the identical mutation in any other RAS family member (e.g., a KRAS G12D vaccine is also a vaccine for HRAS G12D).

Certain self-proteins, such as cancer-testis antigens, are present in cancerous cells at aberrantly high levels and thus can be targets for vaccination to induce an intolerant T cell response against cells displaying peptides derived from these self-proteins on WIC molecules. Examples of these cancer related proteins by their UniProt IDs include CTG1B HUMAN (also known as NY-ESO-1), MAGA1_HUMAN, MAGA3_HUMAN, MAGA4_HUMAN, MAGC1_HUMAN, MAGC3_HUMAN, SSX2_HUMAN, PRAME_HUMAN, KKLC1_HUMAN (also known as CT83), PMEL_HUMAN (as known as gp100), TYRP1_HUMAN (also known as gp75), TYRP2_HUMAN (also known as DCT), and MAR1_HUMAN.

Autoimmune disorders are caused by the loss of self-tolerance by the immune system to self-proteins and are involved in autoimmune disorders such as diabetes, multiple sclerosis, and autoimmune encephalomyelitis. Induction of tolerance for autoimmune related self-peptides can be accomplished by antigen-specific tolerization using the delivery of vaccine antigens with a tolerization protocol. An example of a protocol for the induction of tolerance with a lipid-nanoparticle (LNP) encapsulated (mRNA-LNP) vaccine is described by Krienke et al., 2021 and is incorporated by reference in its entirety herein. Examples of autoimmune disease related proteins include UniProt IDs INS HUMAN (also known as insulin), and MOG HUMAN (also known as Myelin-oligodendrocyte glycoprotein). Individuals with diabetes can suffer from a lack of tolerance to INS HUMAN, and individuals with multiple sclerosis or autoimmune encephalomyelitis can suffer from a lack of tolerance to MOG HUMAN.

A challenge for the design of peptide vaccines is the diversity of human MHC alleles (HLA alleles) that each have specific preferences for the peptide sequences they will display. The Human Leukocyte Antigen (HLA) loci, located within the MHC, encode the HLA class I and class II molecules. There are three classical class I loci (HLA-A, HLA-B, and HLA-C) and three loci that encode class II molecules (HLA-DR, HLA-DQ, and HLA-DP). An individual's HLA type describes the alleles they carry at each of these loci. Peptides of length of between about 8 and about 11 residues can bind to HLA class I (or MHC class I) molecules whereas those of length of between about 13 and about 25 bind to HLA class II (or MHC class II) molecules (Rist et al., 2013; Chicz et al., 1992). Human populations that originate from different geographies have differing frequencies of HLA alleles, and these populations exhibit linkage disequilibrium between HLA loci that result in population specific haplotype frequencies. In some embodiments, methods are disclosed for creating effective vaccines that includes consideration of the HLA allelic frequency in the target population, as well as linkage disequilibrium between HLA genes to achieve a set of peptides that is likely to be robustly displayed.

The present disclosure provides for compositions, systems, and methods of vaccine designs that produce immunity to single or multiple targets. In some embodiments, a target is a neoantigen protein sequence, a pathogen proteome, or any other undesired protein sequence that is non-self and is expected to be bound and displayed by an HLA molecule (also referred to herein as an HLA allele). When a target is present in an individual, it may result in multiple peptide sequences that are displayed by a variety of HLA alleles. In some embodiments, it may be desirable to create a vaccine that includes selected self-peptides, and thus these selected self-peptides are considered to be the target peptides for this purpose.

The term peptide-HLA binding is defined to be the binding of a peptide to an HLA allele, and can either be computationally predicted, experimentally observed, or computationally predicted using experimental observations. The metric of peptide-HLA binding can be expressed as affinity, percentile rank, binary at a predetermined threshold, probability, or other metrics as are known in the art. The term peptide-HLA immunogenicity is defined as the activation of T cells based upon their recognition of a peptide when bound by an HLA allele. Peptide-HLA immunogenicity can vary from individual to individual, and the metric for peptide-HLA immunogenicity can be expressed as a probability, a binary indicator, or other metric that relates to the likelihood that a peptide-HLA combination will be immunogenic. In some embodiments, peptide-HLA immunogenicity is defined as the induction of immune tolerance based upon the recognition of a peptide when bound by an HLA allele. Peptide-HLA immunogenicity can be computationally predicted, experimentally observed, or computationally predicted using experimental observations. In some embodiments, peptide-HLA immunogenicity is based only upon peptide-HLA binding, since peptide-HLA binding is necessary for peptide-HLA immunogenicity. In some embodiments, peptide-HLA immunogenicity data or computational predictions of peptide-HLA immunogenicity can be included and combined with scores for peptide display in the methods disclosed herein. One way of combining the scores is using immunogenicity data for peptides assayed for immunogenicity in diseased or vaccinated individuals and assigning peptides to the HLA allele that displayed them in the individual by choosing the HLA allele that computational methods predict has the highest likelihood of display. For peptides that are not experimentally assayed, computational predictions of display can be used. In some embodiments, different computational methods of predicting peptide-HLA immunogenicity or peptide-HLA binding can be combined (Liu et al., 2020b). For a given set of peptides and a set of HLA alleles, the term peptide-HLA hits is the number of unique combinations of peptides and HLA alleles that exhibit peptide-HLA immunogenicity or binding at a predetermined threshold. For example, a peptide-HLA hit of 2 can mean that one peptide is predicted to be bound (or trigger T cell activation) by two different HLA alleles, two peptides are predicted to be bound (or trigger T cell activation) by two different HLA alleles, or two peptides are predicted to be bound (or trigger T cell activation) by the same HLA allele. For a given set of peptides and HLA frequencies, HLA haplotype frequencies, or HLA diplotype frequencies, the expected number of peptide-HLA hits is the average number of peptide-HLA hits in each set of HLAs that represent an individual, weighted by their frequency of occurrence.

Since immunogenicity may vary from individual to individual, one method to increase the probability of vaccine efficacy is to use a diverse set of target peptides (e.g., at least two peptides) to increase the chances that some subset of them will be immunogenic in a given individual. Prior research using mouse models has shown that most MHC displayed peptides are immunogenic, but immunogenicity varies from individual to individual as described in Croft et al., (2019). In some embodiments, experimental peptide-HLA immunogenicity data are used to determine which target peptides and their modifications will be effective immunogens in a vaccine.

Considerations for the design of peptide vaccines are outlined in Liu et al., Cell Systems 11, Issue 2, p. 131-146 (Liu et al., 2020) and (Liu et al., 2020b) which are incorporated by reference in their entireties herein.

Certain target peptides may not bind with high affinity to a wide range of HLA molecules. To increase the binding of target peptides to HLA molecules, their amino acid composition can be altered to change one or more anchor residues or other residues. Anchor residues are amino acids that interact with an HLA molecule and have the largest influence on the affinity of a peptide for an HLA molecule. Peptides with altered anchor residues are called heteroclitic peptides. In some embodiments, heteroclitic peptides include target peptides with residue modifications at non-anchor positions. In some embodiments, heteroclitic peptides include target peptides with residue modifications that include unnatural amino acids and amino acid derivatives. Modifications to create heteroclitic peptides can improve the binding of peptides to both MHC class I and MHC class II molecules, and the modifications required can be both peptide and MEW class specific. Since peptide anchor residues face the MHC molecule groove, they are less visible than other peptide residues to T cell receptors. Thus, heteroclitic peptides have been observed to induce a T cell response where the stimulated T cells also respond to unmodified peptides. It has been observed that the use of heteroclitic peptides in a vaccine can improve a vaccine's effectiveness (Zirlik et al., 2006). In some embodiments, the immunogenicity of heteroclitic peptides are experimentally determined and their ability to activate T cells that also recognize the corresponding base (also called seed) peptide of the heteroclitic peptide is determined, as is known in the art. In some embodiments, these assays of the immunogenicity and cross-reactivity of heteroclitic peptides are performed when the heteroclitic peptides are displayed by specific HLA alleles.

Peptide Vaccines to Induce Immunity to One or More Targets

In some embodiments, a method is provided for formulating peptide vaccines using a single vaccine design for one or more targets. In some embodiments, a single target is a foreign protein with a specific mutation (e.g., KRAS G12D). In some embodiments, a single target is a self-protein (e.g., a protein that is overexpressed in tumor cells such as cancer/testis antigens). In some embodiments, multiple targets can be used (e.g., both KRAS G12D and KRAS G13D).

In some embodiments, the method includes extracting peptides to construct a candidate set from all target proteome sequences (e.g., entire KRAS G12D protein) as described in Liu et al., (2020).

Figure 2:
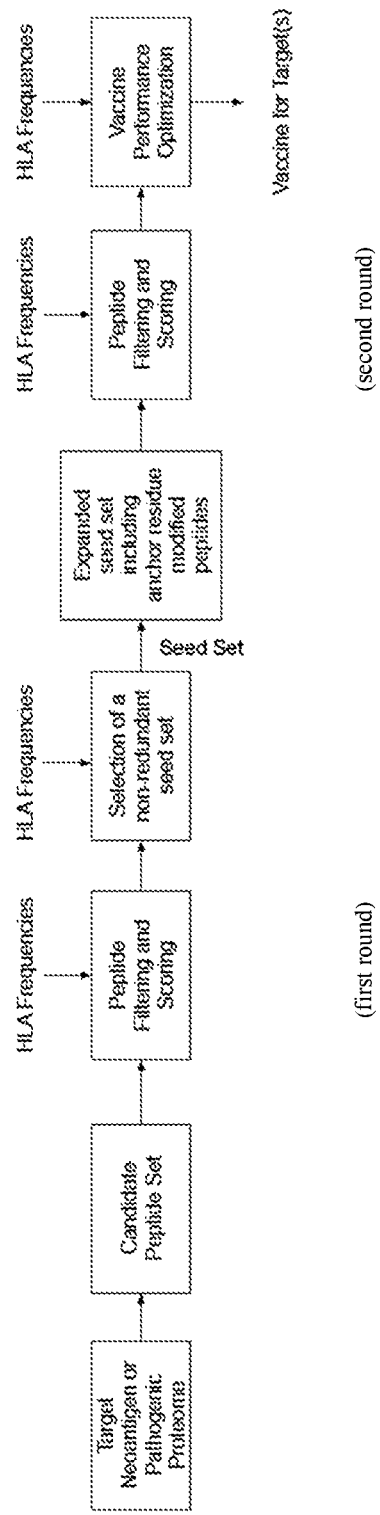
FIG. 2 is a flow chart of a vaccine optimization method with seed set compression.
Figure 3A:
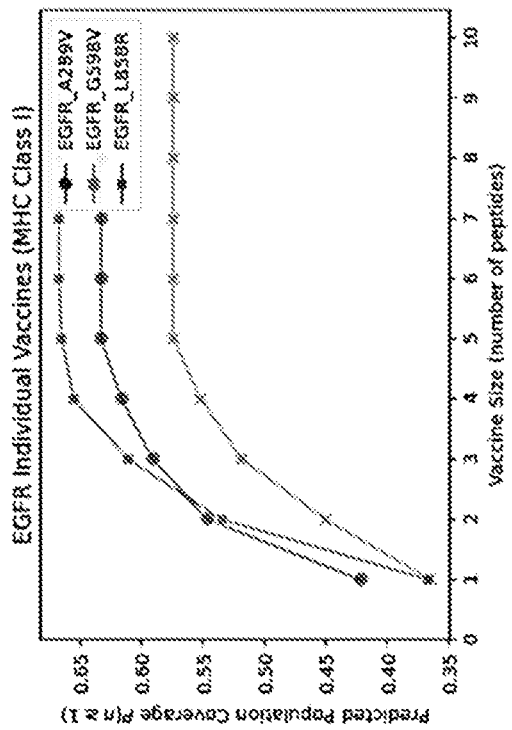
FIGS. 3A-3D shows predicted population coverage for single target MEW class I vaccines by vaccine size for the mutations BRAF V600 and BRAF V600M (3A); EGFR A289V, EGRF G598V, and EGFR L858R (3B); KRAS G12D, KRAS G12V, KRAS G12R, KRAS G12C, KRAS G13D, KRAS G12A, and KRAS G12S (3C); and PIK3CA E542K, PIK3CA E545K, and PIK3CA H1047R (3D).
Figure 3B:
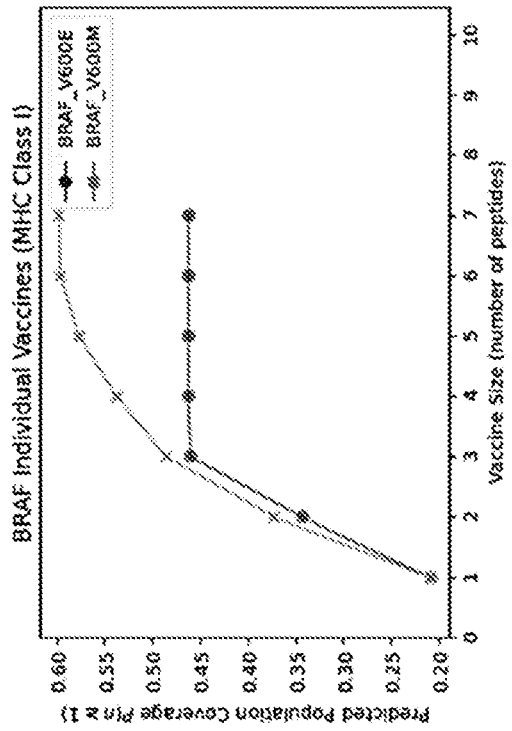
Figure 3C:
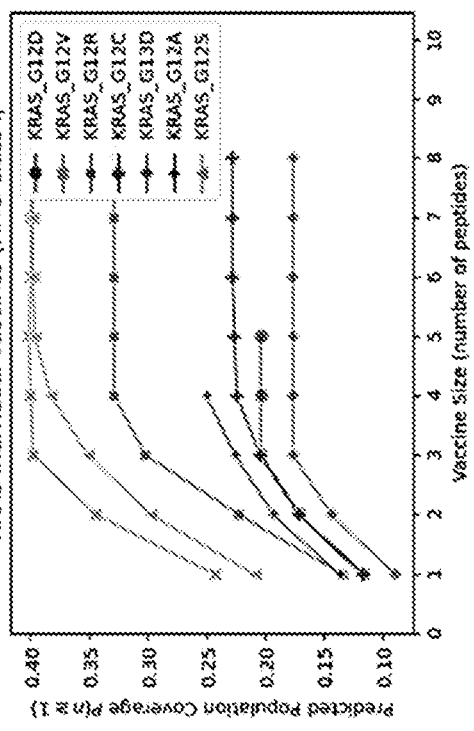
Figure 3D:
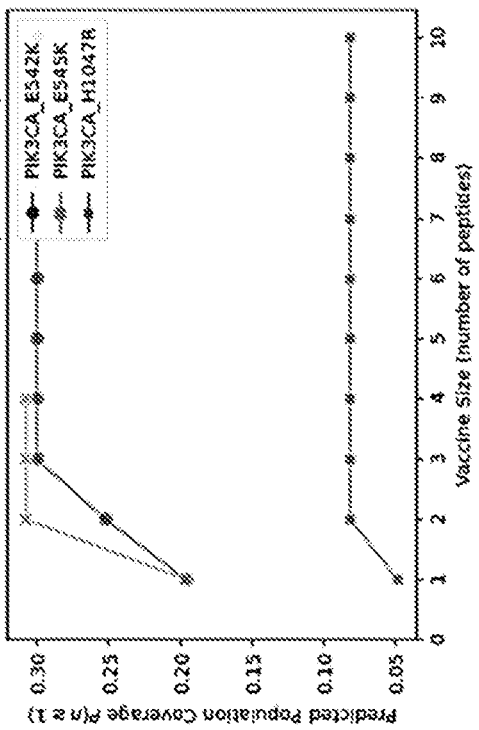

FIGS. 1 and 2 depict flow charts for example vaccine design methods that can be used for MEW class I or MHC class II vaccine design. In some embodiments, extracted target peptides are of amino acid length of between about 8 and about 10 (e.g., for MHC class I binding (Rist et al., 2013)). In some embodiments, the extracted target peptides presented by MEW class I molecules are longer than 10 amino acid residues, such as 11 residues (Trolle et al., 2016). In some embodiments, extracted target peptides are of length between about 13 and about 25 (e.g., for class II binding (Chicz et al., 1992)). In some embodiments, sliding windows of various size ranges described herein are used over the entire proteome. In some embodiments, other target peptide lengths for MEW class I and class II sliding windows can be utilized. In some embodiments, computational predictions of proteasomal cleavage are used to filter or select peptides in the candidate set. One computational method for predicting proteasomal cleavage is described by Nielsen et al., (2005). In some embodiments, peptide mutation rates, glycosylation, cleavage sites, or other criteria can be used to filter peptides as described in Liu et al., (2020). In some embodiments, peptides can be filtered based upon evolutionary sequence variation above a predetermined threshold. Evolutionary sequence variation can be computed with respect to other species, other pathogens, other pathogen strains, or other related organisms. In some embodiments, a first peptide set is the candidate set.

As shown in FIGS. 1-2, in some embodiments, the next step of the method includes scoring the target peptides in the candidate set for peptide-HLA binding to all considered HLA alleles as described in Liu et al., (2020) and Liu et al., (2020b). In some embodiments, a first peptide set is the candidate set after scoring the target peptides. Scoring can be accomplished for human HLA molecules, mouse H-2 molecules, swine SLA molecules, or MHC molecules of any species for which prediction algorithms are available or can be developed. Thus, vaccines targeted at non-human species can be designed with the method. Scoring metrics can include the affinity for a target peptide to an HLA allele in nanomolar, eluted ligand, presentation, and other scores that can be expressed as percentile rank or any other metric. The candidate set may be further filtered to exclude peptides whose predicted binding cores do not contain a particular pathogenic or neoantigen target residue of interest or whose predicted binding cores contain the target residue in an anchor position. The candidate set may also be filtered for target peptides of specific lengths, such as length 9 for MHC class I, for example. In some embodiments, scoring of target peptides is accomplished with experimental data or a combination of experimental data and computational prediction methods. When computational models are unavailable to make peptide-HLA binding predictions for particular (peptide, HLA) pairs, the binding value for such pairs can be defined by the mean, median, minimum, or maximum immunogenicity value taken over supported pairs, a fixed value (such as zero), or inferred using other techniques, including a function of the prediction of the most similar (peptide, HLA) pair available in the scoring model.

In some embodiments, a base set (also referred to as seed set herein) is constructed by selecting peptides from the scored candidate set using individual peptide-HLA binding or immunogenicity criteria (e.g., first peptide set) (FIG. 1). The criteria used for scoring peptide-HLA binding during the scoring procedure can accommodate different goals during the base set selection and vaccine design phases. For example, a target peptide with peptide-HLA binding affinities of 500 nM may be displayed by an individual that is diseased, but at a lower frequency than a target peptide with a 50 nM peptide-HLA binding affinity. During the combinatorial design phase of a vaccine, a more constrained affinity criteria may be used (e.g., when selecting a third peptide set), such a 50 nM, to increase the probability that a vaccine peptide will be found and displayed by HLA molecules. In some embodiments, a relatively less constrained threshold (e.g., less than about 1000 nM or less than about 500 nM) of peptide-HLA immunogenicity or peptide-HLA binding is used for filtering candidate peptides (the first Peptide Filtering and Scoring step in FIGS. 1 and 2) and a relatively more constrained threshold (e.g., less than about 50 nM) is used for filtering expanded set peptides (the second Peptide Filtering and Scoring step in FIGS. 1 and 2). The second threshold (second filtering step) is based on the observation that peptides that are not immunogenic enough for vaccine inclusion may be antigenic (first filtering step) and thus recognized by T cell clonotypes expanded by a vaccine. A peptide is antigenic when it is recognized by a T cell receptor and results in a response such as CD8+ T cell cytotoxicity. Derivatives of an antigenic peptide may be strongly immunogenic, included in a vaccine, and thus activate and expand T cells that recognize the antigenic peptide. The expansion of T cells that recognize an unmodified antigenic peptide can provide an immune response that contributes to disease control. In some embodiments, peptides are scored for third peptide set potential inclusion that have peptide-HLA binding affinities less than about 500 nM. In some embodiments, peptides are selected for the base set that have peptide-HLA binding affinities less than about 1000 nM. Alternatively, predictions of peptide-HLA immunogenicity can be used to qualify target peptides for base set inclusion. In some embodiments, experimental observations of the immunogenicity of peptides in the context of their display by HLA alleles or experimental observation of the binding of peptides to HLA alleles can be used to score peptides for binding to HLA alleles or peptide-HLA immunogenicity. In some embodiments, computational predictions of the immunogenicity of a peptide in the context of display by HLA alleles can used for scoring such as the methods of Ogishi et al., (2019).

In some embodiments, the method further includes running the OptiVax-Robust algorithm as described in Liu et al., (2020) using the HLA haplotype frequencies of a population on the scored candidate set to construct a base set (also referred to as seed set herein) of target peptides (FIG. 2). In some embodiments, HLA diplotype frequencies can be provided to OptiVax. OptiVax-Robust includes algorithms to eliminate peptide redundancy that arises from the sliding window approach with varying window sizes, but other redundancy elimination measures can be used to enforce minimum edit distance constraints between target peptides in the candidate set. The size of the seed set is determined by a point of diminishing returns of population coverage as a function of the number of target peptides in the seed set. Other criteria can also be used, including a minimum number of vaccine target peptides, maximum number of vaccine target peptides, and desired predicted population coverage. In some embodiments, a predetermined population coverage is less than about 0.4, between about 0.4 and 0.5, between about 0.5 and 0.6, between about 0.6 and 0.7, between about 0.7 and 0.8, between about 0.8 and 0.9, or greater than about 0.9. Another possible criterion is a minimum number of expected peptide-HLA binding hits in each individual. In alternate embodiments, the method further includes running the OptiVax-Unlinked algorithm as described in Liu et al., (2020) instead of OptiVax-Robust.

The OptiVax-Robust method uses binary predictions of peptide-HLA immunogenicity, and these binary predictions can be generated as described in Liu et al., (2020b). The OptiVax-Unlinked method uses the probability of target peptide binding to HLA alleles and can be generated as described in Liu et al., (2020). In some embodiments, OptiVax-Unlinked and EvalVax-Unlinked are used with the probabilities of peptide-HLA immunogenicity. Either method can be used for the purposes described herein, and thus the term "OptiVax" refers to either the Robust or Unlinked method. In some embodiments, the HLA haplotype or HLA allele frequencies of a population provided to OptiVax for vaccine design describe the world's population.

In alternative embodiments, the HLA haplotype or HLA allele frequencies of a population provided to OptiVax for vaccine design are specific to a geographic region. In alternative embodiments, the HLA haplotype or HLA allele frequencies of a population provided to OptiVax for vaccine design are specific to an ancestry. In alternative embodiments, the HLA haplotype or HLA allele frequencies of a population provided to OptiVax for vaccine design are specific to a race. In alternative embodiments, the HLA haplotype or HLA allele frequencies of a population provided to OptiVax for vaccine design are specific to individuals with risk factors such as genetic indicators of risk, age, exposure to chemicals, alcohol use, chronic inflammation, diet, hormones, immunosuppression, infectious agents, obesity, radiation, sunlight, or tobacco use. In alternative embodiments, the HLA haplotype or HLA allele frequencies of a population provided to OptiVax for vaccine design are specific to individuals that carry certain HLA alleles. In alternative embodiments, the HLA diplotypes provided to OptiVax for vaccine design describe a single individual and are used to design an individualized vaccine.

In some embodiments, the base (or seed) set of target peptides (e.g., first peptide set) that results from OptiVax application to the candidate set of target peptides describes a set of unmodified target peptides that represent a possible compact vaccine design (Seed Set in FIG. 2). A base peptide is a target peptide that is included in the base or seed peptide set (e.g., first peptide set). In some embodiments, the seed set (e.g., first peptide set) is based upon filtering candidate peptides by predicted or observed affinity or immunogenicity with respect to HLA molecules (Seed Set in FIG. 1). However, to improve the display of the target peptides in a wide range of HLA haplotypes as possible, some embodiments include modifications of the seed (or base) set. In some embodiments, experimental assays can be used to ensure that a modified seed (or base) peptide activates T cells that also recognize the base/seed peptide.

For a given target peptide, the optimal anchor residue selection may depend upon the HLA allele that is binding to and displaying the target peptide and the class of the HLA allele (MHC class I or class II). A seed peptide set (e.g., first peptide set) can become an expanded set by including anchor residue modified peptides of either MHC class I or II peptides (FIGS. 1-2). Thus, one aspect of vaccine design is considering how to select a limited set of heteroclitic peptides that derive from the same target peptide for vaccine inclusion given that different heteroclitic peptides will have different and potentially overlapping population coverages.

In some embodiments, all possible anchor modifications for each base set of target peptide are considered. There are typically two anchor residues in peptides bound by MHC class I molecules, typically at positions 2 and 9 for 9-mer peptides. In some embodiments, anchors for 8-mers, 10-mers, and 11-mers are found at positions 2 and n, where n is the last position (8, 10, and 11, respectively). For MHC class I molecules, the last position n is called the "C" position herein for carboxyl terminus. At each anchor position, 20 possible amino acids are attempted in order to select the best heteroclitic peptides. Thus, for MHC class I binding, 400 (i.e., 20 amino acids by 2 positions=$20^2$) minus 1 heteroclitic peptides are generated for each base target peptide. There are typically four anchor residues in peptides bound by MHC class II molecules, typically at positions 1, 4, 6, and 9 of the 9-mer binding core. Thus, for MHC class II binding there are 160,000 (i.e., 20 amino acids by 4 positions=$20^4$) minus 1 heteroclitic peptides generated for each base target peptide. In some embodiments, more than two (MHC class I) or four (MHC class II) positions are considered as anchors. Other methods, including Bayesian optimization, can be used to select optimal anchor residues to create heteroclitic peptides from each seed (or base) set peptide. Other methods are presented in "Machine learning optimization of peptides for presentation by class II MHCs" by Dai et al., (2020), incorporated in its entirety herein. In some embodiments, the anchor positions are determined by the HLA allele that presents a peptide, and thus the set of heteroclitic peptides includes for each set of HLA specific anchor positions, all possible anchor modifications.

In some embodiments, for all of the target peptides in the base/seed set, new peptide sequences with all possible anchor residue modifications (e.g., MHC class I or class II) are created resulting in a new heteroclitic base set (Expanded set in FIGS. 1-2) that includes all of the modifications. In some embodiments, anchor residue modifications of a peptide are not included in the heteroclitic base set if one or more of the peptide's anchor residue positions contains a substitution mutation that distinguishes the peptide from a self-peptide. In some embodiments, anchor residue modifications of a base/seed peptide are only included in the heteroclitic base set for peptide positions that do not contain a substitution mutation that distinguishes the base/seed peptide from a self-peptide. In some embodiments, anchor residue modifications of a peptide are not included in the heteroclitic base set when one or more of the peptide's mutations does not occur between a pair of its adjacent anchor residues. In some embodiments, for all of the target peptides in the base/seed set, new peptide sequences with anchor residue modifications (e.g., MHC class I or class II) at selected anchor locations are created resulting in a new heteroclitic base set (Expanded set in FIGS. 1-2) that includes the selected modifications. In some embodiments, the anchor residue positions used for modifying peptides are selected from anchor residue positions determined by the HLA alleles considered during vaccine evaluation. In some embodiments, the heteroclitic base set (Expanded set in FIGS. 1-2) also includes the original seed (or base) set (Seed Peptide Set in FIGS. 1-2). In some embodiments, the heteroclitic base set includes amino acid substitutions at non-anchor residues. In some embodiments, modifications of base peptide residues is accomplished to alter binding to T cell receptors to improve therapeutic efficacy (Candia, et al., 2016). In some embodiments, the heteroclitic base set includes amino acid substitutions of non-natural amino acid analogs. The heteroclitic base set is scored for HLA affinity, peptide-HLA immunogenicity, or other metrics as described herein (another round of Peptide Filtering and Scoring as shown in FIGS. 1-2). In some embodiments, the scoring predictions may be further updated for pairs of heteroclitic peptide and HLA allele, eliminating pairs where a heteroclitic peptide is predicted to be displayed by an allele but the seed (or base) peptide from which it was derived is not predicted to be displayed by the allele. The scoring predictions may also be filtered to ensure that predicted binding cores of the heteroclitic peptide displayed by a particular HLA allele align exactly in position with the binding cores of the respective seed (or base) set target peptide for that HLA allele. In some embodiments, the scoring predictions are filtered for an HLA allele to ensure that the heteroclitic peptides considered for that HLA allele are only modified at anchor positions determined by that HLA allele. Scoring produces a metric of peptide-HLA immunogenicity for peptides and HLA alleles that can be either binary, a probability of immunogenicity, or other metric of immunogenicity such as peptide-HLA affinity or percent rank, and can be based on computational predictions, experimental observations, or a combination of both computational predictions and experimental observations. In some embodiments, probabilities of peptide-HLA immunogenicity are utilized by OptiVax-Unlinked. In some embodiments, heteroclitic peptides are included in experimental assays such as MIRA (Klinger et al., 2015) to determine their immunogenicity with respect to specific HLA alleles. In some embodiments, the methods of Liu et al., (2020b), can be used to incorporate MIRA data for heteroclitic peptides into a model of peptide-HLA immunogenicity. In some embodiments, the immunogenicity of heteroclitic peptides are experimentally determined and their ability to activate T cells that also recognize the corresponding seed (or base) peptide of the heteroclitic peptide is performed as is known in the art to qualify the heteroclitic peptide for vaccine inclusion. In some embodiments, these assays of the immunogenicity and cross-reactivity of heteroclitic peptides are performed when the heteroclitic peptides are displayed by specific HLA alleles. In some embodiments, computational predictions of the immunogenicity of a heteroclitic peptide in the context of display by HLA alleles can used for scoring such as the methods of Ogishi et al., (2019). In some embodiments, a peptide in the heteroclitic base set is removed if (1) one of its anchor positions for an HLA allele corresponds to the location of a mutation in the base/seed peptide from which it was derived that distinguishes the base/seed peptide from a self-peptide, and (2) if the peptide-HLA binding or peptide-HLA immunogenicity of the self-peptide is stronger than a specified threshold for self-peptide binding or immunogenicity. This eliminates peptides in the heteroclitic base set that may cross-react with self-peptides as a result of sharing TCR facing residues with self-peptides. In some embodiments, the threshold for self-peptide binding is between approximately 500 nM to 1000 nM.

In some embodiments, redundant peptides in the heteroclitic base set are removed. In some embodiments, a redundant peptide is a first heteroclitic peptide that has peptide-HLA immunogenicity scores or peptide-HLA binding scores that are less immunogenic for all scored HLAs than a second heteroclitic peptide in the heteroclitic base set, where both the first and second heteroclitic peptides are derived from the same base (or seed) peptide. In some embodiments, peptide redundancy is determined by only comparing peptide-HLA immunogenicity scores or peptide-HLA binding scores for HLA alleles where the peptide-HLA immunogenicity scores or peptide-HLA binding scores for both peptides for an HLA allele are more immunogenic than a given threshold (e.g., 50 nM for binding). In some embodiments, a redundant peptide is a first heteroclitic peptide that has an average peptide-HLA immunogenicity score or peptide-HLA binding score that is less immunogenic than the average peptide-HLA immunogenicity score or peptide-HLA binding score of a second heteroclitic peptide in the heteroclitic base set, where both the first and second heteroclitic peptides are derived from the same base (or seed) peptide, and the average scores are computed for HLA alleles where the peptide-HLA immunogenicity scores or peptide-HLA binding scores for both peptides for an HLA allele are more immunogenic than a given threshold (e.g., 50 nM for binding). In some embodiments, a redundant peptide is a first heteroclitic peptide that has a weighted peptide-HLA immunogenicity score or peptide-HLA binding score that is less immunogenic than the weighted peptide-HLA immunogenicity score or peptide-HLA binding score of a second heteroclitic peptide in the heteroclitic base set, where both the first and second heteroclitic peptides are derived from the same base (or seed) peptide, and where the weighting is determined by the frequency of the HLA allele in a human population, and the weighted scores are computed for HLA alleles where the peptide-HLA immunogenicity scores or peptide-HLA binding scores for both peptides for an HLA allele are more immunogenic that a given threshold (e.g., 50 nM for binding).

In some embodiments, the next step involves filtering the heteroclitic base set (the second peptide set) to create a filtered second peptide set by comparing the peptide-HLA immunogenicity scores or peptide-HLA binding scores of the peptides for one or more HLA alleles to a threshold. In some embodiments, an affinity criterion of about 50 nM is used to increase the probability that a vaccine peptide will be found and displayed by HLA molecules. In some embodiments, the affinity criteria is more constrained than 50 nM. In some embodiments, the affinity criteria is more constrained than about 500 nM.

In some embodiments, the next step involves inputting the filtered second peptide set to OptiVax to select a compact set of vaccine peptides that maximizes predicted vaccine performance (Vaccine Performance Optimization; FIGS. 1-2). In some embodiments, predicted vaccine performance is a function of expected peptide-HLA binding affinity (e.g., a function of the distribution of peptide-HLA binding affinities across all peptide-HLA combinations for a given peptide set, or weighted by the occurrence of the HLA alleles in a population or individual). In some embodiments, predicted vaccine performance is the expected population coverage of a vaccine. In some embodiments, predicted vaccine performance is the expected number peptide-HLA hits produced by a vaccine in a population or individual. In some embodiments, predicted vaccine performance requires a minimum expected number of peptide-HLA hits (e.g., 1, 2, 3, 4, 5, 6, 7, 8, or more) produced by a vaccine. In some embodiments, predicted vaccine performance is a function of population coverage and expected number of peptide-HLA hits desired produced by a vaccine. In some embodiments, predicted vaccine performance is a metric that describes the overall immunogenic properties of a vaccine where all of the peptides in the vaccine are scored for peptide-HLA immunogenicity for two or more HLA alleles (e.g., three or more HLA alleles). In some embodiments, predicted vaccine performance excludes immunogenicity contributions by selected HLA alleles above a maximum number of peptide-HLA hits (e.g., 1, 2, 3, 4, 5, 6, 7, 8, or more). In some embodiments, predicted vaccine performance excludes immunogenicity contributions of individual HLA diplotypes above a maximum number of peptide-HLA hits (e.g., 1, 2, 3, 4, 5, 6, 7, 8, or more). In some embodiments, predicted vaccine performance is the fraction of covered HLA alleles, which is the expected fraction of HLA alleles in each individual that have a minimum number of peptides (e.g., 1, 2, 3, 4, 5, 6, 7, 8, or more) with predicted peptide-HLA immunogenicity produced by a vaccine. In some embodiments, predicted vaccine performance is the expected fraction of HLA alleles in a single individual that have a minimum number of peptides (e.g., 1, 2, 3, 4, 5, 6, 7, 8, or more) with predicted peptide-HLA immunogenicity produced by a vaccine.

In some embodiments, a vaccine is designed by the iterative selection of peptides from the heteroclitic base set (also referred to as Expanded set as shown in FIGS. 1-2) at progressively less stringent criteria for predicted peptide immunogenicity or display. In some embodiments, OptiVax is first used to design a vaccine with a desired vaccine performance with specific peptide qualification criteria (e.g., seed peptides from the candidate set must bind to MEW molecules at 500 nM or stronger, and peptides from the expanded set must bind to MEW molecules at 50 nM or stronger). The vaccine that results from this application of OptiVax is then used as the foundation for vaccine augmentation with less stringent criteria (e.g., seed peptides from the candidate set must bind to MEW molecules at 1000 nM or stronger, and peptides from the expanded set must bind to MEW molecules at 100 nM or stronger) to further improve the desired vaccine performance. Methods for vaccine augmentation are described in Liu et al., (2020b), incorporated by reference in its entirety herein. In some embodiments, multiple rounds of vaccine augmentation may be utilized. In some embodiments, the final augmented vaccine is the one selected.

In some embodiments, selection of peptide sets to meet a desired predicted vaccine performance can be accomplished by computational algorithms other than OptiVax. In some embodiments, integer linear programming or mixed-integer linear programming is employed for selecting peptide sets instead of OptiVax. One example of an integer programming method for peptide set selection is described by Toussaint et al., 2008, incorporated by reference in its entirety herein. An example solver for mixed-integer linear programming is Python-MIP than can be used in conjunction with Toussaint et al., 2008.

Predicted vaccine performance refers to a metric. Predicted vaccine performance can be expressed as a single numerical value, a plurality of numerical values, any number of non-numerical values, and a combination thereof. The value or values can be expressed in any mathematical or symbolic term and on any scale (e.g., nominal scale, ordinal scale, interval scale, or ratio scale).

A seed (or base) peptide and all of the modified peptides that are derived from that seed (or base) peptide comprise a single peptide family. In some embodiments, in the component of vaccine performance that is based on peptide-HLA immunogenicity for a given HLA allele, a maximum number of peptides (e.g., 1, 2, 3, 4, 5, 6, 7, 8, or more) that are in the same peptide family are given computational immunogenicity credit for that HLA allele. This limit on peptide family immunogenicity limits the credit caused by many modified versions of the same base peptide. In some embodiments, the methods described herein are included for running OptiVax with an EvalVax objective function that corresponds to a desired metric of predicted vaccine performance. In some embodiments, population coverage means the proportion of a subject population that presents one or more immunogenic peptides that activate T cells responsive to a seed (or base) target peptide. The metric of population coverage is computed using the HLA haplotype frequency in a given population such as a representative human population. In some embodiments, the metric of population coverage is computed using marginal HLA frequencies in a population. Maximizing population coverage means selecting a peptide set (either a base peptide set, a modified peptide set, or a combination of base and modified peptides; e.g., a first peptide set, second peptide set, or third peptide set) that collectively results in the greatest fraction of the population that has at least a minimum number (e.g., 1, 2, 3, 4, 5, 6, 7, 8, or more) of immunogenic peptide-HLA bindings based on proportions of HLA haplotypes in a given population (e.g., representative human population). In some embodiments, this process includes the OptiVax selection of heteroclitic peptides (as described in this disclosure) that activate T cells that respond to their corresponding seed (or base) peptide and the heteroclitic base peptides to improve population coverage. In some embodiments, the seed (or base) target peptides are always included in the final vaccine design. In some embodiments, peptides are only considered as candidates for a vaccine design (e.g., included in a first, second, and/or third peptide set) if they have been observed to be immunogenic in clinical data, animal models, or tissue culture models.

Although heteroclitic peptides are used as exemplary embodiments in this disclosure, any modified peptide could be used in place of a heteroclitic peptide. A modified peptide is a peptide that has one or more amino acid substitutions of a target base/seed peptide. The amino acid substitution could be located at an anchor position or any other non-anchor position.

In some embodiments, a candidate vaccine peptide (e.g., a base peptide or a modified peptide) is eliminated from vaccine inclusion if it activates T cells that recognize self-peptides (e.g., this can be achieved at the first and/or second round of Peptide Filtering and Sorting as shown in FIGS. 1-2). In some embodiments, a candidate vaccine peptide (e.g., a base peptide or a modified peptide) is computationally eliminated from vaccine inclusion if its outward facing amino acids when bound by an HLA allele are similar to outward facing self-peptide residues that are presented by the same HLA allele, where similarity can be defined by identity or defined similarity metrics such as BLOSUM matrices (BLOSUM matrices are known in the art). Testing a vaccine peptide for its ability to activate T cells that recognize self-peptides can be experimentally accomplished by the vaccination of animal models followed by ELISPOT or other immunogenicity assay or with human tissue protocols. In both cases, models with HLA alleles that present the vaccine peptide are used. In some embodiments, human primary blood mononuclear cells (PBMCs) are stimulated with a vaccine peptide, the T cells are allowed to grow, and then T cell activation with a self-peptide is assayed as described in Tapia-Calle et al., (2019) or other methods as known in the art. In some embodiments, the vaccine peptide is excluded from vaccine inclusion if the T cells are activated by the self-peptide. In some embodiments, computational predictions of the ability of a peptide to activate T cells that also recognize self-peptides can be utilized. These predictions can be based upon the modeling of the outward facing residues from the peptide-HLA complex and their interactions with other peptide residues. In some embodiments, a candidate vaccine peptide (e.g., a base peptide or a modified peptide) is eliminated from vaccine inclusion or experimentally tested for cross-reactivity if it is predicted to activate T cells that also recognize self-peptides based upon the structural similarity of the peptide-MHC complex of the candidate peptide (e.g., a base peptide or a modified peptide) and the peptide-MHC complex of a self-peptide. One method for the prediction of peptide-MHC structure is described by Park et al., (2013).

In some embodiments, a candidate heteroclitic vaccine peptide (e.g., a modified peptide) is eliminated from vaccine inclusion if it does not activate T cells that recognize its corresponding base/seed target peptide (second round of Peptide Filtering and Scoring, FIGS. 1-2). Testing a candidate heteroclitic peptide (e.g., a modified peptide) for its ability to activate T cells that recognize its corresponding seed (or base) target peptide with respect to the same HLA allele can be experimentally accomplished by the vaccination of animal models followed by ELISPOT or other immunogenicity assay or with human tissue protocols. In both cases, models with HLA alleles that present the heteroclitic peptide are used. In some embodiments, human PBMCs are stimulated with the heteroclitic peptide, the T cells are allowed to grow, and then T cell activation with the seed (or base) target peptide is assayed as described in Tapia-Calle et al., (2019) or using other methods known in the art. In some embodiments, computational predictions of the ability of a heteroclitic peptide to activate T cells that also recognize the corresponding seed (or base) target peptide can be utilized. These predictions can be based upon the modeling of the outward facing residues from the peptide-HLA complex and their interactions with other peptide residues. In some embodiments, the structural similarity of the peptide-HLA complex of a heteroclitic peptide and the peptide-HLA complex of the corresponding seed (or base) target is used to qualify heteroclitic peptides for vaccine inclusion or to require experimental immunogenicity testing before vaccine inclusion.

TCR Interface Divergence (TCRID) is the Least Root Mean Square Deviation of the difference between a first peptide's TCR facing residues' 3D positions and the corresponding residue positions of a second peptide with respect to a specific HLA allele. In some embodiments, TCRID is used to predict if two peptides when displayed by a given HLA allele will activate the same T cell clonotypes. In some embodiments, FlexPepDock (London et al., 2011, incorporated by reference in its entirety herein) or DINC (Antunes et al., 2018, incorporated by reference in its entirety herein) in conjunction with the crystal structures of HLA molecules can be used to compute TCRID metrics for pairs of peptides given an HLA molecule. In some embodiments, TCRID is computed by (1) determining the 3D peptide-HLA structures for two different peptides bound by a specific HLA allele, (2) aligning the HLA alpha helices of the peptide-HLA structures, and (3) computing the Least Root Mean Square Deviation of the difference between the TCR facing residues of the two peptides with respect to the aligned alpha helix reference frame.

In some embodiments, the second peptide filtering and scoring step in FIGS. 1 and 2 will zero the peptide-HLA binding or immunogenicity score for a heteroclitic peptide for a specific HLA allele when the HLA specific TCRID between the heteroclitic peptide and its corresponding base (or seed) peptide from which it was derived is over a first TCRID threshold. In some embodiments, the second peptide filtering and scoring step in FIGS. 1 and 2 will zero the peptide-HLA binding or immunogenicity score for a heteroclitic peptide for a specific HLA allele when the HLA specific TCRID between the heteroclitic peptide and its corresponding unmutated self-peptide from which it was derived is under a second TCRID threshold. In some embodiments, the first peptide filtering and scoring step in FIGS. 1 and 2 will zero the peptide-HLA binding or immunogenicity score for a candidate peptide and an HLA allele when the HLA specific TCRID between the peptide and its corresponding unmutated self-peptide is under a third TCRID threshold. In some embodiments, any of the TCRID thresholds are determined by experimentally observing or computationally predicting the cross-reactivity of TCR molecules to peptide-HLA complexes.

Figure 4A:
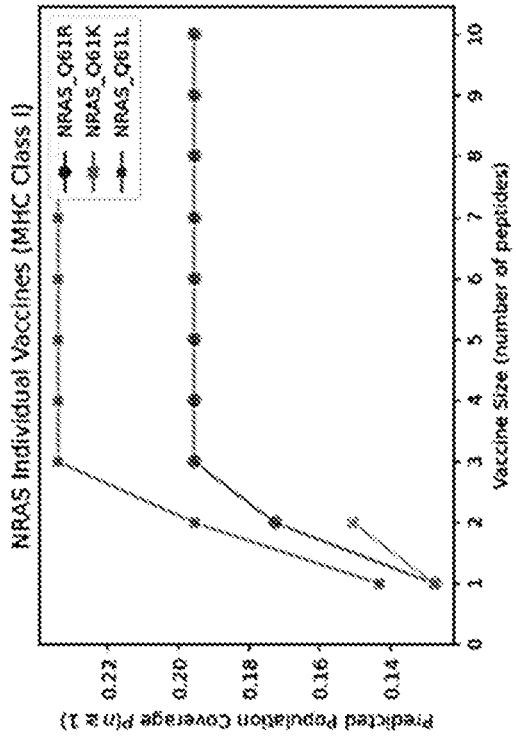
FIGS. 4A-4C shows predicted population coverage for single target MEW class I vaccines by vaccine size for the mutations IDH1 R132H and IDH1 R132C (4A); NRAS Q61R, NRAS Q61K, and NRAS Q61L (4B); and TP53 R158L, TP53 R175H, TP53 R248Q, TP53 R273C, and TP53 R273H (4C).
Figure 4B:
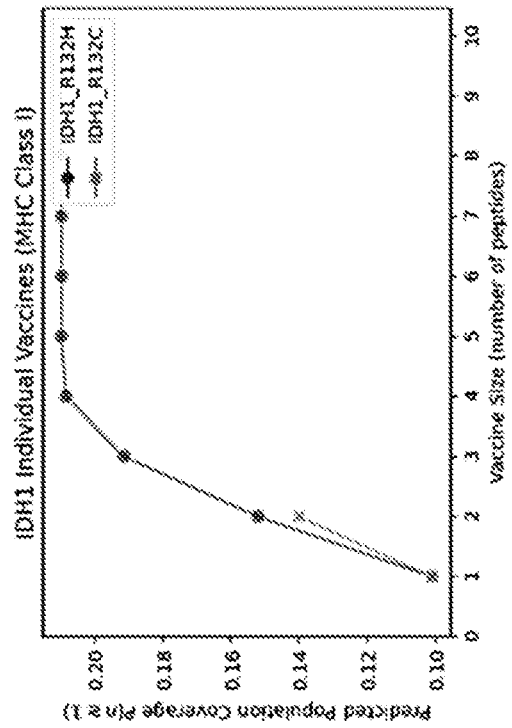
Figure 4C:
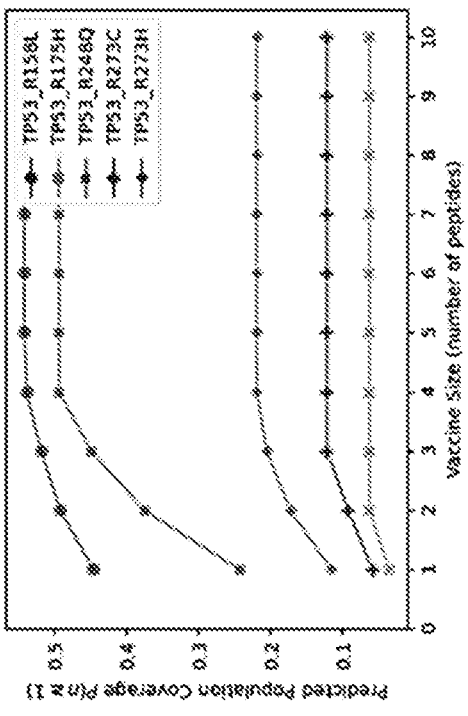
Figure 5B:
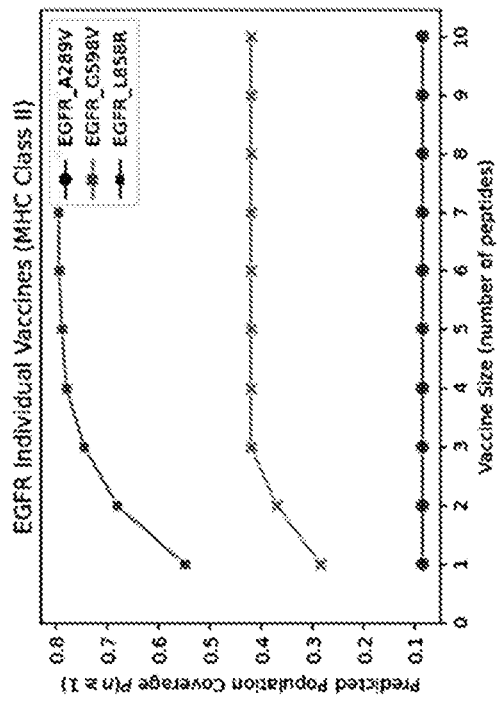
FIGS. 5A-5D shows predicted population coverage for single target MEW class II vaccines by vaccine size for the mutations BRAF V600 and BRAF V600M (5A); EGFR A289V, EGRF G598V, and EGFR L858R, (5B); KRAS G12D, KRAS G12V, KRAS G12R, KRAS G12C, KRAS G13D, KRAS G12A, and KRAS G12S (5C); and PIK3CA E542K, PIK3CA E545K, and PIK3CA H1047R (5D).
Figure 5D:
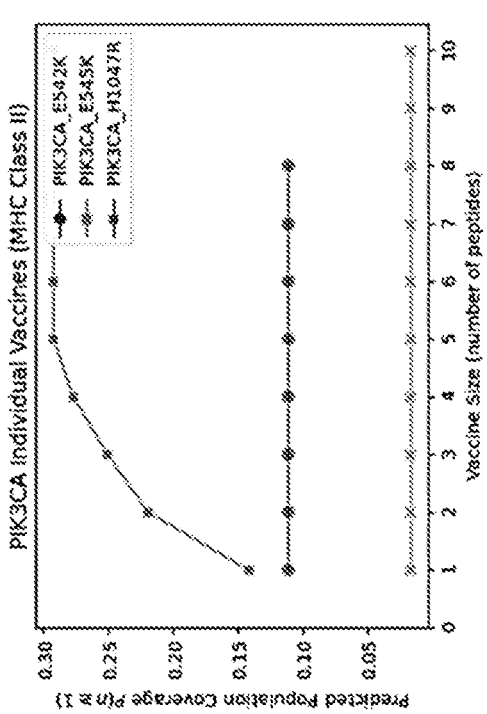
Figure 5A:
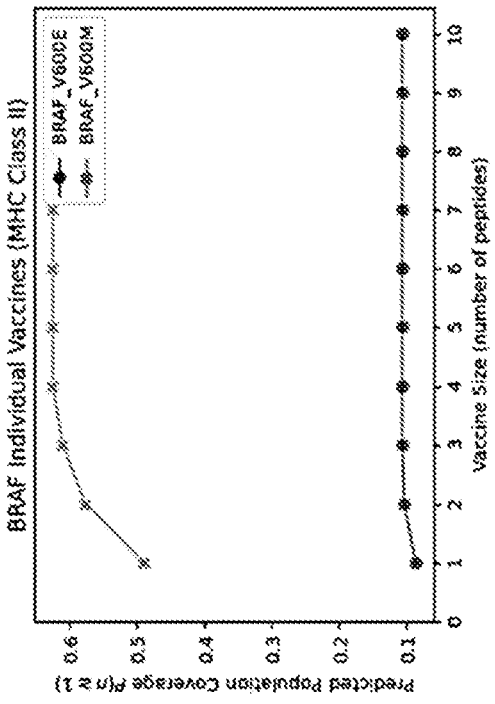
Figure 5C:
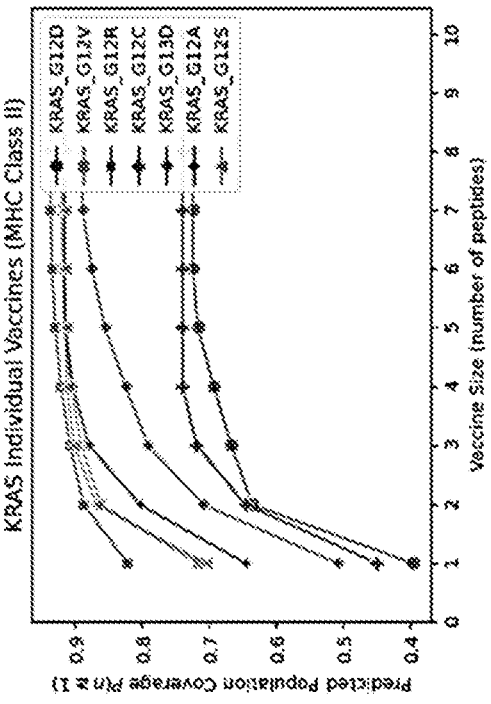
Figure 6A:
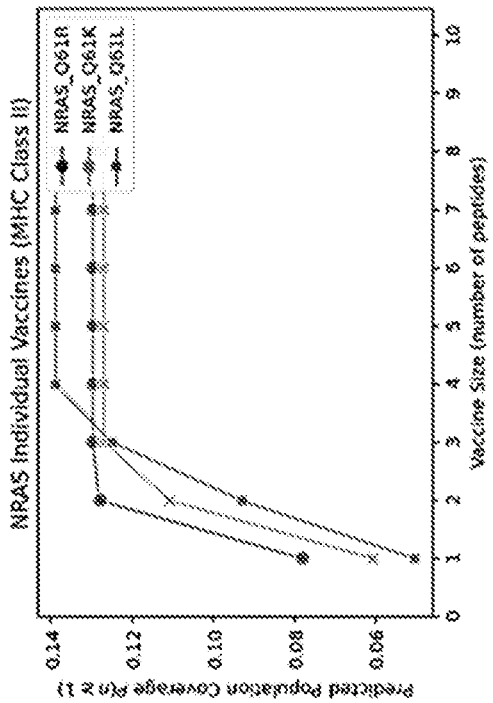
FIGS. 6A-6C shows predicted population coverage for single target MEW class II vaccines by vaccine size for the mutations IDH1 R132H and IDH1 R132C (6A); NRAS Q61R, NRAS Q61K, and NRAS Q61L (6B); and TP53 R158L, TP53 R175H, TP53 R248Q, TP53 R273C, and TP53 R273H (6C).
Figure 6B:
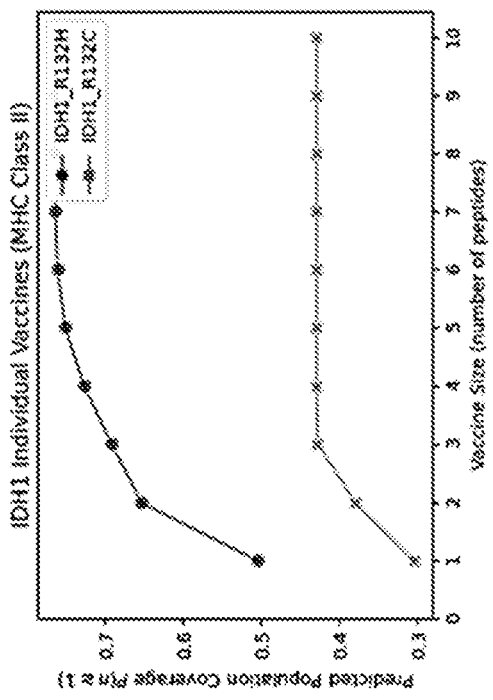
Figure 6C:
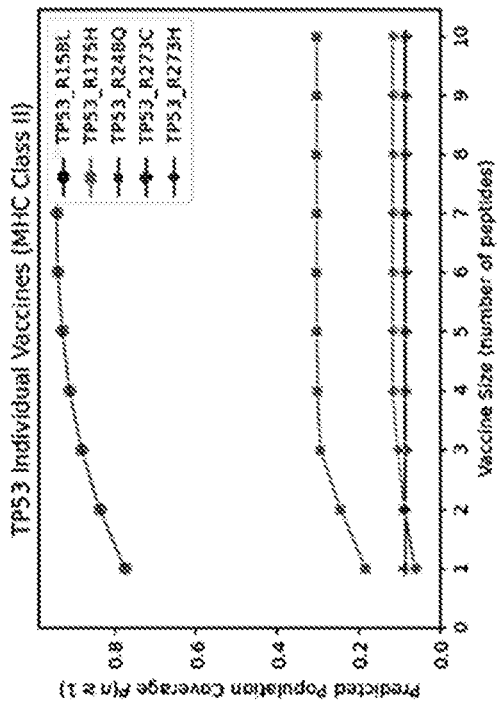

FIGS. 3 and 4 (MHC class I) and FIGS. 5 and 6 (MHC class II) show the predicted population coverage of OptiVax-Robust selected single target-specific vaccines with differing number of peptides designed for the mutations BRAF V600E, BRAF V600M, EGFR A289V, EGRF G598V, EGFR L858R, IDH1 R132H, IDH1 R132C, NRAS Q61R, NRAS Q61K, NRAS Q61L, KRAS G12D, KRAS G12V, KRAS G12R, KRAS G12C, KRAS G13D, KRAS G12A, KRAS G12S, PIK3CA E542K, PIK3CA E545K, PIK3CA H1047R, TP53 R158L, TP53 R175H, TP53 R248Q, TP53 R273C, and TP53 R273H. FIGS. 3-6 show that as the number of peptides increases for a vaccine, its predicted population coverage increases. The population coverage shown in FIGS. 3-6 are of those individuals that have the specific mutation that the vaccine is designed to cover. An increase in peptide count will also typically cause the average number of peptide-HLA hits in each individual to increase within the population.

OptiVax can be used to design a vaccine to maximize the fraction/proportion of the population whose HLA molecules are predicted to bind to and display at least p peptides from the vaccine. In some embodiments, this prediction (e.g., scoring) includes experimental immunogenicity data to directly predict at least p peptides will be immunogenic. The number p is input to OptiVax, and OptiVax can be run multiple times with varying values for p to obtain a predicted optimal target peptide set for different peptide counts p. Larger values of p will increase the redundancy of a vaccine at the cost of more peptides to achieve a desired population coverage. In some embodiments, it may not be possible to achieve a given population coverage given a specific heteroclitic base set. In some embodiments, the number p is a function of the desired size of a vaccine.

The methods described herein can be used to design separate vaccine formulations for MHC class I and class II-based immunity.

In some embodiments, this procedure is used to create a vaccine for an individual. In some embodiments, the target peptides present in the individual are determined by sequencing the individual's tumor RNA or DNA and identifying mutations that produce foreign peptides. One embodiment of this method is described in U.S. Pat. No. 10,738,355, incorporated in its entirety herein. In some embodiments, peptide sequencing methods are used to identify target peptides in the individual. One embodiment of this is described in U.S. Publication No.: 2011/0257890. In some embodiments, the target peptides used for the individual's vaccine are selected when a self-peptide, foreign peptide, or RNA encoding a self-peptide or foreign peptide is observed in a specimen from the individual is present at a predetermined level. The target peptides in the individual are used to construct a vaccine as described in the disclosure herein. For vaccine design, OptiVax is provided a diplotype comprising the HLA type of the individual. In an alternative embodiment, the HLA type of an individual is separated into multiple diplotypes with frequencies that sum to one, where each diplotype comprises one or more HLA alleles from the individual and a notation that the other allele positions should not be evaluated. The use of multiple diplotypes will cause OptiVax's objective function to increase the chance that immunogenic peptides will be displayed by all of the constructed diplotypes. This achieves the objective of maximizing the number of distinct HLA alleles in the individual that exhibit peptide-HLA immunogenicity and thus improves the allelic coverage of the vaccine in the individual.

Figure 14:
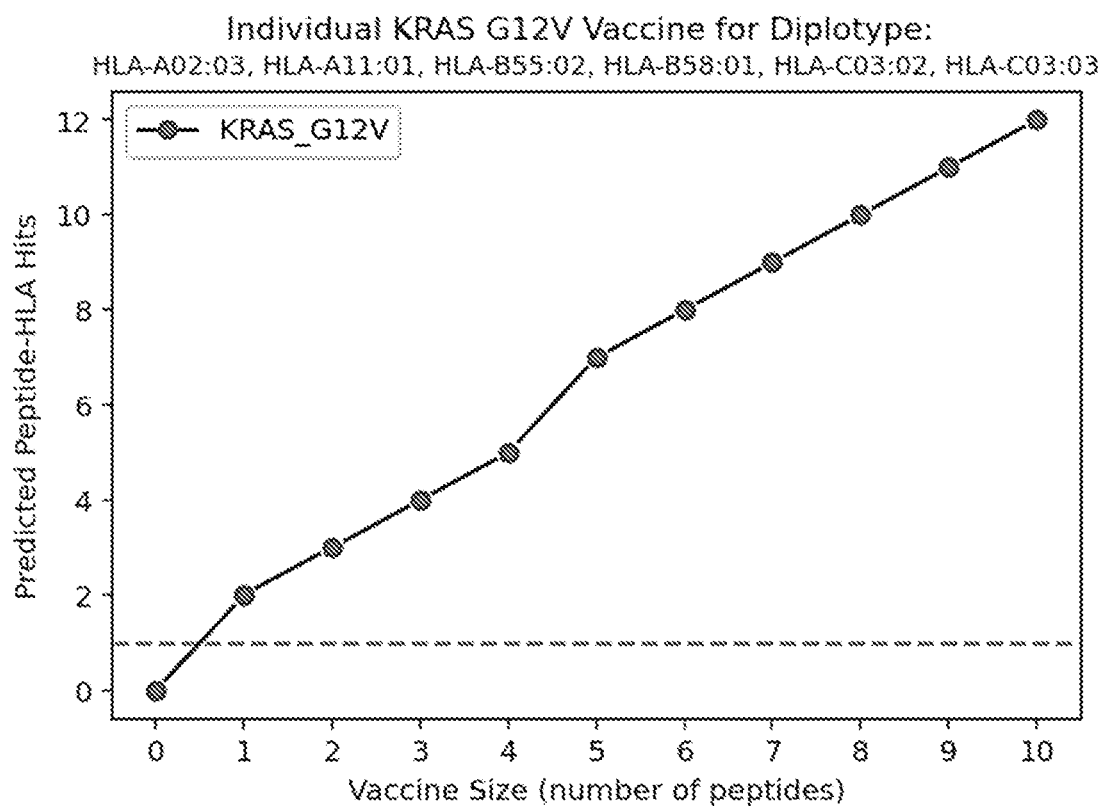
FIG. 14 shows predicated peptide-HLA hits by vaccine size for a KRAS G12V vaccine for the HLA diplotype HLA-A02:03, HLA-A11:01, HLA-B55:02, HLA-B58:01, HLA-C03:02, HLA-C03:03.

FIG. 14 shows the predicted vaccine performance (predicted number of peptide-HLA hits) of ten example G12V MHC class I vaccines for a single individual with the MHC class I HLA diplotype HLA-A02:03, HLA-A11:01, HLA-B55:02, HLA-B58:01, HLA-C03:02, HLA-C03:03. OptiVax was used to design ten G12V MHC class I vaccines for this HLA diplotype with peptide counts ranging from 1 to 10. For the results in FIG. 14, OptiVax was run with six synthetic diplotypes, each equally weighted, each with one HLA allele from the individual's HLA diplotype, and the other allele positions marked to not be evaluated. The 10-peptide vaccine in FIG. 14 comprises SEQ ID NO: 203 (LMVVGAVGV), SEQ ID NO: 208 (GAVGVGKSL), SEQ ID NO: 209 (GPVGVGKSA), SEQ ID NO: 213 (GPVGVGKSV), SEQ ID NO: 11036 (LMVVGAVGI), SEQ ID NO: 11037 (LMVVGAVGL), SEQ ID NO: 11095 (VTGAVGVGK), SEQ ID NO: 11122 (GAVGVGKSM), SEQ ID NO: 11457 (VAGAVGVGM), and SEQ ID NO: 11737 (VVGAVGVGK). Two peptides, SEQ ID NO: 208 (GAVGVGKSL) and SEQ ID NO: 11122 (GAVGVGKSM), are predicted to each bind two of the HLA alleles with an affinity of 50 nM or less.

MHC Class I Vaccine Design Procedure

In some embodiments, MHC class I vaccine design procedures consist of the following computations steps.

In some embodiments, the inputs for the computation are:

$P_{1 \ldots n}$: Peptide sequence (length n) containing the neoantigen or pathogenic target(s) of interest (e.g., KRAS G12D, KRAS G12V, KRAS G12R, KRAS G12C, KRAS G13D). $P_i$ denotes the amino acid at position i.

t: Position of target mutation in P, $t \in [1, \ldots n]$ (e.g., t=12 for KRAS G12D).

s: Substitution mutation $s \in$ [true, false] is true if the mutation is a substitution, and false if the mutation is a deletion or insertion or the peptide does not contain a mutation. When the mutation is a deletion or insertion then t indicates the position immediately before the deletion or insertion.

$\tau_1$: Threshold for potential presentation of peptides by MHC for peptide-WIC scoring (e.g., 500 nM binding affinity)

$\tau_2$: Threshold for predicted display of peptides by WIC for peptide-MHC scoring (e.g., 50 nM binding affinity)

$\mathcal{H}$: Set of HLA alleles (for HLA-A, HLA-B, HLA-C loci)

F: $\mathcal{H}^3 \to \mathbb{R}$ Population haplotype frequencies (for OptiVax optimization and coverage evaluation).

N: Parameter for EvalVax and OptiVax objective function. Specifies minimum number of predicted per-individual hits for population coverage objective to consider the individual covered. Default=1 (computes $P(n \geq 1)$ population coverage).

In some embodiments, Peptide-HLA Scoring Functions used are:

ScorePotential: $P \times \mathcal{H} \to \mathbb{R}$ Scoring function mapping a (peptide, HLA allele) pair to a prediction of peptide-HLA display. If predicted affinity $\leq \tau_1$, then returns 1, else returns 0. Options include MHCflurry, NetMHCpan, PUFFIN, ensembles, or alternative metrics or software may be used, including models calibrated against immunogenicity data.

ScoreDisplay: $P \times \mathcal{H} \to \mathbb{R}$: Scoring function mapping a (peptide, HLA allele) pair to a prediction of peptide-HLA display. If predicted affinity $\leq \tau_2$, then returns 1, else returns 0. Options include MHCflurry, NetMHCpan, PUFFIN, ensembles, or alternative metrics or software may be used, including models calibrated against immunogenicity data.

Next, from the seed protein sequence (P), a set $\mathcal{P}$ of windowed native peptides spanning the protein sequence(s) is constructed. $P_{j \ldots i+(k-1)}$ only produces set members when the subscripts are within the range of the defined seed protein P. In some embodiments, 8-mers, 9-mers, 10-mers, and 11-mers are produced, but this process can be performed with any desired window lengths and the resulting peptide sets combined. In some embodiments, only 9-mers are produced.

$$\mathcal{P} = \bigcup_{k \in [8,\ldots,11]} \mathcal{P}_k$$

$\mathcal{P}_k = \{P_{j \ldots j+(k-1)} | j \in [t-(k-1), \ldots, t], \text{ if } s \text{ then } j \neq \{t-(k-1), t-1\}\}$ The second condition $j \neq \{t-(k-1), t-1\}$ excludes peptides where the mutation at t is in positions P2 or Pk of the windowed k-mer peptide (i.e., the anchor positions) and the mutation is a substitution.

Next, each peptide sequence in $\mathcal{P}$ is scored against all HLA alleles in $\mathcal{H}$ for potential presentation using ScorePotential (with threshold $\tau_1$=500 nM) and store results in a $|\mathcal{P}| \times |\mathcal{H}|$ matrix S:

$S[p,h] = \text{ScorePotential}(p,h) \forall p \in \ h \in \mathcal{H}$

Note that S is a binary matrix where 1 indicates the HLA is predicted to potentially present the peptide, and 0 indicates no potential presentation.

Define Base Set of Peptides $B \subseteq \mathcal{P}$:

$B = \{p \in \mathcal{P} | \exists h \text{ s.t. } S[p,h]=1\}$

Thus, B contains the native peptides that are predicted to be potentially presented by at least 1 HLA.

Create a Set of all Heteroclitic Peptides B' Stemming from Peptides in B:

$$B' = \bigcup_{b \in B} \text{ANCHOR-MODIFIED}(b)$$

where ANCHOR-MODIFIED(b) returns a set of all 399 anchor-modified peptides stemming from b (with all possible modifications to the amino acids at P2 and P9).

Next, all heteroclitic candidate peptides (e.g., modified peptides) in B' are scored against all HLA alleles in $\mathcal{H}$ for predicted display using ScoreDisplay (with threshold $\tau_2$=50 nM), and store results in binary $|B'| \times |\mathcal{H}|$ matrix $S_1'$:

$S1'[b',h] = \text{ScoreDisplay}(b',h) \forall b' \in B', h \in \mathcal{H}$

Next, an updated scoring matrix $S_2'$ is computed for heteroclitic peptides conditioned on the potential presentation of the corresponding base peptides by each HLA:

$$S_2'[b',h] = \begin{cases} S_1'[b',h], & \text{if } S[b,h]=1 \\ 0, & \text{otherwise} \end{cases} \forall b' \in B', h \in \mathcal{H}$$

where each heteroclitic peptide $b' \in B'$ is a mutation of base peptide $b \in B$. This condition enforces that if h was not predicted to potentially present b, then all heteroclitic peptides b' derived from b will not be displayed by h (even if h would otherwise be predicted to display b').

In some embodiments, OptiVax-Robust is used to design a final peptide set (e.g., third peptide set) from the union of base peptides and heteroclitic peptides $B \cup B'$ (with corresponding scoring matrices S and $S_2'$ for B and B', respectively). Let $\mathcal{V}_k$ denote the compact set of vaccine peptides output by OptiVax containing k peptides. Note that $\mathcal{V}_{k+1}$ is not necessarily a superset of $\mathcal{V}_k$. (In alternate embodiments, OptiVax can be used to augment the base set B with peptides from B' using scoring matrix $S_2'$ to return set $\mathcal{A}_k$, and the final vaccine set $\mathcal{V}_{k+|B|}$ consists of peptides B $\mathcal{A}_k$.)

In some embodiments, this procedure is repeated independently for each target of interest, and the resulting independent vaccine sets can be merged into a combined vaccine as described below.

MEW Class II Vaccine Design Procedure

In some embodiments, MEW class II vaccine design procedures consist of the following computations steps.

In some embodiments, the inputs for the computation are:

$P_{1...n}$: Peptide sequence(s) (length n) containing the neoantigen(s) of interest (e.g., KRAS G12D, KRAS G12V, KRAS G12R, KRAS G12C, KRAS G13D). $P_i$ denotes the amino acid at position i.

t: Position of target mutation in P, t∈[1, ..., n] (e.g., t=12 for KRAS G12D).

s: Substitution mutation s∈[true, false] is true if the mutation is a substitution, and false if the mutation is a deletion or insertion or the peptide does not contain a mutation. When the mutation is a deletion or insertion then t indicates the position immediately before the deletion or insertion.

$\tau_1$: Threshold for potential presentation of peptides by MHC for peptide-MHC scoring (e.g., 500 nM binding affinity)

$\tau_2$: Threshold for predicted display of peptides by MHC for peptide-MHC scoring (e.g., 50 nM binding affinity)

$\mathcal{H}$: Set of HLA alleles (for HLA-DR, HLA-DQ, HLA-DP loci)

F: $\mathcal{H}^3 \to \mathbb{R}$ Population haplotype frequencies (for OptiVax optimization and coverage evaluation).

N: Parameter for EvalVax and OptiVax objective function. Specifies minimum number of predicted per-individual hits for population coverage objective to consider the individual covered. Default=1 (computes P(n≥1) population coverage).

In some embodiments, Peptide-HLA Scoring Functions used are:

SCOREPOTENTIAL: $P \times \mathcal{H} \to \mathbb{R}$: Scoring function mapping a (peptide, HLA allele) pair to a prediction of display. If predicted affinity ≤$\tau_1$, then returns 1, else returns 0. Options include NetMHCIIpan, PUFFIN, ensembles, or alternative metrics or software may be used, including models calibrated against immunogenicity data.

SCOREDISPLAY: $P \times \mathcal{H} \to \mathbb{R}$: Scoring function mapping a (peptide, HLA allele) pair to a prediction of peptide-HLA display. If predicted affinity ≤$\tau_2$, then returns 1, else returns 0.

Options include NetMHCIIpan, PUFFIN, ensembles, or alternative metrics or software may be used, including models calibrated against immunogenicity data.

FindCore: $P \times \mathcal{H} \to [1, ..., n]$: Function mapping a (peptide, HLA allele) pair to a prediction of the 9-mer binding core. The core may be specified as the offset position (index) into the peptide where the core begins.

Next, from the seed protein sequence (P), a set $\mathcal{P}$ of peptides spanning the protein sequence are constructed. $P_{j...j+(k-1)}$ only produces set members when the subscripts are within the range of the defined seed protein P. Here, we extract all windowed peptides of length 13-25 spanning the target mutation, but this process can be performed using any desired window lengths (e.g., only 15-mers).

$$\mathcal{P} = \bigcup_{k \in [13,...,25]} \mathcal{P}_k$$

-continued
$$\mathcal{P}_k = \{P_{j...j+(k-1)} | j \in [t-(k-1), ..., t]\}$$

where $\mathcal{P}_k$ contains all sliding windows of length k, which are combined to form $\mathcal{P}$. Note that here (unlike MHC class I), no peptides are excluded based on binding core or anchor residue positions (for MHC class II, filtering is performed as described in this disclosure).

Next, each peptide sequence in P is scored against all HLA alleles in $\mathcal{H}$ for potential presentation using SCOREPOTENTIAL (with threshold $\tau_1$=500 nM) and store results in $|\mathcal{P}| \times |\mathcal{H}|$ matrix $S_1$:

$$S_1[p,h] = \text{SCOREPOTENTIAL}(p,h) \forall p \in \mathcal{P}, h \in \mathcal{H}$$

Note that $S_1$ is a binary matrix where 1 indicates the HLA is predicted to potentially present the peptide, and 0 indicates no potential presentation.

For each (peptide, HLA allele) pair (p, h), identify/predict the 9-mer binding core using FINDCORE. The predicted binding core is recorded in a matrix C:

$$C[p,h] = \text{FINDCORE}(p,h) \forall p \in \mathcal{P}, h \in \mathcal{H}$$

Next, if not(s) then $S_2[p, h] = S_1[p, h]$ otherwise an updated scoring matrix $S_2$ is computed for native peptides in $\mathcal{P}$:

$$S_2[p, h] = \begin{cases} S_1[p, h], & \text{if } C[p, h] \text{ specifies } P_t \text{ at a} \\ & \text{non-anchor position inside core} \quad \forall p \in \mathcal{P}, h \in \mathcal{H} \\ 0, & \text{otherwise} \end{cases}$$

where $P_t$ is the target residue of interest (e.g., the mutation site of KRAS G12D). This condition enforces the target residue to fall within the binding core at a non-anchor position for all (peptide, HLA allele) pairs with non-zero scores in $S_2$, and allows the binding core to vary by allele per peptide (as the binding cores of a particular peptide may differ based on the HLA allele presenting the peptide). Thus, for each pair (p, h), if the predicted binding core C[p, h] specifies the target residue $P_t$ at an anchor position (P1, P4, P6, or P9 of the 9-mer core), or if $P_t$ is not contained within the binding core, then $S_2[p, h]=0$. In an alternate embodiment, $P_t$ can be located outside of the core or inside the core in a non-anchor position. In some embodiments, $P_t$ can only be located at specific positions inside and/or outside of the core. In some embodiments, the binding core predictions in C are accompanied by prediction confidences. In some embodiments, if the confidence for predicted core C[p, h] is below a desired threshold (e.g., 0.5, 0.6, 0.7, 0.8, or 0.9), then $S_2[p, h]=0$.

Next, OptiVax-Robust is run with peptides $\mathcal{P}$ and scoring matrix $S_2$ to identify a non-redundant base set of peptides $B \cup \mathcal{P}$. (In alternate embodiments, B can be chosen as the entire set $\mathcal{P}$ rather than identifying a non-redundant base set.)

Next, a set of all heteroclitic peptides B' is created stemming from peptides in B:

$$B' = \bigcup_{b \in \cup B} \{\text{ANCHOR - MODIFIED}(b, c) \, \forall c | \exists h \text{ s.t. } S_2[b, h] = 1\}$$

where ANCHOR-MODIFIED(b,c) returns a set of all $20^4-1$ anchor-modified peptides stemming from b with all possible modifications to the amino acids at P1, P4, P6, and P9 of the 9-mer binding core c. Thus, for each base peptide b, the heteroclitic set B' contains all anchor-modified peptides b' with modifications to all unique cores of b identified for any HLA alleles that potentially present b with a valid core position as indicated by scoring matrix $S_2$.

Next, all heteroclitic candidate peptides (e.g., modified peptides) in B' are scored against all HLA alleles in $\mathcal{H}$ for predicted display using SCOREDISPLAY (with threshold $\tau_2$=50 nM), and store results in binary |B'|×|$\mathcal{H}$|-C1 matrix $S_1'$:

$$S_1'[b',h] = \text{ScoreDisplay}(b',h) \forall b' \in B', h \in \mathcal{H}$$

For each (heteroclitic peptide, HLA allele) pair (b',h), identify/predict the 9-mer binding core using FINDCORE. The predicted binding core is recorded in a matrix C':

$$C'[b',h] = \text{FindCore}(b',h) \forall b' \in B', h \in \mathcal{H}$$

An updated scoring matrix $S_2'$ is computed for heteroclitic peptides conditioned on the identified binding cores of a heteroclitic and base peptides occurring at the same offset by a particular HLA:

$$S_2'[b', h] = \begin{cases} S_1'[b', h], & \text{if } C'[b', h] = C[b, h] \\ 0, & \text{otherwise} \end{cases} \forall b' \in B', h \in \mathcal{H}$$

where each heteroclitic peptide b'∈B' is a mutation of base peptide b∈B. This condition enforces the binding core of the heteroclitic peptide b' to be at the same relative position as the base peptide b, and, implicitly, enforces that the target residue $P_t$ still falls in a non-anchor position within the 9-mer binding core (Step 3).

An updated scoring matrix $S_3'$ is computed for heteroclitic peptides conditioned on the potential presentation of the corresponding base peptides by each HLA:

$$S_3'[b', h] = \begin{cases} S_2'[b', h], & \text{if } S[b, h] = 1 \\ 0, & \text{otherwise} \end{cases} \forall b' \in B', h \in \mathcal{H}$$

where each heteroclitic peptide b'∈B' is a mutation of base peptide b∈B. This condition enforces that if h was not predicted to display b, then all heteroclitic peptides b' derived from b will not be displayed by h (even if h would otherwise be predicted to display b').

OptiVax-Robust is used to design a final peptide set (e.g., third peptide set) from the union of base peptides and heteroclitic peptides B∪B' (with corresponding scoring matrices $S_2$ and $S_3'$ for B and B', respectively). Let $\mathcal{V}_k$ denote the compact set of vaccine peptides output by OptiVax containing k peptides. Note that $\mathcal{V}_{k+1}$ is not necessarily a superset of $\mathcal{V}_k$. (In alternate embodiments, OptiVax can be used to augment the base set B with peptides from B' using scoring matrix $S_2'$ to return set $\mathcal{A}_k$, and the final vaccine set $\mathcal{V}_{k+|B|}$ consists of peptides B∪$\mathcal{A}_k$.)

In some embodiments, this procedure is repeated independently for each single target of interest, and the resulting independent vaccine sets can be merged into a combined vaccine as described below.

Methods for Combining Multiple Vaccines

The above-described methods will produce an optimized target peptide set (e.g., third peptide set) for one or more individual targets. In some embodiments, a method is provided for designing separate vaccines for MEW class I and class II-based immunity for multiple targets (e.g., two or more targets such as KRAS G12D and KRAS G12V).

In some embodiments, a method is disclosed for producing a combined peptide vaccine for multiple targets by using a table of presentations for a disease that is based upon empirical data from sources such as the Cancer Genome Atlas (TCGA). FIG. 7 shows one embodiment for factoring disease presentation type probabilities (e.g., pancreatic cancer, colorectal cancer, and skin cancer) by probability, for each disease presentation, of target presented for various mutation targets (e.g., KRAS G12D, KRAS G12V, and KRAS G12R). A presentation is a unique set of targets that are presented by one form of a disease (e.g., distinct type of cancer or cancer indication as shown in FIG. 7). For each presentation, FIG. 7 shows an example of the probability of that presentation, and the probability that a given target is observed. For a given presentation, there can be one or more targets, each having a probability. In some embodiments, the method for multi-target vaccine design will allocate peptide resources for inducing disease immunity based on the presentation and respective target probabilities as shown in FIG. 7, for example. In some embodiments, presentations correspond to the prevalence of targets in different human populations or different risk groups. The probability of a target in a population is computed by summing for each possible presentation the probability of that presentation times the probability of the target in that presentation. FIG. 7 shows weights used for merging individual vaccines for each target (row) into combined vaccines for each disease indication (column). Values indicate the observed fraction of cases containing each target mutation. Data are from The Cancer Genome Atlas (TCGA). For each disease indication, TCGA data are filtered to cases where the Primary Site is the indication.

In some embodiments, the same vaccine design will be generated for mutations to different proteins when the base peptides generated by the mutations to the different proteins are identical. For example, in some embodiments of base peptide selection the following mutations have identical vaccine designs because they share the same set of base peptides: HRAS Q61K, NRAS Q61K, and KRAS Q61K; HRAS Q61L, NRAS Q61L, and KRAS Q61L; HRAS Q61R, NRAS Q61R, and KRAS Q61R. Referring to FIG. 7, in some embodiments when two mutations have identical individual vaccine designs their presentation specific probabilities are added when weighting the individual vaccine design for inclusion in a combined vaccine as described below (e.g., for Thyroid Cancer NRAS Q61R and HRAS Q61R).

Figure 8:
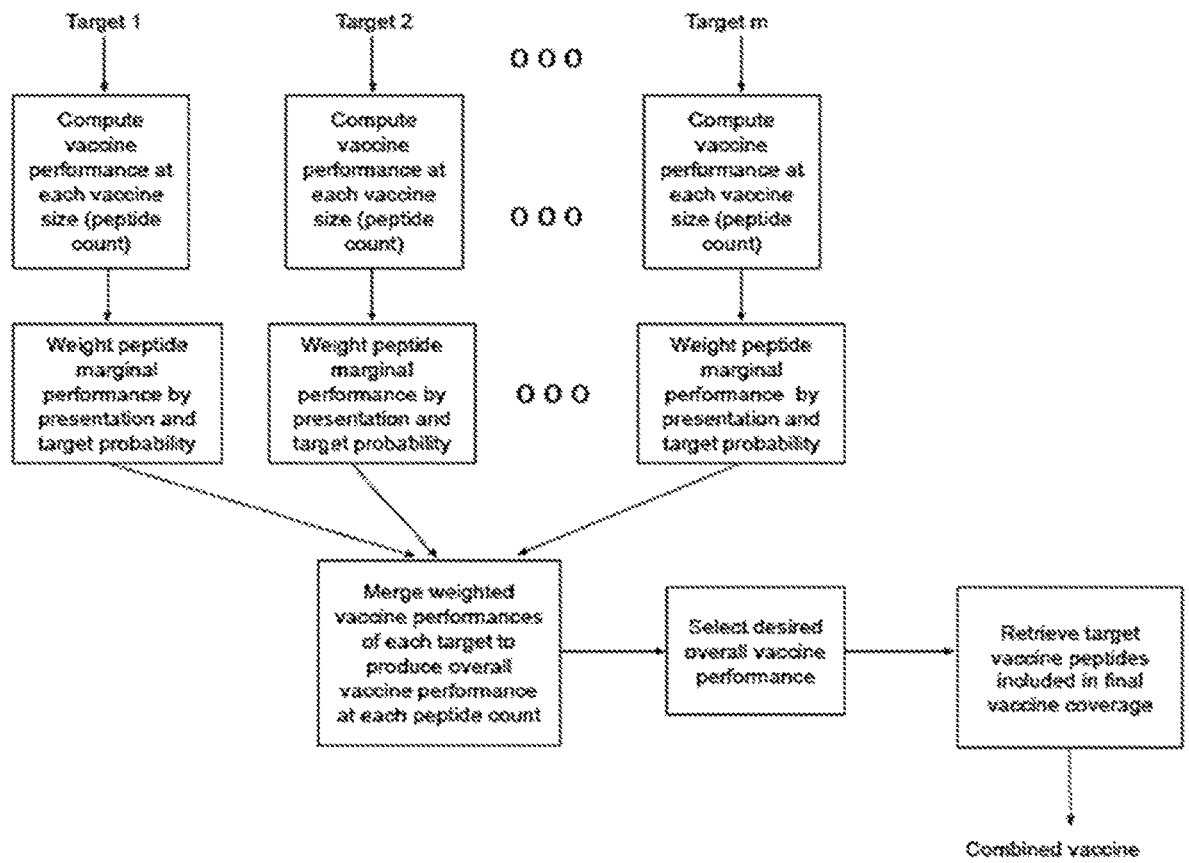
FIG. 8 is a flow chart showing a multiple target (combined) vaccine optimization method.
Figure 9A:
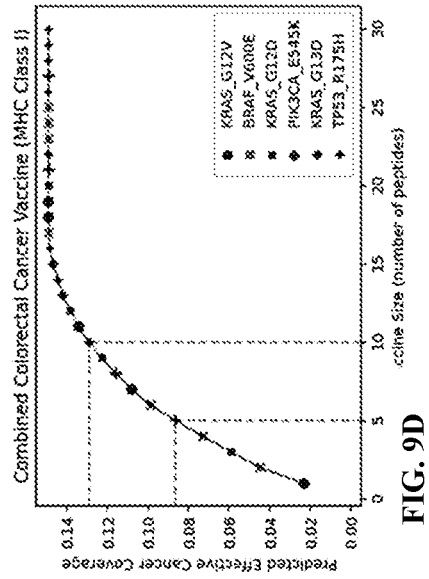
FIGS. 9A-9D shows predicted population coverage for multiple target (combined) MHC class I vaccines by vaccine size for pancreatic cancer (9A), colorectal cancer (9B), brain cancer (9C), and thyroid cancer (9D).
Figure 9B:
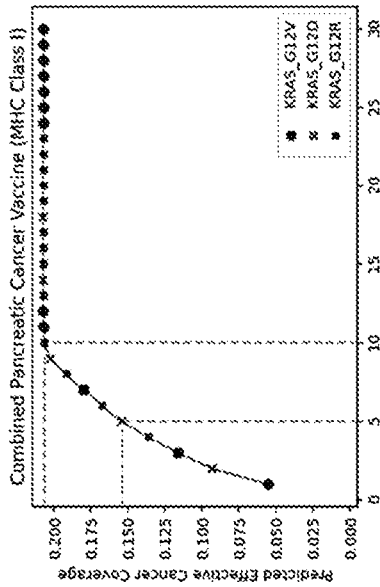
Figure 9C:
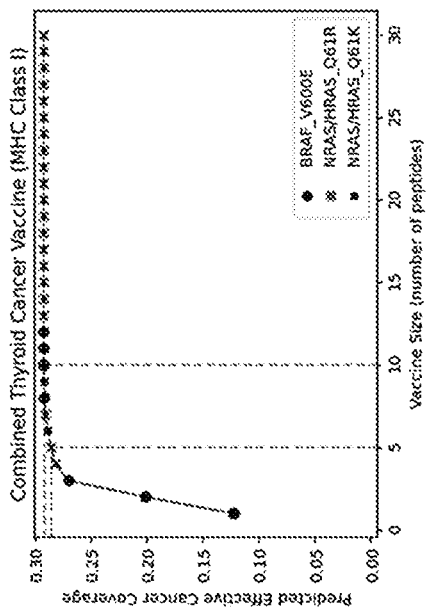
Figure 9D:
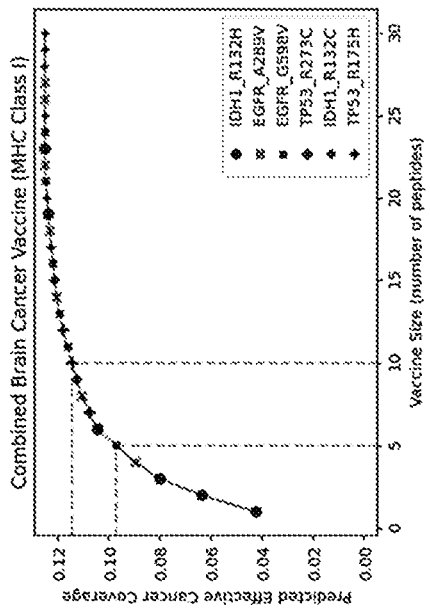

Referring to FIG. 8, in some embodiments, the method first includes designing an individual peptide vaccine for each target to create a combined vaccine design for multiple targets. This initially results in sets of target-specific vaccine designs. In some embodiments, the marginal predicted vaccine performance of each target-specific vaccine at size k is defined by predicted vaccine performance at size k minus the predicted vaccine performance of the vaccine at size k minus one (see FIGS. 3-6). The composition of a vaccine may change as the number of peptides used in the vaccine increases, and thus for computing contributions to a combined vaccine the marginal predicted vaccine performance of each target-specific vaccine is used instead of a specific set of peptides.

In some embodiments, the weighted marginal predicted vaccine performance of a target-specific vaccine design for each target specific vaccine size is computed as shown in FIG. 8. For a given target specific vaccine size, its weighted predicted vaccine performance is computed by multiplying its predicted vaccine performance times the probability of the target in the population (e.g., by using values as shown in FIG. 7). The marginal weighted predicted vaccine performance for a target specific vaccine is its weighted coverage at size k minus its coverage a size k minus one (e.g., see FIG. 3-6). The marginal weighted predicted vaccine performance of a target specific vaccine of size one is its weighted predicted vaccine performance. The marginal weighted predicted vaccine performances for all vaccines are combined into a single list, and the combined list is sorted from largest to least by the weighted marginal predicted vaccine performances of the target specific vaccines as shown in FIG. 8. The combined vaccine of size n is then determined by the first n elements of this list. The peptides for the combined vaccine are determined by the individual peptide target vaccines whose sizes add to n and whose weighted predicted vaccine performances sums to the same sum as the first n elements of the sorted list. This maximizes the predicted vaccine performance of the combined vaccine of size n.

In some embodiments, the combined multiple target vaccine can be designed on its overall predicted coverage for the disease described depending on the presentation table used (e.g., see FIG. 7), by its predicted coverage for a specific indication, and/or by its predicted coverage for a specific target by adjusting the weighting used for predicted vaccine performance accordingly. Once a desired level of coverage is selected, the peptides of the combined vaccine are determined by the contributions of target-specific designs. For example, if the combined vaccine includes a target-specific vaccine of size k, then the vaccine peptides for this target at size k are used in the combined vaccine.

Figure 10A:
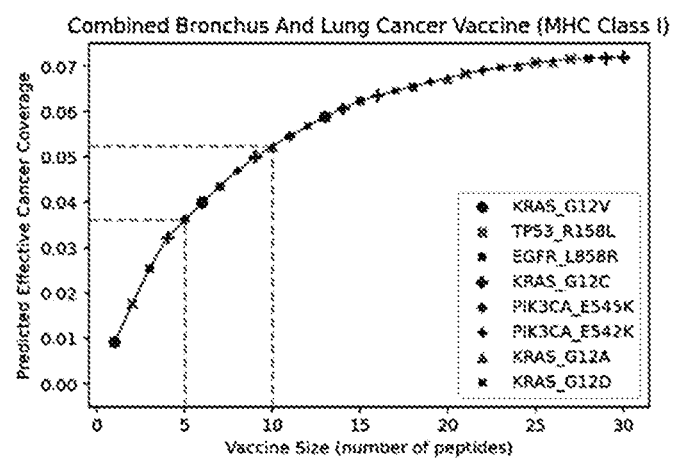
FIGS. 10A-10B shows predicted population coverage for multiple target (combined) MEW class I vaccines by vaccine size for bronchus and lung cancer (10A), and skin cancer (10B).
Figure 10B:
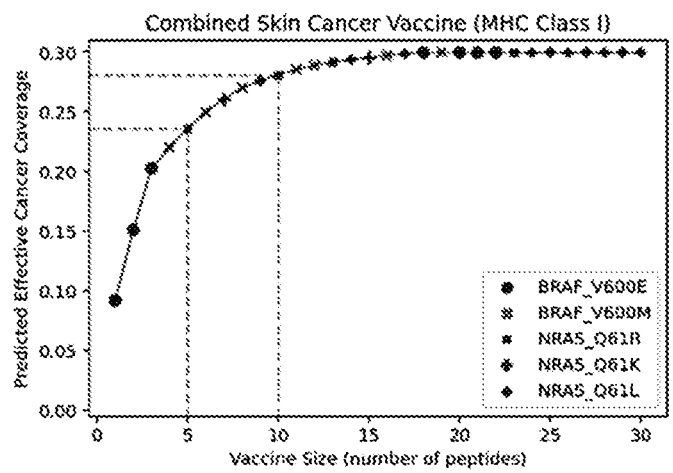
Figure 11B:
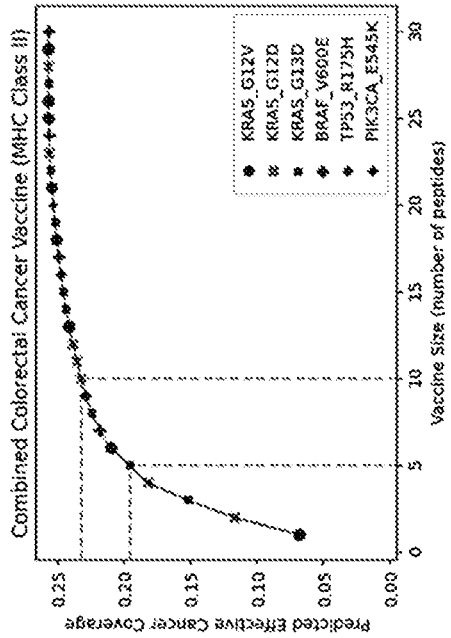
FIGS. 11A-11D shows predicted population coverage for multiple target (combined) MEW class II vaccines by vaccine size for pancreatic cancer (11A), colorectal cancer (11B), brain cancer (11C), and thyroid cancer (11D).
Figure 11D:
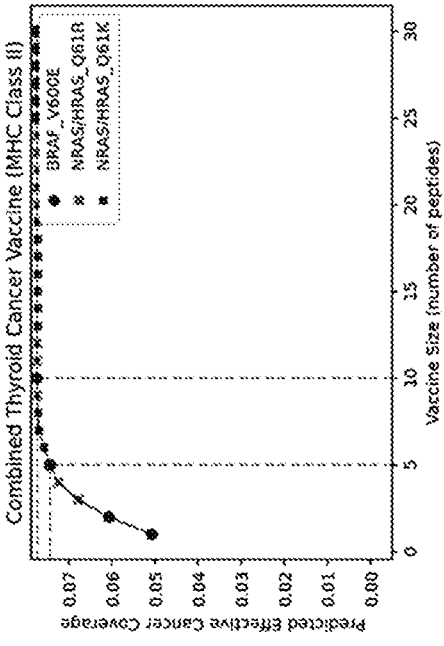
Figure 11A:
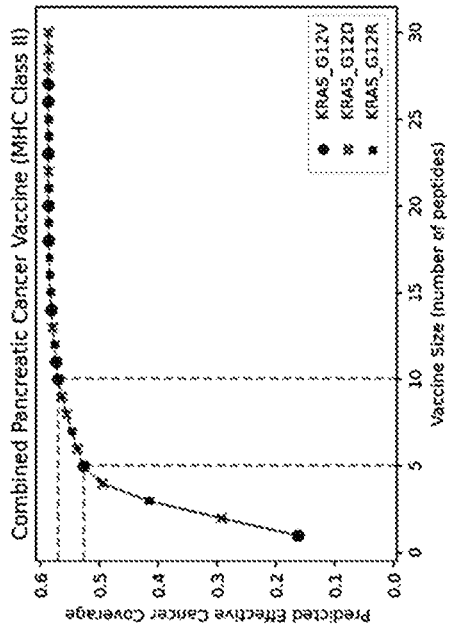
Figure 11C:
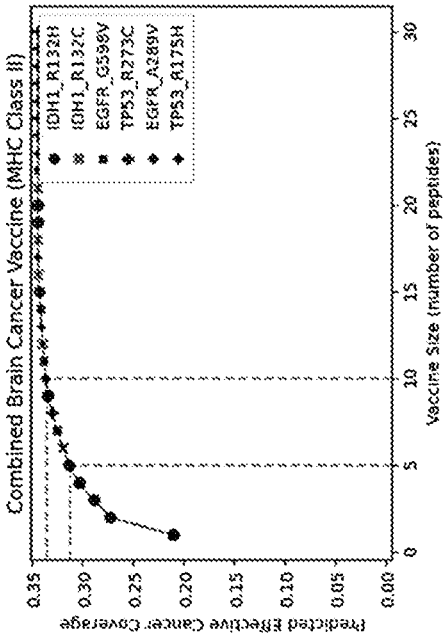
Figure 12A:
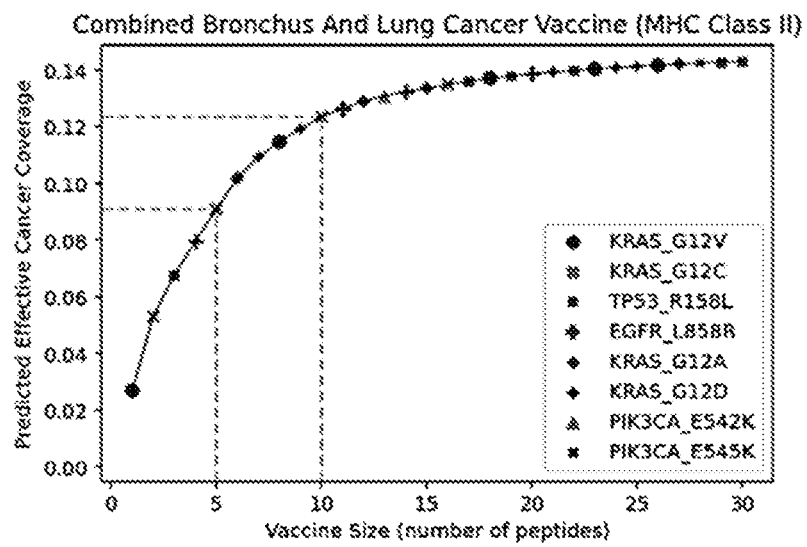
FIGS. 12A-12B shows predicted population coverage for multiple target (combined) MEW class II vaccines by vaccine size for bronchus and lung cancer (12A), and skin cancer (12B).
Figure 12B:
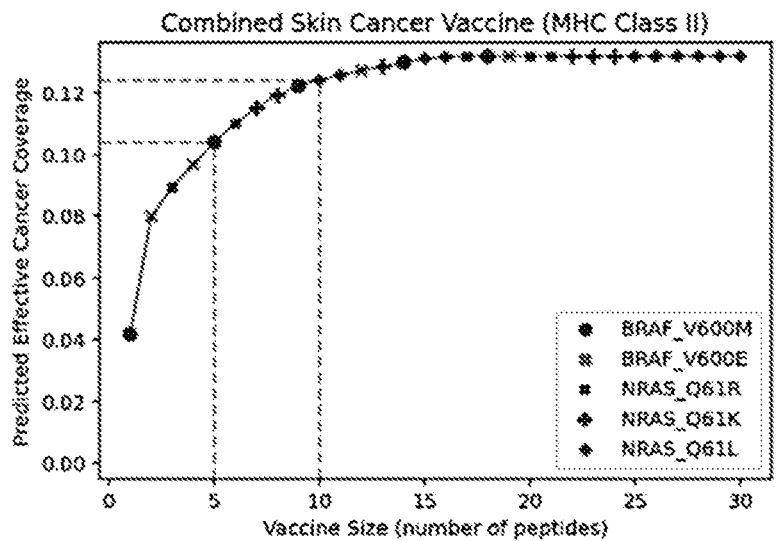

As an example of one embodiment, FIG. 7 shows mutations (e.g., KRAS G12D, G12V, and G12R) and their respective probabilities of occurring in an individual with different cancer indications (e.g., pancreatic cancer). FIGS. 3 and 4 (MHC class I) and FIGS. 5 and 6 (MHC class II) show the population coverage of target-specific vaccines for targets using the methods for vaccines described herein. The marginal population coverage of each target-specific vaccine at a given vaccine size is the improvement in coverage at that size and the size less one. The coverage with no peptides is zero. The marginal coverage of each target-specific vaccine is multiplied by the probability of the target in the population as determined by the proportions as shown in FIG. 7 for a selected indication (e.g., pancreatic cancer). These weighted marginal coverages of all target-specific vaccines are sorted to determine the best target-specific compositions, and the resulting list describes the composition of a combined vaccine for the selected indication at each size k by taking the first k elements of the list. As an example of one embodiment, FIGS. 9 and 10 (MHC Class I) and FIGS. 11 and 12 (MHC Class II) show the target specific contributions at each vaccine size for a combined vaccines for Pancreatic Cancer, Skin Cancer, Thyroid Cancer, Brain Cancer, Colorectal Cancer, and Bronchus and Lung Cancer. The methods for combined vaccine protocol described herein was used to compute the examples in FIGS. 9 to 12. At each combined vaccine size, different components of the target-specific vaccines are utilized for the indication illustrated. Table 1 (below) contains the peptides present in independent (single target) and combined (multiple target) MHC class I vaccine designs. Table 2 (below) contains the contains the peptides present in independent (single target) MHC class II vaccine designs combined (multiple target) MHC class II vaccine designs. Tables 1 and 2 include peptides for Breast Cancer and Ovarian Cancer vaccines for the mutations present in FIG. 7. For alternate embodiments, Sequence Listing provides heteroclitic peptides useful in MHC class I vaccines and MHC class II vaccines for the mutated proteins, specific protein mutations, and indications in Tables 1 and 2. Any subset of the individual/single target vaccines for MHC class I and class II can be combined to create a vaccine for two or more multiple targets.

Combined Vaccine Design Procedure

In some embodiments, the procedure described herein is used to combine individual compact vaccines optimized for different targets into a single optimized combined vaccine.

In some embodiments, the computational inputs for the procedure are:

$\mathcal{T}$: Set of neoantigen or pathogenic targets of interest (e.g., KRAS G12D, KRAS G12V, KRAS G12R)

$\mathcal{V}$: Vaccine sets optimized individually for each target. Let $\mathcal{V}_{t,k}$ denote the optimal vaccine set of exactly k peptides for target $t \in \mathcal{T}$ (e.g., as computed by the procedures describe above). Note that $\mathcal{V}_{t,k+1}$ may not necessarily be a superset of $\mathcal{V}_{t,k}$.

W: $\mathcal{T} \to [0,1]$: Target weighting function mapping each target $t \in \mathcal{T}$ to a probability or weight of t in a particular presentation of interest (e.g., pancreatic cancer; see Exhibit A, Table 1 for example).

POPULATIONCOVERAGE: $\mathcal{V} \to [0,1]$: Function mapping a peptide set into population coverage (e.g., EvalVax). This function may also take as input additional parameters, including HLA haplotype frequencies and a minimum per-individual number of peptide-HLA hits N (here, we compute coverage as $P(n \geq 1)$ using EvalVax-Robust).

For each target t (individually) and vaccine size (peptide count) k, the unweighted population coverage $C_{t,k}$ is computed:

$$c_{t,k} = \text{PopulationCoverage}(\mathcal{V}_{t,k}) \forall t \in \mathcal{T}, k$$

Note that for each target t, $c_{t,k}$ is generally monotonically increasing and concave down for increasing values of k (each additional peptide increases coverage but with decreasing returns).

For each target t (individually), the marginal coverage $m_{t,k}$ is computed of the k-th peptide added to the vaccine set:

$$m_{t,k} = \begin{cases} c_{t,k} & \text{if } k = 1 \\ c_{t,k} - c_{t,k-1}, & \text{otherwise} \end{cases} \forall t \in \mathcal{T}, k$$

Note that for each target t, $m_{t,k}$ should be a monotonically decreasing function in k (by Step 1 above).

The weighted marginal population coverage $\tilde{m}_{t,k}$ is computed using weights of each target in W:

$$\tilde{m}_{t,k} = W(t) \cdot m_{t,k} \forall t \in \mathcal{T}, k$$

The weighted marginal population coverage gives the effective marginal coverage of the k-th peptide in the vaccine weighted by the prevalence of the target in the presentation (by multiplication with the probability/weight of the target in the presentation).

The individual vaccines are combined into a combined vaccine via the MERGEMULTI procedure called on the weighted marginal population coverage lists $\tilde{m}_t = [\tilde{m}_{t,k}, k \in 1, 2, \ldots]$. FIG. 13 shows an example Python implementation of the MERGEMULTI function. This procedure takes as input multiple sorted (descending) lists and merges them into a single sorted (descending) list. Let M indicate the output of MERGEMULTI where each element $M_k$ contains both the marginal weighted coverage and source (target) of the k-th peptide in the combined vaccine. The combined vaccine contains peptides from different targets. In particular, the combined vaccine with k peptides contains $C_{t,k}=\Sigma_{j\le k}\mathbb{1}\{M_k \text{ from } t\}$ peptides from target t. Note that $C_{t,k}\in[0,\ldots,k]$ and $\Sigma_t C_{t,k}=k$ ($c_{t,k}$ gives the distribution of the k peptides in the combined vaccine across the targets).

The optimal combined vaccine set $\hat{V}_k$ is defined as:

$$\hat{V}_k = \bigcup_{t\in\mathcal{T}} v_{t,C_{t,k}}$$

Thus, the combined vaccine with k peptides is the combination of the optimal individual ($C_{t,k}$)-peptide vaccines. The marginal weighted coverage values of the combine vaccine $M_k$ can be cumulatively summed over k to give the overall effective (target-weighted) population coverage of the combined vaccine containing k peptides as $\Sigma_{j\le K} M_k$ (taking into account both the probabilities/weights of the targets in the presentation and the expected population coverage of peptides based on HLA display). The final vaccine size k can vary based upon the specific population coverage goals of the vaccine.

MEW Class I Peptide Sequences

In some embodiments, a peptide vaccine (single target or combined multiple target vaccine) comprises about 1 to 40 MEW class I peptides with each peptide consisting of 8 or more amino acids. In some embodiments, an MHC class I peptide vaccine is intended for one or more of the AKT1, BRAF, EGFR, GTF2I, HRAS, IDH1, KRAS, NRAS, PIK3CA, PTEN, or TP53 mutated protein targets. In some embodiments, an MHC class I peptide vaccine is intended for one or more of the AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, or TP53 Y220C protein mutation targets. In some embodiments, an MEW class I peptide vaccine is intended for one or more of the pancreatic cancer, skin cancer, thyroid cancer, brain cancer, colorectal cancer, bronchus and lung cancer, breast cancer, or ovarian cancer indications.

In some embodiments, the amino acid sequence for a WIC class I peptide vaccine for mutation in the AKT1 protein comprises one or more of the SEQ ID NOs: 1 to 18 and SEQ ID NO: 459. In some embodiments, any one of the peptides in the AKT1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 1 to 18 or SEQ ID NO: 459.

In some embodiments, the amino acid sequence for a WIC class I peptide vaccine for mutation in the AKT1 protein comprises one or more of the SEQ ID NOs: 1 to 18, SEQ ID NO: 459, SEQ ID NOs: 760 to 1768, and SEQ ID NOs: 22386 to 22396. In some embodiments, any one of the peptides in the AKT1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 1 to 18, SEQ ID NO: 459, SEQ ID NOs: 760 to 1768, or SEQ ID NOs: 22386 to 22396.

In some embodiments, the amino acid sequence for a WIC class I peptide vaccine for mutation in the AKT1 protein comprises two or more of the SEQ ID NOs: 1 to 18 and SEQ ID NO: 459. In some embodiments, any one of the peptides in the AKT1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 1 to 18 or SEQ ID NO: 459.

In some embodiments, the amino acid sequence for a WIC class I peptide vaccine for mutation in the AKT1 protein comprises two or more of the SEQ ID NOs: 1 to 18, SEQ ID NO: 459, SEQ ID NOs: 760 to 1768, and SEQ ID NOs: 22386 to 22396. In some embodiments, any one of the peptides in the AKT1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 1 to 18, SEQ ID NO: 459, SEQ ID NOs: 760 to 1768, or SEQ ID NOs: 22386 to 22396.

In some embodiments, the amino acid sequence for a WIC class I peptide vaccine for mutation in the BRAF protein comprises one or more of the SEQ ID NOs: 19 to 50. In some embodiments, any one of the peptides in the BRAF vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 19 to 50.

In some embodiments, the amino acid sequence for a MEW class I peptide vaccine for mutation in the BRAF protein comprises one or more of the SEQ ID NOs: 19 to 50, SEQ ID NOs: 1769 to 3170, and SEQ ID NOs: 22397 to 22417. In some embodiments, any one of the peptides in the BRAF vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 19 to 50, SEQ ID NOs: 1769 to 3170, or SEQ ID NOs: 22397 to 22417.

In some embodiments, the amino acid sequence for a MEW class I peptide vaccine for mutation in the BRAF protein comprises two or more of the SEQ ID NOs: 19 to 50. In some embodiments, any one of the peptides in the BRAF vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 19 to 50.

In some embodiments, the amino acid sequence for a MEW class I peptide vaccine for mutation in the BRAF protein comprises two or more of the SEQ ID NOs: 19 to 50, SEQ ID NOs: 1769 to 3170, and SEQ ID NOs: 22397 to 22417. In some embodiments, any one of the peptides in the BRAF vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 19 to 50, SEQ ID NOs: 1769 to 3170, or SEQ ID NOs: 22397 to 22417.

In some embodiments, the amino acid sequence for a MEW class I peptide vaccine for mutation in the EGFR protein comprises one or more of the SEQ ID NOs: 51 to 98. In some embodiments, any one of the peptides in the EGFR vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 51 to 98.

In some embodiments, the amino acid sequence for a MEW class I peptide vaccine for mutation in the EGFR protein comprises one or more of the SEQ ID NOs: 51 to 98, SEQ ID NOs: 3171 to 5756, and SEQ ID NOs: 22418 to 22449. In some embodiments, any one of the peptides in the EGFR vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 51 to 98, SEQ ID NOs: 3171 to 5756, or SEQ ID NOs: 22418 to 22449.

In some embodiments, the amino acid sequence for a WIC class I peptide vaccine for mutation in the EGFR protein comprises two or more of the SEQ ID NOs: 51 to 98. In some embodiments, any one of the peptides in the EGFR vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 51 to 98.

In some embodiments, the amino acid sequence for a WIC class I peptide vaccine for mutation in the EGFR protein comprises two or more of the SEQ ID NOs: 51 to 98, SEQ ID NOs: 3171 to 5756, and SEQ ID NOs: 22418 to 22449. In some embodiments, any one of the peptides in the EGFR vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 51 to 98, SEQ ID NOs: 3171 to 5756, or SEQ ID NOs: 22418 to 22449.

In some embodiments, the amino acid sequence for a WIC class I peptide vaccine for mutation in the GTF2I protein comprises one or more of the SEQ ID NOs: 99 to 118. In some embodiments, any one of the peptides in the GTF2I vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 99 to 118.

In some embodiments, the amino acid sequence for a WIC class I peptide vaccine for mutation in the GTF2I protein comprises one or more of the SEQ ID NOs: 99 to 118, SEQ ID NOs: 5757 to 6498, and SEQ ID NOs: 22450 to 22466. In some embodiments, any one of the peptides in the GTF2I vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 99 to 118, SEQ ID NOs: 5757 to 6498, or SEQ ID NOs: 22450 to 22466.

In some embodiments, the amino acid sequence for a WIC class I peptide vaccine for mutation in the GTF2I protein comprises two or more of the SEQ ID NOs: 99 to 118. In some embodiments, any one of the peptides in the GTF2I vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 99 to 118.

In some embodiments, the amino acid sequence for a MHC class I peptide vaccine for mutation in the GTF2I protein comprises two or more of the SEQ ID NOs: 99 to 118, SEQ ID NOs: 5757 to 6498, and SEQ ID NOs: 22450 to 22466. In some embodiments, any one of the peptides in the GTF2I vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 99 to 118, SEQ ID NOs: 5757 to 6498, or SEQ ID NOs: 22450 to 22466.

In some embodiments, the amino acid sequence for a MHC class I peptide vaccine for mutation in the IDH1 protein comprises one or more of the SEQ ID NOs: 119 to 140 and SEQ ID NOs: 460 to 461. In some embodiments, any one of the peptides in the IDH1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 119 to 140 or SEQ ID NOs: 460 to 461.

In some embodiments, the amino acid sequence for a MHC class I peptide vaccine for mutation in the IDH1 protein comprises one or more of the SEQ ID NOs: 119 to 140, SEQ ID NOs: 460 to 461, SEQ ID NOs: 6499 to 7098, and SEQ ID NOs: 22467 to 22488. In some embodiments, any one of the peptides in the IDH1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 119 to 140, SEQ ID NOs: 460 to 461, SEQ ID NOs: 6499 to 7098, or SEQ ID NOs: 22467 to 22488.

In some embodiments, the amino acid sequence for a MHC class I peptide vaccine for mutation in the IDH1 protein comprises two or more of the SEQ ID NOs: 119 to 140 and SEQ ID NOs: 460 to 461. In some embodiments, any one of the peptides in the IDH1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 119 to 140 or SEQ ID NOs: 460 to 461.

In some embodiments, the amino acid sequence for a MHC class I peptide vaccine for mutation in the IDH1 protein comprises two or more of the SEQ ID NOs: 119 to 140, SEQ ID NOs: 460 to 461, SEQ ID NOs: 6499 to 7098, and SEQ ID NOs: 22467 to 22488. In some embodiments, any one of the peptides in the IDH1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 119 to 140, SEQ ID NOs: 460 to 461, SEQ ID NOs: 6499 to 7098, or SEQ ID NOs: 22467 to 22488.

In some embodiments, the amino acid sequence for a MEW class I peptide vaccine for mutation in the KRAS protein comprises one or more of the SEQ ID NOs: 141 to 229 and SEQ ID NOs: 462 to 466. In some embodiments, any one of the peptides in the KRAS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 141 to 229 or SEQ ID NOs: 462 to 466.

In some embodiments, the amino acid sequence for a MEW class I peptide vaccine for mutation in the KRAS protein comprises one or more of the SEQ ID NOs: 141 to 229, SEQ ID NOs: 462 to 466, SEQ ID NOs: 7099 to 12814, and SEQ ID NOs: 22489 to 22558. In some embodiments, any one of the peptides in the KRAS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 141 to 229, SEQ ID NOs: 462 to 466, SEQ ID NOs: 7099 to 12814, or SEQ ID NOs: 22489 to 22558.

In some embodiments, the amino acid sequence for a MEW class I peptide vaccine for mutation in the KRAS protein comprises two or more of the SEQ ID NOs: 141 to 229 and SEQ ID NOs: 462 to 466. In some embodiments, any one of the peptides in the KRAS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 141 to 229 or SEQ ID NOs: 462 to 466.

In some embodiments, the amino acid sequence for a MEW class I peptide vaccine for mutation in the KRAS protein comprises two or more of the SEQ ID NOs: 141 to 229, SEQ ID NOs: 462 to 466, SEQ ID NOs: 7099 to 12814, and SEQ ID NOs: 22489 to 22558. In some embodiments, any one of the peptides in the KRAS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 141 to 229, SEQ ID NOs: 462 to 466, SEQ ID NOs: 7099 to 12814, or SEQ ID NOs: 22489 to 22558.

In some embodiments, the amino acid sequence for a MEW class I peptide vaccine for mutation in the NRAS protein comprises one or more of the SEQ ID NOs: 230 to 272. In some embodiments, any one of the peptides in the NRAS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 230 to 272.

In some embodiments, the amino acid sequence for a MEW class I peptide vaccine for mutation in the NRAS protein comprises one or more of the SEQ ID NOs: 230 to 272, SEQ ID NOs: 12815 to 14836, and SEQ ID NOs:

22559 to 22582. In some embodiments, any one of the peptides in the NRAS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 230 to 272, SEQ ID NOs: 12815 to 14836, or SEQ ID NOs: 22559 to 22582.

In some embodiments, the amino acid sequence for a MEW class I peptide vaccine for mutation in the NRAS protein comprises two or more of the SEQ ID NOs: 230 to 272. In some embodiments, any one of the peptides in the NRAS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 230 to 272.

In some embodiments, the amino acid sequence for a MEW class I peptide vaccine for mutation in the NRAS protein comprises two or more of the SEQ ID NOs: 230 to 272, SEQ ID NOs: 12815 to 14836, and SEQ ID NOs: 22559 to 22582. In some embodiments, any one of the peptides in the NRAS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 230 to 272, SEQ ID NOs: 12815 to 14836, or SEQ ID NOs: 22559 to 22582.

In some embodiments, the amino acid sequence for a MEW class I peptide vaccine for mutation in the PIK3CA protein comprises one or more of the SEQ ID NOs: 273 to 322 and SEQ ID NOs: 467 to 468. In some embodiments, any one of the peptides in the PIK3CA vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 273 to 322 or SEQ ID NOs: 467 to 468.

In some embodiments, the amino acid sequence for a WIC class I peptide vaccine for mutation in the PIK3CA protein comprises one or more of the SEQ ID NOs: 273 to 322, SEQ ID NOs: 467 to 468, SEQ ID NOs: 14837 to 17342, and SEQ ID NOs: 22583 to 22622. In some embodiments, any one of the peptides in the PIK3CA vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 273 to 322, SEQ ID NOs: 467 to 468, SEQ ID NOs: 14837 to 17342, or SEQ ID NOs: 22583 to 22622.

In some embodiments, the amino acid sequence for a WIC class I peptide vaccine for mutation in the PIK3CA protein comprises two or more of the SEQ ID NOs: 273 to 322 and SEQ ID NOs: 467 to 468. In some embodiments, any one of the peptides in the PIK3CA vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 273 to 322 or SEQ ID NOs: 467 to 468.

In some embodiments, the amino acid sequence for a WIC class I peptide vaccine for mutation in the PIK3CA protein comprises two or more of the SEQ ID NOs: 273 to 322, SEQ ID NOs: 467 to 468, SEQ ID NOs: 14837 to 17342, and SEQ ID NOs: 22583 to 22622. In some embodiments, any one of the peptides in the PIK3CA vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 273 to 322, SEQ ID NOs: 467 to 468, SEQ ID NOs: 14837 to 17342, or SEQ ID NOs: 22583 to 22622.

In some embodiments, the amino acid sequence for a WIC class I peptide vaccine for mutation in the PTEN protein comprises one or more of the SEQ ID NOs: 323 to 353. In some embodiments, any one of the peptides in the PTEN vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 323 to 353.

In some embodiments, the amino acid sequence for a WIC class I peptide vaccine for mutation in the PTEN protein comprises one or more of the SEQ ID NOs: 323 to 353, SEQ ID NOs: 17343 to 18205, and SEQ ID NOs: 22623 to 22636. In some embodiments, any one of the peptides in the PTEN vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 323 to 353, SEQ ID NOs: 17343 to 18205, or SEQ ID NOs: 22623 to 22636.

In some embodiments, the amino acid sequence for a MEW class I peptide vaccine for mutation in the PTEN protein comprises two or more of the SEQ ID NOs: 323 to 353. In some embodiments, any one of the peptides in the PTEN vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 323 to 353.

In some embodiments, the amino acid sequence for a MEW class I peptide vaccine for mutation in the PTEN protein comprises two or more of the SEQ ID NOs: 323 to 353, SEQ ID NOs: 17343 to 18205, and SEQ ID NOs: 22623 to 22636. In some embodiments, any one of the peptides in the PTEN vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 323 to 353, SEQ ID NOs: 17343 to 18205, or SEQ ID NOs: 22623 to 22636.

In some embodiments, the amino acid sequence for a MEW class I peptide vaccine for mutation in the TP53 protein comprises one or more of the SEQ ID NOs: 354 to 458 and SEQ ID NOs: 469 to 474. In some embodiments, any one of the peptides in the TP53 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 354 to 458 or SEQ ID NOs: 469 to 474.

In some embodiments, the amino acid sequence for a MEW class I peptide vaccine for mutation in the TP53 protein comprises one or more of the SEQ ID NOs: 354 to 458, SEQ ID NOs: 469 to 474, SEQ ID NOs: 18206 to 22385, and SEQ ID NOs: 22637 to 22727. In some embodiments, any one of the peptides in the TP53 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 354 to 458, SEQ ID NOs: 469 to 474, SEQ ID NOs: 18206 to 22385, or SEQ ID NOs: 22637 to 22727.

In some embodiments, the amino acid sequence for a MEW class I peptide vaccine for mutation in the TP53 protein comprises two or more of the SEQ ID NOs: 354 to 458 and SEQ ID NOs: 469 to 474. In some embodiments, any one of the peptides in the TP53 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 354 to 458 or SEQ ID NOs: 469 to 474.

In some embodiments, the amino acid sequence for a WIC class I peptide vaccine for mutation in the TP53 protein comprises two or more of the SEQ ID NOs: 354 to 458, SEQ ID NOs: 469 to 474, SEQ ID NOs: 18206 to 22385, and SEQ ID NOs: 22637 to 22727. In some embodiments, any one of the peptides in the TP53 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 354 to 458, SEQ ID NOs: 469 to 474, SEQ ID NOs: 18206 to 22385, or SEQ ID NOs: 22637 to 22727.

In some embodiments, the amino acid sequence for a WIC class I peptide vaccine for mutation in the RAS protein comprises one or more of the SEQ ID NOs: 141 to 272 and SEQ ID NOs: 462 to 466. In some embodiments, any one of the peptides in the RAS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 141 to 272 or SEQ ID NOs: 462 to 466.

In some embodiments, the amino acid sequence for a WIC class I peptide vaccine for mutation in the RAS protein comprises one or more of the SEQ ID NOs: 141 to 272, SEQ ID NOs: 462 to 466, SEQ ID NOs: 7099 to 14836, and SEQ ID NOs: 22489 to 22582. In some embodiments, any one of the peptides in the RAS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 141 to 272, SEQ ID NOs: 462 to 466, SEQ ID NOs: 7099 to 14836, or SEQ ID NOs: 22489 to 22582.

In some embodiments, the amino acid sequence for a WIC class I peptide vaccine for mutation in the RAS protein comprises two or more of the SEQ ID NOs: 141 to 272 and SEQ ID NOs: 462 to 466. In some embodiments, any one of the peptides in the RAS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 141 to 272 or SEQ ID NOs: 462 to 466.

In some embodiments, the amino acid sequence for a WIC class I peptide vaccine for mutation in the RAS protein comprises two or more of the SEQ ID NOs: 141 to 272, SEQ ID NOs: 462 to 466, SEQ ID NOs: 7099 to 14836, and SEQ ID NOs: 22489 to 22582. In some embodiments, any one of the peptides in the RAS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 141 to 272, SEQ ID NOs: 462 to 466, SEQ ID NOs: 7099 to 14836, or SEQ ID NOs: 22489 to 22582.

In some embodiments, the amino acid sequence for a MEW class I peptide vaccine for the BRAF V600 protein mutation comprises one or more of the SEQ ID NOs: 19 to 33. In some embodiments, any one of the peptides in the BRAF V600 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 19 to 33.

In some embodiments, the amino acid sequence for a MEW class I peptide vaccine for the BRAF V600 protein mutation comprises one or more of the SEQ ID NOs: 19 to 33, SEQ ID NOs: 1769 to 2329, and SEQ ID NOs: 22397 to 22405. In some embodiments, any one of the peptides in the BRAF V600 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 19 to 33, SEQ ID NOs: 1769 to 2329, or SEQ ID NOs: 22397 to 22405.

In some embodiments, the amino acid sequence for a MEW class I peptide vaccine for the BRAF V600 protein mutation comprises two or more of the SEQ ID NOs: 19 to 33. In some embodiments, any one of the peptides in the BRAF V600 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 19 to 33.

In some embodiments, the amino acid sequence for a MEW class I peptide vaccine for the BRAF V600 protein mutation comprises two or more of the SEQ ID NOs: 19 to 33, SEQ ID NOs: 1769 to 2329, and SEQ ID NOs: 22397 to 22405. In some embodiments, any one of the peptides in the BRAF V600 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 19 to 33, SEQ ID NOs: 1769 to 2329, or SEQ ID NOs: 22397 to 22405.

In some embodiments, the amino acid sequence for a WIC class I peptide vaccine for the BRAF V600M protein mutation comprises one or more of the SEQ ID NOs: 34 to 50. In some embodiments, any one of the peptides in the BRAF V600M vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 34 to 50.

In some embodiments, the amino acid sequence for a WIC class I peptide vaccine for the BRAF V600M protein mutation comprises one or more of the SEQ ID NOs: 34 to 50, SEQ ID NOs: 2330 to 3170, and SEQ ID NOs: 22406 to 22417. In some embodiments, any one of the peptides in the BRAF V600M vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 34 to 50, SEQ ID NOs: 2330 to 3170, or SEQ ID NOs: 22406 to 22417.

In some embodiments, the amino acid sequence for a WIC class I peptide vaccine for the BRAF V600M protein mutation comprises two or more of the SEQ ID NOs: 34 to 50. In some embodiments, any one of the peptides in the BRAF V600M vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 34 to 50.

In some embodiments, the amino acid sequence for a WIC class I peptide vaccine for the BRAF V600M protein mutation comprises two or more of the SEQ ID NOs: 34 to 50, SEQ ID NOs: 2330 to 3170, and SEQ ID NOs: 22406 to 22417. In some embodiments, any one of the peptides in the BRAF V600M vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 34 to 50, SEQ ID NOs: 2330 to 3170, or SEQ ID NOs: 22406 to 22417.

In some embodiments, the amino acid sequence for a WIC class I peptide vaccine for the EGFR A289V protein mutation comprises one or more of the SEQ ID NOs: 51 to 66. In some embodiments, any one of the peptides in the EGFR A289V vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 51 to 66.

In some embodiments, the amino acid sequence for a WIC class I peptide vaccine for the EGFR A289V protein mutation comprises one or more of the SEQ ID NOs: 51 to 66, SEQ ID NOs: 3171 to 4055, and SEQ ID NOs: 22418 to 22430. In some embodiments, any one of the peptides in the EGFR A289V vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 51 to 66, SEQ ID NOs: 3171 to 4055, or SEQ ID NOs: 22418 to 22430.

In some embodiments, the amino acid sequence for a WIC class I peptide vaccine for the EGFR A289V protein mutation comprises two or more of the SEQ ID NOs: 51 to 66. In some embodiments, any one of the peptides in the EGFR A289V vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 51 to 66.

In some embodiments, the amino acid sequence for a WIC class I peptide vaccine for the EGFR A289V protein mutation comprises two or more of the SEQ ID NOs: 51 to 66, SEQ ID NOs: 3171 to 4055, and SEQ ID NOs: 22418 to 22430. In some embodiments, any one of the peptides in the EGFR A289V vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 51 to 66, SEQ ID NOs: 3171 to 4055, or SEQ ID NOs: 22418 to 22430.

In some embodiments, the amino acid sequence for a WIC class I peptide vaccine for the EGFR G598V protein mutation comprises one or more of the SEQ ID NOs: 67 to 81. In some embodiments, any one of the peptides in the EGFR G598V vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 67 to 81.

In some embodiments, the amino acid sequence for a WIC class I peptide vaccine for the EGFR G598V protein mutation comprises one or more of the SEQ ID NOs: 67 to 81, SEQ ID NOs: 4056 to 4718, and SEQ ID NOs: 22431 to 22437. In some embodiments, any one of the peptides in the EGFR G598V vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 67 to 81, SEQ ID NOs: 4056 to 4718, or SEQ ID NOs: 22431 to 22437.

In some embodiments, the amino acid sequence for a WIC class I peptide vaccine for the EGFR G598V protein mutation comprises two or more of the SEQ ID NOs: 67 to 81. In some embodiments, any one of the peptides in the EGFR G598V vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 67 to 81.

In some embodiments, the amino acid sequence for a WIC class I peptide vaccine for the EGFR G598V protein mutation comprises two or more of the SEQ ID NOs: 67 to 81, SEQ ID NOs: 4056 to 4718, and SEQ ID NOs: 22431 to 22437. In some embodiments, any one of the peptides in the EGFR G598V vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 67 to 81, SEQ ID NOs: 4056 to 4718, or SEQ ID NOs: 22431 to 22437.

In some embodiments, the amino acid sequence for a WIC class I peptide vaccine for the EGFR L858R protein mutation comprises one or more of the SEQ ID NOs: 82 to 98. In some embodiments, any one of the peptides in the EGFR L858R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 82 to 98.

In some embodiments, the amino acid sequence for a WIC class I peptide vaccine for the EGFR L858R protein mutation comprises one or more of the SEQ ID NOs: 82 to 98, SEQ ID NOs: 4719 to 5756, and SEQ ID NOs: 22438 to 22449. In some embodiments, any one of the peptides in the EGFR L858R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 82 to 98, SEQ ID NOs: 4719 to 5756, or SEQ ID NOs: 22438 to 22449.

In some embodiments, the amino acid sequence for a WIC class I peptide vaccine for the EGFR L858R protein mutation comprises two or more of the SEQ ID NOs: 82 to 98. In some embodiments, any one of the peptides in the EGFR L858R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 82 to 98.

In some embodiments, the amino acid sequence for a MEW class I peptide vaccine for the EGFR L858R protein mutation comprises two or more of the SEQ ID NOs: 82 to 98, SEQ ID NOs: 4719 to 5756, and SEQ ID NOs: 22438 to 22449. In some embodiments, any one of the peptides in the EGFR L858R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 82 to 98, SEQ ID NOs: 4719 to 5756, or SEQ ID NOs: 22438 to 22449.

In some embodiments, the amino acid sequence for a MEW class I peptide vaccine for the IDH1 R132H protein mutation comprises one or more of the SEQ ID NOs: 125 to 140 and SEQ ID NO: 461. In some embodiments, any one of the peptides in the IDH1 R132H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 125 to 140 or SEQ ID NO: 461.

In some embodiments, the amino acid sequence for a MEW class I peptide vaccine for the IDH1 R132H protein mutation comprises one or more of the SEQ ID NOs: 125 to 140, SEQ ID NO: 461, SEQ ID NOs: 6738 to 7098, and SEQ ID NOs: 22477 to 22488. In some embodiments, any one of the peptides in the IDH1 R132H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 125 to 140, SEQ ID NO: 461, SEQ ID NOs: 6738 to 7098, or SEQ ID NOs: 22477 to 22488.

In some embodiments, the amino acid sequence for a MEW class I peptide vaccine for the IDH1 R132H protein mutation comprises two or more of the SEQ ID NOs: 125 to 140 and SEQ ID NO: 461. In some embodiments, any one of the peptides in the IDH1 R132H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 125 to 140 or SEQ ID NO: 461.

In some embodiments, the amino acid sequence for a MEW class I peptide vaccine for the IDH1 R132H protein mutation comprises two or more of the SEQ ID NOs: 125 to 140, SEQ ID NO: 461, SEQ ID NOs: 6738 to 7098, and SEQ ID NOs: 22477 to 22488. In some embodiments, any one of the peptides in the IDH1 R132H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 125 to 140, SEQ ID NO: 461, SEQ ID NOs: 6738 to 7098, or SEQ ID NOs: 22477 to 22488.

In some embodiments, the amino acid sequence for a MHC class I peptide vaccine for the IDH1 R132C protein mutation comprises one or more of the SEQ ID NOs: 119 to 124 and SEQ ID NO: 460. In some embodiments, any one of the peptides in the IDH1 R132C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 119 to 124 or SEQ ID NO: 460.

In some embodiments, the amino acid sequence for a MHC class I peptide vaccine for the IDH1 R132C protein mutation comprises one or more of the SEQ ID NOs: 119 to 124, SEQ ID NO: 460, SEQ ID NOs: 6499 to 6737, and SEQ ID NOs: 22467 to 22476. In some embodiments, any one of the peptides in the IDH1 R132C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 119 to 124, SEQ ID NO: 460, SEQ ID NOs: 6499 to 6737, or SEQ ID NOs: 22467 to 22476.

In some embodiments, the amino acid sequence for a MHC class I peptide vaccine for the IDH1 R132C protein mutation comprises two or more of the SEQ ID NOs: 119 to 124 and SEQ ID NO: 460. In some embodiments, any one of the peptides in the IDH1 R132C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 119 to 124 or SEQ ID NO: 460.

In some embodiments, the amino acid sequence for a MHC class I peptide vaccine for the IDH1 R132C protein mutation comprises two or more of the SEQ ID NOs: 119 to 124, SEQ ID NO: 460, SEQ ID NOs: 6499 to 6737, and SEQ ID NOs: 22467 to 22476. In some embodiments, any one of the peptides in the IDH1 R132C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 119 to 124, SEQ ID NO: 460, SEQ ID NOs: 6499 to 6737, or SEQ ID NOs: 22467 to 22476.

In some embodiments, the amino acid sequence for a MHC class I peptide vaccine for the KRAS G12D protein mutation comprises one or more of the SEQ ID NOs: 167 to 178 and SEQ ID NO: 464. In some embodiments, any one of the peptides in the KRAS G12D vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 167 to 178 or SEQ ID NO: 464.

In some embodiments, the amino acid sequence for a WIC class I peptide vaccine for the KRAS G12D protein mutation comprises one or more of the SEQ ID NOs: 167 to 178, SEQ ID NO: 464, SEQ ID NOs: 8432 to 9733, and SEQ ID NOs: 22507 to 22518. In some embodiments, any one of the peptides in the KRAS G12D vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 167 to 178, SEQ ID NO: 464, SEQ ID NOs: 8432 to 9733, or SEQ ID NOs: 22507 to 22518.

In some embodiments, the amino acid sequence for a WIC class I peptide vaccine for the KRAS G12D protein mutation comprises two or more of the SEQ ID NOs: 167 to 178 and SEQ ID NO: 464. In some embodiments, any one of the peptides in the KRAS G12D vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 167 to 178 or SEQ ID NO: 464.

In some embodiments, the amino acid sequence for a WIC class I peptide vaccine for the KRAS G12D protein mutation comprises two or more of the SEQ ID NOs: 167 to 178, SEQ ID NO: 464, SEQ ID NOs: 8432 to 9733, and SEQ ID NOs: 22507 to 22518. In some embodiments, any one of the peptides in the KRAS G12D vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 167 to 178, SEQ ID NO: 464, SEQ ID NOs: 8432 to 9733, or SEQ ID NOs: 22507 to 22518.

In some embodiments, the amino acid sequence for a WIC class I peptide vaccine for the KRAS G12V protein mutation comprises one or more of the SEQ ID NOs: 203 to 213. In some embodiments, any one of the peptides in the KRAS G12V vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 203 to 213.

In some embodiments, the amino acid sequence for a WIC class I peptide vaccine for the KRAS G12V protein mutation comprises one or more of the SEQ ID NOs: 203 to 213, SEQ ID NOs: 11009 to 11744, and SEQ ID NOs: 22537 to 22546. In some embodiments, any one of the peptides in the KRAS G12V vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 203 to 213, SEQ ID NOs: 11009 to 11744, or SEQ ID NOs: 22537 to 22546.

In some embodiments, the amino acid sequence for a WIC class I peptide vaccine for the KRAS G12V protein mutation comprises two or more of the SEQ ID NOs: 203 to 213. In some embodiments, any one of the peptides in the KRAS G12V vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 203 to 213.

In some embodiments, the amino acid sequence for a WIC class I peptide vaccine for the KRAS G12V protein mutation comprises two or more of the SEQ ID NOs: 203 to 213, SEQ ID NOs: 11009 to 11744, and SEQ ID NOs: 22537 to 22546. In some embodiments, any one of the peptides in the KRAS G12V vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 203 to 213, SEQ ID NOs: 11009 to 11744, or SEQ ID NOs: 22537 to 22546.

In some embodiments, the amino acid sequence for a WIC class I peptide vaccine for the KRAS G12R protein mutation comprises one or more of the SEQ ID NOs: 179 to 191 and SEQ ID NO: 465. In some embodiments, any one of the peptides in the KRAS G12R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 179 to 191 or SEQ ID NO: 465.

In some embodiments, the amino acid sequence for a WIC class I peptide vaccine for the KRAS G12R protein mutation comprises one or more of the SEQ ID NOs: 179 to 191, SEQ ID NO: 465, SEQ ID NOs: 9734 to 10236, and SEQ ID NOs: 22519 to 22527. In some embodiments, any one of the peptides in the KRAS G12R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 179 to 191, SEQ ID NO: 465, SEQ ID NOs: 9734 to 10236, or SEQ ID NOs: 22519 to 22527.

In some embodiments, the amino acid sequence for a WIC class I peptide vaccine for the KRAS G12R protein mutation comprises two or more of the SEQ ID NOs: 179 to 191 and SEQ ID NO: 465. In some embodiments, any one of the peptides in the KRAS G12R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 179 to 191 or SEQ ID NO: 465.

In some embodiments, the amino acid sequence for a WIC class I peptide vaccine for the KRAS G12R protein mutation comprises two or more of the SEQ ID NOs: 179 to 191, SEQ ID NO: 465, SEQ ID NOs: 9734 to 10236, and SEQ ID NOs: 22519 to 22527. In some embodiments, any one of the peptides in the KRAS G12R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 179 to 191, SEQ ID NO: 465, SEQ ID NOs: 9734 to 10236, or SEQ ID NOs: 22519 to 22527.

In some embodiments, the amino acid sequence for a WIC class I peptide vaccine for the KRAS G12C protein mutation comprises one or more of the SEQ ID NOs: 154 to 166 and SEQ ID NO: 463. In some embodiments, any one of the peptides in the KRAS G12C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 154 to 166 or SEQ ID NO: 463.

In some embodiments, the amino acid sequence for a WIC class I peptide vaccine for the KRAS G12C protein mutation comprises one or more of the SEQ ID NOs: 154 to 166, SEQ ID NO: 463, SEQ ID NOs: 7881 to 8431, and SEQ ID NOs: 22498 to 22506. In some embodiments, any one of the peptides in the KRAS G12C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 154 to 166, SEQ ID NO: 463, SEQ ID NOs: 7881 to 8431, or SEQ ID NOs: 22498 to 22506.

In some embodiments, the amino acid sequence for a WIC class I peptide vaccine for the KRAS G12C protein mutation comprises two or more of the SEQ ID NOs: 154 to 166 and SEQ ID NO: 463. In some embodiments, any one of the peptides in the KRAS G12C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 154 to 166 or SEQ ID NO: 463.

In some embodiments, the amino acid sequence for a WIC class I peptide vaccine for the KRAS G12C protein mutation comprises two or more of the SEQ ID NOs: 154 to 166, SEQ ID NO: 463, SEQ ID NOs: 7881 to 8431, and SEQ ID NOs: 22498 to 22506. In some embodiments, any one of the peptides in the KRAS G12C vaccine comprise an amino acid sequence 80, 81, 82, 83, 84, 85, 86, 87, 88, 89, 90, 91, 92, 93, 94, 95, 96, 97, 98 or 99% identical to SEQ ID NOs:

154 to 166, SEQ ID NO: 463, SEQ ID NOs: 7881 to 8431, or SEQ ID NOs: 22498 to 22506.

In some embodiments, the amino acid sequence for a MEW class I peptide vaccine for the KRAS G13D protein mutation comprises one or more of the SEQ ID NOs: 214 to 229 and SEQ ID NO: 466. In some embodiments, any one of the peptides in the KRAS G13D vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 214 to 229 or SEQ ID NO: 466.

In some embodiments, the amino acid sequence for a MEW class I peptide vaccine for the KRAS G13D protein mutation comprises one or more of the SEQ ID NOs: 214 to 229, SEQ ID NO: 466, SEQ ID NOs: 11745 to 12814, and SEQ ID NOs: 22547 to 22558. In some embodiments, any one of the peptides in the KRAS G13D vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 214 to 229, SEQ ID NO: 466, SEQ ID NOs: 11745 to 12814, or SEQ ID NOs: 22547 to 22558.

In some embodiments, the amino acid sequence for a MEW class I peptide vaccine for the KRAS G13D protein mutation comprises two or more of the SEQ ID NOs: 214 to 229 and SEQ ID NO: 466. In some embodiments, any one of the peptides in the KRAS G13D vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 214 to 229 or SEQ ID NO: 466.

In some embodiments, the amino acid sequence for a MEW class I peptide vaccine for the KRAS G13D protein mutation comprises two or more of the SEQ ID NOs: 214 to 229, SEQ ID NO: 466, SEQ ID NOs: 11745 to 12814, and SEQ ID NOs: 22547 to 22558. In some embodiments, any one of the peptides in the KRAS G13D vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 214 to 229, SEQ ID NO: 466, SEQ ID NOs: 11745 to 12814, or SEQ ID NOs: 22547 to 22558.

In some embodiments, the amino acid sequence for a MEW class I peptide vaccine for the KRAS G12A protein mutation comprises one or more of the SEQ ID NOs: 141 to 153 and SEQ ID NO: 462. In some embodiments, any one of the peptides in the KRAS G12A vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 141 to 153 or SEQ ID NO: 462.

In some embodiments, the amino acid sequence for a WIC class I peptide vaccine for the KRAS G12A protein mutation comprises one or more of the SEQ ID NOs: 141 to 153, SEQ ID NO: 462, SEQ ID NOs: 7099 to 7880, and SEQ ID NOs: 22489 to 22497. In some embodiments, any one of the peptides in the KRAS G12A vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 141 to 153, SEQ ID NO: 462, SEQ ID NOs: 7099 to 7880, or SEQ ID NOs: 22489 to 22497.

In some embodiments, the amino acid sequence for a WIC class I peptide vaccine for the KRAS G12A protein mutation comprises two or more of the SEQ ID NOs: 141 to 153 and SEQ ID NO: 462. In some embodiments, any one of the peptides in the KRAS G12A vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 141 to 153 or SEQ ID NO: 462.

In some embodiments, the amino acid sequence for a WIC class I peptide vaccine for the KRAS G12A protein mutation comprises two or more of the SEQ ID NOs: 141 to 153, SEQ ID NO: 462, SEQ ID NOs: 7099 to 7880, and SEQ ID NOs: 22489 to 22497. In some embodiments, any one of the peptides in the KRAS G12A vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 141 to 153, SEQ ID NO: 462, SEQ ID NOs: 7099 to 7880, or SEQ ID NOs: 22489 to 22497.

In some embodiments, the amino acid sequence for a WIC class I peptide vaccine for the KRAS G12S protein mutation comprises one or more of the SEQ ID NOs: 192 to 202. In some embodiments, any one of the peptides in the KRAS G12S vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 192 to 202.

In some embodiments, the amino acid sequence for a WIC class I peptide vaccine for the KRAS G12S protein mutation comprises one or more of the SEQ ID NOs: 192 to 202, SEQ ID NOs: 10237 to 11008, and SEQ ID NOs: 22528 to 22536. In some embodiments, any one of the peptides in the KRAS G12S vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 192 to 202, SEQ ID NOs: 10237 to 11008, or SEQ ID NOs: 22528 to 22536.

In some embodiments, the amino acid sequence for a WIC class I peptide vaccine for the KRAS G12S protein mutation comprises two or more of the SEQ ID NOs: 192 to 202. In some embodiments, any one of the peptides in the KRAS G12S vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 192 to 202.

In some embodiments, the amino acid sequence for a WIC class I peptide vaccine for the KRAS G12S protein mutation comprises two or more of the SEQ ID NOs: 192 to 202, SEQ ID NOs: 10237 to 11008, and SEQ ID NOs: 22528 to 22536. In some embodiments, any one of the peptides in the KRAS G12S vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 192 to 202, SEQ ID NOs: 10237 to 11008, or SEQ ID NOs: 22528 to 22536.

In some embodiments, the amino acid sequence for a WIC class I peptide vaccine for the NRAS Q61R protein mutation comprises one or more of the SEQ ID NOs: 256 to 272. In some embodiments, any one of the peptides in the NRAS Q61R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 256 to 272.

In some embodiments, the amino acid sequence for a WIC class I peptide vaccine for the NRAS Q61R protein mutation comprises one or more of the SEQ ID NOs: 256 to 272, SEQ ID NOs: 14315 to 14836, and SEQ ID NOs: 22577 to 22582. In some embodiments, any one of the peptides in the NRAS Q61R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 256 to 272, SEQ ID NOs: 14315 to 14836, or SEQ ID NOs: 22577 to 22582.

In some embodiments, the amino acid sequence for a WIC class I peptide vaccine for the NRAS Q61R protein mutation comprises two or more of the SEQ ID NOs: 256 to 272. In some embodiments, any one of the peptides in the NRAS Q61R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 256 to 272.

In some embodiments, the amino acid sequence for a MEW class I peptide vaccine for the NRAS Q61R protein mutation comprises two or more of the SEQ ID NOs: 256 to 272, SEQ ID NOs: 14315 to 14836, and SEQ ID NOs: 22577 to 22582. In some embodiments, any one of the peptides in the NRAS Q61R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 256 to 272, SEQ ID NOs: 14315 to 14836, or SEQ ID NOs: 22577 to 22582.

In some embodiments, the amino acid sequence for a MEW class I peptide vaccine for the NRAS Q61K protein mutation comprises one or more of the SEQ ID NOs: 230 to 238. In some embodiments, any one of the peptides in the NRAS Q61K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 230 to 238.

In some embodiments, the amino acid sequence for a MEW class I peptide vaccine for the NRAS Q61K protein mutation comprises one or more of the SEQ ID NOs: 230 to 238, SEQ ID NOs: 12815 to 13434, and SEQ ID NOs: 22559 to 22567. In some embodiments, any one of the peptides in the NRAS Q61K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 230 to 238, SEQ ID NOs: 12815 to 13434, or SEQ ID NOs: 22559 to 22567.

In some embodiments, the amino acid sequence for a MEW class I peptide vaccine for the NRAS Q61K protein mutation comprises two or more of the SEQ ID NOs: 230 to 238. In some embodiments, any one of the peptides in the NRAS Q61K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 230 to 238.

In some embodiments, the amino acid sequence for a MEW class I peptide vaccine for the NRAS Q61K protein mutation comprises two or more of the SEQ ID NOs: 230 to 238, SEQ ID NOs: 12815 to 13434, and SEQ ID NOs: 22559 to 22567. In some embodiments, any one of the peptides in the NRAS Q61K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 230 to 238, SEQ ID NOs: 12815 to 13434, or SEQ ID NOs: 22559 to 22567.

In some embodiments, the amino acid sequence for a MEW class I peptide vaccine for the NRAS Q61L protein mutation comprises one or more of the SEQ ID NOs: 239 to 255. In some embodiments, any one of the peptides in the NRAS Q61L vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 239 to 255.

In some embodiments, the amino acid sequence for a MEW class I peptide vaccine for the NRAS Q61L protein mutation comprises one or more of the SEQ ID NOs: 239 to 255, SEQ ID NOs: 13435 to 14314, and SEQ ID NOs: 22568 to 22576. In some embodiments, any one of the peptides in the NRAS Q61L vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 239 to 255, SEQ ID NOs: 13435 to 14314, or SEQ ID NOs: 22568 to 22576.

In some embodiments, the amino acid sequence for a MEW class I peptide vaccine for the NRAS Q61L protein mutation comprises two or more of the SEQ ID NOs: 239 to 255. In some embodiments, any one of the peptides in the NRAS Q61L vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 239 to 255.

In some embodiments, the amino acid sequence for a MEW class I peptide vaccine for the NRAS Q61L protein mutation comprises two or more of the SEQ ID NOs: 239 to 255, SEQ ID NOs: 13435 to 14314, and SEQ ID NOs: 22568 to 22576. In some embodiments, any one of the peptides in the NRAS Q61L vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 239 to 255, SEQ ID NOs: 13435 to 14314, or SEQ ID NOs: 22568 to 22576.

In some embodiments, the amino acid sequence for a MEW class I peptide vaccine for the PIK3CA E542K protein mutation comprises one or more of the SEQ ID NOs: 273 to 285. In some embodiments, any one of the peptides in the PIK3CA E542K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 273 to 285.

In some embodiments, the amino acid sequence for a MEW class I peptide vaccine for the PIK3CA E542K protein mutation comprises one or more of the SEQ ID NOs: 273 to 285, SEQ ID NOs: 14837 to 15625, and SEQ ID NOs: 22583 to 22592. In some embodiments, any one of the peptides in the PIK3CA E542K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 273 to 285, SEQ ID NOs: 14837 to 15625, or SEQ ID NOs: 22583 to 22592.

In some embodiments, the amino acid sequence for a MEW class I peptide vaccine for the PIK3CA E542K protein mutation comprises two or more of the SEQ ID NOs: 273 to 285. In some embodiments, any one of the peptides in the PIK3CA E542K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 273 to 285.

In some embodiments, the amino acid sequence for a MEW class I peptide vaccine for the PIK3CA E542K protein mutation comprises two or more of the SEQ ID NOs: 273 to 285, SEQ ID NOs: 14837 to 15625, and SEQ ID NOs: 22583 to 22592. In some embodiments, any one of the peptides in the PIK3CA E542K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 273 to 285, SEQ ID NOs: 14837 to 15625, or SEQ ID NOs: 22583 to 22592.

In some embodiments, the amino acid sequence for a MEW class I peptide vaccine for the PIK3CA E545K protein mutation comprises one or more of the SEQ ID NOs: 286 to 293 and SEQ ID NO: 467. In some embodiments, any one of the peptides in the PIK3CA E545K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 286 to 293 or SEQ ID NO: 467.

In some embodiments, the amino acid sequence for a MEW class I peptide vaccine for the PIK3CA E545K protein mutation comprises one or more of the SEQ ID NOs: 286 to 293, SEQ ID NO: 467, SEQ ID NOs: 15626 to 15907, and SEQ ID NOs: 22593 to 22602. In some embodiments, any one of the peptides in the PIK3CA E545K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 286 to 293, SEQ ID NO: 467, SEQ ID NOs: 15626 to 15907, or SEQ ID NOs: 22593 to 22602.

In some embodiments, the amino acid sequence for a MHC class I peptide vaccine for the PIK3CA E545K protein mutation comprises two or more of the SEQ ID NOs: 286 to 293 and SEQ ID NO: 467. In some embodiments, any one of the peptides in the PIK3CA E545K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 286 to 293 or SEQ ID NO: 467.

In some embodiments, the amino acid sequence for a MHC class I peptide vaccine for the PIK3CA E545K protein mutation comprises two or more of the SEQ ID NOs: 286 to 293, SEQ ID NO: 467, SEQ ID NOs: 15626 to 15907, and SEQ ID NOs: 22593 to 22602. In some embodiments, any one of the peptides in the PIK3CA E545K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 286 to 293, SEQ ID NO: 467, SEQ ID NOs: 15626 to 15907, or SEQ ID NOs: 22593 to 22602.

In some embodiments, the amino acid sequence for a MHC class I peptide vaccine for the PIK3CA H1047R protein mutation comprises one or more of the SEQ ID NOs: 294 to 309. In some embodiments, any one of the peptides in the PIK3CA H1047R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 294 to 309.

In some embodiments, the amino acid sequence for a MHC class I peptide vaccine for the PIK3CA H1047R protein mutation comprises one or more of the SEQ ID NOs: 294 to 309, SEQ ID NOs: 15908 to 16276, and SEQ ID NOs: 22603 to 22608. In some embodiments, any one of the peptides in the PIK3CA H1047R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 294 to 309, SEQ ID NOs: 15908 to 16276, or SEQ ID NOs: 22603 to 22608.

In some embodiments, the amino acid sequence for a MHC class I peptide vaccine for the PIK3CA H1047R protein mutation comprises two or more of the SEQ ID NOs: 294 to 309. In some embodiments, any one of the peptides in the PIK3CA H1047R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 294 to 309.

In some embodiments, the amino acid sequence for a MHC class I peptide vaccine for the PIK3CA H1047R protein mutation comprises two or more of the SEQ ID NOs: 294 to 309, SEQ ID NOs: 15908 to 16276, and SEQ ID NOs: 22603 to 22608. In some embodiments, any one of the peptides in the PIK3CA H1047R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 294 to 309, SEQ ID NOs: 15908 to 16276, or SEQ ID NOs: 22603 to 22608.

In some embodiments, the amino acid sequence for a MHC class I peptide vaccine for the TP53 R158L protein mutation comprises one or more of the SEQ ID NOs: 359 to 374 and SEQ ID NOs: 469 to 470. In some embodiments, any one of the peptides in the TP53 R158L vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 359 to 374 or SEQ ID NOs: 469 to 470.

In some embodiments, the amino acid sequence for a MHC class I peptide vaccine for the TP53 R158L protein mutation comprises one or more of the SEQ ID NOs: 359 to 374, SEQ ID NOs: 469 to 470, SEQ ID NOs: 18414 to 19404, and SEQ ID NOs: 22644 to 22657. In some embodiments, any one of the peptides in the TP53 R158L vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 359 to 374, SEQ ID NOs: 469 to 470, SEQ ID NOs: 18414 to 19404, or SEQ ID NOs: 22644 to 22657.

In some embodiments, the amino acid sequence for a MHC class I peptide vaccine for the TP53 R158L protein mutation comprises two or more of the SEQ ID NOs: 359 to 374 and SEQ ID NOs: 469 to 470. In some embodiments, any one of the peptides in the TP53 R158L vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 359 to 374 or SEQ ID NOs: 469 to 470.

In some embodiments, the amino acid sequence for a MHC class I peptide vaccine for the TP53 R158L protein mutation comprises two or more of the SEQ ID NOs: 359 to 374, SEQ ID NOs: 469 to 470, SEQ ID NOs: 18414 to 19404, and SEQ ID NOs: 22644 to 22657. In some embodiments, any one of the peptides in the TP53 R158L vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 359 to 374, SEQ ID NOs: 469 to 470, SEQ ID NOs: 18414 to 19404, or SEQ ID NOs: 22644 to 22657.

In some embodiments, the amino acid sequence for a WIC class I peptide vaccine for the TP53 R175H protein mutation comprises one or more of the SEQ ID NOs: 375 to 386 and SEQ ID NOs: 471 to 472. In some embodiments, any one of the peptides in the TP53 R175H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 375 to 386 or SEQ ID NOs: 471 to 472.

In some embodiments, the amino acid sequence for a WIC class I peptide vaccine for the TP53 R175H protein mutation comprises one or more of the SEQ ID NOs: 375 to 386, SEQ ID NOs: 471 to 472, SEQ ID NOs: 19405 to 19752, and SEQ ID NOs: 22658 to 22665. In some embodiments, any one of the peptides in the TP53 R175H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 375 to 386, SEQ ID NOs: 471 to 472, SEQ ID NOs: 19405 to 19752, or SEQ ID NOs: 22658 to 22665.

In some embodiments, the amino acid sequence for a WIC class I peptide vaccine for the TP53 R175H protein mutation comprises two or more of the SEQ ID NOs: 375 to 386 and SEQ ID NOs: 471 to 472. In some embodiments, any one of the peptides in the TP53 R175H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 375 to 386 or SEQ ID NOs: 471 to 472.

In some embodiments, the amino acid sequence for a WIC class I peptide vaccine for the TP53 R175H protein mutation comprises two or more of the SEQ ID NOs: 375 to 386, SEQ ID NOs: 471 to 472, SEQ ID NOs: 19405 to 19752, and SEQ ID NOs: 22658 to 22665. In some embodiments, any one of the peptides in the TP53 R175H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 375 to 386, SEQ ID NOs: 471 to 472, SEQ ID NOs: 19405 to 19752, or SEQ ID NOs: 22658 to 22665.

In some embodiments, the amino acid sequence for a MEW class I peptide vaccine for the TP53 R248Q protein mutation comprises one or more of the SEQ ID NOs: 387 to 401. In some embodiments, any one of the peptides in the TP53 R248Q vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 387 to 401.

In some embodiments, the amino acid sequence for a MEW class I peptide vaccine for the TP53 R248Q protein mutation comprises one or more of the SEQ ID NOs: 387 to 401, SEQ ID NOs: 19753 to 20608, and SEQ ID NOs: 22666 to 22678. In some embodiments, any one of the peptides in the TP53 R248Q vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 387 to 401, SEQ ID NOs: 19753 to 20608, or SEQ ID NOs: 22666 to 22678.

In some embodiments, the amino acid sequence for a MEW class I peptide vaccine for the TP53 R248Q protein mutation comprises two or more of the SEQ ID NOs: 387 to 401. In some embodiments, any one of the peptides in the TP53 R248Q vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 387 to 401.

In some embodiments, the amino acid sequence for a MEW class I peptide vaccine for the TP53 R248Q protein mutation comprises two or more of the SEQ ID NOs: 387 to 401, SEQ ID NOs: 19753 to 20608, and SEQ ID NOs: 22666 to 22678. In some embodiments, any one of the peptides in the TP53 R248Q vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 387 to 401, SEQ ID NOs: 19753 to 20608, or SEQ ID NOs: 22666 to 22678.

In some embodiments, the amino acid sequence for a MEW class I peptide vaccine for the TP53 R273C protein mutation comprises one or more of the SEQ ID NOs: 422 to 432 and SEQ ID NO: 473. In some embodiments, any one of the peptides in the TP53 R273C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 422 to 432 or SEQ ID NO: 473.

In some embodiments, the amino acid sequence for a MHC class I peptide vaccine for the TP53 R273C protein mutation comprises one or more of the SEQ ID NOs: 422 to 432, SEQ ID NO: 473, SEQ ID NOs: 21192 to 21462, and SEQ ID NOs: 22690 to 22701. In some embodiments, any one of the peptides in the TP53 R273C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 422 to 432, SEQ ID NO: 473, SEQ ID NOs: 21192 to 21462, or SEQ ID NOs: 22690 to 22701.

In some embodiments, the amino acid sequence for a MHC class I peptide vaccine for the TP53 R273C protein mutation comprises two or more of the SEQ ID NOs: 422 to 432 and SEQ ID NO: 473. In some embodiments, any one of the peptides in the TP53 R273C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 422 to 432 or SEQ ID NO: 473.

In some embodiments, the amino acid sequence for a MHC class I peptide vaccine for the TP53 R273C protein mutation comprises two or more of the SEQ ID NOs: 422 to 432, SEQ ID NO: 473, SEQ ID NOs: 21192 to 21462, and SEQ ID NOs: 22690 to 22701. In some embodiments, any one of the peptides in the TP53 R273C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 422 to 432, SEQ ID NO: 473, SEQ ID NOs: 21192 to 21462, or SEQ ID NOs: 22690 to 22701.

In some embodiments, the amino acid sequence for a MHC class I peptide vaccine for the TP53 R273H protein mutation comprises one or more of the SEQ ID NOs: 433 to 446 and SEQ ID NO: 474. In some embodiments, any one of the peptides in the TP53 R273H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 433 to 446 or SEQ ID NO: 474.

In some embodiments, the amino acid sequence for a MHC class I peptide vaccine for the TP53 R273H protein mutation comprises one or more of the SEQ ID NOs: 433 to 446, SEQ ID NO: 474, SEQ ID NOs: 21463 to 21845, and SEQ ID NOs: 22702 to 22713. In some embodiments, any one of the peptides in the TP53 R273H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 433 to 446, SEQ ID NO: 474, SEQ ID NOs: 21463 to 21845, or SEQ ID NOs: 22702 to 22713.

In some embodiments, the amino acid sequence for a MHC class I peptide vaccine for the TP53 R273H protein mutation comprises two or more of the SEQ ID NOs: 433 to 446 and SEQ ID NO: 474. In some embodiments, any one of the peptides in the TP53 R273H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 433 to 446 or SEQ ID NO: 474.

In some embodiments, the amino acid sequence for a MHC class I peptide vaccine for the TP53 R273H protein mutation comprises two or more of the SEQ ID NOs: 433 to 446, SEQ ID NO: 474, SEQ ID NOs: 21463 to 21845, and SEQ ID NOs: 22702 to 22713. In some embodiments, any one of the peptides in the TP53 R273H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 433 to 446, SEQ ID NO: 474, SEQ ID NOs: 21463 to 21845, or SEQ ID NOs: 22702 to 22713.

In some embodiments, the amino acid sequence for a MHC class I peptide vaccine for the TP53 R248W protein mutation comprises one or more of the SEQ ID NOs: 402 to 421. In some embodiments, any one of the peptides in the TP53 R248W vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 402 to 421.

In some embodiments, the amino acid sequence for a MHC class I peptide vaccine for the TP53 R248W protein mutation comprises one or more of the SEQ ID NOs: 402 to 421, SEQ ID NOs: 20609 to 21191, and SEQ ID NOs: 22679 to 22689. In some embodiments, any one of the peptides in the TP53 R248W vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 402 to 421, SEQ ID NOs: 20609 to 21191, or SEQ ID NOs: 22679 to 22689.

In some embodiments, the amino acid sequence for a WIC class I peptide vaccine for the TP53 R248W protein mutation comprises two or more of the SEQ ID NOs: 402 to 421. In some embodiments, any one of the peptides in the TP53 R248W vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 402 to 421.

In some embodiments, the amino acid sequence for a WIC class I peptide vaccine for the TP53 R248W protein mutation comprises two or more of the SEQ ID NOs: 402 to 421, SEQ ID NOs: 20609 to 21191, and SEQ ID NOs: 22679 to 22689. In some embodiments, any one of the peptides in the TP53 R248W vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 402 to 421, SEQ ID NOs: 20609 to 21191, or SEQ ID NOs: 22679 to 22689.

In some embodiments, the amino acid sequence for a WIC class I peptide vaccine for the TP53 R282W protein mutation comprises one or more of the SEQ ID NOs: 447 to 449. In some embodiments, any one of the peptides in the TP53 R282W vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 447 to 449.

In some embodiments, the amino acid sequence for a WIC class I peptide vaccine for the TP53 R282W protein mutation comprises one or more of the SEQ ID NOs: 447 to 449, SEQ ID NOs: 21846 to 21940, and SEQ ID NOs: 22714 to 22720. In some embodiments, any one of the peptides in the TP53 R282W vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 447 to 449, SEQ ID NOs: 21846 to 21940, or SEQ ID NOs: 22714 to 22720.

In some embodiments, the amino acid sequence for a WIC class I peptide vaccine for the TP53 R282W protein mutation comprises two or more of the SEQ ID NOs: 447 to 449. In some embodiments, any one of the peptides in the TP53 R282W vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 447 to 449.

In some embodiments, the amino acid sequence for a WIC class I peptide vaccine for the TP53 R282W protein mutation comprises two or more of the SEQ ID NOs: 447 to 449, SEQ ID NOs: 21846 to 21940, and SEQ ID NOs: 22714 to 22720. In some embodiments, any one of the peptides in the TP53 R282W vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 447 to 449, SEQ ID NOs: 21846 to 21940, or SEQ ID NOs: 22714 to 22720.

In some embodiments, the amino acid sequence for a WIC class I peptide vaccine for the TP53 Y220C protein mutation comprises one or more of the SEQ ID NOs: 450 to 458. In some embodiments, any one of the peptides in the TP53 Y220C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 450 to 458.

In some embodiments, the amino acid sequence for a WIC class I peptide vaccine for the TP53 Y220C protein mutation comprises one or more of the SEQ ID NOs: 450 to 458, SEQ ID NOs: 21941 to 22385, and SEQ ID NOs: 22721 to 22727. In some embodiments, any one of the peptides in the TP53 Y220C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 450 to 458, SEQ ID NOs: 21941 to 22385, or SEQ ID NOs: 22721 to 22727.

In some embodiments, the amino acid sequence for a WIC class I peptide vaccine for the TP53 Y220C protein mutation comprises two or more of the SEQ ID NOs: 450 to 458. In some embodiments, any one of the peptides in the TP53 Y220C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 450 to 458.

In some embodiments, the amino acid sequence for a WIC class I peptide vaccine for the TP53 Y220C protein mutation comprises two or more of the SEQ ID NOs: 450 to 458, SEQ ID NOs: 21941 to 22385, and SEQ ID NOs: 22721 to 22727. In some embodiments, any one of the peptides in the TP53 Y220C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 450 to 458, SEQ ID NOs: 21941 to 22385, or SEQ ID NOs: 22721 to 22727.

In some embodiments, the amino acid sequence for a MHC class I peptide vaccine for the PIK3CA R88Q protein mutation comprises one or more of the SEQ ID NOs: 310 to 322 and SEQ ID NO: 468. In some embodiments, any one of the peptides in the PIK3CA R88Q vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 310 to 322 or SEQ ID NO: 468.

In some embodiments, the amino acid sequence for a MHC class I peptide vaccine for the PIK3CA R88Q protein mutation comprises one or more of the SEQ ID NOs: 310 to 322, SEQ ID NO: 468, SEQ ID NOs: 16277 to 17342, and SEQ ID NOs: 22609 to 22622. In some embodiments, any one of the peptides in the PIK3CA R88Q vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 310 to 322, SEQ ID NO: 468, SEQ ID NOs: 16277 to 17342, or SEQ ID NOs: 22609 to 22622.

In some embodiments, the amino acid sequence for a MHC class I peptide vaccine for the PIK3CA R88Q protein mutation comprises two or more of the SEQ ID NOs: 310 to 322 and SEQ ID NO: 468. In some embodiments, any one of the peptides in the PIK3CA R88Q vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 310 to 322 or SEQ ID NO: 468.

In some embodiments, the amino acid sequence for a MHC class I peptide vaccine for the PIK3CA R88Q protein mutation comprises two or more of the SEQ ID NOs: 310 to 322, SEQ ID NO: 468, SEQ ID NOs: 16277 to 17342, and SEQ ID NOs: 22609 to 22622. In some embodiments, any one of the peptides in the PIK3CA R88Q vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 310 to 322, SEQ ID NO: 468, SEQ ID NOs: 16277 to 17342, or SEQ ID NOs: 22609 to 22622.

In some embodiments, the amino acid sequence for a MHC class I peptide vaccine for the GTF2I L424H protein mutation comprises one or more of the SEQ ID NOs: 99 to 118. In some embodiments, any one of the peptides in the GTF2I L424H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 99 to 118.

In some embodiments, the amino acid sequence for a MHC class I peptide vaccine for the GTF2I L424H protein mutation comprises one or more of the SEQ ID NOs: 99 to 118, SEQ ID NOs: 5757 to 6498, and SEQ ID NOs: 22450 to 22466. In some embodiments, any one of the peptides in the GTF2I L424H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 99 to 118, SEQ ID NOs: 5757 to 6498, or SEQ ID NOs: 22450 to 22466.

In some embodiments, the amino acid sequence for a MHC class I peptide vaccine for the GTF2I L424H protein mutation comprises two or more of the SEQ ID NOs: 99 to 118. In some embodiments, any one of the peptides in the GTF2I L424H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 99 to 118.

In some embodiments, the amino acid sequence for a MHC class I peptide vaccine for the GTF2I L424H protein mutation comprises two or more of the SEQ ID NOs: 99 to 118, SEQ ID NOs: 5757 to 6498, and SEQ ID NOs: 22450 to 22466. In some embodiments, any one of the peptides in the GTF2I L424H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 99 to 118, SEQ ID NOs: 5757 to 6498, or SEQ ID NOs: 22450 to 22466.

In some embodiments, the amino acid sequence for a MHC class I peptide vaccine for the PTEN R130Q protein mutation comprises one or more of the SEQ ID NOs: 338 to 353. In some embodiments, any one of the peptides in the PTEN R130Q vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 338 to 353.

In some embodiments, the amino acid sequence for a MHC class I peptide vaccine for the PTEN R130Q protein mutation comprises one or more of the SEQ ID NOs: 338 to 353, SEQ ID NOs: 17869 to 18205, and SEQ ID NOs: 22630 to 22636. In some embodiments, any one of the peptides in the PTEN R130Q vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 338 to 353, SEQ ID NOs: 17869 to 18205, or SEQ ID NOs: 22630 to 22636.

In some embodiments, the amino acid sequence for a MEW class I peptide vaccine for the PTEN R130Q protein mutation comprises two or more of the SEQ ID NOs: 338 to 353. In some embodiments, any one of the peptides in the PTEN R130Q vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 338 to 353.

In some embodiments, the amino acid sequence for a MEW class I peptide vaccine for the PTEN R130Q protein mutation comprises two or more of the SEQ ID NOs: 338 to 353, SEQ ID NOs: 17869 to 18205, and SEQ ID NOs: 22630 to 22636. In some embodiments, any one of the peptides in the PTEN R130Q vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 338 to 353, SEQ ID NOs: 17869 to 18205, or SEQ ID NOs: 22630 to 22636.

In some embodiments, the amino acid sequence for a MEW class I peptide vaccine for the AKT1 E17K protein mutation comprises one or more of the SEQ ID NOs: 1 to 18 and SEQ ID NO: 459. In some embodiments, any one of the peptides in the AKT1 E17K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 1 to 18 or SEQ ID NO: 459.

In some embodiments, the amino acid sequence for a MEW class I peptide vaccine for the AKT1 E17K protein mutation comprises one or more of the SEQ ID NOs: 1 to 18, SEQ ID NO: 459, SEQ ID NOs: 760 to 1768, and SEQ ID NOs: 22386 to 22396. In some embodiments, any one of the peptides in the AKT1 E17K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 1 to 18, SEQ ID NO: 459, SEQ ID NOs: 760 to 1768, or SEQ ID NOs: 22386 to 22396.

In some embodiments, the amino acid sequence for a MEW class I peptide vaccine for the AKT1 E17K protein mutation comprises two or more of the SEQ ID NOs: 1 to 18 and SEQ ID NO: 459. In some embodiments, any one of the peptides in the AKT1 E17K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 1 to 18 or SEQ ID NO: 459.

In some embodiments, the amino acid sequence for a WIC class I peptide vaccine for the AKT1 E17K protein mutation comprises two or more of the SEQ ID NOs: 1 to 18, SEQ ID NO: 459, SEQ ID NOs: 760 to 1768, and SEQ ID NOs: 22386 to 22396. In some embodiments, any one of the peptides in the AKT1 E17K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 1 to 18, SEQ ID NO: 459, SEQ ID NOs: 760 to 1768, or SEQ ID NOs: 22386 to 22396.

In some embodiments, the amino acid sequence for a WIC class I peptide vaccine for the PTEN R130G protein mutation comprises one or more of the SEQ ID NOs: 323 to 337. In some embodiments, any one of the peptides in the PTEN R130G vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 323 to 337.

In some embodiments, the amino acid sequence for a WIC class I peptide vaccine for the PTEN R130G protein mutation comprises one or more of the SEQ ID NOs: 323 to 337, SEQ ID NOs: 17343 to 17868, and SEQ ID NOs: 22623 to 22629. In some embodiments, any one of the peptides in the PTEN R130G vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 323 to 337, SEQ ID NOs: 17343 to 17868, or SEQ ID NOs: 22623 to 22629.

In some embodiments, the amino acid sequence for a WIC class I peptide vaccine for the PTEN R130G protein mutation comprises two or more of the SEQ ID NOs: 323 to 337. In some embodiments, any one of the peptides in the PTEN R130G vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 323 to 337.

In some embodiments, the amino acid sequence for a WIC class I peptide vaccine for the PTEN R130G protein mutation comprises two or more of the SEQ ID NOs: 323 to 337, SEQ ID NOs: 17343 to 17868, and SEQ ID NOs: 22623 to 22629. In some embodiments, any one of the peptides in the PTEN R130G vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 323 to 337, SEQ ID NOs: 17343 to 17868, or SEQ ID NOs: 22623 to 22629.

In some embodiments, the amino acid sequence for a MEW class I peptide vaccine for the TP53 H179R protein mutation comprises one or more of the SEQ ID NOs: 354 to 358. In some embodiments, any one of the peptides in the TP53 H179R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 354 to 358.

In some embodiments, the amino acid sequence for a MEW class I peptide vaccine for the TP53 H179R protein mutation comprises one or more of the SEQ ID NOs: 354 to 358, SEQ ID NOs: 18206 to 18413, and SEQ ID NOs: 22637 to 22643. In some embodiments, any one of the peptides in the TP53 H179R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 354 to 358, SEQ ID NOs: 18206 to 18413, or SEQ ID NOs: 22637 to 22643.

In some embodiments, the amino acid sequence for a MEW class I peptide vaccine for the TP53 H179R protein mutation comprises two or more of the SEQ ID NOs: 354 to 358. In some embodiments, any one of the peptides in the TP53 H179R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 354 to 358.

In some embodiments, the amino acid sequence for a MEW class I peptide vaccine for the TP53 H179R protein mutation comprises two or more of the SEQ ID NOs: 354 to 358, SEQ ID NOs: 18206 to 18413, and SEQ ID NOs: 22637 to 22643. In some embodiments, any one of the peptides in the TP53 H179R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 354 to 358, SEQ ID NOs: 18206 to 18413, or SEQ ID NOs: 22637 to 22643.

In some embodiments, the amino acid sequence vaccine for a MHC class I peptide vaccine for pancreatic cancer comprises one or more of the SEQ ID NOs: 168 to 169, SEQ ID NO: 171, SEQ ID NOs: 179 to 180, SEQ ID NOs: 182 to 183, SEQ ID NOs: 203 to 204, and SEQ ID NO: 207. In some embodiments, any one of the peptides in the pancreatic cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 168 to 169, SEQ ID NO:

171, SEQ ID NOs: 179 to 180, SEQ ID NOs: 182 to 183, SEQ ID NOs: 203 to 204, or SEQ ID NO: 207.

In some embodiments, the amino acid sequence vaccine for a MHC class I peptide vaccine for pancreatic cancer comprises two or more of the SEQ ID NOs: 168 to 169, SEQ ID NO: 171, SEQ ID NOs: 179 to 180, SEQ ID NOs: 182 to 183, SEQ ID NOs: 203 to 204, and SEQ ID NO: 207. In some embodiments, any one of the peptides in the pancreatic cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 168 to 169, SEQ ID NO: 171, SEQ ID NOs: 179 to 180, SEQ ID NOs: 182 to 183, SEQ ID NOs: 203 to 204, or SEQ ID NO: 207.

In some embodiments, the amino acid sequence vaccine for a MHC class I peptide vaccine for skin cancer comprises one or more of the SEQ ID NOs: 19 to 23, SEQ ID NOs: 34 to 40, SEQ ID NOs: 230 to 231, SEQ ID NO: 239, SEQ ID NOs: 241 to 242, and SEQ ID NOs: 260 to 262. In some embodiments, any one of the peptides in the skin cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 19 to 23, SEQ ID NOs: 34 to 40, SEQ ID NOs: 230 to 231, SEQ ID NO: 239, SEQ ID NOs: 241 to 242, or SEQ ID NOs: 260 to 262.

In some embodiments, the amino acid sequence vaccine for a MHC class I peptide vaccine for skin cancer comprises two or more of the SEQ ID NOs: 19 to 23, SEQ ID NOs: 34 to 40, SEQ ID NOs: 230 to 231, SEQ ID NO: 239, SEQ ID NOs: 241 to 242, and SEQ ID NOs: 260 to 262. In some embodiments, any one of the peptides in the skin cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 19 to 23, SEQ ID NOs: 34 to 40, SEQ ID NOs: 230 to 231, SEQ ID NO: 239, SEQ ID NOs: 241 to 242, or SEQ ID NOs: 260 to 262.

In some embodiments, the amino acid sequence vaccine for a MHC class I peptide vaccine for thyroid cancer comprises one or more of the SEQ ID NOs: 19 to 23, SEQ ID NOs: 230 to 231, and SEQ ID NOs: 260 to 262. In some embodiments, any one of the peptides in the thyroid cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 19 to 23, SEQ ID NOs: 230 to 231, or SEQ ID NOs: 260 to 262.

In some embodiments, the amino acid sequence vaccine for a MHC class I peptide vaccine for thyroid cancer comprises two or more of the SEQ ID NOs: 19 to 23, SEQ ID NOs: 230 to 231, and SEQ ID NOs: 260 to 262. In some embodiments, any one of the peptides in the thyroid cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 19 to 23, SEQ ID NOs: 230 to 231, or SEQ ID NOs: 260 to 262.

In some embodiments, the amino acid sequence vaccine for a MHC class I peptide vaccine for brain cancer comprises one or more of the SEQ ID NOs: 51 to 55, SEQ ID NOs: 67 to 70, SEQ ID NOs: 72 to 73, SEQ ID NOs: 119 to 120, SEQ ID NOs: 125 to 130, SEQ ID NO: 375, SEQ ID NO: 423, SEQ ID NO: 425, and SEQ ID NOs: 471 to 473. In some embodiments, any one of the peptides in the brain cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 51 to 55, SEQ ID NOs: 67 to 70, SEQ ID NOs: 72 to 73, SEQ ID NOs: 119 to 120, SEQ ID NOs: 125 to 130, SEQ ID NO: 375, SEQ ID NO: 423, SEQ ID NO: 425, or SEQ ID NOs: 471 to 473.

In some embodiments, the amino acid sequence vaccine for a MHC class I peptide vaccine for brain cancer comprises two or more of the SEQ ID NOs: 51 to 55, SEQ ID NOs: 67 to 70, SEQ ID NOs: 72 to 73, SEQ ID NOs: 119 to 120, SEQ ID NOs: 125 to 130, SEQ ID NO: 375, SEQ ID NO: 423, SEQ ID NO: 425, and SEQ ID NOs: 471 to 473. In some embodiments, any one of the peptides in the brain cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 51 to 55, SEQ ID NOs: 67 to 70, SEQ ID NOs: 72 to 73, SEQ ID NOs: 119 to 120, SEQ ID NOs: 125 to 130, SEQ ID NO: 375, SEQ ID NO: 423, SEQ ID NO: 425, or SEQ ID NOs: 471 to 473.

In some embodiments, the amino acid sequence vaccine for a MHC class I peptide vaccine for colorectal cancer comprises one or more of the SEQ ID NOs: 20 to 23, SEQ ID NOs: 167 to 169, SEQ ID NO: 171, SEQ ID NOs: 203 to 207, SEQ ID NOs: 215 to 217, SEQ ID NO: 288, SEQ ID NO: 467, and SEQ ID NOs: 471 to 472. In some embodiments, any one of the peptides in the colorectal cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 20 to 23, SEQ ID NOs: 167 to 169, SEQ ID NO: 171, SEQ ID NOs: 203 to 207, SEQ ID NOs: 215 to 217, SEQ ID NO: 288, SEQ ID NO: 467, or SEQ ID NOs: 471 to 472.

In some embodiments, the amino acid sequence vaccine for a MHC class I peptide vaccine for colorectal cancer comprises two or more of the SEQ ID NOs: 20 to 23, SEQ ID NOs: 167 to 169, SEQ ID NO: 171, SEQ ID NOs: 203 to 207, SEQ ID NOs: 215 to 217, SEQ ID NO: 288, SEQ ID NO: 467, and SEQ ID NOs: 471 to 472. In some embodiments, any one of the peptides in the colorectal cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 20 to 23, SEQ ID NOs: 167 to 169, SEQ ID NO: 171, SEQ ID NOs: 203 to 207, SEQ ID NOs: 215 to 217, SEQ ID NO: 288, SEQ ID NO: 467, or SEQ ID NOs: 471 to 472.

In some embodiments, the amino acid sequence vaccine for a MHC class I peptide vaccine for bronchus and lung cancer comprises one or more of the SEQ ID NOs: 82 to 86, SEQ ID NOs: 141 to 144, SEQ ID NOs: 154 to 159, SEQ ID NOs: 168 to 169, SEQ ID NO: 171, SEQ ID NOs: 203 to 204, SEQ ID NO: 207, SEQ ID NOs: 274 to 276, SEQ ID NO: 288, SEQ ID NO: 359, SEQ ID NOs: 362 to 364, and SEQ ID NO: 467. In some embodiments, any one of the peptides in the bronchus and lung cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 82 to 86, SEQ ID NOs: 141 to 144, SEQ ID NOs: 154 to 159, SEQ ID NOs: 168 to 169, SEQ ID NO: 171, SEQ ID NOs: 203 to 204, SEQ ID NO: 207, SEQ ID NOs: 274 to 276, SEQ ID NO: 288, SEQ ID NO: 359, SEQ ID NOs: 362 to 364, or SEQ ID NO: 467.

In some embodiments, the amino acid sequence vaccine for a MHC class I peptide vaccine for bronchus and lung cancer comprises two or more of the SEQ ID NOs: 82 to 86, SEQ ID NOs: 141 to 144, SEQ ID NOs: 154 to 159, SEQ ID NOs: 168 to 169, SEQ ID NO: 171, SEQ ID NOs: 203 to 204, SEQ ID NO: 207, SEQ ID NOs: 274 to 276, SEQ ID NO: 288, SEQ ID NO: 359, SEQ ID NOs: 362 to 364, and SEQ ID NO: 467. In some embodiments, any one of the peptides in the bronchus and lung cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 82 to 86, SEQ ID NOs: 141 to 144, SEQ ID NOs:

154 to 159, SEQ ID NOs: 168 to 169, SEQ ID NO: 171, SEQ ID NOs: 203 to 204, SEQ ID NO: 207, SEQ ID NOs: 274 to 276, SEQ ID NO: 288, SEQ ID NO: 359, SEQ ID NOs: 362 to 364, or SEQ ID NO: 467.

In some embodiments, the amino acid sequence vaccine for a MHC class I peptide vaccine for breast cancer comprises one or more of the SEQ ID NOs: 273 to 309, SEQ ID NOs: 375 to 386, SEQ ID NOs: 422 to 446, SEQ ID NO: 467, and SEQ ID NOs: 471 to 474. In some embodiments, any one of the peptides in the breast cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 273 to 309, SEQ ID NOs: 375 to 386, SEQ ID NOs: 422 to 446, SEQ ID NO: 467, or SEQ ID NOs: 471 to 474.

In some embodiments, the amino acid sequence vaccine for a MHC class I peptide vaccine for breast cancer comprises two or more of the SEQ ID NOs: 273 to 309, SEQ ID NOs: 375 to 386, SEQ ID NOs: 422 to 446, SEQ ID NO: 467, and SEQ ID NOs: 471 to 474. In some embodiments, any one of the peptides in the breast cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 273 to 309, SEQ ID NOs: 375 to 386, SEQ ID NOs: 422 to 446, SEQ ID NO: 467, or SEQ ID NOs: 471 to 474.

In some embodiments, the amino acid sequence vaccine for a MHC class I peptide vaccine for ovarian cancer comprises one or more of the SEQ ID NOs: 273 to 309, SEQ ID NOs: 375 to 386, SEQ ID NOs: 422 to 446, SEQ ID NO: 467, and SEQ ID NOs: 471 to 474. In some embodiments, any one of the peptides in the ovarian cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 273 to 309, SEQ ID NOs: 375 to 386, SEQ ID NOs: 422 to 446, SEQ ID NO: 467, or SEQ ID NOs: 471 to 474.

In some embodiments, the amino acid sequence vaccine for a MHC class I peptide vaccine for ovarian cancer comprises two or more of the SEQ ID NOs: 273 to 309, SEQ ID NOs: 375 to 386, SEQ ID NOs: 422 to 446, SEQ ID NO: 467, and SEQ ID NOs: 471 to 474. In some embodiments, any one of the peptides in the ovarian cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 273 to 309, SEQ ID NOs: 375 to 386, SEQ ID NOs: 422 to 446, SEQ ID NO: 467, or SEQ ID NOs: 471 to 474.

Table 1 shows MHC class I peptide sequences described herein including the respective SEQ ID NO, amino acid sequence corresponding to the SEQ ID NO, protein target (with specific mutation), the seed amino acid sequence (i.e., the amino acid sequence of the wild type protein fragment), the amino acid substitution (if any) for heteroclitic peptides at positions 2 and C (carboxyl terminus), and notes detailing embodiments in which the peptide may be included in a combined peptide vaccine as described herein. In some embodiments, any combination of peptides listed in Table 1 (SEQ ID NOs: 1 to 474) may be used to create a combined peptide vaccine having between about 2 and about 40 peptides. In some embodiments, any one of the peptides (peptides 1 to 474; SEQ ID NOs: 1 to 474) in the combined vaccine comprises an amino acid sequence 80, 81, 82, 83, 84, 85, 86, 87, 88, 89, 90, 91, 92, 93, 94, 95, 96, 97, 98 or 99% identical to any of SEQ ID NOs: 1 to 474.

Additional amino acid sequences of MHC class I vaccine peptides are provided in Sequence Listings (SEQ ID NOs: 760 to 22727). In some embodiments, any combination of MHC class I peptides disclosed herein (SEQ ID NOs: 1 to 474 and SEQ ID NOs: 760 to 22727) may be used to create a combined peptide vaccine having between about 2 and about 40 peptides. In some embodiments, any one of the peptides (SEQ ID NOs: 1 to 474 and SEQ ID NOs: 760 to 22727) in the combined vaccine comprises or contains an amino acid sequence 80, 81, 82, 83, 84, 85, 86, 87, 88, 89, 90, 91, 92, 93, 94, 95, 96, 97, 98 or 99% identical to any of SEQ ID NOs: 1 to 474 or SEQ ID NOs: 760 to 22727.

MHC Class II Peptide Sequences

In some embodiments, a peptide vaccine (single target or combined multiple target vaccine) comprises about 1 to 40 MHC class II peptides with each peptide consisting of about 20 amino acids. In some embodiments, an MHC class II peptide vaccine is intended for one or more of the AKT1, BRAF, EGFR, GTF2I, HRAS, IDH1, KRAS, NRAS, PIK3CA, PTEN, or TP53 mutated protein targets. In some embodiments, an MHC class II peptide vaccine is intended for one or more of the AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, or TP53 Y220C protein mutation targets. In some embodiments, an MHC class II peptide vaccine is intended for one or more of the pancreatic cancer, skin cancer, thyroid cancer, brain cancer, colorectal cancer, bronchus and lung cancer, breast cancer, or ovarian cancer indications.

In some embodiments, the amino acid sequence for a MHC class II peptide vaccine for mutation in the AKT1 protein comprises one or more of the SEQ ID NOs: 475 to 483. In some embodiments, any one of the peptides in the AKT1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 475 to 483.

In some embodiments, the amino acid sequence for a MHC class II peptide vaccine for mutation in the AKT1 protein comprises one or more of the SEQ ID NOs: 475 to 483, SEQ ID NOs: 22728 to 22838, and SEQ ID NOs: 25305 to 25488. In some embodiments, any one of the peptides in the AKT1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 475 to 483, SEQ ID NOs: 22728 to 22838, or SEQ ID NOs: 25305 to 25488.

In some embodiments, the amino acid sequence for a MHC class II peptide vaccine for mutation in the AKT1 protein comprises two or more of the SEQ ID NOs: 475 to 483. In some embodiments, any one of the peptides in the AKT1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 475 to 483.

In some embodiments, the amino acid sequence for a MHC class II peptide vaccine for mutation in the AKT1 protein comprises two or more of the SEQ ID NOs: 475 to 483, SEQ ID NOs: 22728 to 22838, and SEQ ID NOs: 25305 to 25488. In some embodiments, any one of the peptides in the AKT1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 475 to 483, SEQ ID NOs: 22728 to 22838, or SEQ ID NOs: 25305 to 25488.

In some embodiments, the amino acid sequence for a MHC class II peptide vaccine for mutation in the BRAF protein comprises one or more of the SEQ ID NOs: 484 to 502. In some embodiments, any one of the peptides in the BRAF vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 484 to 502.

In some embodiments, the amino acid sequence for a MHC class II peptide vaccine for mutation in the BRAF protein comprises one or more of the SEQ ID NOs: 484 to 502, SEQ ID NOs: 22839 to 22966, and SEQ ID NOs: 25489 to 25616. In some embodiments, any one of the peptides in the BRAF vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 484 to 502, SEQ ID NOs: 22839 to 22966, or SEQ ID NOs: 25489 to 25616.

In some embodiments, the amino acid sequence for a MHC class II peptide vaccine for mutation in the BRAF protein comprises two or more of the SEQ ID NOs: 484 to 502. In some embodiments, any one of the peptides in the BRAF vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 484 to 502.

In some embodiments, the amino acid sequence for a MHC class II peptide vaccine for mutation in the BRAF protein comprises two or more of the SEQ ID NOs: 484 to 502, SEQ ID NOs: 22839 to 22966, and SEQ ID NOs: 25489 to 25616. In some embodiments, any one of the peptides in the BRAF vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 484 to 502, SEQ ID NOs: 22839 to 22966, or SEQ ID NOs: 25489 to 25616.

In some embodiments, the amino acid sequence for a MHC class II peptide vaccine for mutation in the EGFR protein comprises one or more of the SEQ ID NOs: 503 to 527. In some embodiments, any one of the peptides in the EGFR vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 503 to 527.

In some embodiments, the amino acid sequence for a MHC class II peptide vaccine for mutation in the EGFR protein comprises one or more of the SEQ ID NOs: 503 to 527, SEQ ID NOs: 22967 to 23263, and SEQ ID NOs: 25617 to 26046. In some embodiments, any one of the peptides in the EGFR vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 503 to 527, SEQ ID NOs: 22967 to 23263, or SEQ ID NOs: 25617 to 26046.

In some embodiments, the amino acid sequence for a MHC class II peptide vaccine for mutation in the EGFR protein comprises two or more of the SEQ ID NOs: 503 to 527. In some embodiments, any one of the peptides in the EGFR vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 503 to 527.

In some embodiments, the amino acid sequence for a MHC class II peptide vaccine for mutation in the EGFR protein comprises two or more of the SEQ ID NOs: 503 to 527, SEQ ID NOs: 22967 to 23263, and SEQ ID NOs: 25617 to 26046. In some embodiments, any one of the peptides in the EGFR vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 503 to 527, SEQ ID NOs: 22967 to 23263, or SEQ ID NOs: 25617 to 26046.

In some embodiments, the amino acid sequence for a MHC class II peptide vaccine for mutation in the GTF2I protein comprises one or more of the SEQ ID NOs: 528 to 534. In some embodiments, any one of the peptides in the GTF2I vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 528 to 534.

In some embodiments, the amino acid sequence for a MHC class II peptide vaccine for mutation in the GTF2I protein comprises one or more of the SEQ ID NOs: 528 to 534, SEQ ID NOs: 23264 to 23415, and SEQ ID NOs: 26047 to 26375. In some embodiments, any one of the peptides in the GTF2I vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 528 to 534, SEQ ID NOs: 23264 to 23415, or SEQ ID NOs: 26047 to 26375.

In some embodiments, the amino acid sequence for a MHC class II peptide vaccine for mutation in the GTF2I protein comprises two or more of the SEQ ID NOs: 528 to 534. In some embodiments, any one of the peptides in the GTF2I vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 528 to 534.

In some embodiments, the amino acid sequence for a MHC class II peptide vaccine for mutation in the GTF2I protein comprises two or more of the SEQ ID NOs: 528 to 534, SEQ ID NOs: 23264 to 23415, and SEQ ID NOs: 26047 to 26375. In some embodiments, any one of the peptides in the GTF2I vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 528 to 534, SEQ ID NOs: 23264 to 23415, or SEQ ID NOs: 26047 to 26375.

In some embodiments, the amino acid sequence for a MHC class II peptide vaccine for mutation in the IDH1 protein comprises one or more of the SEQ ID NOs: 535 to 553. In some embodiments, any one of the peptides in the IDH1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 535 to 553.

In some embodiments, the amino acid sequence for a MHC class II peptide vaccine for mutation in the IDH1 protein comprises one or more of the SEQ ID NOs: 535 to 553, SEQ ID NOs: 23416 to 23631, and SEQ ID NOs: 26376 to 26614. In some embodiments, any one of the peptides in the IDH1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 535 to 553, SEQ ID NOs: 23416 to 23631, or SEQ ID NOs: 26376 to 26614.

In some embodiments, the amino acid sequence for a MHC class II peptide vaccine for mutation in the IDH1 protein comprises two or more of the SEQ ID NOs: 535 to 553. In some embodiments, any one of the peptides in the IDH1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 535 to 553.

In some embodiments, the amino acid sequence for a MHC class II peptide vaccine for mutation in the IDH1 protein comprises two or more of the SEQ ID NOs: 535 to 553, SEQ ID NOs: 23416 to 23631, and SEQ ID NOs: 26376 to 26614. In some embodiments, any one of the peptides in the IDH1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 535 to 553, SEQ ID NOs: 23416 to 23631, or SEQ ID NOs: 26376 to 26614.

In some embodiments, the amino acid sequence for a MHC class II peptide vaccine for mutation in the KRAS protein comprises one or more of the SEQ ID NOs: 554 to 615 and SEQ ID NO: 759. In some embodiments, any one of the peptides in the KRAS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 554 to 615 or SEQ ID NO: 759.

In some embodiments, the amino acid sequence for a MHC class II peptide vaccine for mutation in the KRAS protein comprises one or more of the SEQ ID NOs: 554 to 615, SEQ ID NO: 759, SEQ ID NOs: 23632 to 24129, and SEQ ID NOs: 26615 to 27328. In some embodiments, any one of the peptides in the KRAS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 554 to 615, SEQ ID NO: 759, SEQ ID NOs: 23632 to 24129, or SEQ ID NOs: 26615 to 27328.

In some embodiments, the amino acid sequence for a MHC class II peptide vaccine for mutation in the KRAS protein comprises two or more of the SEQ ID NOs: 554 to 615 and SEQ ID NO: 759. In some embodiments, any one of the peptides in the KRAS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 554 to 615 or SEQ ID NO: 759.

In some embodiments, the amino acid sequence for a MHC class II peptide vaccine for mutation in the KRAS protein comprises two or more of the SEQ ID NOs: 554 to 615, SEQ ID NO: 759, SEQ ID NOs: 23632 to 24129, and SEQ ID NOs: 26615 to 27328. In some embodiments, any one of the peptides in the KRAS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 554 to 615, SEQ ID NO: 759, SEQ ID NOs: 23632 to 24129, or SEQ ID NOs: 26615 to 27328.

In some embodiments, the amino acid sequence for a MHC class II peptide vaccine for mutation in the NRAS protein comprises one or more of the SEQ ID NOs: 616 to 645. In some embodiments, any one of the peptides in the NRAS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 616 to 645.

In some embodiments, the amino acid sequence for a MHC class II peptide vaccine for mutation in the NRAS protein comprises one or more of the SEQ ID NOs: 616 to 645, SEQ ID NOs: 24130 to 24347, and SEQ ID NOs: 27329 to 27557. In some embodiments, any one of the peptides in the NRAS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 616 to 645, SEQ ID NOs: 24130 to 24347, or SEQ ID NOs: 27329 to 27557.

In some embodiments, the amino acid sequence for a MHC class II peptide vaccine for mutation in the NRAS protein comprises two or more of the SEQ ID NOs: 616 to 645. In some embodiments, any one of the peptides in the NRAS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 616 to 645.

In some embodiments, the amino acid sequence for a MHC class II peptide vaccine for mutation in the NRAS protein comprises two or more of the SEQ ID NOs: 616 to 645, SEQ ID NOs: 24130 to 24347, and SEQ ID NOs: 27329 to 27557. In some embodiments, any one of the peptides in the NRAS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 616 to 645, SEQ ID NOs: 24130 to 24347, or SEQ ID NOs: 27329 to 27557.

In some embodiments, the amino acid sequence for a MHC class II peptide vaccine for mutation in the PIK3CA protein comprises one or more of the SEQ ID NOs: 646 to 675. In some embodiments, any one of the peptides in the PIK3CA vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 646 to 675.

In some embodiments, the amino acid sequence for a MHC class II peptide vaccine for mutation in the PIK3CA protein comprises one or more of the SEQ ID NOs: 646 to 675, SEQ ID NOs: 24348 to 24571, and SEQ ID NOs: 27558 to 27889. In some embodiments, any one of the peptides in the PIK3CA vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 646 to 675, SEQ ID NOs: 24348 to 24571, or SEQ ID NOs: 27558 to 27889.

In some embodiments, the amino acid sequence for a MHC class II peptide vaccine for mutation in the PIK3CA protein comprises two or more of the SEQ ID NOs: 646 to 675. In some embodiments, any one of the peptides in the PIK3CA vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 646 to 675.

In some embodiments, the amino acid sequence for a MHC class II peptide vaccine for mutation in the PIK3CA protein comprises two or more of the SEQ ID NOs: 646 to 675, SEQ ID NOs: 24348 to 24571, and SEQ ID NOs: 27558 to 27889. In some embodiments, any one of the peptides in the PIK3CA vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 646 to 675, SEQ ID NOs: 24348 to 24571, or SEQ ID NOs: 27558 to 27889.

In some embodiments, the amino acid sequence for a MHC class II peptide vaccine for mutation in the PTEN protein comprises one or more of the SEQ ID NOs: 676 to 690. In some embodiments, any one of the peptides in the PTEN vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 676 to 690.

In some embodiments, the amino acid sequence for a MHC class II peptide vaccine for mutation in the PTEN protein comprises one or more of the SEQ ID NOs: 676 to 690, SEQ ID NOs: 24572 to 24724, and SEQ ID NOs: 27890 to 28052. In some embodiments, any one of the peptides in the PTEN vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 676 to 690, SEQ ID NOs: 24572 to 24724, or SEQ ID NOs: 27890 to 28052.

In some embodiments, the amino acid sequence for a MHC class II peptide vaccine for mutation in the PTEN protein comprises two or more of the SEQ ID NOs: 676 to 690. In some embodiments, any one of the peptides in the PTEN vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 676 to 690.

In some embodiments, the amino acid sequence for a MHC class II peptide vaccine for mutation in the PTEN protein comprises two or more of the SEQ ID NOs: 676 to 690, SEQ ID NOs: 24572 to 24724, and SEQ ID NOs: 27890 to 28052. In some embodiments, any one of the peptides in the PTEN vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 676 to 690, SEQ ID NOs: 24572 to 24724, or SEQ ID NOs: 27890 to 28052.

In some embodiments, the amino acid sequence for a MHC class II peptide vaccine for mutation in the TP53 protein comprises one or more of the SEQ ID NOs: 691 to 758. In some embodiments, any one of the peptides in the TP53 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 691 to 758.

In some embodiments, the amino acid sequence for a MHC class II peptide vaccine for mutation in the TP53 protein comprises one or more of the SEQ ID NOs: 691 to 758, SEQ ID NOs: 24725 to 25304, and SEQ ID NOs: 28053 to 28795. In some embodiments, any one of the peptides in the TP53 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 691 to 758, SEQ ID NOs: 24725 to 25304, or SEQ ID NOs: 28053 to 28795.

In some embodiments, the amino acid sequence for a MHC class II peptide vaccine for mutation in the TP53 protein comprises two or more of the SEQ ID NOs: 691 to 758. In some embodiments, any one of the peptides in the TP53 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 691 to 758.

In some embodiments, the amino acid sequence for a MHC class II peptide vaccine for mutation in the TP53 protein comprises two or more of the SEQ ID NOs: 691 to 758, SEQ ID NOs: 24725 to 25304, and SEQ ID NOs: 28053 to 28795. In some embodiments, any one of the peptides in the TP53 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 691 to 758, SEQ ID NOs: 24725 to 25304, or SEQ ID NOs: 28053 to 28795.

In some embodiments, the amino acid sequence for a MHC class II peptide vaccine for mutation in the RAS protein comprises one or more of the SEQ ID NOs: 554 to 645 and SEQ ID NO: 759. In some embodiments, any one of the peptides in the RAS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 554 to 645 or SEQ ID NO: 759.

In some embodiments, the amino acid sequence for a MHC class II peptide vaccine for mutation in the RAS protein comprises one or more of the SEQ ID NOs: 554 to 645, SEQ ID NO: 759, SEQ ID NOs: 23632 to 24347, and SEQ ID NOs: 26615 to 27557. In some embodiments, any one of the peptides in the RAS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 554 to 645, SEQ ID NO: 759, SEQ ID NOs: 23632 to 24347, or SEQ ID NOs: 26615 to 27557.

In some embodiments, the amino acid sequence for a MHC class II peptide vaccine for mutation in the RAS protein comprises two or more of the SEQ ID NOs: 554 to 645 and SEQ ID NO: 759. In some embodiments, any one of the peptides in the RAS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 554 to 645 or SEQ ID NO: 759.

In some embodiments, the amino acid sequence for a MHC class II peptide vaccine for mutation in the RAS protein comprises two or more of the SEQ ID NOs: 554 to 645, SEQ ID NO: 759, SEQ ID NOs: 23632 to 24347, and SEQ ID NOs: 26615 to 27557. In some embodiments, any one of the peptides in the RAS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 554 to 645, SEQ ID NO: 759, SEQ ID NOs: 23632 to 24347, or SEQ ID NOs: 26615 to 27557.

In some embodiments, the amino acid sequence for a MHC class II peptide vaccine for the BRAF V600 protein mutation comprises one or more of the SEQ ID NOs: 484 to 494. In some embodiments, any one of the peptides in the BRAF V600 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 484 to 494.

In some embodiments, the amino acid sequence for a MHC class II peptide vaccine for the BRAF V600 protein mutation comprises one or more of the SEQ ID NOs: 484 to 494, SEQ ID NOs: 22839 to 22876, and SEQ ID NOs: 25489 to 25526. In some embodiments, any one of the peptides in the BRAF V600 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 484 to 494, SEQ ID NOs: 22839 to 22876, or SEQ ID NOs: 25489 to 25526.

In some embodiments, the amino acid sequence for a MHC class II peptide vaccine for the BRAF V600 protein mutation comprises two or more of the SEQ ID NOs: 484 to 494. In some embodiments, any one of the peptides in the BRAF V600 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 484 to 494.

In some embodiments, the amino acid sequence for a MHC class II peptide vaccine for the BRAF V600 protein mutation comprises two or more of the SEQ ID NOs: 484 to 494, SEQ ID NOs: 22839 to 22876, and SEQ ID NOs: 25489 to 25526. In some embodiments, any one of the peptides in the BRAF V600 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 484 to 494, SEQ ID NOs: 22839 to 22876, or SEQ ID NOs: 25489 to 25526.

In some embodiments, the amino acid sequence for a MHC class II peptide vaccine for the BRAF V600M protein mutation comprises one or more of the SEQ ID NOs: 495 to 502. In some embodiments, any one of the peptides in the BRAF V600M vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 495 to 502.

In some embodiments, the amino acid sequence for a MHC class II peptide vaccine for the BRAF V600M protein mutation comprises one or more of the SEQ ID NOs: 495 to 502, SEQ ID NOs: 22877 to 22966, and SEQ ID NOs: 25527 to 25616. In some embodiments, any one of the peptides in the BRAF V600M vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 495 to 502, SEQ ID NOs: 22877 to 22966, or SEQ ID NOs: 25527 to 25616.

In some embodiments, the amino acid sequence for a MHC class II peptide vaccine for the BRAF V600M protein mutation comprises two or more of the SEQ ID NOs: 495 to 502. In some embodiments, any one of the peptides in the BRAF V600M vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 495 to 502.

In some embodiments, the amino acid sequence for a MHC class II peptide vaccine for the BRAF V600M protein mutation comprises two or more of the SEQ ID NOs: 495 to 502, SEQ ID NOs: 22877 to 22966, and SEQ ID NOs: 25527 to 25616. In some embodiments, any one of the peptides in the BRAF V600M vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 495 to 502, SEQ ID NOs: 22877 to 22966, or SEQ ID NOs: 25527 to 25616.

In some embodiments, the amino acid sequence for a MHC class II peptide vaccine for the EGFR A289V protein mutation comprises one or more of the SEQ ID NOs: 503 to 509. In some embodiments, any one of the peptides in the EGFR A289V vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 503 to 509.

In some embodiments, the amino acid sequence for a MHC class II peptide vaccine for the EGFR A289V protein mutation comprises one or more of the SEQ ID NOs: 503 to 509, SEQ ID NOs: 22967 to 23000, and SEQ ID NOs: 25617 to 25653. In some embodiments, any one of the peptides in the EGFR A289V vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 503 to 509, SEQ ID NOs: 22967 to 23000, or SEQ ID NOs: 25617 to 25653.

In some embodiments, the amino acid sequence for a MHC class II peptide vaccine for the EGFR A289V protein mutation comprises two or more of the SEQ ID NOs: 503 to 509. In some embodiments, any one of the peptides in the EGFR A289V vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 503 to 509.

In some embodiments, the amino acid sequence for a MHC class II peptide vaccine for the EGFR A289V protein mutation comprises two or more of the SEQ ID NOs: 503 to 509, SEQ ID NOs: 22967 to 23000, and SEQ ID NOs: 25617 to 25653. In some embodiments, any one of the peptides in the EGFR A289V vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 503 to 509, SEQ ID NOs: 22967 to 23000, or SEQ ID NOs: 25617 to 25653.

In some embodiments, the amino acid sequence for a MHC class II peptide vaccine for the EGFR G598V protein mutation comprises one or more of the SEQ ID NOs: 510 to 519. In some embodiments, any one of the peptides in the EGFR G598V vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 510 to 519.

In some embodiments, the amino acid sequence for a MHC class II peptide vaccine for the EGFR G598V protein mutation comprises one or more of the SEQ ID NOs: 510 to 519, SEQ ID NOs: 23001 to 23089, and SEQ ID NOs: 25654 to 25794. In some embodiments, any one of the peptides in the EGFR G598V vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 510 to 519, SEQ ID NOs: 23001 to 23089, or SEQ ID NOs: 25654 to 25794.

In some embodiments, the amino acid sequence for a MHC class II peptide vaccine for the EGFR G598V protein mutation comprises two or more of the SEQ ID NOs: 510 to 519. In some embodiments, any one of the peptides in the EGFR G598V vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 510 to 519.

In some embodiments, the amino acid sequence for a MHC class II peptide vaccine for the EGFR G598V protein mutation comprises two or more of the SEQ ID NOs: 510 to 519, SEQ ID NOs: 23001 to 23089, and SEQ ID NOs: 25654 to 25794. In some embodiments, any one of the peptides in the EGFR G598V vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 510 to 519, SEQ ID NOs: 23001 to 23089, or SEQ ID NOs: 25654 to 25794.

In some embodiments, the amino acid sequence for a MHC class II peptide vaccine for the EGFR L858R protein mutation comprises one or more of the SEQ ID NOs: 520 to 527. In some embodiments, any one of the peptides in the EGFR L858R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 520 to 527.

In some embodiments, the amino acid sequence for a MHC class II peptide vaccine for the EGFR L858R protein mutation comprises one or more of the SEQ ID NOs: 520 to 527, SEQ ID NOs: 23090 to 23263, and SEQ ID NOs: 25795 to 26046. In some embodiments, any one of the peptides in the EGFR L858R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 520 to 527, SEQ ID NOs: 23090 to 23263, or SEQ ID NOs: 25795 to 26046.

In some embodiments, the amino acid sequence for a MHC class II peptide vaccine for the EGFR L858R protein mutation comprises two or more of the SEQ ID NOs: 520 to 527. In some embodiments, any one of the peptides in the EGFR L858R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 520 to 527.

In some embodiments, the amino acid sequence for a MHC class II peptide vaccine for the EGFR L858R protein mutation comprises two or more of the SEQ ID NOs: 520 to 527, SEQ ID NOs: 23090 to 23263, and SEQ ID NOs: 25795 to 26046. In some embodiments, any one of the peptides in the EGFR L858R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 520 to 527, SEQ ID NOs: 23090 to 23263, or SEQ ID NOs: 25795 to 26046.

In some embodiments, the amino acid sequence for a MHC class II peptide vaccine for the IDH1 R132H protein mutation comprises one or more of the SEQ ID NOs: 543 to 553. In some embodiments, any one of the peptides in the IDH1 R132H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 543 to 553.

In some embodiments, the amino acid sequence for a MHC class II peptide vaccine for the IDH1 R132H protein mutation comprises one or more of the SEQ ID NOs: 543 to 553, SEQ ID NOs: 23505 to 23631, and SEQ ID NOs: 26469 to 26614. In some embodiments, any one of the peptides in the IDH1 R132H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 543 to 553, SEQ ID NOs: 23505 to 23631, or SEQ ID NOs: 26469 to 26614.

In some embodiments, the amino acid sequence for a MHC class II peptide vaccine for the IDH1 R132H protein mutation comprises two or more of the SEQ ID NOs: 543 to 553. In some embodiments, any one of the peptides in the IDH1 R132H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 543 to 553.

In some embodiments, the amino acid sequence for a MHC class II peptide vaccine for the IDH1 R132H protein mutation comprises two or more of the SEQ ID NOs: 543 to 553, SEQ ID NOs: 23505 to 23631, and SEQ ID NOs: 26469 to 26614. In some embodiments, any one of the peptides in the IDH1 R132H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 543 to 553, SEQ ID NOs: 23505 to 23631, or SEQ ID NOs: 26469 to 26614.

In some embodiments, the amino acid sequence for a MHC class II peptide vaccine for the IDH1 R132C protein mutation comprises one or more of the SEQ ID NOs: 535 to 542. In some embodiments, any one of the peptides in the IDH1 R132C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 535 to 542.

In some embodiments, the amino acid sequence for a MHC class II peptide vaccine for the IDH1 R132C protein mutation comprises one or more of the SEQ ID NOs: 535 to 542, SEQ ID NOs: 23416 to 23504, and SEQ ID NOs: 26376 to 26468. In some embodiments, any one of the peptides in the IDH1 R132C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 535 to 542, SEQ ID NOs: 23416 to 23504, or SEQ ID NOs: 26376 to 26468.

In some embodiments, the amino acid sequence for a MHC class II peptide vaccine for the IDH1 R132C protein mutation comprises two or more of the SEQ ID NOs: 535 to 542. In some embodiments, any one of the peptides in the IDH1 R132C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 535 to 542.

In some embodiments, the amino acid sequence for a MHC class II peptide vaccine for the IDH1 R132C protein mutation comprises two or more of the SEQ ID NOs: 535 to 542, SEQ ID NOs: 23416 to 23504, and SEQ ID NOs: 26376 to 26468. In some embodiments, any one of the peptides in the IDH1 R132C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 535 to 542, SEQ ID NOs: 23416 to 23504, or SEQ ID NOs: 26376 to 26468.

In some embodiments, the amino acid sequence for a MHC class II peptide vaccine for the KRAS G12D protein mutation comprises one or more of the SEQ ID NOs: 569 to 577. In some embodiments, any one of the peptides in the KRAS G12D vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 569 to 577.

In some embodiments, the amino acid sequence for a MHC class II peptide vaccine for the KRAS G12D protein mutation comprises one or more of the SEQ ID NOs: 569 to 577, SEQ ID NOs: 23750 to 23809, and SEQ ID NOs: 26757 to 26833. In some embodiments, any one of the peptides in the KRAS G12D vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 569 to 577, SEQ ID NOs: 23750 to 23809, or SEQ ID NOs: 26757 to 26833.

In some embodiments, the amino acid sequence for a MHC class II peptide vaccine for the KRAS G12D protein mutation comprises two or more of the SEQ ID NOs: 569 to 577. In some embodiments, any one of the peptides in the KRAS G12D vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 569 to 577.

In some embodiments, the amino acid sequence for a MHC class II peptide vaccine for the KRAS G12D protein mutation comprises two or more of the SEQ ID NOs: 569 to 577, SEQ ID NOs: 23750 to 23809, and SEQ ID NOs: 26757 to 26833. In some embodiments, any one of the peptides in the KRAS G12D vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 569 to 577, SEQ ID NOs: 23750 to 23809, or SEQ ID NOs: 26757 to 26833.

In some embodiments, the amino acid sequence for a MHC class II peptide vaccine for the KRAS G12V protein mutation comprises one or more of the SEQ ID NOs: 596 to 605. In some embodiments, any one of the peptides in the KRAS G12V vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 596 to 605.

In some embodiments, the amino acid sequence for a MHC class II peptide vaccine for the KRAS G12V protein mutation comprises one or more of the SEQ ID NOs: 596 to 605, SEQ ID NOs: 23958 to 24025, and SEQ ID NOs: 27057 to 27148. In some embodiments, any one of the peptides in the KRAS G12V vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 596 to 605, SEQ ID NOs: 23958 to 24025, or SEQ ID NOs: 27057 to 27148.

In some embodiments, the amino acid sequence for a MHC class II peptide vaccine for the KRAS G12V protein mutation comprises two or more of the SEQ ID NOs: 596 to 605. In some embodiments, any one of the peptides in the KRAS G12V vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 596 to 605.

In some embodiments, the amino acid sequence for a MHC class II peptide vaccine for the KRAS G12V protein mutation comprises two or more of the SEQ ID NOs: 596 to 605, SEQ ID NOs: 23958 to 24025, and SEQ ID NOs: 27057 to 27148. In some embodiments, any one of the peptides in the KRAS G12V vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 596 to 605, SEQ ID NOs: 23958 to 24025, or SEQ ID NOs: 27057 to 27148.

In some embodiments, the amino acid sequence for a MHC class II peptide vaccine for the KRAS G12R protein mutation comprises one or more of the SEQ ID NOs: 578 to 587. In some embodiments, any one of the peptides in the KRAS G12R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 578 to 587.

In some embodiments, the amino acid sequence for a MHC class II peptide vaccine for the KRAS G12R protein mutation comprises one or more of the SEQ ID NOs: 578 to 587, SEQ ID NOs: 23810 to 23889, and SEQ ID NOs: 26834 to 26967. In some embodiments, any one of the peptides in the KRAS G12R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 578 to 587, SEQ ID NOs: 23810 to 23889, or SEQ ID NOs: 26834 to 26967.

In some embodiments, the amino acid sequence for a MHC class II peptide vaccine for the KRAS G12R protein mutation comprises two or more of the SEQ ID NOs: 578 to 587. In some embodiments, any one of the peptides in the KRAS G12R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 578 to 587.

In some embodiments, the amino acid sequence for a MHC class II peptide vaccine for the KRAS G12R protein mutation comprises two or more of the SEQ ID NOs: 578 to 587, SEQ ID NOs: 23810 to 23889, and SEQ ID NOs: 26834 to 26967. In some embodiments, any one of the peptides in the KRAS G12R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 578 to 587, SEQ ID NOs: 23810 to 23889, or SEQ ID NOs: 26834 to 26967.

In some embodiments, the amino acid sequence for a MHC class II peptide vaccine for the KRAS G12C protein mutation comprises one or more of the SEQ ID NOs: 561 to 568. In some embodiments, any one of the peptides in the KRAS G12C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 561 to 568.

In some embodiments, the amino acid sequence for a MHC class II peptide vaccine for the KRAS G12C protein mutation comprises one or more of the SEQ ID NOs: 561 to 568, SEQ ID NOs: 23700 to 23749, and SEQ ID NOs: 26702 to 26756. In some embodiments, any one of the peptides in the KRAS G12C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 561 to 568, SEQ ID NOs: 23700 to 23749, or SEQ ID NOs: 26702 to 26756.

In some embodiments, the amino acid sequence for a MHC class II peptide vaccine for the KRAS G12C protein mutation comprises two or more of the SEQ ID NOs: 561 to 568. In some embodiments, any one of the peptides in the KRAS G12C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 561 to 568.

In some embodiments, the amino acid sequence for a MHC class II peptide vaccine for the KRAS G12C protein mutation comprises two or more of the SEQ ID NOs: 561 to 568, SEQ ID NOs: 23700 to 23749, and SEQ ID NOs: 26702 to 26756. In some embodiments, any one of the peptides in the KRAS G12C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 561 to 568, SEQ ID NOs: 23700 to 23749, or SEQ ID NOs: 26702 to 26756.

In some embodiments, the amino acid sequence for a MHC class II peptide vaccine for the KRAS G13D protein mutation comprises one or more of the SEQ ID NOs: 606 to 615 and SEQ ID NO: 759. In some embodiments, any one of the peptides in the KRAS G13D vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 606 to 615 or SEQ ID NO: 759.

In some embodiments, the amino acid sequence for a MHC class II peptide vaccine for the KRAS G13D protein mutation comprises one or more of the SEQ ID NOs: 606 to 615, SEQ ID NO: 759, SEQ ID NOs: 24026 to 24129, and SEQ ID NOs: 27149 to 27328. In some embodiments, any one of the peptides in the KRAS G13D vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 606 to 615, SEQ ID NO: 759, SEQ ID NOs: 24026 to 24129, or SEQ ID NOs: 27149 to 27328.

In some embodiments, the amino acid sequence for a MHC class II peptide vaccine for the KRAS G13D protein mutation comprises two or more of the SEQ ID NOs: 606 to 615 and SEQ ID NO: 759. In some embodiments, any one of the peptides in the KRAS G13D vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 606 to 615 or SEQ ID NO: 759.

In some embodiments, the amino acid sequence for a MHC class II peptide vaccine for the KRAS G13D protein mutation comprises two or more of the SEQ ID NOs: 606 to 615, SEQ ID NO: 759, SEQ ID NOs: 24026 to 24129, and SEQ ID NOs: 27149 to 27328. In some embodiments, any one of the peptides in the KRAS G13D vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 606 to 615, SEQ ID NO: 759, SEQ ID NOs: 24026 to 24129, or SEQ ID NOs: 27149 to 27328.

In some embodiments, the amino acid sequence for a MHC class II peptide vaccine for the KRAS G12A protein mutation comprises one or more of the SEQ ID NOs: 554 to 560. In some embodiments, any one of the peptides in the KRAS G12A vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 554 to 560.

In some embodiments, the amino acid sequence for a MHC class II peptide vaccine for the KRAS G12A protein mutation comprises one or more of the SEQ ID NOs: 554 to 560, SEQ ID NOs: 23632 to 23699, and SEQ ID NOs: 26615 to 26701. In some embodiments, any one of the peptides in the KRAS G12A vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 554 to 560, SEQ ID NOs: 23632 to 23699, or SEQ ID NOs: 26615 to 26701.

In some embodiments, the amino acid sequence for a MHC class II peptide vaccine for the KRAS G12A protein mutation comprises two or more of the SEQ ID NOs: 554 to 560. In some embodiments, any one of the peptides in the KRAS G12A vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 554 to 560.

In some embodiments, the amino acid sequence for a MHC class II peptide vaccine for the KRAS G12A protein mutation comprises two or more of the SEQ ID NOs: 554 to 560, SEQ ID NOs: 23632 to 23699, and SEQ ID NOs: 26615 to 26701. In some embodiments, any one of the peptides in the KRAS G12A vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 554 to 560, SEQ ID NOs: 23632 to 23699, or SEQ ID NOs: 26615 to 26701.

In some embodiments, the amino acid sequence for a MHC class II peptide vaccine for the KRAS G12S protein mutation comprises one or more of the SEQ ID NOs: 588 to 595. In some embodiments, any one of the peptides in the KRAS G12S vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 588 to 595.

In some embodiments, the amino acid sequence for a MHC class II peptide vaccine for the KRAS G12S protein mutation comprises one or more of the SEQ ID NOs: 588 to 595, SEQ ID NOs: 23890 to 23957, and SEQ ID NOs: 26968 to 27056. In some embodiments, any one of the peptides in the KRAS G12S vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 588 to 595, SEQ ID NOs: 23890 to 23957, or SEQ ID NOs: 26968 to 27056.

In some embodiments, the amino acid sequence for a MHC class II peptide vaccine for the KRAS G12S protein mutation comprises two or more of the SEQ ID NOs: 588 to 595. In some embodiments, any one of the peptides in the KRAS G12S vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 588 to 595.

In some embodiments, the amino acid sequence for a MHC class II peptide vaccine for the KRAS G12S protein mutation comprises two or more of the SEQ ID NOs: 588 to 595, SEQ ID NOs: 23890 to 23957, and SEQ ID NOs: 26968 to 27056. In some embodiments, any one of the peptides in the KRAS G12S vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 588 to 595, SEQ ID NOs: 23890 to 23957, or SEQ ID NOs: 26968 to 27056.

In some embodiments, the amino acid sequence for a MHC class II peptide vaccine for the NRAS Q61R protein mutation comprises one or more of the SEQ ID NOs: 634 to 645. In some embodiments, any one of the peptides in the NRAS Q61R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 634 to 645.

In some embodiments, the amino acid sequence for a MHC class II peptide vaccine for the NRAS Q61R protein mutation comprises one or more of the SEQ ID NOs: 634 to 645, SEQ ID NOs: 24280 to 24347, and SEQ ID NOs: 27490 to 27557. In some embodiments, any one of the peptides in the NRAS Q61R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 634 to 645, SEQ ID NOs: 24280 to 24347, or SEQ ID NOs: 27490 to 27557.

In some embodiments, the amino acid sequence for a MHC class II peptide vaccine for the NRAS Q61R protein mutation comprises two or more of the SEQ ID NOs: 634 to 645. In some embodiments, any one of the peptides in the NRAS Q61R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 634 to 645.

In some embodiments, the amino acid sequence for a MHC class II peptide vaccine for the NRAS Q61R protein mutation comprises two or more of the SEQ ID NOs: 634 to 645, SEQ ID NOs: 24280 to 24347, and SEQ ID NOs: 27490 to 27557. In some embodiments, any one of the peptides in the NRAS Q61R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 634 to 645, SEQ ID NOs: 24280 to 24347, or SEQ ID NOs: 27490 to 27557.

In some embodiments, the amino acid sequence for a MHC class II peptide vaccine for the NRAS Q61K protein mutation comprises one or more of the SEQ ID NOs: 616 to 624. In some embodiments, any one of the peptides in the NRAS Q61K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 616 to 624.

In some embodiments, the amino acid sequence for a MHC class II peptide vaccine for the NRAS Q61K protein mutation comprises one or more of the SEQ ID NOs: 616 to 624, SEQ ID NOs: 24130 to 24194, and SEQ ID NOs: 27329 to 27396. In some embodiments, any one of the peptides in the NRAS Q61K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 616 to 624, SEQ ID NOs: 24130 to 24194, or SEQ ID NOs: 27329 to 27396.

In some embodiments, the amino acid sequence for a MHC class II peptide vaccine for the NRAS Q61K protein mutation comprises two or more of the SEQ ID NOs: 616 to 624. In some embodiments, any one of the peptides in the NRAS Q61K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 616 to 624.

In some embodiments, the amino acid sequence for a MHC class II peptide vaccine for the NRAS Q61K protein mutation comprises two or more of the SEQ ID NOs: 616 to 624, SEQ ID NOs: 24130 to 24194, and SEQ ID NOs: 27329 to 27396. In some embodiments, any one of the peptides in the NRAS Q61K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 616 to 624, SEQ ID NOs: 24130 to 24194, or SEQ ID NOs: 27329 to 27396.

In some embodiments, the amino acid sequence for a MHC class II peptide vaccine for the NRAS Q61L protein mutation comprises one or more of the SEQ ID NOs: 625 to 633. In some embodiments, any one of the peptides in the NRAS Q61L vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 625 to 633.

In some embodiments, the amino acid sequence for a MHC class II peptide vaccine for the NRAS Q61L protein mutation comprises one or more of the SEQ ID NOs: 625 to 633, SEQ ID NOs: 24195 to 24279, and SEQ ID NOs: 27397 to 27489. In some embodiments, any one of the peptides in the NRAS Q61L vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 625 to 633, SEQ ID NOs: 24195 to 24279, or SEQ ID NOs: 27397 to 27489.

In some embodiments, the amino acid sequence for a MHC class II peptide vaccine for the NRAS Q61L protein mutation comprises two or more of the SEQ ID NOs: 625 to 633. In some embodiments, any one of the peptides in the NRAS Q61L vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 625 to 633.

In some embodiments, the amino acid sequence for a MHC class II peptide vaccine for the NRAS Q61L protein mutation comprises two or more of the SEQ ID NOs: 625 to 633, SEQ ID NOs: 24195 to 24279, and SEQ ID NOs: 27397 to 27489. In some embodiments, any one of the peptides in the NRAS Q61L vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 625 to 633, SEQ ID NOs: 24195 to 24279, or SEQ ID NOs: 27397 to 27489.

In some embodiments, the amino acid sequence for a MHC class II peptide vaccine for the PIK3CA E542K protein mutation comprises one or more of the SEQ ID NOs: 646 to 650. In some embodiments, any one of the peptides in the PIK3CA E542K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 646 to 650.

In some embodiments, the amino acid sequence for a MHC class II peptide vaccine for the PIK3CA E542K protein mutation comprises one or more of the SEQ ID NOs:

646 to 650, SEQ ID NOs: 24348 to 24362, and SEQ ID NOs: 27558 to 27572. In some embodiments, any one of the peptides in the PIK3CA E542K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 646 to 650, SEQ ID NOs: 24348 to 24362, or SEQ ID NOs: 27558 to 27572.

In some embodiments, the amino acid sequence for a MHC class II peptide vaccine for the PIK3CA E542K protein mutation comprises two or more of the SEQ ID NOs: 646 to 650. In some embodiments, any one of the peptides in the PIK3CA E542K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 646 to 650.

In some embodiments, the amino acid sequence for a MHC class II peptide vaccine for the PIK3CA E542K protein mutation comprises two or more of the SEQ ID NOs: 646 to 650, SEQ ID NOs: 24348 to 24362, and SEQ ID NOs: 27558 to 27572. In some embodiments, any one of the peptides in the PIK3CA E542K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 646 to 650, SEQ ID NOs: 24348 to 24362, or SEQ ID NOs: 27558 to 27572.

In some embodiments, the amino acid sequence for a MHC class II peptide vaccine for the PIK3CA E545K protein mutation comprises one or more of the SEQ ID NOs: 651 to 657. In some embodiments, any one of the peptides in the PIK3CA E545K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 651 to 657.

In some embodiments, the amino acid sequence for a MHC class II peptide vaccine for the PIK3CA E545K protein mutation comprises one or more of the SEQ ID NOs: 651 to 657, SEQ ID NOs: 24363 to 24388, and SEQ ID NOs: 27573 to 27599. In some embodiments, any one of the peptides in the PIK3CA E545K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 651 to 657, SEQ ID NOs: 24363 to 24388, or SEQ ID NOs: 27573 to 27599.

In some embodiments, the amino acid sequence for a MHC class II peptide vaccine for the PIK3CA E545K protein mutation comprises two or more of the SEQ ID NOs: 651 to 657. In some embodiments, any one of the peptides in the PIK3CA E545K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 651 to 657.

In some embodiments, the amino acid sequence for a MHC class II peptide vaccine for the PIK3CA E545K protein mutation comprises two or more of the SEQ ID NOs: 651 to 657, SEQ ID NOs: 24363 to 24388, and SEQ ID NOs: 27573 to 27599. In some embodiments, any one of the peptides in the PIK3CA E545K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 651 to 657, SEQ ID NOs: 24363 to 24388, or SEQ ID NOs: 27573 to 27599.

In some embodiments, the amino acid sequence for a MHC class II peptide vaccine for the PIK3CA H1047R protein mutation comprises one or more of the SEQ ID NOs: 658 to 667. In some embodiments, any one of the peptides in the PIK3CA H1047R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 658 to 667.

In some embodiments, the amino acid sequence for a MHC class II peptide vaccine for the PIK3CA H1047R protein mutation comprises one or more of the SEQ ID NOs: 658 to 667, SEQ ID NOs: 24389 to 24472, and SEQ ID NOs: 27600 to 27683. In some embodiments, any one of the peptides in the PIK3CA H1047R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 658 to 667, SEQ ID NOs: 24389 to 24472, or SEQ ID NOs: 27600 to 27683.

In some embodiments, the amino acid sequence for a MHC class II peptide vaccine for the PIK3CA H1047R protein mutation comprises two or more of the SEQ ID NOs: 658 to 667. In some embodiments, any one of the peptides in the PIK3CA H1047R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 658 to 667.

In some embodiments, the amino acid sequence for a MHC class II peptide vaccine for the PIK3CA H1047R protein mutation comprises two or more of the SEQ ID NOs: 658 to 667, SEQ ID NOs: 24389 to 24472, and SEQ ID NOs: 27600 to 27683. In some embodiments, any one of the peptides in the PIK3CA H1047R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 658 to 667, SEQ ID NOs: 24389 to 24472, or SEQ ID NOs: 27600 to 27683.

In some embodiments, the amino acid sequence for a MHC class II peptide vaccine for the TP53 R158L protein mutation comprises one or more of the SEQ ID NOs: 700 to 707. In some embodiments, any one of the peptides in the TP53 R158L vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 700 to 707.

In some embodiments, the amino acid sequence for a MHC class II peptide vaccine for the TP53 R158L protein mutation comprises one or more of the SEQ ID NOs: 700 to 707, SEQ ID NOs: 24784 to 24927, and SEQ ID NOs: 28132 to 28372. In some embodiments, any one of the peptides in the TP53 R158L vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 700 to 707, SEQ ID NOs: 24784 to 24927, or SEQ ID NOs: 28132 to 28372.

In some embodiments, the amino acid sequence for a MHC class II peptide vaccine for the TP53 R158L protein mutation comprises two or more of the SEQ ID NOs: 700 to 707. In some embodiments, any one of the peptides in the TP53 R158L vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 700 to 707.

In some embodiments, the amino acid sequence for a MHC class II peptide vaccine for the TP53 R158L protein mutation comprises two or more of the SEQ ID NOs: 700 to 707, SEQ ID NOs: 24784 to 24927, and SEQ ID NOs: 28132 to 28372. In some embodiments, any one of the peptides in the TP53 R158L vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 700 to 707, SEQ ID NOs: 24784 to 24927, or SEQ ID NOs: 28132 to 28372.

In some embodiments, the amino acid sequence for a MHC class II peptide vaccine for the TP53 R175H protein mutation comprises one or more of the SEQ ID NOs: 708 to 717. In some embodiments, any one of the peptides in the TP53 R175H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 708 to 717.

In some embodiments, the amino acid sequence for a MHC class II peptide vaccine for the TP53 R175H protein mutation comprises one or more of the SEQ ID NOs: 708 to 717, SEQ ID NOs: 24928 to 24954, and SEQ ID NOs: 28373 to 28410. In some embodiments, any one of the peptides in the TP53 R175H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 708 to 717, SEQ ID NOs: 24928 to 24954, or SEQ ID NOs: 28373 to 28410.

In some embodiments, the amino acid sequence for a MHC class II peptide vaccine for the TP53 R175H protein mutation comprises two or more of the SEQ ID NOs: 708 to 717. In some embodiments, any one of the peptides in the TP53 R175H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 708 to 717.

In some embodiments, the amino acid sequence for a MHC class II peptide vaccine for the TP53 R175H protein mutation comprises two or more of the SEQ ID NOs: 708 to 717, SEQ ID NOs: 24928 to 24954, and SEQ ID NOs: 28373 to 28410. In some embodiments, any one of the peptides in the TP53 R175H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 708 to 717, SEQ ID NOs: 24928 to 24954, or SEQ ID NOs: 28373 to 28410.

In some embodiments, the amino acid sequence for a MHC class II peptide vaccine for the TP53 R248Q protein mutation comprises one or more of the SEQ ID NOs: 718 to 723. In some embodiments, any one of the peptides in the TP53 R248Q vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 718 to 723.

In some embodiments, the amino acid sequence for a MHC class II peptide vaccine for the TP53 R248Q protein mutation comprises one or more of the SEQ ID NOs: 718 to 723, SEQ ID NOs: 24955 to 25010, and SEQ ID NOs: 28411 to 28468. In some embodiments, any one of the peptides in the TP53 R248Q vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 718 to 723, SEQ ID NOs: 24955 to 25010, or SEQ ID NOs: 28411 to 28468.

In some embodiments, the amino acid sequence for a MHC class II peptide vaccine for the TP53 R248Q protein mutation comprises two or more of the SEQ ID NOs: 718 to 723. In some embodiments, any one of the peptides in the TP53 R248Q vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 718 to 723.

In some embodiments, the amino acid sequence for a MHC class II peptide vaccine for the TP53 R248Q protein mutation comprises two or more of the SEQ ID NOs: 718 to 723, SEQ ID NOs: 24955 to 25010, and SEQ ID NOs: 28411 to 28468. In some embodiments, any one of the peptides in the TP53 R248Q vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 718 to 723, SEQ ID NOs: 24955 to 25010, or SEQ ID NOs: 28411 to 28468.

In some embodiments, the amino acid sequence for a MHC class II peptide vaccine for the TP53 R273C protein mutation comprises one or more of the SEQ ID NOs: 733 to 739. In some embodiments, any one of the peptides in the TP53 R273C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 733 to 739.

In some embodiments, the amino acid sequence for a MHC class II peptide vaccine for the TP53 R273C protein mutation comprises one or more of the SEQ ID NOs: 733 to 739, SEQ ID NOs: 25109 to 25117, and SEQ ID NOs: 28572 to 28580. In some embodiments, any one of the peptides in the TP53 R273C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 733 to 739, SEQ ID NOs: 25109 to 25117, or SEQ ID NOs: 28572 to 28580.

In some embodiments, the amino acid sequence for a MHC class II peptide vaccine for the TP53 R273C protein mutation comprises two or more of the SEQ ID NOs: 733 to 739. In some embodiments, any one of the peptides in the TP53 R273C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 733 to 739.

In some embodiments, the amino acid sequence for a MHC class II peptide vaccine for the TP53 R273C protein mutation comprises two or more of the SEQ ID NOs: 733 to 739, SEQ ID NOs: 25109 to 25117, and SEQ ID NOs: 28572 to 28580. In some embodiments, any one of the peptides in the TP53 R273C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 733 to 739, SEQ ID NOs: 25109 to 25117, or SEQ ID NOs: 28572 to 28580.

In some embodiments, the amino acid sequence for a MHC class II peptide vaccine for the TP53 R273H protein mutation comprises one or more of the SEQ ID NOs: 740 to 748. In some embodiments, any one of the peptides in the TP53 R273H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 740 to 748.

In some embodiments, the amino acid sequence for a MHC class II peptide vaccine for the TP53 R273H protein mutation comprises one or more of the SEQ ID NOs: 740 to 748, SEQ ID NOs: 25118 to 25206, and SEQ ID NOs: 28581 to 28697. In some embodiments, any one of the peptides in the TP53 R273H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 740 to 748, SEQ ID NOs: 25118 to 25206, or SEQ ID NOs: 28581 to 28697.

In some embodiments, the amino acid sequence for a MHC class II peptide vaccine for the TP53 R273H protein mutation comprises two or more of the SEQ ID NOs: 740 to 748. In some embodiments, any one of the peptides in the TP53 R273H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 740 to 748.

In some embodiments, the amino acid sequence for a MHC class II peptide vaccine for the TP53 R273H protein mutation comprises two or more of the SEQ ID NOs: 740 to 748, SEQ ID NOs: 25118 to 25206, and SEQ ID NOs: 28581 to 28697. In some embodiments, any one of the peptides in the TP53 R273H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 740 to 748, SEQ ID NOs: 25118 to 25206, or SEQ ID NOs: 28581 to 28697.

In some embodiments, the amino acid sequence for a MHC class II peptide vaccine for the TP53 R248W protein mutation comprises one or more of the SEQ ID NOs: 724 to 732. In some embodiments, any one of the peptides in the TP53 R248W vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 724 to 732.

In some embodiments, the amino acid sequence for a MHC class II peptide vaccine for the TP53 R248W protein mutation comprises one or more of the SEQ ID NOs: 724 to 732, SEQ ID NOs: 25011 to 25108, and SEQ ID NOs: 28469 to 28571. In some embodiments, any one of the peptides in the TP53 R248W vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 724 to 732, SEQ ID NOs: 25011 to 25108, or SEQ ID NOs: 28469 to 28571.

In some embodiments, the amino acid sequence for a MHC class II peptide vaccine for the TP53 R248W protein mutation comprises two or more of the SEQ ID NOs: 724 to 732. In some embodiments, any one of the peptides in the TP53 R248W vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 724 to 732.

In some embodiments, the amino acid sequence for a MHC class II peptide vaccine for the TP53 R248W protein mutation comprises two or more of the SEQ ID NOs: 724 to 732, SEQ ID NOs: 25011 to 25108, and SEQ ID NOs: 28469 to 28571. In some embodiments, any one of the peptides in the TP53 R248W vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 724 to 732, SEQ ID NOs: 25011 to 25108, or SEQ ID NOs: 28469 to 28571.

In some embodiments, the amino acid sequence for a MHC class II peptide vaccine for the TP53 R282W protein mutation comprises one or more of the SEQ ID NOs: 749 to 750. In some embodiments, any one of the peptides in the TP53 R282W vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 749 to 750.

In some embodiments, the amino acid sequence for a MHC class II peptide vaccine for the TP53 R282W protein mutation comprises one or more of the SEQ ID NOs: 749 to 750, SEQ ID NOs: 25207 to 25218, and SEQ ID NOs: 28698 to 28709. In some embodiments, any one of the peptides in the TP53 R282W vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 749 to 750, SEQ ID NOs: 25207 to 25218, or SEQ ID NOs: 28698 to 28709.

In some embodiments, the amino acid sequence for a MHC class II peptide vaccine for the TP53 R282W protein mutation comprises two or more of the SEQ ID NOs: 749 to 750. In some embodiments, any one of the peptides in the TP53 R282W vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 749 to 750.

In some embodiments, the amino acid sequence for a MHC class II peptide vaccine for the TP53 R282W protein mutation comprises two or more of the SEQ ID NOs: 749 to 750, SEQ ID NOs: 25207 to 25218, and SEQ ID NOs: 28698 to 28709. In some embodiments, any one of the peptides in the TP53 R282W vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 749 to 750, SEQ ID NOs: 25207 to 25218, or SEQ ID NOs: 28698 to 28709.

In some embodiments, the amino acid sequence for a MHC class II peptide vaccine for the TP53 Y220C protein mutation comprises one or more of the SEQ ID NOs: 751 to 758. In some embodiments, any one of the peptides in the TP53 Y220C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 751 to 758.

In some embodiments, the amino acid sequence for a MHC class II peptide vaccine for the TP53 Y220C protein mutation comprises one or more of the SEQ ID NOs: 751 to 758, SEQ ID NOs: 25219 to 25304, and SEQ ID NOs: 28710 to 28795. In some embodiments, any one of the peptides in the TP53 Y220C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 751 to 758, SEQ ID NOs: 25219 to 25304, or SEQ ID NOs: 28710 to 28795.

In some embodiments, the amino acid sequence for a MHC class II peptide vaccine for the TP53 Y220C protein mutation comprises two or more of the SEQ ID NOs: 751 to 758. In some embodiments, any one of the peptides in the TP53 Y220C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 751 to 758.

In some embodiments, the amino acid sequence for a MHC class II peptide vaccine for the TP53 Y220C protein mutation comprises two or more of the SEQ ID NOs: 751 to 758, SEQ ID NOs: 25219 to 25304, and SEQ ID NOs: 28710 to 28795. In some embodiments, any one of the peptides in the TP53 Y220C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 751 to 758, SEQ ID NOs: 25219 to 25304, or SEQ ID NOs: 28710 to 28795.

In some embodiments, the amino acid sequence for a MHC class II peptide vaccine for the PIK3CA R88Q protein mutation comprises one or more of the SEQ ID NOs: 668 to 675. In some embodiments, any one of the peptides in the PIK3CA R88Q vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 668 to 675.

In some embodiments, the amino acid sequence for a MHC class II peptide vaccine for the PIK3CA R88Q protein mutation comprises one or more of the SEQ ID NOs: 668 to 675, SEQ ID NOs: 24473 to 24571, and SEQ ID NOs: 27684 to 27889. In some embodiments, any one of the peptides in the PIK3CA R88Q vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 668 to 675, SEQ ID NOs: 24473 to 24571, or SEQ ID NOs: 27684 to 27889.

In some embodiments, the amino acid sequence for a MHC class II peptide vaccine for the PIK3CA R88Q protein mutation comprises two or more of the SEQ ID NOs: 668 to 675. In some embodiments, any one of the peptides in the PIK3CA R88Q vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 668 to 675.

In some embodiments, the amino acid sequence for a MHC class II peptide vaccine for the PIK3CA R88Q protein mutation comprises two or more of the SEQ ID NOs: 668 to 675, SEQ ID NOs: 24473 to 24571, and SEQ ID NOs: 27684 to 27889. In some embodiments, any one of the peptides in the PIK3CA R88Q vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 668 to 675, SEQ ID NOs: 24473 to 24571, or SEQ ID NOs: 27684 to 27889.

In some embodiments, the amino acid sequence for a MHC class II peptide vaccine for the GTF2I L424H protein mutation comprises one or more of the SEQ ID NOs: 528 to 534. In some embodiments, any one of the peptides in the GTF2I L424H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 528 to 534.

In some embodiments, the amino acid sequence for a MHC class II peptide vaccine for the GTF2I L424H protein mutation comprises one or more of the SEQ ID NOs: 528 to 534, SEQ ID NOs: 23264 to 23415, and SEQ ID NOs: 26047 to 26375. In some embodiments, any one of the peptides in the GTF2I L424H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 528 to 534, SEQ ID NOs: 23264 to 23415, or SEQ ID NOs: 26047 to 26375.

In some embodiments, the amino acid sequence for a MHC class II peptide vaccine for the GTF2I L424H protein mutation comprises two or more of the SEQ ID NOs: 528 to 534. In some embodiments, any one of the peptides in the GTF2I L424H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 528 to 534.

In some embodiments, the amino acid sequence for a MHC class II peptide vaccine for the GTF2I L424H protein mutation comprises two or more of the SEQ ID NOs: 528 to 534, SEQ ID NOs: 23264 to 23415, and SEQ ID NOs: 26047 to 26375. In some embodiments, any one of the peptides in the GTF2I L424H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 528 to 534, SEQ ID NOs: 23264 to 23415, or SEQ ID NOs: 26047 to 26375.

In some embodiments, the amino acid sequence for a MHC class II peptide vaccine for the PTEN R130Q protein mutation comprises one or more of the SEQ ID NOs: 681 to 690. In some embodiments, any one of the peptides in the PTEN R130Q vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 681 to 690.

In some embodiments, the amino acid sequence for a MHC class II peptide vaccine for the PTEN R130Q protein mutation comprises one or more of the SEQ ID NOs: 681 to 690, SEQ ID NOs: 24659 to 24724, and SEQ ID NOs: 27980 to 28052. In some embodiments, any one of the peptides in the PTEN R130Q vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 681 to 690, SEQ ID NOs: 24659 to 24724, or SEQ ID NOs: 27980 to 28052.

In some embodiments, the amino acid sequence for a MHC class II peptide vaccine for the PTEN R130Q protein mutation comprises two or more of the SEQ ID NOs: 681 to 690. In some embodiments, any one of the peptides in the PTEN R130Q vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 681 to 690.

In some embodiments, the amino acid sequence for a MHC class II peptide vaccine for the PTEN R130Q protein mutation comprises two or more of the SEQ ID NOs: 681 to 690, SEQ ID NOs: 24659 to 24724, and SEQ ID NOs: 27980 to 28052. In some embodiments, any one of the peptides in the PTEN R130Q vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 681 to 690, SEQ ID NOs: 24659 to 24724, or SEQ ID NOs: 27980 to 28052.

In some embodiments, the amino acid sequence for a MHC class II peptide vaccine for the AKT1 E17K protein mutation comprises one or more of the SEQ ID NOs: 475 to 483. In some embodiments, any one of the peptides in the AKT1 E17K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 475 to 483.

In some embodiments, the amino acid sequence for a MHC class II peptide vaccine for the AKT1 E17K protein mutation comprises one or more of the SEQ ID NOs: 475 to 483, SEQ ID NOs: 22728 to 22838, and SEQ ID NOs: 25305 to 25488. In some embodiments, any one of the peptides in the AKT1 E17K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 475 to 483, SEQ ID NOs: 22728 to 22838, or SEQ ID NOs: 25305 to 25488.

In some embodiments, the amino acid sequence for a MHC class II peptide vaccine for the AKT1 E17K protein mutation comprises two or more of the SEQ ID NOs: 475 to 483. In some embodiments, any one of the peptides in the AKT1 E17K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 475 to 483.

In some embodiments, the amino acid sequence for a MHC class II peptide vaccine for the AKT1 E17K protein mutation comprises two or more of the SEQ ID NOs: 475 to 483, SEQ ID NOs: 22728 to 22838, and SEQ ID NOs: 25305 to 25488. In some embodiments, any one of the peptides in the AKT1 E17K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 475 to 483, SEQ ID NOs: 22728 to 22838, or SEQ ID NOs: 25305 to 25488.

In some embodiments, the amino acid sequence for a MHC class II peptide vaccine for the PTEN R130G protein mutation comprises one or more of the SEQ ID NOs: 676 to 680. In some embodiments, any one of the peptides in the PTEN R130G vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 676 to 680.

In some embodiments, the amino acid sequence for a MHC class II peptide vaccine for the PTEN R130G protein mutation comprises one or more of the SEQ ID NOs: 676 to 680, SEQ ID NOs: 24572 to 24658, and SEQ ID NOs: 27890 to 27979. In some embodiments, any one of the peptides in the PTEN R130G vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 676 to 680, SEQ ID NOs: 24572 to 24658, or SEQ ID NOs: 27890 to 27979.

In some embodiments, the amino acid sequence for a MHC class II peptide vaccine for the PTEN R130G protein mutation comprises two or more of the SEQ ID NOs: 676 to 680. In some embodiments, any one of the peptides in the PTEN R130G vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 676 to 680.

In some embodiments, the amino acid sequence for a MHC class II peptide vaccine for the PTEN R130G protein mutation comprises two or more of the SEQ ID NOs: 676 to 680, SEQ ID NOs: 24572 to 24658, and SEQ ID NOs: 27890 to 27979. In some embodiments, any one of the peptides in the PTEN R130G vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 676 to 680, SEQ ID NOs: 24572 to 24658, or SEQ ID NOs: 27890 to 27979.

In some embodiments, the amino acid sequence for a MHC class II peptide vaccine for the TP53 H179R protein mutation comprises one or more of the SEQ ID NOs: 691 to 699. In some embodiments, any one of the peptides in the TP53 H179R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 691 to 699.

In some embodiments, the amino acid sequence for a MHC class II peptide vaccine for the TP53 H179R protein mutation comprises one or more of the SEQ ID NOs: 691 to 699, SEQ ID NOs: 24725 to 24783, and SEQ ID NOs: 28053 to 28131. In some embodiments, any one of the peptides in the TP53 H179R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 691 to 699, SEQ ID NOs: 24725 to 24783, or SEQ ID NOs: 28053 to 28131.

In some embodiments, the amino acid sequence for a MHC class II peptide vaccine for the TP53 H179R protein mutation comprises two or more of the SEQ ID NOs: 691 to 699. In some embodiments, any one of the peptides in the TP53 H179R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 691 to 699.

In some embodiments, the amino acid sequence for a MHC class II peptide vaccine for the TP53 H179R protein mutation comprises two or more of the SEQ ID NOs: 691 to 699, SEQ ID NOs: 24725 to 24783, and SEQ ID NOs: 28053 to 28131. In some embodiments, any one of the peptides in the TP53 H179R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 691 to 699, SEQ ID NOs: 24725 to 24783, or SEQ ID NOs: 28053 to 28131.

In some embodiments, the amino acid sequence vaccine for a MHC class II vaccine for pancreatic cancer comprises one or more of the SEQ ID NOs: 569 to 574, SEQ ID NOs: 578 to 584, SEQ ID NOs: 596 to 599, and SEQ ID NOs: 601 to 603. In some embodiments, any one of the peptides in the pancreatic cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 569 to 574, SEQ ID NOs: 578 to 584, SEQ ID NOs: 596 to 599, or SEQ ID NOs: 601 to 603.

In some embodiments, the amino acid sequence vaccine for a MHC class II vaccine for pancreatic cancer comprises two or more of the SEQ ID NOs: 569 to 574, SEQ ID NOs: 578 to 584, SEQ ID NOs: 596 to 599, and SEQ ID NOs: 601 to 603. In some embodiments, any one of the peptides in the pancreatic cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 569 to 574, SEQ ID NOs: 578 to 584, SEQ ID NOs: 596 to 599, or SEQ ID NOs: 601 to 603.

In some embodiments, the amino acid sequence vaccine for a MHC class II vaccine for skin cancer comprises one or more of the SEQ ID NOs: 484 to 485, SEQ ID NOs: 488 to 489, SEQ ID NOs: 495 to 499, SEQ ID NO: 616, SEQ ID NOs: 619 to 620, SEQ ID NOs: 625 to 628, SEQ ID NO: 634, SEQ ID NO: 637, and SEQ ID NOs: 639 to 640. In some embodiments, any one of the peptides in the skin cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 484 to 485, SEQ ID NOs: 488 to 489, SEQ ID NOs: 495 to 499, SEQ ID NO: 616, SEQ ID NOs: 619 to 620, SEQ ID NOs: 625 to 628, SEQ ID NO: 634, SEQ ID NO: 637, or SEQ ID NOs: 639 to 640.

In some embodiments, the amino acid sequence vaccine for a MHC class II vaccine for skin cancer comprises two or more of the SEQ ID NOs: 484 to 485, SEQ ID NOs: 488 to 489, SEQ ID NOs: 495 to 499, SEQ ID NO: 616, SEQ ID NOs: 619 to 620, SEQ ID NOs: 625 to 628, SEQ ID NO: 634, SEQ ID NO: 637, and SEQ ID NOs: 639 to 640. In some embodiments, any one of the peptides in the skin cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 484 to 485, SEQ ID NOs: 488 to 489, SEQ ID NOs: 495 to 499, SEQ ID NO: 616, SEQ ID NOs: 619 to 620, SEQ ID NOs: 625 to 628, SEQ ID NO: 634, SEQ ID NO: 637, or SEQ ID NOs: 639 to 640.

In some embodiments, the amino acid sequence vaccine for a MHC class II vaccine for thyroid cancer comprises one or more of the SEQ ID NOs: 484 to 485, SEQ ID NOs: 488 to 489, SEQ ID NO: 616, SEQ ID NOs: 619 to 620, SEQ ID NO: 634, SEQ ID NO: 637, and SEQ ID NO: 640. In some embodiments, any one of the peptides in the thyroid cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 484 to 485, SEQ ID NOs: 488 to 489, SEQ ID NO: 616, SEQ ID NOs: 619 to 620, SEQ ID NO: 634, SEQ ID NO: 637, or SEQ ID NO: 640.

In some embodiments, the amino acid sequence vaccine for a MHC class II vaccine for thyroid cancer comprises two or more of the SEQ ID NOs: 484 to 485, SEQ ID NOs: 488 to 489, SEQ ID NO: 616, SEQ ID NOs: 619 to 620, SEQ ID NO: 634, SEQ ID NO: 637, and SEQ ID NO: 640. In some embodiments, any one of the peptides in the thyroid cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 484 to 485, SEQ ID NOs: 488 to 489, SEQ ID NO: 616, SEQ ID NOs: 619 to 620, SEQ ID NO: 634, SEQ ID NO: 637, or SEQ ID NO: 640.

In some embodiments, the amino acid sequence vaccine for a MHC class II vaccine for brain cancer comprises one or more of the SEQ ID NO: 508, SEQ ID NO: 510, SEQ ID NO: 512, SEQ ID NO: 514, SEQ ID NOs: 535 to 537, SEQ ID NO: 539, SEQ ID NOs: 543 to 551, SEQ ID NO: 708, SEQ ID NO: 712, and SEQ ID NO: 738. In some embodiments, any one of the peptides in the brain cancer vaccine comprise an amino acid sequence 80, 81, 82, 83, 84, 85, 86, 87, 88, 89, 90, 91, 92, 93, 94, 95, 96, 97, 98 or 99% identical to SEQ ID NO: 508, SEQ ID NO: 510, SEQ ID NO: 512, SEQ ID NO: 514, SEQ ID NOs: 535 to 537, SEQ ID NO: 539, SEQ ID NOs: 543 to 551, SEQ ID NO: 708, SEQ ID NO: 712, or SEQ ID NO: 738.

In some embodiments, the amino acid sequence vaccine for a MHC class II vaccine for brain cancer comprises two or more of the SEQ ID NO: 508, SEQ ID NO: 510, SEQ ID NO: 512, SEQ ID NO: 514, SEQ ID NOs: 535 to 537, SEQ ID NO: 539, SEQ ID NOs: 543 to 551, SEQ ID NO: 708, SEQ ID NO: 712, and SEQ ID NO: 738. In some embodiments, any one of the peptides in the brain cancer vaccine comprise an amino acid sequence 80, 81, 82, 83, 84, 85, 86, 87, 88, 89, 90, 91, 92, 93, 94, 95, 96, 97, 98 or 99% identical to SEQ ID NO: 508, SEQ ID NO: 510, SEQ ID NO: 512, SEQ ID NO: 514, SEQ ID NOs: 535 to 537, SEQ ID NO: 539, SEQ ID NOs: 543 to 551, SEQ ID NO: 708, SEQ ID NO: 712, or SEQ ID NO: 738.

In some embodiments, the amino acid sequence vaccine for a MHC class II vaccine for colorectal cancer comprises one or more of the SEQ ID NOs: 484 to 485, SEQ ID NOs: 488 to 489, SEQ ID NOs: 569 to 575, SEQ ID NOs: 596 to 599, SEQ ID NOs: 601 to 604, SEQ ID NOs: 606 to 612, SEQ ID NO: 656, SEQ ID NO: 708, SEQ ID NO: 712, and SEQ ID NO: 759. In some embodiments, any one of the peptides in the colorectal cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 484 to 485, SEQ ID NOs: 488 to 489, SEQ ID NOs: 569 to 575, SEQ ID NOs: 596 to 599, SEQ ID NOs: 601 to 604, SEQ ID NOs: 606 to 612, SEQ ID NO: 656, SEQ ID NO: 708, SEQ ID NO: 712, or SEQ ID NO: 759.

In some embodiments, the amino acid sequence vaccine for a MHC class II vaccine for colorectal cancer comprises two or more of the SEQ ID NOs: 484 to 485, SEQ ID NOs: 488 to 489, SEQ ID NOs: 569 to 575, SEQ ID NOs: 596 to 599, SEQ ID NOs: 601 to 604, SEQ ID NOs: 606 to 612, SEQ ID NO: 656, SEQ ID NO: 708, SEQ ID NO: 712, and SEQ ID NO: 759. In some embodiments, any one of the peptides in the colorectal cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 484 to 485, SEQ ID NOs: 488 to 489, SEQ ID NOs: 569 to 575, SEQ ID NOs: 596 to 599, SEQ ID NOs: 601 to 604, SEQ ID NOs: 606 to 612, SEQ ID NO: 656, SEQ ID NO: 708, SEQ ID NO: 712, or SEQ ID NO: 759.

In some embodiments, the amino acid sequence vaccine for a MHC class II vaccine for bronchus and lung cancer comprises one or more of the SEQ ID NOs: 520 to 521, SEQ ID NOs: 523 to 524, SEQ ID NOs: 554 to 556, SEQ ID NO: 558, SEQ ID NO: 561, SEQ ID NOs: 563 to 565, SEQ ID NOs: 569 to 573, SEQ ID NOs: 596 to 600, SEQ ID NO: 650, SEQ ID NO: 656, and SEQ ID NOs: 700 to 705. In some embodiments, any one of the peptides in the bronchus and lung cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 520 to 521, SEQ ID NOs: 523 to 524, SEQ ID NOs: 554 to 556, SEQ ID NO: 558, SEQ ID NO: 561, SEQ ID NOs: 563 to 565, SEQ ID NOs: 569 to 573, SEQ ID NOs: 596 to 600, SEQ ID NO: 650, SEQ ID NO: 656, or SEQ ID NOs: 700 to 705.

In some embodiments, the amino acid sequence vaccine for a MHC class II vaccine for bronchus and lung cancer comprises two or more of the SEQ ID NOs: 520 to 521, SEQ ID NOs: 523 to 524, SEQ ID NOs: 554 to 556, SEQ ID NO: 558, SEQ ID NO: 561, SEQ ID NOs: 563 to 565, SEQ ID NOs: 569 to 573, SEQ ID NOs: 596 to 600, SEQ ID NO: 650, SEQ ID NO: 656, and SEQ ID NOs: 700 to 705. In some embodiments, any one of the peptides in the bronchus and lung cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 520 to 521, SEQ ID NOs: 523 to 524, SEQ ID NOs: 554 to 556, SEQ ID NO: 558, SEQ ID NO: 561, SEQ ID NOs: 563 to 565, SEQ ID NOs: 569 to 573, SEQ ID NOs: 596 to 600, SEQ ID NO: 650, SEQ ID NO: 656, or SEQ ID NOs: 700 to 705.

In some embodiments, the amino acid sequence vaccine for a MHC class II vaccine for breast cancer comprises one or more of the SEQ ID NOs: 646 to 667, SEQ ID NOs: 708 to 717, and SEQ ID NOs: 733 to 748. In some embodiments, any one of the peptides in the breast cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 646 to 667, SEQ ID NOs: 708 to 717, or SEQ ID NOs: 733 to 748.

In some embodiments, the amino acid sequence vaccine for a MHC class II vaccine for breast cancer comprises two or more of the SEQ ID NOs: 646 to 667, SEQ ID NOs: 708 to 717, and SEQ ID NOs: 733 to 748. In some embodiments, any one of the peptides in the breast cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 646 to 667, SEQ ID NOs: 708 to 717, or SEQ ID NOs: 733 to 748.

In some embodiments, the amino acid sequence vaccine for a MHC class II vaccine for ovarian cancer comprises one or more of the SEQ ID NOs: 646 to 667, SEQ ID NOs: 708 to 717, and SEQ ID NOs: 733 to 748. In some embodiments, any one of the peptides in the ovarian cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 646 to 667, SEQ ID NOs: 708 to 717, or SEQ ID NOs: 733 to 748.

In some embodiments, the amino acid sequence vaccine for a MHC class II vaccine for ovarian cancer comprises two or more of the SEQ ID NOs: 646 to 667, SEQ ID NOs: 708 to 717, and SEQ ID NOs: 733 to 748. In some embodiments, any one of the peptides in the ovarian cancer vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 646 to 667, SEQ ID NOs: 708 to 717, or SEQ ID NOs: 733 to 748.

Table 2 summarizes MHC class II peptide sequences described herein including the respective SEQ ID NO, amino acid sequence corresponding to the SEQ ID NO, the amino acid sequence corresponding to the peptide's binding core, the protein target (with specific mutation), the seed amino acid sequence (i.e., the amino acid sequence of the wild type KRAS fragment), the seed amino acid sequence of the binding core, and the amino acid substitution (if any) for heteroclitic peptides at positions 1, 4, 6, and 9. Table 2 includes peptide sequences comprising SEQ ID NOs: 475 to 759. SEQ ID NOs: 475 to 759 (Table 2) encode for recombinant peptides. In some embodiments, any combination of peptides listed in Table 2 (SEQ ID NOs: 475 to 759) may be used to create a single target (individual) or combined peptide vaccine having between about 2 and about 40 peptides. In some embodiments, any one of the peptides (peptides 475 to 759; SEQ ID NOs: 475 to 759) in the combined vaccine comprises an amino acid sequence 80, 81, 82, 83, 84, 85, 86, 87, 88, 89, 90, 91, 92, 93, 94, 95, 96, 97, 98 or 99% identical to any of SEQ ID NOs: 475 to 759.

Additional amino acid sequences of MHC class II vaccine peptides are provided in Sequence Listings (SEQ ID NOs: 22728 to 28795). In some embodiments, any combination of MHC class II peptides disclosed herein (SEQ ID NOs: 475 to 759 and SEQ ID NOs: 22728 to 28795) may be used to create a combined peptide vaccine having between about 2 and about 40 peptides. In some embodiments, any one of the peptides (SEQ ID NOs: 475 to 759 and SEQ ID NOs: 22728 to 28795) in the combined vaccine comprises or contains an amino acid sequence 80, 81, 82, 83, 84, 85, 86, 87, 88, 89, 90, 91, 92, 93, 94, 95, 96, 97, 98 or 99% identical to any of SEQ ID NOs: 475 to 759 or SEQ ID NOs: 22728 to 28795.

In some embodiments, the amino acid sequence for a MHC class I and/or MHC class II peptides may be used to create a single target (individual) or combined peptide vaccine for mutation in the AKT1 protein having between about 2 and about 40 peptides. In some embodiments, any one of the peptides in the vaccine for mutation in the AKT1 protein comprises one or more of the SEQ ID NOs: 1 to 18, SEQ ID NO: 459, SEQ ID NOs: 475 to 483, SEQ ID NOs: 760 to 1768, SEQ ID NOs: 22386 to 22396, SEQ ID NOs: 22728 to 22838, and SEQ ID NOs: 25305 to 25488. In some embodiments, any one of the peptides in the AKT1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 1 to 18, SEQ ID NO: 459, SEQ ID NOs:

475 to 483, SEQ ID NOs: 760 to 1768, SEQ ID NOs: 22386 to 22396, SEQ ID NOs: 22728 to 22838, or SEQ ID NOs: 25305 to 25488.

In some embodiments, the amino acid sequence for a MHC class I and/or MHC class II peptides may be used to create a single target (individual) or combined peptide vaccine for mutation in the BRAF protein having between about 2 and about 40 peptides. In some embodiments, any one of the peptides in the vaccine for mutation in the BRAF protein comprises one or more of the SEQ ID NOs: 19 to 50, SEQ ID NOs: 484 to 502, SEQ ID NOs: 1769 to 3170, SEQ ID NOs: 22397 to 22417, SEQ ID NOs: 22839 to 22966, and SEQ ID NOs: 25489 to 25616. In some embodiments, any one of the peptides in the BRAF vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 19 to 50, SEQ ID NOs: 484 to 502, SEQ ID NOs: 1769 to 3170, SEQ ID NOs: 22397 to 22417, SEQ ID NOs: 22839 to 22966, or SEQ ID NOs: 25489 to 25616.

In some embodiments, the amino acid sequence for a MHC class I and/or MHC class II peptides may be used to create a single target (individual) or combined peptide vaccine for mutation in the EGFR protein having between about 2 and about 40 peptides. In some embodiments, any one of the peptides in the vaccine for mutation in the EGFR protein comprises one or more of the SEQ ID NOs: 51 to 98, SEQ ID NOs: 503 to 527, SEQ ID NOs: 3171 to 5756, SEQ ID NOs: 22418 to 22449, SEQ ID NOs: 22967 to 23263, and SEQ ID NOs: 25617 to 26046. In some embodiments, any one of the peptides in the EGFR vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 51 to 98, SEQ ID NOs: 503 to 527, SEQ ID NOs: 3171 to 5756, SEQ ID NOs: 22418 to 22449, SEQ ID NOs: 22967 to 23263, or SEQ ID NOs: 25617 to 26046.

In some embodiments, the amino acid sequence for a MHC class I and/or MHC class II peptides may be used to create a single target (individual) or combined peptide vaccine for mutation in the GTF2I protein having between about 2 and about 40 peptides. In some embodiments, any one of the peptides in the vaccine for mutation in the GTF2I protein comprises one or more of the SEQ ID NOs: 99 to 118, SEQ ID NOs: 528 to 534, SEQ ID NOs: 5757 to 6498, SEQ ID NOs: 22450 to 22466, SEQ ID NOs: 23264 to 23415, and SEQ ID NOs: 26047 to 26375. In some embodiments, any one of the peptides in the GTF2I vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 99 to 118, SEQ ID NOs: 528 to 534, SEQ ID NOs: 5757 to 6498, SEQ ID NOs: 22450 to 22466, SEQ ID NOs: 23264 to 23415, or SEQ ID NOs: 26047 to 26375.

In some embodiments, the amino acid sequence for a MHC class I and/or MHC class II peptides may be used to create a single target (individual) or combined peptide vaccine for mutation in the IDH1 protein having between about 2 and about 40 peptides. In some embodiments, any one of the peptides in the vaccine for mutation in the IDH1 protein comprises one or more of the SEQ ID NOs: 119 to 140, SEQ ID NOs: 460 to 461, SEQ ID NOs: 535 to 553, SEQ ID NOs: 6499 to 7098, SEQ ID NOs: 22467 to 22488, SEQ ID NOs: 23416 to 23631, and SEQ ID NOs: 26376 to 26614. In some embodiments, any one of the peptides in the IDH1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 119 to 140, SEQ ID NOs: 460 to 461, SEQ ID NOs: 535 to 553, SEQ ID NOs: 6499 to 7098, SEQ ID NOs: 22467 to 22488, SEQ ID NOs: 23416 to 23631, or SEQ ID NOs: 26376 to 26614.

In some embodiments, the amino acid sequence for a MHC class I and/or MHC class II peptides may be used to create a single target (individual) or combined peptide vaccine for mutation in the KRAS protein having between about 2 and about 40 peptides. In some embodiments, any one of the peptides in the vaccine for mutation in the KRAS protein comprises one or more of the SEQ ID NOs: 141 to 229, SEQ ID NOs: 462 to 466, SEQ ID NOs: 554 to 615, SEQ ID NO: 759, SEQ ID NOs: 7099 to 12814, SEQ ID NOs: 22489 to 22558, SEQ ID NOs: 23632 to 24129, and SEQ ID NOs: 26615 to 27328. In some embodiments, any one of the peptides in the KRAS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 141 to 229, SEQ ID NOs: 462 to 466, SEQ ID NOs: 554 to 615, SEQ ID NO: 759, SEQ ID NOs: 7099 to 12814, SEQ ID NOs: 22489 to 22558, SEQ ID NOs: 23632 to 24129, or SEQ ID NOs: 26615 to 27328.

In some embodiments, the amino acid sequence for a MHC class I and/or MHC class II peptides may be used to create a single target (individual) or combined peptide vaccine for mutation in the NRAS protein having between about 2 and about 40 peptides. In some embodiments, any one of the peptides in the vaccine for mutation in the NRAS protein comprises one or more of the SEQ ID NOs: 230 to 272, SEQ ID NOs: 616 to 645, SEQ ID NOs: 12815 to 14836, SEQ ID NOs: 22559 to 22582, SEQ ID NOs: 24130 to 24347, and SEQ ID NOs: 27329 to 27557. In some embodiments, any one of the peptides in the NRAS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 230 to 272, SEQ ID NOs: 616 to 645, SEQ ID NOs: 12815 to 14836, SEQ ID NOs: 22559 to 22582, SEQ ID NOs: 24130 to 24347, or SEQ ID NOs: 27329 to 27557.

In some embodiments, the amino acid sequence for a MHC class I and/or MHC class II peptides may be used to create a single target (individual) or combined peptide vaccine for mutation in the PIK3CA protein having between about 2 and about 40 peptides. In some embodiments, any one of the peptides in the vaccine for mutation in the PIK3CA protein comprises one or more of the SEQ ID NOs: 273 to 322, SEQ ID NOs: 467 to 468, SEQ ID NOs: 646 to 675, SEQ ID NOs: 14837 to 17342, SEQ ID NOs: 22583 to 22622, SEQ ID NOs: 24348 to 24571, and SEQ ID NOs: 27558 to 27889. In some embodiments, any one of the peptides in the PIK3CA vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 273 to 322, SEQ ID NOs: 467 to 468, SEQ ID NOs: 646 to 675, SEQ ID NOs: 14837 to 17342, SEQ ID NOs: 22583 to 22622, SEQ ID NOs: 24348 to 24571, or SEQ ID NOs: 27558 to 27889.

In some embodiments, the amino acid sequence for a MHC class I and/or MHC class II peptides may be used to create a single target (individual) or combined peptide vaccine for mutation in the PTEN protein having between about 2 and about 40 peptides. In some embodiments, any one of the peptides in the vaccine for mutation in the PTEN protein comprises one or more of the SEQ ID NOs: 323 to 353, SEQ ID NOs: 676 to 690, SEQ ID NOs: 17343 to 18205, SEQ ID NOs: 22623 to 22636, SEQ ID NOs: 24572 to 24724, and SEQ ID NOs: 27890 to 28052. In some embodiments, any one of the peptides in the PTEN vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 323 to 353, SEQ ID NOs: 676 to 690, SEQ ID NOs: 17343 to 18205, SEQ ID NOs: 22623 to 22636, SEQ ID NOs: 24572 to 24724, or SEQ ID NOs: 27890 to 28052.

In some embodiments, the amino acid sequence for a MHC class I and/or MHC class II peptides may be used to create a single target (individual) or combined peptide vaccine for mutation in the TP53 protein having between about 2 and about 40 peptides. In some embodiments, any one of the peptides in the vaccine for mutation in the TP53 protein comprises one or more of the SEQ ID NOs: 354 to 458, SEQ ID NOs: 469 to 474, SEQ ID NOs: 691 to 758, SEQ ID NOs: 18206 to 22385, SEQ ID NOs: 22637 to 22727, SEQ ID NOs: 24725 to 25304, and SEQ ID NOs: 28053 to 28795. In some embodiments, any one of the peptides in the TP53 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 354 to 458, SEQ ID NOs: 469 to 474, SEQ ID NOs: 691 to 758, SEQ ID NOs: 18206 to 22385, SEQ ID NOs: 22637 to 22727, SEQ ID NOs: 24725 to 25304, or SEQ ID NOs: 28053 to 28795.

In some embodiments, the amino acid sequence for a MHC class I and/or MHC class II peptides may be used to create a single target (individual) or combined peptide vaccine for mutation in the RAS protein having between about 2 and about 40 peptides. In some embodiments, any one of the peptides in the vaccine for mutation in the RAS protein comprises one or more of the SEQ ID NOs: 141 to 272, SEQ ID NOs: 462 to 466, SEQ ID NOs: 554 to 645, SEQ ID NO: 759, SEQ ID NOs: 7099 to 14836, SEQ ID NOs: 22489 to 22582, SEQ ID NOs: 23632 to 24347, and SEQ ID NOs: 26615 to 27557. In some embodiments, any one of the peptides in the RAS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 141 to 272, SEQ ID NOs: 462 to 466, SEQ ID NOs: 554 to 645, SEQ ID NO: 759, SEQ ID NOs: 7099 to 14836, SEQ ID NOs: 22489 to 22582, SEQ ID NOs: 23632 to 24347, or SEQ ID NOs: 26615 to 27557.

In some embodiments, the amino acid sequence for a MHC class I and/or MHC class II peptides may be used to create a single target (individual) or combined peptide vaccine for the BRAF V600 protein mutation having between about 2 and about 40 peptides. In some embodiments, any one of the peptides in the vaccine for the BRAF V600 protein mutation comprises one or more of the SEQ ID NOs: 19 to 33, SEQ ID NOs: 484 to 494, SEQ ID NOs: 1769 to 2329, SEQ ID NOs: 22397 to 22405, SEQ ID NOs: 22839 to 22876, and SEQ ID NOs: 25489 to 25526. In some embodiments, any one of the peptides in the BRAF V600 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 19 to 33, SEQ ID NOs: 484 to 494, SEQ ID NOs: 1769 to 2329, SEQ ID NOs: 22397 to 22405, SEQ ID NOs: 22839 to 22876, or SEQ ID NOs: 25489 to 25526.

In some embodiments, the amino acid sequence for a MHC class I and/or MHC class II peptides may be used to create a single target (individual) or combined peptide vaccine for the BRAF V600M protein mutation having between about 2 and about 40 peptides. In some embodiments, any one of the peptides in the vaccine for the BRAF V600M protein mutation comprises one or more of the SEQ ID NOs: 34 to 50, SEQ ID NOs: 495 to 502, SEQ ID NOs: 2330 to 3170, SEQ ID NOs: 22406 to 22417, SEQ ID NOs: 22877 to 22966, and SEQ ID NOs: 25527 to 25616. In some embodiments, any one of the peptides in the BRAF V600M vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 34 to 50, SEQ ID NOs: 495 to 502, SEQ ID NOs: 2330 to 3170, SEQ ID NOs: 22406 to 22417, SEQ ID NOs: 22877 to 22966, or SEQ ID NOs: 25527 to 25616.

In some embodiments, the amino acid sequence for a MHC class I and/or MHC class II peptides may be used to create a single target (individual) or combined peptide vaccine for the EGFR A289V protein mutation having between about 2 and about 40 peptides. In some embodiments, any one of the peptides in the vaccine for the EGFR A289V protein mutation comprises one or more of the SEQ ID NOs: 51 to 66, SEQ ID NOs: 503 to 509, SEQ ID NOs: 3171 to 4055, SEQ ID NOs: 22418 to 22430, SEQ ID NOs: 22967 to 23000, and SEQ ID NOs: 25617 to 25653. In some embodiments, any one of the peptides in the EGFR A289V vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 51 to 66, SEQ ID NOs: 503 to 509, SEQ ID NOs: 3171 to 4055, SEQ ID NOs: 22418 to 22430, SEQ ID NOs: 22967 to 23000, or SEQ ID NOs: 25617 to 25653.

In some embodiments, the amino acid sequence for a MHC class I and/or MHC class II peptides may be used to create a single target (individual) or combined peptide vaccine for the EGFR G598V protein mutation having between about 2 and about 40 peptides. In some embodiments, any one of the peptides in the vaccine for the EGFR G598V protein mutation comprises one or more of the SEQ ID NOs: 67 to 81, SEQ ID NOs: 510 to 519, SEQ ID NOs: 4056 to 4718, SEQ ID NOs: 22431 to 22437, SEQ ID NOs: 23001 to 23089, and SEQ ID NOs: 25654 to 25794. In some embodiments, any one of the peptides in the EGFR G598V vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 67 to 81, SEQ ID NOs: 510 to 519, SEQ ID NOs: 4056 to 4718, SEQ ID NOs: 22431 to 22437, SEQ ID NOs: 23001 to 23089, or SEQ ID NOs: 25654 to 25794.

In some embodiments, the amino acid sequence for a MHC class I and/or MHC class II peptides may be used to create a single target (individual) or combined peptide vaccine for the EGFR L858R protein mutation having between about 2 and about 40 peptides. In some embodiments, any one of the peptides in the vaccine for the EGFR L858R protein mutation comprises one or more of the SEQ ID NOs: 82 to 98, SEQ ID NOs: 520 to 527, SEQ ID NOs: 4719 to 5756, SEQ ID NOs: 22438 to 22449, SEQ ID NOs: 23090 to 23263, and SEQ ID NOs: 25795 to 26046. In some embodiments, any one of the peptides in the EGFR L858R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 82 to 98, SEQ ID NOs: 520 to 527, SEQ ID NOs: 4719 to 5756, SEQ ID NOs: 22438 to 22449, SEQ ID NOs: 23090 to 23263, or SEQ ID NOs: 25795 to 26046.

In some embodiments, the amino acid sequence for a MHC class I and/or MHC class II peptides may be used to create a single target (individual) or combined peptide vaccine for the IDH1 R132H protein mutation having between about 2 and about 40 peptides. In some embodiments, any one of the peptides in the vaccine for the IDH1 R132H protein mutation comprises one or more of the SEQ ID NOs: 125 to 140, SEQ ID NO: 461, SEQ ID NOs: 543 to 553, SEQ ID NOs: 6738 to 7098, SEQ ID NOs: 22477 to 22488, SEQ ID NOs: 23505 to 23631, and SEQ ID NOs: 26469 to 26614. In some embodiments, any one of the peptides in the IDH1 R132H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 125 to 140, SEQ ID NO: 461, SEQ ID NOs: 543 to 553, SEQ ID NOs: 6738 to 7098, SEQ ID NOs: 22477 to 22488, SEQ ID NOs: 23505 to 23631, or SEQ ID NOs: 26469 to 26614.

In some embodiments, the amino acid sequence for a MHC class I and/or MHC class II peptides may be used to create a single target (individual) or combined peptide vaccine for the IDH1 R132C protein mutation having between about 2 and about 40 peptides. In some embodiments, any one of the peptides in the vaccine for the IDH1 R132C protein mutation comprises one or more of the SEQ ID NOs: 119 to 124, SEQ ID NO: 460, SEQ ID NOs: 535 to 542, SEQ ID NOs: 6499 to 6737, SEQ ID NOs: 22467 to 22476, SEQ ID NOs: 23416 to 23504, and SEQ ID NOs: 26376 to 26468. In some embodiments, any one of the peptides in the IDH1 R132C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 119 to 124, SEQ ID NO: 460, SEQ ID NOs: 535 to 542, SEQ ID NOs: 6499 to 6737, SEQ ID NOs: 22467 to 22476, SEQ ID NOs: 23416 to 23504, or SEQ ID NOs: 26376 to 26468.

In some embodiments, the amino acid sequence for a MHC class I and/or MHC class II peptides may be used to create a single target (individual) or combined peptide vaccine for the KRAS G12D protein mutation having between about 2 and about 40 peptides. In some embodiments, any one of the peptides in the vaccine for the KRAS G12D protein mutation comprises one or more of the SEQ ID NOs: 167 to 178, SEQ ID NO: 464, SEQ ID NOs: 569 to 577, SEQ ID NOs: 8432 to 9733, SEQ ID NOs: 22507 to 22518, SEQ ID NOs: 23750 to 23809, and SEQ ID NOs: 26757 to 26833. In some embodiments, any one of the peptides in the KRAS G12D vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 167 to 178, SEQ ID NO: 464, SEQ ID NOs: 569 to 577, SEQ ID NOs: 8432 to 9733, SEQ ID NOs: 22507 to 22518, SEQ ID NOs: 23750 to 23809, or SEQ ID NOs: 26757 to 26833.

In some embodiments, the amino acid sequence for a MHC class I and/or MHC class II peptides may be used to create a single target (individual) or combined peptide vaccine for the KRAS G12V protein mutation having between about 2 and about 40 peptides. In some embodiments, any one of the peptides in the vaccine for the KRAS G12V protein mutation comprises one or more of the SEQ ID NOs: 203 to 213, SEQ ID NOs: 596 to 605, SEQ ID NOs: 11009 to 11744, SEQ ID NOs: 22537 to 22546, SEQ ID NOs: 23958 to 24025, and SEQ ID NOs: 27057 to 27148. In some embodiments, any one of the peptides in the KRAS G12V vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 203 to 213, SEQ ID NOs: 596 to 605, SEQ ID NOs: 11009 to 11744, SEQ ID NOs: 22537 to 22546, SEQ ID NOs: 23958 to 24025, or SEQ ID NOs: 27057 to 27148.

In some embodiments, the amino acid sequence for a MHC class I and/or MHC class II peptides may be used to create a single target (individual) or combined peptide vaccine for the KRAS G12R protein mutation having between about 2 and about 40 peptides. In some embodiments, any one of the peptides in the vaccine for the KRAS G12R protein mutation comprises one or more of the SEQ ID NOs: 179 to 191, SEQ ID NO: 465, SEQ ID NOs: 578 to 587, SEQ ID NOs: 9734 to 10236, SEQ ID NOs: 22519 to 22527, SEQ ID NOs: 23810 to 23889, and SEQ ID NOs: 26834 to 26967. In some embodiments, any one of the peptides in the KRAS G12R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 179 to 191, SEQ ID NO: 465, SEQ ID NOs: 578 to 587, SEQ ID NOs: 9734 to 10236, SEQ ID NOs: 22519 to 22527, SEQ ID NOs: 23810 to 23889, or SEQ ID NOs: 26834 to 26967.

In some embodiments, the amino acid sequence for a MHC class I and/or MHC class II peptides may be used to create a single target (individual) or combined peptide vaccine for the KRAS G12C protein mutation having between about 2 and about 40 peptides. In some embodiments, any one of the peptides in the vaccine for the KRAS G12C protein mutation comprises one or more of the SEQ ID NOs: 154 to 166, SEQ ID NO: 463, SEQ ID NOs: 561 to 568, SEQ ID NOs: 7881 to 8431, SEQ ID NOs: 22498 to 22506, SEQ ID NOs: 23700 to 23749, and SEQ ID NOs: 26702 to 26756. In some embodiments, any one of the peptides in the KRAS G12C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 154 to 166, SEQ ID NO: 463, SEQ ID NOs: 561 to 568, SEQ ID NOs: 7881 to 8431, SEQ ID NOs: 22498 to 22506, SEQ ID NOs: 23700 to 23749, or SEQ ID NOs: 26702 to 26756.

In some embodiments, the amino acid sequence for a MHC class I and/or MHC class II peptides may be used to create a single target (individual) or combined peptide vaccine for the KRAS G13D protein mutation having between about 2 and about 40 peptides. In some embodiments, any one of the peptides in the vaccine for the KRAS G13D protein mutation comprises one or more of the SEQ ID NOs: 214 to 229, SEQ ID NO: 466, SEQ ID NOs: 606 to 615, SEQ ID NO: 759, SEQ ID NOs: 11745 to 12814, SEQ ID NOs: 22547 to 22558, SEQ ID NOs: 24026 to 24129, and SEQ ID NOs: 27149 to 27328. In some embodiments, any one of the peptides in the KRAS G13D vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 214 to 229, SEQ ID NO: 466, SEQ ID NOs: 606 to 615, SEQ ID NO: 759, SEQ ID NOs: 11745 to 12814, SEQ ID NOs: 22547 to 22558, SEQ ID NOs: 24026 to 24129, or SEQ ID NOs: 27149 to 27328.

In some embodiments, the amino acid sequence for a MHC class I and/or MHC class II peptides may be used to create a single target (individual) or combined peptide vaccine for the KRAS G12A protein mutation having between about 2 and about 40 peptides. In some embodiments, any one of the peptides in the vaccine for the KRAS G12A protein mutation comprises one or more of the SEQ ID NOs: 141 to 153, SEQ ID NO: 462, SEQ ID NOs: 554 to 560, SEQ ID NOs: 7099 to 7880, SEQ ID NOs: 22489 to 22497, SEQ ID NOs: 23632 to 23699, and SEQ ID NOs: 26615 to 26701. In some embodiments, any one of the peptides in the KRAS G12A vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 141 to 153, SEQ ID NO: 462, SEQ ID NOs: 554 to 560, SEQ ID NOs: 7099 to 7880, SEQ ID NOs: 22489 to 22497, SEQ ID NOs: 23632 to 23699, or SEQ ID NOs: 26615 to 26701.

In some embodiments, the amino acid sequence for a MHC class I and/or MHC class II peptides may be used to create a single target (individual) or combined peptide vaccine for the KRAS G12S protein mutation having between about 2 and about 40 peptides. In some embodiments, any one of the peptides in the vaccine for the KRAS G12S protein mutation comprises one or more of the SEQ ID NOs: 192 to 202, SEQ ID NOs: 588 to 595, SEQ ID NOs: 10237 to 11008, SEQ ID NOs: 22528 to 22536, SEQ ID NOs: 23890 to 23957, and SEQ ID NOs: 26968 to 27056. In some embodiments, any one of the peptides in the KRAS G12S vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 192 to 202, SEQ ID NOs: 588 to 595, SEQ ID NOs: 10237 to 11008, SEQ ID NOs: 22528 to 22536, SEQ ID NOs: 23890 to 23957, or SEQ ID NOs: 26968 to 27056.

In some embodiments, the amino acid sequence for a MHC class I and/or MHC class II peptides may be used to create a single target (individual) or combined peptide vaccine for the NRAS Q61R protein mutation having between about 2 and about 40 peptides. In some embodiments, any one of the peptides in the vaccine for the NRAS Q61R protein mutation comprises one or more of the SEQ ID NOs: 256 to 272, SEQ ID NOs: 634 to 645, SEQ ID NOs: 14315 to 14836, SEQ ID NOs: 22577 to 22582, SEQ ID NOs: 24280 to 24347, and SEQ ID NOs: 27490 to 27557. In some embodiments, any one of the peptides in the NRAS Q61R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 256 to 272, SEQ ID NOs: 634 to 645, SEQ ID NOs: 14315 to 14836, SEQ ID NOs: 22577 to 22582, SEQ ID NOs: 24280 to 24347, or SEQ ID NOs: 27490 to 27557.

In some embodiments, the amino acid sequence for a MHC class I and/or MHC class II peptides may be used to create a single target (individual) or combined peptide vaccine for the NRAS Q61K protein mutation having between about 2 and about 40 peptides. In some embodiments, any one of the peptides in the vaccine for the NRAS Q61K protein mutation comprises one or more of the SEQ ID NOs: 230 to 238, SEQ ID NOs: 616 to 624, SEQ ID NOs: 12815 to 13434, SEQ ID NOs: 22559 to 22567, SEQ ID NOs: 24130 to 24194, and SEQ ID NOs: 27329 to 27396. In some embodiments, any one of the peptides in the NRAS Q61K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 230 to 238, SEQ ID NOs: 616 to 624, SEQ ID NOs: 12815 to 13434, SEQ ID NOs: 22559 to 22567, SEQ ID NOs: 24130 to 24194, or SEQ ID NOs: 27329 to 27396.

In some embodiments, the amino acid sequence for a MHC class I and/or MHC class II peptides may be used to create a single target (individual) or combined peptide vaccine for the NRAS Q61L protein mutation having between about 2 and about 40 peptides. In some embodiments, any one of the peptides in the vaccine for the NRAS Q61L protein mutation comprises one or more of the SEQ ID NOs: 239 to 255, SEQ ID NOs: 625 to 633, SEQ ID NOs: 13435 to 14314, SEQ ID NOs: 22568 to 22576, SEQ ID NOs: 24195 to 24279, and SEQ ID NOs: 27397 to 27489. In some embodiments, any one of the peptides in the NRAS Q61L vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 239 to 255, SEQ ID NOs: 625 to 633, SEQ ID NOs: 13435 to 14314, SEQ ID NOs: 22568 to 22576, SEQ ID NOs: 24195 to 24279, or SEQ ID NOs: 27397 to 27489.

In some embodiments, the amino acid sequence for a MHC class I and/or MHC class II peptides may be used to create a single target (individual) or combined peptide vaccine for the PIK3CA E542K protein mutation having between about 2 and about 40 peptides. In some embodiments, any one of the peptides in the vaccine for the PIK3CA E542K protein mutation comprises one or more of the SEQ ID NOs: 273 to 285, SEQ ID NOs: 646 to 650, SEQ ID NOs: 14837 to 15625, SEQ ID NOs: 22583 to 22592, SEQ ID NOs: 24348 to 24362, and SEQ ID NOs: 27558 to 27572. In some embodiments, any one of the peptides in the PIK3CA E542K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 273 to 285, SEQ ID NOs: 646 to 650, SEQ ID NOs: 14837 to 15625, SEQ ID NOs: 22583 to 22592, SEQ ID NOs: 24348 to 24362, or SEQ ID NOs: 27558 to 27572.

In some embodiments, the amino acid sequence for a MHC class I and/or MHC class II peptides may be used to create a single target (individual) or combined peptide vaccine for the PIK3CA E545K protein mutation having between about 2 and about 40 peptides. In some embodiments, any one of the peptides in the vaccine for the PIK3CA E545K protein mutation comprises one or more of the SEQ ID NOs: 286 to 293, SEQ ID NO: 467, SEQ ID NOs: 651 to 657, SEQ ID NOs: 15626 to 15907, SEQ ID NOs: 22593 to 22602, SEQ ID NOs: 24363 to 24388, and SEQ ID NOs: 27573 to 27599. In some embodiments, any one of the peptides in the PIK3CA E545K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 286 to 293, SEQ ID NO: 467, SEQ ID NOs: 651 to 657, SEQ ID NOs: 15626 to 15907, SEQ ID NOs: 22593 to 22602, SEQ ID NOs: 24363 to 24388, or SEQ ID NOs: 27573 to 27599.

In some embodiments, the amino acid sequence for a MHC class I and/or MHC class II peptides may be used to create a single target (individual) or combined peptide vaccine for the PIK3CA H1047R protein mutation having between about 2 and about 40 peptides. In some embodiments, any one of the peptides in the vaccine for the PIK3CA H1047R protein mutation comprises one or more of the SEQ ID NOs: 294 to 309, SEQ ID NOs: 658 to 667, SEQ ID NOs: 15908 to 16276, SEQ ID NOs: 22603 to 22608, SEQ ID NOs: 24389 to 24472, and SEQ ID NOs: 27600 to 27683. In some embodiments, any one of the peptides in the PIK3CA H1047R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 294 to 309, SEQ ID NOs: 658 to 667, SEQ ID NOs: 15908 to 16276, SEQ ID NOs: 22603 to 22608, SEQ ID NOs: 24389 to 24472, or SEQ ID NOs: 27600 to 27683.

In some embodiments, the amino acid sequence for a MHC class I and/or MHC class II peptides may be used to create a single target (individual) or combined peptide vaccine for the TP53 R158L protein mutation having between about 2 and about 40 peptides. In some embodiments, any one of the peptides in the vaccine for the TP53 R158L protein mutation comprises one or more of the SEQ ID NOs: 359 to 374, SEQ ID NOs: 469 to 470, SEQ ID NOs: 700 to 707, SEQ ID NOs: 18414 to 19404, SEQ ID NOs: 22644 to 22657, SEQ ID NOs: 24784 to 24927, and SEQ ID NOs: 28132 to 28372. In some embodiments, any one of the peptides in the TP53 R158L vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 359 to 374, SEQ ID NOs: 469 to 470, SEQ ID NOs: 700 to 707, SEQ ID NOs: 18414 to 19404, SEQ ID NOs: 22644 to 22657, SEQ ID NOs: 24784 to 24927, or SEQ ID NOs: 28132 to 28372.

In some embodiments, the amino acid sequence for a MHC class I and/or MHC class II peptides may be used to create a single target (individual) or combined peptide vaccine for the TP53 R175H protein mutation having between about 2 and about 40 peptides. In some embodiments, any one of the peptides in the vaccine for the TP53 R175H protein mutation comprises one or more of the SEQ ID NOs: 375 to 386, SEQ ID NOs: 471 to 472, SEQ ID NOs: 708 to 717, SEQ ID NOs: 19405 to 19752, SEQ ID NOs: 22658 to 22665, SEQ ID NOs: 24928 to 24954, and SEQ ID NOs: 28373 to 28410. In some embodiments, any one of the peptides in the TP53 R175H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 375 to 386, SEQ ID NOs: 471 to 472, SEQ ID NOs: 708 to 717, SEQ ID NOs: 19405 to 19752, SEQ ID NOs: 22658 to 22665, SEQ ID NOs: 24928 to 24954, or SEQ ID NOs: 28373 to 28410.

In some embodiments, the amino acid sequence for a MHC class I and/or MHC class II peptides may be used to create a single target (individual) or combined peptide vaccine for the TP53 R248Q protein mutation having between about 2 and about 40 peptides. In some embodiments, any one of the peptides in the vaccine for the TP53 R248Q protein mutation comprises one or more of the SEQ ID NOs: 387 to 401, SEQ ID NOs: 718 to 723, SEQ ID NOs: 19753 to 20608, SEQ ID NOs: 22666 to 22678, SEQ ID NOs: 24955 to 25010, and SEQ ID NOs: 28411 to 28468. In some embodiments, any one of the peptides in the TP53 R248Q vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 387 to 401, SEQ ID NOs: 718 to 723, SEQ ID NOs: 19753 to 20608, SEQ ID NOs: 22666 to 22678, SEQ ID NOs: 24955 to 25010, or SEQ ID NOs: 28411 to 28468.

In some embodiments, the amino acid sequence for a MHC class I and/or MHC class II peptides may be used to create a single target (individual) or combined peptide vaccine for the TP53 R273C protein mutation having between about 2 and about 40 peptides. In some embodiments, any one of the peptides in the vaccine for the TP53 R273C protein mutation comprises one or more of the SEQ ID NOs: 422 to 432, SEQ ID NO: 473, SEQ ID NOs: 733 to 739, SEQ ID NOs: 21192 to 21462, SEQ ID NOs: 22690 to 22701, SEQ ID NOs: 25109 to 25117, and SEQ ID NOs: 28572 to 28580. In some embodiments, any one of the peptides in the TP53 R273C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 422 to 432, SEQ ID NO: 473, SEQ ID NOs: 733 to 739, SEQ ID NOs: 21192 to 21462, SEQ ID NOs: 22690 to 22701, SEQ ID NOs: 25109 to 25117, or SEQ ID NOs: 28572 to 28580.

In some embodiments, the amino acid sequence for a MHC class I and/or MHC class II peptides may be used to create a single target (individual) or combined peptide vaccine for the TP53 R273H protein mutation having between about 2 and about 40 peptides. In some embodiments, any one of the peptides in the vaccine for the TP53 R273H protein mutation comprises one or more of the SEQ ID NOs: 433 to 446, SEQ ID NO: 474, SEQ ID NOs: 740 to 748, SEQ ID NOs: 21463 to 21845, SEQ ID NOs: 22702 to 22713, SEQ ID NOs: 25118 to 25206, and SEQ ID NOs: 28581 to 28697. In some embodiments, any one of the peptides in the TP53 R273H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 433 to 446, SEQ ID NO: 474, SEQ ID NOs: 740 to 748, SEQ ID NOs: 21463 to 21845, SEQ ID NOs: 22702 to 22713, SEQ ID NOs: 25118 to 25206, or SEQ ID NOs: 28581 to 28697.

In some embodiments, the amino acid sequence for a MHC class I and/or MHC class II peptides may be used to create a single target (individual) or combined peptide vaccine for the TP53 R248W protein mutation having between about 2 and about 40 peptides. In some embodiments, any one of the peptides in the vaccine for the TP53 R248W protein mutation comprises one or more of the SEQ ID NOs: 402 to 421, SEQ ID NOs: 724 to 732, SEQ ID NOs: 20609 to 21191, SEQ ID NOs: 22679 to 22689, SEQ ID NOs: 25011 to 25108, and SEQ ID NOs: 28469 to 28571. In some embodiments, any one of the peptides in the TP53 R248W vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 402 to 421, SEQ ID NOs: 724 to 732, SEQ ID NOs: 20609 to 21191, SEQ ID NOs: 22679 to 22689, SEQ ID NOs: 25011 to 25108, or SEQ ID NOs: 28469 to 28571.

In some embodiments, the amino acid sequence for a MHC class I and/or MHC class II peptides may be used to create a single target (individual) or combined peptide vaccine for the TP53 R282W protein mutation having between about 2 and about 40 peptides. In some embodiments, any one of the peptides in the vaccine for the TP53 R282W protein mutation comprises one or more of the SEQ ID NOs: 447 to 449, SEQ ID NOs: 749 to 750, SEQ ID NOs: 21846 to 21940, SEQ ID NOs: 22714 to 22720, SEQ ID NOs: 25207 to 25218, and SEQ ID NOs: 28698 to 28709. In some embodiments, any one of the peptides in the TP53 R282W vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 447 to 449, SEQ ID NOs: 749 to 750, SEQ ID NOs: 21846 to 21940, SEQ ID NOs: 22714 to 22720, SEQ ID NOs: 25207 to 25218, or SEQ ID NOs: 28698 to 28709.

In some embodiments, the amino acid sequence for a MHC class I and/or MHC class II peptides may be used to create a single target (individual) or combined peptide vaccine for the TP53 Y220C protein mutation having between about 2 and about 40 peptides. In some embodiments, any one of the peptides in the vaccine for the TP53 Y220C protein mutation comprises one or more of the SEQ ID NOs: 450 to 458, SEQ ID NOs: 751 to 758, SEQ ID NOs: 21941 to 22385, SEQ ID NOs: 22721 to 22727, SEQ ID NOs: 25219 to 25304, and SEQ ID NOs: 28710 to 28795. In some embodiments, any one of the peptides in the TP53 Y220C vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 450 to 458, SEQ ID NOs: 751 to 758, SEQ ID NOs: 21941 to 22385, SEQ ID NOs: 22721 to 22727, SEQ ID NOs: 25219 to 25304, or SEQ ID NOs: 28710 to 28795.

In some embodiments, the amino acid sequence for a MHC class I and/or MHC class II peptides may be used to create a single target (individual) or combined peptide vaccine for the PIK3CA R88Q protein mutation having between about 2 and about 40 peptides. In some embodiments, any one of the peptides in the vaccine for the PIK3CA R88Q protein mutation comprises one or more of the SEQ ID NOs: 310 to 322, SEQ ID NO: 468, SEQ ID NOs: 668 to 675, SEQ ID NOs: 16277 to 17342, SEQ ID NOs: 22609 to 22622, SEQ ID NOs: 24473 to 24571, and SEQ ID NOs: 27684 to 27889. In some embodiments, any one of the peptides in the PIK3CA R88Q vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 310 to 322, SEQ ID NO: 468, SEQ ID NOs: 668 to 675, SEQ ID NOs: 16277 to 17342, SEQ ID NOs: 22609 to 22622, SEQ ID NOs: 24473 to 24571, or SEQ ID NOs: 27684 to 27889.

In some embodiments, the amino acid sequence for a MHC class I and/or MHC class II peptides may be used to create a single target (individual) or combined peptide vaccine for the GTF2I L424H protein mutation having between about 2 and about 40 peptides. In some embodiments, any one of the peptides in the vaccine for the GTF2I L424H protein mutation comprises one or more of the SEQ ID NOs: 99 to 118, SEQ ID NOs: 528 to 534, SEQ ID NOs: 5757 to 6498, SEQ ID NOs: 22450 to 22466, SEQ ID NOs: 23264 to 23415, and SEQ ID NOs: 26047 to 26375. In some embodiments, any one of the peptides in the GTF2I L424H vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 99 to 118, SEQ ID NOs: 528 to 534, SEQ ID NOs: 5757 to 6498, SEQ ID NOs: 22450 to 22466, SEQ ID NOs: 23264 to 23415, or SEQ ID NOs: 26047 to 26375.

In some embodiments, the amino acid sequence for a MHC class I and/or MHC class II peptides may be used to create a single target (individual) or combined peptide vaccine for the PTEN R130Q protein mutation having between about 2 and about 40 peptides. In some embodiments, any one of the peptides in the vaccine for the PTEN R130Q protein mutation comprises one or more of the SEQ ID NOs: 338 to 353, SEQ ID NOs: 681 to 690, SEQ ID NOs: 17869 to 18205, SEQ ID NOs: 22630 to 22636, SEQ ID NOs: 24659 to 24724, and SEQ ID NOs: 27980 to 28052. In some embodiments, any one of the peptides in the PTEN R130Q vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 338 to 353, SEQ ID NOs: 681 to 690, SEQ ID NOs: 17869 to 18205, SEQ ID NOs: 22630 to 22636, SEQ ID NOs: 24659 to 24724, or SEQ ID NOs: 27980 to 28052.

In some embodiments, the amino acid sequence for a MHC class I and/or MHC class II peptides may be used to create a single target (individual) or combined peptide vaccine for the AKT1 E17K protein mutation having between about 2 and about 40 peptides. In some embodiments, any one of the peptides in the vaccine for the AKT1 E17K protein mutation comprises one or more of the SEQ ID NOs: 1 to 18, SEQ ID NO: 459, SEQ ID NOs: 475 to 483, SEQ ID NOs: 760 to 1768, SEQ ID NOs: 22386 to 22396, SEQ ID NOs: 22728 to 22838, and SEQ ID NOs: 25305 to 25488. In some embodiments, any one of the peptides in the AKT1 E17K vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 1 to 18, SEQ ID NO: 459, SEQ ID NOs: 475 to 483, SEQ ID NOs: 760 to 1768, SEQ ID NOs: 22386 to 22396, SEQ ID NOs: 22728 to 22838, or SEQ ID NOs: 25305 to 25488.

In some embodiments, the amino acid sequence for a MHC class I and/or MHC class II peptides may be used to create a single target (individual) or combined peptide vaccine for the PTEN R130G protein mutation having between about 2 and about 40 peptides. In some embodiments, any one of the peptides in the vaccine for the PTEN R130G protein mutation comprises one or more of the SEQ ID NOs: 323 to 337, SEQ ID NOs: 676 to 680, SEQ ID NOs: 17343 to 17868, SEQ ID NOs: 22623 to 22629, SEQ ID NOs: 24572 to 24658, and SEQ ID NOs: 27890 to 27979. In some embodiments, any one of the peptides in the PTEN R130G vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 323 to 337, SEQ ID NOs: 676 to 680, SEQ ID NOs: 17343 to 17868, SEQ ID NOs: 22623 to 22629, SEQ ID NOs: 24572 to 24658, or SEQ ID NOs: 27890 to 27979.

In some embodiments, the amino acid sequence for a MHC class I and/or MHC class II peptides may be used to create a single target (individual) or combined peptide vaccine for the TP53 H179R protein mutation having between about 2 and about 40 peptides. In some embodiments, any one of the peptides in the vaccine for the TP53 H179R protein mutation comprises one or more of the SEQ ID NOs: 354 to 358, SEQ ID NOs: 691 to 699, SEQ ID NOs: 18206 to 18413, SEQ ID NOs: 22637 to 22643, SEQ ID NOs: 24725 to 24783, and SEQ ID NOs: 28053 to 28131. In some embodiments, any one of the peptides in the TP53 H179R vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 354 to 358, SEQ ID NOs: 691 to 699, SEQ ID NOs: 18206 to 18413, SEQ ID NOs: 22637 to 22643, SEQ ID NOs: 24725 to 24783, or SEQ ID NOs: 28053 to 28131.

In some embodiments, any combination of MHC class I and/or MHC class II peptides disclosed herein (SEQ ID NOs: 1 to 28795) may be used to create a single target (individual) or combined peptide vaccine having between about 2 and about 40 peptides. In some embodiments, any one of the peptides (peptides 1 to 28795; SEQ ID NOs: 1 to 28795) in the combined vaccine comprises an amino acid sequence 80, 81, 82, 83, 84, 85, 86, 87, 88, 89, 90, 91, 92, 93, 94, 95, 96, 97, 98 or 99% identical to any of SEQ ID NOs: 1 to 28795.

Vaccines for CT Antigens
MHC Class I Peptide Sequences

In some embodiments, a peptide vaccine (single target or combined multiple target vaccine) comprises about 1 to 40 MHC class I peptides with each peptide consisting of 8 or more amino acids. In some embodiments, an MHC class I peptide vaccine is intended for one or more of the CTG1B, KKLC1, MAGA1, MAGA3, MAGA4, MAGC1, MAGC3, MAR1, PMEL, PRAME, SSX2, TYRP1, or TYRP2 protein targets. In some embodiments, an MHC class I peptide vaccine is intended for one or more of the pancreatic cancer, skin cancer, thyroid cancer, brain cancer, colorectal cancer, bronchus and lung cancer, breast cancer, or ovarian cancer indications.

In some embodiments, the amino acid sequence for a MHC class I peptide vaccine for the CTG1B protein comprises one or more of the SEQ ID NOs: 28796 to 28864. In some embodiments, any one of the peptides in the CTG1B vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 28796 to 28864.

In some embodiments, the amino acid sequence for a MHC class I peptide vaccine for the CTG1B protein comprises one or more of the SEQ ID NOs: 28796 to 34168. In some embodiments, any one of the peptides in the CTG1B vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 28796 to 34168.

In some embodiments, the amino acid sequence for a MHC class I peptide vaccine for the CTG1B protein comprises two or more of the SEQ ID NOs: 28796 to 28864. In some embodiments, any one of the peptides in the CTG1B vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 28796 to 28864.

In some embodiments, the amino acid sequence for a MEW class I peptide vaccine for the CTG1B protein comprises two or more of the SEQ ID NOs: 28796 to 34168. In some embodiments, any one of the peptides in the CTG1B vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 28796 to 34168.

In some embodiments, the amino acid sequence for a MEW class I peptide vaccine for the MAGA1 protein comprises one or more of the SEQ ID NOs: 41321 to 41397. In some embodiments, any one of the peptides in the MAGA1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 41321 to 41397.

In some embodiments, the amino acid sequence for a MEW class I peptide vaccine for the MAGA1 protein comprises one or more of the SEQ ID NOs: 41321 to 51433. In some embodiments, any one of the peptides in the MAGA1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 41321 to 51433.

In some embodiments, the amino acid sequence for a MEW class I peptide vaccine for the MAGA1 protein comprises two or more of the SEQ ID NOs: 41321 to 41397. In some embodiments, any one of the peptides in the MAGA1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 41321 to 41397.

In some embodiments, the amino acid sequence for a MEW class I peptide vaccine for the MAGA1 protein comprises two or more of the SEQ ID NOs: 41321 to 51433. In some embodiments, any one of the peptides in the MAGA1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 41321 to 51433.

In some embodiments, the amino acid sequence for a MEW class I peptide vaccine for the MAGA3 protein comprises one or more of the SEQ ID NO: 41383, SEQ ID NO: 41396, SEQ ID NO: 41770, SEQ ID NO: 49004, and SEQ ID NOs: 51434 to 51510. In some embodiments, any one of the peptides in the MAGA3 vaccine comprise an amino acid sequence 80, 81, 82, 83, 84, 85, 86, 87, 88, 89, 90, 91, 92, 93, 94, 95, 96, 97, 98 or 99% identical to SEQ ID NO: 41383, SEQ ID NO: 41396, SEQ ID NO: 41770, SEQ ID NO: 49004, or SEQ ID NOs: 51434 to 51510.

In some embodiments, the amino acid sequence for a MEW class I peptide vaccine for the MAGA3 protein comprises one or more of the SEQ ID NOs: 41351 to 41352, SEQ ID NO: 41383, SEQ ID NO: 41396, SEQ ID NO: 41410, SEQ ID NO: 41414, SEQ ID NO: 41435, SEQ ID NO: 41450, SEQ ID NO: 41463, SEQ ID NO: 41478, SEQ ID NO: 41489, SEQ ID NO: 41495, SEQ ID NO: 41503, SEQ ID NO: 41513, SEQ ID NO: 41520, SEQ ID NO: 41535, SEQ ID NO: 41541, SEQ ID NO: 41545, SEQ ID NO: 41577, SEQ ID NO: 41588, SEQ ID NO: 41598, SEQ ID NO: 41605, SEQ ID NO: 41617, SEQ ID NO: 41620, SEQ ID NO: 41622, SEQ ID NO: 41627, SEQ ID NO: 41630, SEQ ID NO: 41638, SEQ ID NO: 41647, SEQ ID NO: 41673, SEQ ID NO: 41696, SEQ ID NO: 41703, SEQ ID NO: 41708, SEQ ID NO: 41728, SEQ ID NOs: 41732 to 41733, SEQ ID NO: 41749, SEQ ID NO: 41760, SEQ ID NO: 41766, SEQ ID NO: 41770, SEQ ID NO: 41788, SEQ ID NO: 41791, SEQ ID NO: 41809, SEQ ID NO: 41813, SEQ ID NO: 41817, SEQ ID NO: 41829, SEQ ID NOs: 41847 to 41848, SEQ ID NO: 41853, SEQ ID NO: 41859, SEQ ID NO: 41889, SEQ ID NO: 41894, SEQ ID NO: 41897, SEQ ID NO: 41909, SEQ ID NO: 41923, SEQ ID NO: 41934, SEQ ID NO: 41939, SEQ ID NOs: 41953 to 41954, SEQ ID NO: 41959, SEQ ID NO: 41967, SEQ ID NO: 41970, SEQ ID NO: 41976, SEQ ID NOs: 41984 to 41985, SEQ ID NO: 42007, SEQ ID NO: 42017, SEQ ID NO: 42034, SEQ ID NO: 42044, SEQ ID NO: 42046, SEQ ID NO: 42048, SEQ ID NO: 42056, SEQ ID NO: 42067, SEQ ID NO: 42080, SEQ ID NO: 42088, SEQ ID NO: 42091, SEQ ID NOs: 42119 to 42120, SEQ ID NO: 42129, SEQ ID NO: 42135, SEQ ID NOs: 42140 to 42141, SEQ ID NO: 42155, SEQ ID NO: 42158, SEQ ID NO: 42164, SEQ ID NO: 42170, SEQ ID NO: 42174, SEQ ID NO: 42186, SEQ ID NO: 42209, SEQ ID NO: 42218, SEQ ID NO: 42224, SEQ ID NO: 42229, SEQ ID NO: 42232, SEQ ID NO: 42235, SEQ ID NOs: 42237 to 42238, SEQ ID NO: 42265, SEQ ID NO: 42272, SEQ ID NO: 42278, SEQ ID NO: 42293, SEQ ID NO: 42314, SEQ ID NOs: 42336 to 42337, SEQ ID NO: 42339, SEQ ID NOs: 42372 to 42373, SEQ ID NO: 42376, SEQ ID NO: 42382, SEQ ID NO: 42386, SEQ ID NO: 42408, SEQ ID NO: 42414, SEQ ID NO: 42423, SEQ ID NO: 42429, SEQ ID NOs: 42447 to 42448, SEQ ID NO: 42461, SEQ ID NO: 42466, SEQ ID NO: 42475, SEQ ID NO: 42513, SEQ ID NO: 42540, SEQ ID NO: 42545, SEQ ID NO: 42550, SEQ ID NO: 42553, SEQ ID NOs: 42567 to 42568, SEQ ID NO: 42580, SEQ ID NO: 42585, SEQ ID NO: 42605, SEQ ID NO: 42612, SEQ ID NO: 42627, SEQ ID NO: 42675, SEQ ID NO: 42680, SEQ ID NO: 42685, SEQ ID NO: 42690, SEQ ID NO: 42702, SEQ ID NO: 42711, SEQ ID NO: 42719, SEQ ID NO: 42738, SEQ ID NO: 42743, SEQ ID NO: 42750, SEQ ID NO: 42755, SEQ ID NO: 42777, SEQ ID NO: 42788, SEQ ID NO: 42793, SEQ ID NO: 42851, SEQ ID NO: 42858, SEQ ID NO: 42866, SEQ ID NO: 42903, SEQ ID NO: 42927, SEQ ID NOs: 42936 to 42937, SEQ ID NOs: 42940 to 42941, SEQ ID NO: 42957, SEQ ID NO: 42962, SEQ ID NO: 42966, SEQ ID NO: 42968, SEQ ID NO: 42986, SEQ ID NO: 43002, SEQ ID NO: 43013, SEQ ID NO: 43037, SEQ ID NO: 43052, SEQ ID NOs: 43055 to 43056, SEQ ID NOs: 43063 to 43064, SEQ ID NO: 43096, SEQ ID NO: 43133, SEQ ID NO: 43138, SEQ ID NO: 43156, SEQ ID NO: 43161, SEQ ID NO: 43186, SEQ ID NO: 43199, SEQ ID NO: 43205, SEQ ID NO: 43245, SEQ ID NO: 43251, SEQ ID NO: 43275, SEQ ID NO: 43312, SEQ ID NO: 43327, SEQ ID NO: 43333, SEQ ID NO: 43339, SEQ ID NO: 43342, SEQ ID NO: 43348, SEQ ID NO: 43365, SEQ ID NO: 43371, SEQ ID NO: 43400, SEQ ID NO: 43440, SEQ ID NO: 43451, SEQ ID NO: 43462, SEQ ID NO: 43467, SEQ ID NO: 43487, SEQ ID NOs: 43498 to 43499, SEQ ID NO: 43507, SEQ ID NO: 43522, SEQ ID NO: 43529, SEQ ID NO: 43533, SEQ ID NO: 43545, SEQ ID NO: 43558, SEQ ID NO: 43560, SEQ ID NO: 43583, SEQ ID NO: 43597, SEQ ID NO: 43599, SEQ ID NO: 43610, SEQ ID NO: 43614, SEQ ID NO: 43627, SEQ ID NO: 43697, SEQ ID NO: 43715, SEQ ID NO: 43718, SEQ ID NO: 43768, SEQ ID NO: 43777, SEQ ID NOs: 43825 to 43826, SEQ ID NO: 43836, SEQ ID NO: 43840, SEQ ID NO: 43856, SEQ ID NO: 43860, SEQ ID NO: 43870, SEQ ID NO: 43878, SEQ ID NOs: 43881 to 43882, SEQ ID NO: 43905, SEQ ID NO: 43922, SEQ ID NO: 43930, SEQ ID NO: 43943, SEQ ID NO: 43953, SEQ ID NO: 43958, SEQ ID NO: 43979, SEQ ID NO: 43986, SEQ ID NO: 44002, SEQ ID NO: 44033, SEQ ID NO: 44037, SEQ ID NO: 44048, SEQ ID NO: 44050, SEQ ID NO: 44052, SEQ ID NOs: 44080 to 44081, SEQ ID NOs: 44093 to 44094, SEQ ID NOs: 44114 to 44115, SEQ ID NO: 44120, SEQ ID NO: 44142, SEQ ID NO: 44152, SEQ ID NOs: 44164 to 44166, SEQ ID NO: 44181, SEQ ID NO: 44222, SEQ ID NO: 44244, SEQ ID NO: 44246, SEQ ID NO: 44255, SEQ ID NO: 44261, SEQ ID NO: 44276, SEQ ID NOs: 44286 to 44287, SEQ ID NO: 44296, SEQ ID NO: 44315, SEQ ID NO: 44322, SEQ ID NO: 44324, SEQ ID NO: 44328, SEQ ID NO: 44332, SEQ ID NO: 44339, SEQ ID NO: 44401, SEQ ID NO: 44413, SEQ ID NO: 44435, SEQ ID NO: 44452, SEQ ID NO: 44454, SEQ ID NO: 44463, SEQ ID NO: 44467, SEQ ID NO: 44485, SEQ ID NO: 44504, SEQ ID NO: 44512, SEQ ID NO: 44523, SEQ ID NOs: 44526 to 44527, SEQ ID NO: 44536, SEQ ID NO: 44564, SEQ ID NO: 44605, SEQ ID NO: 44607, SEQ ID NO: 44612, SEQ ID NO: 44629, SEQ ID NOs: 44635 to 44636, SEQ ID NO: 44647, SEQ ID NO: 44650, SEQ ID NO: 44674, SEQ ID NO: 44691, SEQ ID NO: 44696, SEQ ID NO: 44702, SEQ ID NO: 44710, SEQ ID NO: 44713, SEQ ID NO: 44715, SEQ ID NO: 44722, SEQ ID NO: 44730, SEQ ID NO: 44733, SEQ ID NO: 44755, SEQ ID NO: 44770, SEQ ID NO: 44773, SEQ ID NO: 44781, SEQ ID NO: 44783, SEQ ID NO: 44797, SEQ ID NO: 44805, SEQ ID NO: 44822, SEQ ID NO: 44828, SEQ ID NO: 44830, SEQ ID NO: 44832, SEQ ID NO: 44850, SEQ ID NO: 44852, SEQ ID NO: 44854, SEQ ID NO: 44860, SEQ ID NO: 44866, SEQ ID NO: 44898, SEQ ID NO: 44900, SEQ ID NO: 44907, SEQ ID NO: 44933, SEQ ID NO: 44947, SEQ ID NO: 44986, SEQ ID NO: 45003, SEQ ID NO: 45007, SEQ ID NO: 45009, SEQ ID NO: 45012, SEQ ID NO: 45016, SEQ ID NO: 45018, SEQ ID NO: 45027, SEQ ID NO: 45031, SEQ ID NO: 45036, SEQ ID NO: 45044, SEQ ID NO: 45060, SEQ ID NO: 45071, SEQ ID NO: 45077, SEQ ID NO: 45095, SEQ ID NO: 45126, SEQ ID NO: 45132, SEQ ID NO: 45135, SEQ ID NO: 45139, SEQ ID NO: 45143, SEQ ID NO: 45159, SEQ ID NO: 45177, SEQ ID NO: 45197, SEQ ID NO: 45200, SEQ ID NO: 45219, SEQ ID NO: 45228, SEQ ID NO: 45323, SEQ ID NO: 45329, SEQ ID NO: 45351, SEQ ID NO: 45378, SEQ ID NO: 45380, SEQ ID NO: 45389, SEQ ID NO: 45413, SEQ ID NO: 45417, SEQ ID NO: 45438, SEQ ID NO: 45455, SEQ ID NO: 45457, SEQ ID NO: 45467, SEQ ID NO: 45478, SEQ ID NO: 45530, SEQ ID NO: 45562, SEQ ID NO: 45565, SEQ ID NOs: 45583 to 45584, SEQ ID NOs: 45595 to 45596, SEQ ID NO: 45608, SEQ ID NO: 45612, SEQ ID NO: 45616, SEQ ID NO: 45627, SEQ ID NO: 45653, SEQ ID NOs: 45666 to 45667, SEQ ID NO: 45680, SEQ ID NO: 45697, SEQ ID NO: 45705, SEQ ID NO: 45710, SEQ ID NO: 45722, SEQ ID NO: 45736, SEQ ID NO: 45742, SEQ ID NO: 45746, SEQ ID NO: 45765, SEQ ID NO: 45808, SEQ ID NO: 45830, SEQ ID NOs: 45840 to 45841, SEQ ID NO: 45896, SEQ ID NOs: 45904 to 45905, SEQ ID NO: 45913, SEQ ID NO: 45915, SEQ ID NOs: 45940 to 45943, SEQ ID NO: 45945, SEQ ID NOs: 45958 to 45959, SEQ ID NO: 45977, SEQ ID NO: 45983, SEQ ID NO: 45992, SEQ ID NO: 46006, SEQ ID NO: 46012, SEQ ID NO: 46018, SEQ ID NO: 46021, SEQ ID NOs: 46037 to 46038, SEQ ID NO: 46044, SEQ ID NO: 46058, SEQ ID NO: 46071, SEQ ID NO: 46082, SEQ ID NO: 46094, SEQ ID NO: 46096, SEQ ID NO: 46102, SEQ ID NOs: 46108 to 46109, SEQ ID NO: 46122, SEQ ID NO: 46125, SEQ ID NOs: 46133 to 46134, SEQ ID NO: 46146, SEQ ID NO: 46159, SEQ ID NO: 46177, SEQ ID NO: 46182, SEQ ID NO: 46188, SEQ ID NO: 46202, SEQ ID NO: 46219, SEQ ID NO: 46246, SEQ ID NO: 46249, SEQ ID NO: 46270, SEQ ID NO: 46279, SEQ ID NO: 46312, SEQ ID NO: 46339, SEQ ID NO: 46378, SEQ ID NO: 46433, SEQ ID NO: 46442, SEQ ID NO: 46446, SEQ ID NO: 46452, SEQ ID NO: 46454, SEQ ID NO: 46457, SEQ ID NO: 46478, SEQ ID NO: 46484, SEQ ID NO: 46486, SEQ ID NO: 46491, SEQ ID NO: 46506, SEQ ID NO: 46512, SEQ ID NO: 46517, SEQ ID NO: 46530, SEQ ID NO: 46534, SEQ ID NO: 46556, SEQ ID NO: 46560, SEQ ID NO: 46564, SEQ ID NO: 46596, SEQ ID NO: 46602, SEQ ID NO: 46616, SEQ ID NO: 46635, SEQ ID NO: 46656, SEQ ID NO: 46658, SEQ ID NO: 46666, SEQ ID NO: 46676, SEQ ID NO: 46679, SEQ ID NO: 46689, SEQ ID NO: 46705, SEQ ID NO: 46724, SEQ ID NO: 46738, SEQ ID NO: 46767, SEQ ID NO: 46770, SEQ ID NO: 46794, SEQ ID NO: 46810, SEQ ID NO: 46819, SEQ ID NO: 46824, SEQ ID NO: 46831, SEQ ID NO: 46849, SEQ ID NO: 46854, SEQ ID NO: 46870, SEQ ID NO: 46880, SEQ ID NO: 46916, SEQ ID NO: 46935, SEQ ID NO: 46939, SEQ ID NO: 46944, SEQ ID NO: 46958, SEQ ID NO: 46964, SEQ ID NO: 46967, SEQ ID NO: 46978, SEQ ID NO: 46987, SEQ ID NO: 46989, SEQ ID NO: 46991, SEQ ID NO: 46993, SEQ ID NO: 47007, SEQ ID NO: 47034, SEQ ID NO: 47037, SEQ ID NO: 47047, SEQ ID NO: 47057, SEQ ID NO: 47066, SEQ ID NO: 47096, SEQ ID NO: 47098, SEQ ID NO: 47119, SEQ ID NO: 47123, SEQ ID NO: 47137, SEQ ID NO: 47139, SEQ ID NO: 47143, SEQ ID NO: 47150, SEQ ID NO: 47158, SEQ ID NO: 47161, SEQ ID NO: 47170, SEQ ID NO: 47181, SEQ ID NO: 47197, SEQ ID NO: 47209, SEQ ID NO: 47254, SEQ ID NO: 47266, SEQ ID NO: 47272, SEQ ID NO: 47291, SEQ ID NO: 47298, SEQ ID NO: 47300, SEQ ID NO: 47319, SEQ ID NO: 47324, SEQ ID NOs: 47331 to 47332, SEQ ID NO: 47358, SEQ ID NO: 47361, SEQ ID NO: 47393, SEQ ID NO: 47414, SEQ ID NO: 47416, SEQ ID NO: 47422, SEQ ID NO: 47425, SEQ ID NOs: 47432 to 47433, SEQ ID NO: 47445, SEQ ID NO: 47453, SEQ ID NOs: 47460 to 47461, SEQ ID NO: 47477, SEQ ID NO: 47492, SEQ ID NO: 47507, SEQ ID NO: 47509, SEQ ID NO: 47516, SEQ ID NO: 47535, SEQ ID NOs: 47556 to 47557, SEQ ID NOs: 47578 to 47579, SEQ ID NOs: 47591 to 47592, SEQ ID NO: 47597, SEQ ID NO: 47600, SEQ ID NO: 47614, SEQ ID NO: 47626, SEQ ID NO: 47629, SEQ ID NO: 47637, SEQ ID NO: 47639, SEQ ID NO: 47649, SEQ ID NOs: 47689 to 47690, SEQ ID NO: 47713, SEQ ID NO: 47766, SEQ ID NOs: 47814 to 47815, SEQ ID NO: 47827, SEQ ID NO: 47834, SEQ ID NOs: 47852 to 47853, SEQ ID NO: 47855, SEQ ID NO: 47871, SEQ ID NOs: 47875 to 47876, SEQ ID NO: 47891, SEQ ID NO: 47896, SEQ ID NO: 47902, SEQ ID NO: 47923, SEQ ID NO: 47925, SEQ ID NO: 47927, SEQ ID NO: 47929, SEQ ID NO: 47932, SEQ ID NOs: 47962 to 47964, SEQ ID NO: 47972, SEQ ID NO: 47999, SEQ ID NO: 48008, SEQ ID NO: 48028, SEQ ID NOs: 48034 to 48035, SEQ ID NO: 48038, SEQ ID NO: 48056, SEQ ID NO: 48061, SEQ ID NO: 48066, SEQ ID NO: 48118, SEQ ID NO: 48120, SEQ ID NO: 48129, SEQ ID NO: 48140, SEQ ID NO: 48148, SEQ ID NO: 48153, SEQ ID NOs: 48159 to 48160, SEQ ID NO: 48163, SEQ ID NO: 48167, SEQ ID NO: 48178, SEQ ID NO: 48180, SEQ ID NO: 48186, SEQ ID NO: 48218, SEQ ID NO: 48220, SEQ ID NO: 48263, SEQ ID NO: 48286, SEQ ID NO: 48300, SEQ ID NO: 48307, SEQ ID NO: 48315, SEQ ID NO: 48321, SEQ ID NO: 48338, SEQ ID NO: 48341, SEQ ID NO: 48343, SEQ ID NO: 48358, SEQ ID NO: 48362, SEQ ID NO: 48366, SEQ ID NO: 48368, SEQ ID NO: 48418, SEQ ID NO: 48431, SEQ ID NO: 48436, SEQ ID NOs: 48438 to 48439, SEQ ID NOs: 48443 to 48444, SEQ ID NO: 48450, SEQ ID NOs: 48452 to 48453, SEQ ID NO: 48458, SEQ ID NOs: 48461 to 48462, SEQ ID NO: 48507, SEQ ID NO: 48516, SEQ ID NO: 48527, SEQ ID NO: 48537, SEQ ID NO: 48548, SEQ ID NO: 48567, SEQ ID NO: 48574, SEQ ID NO: 48576, SEQ ID NO: 48578, SEQ ID NO: 48594, SEQ ID NO: 48599, SEQ ID NO: 48612, SEQ ID NO: 48614, SEQ ID NO: 48623, SEQ ID NO: 48626, SEQ ID NO: 48630, SEQ ID NO: 48642, SEQ ID NO: 48648, SEQ ID NO: 48656, SEQ ID NOs: 48704 to 48705, SEQ ID NO: 48708, SEQ ID NO: 48739, SEQ ID NO: 48749, SEQ ID NO: 48752, SEQ ID NO: 48754, SEQ ID NO: 48756, SEQ ID NO: 48802, SEQ ID NO: 48832, SEQ ID NO: 48845, SEQ ID NO: 48850, SEQ ID NO: 48852, SEQ ID NO: 48856, SEQ ID NO: 48870, SEQ ID NO: 48888, SEQ ID NO: 48902, SEQ ID NO: 48904, SEQ ID NOs: 48912 to 48913, SEQ ID NO: 48921, SEQ ID NO: 48970, SEQ ID NO: 48974, SEQ ID NO: 48993, SEQ ID NO: 48997, SEQ ID NO: 49004, SEQ ID NO: 49019, SEQ ID NO: 49025, SEQ ID NOs: 49045 to 49046, SEQ ID NO: 49052, SEQ ID NO: 49083, SEQ ID NO: 49086, SEQ ID NOs: 49091 to 49092, SEQ ID NO: 49102, SEQ ID NO: 49106, SEQ ID NO: 49111, SEQ ID NO: 49127, SEQ ID NO: 49152, SEQ ID NO: 49159, SEQ ID NO: 49173, SEQ ID NO: 49197, SEQ ID NO: 49201, SEQ ID NO: 49203, SEQ ID NO: 49207, SEQ ID NO: 49220, SEQ ID NO: 49227, SEQ ID NO: 49230, SEQ ID NO: 49234, SEQ ID NO: 49242, SEQ ID NO: 49256, SEQ ID NO: 49263, SEQ ID NOs: 49273 to 49274, SEQ ID NO: 49278, SEQ ID NO: 49280, SEQ ID NO: 49288, SEQ ID NO: 49290, SEQ ID NOs: 49294 to 49295, SEQ ID NO: 49326, SEQ ID NO: 49362, SEQ ID NOs: 49384 to 49385, SEQ ID NO: 49387, SEQ ID NO: 49393, SEQ ID NO: 49395, SEQ ID NOs: 49427 to 49428, SEQ ID NO: 49444, SEQ ID NO: 49458, SEQ ID NO: 49483, SEQ ID NO: 49487, SEQ ID NO: 49497, SEQ ID NO: 49501, SEQ ID NO: 49517, SEQ ID NO: 49525, SEQ ID NO: 49535, SEQ ID NO: 49537, SEQ ID NO: 49544, SEQ ID NO: 49557, SEQ ID NO: 49569, SEQ ID NO: 49572, SEQ ID NO: 49587, SEQ ID NO: 49594, SEQ ID NO: 49596, SEQ ID NO: 49598, SEQ ID NO: 49606, SEQ ID NO: 49617, SEQ ID NO: 49629, SEQ ID NO: 49646, SEQ ID NO: 49658, SEQ ID NO: 49693, SEQ ID NOs: 49702 to 49703, SEQ ID NO: 49710, SEQ ID NO: 49712, SEQ ID NO: 49719, SEQ ID NO: 49727, SEQ ID NO: 49737, SEQ ID NO: 49740, SEQ ID NO: 49743, SEQ ID NO: 49767, SEQ ID NO: 49778, SEQ ID NO: 49788, SEQ ID NO: 49811, SEQ ID NO: 49848, SEQ ID NO: 49860, SEQ ID NO: 49888, SEQ ID NO: 49908, SEQ ID NO: 49973, SEQ ID NO: 49977, SEQ ID NO: 49980, SEQ ID NOs: 49996 to 49997, SEQ ID NO: 50000, SEQ ID NO: 50012, SEQ ID NOs: 50017 to 50018, SEQ ID NO: 50051, SEQ ID NO: 50056, SEQ ID NO: 50062, SEQ ID NO: 50090, SEQ ID NO: 50093, SEQ ID NO: 50107, SEQ ID NO: 50129, SEQ ID NO: 50132, SEQ ID NO: 50138, SEQ ID NO: 50144, SEQ ID NO: 50167, SEQ ID NO: 50191, SEQ ID NO: 50194, SEQ ID NO: 50196, SEQ ID NO: 50228, SEQ ID NO: 50239, SEQ ID NO: 50263, SEQ ID NO: 50271, SEQ ID NO: 50297, SEQ ID NO: 50305, SEQ ID NO: 50320, SEQ ID NO: 50322, SEQ ID NO: 50326, SEQ ID NO: 50334, SEQ ID NO: 50349, SEQ ID NO: 50375, SEQ ID NO: 50394, SEQ ID NO: 50401, SEQ ID NO: 50414, SEQ ID NO: 50421, SEQ ID NO: 50423, SEQ ID NO: 50435, SEQ ID NOs: 50440 to 50441, SEQ ID NO: 50443, SEQ ID NO: 50510, SEQ ID NO: 50556, SEQ ID NO: 50564, SEQ ID NO: 50591, SEQ ID NO: 50605, SEQ ID NO: 50607, SEQ ID NO: 50611, SEQ ID NO: 50622, SEQ ID NO: 50625, SEQ ID NO: 50627, SEQ ID NO: 50632, SEQ ID NO: 50644, SEQ ID NOs: 50652 to 50653, SEQ ID NOs: 50668 to 50669, SEQ ID NO: 50677, SEQ ID NO: 50696, SEQ ID NO: 50699, SEQ ID NO: 50705, SEQ ID NO: 50709, SEQ ID NO: 50711, SEQ ID NO: 50729, SEQ ID NO: 50731, SEQ ID NO: 50741, SEQ ID NO: 50743, SEQ ID NO: 50748, SEQ ID NO: 50762, SEQ ID NO: 50765, SEQ ID NO: 50767, SEQ ID NO: 50800, SEQ ID NO: 50803, SEQ ID NO: 50807, SEQ ID NO: 50841, SEQ ID NO: 50865, SEQ ID NO: 50872, SEQ ID NO: 50905, SEQ ID NOs: 50955 to 50956, SEQ ID NOs: 50975 to 50977, SEQ ID NO: 50986, SEQ ID NO: 51021, SEQ ID NOs: 51039 to 51040, SEQ ID NOs: 51066 to 51068, SEQ ID NO: 51084, SEQ ID NOs: 51099 to 51100, SEQ ID NOs: 51165 to 51167, SEQ ID NO: 51169, SEQ ID NO: 51190, SEQ ID NOs: 51194 to 51198, SEQ ID NOs: 51267 to 51270, SEQ ID NOs: 51281 to 51282, SEQ ID NO: 51324, SEQ ID NO: 51349, SEQ ID NO: 51379, SEQ ID NOs: 51413 to 51415, SEQ ID NOs: 51420 to 51421, and SEQ ID NOs: 51434 to 60455. In some embodiments, any one of the peptides in the MAGA3 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 41351 to 41352, SEQ ID NO: 41383, SEQ ID NO: 41396, SEQ ID NO: 41410, SEQ ID NO: 41414, SEQ ID NO: 41435, SEQ ID NO: 41450, SEQ ID NO: 41463, SEQ ID NO: 41478, SEQ ID NO: 41489, SEQ ID NO: 41495, SEQ ID NO: 41503, SEQ ID NO: 41513, SEQ ID NO: 41520, SEQ ID NO: 41535, SEQ ID NO: 41541, SEQ ID NO: 41545, SEQ ID NO: 41577, SEQ ID NO: 41588, SEQ ID NO: 41598, SEQ ID NO: 41605, SEQ ID NO: 41617, SEQ ID NO: 41620, SEQ ID NO: 41622, SEQ ID NO: 41627, SEQ ID NO: 41630, SEQ ID NO: 41638, SEQ ID NO: 41647, SEQ ID NO: 41673, SEQ ID NO: 41696, SEQ ID NO: 41703, SEQ ID NO: 41708, SEQ ID NO: 41728, SEQ ID NOs: 41732 to 41733, SEQ ID NO: 41749, SEQ ID NO: 41760, SEQ ID NO: 41766, SEQ ID NO: 41770, SEQ ID NO: 41788, SEQ ID NO: 41791, SEQ ID NO: 41809, SEQ ID NO: 41813, SEQ ID NO: 41817, SEQ ID NO: 41829, SEQ ID NOs: 41847 to 41848, SEQ ID NO: 41853, SEQ ID NO: 41859, SEQ ID NO: 41889, SEQ ID NO: 41894, SEQ ID NO: 41897, SEQ ID NO: 41909, SEQ ID NO: 41923, SEQ ID NO: 41934, SEQ ID NO: 41939, SEQ ID NOs: 41953 to 41954, SEQ ID NO: 41959, SEQ ID NO: 41967, SEQ ID NO: 41970, SEQ ID NO: 41976, SEQ ID NOs: 41984 to 41985, SEQ ID NO: 42007, SEQ ID NO: 42017, SEQ ID NO: 42034, SEQ ID NO: 42044, SEQ ID NO: 42046, SEQ ID NO: 42048, SEQ ID NO: 42056, SEQ ID NO: 42067, SEQ ID NO: 42080, SEQ ID NO: 42088, SEQ ID NO: 42091, SEQ ID NOs: 42119 to 42120, SEQ ID NO: 42129, SEQ ID NO: 42135, SEQ ID NOs: 42140 to 42141, SEQ ID NO: 42155, SEQ ID NO: 42158, SEQ ID NO: 42164, SEQ ID NO: 42170, SEQ ID NO: 42174, SEQ ID NO: 42186, SEQ ID NO: 42209, SEQ ID NO: 42218, SEQ ID NO: 42224, SEQ ID NO: 42229, SEQ ID NO: 42232, SEQ ID NO: 42235, SEQ ID NOs: 42237 to 42238, SEQ ID NO: 42265, SEQ ID NO: 42272, SEQ ID NO: 42278, SEQ ID NO: 42293, SEQ ID NO: 42314, SEQ ID NOs: 42336 to 42337, SEQ ID NO: 42339, SEQ ID NOs: 42372 to 42373, SEQ ID NO: 42376, SEQ ID NO: 42382, SEQ ID NO: 42386, SEQ ID NO: 42408, SEQ ID NO: 42414, SEQ ID NO: 42423, SEQ ID NO: 42429, SEQ ID NOs: 42447 to 42448, SEQ ID NO: 42461, SEQ ID NO: 42466, SEQ ID NO: 42475, SEQ ID NO: 42513, SEQ ID NO: 42540, SEQ ID NO: 42545, SEQ ID NO: 42550, SEQ ID NO: 42553, SEQ ID NOs: 42567 to 42568, SEQ ID NO: 42580, SEQ ID NO: 42585, SEQ ID NO: 42605, SEQ ID NO: 42612, SEQ ID NO: 42627, SEQ ID NO: 42675, SEQ ID NO: 42680, SEQ ID NO: 42685, SEQ ID NO: 42690, SEQ ID NO: 42702, SEQ ID NO:

42711, SEQ ID NO: 42719, SEQ ID NO: 42738, SEQ ID NO: 42743, SEQ ID NO: 42750, SEQ ID NO: 42755, SEQ ID NO: 42777, SEQ ID NO: 42788, SEQ ID NO: 42793, SEQ ID NO: 42851, SEQ ID NO: 42858, SEQ ID NO: 42866, SEQ ID NO: 42903, SEQ ID NO: 42927, SEQ ID NOs: 42936 to 42937, SEQ ID NOs: 42940 to 42941, SEQ ID NO: 42957, SEQ ID NO: 42962, SEQ ID NO: 42966, SEQ ID NO: 42968, SEQ ID NO: 42986, SEQ ID NO: 43002, SEQ ID NO: 43013, SEQ ID NO: 43037, SEQ ID NO: 43052, SEQ ID NOs: 43055 to 43056, SEQ ID NOs: 43063 to 43064, SEQ ID NO: 43096, SEQ ID NO: 43133, SEQ ID NO: 43138, SEQ ID NO: 43156, SEQ ID NO: 43161, SEQ ID NO: 43186, SEQ ID NO: 43199, SEQ ID NO: 43205, SEQ ID NO: 43245, SEQ ID NO: 43251, SEQ ID NO: 43275, SEQ ID NO: 43312, SEQ ID NO: 43327, SEQ ID NO: 43333, SEQ ID NO: 43339, SEQ ID NO: 43342, SEQ ID NO: 43348, SEQ ID NO: 43365, SEQ ID NO: 43371, SEQ ID NO: 43400, SEQ ID NO: 43440, SEQ ID NO: 43451, SEQ ID NO: 43462, SEQ ID NO: 43467, SEQ ID NO: 43487, SEQ ID NOs: 43498 to 43499, SEQ ID NO: 43507, SEQ ID NO: 43522, SEQ ID NO: 43529, SEQ ID NO: 43533, SEQ ID NO: 43545, SEQ ID NO: 43558, SEQ ID NO: 43560, SEQ ID NO: 43583, SEQ ID NO: 43597, SEQ ID NO: 43599, SEQ ID NO: 43610, SEQ ID NO: 43614, SEQ ID NO: 43627, SEQ ID NO: 43697, SEQ ID NO: 43715, SEQ ID NO: 43718, SEQ ID NO: 43768, SEQ ID NO: 43777, SEQ ID NOs: 43825 to 43826, SEQ ID NO: 43836, SEQ ID NO: 43840, SEQ ID NO: 43856, SEQ ID NO: 43860, SEQ ID NO: 43870, SEQ ID NO: 43878, SEQ ID NOs: 43881 to 43882, SEQ ID NO: 43905, SEQ ID NO: 43922, SEQ ID NO: 43930, SEQ ID NO: 43943, SEQ ID NO: 43953, SEQ ID NO: 43958, SEQ ID NO: 43979, SEQ ID NO: 43986, SEQ ID NO: 44002, SEQ ID NO: 44033, SEQ ID NO: 44037, SEQ ID NO: 44048, SEQ ID NO: 44050, SEQ ID NO: 44052, SEQ ID NOs: 44080 to 44081, SEQ ID NOs: 44093 to 44094, SEQ ID NOs: 44114 to 44115, SEQ ID NO: 44120, SEQ ID NO: 44142, SEQ ID NO: 44152, SEQ ID NOs: 44164 to 44166, SEQ ID NO: 44181, SEQ ID NO: 44222, SEQ ID NO: 44244, SEQ ID NO: 44246, SEQ ID NO: 44255, SEQ ID NO: 44261, SEQ ID NO: 44276, SEQ ID NOs: 44286 to 44287, SEQ ID NO: 44296, SEQ ID NO: 44315, SEQ ID NO: 44322, SEQ ID NO: 44324, SEQ ID NO: 44328, SEQ ID NO: 44332, SEQ ID NO: 44339, SEQ ID NO: 44401, SEQ ID NO: 44413, SEQ ID NO: 44435, SEQ ID NO: 44452, SEQ ID NO: 44454, SEQ ID NO: 44463, SEQ ID NO: 44467, SEQ ID NO: 44485, SEQ ID NO: 44504, SEQ ID NO: 44512, SEQ ID NO: 44523, SEQ ID NOs: 44526 to 44527, SEQ ID NO: 44536, SEQ ID NO: 44564, SEQ ID NO: 44605, SEQ ID NO: 44607, SEQ ID NO: 44612, SEQ ID NO: 44629, SEQ ID NOs: 44635 to 44636, SEQ ID NO: 44647, SEQ ID NO: 44650, SEQ ID NO: 44674, SEQ ID NO: 44691, SEQ ID NO: 44696, SEQ ID NO: 44702, SEQ ID NO: 44710, SEQ ID NO: 44713, SEQ ID NO: 44715, SEQ ID NO: 44722, SEQ ID NO: 44730, SEQ ID NO: 44733, SEQ ID NO: 44755, SEQ ID NO: 44770, SEQ ID NO: 44773, SEQ ID NO: 44781, SEQ ID NO: 44783, SEQ ID NO: 44797, SEQ ID NO: 44805, SEQ ID NO: 44822, SEQ ID NO: 44828, SEQ ID NO: 44830, SEQ ID NO: 44832, SEQ ID NO: 44850, SEQ ID NO: 44852, SEQ ID NO: 44854, SEQ ID NO: 44860, SEQ ID NO: 44866, SEQ ID NO: 44898, SEQ ID NO: 44900, SEQ ID NO: 44907, SEQ ID NO: 44933, SEQ ID NO: 44947, SEQ ID NO: 44986, SEQ ID NO: 45003, SEQ ID NO: 45007, SEQ ID NO: 45009, SEQ ID NO: 45012, SEQ ID NO: 45016, SEQ ID NO: 45018, SEQ ID NO: 45027, SEQ ID NO: 45031, SEQ ID NO: 45036, SEQ ID NO: 45044, SEQ ID NO: 45060, SEQ ID NO: 45071, SEQ ID NO: 45077, SEQ ID NO: 45095, SEQ ID NO: 45126, SEQ ID NO: 45132, SEQ ID NO: 45135, SEQ ID NO: 45139, SEQ ID NO: 45143, SEQ ID NO: 45159, SEQ ID NO: 45177, SEQ ID NO: 45197, SEQ ID NO: 45200, SEQ ID NO: 45219, SEQ ID NO: 45228, SEQ ID NO: 45323, SEQ ID NO: 45329, SEQ ID NO: 45351, SEQ ID NO: 45378, SEQ ID NO: 45380, SEQ ID NO: 45389, SEQ ID NO: 45413, SEQ ID NO: 45417, SEQ ID NO: 45438, SEQ ID NO: 45455, SEQ ID NO: 45457, SEQ ID NO: 45467, SEQ ID NO: 45478, SEQ ID NO: 45530, SEQ ID NO: 45562, SEQ ID NO: 45565, SEQ ID NOs: 45583 to 45584, SEQ ID NOs: 45595 to 45596, SEQ ID NO: 45608, SEQ ID NO: 45612, SEQ ID NO: 45616, SEQ ID NO: 45627, SEQ ID NO: 45653, SEQ ID NOs: 45666 to 45667, SEQ ID NO: 45680, SEQ ID NO: 45697, SEQ ID NO: 45705, SEQ ID NO: 45710, SEQ ID NO: 45722, SEQ ID NO: 45736, SEQ ID NO: 45742, SEQ ID NO: 45746, SEQ ID NO: 45765, SEQ ID NO: 45808, SEQ ID NO: 45830, SEQ ID NOs: 45840 to 45841, SEQ ID NO: 45896, SEQ ID NOs: 45904 to 45905, SEQ ID NO: 45913, SEQ ID NO: 45915, SEQ ID NOs: 45940 to 45943, SEQ ID NO: 45945, SEQ ID NOs: 45958 to 45959, SEQ ID NO: 45977, SEQ ID NO: 45983, SEQ ID NO: 45992, SEQ ID NO: 46006, SEQ ID NO: 46012, SEQ ID NO: 46018, SEQ ID NO: 46021, SEQ ID NOs: 46037 to 46038, SEQ ID NO: 46044, SEQ ID NO: 46058, SEQ ID NO: 46071, SEQ ID NO: 46082, SEQ ID NO: 46094, SEQ ID NO: 46096, SEQ ID NO: 46102, SEQ ID NOs: 46108 to 46109, SEQ ID NO: 46122, SEQ ID NO: 46125, SEQ ID NOs: 46133 to 46134, SEQ ID NO: 46146, SEQ ID NO: 46159, SEQ ID NO: 46177, SEQ ID NO: 46182, SEQ ID NO: 46188, SEQ ID NO: 46202, SEQ ID NO: 46219, SEQ ID NO: 46246, SEQ ID NO: 46249, SEQ ID NO: 46270, SEQ ID NO: 46279, SEQ ID NO: 46312, SEQ ID NO: 46339, SEQ ID NO: 46378, SEQ ID NO: 46433, SEQ ID NO: 46442, SEQ ID NO: 46446, SEQ ID NO: 46452, SEQ ID NO: 46454, SEQ ID NO: 46457, SEQ ID NO: 46478, SEQ ID NO: 46484, SEQ ID NO: 46486, SEQ ID NO: 46491, SEQ ID NO: 46506, SEQ ID NO: 46512, SEQ ID NO: 46517, SEQ ID NO: 46530, SEQ ID NO: 46534, SEQ ID NO: 46556, SEQ ID NO: 46560, SEQ ID NO: 46564, SEQ ID NO: 46596, SEQ ID NO: 46602, SEQ ID NO: 46616, SEQ ID NO: 46635, SEQ ID NO: 46656, SEQ ID NO: 46658, SEQ ID NO: 46666, SEQ ID NO: 46676, SEQ ID NO: 46679, SEQ ID NO: 46689, SEQ ID NO: 46705, SEQ ID NO: 46724, SEQ ID NO: 46738, SEQ ID NO: 46767, SEQ ID NO: 46770, SEQ ID NO: 46794, SEQ ID NO: 46810, SEQ ID NO: 46819, SEQ ID NO: 46824, SEQ ID NO: 46831, SEQ ID NO: 46849, SEQ ID NO: 46854, SEQ ID NO: 46870, SEQ ID NO: 46880, SEQ ID NO: 46916, SEQ ID NO: 46935, SEQ ID NO: 46939, SEQ ID NO: 46944, SEQ ID NO: 46958, SEQ ID NO: 46964, SEQ ID NO: 46967, SEQ ID NO: 46978, SEQ ID NO: 46987, SEQ ID NO: 46989, SEQ ID NO: 46991, SEQ ID NO: 46993, SEQ ID NO: 47007, SEQ ID NO: 47034, SEQ ID NO: 47037, SEQ ID NO: 47047, SEQ ID NO: 47057, SEQ ID NO: 47066, SEQ ID NO: 47096, SEQ ID NO: 47098, SEQ ID NO: 47119, SEQ ID NO: 47123, SEQ ID NO: 47137, SEQ ID NO: 47139, SEQ ID NO: 47143, SEQ ID NO: 47150, SEQ ID NO: 47158, SEQ ID NO: 47161, SEQ ID NO: 47170, SEQ ID NO: 47181, SEQ ID NO: 47197, SEQ ID NO: 47209, SEQ ID NO: 47254, SEQ ID NO: 47266, SEQ ID NO: 47272, SEQ ID NO: 47291, SEQ ID NO: 47298, SEQ ID NO: 47300, SEQ ID NO: 47319, SEQ ID NO: 47324, SEQ ID NOs: 47331 to 47332, SEQ ID NO: 47358, SEQ ID NO: 47361, SEQ ID NO: 47393, SEQ ID NO: 47414, SEQ ID NO: 47416, SEQ ID NO: 47422, SEQ ID NO: 47425, SEQ ID NOs: 47432 to

47433, SEQ ID NO: 47445, SEQ ID NO: 47453, SEQ ID NOs: 47460 to 47461, SEQ ID NO: 47477, SEQ ID NO: 47492, SEQ ID NO: 47507, SEQ ID NO: 47509, SEQ ID NO: 47516, SEQ ID NO: 47535, SEQ ID NOs: 47556 to 47557, SEQ ID NOs: 47578 to 47579, SEQ ID NOs: 47591 to 47592, SEQ ID NO: 47597, SEQ ID NO: 47600, SEQ ID NO: 47614, SEQ ID NO: 47626, SEQ ID NO: 47629, SEQ ID NO: 47637, SEQ ID NO: 47639, SEQ ID NO: 47649, SEQ ID NOs: 47689 to 47690, SEQ ID NO: 47713, SEQ ID NO: 47766, SEQ ID NOs: 47814 to 47815, SEQ ID NO: 47827, SEQ ID NO: 47834, SEQ ID NOs: 47852 to 47853, SEQ ID NO: 47855, SEQ ID NO: 47871, SEQ ID NOs: 47875 to 47876, SEQ ID NO: 47891, SEQ ID NO: 47896, SEQ ID NO: 47902, SEQ ID NO: 47923, SEQ ID NO: 47925, SEQ ID NO: 47927, SEQ ID NO: 47929, SEQ ID NO: 47932, SEQ ID NOs: 47962 to 47964, SEQ ID NO: 47972, SEQ ID NO: 47999, SEQ ID NO: 48008, SEQ ID NO: 48028, SEQ ID NOs: 48034 to 48035, SEQ ID NO: 48038, SEQ ID NO: 48056, SEQ ID NO: 48061, SEQ ID NO: 48066, SEQ ID NO: 48118, SEQ ID NO: 48120, SEQ ID NO: 48129, SEQ ID NO: 48140, SEQ ID NO: 48148, SEQ ID NO: 48153, SEQ ID NOs: 48159 to 48160, SEQ ID NO: 48163, SEQ ID NO: 48167, SEQ ID NO: 48178, SEQ ID NO: 48180, SEQ ID NO: 48186, SEQ ID NO: 48218, SEQ ID NO: 48220, SEQ ID NO: 48263, SEQ ID NO: 48286, SEQ ID NO: 48300, SEQ ID NO: 48307, SEQ ID NO: 48315, SEQ ID NO: 48321, SEQ ID NO: 48338, SEQ ID NO: 48341, SEQ ID NO: 48343, SEQ ID NO: 48358, SEQ ID NO: 48362, SEQ ID NO: 48366, SEQ ID NO: 48368, SEQ ID NO: 48418, SEQ ID NO: 48431, SEQ ID NO: 48436, SEQ ID NOs: 48438 to 48439, SEQ ID NOs: 48443 to 48444, SEQ ID NO: 48450, SEQ ID NOs: 48452 to 48453, SEQ ID NO: 48458, SEQ ID NOs: 48461 to 48462, SEQ ID NO: 48507, SEQ ID NO: 48516, SEQ ID NO: 48527, SEQ ID NO: 48537, SEQ ID NO: 48548, SEQ ID NO: 48567, SEQ ID NO: 48574, SEQ ID NO: 48576, SEQ ID NO: 48578, SEQ ID NO: 48594, SEQ ID NO: 48599, SEQ ID NO: 48612, SEQ ID NO: 48614, SEQ ID NO: 48623, SEQ ID NO: 48626, SEQ ID NO: 48630, SEQ ID NO: 48642, SEQ ID NO: 48648, SEQ ID NO: 48656, SEQ ID NOs: 48704 to 48705, SEQ ID NO: 48708, SEQ ID NO: 48739, SEQ ID NO: 48749, SEQ ID NO: 48752, SEQ ID NO: 48754, SEQ ID NO: 48756, SEQ ID NO: 48802, SEQ ID NO: 48832, SEQ ID NO: 48845, SEQ ID NO: 48850, SEQ ID NO: 48852, SEQ ID NO: 48856, SEQ ID NO: 48870, SEQ ID NO: 48888, SEQ ID NO: 48902, SEQ ID NO: 48904, SEQ ID NOs: 48912 to 48913, SEQ ID NO: 48921, SEQ ID NO: 48970, SEQ ID NO: 48974, SEQ ID NO: 48993, SEQ ID NO: 48997, SEQ ID NO: 49004, SEQ ID NO: 49019, SEQ ID NO: 49025, SEQ ID NOs: 49045 to 49046, SEQ ID NO: 49052, SEQ ID NO: 49083, SEQ ID NO: 49086, SEQ ID NOs: 49091 to 49092, SEQ ID NO: 49102, SEQ ID NO: 49106, SEQ ID NO: 49111, SEQ ID NO: 49127, SEQ ID NO: 49152, SEQ ID NO: 49159, SEQ ID NO: 49173, SEQ ID NO: 49197, SEQ ID NO: 49201, SEQ ID NO: 49203, SEQ ID NO: 49207, SEQ ID NO: 49220, SEQ ID NO: 49227, SEQ ID NO: 49230, SEQ ID NO: 49234, SEQ ID NO: 49242, SEQ ID NO: 49256, SEQ ID NO: 49263, SEQ ID NOs: 49273 to 49274, SEQ ID NO: 49278, SEQ ID NO: 49280, SEQ ID NO: 49288, SEQ ID NO: 49290, SEQ ID NOs: 49294 to 49295, SEQ ID NO: 49326, SEQ ID NO: 49362, SEQ ID NOs: 49384 to 49385, SEQ ID NO: 49387, SEQ ID NO: 49393, SEQ ID NO: 49395, SEQ ID NOs: 49427 to 49428, SEQ ID NO: 49444, SEQ ID NO: 49458, SEQ ID NO: 49483, SEQ ID NO: 49487, SEQ ID NO: 49497, SEQ ID NO: 49501, SEQ ID NO: 49517, SEQ ID NO: 49525, SEQ ID NO: 49535, SEQ ID NO: 49537, SEQ ID NO: 49544, SEQ ID NO: 49557, SEQ ID NO: 49569, SEQ ID NO: 49572, SEQ ID NO: 49587, SEQ ID NO: 49594, SEQ ID NO: 49596, SEQ ID NO: 49598, SEQ ID NO: 49606, SEQ ID NO: 49617, SEQ ID NO: 49629, SEQ ID NO: 49646, SEQ ID NO: 49658, SEQ ID NO: 49693, SEQ ID NOs: 49702 to 49703, SEQ ID NO: 49710, SEQ ID NO: 49712, SEQ ID NO: 49719, SEQ ID NO: 49727, SEQ ID NO: 49737, SEQ ID NO: 49740, SEQ ID NO: 49743, SEQ ID NO: 49767, SEQ ID NO: 49778, SEQ ID NO: 49788, SEQ ID NO: 49811, SEQ ID NO: 49848, SEQ ID NO: 49860, SEQ ID NO: 49888, SEQ ID NO: 49908, SEQ ID NO: 49973, SEQ ID NO: 49977, SEQ ID NO: 49980, SEQ ID NOs: 49996 to 49997, SEQ ID NO: 50000, SEQ ID NO: 50012, SEQ ID NOs: 50017 to 50018, SEQ ID NO: 50051, SEQ ID NO: 50056, SEQ ID NO: 50062, SEQ ID NO: 50090, SEQ ID NO: 50093, SEQ ID NO: 50107, SEQ ID NO: 50129, SEQ ID NO: 50132, SEQ ID NO: 50138, SEQ ID NO: 50144, SEQ ID NO: 50167, SEQ ID NO: 50191, SEQ ID NO: 50194, SEQ ID NO: 50196, SEQ ID NO: 50228, SEQ ID NO: 50239, SEQ ID NO: 50263, SEQ ID NO: 50271, SEQ ID NO: 50297, SEQ ID NO: 50305, SEQ ID NO: 50320, SEQ ID NO: 50322, SEQ ID NO: 50326, SEQ ID NO: 50334, SEQ ID NO: 50349, SEQ ID NO: 50375, SEQ ID NO: 50394, SEQ ID NO: 50401, SEQ ID NO: 50414, SEQ ID NO: 50421, SEQ ID NO: 50423, SEQ ID NO: 50435, SEQ ID NOs: 50440 to 50441, SEQ ID NO: 50443, SEQ ID NO: 50510, SEQ ID NO: 50556, SEQ ID NO: 50564, SEQ ID NO: 50591, SEQ ID NO: 50605, SEQ ID NO: 50607, SEQ ID NO: 50611, SEQ ID NO: 50622, SEQ ID NO: 50625, SEQ ID NO: 50627, SEQ ID NO: 50632, SEQ ID NO: 50644, SEQ ID NOs: 50652 to 50653, SEQ ID NOs: 50668 to 50669, SEQ ID NO: 50677, SEQ ID NO: 50696, SEQ ID NO: 50699, SEQ ID NO: 50705, SEQ ID NO: 50709, SEQ ID NO: 50711, SEQ ID NO: 50729, SEQ ID NO: 50731, SEQ ID NO: 50741, SEQ ID NO: 50743, SEQ ID NO: 50748, SEQ ID NO: 50762, SEQ ID NO: 50765, SEQ ID NO: 50767, SEQ ID NO: 50800, SEQ ID NO: 50803, SEQ ID NO: 50807, SEQ ID NO: 50841, SEQ ID NO: 50865, SEQ ID NO: 50872, SEQ ID NO: 50905, SEQ ID NOs: 50955 to 50956, SEQ ID NOs: 50975 to 50977, SEQ ID NO: 50986, SEQ ID NO: 51021, SEQ ID NOs: 51039 to 51040, SEQ ID NOs: 51066 to 51068, SEQ ID NO: 51084, SEQ ID NOs: 51099 to 51100, SEQ ID NOs: 51165 to 51167, SEQ ID NO: 51169, SEQ ID NO: 51190, SEQ ID NOs: 51194 to 51198, SEQ ID NOs: 51267 to 51270, SEQ ID NOs: 51281 to 51282, SEQ ID NO: 51324, SEQ ID NO: 51349, SEQ ID NO: 51379, SEQ ID NOs: 51413 to 51415, SEQ ID NOs: 51420 to 51421, or SEQ ID NOs: 51434 to 60455.

In some embodiments, the amino acid sequence for a MEW class I peptide vaccine for the MAGA3 protein comprises two or more of the SEQ ID NO: 41383, SEQ ID NO: 41396, SEQ ID NO: 41770, SEQ ID NO: 49004, and SEQ ID NOs: 51434 to 51510. In some embodiments, any one of the peptides in the MAGA3 vaccine comprise an amino acid sequence 80, 81, 82, 83, 84, 85, 86, 87, 88, 89, 90, 91, 92, 93, 94, 95, 96, 97, 98 or 99% identical to SEQ ID NO: 41383, SEQ ID NO: 41396, SEQ ID NO: 41770, SEQ ID NO: 49004, or SEQ ID NOs: 51434 to 51510.

In some embodiments, the amino acid sequence for a MEW class I peptide vaccine for the MAGA3 protein comprises two or more of the SEQ ID NOs: 41351 to 41352, SEQ ID NO: 41383, SEQ ID NO: 41396, SEQ ID NO: 41410, SEQ ID NO: 41414, SEQ ID NO: 41435, SEQ ID NO: 41450, SEQ ID NO: 41463, SEQ ID NO: 41478, SEQ ID NO: 41489, SEQ ID NO: 41495, SEQ ID NO: 41503, SEQ ID NO: 41513, SEQ ID NO: 41520, SEQ ID NO:

41535, SEQ ID NO: 41541, SEQ ID NO: 41545, SEQ ID NO: 41577, SEQ ID NO: 41588, SEQ ID NO: 41598, SEQ ID NO: 41605, SEQ ID NO: 41617, SEQ ID NO: 41620, SEQ ID NO: 41622, SEQ ID NO: 41627, SEQ ID NO: 41630, SEQ ID NO: 41638, SEQ ID NO: 41647, SEQ ID NO: 41673, SEQ ID NO: 41696, SEQ ID NO: 41703, SEQ ID NO: 41708, SEQ ID NO: 41728, SEQ ID NOs: 41732 to 41733, SEQ ID NO: 41749, SEQ ID NO: 41760, SEQ ID NO: 41766, SEQ ID NO: 41770, SEQ ID NO: 41788, SEQ ID NO: 41791, SEQ ID NO: 41809, SEQ ID NO: 41813, SEQ ID NO: 41817, SEQ ID NO: 41829, SEQ ID NOs: 41847 to 41848, SEQ ID NO: 41853, SEQ ID NO: 41859, SEQ ID NO: 41889, SEQ ID NO: 41894, SEQ ID NO: 41897, SEQ ID NO: 41909, SEQ ID NO: 41923, SEQ ID NO: 41934, SEQ ID NO: 41939, SEQ ID NOs: 41953 to 41954, SEQ ID NO: 41959, SEQ ID NO: 41967, SEQ ID NO: 41970, SEQ ID NO: 41976, SEQ ID NOs: 41984 to 41985, SEQ ID NO: 42007, SEQ ID NO: 42017, SEQ ID NO: 42034, SEQ ID NO: 42044, SEQ ID NO: 42046, SEQ ID NO: 42048, SEQ ID NO: 42056, SEQ ID NO: 42067, SEQ ID NO: 42080, SEQ ID NO: 42088, SEQ ID NO: 42091, SEQ ID NOs: 42119 to 42120, SEQ ID NO: 42129, SEQ ID NO: 42135, SEQ ID NOs: 42140 to 42141, SEQ ID NO: 42155, SEQ ID NO: 42158, SEQ ID NO: 42164, SEQ ID NO: 42170, SEQ ID NO: 42174, SEQ ID NO: 42186, SEQ ID NO: 42209, SEQ ID NO: 42218, SEQ ID NO: 42224, SEQ ID NO: 42229, SEQ ID NO: 42232, SEQ ID NO: 42235, SEQ ID NOs: 42237 to 42238, SEQ ID NO: 42265, SEQ ID NO: 42272, SEQ ID NO: 42278, SEQ ID NO: 42293, SEQ ID NO: 42314, SEQ ID NOs: 42336 to 42337, SEQ ID NO: 42339, SEQ ID NOs: 42372 to 42373, SEQ ID NO: 42376, SEQ ID NO: 42382, SEQ ID NO: 42386, SEQ ID NO: 42408, SEQ ID NO: 42414, SEQ ID NO: 42423, SEQ ID NO: 42429, SEQ ID NOs: 42447 to 42448, SEQ ID NO: 42461, SEQ ID NO: 42466, SEQ ID NO: 42475, SEQ ID NO: 42513, SEQ ID NO: 42540, SEQ ID NO: 42545, SEQ ID NO: 42550, SEQ ID NO: 42553, SEQ ID NOs: 42567 to 42568, SEQ ID NO: 42580, SEQ ID NO: 42585, SEQ ID NO: 42605, SEQ ID NO: 42612, SEQ ID NO: 42627, SEQ ID NO: 42675, SEQ ID NO: 42680, SEQ ID NO: 42685, SEQ ID NO: 42690, SEQ ID NO: 42702, SEQ ID NO: 42711, SEQ ID NO: 42719, SEQ ID NO: 42738, SEQ ID NO: 42743, SEQ ID NO: 42750, SEQ ID NO: 42755, SEQ ID NO: 42777, SEQ ID NO: 42788, SEQ ID NO: 42793, SEQ ID NO: 42851, SEQ ID NO: 42858, SEQ ID NO: 42866, SEQ ID NO: 42903, SEQ ID NO: 42927, SEQ ID NOs: 42936 to 42937, SEQ ID NOs: 42940 to 42941, SEQ ID NO: 42957, SEQ ID NO: 42962, SEQ ID NO: 42966, SEQ ID NO: 42968, SEQ ID NO: 42986, SEQ ID NO: 43002, SEQ ID NO: 43013, SEQ ID NO: 43037, SEQ ID NO: 43052, SEQ ID NOs: 43055 to 43056, SEQ ID NOs: 43063 to 43064, SEQ ID NO: 43096, SEQ ID NO: 43133, SEQ ID NO: 43138, SEQ ID NO: 43156, SEQ ID NO: 43161, SEQ ID NO: 43186, SEQ ID NO: 43199, SEQ ID NO: 43205, SEQ ID NO: 43245, SEQ ID NO: 43251, SEQ ID NO: 43275, SEQ ID NO: 43312, SEQ ID NO: 43327, SEQ ID NO: 43333, SEQ ID NO: 43339, SEQ ID NO: 43342, SEQ ID NO: 43348, SEQ ID NO: 43365, SEQ ID NO: 43371, SEQ ID NO: 43400, SEQ ID NO: 43440, SEQ ID NO: 43451, SEQ ID NO: 43462, SEQ ID NO: 43467, SEQ ID NO: 43487, SEQ ID NOs: 43498 to 43499, SEQ ID NO: 43507, SEQ ID NO: 43522, SEQ ID NO: 43529, SEQ ID NO: 43533, SEQ ID NO: 43545, SEQ ID NO: 43558, SEQ ID NO: 43560, SEQ ID NO: 43583, SEQ ID NO: 43597, SEQ ID NO: 43599, SEQ ID NO: 43610, SEQ ID NO: 43614, SEQ ID NO: 43627, SEQ ID NO: 43697, SEQ ID NO: 43715, SEQ ID NO: 43718, SEQ ID NO: 43768, SEQ ID NO: 43777, SEQ ID NOs: 43825 to 43826, SEQ ID NO: 43836, SEQ ID NO: 43840, SEQ ID NO: 43856, SEQ ID NO: 43860, SEQ ID NO: 43870, SEQ ID NO: 43878, SEQ ID NOs: 43881 to 43882, SEQ ID NO: 43905, SEQ ID NO: 43922, SEQ ID NO: 43930, SEQ ID NO: 43943, SEQ ID NO: 43953, SEQ ID NO: 43958, SEQ ID NO: 43979, SEQ ID NO: 43986, SEQ ID NO: 44002, SEQ ID NO: 44033, SEQ ID NO: 44037, SEQ ID NO: 44048, SEQ ID NO: 44050, SEQ ID NO: 44052, SEQ ID NOs: 44080 to 44081, SEQ ID NOs: 44093 to 44094, SEQ ID NOs: 44114 to 44115, SEQ ID NO: 44120, SEQ ID NO: 44142, SEQ ID NO: 44152, SEQ ID NOs: 44164 to 44166, SEQ ID NO: 44181, SEQ ID NO: 44222, SEQ ID NO: 44244, SEQ ID NO: 44246, SEQ ID NO: 44255, SEQ ID NO: 44261, SEQ ID NO: 44276, SEQ ID NOs: 44286 to 44287, SEQ ID NO: 44296, SEQ ID NO: 44315, SEQ ID NO: 44322, SEQ ID NO: 44324, SEQ ID NO: 44328, SEQ ID NO: 44332, SEQ ID NO: 44339, SEQ ID NO: 44401, SEQ ID NO: 44413, SEQ ID NO: 44435, SEQ ID NO: 44452, SEQ ID NO: 44454, SEQ ID NO: 44463, SEQ ID NO: 44467, SEQ ID NO: 44485, SEQ ID NO: 44504, SEQ ID NO: 44512, SEQ ID NO: 44523, SEQ ID NOs: 44526 to 44527, SEQ ID NO: 44536, SEQ ID NO: 44564, SEQ ID NO: 44605, SEQ ID NO: 44607, SEQ ID NO: 44612, SEQ ID NO: 44629, SEQ ID NOs: 44635 to 44636, SEQ ID NO: 44647, SEQ ID NO: 44650, SEQ ID NO: 44674, SEQ ID NO: 44691, SEQ ID NO: 44696, SEQ ID NO: 44702, SEQ ID NO: 44710, SEQ ID NO: 44713, SEQ ID NO: 44715, SEQ ID NO: 44722, SEQ ID NO: 44730, SEQ ID NO: 44733, SEQ ID NO: 44755, SEQ ID NO: 44770, SEQ ID NO: 44773, SEQ ID NO: 44781, SEQ ID NO: 44783, SEQ ID NO: 44797, SEQ ID NO: 44805, SEQ ID NO: 44822, SEQ ID NO: 44828, SEQ ID NO: 44830, SEQ ID NO: 44832, SEQ ID NO: 44850, SEQ ID NO: 44852, SEQ ID NO: 44854, SEQ ID NO: 44860, SEQ ID NO: 44866, SEQ ID NO: 44898, SEQ ID NO: 44900, SEQ ID NO: 44907, SEQ ID NO: 44933, SEQ ID NO: 44947, SEQ ID NO: 44986, SEQ ID NO: 45003, SEQ ID NO: 45007, SEQ ID NO: 45009, SEQ ID NO: 45012, SEQ ID NO: 45016, SEQ ID NO: 45018, SEQ ID NO: 45027, SEQ ID NO: 45031, SEQ ID NO: 45036, SEQ ID NO: 45044, SEQ ID NO: 45060, SEQ ID NO: 45071, SEQ ID NO: 45077, SEQ ID NO: 45095, SEQ ID NO: 45126, SEQ ID NO: 45132, SEQ ID NO: 45135, SEQ ID NO: 45139, SEQ ID NO: 45143, SEQ ID NO: 45159, SEQ ID NO: 45177, SEQ ID NO: 45197, SEQ ID NO: 45200, SEQ ID NO: 45219, SEQ ID NO: 45228, SEQ ID NO: 45323, SEQ ID NO: 45329, SEQ ID NO: 45351, SEQ ID NO: 45378, SEQ ID NO: 45380, SEQ ID NO: 45389, SEQ ID NO: 45413, SEQ ID NO: 45417, SEQ ID NO: 45438, SEQ ID NO: 45455, SEQ ID NO: 45457, SEQ ID NO: 45467, SEQ ID NO: 45478, SEQ ID NO: 45530, SEQ ID NO: 45562, SEQ ID NO: 45565, SEQ ID NOs: 45583 to 45584, SEQ ID NOs: 45595 to 45596, SEQ ID NO: 45608, SEQ ID NO: 45612, SEQ ID NO: 45616, SEQ ID NO: 45627, SEQ ID NO: 45653, SEQ ID NOs: 45666 to 45667, SEQ ID NO: 45680, SEQ ID NO: 45697, SEQ ID NO: 45705, SEQ ID NO: 45710, SEQ ID NO: 45722, SEQ ID NO: 45736, SEQ ID NO: 45742, SEQ ID NO: 45746, SEQ ID NO: 45765, SEQ ID NO: 45808, SEQ ID NO: 45830, SEQ ID NOs: 45840 to 45841, SEQ ID NO: 45896, SEQ ID NOs: 45904 to 45905, SEQ ID NO: 45913, SEQ ID NO: 45915, SEQ ID NOs: 45940 to 45943, SEQ ID NO: 45945, SEQ ID NOs: 45958 to 45959, SEQ ID NO: 45977, SEQ ID NO: 45983, SEQ ID NO: 45992, SEQ ID NO: 46006, SEQ ID NO: 46012, SEQ ID NO: 46018, SEQ ID NO: 46021, SEQ ID NOs: 46037 to 46038, SEQ ID NO: 46044, SEQ ID NO:

46058, SEQ ID NO: 46071, SEQ ID NO: 46082, SEQ ID NO: 46094, SEQ ID NO: 46096, SEQ ID NO: 46102, SEQ ID NOs: 46108 to 46109, SEQ ID NO: 46122, SEQ ID NO: 46125, SEQ ID NOs: 46133 to 46134, SEQ ID NO: 46146, SEQ ID NO: 46159, SEQ ID NO: 46177, SEQ ID NO: 46182, SEQ ID NO: 46188, SEQ ID NO: 46202, SEQ ID NO: 46219, SEQ ID NO: 46246, SEQ ID NO: 46249, SEQ ID NO: 46270, SEQ ID NO: 46279, SEQ ID NO: 46312, SEQ ID NO: 46339, SEQ ID NO: 46378, SEQ ID NO: 46433, SEQ ID NO: 46442, SEQ ID NO: 46446, SEQ ID NO: 46452, SEQ ID NO: 46454, SEQ ID NO: 46457, SEQ ID NO: 46478, SEQ ID NO: 46484, SEQ ID NO: 46486, SEQ ID NO: 46491, SEQ ID NO: 46506, SEQ ID NO: 46512, SEQ ID NO: 46517, SEQ ID NO: 46530, SEQ ID NO: 46534, SEQ ID NO: 46556, SEQ ID NO: 46560, SEQ ID NO: 46564, SEQ ID NO: 46596, SEQ ID NO: 46602, SEQ ID NO: 46616, SEQ ID NO: 46635, SEQ ID NO: 46656, SEQ ID NO: 46658, SEQ ID NO: 46666, SEQ ID NO: 46676, SEQ ID NO: 46679, SEQ ID NO: 46689, SEQ ID NO: 46705, SEQ ID NO: 46724, SEQ ID NO: 46738, SEQ ID NO: 46767, SEQ ID NO: 46770, SEQ ID NO: 46794, SEQ ID NO: 46810, SEQ ID NO: 46819, SEQ ID NO: 46824, SEQ ID NO: 46831, SEQ ID NO: 46849, SEQ ID NO: 46854, SEQ ID NO: 46870, SEQ ID NO: 46880, SEQ ID NO: 46916, SEQ ID NO: 46935, SEQ ID NO: 46939, SEQ ID NO: 46944, SEQ ID NO: 46958, SEQ ID NO: 46964, SEQ ID NO: 46967, SEQ ID NO: 46978, SEQ ID NO: 46987, SEQ ID NO: 46989, SEQ ID NO: 46991, SEQ ID NO: 46993, SEQ ID NO: 47007, SEQ ID NO: 47034, SEQ ID NO: 47037, SEQ ID NO: 47047, SEQ ID NO: 47057, SEQ ID NO: 47066, SEQ ID NO: 47096, SEQ ID NO: 47098, SEQ ID NO: 47119, SEQ ID NO: 47123, SEQ ID NO: 47137, SEQ ID NO: 47139, SEQ ID NO: 47143, SEQ ID NO: 47150, SEQ ID NO: 47158, SEQ ID NO: 47161, SEQ ID NO: 47170, SEQ ID NO: 47181, SEQ ID NO: 47197, SEQ ID NO: 47209, SEQ ID NO: 47254, SEQ ID NO: 47266, SEQ ID NO: 47272, SEQ ID NO: 47291, SEQ ID NO: 47298, SEQ ID NO: 47300, SEQ ID NO: 47319, SEQ ID NO: 47324, SEQ ID NOs: 47331 to 47332, SEQ ID NO: 47358, SEQ ID NO: 47361, SEQ ID NO: 47393, SEQ ID NO: 47414, SEQ ID NO: 47416, SEQ ID NO: 47422, SEQ ID NO: 47425, SEQ ID NOs: 47432 to 47433, SEQ ID NO: 47445, SEQ ID NO: 47453, SEQ ID NOs: 47460 to 47461, SEQ ID NO: 47477, SEQ ID NO: 47492, SEQ ID NO: 47507, SEQ ID NO: 47509, SEQ ID NO: 47516, SEQ ID NO: 47535, SEQ ID NOs: 47556 to 47557, SEQ ID NOs: 47578 to 47579, SEQ ID NOs: 47591 to 47592, SEQ ID NO: 47597, SEQ ID NO: 47600, SEQ ID NO: 47614, SEQ ID NO: 47626, SEQ ID NO: 47629, SEQ ID NO: 47637, SEQ ID NO: 47639, SEQ ID NO: 47649, SEQ ID NOs: 47689 to 47690, SEQ ID NO: 47713, SEQ ID NO: 47766, SEQ ID NOs: 47814 to 47815, SEQ ID NO: 47827, SEQ ID NO: 47834, SEQ ID NOs: 47852 to 47853, SEQ ID NO: 47855, SEQ ID NO: 47871, SEQ ID NOs: 47875 to 47876, SEQ ID NO: 47891, SEQ ID NO: 47896, SEQ ID NO: 47902, SEQ ID NO: 47923, SEQ ID NO: 47925, SEQ ID NO: 47927, SEQ ID NO: 47929, SEQ ID NO: 47932, SEQ ID NOs: 47962 to 47964, SEQ ID NO: 47972, SEQ ID NO: 47999, SEQ ID NO: 48008, SEQ ID NO: 48028, SEQ ID NOs: 48034 to 48035, SEQ ID NO: 48038, SEQ ID NO: 48056, SEQ ID NO: 48061, SEQ ID NO: 48066, SEQ ID NO: 48118, SEQ ID NO: 48120, SEQ ID NO: 48129, SEQ ID NO: 48140, SEQ ID NO: 48148, SEQ ID NO: 48153, SEQ ID NOs: 48159 to 48160, SEQ ID NO: 48163, SEQ ID NO: 48167, SEQ ID NO: 48178, SEQ ID NO: 48180, SEQ ID NO: 48186, SEQ ID NO: 48218, SEQ ID NO: 48220, SEQ ID NO: 48263, SEQ ID NO: 48286, SEQ ID NO: 48300, SEQ ID NO: 48307, SEQ ID NO: 48315, SEQ ID NO: 48321, SEQ ID NO: 48338, SEQ ID NO: 48341, SEQ ID NO: 48343, SEQ ID NO: 48358, SEQ ID NO: 48362, SEQ ID NO: 48366, SEQ ID NO: 48368, SEQ ID NO: 48418, SEQ ID NO: 48431, SEQ ID NO: 48436, SEQ ID NOs: 48438 to 48439, SEQ ID NOs: 48443 to 48444, SEQ ID NO: 48450, SEQ ID NOs: 48452 to 48453, SEQ ID NO: 48458, SEQ ID NOs: 48461 to 48462, SEQ ID NO: 48507, SEQ ID NO: 48516, SEQ ID NO: 48527, SEQ ID NO: 48537, SEQ ID NO: 48548, SEQ ID NO: 48567, SEQ ID NO: 48574, SEQ ID NO: 48576, SEQ ID NO: 48578, SEQ ID NO: 48594, SEQ ID NO: 48599, SEQ ID NO: 48612, SEQ ID NO: 48614, SEQ ID NO: 48623, SEQ ID NO: 48626, SEQ ID NO: 48630, SEQ ID NO: 48642, SEQ ID NO: 48648, SEQ ID NO: 48656, SEQ ID NOs: 48704 to 48705, SEQ ID NO: 48708, SEQ ID NO: 48739, SEQ ID NO: 48749, SEQ ID NO: 48752, SEQ ID NO: 48754, SEQ ID NO: 48756, SEQ ID NO: 48802, SEQ ID NO: 48832, SEQ ID NO: 48845, SEQ ID NO: 48850, SEQ ID NO: 48852, SEQ ID NO: 48856, SEQ ID NO: 48870, SEQ ID NO: 48888, SEQ ID NO: 48902, SEQ ID NO: 48904, SEQ ID NOs: 48912 to 48913, SEQ ID NO: 48921, SEQ ID NO: 48970, SEQ ID NO: 48974, SEQ ID NO: 48993, SEQ ID NO: 48997, SEQ ID NO: 49004, SEQ ID NO: 49019, SEQ ID NO: 49025, SEQ ID NOs: 49045 to 49046, SEQ ID NO: 49052, SEQ ID NO: 49083, SEQ ID NO: 49086, SEQ ID NOs: 49091 to 49092, SEQ ID NO: 49102, SEQ ID NO: 49106, SEQ ID NO: 49111, SEQ ID NO: 49127, SEQ ID NO: 49152, SEQ ID NO: 49159, SEQ ID NO: 49173, SEQ ID NO: 49197, SEQ ID NO: 49201, SEQ ID NO: 49203, SEQ ID NO: 49207, SEQ ID NO: 49220, SEQ ID NO: 49227, SEQ ID NO: 49230, SEQ ID NO: 49234, SEQ ID NO: 49242, SEQ ID NO: 49256, SEQ ID NO: 49263, SEQ ID NOs: 49273 to 49274, SEQ ID NO: 49278, SEQ ID NO: 49280, SEQ ID NO: 49288, SEQ ID NO: 49290, SEQ ID NOs: 49294 to 49295, SEQ ID NO: 49326, SEQ ID NO: 49362, SEQ ID NOs: 49384 to 49385, SEQ ID NO: 49387, SEQ ID NO: 49393, SEQ ID NO: 49395, SEQ ID NOs: 49427 to 49428, SEQ ID NO: 49444, SEQ ID NO: 49458, SEQ ID NO: 49483, SEQ ID NO: 49487, SEQ ID NO: 49497, SEQ ID NO: 49501, SEQ ID NO: 49517, SEQ ID NO: 49525, SEQ ID NO: 49535, SEQ ID NO: 49537, SEQ ID NO: 49544, SEQ ID NO: 49557, SEQ ID NO: 49569, SEQ ID NO: 49572, SEQ ID NO: 49587, SEQ ID NO: 49594, SEQ ID NO: 49596, SEQ ID NO: 49598, SEQ ID NO: 49606, SEQ ID NO: 49617, SEQ ID NO: 49629, SEQ ID NO: 49646, SEQ ID NO: 49658, SEQ ID NO: 49693, SEQ ID NOs: 49702 to 49703, SEQ ID NO: 49710, SEQ ID NO: 49712, SEQ ID NO: 49719, SEQ ID NO: 49727, SEQ ID NO: 49737, SEQ ID NO: 49740, SEQ ID NO: 49743, SEQ ID NO: 49767, SEQ ID NO: 49778, SEQ ID NO: 49788, SEQ ID NO: 49811, SEQ ID NO: 49848, SEQ ID NO: 49860, SEQ ID NO: 49888, SEQ ID NO: 49908, SEQ ID NO: 49973, SEQ ID NO: 49977, SEQ ID NO: 49980, SEQ ID NOs: 49996 to 49997, SEQ ID NO: 50000, SEQ ID NO: 50012, SEQ ID NOs: 50017 to 50018, SEQ ID NO: 50051, SEQ ID NO: 50056, SEQ ID NO: 50062, SEQ ID NO: 50090, SEQ ID NO: 50093, SEQ ID NO: 50107, SEQ ID NO: 50129, SEQ ID NO: 50132, SEQ ID NO: 50138, SEQ ID NO: 50144, SEQ ID NO: 50167, SEQ ID NO: 50191, SEQ ID NO: 50194, SEQ ID NO: 50196, SEQ ID NO: 50228, SEQ ID NO: 50239, SEQ ID NO: 50263, SEQ ID NO: 50271, SEQ ID NO: 50297, SEQ ID NO: 50305, SEQ ID NO: 50320, SEQ ID NO: 50322, SEQ ID NO: 50326, SEQ ID NO: 50334, SEQ ID NO: 50349, SEQ ID NO: 50375, SEQ ID NO: 50394, SEQ ID NO: 50401, SEQ ID NO: 50414, SEQ ID NO: 50421,

SEQ ID NO: 50423, SEQ ID NO: 50435, SEQ ID NOs: 50440 to 50441, SEQ ID NO: 50443, SEQ ID NO: 50510, SEQ ID NO: 50556, SEQ ID NO: 50564, SEQ ID NO: 50591, SEQ ID NO: 50605, SEQ ID NO: 50607, SEQ ID NO: 50611, SEQ ID NO: 50622, SEQ ID NO: 50625, SEQ ID NO: 50627, SEQ ID NO: 50632, SEQ ID NO: 50644, SEQ ID NOs: 50652 to 50653, SEQ ID NOs: 50668 to 50669, SEQ ID NO: 50677, SEQ ID NO: 50696, SEQ ID NO: 50699, SEQ ID NO: 50705, SEQ ID NO: 50709, SEQ ID NO: 50711, SEQ ID NO: 50729, SEQ ID NO: 50731, SEQ ID NO: 50741, SEQ ID NO: 50743, SEQ ID NO: 50748, SEQ ID NO: 50762, SEQ ID NO: 50765, SEQ ID NO: 50767, SEQ ID NO: 50800, SEQ ID NO: 50803, SEQ ID NO: 50807, SEQ ID NO: 50841, SEQ ID NO: 50865, SEQ ID NO: 50872, SEQ ID NO: 50905, SEQ ID NOs: 50955 to 50956, SEQ ID NOs: 50975 to 50977, SEQ ID NO: 50986, SEQ ID NO: 51021, SEQ ID NOs: 51039 to 51040, SEQ ID NOs: 51066 to 51068, SEQ ID NO: 51084, SEQ ID NOs: 51099 to 51100, SEQ ID NOs: 51165 to 51167, SEQ ID NO: 51169, SEQ ID NO: 51190, SEQ ID NOs: 51194 to 51198, SEQ ID NOs: 51267 to 51270, SEQ ID NOs: 51281 to 51282, SEQ ID NO: 51324, SEQ ID NO: 51349, SEQ ID NO: 51379, SEQ ID NOs: 51413 to 51415, SEQ ID NOs: 51420 to 51421, and SEQ ID NOs: 51434 to 60455. In some embodiments, any one of the peptides in the MAGA3 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 41351 to 41352, SEQ ID NO: 41383, SEQ ID NO: 41396, SEQ ID NO: 41410, SEQ ID NO: 41414, SEQ ID NO: 41435, SEQ ID NO: 41450, SEQ ID NO: 41463, SEQ ID NO: 41478, SEQ ID NO: 41489, SEQ ID NO: 41495, SEQ ID NO: 41503, SEQ ID NO: 41513, SEQ ID NO: 41520, SEQ ID NO: 41535, SEQ ID NO: 41541, SEQ ID NO: 41545, SEQ ID NO: 41577, SEQ ID NO: 41588, SEQ ID NO: 41598, SEQ ID NO: 41605, SEQ ID NO: 41617, SEQ ID NO: 41620, SEQ ID NO: 41622, SEQ ID NO: 41627, SEQ ID NO: 41630, SEQ ID NO: 41638, SEQ ID NO: 41647, SEQ ID NO: 41673, SEQ ID NO: 41696, SEQ ID NO: 41703, SEQ ID NO: 41708, SEQ ID NO: 41728, SEQ ID NOs: 41732 to 41733, SEQ ID NO: 41749, SEQ ID NO: 41760, SEQ ID NO: 41766, SEQ ID NO: 41770, SEQ ID NO: 41788, SEQ ID NO: 41791, SEQ ID NO: 41809, SEQ ID NO: 41813, SEQ ID NO: 41817, SEQ ID NO: 41829, SEQ ID NOs: 41847 to 41848, SEQ ID NO: 41853, SEQ ID NO: 41859, SEQ ID NO: 41889, SEQ ID NO: 41894, SEQ ID NO: 41897, SEQ ID NO: 41909, SEQ ID NO: 41923, SEQ ID NO: 41934, SEQ ID NO: 41939, SEQ ID NOs: 41953 to 41954, SEQ ID NO: 41959, SEQ ID NO: 41967, SEQ ID NO: 41970, SEQ ID NO: 41976, SEQ ID NOs: 41984 to 41985, SEQ ID NO: 42007, SEQ ID NO: 42017, SEQ ID NO: 42034, SEQ ID NO: 42044, SEQ ID NO: 42046, SEQ ID NO: 42048, SEQ ID NO: 42056, SEQ ID NO: 42067, SEQ ID NO: 42080, SEQ ID NO: 42088, SEQ ID NO: 42091, SEQ ID NOs: 42119 to 42120, SEQ ID NO: 42129, SEQ ID NO: 42135, SEQ ID NOs: 42140 to 42141, SEQ ID NO: 42155, SEQ ID NO: 42158, SEQ ID NO: 42164, SEQ ID NO: 42170, SEQ ID NO: 42174, SEQ ID NO: 42186, SEQ ID NO: 42209, SEQ ID NO: 42218, SEQ ID NO: 42224, SEQ ID NO: 42229, SEQ ID NO: 42232, SEQ ID NO: 42235, SEQ ID NOs: 42237 to 42238, SEQ ID NO: 42265, SEQ ID NO: 42272, SEQ ID NO: 42278, SEQ ID NO: 42293, SEQ ID NO: 42314, SEQ ID NOs: 42336 to 42337, SEQ ID NO: 42339, SEQ ID NOs: 42372 to 42373, SEQ ID NO: 42376, SEQ ID NO: 42382, SEQ ID NO: 42386, SEQ ID NO: 42408, SEQ ID NO: 42414, SEQ ID NO: 42423, SEQ ID NO: 42429, SEQ ID NOs: 42447 to 42448, SEQ ID NO: 42461, SEQ ID NO: 42466, SEQ ID NO: 42475, SEQ ID NO: 42513, SEQ ID NO: 42540, SEQ ID NO: 42545, SEQ ID NO: 42550, SEQ ID NO: 42553, SEQ ID NOs: 42567 to 42568, SEQ ID NO: 42580, SEQ ID NO: 42585, SEQ ID NO: 42605, SEQ ID NO: 42612, SEQ ID NO: 42627, SEQ ID NO: 42675, SEQ ID NO: 42680, SEQ ID NO: 42685, SEQ ID NO: 42690, SEQ ID NO: 42702, SEQ ID NO: 42711, SEQ ID NO: 42719, SEQ ID NO: 42738, SEQ ID NO: 42743, SEQ ID NO: 42750, SEQ ID NO: 42755, SEQ ID NO: 42777, SEQ ID NO: 42788, SEQ ID NO: 42793, SEQ ID NO: 42851, SEQ ID NO: 42858, SEQ ID NO: 42866, SEQ ID NO: 42903, SEQ ID NO: 42927, SEQ ID NOs: 42936 to 42937, SEQ ID NOs: 42940 to 42941, SEQ ID NO: 42957, SEQ ID NO: 42962, SEQ ID NO: 42966, SEQ ID NO: 42968, SEQ ID NO: 42986, SEQ ID NO: 43002, SEQ ID NO: 43013, SEQ ID NO: 43037, SEQ ID NO: 43052, SEQ ID NOs: 43055 to 43056, SEQ ID NOs: 43063 to 43064, SEQ ID NO: 43096, SEQ ID NO: 43133, SEQ ID NO: 43138, SEQ ID NO: 43156, SEQ ID NO: 43161, SEQ ID NO: 43186, SEQ ID NO: 43199, SEQ ID NO: 43205, SEQ ID NO: 43245, SEQ ID NO: 43251, SEQ ID NO: 43275, SEQ ID NO: 43312, SEQ ID NO: 43327, SEQ ID NO: 43333, SEQ ID NO: 43339, SEQ ID NO: 43342, SEQ ID NO: 43348, SEQ ID NO: 43365, SEQ ID NO: 43371, SEQ ID NO: 43400, SEQ ID NO: 43440, SEQ ID NO: 43451, SEQ ID NO: 43462, SEQ ID NO: 43467, SEQ ID NO: 43487, SEQ ID NOs: 43498 to 43499, SEQ ID NO: 43507, SEQ ID NO: 43522, SEQ ID NO: 43529, SEQ ID NO: 43533, SEQ ID NO: 43545, SEQ ID NO: 43558, SEQ ID NO: 43560, SEQ ID NO: 43583, SEQ ID NO: 43597, SEQ ID NO: 43599, SEQ ID NO: 43610, SEQ ID NO: 43614, SEQ ID NO: 43627, SEQ ID NO: 43697, SEQ ID NO: 43715, SEQ ID NO: 43718, SEQ ID NO: 43768, SEQ ID NO: 43777, SEQ ID NOs: 43825 to 43826, SEQ ID NO: 43836, SEQ ID NO: 43840, SEQ ID NO: 43856, SEQ ID NO: 43860, SEQ ID NO: 43870, SEQ ID NO: 43878, SEQ ID NOs: 43881 to 43882, SEQ ID NO: 43905, SEQ ID NO: 43922, SEQ ID NO: 43930, SEQ ID NO: 43943, SEQ ID NO: 43953, SEQ ID NO: 43958, SEQ ID NO: 43979, SEQ ID NO: 43986, SEQ ID NO: 44002, SEQ ID NO: 44033, SEQ ID NO: 44037, SEQ ID NO: 44048, SEQ ID NO: 44050, SEQ ID NO: 44052, SEQ ID NOs: 44080 to 44081, SEQ ID NOs: 44093 to 44094, SEQ ID NOs: 44114 to 44115, SEQ ID NO: 44120, SEQ ID NO: 44142, SEQ ID NO: 44152, SEQ ID NOs: 44164 to 44166, SEQ ID NO: 44181, SEQ ID NO: 44222, SEQ ID NO: 44244, SEQ ID NO: 44246, SEQ ID NO: 44255, SEQ ID NO: 44261, SEQ ID NO: 44276, SEQ ID NOs: 44286 to 44287, SEQ ID NO: 44296, SEQ ID NO: 44315, SEQ ID NO: 44322, SEQ ID NO: 44324, SEQ ID NO: 44328, SEQ ID NO: 44332, SEQ ID NO: 44339, SEQ ID NO: 44401, SEQ ID NO: 44413, SEQ ID NO: 44435, SEQ ID NO: 44452, SEQ ID NO: 44454, SEQ ID NO: 44463, SEQ ID NO: 44467, SEQ ID NO: 44485, SEQ ID NO: 44504, SEQ ID NO: 44512, SEQ ID NO: 44523, SEQ ID NOs: 44526 to 44527, SEQ ID NO: 44536, SEQ ID NO: 44564, SEQ ID NO: 44605, SEQ ID NO: 44607, SEQ ID NO: 44612, SEQ ID NO: 44629, SEQ ID NOs: 44635 to 44636, SEQ ID NO: 44647, SEQ ID NO: 44650, SEQ ID NO: 44674, SEQ ID NO: 44691, SEQ ID NO: 44696, SEQ ID NO: 44702, SEQ ID NO: 44710, SEQ ID NO: 44713, SEQ ID NO: 44715, SEQ ID NO: 44722, SEQ ID NO: 44730, SEQ ID NO: 44733, SEQ ID NO: 44755, SEQ ID NO: 44770, SEQ ID NO: 44773, SEQ ID NO: 44781, SEQ ID NO: 44783, SEQ ID NO: 44797, SEQ ID NO: 44805, SEQ ID NO: 44822, SEQ ID NO: 44828, SEQ ID NO: 44830, SEQ ID NO: 44832, SEQ ID NO: 44850, SEQ ID NO: 44852, SEQ ID NO: 44854, SEQ ID NO: 44860, SEQ ID NO: 44866, SEQ ID NO: 44898, SEQ ID NO: 44900, SEQ ID NO: 44907, SEQ ID NO: 44933, SEQ ID NO: 44947, SEQ ID NO: 44986, SEQ ID NO: 45003, SEQ ID NO: 45007, SEQ ID NO: 45009, SEQ ID NO: 45012, SEQ ID NO: 45016, SEQ ID NO: 45018, SEQ ID NO: 45027, SEQ ID NO: 45031, SEQ ID NO: 45036, SEQ ID NO: 45044, SEQ ID NO: 45060, SEQ ID NO: 45071, SEQ ID NO: 45077, SEQ ID NO: 45095, SEQ ID NO: 45126, SEQ ID NO: 45132, SEQ ID NO: 45135, SEQ ID NO: 45139, SEQ ID NO: 45143, SEQ ID NO: 45159, SEQ ID NO: 45177, SEQ ID NO: 45197, SEQ ID NO: 45200, SEQ ID NO: 45219, SEQ ID NO: 45228, SEQ ID NO: 45323, SEQ ID NO: 45329, SEQ ID NO: 45351, SEQ ID NO: 45378, SEQ ID NO: 45380, SEQ ID NO: 45389, SEQ ID NO: 45413, SEQ ID NO: 45417, SEQ ID NO: 45438, SEQ ID NO: 45455, SEQ ID NO: 45457, SEQ ID NO: 45467, SEQ ID NO: 45478, SEQ ID NO: 45530, SEQ ID NO: 45562, SEQ ID NO: 45565, SEQ ID NOs: 45583 to 45584, SEQ ID NOs: 45595 to 45596, SEQ ID NO: 45608, SEQ ID NO: 45612, SEQ ID NO: 45616, SEQ ID NO: 45627, SEQ ID NO: 45653, SEQ ID NOs: 45666 to 45667, SEQ ID NO: 45680, SEQ ID NO: 45697, SEQ ID NO: 45705, SEQ ID NO: 45710, SEQ ID NO: 45722, SEQ ID NO: 45736, SEQ ID NO: 45742, SEQ ID NO: 45746, SEQ ID NO: 45765, SEQ ID NO: 45808, SEQ ID NO: 45830, SEQ ID NOs: 45840 to 45841, SEQ ID NO: 45896, SEQ ID NOs: 45904 to 45905, SEQ ID NO: 45913, SEQ ID NO: 45915, SEQ ID NOs: 45940 to 45943, SEQ ID NO: 45945, SEQ ID NOs: 45958 to 45959, SEQ ID NO: 45977, SEQ ID NO: 45983, SEQ ID NO: 45992, SEQ ID NO: 46006, SEQ ID NO: 46012, SEQ ID NO: 46018, SEQ ID NO: 46021, SEQ ID NOs: 46037 to 46038, SEQ ID NO: 46044, SEQ ID NO: 46058, SEQ ID NO: 46071, SEQ ID NO: 46082, SEQ ID NO: 46094, SEQ ID NO: 46096, SEQ ID NO: 46102, SEQ ID NOs: 46108 to 46109, SEQ ID NO: 46122, SEQ ID NO: 46125, SEQ ID NOs: 46133 to 46134, SEQ ID NO: 46146, SEQ ID NO: 46159, SEQ ID NO: 46177, SEQ ID NO: 46182, SEQ ID NO: 46188, SEQ ID NO: 46202, SEQ ID NO: 46219, SEQ ID NO: 46246, SEQ ID NO: 46249, SEQ ID NO: 46270, SEQ ID NO: 46279, SEQ ID NO: 46312, SEQ ID NO: 46339, SEQ ID NO: 46378, SEQ ID NO: 46433, SEQ ID NO: 46442, SEQ ID NO: 46446, SEQ ID NO: 46452, SEQ ID NO: 46454, SEQ ID NO: 46457, SEQ ID NO: 46478, SEQ ID NO: 46484, SEQ ID NO: 46486, SEQ ID NO: 46491, SEQ ID NO: 46506, SEQ ID NO: 46512, SEQ ID NO: 46517, SEQ ID NO: 46530, SEQ ID NO: 46534, SEQ ID NO: 46556, SEQ ID NO: 46560, SEQ ID NO: 46564, SEQ ID NO: 46596, SEQ ID NO: 46602, SEQ ID NO: 46616, SEQ ID NO: 46635, SEQ ID NO: 46656, SEQ ID NO: 46658, SEQ ID NO: 46666, SEQ ID NO: 46676, SEQ ID NO: 46679, SEQ ID NO: 46689, SEQ ID NO: 46705, SEQ ID NO: 46724, SEQ ID NO: 46738, SEQ ID NO: 46767, SEQ ID NO: 46770, SEQ ID NO: 46794, SEQ ID NO: 46810, SEQ ID NO: 46819, SEQ ID NO: 46824, SEQ ID NO: 46831, SEQ ID NO: 46849, SEQ ID NO: 46854, SEQ ID NO: 46870, SEQ ID NO: 46880, SEQ ID NO: 46916, SEQ ID NO: 46935, SEQ ID NO: 46939, SEQ ID NO: 46944, SEQ ID NO: 46958, SEQ ID NO: 46964, SEQ ID NO: 46967, SEQ ID NO: 46978, SEQ ID NO: 46987, SEQ ID NO: 46989, SEQ ID NO: 46991, SEQ ID NO: 46993, SEQ ID NO: 47007, SEQ ID NO: 47034, SEQ ID NO: 47037, SEQ ID NO: 47047, SEQ ID NO: 47057, SEQ ID NO: 47066, SEQ ID NO: 47096, SEQ ID NO: 47098, SEQ ID NO: 47119, SEQ ID NO: 47123, SEQ ID NO: 47137, SEQ ID NO: 47139, SEQ ID NO: 47143, SEQ ID NO: 47150, SEQ ID NO: 47158, SEQ ID NO: 47161, SEQ ID NO: 47170, SEQ ID NO: 47181, SEQ ID NO: 47197, SEQ ID NO: 47209, SEQ ID NO: 47254, SEQ ID NO: 47266, SEQ ID NO: 47272, SEQ ID NO: 47291, SEQ ID NO: 47298, SEQ ID NO: 47300, SEQ ID NO: 47319, SEQ ID NO: 47324, SEQ ID NOs: 47331 to 47332, SEQ ID NO: 47358, SEQ ID NO: 47361, SEQ ID NO: 47393, SEQ ID NO: 47414, SEQ ID NO: 47416, SEQ ID NO: 47422, SEQ ID NO: 47425, SEQ ID NOs: 47432 to 47433, SEQ ID NO: 47445, SEQ ID NO: 47453, SEQ ID NOs: 47460 to 47461, SEQ ID NO: 47477, SEQ ID NO: 47492, SEQ ID NO: 47507, SEQ ID NO: 47509, SEQ ID NO: 47516, SEQ ID NO: 47535, SEQ ID NOs: 47556 to 47557, SEQ ID NOs: 47578 to 47579, SEQ ID NOs: 47591 to 47592, SEQ ID NO: 47597, SEQ ID NO: 47600, SEQ ID NO: 47614, SEQ ID NO: 47626, SEQ ID NO: 47629, SEQ ID NO: 47637, SEQ ID NO: 47639, SEQ ID NO: 47649, SEQ ID NOs: 47689 to 47690, SEQ ID NO: 47713, SEQ ID NO: 47766, SEQ ID NOs: 47814 to 47815, SEQ ID NO: 47827, SEQ ID NO: 47834, SEQ ID NOs: 47852 to 47853, SEQ ID NO: 47855, SEQ ID NO: 47871, SEQ ID NOs: 47875 to 47876, SEQ ID NO: 47891, SEQ ID NO: 47896, SEQ ID NO: 47902, SEQ ID NO: 47923, SEQ ID NO: 47925, SEQ ID NO: 47927, SEQ ID NO: 47929, SEQ ID NO: 47932, SEQ ID NOs: 47962 to 47964, SEQ ID NO: 47972, SEQ ID NO: 47999, SEQ ID NO: 48008, SEQ ID NO: 48028, SEQ ID NOs: 48034 to 48035, SEQ ID NO: 48038, SEQ ID NO: 48056, SEQ ID NO: 48061, SEQ ID NO: 48066, SEQ ID NO: 48118, SEQ ID NO: 48120, SEQ ID NO: 48129, SEQ ID NO: 48140, SEQ ID NO: 48148, SEQ ID NO: 48153, SEQ ID NOs: 48159 to 48160, SEQ ID NO: 48163, SEQ ID NO: 48167, SEQ ID NO: 48178, SEQ ID NO: 48180, SEQ ID NO: 48186, SEQ ID NO: 48218, SEQ ID NO: 48220, SEQ ID NO: 48263, SEQ ID NO: 48286, SEQ ID NO: 48300, SEQ ID NO: 48307, SEQ ID NO: 48315, SEQ ID NO: 48321, SEQ ID NO: 48338, SEQ ID NO: 48341, SEQ ID NO: 48343, SEQ ID NO: 48358, SEQ ID NO: 48362, SEQ ID NO: 48366, SEQ ID NO: 48368, SEQ ID NO: 48418, SEQ ID NO: 48431, SEQ ID NO: 48436, SEQ ID NOs: 48438 to 48439, SEQ ID NOs: 48443 to 48444, SEQ ID NO: 48450, SEQ ID NOs: 48452 to 48453, SEQ ID NO: 48458, SEQ ID NOs: 48461 to 48462, SEQ ID NO: 48507, SEQ ID NO: 48516, SEQ ID NO: 48527, SEQ ID NO: 48537, SEQ ID NO: 48548, SEQ ID NO: 48567, SEQ ID NO: 48574, SEQ ID NO: 48576, SEQ ID NO: 48578, SEQ ID NO: 48594, SEQ ID NO: 48599, SEQ ID NO: 48612, SEQ ID NO: 48614, SEQ ID NO: 48623, SEQ ID NO: 48626, SEQ ID NO: 48630, SEQ ID NO: 48642, SEQ ID NO: 48648, SEQ ID NO: 48656, SEQ ID NOs: 48704 to 48705, SEQ ID NO: 48708, SEQ ID NO: 48739, SEQ ID NO: 48749, SEQ ID NO: 48752, SEQ ID NO: 48754, SEQ ID NO: 48756, SEQ ID NO: 48802, SEQ ID NO: 48832, SEQ ID NO: 48845, SEQ ID NO: 48850, SEQ ID NO: 48852, SEQ ID NO: 48856, SEQ ID NO: 48870, SEQ ID NO: 48888, SEQ ID NO: 48902, SEQ ID NO: 48904, SEQ ID NOs: 48912 to 48913, SEQ ID NO: 48921, SEQ ID NO: 48970, SEQ ID NO: 48974, SEQ ID NO: 48993, SEQ ID NO: 48997, SEQ ID NO: 49004, SEQ ID NO: 49019, SEQ ID NO: 49025, SEQ ID NOs: 49045 to 49046, SEQ ID NO: 49052, SEQ ID NO: 49083, SEQ ID NO: 49086, SEQ ID NOs: 49091 to 49092, SEQ ID NO: 49102, SEQ ID NO: 49106, SEQ ID NO: 49111, SEQ ID NO: 49127, SEQ ID NO: 49152, SEQ ID NO: 49159, SEQ ID NO: 49173, SEQ ID NO: 49197, SEQ ID NO: 49201, SEQ ID NO: 49203, SEQ ID NO: 49207, SEQ ID NO: 49220, SEQ ID NO: 49227, SEQ ID NO: 49230, SEQ ID NO: 49234, SEQ ID NO: 49242, SEQ ID NO: 49256, SEQ ID NO: 49263, SEQ ID NOs: 49273 to 49274, SEQ ID NO: 49278, SEQ ID NO: 49280, SEQ ID NO: 49288, SEQ ID NO: 49290, SEQ ID NOs: 49294 to 49295, SEQ ID NO: 49326, SEQ ID NO: 49362, SEQ ID NOs: 49384 to 49385, SEQ ID NO: 49387, SEQ ID NO: 49393, SEQ ID NO: 49395, SEQ ID NOs: 49427 to 49428, SEQ ID NO: 49444, SEQ ID NO: 49458, SEQ ID NO: 49483, SEQ ID NO: 49487, SEQ ID NO: 49497, SEQ ID NO: 49501, SEQ ID NO: 49517, SEQ ID NO: 49525, SEQ ID NO: 49535, SEQ ID NO: 49537, SEQ ID NO: 49544, SEQ ID NO: 49557, SEQ ID NO: 49569, SEQ ID NO: 49572, SEQ ID NO: 49587, SEQ ID NO: 49594, SEQ ID NO: 49596, SEQ ID NO: 49598, SEQ ID NO: 49606, SEQ ID NO: 49617, SEQ ID NO: 49629, SEQ ID NO: 49646, SEQ ID NO: 49658, SEQ ID NO: 49693, SEQ ID NOs: 49702 to 49703, SEQ ID NO: 49710, SEQ ID NO: 49712, SEQ ID NO: 49719, SEQ ID NO: 49727, SEQ ID NO: 49737, SEQ ID NO: 49740, SEQ ID NO: 49743, SEQ ID NO: 49767, SEQ ID NO: 49778, SEQ ID NO: 49788, SEQ ID NO: 49811, SEQ ID NO: 49848, SEQ ID NO: 49860, SEQ ID NO: 49888, SEQ ID NO: 49908, SEQ ID NO: 49973, SEQ ID NO: 49977, SEQ ID NO: 49980, SEQ ID NOs: 49996 to 49997, SEQ ID NO: 50000, SEQ ID NO: 50012, SEQ ID NOs: 50017 to 50018, SEQ ID NO: 50051, SEQ ID NO: 50056, SEQ ID NO: 50062, SEQ ID NO: 50090, SEQ ID NO: 50093, SEQ ID NO: 50107, SEQ ID NO: 50129, SEQ ID NO: 50132, SEQ ID NO: 50138, SEQ ID NO: 50144, SEQ ID NO: 50167, SEQ ID NO: 50191, SEQ ID NO: 50194, SEQ ID NO: 50196, SEQ ID NO: 50228, SEQ ID NO: 50239, SEQ ID NO: 50263, SEQ ID NO: 50271, SEQ ID NO: 50297, SEQ ID NO: 50305, SEQ ID NO: 50320, SEQ ID NO: 50322, SEQ ID NO: 50326, SEQ ID NO: 50334, SEQ ID NO: 50349, SEQ ID NO: 50375, SEQ ID NO: 50394, SEQ ID NO: 50401, SEQ ID NO: 50414, SEQ ID NO: 50421, SEQ ID NO: 50423, SEQ ID NO: 50435, SEQ ID NOs: 50440 to 50441, SEQ ID NO: 50443, SEQ ID NO: 50510, SEQ ID NO: 50556, SEQ ID NO: 50564, SEQ ID NO: 50591, SEQ ID NO: 50605, SEQ ID NO: 50607, SEQ ID NO: 50611, SEQ ID NO: 50622, SEQ ID NO: 50625, SEQ ID NO: 50627, SEQ ID NO: 50632, SEQ ID NO: 50644, SEQ ID NOs: 50652 to 50653, SEQ ID NOs: 50668 to 50669, SEQ ID NO: 50677, SEQ ID NO: 50696, SEQ ID NO: 50699, SEQ ID NO: 50705, SEQ ID NO: 50709, SEQ ID NO: 50711, SEQ ID NO: 50729, SEQ ID NO: 50731, SEQ ID NO: 50741, SEQ ID NO: 50743, SEQ ID NO: 50748, SEQ ID NO: 50762, SEQ ID NO: 50765, SEQ ID NO: 50767, SEQ ID NO: 50800, SEQ ID NO: 50803, SEQ ID NO: 50807, SEQ ID NO: 50841, SEQ ID NO: 50865, SEQ ID NO: 50872, SEQ ID NO: 50905, SEQ ID NOs: 50955 to 50956, SEQ ID NOs: 50975 to 50977, SEQ ID NO: 50986, SEQ ID NO: 51021, SEQ ID NOs: 51039 to 51040, SEQ ID NOs: 51066 to 51068, SEQ ID NO: 51084, SEQ ID NOs: 51099 to 51100, SEQ ID NOs: 51165 to 51167, SEQ ID NO: 51169, SEQ ID NO: 51190, SEQ ID NOs: 51194 to 51198, SEQ ID NOs: 51267 to 51270, SEQ ID NOs: 51281 to 51282, SEQ ID NO: 51324, SEQ ID NO: 51349, SEQ ID NO: 51379, SEQ ID NOs: 51413 to 51415, SEQ ID NOs: 51420 to 51421, or SEQ ID NOs: 51434 to 60455.

In some embodiments, the amino acid sequence for a MEW class I peptide vaccine for the MAGA4 protein comprises one or more of the SEQ ID NO: 41352, SEQ ID NOs: 41357 to 41358, SEQ ID NO: 41377, SEQ ID NO: 41770, SEQ ID NO: 49071, SEQ ID NO: 50632, SEQ ID NO: 50729, SEQ ID NO: 55758, and SEQ ID NOs: 60456 to 60527. In some embodiments, any one of the peptides in the MAGA4 vaccine comprise an amino acid sequence 80, 81, 82, 83, 84, 85, 86, 87, 88, 89, 90, 91, 92, 93, 94, 95, 96, 97, 98 or 99% identical to SEQ ID NO: 41352, SEQ ID NOs: 41357 to 41358, SEQ ID NO: 41377, SEQ ID NO: 41770, SEQ ID NO: 49071, SEQ ID NO: 50632, SEQ ID NO: 50729, SEQ ID NO: 55758, or SEQ ID NOs: 60456 to 60527.

In some embodiments, the amino acid sequence for a MEW class I peptide vaccine for the MAGA4 protein comprises one or more of the SEQ ID NO: 41345, SEQ ID NO: 41347, SEQ ID NO: 41352, SEQ ID NOs: 41357 to 41358, SEQ ID NO: 41366, SEQ ID NO: 41377, SEQ ID NO: 41382, SEQ ID NO: 41392, SEQ ID NO: 41396, SEQ ID NO: 41398, SEQ ID NO: 41406, SEQ ID NO: 41411, SEQ ID NO: 41414, SEQ ID NO: 41433, SEQ ID NO: 41436, SEQ ID NO: 41445, SEQ ID NO: 41449, SEQ ID NO: 41455, SEQ ID NO: 41478, SEQ ID NO: 41487, SEQ ID NOs: 41495 to 41496, SEQ ID NO: 41503, SEQ ID NO: 41515, SEQ ID NO: 41520, SEQ ID NO: 41529, SEQ ID NO: 41549, SEQ ID NO: 41553, SEQ ID NO: 41562, SEQ ID NO: 41569, SEQ ID NO: 41574, SEQ ID NO: 41576, SEQ ID NO: 41579, SEQ ID NOs: 41587 to 41588, SEQ ID NO: 41605, SEQ ID NO: 41617, SEQ ID NO: 41620, SEQ ID NO: 41634, SEQ ID NO: 41650, SEQ ID NO: 41665, SEQ ID NO: 41670, SEQ ID NO: 41672, SEQ ID NO: 41696, SEQ ID NO: 41703, SEQ ID NO: 41709, SEQ ID NO: 41725, SEQ ID NOs: 41732 to 41733, SEQ ID NO: 41748, SEQ ID NO: 41760, SEQ ID NO: 41766, SEQ ID NO: 41768, SEQ ID NO: 41770, SEQ ID NO: 41779, SEQ ID NO: 41791, SEQ ID NO: 41797, SEQ ID NO: 41813, SEQ ID NO: 41819, SEQ ID NO: 41825, SEQ ID NO: 41829, SEQ ID NOs: 41846 to 41847, SEQ ID NO: 41853, SEQ ID NO: 41876, SEQ ID NO: 41889, SEQ ID NO: 41892, SEQ ID NO: 41897, SEQ ID NOs: 41906 to 41907, SEQ ID NO: 41912, SEQ ID NO: 41924, SEQ ID NO: 41940, SEQ ID NO: 41953, SEQ ID NO: 41956, SEQ ID NO: 41967, SEQ ID NO: 41970, SEQ ID NO: 41976, SEQ ID NO: 41985, SEQ ID NO: 41990, SEQ ID NO: 42014, SEQ ID NO: 42017, SEQ ID NO: 42026, SEQ ID NO: 42034, SEQ ID NO: 42037, SEQ ID NO: 42046, SEQ ID NO: 42048, SEQ ID NOs: 42056 to 42057, SEQ ID NO: 42080, SEQ ID NO: 42088, SEQ ID NO: 42091, SEQ ID NO: 42102, SEQ ID NO: 42106, SEQ ID NO: 42115, SEQ ID NO: 42120, SEQ ID NO: 42129, SEQ ID NO: 42135, SEQ ID NO: 42138, SEQ ID NO: 42151, SEQ ID NO: 42158, SEQ ID NOs: 42163 to 42164, SEQ ID NOs: 42167 to 42168, SEQ ID NO: 42170, SEQ ID NO: 42186, SEQ ID NO: 42192, SEQ ID NO: 42195, SEQ ID NO: 42198, SEQ ID NO: 42204, SEQ ID NO: 42209, SEQ ID NO: 42218, SEQ ID NO: 42221, SEQ ID NO: 42224, SEQ ID NO: 42229, SEQ ID NO: 42240, SEQ ID NO: 42263, SEQ ID NO: 42265, SEQ ID NO: 42270, SEQ ID NO: 42316, SEQ ID NOs: 42336 to 42337, SEQ ID NO: 42339, SEQ ID NO: 42351, SEQ ID NO: 42354, SEQ ID NO: 42372, SEQ ID NO: 42378, SEQ ID NOs: 42385 to 42386, SEQ ID NO: 42394, SEQ ID NO: 42405, SEQ ID NO: 42409, SEQ ID NO: 42417, SEQ ID NO: 42423, SEQ ID NO: 42439, SEQ ID NO: 42447, SEQ ID NO: 42453, SEQ ID NO: 42458, SEQ ID NOs: 42460 to 42461, SEQ ID NO: 42466, SEQ ID NOs: 42472 to 42473, SEQ ID NOs: 42519 to 42520, SEQ ID NO: 42525, SEQ ID NO: 42528, SEQ ID NO: 42540, SEQ ID NO: 42545, SEQ ID NO: 42550, SEQ ID NOs: 42563 to 42564, SEQ ID NO: 42580, SEQ ID NO: 42605, SEQ ID NO: 42609, SEQ ID NOs: 42612 to 42613, SEQ ID NO: 42615, SEQ ID NO: 42628, SEQ ID NO: 42637, SEQ ID NO: 42648, SEQ ID NO: 42653, SEQ ID NO: 42675, SEQ ID NO: 42680, SEQ ID NO: 42685, SEQ ID NO: 42696, SEQ ID NO: 42703, SEQ ID NO: 42719, SEQ ID NO: 42735, SEQ ID NO: 42743, SEQ ID NO: 42748, SEQ ID NO: 42750, SEQ ID NO: 42768, SEQ ID NO: 42812, SEQ ID NO: 42814, SEQ ID NO: 42822, SEQ ID NO:

42827, SEQ ID NO: 42831, SEQ ID NO: 42846, SEQ ID NO: 42850, SEQ ID NO: 42872, SEQ ID NO: 42886, SEQ ID NO: 42911, SEQ ID NO: 42914, SEQ ID NO: 42923, SEQ ID NO: 42927, SEQ ID NOs: 42957 to 42958, SEQ ID NO: 42962, SEQ ID NO: 42971, SEQ ID NOs: 42997 to 42998, SEQ ID NO: 43002, SEQ ID NO: 43008, SEQ ID NO: 43035, SEQ ID NO: 43046, SEQ ID NO: 43048, SEQ ID NO: 43064, SEQ ID NO: 43083, SEQ ID NO: 43091, SEQ ID NO: 43093, SEQ ID NO: 43148, SEQ ID NO: 43160, SEQ ID NO: 43170, SEQ ID NO: 43175, SEQ ID NO: 43180, SEQ ID NO: 43186, SEQ ID NO: 43193, SEQ ID NO: 43196, SEQ ID NOs: 43231 to 43232, SEQ ID NO: 43238, SEQ ID NO: 43242, SEQ ID NO: 43248, SEQ ID NO: 43253, SEQ ID NO: 43258, SEQ ID NO: 43267, SEQ ID NO: 43274, SEQ ID NO: 43280, SEQ ID NO: 43285, SEQ ID NO: 43295, SEQ ID NO: 43308, SEQ ID NO: 43311, SEQ ID NO: 43329, SEQ ID NO: 43333, SEQ ID NOs: 43339 to 43340, SEQ ID NO: 43362, SEQ ID NO: 43365, SEQ ID NO: 43384, SEQ ID NO: 43389, SEQ ID NO: 43395, SEQ ID NO: 43401, SEQ ID NO: 43429, SEQ ID NO: 43432, SEQ ID NO: 43440, SEQ ID NOs: 43451 to 43453, SEQ ID NO: 43462, SEQ ID NO: 43464, SEQ ID NO: 43467, SEQ ID NO: 43479, SEQ ID NO: 43482, SEQ ID NO: 43496, SEQ ID NO: 43511, SEQ ID NO: 43513, SEQ ID NO: 43517, SEQ ID NO: 43545, SEQ ID NO: 43564, SEQ ID NO: 43573, SEQ ID NO: 43585, SEQ ID NO: 43587, SEQ ID NO: 43591, SEQ ID NO: 43611, SEQ ID NO: 43632, SEQ ID NO: 43636, SEQ ID NO: 43641, SEQ ID NO: 43643, SEQ ID NO: 43651, SEQ ID NO: 43669, SEQ ID NO: 43688, SEQ ID NO: 43696, SEQ ID NO: 43700, SEQ ID NO: 43703, SEQ ID NO: 43707, SEQ ID NO: 43718, SEQ ID NO: 43760, SEQ ID NO: 43763, SEQ ID NO: 43768, SEQ ID NO: 43777, SEQ ID NO: 43780, SEQ ID NO: 43787, SEQ ID NO: 43801, SEQ ID NO: 43808, SEQ ID NO: 43810, SEQ ID NO: 43825, SEQ ID NO: 43827, SEQ ID NO: 43836, SEQ ID NO: 43860, SEQ ID NO: 43867, SEQ ID NOs: 43881 to 43882, SEQ ID NO: 43884, SEQ ID NO: 43887, SEQ ID NOs: 43898 to 43899, SEQ ID NO: 43905, SEQ ID NO: 43915, SEQ ID NO: 43924, SEQ ID NO: 43932, SEQ ID NO: 43958, SEQ ID NO: 43971, SEQ ID NO: 43974, SEQ ID NO: 43978, SEQ ID NOs: 43982 to 43984, SEQ ID NOs: 43986 to 43987, SEQ ID NO: 43993, SEQ ID NO: 43995, SEQ ID NO: 44012, SEQ ID NO: 44035, SEQ ID NO: 44037, SEQ ID NO: 44048, SEQ ID NO: 44050, SEQ ID NO: 44052, SEQ ID NO: 44055, SEQ ID NO: 44063, SEQ ID NO: 44073, SEQ ID NO: 44080, SEQ ID NO: 44085, SEQ ID NO: 44087, SEQ ID NO: 44089, SEQ ID NO: 44112, SEQ ID NO: 44117, SEQ ID NO: 44123, SEQ ID NOs: 44151 to 44152, SEQ ID NO: 44160, SEQ ID NO: 44181, SEQ ID NO: 44207, SEQ ID NO: 44210, SEQ ID NO: 44244, SEQ ID NO: 44246, SEQ ID NO: 44254, SEQ ID NO: 44263, SEQ ID NOs: 44298 to 44299, SEQ ID NO: 44309, SEQ ID NO: 44324, SEQ ID NO: 44328, SEQ ID NO: 44342, SEQ ID NO: 44345, SEQ ID NO: 44359, SEQ ID NO: 44361, SEQ ID NO: 44383, SEQ ID NO: 44401, SEQ ID NO: 44422, SEQ ID NO: 44440, SEQ ID NO: 44452, SEQ ID NO: 44454, SEQ ID NO: 44456, SEQ ID NO: 44463, SEQ ID NO: 44467, SEQ ID NO: 44485, SEQ ID NO: 44512, SEQ ID NO: 44523, SEQ ID NO: 44545, SEQ ID NO: 44552, SEQ ID NO: 44564, SEQ ID NOs: 44566 to 44567, SEQ ID NOs: 44589 to 44591, SEQ ID NO: 44615, SEQ ID NO: 44623, SEQ ID NO: 44631, SEQ ID NO: 44636, SEQ ID NO: 44649, SEQ ID NO: 44654, SEQ ID NO: 44691, SEQ ID NO: 44713, SEQ ID NO: 44722, SEQ ID NO: 44730, SEQ ID NO: 44754, SEQ ID NO: 44756, SEQ ID NOs: 44762 to 44763, SEQ ID NO: 44773, SEQ ID NO: 44781, SEQ ID NO: 44794, SEQ ID NO: 44850, SEQ ID NOs: 44873 to 44875, SEQ ID NO: 44877, SEQ ID NO: 44884, SEQ ID NO: 44908, SEQ ID NO: 44913, SEQ ID NO: 44940, SEQ ID NO: 44955, SEQ ID NO: 44964, SEQ ID NO: 44971, SEQ ID NO: 44976, SEQ ID NO: 45000, SEQ ID NO: 45027, SEQ ID NO: 45035, SEQ ID NO: 45060, SEQ ID NO: 45062, SEQ ID NO: 45095, SEQ ID NO: 45123, SEQ ID NOs: 45126 to 45127, SEQ ID NO: 45132, SEQ ID NO: 45135, SEQ ID NOs: 45138 to 45139, SEQ ID NO: 45193, SEQ ID NO: 45197, SEQ ID NO: 45200, SEQ ID NO: 45223, SEQ ID NO: 45225, SEQ ID NO: 45244, SEQ ID NO: 45262, SEQ ID NO: 45273, SEQ ID NO: 45292, SEQ ID NO: 45302, SEQ ID NO: 45306, SEQ ID NO: 45314, SEQ ID NO: 45380, SEQ ID NO: 45385, SEQ ID NO: 45389, SEQ ID NO: 45398, SEQ ID NO: 45409, SEQ ID NO: 45438, SEQ ID NO: 45444, SEQ ID NOs: 45450 to 45451, SEQ ID NO: 45478, SEQ ID NO: 45480, SEQ ID NO: 45485, SEQ ID NO: 45490, SEQ ID NO: 45510, SEQ ID NO: 45514, SEQ ID NOs: 45519 to 45520, SEQ ID NO: 45530, SEQ ID NO: 45541, SEQ ID NO: 45552, SEQ ID NO: 45556, SEQ ID NOs: 45562 to 45563, SEQ ID NO: 45568, SEQ ID NO: 45577, SEQ ID NOs: 45580 to 45581, SEQ ID NO: 45584, SEQ ID NO: 45588, SEQ ID NO: 45595, SEQ ID NO: 45599, SEQ ID NO: 45632, SEQ ID NO: 45653, SEQ ID NOs: 45666 to 45667, SEQ ID NO: 45675, SEQ ID NO: 45680, SEQ ID NO: 45687, SEQ ID NO: 45697, SEQ ID NOs: 45699 to 45700, SEQ ID NO: 45712, SEQ ID NO: 45714, SEQ ID NO: 45723, SEQ ID NO: 45746, SEQ ID NO: 45765, SEQ ID NO: 45787, SEQ ID NO: 45793, SEQ ID NO: 45818, SEQ ID NO: 45826, SEQ ID NOs: 45829 to 45830, SEQ ID NO: 45835, SEQ ID NO: 45837, SEQ ID NO: 45846, SEQ ID NO: 45859, SEQ ID NO: 45885, SEQ ID NO: 45894, SEQ ID NO: 45904, SEQ ID NO: 45915, SEQ ID NO: 45930, SEQ ID NO: 45938, SEQ ID NO: 45959, SEQ ID NO: 45983, SEQ ID NO: 46006, SEQ ID NO: 46011, SEQ ID NO: 46014, SEQ ID NO: 46044, SEQ ID NO: 46049, SEQ ID NO: 46054, SEQ ID NO: 46058, SEQ ID NO: 46063, SEQ ID NO: 46071, SEQ ID NO: 46077, SEQ ID NO: 46096, SEQ ID NO: 46103, SEQ ID NO: 46108, SEQ ID NO: 46110, SEQ ID NO: 46125, SEQ ID NO: 46133, SEQ ID NOs: 46170 to 46171, SEQ ID NO: 46195, SEQ ID NO: 46208, SEQ ID NO: 46212, SEQ ID NO: 46219, SEQ ID NO: 46226, SEQ ID NO: 46234, SEQ ID NO: 46236, SEQ ID NO: 46261, SEQ ID NO: 46270, SEQ ID NO: 46273, SEQ ID NO: 46275, SEQ ID NO: 46339, SEQ ID NO: 46364, SEQ ID NO: 46376, SEQ ID NOs: 46400 to 46401, SEQ ID NOs: 46421 to 46422, SEQ ID NO: 46433, SEQ ID NOs: 46442 to 46443, SEQ ID NO: 46446, SEQ ID NOs: 46452 to 46454, SEQ ID NO: 46457, SEQ ID NO: 46459, SEQ ID NO: 46462, SEQ ID NO: 46465, SEQ ID NO: 46478, SEQ ID NO: 46484, SEQ ID NO: 46489, SEQ ID NO: 46499, SEQ ID NO: 46512, SEQ ID NO: 46521, SEQ ID NO: 46530, SEQ ID NO: 46536, SEQ ID NO: 46560, SEQ ID NO: 46564, SEQ ID NO: 46570, SEQ ID NO: 46572, SEQ ID NO: 46575, SEQ ID NO: 46579, SEQ ID NO: 46586, SEQ ID NO: 46602, SEQ ID NO: 46616, SEQ ID NO: 46621, SEQ ID NO: 46628, SEQ ID NO: 46637, SEQ ID NO: 46642, SEQ ID NO: 46648, SEQ ID NO: 46652, SEQ ID NO: 46655, SEQ ID NO: 46660, SEQ ID NO: 46663, SEQ ID NOs: 46665 to 46666, SEQ ID NO: 46676, SEQ ID NOs: 46678 to 46679, SEQ ID NO: 46682, SEQ ID NO: 46685, SEQ ID NO: 46689, SEQ ID NO: 46713, SEQ ID NO: 46715, SEQ ID NO: 46736, SEQ ID NO: 46739, SEQ ID NO: 46770, SEQ ID NO: 46777, SEQ ID NO: 46800, SEQ ID NOs: 46823 to 46825, SEQ ID NO: 46831, SEQ ID NO: 46872, SEQ ID NO: 46880, SEQ ID

NO: 46897, SEQ ID NO: 46916, SEQ ID NO: 46928, SEQ ID NO: 46937, SEQ ID NO: 46950, SEQ ID NO: 46978, SEQ ID NO: 46981, SEQ ID NO: 46983, SEQ ID NO: 46989, SEQ ID NO: 46991, SEQ ID NO: 46993, SEQ ID NO: 47003, SEQ ID NO: 47006, SEQ ID NO: 47017, SEQ ID NO: 47028, SEQ ID NO: 47045, SEQ ID NO: 47047, SEQ ID NO: 47057, SEQ ID NOs: 47079 to 47080, SEQ ID NO: 47082, SEQ ID NO: 47114, SEQ ID NO: 47119, SEQ ID NO: 47123, SEQ ID NOs: 47137 to 47139, SEQ ID NO: 47151, SEQ ID NO: 47158, SEQ ID NO: 47167, SEQ ID NO: 47172, SEQ ID NO: 47186, SEQ ID NO: 47191, SEQ ID NO: 47206, SEQ ID NO: 47224, SEQ ID NO: 47298, SEQ ID NO: 47316, SEQ ID NO: 47324, SEQ ID NOs: 47331 to 47332, SEQ ID NO: 47335, SEQ ID NO: 47356, SEQ ID NO: 47358, SEQ ID NOs: 47360 to 47361, SEQ ID NOs: 47377 to 47378, SEQ ID NO: 47381, SEQ ID NO: 47405, SEQ ID NO: 47412, SEQ ID NO: 47416, SEQ ID NO: 47422, SEQ ID NO: 47425, SEQ ID NO: 47427, SEQ ID NOs: 47432 to 47433, SEQ ID NO: 47445, SEQ ID NO: 47451, SEQ ID NO: 47460, SEQ ID NO: 47482, SEQ ID NO: 47491, SEQ ID NO: 47509, SEQ ID NO: 47516, SEQ ID NOs: 47533 to 47535, SEQ ID NOs: 47538 to 47539, SEQ ID NO: 47555, SEQ ID NO: 47561, SEQ ID NOs: 47575 to 47576, SEQ ID NO: 47582, SEQ ID NO: 47592, SEQ ID NO: 47614, SEQ ID NO: 47625, SEQ ID NO: 47630, SEQ ID NO: 47637, SEQ ID NO: 47643, SEQ ID NO: 47654, SEQ ID NO: 47673, SEQ ID NO: 47689, SEQ ID NO: 47698, SEQ ID NO: 47701, SEQ ID NO: 47727, SEQ ID NO: 47749, SEQ ID NOs: 47759 to 47760, SEQ ID NO: 47767, SEQ ID NO: 47773, SEQ ID NO: 47782, SEQ ID NO: 47790, SEQ ID NO: 47793, SEQ ID NO: 47799, SEQ ID NO: 47806, SEQ ID NO: 47809, SEQ ID NO: 47834, SEQ ID NO: 47840, SEQ ID NO: 47844, SEQ ID NO: 47848, SEQ ID NO: 47855, SEQ ID NO: 47867, SEQ ID NO: 47890, SEQ ID NO: 47895, SEQ ID NO: 47899, SEQ ID NO: 47902, SEQ ID NO: 47923, SEQ ID NO: 47927, SEQ ID NOs: 47959 to 47960, SEQ ID NO: 47964, SEQ ID NO: 47979, SEQ ID NO: 47984, SEQ ID NO: 47986, SEQ ID NOs: 48030 to 48031, SEQ ID NO: 48034, SEQ ID NO: 48059, SEQ ID NO: 48093, SEQ ID NO: 48107, SEQ ID NO: 48113, SEQ ID NO: 48118, SEQ ID NO: 48121, SEQ ID NO: 48129, SEQ ID NOs: 48138 to 48139, SEQ ID NO: 48144, SEQ ID NO: 48158, SEQ ID NO: 48160, SEQ ID NO: 48162, SEQ ID NO: 48175, SEQ ID NO: 48186, SEQ ID NO: 48203, SEQ ID NO: 48210, SEQ ID NO: 48213, SEQ ID NO: 48220, SEQ ID NO: 48224, SEQ ID NO: 48229, SEQ ID NO: 48258, SEQ ID NO: 48266, SEQ ID NO: 48273, SEQ ID NO: 48280, SEQ ID NO: 48286, SEQ ID NO: 48295, SEQ ID NOs: 48300 to 48301, SEQ ID NOs: 48306 to 48307, SEQ ID NO: 48315, SEQ ID NO: 48347, SEQ ID NO: 48353, SEQ ID NO: 48358, SEQ ID NO: 48366, SEQ ID NO: 48371, SEQ ID NO: 48379, SEQ ID NO: 48387, SEQ ID NO: 48400, SEQ ID NO: 48415, SEQ ID NOs: 48418 to 48419, SEQ ID NO: 48436, SEQ ID NOs: 48438 to 48440, SEQ ID NO: 48443, SEQ ID NO: 48452, SEQ ID NOs: 48461 to 48462, SEQ ID NO: 48466, SEQ ID NO: 48469, SEQ ID NO: 48520, SEQ ID NO: 48537, SEQ ID NO: 48545, SEQ ID NO: 48574, SEQ ID NOs: 48576 to 48578, SEQ ID NO: 48594, SEQ ID NO: 48599, SEQ ID NO: 48614, SEQ ID NO: 48627, SEQ ID NO: 48642, SEQ ID NO: 48648, SEQ ID NO: 48654, SEQ ID NO: 48656, SEQ ID NO: 48666, SEQ ID NOs: 48669 to 48670, SEQ ID NO: 48674, SEQ ID NOs: 48680 to 48681, SEQ ID NO: 48684, SEQ ID NO: 48686, SEQ ID NO: 48692, SEQ ID NO: 48701, SEQ ID NO: 48705, SEQ ID NO: 48714, SEQ ID NO: 48717, SEQ ID NO: 48735, SEQ ID NO: 48738, SEQ ID NO: 48749, SEQ ID NO: 48751, SEQ ID NO: 48764, SEQ ID NO: 48769, SEQ ID NO: 48793, SEQ ID NO: 48796, SEQ ID NOs: 48799 to 48800, SEQ ID NOs: 48802 to 48803, SEQ ID NO: 48818, SEQ ID NO: 48832, SEQ ID NO: 48834, SEQ ID NO: 48838, SEQ ID NO: 48845, SEQ ID NO: 48856, SEQ ID NO: 48877, SEQ ID NO: 48884, SEQ ID NO: 48903, SEQ ID NO: 48936, SEQ ID NO: 48947, SEQ ID NOs: 48968 to 48970, SEQ ID NO: 48974, SEQ ID NOs: 48981 to 48982, SEQ ID NO: 48997, SEQ ID NOs: 49013 to 49014, SEQ ID NOs: 49019 to 49020, SEQ ID NO: 49031, SEQ ID NO: 49033, SEQ ID NO: 49043, SEQ ID NO: 49052, SEQ ID NOs: 49061 to 49062, SEQ ID NO: 49068, SEQ ID NO: 49071, SEQ ID NO: 49086, SEQ ID NO: 49102, SEQ ID NO: 49111, SEQ ID NO: 49156, SEQ ID NO: 49164, SEQ ID NO: 49173, SEQ ID NO: 49176, SEQ ID NO: 49183, SEQ ID NO: 49185, SEQ ID NOs: 49200 to 49201, SEQ ID NO: 49209, SEQ ID NO: 49220, SEQ ID NO: 49247, SEQ ID NO: 49251, SEQ ID NO: 49256, SEQ ID NO: 49263, SEQ ID NOs: 49273 to 49274, SEQ ID NOs: 49280 to 49281, SEQ ID NO: 49291, SEQ ID NOs: 49294 to 49295, SEQ ID NO: 49298, SEQ ID NO: 49309, SEQ ID NO: 49319, SEQ ID NO: 49326, SEQ ID NO: 49330, SEQ ID NO: 49340, SEQ ID NOs: 49351 to 49352, SEQ ID NO: 49360, SEQ ID NOs: 49376 to 49377, SEQ ID NO: 49384, SEQ ID NO: 49393, SEQ ID NO: 49395, SEQ ID NO: 49399, SEQ ID NO: 49406, SEQ ID NO: 49411, SEQ ID NOs: 49443 to 49444, SEQ ID NO: 49452, SEQ ID NO: 49462, SEQ ID NO: 49474, SEQ ID NO: 49487, SEQ ID NO: 49499, SEQ ID NO: 49525, SEQ ID NO: 49537, SEQ ID NO: 49540, SEQ ID NO: 49557, SEQ ID NO: 49572, SEQ ID NO: 49584, SEQ ID NO: 49597, SEQ ID NO: 49626, SEQ ID NO: 49630, SEQ ID NO: 49646, SEQ ID NO: 49658, SEQ ID NO: 49671, SEQ ID NO: 49681, SEQ ID NO: 49703, SEQ ID NO: 49728, SEQ ID NO: 49730, SEQ ID NO: 49737, SEQ ID NOs: 49742 to 49743, SEQ ID NOs: 49766 to 49767, SEQ ID NO: 49772, SEQ ID NO: 49782, SEQ ID NOs: 49787 to 49788, SEQ ID NO: 49793, SEQ ID NO: 49796, SEQ ID NO: 49805, SEQ ID NO: 49811, SEQ ID NO: 49823, SEQ ID NO: 49838, SEQ ID NO: 49850, SEQ ID NOs: 49859 to 49860, SEQ ID NO: 49873, SEQ ID NO: 49883, SEQ ID NO: 49892, SEQ ID NO: 49912, SEQ ID NO: 49928, SEQ ID NO: 49948, SEQ ID NO: 49961, SEQ ID NO: 49965, SEQ ID NO: 49987, SEQ ID NO: 49997, SEQ ID NOs: 50017 to 50018, SEQ ID NO: 50020, SEQ ID NO: 50022, SEQ ID NO: 50045, SEQ ID NO: 50062, SEQ ID NO: 50073, SEQ ID NO: 50079, SEQ ID NO: 50090, SEQ ID NO: 50107, SEQ ID NOs: 50111 to 50112, SEQ ID NO: 50123, SEQ ID NO: 50138, SEQ ID NOs: 50165 to 50167, SEQ ID NOs: 50227 to 50228, SEQ ID NO: 50243, SEQ ID NO: 50250, SEQ ID NO: 50254, SEQ ID NO: 50282, SEQ ID NO: 50284, SEQ ID NO: 50290, SEQ ID NO: 50297, SEQ ID NO: 50305, SEQ ID NO: 50309, SEQ ID NO: 50319, SEQ ID NO: 50331, SEQ ID NO: 50334, SEQ ID NO: 50339, SEQ ID NO: 50366, SEQ ID NO: 50388, SEQ ID NO: 50392, SEQ ID NO: 50394, SEQ ID NOs: 50400 to 50401, SEQ ID NO: 50418, SEQ ID NO: 50423, SEQ ID NO: 50428, SEQ ID NO: 50437, SEQ ID NO: 50443, SEQ ID NO: 50450, SEQ ID NO: 50464, SEQ ID NO: 50485, SEQ ID NO: 50494, SEQ ID NO: 50496, SEQ ID NO: 50499, SEQ ID NO: 50526, SEQ ID NO: 50528, SEQ ID NO: 50532, SEQ ID NO: 50538, SEQ ID NO: 50554, SEQ ID NO: 50557, SEQ ID NO: 50560, SEQ ID NO: 50564, SEQ ID NO: 50574, SEQ ID NO: 50585, SEQ ID NO: 50617, SEQ ID NO: 50632, SEQ ID NO: 50634, SEQ ID NO: 50644, SEQ ID NO: 50654, SEQ ID NO: 50678, SEQ ID NO: 50699, SEQ ID NO: 50714, SEQ ID NOs: 50728 to 50729, SEQ ID NO:

50735, SEQ ID NO: 50741, SEQ ID NO: 50744, SEQ ID NO: 50765, SEQ ID NO: 50769, SEQ ID NO: 50793, SEQ ID NO: 50818, SEQ ID NO: 50822, SEQ ID NO: 50826, SEQ ID NO: 50835, SEQ ID NO: 50842, SEQ ID NO: 50847, SEQ ID NO: 50849, SEQ ID NO: 50851, SEQ ID NO: 50893, SEQ ID NO: 50918, SEQ ID NOs: 50935 to 50936, SEQ ID NOs: 50941 to 50944, SEQ ID NOs: 50960 to 50962, SEQ ID NOs: 50975 to 50976, SEQ ID NOs: 51008 to 51009, SEQ ID NO: 51012, SEQ ID NOs: 51021 to 51022, SEQ ID NO: 51046, SEQ ID NO: 51062, SEQ ID NOs: 51068 to 51071, SEQ ID NOs: 51102 to 51104, SEQ ID NO: 51118, SEQ ID NOs: 51168 to 51169, SEQ ID NO: 51214, SEQ ID NO: 51235, SEQ ID NO: 51239, SEQ ID NO: 51241, SEQ ID NO: 51243, SEQ ID NO: 51257, SEQ ID NOs: 51263 to 51266, SEQ ID NOs: 51295 to 51297, SEQ ID NO: 51313, SEQ ID NO: 51405, SEQ ID NOs: 51413 to 51417, SEQ ID NO: 51524, SEQ ID NO: 51526, SEQ ID NO: 51693, SEQ ID NO: 51717, SEQ ID NO: 51762, SEQ ID NO: 51765, SEQ ID NO: 51853, SEQ ID NO: 51878, SEQ ID NO: 52035, SEQ ID NO: 52179, SEQ ID NO: 52275, SEQ ID NO: 52290, SEQ ID NO: 52379, SEQ ID NO: 52463, SEQ ID NO: 52497, SEQ ID NO: 52515, SEQ ID NO: 52652, SEQ ID NO: 52660, SEQ ID NO: 52679, SEQ ID NO: 52686, SEQ ID NO: 52746, SEQ ID NO: 52758, SEQ ID NO: 52816, SEQ ID NO: 52944, SEQ ID NO: 52984, SEQ ID NO: 52988, SEQ ID NO: 52991, SEQ ID NO: 53045, SEQ ID NO: 53118, SEQ ID NO: 53166, SEQ ID NO: 53338, SEQ ID NO: 53382, SEQ ID NO: 53464, SEQ ID NO: 53478, SEQ ID NO: 53511, SEQ ID NO: 53519, SEQ ID NO: 53548, SEQ ID NO: 53581, SEQ ID NO: 53653, SEQ ID NO: 53968, SEQ ID NO: 54024, SEQ ID NO: 54038, SEQ ID NO: 54045, SEQ ID NO: 54080, SEQ ID NO: 54097, SEQ ID NO: 54111, SEQ ID NO: 54238, SEQ ID NO: 54251, SEQ ID NO: 54269, SEQ ID NO: 54409, SEQ ID NO: 54418, SEQ ID NO: 54442, SEQ ID NO: 54473, SEQ ID NO: 54543, SEQ ID NO: 54713, SEQ ID NO: 54719, SEQ ID NO: 54727, SEQ ID NO: 54772, SEQ ID NO: 54788, SEQ ID NO: 54863, SEQ ID NO: 54877, SEQ ID NO: 54945, SEQ ID NO: 54960, SEQ ID NO: 55004, SEQ ID NO: 55109, SEQ ID NO: 55207, SEQ ID NO: 55230, SEQ ID NO: 55300, SEQ ID NO: 55355, SEQ ID NO: 55437, SEQ ID NO: 55516, SEQ ID NO: 55695, SEQ ID NO: 55758, SEQ ID NO: 55801, SEQ ID NO: 55814, SEQ ID NO: 55875, SEQ ID NO: 55879, SEQ ID NO: 55886, SEQ ID NO: 55911, SEQ ID NO: 55986, SEQ ID NO: 56043, SEQ ID NO: 56052, SEQ ID NO: 56175, SEQ ID NO: 56240, SEQ ID NO: 56277, SEQ ID NO: 56352, SEQ ID NO: 56418, SEQ ID NO: 56435, SEQ ID NO: 56521, SEQ ID NO: 56593, SEQ ID NO: 56609, SEQ ID NO: 56629, SEQ ID NOs: 56649 to 56650, SEQ ID NO: 56793, SEQ ID NO: 56836, SEQ ID NO: 56852, SEQ ID NO: 56902, SEQ ID NO: 57155, SEQ ID NO: 57157, SEQ ID NO: 57265, SEQ ID NO: 57278, SEQ ID NO: 57323, SEQ ID NO: 57472, SEQ ID NO: 57535, SEQ ID NO: 57550, SEQ ID NO: 57561, SEQ ID NO: 57568, SEQ ID NO: 57639, SEQ ID NO: 57655, SEQ ID NO: 57790, SEQ ID NO: 57811, SEQ ID NO: 57904, SEQ ID NO: 57944, SEQ ID NO: 58040, SEQ ID NO: 58064, SEQ ID NO: 58075, SEQ ID NO: 58145, SEQ ID NO: 58199, SEQ ID NO: 58223, SEQ ID NO: 58226, SEQ ID NO: 58309, SEQ ID NO: 58349, SEQ ID NO: 58395, SEQ ID NO: 58411, SEQ ID NO: 58433, SEQ ID NO: 58547, SEQ ID NO: 58589, SEQ ID NO: 58679, SEQ ID NOs: 58683 to 58684, SEQ ID NO: 58815, SEQ ID NO: 58823, SEQ ID NO: 58855, SEQ ID NO: 58932, SEQ ID NO: 59223, SEQ ID NO: 59246, SEQ ID NO: 59248, SEQ ID NO: 59530, SEQ ID NO: 59622, SEQ ID NO: 59755, SEQ ID NO: 59757, SEQ ID NO: 59775, SEQ ID NO: 59816, SEQ ID NO: 59821, SEQ ID NO: 59828, SEQ ID NO: 59856, SEQ ID NO: 59871, SEQ ID NO: 59873, SEQ ID NO: 59875, SEQ ID NO: 59960, SEQ ID NO: 59967, SEQ ID NO: 60005, SEQ ID NOs: 60046 to 60047, SEQ ID NO: 60081, SEQ ID NO: 60224, SEQ ID NO: 60228, SEQ ID NO: 60276, SEQ ID NO: 60289, SEQ ID NO: 60292, SEQ ID NOs: 60422 to 60423, SEQ ID NO: 60444, and SEQ ID NOs: 60456 to 68237. In some embodiments, any one of the peptides in the MAGA4 vaccine comprise an amino acid sequence 80, 81, 82, 83, 84, 85, 86, 87, 88, 89, 90, 91, 92, 93, 94, 95, 96, 97, 98 or 99% identical to SEQ ID NO: 41345, SEQ ID NO: 41347, SEQ ID NO: 41352, SEQ ID NOs: 41357 to 41358, SEQ ID NO: 41366, SEQ ID NO: 41377, SEQ ID NO: 41382, SEQ ID NO: 41392, SEQ ID NO: 41396, SEQ ID NO: 41398, SEQ ID NO: 41406, SEQ ID NO: 41411, SEQ ID NO: 41414, SEQ ID NO: 41433, SEQ ID NO: 41436, SEQ ID NO: 41445, SEQ ID NO: 41449, SEQ ID NO: 41455, SEQ ID NO: 41478, SEQ ID NO: 41487, SEQ ID NOs: 41495 to 41496, SEQ ID NO: 41503, SEQ ID NO: 41515, SEQ ID NO: 41520, SEQ ID NO: 41529, SEQ ID NO: 41549, SEQ ID NO: 41553, SEQ ID NO: 41562, SEQ ID NO: 41569, SEQ ID NO: 41574, SEQ ID NO: 41576, SEQ ID NO: 41579, SEQ ID NOs: 41587 to 41588, SEQ ID NO: 41605, SEQ ID NO: 41617, SEQ ID NO: 41620, SEQ ID NO: 41634, SEQ ID NO: 41650, SEQ ID NO: 41665, SEQ ID NO: 41670, SEQ ID NO: 41672, SEQ ID NO: 41696, SEQ ID NO: 41703, SEQ ID NO: 41709, SEQ ID NO: 41725, SEQ ID NOs: 41732 to 41733, SEQ ID NO: 41748, SEQ ID NO: 41760, SEQ ID NO: 41766, SEQ ID NO: 41768, SEQ ID NO: 41770, SEQ ID NO: 41779, SEQ ID NO: 41791, SEQ ID NO: 41797, SEQ ID NO: 41813, SEQ ID NO: 41819, SEQ ID NO: 41825, SEQ ID NO: 41829, SEQ ID NOs: 41846 to 41847, SEQ ID NO: 41853, SEQ ID NO: 41876, SEQ ID NO: 41889, SEQ ID NO: 41892, SEQ ID NO: 41897, SEQ ID NOs: 41906 to 41907, SEQ ID NO: 41912, SEQ ID NO: 41924, SEQ ID NO: 41940, SEQ ID NO: 41953, SEQ ID NO: 41956, SEQ ID NO: 41967, SEQ ID NO: 41970, SEQ ID NO: 41976, SEQ ID NO: 41985, SEQ ID NO: 41990, SEQ ID NO: 42014, SEQ ID NO: 42017, SEQ ID NO: 42026, SEQ ID NO: 42034, SEQ ID NO: 42037, SEQ ID NO: 42046, SEQ ID NO: 42048, SEQ ID NOs: 42056 to 42057, SEQ ID NO: 42080, SEQ ID NO: 42088, SEQ ID NO: 42091, SEQ ID NO: 42102, SEQ ID NO: 42106, SEQ ID NO: 42115, SEQ ID NO: 42120, SEQ ID NO: 42129, SEQ ID NO: 42135, SEQ ID NO: 42138, SEQ ID NO: 42151, SEQ ID NO: 42158, SEQ ID NOs: 42163 to 42164, SEQ ID NOs: 42167 to 42168, SEQ ID NO: 42170, SEQ ID NO: 42186, SEQ ID NO: 42192, SEQ ID NO: 42195, SEQ ID NO: 42198, SEQ ID NO: 42204, SEQ ID NO: 42209, SEQ ID NO: 42218, SEQ ID NO: 42221, SEQ ID NO: 42224, SEQ ID NO: 42229, SEQ ID NO: 42240, SEQ ID NO: 42263, SEQ ID NO: 42265, SEQ ID NO: 42270, SEQ ID NO: 42316, SEQ ID NOs: 42336 to 42337, SEQ ID NO: 42339, SEQ ID NO: 42351, SEQ ID NO: 42354, SEQ ID NO: 42372, SEQ ID NO: 42378, SEQ ID NOs: 42385 to 42386, SEQ ID NO: 42394, SEQ ID NO: 42405, SEQ ID NO: 42409, SEQ ID NO: 42417, SEQ ID NO: 42423, SEQ ID NO: 42439, SEQ ID NO: 42447, SEQ ID NO: 42453, SEQ ID NO: 42458, SEQ ID NOs: 42460 to 42461, SEQ ID NO: 42466, SEQ ID NOs: 42472 to 42473, SEQ ID NOs: 42519 to 42520, SEQ ID NO: 42525, SEQ ID NO: 42528, SEQ ID NO: 42540, SEQ ID NO: 42545, SEQ ID NO: 42550, SEQ ID NOs: 42563 to 42564, SEQ ID NO: 42580, SEQ ID NO: 42605, SEQ ID NO: 42609, SEQ ID NOs: 42612 to 42613, SEQ ID NO: 42615, SEQ ID NO:

42628, SEQ ID NO: 42637, SEQ ID NO: 42648, SEQ ID NO: 42653, SEQ ID NO: 42675, SEQ ID NO: 42680, SEQ ID NO: 42685, SEQ ID NO: 42696, SEQ ID NO: 42703, SEQ ID NO: 42719, SEQ ID NO: 42735, SEQ ID NO: 42743, SEQ ID NO: 42748, SEQ ID NO: 42750, SEQ ID NO: 42768, SEQ ID NO: 42812, SEQ ID NO: 42814, SEQ ID NO: 42822, SEQ ID NO: 42827, SEQ ID NO: 42831, SEQ ID NO: 42846, SEQ ID NO: 42850, SEQ ID NO: 42872, SEQ ID NO: 42886, SEQ ID NO: 42911, SEQ ID NO: 42914, SEQ ID NO: 42923, SEQ ID NO: 42927, SEQ ID NOs: 42957 to 42958, SEQ ID NO: 42962, SEQ ID NO: 42971, SEQ ID NOs: 42997 to 42998, SEQ ID NO: 43002, SEQ ID NO: 43008, SEQ ID NO: 43035, SEQ ID NO: 43046, SEQ ID NO: 43048, SEQ ID NO: 43064, SEQ ID NO: 43083, SEQ ID NO: 43091, SEQ ID NO: 43093, SEQ ID NO: 43148, SEQ ID NO: 43160, SEQ ID NO: 43170, SEQ ID NO: 43175, SEQ ID NO: 43180, SEQ ID NO: 43186, SEQ ID NO: 43193, SEQ ID NO: 43196, SEQ ID NOs: 43231 to 43232, SEQ ID NO: 43238, SEQ ID NO: 43242, SEQ ID NO: 43248, SEQ ID NO: 43253, SEQ ID NO: 43258, SEQ ID NO: 43267, SEQ ID NO: 43274, SEQ ID NO: 43280, SEQ ID NO: 43285, SEQ ID NO: 43295, SEQ ID NO: 43308, SEQ ID NO: 43311, SEQ ID NO: 43329, SEQ ID NO: 43333, SEQ ID NOs: 43339 to 43340, SEQ ID NO: 43362, SEQ ID NO: 43365, SEQ ID NO: 43384, SEQ ID NO: 43389, SEQ ID NO: 43395, SEQ ID NO: 43401, SEQ ID NO: 43429, SEQ ID NO: 43432, SEQ ID NO: 43440, SEQ ID NOs: 43451 to 43453, SEQ ID NO: 43462, SEQ ID NO: 43464, SEQ ID NO: 43467, SEQ ID NO: 43479, SEQ ID NO: 43482, SEQ ID NO: 43496, SEQ ID NO: 43511, SEQ ID NO: 43513, SEQ ID NO: 43517, SEQ ID NO: 43545, SEQ ID NO: 43564, SEQ ID NO: 43573, SEQ ID NO: 43585, SEQ ID NO: 43587, SEQ ID NO: 43591, SEQ ID NO: 43611, SEQ ID NO: 43632, SEQ ID NO: 43636, SEQ ID NO: 43641, SEQ ID NO: 43643, SEQ ID NO: 43651, SEQ ID NO: 43669, SEQ ID NO: 43688, SEQ ID NO: 43696, SEQ ID NO: 43700, SEQ ID NO: 43703, SEQ ID NO: 43707, SEQ ID NO: 43718, SEQ ID NO: 43760, SEQ ID NO: 43763, SEQ ID NO: 43768, SEQ ID NO: 43777, SEQ ID NO: 43780, SEQ ID NO: 43787, SEQ ID NO: 43801, SEQ ID NO: 43808, SEQ ID NO: 43810, SEQ ID NO: 43825, SEQ ID NO: 43827, SEQ ID NO: 43836, SEQ ID NO: 43860, SEQ ID NO: 43867, SEQ ID NOs: 43881 to 43882, SEQ ID NO: 43884, SEQ ID NO: 43887, SEQ ID NOs: 43898 to 43899, SEQ ID NO: 43905, SEQ ID NO: 43915, SEQ ID NO: 43924, SEQ ID NO: 43932, SEQ ID NO: 43958, SEQ ID NO: 43971, SEQ ID NO: 43974, SEQ ID NO: 43978, SEQ ID NOs: 43982 to 43984, SEQ ID NOs: 43986 to 43987, SEQ ID NO: 43993, SEQ ID NO: 43995, SEQ ID NO: 44012, SEQ ID NO: 44035, SEQ ID NO: 44037, SEQ ID NO: 44048, SEQ ID NO: 44050, SEQ ID NO: 44052, SEQ ID NO: 44055, SEQ ID NO: 44063, SEQ ID NO: 44073, SEQ ID NO: 44080, SEQ ID NO: 44085, SEQ ID NO: 44087, SEQ ID NO: 44089, SEQ ID NO: 44112, SEQ ID NO: 44117, SEQ ID NO: 44123, SEQ ID NOs: 44151 to 44152, SEQ ID NO: 44160, SEQ ID NO: 44181, SEQ ID NO: 44207, SEQ ID NO: 44210, SEQ ID NO: 44244, SEQ ID NO: 44246, SEQ ID NO: 44254, SEQ ID NO: 44263, SEQ ID NOs: 44298 to 44299, SEQ ID NO: 44309, SEQ ID NO: 44324, SEQ ID NO: 44328, SEQ ID NO: 44342, SEQ ID NO: 44345, SEQ ID NO: 44359, SEQ ID NO: 44361, SEQ ID NO: 44383, SEQ ID NO: 44401, SEQ ID NO: 44422, SEQ ID NO: 44440, SEQ ID NO: 44452, SEQ ID NO: 44454, SEQ ID NO: 44456, SEQ ID NO: 44463, SEQ ID NO: 44467, SEQ ID NO: 44485, SEQ ID NO: 44512, SEQ ID NO: 44523, SEQ ID NO: 44545, SEQ ID NO: 44552, SEQ ID NO: 44564, SEQ ID NOs: 44566 to 44567, SEQ ID NOs: 44589 to 44591, SEQ ID NO: 44615, SEQ ID NO: 44623, SEQ ID NO: 44631, SEQ ID NO: 44636, SEQ ID NO: 44649, SEQ ID NO: 44654, SEQ ID NO: 44691, SEQ ID NO: 44713, SEQ ID NO: 44722, SEQ ID NO: 44730, SEQ ID NO: 44754, SEQ ID NO: 44756, SEQ ID NOs: 44762 to 44763, SEQ ID NO: 44773, SEQ ID NO: 44781, SEQ ID NO: 44794, SEQ ID NO: 44850, SEQ ID NOs: 44873 to 44875, SEQ ID NO: 44877, SEQ ID NO: 44884, SEQ ID NO: 44908, SEQ ID NO: 44913, SEQ ID NO: 44940, SEQ ID NO: 44955, SEQ ID NO: 44964, SEQ ID NO: 44971, SEQ ID NO: 44976, SEQ ID NO: 45000, SEQ ID NO: 45027, SEQ ID NO: 45035, SEQ ID NO: 45060, SEQ ID NO: 45062, SEQ ID NO: 45095, SEQ ID NO: 45123, SEQ ID NOs: 45126 to 45127, SEQ ID NO: 45132, SEQ ID NO: 45135, SEQ ID NOs: 45138 to 45139, SEQ ID NO: 45193, SEQ ID NO: 45197, SEQ ID NO: 45200, SEQ ID NO: 45223, SEQ ID NO: 45225, SEQ ID NO: 45244, SEQ ID NO: 45262, SEQ ID NO: 45273, SEQ ID NO: 45292, SEQ ID NO: 45302, SEQ ID NO: 45306, SEQ ID NO: 45314, SEQ ID NO: 45380, SEQ ID NO: 45385, SEQ ID NO: 45389, SEQ ID NO: 45398, SEQ ID NO: 45409, SEQ ID NO: 45438, SEQ ID NO: 45444, SEQ ID NOs: 45450 to 45451, SEQ ID NO: 45478, SEQ ID NO: 45480, SEQ ID NO: 45485, SEQ ID NO: 45490, SEQ ID NO: 45510, SEQ ID NO: 45514, SEQ ID NOs: 45519 to 45520, SEQ ID NO: 45530, SEQ ID NO: 45541, SEQ ID NO: 45552, SEQ ID NO: 45556, SEQ ID NOs: 45562 to 45563, SEQ ID NO: 45568, SEQ ID NO: 45577, SEQ ID NOs: 45580 to 45581, SEQ ID NO: 45584, SEQ ID NO: 45588, SEQ ID NO: 45595, SEQ ID NO: 45599, SEQ ID NO: 45632, SEQ ID NO: 45653, SEQ ID NOs: 45666 to 45667, SEQ ID NO: 45675, SEQ ID NO: 45680, SEQ ID NO: 45687, SEQ ID NO: 45697, SEQ ID NOs: 45699 to 45700, SEQ ID NO: 45712, SEQ ID NO: 45714, SEQ ID NO: 45723, SEQ ID NO: 45746, SEQ ID NO: 45765, SEQ ID NO: 45787, SEQ ID NO: 45793, SEQ ID NO: 45818, SEQ ID NO: 45826, SEQ ID NOs: 45829 to 45830, SEQ ID NO: 45835, SEQ ID NO: 45837, SEQ ID NO: 45846, SEQ ID NO: 45859, SEQ ID NO: 45885, SEQ ID NO: 45894, SEQ ID NO: 45904, SEQ ID NO: 45915, SEQ ID NO: 45930, SEQ ID NO: 45938, SEQ ID NO: 45959, SEQ ID NO: 45983, SEQ ID NO: 46006, SEQ ID NO: 46011, SEQ ID NO: 46014, SEQ ID NO: 46044, SEQ ID NO: 46049, SEQ ID NO: 46054, SEQ ID NO: 46058, SEQ ID NO: 46063, SEQ ID NO: 46071, SEQ ID NO: 46077, SEQ ID NO: 46096, SEQ ID NO: 46103, SEQ ID NO: 46108, SEQ ID NO: 46110, SEQ ID NO: 46125, SEQ ID NO: 46133, SEQ ID NOs: 46170 to 46171, SEQ ID NO: 46195, SEQ ID NO: 46208, SEQ ID NO: 46212, SEQ ID NO: 46219, SEQ ID NO: 46226, SEQ ID NO: 46234, SEQ ID NO: 46236, SEQ ID NO: 46261, SEQ ID NO: 46270, SEQ ID NO: 46273, SEQ ID NO: 46275, SEQ ID NO: 46339, SEQ ID NO: 46364, SEQ ID NO: 46376, SEQ ID NOs: 46400 to 46401, SEQ ID NOs: 46421 to 46422, SEQ ID NO: 46433, SEQ ID NOs: 46442 to 46443, SEQ ID NO: 46446, SEQ ID NOs: 46452 to 46454, SEQ ID NO: 46457, SEQ ID NO: 46459, SEQ ID NO: 46462, SEQ ID NO: 46465, SEQ ID NO: 46478, SEQ ID NO: 46484, SEQ ID NO: 46489, SEQ ID NO: 46499, SEQ ID NO: 46512, SEQ ID NO: 46521, SEQ ID NO: 46530, SEQ ID NO: 46536, SEQ ID NO: 46560, SEQ ID NO: 46564, SEQ ID NO: 46570, SEQ ID NO: 46572, SEQ ID NO: 46575, SEQ ID NO: 46579, SEQ ID NO: 46586, SEQ ID NO: 46602, SEQ ID NO: 46616, SEQ ID NO: 46621, SEQ ID NO: 46628, SEQ ID NO: 46637, SEQ ID NO: 46642, SEQ ID NO: 46648, SEQ ID NO: 46652, SEQ ID NO: 46655, SEQ ID NO: 46660, SEQ ID NO: 46663,

SEQ ID NOs: 46665 to 46666, SEQ ID NO: 46676, SEQ ID NOs: 46678 to 46679, SEQ ID NO: 46682, SEQ ID NO: 46685, SEQ ID NO: 46689, SEQ ID NO: 46713, SEQ ID NO: 46715, SEQ ID NO: 46736, SEQ ID NO: 46739, SEQ ID NO: 46770, SEQ ID NO: 46777, SEQ ID NO: 46800, SEQ ID NOs: 46823 to 46825, SEQ ID NO: 46831, SEQ ID NO: 46872, SEQ ID NO: 46880, SEQ ID NO: 46897, SEQ ID NO: 46916, SEQ ID NO: 46928, SEQ ID NO: 46937, SEQ ID NO: 46950, SEQ ID NO: 46978, SEQ ID NO: 46981, SEQ ID NO: 46983, SEQ ID NO: 46989, SEQ ID NO: 46991, SEQ ID NO: 46993, SEQ ID NO: 47003, SEQ ID NO: 47006, SEQ ID NO: 47017, SEQ ID NO: 47028, SEQ ID NO: 47045, SEQ ID NO: 47047, SEQ ID NO: 47057, SEQ ID NOs: 47079 to 47080, SEQ ID NO: 47082, SEQ ID NO: 47114, SEQ ID NO: 47119, SEQ ID NO: 47123, SEQ ID NOs: 47137 to 47139, SEQ ID NO: 47151, SEQ ID NO: 47158, SEQ ID NO: 47167, SEQ ID NO: 47172, SEQ ID NO: 47186, SEQ ID NO: 47191, SEQ ID NO: 47206, SEQ ID NO: 47224, SEQ ID NO: 47298, SEQ ID NO: 47316, SEQ ID NO: 47324, SEQ ID NOs: 47331 to 47332, SEQ ID NO: 47335, SEQ ID NO: 47356, SEQ ID NO: 47358, SEQ ID NOs: 47360 to 47361, SEQ ID NOs: 47377 to 47378, SEQ ID NO: 47381, SEQ ID NO: 47405, SEQ ID NO: 47412, SEQ ID NO: 47416, SEQ ID NO: 47422, SEQ ID NO: 47425, SEQ ID NO: 47427, SEQ ID NOs: 47432 to 47433, SEQ ID NO: 47445, SEQ ID NO: 47451, SEQ ID NO: 47460, SEQ ID NO: 47482, SEQ ID NO: 47491, SEQ ID NO: 47509, SEQ ID NO: 47516, SEQ ID NOs: 47533 to 47535, SEQ ID NOs: 47538 to 47539, SEQ ID NO: 47555, SEQ ID NO: 47561, SEQ ID NOs: 47575 to 47576, SEQ ID NO: 47582, SEQ ID NO: 47592, SEQ ID NO: 47614, SEQ ID NO: 47625, SEQ ID NO: 47630, SEQ ID NO: 47637, SEQ ID NO: 47643, SEQ ID NO: 47654, SEQ ID NO: 47673, SEQ ID NO: 47689, SEQ ID NO: 47698, SEQ ID NO: 47701, SEQ ID NO: 47727, SEQ ID NO: 47749, SEQ ID NOs: 47759 to 47760, SEQ ID NO: 47767, SEQ ID NO: 47773, SEQ ID NO: 47782, SEQ ID NO: 47790, SEQ ID NO: 47793, SEQ ID NO: 47799, SEQ ID NO: 47806, SEQ ID NO: 47809, SEQ ID NO: 47834, SEQ ID NO: 47840, SEQ ID NO: 47844, SEQ ID NO: 47848, SEQ ID NO: 47855, SEQ ID NO: 47867, SEQ ID NO: 47890, SEQ ID NO: 47895, SEQ ID NO: 47899, SEQ ID NO: 47902, SEQ ID NO: 47923, SEQ ID NO: 47927, SEQ ID NOs: 47959 to 47960, SEQ ID NO: 47964, SEQ ID NO: 47979, SEQ ID NO: 47984, SEQ ID NO: 47986, SEQ ID NOs: 48030 to 48031, SEQ ID NO: 48034, SEQ ID NO: 48059, SEQ ID NO: 48093, SEQ ID NO: 48107, SEQ ID NO: 48113, SEQ ID NO: 48118, SEQ ID NO: 48121, SEQ ID NO: 48129, SEQ ID NOs: 48138 to 48139, SEQ ID NO: 48144, SEQ ID NO: 48158, SEQ ID NO: 48160, SEQ ID NO: 48162, SEQ ID NO: 48175, SEQ ID NO: 48186, SEQ ID NO: 48203, SEQ ID NO: 48210, SEQ ID NO: 48213, SEQ ID NO: 48220, SEQ ID NO: 48224, SEQ ID NO: 48229, SEQ ID NO: 48258, SEQ ID NO: 48266, SEQ ID NO: 48273, SEQ ID NO: 48280, SEQ ID NO: 48286, SEQ ID NO: 48295, SEQ ID NOs: 48300 to 48301, SEQ ID NOs: 48306 to 48307, SEQ ID NO: 48315, SEQ ID NO: 48347, SEQ ID NO: 48353, SEQ ID NO: 48358, SEQ ID NO: 48366, SEQ ID NO: 48371, SEQ ID NO: 48379, SEQ ID NO: 48387, SEQ ID NO: 48400, SEQ ID NO: 48415, SEQ ID NOs: 48418 to 48419, SEQ ID NO: 48436, SEQ ID NOs: 48438 to 48440, SEQ ID NO: 48443, SEQ ID NO: 48452, SEQ ID NOs: 48461 to 48462, SEQ ID NO: 48466, SEQ ID NO: 48469, SEQ ID NO: 48520, SEQ ID NO: 48537, SEQ ID NO: 48545, SEQ ID NO: 48574, SEQ ID NOs: 48576 to 48578, SEQ ID NO: 48594, SEQ ID NO: 48599, SEQ ID NO: 48614, SEQ ID NO: 48627, SEQ ID NO: 48642, SEQ ID NO: 48648, SEQ ID NO: 48654, SEQ ID NO: 48656, SEQ ID NO: 48666, SEQ ID NOs: 48669 to 48670, SEQ ID NO: 48674, SEQ ID NOs: 48680 to 48681, SEQ ID NO: 48684, SEQ ID NO: 48686, SEQ ID NO: 48692, SEQ ID NO: 48701, SEQ ID NO: 48705, SEQ ID NO: 48714, SEQ ID NO: 48717, SEQ ID NO: 48735, SEQ ID NO: 48738, SEQ ID NO: 48749, SEQ ID NO: 48751, SEQ ID NO: 48764, SEQ ID NO: 48769, SEQ ID NO: 48793, SEQ ID NO: 48796, SEQ ID NOs: 48799 to 48800, SEQ ID NOs: 48802 to 48803, SEQ ID NO: 48818, SEQ ID NO: 48832, SEQ ID NO: 48834, SEQ ID NO: 48838, SEQ ID NO: 48845, SEQ ID NO: 48856, SEQ ID NO: 48877, SEQ ID NO: 48884, SEQ ID NO: 48903, SEQ ID NO: 48936, SEQ ID NO: 48947, SEQ ID NOs: 48968 to 48970, SEQ ID NO: 48974, SEQ ID NOs: 48981 to 48982, SEQ ID NO: 48997, SEQ ID NOs: 49013 to 49014, SEQ ID NOs: 49019 to 49020, SEQ ID NO: 49031, SEQ ID NO: 49033, SEQ ID NO: 49043, SEQ ID NO: 49052, SEQ ID NOs: 49061 to 49062, SEQ ID NO: 49068, SEQ ID NO: 49071, SEQ ID NO: 49086, SEQ ID NO: 49102, SEQ ID NO: 49111, SEQ ID NO: 49156, SEQ ID NO: 49164, SEQ ID NO: 49173, SEQ ID NO: 49176, SEQ ID NO: 49183, SEQ ID NO: 49185, SEQ ID NOs: 49200 to 49201, SEQ ID NO: 49209, SEQ ID NO: 49220, SEQ ID NO: 49247, SEQ ID NO: 49251, SEQ ID NO: 49256, SEQ ID NO: 49263, SEQ ID NOs: 49273 to 49274, SEQ ID NOs: 49280 to 49281, SEQ ID NO: 49291, SEQ ID NOs: 49294 to 49295, SEQ ID NO: 49298, SEQ ID NO: 49309, SEQ ID NO: 49319, SEQ ID NO: 49326, SEQ ID NO: 49330, SEQ ID NO: 49340, SEQ ID NOs: 49351 to 49352, SEQ ID NO: 49360, SEQ ID NOs: 49376 to 49377, SEQ ID NO: 49384, SEQ ID NO: 49393, SEQ ID NO: 49395, SEQ ID NO: 49399, SEQ ID NO: 49406, SEQ ID NO: 49411, SEQ ID NOs: 49443 to 49444, SEQ ID NO: 49452, SEQ ID NO: 49462, SEQ ID NO: 49474, SEQ ID NO: 49487, SEQ ID NO: 49499, SEQ ID NO: 49525, SEQ ID NO: 49537, SEQ ID NO: 49540, SEQ ID NO: 49557, SEQ ID NO: 49572, SEQ ID NO: 49584, SEQ ID NO: 49597, SEQ ID NO: 49626, SEQ ID NO: 49630, SEQ ID NO: 49646, SEQ ID NO: 49658, SEQ ID NO: 49671, SEQ ID NO: 49681, SEQ ID NO: 49703, SEQ ID NO: 49728, SEQ ID NO: 49730, SEQ ID NO: 49737, SEQ ID NOs: 49742 to 49743, SEQ ID NOs: 49766 to 49767, SEQ ID NO: 49772, SEQ ID NO: 49782, SEQ ID NOs: 49787 to 49788, SEQ ID NO: 49793, SEQ ID NO: 49796, SEQ ID NO: 49805, SEQ ID NO: 49811, SEQ ID NO: 49823, SEQ ID NO: 49838, SEQ ID NO: 49850, SEQ ID NOs: 49859 to 49860, SEQ ID NO: 49873, SEQ ID NO: 49883, SEQ ID NO: 49892, SEQ ID NO: 49912, SEQ ID NO: 49928, SEQ ID NO: 49948, SEQ ID NO: 49961, SEQ ID NO: 49965, SEQ ID NO: 49987, SEQ ID NO: 49997, SEQ ID NOs: 50017 to 50018, SEQ ID NO: 50020, SEQ ID NO: 50022, SEQ ID NO: 50045, SEQ ID NO: 50062, SEQ ID NO: 50073, SEQ ID NO: 50079, SEQ ID NO: 50090, SEQ ID NO: 50107, SEQ ID NOs: 50111 to 50112, SEQ ID NO: 50123, SEQ ID NO: 50138, SEQ ID NOs: 50165 to 50167, SEQ ID NOs: 50227 to 50228, SEQ ID NO: 50243, SEQ ID NO: 50250, SEQ ID NO: 50254, SEQ ID NO: 50282, SEQ ID NO: 50284, SEQ ID NO: 50290, SEQ ID NO: 50297, SEQ ID NO: 50305, SEQ ID NO: 50309, SEQ ID NO: 50319, SEQ ID NO: 50331, SEQ ID NO: 50334, SEQ ID NO: 50339, SEQ ID NO: 50366, SEQ ID NO: 50388, SEQ ID NO: 50392, SEQ ID NO: 50394, SEQ ID NOs: 50400 to 50401, SEQ ID NO: 50418, SEQ ID NO: 50423, SEQ ID NO: 50428, SEQ ID NO: 50437, SEQ ID NO: 50443, SEQ ID NO: 50450, SEQ ID NO: 50464, SEQ ID NO: 50485, SEQ ID NO: 50494, SEQ ID NO: 50496, SEQ ID NO: 50499, SEQ ID NO:

50526, SEQ ID NO: 50528, SEQ ID NO: 50532, SEQ ID NO: 50538, SEQ ID NO: 50554, SEQ ID NO: 50557, SEQ ID NO: 50560, SEQ ID NO: 50564, SEQ ID NO: 50574, SEQ ID NO: 50585, SEQ ID NO: 50617, SEQ ID NO: 50632, SEQ ID NO: 50634, SEQ ID NO: 50644, SEQ ID NO: 50654, SEQ ID NO: 50678, SEQ ID NO: 50699, SEQ ID NO: 50714, SEQ ID NOs: 50728 to 50729, SEQ ID NO: 50735, SEQ ID NO: 50741, SEQ ID NO: 50744, SEQ ID NO: 50765, SEQ ID NO: 50769, SEQ ID NO: 50793, SEQ ID NO: 50818, SEQ ID NO: 50822, SEQ ID NO: 50826, SEQ ID NO: 50835, SEQ ID NO: 50842, SEQ ID NO: 50847, SEQ ID NO: 50849, SEQ ID NO: 50851, SEQ ID NO: 50893, SEQ ID NO: 50918, SEQ ID NOs: 50935 to 50936, SEQ ID NOs: 50941 to 50944, SEQ ID NOs: 50960 to 50962, SEQ ID NOs: 50975 to 50976, SEQ ID NOs: 51008 to 51009, SEQ ID NO: 51012, SEQ ID NOs: 51021 to 51022, SEQ ID NO: 51046, SEQ ID NO: 51062, SEQ ID NOs: 51068 to 51071, SEQ ID NOs: 51102 to 51104, SEQ ID NO: 51118, SEQ ID NOs: 51168 to 51169, SEQ ID NO: 51214, SEQ ID NO: 51235, SEQ ID NO: 51239, SEQ ID NO: 51241, SEQ ID NO: 51243, SEQ ID NO: 51257, SEQ ID NOs: 51263 to 51266, SEQ ID NOs: 51295 to 51297, SEQ ID NO: 51313, SEQ ID NO: 51405, SEQ ID NOs: 51413 to 51417, SEQ ID NO: 51524, SEQ ID NO: 51526, SEQ ID NO: 51693, SEQ ID NO: 51717, SEQ ID NO: 51762, SEQ ID NO: 51765, SEQ ID NO: 51853, SEQ ID NO: 51878, SEQ ID NO: 52035, SEQ ID NO: 52179, SEQ ID NO: 52275, SEQ ID NO: 52290, SEQ ID NO: 52379, SEQ ID NO: 52463, SEQ ID NO: 52497, SEQ ID NO: 52515, SEQ ID NO: 52652, SEQ ID NO: 52660, SEQ ID NO: 52679, SEQ ID NO: 52686, SEQ ID NO: 52746, SEQ ID NO: 52758, SEQ ID NO: 52816, SEQ ID NO: 52944, SEQ ID NO: 52984, SEQ ID NO: 52988, SEQ ID NO: 52991, SEQ ID NO: 53045, SEQ ID NO: 53118, SEQ ID NO: 53166, SEQ ID NO: 53338, SEQ ID NO: 53382, SEQ ID NO: 53464, SEQ ID NO: 53478, SEQ ID NO: 53511, SEQ ID NO: 53519, SEQ ID NO: 53548, SEQ ID NO: 53581, SEQ ID NO: 53653, SEQ ID NO: 53968, SEQ ID NO: 54024, SEQ ID NO: 54038, SEQ ID NO: 54045, SEQ ID NO: 54080, SEQ ID NO: 54097, SEQ ID NO: 54111, SEQ ID NO: 54238, SEQ ID NO: 54251, SEQ ID NO: 54269, SEQ ID NO: 54409, SEQ ID NO: 54418, SEQ ID NO: 54442, SEQ ID NO: 54473, SEQ ID NO: 54543, SEQ ID NO: 54713, SEQ ID NO: 54719, SEQ ID NO: 54727, SEQ ID NO: 54772, SEQ ID NO: 54788, SEQ ID NO: 54863, SEQ ID NO: 54877, SEQ ID NO: 54945, SEQ ID NO: 54960, SEQ ID NO: 55004, SEQ ID NO: 55109, SEQ ID NO: 55207, SEQ ID NO: 55230, SEQ ID NO: 55300, SEQ ID NO: 55355, SEQ ID NO: 55437, SEQ ID NO: 55516, SEQ ID NO: 55695, SEQ ID NO: 55758, SEQ ID NO: 55801, SEQ ID NO: 55814, SEQ ID NO: 55875, SEQ ID NO: 55879, SEQ ID NO: 55886, SEQ ID NO: 55911, SEQ ID NO: 55986, SEQ ID NO: 56043, SEQ ID NO: 56052, SEQ ID NO: 56175, SEQ ID NO: 56240, SEQ ID NO: 56277, SEQ ID NO: 56352, SEQ ID NO: 56418, SEQ ID NO: 56435, SEQ ID NO: 56521, SEQ ID NO: 56593, SEQ ID NO: 56609, SEQ ID NO: 56629, SEQ ID NOs: 56649 to 56650, SEQ ID NO: 56793, SEQ ID NO: 56836, SEQ ID NO: 56852, SEQ ID NO: 56902, SEQ ID NO: 57155, SEQ ID NO: 57157, SEQ ID NO: 57265, SEQ ID NO: 57278, SEQ ID NO: 57323, SEQ ID NO: 57472, SEQ ID NO: 57535, SEQ ID NO: 57550, SEQ ID NO: 57561, SEQ ID NO: 57568, SEQ ID NO: 57639, SEQ ID NO: 57655, SEQ ID NO: 57790, SEQ ID NO: 57811, SEQ ID NO: 57904, SEQ ID NO: 57944, SEQ ID NO: 58040, SEQ ID NO: 58064, SEQ ID NO: 58075, SEQ ID NO: 58145, SEQ ID NO: 58199, SEQ ID NO: 58223, SEQ ID NO: 58226, SEQ ID NO: 58309, SEQ ID NO: 58349, SEQ ID NO: 58395, SEQ ID NO: 58411, SEQ ID NO: 58433, SEQ ID NO: 58547, SEQ ID NO: 58589, SEQ ID NO: 58679, SEQ ID NOs: 58683 to 58684, SEQ ID NO: 58815, SEQ ID NO: 58823, SEQ ID NO: 58855, SEQ ID NO: 58932, SEQ ID NO: 59223, SEQ ID NO: 59246, SEQ ID NO: 59248, SEQ ID NO: 59530, SEQ ID NO: 59622, SEQ ID NO: 59755, SEQ ID NO: 59757, SEQ ID NO: 59775, SEQ ID NO: 59816, SEQ ID NO: 59821, SEQ ID NO: 59828, SEQ ID NO: 59856, SEQ ID NO: 59871, SEQ ID NO: 59873, SEQ ID NO: 59875, SEQ ID NO: 59960, SEQ ID NO: 59967, SEQ ID NO: 60005, SEQ ID NOs: 60046 to 60047, SEQ ID NO: 60081, SEQ ID NO: 60224, SEQ ID NO: 60228, SEQ ID NO: 60276, SEQ ID NO: 60289, SEQ ID NO: 60292, SEQ ID NOs: 60422 to 60423, SEQ ID NO: 60444, or SEQ ID NOs: 60456 to 68237.

In some embodiments, the amino acid sequence for a MEW class I peptide vaccine for the MAGA4 protein comprises two or more of the SEQ ID NO: 41352, SEQ ID NOs: 41357 to 41358, SEQ ID NO: 41377, SEQ ID NO: 41770, SEQ ID NO: 49071, SEQ ID NO: 50632, SEQ ID NO: 50729, SEQ ID NO: 55758, and SEQ ID NOs: 60456 to 60527. In some embodiments, any one of the peptides in the MAGA4 vaccine comprise an amino acid sequence 80, 81, 82, 83, 84, 85, 86, 87, 88, 89, 90, 91, 92, 93, 94, 95, 96, 97, 98 or 99% identical to SEQ ID NO: 41352, SEQ ID NOs: 41357 to 41358, SEQ ID NO: 41377, SEQ ID NO: 41770, SEQ ID NO: 49071, SEQ ID NO: 50632, SEQ ID NO: 50729, SEQ ID NO: 55758, or SEQ ID NOs: 60456 to 60527.

In some embodiments, the amino acid sequence for a MEW class I peptide vaccine for the MAGA4 protein comprises two or more of the SEQ ID NO: 41345, SEQ ID NO: 41347, SEQ ID NO: 41352, SEQ ID NOs: 41357 to 41358, SEQ ID NO: 41366, SEQ ID NO: 41377, SEQ ID NO: 41382, SEQ ID NO: 41392, SEQ ID NO: 41396, SEQ ID NO: 41398, SEQ ID NO: 41406, SEQ ID NO: 41411, SEQ ID NO: 41414, SEQ ID NO: 41433, SEQ ID NO: 41436, SEQ ID NO: 41445, SEQ ID NO: 41449, SEQ ID NO: 41455, SEQ ID NO: 41478, SEQ ID NO: 41487, SEQ ID NOs: 41495 to 41496, SEQ ID NO: 41503, SEQ ID NO: 41515, SEQ ID NO: 41520, SEQ ID NO: 41529, SEQ ID NO: 41549, SEQ ID NO: 41553, SEQ ID NO: 41562, SEQ ID NO: 41569, SEQ ID NO: 41574, SEQ ID NO: 41576, SEQ ID NO: 41579, SEQ ID NOs: 41587 to 41588, SEQ ID NO: 41605, SEQ ID NO: 41617, SEQ ID NO: 41620, SEQ ID NO: 41634, SEQ ID NO: 41650, SEQ ID NO: 41665, SEQ ID NO: 41670, SEQ ID NO: 41672, SEQ ID NO: 41696, SEQ ID NO: 41703, SEQ ID NO: 41709, SEQ ID NO: 41725, SEQ ID NOs: 41732 to 41733, SEQ ID NO: 41748, SEQ ID NO: 41760, SEQ ID NO: 41766, SEQ ID NO: 41768, SEQ ID NO: 41770, SEQ ID NO: 41779, SEQ ID NO: 41791, SEQ ID NO: 41797, SEQ ID NO: 41813, SEQ ID NO: 41819, SEQ ID NO: 41825, SEQ ID NO: 41829, SEQ ID NOs: 41846 to 41847, SEQ ID NO: 41853, SEQ ID NO: 41876, SEQ ID NO: 41889, SEQ ID NO: 41892, SEQ ID NO: 41897, SEQ ID NOs: 41906 to 41907, SEQ ID NO: 41912, SEQ ID NO: 41924, SEQ ID NO: 41940, SEQ ID NO: 41953, SEQ ID NO: 41956, SEQ ID NO: 41967, SEQ ID NO: 41970, SEQ ID NO: 41976, SEQ ID NO: 41985, SEQ ID NO: 41990, SEQ ID NO: 42014, SEQ ID NO: 42017, SEQ ID NO: 42026, SEQ ID NO: 42034, SEQ ID NO: 42037, SEQ ID NO: 42046, SEQ ID NO: 42048, SEQ ID NOs: 42056 to 42057, SEQ ID NO: 42080, SEQ ID NO: 42088, SEQ ID NO: 42091, SEQ ID NO: 42102, SEQ ID NO: 42106, SEQ ID NO: 42115, SEQ ID NO: 42120, SEQ ID NO: 42129, SEQ ID NO: 42135, SEQ ID NO: 42138, SEQ ID NO: 42151, SEQ ID NO: 42158, SEQ ID NOs: 42163 to 42164, SEQ ID NOs: 42167 to 42168, SEQ ID NO: 42170, SEQ ID NO: 42186, SEQ ID NO: 42192, SEQ ID NO: 42195, SEQ ID NO: 42198, SEQ ID NO: 42204, SEQ ID NO: 42209, SEQ ID NO: 42218, SEQ ID NO: 42221, SEQ ID NO: 42224, SEQ ID NO: 42229, SEQ ID NO: 42240, SEQ ID NO: 42263, SEQ ID NO: 42265, SEQ ID NO: 42270, SEQ ID NO: 42316, SEQ ID NOs: 42336 to 42337, SEQ ID NO: 42339, SEQ ID NO: 42351, SEQ ID NO: 42354, SEQ ID NO: 42372, SEQ ID NO: 42378, SEQ ID NOs: 42385 to 42386, SEQ ID NO: 42394, SEQ ID NO: 42405, SEQ ID NO: 42409, SEQ ID NO: 42417, SEQ ID NO: 42423, SEQ ID NO: 42439, SEQ ID NO: 42447, SEQ ID NO: 42453, SEQ ID NO: 42458, SEQ ID NOs: 42460 to 42461, SEQ ID NO: 42466, SEQ ID NOs: 42472 to 42473, SEQ ID NOs: 42519 to 42520, SEQ ID NO: 42525, SEQ ID NO: 42528, SEQ ID NO: 42540, SEQ ID NO: 42545, SEQ ID NO: 42550, SEQ ID NOs: 42563 to 42564, SEQ ID NO: 42580, SEQ ID NO: 42605, SEQ ID NO: 42609, SEQ ID NOs: 42612 to 42613, SEQ ID NO: 42615, SEQ ID NO: 42628, SEQ ID NO: 42637, SEQ ID NO: 42648, SEQ ID NO: 42653, SEQ ID NO: 42675, SEQ ID NO: 42680, SEQ ID NO: 42685, SEQ ID NO: 42696, SEQ ID NO: 42703, SEQ ID NO: 42719, SEQ ID NO: 42735, SEQ ID NO: 42743, SEQ ID NO: 42748, SEQ ID NO: 42750, SEQ ID NO: 42768, SEQ ID NO: 42812, SEQ ID NO: 42814, SEQ ID NO: 42822, SEQ ID NO: 42827, SEQ ID NO: 42831, SEQ ID NO: 42846, SEQ ID NO: 42850, SEQ ID NO: 42872, SEQ ID NO: 42886, SEQ ID NO: 42911, SEQ ID NO: 42914, SEQ ID NO: 42923, SEQ ID NO: 42927, SEQ ID NOs: 42957 to 42958, SEQ ID NO: 42962, SEQ ID NO: 42971, SEQ ID NOs: 42997 to 42998, SEQ ID NO: 43002, SEQ ID NO: 43008, SEQ ID NO: 43035, SEQ ID NO: 43046, SEQ ID NO: 43048, SEQ ID NO: 43064, SEQ ID NO: 43083, SEQ ID NO: 43091, SEQ ID NO: 43093, SEQ ID NO: 43148, SEQ ID NO: 43160, SEQ ID NO: 43170, SEQ ID NO: 43175, SEQ ID NO: 43180, SEQ ID NO: 43186, SEQ ID NO: 43193, SEQ ID NO: 43196, SEQ ID NOs: 43231 to 43232, SEQ ID NO: 43238, SEQ ID NO: 43242, SEQ ID NO: 43248, SEQ ID NO: 43253, SEQ ID NO: 43258, SEQ ID NO: 43267, SEQ ID NO: 43274, SEQ ID NO: 43280, SEQ ID NO: 43285, SEQ ID NO: 43295, SEQ ID NO: 43308, SEQ ID NO: 43311, SEQ ID NO: 43329, SEQ ID NO: 43333, SEQ ID NOs: 43339 to 43340, SEQ ID NO: 43362, SEQ ID NO: 43365, SEQ ID NO: 43384, SEQ ID NO: 43389, SEQ ID NO: 43395, SEQ ID NO: 43401, SEQ ID NO: 43429, SEQ ID NO: 43432, SEQ ID NO: 43440, SEQ ID NOs: 43451 to 43453, SEQ ID NO: 43462, SEQ ID NO: 43464, SEQ ID NO: 43467, SEQ ID NO: 43479, SEQ ID NO: 43482, SEQ ID NO: 43496, SEQ ID NO: 43511, SEQ ID NO: 43513, SEQ ID NO: 43517, SEQ ID NO: 43545, SEQ ID NO: 43564, SEQ ID NO: 43573, SEQ ID NO: 43585, SEQ ID NO: 43587, SEQ ID NO: 43591, SEQ ID NO: 43611, SEQ ID NO: 43632, SEQ ID NO: 43636, SEQ ID NO: 43641, SEQ ID NO: 43643, SEQ ID NO: 43651, SEQ ID NO: 43669, SEQ ID NO: 43688, SEQ ID NO: 43696, SEQ ID NO: 43700, SEQ ID NO: 43703, SEQ ID NO: 43707, SEQ ID NO: 43718, SEQ ID NO: 43760, SEQ ID NO: 43763, SEQ ID NO: 43768, SEQ ID NO: 43777, SEQ ID NO: 43780, SEQ ID NO: 43787, SEQ ID NO: 43801, SEQ ID NO: 43808, SEQ ID NO: 43810, SEQ ID NO: 43825, SEQ ID NO: 43827, SEQ ID NO: 43836, SEQ ID NO: 43860, SEQ ID NOs: 43867, SEQ ID NOs: 43881 to 43882, SEQ ID NO: 43884, SEQ ID NO: 43887, SEQ ID NOs: 43898 to 43899, SEQ ID NO: 43905, SEQ ID NO: 43915, SEQ ID NO: 43924, SEQ ID NO: 43932, SEQ ID NO: 43958, SEQ ID NO: 43971, SEQ ID NO: 43974, SEQ ID NO: 43978, SEQ ID NOs: 43982 to 43984, SEQ ID NOs: 43986 to 43987, SEQ ID NO: 43993, SEQ ID NO: 43995, SEQ ID NO: 44012, SEQ ID NO: 44035, SEQ ID NO: 44037, SEQ ID NO: 44048, SEQ ID NO: 44050, SEQ ID NO: 44052, SEQ ID NO: 44055, SEQ ID NO: 44063, SEQ ID NO: 44073, SEQ ID NO: 44080, SEQ ID NO: 44085, SEQ ID NO: 44087, SEQ ID NO: 44089, SEQ ID NO: 44112, SEQ ID NO: 44117, SEQ ID NO: 44123, SEQ ID NOs: 44151 to 44152, SEQ ID NO: 44160, SEQ ID NO: 44181, SEQ ID NO: 44207, SEQ ID NO: 44210, SEQ ID NO: 44244, SEQ ID NO: 44246, SEQ ID NO: 44254, SEQ ID NO: 44263, SEQ ID NOs: 44298 to 44299, SEQ ID NO: 44309, SEQ ID NO: 44324, SEQ ID NO: 44328, SEQ ID NO: 44342, SEQ ID NO: 44345, SEQ ID NO: 44359, SEQ ID NO: 44361, SEQ ID NO: 44383, SEQ ID NO: 44401, SEQ ID NO: 44422, SEQ ID NO: 44440, SEQ ID NO: 44452, SEQ ID NO: 44454, SEQ ID NO: 44456, SEQ ID NO: 44463, SEQ ID NO: 44467, SEQ ID NO: 44485, SEQ ID NO: 44512, SEQ ID NO: 44523, SEQ ID NO: 44545, SEQ ID NO: 44552, SEQ ID NO: 44564, SEQ ID NOs: 44566 to 44567, SEQ ID NOs: 44589 to 44591, SEQ ID NO: 44615, SEQ ID NO: 44623, SEQ ID NO: 44631, SEQ ID NO: 44636, SEQ ID NO: 44649, SEQ ID NO: 44654, SEQ ID NO: 44691, SEQ ID NO: 44713, SEQ ID NO: 44722, SEQ ID NO: 44730, SEQ ID NO: 44754, SEQ ID NO: 44756, SEQ ID NOs: 44762 to 44763, SEQ ID NO: 44773, SEQ ID NO: 44781, SEQ ID NO: 44794, SEQ ID NO: 44850, SEQ ID NOs: 44873 to 44875, SEQ ID NO: 44877, SEQ ID NO: 44884, SEQ ID NO: 44908, SEQ ID NO: 44913, SEQ ID NO: 44940, SEQ ID NO: 44955, SEQ ID NO: 44964, SEQ ID NO: 44971, SEQ ID NO: 44976, SEQ ID NO: 45000, SEQ ID NO: 45027, SEQ ID NO: 45035, SEQ ID NO: 45060, SEQ ID NO: 45062, SEQ ID NO: 45095, SEQ ID NO: 45123, SEQ ID NOs: 45126 to 45127, SEQ ID NO: 45132, SEQ ID NO: 45135, SEQ ID NOs: 45138 to 45139, SEQ ID NO: 45193, SEQ ID NO: 45197, SEQ ID NO: 45200, SEQ ID NO: 45223, SEQ ID NO: 45225, SEQ ID NO: 45244, SEQ ID NO: 45262, SEQ ID NO: 45273, SEQ ID NO: 45292, SEQ ID NO: 45302, SEQ ID NO: 45306, SEQ ID NO: 45314, SEQ ID NO: 45380, SEQ ID NO: 45385, SEQ ID NO: 45389, SEQ ID NO: 45398, SEQ ID NO: 45409, SEQ ID NO: 45438, SEQ ID NO: 45444, SEQ ID NOs: 45450 to 45451, SEQ ID NO: 45478, SEQ ID NO: 45480, SEQ ID NO: 45485, SEQ ID NO: 45490, SEQ ID NO: 45510, SEQ ID NO: 45514, SEQ ID NOs: 45519 to 45520, SEQ ID NO: 45530, SEQ ID NO: 45541, SEQ ID NO: 45552, SEQ ID NO: 45556, SEQ ID NOs: 45562 to 45563, SEQ ID NO: 45568, SEQ ID NO: 45577, SEQ ID NOs: 45580 to 45581, SEQ ID NO: 45584, SEQ ID NO: 45588, SEQ ID NO: 45595, SEQ ID NO: 45599, SEQ ID NO: 45632, SEQ ID NO: 45653, SEQ ID NOs: 45666 to 45667, SEQ ID NO: 45675, SEQ ID NO: 45680, SEQ ID NO: 45687, SEQ ID NO: 45697, SEQ ID NOs: 45699 to 45700, SEQ ID NO: 45712, SEQ ID NO: 45714, SEQ ID NO: 45723, SEQ ID NO: 45746, SEQ ID NO: 45765, SEQ ID NO: 45787, SEQ ID NO: 45793, SEQ ID NO: 45818, SEQ ID NO: 45826, SEQ ID NOs: 45829 to 45830, SEQ ID NO: 45835, SEQ ID NO: 45837, SEQ ID NO: 45846, SEQ ID NO: 45859, SEQ ID NO: 45885, SEQ ID NO: 45894, SEQ ID NO: 45904, SEQ ID NO: 45915, SEQ ID NO: 45930, SEQ ID NO: 45938, SEQ ID NO: 45959, SEQ ID NO: 45983, SEQ ID NO: 46006, SEQ ID NO: 46011, SEQ ID NO: 46014, SEQ ID NO: 46044, SEQ ID NO: 46049, SEQ ID NO: 46054, SEQ ID NO: 46058, SEQ ID NO: 46063, SEQ ID NO: 46071, SEQ ID NO: 46077, SEQ ID NO: 46096, SEQ ID NO: 46103, SEQ ID NO: 46108, SEQ ID NO: 46110, SEQ ID NO: 46125, SEQ ID NO: 46133, SEQ ID NOs: 46170 to 46171, SEQ ID NO: 46195, SEQ ID NO: 46208, SEQ ID NO: 46212, SEQ ID NO: 46219, SEQ ID NO: 46226, SEQ ID NO: 46234, SEQ ID NO: 46236, SEQ ID NO: 46261, SEQ ID NO: 46270, SEQ ID NO: 46273, SEQ ID NO: 46275, SEQ ID NO: 46339, SEQ ID NO: 46364, SEQ ID NO: 46376, SEQ ID NOs: 46400 to 46401, SEQ ID NOs: 46421 to 46422, SEQ ID NO: 46433, SEQ ID NOs: 46442 to 46443, SEQ ID NO: 46446, SEQ ID NOs: 46452 to 46454, SEQ ID NO: 46457, SEQ ID NO: 46459, SEQ ID NO: 46462, SEQ ID NO: 46465, SEQ ID NO: 46478, SEQ ID NO: 46484, SEQ ID NO: 46489, SEQ ID NO: 46499, SEQ ID NO: 46512, SEQ ID NO: 46521, SEQ ID NO: 46530, SEQ ID NO: 46536, SEQ ID NO: 46560, SEQ ID NO: 46564, SEQ ID NO: 46570, SEQ ID NO: 46572, SEQ ID NO: 46575, SEQ ID NO: 46579, SEQ ID NO: 46586, SEQ ID NO: 46602, SEQ ID NO: 46616, SEQ ID NO: 46621, SEQ ID NO: 46628, SEQ ID NO: 46637, SEQ ID NO: 46642, SEQ ID NO: 46648, SEQ ID NO: 46652, SEQ ID NO: 46655, SEQ ID NO: 46660, SEQ ID NO: 46663, SEQ ID NOs: 46665 to 46666, SEQ ID NO: 46676, SEQ ID NOs: 46678 to 46679, SEQ ID NO: 46682, SEQ ID NO: 46685, SEQ ID NO: 46689, SEQ ID NO: 46713, SEQ ID NO: 46715, SEQ ID NO: 46736, SEQ ID NO: 46739, SEQ ID NO: 46770, SEQ ID NO: 46777, SEQ ID NO: 46800, SEQ ID NOs: 46823 to 46825, SEQ ID NO: 46831, SEQ ID NO: 46872, SEQ ID NO: 46880, SEQ ID NO: 46897, SEQ ID NO: 46916, SEQ ID NO: 46928, SEQ ID NO: 46937, SEQ ID NO: 46950, SEQ ID NO: 46978, SEQ ID NO: 46981, SEQ ID NO: 46983, SEQ ID NO: 46989, SEQ ID NO: 46991, SEQ ID NO: 46993, SEQ ID NO: 47003, SEQ ID NO: 47006, SEQ ID NO: 47017, SEQ ID NO: 47028, SEQ ID NO: 47045, SEQ ID NO: 47047, SEQ ID NO: 47057, SEQ ID NOs: 47079 to 47080, SEQ ID NO: 47082, SEQ ID NO: 47114, SEQ ID NO: 47119, SEQ ID NO: 47123, SEQ ID NOs: 47137 to 47139, SEQ ID NO: 47151, SEQ ID NO: 47158, SEQ ID NO: 47167, SEQ ID NO: 47172, SEQ ID NO: 47186, SEQ ID NO: 47191, SEQ ID NO: 47206, SEQ ID NO: 47224, SEQ ID NO: 47298, SEQ ID NO: 47316, SEQ ID NO: 47324, SEQ ID NOs: 47331 to 47332, SEQ ID NO: 47335, SEQ ID NO: 47356, SEQ ID NO: 47358, SEQ ID NOs: 47360 to 47361, SEQ ID NOs: 47377 to 47378, SEQ ID NO: 47381, SEQ ID NO: 47405, SEQ ID NO: 47412, SEQ ID NO: 47416, SEQ ID NO: 47422, SEQ ID NO: 47425, SEQ ID NO: 47427, SEQ ID NOs: 47432 to 47433, SEQ ID NO: 47445, SEQ ID NO: 47451, SEQ ID NO: 47460, SEQ ID NO: 47482, SEQ ID NO: 47491, SEQ ID NO: 47509, SEQ ID NO: 47516, SEQ ID NOs: 47533 to 47535, SEQ ID NOs: 47538 to 47539, SEQ ID NO: 47555, SEQ ID NO: 47561, SEQ ID NOs: 47575 to 47576, SEQ ID NO: 47582, SEQ ID NO: 47592, SEQ ID NO: 47614, SEQ ID NO: 47625, SEQ ID NO: 47630, SEQ ID NO: 47637, SEQ ID NO: 47643, SEQ ID NO: 47654, SEQ ID NO: 47673, SEQ ID NO: 47689, SEQ ID NO: 47698, SEQ ID NO: 47701, SEQ ID NO: 47727, SEQ ID NO: 47749, SEQ ID NOs: 47759 to 47760, SEQ ID NO: 47767, SEQ ID NO: 47773, SEQ ID NO: 47782, SEQ ID NO: 47790, SEQ ID NO: 47793, SEQ ID NO: 47799, SEQ ID NO: 47806, SEQ ID NO: 47809, SEQ ID NO: 47834, SEQ ID NO: 47840, SEQ ID NO: 47844, SEQ ID NO: 47848, SEQ ID NO: 47855, SEQ ID NO: 47867, SEQ ID NO: 47890, SEQ ID NO: 47895, SEQ ID NO: 47899, SEQ ID NO: 47902, SEQ ID NO: 47923, SEQ ID NO: 47927, SEQ ID NOs: 47959 to 47960, SEQ ID NO: 47964, SEQ ID NO: 47979, SEQ ID NO: 47984, SEQ ID NO: 47986, SEQ ID NOs: 48030 to 48031, SEQ ID NO: 48034, SEQ ID NO: 48059, SEQ ID NO: 48093, SEQ ID NO: 48107, SEQ ID NO: 48113, SEQ ID NO: 48118, SEQ ID NO: 48121, SEQ ID NO: 48129, SEQ ID NOs: 48138 to 48139, SEQ ID NO: 48144, SEQ ID NO: 48158, SEQ ID NO: 48160, SEQ ID NO: 48162, SEQ ID NO: 48175, SEQ ID NO: 48186, SEQ ID NO: 48203, SEQ ID NO: 48210, SEQ ID NO: 48213, SEQ ID NO: 48220, SEQ ID NO: 48224, SEQ ID NO: 48229, SEQ ID NO: 48258, SEQ ID NO: 48266, SEQ ID NO: 48273, SEQ ID NO: 48280, SEQ ID NO: 48286, SEQ ID NO: 48295, SEQ ID NOs: 48300 to 48301, SEQ ID NOs: 48306 to 48307, SEQ ID NO: 48315, SEQ ID NO: 48347, SEQ ID NO: 48353, SEQ ID NO: 48358, SEQ ID NO: 48366, SEQ ID NO: 48371, SEQ ID NO: 48379, SEQ ID NO: 48387, SEQ ID NO: 48400, SEQ ID NO: 48415, SEQ ID NOs: 48418 to 48419, SEQ ID NO: 48436, SEQ ID NOs: 48438 to 48440, SEQ ID NO: 48443, SEQ ID NO: 48452, SEQ ID NOs: 48461 to 48462, SEQ ID NO: 48466, SEQ ID NO: 48469, SEQ ID NO: 48520, SEQ ID NO: 48537, SEQ ID NO: 48545, SEQ ID NO: 48574, SEQ ID NOs: 48576 to 48578, SEQ ID NO: 48594, SEQ ID NO: 48599, SEQ ID NO: 48614, SEQ ID NO: 48627, SEQ ID NO: 48642, SEQ ID NO: 48648, SEQ ID NO: 48654, SEQ ID NO: 48656, SEQ ID NO: 48666, SEQ ID NOs: 48669 to 48670, SEQ ID NO: 48674, SEQ ID NOs: 48680 to 48681, SEQ ID NO: 48684, SEQ ID NO: 48686, SEQ ID NO: 48692, SEQ ID NO: 48701, SEQ ID NO: 48705, SEQ ID NO: 48714, SEQ ID NO: 48717, SEQ ID NO: 48735, SEQ ID NO: 48738, SEQ ID NO: 48749, SEQ ID NO: 48751, SEQ ID NO: 48764, SEQ ID NO: 48769, SEQ ID NO: 48793, SEQ ID NO: 48796, SEQ ID NOs: 48799 to 48800, SEQ ID NOs: 48802 to 48803, SEQ ID NO: 48818, SEQ ID NO: 48832, SEQ ID NO: 48834, SEQ ID NO: 48838, SEQ ID NO: 48845, SEQ ID NO: 48856, SEQ ID NO: 48877, SEQ ID NO: 48884, SEQ ID NO: 48903, SEQ ID NO: 48936, SEQ ID NO: 48947, SEQ ID NOs: 48968 to 48970, SEQ ID NO: 48974, SEQ ID NOs: 48981 to 48982, SEQ ID NO: 48997, SEQ ID NOs: 49013 to 49014, SEQ ID NOs: 49019 to 49020, SEQ ID NO: 49031, SEQ ID NO: 49033, SEQ ID NO: 49043, SEQ ID NO: 49052, SEQ ID NOs: 49061 to 49062, SEQ ID NO: 49068, SEQ ID NO: 49071, SEQ ID NO: 49086, SEQ ID NO: 49102, SEQ ID NO: 49111, SEQ ID NO: 49156, SEQ ID NO: 49164, SEQ ID NO: 49173, SEQ ID NO: 49176, SEQ ID NO: 49183, SEQ ID NO: 49185, SEQ ID NOs: 49200 to 49201, SEQ ID NO: 49209, SEQ ID NO: 49220, SEQ ID NO: 49247, SEQ ID NO: 49251, SEQ ID NO: 49256, SEQ ID NO: 49263, SEQ ID NOs: 49273 to 49274, SEQ ID NOs: 49280 to 49281, SEQ ID NO: 49291, SEQ ID NOs: 49294 to 49295, SEQ ID NO: 49298, SEQ ID NO: 49309, SEQ ID NO: 49319, SEQ ID NO: 49326, SEQ ID NO: 49330, SEQ ID NO: 49340, SEQ ID NOs: 49351 to 49352, SEQ ID NO: 49360, SEQ ID NOs: 49376 to 49377, SEQ ID NO: 49384, SEQ ID NO: 49393, SEQ ID NO: 49395, SEQ ID NO: 49399, SEQ ID NO: 49406, SEQ ID NO: 49411, SEQ ID NOs: 49443 to 49444, SEQ ID NO: 49452, SEQ ID NO: 49462, SEQ ID NO: 49474, SEQ ID NO: 49487, SEQ ID NO: 49499, SEQ ID NO: 49525, SEQ ID NO: 49537, SEQ ID NO: 49540, SEQ ID NO: 49557, SEQ ID NO: 49572, SEQ ID NO: 49584, SEQ ID NO: 49597, SEQ ID NO: 49626, SEQ ID NO: 49630, SEQ ID NO: 49646, SEQ ID NO: 49658, SEQ ID NO: 49671, SEQ ID NO: 49681, SEQ ID NO: 49703, SEQ ID NO: 49728, SEQ ID NO: 49730, SEQ ID NO: 49737, SEQ ID NOs: 49742 to 49743, SEQ ID NOs: 49766 to 49767, SEQ ID NO: 49772, SEQ ID NO: 49782, SEQ ID NOs: 49787 to 49788, SEQ ID NO: 49793, SEQ ID NO: 49796, SEQ ID NO: 49805, SEQ ID NO: 49811, SEQ ID NO: 49823, SEQ ID NO: 49838, SEQ ID NO: 49850, SEQ ID NOs: 49859 to 49860, SEQ ID NO:

49873, SEQ ID NO: 49883, SEQ ID NO: 49892, SEQ ID NO: 49912, SEQ ID NO: 49928, SEQ ID NO: 49948, SEQ ID NO: 49961, SEQ ID NO: 49965, SEQ ID NO: 49987, SEQ ID NO: 49997, SEQ ID NOs: 50017 to 50018, SEQ ID NO: 50020, SEQ ID NO: 50022, SEQ ID NO: 50045, SEQ ID NO: 50062, SEQ ID NO: 50073, SEQ ID NO: 50079, SEQ ID NO: 50090, SEQ ID NO: 50107, SEQ ID NOs: 50111 to 50112, SEQ ID NO: 50123, SEQ ID NO: 50138, SEQ ID NOs: 50165 to 50167, SEQ ID NOs: 50227 to 50228, SEQ ID NO: 50243, SEQ ID NO: 50250, SEQ ID NO: 50254, SEQ ID NO: 50282, SEQ ID NO: 50284, SEQ ID NO: 50290, SEQ ID NO: 50297, SEQ ID NO: 50305, SEQ ID NO: 50309, SEQ ID NO: 50319, SEQ ID NO: 50331, SEQ ID NO: 50334, SEQ ID NO: 50339, SEQ ID NO: 50366, SEQ ID NO: 50388, SEQ ID NO: 50392, SEQ ID NO: 50394, SEQ ID NOs: 50400 to 50401, SEQ ID NO: 50418, SEQ ID NO: 50423, SEQ ID NO: 50428, SEQ ID NO: 50437, SEQ ID NO: 50443, SEQ ID NO: 50450, SEQ ID NO: 50464, SEQ ID NO: 50485, SEQ ID NO: 50494, SEQ ID NO: 50496, SEQ ID NO: 50499, SEQ ID NO: 50526, SEQ ID NO: 50528, SEQ ID NO: 50532, SEQ ID NO: 50538, SEQ ID NO: 50554, SEQ ID NO: 50557, SEQ ID NO: 50560, SEQ ID NO: 50564, SEQ ID NO: 50574, SEQ ID NO: 50585, SEQ ID NO: 50617, SEQ ID NO: 50632, SEQ ID NO: 50634, SEQ ID NO: 50644, SEQ ID NO: 50654, SEQ ID NO: 50678, SEQ ID NO: 50699, SEQ ID NO: 50714, SEQ ID NOs: 50728 to 50729, SEQ ID NO: 50735, SEQ ID NO: 50741, SEQ ID NO: 50744, SEQ ID NO: 50765, SEQ ID NO: 50769, SEQ ID NO: 50793, SEQ ID NO: 50818, SEQ ID NO: 50822, SEQ ID NO: 50826, SEQ ID NO: 50835, SEQ ID NO: 50842, SEQ ID NO: 50847, SEQ ID NO: 50849, SEQ ID NO: 50851, SEQ ID NO: 50893, SEQ ID NO: 50918, SEQ ID NOs: 50935 to 50936, SEQ ID NOs: 50941 to 50944, SEQ ID NOs: 50960 to 50962, SEQ ID NOs: 50975 to 50976, SEQ ID NOs: 51008 to 51009, SEQ ID NO: 51012, SEQ ID NOs: 51021 to 51022, SEQ ID NO: 51046, SEQ ID NO: 51062, SEQ ID NOs: 51068 to 51071, SEQ ID NOs: 51102 to 51104, SEQ ID NO: 51118, SEQ ID NOs: 51168 to 51169, SEQ ID NO: 51214, SEQ ID NO: 51235, SEQ ID NO: 51239, SEQ ID NO: 51241, SEQ ID NO: 51243, SEQ ID NO: 51257, SEQ ID NOs: 51263 to 51266, SEQ ID NOs: 51295 to 51297, SEQ ID NO: 51313, SEQ ID NO: 51405, SEQ ID NOs: 51413 to 51417, SEQ ID NO: 51524, SEQ ID NO: 51526, SEQ ID NO: 51693, SEQ ID NO: 51717, SEQ ID NO: 51762, SEQ ID NO: 51765, SEQ ID NO: 51853, SEQ ID NO: 51878, SEQ ID NO: 52035, SEQ ID NO: 52179, SEQ ID NO: 52275, SEQ ID NO: 52290, SEQ ID NO: 52379, SEQ ID NO: 52463, SEQ ID NO: 52497, SEQ ID NO: 52515, SEQ ID NO: 52652, SEQ ID NO: 52660, SEQ ID NO: 52679, SEQ ID NO: 52686, SEQ ID NO: 52746, SEQ ID NO: 52758, SEQ ID NO: 52816, SEQ ID NO: 52944, SEQ ID NO: 52984, SEQ ID NO: 52988, SEQ ID NO: 52991, SEQ ID NO: 53045, SEQ ID NO: 53118, SEQ ID NO: 53166, SEQ ID NO: 53338, SEQ ID NO: 53382, SEQ ID NO: 53464, SEQ ID NO: 53478, SEQ ID NO: 53511, SEQ ID NO: 53519, SEQ ID NO: 53548, SEQ ID NO: 53581, SEQ ID NO: 53653, SEQ ID NO: 53968, SEQ ID NO: 54024, SEQ ID NO: 54038, SEQ ID NO: 54045, SEQ ID NO: 54080, SEQ ID NO: 54097, SEQ ID NO: 54111, SEQ ID NO: 54238, SEQ ID NO: 54251, SEQ ID NO: 54269, SEQ ID NO: 54409, SEQ ID NO: 54418, SEQ ID NO: 54442, SEQ ID NO: 54473, SEQ ID NO: 54543, SEQ ID NO: 54713, SEQ ID NO: 54719, SEQ ID NO: 54727, SEQ ID NO: 54772, SEQ ID NO: 54788, SEQ ID NO: 54863, SEQ ID NO: 54877, SEQ ID NO: 54945, SEQ ID NO: 54960, SEQ ID NO: 55004, SEQ ID NO: 55109, SEQ ID NO: 55207, SEQ ID NO: 55230, SEQ ID NO: 55300, SEQ ID NO: 55355, SEQ ID NO: 55437, SEQ ID NO: 55516, SEQ ID NO: 55695, SEQ ID NO: 55758, SEQ ID NO: 55801, SEQ ID NO: 55814, SEQ ID NO: 55875, SEQ ID NO: 55879, SEQ ID NO: 55886, SEQ ID NO: 55911, SEQ ID NO: 55986, SEQ ID NO: 56043, SEQ ID NO: 56052, SEQ ID NO: 56175, SEQ ID NO: 56240, SEQ ID NO: 56277, SEQ ID NO: 56352, SEQ ID NO: 56418, SEQ ID NO: 56435, SEQ ID NO: 56521, SEQ ID NO: 56593, SEQ ID NO: 56609, SEQ ID NO: 56629, SEQ ID NOs: 56649 to 56650, SEQ ID NO: 56793, SEQ ID NO: 56836, SEQ ID NO: 56852, SEQ ID NO: 56902, SEQ ID NO: 57155, SEQ ID NO: 57157, SEQ ID NO: 57265, SEQ ID NO: 57278, SEQ ID NO: 57323, SEQ ID NO: 57472, SEQ ID NO: 57535, SEQ ID NO: 57550, SEQ ID NO: 57561, SEQ ID NO: 57568, SEQ ID NO: 57639, SEQ ID NO: 57655, SEQ ID NO: 57790, SEQ ID NO: 57811, SEQ ID NO: 57904, SEQ ID NO: 57944, SEQ ID NO: 58040, SEQ ID NO: 58064, SEQ ID NO: 58075, SEQ ID NO: 58145, SEQ ID NO: 58199, SEQ ID NO: 58223, SEQ ID NO: 58226, SEQ ID NO: 58309, SEQ ID NO: 58349, SEQ ID NO: 58395, SEQ ID NO: 58411, SEQ ID NO: 58433, SEQ ID NO: 58547, SEQ ID NO: 58589, SEQ ID NO: 58679, SEQ ID NOs: 58683 to 58684, SEQ ID NO: 58815, SEQ ID NO: 58823, SEQ ID NO: 58855, SEQ ID NO: 58932, SEQ ID NO: 59223, SEQ ID NO: 59246, SEQ ID NO: 59248, SEQ ID NO: 59530, SEQ ID NO: 59622, SEQ ID NO: 59755, SEQ ID NO: 59757, SEQ ID NO: 59775, SEQ ID NO: 59816, SEQ ID NO: 59821, SEQ ID NO: 59828, SEQ ID NO: 59856, SEQ ID NO: 59871, SEQ ID NO: 59873, SEQ ID NO: 59875, SEQ ID NO: 59960, SEQ ID NO: 59967, SEQ ID NO: 60005, SEQ ID NOs: 60046 to 60047, SEQ ID NO: 60081, SEQ ID NO: 60224, SEQ ID NO: 60228, SEQ ID NO: 60276, SEQ ID NO: 60289, SEQ ID NO: 60292, SEQ ID NOs: 60422 to 60423, SEQ ID NO: 60444, and SEQ ID NOs: 60456 to 68237. In some embodiments, any one of the peptides in the MAGA4 vaccine comprise an amino acid sequence 80, 81, 82, 83, 84, 85, 86, 87, 88, 89, 90, 91, 92, 93, 94, 95, 96, 97, 98 or 99% identical to SEQ ID NO: 41345, SEQ ID NO: 41347, SEQ ID NO: 41352, SEQ ID NOs: 41357 to 41358, SEQ ID NO: 41366, SEQ ID NO: 41377, SEQ ID NO: 41382, SEQ ID NO: 41392, SEQ ID NO: 41396, SEQ ID NO: 41398, SEQ ID NO: 41406, SEQ ID NO: 41411, SEQ ID NO: 41414, SEQ ID NO: 41433, SEQ ID NO: 41436, SEQ ID NO: 41445, SEQ ID NO: 41449, SEQ ID NO: 41455, SEQ ID NO: 41478, SEQ ID NO: 41487, SEQ ID NOs: 41495 to 41496, SEQ ID NO: 41503, SEQ ID NO: 41515, SEQ ID NO: 41520, SEQ ID NO: 41529, SEQ ID NO: 41549, SEQ ID NO: 41553, SEQ ID NO: 41562, SEQ ID NO: 41569, SEQ ID NO: 41574, SEQ ID NO: 41576, SEQ ID NO: 41579, SEQ ID NOs: 41587 to 41588, SEQ ID NO: 41605, SEQ ID NO: 41617, SEQ ID NO: 41620, SEQ ID NO: 41634, SEQ ID NO: 41650, SEQ ID NO: 41665, SEQ ID NO: 41670, SEQ ID NO: 41672, SEQ ID NO: 41696, SEQ ID NO: 41703, SEQ ID NO: 41709, SEQ ID NO: 41725, SEQ ID NOs: 41732 to 41733, SEQ ID NO: 41748, SEQ ID NO: 41760, SEQ ID NO: 41766, SEQ ID NO: 41768, SEQ ID NO: 41770, SEQ ID NO: 41779, SEQ ID NO: 41791, SEQ ID NO: 41797, SEQ ID NO: 41813, SEQ ID NO: 41819, SEQ ID NO: 41825, SEQ ID NO: 41829, SEQ ID NOs: 41846 to 41847, SEQ ID NO: 41853, SEQ ID NO: 41876, SEQ ID NO: 41889, SEQ ID NO: 41892, SEQ ID NO: 41897, SEQ ID NOs: 41906 to 41907, SEQ ID NO: 41912, SEQ ID NO: 41924, SEQ ID NO: 41940, SEQ ID NO: 41953, SEQ ID NO: 41956, SEQ ID NO: 41967, SEQ ID NO: 41970, SEQ ID NO: 41976, SEQ ID NO: 41985, SEQ ID NO: 41990, SEQ ID NO: 42014, SEQ ID NO: 42017, SEQ ID NO: 42026, SEQ ID NO: 42034, SEQ ID NO: 42037, SEQ ID NO: 42046, SEQ ID NO: 42048, SEQ ID NOs: 42056 to 42057, SEQ ID NO: 42080, SEQ ID NO: 42088, SEQ ID NO: 42091, SEQ ID NO: 42102, SEQ ID NO: 42106, SEQ ID NO: 42115, SEQ ID NO: 42120, SEQ ID NO: 42129, SEQ ID NO: 42135, SEQ ID NO: 42138, SEQ ID NO: 42151, SEQ ID NO: 42158, SEQ ID NOs: 42163 to 42164, SEQ ID NOs: 42167 to 42168, SEQ ID NO: 42170, SEQ ID NO: 42186, SEQ ID NO: 42192, SEQ ID NO: 42195, SEQ ID NO: 42198, SEQ ID NO: 42204, SEQ ID NO: 42209, SEQ ID NO: 42218, SEQ ID NO: 42221, SEQ ID NO: 42224, SEQ ID NO: 42229, SEQ ID NO: 42240, SEQ ID NO: 42263, SEQ ID NO: 42265, SEQ ID NO: 42270, SEQ ID NO: 42316, SEQ ID NOs: 42336 to 42337, SEQ ID NO: 42339, SEQ ID NO: 42351, SEQ ID NO: 42354, SEQ ID NO: 42372, SEQ ID NO: 42378, SEQ ID NOs: 42385 to 42386, SEQ ID NO: 42394, SEQ ID NO: 42405, SEQ ID NO: 42409, SEQ ID NO: 42417, SEQ ID NO: 42423, SEQ ID NO: 42439, SEQ ID NO: 42447, SEQ ID NO: 42453, SEQ ID NO: 42458, SEQ ID NOs: 42460 to 42461, SEQ ID NO: 42466, SEQ ID NOs: 42472 to 42473, SEQ ID NOs: 42519 to 42520, SEQ ID NO: 42525, SEQ ID NO: 42528, SEQ ID NO: 42540, SEQ ID NO: 42545, SEQ ID NO: 42550, SEQ ID NOs: 42563 to 42564, SEQ ID NO: 42580, SEQ ID NO: 42605, SEQ ID NO: 42609, SEQ ID NOs: 42612 to 42613, SEQ ID NO: 42615, SEQ ID NO: 42628, SEQ ID NO: 42637, SEQ ID NO: 42648, SEQ ID NO: 42653, SEQ ID NO: 42675, SEQ ID NO: 42680, SEQ ID NO: 42685, SEQ ID NO: 42696, SEQ ID NO: 42703, SEQ ID NO: 42719, SEQ ID NO: 42735, SEQ ID NO: 42743, SEQ ID NO: 42748, SEQ ID NO: 42750, SEQ ID NO: 42768, SEQ ID NO: 42812, SEQ ID NO: 42814, SEQ ID NO: 42822, SEQ ID NO: 42827, SEQ ID NO: 42831, SEQ ID NO: 42846, SEQ ID NO: 42850, SEQ ID NO: 42872, SEQ ID NO: 42886, SEQ ID NO: 42911, SEQ ID NO: 42914, SEQ ID NO: 42923, SEQ ID NO: 42927, SEQ ID NOs: 42957 to 42958, SEQ ID NO: 42962, SEQ ID NO: 42971, SEQ ID NOs: 42997 to 42998, SEQ ID NO: 43002, SEQ ID NO: 43008, SEQ ID NO: 43035, SEQ ID NO: 43046, SEQ ID NO: 43048, SEQ ID NO: 43064, SEQ ID NO: 43083, SEQ ID NO: 43091, SEQ ID NO: 43093, SEQ ID NO: 43148, SEQ ID NO: 43160, SEQ ID NO: 43170, SEQ ID NO: 43175, SEQ ID NO: 43180, SEQ ID NO: 43186, SEQ ID NO: 43193, SEQ ID NO: 43196, SEQ ID NOs: 43231 to 43232, SEQ ID NO: 43238, SEQ ID NO: 43242, SEQ ID NO: 43248, SEQ ID NO: 43253, SEQ ID NO: 43258, SEQ ID NO: 43267, SEQ ID NO: 43274, SEQ ID NO: 43280, SEQ ID NO: 43285, SEQ ID NO: 43295, SEQ ID NO: 43308, SEQ ID NO: 43311, SEQ ID NO: 43329, SEQ ID NO: 43333, SEQ ID NOs: 43339 to 43340, SEQ ID NO: 43362, SEQ ID NO: 43365, SEQ ID NO: 43384, SEQ ID NO: 43389, SEQ ID NO: 43395, SEQ ID NO: 43401, SEQ ID NO: 43429, SEQ ID NO: 43432, SEQ ID NO: 43440, SEQ ID NOs: 43451 to 43453, SEQ ID NO: 43462, SEQ ID NO: 43464, SEQ ID NO: 43467, SEQ ID NO: 43479, SEQ ID NO: 43482, SEQ ID NO: 43496, SEQ ID NO: 43511, SEQ ID NO: 43513, SEQ ID NO: 43517, SEQ ID NO: 43545, SEQ ID NO: 43564, SEQ ID NO: 43573, SEQ ID NO: 43585, SEQ ID NO: 43587, SEQ ID NO: 43591, SEQ ID NO: 43611, SEQ ID NO: 43632, SEQ ID NO: 43636, SEQ ID NO: 43641, SEQ ID NO: 43643, SEQ ID NO: 43651, SEQ ID NO: 43669, SEQ ID NO: 43688, SEQ ID NO: 43696, SEQ ID NO: 43700, SEQ ID NO: 43703, SEQ ID NO: 43707, SEQ ID NO: 43718, SEQ ID NO: 43760, SEQ ID NO: 43763, SEQ ID NO: 43768, SEQ ID NO: 43777, SEQ ID NO: 43780, SEQ ID NO: 43787, SEQ ID NO: 43801, SEQ ID NO: 43808, SEQ ID NO: 43810, SEQ ID NO: 43825, SEQ ID NO: 43827, SEQ ID NO: 43836, SEQ ID NO: 43860, SEQ ID NO: 43867, SEQ ID NOs: 43881 to 43882, SEQ ID NO: 43884, SEQ ID NO: 43887, SEQ ID NOs: 43898 to 43899, SEQ ID NO: 43905, SEQ ID NO: 43915, SEQ ID NO: 43924, SEQ ID NO: 43932, SEQ ID NO: 43958, SEQ ID NO: 43971, SEQ ID NO: 43974, SEQ ID NO: 43978, SEQ ID NOs: 43982 to 43984, SEQ ID NOs: 43986 to 43987, SEQ ID NO: 43993, SEQ ID NO: 43995, SEQ ID NO: 44012, SEQ ID NO: 44035, SEQ ID NO: 44037, SEQ ID NO: 44048, SEQ ID NO: 44050, SEQ ID NO: 44052, SEQ ID NO: 44055, SEQ ID NO: 44063, SEQ ID NO: 44073, SEQ ID NO: 44080, SEQ ID NO: 44085, SEQ ID NO: 44087, SEQ ID NO: 44089, SEQ ID NO: 44112, SEQ ID NO: 44117, SEQ ID NO: 44123, SEQ ID NOs: 44151 to 44152, SEQ ID NO: 44160, SEQ ID NO: 44181, SEQ ID NO: 44207, SEQ ID NO: 44210, SEQ ID NO: 44244, SEQ ID NO: 44246, SEQ ID NO: 44254, SEQ ID NO: 44263, SEQ ID NOs: 44298 to 44299, SEQ ID NO: 44309, SEQ ID NO: 44324, SEQ ID NO: 44328, SEQ ID NO: 44342, SEQ ID NO: 44345, SEQ ID NO: 44359, SEQ ID NO: 44361, SEQ ID NO: 44383, SEQ ID NO: 44401, SEQ ID NO: 44422, SEQ ID NO: 44440, SEQ ID NO: 44452, SEQ ID NO: 44454, SEQ ID NO: 44456, SEQ ID NO: 44463, SEQ ID NO: 44467, SEQ ID NO: 44485, SEQ ID NO: 44512, SEQ ID NO: 44523, SEQ ID NO: 44545, SEQ ID NO: 44552, SEQ ID NO: 44564, SEQ ID NOs: 44566 to 44567, SEQ ID NOs: 44589 to 44591, SEQ ID NO: 44615, SEQ ID NO: 44623, SEQ ID NO: 44631, SEQ ID NO: 44636, SEQ ID NO: 44649, SEQ ID NO: 44654, SEQ ID NO: 44691, SEQ ID NO: 44713, SEQ ID NO: 44722, SEQ ID NO: 44730, SEQ ID NO: 44754, SEQ ID NO: 44756, SEQ ID NOs: 44762 to 44763, SEQ ID NO: 44773, SEQ ID NO: 44781, SEQ ID NO: 44794, SEQ ID NO: 44850, SEQ ID NOs: 44873 to 44875, SEQ ID NO: 44877, SEQ ID NO: 44884, SEQ ID NO: 44908, SEQ ID NO: 44913, SEQ ID NO: 44940, SEQ ID NO: 44955, SEQ ID NO: 44964, SEQ ID NO: 44971, SEQ ID NO: 44976, SEQ ID NO: 45000, SEQ ID NO: 45027, SEQ ID NO: 45035, SEQ ID NO: 45060, SEQ ID NO: 45062, SEQ ID NO: 45095, SEQ ID NO: 45123, SEQ ID NOs: 45126 to 45127, SEQ ID NO: 45132, SEQ ID NO: 45135, SEQ ID NOs: 45138 to 45139, SEQ ID NO: 45193, SEQ ID NO: 45197, SEQ ID NO: 45200, SEQ ID NO: 45223, SEQ ID NO: 45225, SEQ ID NO: 45244, SEQ ID NO: 45262, SEQ ID NO: 45273, SEQ ID NO: 45292, SEQ ID NO: 45302, SEQ ID NO: 45306, SEQ ID NO: 45314, SEQ ID NO: 45380, SEQ ID NO: 45385, SEQ ID NO: 45389, SEQ ID NO: 45398, SEQ ID NO: 45409, SEQ ID NO: 45438, SEQ ID NO: 45444, SEQ ID NOs: 45450 to 45451, SEQ ID NO: 45478, SEQ ID NO: 45480, SEQ ID NO: 45485, SEQ ID NO: 45490, SEQ ID NO: 45510, SEQ ID NO: 45514, SEQ ID NOs: 45519 to 45520, SEQ ID NO: 45530, SEQ ID NO: 45541, SEQ ID NO: 45552, SEQ ID NO: 45556, SEQ ID NOs: 45562 to 45563, SEQ ID NO: 45568, SEQ ID NO: 45577, SEQ ID NOs: 45580 to 45581, SEQ ID NO: 45584, SEQ ID NO: 45588, SEQ ID NO: 45595, SEQ ID NO: 45599, SEQ ID NO: 45632, SEQ ID NO: 45653, SEQ ID NOs: 45666 to 45667, SEQ ID NO: 45675, SEQ ID NO: 45680, SEQ ID NO: 45687, SEQ ID NO: 45697, SEQ ID NOs: 45699 to 45700, SEQ ID NO: 45712, SEQ ID NO: 45714, SEQ ID NO: 45723, SEQ ID NO: 45746, SEQ ID NO: 45765, SEQ ID NO: 45787, SEQ ID NO: 45793, SEQ ID NO: 45818, SEQ ID NO: 45826, SEQ ID NOs: 45829 to 45830, SEQ ID NO: 45835, SEQ ID NO: 45837, SEQ ID NO: 45846, SEQ ID NO: 45859, SEQ ID NO: 45885, SEQ ID NO: 45894, SEQ ID NO: 45904, SEQ ID NO: 45915, SEQ ID NO: 45930, SEQ ID NO: 45938, SEQ ID NO: 45959, SEQ ID NO: 45983, SEQ ID NO: 46006, SEQ ID NO: 46011, SEQ ID NO: 46014, SEQ ID NO: 46044, SEQ ID NO: 46049, SEQ ID NO: 46054, SEQ ID NO: 46058, SEQ ID NO: 46063, SEQ ID NO: 46071, SEQ ID NO: 46077, SEQ ID NO: 46096, SEQ ID NO: 46103, SEQ ID NO: 46108, SEQ ID NO: 46110, SEQ ID NO: 46125, SEQ ID NO: 46133, SEQ ID NOs: 46170 to 46171, SEQ ID NO: 46195, SEQ ID NO: 46208, SEQ ID NO: 46212, SEQ ID NO: 46219, SEQ ID NO: 46226, SEQ ID NO: 46234, SEQ ID NO: 46236, SEQ ID NO: 46261, SEQ ID NO: 46270, SEQ ID NO: 46273, SEQ ID NO: 46275, SEQ ID NO: 46339, SEQ ID NO: 46364, SEQ ID NO: 46376, SEQ ID NOs: 46400 to 46401, SEQ ID NOs: 46421 to 46422, SEQ ID NO: 46433, SEQ ID NOs: 46442 to 46443, SEQ ID NO: 46446, SEQ ID NOs: 46452 to 46454, SEQ ID NO: 46457, SEQ ID NO: 46459, SEQ ID NO: 46462, SEQ ID NO: 46465, SEQ ID NO: 46478, SEQ ID NO: 46484, SEQ ID NO: 46489, SEQ ID NO: 46499, SEQ ID NO: 46512, SEQ ID NO: 46521, SEQ ID NO: 46530, SEQ ID NO: 46536, SEQ ID NO: 46560, SEQ ID NO: 46564, SEQ ID NO: 46570, SEQ ID NO: 46572, SEQ ID NO: 46575, SEQ ID NO: 46579, SEQ ID NO: 46586, SEQ ID NO: 46602, SEQ ID NO: 46616, SEQ ID NO: 46621, SEQ ID NO: 46628, SEQ ID NO: 46637, SEQ ID NO: 46642, SEQ ID NO: 46648, SEQ ID NO: 46652, SEQ ID NO: 46655, SEQ ID NO: 46660, SEQ ID NO: 46663, SEQ ID NOs: 46665 to 46666, SEQ ID NO: 46676, SEQ ID NOs: 46678 to 46679, SEQ ID NO: 46682, SEQ ID NO: 46685, SEQ ID NO: 46689, SEQ ID NO: 46713, SEQ ID NO: 46715, SEQ ID NO: 46736, SEQ ID NO: 46739, SEQ ID NO: 46770, SEQ ID NO: 46777, SEQ ID NO: 46800, SEQ ID NOs: 46823 to 46825, SEQ ID NO: 46831, SEQ ID NO: 46872, SEQ ID NO: 46880, SEQ ID NO: 46897, SEQ ID NO: 46916, SEQ ID NO: 46928, SEQ ID NO: 46937, SEQ ID NO: 46950, SEQ ID NO: 46978, SEQ ID NO: 46981, SEQ ID NO: 46983, SEQ ID NO: 46989, SEQ ID NO: 46991, SEQ ID NO: 46993, SEQ ID NO: 47003, SEQ ID NO: 47006, SEQ ID NO: 47017, SEQ ID NO: 47028, SEQ ID NO: 47045, SEQ ID NO: 47047, SEQ ID NO: 47057, SEQ ID NOs: 47079 to 47080, SEQ ID NO: 47082, SEQ ID NO: 47114, SEQ ID NO: 47119, SEQ ID NO: 47123, SEQ ID NOs: 47137 to 47139, SEQ ID NO: 47151, SEQ ID NO: 47158, SEQ ID NO: 47167, SEQ ID NO: 47172, SEQ ID NO: 47186, SEQ ID NO: 47191, SEQ ID NO: 47206, SEQ ID NO: 47224, SEQ ID NO: 47298, SEQ ID NO: 47316, SEQ ID NO: 47324, SEQ ID NOs: 47331 to 47332, SEQ ID NO: 47335, SEQ ID NO: 47356, SEQ ID NO: 47358, SEQ ID NOs: 47360 to 47361, SEQ ID NOs: 47377 to 47378, SEQ ID NO: 47381, SEQ ID NO: 47405, SEQ ID NO: 47412, SEQ ID NO: 47416, SEQ ID NO: 47422, SEQ ID NO: 47425, SEQ ID NO: 47427, SEQ ID NOs: 47432 to 47433, SEQ ID NO: 47445, SEQ ID NO: 47451, SEQ ID NO: 47460, SEQ ID NO: 47482, SEQ ID NO: 47491, SEQ ID NO: 47509, SEQ ID NO: 47516, SEQ ID NOs: 47533 to 47535, SEQ ID NOs: 47538 to 47539, SEQ ID NO: 47555, SEQ ID NO: 47561, SEQ ID NOs: 47575 to 47576, SEQ ID NO: 47582, SEQ ID NO: 47592, SEQ ID NO: 47614, SEQ ID NO: 47625, SEQ ID NO: 47630, SEQ ID NO: 47637, SEQ ID NO: 47643, SEQ ID NO: 47654, SEQ ID NO: 47673, SEQ ID NO: 47689, SEQ ID NO: 47698, SEQ ID NO: 47701, SEQ ID NO: 47727, SEQ ID NO: 47749, SEQ ID NOs: 47759 to 47760, SEQ ID NO: 47767, SEQ ID NO: 47773, SEQ ID NO: 47782, SEQ ID NO: 47790, SEQ ID NO: 47793, SEQ ID NO: 47799, SEQ ID NO: 47806, SEQ ID NO: 47809, SEQ ID NO: 47834, SEQ ID NO: 47840, SEQ ID NO: 47844, SEQ ID NO: 47848, SEQ ID NO: 47855, SEQ ID NO: 47867, SEQ ID NO: 47890, SEQ ID NO: 47895, SEQ ID NO: 47899, SEQ ID NO: 47902, SEQ ID NO: 47923, SEQ ID NO: 47927, SEQ ID NOs: 47959 to 47960, SEQ ID NO: 47964, SEQ ID NO: 47979, SEQ ID NO: 47984, SEQ ID NO: 47986, SEQ ID NOs: 48030 to 48031, SEQ ID NO: 48034, SEQ ID NO: 48059, SEQ ID NO: 48093, SEQ ID NO: 48107, SEQ ID NO: 48113, SEQ ID NO: 48118, SEQ ID NO: 48121, SEQ ID NO: 48129, SEQ ID NOs: 48138 to 48139, SEQ ID NO: 48144, SEQ ID NO: 48158, SEQ ID NO: 48160, SEQ ID NO: 48162, SEQ ID NO: 48175, SEQ ID NO: 48186, SEQ ID NO: 48203, SEQ ID NO: 48210, SEQ ID NO: 48213, SEQ ID NO: 48220, SEQ ID NO: 48224, SEQ ID NO: 48229, SEQ ID NO: 48258, SEQ ID NO: 48266, SEQ ID NO: 48273, SEQ ID NO: 48280, SEQ ID NO: 48286, SEQ ID NO: 48295, SEQ ID NOs: 48300 to 48301, SEQ ID NOs: 48306 to 48307, SEQ ID NO: 48315, SEQ ID NO: 48347, SEQ ID NO: 48353, SEQ ID NO: 48358, SEQ ID NO: 48366, SEQ ID NO: 48371, SEQ ID NO: 48379, SEQ ID NO: 48387, SEQ ID NO: 48400, SEQ ID NO: 48415, SEQ ID NOs: 48418 to 48419, SEQ ID NO: 48436, SEQ ID NOs: 48438 to 48440, SEQ ID NO: 48443, SEQ ID NO: 48452, SEQ ID NOs: 48461 to 48462, SEQ ID NO: 48466, SEQ ID NO: 48469, SEQ ID NO: 48520, SEQ ID NO: 48537, SEQ ID NO: 48545, SEQ ID NO: 48574, SEQ ID NOs: 48576 to 48578, SEQ ID NO: 48594, SEQ ID NO: 48599, SEQ ID NO: 48614, SEQ ID NO: 48627, SEQ ID NO: 48642, SEQ ID NO: 48648, SEQ ID NO: 48654, SEQ ID NO: 48656, SEQ ID NO: 48666, SEQ ID NOs: 48669 to 48670, SEQ ID NO: 48674, SEQ ID NOs: 48680 to 48681, SEQ ID NO: 48684, SEQ ID NO: 48686, SEQ ID NO: 48692, SEQ ID NO: 48701, SEQ ID NO: 48705, SEQ ID NO: 48714, SEQ ID NO: 48717, SEQ ID NO: 48735, SEQ ID NO: 48738, SEQ ID NO: 48749, SEQ ID NO: 48751, SEQ ID NO: 48764, SEQ ID NO: 48769, SEQ ID NO: 48793, SEQ ID NO: 48796, SEQ ID NOs: 48799 to 48800, SEQ ID NOs: 48802 to 48803, SEQ ID NO: 48818, SEQ ID NO: 48832, SEQ ID NO: 48834, SEQ ID NO: 48838, SEQ ID NO: 48845, SEQ ID NO: 48856, SEQ ID NO: 48877, SEQ ID NO: 48884, SEQ ID NO: 48903, SEQ ID NO: 48936, SEQ ID NO: 48947, SEQ ID NOs: 48968 to 48970, SEQ ID NO: 48974, SEQ ID NOs: 48981 to 48982, SEQ ID NO: 48997, SEQ ID NOs: 49013 to 49014, SEQ ID NOs: 49019 to 49020, SEQ ID NO: 49031, SEQ ID NO: 49033, SEQ ID NO: 49043, SEQ ID NO: 49052, SEQ ID NOs: 49061 to 49062, SEQ ID NO: 49068, SEQ ID NO: 49071, SEQ ID NO: 49086, SEQ ID NO: 49102, SEQ ID NO: 49111, SEQ ID NO: 49156, SEQ ID NO: 49164, SEQ ID NO: 49173, SEQ ID NO: 49176, SEQ ID NO: 49183, SEQ ID NO: 49185, SEQ ID NOs: 49200 to 49201, SEQ ID NO: 49209, SEQ ID NO: 49220, SEQ ID NO: 49247, SEQ ID NO: 49251, SEQ ID NO: 49256, SEQ ID NO: 49263, SEQ ID NOs: 49273 to 49274, SEQ ID NOs: 49280 to 49281, SEQ ID NO: 49291, SEQ ID NOs: 49294 to 49295, SEQ ID NO: 49298, SEQ ID NO: 49309, SEQ ID NO: 49319, SEQ ID NO: 49326, SEQ ID NO: 49330, SEQ ID NO: 49340, SEQ ID NOs: 49351 to 49352, SEQ ID NO: 49360, SEQ ID NOs: 49376 to 49377, SEQ ID NO: 49384, SEQ ID NO: 49393, SEQ ID NO: 49395, SEQ ID NO: 49399, SEQ ID NO: 49406, SEQ ID NO: 49411, SEQ ID NOs: 49443 to 49444, SEQ ID NO: 49452, SEQ ID NO: 49462, SEQ ID NO: 49474, SEQ ID NO: 49487, SEQ ID NO: 49499, SEQ ID NO: 49525, SEQ ID NO: 49537, SEQ ID NO: 49540, SEQ ID NO: 49557, SEQ ID NO: 49572, SEQ ID NO: 49584, SEQ ID NO: 49597, SEQ ID NO: 49626, SEQ ID NO: 49630, SEQ ID NO: 49646, SEQ ID NO: 49658, SEQ ID NO: 49671, SEQ ID NO: 49681, SEQ ID NO: 49703, SEQ ID NO: 49728, SEQ ID NO: 49730, SEQ ID NO: 49737, SEQ ID NOs: 49742 to 49743, SEQ ID NOs: 49766 to 49767, SEQ ID NO: 49772, SEQ ID NO: 49782, SEQ ID NOs: 49787 to 49788, SEQ ID NO: 49793, SEQ ID NO: 49796, SEQ ID NO: 49805, SEQ ID NO: 49811, SEQ ID NO: 49823, SEQ ID NO: 49838, SEQ ID NO: 49850, SEQ ID NOs: 49859 to 49860, SEQ ID NO: 49873, SEQ ID NO: 49883, SEQ ID NO: 49892, SEQ ID NO: 49912, SEQ ID NO: 49928, SEQ ID NO: 49948, SEQ ID NO: 49961, SEQ ID NO: 49965, SEQ ID NO: 49987, SEQ ID NO: 49997, SEQ ID NOs: 50017 to 50018, SEQ ID NO: 50020, SEQ ID NO: 50022, SEQ ID NO: 50045, SEQ ID NO: 50062, SEQ ID NO: 50073, SEQ ID NO: 50079, SEQ ID NO: 50090, SEQ ID NO: 50107, SEQ ID NOs: 50111 to 50112, SEQ ID NO: 50123, SEQ ID NO: 50138, SEQ ID NOs: 50165 to 50167, SEQ ID NOs: 50227 to 50228, SEQ ID NO: 50243, SEQ ID NO: 50250, SEQ ID NO: 50254, SEQ ID NO: 50282, SEQ ID NO: 50284, SEQ ID NO: 50290, SEQ ID NO: 50297, SEQ ID NO: 50305, SEQ ID NO: 50309, SEQ ID NO: 50319, SEQ ID NO: 50331, SEQ ID NO: 50334, SEQ ID NO: 50339, SEQ ID NO: 50366, SEQ ID NO: 50388, SEQ ID NO: 50392, SEQ ID NO: 50394, SEQ ID NOs: 50400 to 50401, SEQ ID NO: 50418, SEQ ID NO: 50423, SEQ ID NO: 50428, SEQ ID NO: 50437, SEQ ID NO: 50443, SEQ ID NO: 50450, SEQ ID NO: 50464, SEQ ID NO: 50485, SEQ ID NO: 50494, SEQ ID NO: 50496, SEQ ID NO: 50499, SEQ ID NO: 50526, SEQ ID NO: 50528, SEQ ID NO: 50532, SEQ ID NO: 50538, SEQ ID NO: 50554, SEQ ID NO: 50557, SEQ ID NO: 50560, SEQ ID NO: 50564, SEQ ID NO: 50574, SEQ ID NO: 50585, SEQ ID NO: 50617, SEQ ID NO: 50632, SEQ ID NO: 50634, SEQ ID NO: 50644, SEQ ID NO: 50654, SEQ ID NO: 50678, SEQ ID NO: 50699, SEQ ID NO: 50714, SEQ ID NOs: 50728 to 50729, SEQ ID NO: 50735, SEQ ID NO: 50741, SEQ ID NO: 50744, SEQ ID NO: 50765, SEQ ID NO: 50769, SEQ ID NO: 50793, SEQ ID NO: 50818, SEQ ID NO: 50822, SEQ ID NO: 50826, SEQ ID NO: 50835, SEQ ID NO: 50842, SEQ ID NO: 50847, SEQ ID NO: 50849, SEQ ID NO: 50851, SEQ ID NO: 50893, SEQ ID NO: 50918, SEQ ID NOs: 50935 to 50936, SEQ ID NOs: 50941 to 50944, SEQ ID NOs: 50960 to 50962, SEQ ID NOs: 50975 to 50976, SEQ ID NOs: 51008 to 51009, SEQ ID NO: 51012, SEQ ID NOs: 51021 to 51022, SEQ ID NO: 51046, SEQ ID NO: 51062, SEQ ID NOs: 51068 to 51071, SEQ ID NOs: 51102 to 51104, SEQ ID NO: 51118, SEQ ID NOs: 51168 to 51169, SEQ ID NO: 51214, SEQ ID NO: 51235, SEQ ID NO: 51239, SEQ ID NO: 51241, SEQ ID NO: 51243, SEQ ID NO: 51257, SEQ ID NOs: 51263 to 51266, SEQ ID NOs: 51295 to 51297, SEQ ID NO: 51313, SEQ ID NO: 51405, SEQ ID NOs: 51413 to 51417, SEQ ID NO: 51524, SEQ ID NO: 51526, SEQ ID NO: 51693, SEQ ID NO: 51717, SEQ ID NO: 51762, SEQ ID NO: 51765, SEQ ID NO: 51853, SEQ ID NO: 51878, SEQ ID NO: 52035, SEQ ID NO: 52179, SEQ ID NO: 52275, SEQ ID NO: 52290, SEQ ID NO: 52379, SEQ ID NO: 52463, SEQ ID NO: 52497, SEQ ID NO: 52515, SEQ ID NO: 52652, SEQ ID NO: 52660, SEQ ID NO: 52679, SEQ ID NO: 52686, SEQ ID NO: 52746, SEQ ID NO: 52758, SEQ ID NO: 52816, SEQ ID NO: 52944, SEQ ID NO: 52984, SEQ ID NO: 52988, SEQ ID NO: 52991, SEQ ID NO: 53045, SEQ ID NO: 53118, SEQ ID NO: 53166, SEQ ID NO: 53338, SEQ ID NO: 53382, SEQ ID NO: 53464, SEQ ID NO: 53478, SEQ ID NO: 53511, SEQ ID NO: 53519, SEQ ID NO: 53548, SEQ ID NO: 53581, SEQ ID NO: 53653, SEQ ID NO: 53968, SEQ ID NO: 54024, SEQ ID NO: 54038, SEQ ID NO: 54045, SEQ ID NO: 54080, SEQ ID NO: 54097, SEQ ID NO: 54111, SEQ ID NO: 54238, SEQ ID NO: 54251, SEQ ID NO: 54269, SEQ ID NO: 54409, SEQ ID NO: 54418, SEQ ID NO: 54442, SEQ ID NO: 54473, SEQ ID NO: 54543, SEQ ID NO: 54713, SEQ ID NO: 54719, SEQ ID NO: 54727, SEQ ID NO: 54772, SEQ ID NO: 54788, SEQ ID NO: 54863, SEQ ID NO: 54877, SEQ ID NO: 54945, SEQ ID NO: 54960, SEQ ID NO: 55004, SEQ ID NO: 55109, SEQ ID NO: 55207, SEQ ID NO: 55230, SEQ ID NO: 55300, SEQ ID NO: 55355, SEQ ID NO: 55437, SEQ ID NO: 55516, SEQ ID NO: 55695, SEQ ID NO: 55758, SEQ ID NO: 55801, SEQ ID NO: 55814, SEQ ID NO: 55875, SEQ ID NO: 55879, SEQ ID NO: 55886, SEQ ID NO: 55911, SEQ ID NO: 55986, SEQ ID NO: 56043, SEQ ID NO: 56052, SEQ ID NO: 56175, SEQ ID NO: 56240, SEQ ID NO: 56277, SEQ ID NO: 56352, SEQ ID NO: 56418, SEQ ID NO: 56435, SEQ ID NO: 56521, SEQ ID NO: 56593, SEQ ID NO: 56609, SEQ ID NO: 56629, SEQ ID NOs: 56649 to 56650, SEQ ID NO: 56793, SEQ ID NO: 56836, SEQ ID NO: 56852, SEQ ID NO: 56902, SEQ ID NO: 57155, SEQ ID NO: 57157, SEQ ID NO: 57265, SEQ ID NO: 57278, SEQ ID NO: 57323, SEQ ID NO: 57472, SEQ ID NO: 57535, SEQ ID NO: 57550, SEQ ID NO: 57561, SEQ ID NO: 57568, SEQ ID NO: 57639, SEQ ID NO: 57655, SEQ ID NO: 57790, SEQ ID NO: 57811, SEQ ID NO: 57904, SEQ ID NO: 57944, SEQ ID NO: 58040, SEQ ID NO: 58064, SEQ ID NO: 58075, SEQ ID NO: 58145, SEQ ID NO: 58199, SEQ ID NO: 58223, SEQ ID NO: 58226, SEQ ID NO: 58309, SEQ ID NO: 58349, SEQ ID NO: 58395, SEQ ID NO: 58411, SEQ ID NO: 58433, SEQ ID NO: 58547, SEQ ID NO: 58589, SEQ ID NO: 58679, SEQ ID NOs: 58683 to 58684, SEQ ID NO: 58815, SEQ ID NO: 58823, SEQ ID NO: 58855, SEQ ID NO: 58932, SEQ ID NO: 59223, SEQ ID NO: 59246, SEQ ID NO: 59248, SEQ ID NO: 59530, SEQ ID NO: 59622, SEQ ID NO: 59755, SEQ ID NO: 59757, SEQ ID NO: 59775, SEQ ID NO: 59816, SEQ ID NO: 59821, SEQ ID NO: 59828, SEQ ID NO: 59856, SEQ ID NO: 59871, SEQ ID NO: 59873, SEQ ID NO: 59875, SEQ ID NO: 59960, SEQ ID NO: 59967, SEQ ID NO: 60005, SEQ ID NOs: 60046 to 60047, SEQ ID NO: 60081, SEQ ID NO: 60224, SEQ ID NO: 60228, SEQ ID NO: 60276, SEQ ID NO: 60289, SEQ ID NO: 60292, SEQ ID NOs: 60422 to 60423, SEQ ID NO: 60444, or SEQ ID NOs: 60456 to 68237.

In some embodiments, the amino acid sequence for a MEW class I peptide vaccine for the MAGC1 protein comprises one or more of the SEQ ID NO: 49395, SEQ ID NO: 50632, and SEQ ID NOs: 68238 to 68321. In some embodiments, any one of the peptides in the MAGC1 vaccine comprise an amino acid sequence 80, 81, 82, 83, 84, 85, 86, 87, 88, 89, 90, 91, 92, 93, 94, 95, 96, 97, 98 or 99% identical to SEQ ID NO: 49395, SEQ ID NO: 50632, or SEQ ID NOs: 68238 to 68321.

In some embodiments, the amino acid sequence for a MEW class I peptide vaccine for the MAGC1 protein comprises one or more of the SEQ ID NO: 41352, SEQ ID NO: 41478, SEQ ID NO: 41495, SEQ ID NO: 41725, SEQ ID NO: 41847, SEQ ID NO: 42129, SEQ ID NO: 42135, SEQ ID NO: 42168, SEQ ID NO: 42170, SEQ ID NO: 42195, SEQ ID NO: 42218, SEQ ID NO: 42229, SEQ ID NO: 42458, SEQ ID NO: 42545, SEQ ID NO: 42628, SEQ ID NO: 42653, SEQ ID NO: 42685, SEQ ID NO: 42703, SEQ ID NO: 42872, SEQ ID NO: 43008, SEQ ID NO: 43046, SEQ ID NO: 43083, SEQ ID NO: 43333, SEQ ID NO: 43429, SEQ ID NO: 43564, SEQ ID NO: 43780, SEQ ID NO: 43836, SEQ ID NO: 43881, SEQ ID NO: 43898, SEQ ID NO: 43932, SEQ ID NO: 44048, SEQ ID NO: 44181, SEQ ID NO: 44328, SEQ ID NO: 44456, SEQ ID NO: 44523, SEQ ID NO: 44566, SEQ ID NO: 44773, SEQ ID NO: 44877, SEQ ID NO: 45197, SEQ ID NO: 45385, SEQ ID NO: 45450, SEQ ID NO: 45556, SEQ ID NO: 45580, SEQ ID NO: 45584, SEQ ID NO: 45599, SEQ ID NO: 45765, SEQ ID NO: 45829, SEQ ID NO: 45894, SEQ ID NO: 45915, SEQ ID NO: 46273, SEQ ID NO: 46400, SEQ ID NO: 46421, SEQ ID NO: 46457, SEQ ID NO: 46459, SEQ ID NO: 46484, SEQ ID NO: 46666, SEQ ID NO: 46678, SEQ ID NO: 46689, SEQ ID NO: 46981, SEQ ID NO: 46991, SEQ ID NO: 46993, SEQ ID NO: 47047, SEQ ID NO: 47151, SEQ ID NO: 47324, SEQ ID NO: 47432, SEQ ID NO: 47592, SEQ ID NO: 47673, SEQ ID NO: 47895, SEQ ID NO: 47960, SEQ ID NO: 47964, SEQ ID NO: 47979, SEQ ID NO: 47984, SEQ ID NO: 48034, SEQ ID NO: 48113, SEQ ID NO: 48118, SEQ ID NO: 48300, SEQ ID NO: 48436, SEQ ID NOs: 48461 to 48462, SEQ ID NO: 48469, SEQ ID NO: 48574, SEQ ID NO: 48680, SEQ ID NO: 48796, SEQ ID NO: 48832, SEQ ID NO: 48838, SEQ ID NO: 48845, SEQ ID NO: 48877, SEQ ID NO: 48947, SEQ ID NO: 49019, SEQ ID NO: 49111, SEQ ID NO: 49176, SEQ ID NO: 49263, SEQ ID NO: 49395, SEQ ID NO: 49462, SEQ ID NO: 49557, SEQ ID NO: 49823, SEQ ID NO: 49883, SEQ ID NO: 50062, SEQ ID NO: 50167, SEQ ID NO: 50305, SEQ ID NO: 50394, SEQ ID NO: 50401, SEQ ID NO: 50423, SEQ ID NO: 50428, SEQ ID NO: 50443, SEQ ID NO: 50450, SEQ ID NO: 50564, SEQ ID NO: 50574, SEQ ID NO: 50632, SEQ ID NO: 50678, and SEQ ID NOs: 68238 to 95592. In some embodiments, any one of the peptides in the MAGC1 vaccine comprise an amino acid sequence 80, 81, 82, 83, 84, 85, 86, 87, 88, 89, 90, 91, 92, 93, 94, 95, 96, 97, 98 or 99% identical to SEQ ID NO: 41352, SEQ ID NO: 41478, SEQ ID NO: 41495, SEQ ID NO: 41725, SEQ ID NO: 41847, SEQ ID NO: 42129, SEQ ID NO: 42135, SEQ ID NO: 42168, SEQ ID NO: 42170, SEQ ID NO: 42195, SEQ ID NO: 42218, SEQ ID NO: 42229, SEQ ID NO: 42458, SEQ ID NO: 42545, SEQ ID NO: 42628, SEQ ID NO: 42653, SEQ ID NO: 42685, SEQ ID NO: 42703, SEQ ID NO: 42872, SEQ ID NO: 43008, SEQ ID NO: 43046, SEQ ID NO: 43083, SEQ ID NO: 43333, SEQ ID NO: 43429, SEQ ID NO: 43564, SEQ ID NO: 43780, SEQ ID NO: 43836, SEQ ID NO: 43881, SEQ ID NO: 43898, SEQ ID NO: 43932, SEQ ID NO: 44048, SEQ ID NO: 44181, SEQ ID NO: 44328, SEQ ID NO: 44456, SEQ ID NO: 44523, SEQ ID NO: 44566, SEQ ID NO: 44773, SEQ ID NO: 44877, SEQ ID NO: 45197, SEQ ID NO: 45385, SEQ ID NO: 45450, SEQ ID NO: 45556, SEQ ID NO: 45580, SEQ ID NO: 45584, SEQ ID NO: 45599, SEQ ID NO: 45765, SEQ ID NO: 45829, SEQ ID NO: 45894, SEQ ID NO: 45915, SEQ ID NO: 46273, SEQ ID NO: 46400, SEQ ID NO: 46421, SEQ ID NO: 46457, SEQ ID NO: 46459, SEQ ID NO: 46484, SEQ ID NO: 46666, SEQ ID NO: 46678, SEQ ID NO: 46689, SEQ ID NO: 46981, SEQ ID NO: 46991, SEQ ID NO: 46993, SEQ ID NO: 47047, SEQ ID NO: 47151, SEQ ID NO: 47324, SEQ ID NO: 47432, SEQ ID NO: 47592, SEQ ID NO: 47673, SEQ ID NO: 47895, SEQ ID NO: 47960, SEQ ID NO: 47964, SEQ ID NO: 47979, SEQ ID NO: 47984, SEQ ID NO: 48034, SEQ ID NO: 48113, SEQ ID NO: 48118, SEQ ID NO: 48300, SEQ ID NO: 48436, SEQ ID NOs: 48461 to 48462, SEQ ID NO: 48469, SEQ ID NO: 48574, SEQ ID NO: 48680, SEQ ID NO: 48796, SEQ ID NO: 48832, SEQ ID NO: 48838, SEQ ID NO: 48845, SEQ ID NO: 48877, SEQ ID NO: 48947, SEQ ID NO: 49019, SEQ ID NO: 49111, SEQ ID NO: 49176, SEQ ID NO: 49263, SEQ ID NO: 49395, SEQ ID NO: 49462, SEQ ID NO: 49557, SEQ ID NO: 49823, SEQ ID NO: 49883, SEQ ID NO: 50062, SEQ ID NO: 50167, SEQ ID NO: 50305, SEQ ID NO: 50394, SEQ ID NO: 50401, SEQ ID NO: 50423, SEQ ID NO: 50428, SEQ ID NO: 50443, SEQ ID NO: 50450, SEQ ID NO: 50564, SEQ ID NO: 50574, SEQ ID NO: 50632, SEQ ID NO: 50678, or SEQ ID NOs: 68238 to 95592.

In some embodiments, the amino acid sequence for a MEW class I peptide vaccine for the MAGC1 protein comprises two or more of the SEQ ID NO: 49395, SEQ ID NO: 50632, and SEQ ID NOs: 68238 to 68321. In some embodiments, any one of the peptides in the MAGC1 vaccine comprise an amino acid sequence 80, 81, 82, 83, 84, 85, 86, 87, 88, 89, 90, 91, 92, 93, 94, 95, 96, 97, 98 or 99% identical to SEQ ID NO: 49395, SEQ ID NO: 50632, or SEQ ID NOs: 68238 to 68321.

In some embodiments, the amino acid sequence for a MEW class I peptide vaccine for the MAGC1 protein comprises two or more of the SEQ ID NO: 41352, SEQ ID NO: 41478, SEQ ID NO: 41495, SEQ ID NO: 41725, SEQ ID NO: 41847, SEQ ID NO: 42129, SEQ ID NO: 42135, SEQ ID NO: 42168, SEQ ID NO: 42170, SEQ ID NO: 42195, SEQ ID NO: 42218, SEQ ID NO: 42229, SEQ ID NO: 42458, SEQ ID NO: 42545, SEQ ID NO: 42628, SEQ ID NO: 42653, SEQ ID NO: 42685, SEQ ID NO: 42703, SEQ ID NO: 42872, SEQ ID NO: 43008, SEQ ID NO: 43046, SEQ ID NO: 43083, SEQ ID NO: 43333, SEQ ID NO: 43429, SEQ ID NO: 43564, SEQ ID NO: 43780, SEQ ID NO: 43836, SEQ ID NO: 43881, SEQ ID NO: 43898, SEQ ID NO: 43932, SEQ ID NO: 44048, SEQ ID NO: 44181, SEQ ID NO: 44328, SEQ ID NO: 44456, SEQ ID NO: 44523, SEQ ID NO: 44566, SEQ ID NO: 44773, SEQ ID NO: 44877, SEQ ID NO: 45197, SEQ ID NO: 45385, SEQ ID NO: 45450, SEQ ID NO: 45556, SEQ ID NO: 45580, SEQ ID NO: 45584, SEQ ID NO: 45599, SEQ ID NO: 45765, SEQ ID NO: 45829, SEQ ID NO: 45894, SEQ ID NO: 45915, SEQ ID NO: 46273, SEQ ID NO: 46400, SEQ ID NO: 46421, SEQ ID NO: 46457, SEQ ID NO: 46459, SEQ ID NO: 46484, SEQ ID NO: 46666, SEQ ID NO: 46678, SEQ ID NO: 46689, SEQ ID NO: 46981, SEQ ID NO: 46991, SEQ ID NO: 46993, SEQ ID NO: 47047, SEQ ID NO: 47151, SEQ ID NO: 47324, SEQ ID NO: 47432, SEQ ID NO: 47592, SEQ ID NO: 47673, SEQ ID NO: 47895, SEQ ID NO: 47960, SEQ ID NO: 47964, SEQ ID NO: 47979, SEQ ID NO: 47984, SEQ ID NO: 48034, SEQ ID NO: 48113, SEQ ID NO: 48118, SEQ ID NO: 48300, SEQ ID NO: 48436, SEQ ID NOs: 48461 to 48462, SEQ ID NO: 48469, SEQ ID NO: 48574, SEQ ID NO: 48680, SEQ ID NO: 48796, SEQ ID NO: 48832, SEQ ID NO: 48838, SEQ ID NO: 48845, SEQ ID NO: 48877, SEQ ID NO: 48947, SEQ ID NO: 49019, SEQ ID NO: 49111, SEQ ID NO: 49176, SEQ ID NO: 49263, SEQ ID NO: 49395, SEQ ID NO: 49462, SEQ ID NO: 49557, SEQ ID NO: 49823, SEQ ID NO: 49883, SEQ ID NO: 50062, SEQ ID NO: 50167, SEQ ID NO: 50305, SEQ ID NO: 50394, SEQ ID NO: 50401, SEQ ID NO: 50423, SEQ ID NO: 50428, SEQ ID NO: 50443, SEQ ID NO: 50450, SEQ ID NO: 50564, SEQ ID NO: 50574, SEQ ID NO: 50632, SEQ ID NO: 50678, and SEQ ID NOs: 68238 to 95592. In some embodiments, any one of the peptides in the MAGC1 vaccine comprise an amino acid sequence 80, 81, 82, 83, 84, 85, 86, 87, 88, 89, 90, 91, 92, 93, 94, 95, 96, 97, 98 or 99% identical to SEQ ID NO: 41352, SEQ ID NO: 41478, SEQ ID NO: 41495, SEQ ID NO: 41725, SEQ ID NO: 41847, SEQ ID NO: 42129, SEQ ID NO: 42135, SEQ ID NO: 42168, SEQ ID NO: 42170, SEQ ID NO: 42195, SEQ ID NO: 42218, SEQ ID NO: 42229, SEQ ID NO: 42458, SEQ ID NO: 42545, SEQ ID NO: 42628, SEQ ID NO: 42653, SEQ ID NO: 42685, SEQ ID NO: 42703, SEQ ID NO:

42872, SEQ ID NO: 43008, SEQ ID NO: 43046, SEQ ID NO: 43083, SEQ ID NO: 43333, SEQ ID NO: 43429, SEQ ID NO: 43564, SEQ ID NO: 43780, SEQ ID NO: 43836, SEQ ID NO: 43881, SEQ ID NO: 43898, SEQ ID NO: 43932, SEQ ID NO: 44048, SEQ ID NO: 44181, SEQ ID NO: 44328, SEQ ID NO: 44456, SEQ ID NO: 44523, SEQ ID NO: 44566, SEQ ID NO: 44773, SEQ ID NO: 44877, SEQ ID NO: 45197, SEQ ID NO: 45385, SEQ ID NO: 45450, SEQ ID NO: 45556, SEQ ID NO: 45580, SEQ ID NO: 45584, SEQ ID NO: 45599, SEQ ID NO: 45765, SEQ ID NO: 45829, SEQ ID NO: 45894, SEQ ID NO: 45915, SEQ ID NO: 46273, SEQ ID NO: 46400, SEQ ID NO: 46421, SEQ ID NO: 46457, SEQ ID NO: 46459, SEQ ID NO: 46484, SEQ ID NO: 46666, SEQ ID NO: 46678, SEQ ID NO: 46689, SEQ ID NO: 46981, SEQ ID NO: 46991, SEQ ID NO: 46993, SEQ ID NO: 47047, SEQ ID NO: 47151, SEQ ID NO: 47324, SEQ ID NO: 47432, SEQ ID NO: 47592, SEQ ID NO: 47673, SEQ ID NO: 47895, SEQ ID NO: 47960, SEQ ID NO: 47964, SEQ ID NO: 47979, SEQ ID NO: 47984, SEQ ID NO: 48034, SEQ ID NO: 48113, SEQ ID NO: 48118, SEQ ID NO: 48300, SEQ ID NO: 48436, SEQ ID NOs: 48461 to 48462, SEQ ID NO: 48469, SEQ ID NO: 48574, SEQ ID NO: 48680, SEQ ID NO: 48796, SEQ ID NO: 48832, SEQ ID NO: 48838, SEQ ID NO: 48845, SEQ ID NO: 48877, SEQ ID NO: 48947, SEQ ID NO: 49019, SEQ ID NO: 49111, SEQ ID NO: 49176, SEQ ID NO: 49263, SEQ ID NO: 49395, SEQ ID NO: 49462, SEQ ID NO: 49557, SEQ ID NO: 49823, SEQ ID NO: 49883, SEQ ID NO: 50062, SEQ ID NO: 50167, SEQ ID NO: 50305, SEQ ID NO: 50394, SEQ ID NO: 50401, SEQ ID NO: 50423, SEQ ID NO: 50428, SEQ ID NO: 50443, SEQ ID NO: 50450, SEQ ID NO: 50564, SEQ ID NO: 50574, SEQ ID NO: 50632, SEQ ID NO: 50678, or SEQ ID NOs: 68238 to 95592.

In some embodiments, the amino acid sequence for a MEW class I peptide vaccine for the MAGC3 protein comprises one or more of the SEQ ID NO: 68285, SEQ ID NO: 68290, SEQ ID NO: 68305, SEQ ID NO: 77091, SEQ ID NO: 77210, SEQ ID NO: 84188, SEQ ID NO: 87951, SEQ ID NO: 88144, and SEQ ID NOs: 95593 to 95664. In some embodiments, any one of the peptides in the MAGC3 vaccine comprise an amino acid sequence 80, 81, 82, 83, 84, 85, 86, 87, 88, 89, 90, 91, 92, 93, 94, 95, 96, 97, 98 or 99% identical to SEQ ID NO: 68285, SEQ ID NO: 68290, SEQ ID NO: 68305, SEQ ID NO: 77091, SEQ ID NO: 77210, SEQ ID NO: 84188, SEQ ID NO: 87951, SEQ ID NO: 88144, or SEQ ID NOs: 95593 to 95664.

In some embodiments, the amino acid sequence for a MEW class I peptide vaccine for the MAGC3 protein comprises one or more of the SEQ ID NO: 41647, SEQ ID NO: 50668, SEQ ID NO: 50905, SEQ ID NOs: 51039 to 51040, SEQ ID NO: 68257, SEQ ID NO: 68285, SEQ ID NO: 68288, SEQ ID NO: 68290, SEQ ID NO: 68305, SEQ ID NO: 68389, SEQ ID NO: 68419, SEQ ID NO: 68470, SEQ ID NO: 68510, SEQ ID NO: 68519, SEQ ID NO: 68592, SEQ ID NO: 68603, SEQ ID NO: 68684, SEQ ID NO: 68688, SEQ ID NO: 68747, SEQ ID NO: 68760, SEQ ID NO: 68778, SEQ ID NO: 68786, SEQ ID NO: 68855, SEQ ID NO: 68898, SEQ ID NO: 68900, SEQ ID NO: 68927, SEQ ID NO: 68961, SEQ ID NO: 69026, SEQ ID NO: 69041, SEQ ID NO: 69047, SEQ ID NO: 69148, SEQ ID NO: 69173, SEQ ID NO: 69180, SEQ ID NO: 69192, SEQ ID NO: 69227, SEQ ID NO: 69311, SEQ ID NO: 69330, SEQ ID NO: 69333, SEQ ID NO: 69346, SEQ ID NO: 69356, SEQ ID NO: 69393, SEQ ID NO: 69421, SEQ ID NO: 69437, SEQ ID NO: 69451, SEQ ID NO: 69500, SEQ ID NO: 69505, SEQ ID NO: 69517, SEQ ID NO: 69540, SEQ ID NO: 69559, SEQ ID NO: 69571, SEQ ID NO: 69586, SEQ ID NO: 69589, SEQ ID NO: 69591, SEQ ID NO: 69619, SEQ ID NO: 69631, SEQ ID NO: 69633, SEQ ID NO: 69644, SEQ ID NO: 69649, SEQ ID NO: 69747, SEQ ID NO: 69764, SEQ ID NO: 69767, SEQ ID NO: 69790, SEQ ID NO: 69832, SEQ ID NO: 69836, SEQ ID NO: 69882, SEQ ID NO: 69999, SEQ ID NO: 70012, SEQ ID NO: 70036, SEQ ID NO: 70050, SEQ ID NO: 70066, SEQ ID NO: 70069, SEQ ID NO: 70109, SEQ ID NO: 70159, SEQ ID NO: 70165, SEQ ID NO: 70175, SEQ ID NO: 70177, SEQ ID NO: 70188, SEQ ID NO: 70284, SEQ ID NO: 70323, SEQ ID NO: 70326, SEQ ID NO: 70428, SEQ ID NO: 70455, SEQ ID NO: 70570, SEQ ID NO: 70606, SEQ ID NO: 70635, SEQ ID NO: 70676, SEQ ID NO: 70692, SEQ ID NO: 70716, SEQ ID NO: 70728, SEQ ID NO: 70735, SEQ ID NO: 70750, SEQ ID NO: 70764, SEQ ID NO: 70770, SEQ ID NO: 70806, SEQ ID NO: 70968, SEQ ID NO: 70997, SEQ ID NO: 71049, SEQ ID NO: 71075, SEQ ID NO: 71090, SEQ ID NO: 71117, SEQ ID NO: 71151, SEQ ID NO: 71176, SEQ ID NO: 71193, SEQ ID NO: 71203, SEQ ID NO: 71239, SEQ ID NO: 71247, SEQ ID NO: 71249, SEQ ID NO: 71275, SEQ ID NO: 71287, SEQ ID NO: 71328, SEQ ID NOs: 71359 to 71360, SEQ ID NOs: 71367 to 71368, SEQ ID NO: 71392, SEQ ID NO: 71414, SEQ ID NO: 71449, SEQ ID NO: 71476, SEQ ID NO: 71482, SEQ ID NO: 71543, SEQ ID NO: 71547, SEQ ID NO: 71560, SEQ ID NO: 71585, SEQ ID NO: 71612, SEQ ID NO: 71620, SEQ ID NO: 71628, SEQ ID NO: 71636, SEQ ID NO: 71673, SEQ ID NOs: 71688 to 71689, SEQ ID NO: 71696, SEQ ID NO: 71700, SEQ ID NO: 71718, SEQ ID NO: 71725, SEQ ID NO: 71807, SEQ ID NO: 71919, SEQ ID NO: 71935, SEQ ID NO: 71943, SEQ ID NO: 71948, SEQ ID NOs: 71987 to 71988, SEQ ID NO: 72045, SEQ ID NO: 72055, SEQ ID NO: 72076, SEQ ID NO: 72085, SEQ ID NO: 72102, SEQ ID NO: 72159, SEQ ID NO: 72183, SEQ ID NO: 72216, SEQ ID NO: 72241, SEQ ID NO: 72331, SEQ ID NO: 72364, SEQ ID NO: 72372, SEQ ID NO: 72390, SEQ ID NO: 72448, SEQ ID NO: 72528, SEQ ID NO: 72595, SEQ ID NO: 72604, SEQ ID NO: 72648, SEQ ID NO: 72667, SEQ ID NO: 72685, SEQ ID NO: 72721, SEQ ID NO: 72751, SEQ ID NO: 72755, SEQ ID NO: 72805, SEQ ID NO: 72810, SEQ ID NO: 72831, SEQ ID NO: 72837, SEQ ID NO: 72862, SEQ ID NO: 72885, SEQ ID NO: 72989, SEQ ID NO: 73014, SEQ ID NOs: 73045 to 73046, SEQ ID NO: 73086, SEQ ID NO: 73094, SEQ ID NO: 73113, SEQ ID NO: 73122, SEQ ID NO: 73161, SEQ ID NO: 73191, SEQ ID NO: 73224, SEQ ID NOs: 73232 to 73233, SEQ ID NO: 73238, SEQ ID NO: 73290, SEQ ID NO: 73327, SEQ ID NO: 73377, SEQ ID NO: 73382, SEQ ID NO: 73404, SEQ ID NO: 73406, SEQ ID NO: 73422, SEQ ID NOs: 73428 to 73429, SEQ ID NO: 73466, SEQ ID NO: 73475, SEQ ID NO: 73521, SEQ ID NO: 73523, SEQ ID NO: 73532, SEQ ID NO: 73550, SEQ ID NO: 73560, SEQ ID NO: 73591, SEQ ID NO: 73597, SEQ ID NO: 73644, SEQ ID NO: 73657, SEQ ID NO: 73660, SEQ ID NO: 73689, SEQ ID NO: 73729, SEQ ID NO: 73733, SEQ ID NO: 73873, SEQ ID NO: 73886, SEQ ID NO: 73930, SEQ ID NO: 73957, SEQ ID NOs: 73991 to 73992, SEQ ID NO: 74045, SEQ ID NO: 74047, SEQ ID NO: 74072, SEQ ID NO: 74080, SEQ ID NOs: 74096 to 74097, SEQ ID NO: 74107, SEQ ID NO: 74203, SEQ ID NO: 74208, SEQ ID NO: 74210, SEQ ID NO: 74238, SEQ ID NO: 74302, SEQ ID NO: 74350, SEQ ID NO: 74352, SEQ ID NO: 74411, SEQ ID NO: 74448, SEQ ID NO: 74473, SEQ ID NO: 74482, SEQ ID NO: 74515, SEQ ID NO: 74527, SEQ ID NO: 74560, SEQ ID NO: 74616, SEQ ID NO: 74649, SEQ ID NO: 74672, SEQ ID NO: 74674, SEQ ID NO: 74737, SEQ ID NO: 74782, SEQ ID NO: 74808, SEQ ID NO: 74810, SEQ ID NO: 74835, SEQ ID NO: 74886, SEQ ID NO: 74901, SEQ ID NO: 74946, SEQ ID NOs: 74975 to 74976, SEQ ID NO: 75017, SEQ ID NO: 75021, SEQ ID NO: 75040, SEQ ID NO: 75049, SEQ ID NO: 75063, SEQ ID NO: 75066, SEQ ID NO: 75072, SEQ ID NO: 75092, SEQ ID NO: 75094, SEQ ID NO: 75099, SEQ ID NO: 75111, SEQ ID NO: 75148, SEQ ID NO: 75245, SEQ ID NO: 75269, SEQ ID NO: 75388, SEQ ID NO: 75403, SEQ ID NO: 75429, SEQ ID NO: 75455, SEQ ID NO: 75470, SEQ ID NO: 75489, SEQ ID NO: 75506, SEQ ID NO: 75529, SEQ ID NO: 75547, SEQ ID NO: 75551, SEQ ID NOs: 75576 to 75577, SEQ ID NO: 75595, SEQ ID NO: 75701, SEQ ID NO: 75716, SEQ ID NO: 75747, SEQ ID NO: 75757, SEQ ID NO: 75762, SEQ ID NO: 75766, SEQ ID NO: 75874, SEQ ID NO: 75915, SEQ ID NO: 75933, SEQ ID NO: 75975, SEQ ID NO: 75979, SEQ ID NO: 76016, SEQ ID NO: 76023, SEQ ID NO: 76034, SEQ ID NO: 76040, SEQ ID NO: 76064, SEQ ID NO: 76076, SEQ ID NO: 76102, SEQ ID NOs: 76147 to 76148, SEQ ID NO: 76189, SEQ ID NO: 76199, SEQ ID NO: 76369, SEQ ID NO: 76375, SEQ ID NO: 76397, SEQ ID NO: 76410, SEQ ID NO: 76435, SEQ ID NO: 76446, SEQ ID NO: 76451, SEQ ID NOs: 76456 to 76458, SEQ ID NO: 76492, SEQ ID NO: 76544, SEQ ID NO: 76569, SEQ ID NO: 76574, SEQ ID NO: 76611, SEQ ID NO: 76654, SEQ ID NO: 76710, SEQ ID NO: 76753, SEQ ID NO: 76769, SEQ ID NO: 76781, SEQ ID NO: 76797, SEQ ID NO: 76803, SEQ ID NO: 76858, SEQ ID NO: 76860, SEQ ID NO: 76879, SEQ ID NO: 76943, SEQ ID NO: 76971, SEQ ID NO: 76981, SEQ ID NO: 77091, SEQ ID NO: 77133, SEQ ID NOs: 77193 to 77194, SEQ ID NO: 77210, SEQ ID NO: 77219, SEQ ID NO: 77237, SEQ ID NO: 77246, SEQ ID NO: 77251, SEQ ID NO: 77281, SEQ ID NO: 77293, SEQ ID NO: 77323, SEQ ID NO: 77334, SEQ ID NO: 77339, SEQ ID NO: 77396, SEQ ID NO: 77423, SEQ ID NO: 77433, SEQ ID NO: 77437, SEQ ID NO: 77442, SEQ ID NO: 77453, SEQ ID NO: 77485, SEQ ID NO: 77579, SEQ ID NO: 77627, SEQ ID NO: 77639, SEQ ID NO: 77644, SEQ ID NO: 77703, SEQ ID NO: 77773, SEQ ID NO: 77814, SEQ ID NO: 77868, SEQ ID NO: 77874, SEQ ID NO: 77900, SEQ ID NO: 77925, SEQ ID NO: 77995, SEQ ID NO: 78017, SEQ ID NO: 78083, SEQ ID NO: 78086, SEQ ID NO: 78090, SEQ ID NO: 78131, SEQ ID NO: 78139, SEQ ID NO: 78228, SEQ ID NO: 78248, SEQ ID NO: 78260, SEQ ID NO: 78346, SEQ ID NO: 78352, SEQ ID NO: 78377, SEQ ID NO: 78416, SEQ ID NO: 78421, SEQ ID NO: 78440, SEQ ID NO: 78521, SEQ ID NO: 78530, SEQ ID NO: 78532, SEQ ID NO: 78546, SEQ ID NO: 78600, SEQ ID NO: 78631, SEQ ID NO: 78671, SEQ ID NO: 78709, SEQ ID NO: 78714, SEQ ID NO: 78730, SEQ ID NO: 78738, SEQ ID NO: 78810, SEQ ID NO: 78855, SEQ ID NO: 78883, SEQ ID NO: 78917, SEQ ID NOs: 78919 to 78920, SEQ ID NO: 78928, SEQ ID NO: 79035, SEQ ID NO: 79048, SEQ ID NO: 79056, SEQ ID NO: 79086, SEQ ID NO: 79091, SEQ ID NO: 79095, SEQ ID NO: 79107, SEQ ID NO: 79109, SEQ ID NO: 79136, SEQ ID NO: 79142, SEQ ID NO: 79147, SEQ ID NO: 79151, SEQ ID NO: 79194, SEQ ID NO: 79196, SEQ ID NO: 79227, SEQ ID NO: 79247, SEQ ID NO: 79253, SEQ ID NO: 79255, SEQ ID NO: 79269, SEQ ID NO: 79310, SEQ ID NO: 79331, SEQ ID NO: 79357, SEQ ID NO: 79406, SEQ ID NO: 79437, SEQ ID NO: 79448, SEQ ID NO: 79453, SEQ ID NO: 79480, SEQ ID NO: 79483, SEQ ID NO: 79486, SEQ ID NO: 79504, SEQ ID NO: 79508, SEQ ID NO: 79516, SEQ ID NO: 79548, SEQ ID NO: 79575, SEQ ID NO: 79588, SEQ ID NO: 79592, SEQ ID NO: 79609, SEQ ID NO: 79626, SEQ ID NO: 79640, SEQ ID NO: 79697, SEQ ID NO: 79746, SEQ ID NO: 79751, SEQ ID NO: 79766, SEQ ID NO: 79784, SEQ ID NO: 79787, SEQ ID NO: 79816, SEQ ID NO: 79834, SEQ ID NO: 79853, SEQ ID NO: 79858, SEQ ID NO: 79861, SEQ ID NO: 79874, SEQ ID NO: 79877, SEQ ID NO: 79906, SEQ ID NO: 79909, SEQ ID NO: 79939, SEQ ID NO: 79958, SEQ ID NO: 79987, SEQ ID NO: 80000, SEQ ID NO: 80027, SEQ ID NO: 80040, SEQ ID NO: 80139, SEQ ID NO: 80141, SEQ ID NO: 80212, SEQ ID NO: 80232, SEQ ID NO: 80237, SEQ ID NO: 80241, SEQ ID NO: 80318, SEQ ID NO: 80320, SEQ ID NOs: 80367 to 80368, SEQ ID NO: 80398, SEQ ID NO: 80421, SEQ ID NO: 80461, SEQ ID NO: 80486, SEQ ID NO: 80513, SEQ ID NO: 80527, SEQ ID NO: 80555, SEQ ID NO: 80574, SEQ ID NO: 80583, SEQ ID NO: 80627, SEQ ID NO: 80673, SEQ ID NOs: 80703 to 80704, SEQ ID NOs: 80718 to 80719, SEQ ID NO: 80725, SEQ ID NO: 80796, SEQ ID NO: 80804, SEQ ID NO: 80833, SEQ ID NO: 80869, SEQ ID NO: 80903, SEQ ID NO: 80931, SEQ ID NO: 80936, SEQ ID NO: 80946, SEQ ID NO: 80990, SEQ ID NO: 81021, SEQ ID NO: 81042, SEQ ID NO: 81046, SEQ ID NO: 81054, SEQ ID NO: 81066, SEQ ID NO: 81145, SEQ ID NO: 81166, SEQ ID NO: 81168, SEQ ID NO: 81175, SEQ ID NO: 81185, SEQ ID NO: 81207, SEQ ID NO: 81251, SEQ ID NO: 81259, SEQ ID NO: 81302, SEQ ID NO: 81337, SEQ ID NO: 81342, SEQ ID NO: 81386, SEQ ID NO: 81428, SEQ ID NO: 81446, SEQ ID NO: 81458, SEQ ID NO: 81488, SEQ ID NO: 81505, SEQ ID NO: 81517, SEQ ID NO: 81566, SEQ ID NO: 81687, SEQ ID NO: 81690, SEQ ID NO: 81694, SEQ ID NO: 81713, SEQ ID NO: 81755, SEQ ID NO: 81825, SEQ ID NO: 81856, SEQ ID NO: 81873, SEQ ID NO: 81904, SEQ ID NO: 81916, SEQ ID NO: 81938, SEQ ID NO: 81951, SEQ ID NO: 81963, SEQ ID NO: 82045, SEQ ID NO: 82085, SEQ ID NO: 82117, SEQ ID NO: 82136, SEQ ID NO: 82193, SEQ ID NO: 82239, SEQ ID NO: 82241, SEQ ID NO: 82259, SEQ ID NO: 82320, SEQ ID NO: 82382, SEQ ID NO: 82417, SEQ ID NO: 82459, SEQ ID NO: 82474, SEQ ID NO: 82514, SEQ ID NO: 82556, SEQ ID NO: 82581, SEQ ID NO: 82596, SEQ ID NO: 82633, SEQ ID NO: 82644, SEQ ID NO: 82649, SEQ ID NO: 82676, SEQ ID NO: 82681, SEQ ID NO: 82718, SEQ ID NO: 82731, SEQ ID NO: 82769, SEQ ID NO: 82817, SEQ ID NO: 82870, SEQ ID NO: 82872, SEQ ID NO: 82885, SEQ ID NOs: 82920 to 82921, SEQ ID NO: 82955, SEQ ID NO: 82960, SEQ ID NO: 82985, SEQ ID NO: 82988, SEQ ID NO: 83013, SEQ ID NO: 83018, SEQ ID NO: 83051, SEQ ID NO: 83062, SEQ ID NO: 83099, SEQ ID NO: 83149, SEQ ID NO: 83185, SEQ ID NO: 83193, SEQ ID NO: 83208, SEQ ID NO: 83225, SEQ ID NO: 83235, SEQ ID NO: 83243, SEQ ID NO: 83260, SEQ ID NO: 83269, SEQ ID NO: 83286, SEQ ID NO: 83293, SEQ ID NO: 83349, SEQ ID NO: 83383, SEQ ID NO: 83409, SEQ ID NO: 83426, SEQ ID NO: 83438, SEQ ID NO: 83549, SEQ ID NO: 83605, SEQ ID NO: 83686, SEQ ID NO: 83704, SEQ ID NO: 83714, SEQ ID NO: 83806, SEQ ID NO: 83811, SEQ ID NO: 83821, SEQ ID NOs: 83863 to 83864, SEQ ID NO: 83872, SEQ ID NO: 83891, SEQ ID NO: 83899, SEQ ID NO: 83901, SEQ ID NO: 83921, SEQ ID NO: 83970, SEQ ID NO: 83974, SEQ ID NO: 83988, SEQ ID NO: 84002, SEQ ID NO: 84025, SEQ ID NO: 84070, SEQ ID NO: 84090, SEQ ID NO: 84154, SEQ ID NO: 84182, SEQ ID NOs: 84187 to 84188, SEQ ID NO: 84201, SEQ ID NO: 84212, SEQ ID NO: 84232, SEQ ID NO: 84238, SEQ ID NO: 84248, SEQ ID NO: 84306, SEQ ID NO: 84324, SEQ ID NO: 84348, SEQ ID NO: 84376, SEQ ID NO: 84387, SEQ ID NO: 84390, SEQ ID NO: 84422, SEQ ID NO: 84428, SEQ ID NO: 84437, SEQ ID NO: 84445, SEQ ID NO: 84489, SEQ ID NO: 84501, SEQ ID NO: 84534, SEQ ID NO: 84558, SEQ ID NO: 84593, SEQ ID NO: 84676, SEQ ID NO: 84782, SEQ ID NO: 84795, SEQ ID NO: 84822, SEQ ID NO: 84885, SEQ ID NO: 84991, SEQ ID NO: 85010, SEQ ID NO: 85024, SEQ ID NO: 85054, SEQ ID NO: 85056, SEQ ID NO: 85060, SEQ ID NO: 85101, SEQ ID NO: 85117, SEQ ID NO: 85146, SEQ ID NO: 85219, SEQ ID NOs: 85242 to 85243, SEQ ID NO: 85266, SEQ ID NO: 85310, SEQ ID NO: 85349, SEQ ID NO: 85361, SEQ ID NO: 85370, SEQ ID NO: 85379, SEQ ID NO: 85399, SEQ ID NO: 85417, SEQ ID NO: 85435, SEQ ID NO: 85447, SEQ ID NO: 85463, SEQ ID NO: 85519, SEQ ID NO: 85528, SEQ ID NO: 85530, SEQ ID NO: 85602, SEQ ID NO: 85624, SEQ ID NO: 85629, SEQ ID NO: 85725, SEQ ID NO: 85737, SEQ ID NO: 85848, SEQ ID NO: 85878, SEQ ID NO: 85910, SEQ ID NO: 85959, SEQ ID NO: 85963, SEQ ID NO: 85967, SEQ ID NOs: 85985 to 85986, SEQ ID NO: 86003, SEQ ID NO: 86076, SEQ ID NO: 86159, SEQ ID NO: 86208, SEQ ID NO: 86248, SEQ ID NO: 86279, SEQ ID NO: 86343, SEQ ID NO: 86366, SEQ ID NO: 86417, SEQ ID NO: 86431, SEQ ID NO: 86433, SEQ ID NO: 86473, SEQ ID NO: 86523, SEQ ID NOs: 86526 to 86527, SEQ ID NO: 86541, SEQ ID NO: 86567, SEQ ID NO: 86586, SEQ ID NO: 86589, SEQ ID NO: 86599, SEQ ID NO: 86633, SEQ ID NO: 86665, SEQ ID NO: 86688, SEQ ID NO: 86698, SEQ ID NO: 86725, SEQ ID NO: 86761, SEQ ID NO: 86775, SEQ ID NO: 86825, SEQ ID NO: 86914, SEQ ID NO: 86929, SEQ ID NO: 86940, SEQ ID NO: 86969, SEQ ID NO: 86994, SEQ ID NO: 87027, SEQ ID NO: 87041, SEQ ID NO: 87157, SEQ ID NO: 87160, SEQ ID NO: 87185, SEQ ID NO: 87251, SEQ ID NO: 87255, SEQ ID NO: 87300, SEQ ID NO: 87321, SEQ ID NO: 87358, SEQ ID NO: 87425, SEQ ID NO: 87427, SEQ ID NO: 87431, SEQ ID NO: 87474, SEQ ID NO: 87536, SEQ ID NO: 87550, SEQ ID NO: 87576, SEQ ID NO: 87603, SEQ ID NO: 87623, SEQ ID NO: 87626, SEQ ID NO: 87638, SEQ ID NO: 87708, SEQ ID NO: 87733, SEQ ID NO: 87785, SEQ ID NO: 87799, SEQ ID NO: 87818, SEQ ID NOs: 87865 to 87866, SEQ ID NO: 87875, SEQ ID NO: 87917, SEQ ID NO: 87946, SEQ ID NO: 87951, SEQ ID NO: 88016, SEQ ID NO: 88061, SEQ ID NO: 88120, SEQ ID NO: 88122, SEQ ID NO: 88125, SEQ ID NO: 88144, SEQ ID NO: 88178, SEQ ID NO: 88180, SEQ ID NO: 88186, SEQ ID NO: 88203, SEQ ID NO: 88241, SEQ ID NO: 88272, SEQ ID NO: 88285, SEQ ID NO: 88288, SEQ ID NO: 88359, SEQ ID NO: 88384, SEQ ID NO: 88390, SEQ ID NO: 88474, SEQ ID NO: 88522, SEQ ID NO: 88563, SEQ ID NO: 88643, SEQ ID NO: 88659, SEQ ID NO: 88708, SEQ ID NO: 88710, SEQ ID NO: 88731, SEQ ID NO: 88751, SEQ ID NO: 88806, SEQ ID NO: 88975, SEQ ID NO: 88999, SEQ ID NO: 89010, SEQ ID NO: 89012, SEQ ID NO: 89028, SEQ ID NO: 89035, SEQ ID NO: 89037, SEQ ID NO: 89039, SEQ ID NO: 89045, SEQ ID NO: 89073, SEQ ID NO: 89118, SEQ ID NO: 89126, SEQ ID NO: 89135, SEQ ID NO: 89138, SEQ ID NO: 89147, SEQ ID NO: 89168, SEQ ID NO: 89193, SEQ ID NO: 89228, SEQ ID NO: 89235, SEQ ID NO: 89269, SEQ ID NO: 89286, SEQ ID NO: 89291, SEQ ID NO: 89339, SEQ ID NO: 89342, SEQ ID NO: 89394, SEQ ID NO: 89453, SEQ ID NO: 89492, SEQ ID NO: 89510, SEQ ID NO: 89555, SEQ ID NO: 89595, SEQ ID NO: 89670, SEQ ID NO: 89695, SEQ ID NO: 89785, SEQ ID NO: 89836, SEQ ID NO: 89842, SEQ ID NO: 89921, SEQ ID NO: 89929, SEQ ID NO: 89935, SEQ ID NO: 89938, SEQ ID NO: 89950, SEQ ID NO: 89953, SEQ ID NO: 89960, SEQ ID NO: 89987, SEQ ID NO: 89992, SEQ ID NO: 90030, SEQ ID NO: 90056, SEQ ID NO: 90066, SEQ ID NO: 90085, SEQ ID NO: 90089, SEQ ID NO: 90115, SEQ ID NO: 90120, SEQ ID NO: 90133, SEQ ID NO: 90157, SEQ ID NO: 90159, SEQ ID NO: 90191, SEQ ID NO: 90268, SEQ ID NO: 90274, SEQ ID NO: 90280, SEQ ID NO: 90287, SEQ ID NO: 90315, SEQ ID NO: 90408, SEQ ID NO: 90417, SEQ ID NO: 90443, SEQ ID NO: 90466, SEQ ID NO: 90507, SEQ ID NO: 90555, SEQ ID NO: 90593, SEQ ID NO: 90599, SEQ ID NO: 90621, SEQ ID NO: 90634, SEQ ID NO: 90653, SEQ ID NO: 90696, SEQ ID NO: 90758, SEQ ID NO: 90777, SEQ ID NO: 90835, SEQ ID NO: 90882, SEQ ID NO: 90898, SEQ ID NO: 90938, SEQ ID NO: 90954, SEQ ID NO: 90999, SEQ ID NO: 91045, SEQ ID NO: 91060, SEQ ID NO: 91072, SEQ ID NO: 91076, SEQ ID NO: 91105, SEQ ID NO: 91132, SEQ ID NO: 91222, SEQ ID NO: 91226, SEQ ID NO: 91229, SEQ ID NO: 91306, SEQ ID NO: 91309, SEQ ID NO: 91315, SEQ ID NO: 91346, SEQ ID NO: 91419, SEQ ID NO: 91449, SEQ ID NO: 91498, SEQ ID NO: 91563, SEQ ID NO: 91588, SEQ ID NO: 91681, SEQ ID NO: 91766, SEQ ID NOs: 91775 to 91776, SEQ ID NO: 91780, SEQ ID NO: 91799, SEQ ID NO: 91845, SEQ ID NO: 91852, SEQ ID NOs: 91885 to 91886, SEQ ID NO: 91930, SEQ ID NO: 91935, SEQ ID NO: 91953, SEQ ID NO: 91966, SEQ ID NO: 91984, SEQ ID NO: 92026, SEQ ID NO: 92030, SEQ ID NO: 92069, SEQ ID NO: 92100, SEQ ID NO: 92111, SEQ ID NO: 92189, SEQ ID NO: 92249, SEQ ID NO: 92296, SEQ ID NO: 92400, SEQ ID NO: 92404, SEQ ID NO: 92409, SEQ ID NO: 92429, SEQ ID NO: 92474, SEQ ID NO: 92500, SEQ ID NO: 92515, SEQ ID NO: 92538, SEQ ID NO: 92646, SEQ ID NO: 92659, SEQ ID NO: 92671, SEQ ID NO: 92673, SEQ ID NO: 92675, SEQ ID NO: 92684, SEQ ID NO: 92704, SEQ ID NO: 92832, SEQ ID NO: 92835, SEQ ID NO: 92854, SEQ ID NO: 92858, SEQ ID NO: 92877, SEQ ID NO: 92918, SEQ ID NO: 92920, SEQ ID NO: 93004, SEQ ID NO: 93036, SEQ ID NO: 93042, SEQ ID NO: 93071, SEQ ID NO: 93089, SEQ ID NO: 93136, SEQ ID NO: 93180, SEQ ID NO: 93251, SEQ ID NO: 93325, SEQ ID NO: 93335, SEQ ID NO: 93344, SEQ ID NO: 93356, SEQ ID NO: 93382, SEQ ID NO: 93408, SEQ ID NO: 93420, SEQ ID NO: 93503, SEQ ID NO: 93537, SEQ ID NO: 93617, SEQ ID NO: 93658, SEQ ID NO: 93697, SEQ ID NO: 93710, SEQ ID NO: 93877, SEQ ID NO: 93885, SEQ ID NO: 93888, SEQ ID NO: 93893, SEQ ID NO: 93903, SEQ ID NO: 93912, SEQ ID NO: 93926, SEQ ID NO: 93933, SEQ ID NO: 93982, SEQ ID NO: 93987, SEQ ID NO: 94000, SEQ ID NO: 94054, SEQ ID NO: 94058, SEQ ID NO: 94087, SEQ ID NO: 94090, SEQ ID NO: 94102, SEQ ID NO: 94143, SEQ ID NO: 94269, SEQ ID NO: 94367, SEQ ID NO: 94465, SEQ ID NO: 94477, SEQ ID NO: 94525, SEQ ID NO: 94587, and SEQ ID NOs: 95593 to 113807. In some embodiments, any one of the peptides in the MAGC3 vaccine comprise an amino acid sequence 80, 81, 82, 83, 84, 85, 86, 87, 88, 89, 90, 91, 92, 93, 94, 95, 96, 97, 98 or 99% identical to SEQ ID NO: 41647, SEQ ID NO: 50668, SEQ ID NO: 50905, SEQ ID NOs: 51039 to 51040, SEQ ID NO: 68257, SEQ ID NO: 68285, SEQ ID NO: 68288, SEQ ID NO: 68290, SEQ ID NO: 68305, SEQ ID NO: 68389, SEQ ID NO: 68419, SEQ ID NO: 68470, SEQ ID NO: 68510, SEQ ID NO: 68519, SEQ ID NO: 68592, SEQ ID NO: 68603, SEQ ID NO: 68684, SEQ ID NO: 68688, SEQ ID NO: 68747, SEQ ID NO: 68760, SEQ ID NO: 68778, SEQ ID NO: 68786, SEQ ID NO: 68855, SEQ ID NO: 68898, SEQ ID NO: 68900, SEQ ID NO: 68927, SEQ ID NO: 68961, SEQ ID NO: 69026, SEQ ID NO: 69041, SEQ ID NO: 69047, SEQ ID NO: 69148, SEQ ID NO: 69173, SEQ ID NO: 69180, SEQ ID NO: 69192, SEQ ID NO: 69227, SEQ ID NO: 69311, SEQ ID NO: 69330, SEQ ID NO: 69333, SEQ ID NO: 69346, SEQ ID NO: 69356, SEQ ID NO: 69393, SEQ ID NO: 69421, SEQ ID NO: 69437, SEQ ID NO: 69451, SEQ ID NO: 69500, SEQ ID NO: 69505, SEQ ID NO: 69517, SEQ ID NO: 69540, SEQ ID NO: 69559, SEQ ID NO: 69571, SEQ ID NO: 69586, SEQ ID NO: 69589, SEQ ID NO: 69591, SEQ ID NO: 69619, SEQ ID NO: 69631, SEQ ID NO: 69633, SEQ ID NO: 69644, SEQ ID NO: 69649, SEQ ID NO: 69747, SEQ ID NO: 69764, SEQ ID NO: 69767, SEQ ID NO: 69790, SEQ ID NO: 69832, SEQ ID NO: 69836, SEQ ID NO: 69882, SEQ ID NO: 69999, SEQ ID NO: 70012, SEQ ID NO: 70036, SEQ ID NO: 70050, SEQ ID NO: 70066, SEQ ID NO: 70069, SEQ ID NO: 70109, SEQ ID NO: 70159, SEQ ID NO: 70165, SEQ ID NO: 70175, SEQ ID NO: 70177, SEQ ID NO: 70188, SEQ ID NO: 70284, SEQ ID NO: 70323, SEQ ID NO: 70326, SEQ ID NO: 70428, SEQ ID NO: 70455, SEQ ID NO: 70570, SEQ ID NO: 70606, SEQ ID NO: 70635, SEQ ID NO: 70676, SEQ ID NO: 70692, SEQ ID NO: 70716, SEQ ID NO: 70728, SEQ ID NO: 70735, SEQ ID NO: 70750, SEQ ID NO: 70764, SEQ ID NO: 70770, SEQ ID NO: 70806, SEQ ID NO: 70968, SEQ ID NO: 70997, SEQ ID NO: 71049, SEQ ID NO: 71075, SEQ ID NO: 71090, SEQ ID NO: 71117, SEQ ID NO: 71151, SEQ ID NO: 71176, SEQ ID NO: 71193, SEQ ID NO: 71203, SEQ ID NO: 71239, SEQ ID NO: 71247, SEQ ID NO: 71249, SEQ ID NO: 71275, SEQ ID NO: 71287, SEQ ID NO: 71328, SEQ ID NOs: 71359 to 71360, SEQ ID NOs: 71367 to 71368, SEQ ID NO: 71392, SEQ ID NO: 71414, SEQ ID NO: 71449, SEQ ID NO: 71476, SEQ ID NO: 71482, SEQ ID NO: 71543, SEQ ID NO: 71547, SEQ ID NO: 71560, SEQ ID NO: 71585, SEQ ID NO: 71612, SEQ ID NO: 71620, SEQ ID NO: 71628, SEQ ID NO: 71636, SEQ ID NO: 71673, SEQ ID NOs: 71688 to 71689, SEQ ID NO: 71696, SEQ ID NO: 71700, SEQ ID NO: 71718, SEQ ID NO: 71725, SEQ ID NO: 71807, SEQ ID NO: 71919, SEQ ID NO: 71935, SEQ ID NO: 71943, SEQ ID NO: 71948, SEQ ID NOs: 71987 to 71988, SEQ ID NO: 72045, SEQ ID NO: 72055, SEQ ID NO: 72076, SEQ ID NO: 72085, SEQ ID NO: 72102, SEQ ID NO: 72159, SEQ ID NO: 72183, SEQ ID NO: 72216, SEQ ID NO: 72241, SEQ ID NO: 72331, SEQ ID NO: 72364, SEQ ID NO: 72372, SEQ ID NO: 72390, SEQ ID NO: 72448, SEQ ID NO: 72528, SEQ ID NO: 72595, SEQ ID NO: 72604, SEQ ID NO: 72648, SEQ ID NO: 72667, SEQ ID NO: 72685, SEQ ID NO: 72721, SEQ ID NO: 72751, SEQ ID NO: 72755, SEQ ID NO: 72805, SEQ ID NO: 72810, SEQ ID NO: 72831, SEQ ID NO: 72837, SEQ ID NO: 72862, SEQ ID NO: 72885, SEQ ID NO: 72989, SEQ ID NO: 73014, SEQ ID NOs: 73045 to 73046, SEQ ID NO: 73086, SEQ ID NO: 73094, SEQ ID NO: 73113, SEQ ID NO: 73122, SEQ ID NO: 73161, SEQ ID NO: 73191, SEQ ID NO: 73224, SEQ ID NOs: 73232 to 73233, SEQ ID NO: 73238, SEQ ID NO: 73290, SEQ ID NO: 73327, SEQ ID NO: 73377, SEQ ID NO: 73382, SEQ ID NO: 73404, SEQ ID NO: 73406, SEQ ID NO: 73422, SEQ ID NOs: 73428 to 73429, SEQ ID NO: 73466, SEQ ID NO: 73475, SEQ ID NO: 73521, SEQ ID NO: 73523, SEQ ID NO: 73532, SEQ ID NO: 73550, SEQ ID NO: 73560, SEQ ID NO: 73591, SEQ ID NO: 73597, SEQ ID NO: 73644, SEQ ID NO: 73657, SEQ ID NO: 73660, SEQ ID NO: 73689, SEQ ID NO: 73729, SEQ ID NO: 73733, SEQ ID NO: 73873, SEQ ID NO: 73886, SEQ ID NO: 73930, SEQ ID NO: 73957, SEQ ID NOs: 73991 to 73992, SEQ ID NO: 74045, SEQ ID NO: 74047, SEQ ID NO: 74072, SEQ ID NO: 74080, SEQ ID NOs: 74096 to 74097, SEQ ID NO: 74107, SEQ ID NO: 74203, SEQ ID NO: 74208, SEQ ID NO: 74210, SEQ ID NO: 74238, SEQ ID NO: 74302, SEQ ID NO: 74350, SEQ ID NO: 74352, SEQ ID NO: 74411, SEQ ID NO: 74448, SEQ ID NO: 74473, SEQ ID NO: 74482, SEQ ID NO: 74515, SEQ ID NO: 74527, SEQ ID NO: 74560, SEQ ID NO: 74616, SEQ ID NO: 74649, SEQ ID NO: 74672, SEQ ID NO: 74674, SEQ ID NO: 74737, SEQ ID NO: 74782, SEQ ID NO: 74808, SEQ ID NO: 74810, SEQ ID NO: 74835, SEQ ID NO: 74886, SEQ ID NO: 74901, SEQ ID NO: 74946, SEQ ID NOs: 74975 to 74976, SEQ ID NO: 75017, SEQ ID NO: 75021, SEQ ID NO: 75040, SEQ ID NO: 75049, SEQ ID NO: 75063, SEQ ID NO: 75066, SEQ ID NO: 75072, SEQ ID NO: 75092, SEQ ID NO: 75094, SEQ ID NO: 75099, SEQ ID NO: 75111, SEQ ID NO: 75148, SEQ ID NO: 75245, SEQ ID NO: 75269, SEQ ID NO: 75388, SEQ ID NO: 75403, SEQ ID NO: 75429, SEQ ID NO: 75455, SEQ ID NO: 75470, SEQ ID NO: 75489, SEQ ID NO: 75506, SEQ ID NO: 75529, SEQ ID NO: 75547, SEQ ID NO: 75551, SEQ ID NOs: 75576 to 75577, SEQ ID NO: 75595, SEQ ID NO: 75701, SEQ ID NO: 75716, SEQ ID NO: 75747, SEQ ID NO: 75757, SEQ ID NO: 75762, SEQ ID NO: 75766, SEQ ID NO: 75874, SEQ ID NO: 75915, SEQ ID NO: 75933, SEQ ID NO: 75975, SEQ ID NO: 75979, SEQ ID NO: 76016, SEQ ID NO: 76023, SEQ ID NO: 76034, SEQ ID NO: 76040, SEQ ID NO: 76064, SEQ ID NO: 76076, SEQ ID NO: 76102, SEQ ID NOs: 76147 to 76148, SEQ ID NO: 76189, SEQ ID NO: 76199, SEQ ID NO: 76369, SEQ ID NO: 76375, SEQ ID NO: 76397, SEQ ID NO: 76410, SEQ ID NO: 76435, SEQ ID NO: 76446, SEQ ID NO: 76451, SEQ ID NOs: 76456 to 76458, SEQ ID NO: 76492, SEQ ID NO: 76544, SEQ ID NO: 76569, SEQ ID NO: 76574, SEQ ID NO: 76611, SEQ ID NO: 76654, SEQ ID NO: 76710, SEQ ID NO: 76753, SEQ ID NO: 76769, SEQ ID NO: 76781, SEQ ID NO: 76797, SEQ ID NO: 76803, SEQ ID NO: 76858, SEQ ID NO: 76860, SEQ ID NO: 76879, SEQ ID NO: 76943, SEQ ID NO: 76971, SEQ ID NO: 76981, SEQ ID NO: 77091, SEQ ID NO: 77133, SEQ ID NOs: 77193 to 77194, SEQ ID NO: 77210, SEQ ID NO: 77219, SEQ ID NO: 77237, SEQ ID NO: 77246, SEQ ID NO: 77251, SEQ ID NO: 77281, SEQ ID NO: 77293, SEQ ID NO: 77323, SEQ ID NO: 77334, SEQ ID NO: 77339, SEQ ID NO: 77396, SEQ ID NO: 77423, SEQ ID NO: 77433, SEQ ID NO: 77437, SEQ ID NO: 77442, SEQ ID NO: 77453, SEQ ID NO: 77485, SEQ ID NO: 77579, SEQ ID NO: 77627, SEQ ID NO: 77639, SEQ ID NO: 77644, SEQ ID NO: 77703, SEQ ID NO: 77773, SEQ ID NO: 77814, SEQ ID NO: 77868, SEQ ID NO: 77874, SEQ ID NO: 77900, SEQ ID NO: 77925, SEQ ID NO: 77995, SEQ ID NO: 78017, SEQ ID NO: 78083, SEQ ID NO: 78086, SEQ ID NO: 78090, SEQ ID NO: 78131, SEQ ID NO: 78139, SEQ ID NO: 78228, SEQ ID NO: 78248, SEQ ID NO: 78260, SEQ ID NO: 78346, SEQ ID NO: 78352, SEQ ID NO: 78377, SEQ ID NO: 78416, SEQ ID NO: 78421, SEQ ID NO: 78440, SEQ ID NO: 78521, SEQ ID NO: 78530, SEQ ID NO: 78532, SEQ ID NO: 78546, SEQ ID NO: 78600, SEQ ID NO: 78631, SEQ ID NO: 78671, SEQ ID NO: 78709, SEQ ID NO: 78714, SEQ ID NO: 78730, SEQ ID NO: 78738, SEQ ID NO: 78810, SEQ ID NO: 78855, SEQ ID NO: 78883, SEQ ID NO: 78917, SEQ ID NOs: 78919 to 78920, SEQ ID NO: 78928, SEQ ID NO: 79035, SEQ ID NO: 79048, SEQ ID NO: 79056, SEQ ID NO: 79086, SEQ ID NO: 79091, SEQ ID NO: 79095, SEQ ID NO: 79107, SEQ ID NO: 79109, SEQ ID NO: 79136, SEQ ID NO: 79142, SEQ ID NO: 79147, SEQ ID NO: 79151, SEQ ID NO: 79194, SEQ ID NO: 79196, SEQ ID NO: 79227, SEQ ID NO: 79247, SEQ ID NO: 79253, SEQ ID NO: 79255, SEQ ID NO: 79269, SEQ ID NO: 79310, SEQ ID NO: 79331, SEQ ID NO: 79357, SEQ ID NO: 79406, SEQ ID NO: 79437, SEQ ID NO: 79448, SEQ ID NO: 79453, SEQ ID NO: 79480, SEQ ID NO: 79483, SEQ ID NO: 79486, SEQ ID NO: 79504, SEQ ID NO: 79508, SEQ ID NO: 79516, SEQ ID NO: 79548, SEQ ID NO: 79575, SEQ ID NO: 79588, SEQ ID NO: 79592, SEQ ID NO: 79609, SEQ ID NO: 79626, SEQ ID NO: 79640, SEQ ID NO: 79697, SEQ ID NO: 79746, SEQ ID NO: 79751, SEQ ID NO: 79766, SEQ ID NO: 79784, SEQ ID NO: 79787, SEQ ID NO: 79816, SEQ ID NO: 79834, SEQ ID NO: 79853, SEQ ID NO: 79858, SEQ ID NO: 79861, SEQ ID NO: 79874, SEQ ID NO: 79877, SEQ ID NO: 79906, SEQ ID NO: 79909, SEQ ID NO: 79939, SEQ ID NO: 79958, SEQ ID NO: 79987, SEQ ID NO: 80000, SEQ ID NO: 80027, SEQ ID NO: 80040, SEQ ID NO: 80139, SEQ ID NO: 80141, SEQ ID NO: 80212, SEQ ID NO: 80232, SEQ ID NO: 80237, SEQ ID NO: 80241, SEQ ID NO: 80318, SEQ ID NO: 80320, SEQ ID NOs: 80367 to 80368, SEQ ID NO: 80398, SEQ ID NO: 80421, SEQ ID NO: 80461, SEQ ID NO: 80486, SEQ ID NO: 80513, SEQ ID NO: 80527, SEQ ID NO: 80555, SEQ ID NO: 80574, SEQ ID NO: 80583, SEQ ID NO: 80627, SEQ ID NO: 80673, SEQ ID NOs: 80703 to 80704, SEQ ID NOs: 80718 to 80719, SEQ ID NO: 80725, SEQ ID NO: 80796, SEQ ID NO: 80804, SEQ ID NO: 80833, SEQ ID NO: 80869, SEQ ID NO: 80903, SEQ ID NO: 80931, SEQ ID NO: 80936, SEQ ID NO: 80946, SEQ ID NO: 80990, SEQ ID NO: 81021, SEQ ID NO: 81042, SEQ ID NO: 81046, SEQ ID NO: 81054, SEQ ID NO: 81066, SEQ ID NO: 81145, SEQ ID NO: 81166, SEQ ID NO: 81168, SEQ ID NO: 81175, SEQ ID NO: 81185, SEQ ID NO: 81207, SEQ ID NO: 81251, SEQ ID NO: 81259, SEQ ID NO: 81302, SEQ ID NO: 81337, SEQ ID NO: 81342, SEQ ID NO: 81386, SEQ ID NO: 81428, SEQ ID NO: 81446, SEQ ID NO: 81458, SEQ ID NO: 81488, SEQ ID NO: 81505, SEQ ID NO: 81517, SEQ ID NO: 81566, SEQ ID NO: 81687, SEQ ID NO: 81690, SEQ ID NO: 81694, SEQ ID NO: 81713, SEQ ID NO: 81755, SEQ ID NO: 81825, SEQ ID NO: 81856, SEQ ID NO: 81873, SEQ ID NO: 81904, SEQ ID NO: 81916, SEQ ID NO: 81938, SEQ ID NO: 81951, SEQ ID NO: 81963, SEQ ID NO: 82045, SEQ ID NO: 82085, SEQ ID NO: 82117, SEQ ID NO: 82136, SEQ ID NO: 82193, SEQ ID NO: 82239, SEQ ID NO: 82241, SEQ ID NO: 82259, SEQ ID NO: 82320, SEQ ID NO: 82382, SEQ ID NO: 82417, SEQ ID NO: 82459, SEQ ID NO: 82474, SEQ ID NO: 82514, SEQ ID NO: 82556, SEQ ID NO: 82581, SEQ ID NO: 82596, SEQ ID NO: 82633, SEQ ID NO: 82644, SEQ ID NO: 82649, SEQ ID NO: 82676, SEQ ID NO: 82681, SEQ ID NO: 82718, SEQ ID NO: 82731, SEQ ID NO: 82769, SEQ ID NO: 82817, SEQ ID NO: 82870, SEQ ID NO: 82872, SEQ ID NO: 82885, SEQ ID NOs: 82920 to 82921, SEQ ID NO: 82955, SEQ ID NO: 82960, SEQ ID NO: 82985, SEQ ID NO: 82988, SEQ ID NO: 83013, SEQ ID NO: 83018, SEQ ID NO: 83051, SEQ ID NO: 83062, SEQ ID NO: 83099, SEQ ID NO: 83149, SEQ ID NO: 83185, SEQ ID NO: 83193, SEQ ID NO: 83208, SEQ ID NO: 83225, SEQ ID NO: 83235, SEQ ID NO: 83243, SEQ ID NO: 83260, SEQ ID NO: 83269, SEQ ID NO: 83286, SEQ ID NO: 83293, SEQ ID NO: 83349, SEQ ID NO: 83383, SEQ ID NO: 83409, SEQ ID NO: 83426, SEQ ID NO: 83438, SEQ ID NO: 83549, SEQ ID NO: 83605, SEQ ID NO: 83686, SEQ ID NO: 83704, SEQ ID NO: 83714, SEQ ID NO: 83806, SEQ ID NO: 83811, SEQ ID NO: 83821, SEQ ID NOs: 83863 to 83864, SEQ ID NO: 83872, SEQ ID NO: 83891, SEQ ID NO: 83899, SEQ ID NO: 83901, SEQ ID NO: 83921, SEQ ID NO: 83970, SEQ ID NO: 83974, SEQ ID NO: 83988, SEQ ID NO: 84002, SEQ ID NO: 84025, SEQ ID NO: 84070, SEQ ID NO: 84090, SEQ ID NO: 84154, SEQ ID NO: 84182, SEQ ID NOs: 84187 to 84188, SEQ ID NO: 84201, SEQ ID NO: 84212, SEQ ID NO: 84232, SEQ ID NO: 84238, SEQ ID NO: 84248, SEQ ID NO: 84306, SEQ ID NO: 84324, SEQ ID NO: 84348, SEQ ID NO: 84376, SEQ ID NO: 84387, SEQ ID NO: 84390, SEQ ID NO: 84422, SEQ ID NO: 84428, SEQ ID NO: 84437, SEQ ID NO: 84445, SEQ ID NO: 84489, SEQ ID NO: 84501, SEQ ID NO: 84534, SEQ ID NO: 84558, SEQ ID NO: 84593, SEQ ID NO: 84676, SEQ ID NO: 84782, SEQ ID NO: 84795, SEQ ID NO: 84822, SEQ ID NO: 84885, SEQ ID NO: 84991, SEQ ID NO: 85010, SEQ ID NO: 85024, SEQ ID NO: 85054, SEQ ID NO: 85056, SEQ ID NO: 85060, SEQ ID NO: 85101, SEQ ID NO: 85117, SEQ ID NO: 85146, SEQ ID NO: 85219, SEQ ID NOs: 85242 to 85243, SEQ ID NO: 85266, SEQ ID NO: 85310, SEQ ID NO: 85349, SEQ ID NO: 85361, SEQ ID NO: 85370, SEQ ID NO: 85379, SEQ ID NO: 85399, SEQ ID NO: 85417, SEQ ID NO: 85435, SEQ ID NO: 85447, SEQ ID NO: 85463, SEQ ID NO: 85519, SEQ ID NO: 85528, SEQ ID NO: 85530, SEQ ID NO: 85602, SEQ ID NO: 85624, SEQ ID NO: 85629, SEQ ID NO: 85725, SEQ ID NO: 85737, SEQ ID NO: 85848, SEQ ID NO: 85878, SEQ ID NO: 85910, SEQ ID NO: 85959, SEQ ID NO: 85963, SEQ ID NO: 85967, SEQ ID NOs: 85985 to 85986, SEQ ID NO: 86003, SEQ ID NO: 86076, SEQ ID NO: 86159, SEQ ID NO: 86208, SEQ ID NO: 86248, SEQ ID NO: 86279, SEQ ID NO: 86343, SEQ ID NO: 86366, SEQ ID NO: 86417, SEQ ID NO: 86431, SEQ ID NO: 86433, SEQ ID NO: 86473, SEQ ID NO: 86523, SEQ ID NOs: 86526 to 86527, SEQ ID NO: 86541, SEQ ID NO: 86567, SEQ ID NO: 86586, SEQ ID NO: 86589, SEQ ID NO: 86599, SEQ ID NO: 86633, SEQ ID NO: 86665, SEQ ID NO: 86688, SEQ ID NO: 86698, SEQ ID NO: 86725, SEQ ID NO: 86761, SEQ ID NO: 86775, SEQ ID NO: 86825, SEQ ID NO: 86914, SEQ ID NO: 86929, SEQ ID NO: 86940, SEQ ID NO: 86969, SEQ ID NO: 86994, SEQ ID NO: 87027, SEQ ID NO: 87041, SEQ ID NO: 87157, SEQ ID NO: 87160, SEQ ID NO: 87185, SEQ ID NO: 87251, SEQ ID NO: 87255, SEQ ID NO: 87300, SEQ ID NO: 87321, SEQ ID NO: 87358, SEQ ID NO: 87425, SEQ ID NO: 87427, SEQ ID NO: 87431, SEQ ID NO: 87474, SEQ ID NO: 87536, SEQ ID NO: 87550, SEQ ID NO: 87576, SEQ ID NO: 87603, SEQ ID NO: 87623, SEQ ID NO: 87626, SEQ ID NO: 87638, SEQ ID NO: 87708, SEQ ID NO: 87733, SEQ ID NO: 87785, SEQ ID NO: 87799, SEQ ID NO: 87818, SEQ ID NOs: 87865 to 87866, SEQ ID NO: 87875, SEQ ID NO: 87917, SEQ ID NO: 87946, SEQ ID NO: 87951, SEQ ID NO: 88016, SEQ ID NO: 88061, SEQ ID NO: 88120, SEQ ID NO: 88122, SEQ ID NO: 88125, SEQ ID NO: 88144, SEQ ID NO: 88178, SEQ ID NO: 88180, SEQ ID NO: 88186, SEQ ID NO: 88203, SEQ ID NO: 88241, SEQ ID NO: 88272, SEQ ID NO: 88285, SEQ ID NO: 88288, SEQ ID NO: 88359, SEQ ID NO: 88384, SEQ ID NO: 88390, SEQ ID NO: 88474, SEQ ID NO: 88522, SEQ ID NO: 88563, SEQ ID NO: 88643, SEQ ID NO: 88659, SEQ ID NO: 88708, SEQ ID NO: 88710, SEQ ID NO: 88731, SEQ ID NO: 88751, SEQ ID NO: 88806, SEQ ID NO: 88975, SEQ ID NO: 88999, SEQ ID NO: 89010, SEQ ID NO: 89012, SEQ ID NO: 89028, SEQ ID NO: 89035, SEQ ID NO: 89037, SEQ ID NO: 89039, SEQ ID NO: 89045, SEQ ID NO: 89073, SEQ ID NO: 89118, SEQ ID NO: 89126, SEQ ID NO: 89135, SEQ ID NO: 89138, SEQ ID NO: 89147, SEQ ID NO: 89168, SEQ ID NO: 89193, SEQ ID NO: 89228, SEQ ID NO: 89235, SEQ ID NO: 89269, SEQ ID NO: 89286, SEQ ID NO: 89291, SEQ ID NO: 89339, SEQ ID NO: 89342, SEQ ID NO: 89394, SEQ ID NO: 89453, SEQ ID NO: 89492, SEQ ID NO: 89510, SEQ ID NO: 89555, SEQ ID NO: 89595, SEQ ID NO: 89670, SEQ ID NO: 89695, SEQ ID NO: 89785, SEQ ID NO: 89836, SEQ ID NO: 89842, SEQ ID NO: 89921, SEQ ID NO: 89929, SEQ ID NO: 89935, SEQ ID NO: 89938, SEQ ID NO: 89950, SEQ ID NO: 89953, SEQ ID NO: 89960, SEQ ID NO: 89987, SEQ ID NO: 89992, SEQ ID NO: 90030, SEQ ID NO: 90056, SEQ ID NO: 90066, SEQ ID NO: 90085, SEQ ID NO: 90089, SEQ ID NO: 90115, SEQ ID NO: 90120, SEQ ID NO: 90133, SEQ ID NO: 90157, SEQ ID NO: 90159, SEQ ID NO: 90191, SEQ ID NO: 90268, SEQ ID NO: 90274, SEQ ID NO: 90280, SEQ ID NO: 90287, SEQ ID NO: 90315, SEQ ID NO: 90408, SEQ ID NO: 90417, SEQ ID NO: 90443, SEQ ID NO: 90466, SEQ ID NO: 90507, SEQ ID NO: 90555, SEQ ID NO: 90593, SEQ ID NO: 90599, SEQ ID NO: 90621, SEQ ID NO: 90634, SEQ ID NO: 90653, SEQ ID NO: 90696, SEQ ID NO: 90758, SEQ ID NO: 90777, SEQ ID NO: 90835, SEQ ID NO: 90882, SEQ ID NO: 90898, SEQ ID NO: 90938, SEQ ID NO: 90954, SEQ ID NO: 90999, SEQ ID NO: 91045, SEQ ID NO: 91060, SEQ ID NO: 91072, SEQ ID NO: 91076, SEQ ID NO: 91105, SEQ ID NO: 91132, SEQ ID NO: 91222, SEQ ID NO: 91226, SEQ ID NO: 91229, SEQ ID NO: 91306, SEQ ID NO: 91309, SEQ ID NO: 91315, SEQ ID NO: 91346, SEQ ID NO: 91419, SEQ ID NO: 91449, SEQ ID NO: 91498, SEQ ID NO: 91563, SEQ ID NO: 91588, SEQ ID NO: 91681, SEQ ID NO: 91766, SEQ ID NOs: 91775 to 91776, SEQ ID NO: 91780, SEQ ID NO: 91799, SEQ ID NO: 91845, SEQ ID NO: 91852, SEQ ID NOs: 91885 to 91886, SEQ ID NO: 91930, SEQ ID NO: 91935, SEQ ID NO: 91953, SEQ ID NO: 91966, SEQ ID NO: 91984, SEQ ID NO: 92026, SEQ ID NO: 92030, SEQ ID NO: 92069, SEQ ID NO: 92100, SEQ ID NO: 92111, SEQ ID NO: 92189, SEQ ID NO: 92249, SEQ ID NO: 92296, SEQ ID NO: 92400, SEQ ID NO: 92404, SEQ ID NO: 92409, SEQ ID NO: 92429, SEQ ID NO: 92474, SEQ ID NO: 92500, SEQ ID NO: 92515, SEQ ID NO: 92538, SEQ ID NO: 92646, SEQ ID NO: 92659, SEQ ID NO: 92671, SEQ ID NO: 92673, SEQ ID NO: 92675, SEQ ID NO: 92684, SEQ ID NO: 92704, SEQ ID NO: 92832, SEQ ID NO: 92835, SEQ ID NO: 92854, SEQ ID NO: 92858, SEQ ID NO: 92877, SEQ ID NO: 92918, SEQ ID NO: 92920, SEQ ID NO: 93004, SEQ ID NO: 93036, SEQ ID NO: 93042, SEQ ID NO: 93071, SEQ ID NO: 93089, SEQ ID NO: 93136, SEQ ID NO: 93180, SEQ ID NO: 93251, SEQ ID NO: 93325, SEQ ID NO: 93335, SEQ ID NO: 93344, SEQ ID NO: 93356, SEQ ID NO: 93382, SEQ ID NO: 93408, SEQ ID NO: 93420, SEQ ID NO: 93503, SEQ ID NO: 93537, SEQ ID NO: 93617, SEQ ID NO: 93658, SEQ ID NO: 93697, SEQ ID NO: 93710, SEQ ID NO: 93877, SEQ ID NO: 93885, SEQ ID NO: 93888, SEQ ID NO: 93893, SEQ ID NO: 93903, SEQ ID NO: 93912, SEQ ID NO: 93926, SEQ ID NO: 93933, SEQ ID NO: 93982, SEQ ID NO: 93987, SEQ ID NO: 94000, SEQ ID NO: 94054, SEQ ID NO: 94058, SEQ ID NO: 94087, SEQ ID NO: 94090, SEQ ID NO: 94102, SEQ ID NO: 94143, SEQ ID NO: 94269, SEQ ID NO: 94367, SEQ ID NO: 94465, SEQ ID NO: 94477, SEQ ID NO: 94525, SEQ ID NO: 94587, or SEQ ID NOs: 95593 to 113807.

In some embodiments, the amino acid sequence for a MEW class I peptide vaccine for the MAGC3 protein comprises two or more of the SEQ ID NO: 68285, SEQ ID NO: 68290, SEQ ID NO: 68305, SEQ ID NO: 77091, SEQ ID NO: 77210, SEQ ID NO: 84188, SEQ ID NO: 87951, SEQ ID NO: 88144, and SEQ ID NOs: 95593 to 95664. In some embodiments, any one of the peptides in the MAGC3 vaccine comprise an amino acid sequence 80, 81, 82, 83, 84, 85, 86, 87, 88, 89, 90, 91, 92, 93, 94, 95, 96, 97, 98 or 99% identical to SEQ ID NO: 68285, SEQ ID NO: 68290, SEQ ID NO: 68305, SEQ ID NO: 77091, SEQ ID NO: 77210, SEQ ID NO: 84188, SEQ ID NO: 87951, SEQ ID NO: 88144, or SEQ ID NOs: 95593 to 95664.

In some embodiments, the amino acid sequence for a MEW class I peptide vaccine for the MAGC3 protein comprises two or more of the SEQ ID NO: 41647, SEQ ID NO: 50668, SEQ ID NO: 50905, SEQ ID NOs: 51039 to 51040, SEQ ID NO: 68257, SEQ ID NO: 68285, SEQ ID NO: 68288, SEQ ID NO: 68290, SEQ ID NO: 68305, SEQ ID NO: 68389, SEQ ID NO: 68419, SEQ ID NO: 68470, SEQ ID NO: 68510, SEQ ID NO: 68519, SEQ ID NO: 68592, SEQ ID NO: 68603, SEQ ID NO: 68684, SEQ ID NO: 68688, SEQ ID NO: 68747, SEQ ID NO: 68760, SEQ ID NO: 68778, SEQ ID NO: 68786, SEQ ID NO: 68855, SEQ ID NO: 68898, SEQ ID NO: 68900, SEQ ID NO: 68927, SEQ ID NO: 68961, SEQ ID NO: 69026, SEQ ID NO: 69041, SEQ ID NO: 69047, SEQ ID NO: 69148, SEQ ID NO: 69173, SEQ ID NO: 69180, SEQ ID NO: 69192, SEQ ID NO: 69227, SEQ ID NO: 69311, SEQ ID NO: 69330, SEQ ID NO: 69333, SEQ ID NO: 69346, SEQ ID NO: 69356, SEQ ID NO: 69393, SEQ ID NO: 69421, SEQ ID NO: 69437, SEQ ID NO: 69451, SEQ ID NO: 69500, SEQ ID NO: 69505, SEQ ID NO: 69517, SEQ ID NO: 69540, SEQ ID NO: 69559, SEQ ID NO: 69571, SEQ ID NO: 69586, SEQ ID NO: 69589, SEQ ID NO: 69591, SEQ ID NO: 69619, SEQ ID NO: 69631, SEQ ID NO: 69633, SEQ ID NO: 69644, SEQ ID NO: 69649, SEQ ID NO: 69747, SEQ ID NO: 69764, SEQ ID NO: 69767, SEQ ID NO: 69790, SEQ ID NO: 69832, SEQ ID NO: 69836, SEQ ID NO: 69882, SEQ ID NO: 69999, SEQ ID NO: 70012, SEQ ID NO: 70036, SEQ ID NO: 70050, SEQ ID NO: 70066, SEQ ID NO: 70069, SEQ ID NO: 70109, SEQ ID NO: 70159, SEQ ID NO: 70165, SEQ ID NO: 70175, SEQ ID NO: 70177, SEQ ID NO: 70188, SEQ ID NO: 70284, SEQ ID NO: 70323, SEQ ID NO: 70326, SEQ ID NO: 70428, SEQ ID NO: 70455, SEQ ID NO: 70570, SEQ ID NO: 70606, SEQ ID NO: 70635, SEQ ID NO: 70676, SEQ ID NO: 70692, SEQ ID NO: 70716, SEQ ID NO: 70728, SEQ ID NO: 70735, SEQ ID NO: 70750, SEQ ID NO: 70764, SEQ ID NO: 70770, SEQ ID NO: 70806, SEQ ID NO: 70968, SEQ ID NO: 70997, SEQ ID NO: 71049, SEQ ID NO: 71075, SEQ ID NO: 71090, SEQ ID NO: 71117, SEQ ID NO: 71151, SEQ ID NO: 71176, SEQ ID NO: 71193, SEQ ID NO: 71203, SEQ ID NO: 71239, SEQ ID NO: 71247, SEQ ID NO: 71249, SEQ ID NO: 71275, SEQ ID NO: 71287, SEQ ID NO: 71328, SEQ ID NOs: 71359 to 71360, SEQ ID NOs: 71367 to 71368, SEQ ID NO: 71392, SEQ ID NO: 71414, SEQ ID NO: 71449, SEQ ID NO: 71476, SEQ ID NO: 71482, SEQ ID NO: 71543, SEQ ID NO: 71547, SEQ ID NO: 71560, SEQ ID NO: 71585, SEQ ID NO: 71612, SEQ ID NO: 71620, SEQ ID NO: 71628, SEQ ID NO: 71636, SEQ ID NO: 71673, SEQ ID NOs: 71688 to 71689, SEQ ID NO: 71696, SEQ ID NO: 71700, SEQ ID NO: 71718, SEQ ID NO: 71725, SEQ ID NO: 71807, SEQ ID NO: 71919, SEQ ID NO: 71935, SEQ ID NO: 71943, SEQ ID NO: 71948, SEQ ID NOs: 71987 to 71988, SEQ ID NO: 72045, SEQ ID NO: 72055, SEQ ID NO: 72076, SEQ ID NO: 72085, SEQ ID NO: 72102, SEQ ID NO: 72159, SEQ ID NO: 72183, SEQ ID NO: 72216, SEQ ID NO: 72241, SEQ ID NO: 72331, SEQ ID NO: 72364, SEQ ID NO: 72372, SEQ ID NO: 72390, SEQ ID NO: 72448, SEQ ID NO: 72528, SEQ ID NO: 72595, SEQ ID NO: 72604, SEQ ID NO: 72648, SEQ ID NO: 72667, SEQ ID NO: 72685, SEQ ID NO: 72721, SEQ ID NO: 72751, SEQ ID NO: 72755, SEQ ID NO: 72805, SEQ ID NO: 72810, SEQ ID NO: 72831, SEQ ID NO: 72837, SEQ ID NO: 72862, SEQ ID NO: 72885, SEQ ID NO: 72989, SEQ ID NO: 73014, SEQ ID NOs: 73045 to 73046, SEQ ID NO: 73086, SEQ ID NO: 73094, SEQ ID NO: 73113, SEQ ID NO: 73122, SEQ ID NO: 73161, SEQ ID NO: 73191, SEQ ID NO: 73224, SEQ ID NOs: 73232 to 73233, SEQ ID NO: 73238, SEQ ID NO: 73290, SEQ ID NO: 73327, SEQ ID NO: 73377, SEQ ID NO: 73382, SEQ ID NO: 73404, SEQ ID NO: 73406, SEQ ID NO: 73422, SEQ ID NOs: 73428 to 73429, SEQ ID NO: 73466, SEQ ID NO: 73475, SEQ ID NO: 73521, SEQ ID NO: 73523, SEQ ID NO: 73532, SEQ ID NO: 73550, SEQ ID NO: 73560, SEQ ID NO: 73591, SEQ ID NO: 73597, SEQ ID NO: 73644, SEQ ID NO: 73657, SEQ ID NO: 73660, SEQ ID NO: 73689, SEQ ID NO: 73729, SEQ ID NO: 73733, SEQ ID NO: 73873, SEQ ID NO: 73886, SEQ ID NO: 73930, SEQ ID NO: 73957, SEQ ID NOs: 73991 to 73992, SEQ ID NO: 74045, SEQ ID NO: 74047, SEQ ID NO: 74072, SEQ ID NO: 74080, SEQ ID NOs: 74096 to 74097, SEQ ID NO: 74107, SEQ ID NO: 74203, SEQ ID NO: 74208, SEQ ID NO: 74210, SEQ ID NO: 74238, SEQ ID NO: 74302, SEQ ID NO: 74350, SEQ ID NO: 74352, SEQ ID NO: 74411, SEQ ID NO: 74448, SEQ ID NO: 74473, SEQ ID NO: 74482, SEQ ID NO: 74515, SEQ ID NO: 74527, SEQ ID NO: 74560, SEQ ID NO: 74616, SEQ ID NO: 74649, SEQ ID NO: 74672, SEQ ID NO: 74674, SEQ ID NO: 74737, SEQ ID NO: 74782, SEQ ID NO: 74808, SEQ ID NO: 74810, SEQ ID NO: 74835, SEQ ID NO: 74886, SEQ ID NO: 74901, SEQ ID NO: 74946, SEQ ID NOs: 74975 to 74976, SEQ ID NO: 75017, SEQ ID NO: 75021, SEQ ID NO: 75040, SEQ ID NO: 75049, SEQ ID NO: 75063, SEQ ID NO: 75066, SEQ ID NO: 75072, SEQ ID NO: 75092, SEQ ID NO: 75094, SEQ ID NO: 75099, SEQ ID NO: 75111, SEQ ID NO: 75148, SEQ ID NO: 75245, SEQ ID NO: 75269, SEQ ID NO: 75388, SEQ ID NO: 75403, SEQ ID NO: 75429, SEQ ID NO: 75455, SEQ ID NO: 75470, SEQ ID NO: 75489, SEQ ID NO: 75506, SEQ ID NO: 75529, SEQ ID NO: 75547, SEQ ID NO: 75551, SEQ ID NOs: 75576 to 75577, SEQ ID NO: 75595, SEQ ID NO: 75701, SEQ ID NO: 75716, SEQ ID NO: 75747, SEQ ID NO: 75757, SEQ ID NO: 75762, SEQ ID NO: 75766, SEQ ID NO: 75874, SEQ ID NO: 75915, SEQ ID NO: 75933, SEQ ID NO: 75975, SEQ ID NO: 75979, SEQ ID NO: 76016, SEQ ID NO: 76023, SEQ ID NO: 76034, SEQ ID NO: 76040, SEQ ID NO: 76064, SEQ ID NO: 76076, SEQ ID NO: 76102, SEQ ID NOs: 76147 to 76148, SEQ ID NO: 76189, SEQ ID NO: 76199, SEQ ID NO: 76369, SEQ ID NO: 76375, SEQ ID NO: 76397, SEQ ID NO: 76410, SEQ ID NO: 76435, SEQ ID NO: 76446, SEQ ID NO: 76451, SEQ ID NOs: 76456 to 76458, SEQ ID NO: 76492, SEQ ID NO: 76544, SEQ ID NO: 76569, SEQ ID NO: 76574, SEQ ID NO: 76611, SEQ ID NO: 76654, SEQ ID NO: 76710, SEQ ID NO: 76753, SEQ ID NO: 76769, SEQ ID NO: 76781, SEQ ID NO: 76797, SEQ ID NO: 76803, SEQ ID NO: 76858, SEQ ID NO: 76860, SEQ ID NO: 76879, SEQ ID NO: 76943, SEQ ID NO: 76971, SEQ ID NO: 76981, SEQ ID NO: 77091, SEQ ID NO: 77133, SEQ ID NOs: 77193 to 77194, SEQ ID NO: 77210, SEQ ID NO: 77219, SEQ ID NO: 77237, SEQ ID NO: 77246, SEQ ID NO: 77251, SEQ ID NO: 77281, SEQ ID NO: 77293, SEQ ID NO: 77323, SEQ ID NO: 77334, SEQ ID NO: 77339, SEQ ID NO: 77396, SEQ ID NO: 77423, SEQ ID NO: 77433, SEQ ID NO: 77437, SEQ ID NO: 77442, SEQ ID NO: 77453, SEQ ID NO: 77485, SEQ ID NO: 77579, SEQ ID NO: 77627, SEQ ID NO: 77639, SEQ ID NO: 77644, SEQ ID NO: 77703, SEQ ID NO: 77773, SEQ ID NO: 77814, SEQ ID NO: 77868, SEQ ID NO: 77874, SEQ ID NO: 77900, SEQ ID NO: 77925, SEQ ID NO: 77995, SEQ ID NO: 78017, SEQ ID NO: 78083, SEQ ID NO: 78086, SEQ ID NO: 78090, SEQ ID NO: 78131, SEQ ID NO: 78139, SEQ ID NO: 78228, SEQ ID NO: 78248, SEQ ID NO: 78260, SEQ ID NO: 78346, SEQ ID NO: 78352, SEQ ID NO: 78377, SEQ ID NO: 78416, SEQ ID NO: 78421, SEQ ID NO: 78440, SEQ ID NO: 78521, SEQ ID NO: 78530, SEQ ID NO: 78532, SEQ ID NO: 78546, SEQ ID NO: 78600, SEQ ID NO: 78631, SEQ ID NO: 78671, SEQ ID NO: 78709, SEQ ID NO: 78714, SEQ ID NO: 78730, SEQ ID NO: 78738, SEQ ID NO: 78810, SEQ ID NO: 78855, SEQ ID NO: 78883, SEQ ID NO: 78917, SEQ ID NOs: 78919 to 78920, SEQ ID NO: 78928, SEQ ID NO: 79035, SEQ ID NO: 79048, SEQ ID NO: 79056, SEQ ID NO: 79086, SEQ ID NO: 79091, SEQ ID NO: 79095, SEQ ID NO: 79107, SEQ ID NO: 79109, SEQ ID NO: 79136, SEQ ID NO: 79142, SEQ ID NO: 79147, SEQ ID NO: 79151, SEQ ID NO: 79194, SEQ ID NO: 79196, SEQ ID NO: 79227, SEQ ID NO: 79247, SEQ ID NO: 79253, SEQ ID NO: 79255, SEQ ID NO: 79269, SEQ ID NO: 79310, SEQ ID NO: 79331, SEQ ID NO: 79357, SEQ ID NO: 79406, SEQ ID NO: 79437, SEQ ID NO: 79448, SEQ ID NO: 79453, SEQ ID NO: 79480, SEQ ID NO: 79483, SEQ ID NO: 79486, SEQ ID NO: 79504, SEQ ID NO: 79508, SEQ ID NO: 79516, SEQ ID NO: 79548, SEQ ID NO: 79575, SEQ ID NO: 79588, SEQ ID NO: 79592, SEQ ID NO: 79609, SEQ ID NO: 79626, SEQ ID NO: 79640, SEQ ID NO: 79697, SEQ ID NO: 79746, SEQ ID NO: 79751, SEQ ID NO: 79766, SEQ ID NO: 79784, SEQ ID NO: 79787, SEQ ID NO: 79816, SEQ ID NO: 79834, SEQ ID NO: 79853, SEQ ID NO: 79858, SEQ ID NO: 79861, SEQ ID NO: 79874, SEQ ID NO: 79877, SEQ ID NO: 79906, SEQ ID NO: 79909, SEQ ID NO: 79939, SEQ ID NO: 79958, SEQ ID NO: 79987, SEQ ID NO: 80000, SEQ ID NO: 80027, SEQ ID NO: 80040, SEQ ID NO: 80139, SEQ ID NO: 80141, SEQ ID NO: 80212, SEQ ID NO: 80232, SEQ ID NO: 80237, SEQ ID NO: 80241, SEQ ID NO: 80318, SEQ ID NO: 80320, SEQ ID NOs: 80367 to 80368, SEQ ID NO: 80398, SEQ ID NO: 80421, SEQ ID NO: 80461, SEQ ID NO: 80486, SEQ ID NO: 80513, SEQ ID NO: 80527, SEQ ID NO: 80555, SEQ ID NO: 80574, SEQ ID NO: 80583, SEQ ID NO: 80627, SEQ ID NO: 80673, SEQ ID NOs: 80703 to 80704, SEQ ID NOs: 80718 to 80719, SEQ ID NO: 80725, SEQ ID NO: 80796, SEQ ID NO: 80804, SEQ ID NO: 80833, SEQ ID NO: 80869, SEQ ID NO: 80903, SEQ ID NO: 80931, SEQ ID NO: 80936, SEQ ID NO: 80946, SEQ ID NO: 80990, SEQ ID NO: 81021, SEQ ID NO: 81042, SEQ ID NO: 81046, SEQ ID NO: 81054, SEQ ID NO: 81066, SEQ ID NO: 81145, SEQ ID NO: 81166, SEQ ID NO: 81168, SEQ ID NO: 81175, SEQ ID NO: 81185, SEQ ID NO: 81207, SEQ ID NO: 81251, SEQ ID NO: 81259, SEQ ID NO: 81302, SEQ ID NO: 81337, SEQ ID NO: 81342, SEQ ID NO: 81386, SEQ ID NO: 81428, SEQ ID NO: 81446, SEQ ID NO: 81458, SEQ ID NO: 81488, SEQ ID NO: 81505, SEQ ID NO: 81517, SEQ ID NO: 81566, SEQ ID NO: 81687, SEQ ID NO: 81690, SEQ ID NO: 81694, SEQ ID NO: 81713, SEQ ID NO: 81755, SEQ ID NO: 81825, SEQ ID NO: 81856, SEQ ID NO: 81873, SEQ ID NO: 81904, SEQ ID NO: 81916, SEQ ID NO: 81938, SEQ ID NO: 81951, SEQ ID NO: 81963, SEQ ID NO: 82045, SEQ ID NO: 82085, SEQ ID NO: 82117, SEQ ID NO: 82136, SEQ ID NO: 82193, SEQ ID NO: 82239, SEQ ID NO: 82241, SEQ ID NO: 82259, SEQ ID NO: 82320, SEQ ID NO: 82382, SEQ ID NO: 82417, SEQ ID NO: 82459, SEQ ID NO: 82474, SEQ ID NO: 82514, SEQ ID NO: 82556, SEQ ID NO: 82581, SEQ ID NO: 82596, SEQ ID NO: 82633, SEQ ID NO: 82644, SEQ ID NO: 82649, SEQ ID NO: 82676, SEQ ID NO: 82681, SEQ ID NO: 82718, SEQ ID NO: 82731, SEQ ID NO: 82769, SEQ ID NO: 82817, SEQ ID NO: 82870, SEQ ID NO: 82872, SEQ ID NO: 82885, SEQ ID NOs: 82920 to 82921, SEQ ID NO: 82955, SEQ ID NO: 82960, SEQ ID NO: 82985, SEQ ID NO: 82988, SEQ ID NO: 83013, SEQ ID NO: 83018, SEQ ID NO: 83051, SEQ ID NO: 83062, SEQ ID NO: 83099, SEQ ID NO: 83149, SEQ ID NO: 83185, SEQ ID NO: 83193, SEQ ID NO: 83208, SEQ ID NO: 83225, SEQ ID NO: 83235, SEQ ID NO: 83243, SEQ ID NO: 83260, SEQ ID NO: 83269, SEQ ID NO: 83286, SEQ ID NO: 83293, SEQ ID NO: 83349, SEQ ID NO: 83383, SEQ ID NO: 83409, SEQ ID NO: 83426, SEQ ID NO: 83438, SEQ ID NO: 83549, SEQ ID NO: 83605, SEQ ID NO: 83686, SEQ ID NO: 83704, SEQ ID NO: 83714, SEQ ID NO: 83806, SEQ ID NO: 83811, SEQ ID NO: 83821, SEQ ID NOs: 83863 to 83864, SEQ ID NO: 83872, SEQ ID NO: 83891, SEQ ID NO: 83899, SEQ ID NO: 83901, SEQ ID NO: 83921, SEQ ID NO: 83970, SEQ ID NO: 83974, SEQ ID NO: 83988, SEQ ID NO: 84002, SEQ ID NO: 84025, SEQ ID NO: 84070, SEQ ID NO: 84090, SEQ ID NO: 84154, SEQ ID NO: 84182, SEQ ID NOs: 84187 to 84188, SEQ ID NO: 84201, SEQ ID NO: 84212, SEQ ID NO: 84232, SEQ ID NO: 84238, SEQ ID NO: 84248, SEQ ID NO: 84306, SEQ ID NO: 84324, SEQ ID NO: 84348, SEQ ID NO: 84376, SEQ ID NO: 84387, SEQ ID NO: 84390, SEQ ID NO: 84422, SEQ ID NO: 84428, SEQ ID NO: 84437, SEQ ID NO: 84445, SEQ ID NO: 84489, SEQ ID NO: 84501, SEQ ID NO: 84534, SEQ ID NO: 84558, SEQ ID NO: 84593, SEQ ID NO: 84676, SEQ ID NO: 84782, SEQ ID NO: 84795, SEQ ID NO: 84822, SEQ ID NO: 84885, SEQ ID NO: 84991, SEQ ID NO: 85010, SEQ ID NO: 85024, SEQ ID NO: 85054, SEQ ID NO: 85056, SEQ ID NO: 85060, SEQ ID NO: 85101, SEQ ID NO: 85117, SEQ ID NO: 85146, SEQ ID NO: 85219, SEQ ID NOs: 85242 to 85243, SEQ ID NO: 85266, SEQ ID NO: 85310, SEQ ID NO: 85349, SEQ ID NO: 85361, SEQ ID NO: 85370, SEQ ID NO: 85379, SEQ ID NO: 85399, SEQ ID NO: 85417, SEQ ID NO: 85435, SEQ ID NO: 85447, SEQ ID NO: 85463, SEQ ID NO: 85519, SEQ ID NO: 85528, SEQ ID NO: 85530, SEQ ID NO: 85602, SEQ ID NO: 85624, SEQ ID NO: 85629, SEQ ID NO: 85725, SEQ ID NO: 85737, SEQ ID NO: 85848, SEQ ID NO: 85878, SEQ ID NO: 85910, SEQ ID NO: 85959, SEQ ID NO: 85963, SEQ ID NO: 85967, SEQ ID NOs: 85985 to 85986, SEQ ID NO: 86003, SEQ ID NO: 86076, SEQ ID NO: 86159, SEQ ID NO: 86208, SEQ ID NO: 86248, SEQ ID NO: 86279, SEQ ID NO: 86343, SEQ ID NO: 86366, SEQ ID NO: 86417, SEQ ID NO: 86431, SEQ ID NO: 86433, SEQ ID NO: 86473, SEQ ID NO: 86523, SEQ ID NOs: 86526 to 86527, SEQ ID NO: 86541, SEQ ID NO: 86567, SEQ ID NO: 86586, SEQ ID NO: 86589, SEQ ID NO: 86599, SEQ ID NO: 86633, SEQ ID NO: 86665, SEQ ID NO: 86688, SEQ ID NO: 86698, SEQ ID NO: 86725, SEQ ID NO: 86761, SEQ ID NO: 86775, SEQ ID NO: 86825, SEQ ID NO: 86914, SEQ ID NO: 86929, SEQ ID NO: 86940, SEQ ID NO: 86969, SEQ ID NO: 86994, SEQ ID NO: 87027, SEQ ID NO: 87041, SEQ ID NO: 87157, SEQ ID NO: 87160, SEQ ID NO: 87185, SEQ ID NO: 87251, SEQ ID NO: 87255, SEQ ID NO: 87300, SEQ ID NO: 87321, SEQ ID NO: 87358, SEQ ID NO: 87425, SEQ ID NO: 87427, SEQ ID NO: 87431, SEQ ID NO: 87474, SEQ ID NO: 87536, SEQ ID NO: 87550, SEQ ID NO: 87576, SEQ ID NO: 87603, SEQ ID NO: 87623, SEQ ID NO: 87626, SEQ ID NO: 87638, SEQ ID NO: 87708, SEQ ID NO: 87733, SEQ ID NO: 87775, SEQ ID NO: 87799, SEQ ID NO: 87818, SEQ ID NOs: 87865 to 87866, SEQ ID NO: 87875, SEQ ID NO: 87917, SEQ ID NO: 87946, SEQ ID NO: 87951, SEQ ID NO: 88016, SEQ ID NO: 88061, SEQ ID NO: 88120, SEQ ID NO: 88122, SEQ ID NO: 88125, SEQ ID NO: 88144, SEQ ID NO: 88178, SEQ ID NO: 88180, SEQ ID NO: 88186, SEQ ID NO: 88203, SEQ ID NO: 88241, SEQ ID NO: 88272, SEQ ID NO: 88285, SEQ ID NO: 88288, SEQ ID NO: 88359, SEQ ID NO: 88384, SEQ ID NO: 88390, SEQ ID NO: 88474, SEQ ID NO: 88522, SEQ ID NO: 88563, SEQ ID NO: 88643, SEQ ID NO: 88659, SEQ ID NO: 88708, SEQ ID NO: 88710, SEQ ID NO: 88731, SEQ ID NO: 88751, SEQ ID NO: 88806, SEQ ID NO: 88975, SEQ ID NO: 88999, SEQ ID NO: 89010, SEQ ID NO: 89012, SEQ ID NO: 89028, SEQ ID NO: 89035, SEQ ID NO: 89037, SEQ ID NO: 89039, SEQ ID NO: 89045, SEQ ID NO: 89073, SEQ ID NO: 89118, SEQ ID NO: 89126, SEQ ID NO: 89135, SEQ ID NO: 89138, SEQ ID NO: 89147, SEQ ID NO: 89168, SEQ ID NO: 89193, SEQ ID NO: 89228, SEQ ID NO: 89235, SEQ ID NO: 89269, SEQ ID NO: 89286, SEQ ID NO: 89291, SEQ ID NO: 89339, SEQ ID NO: 89342, SEQ ID NO: 89394, SEQ ID NO: 89453, SEQ ID NO: 89492, SEQ ID NO: 89510, SEQ ID NO: 89555, SEQ ID NO: 89595, SEQ ID NO: 89670, SEQ ID NO: 89695, SEQ ID NO: 89785, SEQ ID NO: 89836, SEQ ID NO: 89842, SEQ ID NO: 89921, SEQ ID NO: 89929, SEQ ID NO: 89935, SEQ ID NO: 89938, SEQ ID NO: 89950, SEQ ID NO: 89953, SEQ ID NO: 89960, SEQ ID NO: 89987, SEQ ID NO: 89992, SEQ ID NO: 90030, SEQ ID NO: 90056, SEQ ID NO: 90066, SEQ ID NO: 90085, SEQ ID NO: 90089, SEQ ID NO: 90115, SEQ ID NO: 90120, SEQ ID NO: 90133, SEQ ID NO: 90157, SEQ ID NO: 90159, SEQ ID NO: 90191, SEQ ID NO: 90268, SEQ ID NO: 90274, SEQ ID NO: 90280, SEQ ID NO: 90287, SEQ ID NO: 90315, SEQ ID NO: 90408, SEQ ID NO: 90417, SEQ ID NO: 90443, SEQ ID NO: 90466, SEQ ID NO: 90507, SEQ ID NO: 90555, SEQ ID NO: 90593, SEQ ID NO: 90599, SEQ ID NO: 90621, SEQ ID NO: 90634, SEQ ID NO: 90653, SEQ ID NO: 90696, SEQ ID NO: 90758, SEQ ID NO: 90777, SEQ ID NO: 90835, SEQ ID NO: 90882, SEQ ID NO: 90898, SEQ ID NO: 90938, SEQ ID NO: 90954, SEQ ID NO: 90999, SEQ ID NO: 91045, SEQ ID NO: 91060, SEQ ID NO: 91072, SEQ ID NO: 91076, SEQ ID NO: 91105, SEQ ID NO: 91132, SEQ ID NO: 91222, SEQ ID NO: 91226, SEQ ID NO: 91229, SEQ ID NO: 91306, SEQ ID NO: 91309, SEQ ID NO: 91315, SEQ ID NO: 91346, SEQ ID NO: 91419, SEQ ID NO: 91449, SEQ ID NO: 91498, SEQ ID NO: 91563, SEQ ID NO: 91588, SEQ ID NO: 91681, SEQ ID NO: 91766, SEQ ID NOs: 91775 to 91776, SEQ ID NO: 91780, SEQ ID NO: 91799, SEQ ID NO: 91845, SEQ ID NO: 91852, SEQ ID NOs: 91885 to 91886, SEQ ID NO: 91930, SEQ ID NO: 91935, SEQ ID NO: 91953, SEQ ID NO: 91966, SEQ ID NO: 91984, SEQ ID NO: 92026, SEQ ID NO: 92030, SEQ ID NO: 92069, SEQ ID NO: 92100, SEQ ID NO: 92111, SEQ ID NO: 92189, SEQ ID NO: 92249, SEQ ID NO: 92296, SEQ ID NO: 92400, SEQ ID NO: 92404, SEQ ID NO: 92409, SEQ ID NO: 92429, SEQ ID NO: 92474, SEQ ID NO: 92500, SEQ ID NO: 92515, SEQ ID NO: 92538, SEQ ID NO: 92646, SEQ ID NO: 92659, SEQ ID NO: 92671, SEQ ID NO: 92673, SEQ ID NO: 92675, SEQ ID NO: 92684, SEQ ID NO: 92704, SEQ ID NO: 92832, SEQ ID NO: 92835, SEQ ID NO: 92854, SEQ ID NO: 92858, SEQ ID NO: 92877, SEQ ID NO: 92918, SEQ ID NO: 92920, SEQ ID NO:

93004, SEQ ID NO: 93036, SEQ ID NO: 93042, SEQ ID NO: 93071, SEQ ID NO: 93089, SEQ ID NO: 93136, SEQ ID NO: 93180, SEQ ID NO: 93251, SEQ ID NO: 93325, SEQ ID NO: 93335, SEQ ID NO: 93344, SEQ ID NO: 93356, SEQ ID NO: 93382, SEQ ID NO: 93408, SEQ ID NO: 93420, SEQ ID NO: 93503, SEQ ID NO: 93537, SEQ ID NO: 93617, SEQ ID NO: 93658, SEQ ID NO: 93697, SEQ ID NO: 93710, SEQ ID NO: 93877, SEQ ID NO: 93885, SEQ ID NO: 93888, SEQ ID NO: 93893, SEQ ID NO: 93903, SEQ ID NO: 93912, SEQ ID NO: 93926, SEQ ID NO: 93933, SEQ ID NO: 93982, SEQ ID NO: 93987, SEQ ID NO: 94000, SEQ ID NO: 94054, SEQ ID NO: 94058, SEQ ID NO: 94087, SEQ ID NO: 94090, SEQ ID NO: 94102, SEQ ID NO: 94143, SEQ ID NO: 94269, SEQ ID NO: 94367, SEQ ID NO: 94465, SEQ ID NO: 94477, SEQ ID NO: 94525, SEQ ID NO: 94587, and SEQ ID NOs: 95593 to 113807. In some embodiments, any one of the peptides in the MAGC3 vaccine comprise an amino acid sequence 80, 81, 82, 83, 84, 85, 86, 87, 88, 89, 90, 91, 92, 93, 94, 95, 96, 97, 98 or 99% identical to SEQ ID NO: 41647, SEQ ID NO: 50668, SEQ ID NO: 50905, SEQ ID NOs: 51039 to 51040, SEQ ID NO: 68257, SEQ ID NO: 68285, SEQ ID NO: 68288, SEQ ID NO: 68290, SEQ ID NO: 68305, SEQ ID NO: 68389, SEQ ID NO: 68419, SEQ ID NO: 68470, SEQ ID NO: 68510, SEQ ID NO: 68519, SEQ ID NO: 68592, SEQ ID NO: 68603, SEQ ID NO: 68684, SEQ ID NO: 68688, SEQ ID NO: 68747, SEQ ID NO: 68760, SEQ ID NO: 68778, SEQ ID NO: 68786, SEQ ID NO: 68855, SEQ ID NO: 68898, SEQ ID NO: 68900, SEQ ID NO: 68927, SEQ ID NO: 68961, SEQ ID NO: 69026, SEQ ID NO: 69041, SEQ ID NO: 69047, SEQ ID NO: 69148, SEQ ID NO: 69173, SEQ ID NO: 69180, SEQ ID NO: 69192, SEQ ID NO: 69227, SEQ ID NO: 69311, SEQ ID NO: 69330, SEQ ID NO: 69333, SEQ ID NO: 69346, SEQ ID NO: 69356, SEQ ID NO: 69393, SEQ ID NO: 69421, SEQ ID NO: 69437, SEQ ID NO: 69451, SEQ ID NO: 69500, SEQ ID NO: 69505, SEQ ID NO: 69517, SEQ ID NO: 69540, SEQ ID NO: 69559, SEQ ID NO: 69571, SEQ ID NO: 69586, SEQ ID NO: 69589, SEQ ID NO: 69591, SEQ ID NO: 69619, SEQ ID NO: 69631, SEQ ID NO: 69633, SEQ ID NO: 69644, SEQ ID NO: 69649, SEQ ID NO: 69747, SEQ ID NO: 69764, SEQ ID NO: 69767, SEQ ID NO: 69790, SEQ ID NO: 69832, SEQ ID NO: 69836, SEQ ID NO: 69882, SEQ ID NO: 69999, SEQ ID NO: 70012, SEQ ID NO: 70036, SEQ ID NO: 70050, SEQ ID NO: 70066, SEQ ID NO: 70069, SEQ ID NO: 70109, SEQ ID NO: 70159, SEQ ID NO: 70165, SEQ ID NO: 70175, SEQ ID NO: 70177, SEQ ID NO: 70188, SEQ ID NO: 70284, SEQ ID NO: 70323, SEQ ID NO: 70326, SEQ ID NO: 70428, SEQ ID NO: 70455, SEQ ID NO: 70570, SEQ ID NO: 70606, SEQ ID NO: 70635, SEQ ID NO: 70676, SEQ ID NO: 70692, SEQ ID NO: 70716, SEQ ID NO: 70728, SEQ ID NO: 70735, SEQ ID NO: 70750, SEQ ID NO: 70764, SEQ ID NO: 70770, SEQ ID NO: 70806, SEQ ID NO: 70968, SEQ ID NO: 70997, SEQ ID NO: 71049, SEQ ID NO: 71075, SEQ ID NO: 71090, SEQ ID NO: 71117, SEQ ID NO: 71151, SEQ ID NO: 71176, SEQ ID NO: 71193, SEQ ID NO: 71203, SEQ ID NO: 71239, SEQ ID NO: 71247, SEQ ID NO: 71249, SEQ ID NO: 71275, SEQ ID NO: 71287, SEQ ID NO: 71328, SEQ ID NOs: 71359 to 71360, SEQ ID NOs: 71367 to 71368, SEQ ID NO: 71392, SEQ ID NO: 71414, SEQ ID NO: 71449, SEQ ID NO: 71476, SEQ ID NO: 71482, SEQ ID NO: 71543, SEQ ID NO: 71547, SEQ ID NO: 71560, SEQ ID NO: 71585, SEQ ID NO: 71612, SEQ ID NO: 71620, SEQ ID NO: 71628, SEQ ID NO: 71636, SEQ ID NO: 71673, SEQ ID NOs: 71688 to 71689, SEQ ID NO: 71696, SEQ ID NO: 71700, SEQ ID NO: 71718, SEQ ID NO: 71725, SEQ ID NO: 71807, SEQ ID NO: 71919, SEQ ID NO: 71935, SEQ ID NO: 71943, SEQ ID NO: 71948, SEQ ID NOs: 71987 to 71988, SEQ ID NO: 72045, SEQ ID NO: 72055, SEQ ID NO: 72076, SEQ ID NO: 72085, SEQ ID NO: 72102, SEQ ID NO: 72159, SEQ ID NO: 72183, SEQ ID NO: 72216, SEQ ID NO: 72241, SEQ ID NO: 72331, SEQ ID NO: 72364, SEQ ID NO: 72372, SEQ ID NO: 72390, SEQ ID NO: 72448, SEQ ID NO: 72528, SEQ ID NO: 72595, SEQ ID NO: 72604, SEQ ID NO: 72648, SEQ ID NO: 72667, SEQ ID NO: 72685, SEQ ID NO: 72721, SEQ ID NO: 72751, SEQ ID NO: 72755, SEQ ID NO: 72805, SEQ ID NO: 72810, SEQ ID NO: 72831, SEQ ID NO: 72837, SEQ ID NO: 72862, SEQ ID NO: 72885, SEQ ID NO: 72989, SEQ ID NO: 73014, SEQ ID NOs: 73045 to 73046, SEQ ID NO: 73086, SEQ ID NO: 73094, SEQ ID NO: 73113, SEQ ID NO: 73122, SEQ ID NO: 73161, SEQ ID NO: 73191, SEQ ID NO: 73224, SEQ ID NOs: 73232 to 73233, SEQ ID NO: 73238, SEQ ID NO: 73290, SEQ ID NO: 73327, SEQ ID NO: 73377, SEQ ID NO: 73382, SEQ ID NO: 73404, SEQ ID NO: 73406, SEQ ID NO: 73422, SEQ ID NOs: 73428 to 73429, SEQ ID NO: 73466, SEQ ID NO: 73475, SEQ ID NO: 73521, SEQ ID NO: 73523, SEQ ID NO: 73532, SEQ ID NO: 73550, SEQ ID NO: 73560, SEQ ID NO: 73591, SEQ ID NO: 73597, SEQ ID NO: 73644, SEQ ID NO: 73657, SEQ ID NO: 73660, SEQ ID NO: 73689, SEQ ID NO: 73729, SEQ ID NO: 73733, SEQ ID NO: 73873, SEQ ID NO: 73886, SEQ ID NO: 73930, SEQ ID NO: 73957, SEQ ID NOs: 73991 to 73992, SEQ ID NO: 74045, SEQ ID NO: 74047, SEQ ID NO: 74072, SEQ ID NO: 74080, SEQ ID NOs: 74096 to 74097, SEQ ID NO: 74107, SEQ ID NO: 74203, SEQ ID NO: 74208, SEQ ID NO: 74210, SEQ ID NO: 74238, SEQ ID NO: 74302, SEQ ID NO: 74350, SEQ ID NO: 74352, SEQ ID NO: 74411, SEQ ID NO: 74448, SEQ ID NO: 74473, SEQ ID NO: 74482, SEQ ID NO: 74515, SEQ ID NO: 74527, SEQ ID NO: 74560, SEQ ID NO: 74616, SEQ ID NO: 74649, SEQ ID NO: 74672, SEQ ID NO: 74674, SEQ ID NO: 74737, SEQ ID NO: 74782, SEQ ID NO: 74808, SEQ ID NO: 74810, SEQ ID NO: 74835, SEQ ID NO: 74886, SEQ ID NO: 74901, SEQ ID NO: 74946, SEQ ID NOs: 74975 to 74976, SEQ ID NO: 75017, SEQ ID NO: 75021, SEQ ID NO: 75040, SEQ ID NO: 75049, SEQ ID NO: 75063, SEQ ID NO: 75066, SEQ ID NO: 75072, SEQ ID NO: 75092, SEQ ID NO: 75094, SEQ ID NO: 75099, SEQ ID NO: 75111, SEQ ID NO: 75148, SEQ ID NO: 75245, SEQ ID NO: 75269, SEQ ID NO: 75388, SEQ ID NO: 75403, SEQ ID NO: 75429, SEQ ID NO: 75455, SEQ ID NO: 75470, SEQ ID NO: 75489, SEQ ID NO: 75506, SEQ ID NO: 75529, SEQ ID NO: 75547, SEQ ID NO: 75551, SEQ ID NOs: 75576 to 75577, SEQ ID NO: 75595, SEQ ID NO: 75701, SEQ ID NO: 75716, SEQ ID NO: 75747, SEQ ID NO: 75757, SEQ ID NO: 75762, SEQ ID NO: 75766, SEQ ID NO: 75874, SEQ ID NO: 75915, SEQ ID NO: 75933, SEQ ID NO: 75975, SEQ ID NO: 75979, SEQ ID NO: 76016, SEQ ID NO: 76023, SEQ ID NO: 76034, SEQ ID NO: 76040, SEQ ID NO: 76064, SEQ ID NO: 76076, SEQ ID NO: 76102, SEQ ID NOs: 76147 to 76148, SEQ ID NO: 76189, SEQ ID NO: 76199, SEQ ID NO: 76369, SEQ ID NO: 76375, SEQ ID NO: 76397, SEQ ID NO: 76410, SEQ ID NO: 76435, SEQ ID NO: 76446, SEQ ID NO: 76451, SEQ ID NOs: 76456 to 76458, SEQ ID NO: 76492, SEQ ID NO: 76544, SEQ ID NO: 76569, SEQ ID NO: 76574, SEQ ID NO: 76611, SEQ ID NO: 76654, SEQ ID NO: 76710, SEQ ID NO: 76753, SEQ ID NO: 76769, SEQ ID NO: 76781, SEQ ID NO: 76797, SEQ ID NO: 76803, SEQ ID NO: 76858, SEQ ID NO: 76860, SEQ ID NO: 76879, SEQ ID NO: 76943, SEQ ID NO: 76971, SEQ ID NO: 76981, SEQ ID NO: 77091, SEQ ID NO: 77133, SEQ ID NOs: 77193 to 77194, SEQ ID NO: 77210, SEQ ID NO: 77219, SEQ ID NO: 77237, SEQ ID NO: 77246, SEQ ID NO: 77251, SEQ ID NO: 77281, SEQ ID NO: 77293, SEQ ID NO: 77323, SEQ ID NO: 77334, SEQ ID NO: 77339, SEQ ID NO: 77396, SEQ ID NO: 77423, SEQ ID NO: 77433, SEQ ID NO: 77437, SEQ ID NO: 77442, SEQ ID NO: 77453, SEQ ID NO: 77485, SEQ ID NO: 77579, SEQ ID NO: 77627, SEQ ID NO: 77639, SEQ ID NO: 77644, SEQ ID NO: 77703, SEQ ID NO: 77773, SEQ ID NO: 77814, SEQ ID NO: 77868, SEQ ID NO: 77874, SEQ ID NO: 77900, SEQ ID NO: 77925, SEQ ID NO: 77995, SEQ ID NO: 78017, SEQ ID NO: 78083, SEQ ID NO: 78086, SEQ ID NO: 78090, SEQ ID NO: 78131, SEQ ID NO: 78139, SEQ ID NO: 78228, SEQ ID NO: 78248, SEQ ID NO: 78260, SEQ ID NO: 78346, SEQ ID NO: 78352, SEQ ID NO: 78377, SEQ ID NO: 78416, SEQ ID NO: 78421, SEQ ID NO: 78440, SEQ ID NO: 78521, SEQ ID NO: 78530, SEQ ID NO: 78532, SEQ ID NO: 78546, SEQ ID NO: 78600, SEQ ID NO: 78631, SEQ ID NO: 78671, SEQ ID NO: 78709, SEQ ID NO: 78714, SEQ ID NO: 78730, SEQ ID NO: 78738, SEQ ID NO: 78810, SEQ ID NO: 78855, SEQ ID NO: 78883, SEQ ID NO: 78917, SEQ ID NOs: 78919 to 78920, SEQ ID NO: 78928, SEQ ID NO: 79035, SEQ ID NO: 79048, SEQ ID NO: 79056, SEQ ID NO: 79086, SEQ ID NO: 79091, SEQ ID NO: 79095, SEQ ID NO: 79107, SEQ ID NO: 79109, SEQ ID NO: 79136, SEQ ID NO: 79142, SEQ ID NO: 79147, SEQ ID NO: 79151, SEQ ID NO: 79194, SEQ ID NO: 79196, SEQ ID NO: 79227, SEQ ID NO: 79247, SEQ ID NO: 79253, SEQ ID NO: 79255, SEQ ID NO: 79269, SEQ ID NO: 79310, SEQ ID NO: 79331, SEQ ID NO: 79357, SEQ ID NO: 79406, SEQ ID NO: 79437, SEQ ID NO: 79448, SEQ ID NO: 79453, SEQ ID NO: 79480, SEQ ID NO: 79483, SEQ ID NO: 79486, SEQ ID NO: 79504, SEQ ID NO: 79508, SEQ ID NO: 79516, SEQ ID NO: 79548, SEQ ID NO: 79575, SEQ ID NO: 79588, SEQ ID NO: 79592, SEQ ID NO: 79609, SEQ ID NO: 79626, SEQ ID NO: 79640, SEQ ID NO: 79697, SEQ ID NO: 79746, SEQ ID NO: 79751, SEQ ID NO: 79766, SEQ ID NO: 79784, SEQ ID NO: 79787, SEQ ID NO: 79816, SEQ ID NO: 79834, SEQ ID NO: 79853, SEQ ID NO: 79858, SEQ ID NO: 79861, SEQ ID NO: 79874, SEQ ID NO: 79877, SEQ ID NO: 79906, SEQ ID NO: 79909, SEQ ID NO: 79939, SEQ ID NO: 79958, SEQ ID NO: 79987, SEQ ID NO: 80000, SEQ ID NO: 80027, SEQ ID NO: 80040, SEQ ID NO: 80139, SEQ ID NO: 80141, SEQ ID NO: 80212, SEQ ID NO: 80232, SEQ ID NO: 80237, SEQ ID NO: 80241, SEQ ID NO: 80318, SEQ ID NO: 80320, SEQ ID NOs: 80367 to 80368, SEQ ID NO: 80398, SEQ ID NO: 80421, SEQ ID NO: 80461, SEQ ID NO: 80486, SEQ ID NO: 80513, SEQ ID NO: 80527, SEQ ID NO: 80555, SEQ ID NO: 80574, SEQ ID NO: 80583, SEQ ID NO: 80627, SEQ ID NO: 80673, SEQ ID NOs: 80703 to 80704, SEQ ID NOs: 80718 to 80719, SEQ ID NO: 80725, SEQ ID NO: 80796, SEQ ID NO: 80804, SEQ ID NO: 80833, SEQ ID NO: 80869, SEQ ID NO: 80903, SEQ ID NO: 80931, SEQ ID NO: 80936, SEQ ID NO: 80946, SEQ ID NO: 80990, SEQ ID NO: 81021, SEQ ID NO: 81042, SEQ ID NO: 81046, SEQ ID NO: 81054, SEQ ID NO: 81066, SEQ ID NO: 81145, SEQ ID NO: 81166, SEQ ID NO: 81168, SEQ ID NO: 81175, SEQ ID NO: 81185, SEQ ID NO: 81207, SEQ ID NO: 81251, SEQ ID NO: 81259, SEQ ID NO: 81302, SEQ ID NO: 81337, SEQ ID NO: 81342, SEQ ID NO: 81386, SEQ ID NO: 81428, SEQ ID NO: 81446, SEQ ID NO: 81458, SEQ ID NO: 81488, SEQ ID NO: 81505, SEQ ID NO: 81517, SEQ ID NO: 81566, SEQ ID NO: 81687, SEQ ID NO: 81690, SEQ ID NO: 81694, SEQ ID NO: 81713, SEQ ID NO: 81755, SEQ ID NO: 81825, SEQ ID NO: 81856, SEQ ID NO: 81873, SEQ ID NO: 81904, SEQ ID NO: 81916, SEQ ID NO: 81938, SEQ ID NO: 81951, SEQ ID NO: 81963, SEQ ID NO: 82045, SEQ ID NO: 82085, SEQ ID NO: 82117, SEQ ID NO: 82136, SEQ ID NO: 82193, SEQ ID NO: 82239, SEQ ID NO: 82241, SEQ ID NO: 82259, SEQ ID NO: 82320, SEQ ID NO: 82382, SEQ ID NO: 82417, SEQ ID NO: 82459, SEQ ID NO: 82474, SEQ ID NO: 82514, SEQ ID NO: 82556, SEQ ID NO: 82581, SEQ ID NO: 82596, SEQ ID NO: 82633, SEQ ID NO: 82644, SEQ ID NO: 82649, SEQ ID NO: 82676, SEQ ID NO: 82681, SEQ ID NO: 82718, SEQ ID NO: 82731, SEQ ID NO: 82769, SEQ ID NO: 82817, SEQ ID NO: 82870, SEQ ID NO: 82872, SEQ ID NO: 82885, SEQ ID NOs: 82920 to 82921, SEQ ID NO: 82955, SEQ ID NO: 82960, SEQ ID NO: 82985, SEQ ID NO: 82988, SEQ ID NO: 83013, SEQ ID NO: 83018, SEQ ID NO: 83051, SEQ ID NO: 83062, SEQ ID NO: 83099, SEQ ID NO: 83149, SEQ ID NO: 83185, SEQ ID NO: 83193, SEQ ID NO: 83208, SEQ ID NO: 83225, SEQ ID NO: 83235, SEQ ID NO: 83243, SEQ ID NO: 83260, SEQ ID NO: 83269, SEQ ID NO: 83286, SEQ ID NO: 83293, SEQ ID NO: 83349, SEQ ID NO: 83383, SEQ ID NO: 83409, SEQ ID NO: 83426, SEQ ID NO: 83438, SEQ ID NO: 83549, SEQ ID NO: 83605, SEQ ID NO: 83686, SEQ ID NO: 83704, SEQ ID NO: 83714, SEQ ID NO: 83806, SEQ ID NO: 83811, SEQ ID NO: 83821, SEQ ID NOs: 83863 to 83864, SEQ ID NO: 83872, SEQ ID NO: 83891, SEQ ID NO: 83899, SEQ ID NO: 83901, SEQ ID NO: 83921, SEQ ID NO: 83970, SEQ ID NO: 83974, SEQ ID NO: 83988, SEQ ID NO: 84002, SEQ ID NO: 84025, SEQ ID NO: 84070, SEQ ID NO: 84090, SEQ ID NO: 84154, SEQ ID NO: 84182, SEQ ID NOs: 84187 to 84188, SEQ ID NO: 84201, SEQ ID NO: 84212, SEQ ID NO: 84232, SEQ ID NO: 84238, SEQ ID NO: 84248, SEQ ID NO: 84306, SEQ ID NO: 84324, SEQ ID NO: 84348, SEQ ID NO: 84376, SEQ ID NO: 84387, SEQ ID NO: 84390, SEQ ID NO: 84422, SEQ ID NO: 84428, SEQ ID NO: 84437, SEQ ID NO: 84445, SEQ ID NO: 84489, SEQ ID NO: 84501, SEQ ID NO: 84534, SEQ ID NO: 84558, SEQ ID NO: 84593, SEQ ID NO: 84676, SEQ ID NO: 84782, SEQ ID NO: 84795, SEQ ID NO: 84822, SEQ ID NO: 84885, SEQ ID NO: 84991, SEQ ID NO: 85010, SEQ ID NO: 85024, SEQ ID NO: 85054, SEQ ID NO: 85056, SEQ ID NO: 85060, SEQ ID NO: 85101, SEQ ID NO: 85117, SEQ ID NO: 85146, SEQ ID NO: 85219, SEQ ID NOs: 85242 to 85243, SEQ ID NO: 85266, SEQ ID NO: 85310, SEQ ID NO: 85349, SEQ ID NO: 85361, SEQ ID NO: 85370, SEQ ID NO: 85379, SEQ ID NO: 85399, SEQ ID NO: 85417, SEQ ID NO: 85435, SEQ ID NO: 85447, SEQ ID NO: 85463, SEQ ID NO: 85519, SEQ ID NO: 85528, SEQ ID NO: 85530, SEQ ID NO: 85602, SEQ ID NO: 85624, SEQ ID NO: 85629, SEQ ID NO: 85725, SEQ ID NO: 85737, SEQ ID NO: 85848, SEQ ID NO: 85878, SEQ ID NO: 85910, SEQ ID NO: 85959, SEQ ID NO: 85963, SEQ ID NO: 85967, SEQ ID NOs: 85985 to 85986, SEQ ID NO: 86003, SEQ ID NO: 86076, SEQ ID NO: 86159, SEQ ID NO: 86208, SEQ ID NO: 86248, SEQ ID NO: 86279, SEQ ID NO: 86343, SEQ ID NO: 86366, SEQ ID NO: 86417, SEQ ID NO: 86431, SEQ ID NO: 86433, SEQ ID NO: 86473, SEQ ID NO: 86523, SEQ ID NOs: 86526 to 86527, SEQ ID NO: 86541, SEQ ID NO: 86567, SEQ ID NO: 86586, SEQ ID NO: 86589, SEQ ID NO: 86599, SEQ ID NO: 86633, SEQ ID NO: 86665, SEQ ID NO: 86688, SEQ ID NO: 86698, SEQ ID NO: 86725, SEQ ID NO: 86761, SEQ ID NO: 86775, SEQ ID NO:

86825, SEQ ID NO: 86914, SEQ ID NO: 86929, SEQ ID NO: 86940, SEQ ID NO: 86969, SEQ ID NO: 86994, SEQ ID NO: 87027, SEQ ID NO: 87041, SEQ ID NO: 87157, SEQ ID NO: 87160, SEQ ID NO: 87185, SEQ ID NO: 87251, SEQ ID NO: 87255, SEQ ID NO: 87300, SEQ ID NO: 87321, SEQ ID NO: 87358, SEQ ID NO: 87425, SEQ ID NO: 87427, SEQ ID NO: 87431, SEQ ID NO: 87474, SEQ ID NO: 87536, SEQ ID NO: 87550, SEQ ID NO: 87576, SEQ ID NO: 87603, SEQ ID NO: 87623, SEQ ID NO: 87626, SEQ ID NO: 87638, SEQ ID NO: 87708, SEQ ID NO: 87733, SEQ ID NO: 87785, SEQ ID NO: 87799, SEQ ID NO: 87818, SEQ ID NOs: 87865 to 87866, SEQ ID NO: 87875, SEQ ID NO: 87917, SEQ ID NO: 87946, SEQ ID NO: 87951, SEQ ID NO: 88016, SEQ ID NO: 88061, SEQ ID NO: 88120, SEQ ID NO: 88122, SEQ ID NO: 88125, SEQ ID NO: 88144, SEQ ID NO: 88178, SEQ ID NO: 88180, SEQ ID NO: 88186, SEQ ID NO: 88203, SEQ ID NO: 88241, SEQ ID NO: 88272, SEQ ID NO: 88285, SEQ ID NO: 88288, SEQ ID NO: 88359, SEQ ID NO: 88384, SEQ ID NO: 88390, SEQ ID NO: 88474, SEQ ID NO: 88522, SEQ ID NO: 88563, SEQ ID NO: 88643, SEQ ID NO: 88659, SEQ ID NO: 88708, SEQ ID NO: 88710, SEQ ID NO: 88731, SEQ ID NO: 88751, SEQ ID NO: 88806, SEQ ID NO: 88975, SEQ ID NO: 88999, SEQ ID NO: 89010, SEQ ID NO: 89012, SEQ ID NO: 89028, SEQ ID NO: 89035, SEQ ID NO: 89037, SEQ ID NO: 89039, SEQ ID NO: 89045, SEQ ID NO: 89073, SEQ ID NO: 89118, SEQ ID NO: 89126, SEQ ID NO: 89135, SEQ ID NO: 89138, SEQ ID NO: 89147, SEQ ID NO: 89168, SEQ ID NO: 89193, SEQ ID NO: 89228, SEQ ID NO: 89235, SEQ ID NO: 89269, SEQ ID NO: 89286, SEQ ID NO: 89291, SEQ ID NO: 89339, SEQ ID NO: 89342, SEQ ID NO: 89394, SEQ ID NO: 89453, SEQ ID NO: 89492, SEQ ID NO: 89510, SEQ ID NO: 89555, SEQ ID NO: 89595, SEQ ID NO: 89670, SEQ ID NO: 89695, SEQ ID NO: 89785, SEQ ID NO: 89836, SEQ ID NO: 89842, SEQ ID NO: 89921, SEQ ID NO: 89929, SEQ ID NO: 89935, SEQ ID NO: 89938, SEQ ID NO: 89950, SEQ ID NO: 89953, SEQ ID NO: 89960, SEQ ID NO: 89987, SEQ ID NO: 89992, SEQ ID NO: 90030, SEQ ID NO: 90056, SEQ ID NO: 90066, SEQ ID NO: 90085, SEQ ID NO: 90089, SEQ ID NO: 90115, SEQ ID NO: 90120, SEQ ID NO: 90133, SEQ ID NO: 90157, SEQ ID NO: 90159, SEQ ID NO: 90191, SEQ ID NO: 90268, SEQ ID NO: 90274, SEQ ID NO: 90280, SEQ ID NO: 90287, SEQ ID NO: 90315, SEQ ID NO: 90408, SEQ ID NO: 90417, SEQ ID NO: 90443, SEQ ID NO: 90466, SEQ ID NO: 90507, SEQ ID NO: 90555, SEQ ID NO: 90593, SEQ ID NO: 90599, SEQ ID NO: 90621, SEQ ID NO: 90634, SEQ ID NO: 90653, SEQ ID NO: 90696, SEQ ID NO: 90758, SEQ ID NO: 90777, SEQ ID NO: 90835, SEQ ID NO: 90882, SEQ ID NO: 90898, SEQ ID NO: 90938, SEQ ID NO: 90954, SEQ ID NO: 90999, SEQ ID NO: 91045, SEQ ID NO: 91060, SEQ ID NO: 91072, SEQ ID NO: 91076, SEQ ID NO: 91105, SEQ ID NO: 91132, SEQ ID NO: 91222, SEQ ID NO: 91226, SEQ ID NO: 91229, SEQ ID NO: 91306, SEQ ID NO: 91309, SEQ ID NO: 91315, SEQ ID NO: 91346, SEQ ID NO: 91419, SEQ ID NO: 91449, SEQ ID NO: 91498, SEQ ID NO: 91563, SEQ ID NO: 91588, SEQ ID NO: 91681, SEQ ID NO: 91766, SEQ ID NOs: 91775 to 91776, SEQ ID NO: 91780, SEQ ID NO: 91799, SEQ ID NO: 91845, SEQ ID NO: 91852, SEQ ID NOs: 91885 to 91886, SEQ ID NO: 91930, SEQ ID NO: 91935, SEQ ID NO: 91953, SEQ ID NO: 91966, SEQ ID NO: 91984, SEQ ID NO: 92026, SEQ ID NO: 92030, SEQ ID NO: 92069, SEQ ID NO: 92100, SEQ ID NO: 92111, SEQ ID NO: 92189, SEQ ID NO: 92249, SEQ ID NO: 92296, SEQ ID NO: 92400, SEQ ID NO: 92404, SEQ ID NO: 92409, SEQ ID NO: 92429, SEQ ID NO: 92474, SEQ ID NO: 92500, SEQ ID NO: 92515, SEQ ID NO: 92538, SEQ ID NO: 92646, SEQ ID NO: 92659, SEQ ID NO: 92671, SEQ ID NO: 92673, SEQ ID NO: 92675, SEQ ID NO: 92684, SEQ ID NO: 92704, SEQ ID NO: 92832, SEQ ID NO: 92835, SEQ ID NO: 92854, SEQ ID NO: 92858, SEQ ID NO: 92877, SEQ ID NO: 92918, SEQ ID NO: 92920, SEQ ID NO: 93004, SEQ ID NO: 93036, SEQ ID NO: 93042, SEQ ID NO: 93071, SEQ ID NO: 93089, SEQ ID NO: 93136, SEQ ID NO: 93180, SEQ ID NO: 93251, SEQ ID NO: 93325, SEQ ID NO: 93335, SEQ ID NO: 93344, SEQ ID NO: 93356, SEQ ID NO: 93382, SEQ ID NO: 93408, SEQ ID NO: 93420, SEQ ID NO: 93503, SEQ ID NO: 93537, SEQ ID NO: 93617, SEQ ID NO: 93658, SEQ ID NO: 93697, SEQ ID NO: 93710, SEQ ID NO: 93877, SEQ ID NO: 93885, SEQ ID NO: 93888, SEQ ID NO: 93893, SEQ ID NO: 93903, SEQ ID NO: 93912, SEQ ID NO: 93926, SEQ ID NO: 93933, SEQ ID NO: 93982, SEQ ID NO: 93987, SEQ ID NO: 94000, SEQ ID NO: 94054, SEQ ID NO: 94058, SEQ ID NO: 94087, SEQ ID NO: 94090, SEQ ID NO: 94102, SEQ ID NO: 94143, SEQ ID NO: 94269, SEQ ID NO: 94367, SEQ ID NO: 94465, SEQ ID NO: 94477, SEQ ID NO: 94525, SEQ ID NO: 94587, or SEQ ID NOs: 95593 to 113807.

In some embodiments, the amino acid sequence for a MEW class I peptide vaccine for the SSX2 protein comprises one or more of the SEQ ID NOs: 162383 to 162453. In some embodiments, any one of the peptides in the SSX2 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 162383 to 162453.

In some embodiments, the amino acid sequence for a MEW class I peptide vaccine for the SSX2 protein comprises one or more of the SEQ ID NOs: 162383 to 166443. In some embodiments, any one of the peptides in the SSX2 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 162383 to 166443.

In some embodiments, the amino acid sequence for a MEW class I peptide vaccine for the SSX2 protein comprises two or more of the SEQ ID NOs: 162383 to 162453. In some embodiments, any one of the peptides in the SSX2 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 162383 to 162453.

In some embodiments, the amino acid sequence for a WIC class I peptide vaccine for the SSX2 protein comprises two or more of the SEQ ID NOs: 162383 to 166443. In some embodiments, any one of the peptides in the SSX2 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 162383 to 166443.

In some embodiments, the amino acid sequence for a WIC class I peptide vaccine for the PRAME protein comprises one or more of the SEQ ID NOs: 144109 to 144188. In some embodiments, any one of the peptides in the PRAME vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 144109 to 144188.

In some embodiments, the amino acid sequence for a WIC class I peptide vaccine for the PRAME protein comprises one or more of the SEQ ID NOs: 144109 to 162382. In some embodiments, any one of the peptides in the PRAME vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 144109 to 162382.

In some embodiments, the amino acid sequence for a WIC class I peptide vaccine for the PRAME protein comprises two or more of the SEQ ID NOs: 144109 to 144188. In some embodiments, any one of the peptides in the PRAME vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 144109 to 144188.

In some embodiments, the amino acid sequence for a WIC class I peptide vaccine for the PRAME protein comprises two or more of the SEQ ID NOs: 144109 to 162382. In some embodiments, any one of the peptides in the PRAME vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 144109 to 162382.

In some embodiments, the amino acid sequence for a WIC class I peptide vaccine for the KKLC1 protein comprises one or more of the SEQ ID NOs: 37110 to 37174. In some embodiments, any one of the peptides in the KKLC1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 37110 to 37174.

In some embodiments, the amino acid sequence for a WIC class I peptide vaccine for the KKLC1 protein comprises one or more of the SEQ ID NOs: 37110 to 41320. In some embodiments, any one of the peptides in the KKLC1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 37110 to 41320.

In some embodiments, the amino acid sequence for a WIC class I peptide vaccine for the KKLC1 protein comprises two or more of the SEQ ID NOs: 37110 to 37174. In some embodiments, any one of the peptides in the KKLC1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 37110 to 37174.

In some embodiments, the amino acid sequence for a WIC class I peptide vaccine for the KKLC1 protein comprises two or more of the SEQ ID NOs: 37110 to 41320. In some embodiments, any one of the peptides in the KKLC1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 37110 to 41320.

In some embodiments, the amino acid sequence for a WIC class I peptide vaccine for the PMEL protein comprises one or more of the SEQ ID NOs: 125134 to 125218. In some embodiments, any one of the peptides in the PMEL vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 125134 to 125218.

In some embodiments, the amino acid sequence for a WIC class I peptide vaccine for the PMEL protein comprises one or more of the SEQ ID NOs: 125134 to 144108. In some embodiments, any one of the peptides in the PMEL vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 125134 to 144108.

In some embodiments, the amino acid sequence for a WIC class I peptide vaccine for the PMEL protein comprises two or more of the SEQ ID NOs: 125134 to 125218. In some embodiments, any one of the peptides in the PMEL vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 125134 to 125218.

In some embodiments, the amino acid sequence for a WIC class I peptide vaccine for the PMEL protein comprises two or more of the SEQ ID NOs: 125134 to 144108. In some embodiments, any one of the peptides in the PMEL vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 125134 to 144108.

In some embodiments, the amino acid sequence for a WIC class I peptide vaccine for the TYRP1 protein comprises one or more of the SEQ ID NOs: 166444 to 166531. In some embodiments, any one of the peptides in the TYRP1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 166444 to 166531.

In some embodiments, the amino acid sequence for a WIC class I peptide vaccine for the TYRP1 protein comprises one or more of the SEQ ID NOs: 166444 to 182573. In some embodiments, any one of the peptides in the TYRP1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 166444 to 182573.

In some embodiments, the amino acid sequence for a WIC class I peptide vaccine for the TYRP1 protein comprises two or more of the SEQ ID NOs: 166444 to 166531. In some embodiments, any one of the peptides in the TYRP1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 166444 to 166531.

In some embodiments, the amino acid sequence for a WIC class I peptide vaccine for the TYRP1 protein comprises two or more of the SEQ ID NOs: 166444 to 182573. In some embodiments, any one of the peptides in the TYRP1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 166444 to 182573.

In some embodiments, the amino acid sequence for a MEW class I peptide vaccine for the TYRP2 protein comprises one or more of the SEQ ID NO: 166476, SEQ ID NO: 167118, SEQ ID NO: 169740, SEQ ID NO: 173412, SEQ ID NO: 179404, and SEQ ID NOs: 182574 to 182654. In some embodiments, any one of the peptides in the TYRP2 vaccine comprise an amino acid sequence 80, 81, 82, 83, 84, 85, 86, 87, 88, 89, 90, 91, 92, 93, 94, 95, 96, 97, 98 or 99% identical to SEQ ID NO: 166476, SEQ ID NO: 167118, SEQ ID NO: 169740, SEQ ID NO: 173412, SEQ ID NO: 179404, or SEQ ID NOs: 182574 to 182654.

In some embodiments, the amino acid sequence for a MEW class I peptide vaccine for the TYRP2 protein comprises one or more of the SEQ ID NOs: 166476 to 166477, SEQ ID NO: 166486, SEQ ID NO: 166513, SEQ ID NO: 166591, SEQ ID NO: 166606, SEQ ID NO: 166629, SEQ ID NO: 166641, SEQ ID NO: 166667, SEQ ID NOs: 166678 to 166679, SEQ ID NO: 166795, SEQ ID NO: 166799, SEQ ID NO: 166834, SEQ ID NO: 166854, SEQ ID NO: 166909, SEQ ID NO: 166912, SEQ ID NO: 166942, SEQ ID NOs: 166991 to 166992, SEQ ID NO: 167062, SEQ ID NO: 167067, SEQ ID NOs: 167073 to 167074, SEQ ID NO: 167106, SEQ ID NO: 167118, SEQ ID NO: 167151, SEQ ID NO: 167177, SEQ ID NO: 167241, SEQ ID NO: 167271, SEQ ID NO: 167395, SEQ ID NO: 167491, SEQ ID NO: 167505, SEQ ID NO: 167687, SEQ ID NO: 167736, SEQ ID NO: 167740, SEQ ID NO: 167743, SEQ ID NO: 167755, SEQ ID NO: 167810, SEQ ID NO: 167831, SEQ ID NO: 167837, SEQ ID NO: 167844, SEQ ID NOs: 167847 to 167848, SEQ ID NO: 167859, SEQ ID NO: 167880, SEQ ID NO: 167891, SEQ ID NO: 167897, SEQ ID NO: 167933, SEQ ID NO: 168094, SEQ ID NOs: 168111 to 168112, SEQ ID NO: 168132, SEQ ID NO: 168144, SEQ ID NO: 168167, SEQ ID NO: 168211, SEQ ID NO: 168252, SEQ ID NO: 168268, SEQ ID NO: 168343, SEQ ID NO: 168354, SEQ ID NO: 168376, SEQ ID NO: 168396, SEQ ID NO: 168410, SEQ ID NO: 168423, SEQ ID NO: 168460, SEQ ID NO: 168484, SEQ ID NO: 168496, SEQ ID NO: 168616, SEQ ID NO: 168626, SEQ ID NO: 168646, SEQ ID NO: 168660, SEQ ID NO: 168681, SEQ ID NO: 168703, SEQ ID NO: 168711, SEQ ID NO: 168725, SEQ ID NO: 168728, SEQ ID NO: 168760, SEQ ID NOs: 168792 to 168793, SEQ ID NO: 168815, SEQ ID NO: 168851, SEQ ID NO: 168863, SEQ ID NO: 168867, SEQ ID NO: 168871, SEQ ID NO: 168924, SEQ ID NO: 168927, SEQ ID NO: 168947, SEQ ID NO: 168974, SEQ ID NO: 169000, SEQ ID NO: 169024, SEQ ID NO: 169035, SEQ ID NO: 169112, SEQ ID NO: 169150, SEQ ID NO: 169187, SEQ ID NO: 169233, SEQ ID NO: 169240, SEQ ID NO: 169247, SEQ ID NO: 169275, SEQ ID NO: 169375, SEQ ID NO: 169403, SEQ ID NO: 169428, SEQ ID NO: 169460, SEQ ID NO: 169474, SEQ ID NO: 169500, SEQ ID NO: 169530, SEQ ID NO: 169542, SEQ ID NO: 169546, SEQ ID NO: 169548, SEQ ID NO: 169553, SEQ ID NO: 169555, SEQ ID NO: 169563, SEQ ID NO: 169565, SEQ ID NO: 169578, SEQ ID NO: 169584, SEQ ID NO: 169605, SEQ ID NO: 169641, SEQ ID NO: 169665, SEQ ID NO: 169673, SEQ ID NO: 169682, SEQ ID NO: 169700, SEQ ID NO: 169704, SEQ ID NO: 169740, SEQ ID NO: 169768, SEQ ID NO: 169850, SEQ ID NO: 169858, SEQ ID NO: 169867, SEQ ID NO: 169871, SEQ ID NO: 169886, SEQ ID NO: 169915, SEQ ID NO: 169966, SEQ ID NO: 170057, SEQ ID NO: 170061, SEQ ID NO: 170081, SEQ ID NOs: 170178 to 170179, SEQ ID NO: 170261, SEQ ID NO: 170268, SEQ ID NO: 170278, SEQ ID NO: 170290, SEQ ID NO: 170320, SEQ ID NO: 170329, SEQ ID NO: 170390, SEQ ID NO: 170443, SEQ ID NO: 170488, SEQ ID NO: 170543, SEQ ID NO: 170574, SEQ ID NO: 170679, SEQ ID NO: 170704, SEQ ID NOs: 170706 to 170707, SEQ ID NO: 170735, SEQ ID NO: 170754, SEQ ID NO: 170771, SEQ ID NOs: 170809 to 170810, SEQ ID NO: 170834, SEQ ID NO: 170847, SEQ ID NO: 170876, SEQ ID NOs: 170902 to 170903, SEQ ID NO: 170964, SEQ ID NO: 170968, SEQ ID NO: 170970, SEQ ID NO: 170976, SEQ ID NO: 170981, SEQ ID NO: 171011, SEQ ID NO: 171029, SEQ ID NO: 171080, SEQ ID NO: 171085, SEQ ID NO: 171091, SEQ ID NO: 171174, SEQ ID NO: 171182, SEQ ID NO: 171212, SEQ ID NO: 171229, SEQ ID NO: 171242, SEQ ID NO: 171256, SEQ ID NO: 171260, SEQ ID NO: 171263, SEQ ID NO: 171291, SEQ ID NO: 171329, SEQ ID NO: 171334, SEQ ID NO: 171340, SEQ ID NO: 171406, SEQ ID NO: 171412, SEQ ID NO: 171428, SEQ ID NO: 171462, SEQ ID NO: 171474, SEQ ID NO: 171485, SEQ ID NO: 171490, SEQ ID NO: 171526, SEQ ID NO: 171536, SEQ ID NO: 171550, SEQ ID NO: 171581, SEQ ID NO: 171608, SEQ ID NO: 171625, SEQ ID NO: 171655, SEQ ID NO: 171662, SEQ ID NO: 171709, SEQ ID NO: 171732, SEQ ID NO: 171746, SEQ ID NO: 171752, SEQ ID NO: 171768, SEQ ID NO: 171786, SEQ ID NO: 171788, SEQ ID NO: 171814, SEQ ID NO: 171855, SEQ ID NO: 171863, SEQ ID NO: 171980, SEQ ID NO: 172007, SEQ ID NO: 172010, SEQ ID NO: 172062, SEQ ID NO: 172161, SEQ ID NO: 172181, SEQ ID NO: 172203, SEQ ID NO: 172225, SEQ ID NO: 172231, SEQ ID NO: 172255, SEQ ID NO: 172272, SEQ ID NO: 172276, SEQ ID NO: 172294, SEQ ID NO: 172348, SEQ ID NO: 172372, SEQ ID NO: 172375, SEQ ID NO: 172378, SEQ ID NO: 172387, SEQ ID NO: 172389, SEQ ID NO: 172421, SEQ ID NOs: 172439 to 172440, SEQ ID NO: 172484, SEQ ID NO: 172495, SEQ ID NO: 172563, SEQ ID NO: 172594, SEQ ID NO: 172660, SEQ ID NO: 172693, SEQ ID NO: 172702, SEQ ID NO: 172704, SEQ ID NO: 172709, SEQ ID NO: 172717, SEQ ID NO: 172726, SEQ ID NO: 172742, SEQ ID NO: 172793, SEQ ID NO: 172801, SEQ ID NO: 172816, SEQ ID NO: 172849, SEQ ID NO: 172862, SEQ ID NO: 172900, SEQ ID NO: 172907, SEQ ID NO: 172919, SEQ ID NO: 172926, SEQ ID NO: 172990, SEQ ID NO: 172994, SEQ ID NO: 172999, SEQ ID NO: 173004, SEQ ID NO: 173007, SEQ ID NO: 173084, SEQ ID NO: 173202, SEQ ID NO: 173206, SEQ ID NO: 173284, SEQ ID NO: 173288, SEQ ID NO: 173318, SEQ ID NO: 173321, SEQ ID NO: 173412, SEQ ID NO: 173433, SEQ ID NO: 173452, SEQ ID NO: 173467, SEQ ID NOs: 173469 to 173470, SEQ ID NO: 173494, SEQ ID NO: 173497, SEQ ID NO: 173516, SEQ ID NO: 173611, SEQ ID NO: 173633, SEQ ID NO: 173713, SEQ ID NO: 173726, SEQ ID NO: 173762, SEQ ID NO: 173792, SEQ ID NO: 173837, SEQ ID NO: 173849, SEQ ID NO: 173858, SEQ ID NO: 173864, SEQ ID NO: 173884, SEQ ID NO: 173918, SEQ ID NO: 173923, SEQ ID NO: 173929, SEQ ID NO: 173958, SEQ ID NO: 173993, SEQ ID NO: 174020, SEQ ID NO: 174026, SEQ ID NO: 174044, SEQ ID NO: 174047, SEQ ID NO: 174110, SEQ ID NO: 174116, SEQ ID NO: 174161, SEQ ID NO: 174164, SEQ ID NO: 174168, SEQ ID NO: 174180, SEQ ID NO: 174190, SEQ ID NO: 174210, SEQ ID NO: 174228, SEQ ID NO: 174260, SEQ ID NO: 174265, SEQ ID NO: 174277, SEQ ID NO: 174283, SEQ ID NO: 174301, SEQ ID NO: 174311, SEQ ID NO: 174316, SEQ ID NO: 174356, SEQ ID NO: 174387, SEQ ID NO: 174424, SEQ ID NO: 174452, SEQ ID NO: 174486, SEQ ID NO: 174491, SEQ ID NO: 174507, SEQ ID NO: 174510, SEQ ID NO: 174595, SEQ ID NO: 174611, SEQ ID NO: 174633, SEQ ID NO: 174679, SEQ ID NO: 174702, SEQ ID NO: 174724, SEQ ID NO: 174747, SEQ ID NO: 174756, SEQ ID NO: 174779, SEQ ID NO: 174847, SEQ ID NO: 174880, SEQ ID NO: 174904, SEQ ID NO: 174956, SEQ ID NO: 174960, SEQ ID NO: 174978, SEQ ID NO: 175027, SEQ ID NO: 175063, SEQ ID NO: 175076, SEQ ID NO: 175129, SEQ ID NO: 175160, SEQ ID NO: 175175, SEQ ID NO: 175186, SEQ ID NO: 175191, SEQ ID NO: 175251, SEQ ID NO: 175269, SEQ ID NO: 175292, SEQ ID NO: 175295, SEQ ID NO: 175300, SEQ ID NO: 175416, SEQ ID NO: 175423, SEQ ID NO: 175506, SEQ ID NO: 175541, SEQ ID NO: 175557, SEQ ID NO: 175585, SEQ ID NO: 175625, SEQ ID NO: 175649, SEQ ID NO: 175671, SEQ ID NOs: 175721 to 175722, SEQ ID NO: 175820, SEQ ID NO: 175886, SEQ ID NO: 175902, SEQ ID NO: 175951, SEQ ID NOs: 175960 to 175961, SEQ ID NO: 175968, SEQ ID NO: 175975, SEQ ID NO: 175993, SEQ ID NO: 176018, SEQ ID NO: 176041, SEQ ID NO: 176051, SEQ ID NO: 176112, SEQ ID NO: 176118, SEQ ID NO: 176149, SEQ ID NO: 176179, SEQ ID NO: 176248, SEQ ID NO: 176306, SEQ ID NO: 176309, SEQ ID NO: 176312, SEQ ID NO: 176335, SEQ ID NO: 176338, SEQ ID NO: 176355, SEQ ID NO: 176369, SEQ ID NO: 176379, SEQ ID NO: 176452, SEQ ID NO: 176466, SEQ ID NO: 176503, SEQ ID NO: 176548, SEQ ID NO: 176560, SEQ ID NO: 176611, SEQ ID NO: 176621, SEQ ID NO: 176639, SEQ ID NO: 176693, SEQ ID NO: 176700, SEQ ID NO: 176713, SEQ ID NO: 176764, SEQ ID NOs: 176795 to 176796, SEQ ID NO: 176806, SEQ ID NO: 176815, SEQ ID NO: 176953, SEQ ID NO: 176958, SEQ ID NO: 176969, SEQ ID NO: 176980, SEQ ID NO: 176991, SEQ ID NO: 177016, SEQ ID NO: 177033, SEQ ID NO: 177044, SEQ ID NO: 177061, SEQ ID NO: 177065, SEQ ID NO: 177080, SEQ ID NO: 177088, SEQ ID NO: 177102, SEQ ID NO: 177119, SEQ ID NO: 177343, SEQ ID NO: 177358, SEQ ID NO: 177390, SEQ ID NO: 177430, SEQ ID NO: 177437, SEQ ID NO: 177465, SEQ ID NOs: 177482 to 177483, SEQ ID NO: 177492, SEQ ID NO: 177495, SEQ ID NO: 177522, SEQ ID NO: 177585, SEQ ID NO: 177604, SEQ ID NO: 177611, SEQ ID NO: 177664, SEQ ID NO: 177669, SEQ ID NO: 177701, SEQ ID NO: 177707, SEQ ID NO: 177710, SEQ ID NO: 177712, SEQ ID NO: 177714, SEQ ID NO: 177734, SEQ ID NO: 177808, SEQ ID NO: 177841, SEQ ID NO: 177848, SEQ ID NO: 177892, SEQ ID NO: 177918, SEQ ID NO: 177958, SEQ ID NOs: 177989 to 177990, SEQ ID NO: 178023, SEQ ID NO: 178032, SEQ ID NO: 178035, SEQ ID NO: 178039, SEQ ID NO: 178122, SEQ ID NO: 178161, SEQ ID NO: 178195, SEQ ID NO: 178208, SEQ ID NO: 178244, SEQ ID NO: 178272, SEQ ID NO: 178293, SEQ ID NO: 178310, SEQ ID NO: 178338, SEQ ID NO: 178353, SEQ ID NO: 178385, SEQ ID NO: 178399, SEQ ID NO: 178477, SEQ ID NO: 178519, SEQ ID NO: 178568, SEQ ID NO: 178587, SEQ ID NO: 178600, SEQ ID NO: 178612, SEQ ID NO: 178615, SEQ ID NO: 178651, SEQ ID NO: 178726, SEQ ID NO: 178740, SEQ ID NO: 178743, SEQ ID NO: 178750, SEQ ID NO: 178821, SEQ ID NO: 178886, SEQ ID NO: 178895, SEQ ID NO: 178911, SEQ ID NO: 178942, SEQ ID NO: 178946, SEQ ID NO: 178948, SEQ ID NO: 178966, SEQ ID NO: 179020, SEQ ID NO: 179031, SEQ ID NO: 179034, SEQ ID NO: 179130, SEQ ID NO: 179134, SEQ ID NO: 179151, SEQ ID NO: 179154, SEQ ID NO: 179224, SEQ ID NO: 179257, SEQ ID NO: 179387, SEQ ID NO: 179404, SEQ ID NO: 179444, SEQ ID NO: 179455, SEQ ID NO: 179462, SEQ ID NO: 179483, SEQ ID NO: 179544, SEQ ID NO: 179586, SEQ ID NO: 179600, SEQ ID NO: 179612, SEQ ID NO: 179619, SEQ ID NO: 179632, SEQ ID NO: 179677, SEQ ID NO: 179695, SEQ ID NO: 179697, SEQ ID NO: 179760, SEQ ID NO: 179863, SEQ ID NO: 179898, SEQ ID NO: 179904, SEQ ID NO: 179934, SEQ ID NO: 179957, SEQ ID NO: 179981, SEQ ID NO: 180013, SEQ ID NO: 180019, SEQ ID NO: 180036, SEQ ID NO: 180077, SEQ ID NO: 180086, SEQ ID NO: 180167, SEQ ID NO: 180257, SEQ ID NO: 180259, SEQ ID NO: 180271, SEQ ID NO: 180291, SEQ ID NO: 180327, SEQ ID NO: 180348, SEQ ID NO: 180378, SEQ ID NO: 180396, SEQ ID NO: 180430, SEQ ID NO: 180452, SEQ ID NO: 180458, SEQ ID NO: 180481, SEQ ID NO: 180489, SEQ ID NO: 180492, SEQ ID NO: 180528, SEQ ID NO: 180551, SEQ ID NO: 180567, SEQ ID NO: 180577, SEQ ID NO: 180597, SEQ ID NO: 180622, SEQ ID NO: 180683, SEQ ID NO: 180694, SEQ ID NOs: 180720 to 180721, SEQ ID NO: 180772, SEQ ID NO: 180799, SEQ ID NO: 180823, SEQ ID NO: 180843, SEQ ID NO: 180848, SEQ ID NO: 180858, SEQ ID NO: 180866, SEQ ID NO: 180879, SEQ ID NO: 180977, SEQ ID NOs: 181032 to 181033, SEQ ID NO: 181173, SEQ ID NO: 181204, SEQ ID NO: 181259, SEQ ID NO: 181406, SEQ ID NO: 181630, SEQ ID NO: 181685, SEQ ID NO: 181792, SEQ ID NO: 181963, SEQ ID NO: 181984, SEQ ID NOs: 182157 to 182159, SEQ ID NO: 182471, and SEQ ID NOs: 182574 to 197896. In some embodiments, any one of the peptides in the TYRP2 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 166476 to 166477, SEQ ID NO: 166486, SEQ ID NO: 166513, SEQ ID NO: 166591, SEQ ID NO: 166606, SEQ ID NO: 166629, SEQ ID NO: 166641, SEQ ID NO: 166667, SEQ ID NOs: 166678 to 166679, SEQ ID NO: 166795, SEQ ID NO: 166799, SEQ ID NO: 166834, SEQ ID NO: 166854, SEQ ID NO: 166909, SEQ ID NO: 166912, SEQ ID NO: 166942, SEQ ID NOs: 166991 to 166992, SEQ ID NO: 167062, SEQ ID NO: 167067, SEQ ID NOs: 167073 to 167074, SEQ ID NO: 167106, SEQ ID NO: 167118, SEQ ID NO: 167151, SEQ ID NO: 167177, SEQ ID NO: 167241, SEQ ID NO: 167271, SEQ ID NO: 167395, SEQ ID NO: 167491, SEQ ID NO: 167505, SEQ ID NO: 167687, SEQ ID NO: 167736, SEQ ID NO: 167740, SEQ ID NO: 167743, SEQ ID NO: 167755, SEQ ID NO: 167810, SEQ ID NO: 167831, SEQ ID NO: 167837, SEQ ID NO: 167844, SEQ ID NOs: 167847 to 167848, SEQ ID NO: 167859, SEQ ID NO: 167880, SEQ ID NO: 167891, SEQ ID NO: 167897, SEQ ID NO: 167933, SEQ ID NO: 168094, SEQ ID NOs: 168111 to 168112, SEQ ID NO: 168132, SEQ ID NO: 168144, SEQ ID NO: 168167, SEQ ID NO: 168211, SEQ ID NO: 168252, SEQ ID NO: 168268, SEQ ID NO: 168343, SEQ ID NO: 168354, SEQ ID NO: 168376, SEQ ID NO: 168396, SEQ ID NO: 168410, SEQ ID NO: 168423, SEQ ID NO: 168460, SEQ ID NO: 168484, SEQ ID NO: 168496, SEQ ID NO: 168616, SEQ ID NO: 168626, SEQ ID NO: 168646, SEQ ID NO: 168660, SEQ ID NO: 168681, SEQ ID NO: 168703, SEQ ID NO: 168711, SEQ ID NO: 168725, SEQ ID NO: 168728, SEQ ID NO: 168760, SEQ ID NOs: 168792 to 168793, SEQ ID NO: 168815, SEQ ID NO: 168851, SEQ ID NO: 168863, SEQ ID NO: 168867, SEQ ID NO: 168871, SEQ ID NO: 168924, SEQ ID NO: 168927, SEQ ID NO: 168947, SEQ ID NO: 168974, SEQ ID NO: 169000, SEQ ID NO: 169024, SEQ ID NO: 169035, SEQ ID NO: 169112, SEQ ID NO: 169150, SEQ ID NO: 169187, SEQ ID NO: 169233, SEQ ID NO: 169240, SEQ ID NO: 169247, SEQ ID NO: 169275, SEQ ID NO: 169375, SEQ ID NO: 169403, SEQ ID NO: 169428, SEQ ID NO: 169460, SEQ ID NO: 169474, SEQ ID NO: 169500, SEQ ID NO: 169530, SEQ ID NO: 169542, SEQ ID NO: 169546, SEQ ID NO: 169548, SEQ ID NO: 169553, SEQ ID NO: 169555, SEQ ID NO: 169563, SEQ ID NO: 169565, SEQ ID NO: 169578, SEQ ID NO: 169584, SEQ ID NO: 169605, SEQ ID NO: 169641, SEQ ID NO: 169665, SEQ ID NO: 169673, SEQ ID NO: 169682, SEQ ID NO: 169700, SEQ ID NO: 169704, SEQ ID NO: 169740, SEQ ID NO: 169768, SEQ ID NO: 169850, SEQ ID NO: 169858, SEQ ID NO: 169867, SEQ ID NO: 169871, SEQ ID NO: 169886, SEQ ID NO: 169915, SEQ ID NO: 169966, SEQ ID NO: 170057, SEQ ID NO: 170061, SEQ ID NO: 170081, SEQ ID NOs: 170178 to 170179, SEQ ID NO: 170261, SEQ ID NO: 170268, SEQ ID NO: 170278, SEQ ID NO: 170290, SEQ ID NO: 170320, SEQ ID NO: 170329, SEQ ID NO: 170390, SEQ ID NO: 170443, SEQ ID NO: 170488, SEQ ID NO: 170543, SEQ ID NO: 170574, SEQ ID NO: 170679, SEQ ID NO: 170704, SEQ ID NOs: 170706 to 170707, SEQ ID NO: 170735, SEQ ID NO: 170754, SEQ ID NO: 170771, SEQ ID NOs: 170809 to 170810, SEQ ID NO: 170834, SEQ ID NO: 170847, SEQ ID NO: 170876, SEQ ID NOs: 170902 to 170903, SEQ ID NO: 170964, SEQ ID NO: 170968, SEQ ID NO: 170970, SEQ ID NO: 170976, SEQ ID NO: 170981, SEQ ID NO: 171011, SEQ ID NO: 171029, SEQ ID NO: 171080, SEQ ID NO: 171085, SEQ ID NO: 171091, SEQ ID NO: 171174, SEQ ID NO: 171182, SEQ ID NO: 171212, SEQ ID NO: 171229, SEQ ID NO: 171242, SEQ ID NO: 171256, SEQ ID NO: 171260, SEQ ID NO: 171263, SEQ ID NO: 171291, SEQ ID NO: 171329, SEQ ID NO: 171334, SEQ ID NO: 171340, SEQ ID NO: 171406, SEQ ID NO: 171412, SEQ ID NO: 171428, SEQ ID NO: 171462, SEQ ID NO: 171474, SEQ ID NO: 171485, SEQ ID NO: 171490, SEQ ID NO: 171526, SEQ ID NO: 171536, SEQ ID NO: 171550, SEQ ID NO: 171581, SEQ ID NO: 171608, SEQ ID NO: 171625, SEQ ID NO: 171655, SEQ ID NO: 171662, SEQ ID NO: 171709, SEQ ID NO: 171732, SEQ ID NO: 171746, SEQ ID NO: 171752, SEQ ID NO: 171768, SEQ ID NO: 171786, SEQ ID NO: 171788, SEQ ID NO: 171814, SEQ ID NO: 171855, SEQ ID NO: 171863, SEQ ID NO: 171980, SEQ ID NO: 172007, SEQ ID NO: 172010, SEQ ID NO: 172062, SEQ ID NO: 172161, SEQ ID NO: 172181, SEQ ID NO: 172203, SEQ ID NO: 172225, SEQ ID NO: 172231, SEQ ID NO: 172255, SEQ ID NO: 172272, SEQ ID NO: 172276, SEQ ID NO: 172294, SEQ ID NO: 172348, SEQ ID NO: 172372, SEQ ID NO: 172375, SEQ ID NO: 172378, SEQ ID NO: 172387, SEQ ID NO: 172389, SEQ ID NO: 172421, SEQ ID NOs: 172439 to 172440, SEQ ID NO: 172484, SEQ ID NO: 172495, SEQ ID NO: 172563, SEQ ID NO: 172594, SEQ ID NO: 172660, SEQ ID NO: 172693, SEQ ID NO: 172702, SEQ ID NO: 172704, SEQ ID NO: 172709, SEQ ID NO: 172717, SEQ ID NO: 172726, SEQ ID NO: 172742, SEQ ID NO: 172793, SEQ ID NO: 172801, SEQ ID NO: 172816, SEQ ID NO: 172849, SEQ ID NO: 172862, SEQ ID NO: 172900, SEQ ID NO: 172907, SEQ ID NO: 172919, SEQ ID NO: 172926, SEQ ID NO: 172990, SEQ ID NO: 172994, SEQ ID NO: 172999, SEQ ID NO: 173004, SEQ ID NO: 173007, SEQ ID NO: 173084, SEQ ID NO: 173202, SEQ ID NO: 173206, SEQ ID NO: 173284, SEQ ID NO: 173288, SEQ ID NO: 173318, SEQ ID NO: 173321, SEQ ID NO: 173412, SEQ ID NO: 173433, SEQ ID NO: 173452, SEQ ID NO: 173467, SEQ ID NOs: 173469 to 173470, SEQ ID NO: 173494, SEQ ID NO: 173497, SEQ ID NO: 173516, SEQ ID NO: 173611, SEQ ID NO: 173633, SEQ ID NO: 173713, SEQ ID NO: 173726, SEQ ID NO: 173762, SEQ ID NO: 173792, SEQ ID NO: 173837, SEQ ID NO: 173849, SEQ ID NO: 173858, SEQ ID NO: 173864, SEQ ID NO: 173884, SEQ ID NO: 173918, SEQ ID NO: 173923, SEQ ID NO: 173929, SEQ ID NO: 173958, SEQ ID NO: 173993, SEQ ID NO: 174020, SEQ ID NO: 174026, SEQ ID NO: 174044, SEQ ID NO: 174047, SEQ ID NO: 174110, SEQ ID NO: 174116, SEQ ID NO: 174161, SEQ ID NO: 174164, SEQ ID NO: 174168, SEQ ID NO: 174180, SEQ ID NO: 174190, SEQ ID NO: 174210, SEQ ID NO: 174228, SEQ ID NO: 174260, SEQ ID NO: 174265, SEQ ID NO: 174277, SEQ ID NO: 174283, SEQ ID NO: 174301, SEQ ID NO: 174311, SEQ ID NO: 174316, SEQ ID NO: 174356, SEQ ID NO: 174387, SEQ ID NO: 174424, SEQ ID NO: 174452, SEQ ID NO: 174486, SEQ ID NO: 174491, SEQ ID NO: 174507, SEQ ID NO: 174510, SEQ ID NO: 174595, SEQ ID NO: 174611, SEQ ID NO: 174633, SEQ ID NO: 174679, SEQ ID NO: 174702, SEQ ID NO: 174724, SEQ ID NO: 174747, SEQ ID NO: 174756, SEQ ID NO: 174779, SEQ ID NO: 174847, SEQ ID NO: 174880, SEQ ID NO: 174904, SEQ ID NO: 174956, SEQ ID NO: 174960, SEQ ID NO: 174978, SEQ ID NO: 175027, SEQ ID NO: 175063, SEQ ID NO: 175076, SEQ ID NO: 175129, SEQ ID NO: 175160, SEQ ID NO: 175175, SEQ ID NO: 175186, SEQ ID NO: 175191, SEQ ID NO: 175251, SEQ ID NO: 175269, SEQ ID NO: 175292, SEQ ID NO: 175295, SEQ ID NO: 175300, SEQ ID NO: 175416, SEQ ID NO: 175423, SEQ ID NO: 175506, SEQ ID NO: 175541, SEQ ID NO: 175557, SEQ ID NO: 175585, SEQ ID NO: 175625, SEQ ID NO: 175649, SEQ ID NO: 175671, SEQ ID NOs: 175721 to 175722, SEQ ID NO: 175820, SEQ ID NO: 175886, SEQ ID NO: 175902, SEQ ID NO: 175951, SEQ ID NOs: 175960 to 175961, SEQ ID NO: 175968, SEQ ID NO: 175975, SEQ ID NO: 175993, SEQ ID NO: 176018, SEQ ID NO: 176041, SEQ ID NO: 176051, SEQ ID NO: 176112, SEQ ID NO: 176118, SEQ ID NO: 176149, SEQ ID NO: 176179, SEQ ID NO: 176248, SEQ ID NO: 176306, SEQ ID NO: 176309, SEQ ID NO: 176312, SEQ ID NO: 176335, SEQ ID NO: 176338, SEQ ID NO: 176355, SEQ ID NO: 176369, SEQ ID NO: 176379, SEQ ID NO: 176452, SEQ ID NO: 176466, SEQ ID NO: 176503, SEQ ID NO: 176548, SEQ ID NO: 176560, SEQ ID NO: 176611, SEQ ID NO: 176621, SEQ ID NO: 176639, SEQ ID NO: 176693, SEQ ID NO: 176700, SEQ ID NO: 176713, SEQ ID NO: 176764, SEQ ID NOs: 176795 to 176796, SEQ ID NO: 176806, SEQ ID NO: 176815, SEQ ID NO: 176953, SEQ ID NO: 176958, SEQ ID NO: 176969, SEQ ID NO: 176980, SEQ ID NO: 176991, SEQ ID NO: 177016, SEQ ID NO: 177033, SEQ ID NO: 177044, SEQ ID NO: 177061, SEQ ID NO: 177065, SEQ ID NO: 177080, SEQ ID NO: 177088, SEQ ID NO: 177102, SEQ ID NO: 177119, SEQ ID NO: 177343, SEQ ID NO: 177358, SEQ ID NO: 177390, SEQ ID NO: 177430, SEQ ID NO: 177437, SEQ ID NO: 177465, SEQ ID NOs: 177482 to 177483, SEQ ID NO: 177492, SEQ ID NO: 177495, SEQ ID NO: 177522, SEQ ID NO: 177585, SEQ ID NO: 177604, SEQ ID NO: 177611, SEQ ID NO: 177664, SEQ ID NO: 177669, SEQ ID NO: 177701, SEQ ID NO: 177707, SEQ ID NO: 177710, SEQ ID NO: 177712, SEQ ID NO: 177714, SEQ ID NO: 177734, SEQ ID NO: 177808, SEQ ID NO: 177841, SEQ ID NO: 177848, SEQ ID NO: 177892, SEQ ID NO: 177918, SEQ ID NO: 177958, SEQ ID NOs: 177989 to 177990, SEQ ID NO: 178023, SEQ ID NO: 178032, SEQ ID NO: 178035, SEQ ID NO: 178039, SEQ ID NO: 178122, SEQ ID NO: 178161, SEQ ID NO: 178195, SEQ ID NO: 178208, SEQ ID NO: 178244, SEQ ID NO: 178272, SEQ ID NO: 178293, SEQ ID NO: 178310, SEQ ID NO: 178338, SEQ ID NO: 178353, SEQ ID NO: 178385, SEQ ID NO: 178399, SEQ ID NO: 178477, SEQ ID NO: 178519, SEQ ID NO: 178568, SEQ ID NO: 178587, SEQ ID NO: 178600, SEQ ID NO: 178612, SEQ ID NO: 178615, SEQ ID NO: 178651, SEQ ID NO: 178726, SEQ ID NO: 178740, SEQ ID NO: 178743, SEQ ID NO: 178750, SEQ ID NO: 178821, SEQ ID NO: 178886, SEQ ID NO: 178895, SEQ ID NO: 178911, SEQ ID NO: 178942, SEQ ID NO: 178946, SEQ ID NO: 178948, SEQ ID NO: 178966, SEQ ID NO: 179020, SEQ ID NO: 179031, SEQ ID NO: 179034, SEQ ID NO: 179130, SEQ ID NO: 179134, SEQ ID NO: 179151, SEQ ID NO: 179154, SEQ ID NO: 179224, SEQ ID NO: 179257, SEQ ID NO: 179387, SEQ ID NO: 179404, SEQ ID NO: 179444, SEQ ID NO: 179455, SEQ ID NO: 179462, SEQ ID NO: 179483, SEQ ID NO: 179544, SEQ ID NO: 179586, SEQ ID NO: 179600, SEQ ID NO: 179612, SEQ ID NO: 179619, SEQ ID NO: 179632, SEQ ID NO: 179677, SEQ ID NO: 179695, SEQ ID NO: 179697, SEQ ID NO: 179760, SEQ ID NO: 179863, SEQ ID NO: 179898, SEQ ID NO: 179904, SEQ ID NO: 179934, SEQ ID NO: 179957, SEQ ID NO: 179981, SEQ ID NO: 180013, SEQ ID NO: 180019, SEQ ID NO: 180036, SEQ ID NO: 180077, SEQ ID NO: 180086, SEQ ID NO: 180167, SEQ ID NO: 180257, SEQ ID NO: 180259, SEQ ID NO: 180271, SEQ ID NO: 180291, SEQ ID NO: 180327, SEQ ID NO: 180348, SEQ ID NO: 180378, SEQ ID NO: 180396, SEQ ID NO: 180430, SEQ ID NO: 180452, SEQ ID NO: 180458, SEQ ID NO: 180481, SEQ ID NO: 180489, SEQ ID NO: 180492, SEQ ID NO: 180528, SEQ ID NO: 180551, SEQ ID NO: 180567, SEQ ID NO: 180577, SEQ ID NO: 180597, SEQ ID NO: 180622, SEQ ID NO: 180683, SEQ ID NO: 180694, SEQ ID NOs: 180720 to 180721, SEQ ID NO: 180772, SEQ ID NO: 180799, SEQ ID NO: 180823, SEQ ID NO: 180843, SEQ ID NO: 180848, SEQ ID NO: 180858, SEQ ID NO: 180866, SEQ ID NO: 180879, SEQ ID NO: 180977, SEQ ID NOs: 181032 to 181033, SEQ ID NO: 181173, SEQ ID NO: 181204, SEQ ID NO: 181259, SEQ ID NO: 181406, SEQ ID NO: 181630, SEQ ID NO: 181685, SEQ ID NO: 181792, SEQ ID NO: 181963, SEQ ID NO: 181984, SEQ ID NOs: 182157 to 182159, SEQ ID NO: 182471, or SEQ ID NOs: 182574 to 197896.

In some embodiments, the amino acid sequence for a MEW class I peptide vaccine for the TYRP2 protein comprises two or more of the SEQ ID NO: 166476, SEQ ID NO: 167118, SEQ ID NO: 169740, SEQ ID NO: 173412, SEQ ID NO: 179404, and SEQ ID NOs: 182574 to 182654. In some embodiments, any one of the peptides in the TYRP2 vaccine comprise an amino acid sequence 80, 81, 82, 83, 84, 85, 86, 87, 88, 89, 90, 91, 92, 93, 94, 95, 96, 97, 98 or 99% identical to SEQ ID NO: 166476, SEQ ID NO: 167118, SEQ ID NO: 169740, SEQ ID NO: 173412, SEQ ID NO: 179404, or SEQ ID NOs: 182574 to 182654.

In some embodiments, the amino acid sequence for a MEW class I peptide vaccine for the TYRP2 protein comprises two or more of the SEQ ID NOs: 166476 to 166477, SEQ ID NO: 166486, SEQ ID NO: 166513, SEQ ID NO: 166591, SEQ ID NO: 166606, SEQ ID NO: 166629, SEQ ID NO: 166641, SEQ ID NO: 166667, SEQ ID NOs: 166678 to 166679, SEQ ID NO: 166795, SEQ ID NO: 166799, SEQ ID NO: 166834, SEQ ID NO: 166854, SEQ ID NO: 166909, SEQ ID NO: 166912, SEQ ID NO: 166942, SEQ ID NOs: 166991 to 166992, SEQ ID NO: 167062, SEQ ID NO: 167067, SEQ ID NOs: 167073 to 167074, SEQ ID NO: 167106, SEQ ID NO: 167118, SEQ ID NO: 167151, SEQ ID NO: 167177, SEQ ID NO: 167241, SEQ ID NO: 167271, SEQ ID NO: 167395, SEQ ID NO: 167491, SEQ ID NO: 167505, SEQ ID NO: 167687, SEQ ID NO: 167736, SEQ ID NO: 167740, SEQ ID NO: 167743, SEQ ID NO: 167755, SEQ ID NO: 167810, SEQ ID NO: 167831, SEQ ID NO: 167837, SEQ ID NO: 167844, SEQ ID NOs: 167847 to 167848, SEQ ID NO: 167859, SEQ ID NO: 167880, SEQ ID NO: 167891, SEQ ID NO: 167897, SEQ ID NO: 167933, SEQ ID NO: 168094, SEQ ID NOs: 168111 to 168112, SEQ ID NO: 168132, SEQ ID NO: 168144, SEQ ID NO: 168167, SEQ ID NO: 168211, SEQ ID NO: 168252, SEQ ID NO: 168268, SEQ ID NO: 168343, SEQ ID NO: 168354, SEQ ID NO: 168376, SEQ ID NO: 168396, SEQ ID NO: 168410, SEQ ID NO: 168423, SEQ ID NO: 168460, SEQ ID NO: 168484, SEQ ID NO: 168496, SEQ ID NO: 168616, SEQ ID NO: 168626, SEQ ID NO: 168646, SEQ ID NO: 168660, SEQ ID NO: 168681, SEQ ID NO: 168703, SEQ ID NO: 168711, SEQ ID NO: 168725, SEQ ID NO: 168728, SEQ ID NO: 168760, SEQ ID NOs: 168792 to 168793, SEQ ID NO: 168815, SEQ ID NO: 168851, SEQ ID NO: 168863, SEQ ID NO: 168867, SEQ ID NO: 168871, SEQ ID NO: 168924, SEQ ID NO: 168927, SEQ ID NO: 168947, SEQ ID NO: 168974, SEQ ID NO: 169000, SEQ ID NO: 169024, SEQ ID NO: 169035, SEQ ID NO: 169112, SEQ ID NO: 169150, SEQ ID NO: 169187, SEQ ID NO: 169233, SEQ ID NO: 169240, SEQ ID NO: 169247, SEQ ID NO: 169275, SEQ ID NO: 169375, SEQ ID NO: 169403, SEQ ID NO: 169428, SEQ ID NO: 169460, SEQ ID NO: 169474, SEQ ID NO: 169500, SEQ ID NO: 169530, SEQ ID NO: 169542, SEQ ID NO: 169546, SEQ ID NO: 169548, SEQ ID NO: 169553, SEQ ID NO: 169555, SEQ ID NO: 169563, SEQ ID NO: 169565, SEQ ID NO: 169578, SEQ ID NO: 169584, SEQ ID NO: 169605, SEQ ID NO: 169641, SEQ ID NO: 169665, SEQ ID NO: 169673, SEQ ID NO: 169682, SEQ ID NO: 169700, SEQ ID NO: 169704, SEQ ID NO: 169740, SEQ ID NO: 169768, SEQ ID NO: 169850, SEQ ID NO: 169858, SEQ ID NO: 169867, SEQ ID NO: 169871, SEQ ID NO: 169886, SEQ ID NO: 169915, SEQ ID NO: 169966, SEQ ID NO: 170057, SEQ ID NO: 170061, SEQ ID NO: 170081, SEQ ID NOs: 170178 to 170179, SEQ ID NO: 170261, SEQ ID NO: 170268, SEQ ID NO: 170278, SEQ ID NO: 170290, SEQ ID NO: 170320, SEQ ID NO: 170329, SEQ ID NO: 170390, SEQ ID NO: 170443, SEQ ID NO: 170488, SEQ ID NO: 170543, SEQ ID NO: 170574, SEQ ID NO: 170679, SEQ ID NO: 170704, SEQ ID NOs: 170706 to 170707, SEQ ID NO: 170735, SEQ ID NO: 170754, SEQ ID NO: 170771, SEQ ID NOs: 170809 to 170810, SEQ ID NO: 170834, SEQ ID NO: 170847, SEQ ID NO: 170876, SEQ ID NOs: 170902 to 170903, SEQ ID NO: 170964, SEQ ID NO: 170968, SEQ ID NO: 170970, SEQ ID NO: 170976, SEQ ID NO: 170981, SEQ ID NO: 171011, SEQ ID NO: 171029, SEQ ID NO: 171080, SEQ ID NO: 171085, SEQ ID NO: 171091, SEQ ID NO: 171174, SEQ ID NO: 171182, SEQ ID NO: 171212, SEQ ID NO: 171229, SEQ ID NO: 171242, SEQ ID NO: 171256, SEQ ID NO: 171260, SEQ ID NO: 171263, SEQ ID NO: 171291, SEQ ID NO: 171329, SEQ ID NO: 171334, SEQ ID NO: 171340, SEQ ID NO: 171406, SEQ ID NO: 171412, SEQ ID NO: 171428, SEQ ID NO: 171462, SEQ ID NO: 171474, SEQ ID NO: 171485, SEQ ID NO: 171490, SEQ ID NO: 171526, SEQ ID NO: 171536, SEQ ID NO: 171550, SEQ ID NO: 171581, SEQ ID NO: 171608, SEQ ID NO: 171625, SEQ ID NO: 171655, SEQ ID NO: 171662, SEQ ID NO: 171709, SEQ ID NO: 171732, SEQ ID NO: 171746, SEQ ID NO: 171752, SEQ ID NO: 171768, SEQ ID NO: 171786, SEQ ID NO: 171788, SEQ ID NO: 171814, SEQ ID NO: 171855, SEQ ID NO: 171863, SEQ ID NO: 171980, SEQ ID NO: 172007, SEQ ID NO: 172010, SEQ ID NO: 172062, SEQ ID NO: 172161, SEQ ID NO: 172181, SEQ ID NO: 172203, SEQ ID NO: 172225, SEQ ID NO: 172231, SEQ ID NO: 172255, SEQ ID NO: 172272, SEQ ID NO: 172276, SEQ ID NO: 172294, SEQ ID NO: 172348, SEQ ID NO: 172372, SEQ ID NO: 172375, SEQ ID NO: 172378, SEQ ID NO: 172387, SEQ ID NO: 172389, SEQ ID NO: 172421, SEQ ID NOs: 172439 to 172440, SEQ ID NO: 172484, SEQ ID NO: 172495, SEQ ID NO: 172563, SEQ ID NO: 172594, SEQ ID NO: 172660, SEQ ID NO: 172693, SEQ ID NO: 172702, SEQ ID NO: 172704, SEQ ID NO: 172709, SEQ ID NO: 172717, SEQ ID NO: 172726, SEQ ID NO: 172742, SEQ ID NO: 172793, SEQ ID NO: 172801, SEQ ID NO: 172816, SEQ ID NO: 172849, SEQ ID NO: 172862, SEQ ID NO: 172900, SEQ ID NO: 172907, SEQ ID NO: 172919, SEQ ID NO: 172926, SEQ ID NO: 172990, SEQ ID NO: 172994, SEQ ID NO: 172999, SEQ ID NO: 173004, SEQ ID NO: 173007, SEQ ID NO: 173084, SEQ ID NO: 173202, SEQ ID NO: 173206, SEQ ID NO: 173284, SEQ ID NO: 173288, SEQ ID NO: 173318, SEQ ID NO: 173321, SEQ ID NO: 173412, SEQ ID NO: 173433, SEQ ID NO: 173452, SEQ ID NO: 173467, SEQ ID NOs: 173469 to 173470, SEQ ID NO: 173494, SEQ ID NO: 173497, SEQ ID NO: 173516, SEQ ID NO: 173611, SEQ ID NO: 173633, SEQ ID NO: 173713, SEQ ID NO: 173726, SEQ ID NO: 173762, SEQ ID NO: 173792, SEQ ID NO: 173837, SEQ ID NO: 173849, SEQ ID NO: 173858, SEQ ID NO: 173864, SEQ ID NO: 173884, SEQ ID NO: 173918, SEQ ID NO: 173923, SEQ ID NO: 173929, SEQ ID NO: 173958, SEQ ID NO: 173993, SEQ ID NO: 174020, SEQ ID NO: 174026, SEQ ID NO: 174044, SEQ ID NO: 174047, SEQ ID NO: 174110, SEQ ID NO: 174116, SEQ ID NO: 174161, SEQ ID NO: 174164, SEQ ID NO: 174168, SEQ ID NO: 174180, SEQ ID NO: 174190, SEQ ID NO: 174210, SEQ ID NO: 174228, SEQ ID NO: 174260, SEQ ID NO: 174265, SEQ ID NO: 174277, SEQ ID NO: 174283, SEQ ID NO: 174301, SEQ ID NO: 174311, SEQ ID NO: 174316, SEQ ID NO: 174356, SEQ ID NO: 174387, SEQ ID NO: 174424, SEQ ID NO: 174452, SEQ ID NO: 174486, SEQ ID NO: 174491, SEQ ID NO: 174507, SEQ ID NO: 174510, SEQ ID NO: 174595, SEQ ID NO: 174611, SEQ ID NO: 174633, SEQ ID NO: 174679, SEQ ID NO: 174702, SEQ ID NO: 174724, SEQ ID NO: 174747, SEQ ID NO: 174756, SEQ ID NO: 174779, SEQ ID NO: 174847, SEQ ID NO: 174880, SEQ ID NO: 174904, SEQ ID NO: 174956, SEQ ID NO: 174960, SEQ ID NO: 174978, SEQ ID NO: 175027, SEQ ID NO: 175063, SEQ ID NO: 175076, SEQ ID NO: 175129, SEQ ID NO: 175160, SEQ ID NO: 175175, SEQ ID NO: 175186, SEQ ID NO: 175191, SEQ ID NO: 175251, SEQ ID NO: 175269, SEQ ID NO: 175292, SEQ ID NO: 175295, SEQ ID NO: 175300, SEQ ID NO: 175416, SEQ ID NO: 175423, SEQ ID NO: 175506, SEQ ID NO: 175541, SEQ ID NO: 175557, SEQ ID NO: 175585, SEQ ID NO:

175625, SEQ ID NO: 175649, SEQ ID NO: 175671, SEQ ID NOs: 175721 to 175722, SEQ ID NO: 175820, SEQ ID NO: 175886, SEQ ID NO: 175902, SEQ ID NO: 175951, SEQ ID NOs: 175960 to 175961, SEQ ID NO: 175968, SEQ ID NO: 175975, SEQ ID NO: 175993, SEQ ID NO: 176018, SEQ ID NO: 176041, SEQ ID NO: 176051, SEQ ID NO: 176112, SEQ ID NO: 176118, SEQ ID NO: 176149, SEQ ID NO: 176179, SEQ ID NO: 176248, SEQ ID NO: 176306, SEQ ID NO: 176309, SEQ ID NO: 176312, SEQ ID NO: 176335, SEQ ID NO: 176338, SEQ ID NO: 176355, SEQ ID NO: 176369, SEQ ID NO: 176379, SEQ ID NO: 176452, SEQ ID NO: 176466, SEQ ID NO: 176503, SEQ ID NO: 176548, SEQ ID NO: 176560, SEQ ID NO: 176611, SEQ ID NO: 176621, SEQ ID NO: 176639, SEQ ID NO: 176693, SEQ ID NO: 176700, SEQ ID NO: 176713, SEQ ID NO: 176764, SEQ ID NOs: 176795 to 176796, SEQ ID NO: 176806, SEQ ID NO: 176815, SEQ ID NO: 176953, SEQ ID NO: 176958, SEQ ID NO: 176969, SEQ ID NO: 176980, SEQ ID NO: 176991, SEQ ID NO: 177016, SEQ ID NO: 177033, SEQ ID NO: 177044, SEQ ID NO: 177061, SEQ ID NO: 177065, SEQ ID NO: 177080, SEQ ID NO: 177088, SEQ ID NO: 177102, SEQ ID NO: 177119, SEQ ID NO: 177343, SEQ ID NO: 177358, SEQ ID NO: 177390, SEQ ID NO: 177430, SEQ ID NO: 177437, SEQ ID NO: 177465, SEQ ID NOs: 177482 to 177483, SEQ ID NO: 177492, SEQ ID NO: 177495, SEQ ID NO: 177522, SEQ ID NO: 177585, SEQ ID NO: 177604, SEQ ID NO: 177611, SEQ ID NO: 177664, SEQ ID NO: 177669, SEQ ID NO: 177701, SEQ ID NO: 177707, SEQ ID NO: 177710, SEQ ID NO: 177712, SEQ ID NO: 177714, SEQ ID NO: 177734, SEQ ID NO: 177808, SEQ ID NO: 177841, SEQ ID NO: 177848, SEQ ID NO: 177892, SEQ ID NO: 177918, SEQ ID NO: 177958, SEQ ID NOs: 177989 to 177990, SEQ ID NO: 178023, SEQ ID NO: 178032, SEQ ID NO: 178035, SEQ ID NO: 178039, SEQ ID NO: 178122, SEQ ID NO: 178161, SEQ ID NO: 178195, SEQ ID NO: 178208, SEQ ID NO: 178244, SEQ ID NO: 178272, SEQ ID NO: 178293, SEQ ID NO: 178310, SEQ ID NO: 178338, SEQ ID NO: 178353, SEQ ID NO: 178385, SEQ ID NO: 178399, SEQ ID NO: 178477, SEQ ID NO: 178519, SEQ ID NO: 178568, SEQ ID NO: 178587, SEQ ID NO: 178600, SEQ ID NO: 178612, SEQ ID NO: 178615, SEQ ID NO: 178651, SEQ ID NO: 178726, SEQ ID NO: 178740, SEQ ID NO: 178743, SEQ ID NO: 178750, SEQ ID NO: 178821, SEQ ID NO: 178886, SEQ ID NO: 178895, SEQ ID NO: 178911, SEQ ID NO: 178942, SEQ ID NO: 178946, SEQ ID NO: 178948, SEQ ID NO: 178966, SEQ ID NO: 179020, SEQ ID NO: 179031, SEQ ID NO: 179034, SEQ ID NO: 179130, SEQ ID NO: 179134, SEQ ID NO: 179151, SEQ ID NO: 179154, SEQ ID NO: 179224, SEQ ID NO: 179257, SEQ ID NO: 179387, SEQ ID NO: 179404, SEQ ID NO: 179444, SEQ ID NO: 179455, SEQ ID NO: 179462, SEQ ID NO: 179483, SEQ ID NO: 179544, SEQ ID NO: 179586, SEQ ID NO: 179600, SEQ ID NO: 179612, SEQ ID NO: 179619, SEQ ID NO: 179632, SEQ ID NO: 179677, SEQ ID NO: 179695, SEQ ID NO: 179697, SEQ ID NO: 179760, SEQ ID NO: 179863, SEQ ID NO: 179898, SEQ ID NO: 179904, SEQ ID NO: 179934, SEQ ID NO: 179957, SEQ ID NO: 179981, SEQ ID NO: 180013, SEQ ID NO: 180019, SEQ ID NO: 180036, SEQ ID NO: 180077, SEQ ID NO: 180086, SEQ ID NO: 180167, SEQ ID NO: 180257, SEQ ID NO: 180259, SEQ ID NO: 180271, SEQ ID NO: 180291, SEQ ID NO: 180327, SEQ ID NO: 180348, SEQ ID NO: 180378, SEQ ID NO: 180396, SEQ ID NO: 180430, SEQ ID NO: 180452, SEQ ID NO: 180458, SEQ ID NO: 180481, SEQ ID NO: 180489, SEQ ID NO: 180492, SEQ ID NO: 180528, SEQ ID NO: 180551, SEQ ID NO: 180567, SEQ ID NO: 180577, SEQ ID NO: 180597, SEQ ID NO: 180622, SEQ ID NO: 180683, SEQ ID NO: 180694, SEQ ID NOs: 180720 to 180721, SEQ ID NO: 180772, SEQ ID NO: 180799, SEQ ID NO: 180823, SEQ ID NO: 180843, SEQ ID NO: 180848, SEQ ID NO: 180858, SEQ ID NO: 180866, SEQ ID NO: 180879, SEQ ID NO: 180977, SEQ ID NOs: 181032 to 181033, SEQ ID NO: 181173, SEQ ID NO: 181204, SEQ ID NO: 181259, SEQ ID NO: 181406, SEQ ID NO: 181630, SEQ ID NO: 181685, SEQ ID NO: 181792, SEQ ID NO: 181963, SEQ ID NO: 181984, SEQ ID NOs: 182157 to 182159, SEQ ID NO: 182471, and SEQ ID NOs: 182574 to 197896. In some embodiments, any one of the peptides in the TYRP2 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 166476 to 166477, SEQ ID NO: 166486, SEQ ID NO: 166513, SEQ ID NO: 166591, SEQ ID NO: 166606, SEQ ID NO: 166629, SEQ ID NO: 166641, SEQ ID NO: 166667, SEQ ID NOs: 166678 to 166679, SEQ ID NO: 166795, SEQ ID NO: 166799, SEQ ID NO: 166834, SEQ ID NO: 166854, SEQ ID NO: 166909, SEQ ID NO: 166912, SEQ ID NO: 166942, SEQ ID NOs: 166991 to 166992, SEQ ID NO: 167062, SEQ ID NO: 167067, SEQ ID NOs: 167073 to 167074, SEQ ID NO: 167106, SEQ ID NO: 167118, SEQ ID NO: 167151, SEQ ID NO: 167177, SEQ ID NO: 167241, SEQ ID NO: 167271, SEQ ID NO: 167395, SEQ ID NO: 167491, SEQ ID NO: 167505, SEQ ID NO: 167687, SEQ ID NO: 167736, SEQ ID NO: 167740, SEQ ID NO: 167743, SEQ ID NO: 167755, SEQ ID NO: 167810, SEQ ID NO: 167831, SEQ ID NO: 167837, SEQ ID NO: 167844, SEQ ID NOs: 167847 to 167848, SEQ ID NO: 167859, SEQ ID NO: 167880, SEQ ID NO: 167891, SEQ ID NO: 167897, SEQ ID NO: 167933, SEQ ID NO: 168094, SEQ ID NOs: 168111 to 168112, SEQ ID NO: 168132, SEQ ID NO: 168144, SEQ ID NO: 168167, SEQ ID NO: 168211, SEQ ID NO: 168252, SEQ ID NO: 168268, SEQ ID NO: 168343, SEQ ID NO: 168354, SEQ ID NO: 168376, SEQ ID NO: 168396, SEQ ID NO: 168410, SEQ ID NO: 168423, SEQ ID NO: 168460, SEQ ID NO: 168484, SEQ ID NO: 168496, SEQ ID NO: 168616, SEQ ID NO: 168626, SEQ ID NO: 168646, SEQ ID NO: 168660, SEQ ID NO: 168681, SEQ ID NO: 168703, SEQ ID NO: 168711, SEQ ID NO: 168725, SEQ ID NO: 168728, SEQ ID NO: 168760, SEQ ID NOs: 168792 to 168793, SEQ ID NO: 168815, SEQ ID NO: 168851, SEQ ID NO: 168863, SEQ ID NO: 168867, SEQ ID NO: 168871, SEQ ID NO: 168924, SEQ ID NO: 168927, SEQ ID NO: 168947, SEQ ID NO: 168974, SEQ ID NO: 169000, SEQ ID NO: 169024, SEQ ID NO: 169035, SEQ ID NO: 169112, SEQ ID NO: 169150, SEQ ID NO: 169187, SEQ ID NO: 169233, SEQ ID NO: 169240, SEQ ID NO: 169247, SEQ ID NO: 169275, SEQ ID NO: 169375, SEQ ID NO: 169403, SEQ ID NO: 169428, SEQ ID NO: 169460, SEQ ID NO: 169474, SEQ ID NO: 169500, SEQ ID NO: 169530, SEQ ID NO: 169542, SEQ ID NO: 169546, SEQ ID NO: 169548, SEQ ID NO: 169553, SEQ ID NO: 169555, SEQ ID NO: 169563, SEQ ID NO: 169565, SEQ ID NO: 169578, SEQ ID NO: 169584, SEQ ID NO: 169605, SEQ ID NO: 169641, SEQ ID NO: 169665, SEQ ID NO: 169673, SEQ ID NO: 169682, SEQ ID NO: 169700, SEQ ID NO: 169704, SEQ ID NO: 169740, SEQ ID NO: 169768, SEQ ID NO: 169850, SEQ ID NO: 169858, SEQ ID NO: 169867, SEQ ID NO: 169871, SEQ ID NO: 169886, SEQ ID NO: 169915, SEQ ID NO: 169966, SEQ ID NO: 170057, SEQ ID NO: 170061, SEQ ID NO: 170081, SEQ ID NOs: 170178 to 170179, SEQ ID NO: 170261, SEQ ID NO: 170268, SEQ ID NO: 170278, SEQ ID NO: 170290, SEQ ID NO: 170320, SEQ ID NO: 170329, SEQ ID NO: 170390, SEQ ID NO: 170443, SEQ ID NO: 170488, SEQ ID NO: 170543, SEQ ID NO: 170574, SEQ ID NO: 170679, SEQ ID NO: 170704, SEQ ID NOs: 170706 to 170707, SEQ ID NO: 170735, SEQ ID NO: 170754, SEQ ID NO: 170771, SEQ ID NOs: 170809 to 170810, SEQ ID NO: 170834, SEQ ID NO: 170847, SEQ ID NO: 170876, SEQ ID NOs: 170902 to 170903, SEQ ID NO: 170964, SEQ ID NO: 170968, SEQ ID NO: 170970, SEQ ID NO: 170976, SEQ ID NO: 170981, SEQ ID NO: 171011, SEQ ID NO: 171029, SEQ ID NO: 171080, SEQ ID NO: 171085, SEQ ID NO: 171091, SEQ ID NO: 171174, SEQ ID NO: 171182, SEQ ID NO: 171212, SEQ ID NO: 171229, SEQ ID NO: 171242, SEQ ID NO: 171256, SEQ ID NO: 171260, SEQ ID NO: 171263, SEQ ID NO: 171291, SEQ ID NO: 171329, SEQ ID NO: 171334, SEQ ID NO: 171340, SEQ ID NO: 171406, SEQ ID NO: 171412, SEQ ID NO: 171428, SEQ ID NO: 171462, SEQ ID NO: 171474, SEQ ID NO: 171485, SEQ ID NO: 171490, SEQ ID NO: 171526, SEQ ID NO: 171536, SEQ ID NO: 171550, SEQ ID NO: 171581, SEQ ID NO: 171608, SEQ ID NO: 171625, SEQ ID NO: 171655, SEQ ID NO: 171662, SEQ ID NO: 171709, SEQ ID NO: 171732, SEQ ID NO: 171746, SEQ ID NO: 171752, SEQ ID NO: 171768, SEQ ID NO: 171786, SEQ ID NO: 171788, SEQ ID NO: 171814, SEQ ID NO: 171855, SEQ ID NO: 171863, SEQ ID NO: 171980, SEQ ID NO: 172007, SEQ ID NO: 172010, SEQ ID NO: 172062, SEQ ID NO: 172161, SEQ ID NO: 172181, SEQ ID NO: 172203, SEQ ID NO: 172225, SEQ ID NO: 172231, SEQ ID NO: 172255, SEQ ID NO: 172272, SEQ ID NO: 172276, SEQ ID NO: 172294, SEQ ID NO: 172348, SEQ ID NO: 172372, SEQ ID NO: 172375, SEQ ID NO: 172378, SEQ ID NO: 172387, SEQ ID NO: 172389, SEQ ID NO: 172421, SEQ ID NOs: 172439 to 172440, SEQ ID NO: 172484, SEQ ID NO: 172495, SEQ ID NO: 172563, SEQ ID NO: 172594, SEQ ID NO: 172660, SEQ ID NO: 172693, SEQ ID NO: 172702, SEQ ID NO: 172704, SEQ ID NO: 172709, SEQ ID NO: 172717, SEQ ID NO: 172726, SEQ ID NO: 172742, SEQ ID NO: 172793, SEQ ID NO: 172801, SEQ ID NO: 172816, SEQ ID NO: 172849, SEQ ID NO: 172862, SEQ ID NO: 172900, SEQ ID NO: 172907, SEQ ID NO: 172919, SEQ ID NO: 172926, SEQ ID NO: 172990, SEQ ID NO: 172994, SEQ ID NO: 172999, SEQ ID NO: 173004, SEQ ID NO: 173007, SEQ ID NO: 173084, SEQ ID NO: 173202, SEQ ID NO: 173206, SEQ ID NO: 173284, SEQ ID NO: 173288, SEQ ID NO: 173318, SEQ ID NO: 173321, SEQ ID NO: 173412, SEQ ID NO: 173433, SEQ ID NO: 173452, SEQ ID NO: 173467, SEQ ID NOs: 173469 to 173470, SEQ ID NO: 173494, SEQ ID NO: 173497, SEQ ID NO: 173516, SEQ ID NO: 173611, SEQ ID NO: 173633, SEQ ID NO: 173713, SEQ ID NO: 173726, SEQ ID NO: 173762, SEQ ID NO: 173792, SEQ ID NO: 173837, SEQ ID NO: 173849, SEQ ID NO: 173858, SEQ ID NO: 173864, SEQ ID NO: 173884, SEQ ID NO: 173918, SEQ ID NO: 173923, SEQ ID NO: 173929, SEQ ID NO: 173958, SEQ ID NO: 173993, SEQ ID NO: 174020, SEQ ID NO: 174026, SEQ ID NO: 174044, SEQ ID NO: 174047, SEQ ID NO: 174110, SEQ ID NO: 174116, SEQ ID NO: 174161, SEQ ID NO: 174164, SEQ ID NO: 174168, SEQ ID NO: 174180, SEQ ID NO: 174190, SEQ ID NO: 174210, SEQ ID NO: 174228, SEQ ID NO: 174260, SEQ ID NO: 174265, SEQ ID NO: 174277, SEQ ID NO: 174283, SEQ ID NO: 174301, SEQ ID NO: 174311, SEQ ID NO: 174316, SEQ ID NO: 174356, SEQ ID NO: 174387, SEQ ID NO: 174424, SEQ ID NO: 174452, SEQ ID NO: 174486, SEQ ID NO: 174491, SEQ ID NO: 174507, SEQ ID NO: 174510, SEQ ID NO: 174595, SEQ ID NO: 174611, SEQ ID NO: 174633, SEQ ID NO: 174679, SEQ ID NO: 174702, SEQ ID NO: 174724, SEQ ID NO: 174747, SEQ ID NO: 174756, SEQ ID NO: 174779, SEQ ID NO: 174847, SEQ ID NO: 174880, SEQ ID NO: 174904, SEQ ID NO: 174956, SEQ ID NO: 174960, SEQ ID NO: 174978, SEQ ID NO: 175027, SEQ ID NO: 175063, SEQ ID NO: 175076, SEQ ID NO: 175129, SEQ ID NO: 175160, SEQ ID NO: 175175, SEQ ID NO: 175186, SEQ ID NO: 175191, SEQ ID NO: 175251, SEQ ID NO: 175269, SEQ ID NO: 175292, SEQ ID NO: 175295, SEQ ID NO: 175300, SEQ ID NO: 175416, SEQ ID NO: 175423, SEQ ID NO: 175506, SEQ ID NO: 175541, SEQ ID NO: 175557, SEQ ID NO: 175585, SEQ ID NO: 175625, SEQ ID NO: 175649, SEQ ID NO: 175671, SEQ ID NOs: 175721 to 175722, SEQ ID NO: 175820, SEQ ID NO: 175886, SEQ ID NO: 175902, SEQ ID NO: 175951, SEQ ID NOs: 175960 to 175961, SEQ ID NO: 175968, SEQ ID NO: 175975, SEQ ID NO: 175993, SEQ ID NO: 176018, SEQ ID NO: 176041, SEQ ID NO: 176051, SEQ ID NO: 176112, SEQ ID NO: 176118, SEQ ID NO: 176149, SEQ ID NO: 176179, SEQ ID NO: 176248, SEQ ID NO: 176306, SEQ ID NO: 176309, SEQ ID NO: 176312, SEQ ID NO: 176335, SEQ ID NO: 176338, SEQ ID NO: 176355, SEQ ID NO: 176369, SEQ ID NO: 176379, SEQ ID NO: 176452, SEQ ID NO: 176466, SEQ ID NO: 176503, SEQ ID NO: 176548, SEQ ID NO: 176560, SEQ ID NO: 176611, SEQ ID NO: 176621, SEQ ID NO: 176639, SEQ ID NO: 176693, SEQ ID NO: 176700, SEQ ID NO: 176713, SEQ ID NO: 176764, SEQ ID NOs: 176795 to 176796, SEQ ID NO: 176806, SEQ ID NO: 176815, SEQ ID NO: 176953, SEQ ID NO: 176958, SEQ ID NO: 176969, SEQ ID NO: 176980, SEQ ID NO: 176991, SEQ ID NO: 177016, SEQ ID NO: 177033, SEQ ID NO: 177044, SEQ ID NO: 177061, SEQ ID NO: 177065, SEQ ID NO: 177080, SEQ ID NO: 177088, SEQ ID NO: 177102, SEQ ID NO: 177119, SEQ ID NO: 177343, SEQ ID NO: 177358, SEQ ID NO: 177390, SEQ ID NO: 177430, SEQ ID NO: 177437, SEQ ID NO: 177465, SEQ ID NOs: 177482 to 177483, SEQ ID NO: 177492, SEQ ID NO: 177495, SEQ ID NO: 177522, SEQ ID NO: 177585, SEQ ID NO: 177604, SEQ ID NO: 177611, SEQ ID NO: 177664, SEQ ID NO: 177669, SEQ ID NO: 177701, SEQ ID NO: 177707, SEQ ID NO: 177710, SEQ ID NO: 177712, SEQ ID NO: 177714, SEQ ID NO: 177734, SEQ ID NO: 177808, SEQ ID NO: 177841, SEQ ID NO: 177848, SEQ ID NO: 177892, SEQ ID NO: 177918, SEQ ID NO: 177958, SEQ ID NOs: 177989 to 177990, SEQ ID NO: 178023, SEQ ID NO: 178032, SEQ ID NO: 178035, SEQ ID NO: 178039, SEQ ID NO: 178122, SEQ ID NO: 178161, SEQ ID NO: 178195, SEQ ID NO: 178208, SEQ ID NO: 178244, SEQ ID NO: 178272, SEQ ID NO: 178293, SEQ ID NO: 178310, SEQ ID NO: 178338, SEQ ID NO: 178353, SEQ ID NO: 178385, SEQ ID NO: 178399, SEQ ID NO: 178477, SEQ ID NO: 178519, SEQ ID NO: 178568, SEQ ID NO: 178587, SEQ ID NO: 178600, SEQ ID NO: 178612, SEQ ID NO: 178615, SEQ ID NO: 178651, SEQ ID NO: 178726, SEQ ID NO: 178740, SEQ ID NO: 178743, SEQ ID NO: 178750, SEQ ID NO: 178821, SEQ ID NO: 178886, SEQ ID NO: 178895, SEQ ID NO: 178911, SEQ ID NO: 178942, SEQ ID NO: 178946, SEQ ID NO: 178948, SEQ ID NO: 178966, SEQ ID NO: 179020, SEQ ID NO: 179031, SEQ ID NO: 179034, SEQ ID NO: 179130, SEQ ID NO: 179134, SEQ ID NO: 179151, SEQ ID NO: 179154, SEQ ID NO: 179224, SEQ ID NO: 179257, SEQ ID NO: 179387, SEQ ID NO: 179404, SEQ ID NO: 179444, SEQ ID NO: 179455, SEQ ID NO: 179462, SEQ ID NO: 179483, SEQ ID NO: 179544, SEQ ID NO: 179586, SEQ ID NO: 179600, SEQ ID NO: 179612, SEQ ID NO: 179619, SEQ ID NO: 179632, SEQ ID NO: 179677, SEQ ID NO: 179695, SEQ ID NO: 179697, SEQ ID NO: 179760, SEQ ID NO: 179863, SEQ ID NO: 179898, SEQ ID NO: 179904, SEQ ID NO: 179934, SEQ ID NO: 179957, SEQ ID NO: 179981, SEQ ID NO: 180013, SEQ ID NO: 180019, SEQ ID NO: 180036, SEQ ID NO: 180077, SEQ ID NO: 180086, SEQ ID NO: 180167, SEQ ID NO: 180257, SEQ ID NO: 180259, SEQ ID NO: 180271, SEQ ID NO: 180291, SEQ ID NO: 180327, SEQ ID NO: 180348, SEQ ID NO: 180378, SEQ ID NO: 180396, SEQ ID NO: 180430, SEQ ID NO: 180452, SEQ ID NO: 180458, SEQ ID NO: 180481, SEQ ID NO: 180489, SEQ ID NO: 180492, SEQ ID NO: 180528, SEQ ID NO: 180551, SEQ ID NO: 180567, SEQ ID NO: 180577, SEQ ID NO: 180597, SEQ ID NO: 180622, SEQ ID NO: 180683, SEQ ID NO: 180694, SEQ ID NOs: 180720 to 180721, SEQ ID NO: 180772, SEQ ID NO: 180799, SEQ ID NO: 180823, SEQ ID NO: 180843, SEQ ID NO: 180848, SEQ ID NO: 180858, SEQ ID NO: 180866, SEQ ID NO: 180879, SEQ ID NO: 180977, SEQ ID NOs: 181032 to 181033, SEQ ID NO: 181173, SEQ ID NO: 181204, SEQ ID NO: 181259, SEQ ID NO: 181406, SEQ ID NO: 181630, SEQ ID NO: 181685, SEQ ID NO: 181792, SEQ ID NO: 181963, SEQ ID NO: 181984, SEQ ID NOs: 182157 to 182159, SEQ ID NO: 182471, or SEQ ID NOs: 182574 to 197896.

In some embodiments, the amino acid sequence for a MEW class I peptide vaccine for the MAR1 protein comprises one or more of the SEQ ID NOs: 113808 to 113869. In some embodiments, any one of the peptides in the MAR1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 113808 to 113869.

In some embodiments, the amino acid sequence for a MEW class I peptide vaccine for the MAR1 protein comprises one or more of the SEQ ID NOs: 113808 to 116477. In some embodiments, any one of the peptides in the MAR1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 113808 to 116477.

In some embodiments, the amino acid sequence for a MEW class I peptide vaccine for the MAR1 protein comprises two or more of the SEQ ID NOs: 113808 to 113869. In some embodiments, any one of the peptides in the MAR1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 113808 to 113869.

In some embodiments, the amino acid sequence for a MEW class I peptide vaccine for the MAR1 protein comprises two or more of the SEQ ID NOs: 113808 to 116477. In some embodiments, any one of the peptides in the MAR1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 113808 to 116477.

Additional amino acid sequences of MHC class I vaccine peptides are provided in Sequence Listings (SEQ ID NOs: 760 to 22727, SEQ ID NOs: 28865 to 34168, SEQ ID NOs: 37175 to 41320, SEQ ID NO: 41345, SEQ ID NO: 41347, SEQ ID NOs: 41351 to 41352, SEQ ID NO: 41366, SEQ ID NO: 41382, SEQ ID NO: 41392, SEQ ID NO: 41396, SEQ ID NOs: 41398 to 51433, SEQ ID NOs: 51511 to 60455, SEQ ID NOs: 60528 to 68237, SEQ ID NO: 68257, SEQ ID NO: 68288, SEQ ID NOs: 68322 to 95592, SEQ ID NOs: 95665 to 113807, SEQ ID NOs: 113870 to 116477, SEQ ID NOs: 125219 to 144108, SEQ ID NOs: 144189 to 162382, SEQ ID NOs: 162454 to 166443, SEQ ID NO: 166477, SEQ ID NO: 166486, SEQ ID NO: 166513, SEQ ID NOs: 166532 to 182573, and SEQ ID NOs: 182655 to 197896). In some embodiments, any combination of MHC class I peptides disclosed herein (SEQ ID NOs: 1 to 474, SEQ ID NOs: 760 to 22727, SEQ ID NOs: 28796 to 34168, SEQ ID NOs: 37110 to 116477, and SEQ ID NOs: 125134 to 197896) may be used to create a combined peptide vaccine having between about 2 and about 40 peptides. In some embodiments, any one of the peptides (SEQ ID NOs: 1 to 474, SEQ ID NOs: 760 to 22727, SEQ ID NOs: 28796 to 34168, SEQ ID NOs: 37110 to 116477, and SEQ ID NOs: 125134 to 197896) in the combined vaccine comprises or contains an amino acid sequence 80, 81, 82, 83, 84, 85, 86, 87, 88, 89, 90, 91, 92, 93, 94, 95, 96, 97, 98 or 99% identical to any of SEQ ID NOs: 1 to 474, SEQ ID NOs: 760 to 22727, SEQ ID NOs: 28796 to 34168, SEQ ID NOs: 37110 to 116477, or SEQ ID NOs: 125134 to 197896.

WIC Class II Peptide Sequences

In some embodiments, a peptide vaccine (single target or combined multiple target vaccine) comprises about 1 to 40 MHC class II peptides with each peptide consisting of about 20 amino acids. In some embodiments, an MHC class II peptide vaccine is intended for one or more of the CTG1B, KKLC1, MAGA1, MAGA3, MAGA4, MAGC1, MAGC3, MAR1, PMEL, PRAME, SSX2, TYRP1, or TYRP2 protein targets. In some embodiments, an MHC class II peptide vaccine is intended for one or more of the pancreatic cancer, skin cancer, thyroid cancer, brain cancer, colorectal cancer, bronchus and lung cancer, breast cancer, or ovarian cancer indications.

In some embodiments, the amino acid sequence for a MHC class II peptide vaccine for the CTG1B protein comprises one or more of the SEQ ID NOs: 197897 to 197910. In some embodiments, any one of the peptides in the CTG1B vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 197897 to 197910.

In some embodiments, the amino acid sequence for a MHC class II peptide vaccine for the CTG1B protein comprises one or more of the SEQ ID NOs: 197897 to 203516. In some embodiments, any one of the peptides in the CTG1B vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 197897 to 203516.

In some embodiments, the amino acid sequence for a MHC class II peptide vaccine for the CTG1B protein comprises two or more of the SEQ ID NOs: 197897 to 197910. In some embodiments, any one of the peptides in the CTG1B vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 197897 to 197910.

In some embodiments, the amino acid sequence for a MHC class II peptide vaccine for the CTG1B protein comprises two or more of the SEQ ID NOs: 197897 to 203516. In some embodiments, any one of the peptides in the CTG1B vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 197897 to 203516.

In some embodiments, the amino acid sequence for a MHC class II peptide vaccine for the MAGA1 protein comprises one or more of the SEQ ID NOs: 211901 to 211917. In some embodiments, any one of the peptides in the MAGA1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 211901 to 211917.

In some embodiments, the amino acid sequence for a MHC class II peptide vaccine for the MAGA1 protein comprises one or more of the SEQ ID NOs: 211901 to 223622. In some embodiments, any one of the peptides in the MAGA1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 211901 to 223622.

In some embodiments, the amino acid sequence for a MHC class II peptide vaccine for the MAGA1 protein comprises two or more of the SEQ ID NOs: 211901 to 211917. In some embodiments, any one of the peptides in the MAGA1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 211901 to 211917.

In some embodiments, the amino acid sequence for a MHC class II peptide vaccine for the MAGA1 protein comprises two or more of the SEQ ID NOs: 211901 to 223622. In some embodiments, any one of the peptides in the MAGA1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 211901 to 223622.

In some embodiments, the amino acid sequence for a MHC class II peptide vaccine for the MAGA3 protein comprises one or more of the SEQ ID NOs: 223623 to 223640. In some embodiments, any one of the peptides in the MAGA3 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 223623 to 223640.

In some embodiments, the amino acid sequence for a MHC class II peptide vaccine for the MAGA3 protein comprises one or more of the SEQ ID NOs: 212187 to 212190, SEQ ID NOs: 212668 to 212673, SEQ ID NOs: 212836 to 212837, SEQ ID NOs: 213320 to 213323, SEQ ID NO: 213359, SEQ ID NOs: 213380 to 213382, SEQ ID NOs: 213391 to 213395, SEQ ID NO: 213432, SEQ ID NOs: 214285 to 214290, SEQ ID NOs: 215204 to 215205, SEQ ID NOs: 215677 to 215682, SEQ ID NO: 216240, SEQ ID NO: 216385, SEQ ID NO: 216393, SEQ ID NO: 216397, SEQ ID NOs: 217119 to 217137, SEQ ID NO: 217185, SEQ ID NO: 217187, SEQ ID NO: 217190, SEQ ID NOs: 217659 to 217660, SEQ ID NOs: 219238 to 219245, SEQ ID NOs: 219322 to 219323, SEQ ID NOs: 219380 to 219386, SEQ ID NOs: 219432 to 219446, SEQ ID NOs: 219545 to 219546, SEQ ID NO: 219774, SEQ ID NO: 219777, SEQ ID NO: 220091, SEQ ID NOs: 221996 to 222005, SEQ ID NO: 223185, SEQ ID NO: 223187, SEQ ID NO: 223251, SEQ ID NO: 223253, SEQ ID NO: 223258, SEQ ID NO: 223261, SEQ ID NO: 223264, SEQ ID NO: 223268, SEQ ID NO: 223272, SEQ ID NO: 223274, SEQ ID NO: 223277, and SEQ ID NOs: 223623 to 236015. In some embodiments, any one of the peptides in the MAGA3 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 212187 to 212190, SEQ ID NOs: 212668 to 212673, SEQ ID NOs: 212836 to 212837, SEQ ID NOs: 213320 to 213323, SEQ ID NO: 213359, SEQ ID NOs: 213380 to 213382, SEQ ID NOs: 213391 to 213395, SEQ ID NO: 213432, SEQ ID NOs: 214285 to 214290, SEQ ID NOs: 215204 to 215205, SEQ ID NOs: 215677 to 215682, SEQ ID NO: 216240, SEQ ID NO: 216385, SEQ ID NO: 216393, SEQ ID NO: 216397, SEQ ID NOs: 217119 to 217137, SEQ ID NO: 217185, SEQ ID NO: 217187, SEQ ID NO: 217190, SEQ ID NOs: 217659 to 217660, SEQ ID NOs: 219238 to 219245, SEQ ID NOs: 219322 to 219323, SEQ ID NOs: 219380 to 219386, SEQ ID NOs: 219432 to 219446, SEQ ID NOs: 219545 to 219546, SEQ ID NO: 219774, SEQ ID NO: 219777, SEQ ID NO: 220091, SEQ ID NOs: 221996 to 222005, SEQ ID NO: 223185, SEQ ID NO: 223187, SEQ ID NO: 223251, SEQ ID NO: 223253, SEQ ID NO: 223258, SEQ ID NO: 223261, SEQ ID NO: 223264, SEQ ID NO: 223268, SEQ ID NO: 223272, SEQ ID NO: 223274, SEQ ID NO: 223277, or SEQ ID NOs: 223623 to 236015.

In some embodiments, the amino acid sequence for a MHC class II peptide vaccine for the MAGA3 protein comprises two or more of the SEQ ID NOs: 223623 to 223640. In some embodiments, any one of the peptides in the MAGA3 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 223623 to 223640.

In some embodiments, the amino acid sequence for a MHC class II peptide vaccine for the MAGA3 protein comprises two or more of the SEQ ID NOs: 212187 to 212190, SEQ ID NOs: 212668 to 212673, SEQ ID NOs: 212836 to 212837, SEQ ID NOs: 213320 to 213323, SEQ ID NO: 213359, SEQ ID NOs: 213380 to 213382, SEQ ID NOs: 213391 to 213395, SEQ ID NO: 213432, SEQ ID NOs: 214285 to 214290, SEQ ID NOs: 215204 to 215205, SEQ ID NOs: 215677 to 215682, SEQ ID NO: 216240, SEQ ID NO: 216385, SEQ ID NO: 216393, SEQ ID NO: 216397, SEQ ID NOs: 217119 to 217137, SEQ ID NO: 217185, SEQ ID NO: 217187, SEQ ID NO: 217190, SEQ ID NOs: 217659 to 217660, SEQ ID NOs: 219238 to 219245, SEQ ID NOs: 219322 to 219323, SEQ ID NOs: 219380 to 219386, SEQ ID NOs: 219432 to 219446, SEQ ID NOs: 219545 to 219546, SEQ ID NO: 219774, SEQ ID NO: 219777, SEQ ID NO: 220091, SEQ ID NOs: 221996 to 222005, SEQ ID NO: 223185, SEQ ID NO: 223187, SEQ ID NO: 223251, SEQ ID NO: 223253, SEQ ID NO: 223258, SEQ ID NO: 223261, SEQ ID NO: 223264, SEQ ID NO: 223268, SEQ ID NO: 223272, SEQ ID NO: 223274, SEQ ID NO: 223277, and SEQ ID NOs: 223623 to 236015. In some embodiments, any one of the peptides in the MAGA3 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 212187 to 212190, SEQ ID NOs: 212668 to 212673, SEQ ID NOs: 212836 to 212837, SEQ ID NOs: 213320 to 213323, SEQ ID NO: 213359, SEQ ID NOs: 213380 to 213382, SEQ ID NOs: 213391 to 213395, SEQ ID NO: 213432, SEQ ID NOs: 214285 to 214290, SEQ ID NOs: 215204 to 215205, SEQ ID NOs: 215677 to 215682, SEQ ID NO: 216240, SEQ ID NO: 216385, SEQ ID NO: 216393, SEQ ID NO: 216397, SEQ ID NOs: 217119 to 217137, SEQ ID NO: 217185, SEQ ID NO: 217187, SEQ ID NO: 217190, SEQ ID NOs: 217659 to 217660, SEQ ID NOs: 219238 to 219245, SEQ ID NOs: 219322 to 219323, SEQ ID NOs: 219380 to 219386, SEQ ID NOs: 219432 to 219446, SEQ ID NOs: 219545 to 219546, SEQ ID NO: 219774, SEQ ID NO: 219777, SEQ ID NO: 220091, SEQ ID NOs: 221996 to 222005, SEQ ID NO: 223185, SEQ ID NO: 223187, SEQ ID NO: 223251, SEQ ID NO: 223253, SEQ ID NO: 223258, SEQ ID NO: 223261, SEQ ID NO: 223264, SEQ ID NO: 223268, SEQ ID NO: 223272, SEQ ID NO: 223274, SEQ ID NO: 223277, or SEQ ID NOs: 223623 to 236015.

In some embodiments, the amino acid sequence for a MHC class II peptide vaccine for the MAGA4 protein comprises one or more of the SEQ ID NOs: 236016 to 236033. In some embodiments, any one of the peptides in the MAGA4 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 236016 to 236033.

In some embodiments, the amino acid sequence for a MHC class II peptide vaccine for the MAGA4 protein comprises one or more of the SEQ ID NO: 211911, SEQ ID NOs: 212086 to 212095, SEQ ID NOs: 212435 to 212440, SEQ ID NOs: 212681 to 212684, SEQ ID NOs: 212858 to 212860, SEQ ID NOs: 213516 to 213517, SEQ ID NOs: 213529 to 213531, SEQ ID NOs: 213602 to 213611, SEQ ID NOs: 213719 to 213720, SEQ ID NO: 213899, SEQ ID NOs: 214004 to 214012, SEQ ID NO: 214607, SEQ ID NOs: 214647 to 214649, SEQ ID NOs: 214672 to 214679, SEQ ID NOs: 214774 to 214775, SEQ ID NO: 214777, SEQ ID NO: 214779, SEQ ID NO: 214782, SEQ ID NOs: 215373 to 215415, SEQ ID NO: 215494, SEQ ID NO: 215497, SEQ ID NO: 215679, SEQ ID NO: 216244, SEQ ID NO: 216246, SEQ ID NOs: 216383 to 216401, SEQ ID NOs: 217184 to 217192, SEQ ID NO: 217200, SEQ ID NO: 217362, SEQ ID NOs: 217708 to 217712, SEQ ID NO: 217719, SEQ ID NO: 219238, SEQ ID NOs: 219742 to 219744, SEQ ID NO: 219747, SEQ ID NO: 219749, SEQ ID NO: 219751, SEQ ID NOs: 219773 to 219781, SEQ ID NOs: 219994 to 220030, SEQ ID NOs: 220318 to 220319, SEQ ID NO: 220327, SEQ ID NO: 220670, SEQ ID NO: 220815, SEQ ID NO: 220820, SEQ ID NOs: 221197 to 221234, SEQ ID NO: 221998, SEQ ID NO: 222000, SEQ ID NO: 223092, SEQ ID NO: 223095, SEQ ID NO: 223097, SEQ ID NO: 223099, SEQ ID NO: 223119, SEQ ID NO: 223121, SEQ ID NOs: 223184 to 223190, SEQ ID NOs: 223250 to 223283, SEQ ID NO: 223319, SEQ ID NO: 230922, SEQ ID NOs: 232805 to 232806, SEQ ID NO: 232846, and SEQ ID NOs: 236016 to 247058. In some embodiments, any one of the peptides in the MAGA4 vaccine comprise an amino acid sequence 80, 81, 82, 83, 84, 85, 86, 87, 88, 89, 90, 91, 92, 93, 94, 95, 96, 97, 98 or 99% identical to SEQ ID NO: 211911, SEQ ID NOs: 212086 to 212095, SEQ ID NOs: 212435 to 212440, SEQ ID NOs: 212681 to 212684, SEQ ID NOs: 212858 to 212860, SEQ ID NOs: 213516 to 213517, SEQ ID NOs: 213529 to 213531, SEQ ID NOs: 213602 to 213611, SEQ ID NOs: 213719 to 213720, SEQ ID NO: 213899, SEQ ID NOs: 214004 to 214012, SEQ ID NO: 214607, SEQ ID NOs: 214647 to 214649, SEQ ID NOs: 214672 to 214679, SEQ ID NOs: 214774 to 214775, SEQ ID NO: 214777, SEQ ID NO: 214779, SEQ ID NO: 214782, SEQ ID NOs: 215373 to 215415, SEQ ID NO: 215494, SEQ ID NO: 215497, SEQ ID NO: 215679, SEQ ID NO: 216244, SEQ ID NO: 216246, SEQ ID NOs: 216383 to 216401, SEQ ID NOs: 217184 to 217192, SEQ ID NO: 217200, SEQ ID NO: 217362, SEQ ID NOs: 217708 to 217712, SEQ ID NO: 217719, SEQ ID NO: 219238, SEQ ID NOs: 219742 to 219744, SEQ ID NO: 219747, SEQ ID NO: 219749, SEQ ID NO: 219751, SEQ ID NOs: 219773 to 219781, SEQ ID NOs: 219994 to 220030, SEQ ID NOs: 220318 to 220319, SEQ ID NO: 220327, SEQ ID NO: 220670, SEQ ID NO: 220815, SEQ ID NO: 220820, SEQ ID NOs: 221197 to 221234, SEQ ID NO: 221998, SEQ ID NO: 222000, SEQ ID NO: 223092, SEQ ID NO: 223095, SEQ ID NO: 223097, SEQ ID NO: 223099, SEQ ID NO: 223119, SEQ ID NO: 223121, SEQ ID NOs: 223184 to 223190, SEQ ID NOs: 223250 to 223283, SEQ ID NO: 223319, SEQ ID NO: 230922, SEQ ID NOs: 232805 to 232806, SEQ ID NO: 232846, or SEQ ID NOs: 236016 to 247058.

In some embodiments, the amino acid sequence for a MHC class II peptide vaccine for the MAGA4 protein comprises two or more of the SEQ ID NOs: 236016 to 236033. In some embodiments, any one of the peptides in the MAGA4 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 236016 to 236033.

In some embodiments, the amino acid sequence for a MHC class II peptide vaccine for the MAGA4 protein comprises two or more of the SEQ ID NO: 211911, SEQ ID NOs: 212086 to 212095, SEQ ID NOs: 212435 to 212440, SEQ ID NOs: 212681 to 212684, SEQ ID NOs: 212858 to 212860, SEQ ID NOs: 213516 to 213517, SEQ ID NOs: 213529 to 213531, SEQ ID NOs: 213602 to 213611, SEQ ID NOs: 213719 to 213720, SEQ ID NO: 213899, SEQ ID NOs: 214004 to 214012, SEQ ID NO: 214607, SEQ ID NOs: 214647 to 214649, SEQ ID NOs: 214672 to 214679, SEQ ID NOs: 214774 to 214775, SEQ ID NO: 214777, SEQ ID NO: 214779, SEQ ID NO: 214782, SEQ ID NOs: 215373 to 215415, SEQ ID NO: 215494, SEQ ID NO: 215497, SEQ ID NO: 215679, SEQ ID NO: 216244, SEQ ID NO: 216246, SEQ ID NOs: 216383 to 216401, SEQ ID NOs: 217184 to 217192, SEQ ID NO: 217200, SEQ ID NO: 217362, SEQ ID NOs: 217708 to 217712, SEQ ID NO: 217719, SEQ ID NO: 219238, SEQ ID NOs: 219742 to 219744, SEQ ID NO: 219747, SEQ ID NO: 219749, SEQ ID NO: 219751, SEQ ID NOs: 219773 to 219781, SEQ ID NOs: 219994 to 220030, SEQ ID NOs: 220318 to 220319, SEQ ID NO: 220327, SEQ ID NO: 220670, SEQ ID NO: 220815, SEQ ID NO: 220820, SEQ ID NOs: 221197 to 221234, SEQ ID NO: 221998, SEQ ID NO: 222000, SEQ ID NO: 223092, SEQ ID NO: 223095, SEQ ID NO: 223097, SEQ ID NO: 223099, SEQ ID NO: 223119, SEQ ID NO: 223121, SEQ ID NOs: 223184 to 223190, SEQ ID NOs: 223250 to 223283, SEQ ID NO: 223319, SEQ ID NO: 230922, SEQ ID NOs: 232805 to 232806, SEQ ID NO: 232846, or SEQ ID NOs: 236016 to 247058.

In some embodiments, the amino acid sequence for a MHC class II peptide vaccine for the MAGC1 protein comprises one or more of the SEQ ID NOs: 247059 to 247093. In some embodiments, any one of the peptides in the MAGC1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 247059 to 247093.

In some embodiments, the amino acid sequence for a MHC class II peptide vaccine for the MAGC1 protein comprises one or more of the SEQ ID NOs: 247059 to 281349. In some embodiments, any one of the peptides in the MAGC1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 247059 to 281349.

In some embodiments, the amino acid sequence for a MHC class II peptide vaccine for the MAGC1 protein comprises two or more of the SEQ ID NOs: 247059 to 247093. In some embodiments, any one of the peptides in the MAGC1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 247059 to 247093.

In some embodiments, the amino acid sequence for a MHC class II peptide vaccine for the MAGC1 protein comprises two or more of the SEQ ID NOs: 247059 to 281349. In some embodiments, any one of the peptides in the MAGC1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 247059 to 281349.

In some embodiments, the amino acid sequence for a MHC class II peptide vaccine for the MAGC3 protein comprises one or more of the SEQ ID NOs: 281350 to 281378. In some embodiments, any one of the peptides in the MAGC3 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 281350 to 281378.

In some embodiments, the amino acid sequence for a MHC class II peptide vaccine for the MAGC3 protein comprises one or more of the SEQ ID NO: 217120, SEQ ID NO: 247270, SEQ ID NO: 248009, SEQ ID NOs: 248159 to 248160, SEQ ID NOs: 248735 to 248738, SEQ ID NOs: 249358 to 249362, SEQ ID NOs: 249690 to 249691, SEQ ID NOs: 252562 to 252564, SEQ ID NOs: 252836 to 252837, SEQ ID NO: 256214, SEQ ID NO: 256221, SEQ ID NO: 256226, SEQ ID NO: 256229, SEQ ID NO: 256235, SEQ ID NO: 256705, SEQ ID NO: 257337, SEQ ID NO: 257341, SEQ ID NO: 257345, SEQ ID NO: 257995, SEQ ID NO: 258292, SEQ ID NO: 258295, SEQ ID NOs: 258614 to 258616, SEQ ID NO: 259467, SEQ ID NO: 259471, SEQ ID NO: 259474, SEQ ID NO: 260118, SEQ ID NO: 260122, SEQ ID NO: 260126, SEQ ID NO: 260131, SEQ ID NO: 260138, SEQ ID NO: 260145, SEQ ID NO: 260153, SEQ ID NOs: 260367 to 260384, SEQ ID NO: 260407, SEQ ID NO: 260412, SEQ ID NO: 261788, SEQ ID NO: 261790, SEQ ID NOs: 261792 to 261793, SEQ ID NO: 261795, SEQ ID NO: 261798, SEQ ID NO: 261800, SEQ ID NO: 261803, SEQ ID NO: 261805, SEQ ID NO: 261809, SEQ ID NO: 261811, SEQ ID NO: 261814, SEQ ID NO: 261816, SEQ ID NO: 261821, SEQ ID NO: 261823, SEQ ID NO: 261830, SEQ ID NO: 261832, SEQ ID NO: 261837, SEQ ID NO: 261839, SEQ ID NO: 262119, SEQ ID NO: 262122, SEQ ID NOs: 262261 to 262285, SEQ ID NO: 262313, SEQ ID NO: 262318, SEQ ID NOs: 263471 to 263474, SEQ ID NO: 263494, SEQ ID NO: 263498, SEQ ID NOs: 266653 to 266654, SEQ ID NO: 269139, SEQ ID NO: 269143, SEQ ID NO: 269149, SEQ ID NO: 269156, SEQ ID NO: 269169, SEQ ID NOs: 270516 to 270517, SEQ ID NOs: 270519 to 270520, SEQ ID NOs: 270523 to 270524, SEQ ID NOs: 270527 to 270528, SEQ ID NO: 272016, SEQ ID NO: 272020, SEQ ID NOs: 272214 to 272222, SEQ ID NO: 272243, SEQ ID NO: 272248, SEQ ID NO: 272896, SEQ ID NOs: 273018 to 273020, SEQ ID NOs: 278350 to 278351, SEQ ID NO: 278355, SEQ ID NOs: 278358 to 278359, SEQ ID NOs: 278361 to 278362, SEQ ID NO: 278364, SEQ ID NO: 278367, SEQ ID NO: 278369, SEQ ID NO: 278371, SEQ ID NO: 278373, SEQ ID NO: 278375, SEQ ID NO: 278377, SEQ ID NO: 278383, SEQ ID NO: 278385, SEQ ID NO: 278388, SEQ ID NO: 278390, SEQ ID NO: 278394, SEQ ID NO: 278396, SEQ ID NOs: 281013 to 281014, SEQ ID NO: 281018, SEQ ID NO: 281022, SEQ ID NO: 281026, SEQ ID NO: 281031, SEQ ID NOs: 281037 to 281038, SEQ ID NOs: 281044 to 281045, SEQ ID NOs: 281052 to 281053, SEQ ID NOs: 281151 to 281152, SEQ ID NO: 281155, SEQ ID NO: 281159, SEQ ID NOs: 281162 to 281163, SEQ ID NOs: 281165 to 281166, SEQ ID NO: 281169, SEQ ID NO: 281171, SEQ ID NO: 281174, SEQ ID NO: 281176, SEQ ID NO: 281179, SEQ ID NO: 281181, SEQ ID NO: 281184, SEQ ID NO: 281186, SEQ ID NO: 281190, SEQ ID NO: 281192, SEQ ID NO: 281197, SEQ ID NO: 281199, or SEQ ID NOs: 281350 to 305565.

In some embodiments, the amino acid sequence for a MHC class II peptide vaccine for the MAGC3 protein comprises two or more of the SEQ ID NOs: 281350 to 281378. In some embodiments, any one of the peptides in the MAGC3 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 281350 to 281378.

In some embodiments, the amino acid sequence for a MHC class II peptide vaccine for the MAGC3 protein comprises two or more of the SEQ ID NO: 217120, SEQ ID NO: 247270, SEQ ID NO: 248009, SEQ ID NOs: 248159 to 248160, SEQ ID NOs: 248735 to 248738, SEQ ID NOs: 249358 to 249362, SEQ ID NOs: 249690 to 249691, SEQ ID NOs: 252562 to 252564, SEQ ID NOs: 252836 to 252837, SEQ ID NO: 256214, SEQ ID NO: 256221, SEQ ID NO: 256226, SEQ ID NO: 256229, SEQ ID NO: 256235, SEQ ID NO: 256705, SEQ ID NO: 257337, SEQ ID NO: 257341, SEQ ID NO: 257345, SEQ ID NO: 257995, SEQ ID NO: 258292, SEQ ID NO: 258295, SEQ ID NOs: 258614 to 258616, SEQ ID NO: 259467, SEQ ID NO: 259471, SEQ ID NO: 259474, SEQ ID NO: 260118, SEQ ID NO: 260122, SEQ ID NO: 260126, SEQ ID NO: 260131, SEQ ID NO: 260138, SEQ ID NO: 260145, SEQ ID NO: 260153, SEQ ID NOs: 260367 to 260384, SEQ ID NO: 260407, SEQ ID NO: 260412, SEQ ID NO: 261788, SEQ ID NO: 261790, SEQ ID NOs: 261792 to 261793, SEQ ID NO: 261795, SEQ ID NO: 261798, SEQ ID NO: 261800, SEQ ID NO: 261803, SEQ ID NO: 261805, SEQ ID NO: 261809, SEQ ID NO: 261811, SEQ ID NO: 261814, SEQ ID NO: 261816, SEQ ID NO: 261821, SEQ ID NO: 261823, SEQ ID NO: 261830, SEQ ID NO: 261832, SEQ ID NO: 261837, SEQ ID NO: 261839, SEQ ID NO: 262119, SEQ ID NO: 262122, SEQ ID NOs: 262261 to 262285, SEQ ID NO: 262313, SEQ ID NO: 262318, SEQ ID NOs: 263471 to 263474, SEQ ID NO: 263494, SEQ ID NO: 263498, SEQ ID NOs: 266653 to 266654, SEQ ID NO: 269139, SEQ ID NO: 269143, SEQ ID NO: 269149, SEQ ID NO: 269156, SEQ ID NO: 269169, SEQ ID NOs: 270516 to 270517, SEQ ID NOs: 270519 to 270520, SEQ ID NOs: 270523 to 270524, SEQ ID NOs: 270527 to 270528, SEQ ID NO: 272016, SEQ ID NO: 272020, SEQ ID NOs: 272214 to 272222, SEQ ID NO: 272243, SEQ ID NO: 272248, SEQ ID NO: 272896, SEQ ID NOs: 273018 to 273020, SEQ ID NOs: 278350 to 278351, SEQ ID NO: 278355, SEQ ID NOs: 278358 to 278359, SEQ ID NOs: 278361 to 278362, SEQ ID NO: 278364, SEQ ID NO: 278367, SEQ ID NO: 278369, SEQ ID NO: 278371, SEQ ID NO: 278373, SEQ ID NO: 278375, SEQ ID NO: 278377, SEQ ID NO: 278383, SEQ ID NO: 278385, SEQ ID NO: 278388, SEQ ID NO: 278390, SEQ ID NO: 278394, SEQ ID NO: 278396, SEQ ID NOs: 281013 to 281014, SEQ ID NO: 281018, SEQ ID NO: 281022, SEQ ID NO: 281026, SEQ ID NO: 281031, SEQ ID NOs: 281037 to 281038, SEQ ID NOs: 281044 to 281045, SEQ ID NOs: 281052 to 281053, SEQ ID NOs: 281151 to 281152, SEQ ID NO: 281155, SEQ ID NO: 281159, SEQ ID NOs: 281162 to 281163, SEQ ID NOs: 281165 to 281166, SEQ ID NO: 281169, SEQ ID NO: 281171, SEQ ID NO: 281174, SEQ ID NO: 281176, SEQ ID NO: 281179, SEQ ID NO: 281181, SEQ ID NO: 281184, SEQ ID NO: 281186, SEQ ID NO: 281190, SEQ ID NO: 281192, SEQ ID NO: 281197, SEQ ID NO: 281199, or SEQ ID NOs: 281350 to 305565.

In some embodiments, the amino acid sequence for a MHC class II peptide vaccine for the SSX2 protein comprises one or more of the SEQ ID NOs: 369027 to 369036. In some embodiments, any one of the peptides in the SSX2 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 369027 to 369036.

In some embodiments, the amino acid sequence for a MHC class II peptide vaccine for the SSX2 protein comprises one or more of the SEQ ID NOs: 369027 to 373347. In some embodiments, any one of the peptides in the SSX2 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 369027 to 373347.

In some embodiments, the amino acid sequence for a MHC class II peptide vaccine for the SSX2 protein comprises two or more of the SEQ ID NOs: 369027 to 369036. In some embodiments, any one of the peptides in the SSX2 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 369027 to 369036.

In some embodiments, the amino acid sequence for a MHC class II peptide vaccine for the SSX2 protein comprises two or more of the SEQ ID NOs: 369027 to 373347. In some embodiments, any one of the peptides in the SSX2 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 369027 to 373347.

In some embodiments, the amino acid sequence for a MHC class II peptide vaccine for the PRAME protein comprises one or more of the SEQ ID NOs: 342521 to 342555. In some embodiments, any one of the peptides in the PRAME vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 342521 to 342555.

In some embodiments, the amino acid sequence for a MHC class II peptide vaccine for the PRAME protein comprises one or more of the SEQ ID NOs: 342521 to 369026. In some embodiments, any one of the peptides in the PRAME vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 342521 to 369026.

In some embodiments, the amino acid sequence for a MHC class II peptide vaccine for the PRAME protein comprises two or more of the SEQ ID NOs: 342521 to 342555. In some embodiments, any one of the peptides in the PRAME vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 342521 to 342555.

In some embodiments, the amino acid sequence for a MHC class II peptide vaccine for the PRAME protein comprises two or more of the SEQ ID NOs: 342521 to 369026. In some embodiments, any one of the peptides in the PRAME vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 342521 to 369026.

In some embodiments, the amino acid sequence for a MHC class II peptide vaccine for the KKLC1 protein comprises one or more of the SEQ ID NOs: 206663 to 206675. In some embodiments, any one of the peptides in the KKLC1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 206663 to 206675.

In some embodiments, the amino acid sequence for a MHC class II peptide vaccine for the KKLC1 protein comprises one or more of the SEQ ID NOs: 206663 to 211900. In some embodiments, any one of the peptides in the KKLC1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 206663 to 211900.

In some embodiments, the amino acid sequence for a MHC class II peptide vaccine for the KKLC1 protein comprises two or more of the SEQ ID NOs: 206663 to 206675. In some embodiments, any one of the peptides in the KKLC1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 206663 to 206675.

In some embodiments, the amino acid sequence for a MHC class II peptide vaccine for the KKLC1 protein comprises two or more of the SEQ ID NOs: 206663 to 211900. In some embodiments, any one of the peptides in the KKLC1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 206663 to 211900.

In some embodiments, the amino acid sequence for a MHC class II peptide vaccine for the PMEL protein comprises one or more of the SEQ ID NOs: 317360 to 317390. In some embodiments, any one of the peptides in the PMEL vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 317360 to 317390.

In some embodiments, the amino acid sequence for a MHC class II peptide vaccine for the PMEL protein comprises one or more of the SEQ ID NOs: 317360 to 342520. In some embodiments, any one of the peptides in the PMEL vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 317360 to 342520.

In some embodiments, the amino acid sequence for a MHC class II peptide vaccine for the PMEL protein comprises two or more of the SEQ ID NOs: 317360 to 317390. In some embodiments, any one of the peptides in the PMEL vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 317360 to 317390.

In some embodiments, the amino acid sequence for a MHC class II peptide vaccine for the PMEL protein comprises two or more of the SEQ ID NOs: 317360 to 342520. In some embodiments, any one of the peptides in the PMEL vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 317360 to 342520.

In some embodiments, the amino acid sequence for a MHC class II peptide vaccine for the TYRP1 protein comprises one or more of the SEQ ID NOs: 373348 to 373373. In some embodiments, any one of the peptides in the TYRP1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 373348 to 373373.

In some embodiments, the amino acid sequence for a MHC class II peptide vaccine for the TYRP1 protein comprises one or more of the SEQ ID NOs: 373348 to 392433. In some embodiments, any one of the peptides in the TYRP1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 373348 to 392433.

In some embodiments, the amino acid sequence for a MHC class II peptide vaccine for the TYRP1 protein comprises two or more of the SEQ ID NOs: 373348 to 373373. In some embodiments, any one of the peptides in the TYRP1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 373348 to 373373.

In some embodiments, the amino acid sequence for a MHC class II peptide vaccine for the TYRP1 protein comprises two or more of the SEQ ID NOs: 373348 to 392433. In some embodiments, any one of the peptides in the TYRP1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 373348 to 392433.

In some embodiments, the amino acid sequence for a MHC class II peptide vaccine for the TYRP2 protein comprises one or more of the SEQ ID NOs: 392434 to 392455. In some embodiments, any one of the peptides in the TYRP2 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 392434 to 392455.

In some embodiments, the amino acid sequence for a MHC class II peptide vaccine for the TYRP2 protein comprises one or more of the SEQ ID NO: 379327, SEQ ID NO: 379329, SEQ ID NO: 379332, SEQ ID NO: 379334, SEQ ID NO: 379770, SEQ ID NO: 381531, SEQ ID NO: 382109, SEQ ID NO: 383301, SEQ ID NO: 383305, SEQ ID NO: 383310, SEQ ID NO: 386111, SEQ ID NO: 387057, SEQ ID NO: 387062, and SEQ ID NOs: 392434 to 410309. In some embodiments, any one of the peptides in the TYRP2 vaccine comprise an amino acid sequence 80, 81, 82, 83, 84, 85, 86, 87, 88, 89, 90, 91, 92, 93, 94, 95, 96, 97, 98 or 99% identical to SEQ ID NO: 379327, SEQ ID NO: 379329, SEQ ID NO: 379332, SEQ ID NO: 379334, SEQ ID NO: 379770, SEQ ID NO: 381531, SEQ ID NO: 382109, SEQ ID NO: 383301, SEQ ID NO: 383305, SEQ ID NO: 383310, SEQ ID NO: 386111, SEQ ID NO: 387057, SEQ ID NO: 387062, or SEQ ID NOs: 392434 to 410309.

In some embodiments, the amino acid sequence for a MHC class II peptide vaccine for the TYRP2 protein comprises two or more of the SEQ ID NOs: 392434 to 392455. In some embodiments, any one of the peptides in the TYRP2 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 392434 to 392455.

In some embodiments, the amino acid sequence for a MHC class II peptide vaccine for the TYRP2 protein comprises two or more of the SEQ ID NO: 379327, SEQ ID NO: 379329, SEQ ID NO: 379332, SEQ ID NO: 379334, SEQ ID NO: 379770, SEQ ID NO: 381531, SEQ ID NO: 382109, SEQ ID NO: 383301, SEQ ID NO: 383305, SEQ ID NO: 383310, SEQ ID NO: 386111, SEQ ID NO: 387057, SEQ ID NO: 387062, and SEQ ID NOs: 392434 to 410309. In some embodiments, any one of the peptides in the TYRP2 vaccine comprise an amino acid sequence 80, 81, 82, 83, 84, 85, 86, 87, 88, 89, 90, 91, 92, 93, 94, 95, 96, 97, 98 or 99% identical to SEQ ID NO: 379327, SEQ ID NO: 379329, SEQ ID NO: 379332, SEQ ID NO: 379334, SEQ ID NO: 379770, SEQ ID NO: 381531, SEQ ID NO: 382109, SEQ ID NO: 383301, SEQ ID NO: 383305, SEQ ID NO: 383310, SEQ ID NO: 386111, SEQ ID NO: 387057, SEQ ID NO: 387062, or SEQ ID NOs: 392434 to 410309.

In some embodiments, the amino acid sequence for a MHC class II peptide vaccine for the MAR1 protein comprises one or more of the SEQ ID NOs: 305566 to 305571. In some embodiments, any one of the peptides in the MAR1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 305566 to 305571.

In some embodiments, the amino acid sequence for a MHC class II peptide vaccine for the MAR1 protein comprises one or more of the SEQ ID NOs: 305566 to 307669. In some embodiments, any one of the peptides in the MAR1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 305566 to 307669.

In some embodiments, the amino acid sequence for a MHC class II peptide vaccine for the MAR1 protein comprises two or more of the SEQ ID NOs: 305566 to 305571. In some embodiments, any one of the peptides in the MAR1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 305566 to 305571.

In some embodiments, the amino acid sequence for a MHC class II peptide vaccine for the MAR1 protein comprises two or more of the SEQ ID NOs: 305566 to 307669. In some embodiments, any one of the peptides in the MAR1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 305566 to 307669.

Additional amino acid sequences of MHC class II vaccine peptides are provided in Sequence Listings (SEQ ID NOs: 22728 to 28795, SEQ ID NOs: 197911 to 203516, SEQ ID NOs: 206676 to 211900, SEQ ID NO: 211911, SEQ ID NOs: 211918 to 223622, SEQ ID NOs: 223641 to 236015, SEQ ID NOs: 236034 to 247058, SEQ ID NOs: 247094 to 281349, SEQ ID NOs: 281379 to 305565, SEQ ID NOs: 305572 to 307669, SEQ ID NOs: 317391 to 342520, SEQ ID NOs: 342556 to 369026, SEQ ID NOs: 369037 to 373347, SEQ ID NOs: 373374 to 392433, and SEQ ID NOs: 392456 to 410309). In some embodiments, any combination of MHC class II peptides disclosed herein (SEQ ID NOs: 475 to 759, SEQ ID NOs: 22728 to 28795, SEQ ID NOs: 197897 to 203516, SEQ ID NOs: 206663 to 307669, and SEQ ID NOs: 317360 to 410309) may be used to create a combined peptide vaccine having between about 2 and about 40 peptides. In some embodiments, any one of the peptides (SEQ ID NOs: 475 to 759, SEQ ID NOs: 22728 to 28795, SEQ ID NOs: 197897 to 203516, SEQ ID NOs: 206663 to 307669, and SEQ ID NOs: 317360 to 410309) in the combined vaccine comprises or contains an amino acid sequence 80, 81, 82, 83, 84, 85, 86, 87, 88, 89, 90, 91, 92, 93, 94, 95, 96, 97, 98 or 99% identical to any of SEQ ID NOs: 475 to 759, SEQ ID NOs: 22728 to 28795, SEQ ID NOs: 197897 to 203516, SEQ ID NOs: 206663 to 307669, or SEQ ID NOs: 317360 to 410309.

In some embodiments, the amino acid sequence for a MHC class I and/or MHC class II peptides may be used to create a single target (individual) or combined peptide vaccine for the CTG1B protein having between about 2 and about 40 peptides. In some embodiments, any one of the peptides in the vaccine for the CTG1B protein comprises one or more of the SEQ ID NOs: 28796 to 34168 and SEQ ID NOs: 197897 to 203516. In some embodiments, any one of the peptides in the CTG1B vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 28796 to 34168 or SEQ ID NOs: 197897 to 203516.

In some embodiments, the amino acid sequence for a MHC class I and/or MHC class II peptides may be used to create a single target (individual) or combined peptide vaccine for the MAGA1 protein having between about 2 and about 40 peptides. In some embodiments, any one of the peptides in the vaccine for the MAGA1 protein comprises one or more of the SEQ ID NOs: 41321 to 51433 and SEQ ID NOs: 211901 to 223622. In some embodiments, any one of the peptides in the MAGA1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 41321 to 51433 or SEQ ID NOs: 211901 to 223622.

In some embodiments, the amino acid sequence for a MHC class I and/or MHC class II peptides may be used to create a single target (individual) or combined peptide vaccine for the MAGA3 protein having between about 2 and about 40 peptides. In some embodiments, any one of the peptides in the vaccine for the MAGA3 protein comprises one or more of the SEQ ID NOs: 41351 to 41352, SEQ ID NO: 41383, SEQ ID NO: 41396, SEQ ID NO: 41410, SEQ ID NO: 41414, SEQ ID NO: 41435, SEQ ID NO: 41450, SEQ ID NO: 41463, SEQ ID NO: 41478, SEQ ID NO: 41489, SEQ ID NO: 41495, SEQ ID NO: 41503, SEQ ID NO: 41513, SEQ ID NO: 41520, SEQ ID NO: 41535, SEQ ID NO: 41541, SEQ ID NO: 41545, SEQ ID NO: 41577, SEQ ID NO: 41588, SEQ ID NO: 41598, SEQ ID NO: 41605, SEQ ID NO: 41617, SEQ ID NO: 41620, SEQ ID NO: 41622, SEQ ID NO: 41627, SEQ ID NO: 41630, SEQ ID NO: 41638, SEQ ID NO: 41647, SEQ ID NO: 41673, SEQ ID NO: 41696, SEQ ID NO: 41703, SEQ ID NO: 41708, SEQ ID NO: 41728, SEQ ID NOs: 41732 to 41733, SEQ ID NO: 41749, SEQ ID NO: 41760, SEQ ID NO: 41766, SEQ ID NO: 41770, SEQ ID NO: 41788, SEQ ID NO: 41791, SEQ ID NO: 41809, SEQ ID NO: 41813, SEQ ID NO: 41817, SEQ ID NO: 41829, SEQ ID NOs: 41847 to 41848, SEQ ID NO: 41853, SEQ ID NO: 41859, SEQ ID NO: 41889, SEQ ID NO: 41894, SEQ ID NO: 41897, SEQ ID NO: 41909, SEQ ID NO: 41923, SEQ ID NO: 41934, SEQ ID NO: 41939, SEQ ID NOs: 41953 to 41954, SEQ ID NO: 41959, SEQ ID NO: 41967, SEQ ID NO: 41970, SEQ ID NO: 41976, SEQ ID NOs: 41984 to 41985, SEQ ID NO: 42007, SEQ ID NO: 42017, SEQ ID NO: 42034, SEQ ID NO: 42044, SEQ ID NO: 42046, SEQ ID NO: 42048, SEQ ID NO: 42056, SEQ ID NO: 42067, SEQ ID NO: 42080, SEQ ID NO: 42088, SEQ ID NO: 42091, SEQ ID NOs: 42119 to 42120, SEQ ID NO: 42129, SEQ ID NO: 42135, SEQ ID NOs: 42140 to 42141, SEQ ID NO: 42155, SEQ ID NO: 42158, SEQ ID NO: 42164, SEQ ID NO: 42170, SEQ ID NO: 42174, SEQ ID NO: 42186, SEQ ID NO: 42209, SEQ ID NO: 42218, SEQ ID NO: 42224, SEQ ID NO: 42229, SEQ ID NO: 42232, SEQ ID NO: 42235, SEQ ID NOs: 42237 to 42238, SEQ ID NO: 42265, SEQ ID NO: 42272, SEQ ID NO: 42278, SEQ ID NO: 42293, SEQ ID NO: 42314, SEQ ID NOs: 42336 to 42337, SEQ ID NO: 42339, SEQ ID NOs: 42372 to 42373, SEQ ID NO: 42376, SEQ ID NO: 42382, SEQ ID NO: 42386, SEQ ID NO: 42408, SEQ ID NO: 42414, SEQ ID NO: 42423, SEQ ID NO: 42429, SEQ ID NOs: 42447 to 42448, SEQ ID NO: 42461, SEQ ID NO: 42466, SEQ ID NO: 42475, SEQ ID NO: 42513, SEQ ID NO: 42540, SEQ ID NO: 42545, SEQ ID NO: 42550, SEQ ID NO: 42553, SEQ ID NOs: 42567 to 42568, SEQ ID NO: 42580, SEQ ID NO: 42585, SEQ ID NO: 42605, SEQ ID NO: 42612, SEQ ID NO: 42627, SEQ ID NO: 42675, SEQ ID NO: 42680, SEQ ID NO: 42685, SEQ ID NO: 42690, SEQ ID NO: 42702, SEQ ID NO: 42711, SEQ ID NO: 42719, SEQ ID NO: 42738, SEQ ID NO: 42743, SEQ ID NO: 42750, SEQ ID NO: 42755, SEQ ID NO: 42777, SEQ ID NO: 42788, SEQ ID NO: 42793, SEQ ID NO: 42851, SEQ ID NO: 42858, SEQ ID NO: 42866, SEQ ID NO: 42903, SEQ ID NO: 42927, SEQ ID NOs: 42936 to 42937, SEQ ID NOs: 42940 to 42941, SEQ ID NO: 42957, SEQ ID NO: 42962, SEQ ID NO: 42966, SEQ ID NO: 42968, SEQ ID NO: 42986, SEQ ID NO: 43002, SEQ ID NO: 43013, SEQ ID NO: 43037, SEQ ID NO: 43052, SEQ ID NOs: 43055 to 43056, SEQ ID NOs: 43063 to 43064, SEQ ID NO: 43096, SEQ ID NO: 43133, SEQ ID NO: 43138, SEQ ID NO: 43156, SEQ ID NO: 43161, SEQ ID NO: 43186, SEQ ID NO: 43199, SEQ ID NO: 43205, SEQ ID NO: 43245, SEQ ID NO: 43251, SEQ ID NO: 43275, SEQ ID NO: 43312, SEQ ID NO: 43327, SEQ ID NO: 43333, SEQ ID NO: 43339, SEQ ID NO: 43342, SEQ ID NO: 43348, SEQ ID NO: 43365, SEQ ID NO: 43371, SEQ ID NO: 43400, SEQ ID NO: 43440, SEQ ID NO: 43451, SEQ ID NO: 43462, SEQ ID NO: 43467, SEQ ID NO: 43487, SEQ ID NOs: 43498 to 43499, SEQ ID NO: 43507, SEQ ID NO: 43522, SEQ ID NO: 43529, SEQ ID NO: 43533, SEQ ID NO: 43545, SEQ ID NO: 43558, SEQ ID NO: 43560, SEQ ID NO: 43583, SEQ ID NO: 43597, SEQ ID NO: 43599, SEQ ID NO: 43610, SEQ ID NO: 43614, SEQ ID NO: 43627, SEQ ID NO: 43697, SEQ ID NO: 43715, SEQ ID NO: 43718, SEQ ID NO: 43768, SEQ ID NO: 43777, SEQ ID NOs: 43825 to 43826, SEQ ID NO: 43836, SEQ ID NO: 43840, SEQ ID NO: 43856, SEQ ID NO: 43860, SEQ ID NO: 43870, SEQ ID NO: 43878, SEQ ID NOs: 43881 to 43882, SEQ ID NO: 43905, SEQ ID NO: 43922, SEQ ID NO: 43930, SEQ ID NO: 43943, SEQ ID NO: 43953, SEQ ID NO: 43958, SEQ ID NO: 43979, SEQ ID NO: 43986, SEQ ID NO: 44002, SEQ ID NO: 44033, SEQ ID NO: 44037, SEQ ID NO: 44048, SEQ ID NO: 44050, SEQ ID NO: 44052, SEQ ID NOs: 44080 to 44081, SEQ ID NOs: 44093 to 44094, SEQ ID NOs: 44114 to 44115, SEQ ID NO: 44120, SEQ ID NO: 44142, SEQ ID NO: 44152, SEQ ID NOs: 44164 to 44166, SEQ ID NO: 44181, SEQ ID NO: 44222, SEQ ID NO: 44244, SEQ ID NO: 44246, SEQ ID NO: 44255, SEQ ID NO: 44261, SEQ ID NO: 44276, SEQ ID NOs: 44286 to 44287, SEQ ID NO: 44296, SEQ ID NO: 44315, SEQ ID NO: 44322, SEQ ID NO: 44324, SEQ ID NO: 44328, SEQ ID NO: 44332, SEQ ID NO: 44339, SEQ ID NO: 44401, SEQ ID NO: 44413, SEQ ID NO: 44435, SEQ ID NO: 44452, SEQ ID NO: 44454, SEQ ID NO: 44463, SEQ ID NO: 44467, SEQ ID NO: 44485, SEQ ID NO: 44504, SEQ ID NO: 44512, SEQ ID NO: 44523, SEQ ID NOs: 44526 to 44527, SEQ ID NO: 44536, SEQ ID NO: 44564, SEQ ID NO: 44605, SEQ ID NO: 44607, SEQ ID NO: 44612, SEQ ID NO: 44629, SEQ ID NOs: 44635 to 44636, SEQ ID NO: 44647, SEQ ID NO: 44650, SEQ ID NO: 44674, SEQ ID NO: 44691, SEQ ID NO: 44696, SEQ ID NO: 44702, SEQ ID NO: 44710, SEQ ID NO: 44713, SEQ ID NO: 44715, SEQ ID NO: 44722, SEQ ID NO: 44730, SEQ ID NO: 44733, SEQ ID NO: 44755, SEQ ID NO: 44770, SEQ ID NO: 44773, SEQ ID NO: 44781, SEQ ID NO: 44783, SEQ ID NO: 44797, SEQ ID NO: 44805, SEQ ID NO: 44822, SEQ ID NO: 44828, SEQ ID NO: 44830, SEQ ID NO: 44832, SEQ ID NO: 44850, SEQ ID NO: 44852, SEQ ID NO: 44854, SEQ ID NO: 44860, SEQ ID NO: 44866, SEQ ID NO: 44898, SEQ ID NO: 44900, SEQ ID NO: 44907, SEQ ID NO: 44933, SEQ ID NO: 44947, SEQ ID NO: 44986, SEQ ID NO: 45003, SEQ ID NO: 45007, SEQ ID NO: 45009, SEQ ID NO: 45012, SEQ ID NO: 45016, SEQ ID NO: 45018, SEQ ID NO: 45027, SEQ ID NO: 45031, SEQ ID NO: 45036, SEQ ID NO: 45044, SEQ ID NO: 45060, SEQ ID NO: 45071, SEQ ID NO: 45077, SEQ ID NO: 45095, SEQ ID NO: 45126, SEQ ID NO: 45132, SEQ ID NO: 45135, SEQ ID NO: 45139, SEQ ID NO: 45143, SEQ ID NO: 45159, SEQ ID NO: 45177, SEQ ID NO: 45197, SEQ ID NO: 45200, SEQ ID NO: 45219, SEQ ID NO: 45228, SEQ ID NO: 45323, SEQ ID NO: 45329, SEQ ID NO: 45351, SEQ ID NO: 45378, SEQ ID NO: 45380, SEQ ID NO: 45389, SEQ ID NO: 45413, SEQ ID NO: 45417, SEQ ID NO: 45438, SEQ ID NO: 45455, SEQ ID NO: 45457, SEQ ID NO: 45467, SEQ ID NO: 45478, SEQ ID NO: 45530, SEQ ID NO: 45562, SEQ ID NO: 45565, SEQ ID NOs: 45583 to 45584, SEQ ID NOs: 45595 to 45596, SEQ ID NO: 45608, SEQ ID NO: 45612, SEQ ID NO: 45616, SEQ ID NO: 45627, SEQ ID NO: 45653, SEQ ID NOs: 45666 to 45667, SEQ ID NO: 45680, SEQ ID NO: 45697, SEQ ID NO: 45705, SEQ ID NO: 45710, SEQ ID NO: 45722, SEQ ID NO: 45736, SEQ ID NO: 45742, SEQ ID NO: 45746, SEQ ID NO: 45765, SEQ ID NO: 45808, SEQ ID NO: 45830, SEQ ID NOs: 45840 to 45841, SEQ ID NO: 45896, SEQ ID NOs: 45904 to 45905, SEQ ID NO: 45913, SEQ ID NO: 45915, SEQ ID NOs: 45940 to 45943, SEQ ID NO: 45945, SEQ ID NOs: 45958 to 45959, SEQ ID NO: 45977, SEQ ID NO: 45983, SEQ ID NO: 45992, SEQ ID NO: 46006, SEQ ID NO: 46012, SEQ ID NO: 46018, SEQ ID NO: 46021, SEQ ID NOs: 46037 to 46038, SEQ ID NO: 46044, SEQ ID NO: 46058, SEQ ID NO: 46071, SEQ ID NO: 46082, SEQ ID NO: 46094, SEQ ID NO: 46096, SEQ ID NO: 46102, SEQ ID NOs: 46108 to 46109, SEQ ID NO: 46122, SEQ ID NO: 46125, SEQ ID NOs: 46133 to 46134, SEQ ID NO: 46146, SEQ ID NO: 46159, SEQ ID NO: 46177, SEQ ID NO: 46182, SEQ ID NO: 46188, SEQ ID NO: 46202, SEQ ID NO: 46219, SEQ ID NO: 46246, SEQ ID NO: 46249, SEQ ID NO: 46270, SEQ ID NO: 46279, SEQ ID NO: 46312, SEQ ID NO: 46339, SEQ ID NO: 46378, SEQ ID NO: 46433, SEQ ID NO: 46442, SEQ ID NO: 46446, SEQ ID NO: 46452, SEQ ID NO: 46454, SEQ ID NO: 46457, SEQ ID NO: 46478, SEQ ID NO: 46484, SEQ ID NO: 46486, SEQ ID NO: 46491, SEQ ID NO: 46506, SEQ ID NO: 46512, SEQ ID NO: 46517, SEQ ID NO: 46530, SEQ ID NO: 46534, SEQ ID NO: 46556, SEQ ID NO: 46560, SEQ ID NO: 46564, SEQ ID NO: 46596, SEQ ID NO: 46602, SEQ ID NO: 46616, SEQ ID NO: 46635, SEQ ID NO: 46656, SEQ ID NO: 46658, SEQ ID NO: 46666, SEQ ID NO: 46676, SEQ ID NO: 46679, SEQ ID NO: 46689, SEQ ID NO: 46705, SEQ ID NO: 46724, SEQ ID NO: 46738, SEQ ID NO: 46767, SEQ ID NO: 46770, SEQ ID NO: 46794, SEQ ID NO: 46810, SEQ ID NO: 46819, SEQ ID NO: 46824, SEQ ID NO: 46831, SEQ ID NO: 46849, SEQ ID NO: 46854, SEQ ID NO: 46870, SEQ ID NO: 46880, SEQ ID NO: 46916, SEQ ID NO: 46935, SEQ ID NO: 46939, SEQ ID NO: 46944, SEQ ID NO: 46958, SEQ ID NO: 46964, SEQ ID NO: 46967, SEQ ID NO: 46978, SEQ ID NO: 46987, SEQ ID NO: 46989, SEQ ID NO: 46991, SEQ ID NO: 46993, SEQ ID NO: 47007, SEQ ID NO: 47034, SEQ ID NO: 47037, SEQ ID NO: 47047, SEQ ID NO: 47057, SEQ ID NO: 47066, SEQ ID NO: 47096, SEQ ID NO: 47098, SEQ ID NO: 47119, SEQ ID NO: 47123, SEQ ID NO: 47137, SEQ ID NO: 47139, SEQ ID NO: 47143, SEQ ID NO: 47150, SEQ ID NO: 47158, SEQ ID NO: 47161, SEQ ID NO: 47170, SEQ ID NO: 47181, SEQ ID NO: 47197, SEQ ID NO: 47209, SEQ ID NO: 47254, SEQ ID NO: 47266, SEQ ID NO: 47272, SEQ ID NO: 47291, SEQ ID NO: 47298, SEQ ID NO: 47300, SEQ ID NO: 47319, SEQ ID NO: 47324, SEQ ID NOs: 47331 to 47332, SEQ ID NO: 47358, SEQ ID NO: 47361, SEQ ID NO: 47393, SEQ ID NO: 47414, SEQ ID NO: 47416, SEQ ID NO: 47422, SEQ ID NO: 47425, SEQ ID NOs: 47432 to 47433, SEQ ID NO: 47445, SEQ ID NO: 47453, SEQ ID NOs: 47460 to 47461, SEQ ID NO: 47477, SEQ ID NO: 47492, SEQ ID NO: 47507, SEQ ID NO: 47509, SEQ ID NO: 47516, SEQ ID NO: 47535, SEQ ID NOs: 47556 to 47557, SEQ ID NOs: 47578 to 47579, SEQ ID NOs: 47591 to 47592, SEQ ID NO: 47597, SEQ ID NO: 47600, SEQ ID NO: 47614, SEQ ID NO: 47626, SEQ ID NO: 47629, SEQ ID NO: 47637, SEQ ID NO: 47639, SEQ ID NO: 47649, SEQ ID NOs: 47689 to 47690, SEQ ID NO: 47713, SEQ ID NO: 47766, SEQ ID NOs: 47814 to 47815, SEQ ID NO: 47827, SEQ ID NO: 47834, SEQ ID NOs: 47852 to 47853, SEQ ID NO: 47855, SEQ ID NO: 47871, SEQ ID NOs: 47875 to 47876, SEQ ID NO: 47891, SEQ ID NO: 47896, SEQ ID NO: 47902, SEQ ID NO: 47923, SEQ ID NO: 47925, SEQ ID NO: 47927, SEQ ID NO: 47929, SEQ ID NO: 47932, SEQ ID NOs: 47962 to 47964, SEQ ID NO: 47972, SEQ ID NO: 47999, SEQ ID NO: 48008, SEQ ID NO: 48028, SEQ ID NOs: 48034 to 48035, SEQ ID NO: 48038, SEQ ID NO: 48056, SEQ ID NO: 48061, SEQ ID NO: 48066, SEQ ID NO: 48118, SEQ ID NO: 48120, SEQ ID NO: 48129, SEQ ID NO: 48140, SEQ ID NO: 48148, SEQ ID NO: 48153, SEQ ID NOs: 48159 to 48160, SEQ ID NO: 48163, SEQ ID NO: 48167, SEQ ID NO: 48178, SEQ ID NO: 48180, SEQ ID NO: 48186, SEQ ID NO: 48218, SEQ ID NO: 48220, SEQ ID NO: 48263, SEQ ID NO: 48286, SEQ ID NO: 48300, SEQ ID NO: 48307, SEQ ID NO: 48315, SEQ ID NO: 48321, SEQ ID NO: 48338, SEQ ID NO: 48341, SEQ ID NO: 48343, SEQ ID NO: 48358, SEQ ID NO: 48362, SEQ ID NO: 48366, SEQ ID NO: 48368, SEQ ID NO: 48418, SEQ ID NO: 48431, SEQ ID NO: 48436, SEQ ID NOs: 48438 to 48439, SEQ ID NOs: 48443 to 48444, SEQ ID NO: 48450, SEQ ID NOs: 48452 to 48453, SEQ ID NO: 48458, SEQ ID NOs: 48461 to 48462, SEQ ID NO: 48507, SEQ ID NO: 48516, SEQ ID NO: 48527, SEQ ID NO: 48537, SEQ ID NO: 48548, SEQ ID NO: 48567, SEQ ID NO: 48574, SEQ ID NO: 48576, SEQ ID NO: 48578, SEQ ID NO: 48594, SEQ ID NO: 48599, SEQ ID NO: 48612, SEQ ID NO: 48614, SEQ ID NO: 48623, SEQ ID NO: 48626, SEQ ID NO: 48630, SEQ ID NO: 48642, SEQ ID NO: 48648, SEQ ID NO: 48656, SEQ ID NOs: 48704 to 48705, SEQ ID NO: 48708, SEQ ID NO: 48739, SEQ ID NO: 48749, SEQ ID NO: 48752, SEQ ID NO: 48754, SEQ ID NO: 48756, SEQ ID NO: 48802, SEQ ID NO: 48832, SEQ ID NO: 48845, SEQ ID NO: 48850, SEQ ID NO: 48852, SEQ ID NO: 48856, SEQ ID NO: 48870, SEQ ID NO: 48888, SEQ ID NO: 48902, SEQ ID NO: 48904, SEQ ID NOs: 48912 to 48913, SEQ ID NO: 48921, SEQ ID NO: 48970, SEQ ID NO: 48974, SEQ ID NO: 48993, SEQ ID NO: 48997, SEQ ID NO: 49004, SEQ ID NO: 49019, SEQ ID NO: 49025, SEQ ID NOs: 49045 to 49046, SEQ ID NO: 49052, SEQ ID NO: 49083, SEQ ID NO: 49086, SEQ ID NOs: 49091 to 49092, SEQ ID NO: 49102, SEQ ID NO: 49106, SEQ ID NO: 49111, SEQ ID NO: 49127, SEQ ID NO: 49152, SEQ ID NO: 49159, SEQ ID NO: 49173, SEQ ID NO: 49197, SEQ ID NO: 49201, SEQ ID NO: 49203, SEQ ID NO: 49207, SEQ ID NO: 49220, SEQ ID NO: 49227, SEQ ID NO: 49230, SEQ ID NO: 49234, SEQ ID NO: 49242, SEQ ID NO: 49256, SEQ ID NO: 49263, SEQ ID NOs: 49273 to 49274, SEQ ID NO: 49278, SEQ ID NO: 49280, SEQ ID NO: 49288, SEQ ID NO: 49290, SEQ ID NOs: 49294 to 49295, SEQ ID NO: 49326, SEQ ID NO: 49362, SEQ ID NOs: 49384 to 49385, SEQ ID NO: 49387, SEQ ID NO: 49393, SEQ ID NO: 49395, SEQ ID NOs: 49427 to 49428, SEQ ID NO: 49444, SEQ ID NO: 49458, SEQ ID NO: 49483, SEQ ID NO: 49487, SEQ ID NO: 49497, SEQ ID NO: 49501, SEQ ID NO: 49517, SEQ ID NO: 49525, SEQ ID NO: 49535, SEQ ID NO: 49537, SEQ ID NO: 49544, SEQ ID NO: 49557, SEQ ID NO: 49569, SEQ ID NO: 49572, SEQ ID NO: 49587, SEQ ID NO: 49594, SEQ ID NO: 49596, SEQ ID NO: 49598, SEQ ID NO: 49606, SEQ ID NO: 49617, SEQ ID NO: 49629, SEQ ID NO: 49646, SEQ ID NO: 49658, SEQ ID NO: 49693, SEQ ID NOs: 49702 to 49703, SEQ ID NO: 49710, SEQ ID NO: 49712, SEQ ID NO: 49719, SEQ ID NO: 49727, SEQ ID NO: 49737, SEQ ID NO: 49740, SEQ ID NO: 49743, SEQ ID NO: 49767, SEQ ID NO: 49778, SEQ ID NO: 49788, SEQ ID NO: 49811, SEQ ID NO: 49848, SEQ ID NO: 49860, SEQ ID NO: 49888, SEQ ID NO: 49908, SEQ ID NO: 49973, SEQ ID NO: 49977, SEQ ID NO: 49980, SEQ ID NOs: 49996 to 49997, SEQ ID NO: 50000, SEQ ID NO: 50012, SEQ ID NOs: 50017 to 50018, SEQ ID NO: 50051, SEQ ID NO: 50056, SEQ ID NO: 50062, SEQ ID NO: 50090, SEQ ID NO: 50093, SEQ ID NO: 50107, SEQ ID NO: 50129, SEQ ID NO: 50132, SEQ ID NO: 50138, SEQ ID NO: 50144, SEQ ID NO: 50167, SEQ ID NO: 50191, SEQ ID NO: 50194, SEQ ID NO: 50196, SEQ ID NO: 50228, SEQ ID NO: 50239, SEQ ID NO: 50263, SEQ ID NO: 50271, SEQ ID NO: 50297, SEQ ID NO: 50305, SEQ ID NO: 50320, SEQ ID NO: 50322, SEQ ID NO: 50326, SEQ ID NO: 50334, SEQ ID NO: 50349, SEQ ID NO: 50375, SEQ ID NO: 50394, SEQ ID NO: 50401, SEQ ID NO: 50414, SEQ ID NO: 50421, SEQ ID NO: 50423, SEQ ID NO: 50435, SEQ ID NOs: 50440 to 50441, SEQ ID NO: 50443, SEQ ID NO: 50510, SEQ ID NO: 50556, SEQ ID NO: 50564, SEQ ID NO: 50591, SEQ ID NO: 50605, SEQ ID NO: 50607, SEQ ID NO: 50611, SEQ ID NO: 50622, SEQ ID NO: 50625, SEQ ID NO: 50627, SEQ ID NO: 50632, SEQ ID NO: 50644, SEQ ID NOs: 50652 to 50653, SEQ ID NOs: 50668 to 50669, SEQ ID NO: 50677, SEQ ID NO: 50696, SEQ ID NO: 50699, SEQ ID NO: 50705, SEQ ID NO: 50709, SEQ ID NO: 50711, SEQ ID NO: 50729, SEQ ID NO: 50731, SEQ ID NO: 50741, SEQ ID NO: 50743, SEQ ID NO: 50748, SEQ ID NO: 50762, SEQ ID NO: 50765, SEQ ID NO: 50767, SEQ ID NO: 50800, SEQ ID NO: 50803, SEQ ID NO: 50807, SEQ ID NO: 50841, SEQ ID NO: 50865, SEQ ID NO: 50872, SEQ ID NO: 50905, SEQ ID NOs: 50955 to 50956, SEQ ID NOs: 50975 to 50977, SEQ ID NO: 50986, SEQ ID NO: 51021, SEQ ID NOs: 51039 to 51040, SEQ ID NOs: 51066 to 51068, SEQ ID NO: 51084, SEQ ID NOs: 51099 to 51100, SEQ ID NOs: 51165 to 51167, SEQ ID NO: 51169, SEQ ID NO: 51190, SEQ ID NOs: 51194 to 51198, SEQ ID NOs: 51267 to 51270, SEQ ID NOs: 51281 to 51282, SEQ ID NO: 51324, SEQ ID NO: 51349, SEQ ID NO: 51379, SEQ ID NOs: 51413 to 51415, SEQ ID NOs: 51420 to 51421, SEQ ID NOs: 51434 to 60455, SEQ ID NOs: 212187 to 212190, SEQ ID NOs: 212668 to 212673, SEQ ID NOs: 212836 to 212837, SEQ ID NOs: 213320 to 213323, SEQ ID NO: 213359, SEQ ID NOs: 213380 to 213382, SEQ ID NOs: 213391 to 213395, SEQ ID NO: 213432, SEQ ID NOs: 214285 to 214290, SEQ ID NOs: 215204 to 215205, SEQ ID NOs: 215677 to 215682, SEQ ID NO: 216240, SEQ ID NO: 216385, SEQ ID NO: 216393, SEQ ID NO: 216397, SEQ ID NOs: 217119 to 217137, SEQ ID NO: 217185, SEQ ID NO: 217187, SEQ ID NO: 217190, SEQ ID NOs: 217659 to 217660, SEQ ID NOs: 219238 to 219245, SEQ ID NOs: 219322 to 219323, SEQ ID NOs: 219380 to 219386, SEQ ID NOs: 219432 to 219446, SEQ ID NOs: 219545 to 219546, SEQ ID NO: 219774, SEQ ID NO: 219777, SEQ ID NO: 220091, SEQ ID NOs: 221996 to 222005, SEQ ID NO: 223185, SEQ ID NO: 223187, SEQ ID NO: 223251, SEQ ID NO: 223253, SEQ ID NO: 223258, SEQ ID NO: 223261, SEQ ID NO: 223264, SEQ ID NO: 223268, SEQ ID NO: 223272, SEQ ID NO: 223274, SEQ ID NO: 223277, and SEQ ID NOs: 223623 to 236015. In some embodiments, any one of the peptides in the MAGA3 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 41351 to 41352, SEQ ID NO: 41383, SEQ ID NO: 41396, SEQ ID NO: 41410, SEQ ID NO: 41414, SEQ ID NO: 41435, SEQ ID NO: 41450, SEQ ID NO: 41463, SEQ ID NO: 41478, SEQ ID NO: 41489, SEQ ID NO: 41495, SEQ ID NO: 41503, SEQ ID NO: 41513, SEQ ID NO: 41520, SEQ ID NO: 41535, SEQ ID NO: 41541, SEQ ID NO: 41545, SEQ ID NO: 41577, SEQ ID NO: 41588, SEQ ID NO: 41598, SEQ ID NO: 41605, SEQ ID NO: 41617, SEQ ID NO: 41620, SEQ ID NO: 41622, SEQ ID NO: 41627, SEQ ID NO: 41630, SEQ ID NO: 41638, SEQ ID NO: 41647, SEQ ID NO: 41673, SEQ ID NO: 41696, SEQ ID NO: 41703, SEQ ID NO: 41708, SEQ ID NO: 41728, SEQ ID NOs: 41732 to 41733, SEQ ID NO: 41749, SEQ ID NO: 41760, SEQ ID NO: 41766, SEQ ID NO: 41770, SEQ ID NO: 41788, SEQ ID NO: 41791, SEQ ID NO: 41809, SEQ ID NO: 41813, SEQ ID NO: 41817, SEQ ID NO: 41829, SEQ ID NOs: 41847 to 41848, SEQ ID NO: 41853, SEQ ID NO: 41859, SEQ ID NO: 41889, SEQ ID NO: 41894, SEQ ID NO: 41897, SEQ ID NO: 41909, SEQ ID NO: 41923, SEQ ID NO: 41934, SEQ ID NO: 41939, SEQ ID NOs: 41953 to 41954, SEQ ID NO: 41959, SEQ ID NO: 41967, SEQ ID NO: 41970, SEQ ID NO: 41976, SEQ ID NOs: 41984 to 41985, SEQ ID NO: 42007, SEQ ID NO: 42017, SEQ ID NO: 42034, SEQ ID NO: 42044, SEQ ID NO: 42046, SEQ ID NO: 42048, SEQ ID NO: 42056, SEQ ID NO: 42067, SEQ ID NO: 42080, SEQ ID NO: 42088, SEQ ID NO: 42091, SEQ ID NOs: 42119 to 42120, SEQ ID NO: 42129, SEQ ID NO: 42135, SEQ ID NOs: 42140 to 42141, SEQ ID NO: 42155, SEQ ID NO: 42158, SEQ ID NO: 42164, SEQ ID NO: 42170, SEQ ID NO: 42174, SEQ ID NO: 42186, SEQ ID NO: 42209, SEQ ID NO: 42218, SEQ ID NO: 42224, SEQ ID NO: 42229, SEQ ID NO: 42232, SEQ ID NO: 42235, SEQ ID NOs: 42237 to 42238, SEQ ID NO: 42265, SEQ ID NO: 42272, SEQ ID NO: 42278, SEQ ID NO: 42293, SEQ ID NO: 42314, SEQ ID NOs: 42336 to 42337, SEQ ID NO: 42339, SEQ ID NOs: 42372 to 42373, SEQ ID NO: 42376, SEQ ID NO: 42382, SEQ ID NO: 42386, SEQ ID NO: 42408, SEQ ID NO: 42414, SEQ ID NO: 42423, SEQ ID NO: 42429, SEQ ID NOs: 42447 to 42448, SEQ ID NO: 42461, SEQ ID NO: 42466, SEQ ID NO: 42475, SEQ ID NO: 42513, SEQ ID NO: 42540, SEQ ID NO: 42545, SEQ ID NO: 42550, SEQ ID NO: 42553, SEQ ID NOs: 42567 to 42568, SEQ ID NO: 42580, SEQ ID NO: 42585, SEQ ID NO: 42605, SEQ ID NO: 42612, SEQ ID NO: 42627, SEQ ID NO: 42675, SEQ ID NO: 42680, SEQ ID NO: 42685, SEQ ID NO: 42690, SEQ ID NO: 42702, SEQ ID NO: 42711, SEQ ID NO: 42719, SEQ ID NO: 42738, SEQ ID NO: 42743, SEQ ID NO: 42750, SEQ ID NO: 42755, SEQ ID NO: 42777, SEQ ID NO: 42788, SEQ ID NO: 42793, SEQ ID NO: 42851, SEQ ID NO: 42858, SEQ ID NO: 42866, SEQ ID NO: 42903, SEQ ID NO: 42927, SEQ ID NOs: 42936 to 42937, SEQ ID NOs: 42940 to 42941, SEQ ID NO: 42957, SEQ ID NO: 42962, SEQ ID NO: 42966, SEQ ID NO: 42968, SEQ ID NO: 42986, SEQ ID NO: 43002, SEQ ID NO: 43013, SEQ ID NO: 43037, SEQ ID NO: 43052, SEQ ID NOs: 43055 to 43056, SEQ ID NOs: 43063 to 43064, SEQ ID NO: 43096, SEQ ID NO: 43133, SEQ ID NO: 43138, SEQ ID NO: 43156, SEQ ID NO: 43161, SEQ ID NO: 43186, SEQ ID NO: 43199, SEQ ID NO: 43205, SEQ ID NO: 43245, SEQ ID NO: 43251, SEQ ID NO: 43275, SEQ ID NO: 43312, SEQ ID NO: 43327, SEQ ID NO: 43333, SEQ ID NO: 43339, SEQ ID NO: 43342, SEQ ID NO: 43348, SEQ ID NO: 43365, SEQ ID NO: 43371, SEQ ID NO: 43400, SEQ ID NO: 43440, SEQ ID NO: 43451, SEQ ID NO: 43462, SEQ ID NO: 43467, SEQ ID NO: 43487, SEQ ID NOs: 43498 to 43499, SEQ ID NO: 43507, SEQ ID NO: 43522, SEQ ID NO: 43529, SEQ ID NO: 43533, SEQ ID NO: 43545, SEQ ID NO: 43558, SEQ ID NO: 43560, SEQ ID NO: 43583, SEQ ID NO: 43597, SEQ ID NO: 43599, SEQ ID NO: 43610, SEQ ID NO: 43614, SEQ ID NO: 43627, SEQ ID NO: 43697, SEQ ID NO: 43715, SEQ ID NO: 43718, SEQ ID NO: 43768, SEQ ID NO: 43777, SEQ ID NOs: 43825 to 43826, SEQ ID NO: 43836, SEQ ID NO: 43840, SEQ ID NO: 43856, SEQ ID NO: 43860, SEQ ID NO: 43870, SEQ ID NO: 43878, SEQ ID NOs: 43881 to 43882, SEQ ID NO: 43905, SEQ ID NO: 43922, SEQ ID NO: 43930, SEQ ID NO: 43943, SEQ ID NO: 43953, SEQ ID NO: 43958, SEQ ID NO: 43979, SEQ ID NO: 43986, SEQ ID NO: 44002, SEQ ID NO: 44033, SEQ ID NO: 44037, SEQ ID NO: 44048, SEQ ID NO: 44050, SEQ ID NO: 44052, SEQ ID NOs: 44080 to 44081, SEQ ID NOs: 44093 to 44094, SEQ ID NOs: 44114 to 44115, SEQ ID NO: 44120, SEQ ID NO: 44142, SEQ ID NO: 44152, SEQ ID NOs: 44164 to 44166, SEQ ID NO: 44181, SEQ ID NO: 44222, SEQ ID NO: 44244, SEQ ID NO: 44246, SEQ ID NO: 44255, SEQ ID NO: 44261, SEQ ID NO: 44276, SEQ ID NOs: 44286 to 44287, SEQ ID NO: 44296, SEQ ID NO: 44315, SEQ ID NO: 44322, SEQ ID NO: 44324, SEQ ID NO: 44328, SEQ ID NO: 44332, SEQ ID NO: 44339, SEQ ID NO: 44401, SEQ ID NO: 44413, SEQ ID NO: 44435, SEQ ID NO: 44452, SEQ ID NO: 44454, SEQ ID NO: 44463, SEQ ID NO: 44467, SEQ ID NO: 44485, SEQ ID NO: 44504, SEQ ID NO: 44512, SEQ ID NO: 44523, SEQ ID NOs: 44526 to 44527, SEQ ID NO: 44536, SEQ ID NO: 44564, SEQ ID NO: 44605, SEQ ID NO: 44607, SEQ ID NO: 44612, SEQ ID NO: 44629, SEQ ID NOs: 44635 to 44636, SEQ ID NO: 44647, SEQ ID NO: 44650, SEQ ID NO: 44674, SEQ ID NO: 44691, SEQ ID NO: 44696, SEQ ID NO: 44702, SEQ ID NO: 44710, SEQ ID NO: 44713, SEQ ID NO: 44715, SEQ ID NO: 44722, SEQ ID NO: 44730, SEQ ID NO: 44733, SEQ ID NO: 44755, SEQ ID NO: 44770, SEQ ID NO: 44773, SEQ ID NO: 44781, SEQ ID NO: 44783, SEQ ID NO: 44797, SEQ ID NO: 44805, SEQ ID NO: 44822, SEQ ID NO: 44828, SEQ ID NO: 44830, SEQ ID NO: 44832, SEQ ID NO: 44850, SEQ ID NO: 44852, SEQ ID NO: 44854, SEQ ID NO: 44860, SEQ ID NO: 44866, SEQ ID NO: 44898, SEQ ID NO: 44900, SEQ ID NO: 44907, SEQ ID NO: 44933, SEQ ID NO: 44947, SEQ ID NO: 44986, SEQ ID NO: 45003, SEQ ID NO: 45007, SEQ ID NO: 45009, SEQ ID NO: 45012, SEQ ID NO: 45016, SEQ ID NO: 45018, SEQ ID NO: 45027, SEQ ID NO: 45031, SEQ ID NO: 45036, SEQ ID NO: 45044, SEQ ID NO: 45060, SEQ ID NO: 45071, SEQ ID NO: 45077, SEQ ID NO: 45095, SEQ ID NO: 45126, SEQ ID NO: 45132, SEQ ID NO: 45135, SEQ ID NO: 45139, SEQ ID NO: 45143, SEQ ID NO: 45159, SEQ ID NO: 45177, SEQ ID NO: 45197, SEQ ID NO: 45200, SEQ ID NO: 45219, SEQ ID NO: 45228, SEQ ID NO: 45323, SEQ ID NO: 45329, SEQ ID NO: 45351, SEQ ID NO: 45378, SEQ ID NO: 45380, SEQ ID NO: 45389, SEQ ID NO: 45413, SEQ ID NO: 45417, SEQ ID NO: 45438, SEQ ID NO: 45455, SEQ ID NO: 45457, SEQ ID NO: 45467, SEQ ID NO: 45478, SEQ ID NO: 45530, SEQ ID NO: 45562, SEQ ID NO: 45565, SEQ ID NOs: 45583 to 45584, SEQ ID NOs: 45595 to 45596, SEQ ID NO: 45608, SEQ ID NO: 45612, SEQ ID NO: 45616, SEQ ID NO: 45627, SEQ ID NO: 45653, SEQ ID NOs: 45666 to 45667, SEQ ID NO: 45680, SEQ ID NO: 45697, SEQ ID NO: 45705, SEQ ID NO: 45710, SEQ ID NO: 45722, SEQ ID NO: 45736, SEQ ID NO: 45742, SEQ ID NO: 45746, SEQ ID NO: 45765, SEQ ID NO: 45808, SEQ ID NO: 45830, SEQ ID NOs: 45840 to 45841, SEQ ID NO: 45896, SEQ ID NOs: 45904 to 45905, SEQ ID NO: 45913, SEQ ID NO: 45915, SEQ ID NOs: 45940 to 45943, SEQ ID NO: 45945, SEQ ID NOs: 45958 to 45959, SEQ ID NO: 45977, SEQ ID NO: 45983, SEQ ID NO: 45992, SEQ ID NO: 46006, SEQ ID NO: 46012, SEQ ID NO: 46018, SEQ ID NO: 46021, SEQ ID NOs: 46037 to 46038, SEQ ID NO: 46044, SEQ ID NO: 46058, SEQ ID NO: 46071, SEQ ID NO: 46082, SEQ ID NO: 46094, SEQ ID NO: 46096, SEQ ID NO: 46102, SEQ ID NOs: 46108 to 46109, SEQ ID NO: 46122, SEQ ID NO: 46125, SEQ ID NOs: 46133 to 46134, SEQ ID NO: 46146, SEQ ID NO: 46159, SEQ ID NO: 46177, SEQ ID NO: 46182, SEQ ID NO: 46188, SEQ ID NO: 46202, SEQ ID NO: 46219, SEQ ID NO: 46246, SEQ ID NO: 46249, SEQ ID NO: 46270, SEQ ID NO: 46279, SEQ ID NO: 46312, SEQ ID NO: 46339, SEQ ID NO: 46378, SEQ ID NO: 46433, SEQ ID NO: 46442, SEQ ID NO: 46446, SEQ ID NO: 46452, SEQ ID NO: 46454, SEQ ID NO: 46457, SEQ ID NO: 46478, SEQ ID NO: 46484, SEQ ID NO: 46486, SEQ ID NO: 46491, SEQ ID NO: 46506, SEQ ID NO: 46512, SEQ ID NO: 46517, SEQ ID NO: 46530, SEQ ID NO: 46534, SEQ ID NO: 46556, SEQ ID NO: 46560, SEQ ID NO: 46564, SEQ ID NO: 46596, SEQ ID NO: 46602, SEQ ID NO: 46616, SEQ ID NO: 46635, SEQ ID NO: 46656, SEQ ID NO: 46658, SEQ ID NO: 46666, SEQ ID NO: 46676, SEQ ID NO: 46679, SEQ ID NO: 46689, SEQ ID NO: 46705, SEQ ID NO: 46724, SEQ ID NO: 46738, SEQ ID NO: 46767, SEQ ID NO: 46770, SEQ ID NO: 46794, SEQ ID NO: 46810, SEQ ID NO: 46819, SEQ ID NO: 46824, SEQ ID NO: 46831, SEQ ID NO: 46849, SEQ ID NO: 46854, SEQ ID NO: 46870, SEQ ID NO: 46880, SEQ ID NO: 46916, SEQ ID NO: 46935, SEQ ID NO: 46939, SEQ ID NO: 46944, SEQ ID NO: 46958, SEQ ID NO: 46964, SEQ ID NO: 46967, SEQ ID NO: 46978, SEQ ID NO: 46987, SEQ ID NO: 46989, SEQ ID NO: 46991, SEQ ID NO: 46993, SEQ ID NO: 47007, SEQ ID NO: 47034, SEQ ID NO: 47037, SEQ ID NO: 47047, SEQ ID NO: 47057, SEQ ID NO: 47066, SEQ ID NO: 47096, SEQ ID NO: 47098, SEQ ID NO: 47119, SEQ ID NO: 47123, SEQ ID NO: 47137, SEQ ID NO: 47139, SEQ ID NO: 47143, SEQ ID NO: 47150, SEQ ID NO: 47158, SEQ ID NO: 47161, SEQ ID NO: 47170, SEQ ID NO: 47181, SEQ ID NO: 47197, SEQ ID NO: 47209, SEQ ID NO: 47254, SEQ ID NO: 47266, SEQ ID NO: 47272, SEQ ID NO: 47291, SEQ ID NO: 47298, SEQ ID NO: 47300, SEQ ID NO: 47319, SEQ ID NO: 47324, SEQ ID NOs: 47331 to 47332, SEQ ID NO: 47358, SEQ ID NO: 47361, SEQ ID NO: 47393, SEQ ID NO: 47414, SEQ ID NO: 47416, SEQ ID NO: 47422, SEQ ID NO: 47425, SEQ ID NOs: 47432 to 47433, SEQ ID NO: 47445, SEQ ID NO: 47453, SEQ ID NOs: 47460 to 47461, SEQ ID NO: 47477, SEQ ID NO: 47492, SEQ ID NO: 47507, SEQ ID NO: 47509, SEQ ID NO: 47516, SEQ ID NO: 47535, SEQ ID NOs: 47556 to 47557, SEQ ID NOs: 47578 to 47579, SEQ ID NOs: 47591 to 47592, SEQ ID NO: 47597, SEQ ID NO: 47600, SEQ ID NO: 47614, SEQ ID NO: 47626, SEQ ID NO: 47629, SEQ ID NO: 47637, SEQ ID NO: 47639, SEQ ID NO: 47649, SEQ ID NOs: 47689 to 47690, SEQ ID NO: 47713, SEQ ID NO: 47766, SEQ ID NOs: 47814 to 47815, SEQ ID NO: 47827, SEQ ID NO: 47834, SEQ ID NOs: 47852 to 47853, SEQ ID NO: 47855, SEQ ID NO: 47871, SEQ ID NOs: 47875 to 47876, SEQ ID NO: 47891, SEQ ID NO: 47896, SEQ ID NO: 47902, SEQ ID NO: 47923, SEQ ID NO: 47925, SEQ ID NO: 47927, SEQ ID NO: 47929, SEQ ID NO: 47932, SEQ ID NOs: 47962 to 47964, SEQ ID NO: 47972, SEQ ID NO: 47999, SEQ ID NO: 48008, SEQ ID NO: 48028, SEQ ID NOs: 48034 to 48035, SEQ ID NO: 48038, SEQ ID NO: 48056, SEQ ID NO: 48061, SEQ ID NO: 48066, SEQ ID NO: 48118, SEQ ID NO: 48120, SEQ ID NO: 48129, SEQ ID NO: 48140, SEQ ID NO: 48148, SEQ ID NO: 48153, SEQ ID NOs: 48159 to 48160, SEQ ID NO: 48163, SEQ ID NO: 48167, SEQ ID NO: 48178, SEQ ID NO: 48180, SEQ ID NO: 48186, SEQ ID NO: 48218, SEQ ID NO: 48220, SEQ ID NO: 48263, SEQ ID NO: 48286, SEQ ID NO: 48300, SEQ ID NO: 48307, SEQ ID NO: 48315, SEQ ID NO: 48321, SEQ ID NO: 48338, SEQ ID NO: 48341, SEQ ID NO: 48343, SEQ ID NO: 48358, SEQ ID NO: 48362, SEQ ID NO: 48366, SEQ ID NO: 48368, SEQ ID NO: 48418, SEQ ID NO: 48431, SEQ ID NO: 48436, SEQ ID NOs: 48438 to 48439, SEQ ID NOs: 48443 to 48444, SEQ ID NO: 48450, SEQ ID NOs: 48452 to 48453, SEQ ID NO: 48458, SEQ ID NOs: 48461 to 48462, SEQ ID NO: 48507, SEQ ID NO: 48516, SEQ ID NO: 48527, SEQ ID NO: 48537, SEQ ID NO: 48548, SEQ ID NO: 48567, SEQ ID NO: 48574, SEQ ID NO: 48576, SEQ ID NO: 48578, SEQ ID NO: 48594, SEQ ID NO: 48599, SEQ ID NO: 48612, SEQ ID NO: 48614, SEQ ID NO: 48623, SEQ ID NO: 48626, SEQ ID NO: 48630, SEQ ID NO: 48642, SEQ ID NO: 48648, SEQ ID NO: 48656, SEQ ID NOs: 48704 to 48705, SEQ ID NO: 48708, SEQ ID NO: 48739, SEQ ID NO: 48749, SEQ ID NO: 48752, SEQ ID NO: 48754, SEQ ID NO: 48756, SEQ ID NO: 48802, SEQ ID NO: 48832, SEQ ID NO: 48845, SEQ ID NO: 48850, SEQ ID NO: 48852, SEQ ID NO: 48856, SEQ ID NO: 48870, SEQ ID NO: 48888, SEQ ID NO: 48902, SEQ ID NO: 48904, SEQ ID NOs: 48912 to 48913, SEQ ID NO: 48921, SEQ ID NO: 48970, SEQ ID NO: 48974, SEQ ID NO: 48993, SEQ ID NO: 48997, SEQ ID NO: 49004, SEQ ID NO: 49019, SEQ ID NO: 49025, SEQ ID NOs: 49045 to 49046, SEQ ID NO: 49052, SEQ ID NO: 49083, SEQ ID NO: 49086, SEQ ID NOs: 49091 to 49092, SEQ ID NO: 49102, SEQ ID NO: 49106, SEQ ID NO: 49111, SEQ ID NO: 49127, SEQ ID NO: 49152, SEQ ID NO: 49159, SEQ ID NO: 49173, SEQ ID NO: 49197, SEQ ID NO: 49201, SEQ ID NO: 49203, SEQ ID NO: 49207, SEQ ID NO: 49220, SEQ ID NO: 49227, SEQ ID NO: 49230, SEQ ID NO: 49234, SEQ ID NO: 49242, SEQ ID NO: 49256, SEQ ID NO: 49263, SEQ ID NOs: 49273 to 49274, SEQ ID NO: 49278, SEQ ID NO: 49280, SEQ ID NO: 49288, SEQ ID NO: 49290, SEQ ID NOs: 49294 to 49295, SEQ ID NO: 49326, SEQ ID NO: 49362, SEQ ID NOs: 49384 to 49385, SEQ ID NO: 49387, SEQ ID NO: 49393, SEQ ID NO: 49395, SEQ ID NOs: 49427 to 49428, SEQ ID NO: 49444, SEQ ID NO: 49458, SEQ ID NO: 49483, SEQ ID NO: 49487, SEQ ID NO: 49497, SEQ ID NO: 49501, SEQ ID NO: 49517, SEQ ID NO: 49525, SEQ ID NO: 49535, SEQ ID NO: 49537, SEQ ID NO: 49544, SEQ ID NO: 49557, SEQ ID NO: 49569, SEQ ID NO: 49572, SEQ ID NO: 49587, SEQ ID NO: 49594, SEQ ID NO: 49596, SEQ ID NO: 49598, SEQ ID NO: 49606, SEQ ID NO: 49617, SEQ ID NO: 49629, SEQ ID NO: 49646, SEQ ID NO: 49658, SEQ ID NO: 49693, SEQ ID NOs: 49702 to 49703, SEQ ID NO: 49710, SEQ ID NO: 49712, SEQ ID NO: 49719, SEQ ID NO: 49727, SEQ ID NO: 49737, SEQ ID NO: 49740, SEQ ID NO: 49743, SEQ ID NO: 49767, SEQ ID NO: 49778, SEQ ID NO: 49788, SEQ ID NO: 49811, SEQ ID NO: 49848, SEQ ID NO: 49860, SEQ ID NO: 49888, SEQ ID NO: 49908, SEQ ID NO: 49973, SEQ ID NO: 49977, SEQ ID NO: 49980, SEQ ID NOs: 49996 to 49997, SEQ ID NO: 50000, SEQ ID NO: 50012, SEQ ID NOs: 50017 to 50018, SEQ ID NO: 50051, SEQ ID NO: 50056, SEQ ID NO: 50062, SEQ ID NO: 50090, SEQ ID NO: 50093, SEQ ID NO: 50107, SEQ ID NO: 50129, SEQ ID NO: 50132, SEQ ID NO: 50138, SEQ ID NO: 50144, SEQ ID NO: 50167, SEQ ID NO: 50191, SEQ ID NO: 50194, SEQ ID NO: 50196, SEQ ID NO: 50228, SEQ ID NO: 50239, SEQ ID NO: 50263, SEQ ID NO: 50271, SEQ ID NO: 50297, SEQ ID NO: 50305, SEQ ID NO: 50320, SEQ ID NO: 50322, SEQ ID NO: 50326, SEQ ID NO: 50334, SEQ ID NO: 50349, SEQ ID NO: 50375, SEQ ID NO: 50394, SEQ ID NO: 50401, SEQ ID NO: 50414, SEQ ID NO: 50421, SEQ ID NO: 50423, SEQ ID NO: 50435, SEQ ID NOs: 50440 to 50441, SEQ ID NO: 50443, SEQ ID NO: 50510, SEQ ID NO: 50556, SEQ ID NO: 50564, SEQ ID NO: 50591, SEQ ID NO: 50605, SEQ ID NO: 50607, SEQ ID NO: 50611, SEQ ID NO: 50622, SEQ ID NO: 50625, SEQ ID NO: 50627, SEQ ID NO: 50632, SEQ ID NO: 50644, SEQ ID NOs: 50652 to 50653, SEQ ID NOs: 50668 to 50669, SEQ ID NO: 50677, SEQ ID NO: 50696, SEQ ID NO: 50699, SEQ ID NO: 50705, SEQ ID NO: 50709, SEQ ID NO: 50711, SEQ ID NO: 50729, SEQ ID NO: 50731, SEQ ID NO: 50741, SEQ ID NO: 50743, SEQ ID NO: 50748, SEQ ID NO: 50762, SEQ ID NO: 50765, SEQ ID NO: 50767, SEQ ID NO: 50800, SEQ ID NO: 50803, SEQ ID NO: 50807, SEQ ID NO: 50841, SEQ ID NO: 50865, SEQ ID NO: 50872, SEQ ID NO: 50905, SEQ ID NOs: 50955 to 50956, SEQ ID NOs: 50975 to 50977, SEQ ID NO: 50986, SEQ ID NO: 51021, SEQ ID NOs: 51039 to 51040, SEQ ID NOs: 51066 to 51068, SEQ ID NO: 51084, SEQ ID NOs: 51099 to 51100, SEQ ID NOs: 51165 to 51167, SEQ ID NO: 51169, SEQ ID NO: 51190, SEQ ID NOs: 51194 to 51198, SEQ ID NOs: 51267 to 51270, SEQ ID NOs: 51281 to 51282, SEQ ID NO: 51324, SEQ ID NO: 51349, SEQ ID NO: 51379, SEQ ID NOs: 51413 to 51415, SEQ ID NOs: 51420 to 51421, SEQ ID NOs: 51434 to 60455, SEQ ID NOs: 212187 to 212190, SEQ ID NOs: 212668 to 212673, SEQ ID NOs: 212836 to 212837, SEQ ID NOs: 213320 to 213323, SEQ ID NO: 213359, SEQ ID NOs: 213380 to 213382, SEQ ID NOs: 213391 to 213395, SEQ ID NO: 213432, SEQ ID NOs: 214285 to 214290, SEQ ID NOs: 215204 to 215205, SEQ ID NOs: 215677 to 215682, SEQ ID NO: 216240, SEQ ID NO: 216385, SEQ ID NO: 216393, SEQ ID NO: 216397, SEQ ID NOs: 217119 to 217137, SEQ ID NO: 217185, SEQ ID NO: 217187, SEQ ID NO: 217190, SEQ ID NOs: 217659 to 217660, SEQ ID NOs: 219238 to 219245, SEQ ID NOs: 219322 to 219323, SEQ ID NOs: 219380 to 219386, SEQ ID NOs: 219432 to 219446, SEQ ID NOs: 219545 to 219546, SEQ ID NO: 219774, SEQ ID NO: 219777, SEQ ID NO: 220091, SEQ ID NOs: 221996 to 222005, SEQ ID NO: 223185, SEQ ID NO: 223187, SEQ ID NO: 223251, SEQ ID NO: 223253, SEQ ID NO: 223258, SEQ ID NO: 223261, SEQ ID NO: 223264, SEQ ID NO: 223268, SEQ ID NO: 223272, SEQ ID NO: 223274, SEQ ID NO: 223277, or SEQ ID NOs: 223623 to 236015.

In some embodiments, the amino acid sequence for a MHC class I and/or MHC class II peptides may be used to create a single target (individual) or combined peptide vaccine for the MAGA4 protein having between about 2 and about 40 peptides. In some embodiments, any one of the peptides in the vaccine for the MAGA4 protein comprises one or more of the SEQ ID NO: 41345, SEQ ID NO: 41347, SEQ ID NO: 41352, SEQ ID NOs: 41357 to 41358, SEQ ID NO: 41366, SEQ ID NO: 41377, SEQ ID NO: 41382, SEQ ID NO: 41392, SEQ ID NO: 41396, SEQ ID NO: 41398, SEQ ID NO: 41406, SEQ ID NO: 41411, SEQ ID NO: 41414, SEQ ID NO: 41433, SEQ ID NO: 41436, SEQ ID NO: 41445, SEQ ID NO: 41449, SEQ ID NO: 41455, SEQ ID NO: 41478, SEQ ID NO: 41487, SEQ ID NOs: 41495 to 41496, SEQ ID NO: 41503, SEQ ID NO: 41515, SEQ ID NO: 41520, SEQ ID NO: 41529, SEQ ID NO: 41549, SEQ ID NO: 41553, SEQ ID NO: 41562, SEQ ID NO: 41569, SEQ ID NO: 41574, SEQ ID NO: 41576, SEQ ID NO: 41579, SEQ ID NOs: 41587 to 41588, SEQ ID NO: 41605, SEQ ID NO: 41617, SEQ ID NO: 41620, SEQ ID NO: 41634, SEQ ID NO: 41650, SEQ ID NO: 41665, SEQ ID NO: 41670, SEQ ID NO: 41672, SEQ ID NO: 41696, SEQ ID NO: 41703, SEQ ID NO: 41709, SEQ ID NO: 41725, SEQ ID NOs: 41732 to 41733, SEQ ID NO: 41748, SEQ ID NO: 41760, SEQ ID NO: 41766, SEQ ID NO: 41768, SEQ ID NO: 41770, SEQ ID NO: 41779, SEQ ID NO: 41791, SEQ ID NO: 41797, SEQ ID NO: 41813, SEQ ID NO: 41819, SEQ ID NO: 41825, SEQ ID NO: 41829, SEQ ID NOs: 41846 to 41847, SEQ ID NO: 41853, SEQ ID NO: 41876, SEQ ID NO: 41889, SEQ ID NO: 41892, SEQ ID NO: 41897, SEQ ID NOs: 41906 to 41907, SEQ ID NO: 41912, SEQ ID NO: 41924, SEQ ID NO: 41940, SEQ ID NO: 41953, SEQ ID NO: 41956, SEQ ID NO: 41967, SEQ ID NO: 41970, SEQ ID NO: 41976, SEQ ID NO: 41985, SEQ ID NO: 41990, SEQ ID NO: 42014, SEQ ID NO: 42017, SEQ ID NO: 42026, SEQ ID NO: 42034, SEQ ID NO: 42037, SEQ ID NO: 42046, SEQ ID NO: 42048, SEQ ID NOs: 42056 to 42057, SEQ ID NO: 42080, SEQ ID NO: 42088, SEQ ID NO: 42091, SEQ ID NO: 42102, SEQ ID NO: 42106, SEQ ID NO: 42115, SEQ ID NO: 42120, SEQ ID NO: 42129, SEQ ID NO: 42135, SEQ ID NO: 42138, SEQ ID NO: 42151, SEQ ID NO: 42158, SEQ ID NOs: 42163 to 42164, SEQ ID NOs: 42167 to 42168, SEQ ID NO: 42170, SEQ ID NO: 42186, SEQ ID NO: 42192, SEQ ID NO: 42195, SEQ ID NO: 42198, SEQ ID NO: 42204, SEQ ID NO: 42209, SEQ ID NO: 42218, SEQ ID NO: 42221, SEQ ID NO: 42224, SEQ ID NO: 42229, SEQ ID NO: 42240, SEQ ID NO: 42263, SEQ ID NO: 42265, SEQ ID NO: 42270, SEQ ID NO: 42316, SEQ ID NOs: 42336 to 42337, SEQ ID NO: 42339, SEQ ID NO: 42351, SEQ ID NO: 42354, SEQ ID NO: 42372, SEQ ID NO: 42378, SEQ ID NOs: 42385 to 42386, SEQ ID NO: 42394, SEQ ID NO: 42405, SEQ ID NO: 42409, SEQ ID NO: 42417, SEQ ID NO: 42423, SEQ ID NO: 42439, SEQ ID NO: 42447, SEQ ID NO: 42453, SEQ ID NO: 42458, SEQ ID NOs: 42460 to 42461, SEQ ID NO: 42466, SEQ ID NOs: 42472 to 42473, SEQ ID NOs: 42519 to 42520, SEQ ID NO: 42525, SEQ ID NO: 42528, SEQ ID NO: 42540, SEQ ID NO: 42545, SEQ ID NO: 42550, SEQ ID NOs: 42563 to 42564, SEQ ID NO: 42580, SEQ ID NO: 42605, SEQ ID NO: 42609, SEQ ID NOs: 42612 to 42613, SEQ ID NO: 42615, SEQ ID NO: 42628, SEQ ID NO: 42637, SEQ ID NO: 42648, SEQ ID NO: 42653, SEQ ID NO: 42675, SEQ ID NO: 42680, SEQ ID NO: 42685, SEQ ID NO: 42696, SEQ ID NO: 42703, SEQ ID NO: 42719, SEQ ID NO: 42735, SEQ ID NO: 42743, SEQ ID NO: 42748, SEQ ID NO: 42750, SEQ ID NO: 42768, SEQ ID NO: 42812, SEQ ID NO: 42814, SEQ ID NO: 42822, SEQ ID NO: 42827, SEQ ID NO: 42831, SEQ ID NO: 42846, SEQ ID NO: 42850, SEQ ID NO: 42872, SEQ ID NO: 42886, SEQ ID NO: 42911, SEQ ID NO: 42914, SEQ ID NO: 42923, SEQ ID NO: 42927, SEQ ID NOs: 42957 to 42958, SEQ ID NO: 42962, SEQ ID NO: 42971, SEQ ID NOs: 42997 to 42998, SEQ ID NO: 43002, SEQ ID NO: 43008, SEQ ID NO: 43035, SEQ ID NO: 43046, SEQ ID NO: 43048, SEQ ID NO: 43064, SEQ ID NO: 43083, SEQ ID NO: 43091, SEQ ID NO: 43093, SEQ ID NO: 43148, SEQ ID NO: 43160, SEQ ID NO: 43170, SEQ ID NO: 43175, SEQ ID NO: 43180, SEQ ID NO: 43186, SEQ ID NO: 43193, SEQ ID NO: 43196, SEQ ID NOs: 43231 to 43232, SEQ ID NO: 43238, SEQ ID NO: 43242, SEQ ID NO: 43248, SEQ ID NO: 43253, SEQ ID NO: 43258, SEQ ID NO: 43267, SEQ ID NO: 43274, SEQ ID NO: 43280, SEQ ID NO: 43285, SEQ ID NO: 43295, SEQ ID NO: 43308, SEQ ID NO: 43311, SEQ ID NO: 43329, SEQ ID NO: 43333, SEQ ID NOs: 43339 to 43340, SEQ ID NO: 43362, SEQ ID NO: 43365, SEQ ID NO: 43384, SEQ ID NO: 43389, SEQ ID NO: 43395, SEQ ID NO: 43401, SEQ ID NO: 43429, SEQ ID NO: 43432, SEQ ID NO: 43440, SEQ ID NOs: 43451 to 43453, SEQ ID NO: 43462, SEQ ID NO: 43464, SEQ ID NO: 43467, SEQ ID NO: 43479, SEQ ID NO: 43482, SEQ ID NO: 43496, SEQ ID NO: 43511, SEQ ID NO: 43513, SEQ ID NO: 43517, SEQ ID NO: 43545, SEQ ID NO: 43564, SEQ ID NO: 43573, SEQ ID NO: 43585, SEQ ID NO: 43587, SEQ ID NO: 43591, SEQ ID NO: 43611, SEQ ID NO: 43632, SEQ ID NO: 43636, SEQ ID NO: 43641, SEQ ID NO: 43643, SEQ ID NO: 43651, SEQ ID NO: 43669, SEQ ID NO: 43688, SEQ ID NO: 43696, SEQ ID NO: 43700, SEQ ID NO: 43703, SEQ ID NO: 43707, SEQ ID NO: 43718, SEQ ID NO: 43760, SEQ ID NO: 43763, SEQ ID NO: 43768, SEQ ID NO: 43777, SEQ ID NO: 43780, SEQ ID NO: 43787, SEQ ID NO: 43801, SEQ ID NO: 43808, SEQ ID NO: 43810, SEQ ID NO: 43825, SEQ ID NO: 43827, SEQ ID NO: 43836, SEQ ID NO: 43860, SEQ ID NO: 43867, SEQ ID NOs: 43881 to 43882, SEQ ID NO: 43884, SEQ ID NO: 43887, SEQ ID NOs: 43898 to 43899, SEQ ID NO: 43905, SEQ ID NO: 43915, SEQ ID NO: 43924, SEQ ID NO: 43932, SEQ ID NO: 43958, SEQ ID NO: 43971, SEQ ID NO: 43974, SEQ ID NO: 43978, SEQ ID NOs: 43982 to 43984, SEQ ID NOs: 43986 to 43987, SEQ ID NO: 43993, SEQ ID NO: 43995, SEQ ID NO: 44012, SEQ ID NO: 44035, SEQ ID NO: 44037, SEQ ID NO: 44048, SEQ ID NO: 44050, SEQ ID NO: 44052, SEQ ID NO: 44055, SEQ ID NO: 44063, SEQ ID NO: 44073, SEQ ID NO: 44080, SEQ ID NO: 44085, SEQ ID NO: 44087, SEQ ID NO: 44089, SEQ ID NO: 44112, SEQ ID NO: 44117, SEQ ID NO: 44123, SEQ ID NOs: 44151 to 44152, SEQ ID NO: 44160, SEQ ID NO: 44181, SEQ ID NO: 44207, SEQ ID NO: 44210, SEQ ID NO: 44244, SEQ ID NO: 44246, SEQ ID NO: 44254, SEQ ID NO: 44263, SEQ ID NOs: 44298 to 44299, SEQ ID NO: 44309, SEQ ID NO: 44324, SEQ ID NO: 44328, SEQ ID NO: 44342, SEQ ID NO: 44345, SEQ ID NO: 44359, SEQ ID NO: 44361, SEQ ID NO: 44383, SEQ ID NO: 44401, SEQ ID NO: 44422, SEQ ID NO: 44440, SEQ ID NO: 44452, SEQ ID NO: 44454, SEQ ID NO: 44456, SEQ ID NO: 44463, SEQ ID NO: 44467, SEQ ID NO: 44485, SEQ ID NO: 44512, SEQ ID NO: 44523, SEQ ID NO: 44545, SEQ ID NO: 44552, SEQ ID NO: 44564, SEQ ID NOs: 44566 to 44567, SEQ ID NOs: 44589 to 44591, SEQ ID NO: 44615, SEQ ID NO: 44623, SEQ ID NO: 44631, SEQ ID NO: 44636, SEQ ID NO: 44649, SEQ ID NO: 44654, SEQ ID NO: 44691, SEQ ID NO: 44713, SEQ ID NO: 44722, SEQ ID NO: 44730, SEQ ID NO: 44754, SEQ ID NO: 44756, SEQ ID NOs: 44762 to 44763, SEQ ID NO: 44773, SEQ ID NO: 44781, SEQ ID NO: 44794, SEQ ID NO: 44850, SEQ ID NOs: 44873 to 44875, SEQ ID NO: 44877, SEQ ID NO: 44884, SEQ ID NO: 44908, SEQ ID NO: 44913, SEQ ID NO: 44940, SEQ ID NO: 44955, SEQ ID NO: 44964, SEQ ID NO: 44971, SEQ ID NO: 44976, SEQ ID NO: 45000, SEQ ID NO: 45027, SEQ ID NO: 45035, SEQ ID NO: 45060, SEQ ID NO: 45062, SEQ ID NO: 45095, SEQ ID NO: 45123, SEQ ID NOs: 45126 to 45127, SEQ ID NO: 45132, SEQ ID NO: 45135, SEQ ID NOs: 45138 to 45139, SEQ ID NO: 45193, SEQ ID NO: 45197, SEQ ID NO: 45200, SEQ ID NO: 45223, SEQ ID NO: 45225, SEQ ID NO: 45244, SEQ ID NO: 45262, SEQ ID NO: 45273, SEQ ID NO: 45292, SEQ ID NO: 45302, SEQ ID NO: 45306, SEQ ID NO: 45314, SEQ ID NO: 45380, SEQ ID NO: 45385, SEQ ID NO: 45389, SEQ ID NO: 45398, SEQ ID NO: 45409, SEQ ID NO: 45438, SEQ ID NO: 45444, SEQ ID NOs: 45450 to 45451, SEQ ID NO: 45478, SEQ ID NO: 45480, SEQ ID NO: 45485, SEQ ID NO: 45490, SEQ ID NO: 45510, SEQ ID NO: 45514, SEQ ID NOs: 45519 to 45520, SEQ ID NO: 45530, SEQ ID NO: 45541, SEQ ID NO: 45552, SEQ ID NO: 45556, SEQ ID NOs: 45562 to 45563, SEQ ID NO: 45568, SEQ ID NO: 45577, SEQ ID NOs: 45580 to 45581, SEQ ID NO: 45584, SEQ ID NO: 45588, SEQ ID NO: 45595, SEQ ID NO: 45599, SEQ ID NO: 45632, SEQ ID NO: 45653, SEQ ID NOs: 45666 to 45667, SEQ ID NO: 45675, SEQ ID NO: 45680, SEQ ID NO: 45687, SEQ ID NO: 45697, SEQ ID NOs: 45699 to 45700, SEQ ID NO: 45712, SEQ ID NO: 45714, SEQ ID NO: 45723, SEQ ID NO: 45746, SEQ ID NO: 45765, SEQ ID NO: 45787, SEQ ID NO: 45793, SEQ ID NO: 45818, SEQ ID NO: 45826, SEQ ID NOs: 45829 to 45830, SEQ ID NO: 45835, SEQ ID NO: 45837, SEQ ID NO: 45846, SEQ ID NO: 45859, SEQ ID NO: 45885, SEQ ID NO: 45894, SEQ ID NO: 45904, SEQ ID NO: 45915, SEQ ID NO: 45930, SEQ ID NO: 45938, SEQ ID NO: 45959, SEQ ID NO: 45983, SEQ ID NO: 46006, SEQ ID NO: 46011, SEQ ID NO: 46014, SEQ ID NO: 46044, SEQ ID NO: 46049, SEQ ID NO: 46054, SEQ ID NO: 46058, SEQ ID NO: 46063, SEQ ID NO: 46071, SEQ ID NO: 46077, SEQ ID NO: 46096, SEQ ID NO: 46103, SEQ ID NO: 46108, SEQ ID NO: 46110, SEQ ID NO: 46125, SEQ ID NO: 46133, SEQ ID NOs: 46170 to 46171, SEQ ID NO: 46195, SEQ ID NO: 46208, SEQ ID NO: 46212, SEQ ID NO: 46219, SEQ ID NO: 46226, SEQ ID NO: 46234, SEQ ID NO: 46236, SEQ ID NO: 46261, SEQ ID NO: 46270, SEQ ID NO: 46273, SEQ ID NO: 46275, SEQ ID NO: 46339, SEQ ID NO: 46364, SEQ ID NO: 46376, SEQ ID NOs: 46400 to 46401, SEQ ID NOs: 46421 to 46422, SEQ ID NO: 46433, SEQ ID NOs: 46442 to 46443, SEQ ID NO: 46446, SEQ ID NOs: 46452 to 46454, SEQ ID NO: 46457, SEQ ID NO: 46459, SEQ ID NO: 46462, SEQ ID NO: 46465, SEQ ID NO: 46478, SEQ ID NO: 46484, SEQ ID NO: 46489, SEQ ID NO: 46499, SEQ ID NO: 46512, SEQ ID NO: 46521, SEQ ID NO: 46530, SEQ ID NO: 46536, SEQ ID NO: 46560, SEQ ID NO: 46564, SEQ ID NO: 46570, SEQ ID NO: 46572, SEQ ID NO: 46575, SEQ ID NO: 46579, SEQ ID NO: 46586, SEQ ID NO: 46602, SEQ ID NO: 46616, SEQ ID NO: 46621, SEQ ID NO: 46628, SEQ ID NO: 46637, SEQ ID NO: 46642, SEQ ID NO: 46648, SEQ ID NO: 46652, SEQ ID NO: 46655, SEQ ID NO: 46660, SEQ ID NO: 46663, SEQ ID NOs: 46665 to 46666, SEQ ID NO: 46676, SEQ ID NOs: 46678 to 46679, SEQ ID NO: 46682, SEQ ID NO: 46685, SEQ ID NO: 46689, SEQ ID NO: 46713, SEQ ID NO: 46715, SEQ ID NO: 46736, SEQ ID NO: 46739, SEQ ID NO: 46770, SEQ ID NO: 46777, SEQ ID NO: 46800, SEQ ID NOs: 46823 to 46825, SEQ ID NO: 46831, SEQ ID NO: 46872, SEQ ID NO: 46880, SEQ ID NO: 46897, SEQ ID NO: 46916, SEQ ID NO: 46928, SEQ ID NO: 46937, SEQ ID NO: 46950, SEQ ID NO: 46978, SEQ ID NO: 46981, SEQ ID NO: 46983, SEQ ID NO: 46989, SEQ ID NO: 46991, SEQ ID NO: 46993, SEQ ID NO: 47003, SEQ ID NO: 47006, SEQ ID NO: 47017, SEQ ID NO: 47028, SEQ ID NO: 47045, SEQ ID NO: 47047, SEQ ID NO: 47057, SEQ ID NOs: 47079 to 47080, SEQ ID NO: 47082, SEQ ID NO: 47114, SEQ ID NO: 47119, SEQ ID NO: 47123, SEQ ID NOs: 47137 to 47139, SEQ ID NO: 47151, SEQ ID NO: 47158, SEQ ID NO: 47167, SEQ ID NO: 47172, SEQ ID NO: 47186, SEQ ID NO: 47191, SEQ ID NO: 47206, SEQ ID NO: 47224, SEQ ID NO: 47298, SEQ ID NO: 47316, SEQ ID NO: 47324, SEQ ID NOs: 47331 to 47332, SEQ ID NO: 47335, SEQ ID NO: 47356, SEQ ID NO: 47358, SEQ ID NOs: 47360 to 47361, SEQ ID NOs: 47377 to 47378, SEQ ID NO: 47381, SEQ ID NO: 47405, SEQ ID NO: 47412, SEQ ID NO: 47416, SEQ ID NO: 47422, SEQ ID NO: 47425, SEQ ID NO: 47427, SEQ ID NOs: 47432 to 47433, SEQ ID NO: 47445, SEQ ID NO: 47451, SEQ ID NO: 47460, SEQ ID NO: 47482, SEQ ID NO: 47491, SEQ ID NO: 47509, SEQ ID NO: 47516, SEQ ID NOs: 47533 to 47535, SEQ ID NOs: 47538 to 47539, SEQ ID NO: 47555, SEQ ID NO: 47561, SEQ ID NOs: 47575 to 47576, SEQ ID NO: 47582, SEQ ID NO: 47592, SEQ ID NO: 47614, SEQ ID NO: 47625, SEQ ID NO: 47630, SEQ ID NO: 47637, SEQ ID NO: 47643, SEQ ID NO: 47654, SEQ ID NO: 47673, SEQ ID NO: 47689, SEQ ID NO: 47698, SEQ ID NO: 47701, SEQ ID NO: 47727, SEQ ID NO: 47749, SEQ ID NOs: 47759 to 47760, SEQ ID NO: 47767, SEQ ID NO: 47773, SEQ ID NO: 47782, SEQ ID NO: 47790, SEQ ID NO: 47793, SEQ ID NO: 47799, SEQ ID NO: 47806, SEQ ID NO: 47809, SEQ ID NO: 47834, SEQ ID NO: 47840, SEQ ID NO: 47844, SEQ ID NO: 47848, SEQ ID NO: 47855, SEQ ID NO: 47867, SEQ ID NO: 47890, SEQ ID NO: 47895, SEQ ID NO: 47899, SEQ ID NO: 47902, SEQ ID NO: 47923, SEQ ID NO: 47927, SEQ ID NOs: 47959 to 47960, SEQ ID NO: 47964, SEQ ID NO: 47979, SEQ ID NO: 47984, SEQ ID NO: 47986, SEQ ID NOs: 48030 to 48031, SEQ ID NO: 48034, SEQ ID NO: 48059, SEQ ID NO: 48093, SEQ ID NO: 48107, SEQ ID NO: 48113, SEQ ID NO: 48118, SEQ ID NO: 48121, SEQ ID NO: 48129, SEQ ID NOs: 48138 to 48139, SEQ ID NO: 48144, SEQ ID NO: 48158, SEQ ID NO: 48160, SEQ ID NO: 48162, SEQ ID NO: 48175, SEQ ID NO: 48186, SEQ ID NO: 48203, SEQ ID NO: 48210, SEQ ID NO: 48213, SEQ ID NO: 48220, SEQ ID NO: 48224, SEQ ID NO: 48229, SEQ ID NO: 48258, SEQ ID NO: 48266, SEQ ID NO: 48273, SEQ ID NO: 48280, SEQ ID NO: 48286, SEQ ID NO: 48295, SEQ ID NO: 48300 to 48301, SEQ ID NOs: 48306 to 48307, SEQ ID NO: 48315, SEQ ID NO: 48347, SEQ ID NO: 48353, SEQ ID NO: 48358, SEQ ID NO: 48366, SEQ ID NO: 48371, SEQ ID NO: 48379, SEQ ID NO: 48387, SEQ ID NO: 48400, SEQ ID NO: 48415, SEQ ID NOs: 48418 to 48419, SEQ ID NO: 48436, SEQ ID NOs: 48438 to 48440, SEQ ID NO: 48443, SEQ ID NO: 48452, SEQ ID NOs: 48461 to 48462, SEQ ID NO: 48466, SEQ ID NO: 48469, SEQ ID NO: 48520, SEQ ID NO: 48537, SEQ ID NO: 48545, SEQ ID NO: 48574, SEQ ID NOs: 48576 to 48578, SEQ ID NO: 48594, SEQ ID NO: 48599, SEQ ID NO: 48614, SEQ ID NO: 48627, SEQ ID NO: 48642, SEQ ID NO: 48648, SEQ ID NO: 48654, SEQ ID NO: 48656, SEQ ID NO: 48666, SEQ ID NOs: 48669 to 48670, SEQ ID NO: 48674, SEQ ID NOs: 48680 to 48681, SEQ ID NO: 48684, SEQ ID NO: 48686, SEQ ID NO: 48692, SEQ ID NO: 48701, SEQ ID NO: 48705, SEQ ID NO: 48714, SEQ ID NO: 48717, SEQ ID NO: 48735, SEQ ID NO: 48738, SEQ ID NO: 48749, SEQ ID NO: 48751, SEQ ID NO: 48764, SEQ ID NO: 48769, SEQ ID NO: 48793, SEQ ID NO: 48796, SEQ ID NOs: 48799 to 48800, SEQ ID NOs: 48802 to 48803, SEQ ID NO: 48818, SEQ ID NO: 48832, SEQ ID NO: 48834, SEQ ID NO: 48838, SEQ ID NO: 48845, SEQ ID NO: 48856, SEQ ID NO: 48877, SEQ ID NO: 48884, SEQ ID NO: 48903, SEQ ID NO: 48936, SEQ ID NO: 48947, SEQ ID NOs: 48968 to 48970, SEQ ID NO: 48974, SEQ ID NOs: 48981 to 48982, SEQ ID NO: 48997, SEQ ID NOs: 49013 to 49014, SEQ ID NOs: 49019 to 49020, SEQ ID NO: 49031, SEQ ID NO: 49033, SEQ ID NO: 49043, SEQ ID NO: 49052, SEQ ID NOs: 49061 to 49062, SEQ ID NO: 49068, SEQ ID NO: 49071, SEQ ID NO: 49086, SEQ ID NO: 49102, SEQ ID NO: 49111, SEQ ID NO: 49156, SEQ ID NO: 49164, SEQ ID NO: 49173, SEQ ID NO: 49176, SEQ ID NO: 49183, SEQ ID NO: 49185, SEQ ID NOs: 49200 to 49201, SEQ ID NO: 49209, SEQ ID NO: 49220, SEQ ID NO: 49247, SEQ ID NO: 49251, SEQ ID NO: 49256, SEQ ID NO: 49263, SEQ ID NOs: 49273 to 49274, SEQ ID NOs: 49280 to 49281, SEQ ID NO: 49291, SEQ ID NOs: 49294 to 49295, SEQ ID NO: 49298, SEQ ID NO: 49309, SEQ ID NO: 49319, SEQ ID NO: 49326, SEQ ID NO: 49330, SEQ ID NO: 49340, SEQ ID NOs: 49351 to 49352, SEQ ID NO: 49360, SEQ ID NOs: 49376 to 49377, SEQ ID NO: 49384, SEQ ID NO: 49393, SEQ ID NO: 49395, SEQ ID NO: 49399, SEQ ID NO: 49406, SEQ ID NO: 49411, SEQ ID NOs: 49443 to 49444, SEQ ID NO: 49452, SEQ ID NO: 49462, SEQ ID NO: 49474, SEQ ID NO: 49487, SEQ ID NO: 49499, SEQ ID NO: 49525, SEQ ID NO: 49537, SEQ ID NO: 49540, SEQ ID NO: 49557, SEQ ID NO: 49572, SEQ ID NO: 49584, SEQ ID NO: 49597, SEQ ID NO: 49626, SEQ ID NO: 49630, SEQ ID NO: 49646, SEQ ID NO: 49658, SEQ ID NO: 49671, SEQ ID NO: 49681, SEQ ID NO: 49703, SEQ ID NO: 49728, SEQ ID NO: 49730, SEQ ID NO: 49737, SEQ ID NOs: 49742 to 49743, SEQ ID NOs: 49766 to 49767, SEQ ID NO: 49772, SEQ ID NO: 49782, SEQ ID NOs: 49787 to 49788, SEQ ID NO: 49793, SEQ ID NO: 49796, SEQ ID NO: 49805, SEQ ID NO: 49811, SEQ ID NO: 49823, SEQ ID NO: 49838, SEQ ID NO: 49850, SEQ ID NOs: 49859 to 49860, SEQ ID NO: 49873, SEQ ID NO: 49883, SEQ ID NO: 49892, SEQ ID NO: 49912, SEQ ID NO: 49928, SEQ ID NO: 49948, SEQ ID NO: 49961, SEQ ID NO: 49965, SEQ ID NO: 49987, SEQ ID NO: 49997, SEQ ID NOs: 50017 to 50018, SEQ ID NO: 50020, SEQ ID NO: 50022, SEQ ID NO: 50045, SEQ ID NO: 50062, SEQ ID NO: 50073, SEQ ID NO: 50079, SEQ ID NO: 50090, SEQ ID NO: 50107, SEQ ID NOs: 50111 to 50112, SEQ ID NO: 50123, SEQ ID NO: 50138, SEQ ID NOs: 50165 to 50167, SEQ ID NOs: 50227 to 50228, SEQ ID NO: 50243, SEQ ID NO: 50250, SEQ ID NO: 50254, SEQ ID NO: 50282, SEQ ID NO: 50284, SEQ ID NO: 50290, SEQ ID NO: 50297, SEQ ID NO: 50305, SEQ ID NO: 50309, SEQ ID NO: 50319, SEQ ID NO: 50331, SEQ ID NO: 50334, SEQ ID NO: 50339, SEQ ID NO: 50366, SEQ ID NO: 50388, SEQ ID NO: 50392, SEQ ID NO: 50394, SEQ ID NOs: 50400 to 50401, SEQ ID NO: 50418, SEQ ID NO: 50423, SEQ ID NO: 50428, SEQ ID NO: 50437, SEQ ID NO: 50443, SEQ ID NO: 50450, SEQ ID NO: 50464, SEQ ID NO: 50485, SEQ ID NO: 50494, SEQ ID NO: 50496, SEQ ID NO: 50499, SEQ ID NO: 50526, SEQ ID NO: 50528, SEQ ID NO: 50532, SEQ ID NO: 50538, SEQ ID NO: 50554, SEQ ID NO: 50557, SEQ ID NO: 50560, SEQ ID NO: 50564, SEQ ID NO: 50574, SEQ ID NO: 50585, SEQ ID NO: 50617, SEQ ID NO: 50632, SEQ ID NO: 50634, SEQ ID NO: 50644, SEQ ID NO: 50654, SEQ ID NO: 50678, SEQ ID NO: 50699, SEQ ID NO: 50714, SEQ ID NOs: 50728 to 50729, SEQ ID NO: 50735, SEQ ID NO: 50741, SEQ ID NO: 50744, SEQ ID NO: 50765, SEQ ID NO: 50769, SEQ ID NO: 50793, SEQ ID NO: 50818, SEQ ID NO: 50822, SEQ ID NO: 50826, SEQ ID NO: 50835, SEQ ID NO: 50842, SEQ ID NO: 50847, SEQ ID NO: 50849, SEQ ID NO: 50851, SEQ ID NO: 50893, SEQ ID NO: 50918, SEQ ID NOs: 50935 to 50936, SEQ ID NOs: 50941 to 50944, SEQ ID NOs: 50960 to 50962, SEQ ID NOs: 50975 to 50976, SEQ ID NOs: 51008 to 51009, SEQ ID NO: 51012, SEQ ID NOs: 51021 to 51022, SEQ ID NO: 51046, SEQ ID NO: 51062, SEQ ID NOs: 51068 to 51071, SEQ ID NOs: 51102 to 51104, SEQ ID NO: 51118, SEQ ID NOs: 51168 to 51169, SEQ ID NO: 51214, SEQ ID NO: 51235, SEQ ID NO: 51239, SEQ ID NO: 51241, SEQ ID NO: 51243, SEQ ID NO: 51257, SEQ ID NOs: 51263 to 51266, SEQ ID NOs: 51295 to 51297, SEQ ID NO: 51313, SEQ ID NO: 51405, SEQ ID NOs: 51413 to 51417, SEQ ID NO: 51524, SEQ ID NO: 51526, SEQ ID NO: 51693, SEQ ID NO: 51717, SEQ ID NO: 51762, SEQ ID NO: 51765, SEQ ID NO: 51853, SEQ ID NO: 51878, SEQ ID NO: 52035, SEQ ID NO: 52179, SEQ ID NO: 52275, SEQ ID NO: 52290, SEQ ID NO: 52379, SEQ ID NO: 52463, SEQ ID NO: 52497, SEQ ID NO: 52515, SEQ ID NO: 52652, SEQ ID NO: 52660, SEQ ID NO: 52679, SEQ ID NO: 52686, SEQ ID NO: 52746, SEQ ID NO: 52758, SEQ ID NO: 52816, SEQ ID NO: 52944, SEQ ID NO: 52984, SEQ ID NO: 52988, SEQ ID NO: 52991, SEQ ID NO: 53045, SEQ ID NO: 53118, SEQ ID NO: 53166, SEQ ID NO: 53338, SEQ ID NO: 53382, SEQ ID NO: 53464, SEQ ID NO: 53478, SEQ ID NO: 53511, SEQ ID NO: 53519, SEQ ID NO: 53548, SEQ ID NO: 53581, SEQ ID NO: 53653, SEQ ID NO: 53968, SEQ ID NO: 54024, SEQ ID NO: 54038, SEQ ID NO: 54045, SEQ ID NO: 54080, SEQ ID NO: 54097, SEQ ID NO: 54111, SEQ ID NO: 54238, SEQ ID NO: 54251, SEQ ID NO: 54269, SEQ ID NO: 54409, SEQ ID NO: 54418, SEQ ID NO: 54442, SEQ ID NO: 54473, SEQ ID NO: 54543, SEQ ID NO: 54713, SEQ ID NO: 54719, SEQ ID NO: 54727, SEQ ID NO: 54772, SEQ ID NO: 54788, SEQ ID NO: 54863, SEQ ID NO: 54877, SEQ ID NO: 54945, SEQ ID NO: 54960, SEQ ID NO: 55004, SEQ ID NO: 55109, SEQ ID NO: 55207, SEQ ID NO: 55230, SEQ ID NO: 55300, SEQ ID NO: 55355, SEQ ID NO: 55437, SEQ ID NO: 55516, SEQ ID NO: 55695, SEQ ID NO: 55758, SEQ ID NO: 55801, SEQ ID NO: 55814, SEQ ID NO: 55875, SEQ ID NO: 55879, SEQ ID NO: 55886, SEQ ID NO: 55911, SEQ ID NO: 55986, SEQ ID NO: 56043, SEQ ID NO: 56052, SEQ ID NO: 56175, SEQ ID NO: 56240, SEQ ID NO: 56277, SEQ ID NO: 56352, SEQ ID NO: 56418, SEQ ID NO: 56435, SEQ ID NO: 56521, SEQ ID NO: 56593, SEQ ID NO: 56609, SEQ ID NO: 56629, SEQ ID NOs: 56649 to 56650, SEQ ID NO: 56793, SEQ ID NO: 56836, SEQ ID NO: 56852, SEQ ID NO: 56902, SEQ ID NO: 57155, SEQ ID NO: 57157, SEQ ID NO: 57265, SEQ ID NO: 57278, SEQ ID NO: 57323, SEQ ID NO: 57472, SEQ ID NO: 57535, SEQ ID NO: 57550, SEQ ID NO: 57561, SEQ ID NO: 57568, SEQ ID NO: 57639, SEQ ID NO: 57655, SEQ ID NO: 57790, SEQ ID NO: 57811, SEQ ID NO: 57904, SEQ ID NO: 57944, SEQ ID NO: 58040, SEQ ID NO: 58064, SEQ ID NO: 58075, SEQ ID NO: 58145, SEQ ID NO: 58199, SEQ ID NO: 58223, SEQ ID NO: 58226, SEQ ID NO: 58309, SEQ ID NO: 58349, SEQ ID NO: 58395, SEQ ID NO: 58411, SEQ ID NO: 58433, SEQ ID NO: 58547, SEQ ID NO: 58589, SEQ ID NO: 58679, SEQ ID NOs: 58683 to 58684, SEQ ID NO: 58815, SEQ ID NO: 58823, SEQ ID NO: 58855, SEQ ID NO: 58932, SEQ ID NO: 59223, SEQ ID NO: 59246, SEQ ID NO: 59248, SEQ ID NO: 59530, SEQ ID NO: 59622, SEQ ID NO: 59755, SEQ ID NO: 59757, SEQ ID NO: 59775, SEQ ID NO: 59816, SEQ ID NO: 59821, SEQ ID NO: 59828, SEQ ID NO: 59856, SEQ ID NO: 59871, SEQ ID NO: 59873, SEQ ID NO: 59875, SEQ ID NO: 59960, SEQ ID NO: 59967, SEQ ID NO: 60005, SEQ ID NOs: 60046 to 60047, SEQ ID NO: 60081, SEQ ID NO: 60224, SEQ ID NO: 60228, SEQ ID NO: 60276, SEQ ID NO: 60289, SEQ ID NO: 60292, SEQ ID NOs: 60422 to 60423, SEQ ID NO: 60444, SEQ ID NOs: 60456 to 68237, SEQ ID NO: 211911, SEQ ID NOs: 212086 to 212095, SEQ ID NOs: 212435 to 212440, SEQ ID NOs: 212681 to 212684, SEQ ID NOs: 212858 to 212860, SEQ ID NOs: 213516 to 213517, SEQ ID NOs: 213529 to 213531, SEQ ID NOs: 213602 to 213611, SEQ ID NOs: 213719 to 213720, SEQ ID NO: 213899, SEQ ID NOs: 214004 to 214012, SEQ ID NO: 214607, SEQ ID NOs: 214647 to 214649, SEQ ID NOs: 214672 to 214679, SEQ ID NOs: 214774 to 214775, SEQ ID NO: 214777, SEQ ID NO: 214779, SEQ ID NO: 214782, SEQ ID NOs: 215373 to 215415, SEQ ID NO: 215494, SEQ ID NO: 215497, SEQ ID NO: 215679, SEQ ID NO: 216244, SEQ ID NO: 216246, SEQ ID NOs: 216383 to 216401, SEQ ID NOs: 217184 to 217192, SEQ ID NO: 217200, SEQ ID NO: 217362, SEQ ID NOs: 217708 to 217712, SEQ ID NO: 217719, SEQ ID NO: 219238, SEQ ID NOs: 219742 to 219744, SEQ ID NO: 219747, SEQ ID NO: 219749, SEQ ID NO: 219751, SEQ ID NOs: 219773 to 219781, SEQ ID NOs: 219994 to 220030, SEQ ID NOs: 220318 to 220319, SEQ ID NO: 220327, SEQ ID NO: 220670, SEQ ID NO: 220815, SEQ ID NO: 220820, SEQ ID NOs: 221197 to 221234, SEQ ID NO: 221998, SEQ ID NO: 222000, SEQ ID NO: 223092, SEQ ID NO: 223095, SEQ ID NO: 223097, SEQ ID NO: 223099, SEQ ID NO: 223119, SEQ ID NO: 223121, SEQ ID NOs: 223184 to 223190, SEQ ID NOs: 223250 to 223283, SEQ ID NO: 223319, SEQ ID NO: 230922, SEQ ID NOs: 232805 to 232806, SEQ ID NO: 232846, and SEQ ID NOs: 236016 to 247058. In some embodiments, any one of the peptides in the MAGA4 vaccine comprise an amino acid sequence 80, 81, 82, 83, 84, 85, 86, 87, 88, 89, 90, 91, 92, 93, 94, 95, 96, 97, 98 or 99% identical to SEQ ID NO: 41345, SEQ ID NO: 41347, SEQ ID NO: 41352, SEQ ID NOs: 41357 to 41358, SEQ ID NO: 41366, SEQ ID NO: 41377, SEQ ID NO: 41382, SEQ ID NO: 41392, SEQ ID NO: 41396, SEQ ID NO: 41398, SEQ ID NO: 41406, SEQ ID NO: 41411, SEQ ID NO: 41414, SEQ ID NO: 41433, SEQ ID NO: 41436, SEQ ID NO: 41445, SEQ ID NO: 41449, SEQ ID NO: 41455, SEQ ID NO: 41478, SEQ ID NO: 41487, SEQ ID NOs: 41495 to 41496, SEQ ID NO: 41503, SEQ ID NO: 41515, SEQ ID NO: 41520, SEQ ID NO: 41529, SEQ ID NO: 41549, SEQ ID NO: 41553, SEQ ID NO: 41562, SEQ ID NO: 41569, SEQ ID NO: 41574, SEQ ID NO: 41576, SEQ ID NO: 41579, SEQ ID NOs: 41587 to 41588, SEQ ID NO: 41605, SEQ ID NO: 41617, SEQ ID NO: 41620, SEQ ID NO: 41634, SEQ ID NO: 41650, SEQ ID NO: 41665, SEQ ID NO: 41670, SEQ ID NO: 41672, SEQ ID NO: 41696, SEQ ID NO: 41703, SEQ ID NO: 41709, SEQ ID NO: 41725, SEQ ID NOs: 41732 to 41733, SEQ ID NO: 41748, SEQ ID NO: 41760, SEQ ID NO: 41766, SEQ ID NO: 41768, SEQ ID NO: 41770, SEQ ID NO: 41779, SEQ ID NO: 41791, SEQ ID NO: 41797, SEQ ID NO: 41813, SEQ ID NO: 41819, SEQ ID NO: 41825, SEQ ID NO: 41829, SEQ ID NOs: 41846 to 41847, SEQ ID NO: 41853, SEQ ID NO: 41876, SEQ ID NO: 41889, SEQ ID NO: 41892, SEQ ID NO: 41897, SEQ ID NOs: 41906 to 41907, SEQ ID NO: 41912, SEQ ID NO: 41924, SEQ ID NO: 41940, SEQ ID NO: 41953, SEQ ID NO: 41956, SEQ ID NO: 41967, SEQ ID NO: 41970, SEQ ID NO: 41976, SEQ ID NO: 41985, SEQ ID NO: 41990, SEQ ID NO: 42014, SEQ ID NO: 42017, SEQ ID NO: 42026, SEQ ID NO: 42034, SEQ ID NO: 42037, SEQ ID NO: 42046, SEQ ID NO: 42048, SEQ ID NOs: 42056 to 42057, SEQ ID NO: 42080, SEQ ID NO: 42088, SEQ ID NO: 42091, SEQ ID NO: 42102, SEQ ID NO: 42106, SEQ ID NO: 42115, SEQ ID NO: 42120, SEQ ID NO: 42129, SEQ ID NO: 42135, SEQ ID NO: 42138, SEQ ID NO: 42151, SEQ ID NO: 42158, SEQ ID NOs: 42163 to 42164, SEQ ID NOs: 42167 to 42168, SEQ ID NO: 42170, SEQ ID NO: 42186, SEQ ID NO: 42192, SEQ ID NO: 42195, SEQ ID NO: 42198, SEQ ID NO: 42204, SEQ ID NO: 42209, SEQ ID NO: 42218, SEQ ID NO: 42221, SEQ ID NO: 42224, SEQ ID NO: 42229, SEQ ID NO: 42240, SEQ ID NO: 42263, SEQ ID NO: 42265, SEQ ID NO: 42270, SEQ ID NO: 42316, SEQ ID NOs: 42336 to 42337, SEQ ID NO: 42339, SEQ ID NO: 42351, SEQ ID NO: 42354, SEQ ID NO: 42372, SEQ ID NO: 42378, SEQ ID NOs: 42385 to 42386, SEQ ID NO: 42394, SEQ ID NO: 42405, SEQ ID NO: 42409, SEQ ID NO: 42417, SEQ ID NO: 42423, SEQ ID NO: 42439, SEQ ID NO: 42447, SEQ ID NO: 42453, SEQ ID NO: 42458, SEQ ID NOs: 42460 to 42461, SEQ ID NO: 42466, SEQ ID NOs: 42472 to 42473, SEQ ID NOs: 42519 to 42520, SEQ ID NO: 42525, SEQ ID NO: 42528, SEQ ID NO: 42540, SEQ ID NO: 42545, SEQ ID NO: 42550, SEQ ID NOs: 42563 to 42564, SEQ ID NO: 42580, SEQ ID NO: 42605, SEQ ID NO: 42609, SEQ ID NOs: 42612 to 42613, SEQ ID NO: 42615, SEQ ID NO: 42628, SEQ ID NO: 42637, SEQ ID NO: 42648, SEQ ID NO: 42653, SEQ ID NO: 42675, SEQ ID NO: 42680, SEQ ID NO: 42685, SEQ ID NO: 42696, SEQ ID NO: 42703, SEQ ID NO: 42719, SEQ ID NO: 42735, SEQ ID NO: 42743, SEQ ID NO: 42748, SEQ ID NO: 42750, SEQ ID NO: 42768, SEQ ID NO: 42812, SEQ ID NO: 42814, SEQ ID NO: 42822, SEQ ID NO: 42827, SEQ ID NO: 42831, SEQ ID NO: 42846, SEQ ID NO: 42850, SEQ ID NO: 42872, SEQ ID NO: 42886, SEQ ID NO: 42911, SEQ ID NO: 42914, SEQ ID NO: 42923, SEQ ID NO: 42927, SEQ ID NOs: 42957 to 42958, SEQ ID NO: 42962, SEQ ID NO: 42971, SEQ ID NOs: 42997 to 42998, SEQ ID NO: 43002, SEQ ID NO: 43008, SEQ ID NO: 43035, SEQ ID NO: 43046, SEQ ID NO: 43048, SEQ ID NO: 43064, SEQ ID NO: 43083, SEQ ID NO: 43091, SEQ ID NO: 43093, SEQ ID NO: 43148, SEQ ID NO: 43160, SEQ ID NO: 43170, SEQ ID NO: 43175, SEQ ID NO: 43180, SEQ ID NO: 43186, SEQ ID NO: 43193, SEQ ID NO: 43196, SEQ ID NOs: 43231 to 43232, SEQ ID NO: 43238, SEQ ID NO: 43242, SEQ ID NO: 43248, SEQ ID NO: 43253, SEQ ID NO: 43258, SEQ ID NO: 43267, SEQ ID NO: 43274, SEQ ID NO: 43280, SEQ ID NO: 43285, SEQ ID NO: 43295, SEQ ID NO: 43308, SEQ ID NO: 43311, SEQ ID NO: 43329, SEQ ID NO: 43333, SEQ ID NOs: 43339 to 43340, SEQ ID NO: 43362, SEQ ID NO: 43365, SEQ ID NO: 43384, SEQ ID NO: 43389, SEQ ID NO: 43395, SEQ ID NO: 43401, SEQ ID NO: 43429, SEQ ID NO: 43432, SEQ ID NO: 43440, SEQ ID NOs: 43451 to 43453, SEQ ID NO: 43462, SEQ ID NO: 43464, SEQ ID NO: 43467, SEQ ID NO: 43479, SEQ ID NO: 43482, SEQ ID NO: 43496, SEQ ID NO: 43511, SEQ ID NO: 43513, SEQ ID NO: 43517, SEQ ID NO: 43545, SEQ ID NO: 43564, SEQ ID NO: 43573, SEQ ID NO: 43585, SEQ ID NO: 43587, SEQ ID NO: 43591, SEQ ID NO: 43611, SEQ ID NO: 43632, SEQ ID NO: 43636, SEQ ID NO: 43641, SEQ ID NO: 43643, SEQ ID NO: 43651, SEQ ID NO: 43669, SEQ ID NO: 43688, SEQ ID NO: 43696, SEQ ID NO: 43700, SEQ ID NO: 43703, SEQ ID NO: 43707, SEQ ID NO: 43718, SEQ ID NO: 43760, SEQ ID NO: 43763, SEQ ID NO: 43768, SEQ ID NO: 43777, SEQ ID NO: 43780, SEQ ID NO: 43787, SEQ ID NO: 43801, SEQ ID NO: 43808, SEQ ID NO: 43810, SEQ ID NO: 43825, SEQ ID NO: 43827, SEQ ID NO: 43836, SEQ ID NO: 43860, SEQ ID NO: 43867, SEQ ID NOs: 43881 to 43882, SEQ ID NO: 43884, SEQ ID NO: 43887, SEQ ID NOs: 43898 to 43899, SEQ ID NO: 43905, SEQ ID NO: 43915, SEQ ID NO: 43924, SEQ ID NO: 43932, SEQ ID NO: 43958, SEQ ID NO: 43971, SEQ ID NO: 43974, SEQ ID NO: 43978, SEQ ID NOs: 43982 to 43984, SEQ ID NOs: 43986 to 43987, SEQ ID NO: 43993, SEQ ID NO: 43995, SEQ ID NO: 44012, SEQ ID NO: 44035, SEQ ID NO: 44037, SEQ ID NO: 44048, SEQ ID NO: 44050, SEQ ID NO: 44052, SEQ ID NO: 44055, SEQ ID NO: 44063, SEQ ID NO: 44073, SEQ ID NO: 44080, SEQ ID NO: 44085, SEQ ID NO: 44087, SEQ ID NO: 44089, SEQ ID NO: 44112, SEQ ID NO: 44117, SEQ ID NO: 44123, SEQ ID NOs: 44151 to 44152, SEQ ID NO: 44160, SEQ ID NO: 44181, SEQ ID NO: 44207, SEQ ID NO: 44210, SEQ ID NO: 44244, SEQ ID NO: 44246, SEQ ID NO: 44254, SEQ ID NO: 44263, SEQ ID NOs: 44298 to 44299, SEQ ID NO: 44309, SEQ ID NO: 44324, SEQ ID NO: 44328, SEQ ID NO: 44342, SEQ ID NO: 44345, SEQ ID NO: 44359, SEQ ID NO: 44361, SEQ ID NO: 44383, SEQ ID NO: 44401, SEQ ID NO: 44422, SEQ ID NO: 44440, SEQ ID NO: 44452, SEQ ID NO: 44454, SEQ ID NO: 44456, SEQ ID NO: 44463, SEQ ID NO: 44467, SEQ ID NO: 44485, SEQ ID NO: 44512, SEQ ID NO: 44523, SEQ ID NO: 44545, SEQ ID NO: 44552, SEQ ID NO: 44564, SEQ ID NOs: 44566 to 44567, SEQ ID NOs: 44589 to 44591, SEQ ID NO: 44615, SEQ ID NO: 44623, SEQ ID NO: 44631, SEQ ID NO: 44636, SEQ ID NO: 44649, SEQ ID NO: 44654, SEQ ID NO: 44691, SEQ ID NO: 44713, SEQ ID NO: 44722, SEQ ID NO: 44730, SEQ ID NO: 44754, SEQ ID NO: 44756, SEQ ID NOs: 44762 to 44763, SEQ ID NO: 44773, SEQ ID NO: 44781, SEQ ID NO: 44794, SEQ ID NO: 44850, SEQ ID NOs: 44873 to 44875, SEQ ID NO: 44877, SEQ ID NO: 44884, SEQ ID NO: 44908, SEQ ID NO: 44913, SEQ ID NO: 44940, SEQ ID NO: 44955, SEQ ID NO: 44964, SEQ ID NO: 44971, SEQ ID NO: 44976, SEQ ID NO: 45000, SEQ ID NO: 45027, SEQ ID NO: 45035, SEQ ID NO: 45060, SEQ ID NO: 45062, SEQ ID NO: 45095, SEQ ID NO: 45123, SEQ ID NOs: 45126 to 45127, SEQ ID NO: 45132, SEQ ID NO: 45135, SEQ ID NOs: 45138 to 45139, SEQ ID NO: 45193, SEQ ID NO: 45197, SEQ ID NO: 45200, SEQ ID NO: 45223, SEQ ID NO: 45225, SEQ ID NO: 45244, SEQ ID NO: 45262, SEQ ID NO: 45273, SEQ ID NO: 45292, SEQ ID NO: 45302, SEQ ID NO: 45306, SEQ ID NO: 45314, SEQ ID NO: 45380, SEQ ID NO: 45385, SEQ ID NO: 45389, SEQ ID NO: 45398, SEQ ID NO: 45409, SEQ ID NO: 45438, SEQ ID NO: 45444, SEQ ID NOs: 45450 to 45451, SEQ ID NO: 45478, SEQ ID NO: 45480, SEQ ID NO: 45485, SEQ ID NO: 45490, SEQ ID NO: 45510, SEQ ID NO: 45514, SEQ ID NOs: 45519 to 45520, SEQ ID NO: 45530, SEQ ID NO: 45541, SEQ ID NO: 45552, SEQ ID NO: 45556, SEQ ID NOs: 45562 to 45563, SEQ ID NO: 45568, SEQ ID NO: 45577, SEQ ID NOs: 45580 to 45581, SEQ ID NO: 45584, SEQ ID NO: 45588, SEQ ID NO: 45595, SEQ ID NO: 45599, SEQ ID NO: 45632, SEQ ID NO: 45653, SEQ ID NOs: 45666 to 45667, SEQ ID NO: 45675, SEQ ID NO: 45680, SEQ ID NO: 45687, SEQ ID NO: 45697, SEQ ID NOs: 45699 to 45700, SEQ ID NO: 45712, SEQ ID NO: 45714, SEQ ID NO: 45723, SEQ ID NO: 45746, SEQ ID NO: 45765, SEQ ID NO: 45787, SEQ ID NO: 45793, SEQ ID NO: 45818, SEQ ID NO: 45826, SEQ ID NOs: 45829 to 45830, SEQ ID NO: 45835, SEQ ID NO: 45837, SEQ ID NO: 45846, SEQ ID NO: 45859, SEQ ID NO: 45885, SEQ ID NO: 45894, SEQ ID NO: 45904, SEQ ID NO: 45915, SEQ ID NO: 45930, SEQ ID NO: 45938, SEQ ID NO: 45959, SEQ ID NO: 45983, SEQ ID NO: 46006, SEQ ID NO: 46011, SEQ ID NO: 46014, SEQ ID NO: 46044, SEQ ID NO: 46049, SEQ ID NO: 46054, SEQ ID NO: 46058, SEQ ID NO: 46063, SEQ ID NO: 46071, SEQ ID NO: 46077, SEQ ID NO: 46096, SEQ ID NO: 46103, SEQ ID NO: 46108, SEQ ID NO: 46110, SEQ ID NO: 46125, SEQ ID NO: 46133, SEQ ID NOs: 46170 to 46171, SEQ ID NO: 46195, SEQ ID NO: 46208, SEQ ID NO: 46212, SEQ ID NO: 46219, SEQ ID NO: 46226, SEQ ID NO: 46234, SEQ ID NO: 46236, SEQ ID NO: 46261, SEQ ID NO: 46270, SEQ ID NO: 46273, SEQ ID NO: 46275, SEQ ID NO: 46339, SEQ ID NO: 46364, SEQ ID NO: 46376, SEQ ID NOs: 46400 to 46401, SEQ ID NOs: 46421 to 46422, SEQ ID NO: 46433, SEQ ID NOs: 46442 to 46443, SEQ ID NO: 46446, SEQ ID NOs: 46452 to 46454, SEQ ID NO: 46457, SEQ ID NO: 46459, SEQ ID NO: 46462, SEQ ID NO: 46465, SEQ ID NO: 46478, SEQ ID NO: 46484, SEQ ID NO: 46489, SEQ ID NO: 46499, SEQ ID NO: 46512, SEQ ID NO: 46521, SEQ ID NO: 46530, SEQ ID NO: 46536, SEQ ID NO: 46560, SEQ ID NO: 46564, SEQ ID NO: 46570, SEQ ID NO: 46572, SEQ ID NO: 46575, SEQ ID NO: 46579, SEQ ID NO: 46586, SEQ ID NO: 46602, SEQ ID NO: 46616, SEQ ID NO: 46621, SEQ ID NO: 46628, SEQ ID NO: 46637, SEQ ID NO: 46642, SEQ ID NO: 46648, SEQ ID NO: 46652, SEQ ID NO: 46655, SEQ ID NO: 46660, SEQ ID NO: 46663, SEQ ID NOs: 46665 to 46666, SEQ ID NO: 46676, SEQ ID NOs: 46678 to 46679, SEQ ID NO: 46682, SEQ ID NO: 46685, SEQ ID NO: 46689, SEQ ID NO: 46713, SEQ ID NO: 46715, SEQ ID NO: 46736, SEQ ID NO: 46739, SEQ ID NO: 46770, SEQ ID NO: 46777, SEQ ID NO: 46800, SEQ ID NOs: 46823 to 46825, SEQ ID NO: 46831, SEQ ID NO: 46872, SEQ ID NO: 46880, SEQ ID NO: 46897, SEQ ID NO: 46916, SEQ ID NO: 46928, SEQ ID NO: 46937, SEQ ID NO: 46950, SEQ ID NO: 46978, SEQ ID NO: 46981, SEQ ID NO: 46983, SEQ ID NO: 46989, SEQ ID NO: 46991, SEQ ID NO: 46993, SEQ ID NO: 47003, SEQ ID NO: 47006, SEQ ID NO: 47017, SEQ ID NO: 47028, SEQ ID NO: 47045, SEQ ID NO: 47047, SEQ ID NO: 47057, SEQ ID NOs: 47079 to 47080, SEQ ID NO: 47082, SEQ ID NO: 47114, SEQ ID NO: 47119, SEQ ID NO: 47123, SEQ ID NOs: 47137 to 47139, SEQ ID NO: 47151, SEQ ID NO: 47158, SEQ ID NO: 47167, SEQ ID NO: 47172, SEQ ID NO: 47186, SEQ ID NO: 47191, SEQ ID NO: 47206, SEQ ID NO: 47224, SEQ ID NO: 47298, SEQ ID NO: 47316, SEQ ID NO: 47324, SEQ ID NOs: 47331 to 47332, SEQ ID NO: 47335, SEQ ID NO: 47356, SEQ ID NO: 47358, SEQ ID NOs: 47360 to 47361, SEQ ID NOs: 47377 to 47378, SEQ ID NO: 47381, SEQ ID NO: 47405, SEQ ID NO: 47412, SEQ ID NO: 47416, SEQ ID NO: 47422, SEQ ID NO: 47425, SEQ ID NO: 47427, SEQ ID NOs: 47432 to 47433, SEQ ID NO: 47445, SEQ ID NO: 47451, SEQ ID NO: 47460, SEQ ID NO: 47482, SEQ ID NO: 47491, SEQ ID NO: 47509, SEQ ID NO: 47516, SEQ ID NOs: 47533 to 47535, SEQ ID NOs: 47538 to 47539, SEQ ID NO: 47555, SEQ ID NO: 47561, SEQ ID NOs: 47575 to 47576, SEQ ID NO: 47582, SEQ ID NO: 47592, SEQ ID NO: 47614, SEQ ID NO: 47625, SEQ ID NO: 47630, SEQ ID NO: 47637, SEQ ID NO: 47643, SEQ ID NO: 47654, SEQ ID NO: 47673, SEQ ID NO: 47689, SEQ ID NO: 47698, SEQ ID NO: 47701, SEQ ID NO: 47727, SEQ ID NO: 47749, SEQ ID NOs: 47759 to 47760, SEQ ID NO: 47767, SEQ ID NO: 47773, SEQ ID NO: 47782, SEQ ID NO: 47790, SEQ ID NO: 47793, SEQ ID NO: 47799, SEQ ID NO: 47806, SEQ ID NO: 47809, SEQ ID NO: 47834, SEQ ID NO: 47840, SEQ ID NO: 47844, SEQ ID NO: 47848, SEQ ID NO: 47855, SEQ ID NO: 47867, SEQ ID NO: 47890, SEQ ID NO: 47895, SEQ ID NO: 47899, SEQ ID NO: 47902, SEQ ID NO: 47923, SEQ ID NO: 47927, SEQ ID NOs: 47959 to 47960, SEQ ID NO: 47964, SEQ ID NO: 47979, SEQ ID NO: 47984, SEQ ID NO: 47986, SEQ ID NOs: 48030 to 48031, SEQ ID NO: 48034, SEQ ID NO: 48059, SEQ ID NO: 48093, SEQ ID NO: 48107, SEQ ID NO: 48113, SEQ ID NO: 48118, SEQ ID NO: 48121, SEQ ID NO: 48129, SEQ ID NOs: 48138 to 48139, SEQ ID NO: 48144, SEQ ID NO: 48158, SEQ ID NO: 48160, SEQ ID NO: 48162, SEQ ID NO: 48175, SEQ ID NO: 48186, SEQ ID NO: 48203, SEQ ID NO: 48210, SEQ ID NO: 48213, SEQ ID NO: 48220, SEQ ID NO: 48224, SEQ ID NO: 48229, SEQ ID NO: 48258, SEQ ID NO: 48266, SEQ ID NO: 48273, SEQ ID NO: 48280, SEQ ID NO: 48286, SEQ ID NO: 48295, SEQ ID NOs: 48300 to 48301, SEQ ID NOs: 48306 to 48307, SEQ ID NO: 48315, SEQ ID NO: 48347, SEQ ID NO: 48353, SEQ ID NO: 48358, SEQ ID NO: 48366, SEQ ID NO: 48371, SEQ ID NO: 48379, SEQ ID NO: 48387, SEQ ID NO: 48400, SEQ ID NO: 48415, SEQ ID NOs: 48418 to 48419, SEQ ID NO: 48436, SEQ ID NOs: 48438 to 48440, SEQ ID NO: 48443, SEQ ID NO: 48452, SEQ ID NOs: 48461 to 48462, SEQ ID NO: 48466, SEQ ID NO: 48469, SEQ ID NO: 48520, SEQ ID NO: 48537, SEQ ID NO: 48545, SEQ ID NO: 48574, SEQ ID NOs: 48576 to 48578, SEQ ID NO: 48594, SEQ ID NO: 48599, SEQ ID NO: 48614, SEQ ID NO: 48627, SEQ ID NO: 48642, SEQ ID NO: 48648, SEQ ID NO: 48654, SEQ ID NO: 48656, SEQ ID NO: 48666, SEQ ID NOs: 48669 to 48670, SEQ ID NO: 48674, SEQ ID NOs: 48680 to 48681, SEQ ID NO: 48684, SEQ ID NO: 48686, SEQ ID NO: 48692, SEQ ID NO: 48701, SEQ ID NO: 48705, SEQ ID NO: 48714, SEQ ID NO: 48717, SEQ ID NO: 48735, SEQ ID NO: 48738, SEQ ID NO: 48749, SEQ ID NO: 48751, SEQ ID NO: 48764, SEQ ID NO: 48769, SEQ ID NO: 48793, SEQ ID NO: 48796, SEQ ID NOs: 48799 to 48800, SEQ ID NOs: 48802 to 48803, SEQ ID NO: 48818, SEQ ID NO: 48832, SEQ ID NO: 48834, SEQ ID NO: 48838, SEQ ID NO: 48845, SEQ ID NO: 48856, SEQ ID NO: 48877, SEQ ID NO: 48884, SEQ ID NO: 48903, SEQ ID NO: 48936, SEQ ID NO: 48947, SEQ ID NOs: 48968 to 48970, SEQ ID NO: 48974, SEQ ID NOs: 48981 to 48982, SEQ ID NO: 48997, SEQ ID NOs: 49013 to 49014, SEQ ID NOs: 49019 to 49020, SEQ ID NO: 49031, SEQ ID NO: 49033, SEQ ID NO: 49043, SEQ ID NO: 49052, SEQ ID NOs: 49061 to 49062, SEQ ID NO: 49068, SEQ ID NO: 49071, SEQ ID NO: 49086, SEQ ID NO: 49102, SEQ ID NO: 49111, SEQ ID NO: 49156, SEQ ID NO: 49164, SEQ ID NO: 49173, SEQ ID NO: 49176, SEQ ID NO: 49183, SEQ ID NO: 49185, SEQ ID NOs: 49200 to 49201, SEQ ID NO: 49209, SEQ ID NO: 49220, SEQ ID NO: 49247, SEQ ID NO: 49251, SEQ ID NO: 49256, SEQ ID NO: 49263, SEQ ID NOs: 49273 to 49274, SEQ ID NOs: 49280 to 49281, SEQ ID NO: 49291, SEQ ID NOs: 49294 to 49295, SEQ ID NO: 49298, SEQ ID NO: 49309, SEQ ID NO: 49319, SEQ ID NO: 49326, SEQ ID NO: 49330, SEQ ID NO: 49340, SEQ ID NOs: 49351 to 49352, SEQ ID NO: 49360, SEQ ID NOs: 49376 to 49377, SEQ ID NO: 49384, SEQ ID NO: 49393, SEQ ID NO: 49395, SEQ ID NO: 49399, SEQ ID NO: 49406, SEQ ID NO: 49411, SEQ ID NOs: 49443 to 49444, SEQ ID NO: 49452, SEQ ID NO: 49462, SEQ ID NO: 49474, SEQ ID NO: 49487, SEQ ID NO: 49499, SEQ ID NO: 49525, SEQ ID NO: 49537, SEQ ID NO: 49540, SEQ ID NO: 49557, SEQ ID NO: 49572, SEQ ID NO: 49584, SEQ ID NO: 49597, SEQ ID NO: 49626, SEQ ID NO: 49630, SEQ ID NO: 49646, SEQ ID NO: 49658, SEQ ID NO: 49671, SEQ ID NO: 49681, SEQ ID NO: 49703, SEQ ID NO: 49728, SEQ ID NO: 49730, SEQ ID NO: 49737, SEQ ID NOs: 49742 to 49743, SEQ ID NOs: 49766 to 49767, SEQ ID NO: 49772, SEQ ID NO: 49782, SEQ ID NOs: 49787 to 49788, SEQ ID NO: 49793, SEQ ID NO: 49796, SEQ ID NO: 49805, SEQ ID NO: 49811, SEQ ID NO: 49823, SEQ ID NO: 49838, SEQ ID NO: 49850, SEQ ID NOs: 49859 to 49860, SEQ ID NO: 49873, SEQ ID NO: 49883, SEQ ID NO: 49892, SEQ ID NO: 49912, SEQ ID NO: 49928, SEQ ID NO: 49948, SEQ ID NO: 49961, SEQ ID NO: 49965, SEQ ID NO: 49987, SEQ ID NO: 49997, SEQ ID NOs: 50017 to 50018, SEQ ID NO: 50020, SEQ ID NO: 50022, SEQ ID NO: 50045, SEQ ID NO: 50062, SEQ ID NO: 50073, SEQ ID NO: 50079, SEQ ID NO: 50090, SEQ ID NO: 50107, SEQ ID NOs: 50111 to 50112, SEQ ID NO: 50123, SEQ ID NO: 50138, SEQ ID NOs: 50165 to 50167, SEQ ID NOs: 50227 to 50228, SEQ ID NO: 50243, SEQ ID NO: 50250, SEQ ID NO: 50254, SEQ ID NO: 50282, SEQ ID NO: 50284, SEQ ID NO: 50290, SEQ ID NO: 50297, SEQ ID NO: 50305, SEQ ID NO: 50309, SEQ ID NO: 50319, SEQ ID NO: 50331, SEQ ID NO: 50334, SEQ ID NO: 50339, SEQ ID NO: 50366, SEQ ID NO: 50388, SEQ ID NO: 50392, SEQ ID NO: 50394, SEQ ID NOs: 50400 to 50401, SEQ ID NO: 50418, SEQ ID NO: 50423, SEQ ID NO: 50428, SEQ ID NO: 50437, SEQ ID NO: 50443, SEQ ID NO: 50450, SEQ ID NO: 50464, SEQ ID NO: 50485, SEQ ID NO: 50494, SEQ ID NO: 50496, SEQ ID NO: 50499, SEQ ID NO: 50526, SEQ ID NO: 50528, SEQ ID NO: 50532, SEQ ID NO: 50538, SEQ ID NO: 50554, SEQ ID NO: 50557, SEQ ID NO: 50560, SEQ ID NO: 50564, SEQ ID NO: 50574, SEQ ID NO: 50585, SEQ ID NO: 50617, SEQ ID NO: 50632, SEQ ID NO: 50634, SEQ ID NO: 50644, SEQ ID NO: 50654, SEQ ID NO: 50678, SEQ ID NO: 50699, SEQ ID NO: 50714, SEQ ID NOs: 50728 to 50729, SEQ ID NO: 50735, SEQ ID NO: 50741, SEQ ID NO: 50744, SEQ ID NO: 50765, SEQ ID NO: 50769, SEQ ID NO: 50793, SEQ ID NO: 50818, SEQ ID NO: 50822, SEQ ID NO: 50826, SEQ ID NO: 50835, SEQ ID NO: 50842, SEQ ID NO: 50847, SEQ ID NO: 50849, SEQ ID NO: 50851, SEQ ID NO: 50893, SEQ ID NO: 50918, SEQ ID NOs: 50935 to 50936, SEQ ID NOs: 50941 to 50944, SEQ ID NOs: 50960 to 50962, SEQ ID NOs: 50975 to 50976, SEQ ID NOs: 51008 to 51009, SEQ ID NO: 51012, SEQ ID NOs: 51021 to 51022, SEQ ID NO: 51046, SEQ ID NO: 51062, SEQ ID NOs: 51068 to 51071, SEQ ID NOs: 51102 to 51104, SEQ ID NO: 51118, SEQ ID NOs: 51168 to 51169, SEQ ID NO: 51214, SEQ ID NO: 51235, SEQ ID NO: 51239, SEQ ID NO: 51241, SEQ ID NO: 51243, SEQ ID NO: 51257, SEQ ID NOs: 51263 to 51266, SEQ ID NOs: 51295 to 51297, SEQ ID NO: 51313, SEQ ID NO: 51405, SEQ ID NOs: 51413 to 51417, SEQ ID NO: 51524, SEQ ID NO: 51526, SEQ ID NO: 51693, SEQ ID NO: 51717, SEQ ID NO: 51762, SEQ ID NO: 51765, SEQ ID NO: 51853, SEQ ID NO: 51878, SEQ ID NO: 52035, SEQ ID NO: 52179, SEQ ID NO: 52275, SEQ ID NO: 52290, SEQ ID NO: 52379, SEQ ID NO: 52463, SEQ ID NO: 52497, SEQ ID NO: 52515, SEQ ID NO: 52652, SEQ ID NO: 52660, SEQ ID NO: 52679, SEQ ID NO: 52686, SEQ ID NO: 52746, SEQ ID NO: 52758, SEQ ID NO: 52816, SEQ ID NO: 52944, SEQ ID NO: 52984, SEQ ID NO: 52988, SEQ ID NO: 52991, SEQ ID NO: 53045, SEQ ID NO: 53118, SEQ ID NO: 53166, SEQ ID NO: 53338, SEQ ID NO: 53382, SEQ ID NO: 53464, SEQ ID NO: 53478, SEQ ID NO: 53511, SEQ ID NO: 53519, SEQ ID NO: 53548, SEQ ID NO: 53581, SEQ ID NO: 53653, SEQ ID NO: 53968, SEQ ID NO: 54024, SEQ ID NO: 54038, SEQ ID NO: 54045, SEQ ID NO: 54080, SEQ ID NO: 54097, SEQ ID NO: 54111, SEQ ID NO: 54238, SEQ ID NO: 54251, SEQ ID NO: 54269, SEQ ID NO: 54409, SEQ ID NO: 54418, SEQ ID NO: 54442, SEQ ID NO: 54473, SEQ ID NO: 54543, SEQ ID NO: 54713, SEQ ID NO: 54719, SEQ ID NO: 54727, SEQ ID NO: 54772, SEQ ID NO: 54788, SEQ ID NO: 54863, SEQ ID NO: 54877, SEQ ID NO: 54945, SEQ ID NO: 54960, SEQ ID NO: 55004, SEQ ID NO: 55109, SEQ ID NO: 55207, SEQ ID NO: 55230, SEQ ID NO: 55300, SEQ ID NO: 55355, SEQ ID NO: 55437, SEQ ID NO: 55516, SEQ ID NO: 55695, SEQ ID NO: 55758, SEQ ID NO: 55801, SEQ ID NO: 55814, SEQ ID NO: 55875, SEQ ID NO: 55879, SEQ ID NO: 55886, SEQ ID NO: 55911, SEQ ID NO: 55986, SEQ ID NO: 56043, SEQ ID NO: 56052, SEQ ID NO: 56175, SEQ ID NO: 56240, SEQ ID NO: 56277, SEQ ID NO: 56352, SEQ ID NO: 56418, SEQ ID NO: 56435, SEQ ID NO: 56521, SEQ ID NO: 56593, SEQ ID NO: 56609, SEQ ID NO: 56629, SEQ ID NOs: 56649 to 56650, SEQ ID NO: 56793, SEQ ID NO: 56836, SEQ ID NO: 56852, SEQ ID NO: 56902, SEQ ID NO: 57155, SEQ ID NO: 57157, SEQ ID NO: 57265, SEQ ID NO: 57278, SEQ ID NO: 57323, SEQ ID NO: 57472, SEQ ID NO: 57535, SEQ ID NO: 57550, SEQ ID NO: 57561, SEQ ID NO: 57568, SEQ ID NO: 57639, SEQ ID NO: 57655, SEQ ID NO: 57790, SEQ ID NO: 57811, SEQ ID NO: 57904, SEQ ID NO: 57944, SEQ ID NO: 58040, SEQ ID NO: 58064, SEQ ID NO: 58075, SEQ ID NO: 58145, SEQ ID NO: 58199, SEQ ID NO: 58223, SEQ ID NO: 58226, SEQ ID NO: 58309, SEQ ID NO: 58349, SEQ ID NO: 58395, SEQ ID NO: 58411, SEQ ID NO: 58433, SEQ ID NO: 58547, SEQ ID NO: 58589, SEQ ID NO: 58679, SEQ ID NOs: 58683 to 58684, SEQ ID NO: 58815, SEQ ID NO: 58823, SEQ ID NO: 58855, SEQ ID NO: 58932, SEQ ID NO: 59223, SEQ ID NO: 59246, SEQ ID NO: 59248, SEQ ID NO: 59530, SEQ ID NO: 59622, SEQ ID NO: 59755, SEQ ID NO: 59757, SEQ ID NO: 59775, SEQ ID NO: 59816, SEQ ID NO: 59821, SEQ ID NO: 59828, SEQ ID NO: 59856, SEQ ID NO: 59871, SEQ ID NO: 59873, SEQ ID NO: 59875, SEQ ID NO: 59960, SEQ ID NO: 59967, SEQ ID NO: 60005, SEQ ID NOs: 60046 to 60047, SEQ ID NO: 60081, SEQ ID NO: 60224, SEQ ID NO: 60228, SEQ ID NO: 60276, SEQ ID NO: 60289, SEQ ID NO: 60292, SEQ ID NOs: 60422 to 60423, SEQ ID NO: 60444, SEQ ID NOs: 60456 to 68237, SEQ ID NO: 211911, SEQ ID NOs: 212086 to 212095, SEQ ID NOs: 212435 to 212440, SEQ ID NOs: 212681 to 212684, SEQ ID NOs: 212858 to 212860, SEQ ID NOs: 213516 to 213517, SEQ ID NOs: 213529 to 213531, SEQ ID NOs: 213602 to 213611, SEQ ID NOs: 213719 to 213720, SEQ ID NO: 213899, SEQ ID NOs: 214004 to 214012, SEQ ID NO: 214607, SEQ ID NOs: 214647 to 214649, SEQ ID NOs: 214672 to 214679, SEQ ID NOs: 214774 to 214775, SEQ ID NO: 214777, SEQ ID NO: 214779, SEQ ID NO: 214782, SEQ ID NOs: 215373 to 215415, SEQ ID NO: 215494, SEQ ID NO: 215497, SEQ ID NO: 215679, SEQ ID NO: 216244, SEQ ID NO: 216246, SEQ ID NOs: 216383 to 216401, SEQ ID NOs: 217184 to 217192, SEQ ID NO: 217200, SEQ ID NO: 217362, SEQ ID NOs: 217708 to 217712, SEQ ID NO: 217719, SEQ ID NO: 219238, SEQ ID NOs: 219742 to 219744, SEQ ID NO: 219747, SEQ ID NO: 219749, SEQ ID NO: 219751, SEQ ID NOs: 219773 to 219781, SEQ ID NOs: 219994 to 220030, SEQ ID NOs: 220318 to 220319, SEQ ID NO: 220327, SEQ ID NO: 220670, SEQ ID NO: 220815, SEQ ID NO: 220820, SEQ ID NOs: 221197 to 221234, SEQ ID NO: 221998, SEQ ID NO: 222000, SEQ ID NO: 223092, SEQ ID NO: 223095, SEQ ID NO: 223097, SEQ ID NO: 223099, SEQ ID NO: 223119, SEQ ID NO: 223121, SEQ ID NOs: 223184 to 223190, SEQ ID NOs: 223250 to 223283, SEQ ID NO: 223319, SEQ ID NO: 230922, SEQ ID NOs: 232805 to 232806, SEQ ID NO: 232846, or SEQ ID NOs: 236016 to 247058.

In some embodiments, the amino acid sequence for a MHC class I and/or MHC class II peptides may be used to create a single target (individual) or combined peptide vaccine for the MAGC1 protein having between about 2 and about 40 peptides. In some embodiments, any one of the peptides in the vaccine for the MAGC1 protein comprises one or more of the SEQ ID NO: 41352, SEQ ID NO: 41478, SEQ ID NO: 41495, SEQ ID NO: 41725, SEQ ID NO: 41847, SEQ ID NO: 42129, SEQ ID NO: 42135, SEQ ID NO: 42168, SEQ ID NO: 42170, SEQ ID NO: 42195, SEQ ID NO: 42218, SEQ ID NO: 42229, SEQ ID NO: 42458, SEQ ID NO: 42545, SEQ ID NO: 42628, SEQ ID NO: 42653, SEQ ID NO: 42685, SEQ ID NO: 42703, SEQ ID NO: 42872, SEQ ID NO: 43008, SEQ ID NO: 43046, SEQ ID NO: 43083, SEQ ID NO: 43333, SEQ ID NO: 43429, SEQ ID NO: 43564, SEQ ID NO: 43780, SEQ ID NO: 43836, SEQ ID NO: 43881, SEQ ID NO: 43898, SEQ ID NO: 43932, SEQ ID NO: 44048, SEQ ID NO: 44181, SEQ ID NO: 44328, SEQ ID NO: 44456, SEQ ID NO: 44523, SEQ ID NO: 44566, SEQ ID NO: 44773, SEQ ID NO: 44877, SEQ ID NO: 45197, SEQ ID NO: 45385, SEQ ID NO: 45450, SEQ ID NO: 45556, SEQ ID NO: 45580, SEQ ID NO: 45584, SEQ ID NO: 45599, SEQ ID NO: 45765, SEQ ID NO: 45829, SEQ ID NO: 45894, SEQ ID NO: 45915, SEQ ID NO: 46273, SEQ ID NO: 46400, SEQ ID NO: 46421, SEQ ID NO: 46457, SEQ ID NO: 46459, SEQ ID NO: 46484, SEQ ID NO: 46666, SEQ ID NO: 46678, SEQ ID NO: 46689, SEQ ID NO: 46981, SEQ ID NO: 46991, SEQ ID NO: 46993, SEQ ID NO: 47047, SEQ ID NO: 47151, SEQ ID NO: 47324, SEQ ID NO: 47432, SEQ ID NO: 47592, SEQ ID NO: 47673, SEQ ID NO: 47895, SEQ ID NO: 47960, SEQ ID NO: 47964, SEQ ID NO: 47979, SEQ ID NO: 47984, SEQ ID NO: 48034, SEQ ID NO: 48113, SEQ ID NO: 48118, SEQ ID NO: 48300, SEQ ID NO: 48436, SEQ ID NOs: 48461 to 48462, SEQ ID NO: 48469, SEQ ID NO: 48574, SEQ ID NO: 48680, SEQ ID NO: 48796, SEQ ID NO: 48832, SEQ ID NO: 48838, SEQ ID NO: 48845, SEQ ID NO: 48877, SEQ ID NO: 48947, SEQ ID NO: 49019, SEQ ID NO: 49111, SEQ ID NO: 49176, SEQ ID NO: 49263, SEQ ID NO: 49395, SEQ ID NO: 49462, SEQ ID NO: 49557, SEQ ID NO: 49823, SEQ ID NO: 49883, SEQ ID NO: 50062, SEQ ID NO: 50167, SEQ ID NO: 50305, SEQ ID NO: 50394, SEQ ID NO: 50401, SEQ ID NO: 50423, SEQ ID NO: 50428, SEQ ID NO: 50443, SEQ ID NO: 50450, SEQ ID NO: 50564, SEQ ID NO: 50574, SEQ ID NO: 50632, SEQ ID NO: 50678, SEQ ID NOs: 68238 to 95592, and SEQ ID NOs: 247059 to 281349. In some embodiments, any one of the peptides in the MAGC1 vaccine comprise an amino acid sequence 80, 81, 82, 83, 84, 85, 86, 87, 88, 89, 90, 91, 92, 93, 94, 95, 96, 97, 98 or 99% identical to SEQ ID NO: 41352, SEQ ID NO: 41478, SEQ ID NO: 41495, SEQ ID NO: 41725, SEQ ID NO: 41847, SEQ ID NO: 42129, SEQ ID NO: 42135, SEQ ID NO: 42168, SEQ ID NO: 42170, SEQ ID NO: 42195, SEQ ID NO: 42218, SEQ ID NO: 42229, SEQ ID NO: 42458, SEQ ID NO: 42545, SEQ ID NO: 42628, SEQ ID NO: 42653, SEQ ID NO: 42685, SEQ ID NO: 42703, SEQ ID NO: 42872, SEQ ID NO: 43008, SEQ ID NO: 43046, SEQ ID NO: 43083, SEQ ID NO: 43333, SEQ ID NO: 43429, SEQ ID NO: 43564, SEQ ID NO: 43780, SEQ ID NO: 43836, SEQ ID NO: 43881, SEQ ID NO: 43898, SEQ ID NO: 43932, SEQ ID NO: 44048, SEQ ID NO: 44181, SEQ ID NO: 44328, SEQ ID NO: 44456, SEQ ID NO: 44523, SEQ ID NO: 44566, SEQ ID NO: 44773, SEQ ID NO: 44877, SEQ ID NO: 45197, SEQ ID NO: 45385, SEQ ID NO: 45450, SEQ ID NO: 45556, SEQ ID NO: 45580, SEQ ID NO: 45584, SEQ ID NO: 45599, SEQ ID NO: 45765, SEQ ID NO: 45829, SEQ ID NO: 45894, SEQ ID NO: 45915, SEQ ID NO: 46273, SEQ ID NO: 46400, SEQ ID NO: 46421, SEQ ID NO: 46457, SEQ ID NO: 46459, SEQ ID NO: 46484, SEQ ID NO: 46666, SEQ ID NO: 46678, SEQ ID NO: 46689, SEQ ID NO: 46981, SEQ ID NO: 46991, SEQ ID NO: 46993, SEQ ID NO: 47047, SEQ ID NO: 47151, SEQ ID NO: 47324, SEQ ID NO: 47432, SEQ ID NO: 47592, SEQ ID NO: 47673, SEQ ID NO: 47895, SEQ ID NO: 47960, SEQ ID NO: 47964, SEQ ID NO: 47979, SEQ ID NO: 47984, SEQ ID NO: 48034, SEQ ID NO: 48113, SEQ ID NO: 48118, SEQ ID NO: 48300, SEQ ID NO: 48436, SEQ ID NOs: 48461 to 48462, SEQ ID NO: 48469, SEQ ID NO: 48574, SEQ ID NO: 48680, SEQ ID NO: 48796, SEQ ID NO: 48832, SEQ ID NO: 48838, SEQ ID NO: 48845, SEQ ID NO: 48877, SEQ ID NO: 48947, SEQ ID NO: 49019, SEQ ID NO: 49111, SEQ ID NO: 49176, SEQ ID NO: 49263, SEQ ID NO: 49395, SEQ ID NO: 49462, SEQ ID NO: 49557, SEQ ID NO: 49823, SEQ ID NO: 49883, SEQ ID NO: 50062, SEQ ID NO: 50167, SEQ ID NO: 50305, SEQ ID NO: 50394, SEQ ID NO: 50401, SEQ ID NO: 50423, SEQ ID NO: 50428, SEQ ID NO: 50443, SEQ ID NO: 50450, SEQ ID NO: 50564, SEQ ID NO: 50574, SEQ ID NO: 50632, SEQ ID NO: 50678, SEQ ID NOs: 68238 to 95592, or SEQ ID NOs: 247059 to 281349.

In some embodiments, the amino acid sequence for a MHC class I and/or MHC class II peptides may be used to create a single target (individual) or combined peptide vaccine for the MAGC3 protein having between about 2 and about 40 peptides. In some embodiments, any one of the peptides in the vaccine for the MAGC3 protein comprises one or more of the SEQ ID NO: 41647, SEQ ID NO: 50668, SEQ ID NO: 50905, SEQ ID NOs: 51039 to 51040, SEQ ID NO: 68257, SEQ ID NO: 68285, SEQ ID NO: 68288, SEQ ID NO: 68290, SEQ ID NO: 68305, SEQ ID NO: 68389, SEQ ID NO: 68419, SEQ ID NO: 68470, SEQ ID NO: 68510, SEQ ID NO: 68519, SEQ ID NO: 68592, SEQ ID NO: 68603, SEQ ID NO: 68684, SEQ ID NO: 68688, SEQ ID NO: 68747, SEQ ID NO: 68760, SEQ ID NO: 68778, SEQ ID NO: 68786, SEQ ID NO: 68855, SEQ ID NO: 68898, SEQ ID NO: 68900, SEQ ID NO: 68927, SEQ ID NO: 68961, SEQ ID NO: 69026, SEQ ID NO: 69041, SEQ ID NO: 69047, SEQ ID NO: 69148, SEQ ID NO: 69173, SEQ ID NO: 69180, SEQ ID NO: 69192, SEQ ID NO: 69227, SEQ ID NO: 69311, SEQ ID NO: 69330, SEQ ID NO: 69333, SEQ ID NO: 69346, SEQ ID NO: 69356, SEQ ID NO: 69393, SEQ ID NO: 69421, SEQ ID NO: 69437, SEQ ID NO: 69451, SEQ ID NO: 69500, SEQ ID NO: 69505, SEQ ID NO: 69517, SEQ ID NO: 69540, SEQ ID NO: 69559, SEQ ID NO: 69571, SEQ ID NO: 69586, SEQ ID NO: 69589, SEQ ID NO: 69591, SEQ ID NO: 69619, SEQ ID NO: 69631, SEQ ID NO: 69633, SEQ ID NO: 69644, SEQ ID NO: 69649, SEQ ID NO: 69747, SEQ ID NO: 69764, SEQ ID NO: 69767, SEQ ID NO: 69790, SEQ ID NO: 69832, SEQ ID NO: 69836, SEQ ID NO: 69882, SEQ ID NO: 69999, SEQ ID NO: 70012, SEQ ID NO: 70036, SEQ ID NO: 70050, SEQ ID NO: 70066, SEQ ID NO: 70069, SEQ ID NO: 70109, SEQ ID NO: 70159, SEQ ID NO: 70165, SEQ ID NO: 70175, SEQ ID NO: 70177, SEQ ID NO: 70188, SEQ ID NO: 70284, SEQ ID NO: 70323, SEQ ID NO: 70326, SEQ ID NO: 70428, SEQ ID NO: 70455, SEQ ID NO: 70570, SEQ ID NO: 70606, SEQ ID NO: 70635, SEQ ID NO: 70676, SEQ ID NO: 70692, SEQ ID NO: 70716, SEQ ID NO: 70728, SEQ ID NO: 70735, SEQ ID NO: 70750, SEQ ID NO: 70764, SEQ ID NO: 70770, SEQ ID NO: 70806, SEQ ID NO: 70968, SEQ ID NO: 70997, SEQ ID NO: 71049, SEQ ID NO: 71075, SEQ ID NO: 71090, SEQ ID NO: 71117, SEQ ID NO: 71151, SEQ ID NO: 71176, SEQ ID NO: 71193, SEQ ID NO: 71203, SEQ ID NO: 71239, SEQ ID NO: 71247, SEQ ID NO: 71249, SEQ ID NO: 71275, SEQ ID NO: 71287, SEQ ID NO: 71328, SEQ ID NOs: 71359 to 71360, SEQ ID NOs: 71367 to 71368, SEQ ID NO: 71392, SEQ ID NO: 71414, SEQ ID NO: 71449, SEQ ID NO: 71476, SEQ ID NO: 71482, SEQ ID NO: 71543, SEQ ID NO: 71547, SEQ ID NO: 71560, SEQ ID NO: 71585, SEQ ID NO: 71612, SEQ ID NO: 71620, SEQ ID NO: 71628, SEQ ID NO: 71636, SEQ ID NO: 71673, SEQ ID NOs: 71688 to 71689, SEQ ID NO: 71696, SEQ ID NO: 71700, SEQ ID NO: 71718, SEQ ID NO: 71725, SEQ ID NO: 71807, SEQ ID NO: 71919, SEQ ID NO: 71935, SEQ ID NO: 71943, SEQ ID NO: 71948, SEQ ID NOs: 71987 to 71988, SEQ ID NO: 72045, SEQ ID NO: 72055, SEQ ID NO: 72076, SEQ ID NO: 72085, SEQ ID NO: 72102, SEQ ID NO: 72159, SEQ ID NO: 72183, SEQ ID NO: 72216, SEQ ID NO: 72241, SEQ ID NO: 72331, SEQ ID NO: 72364, SEQ ID NO: 72372, SEQ ID NO: 72390, SEQ ID NO: 72448, SEQ ID NO: 72528, SEQ ID NO: 72595, SEQ ID NO: 72604, SEQ ID NO: 72648, SEQ ID NO: 72667, SEQ ID NO: 72685, SEQ ID NO: 72721, SEQ ID NO: 72751, SEQ ID NO: 72755, SEQ ID NO: 72805, SEQ ID NO: 72810, SEQ ID NO: 72831, SEQ ID NO: 72837, SEQ ID NO: 72862, SEQ ID NO: 72885, SEQ ID NO: 72989, SEQ ID NO: 73014, SEQ ID NOs: 73045 to 73046, SEQ ID NO: 73086, SEQ ID NO: 73094, SEQ ID NO: 73113, SEQ ID NO: 73122, SEQ ID NO: 73161, SEQ ID NO: 73191, SEQ ID NO: 73224, SEQ ID NOs: 73232 to 73233, SEQ ID NO: 73238, SEQ ID NO: 73290, SEQ ID NO: 73327, SEQ ID NO: 73377, SEQ ID NO: 73382, SEQ ID NO: 73404, SEQ ID NO: 73406, SEQ ID NO: 73422, SEQ ID NOs: 73428 to 73429, SEQ ID NO: 73466, SEQ ID NO: 73475, SEQ ID NO: 73521, SEQ ID NO: 73523, SEQ ID NO: 73532, SEQ ID NO: 73550, SEQ ID NO: 73560, SEQ ID NO: 73591, SEQ ID NO: 73597, SEQ ID NO: 73644, SEQ ID NO: 73657, SEQ ID NO: 73660, SEQ ID NO: 73689, SEQ ID NO: 73729, SEQ ID NO: 73733, SEQ ID NO: 73873, SEQ ID NO: 73886, SEQ ID NO: 73930, SEQ ID NO: 73957, SEQ ID NOs: 73991 to 73992, SEQ ID NO: 74045, SEQ ID NO: 74047, SEQ ID NO: 74072, SEQ ID NO: 74080, SEQ ID NOs: 74096 to 74097, SEQ ID NO: 74107, SEQ ID NO: 74203, SEQ ID NO: 74208, SEQ ID NO: 74210, SEQ ID NO: 74238, SEQ ID NO: 74302, SEQ ID NO: 74350, SEQ ID NO: 74352, SEQ ID NO: 74411, SEQ ID NO: 74448, SEQ ID NO: 74473, SEQ ID NO: 74482, SEQ ID NO: 74515, SEQ ID NO: 74527, SEQ ID NO: 74560, SEQ ID NO: 74616, SEQ ID NO: 74649, SEQ ID NO: 74672, SEQ ID NO: 74674, SEQ ID NO: 74737, SEQ ID NO: 74782, SEQ ID NO: 74808, SEQ ID NO: 74810, SEQ ID NO: 74835, SEQ ID NO: 74886, SEQ ID NO: 74901, SEQ ID NO: 74946, SEQ ID NOs: 74975 to 74976, SEQ ID NO: 75017, SEQ ID NO: 75021, SEQ ID NO: 75040, SEQ ID NO: 75049, SEQ ID NO: 75063, SEQ ID NO: 75066, SEQ ID NO: 75072, SEQ ID NO: 75092, SEQ ID NO: 75094, SEQ ID NO: 75099, SEQ ID NO: 75111, SEQ ID NO: 75148, SEQ ID NO: 75245, SEQ ID NO: 75269, SEQ ID NO: 75388, SEQ ID NO: 75403, SEQ ID NO: 75429, SEQ ID NO: 75455, SEQ ID NO: 75470, SEQ ID NO: 75489, SEQ ID NO: 75506, SEQ ID NO: 75529, SEQ ID NO: 75547, SEQ ID NO: 75551, SEQ ID NOs: 75576 to 75577, SEQ ID NO: 75595, SEQ ID NO: 75701, SEQ ID NO: 75716, SEQ ID NO: 75747, SEQ ID NO: 75757, SEQ ID NO: 75762, SEQ ID NO: 75766, SEQ ID NO: 75874, SEQ ID NO: 75915, SEQ ID NO: 75933, SEQ ID NO: 75975, SEQ ID NO: 75979, SEQ ID NO: 76016, SEQ ID NO: 76023, SEQ ID NO: 76034, SEQ ID NO: 76040, SEQ ID NO: 76064, SEQ ID NO: 76076, SEQ ID NO: 76102, SEQ ID NOs: 76147 to 76148, SEQ ID NO: 76189, SEQ ID NO: 76199, SEQ ID NO: 76369, SEQ ID NO: 76375, SEQ ID NO: 76397, SEQ ID NO: 76410, SEQ ID NO: 76435, SEQ ID NO: 76446, SEQ ID NO: 76451, SEQ ID NOs: 76456 to 76458, SEQ ID NO: 76492, SEQ ID NO: 76544, SEQ ID NO: 76569, SEQ ID NO: 76574, SEQ ID NO: 76611, SEQ ID NO: 76654, SEQ ID NO: 76710, SEQ ID NO: 76753, SEQ ID NO: 76769, SEQ ID NO: 76781, SEQ ID NO: 76797, SEQ ID NO: 76803, SEQ ID NO: 76858, SEQ ID NO: 76860, SEQ ID NO: 76879, SEQ ID NO: 76943, SEQ ID NO: 76971, SEQ ID NO: 76981, SEQ ID NO: 77091, SEQ ID NO: 77133, SEQ ID NOs: 77193 to 77194, SEQ ID NO: 77210, SEQ ID NO: 77219, SEQ ID NO: 77237, SEQ ID NO: 77246, SEQ ID NO: 77251, SEQ ID NO: 77281, SEQ ID NO: 77293, SEQ ID NO: 77323, SEQ ID NO: 77334, SEQ ID NO: 77339, SEQ ID NO: 77396, SEQ ID NO: 77423, SEQ ID NO: 77433, SEQ ID NO: 77437, SEQ ID NO: 77442, SEQ ID NO: 77453, SEQ ID NO: 77485, SEQ ID NO: 77579, SEQ ID NO: 77627, SEQ ID NO: 77639, SEQ ID NO: 77644, SEQ ID NO: 77703, SEQ ID NO: 77773, SEQ ID NO: 77814, SEQ ID NO: 77868, SEQ ID NO: 77874, SEQ ID NO: 77900, SEQ ID NO: 77925, SEQ ID NO: 77995, SEQ ID NO: 78017, SEQ ID NO: 78083, SEQ ID NO: 78086, SEQ ID NO: 78090, SEQ ID NO: 78131, SEQ ID NO: 78139, SEQ ID NO: 78228, SEQ ID NO: 78248, SEQ ID NO: 78260, SEQ ID NO: 78346, SEQ ID NO: 78352, SEQ ID NO: 78377, SEQ ID NO: 78416, SEQ ID NO: 78421, SEQ ID NO: 78440, SEQ ID NO: 78521, SEQ ID NO: 78530, SEQ ID NO: 78532, SEQ ID NO: 78546, SEQ ID NO: 78600, SEQ ID NO: 78631, SEQ ID NO: 78671, SEQ ID NO: 78709, SEQ ID NO: 78714, SEQ ID NO: 78730, SEQ ID NO: 78738, SEQ ID NO: 78810, SEQ ID NO: 78855, SEQ ID NO: 78883, SEQ ID NO: 78917, SEQ ID NOs: 78919 to 78920, SEQ ID NO: 78928, SEQ ID NO: 79035, SEQ ID NO: 79048, SEQ ID NO: 79056, SEQ ID NO: 79086, SEQ ID NO: 79091, SEQ ID NO: 79095, SEQ ID NO: 79107, SEQ ID NO: 79109, SEQ ID NO: 79136, SEQ ID NO: 79142, SEQ ID NO: 79147, SEQ ID NO: 79151, SEQ ID NO: 79194, SEQ ID NO: 79196, SEQ ID NO: 79227, SEQ ID NO: 79247, SEQ ID NO: 79253, SEQ ID NO: 79255, SEQ ID NO: 79269, SEQ ID NO: 79310, SEQ ID NO: 79331, SEQ ID NO: 79357, SEQ ID NO: 79406, SEQ ID NO: 79437, SEQ ID NO: 79448, SEQ ID NO: 79453, SEQ ID NO: 79480, SEQ ID NO: 79483, SEQ ID NO: 79486, SEQ ID NO: 79504, SEQ ID NO: 79508, SEQ ID NO: 79516, SEQ ID NO: 79548, SEQ ID NO: 79575, SEQ ID NO: 79588, SEQ ID NO: 79592, SEQ ID NO: 79609, SEQ ID NO: 79626, SEQ ID NO: 79640, SEQ ID NO: 79697, SEQ ID NO: 79746, SEQ ID NO: 79751, SEQ ID NO: 79766, SEQ ID NO: 79784, SEQ ID NO: 79787, SEQ ID NO: 79816, SEQ ID NO: 79834, SEQ ID NO: 79853, SEQ ID NO: 79858, SEQ ID NO: 79861, SEQ ID NO: 79874, SEQ ID NO: 79877, SEQ ID NO: 79906, SEQ ID NO: 79909, SEQ ID NO: 79939, SEQ ID NO: 79958, SEQ ID NO: 79987, SEQ ID NO: 80000, SEQ ID NO: 80027, SEQ ID NO: 80040, SEQ ID NO: 80139, SEQ ID NO: 80141, SEQ ID NO: 80212, SEQ ID NO: 80232, SEQ ID NO: 80237, SEQ ID NO: 80241, SEQ ID NO: 80318, SEQ ID NO: 80320, SEQ ID NOs: 80367 to 80368, SEQ ID NO: 80398, SEQ ID NO: 80421, SEQ ID NO: 80461, SEQ ID NO: 80486, SEQ ID NO: 80513, SEQ ID NO: 80527, SEQ ID NO: 80555, SEQ ID NO: 80574, SEQ ID NO: 80583, SEQ ID NO: 80627, SEQ ID NO: 80673, SEQ ID NOs: 80703 to 80704, SEQ ID NOs: 80718 to 80719, SEQ ID NO: 80725, SEQ ID NO: 80796, SEQ ID NO: 80804, SEQ ID NO: 80833, SEQ ID NO: 80869, SEQ ID NO: 80903, SEQ ID NO: 80931, SEQ ID NO: 80936, SEQ ID NO: 80946, SEQ ID NO: 80990, SEQ ID NO: 81021, SEQ ID NO: 81042, SEQ ID NO: 81046, SEQ ID NO: 81054, SEQ ID NO: 81066, SEQ ID NO: 81145, SEQ ID NO: 81166, SEQ ID NO: 81168, SEQ ID NO: 81175, SEQ ID NO: 81185, SEQ ID NO: 81207, SEQ ID NO: 81251, SEQ ID NO: 81259, SEQ ID NO: 81302, SEQ ID NO: 81337, SEQ ID NO: 81342, SEQ ID NO: 81386, SEQ ID NO: 81428, SEQ ID NO: 81446, SEQ ID NO: 81458, SEQ ID NO: 81488, SEQ ID NO: 81505, SEQ ID NO: 81517, SEQ ID NO: 81566, SEQ ID NO: 81687, SEQ ID NO: 81690, SEQ ID NO: 81694, SEQ ID NO: 81713, SEQ ID NO: 81755, SEQ ID NO: 81825, SEQ ID NO: 81856, SEQ ID NO: 81873, SEQ ID NO: 81904, SEQ ID NO: 81916, SEQ ID NO: 81938, SEQ ID NO: 81951, SEQ ID NO: 81963, SEQ ID NO: 82045, SEQ ID NO: 82085, SEQ ID NO: 82117, SEQ ID NO: 82136, SEQ ID NO: 82193, SEQ ID NO: 82239, SEQ ID NO: 82241, SEQ ID NO: 82259, SEQ ID NO: 82320, SEQ ID NO: 82382, SEQ ID NO: 82417, SEQ ID NO: 82459, SEQ ID NO: 82474, SEQ ID NO: 82514, SEQ ID NO: 82556, SEQ ID NO: 82581, SEQ ID NO: 82596, SEQ ID NO: 82633, SEQ ID NO: 82644, SEQ ID NO: 82649, SEQ ID NO: 82676, SEQ ID NO: 82681, SEQ ID NO: 82718, SEQ ID NO: 82731, SEQ ID NO: 82769, SEQ ID NO: 82817, SEQ ID NO: 82870, SEQ ID NO: 82872, SEQ ID NO: 82885, SEQ ID NOs: 82920 to 82921, SEQ ID NO: 82955, SEQ ID NO: 82960, SEQ ID NO: 82985, SEQ ID NO: 82988, SEQ ID NO: 83013, SEQ ID NO: 83018, SEQ ID NO: 83051, SEQ ID NO: 83062, SEQ ID NO: 83099, SEQ ID NO: 83149, SEQ ID NO: 83185, SEQ ID NO: 83193, SEQ ID NO: 83208, SEQ ID NO: 83225, SEQ ID NO: 83235, SEQ ID NO: 83243, SEQ ID NO: 83260, SEQ ID NO: 83269, SEQ ID NO: 83286, SEQ ID NO: 83293, SEQ ID NO: 83349, SEQ ID NO: 83383, SEQ ID NO: 83409, SEQ ID NO: 83426, SEQ ID NO: 83438, SEQ ID NO: 83549, SEQ ID NO: 83605, SEQ ID NO: 83686, SEQ ID NO: 83704, SEQ ID NO: 83714, SEQ ID NO: 83806, SEQ ID NO: 83811, SEQ ID NO: 83821, SEQ ID NOs: 83863 to 83864, SEQ ID NO: 83872, SEQ ID NO: 83891, SEQ ID NO: 83899, SEQ ID NO: 83901, SEQ ID NO: 83921, SEQ ID NO: 83970, SEQ ID NO: 83974, SEQ ID NO: 83988, SEQ ID NO: 84002, SEQ ID NO: 84025, SEQ ID NO: 84070, SEQ ID NO: 84090, SEQ ID NO: 84154, SEQ ID NO: 84182, SEQ ID NOs: 84187 to 84188, SEQ ID NO: 84201, SEQ ID NO: 84212, SEQ ID NO: 84232, SEQ ID NO: 84238, SEQ ID NO: 84248, SEQ ID NO: 84306, SEQ ID NO: 84324, SEQ ID NO: 84348, SEQ ID NO: 84376, SEQ ID NO: 84387, SEQ ID NO: 84390, SEQ ID NO: 84422, SEQ ID NO: 84428, SEQ ID NO: 84437, SEQ ID NO: 84445, SEQ ID NO: 84489, SEQ ID NO: 84501, SEQ ID NO: 84534, SEQ ID NO: 84558, SEQ ID NO: 84593, SEQ ID NO: 84676, SEQ ID NO: 84782, SEQ ID NO: 84795, SEQ ID NO: 84822, SEQ ID NO: 84885, SEQ ID NO: 84991, SEQ ID NO: 85010, SEQ ID NO: 85024, SEQ ID NO: 85054, SEQ ID NO: 85056, SEQ ID NO: 85060, SEQ ID NO: 85101, SEQ ID NO: 85117, SEQ ID NO: 85146, SEQ ID NO: 85219, SEQ ID NOs: 85242 to 85243, SEQ ID NO: 85266, SEQ ID NO: 85310, SEQ ID NO: 85349, SEQ ID NO: 85361, SEQ ID NO: 85370, SEQ ID NO: 85379, SEQ ID NO: 85399, SEQ ID NO: 85417, SEQ ID NO: 85435, SEQ ID NO: 85447, SEQ ID NO: 85463, SEQ ID NO: 85519, SEQ ID NO: 85528, SEQ ID NO: 85530, SEQ ID NO: 85602, SEQ ID NO: 85624, SEQ ID NO: 85629, SEQ ID NO: 85725, SEQ ID NO: 85737, SEQ ID NO: 85848, SEQ ID NO: 85878, SEQ ID NO: 85910, SEQ ID NO: 85959, SEQ ID NO: 85963, SEQ ID NO: 85967, SEQ ID NOs: 85985 to 85986, SEQ ID NO: 86003, SEQ ID NO: 86076, SEQ ID NO: 86159, SEQ ID NO: 86208, SEQ ID NO: 86248, SEQ ID NO: 86279, SEQ ID NO: 86343, SEQ ID NO: 86366, SEQ ID NO: 86417, SEQ ID NO: 86431, SEQ ID NO: 86433, SEQ ID NO: 86473, SEQ ID NO: 86523, SEQ ID NOs: 86526 to 86527, SEQ ID NO: 86541, SEQ ID NO: 86567, SEQ ID NO: 86586, SEQ ID NO: 86589, SEQ ID NO: 86599, SEQ ID NO: 86633, SEQ ID NO: 86665, SEQ ID NO: 86688, SEQ ID NO: 86698, SEQ ID NO: 86725, SEQ ID NO: 86761, SEQ ID NO: 86775, SEQ ID NO: 86825, SEQ ID NO: 86914, SEQ ID NO: 86929, SEQ ID NO: 86940, SEQ ID NO: 86969, SEQ ID NO: 86994, SEQ ID NO: 87027, SEQ ID NO: 87041, SEQ ID NO: 87157, SEQ ID NO: 87160, SEQ ID NO: 87185, SEQ ID NO: 87251, SEQ ID NO: 87255, SEQ ID NO: 87300, SEQ ID NO: 87321, SEQ ID NO: 87358, SEQ ID NO: 87425, SEQ ID NO: 87427, SEQ ID NO: 87431, SEQ ID NO: 87474, SEQ ID NO: 87536, SEQ ID NO: 87550, SEQ ID NO: 87576, SEQ ID NO: 87603, SEQ ID NO: 87623, SEQ ID NO: 87626, SEQ ID NO: 87638, SEQ ID NO: 87708, SEQ ID NO: 87733, SEQ ID NO: 87785, SEQ ID NO: 87799, SEQ ID NO: 87818, SEQ ID NOs: 87865 to 87866, SEQ ID NO: 87875, SEQ ID NO: 87917, SEQ ID NO: 87946, SEQ ID NO: 87951, SEQ ID NO: 88016, SEQ ID NO: 88061, SEQ ID NO: 88120, SEQ ID NO: 88122, SEQ ID NO: 88125, SEQ ID NO: 88144, SEQ ID NO: 88178, SEQ ID NO: 88180, SEQ ID NO: 88186, SEQ ID NO: 88203, SEQ ID NO: 88241, SEQ ID NO: 88272, SEQ ID NO: 88285, SEQ ID NO: 88288, SEQ ID NO: 88359, SEQ ID NO: 88384, SEQ ID NO: 88390, SEQ ID NO: 88474, SEQ ID NO: 88522, SEQ ID NO: 88563, SEQ ID NO: 88643, SEQ ID NO: 88659, SEQ ID NO: 88708, SEQ ID NO: 88710, SEQ ID NO: 88731, SEQ ID NO: 88751, SEQ ID NO: 88806, SEQ ID NO: 88975, SEQ ID NO: 88999, SEQ ID NO: 89010, SEQ ID NO: 89012, SEQ ID NO: 89028, SEQ ID NO: 89035, SEQ ID NO: 89037, SEQ ID NO: 89039, SEQ ID NO: 89045, SEQ ID NO: 89073, SEQ ID NO: 89118, SEQ ID NO: 89126, SEQ ID NO: 89135, SEQ ID NO: 89138, SEQ ID NO: 89147, SEQ ID NO: 89168, SEQ ID NO: 89193, SEQ ID NO: 89228, SEQ ID NO: 89235, SEQ ID NO: 89269, SEQ ID NO: 89286, SEQ ID NO: 89291, SEQ ID NO: 89339, SEQ ID NO: 89342, SEQ ID NO: 89394, SEQ ID NO: 89453, SEQ ID NO: 89492, SEQ ID NO: 89510, SEQ ID NO: 89555, SEQ ID NO: 89595, SEQ ID NO: 89670, SEQ ID NO: 89695, SEQ ID NO: 89785, SEQ ID NO: 89836, SEQ ID NO: 89842, SEQ ID NO: 89921, SEQ ID NO: 89929, SEQ ID NO: 89935, SEQ ID NO: 89938, SEQ ID NO: 89950, SEQ ID NO: 89953, SEQ ID NO: 89960, SEQ ID NO: 89987, SEQ ID NO: 89992, SEQ ID NO: 90030, SEQ ID NO: 90056, SEQ ID NO: 90066, SEQ ID NO: 90085, SEQ ID NO: 90089, SEQ ID NO: 90115, SEQ ID NO: 90120, SEQ ID NO: 90133, SEQ ID NO: 90157, SEQ ID NO: 90159, SEQ ID NO: 90191, SEQ ID NO: 90268, SEQ ID NO: 90274, SEQ ID NO: 90280, SEQ ID NO: 90287, SEQ ID NO: 90315, SEQ ID NO: 90408, SEQ ID NO: 90417, SEQ ID NO: 90443, SEQ ID NO: 90466, SEQ ID NO: 90507, SEQ ID NO: 90555, SEQ ID NO: 90593, SEQ ID NO: 90599, SEQ ID NO: 90621, SEQ ID NO: 90634, SEQ ID NO: 90653, SEQ ID NO: 90696, SEQ ID NO: 90758, SEQ ID NO: 90777, SEQ ID NO: 90835, SEQ ID NO: 90882, SEQ ID NO: 90898, SEQ ID NO: 90938, SEQ ID NO: 90954, SEQ ID NO: 90999, SEQ ID NO: 91045, SEQ ID NO: 91060, SEQ ID NO: 91072, SEQ ID NO: 91076, SEQ ID NO: 91105, SEQ ID NO: 91132, SEQ ID NO: 91222, SEQ ID NO: 91226, SEQ ID NO: 91229, SEQ ID NO: 91306, SEQ ID NO: 91309, SEQ ID NO: 91315, SEQ ID NO: 91346, SEQ ID NO: 91419, SEQ ID NO: 91449, SEQ ID NO: 91498, SEQ ID NO: 91563, SEQ ID NO: 91588, SEQ ID NO: 91681, SEQ ID NO: 91766, SEQ ID NOs: 91775 to 91776, SEQ ID NO: 91780, SEQ ID NO: 91799, SEQ ID NO: 91845, SEQ ID NO: 91852, SEQ ID NOs: 91885 to 91886, SEQ ID NO: 91930, SEQ ID NO: 91935, SEQ ID NO: 91953, SEQ ID NO: 91966, SEQ ID NO: 91984, SEQ ID NO: 92026, SEQ ID NO: 92030, SEQ ID NO: 92069, SEQ ID NO: 92100, SEQ ID NO: 92111, SEQ ID NO: 92189, SEQ ID NO: 92249, SEQ ID NO: 92296, SEQ ID NO: 92400, SEQ ID NO: 92404, SEQ ID NO: 92409, SEQ ID NO: 92429, SEQ ID NO: 92474, SEQ ID NO: 92500, SEQ ID NO: 92515, SEQ ID NO: 92538, SEQ ID NO: 92646, SEQ ID NO: 92659, SEQ ID NO: 92671, SEQ ID NO: 92673, SEQ ID NO: 92675, SEQ ID NO: 92684, SEQ ID NO: 92704, SEQ ID NO: 92832, SEQ ID NO: 92835, SEQ ID NO: 92854, SEQ ID NO: 92858, SEQ ID NO: 92877, SEQ ID NO: 92918, SEQ ID NO: 92920, SEQ ID NO: 93004, SEQ ID NO: 93036, SEQ ID NO: 93042, SEQ ID NO: 93071, SEQ ID NO: 93089, SEQ ID NO: 93136, SEQ ID NO: 93180, SEQ ID NO: 93251, SEQ ID NO: 93325, SEQ ID NO: 93335, SEQ ID NO: 93344, SEQ ID NO: 93356, SEQ ID NO: 93382, SEQ ID NO: 93408, SEQ ID NO: 93420, SEQ ID NO: 93503, SEQ ID NO: 93537, SEQ ID NO: 93617, SEQ ID NO: 93658, SEQ ID NO: 93697, SEQ ID NO: 93710, SEQ ID NO: 93877, SEQ ID NO: 93885, SEQ ID NO: 93888, SEQ ID NO: 93893, SEQ ID NO: 93903, SEQ ID NO: 93912, SEQ ID NO: 93926, SEQ ID NO: 93933, SEQ ID NO: 93982, SEQ ID NO: 93987, SEQ ID NO: 94000, SEQ ID NO: 94054, SEQ ID NO: 94058, SEQ ID NO: 94087, SEQ ID NO: 94090, SEQ ID NO: 94102, SEQ ID NO: 94143, SEQ ID NO: 94269, SEQ ID NO: 94367, SEQ ID NO: 94465, SEQ ID NO: 94477, SEQ ID NO: 94525, SEQ ID NO: 94587, SEQ ID NOs: 95593 to 113807, SEQ ID NO: 217120, SEQ ID NO: 247270, SEQ ID NO: 248009, SEQ ID NOs: 248159 to 248160, SEQ ID NOs: 248735 to 248738, SEQ ID NOs: 249358 to 249362, SEQ ID NOs: 249690 to 249691, SEQ ID NOs: 252562 to 252564, SEQ ID NOs: 252836 to 252837, SEQ ID NO: 256214, SEQ ID NO: 256221, SEQ ID NO: 256226, SEQ ID NO: 256229, SEQ ID NO: 256235, SEQ ID NO: 256705, SEQ ID NO: 257337, SEQ ID NO: 257341, SEQ ID NO: 257345, SEQ ID NO: 257995, SEQ ID NO: 258292, SEQ ID NO: 258295, SEQ ID NOs: 258614 to 258616, SEQ ID NO: 259467, SEQ ID NO: 259471, SEQ ID NO: 259474, SEQ ID NO: 260118, SEQ ID NO: 260122, SEQ ID NO: 260126, SEQ ID NO: 260131, SEQ ID NO: 260138, SEQ ID NO: 260145, SEQ ID NO: 260153, SEQ ID NOs: 260367 to 260384, SEQ ID NO: 260407, SEQ ID NO: 260412, SEQ ID NO: 261788, SEQ ID NO: 261790, SEQ ID NOs: 261792 to 261793, SEQ ID NO: 261795, SEQ ID NO: 261798, SEQ ID NO: 261800, SEQ ID NO: 261803, SEQ ID NO: 261805, SEQ ID NO: 261809, SEQ ID NO: 261811, SEQ ID NO: 261814, SEQ ID NO: 261816, SEQ ID NO: 261821, SEQ ID NO: 261823, SEQ ID NO: 261830, SEQ ID NO: 261832, SEQ ID NO: 261837, SEQ ID NO: 261839, SEQ ID NO: 262119, SEQ ID NO: 262122, SEQ ID NOs: 262261 to 262285, SEQ ID NO: 262313, SEQ ID NO: 262318, SEQ ID NOs: 263471 to 263474, SEQ ID NO: 263494, SEQ ID NO: 263498, SEQ ID NOs: 266653 to 266654, SEQ ID NO: 269139, SEQ ID NO: 269143, SEQ ID NO: 269149, SEQ ID NO: 269156, SEQ ID NO: 269169, SEQ ID NOs: 270516 to 270517, SEQ ID NOs: 270519 to 270520, SEQ ID NOs: 270523 to 270524, SEQ ID NOs: 270527 to 270528, SEQ ID NO: 272016, SEQ ID NO: 272020, SEQ ID NOs: 272214 to 272222, SEQ ID NO: 272243, SEQ ID NO: 272248, SEQ ID NO: 272896, SEQ ID NOs: 273018 to 273020, SEQ ID NOs: 278350 to 278351, SEQ ID NO: 278355, SEQ ID NOs: 278358 to 278359, SEQ ID NOs: 278361 to 278362, SEQ ID NO: 278364, SEQ ID NO: 278367, SEQ ID NO: 278369, SEQ ID NO: 278371, SEQ ID NO: 278373, SEQ ID NO: 278375, SEQ ID NO: 278377, SEQ ID NO: 278383, SEQ ID NO: 278385, SEQ ID NO: 278388, SEQ ID NO: 278390, SEQ ID NO: 278394, SEQ ID NO: 278396, SEQ ID NOs: 281013 to 281014, SEQ ID NO: 281018, SEQ ID NO: 281022, SEQ ID NO: 281026, SEQ ID NO: 281031, SEQ ID NOs: 281037 to 281038, SEQ ID NOs: 281044 to 281045, SEQ ID NOs: 281052 to 281053, SEQ ID NOs: 281151 to 281152, SEQ ID NO: 281155, SEQ ID NO: 281159, SEQ ID NOs: 281162 to 281163, SEQ ID NOs: 281165 to 281166, SEQ ID NO: 281169, SEQ ID NO: 281171, SEQ ID NO: 281174, SEQ ID NO: 281176, SEQ ID NO: 281179, SEQ ID NO: 281181, SEQ ID NO: 281184, SEQ ID NO: 281186, SEQ ID NO: 281190, SEQ ID NO: 281192, SEQ ID NO: 281197, SEQ ID NO: 281199, and SEQ ID NOs: 281350 to 305565. In some embodiments, any one of the peptides in the MAGC3 vaccine comprise an amino acid sequence 80, 81, 82, 83, 84, 85, 86, 87, 88, 89, 90, 91, 92, 93, 94, 95, 96, 97, 98 or 99% identical to SEQ ID NO: 41647, SEQ ID NO: 50668, SEQ ID NO: 50905, SEQ ID NOs: 51039 to 51040, SEQ ID NO: 68257, SEQ ID NO: 68285, SEQ ID NO: 68288, SEQ ID NO: 68290, SEQ ID NO: 68305, SEQ ID NO: 68389, SEQ ID NO: 68419, SEQ ID NO: 68470, SEQ ID NO: 68510, SEQ ID NO: 68519, SEQ ID NO: 68592, SEQ ID NO: 68603, SEQ ID NO: 68684, SEQ ID NO: 68688, SEQ ID NO: 68747, SEQ ID NO: 68760, SEQ ID NO: 68778, SEQ ID NO: 68786, SEQ ID NO: 68855, SEQ ID NO: 68898, SEQ ID NO: 68900, SEQ ID NO: 68927, SEQ ID NO: 68961, SEQ ID NO: 69026, SEQ ID NO: 69041, SEQ ID NO: 69047, SEQ ID NO: 69148, SEQ ID NO: 69173, SEQ ID NO: 69180, SEQ ID NO: 69192, SEQ ID NO: 69227, SEQ ID NO: 69311, SEQ ID NO: 69330, SEQ ID NO: 69333, SEQ ID NO: 69346, SEQ ID NO: 69356, SEQ ID NO: 69393, SEQ ID NO: 69421, SEQ ID NO: 69437, SEQ ID NO: 69451, SEQ ID NO: 69500, SEQ ID NO: 69505, SEQ ID NO: 69517, SEQ ID NO: 69540, SEQ ID NO: 69559, SEQ ID NO: 69571, SEQ ID NO: 69586, SEQ ID NO: 69589, SEQ ID NO: 69591, SEQ ID NO: 69619, SEQ ID NO: 69631, SEQ ID NO: 69633, SEQ ID NO: 69644, SEQ ID NO: 69649, SEQ ID NO: 69747, SEQ ID NO: 69764, SEQ ID NO: 69767, SEQ ID NO: 69790, SEQ ID NO: 69832, SEQ ID NO: 69836, SEQ ID NO: 69882, SEQ ID NO: 69999, SEQ ID NO: 70012, SEQ ID NO: 70036, SEQ ID NO: 70050, SEQ ID NO: 70066, SEQ ID NO:

70069, SEQ ID NO: 70109, SEQ ID NO: 70159, SEQ ID NO: 70165, SEQ ID NO: 70175, SEQ ID NO: 70177, SEQ ID NO: 70188, SEQ ID NO: 70284, SEQ ID NO: 70323, SEQ ID NO: 70326, SEQ ID NO: 70428, SEQ ID NO: 70455, SEQ ID NO: 70570, SEQ ID NO: 70606, SEQ ID NO: 70635, SEQ ID NO: 70676, SEQ ID NO: 70692, SEQ ID NO: 70716, SEQ ID NO: 70728, SEQ ID NO: 70735, SEQ ID NO: 70750, SEQ ID NO: 70764, SEQ ID NO: 70770, SEQ ID NO: 70806, SEQ ID NO: 70968, SEQ ID NO: 70997, SEQ ID NO: 71049, SEQ ID NO: 71075, SEQ ID NO: 71090, SEQ ID NO: 71117, SEQ ID NO: 71151, SEQ ID NO: 71176, SEQ ID NO: 71193, SEQ ID NO: 71203, SEQ ID NO: 71239, SEQ ID NO: 71247, SEQ ID NO: 71249, SEQ ID NO: 71275, SEQ ID NO: 71287, SEQ ID NO: 71328, SEQ ID NOs: 71359 to 71360, SEQ ID NOs: 71367 to 71368, SEQ ID NO: 71392, SEQ ID NO: 71414, SEQ ID NO: 71449, SEQ ID NO: 71476, SEQ ID NO: 71482, SEQ ID NO: 71543, SEQ ID NO: 71547, SEQ ID NO: 71560, SEQ ID NO: 71585, SEQ ID NO: 71612, SEQ ID NO: 71620, SEQ ID NO: 71628, SEQ ID NO: 71636, SEQ ID NO: 71673, SEQ ID NOs: 71688 to 71689, SEQ ID NO: 71696, SEQ ID NO: 71700, SEQ ID NO: 71718, SEQ ID NO: 71725, SEQ ID NO: 71807, SEQ ID NO: 71919, SEQ ID NO: 71935, SEQ ID NO: 71943, SEQ ID NO: 71948, SEQ ID NOs: 71987 to 71988, SEQ ID NO: 72045, SEQ ID NO: 72055, SEQ ID NO: 72076, SEQ ID NO: 72085, SEQ ID NO: 72102, SEQ ID NO: 72159, SEQ ID NO: 72183, SEQ ID NO: 72216, SEQ ID NO: 72241, SEQ ID NO: 72331, SEQ ID NO: 72364, SEQ ID NO: 72372, SEQ ID NO: 72390, SEQ ID NO: 72448, SEQ ID NO: 72528, SEQ ID NO: 72595, SEQ ID NO: 72604, SEQ ID NO: 72648, SEQ ID NO: 72667, SEQ ID NO: 72685, SEQ ID NO: 72721, SEQ ID NO: 72751, SEQ ID NO: 72755, SEQ ID NO: 72805, SEQ ID NO: 72810, SEQ ID NO: 72831, SEQ ID NO: 72837, SEQ ID NO: 72862, SEQ ID NO: 72885, SEQ ID NO: 72989, SEQ ID NO: 73014, SEQ ID NOs: 73045 to 73046, SEQ ID NO: 73086, SEQ ID NO: 73094, SEQ ID NO: 73113, SEQ ID NO: 73122, SEQ ID NO: 73161, SEQ ID NO: 73191, SEQ ID NO: 73224, SEQ ID NOs: 73232 to 73233, SEQ ID NO: 73238, SEQ ID NO: 73290, SEQ ID NO: 73327, SEQ ID NO: 73377, SEQ ID NO: 73382, SEQ ID NO: 73404, SEQ ID NO: 73406, SEQ ID NO: 73422, SEQ ID NOs: 73428 to 73429, SEQ ID NO: 73466, SEQ ID NO: 73475, SEQ ID NO: 73521, SEQ ID NO: 73523, SEQ ID NO: 73532, SEQ ID NO: 73550, SEQ ID NO: 73560, SEQ ID NO: 73591, SEQ ID NO: 73597, SEQ ID NO: 73644, SEQ ID NO: 73657, SEQ ID NO: 73660, SEQ ID NO: 73689, SEQ ID NO: 73729, SEQ ID NO: 73733, SEQ ID NO: 73873, SEQ ID NO: 73886, SEQ ID NO: 73930, SEQ ID NO: 73957, SEQ ID NOs: 73991 to 73992, SEQ ID NO: 74045, SEQ ID NO: 74047, SEQ ID NO: 74072, SEQ ID NO: 74080, SEQ ID NOs: 74096 to 74097, SEQ ID NO: 74107, SEQ ID NO: 74203, SEQ ID NO: 74208, SEQ ID NO: 74210, SEQ ID NO: 74238, SEQ ID NO: 74302, SEQ ID NO: 74350, SEQ ID NO: 74352, SEQ ID NO: 74411, SEQ ID NO: 74448, SEQ ID NO: 74473, SEQ ID NO: 74482, SEQ ID NO: 74515, SEQ ID NO: 74527, SEQ ID NO: 74560, SEQ ID NO: 74616, SEQ ID NO: 74649, SEQ ID NO: 74672, SEQ ID NO: 74674, SEQ ID NO: 74737, SEQ ID NO: 74782, SEQ ID NO: 74808, SEQ ID NO: 74810, SEQ ID NO: 74835, SEQ ID NO: 74886, SEQ ID NO: 74901, SEQ ID NO: 74946, SEQ ID NOs: 74975 to 74976, SEQ ID NO: 75017, SEQ ID NO: 75021, SEQ ID NO: 75040, SEQ ID NO: 75049, SEQ ID NO: 75063, SEQ ID NO: 75066, SEQ ID NO: 75072, SEQ ID NO: 75092, SEQ ID NO: 75094, SEQ ID NO: 75099, SEQ ID NO: 75111, SEQ ID NO: 75148, SEQ ID NO: 75245, SEQ ID NO: 75269, SEQ ID NO: 75388, SEQ ID NO: 75403, SEQ ID NO: 75429, SEQ ID NO: 75455, SEQ ID NO: 75470, SEQ ID NO: 75489, SEQ ID NO: 75506, SEQ ID NO: 75529, SEQ ID NO: 75547, SEQ ID NO: 75551, SEQ ID NOs: 75576 to 75577, SEQ ID NO: 75595, SEQ ID NO: 75701, SEQ ID NO: 75716, SEQ ID NO: 75747, SEQ ID NO: 75757, SEQ ID NO: 75762, SEQ ID NO: 75766, SEQ ID NO: 75874, SEQ ID NO: 75915, SEQ ID NO: 75933, SEQ ID NO: 75975, SEQ ID NO: 75979, SEQ ID NO: 76016, SEQ ID NO: 76023, SEQ ID NO: 76034, SEQ ID NO: 76040, SEQ ID NO: 76064, SEQ ID NO: 76076, SEQ ID NO: 76102, SEQ ID NOs: 76147 to 76148, SEQ ID NO: 76189, SEQ ID NO: 76199, SEQ ID NO: 76369, SEQ ID NO: 76375, SEQ ID NO: 76397, SEQ ID NO: 76410, SEQ ID NO: 76435, SEQ ID NO: 76446, SEQ ID NO: 76451, SEQ ID NOs: 76456 to 76458, SEQ ID NO: 76492, SEQ ID NO: 76544, SEQ ID NO: 76569, SEQ ID NO: 76574, SEQ ID NO: 76611, SEQ ID NO: 76654, SEQ ID NO: 76710, SEQ ID NO: 76753, SEQ ID NO: 76769, SEQ ID NO: 76781, SEQ ID NO: 76797, SEQ ID NO: 76803, SEQ ID NO: 76858, SEQ ID NO: 76860, SEQ ID NO: 76879, SEQ ID NO: 76943, SEQ ID NO: 76971, SEQ ID NO: 76981, SEQ ID NO: 77091, SEQ ID NO: 77133, SEQ ID NOs: 77193 to 77194, SEQ ID NO: 77210, SEQ ID NO: 77219, SEQ ID NO: 77237, SEQ ID NO: 77246, SEQ ID NO: 77251, SEQ ID NO: 77281, SEQ ID NO: 77293, SEQ ID NO: 77323, SEQ ID NO: 77334, SEQ ID NO: 77339, SEQ ID NO: 77396, SEQ ID NO: 77423, SEQ ID NO: 77433, SEQ ID NO: 77437, SEQ ID NO: 77442, SEQ ID NO: 77453, SEQ ID NO: 77485, SEQ ID NO: 77579, SEQ ID NO: 77627, SEQ ID NO: 77639, SEQ ID NO: 77644, SEQ ID NO: 77703, SEQ ID NO: 77773, SEQ ID NO: 77814, SEQ ID NO: 77868, SEQ ID NO: 77874, SEQ ID NO: 77900, SEQ ID NO: 77925, SEQ ID NO: 77995, SEQ ID NO: 78017, SEQ ID NO: 78083, SEQ ID NO: 78086, SEQ ID NO: 78090, SEQ ID NO: 78131, SEQ ID NO: 78139, SEQ ID NO: 78228, SEQ ID NO: 78248, SEQ ID NO: 78260, SEQ ID NO: 78346, SEQ ID NO: 78352, SEQ ID NO: 78377, SEQ ID NO: 78416, SEQ ID NO: 78421, SEQ ID NO: 78440, SEQ ID NO: 78521, SEQ ID NO: 78530, SEQ ID NO: 78532, SEQ ID NO: 78546, SEQ ID NO: 78600, SEQ ID NO: 78631, SEQ ID NO: 78671, SEQ ID NO: 78709, SEQ ID NO: 78714, SEQ ID NO: 78730, SEQ ID NO: 78738, SEQ ID NO: 78810, SEQ ID NO: 78855, SEQ ID NO: 78883, SEQ ID NO: 78917, SEQ ID NOs: 78919 to 78920, SEQ ID NO: 78928, SEQ ID NO: 79035, SEQ ID NO: 79048, SEQ ID NO: 79056, SEQ ID NO: 79086, SEQ ID NO: 79091, SEQ ID NO: 79095, SEQ ID NO: 79107, SEQ ID NO: 79109, SEQ ID NO: 79136, SEQ ID NO: 79142, SEQ ID NO: 79147, SEQ ID NO: 79151, SEQ ID NO: 79194, SEQ ID NO: 79196, SEQ ID NO: 79227, SEQ ID NO: 79247, SEQ ID NO: 79253, SEQ ID NO: 79255, SEQ ID NO: 79269, SEQ ID NO: 79310, SEQ ID NO: 79331, SEQ ID NO: 79357, SEQ ID NO: 79406, SEQ ID NO: 79437, SEQ ID NO: 79448, SEQ ID NO: 79453, SEQ ID NO: 79480, SEQ ID NO: 79483, SEQ ID NO: 79486, SEQ ID NO: 79504, SEQ ID NO: 79508, SEQ ID NO: 79516, SEQ ID NO: 79548, SEQ ID NO: 79575, SEQ ID NO: 79588, SEQ ID NO: 79592, SEQ ID NO: 79609, SEQ ID NO: 79626, SEQ ID NO: 79640, SEQ ID NO: 79697, SEQ ID NO: 79746, SEQ ID NO: 79751, SEQ ID NO: 79766, SEQ ID NO: 79784, SEQ ID NO: 79787, SEQ ID NO: 79816, SEQ ID NO: 79834, SEQ ID NO: 79853, SEQ ID NO: 79858, SEQ ID NO: 79861, SEQ ID NO: 79874, SEQ ID NO: 79877, SEQ ID NO: 79906, SEQ ID NO: 79909, SEQ ID NO: 79939, SEQ ID NO: 79958, SEQ ID NO: 79987, SEQ ID NO:

80000, SEQ ID NO: 80027, SEQ ID NO: 80040, SEQ ID NO: 80139, SEQ ID NO: 80141, SEQ ID NO: 80212, SEQ ID NO: 80232, SEQ ID NO: 80237, SEQ ID NO: 80241, SEQ ID NO: 80318, SEQ ID NO: 80320, SEQ ID NOs: 80367 to 80368, SEQ ID NO: 80398, SEQ ID NO: 80421, SEQ ID NO: 80461, SEQ ID NO: 80486, SEQ ID NO: 80513, SEQ ID NO: 80527, SEQ ID NO: 80555, SEQ ID NO: 80574, SEQ ID NO: 80583, SEQ ID NO: 80627, SEQ ID NO: 80673, SEQ ID NOs: 80703 to 80704, SEQ ID NOs: 80718 to 80719, SEQ ID NO: 80725, SEQ ID NO: 80796, SEQ ID NO: 80804, SEQ ID NO: 80833, SEQ ID NO: 80869, SEQ ID NO: 80903, SEQ ID NO: 80931, SEQ ID NO: 80936, SEQ ID NO: 80946, SEQ ID NO: 80990, SEQ ID NO: 81021, SEQ ID NO: 81042, SEQ ID NO: 81046, SEQ ID NO: 81054, SEQ ID NO: 81066, SEQ ID NO: 81145, SEQ ID NO: 81166, SEQ ID NO: 81168, SEQ ID NO: 81175, SEQ ID NO: 81185, SEQ ID NO: 81207, SEQ ID NO: 81251, SEQ ID NO: 81259, SEQ ID NO: 81302, SEQ ID NO: 81337, SEQ ID NO: 81342, SEQ ID NO: 81386, SEQ ID NO: 81428, SEQ ID NO: 81446, SEQ ID NO: 81458, SEQ ID NO: 81488, SEQ ID NO: 81505, SEQ ID NO: 81517, SEQ ID NO: 81566, SEQ ID NO: 81687, SEQ ID NO: 81690, SEQ ID NO: 81694, SEQ ID NO: 81713, SEQ ID NO: 81755, SEQ ID NO: 81825, SEQ ID NO: 81856, SEQ ID NO: 81873, SEQ ID NO: 81904, SEQ ID NO: 81916, SEQ ID NO: 81938, SEQ ID NO: 81951, SEQ ID NO: 81963, SEQ ID NO: 82045, SEQ ID NO: 82085, SEQ ID NO: 82117, SEQ ID NO: 82136, SEQ ID NO: 82193, SEQ ID NO: 82239, SEQ ID NO: 82241, SEQ ID NO: 82259, SEQ ID NO: 82320, SEQ ID NO: 82382, SEQ ID NO: 82417, SEQ ID NO: 82459, SEQ ID NO: 82474, SEQ ID NO: 82514, SEQ ID NO: 82556, SEQ ID NO: 82581, SEQ ID NO: 82596, SEQ ID NO: 82633, SEQ ID NO: 82644, SEQ ID NO: 82649, SEQ ID NO: 82676, SEQ ID NO: 82681, SEQ ID NO: 82718, SEQ ID NO: 82731, SEQ ID NO: 82769, SEQ ID NO: 82817, SEQ ID NO: 82870, SEQ ID NO: 82872, SEQ ID NO: 82885, SEQ ID NOs: 82920 to 82921, SEQ ID NO: 82955, SEQ ID NO: 82960, SEQ ID NO: 82985, SEQ ID NO: 82988, SEQ ID NO: 83013, SEQ ID NO: 83018, SEQ ID NO: 83051, SEQ ID NO: 83062, SEQ ID NO: 83099, SEQ ID NO: 83149, SEQ ID NO: 83185, SEQ ID NO: 83193, SEQ ID NO: 83208, SEQ ID NO: 83225, SEQ ID NO: 83235, SEQ ID NO: 83243, SEQ ID NO: 83260, SEQ ID NO: 83269, SEQ ID NO: 83286, SEQ ID NO: 83293, SEQ ID NO: 83349, SEQ ID NO: 83383, SEQ ID NO: 83409, SEQ ID NO: 83426, SEQ ID NO: 83438, SEQ ID NO: 83549, SEQ ID NO: 83605, SEQ ID NO: 83686, SEQ ID NO: 83704, SEQ ID NO: 83714, SEQ ID NO: 83806, SEQ ID NO: 83811, SEQ ID NO: 83821, SEQ ID NOs: 83863 to 83864, SEQ ID NO: 83872, SEQ ID NO: 83891, SEQ ID NO: 83899, SEQ ID NO: 83901, SEQ ID NO: 83921, SEQ ID NO: 83970, SEQ ID NO: 83974, SEQ ID NO: 83988, SEQ ID NO: 84002, SEQ ID NO: 84025, SEQ ID NO: 84070, SEQ ID NO: 84090, SEQ ID NO: 84154, SEQ ID NO: 84182, SEQ ID NOs: 84187 to 84188, SEQ ID NO: 84201, SEQ ID NO: 84212, SEQ ID NO: 84232, SEQ ID NO: 84238, SEQ ID NO: 84248, SEQ ID NO: 84306, SEQ ID NO: 84324, SEQ ID NO: 84348, SEQ ID NO: 84376, SEQ ID NO: 84387, SEQ ID NO: 84390, SEQ ID NO: 84422, SEQ ID NO: 84428, SEQ ID NO: 84437, SEQ ID NO: 84445, SEQ ID NO: 84489, SEQ ID NO: 84501, SEQ ID NO: 84534, SEQ ID NO: 84558, SEQ ID NO: 84593, SEQ ID NO: 84676, SEQ ID NO: 84782, SEQ ID NO: 84795, SEQ ID NO: 84822, SEQ ID NO: 84885, SEQ ID NO: 84991, SEQ ID NO: 85010, SEQ ID NO: 85024, SEQ ID NO: 85054, SEQ ID NO: 85056, SEQ ID NO: 85060, SEQ ID NO: 85101, SEQ ID NO: 85117, SEQ ID NO: 85146, SEQ ID NO: 85219, SEQ ID NOs: 85242 to 85243, SEQ ID NO: 85266, SEQ ID NO: 85310, SEQ ID NO: 85349, SEQ ID NO: 85361, SEQ ID NO: 85370, SEQ ID NO: 85379, SEQ ID NO: 85399, SEQ ID NO: 85417, SEQ ID NO: 85435, SEQ ID NO: 85447, SEQ ID NO: 85463, SEQ ID NO: 85519, SEQ ID NO: 85528, SEQ ID NO: 85530, SEQ ID NO: 85602, SEQ ID NO: 85624, SEQ ID NO: 85629, SEQ ID NO: 85725, SEQ ID NO: 85737, SEQ ID NO: 85848, SEQ ID NO: 85878, SEQ ID NO: 85910, SEQ ID NO: 85959, SEQ ID NO: 85963, SEQ ID NO: 85967, SEQ ID NOs: 85985 to 85986, SEQ ID NO: 86003, SEQ ID NO: 86076, SEQ ID NO: 86159, SEQ ID NO: 86208, SEQ ID NO: 86248, SEQ ID NO: 86279, SEQ ID NO: 86343, SEQ ID NO: 86366, SEQ ID NO: 86417, SEQ ID NO: 86431, SEQ ID NO: 86433, SEQ ID NO: 86473, SEQ ID NO: 86523, SEQ ID NOs: 86526 to 86527, SEQ ID NO: 86541, SEQ ID NO: 86567, SEQ ID NO: 86586, SEQ ID NO: 86589, SEQ ID NO: 86599, SEQ ID NO: 86633, SEQ ID NO: 86665, SEQ ID NO: 86688, SEQ ID NO: 86698, SEQ ID NO: 86725, SEQ ID NO: 86761, SEQ ID NO: 86775, SEQ ID NO: 86825, SEQ ID NO: 86914, SEQ ID NO: 86929, SEQ ID NO: 86940, SEQ ID NO: 86969, SEQ ID NO: 86994, SEQ ID NO: 87027, SEQ ID NO: 87041, SEQ ID NO: 87157, SEQ ID NO: 87160, SEQ ID NO: 87185, SEQ ID NO: 87251, SEQ ID NO: 87255, SEQ ID NO: 87300, SEQ ID NO: 87321, SEQ ID NO: 87358, SEQ ID NO: 87425, SEQ ID NO: 87427, SEQ ID NO: 87431, SEQ ID NO: 87474, SEQ ID NO: 87536, SEQ ID NO: 87550, SEQ ID NO: 87576, SEQ ID NO: 87603, SEQ ID NO: 87623, SEQ ID NO: 87626, SEQ ID NO: 87638, SEQ ID NO: 87708, SEQ ID NO: 87733, SEQ ID NO: 87785, SEQ ID NO: 87799, SEQ ID NO: 87818, SEQ ID NOs: 87865 to 87866, SEQ ID NO: 87875, SEQ ID NO: 87917, SEQ ID NO: 87946, SEQ ID NO: 87951, SEQ ID NO: 88016, SEQ ID NO: 88061, SEQ ID NO: 88120, SEQ ID NO: 88122, SEQ ID NO: 88125, SEQ ID NO: 88144, SEQ ID NO: 88178, SEQ ID NO: 88180, SEQ ID NO: 88186, SEQ ID NO: 88203, SEQ ID NO: 88241, SEQ ID NO: 88272, SEQ ID NO: 88285, SEQ ID NO: 88288, SEQ ID NO: 88359, SEQ ID NO: 88384, SEQ ID NO: 88390, SEQ ID NO: 88474, SEQ ID NO: 88522, SEQ ID NO: 88563, SEQ ID NO: 88643, SEQ ID NO: 88659, SEQ ID NO: 88708, SEQ ID NO: 88710, SEQ ID NO: 88731, SEQ ID NO: 88751, SEQ ID NO: 88806, SEQ ID NO: 88975, SEQ ID NO: 88999, SEQ ID NO: 89010, SEQ ID NO: 89012, SEQ ID NO: 89028, SEQ ID NO: 89035, SEQ ID NO: 89037, SEQ ID NO: 89039, SEQ ID NO: 89045, SEQ ID NO: 89073, SEQ ID NO: 89118, SEQ ID NO: 89126, SEQ ID NO: 89135, SEQ ID NO: 89138, SEQ ID NO: 89147, SEQ ID NO: 89168, SEQ ID NO: 89193, SEQ ID NO: 89228, SEQ ID NO: 89235, SEQ ID NO: 89269, SEQ ID NO: 89286, SEQ ID NO: 89291, SEQ ID NO: 89339, SEQ ID NO: 89342, SEQ ID NO: 89394, SEQ ID NO: 89453, SEQ ID NO: 89492, SEQ ID NO: 89510, SEQ ID NO: 89555, SEQ ID NO: 89595, SEQ ID NO: 89670, SEQ ID NO: 89695, SEQ ID NO: 89785, SEQ ID NO: 89836, SEQ ID NO: 89842, SEQ ID NO: 89921, SEQ ID NO: 89929, SEQ ID NO: 89935, SEQ ID NO: 89938, SEQ ID NO: 89950, SEQ ID NO: 89953, SEQ ID NO: 89960, SEQ ID NO: 89987, SEQ ID NO: 89992, SEQ ID NO: 90030, SEQ ID NO: 90056, SEQ ID NO: 90066, SEQ ID NO: 90085, SEQ ID NO: 90089, SEQ ID NO: 90115, SEQ ID NO: 90120, SEQ ID NO: 90133, SEQ ID NO: 90157, SEQ ID NO: 90159, SEQ ID NO: 90191, SEQ ID NO: 90268, SEQ ID NO: 90274, SEQ ID NO: 90280, SEQ ID NO: 90287, SEQ ID NO: 90315, SEQ ID NO: 90408, SEQ ID NO: 90417, SEQ ID

NO: 90443, SEQ ID NO: 90466, SEQ ID NO: 90507, SEQ ID NO: 90555, SEQ ID NO: 90593, SEQ ID NO: 90599, SEQ ID NO: 90621, SEQ ID NO: 90634, SEQ ID NO: 90653, SEQ ID NO: 90696, SEQ ID NO: 90758, SEQ ID NO: 90777, SEQ ID NO: 90835, SEQ ID NO: 90882, SEQ ID NO: 90898, SEQ ID NO: 90938, SEQ ID NO: 90954, SEQ ID NO: 90999, SEQ ID NO: 91045, SEQ ID NO: 91060, SEQ ID NO: 91072, SEQ ID NO: 91076, SEQ ID NO: 91105, SEQ ID NO: 91132, SEQ ID NO: 91222, SEQ ID NO: 91226, SEQ ID NO: 91229, SEQ ID NO: 91306, SEQ ID NO: 91309, SEQ ID NO: 91315, SEQ ID NO: 91346, SEQ ID NO: 91419, SEQ ID NO: 91449, SEQ ID NO: 91498, SEQ ID NO: 91563, SEQ ID NO: 91588, SEQ ID NO: 91681, SEQ ID NO: 91766, SEQ ID NOs: 91775 to 91776, SEQ ID NO: 91780, SEQ ID NO: 91799, SEQ ID NO: 91845, SEQ ID NO: 91852, SEQ ID NOs: 91885 to 91886, SEQ ID NO: 91930, SEQ ID NO: 91935, SEQ ID NO: 91953, SEQ ID NO: 91966, SEQ ID NO: 91984, SEQ ID NO: 92026, SEQ ID NO: 92030, SEQ ID NO: 92069, SEQ ID NO: 92100, SEQ ID NO: 92111, SEQ ID NO: 92189, SEQ ID NO: 92249, SEQ ID NO: 92296, SEQ ID NO: 92400, SEQ ID NO: 92404, SEQ ID NO: 92409, SEQ ID NO: 92429, SEQ ID NO: 92474, SEQ ID NO: 92500, SEQ ID NO: 92515, SEQ ID NO: 92538, SEQ ID NO: 92646, SEQ ID NO: 92659, SEQ ID NO: 92671, SEQ ID NO: 92673, SEQ ID NO: 92675, SEQ ID NO: 92684, SEQ ID NO: 92704, SEQ ID NO: 92832, SEQ ID NO: 92835, SEQ ID NO: 92854, SEQ ID NO: 92858, SEQ ID NO: 92877, SEQ ID NO: 92918, SEQ ID NO: 92920, SEQ ID NO: 93004, SEQ ID NO: 93036, SEQ ID NO: 93042, SEQ ID NO: 93071, SEQ ID NO: 93089, SEQ ID NO: 93136, SEQ ID NO: 93180, SEQ ID NO: 93251, SEQ ID NO: 93325, SEQ ID NO: 93335, SEQ ID NO: 93344, SEQ ID NO: 93356, SEQ ID NO: 93382, SEQ ID NO: 93408, SEQ ID NO: 93420, SEQ ID NO: 93503, SEQ ID NO: 93537, SEQ ID NO: 93617, SEQ ID NO: 93658, SEQ ID NO: 93697, SEQ ID NO: 93710, SEQ ID NO: 93877, SEQ ID NO: 93885, SEQ ID NO: 93888, SEQ ID NO: 93893, SEQ ID NO: 93903, SEQ ID NO: 93912, SEQ ID NO: 93926, SEQ ID NO: 93933, SEQ ID NO: 93982, SEQ ID NO: 93987, SEQ ID NO: 94000, SEQ ID NO: 94054, SEQ ID NO: 94058, SEQ ID NO: 94087, SEQ ID NO: 94090, SEQ ID NO: 94102, SEQ ID NO: 94143, SEQ ID NO: 94269, SEQ ID NO: 94367, SEQ ID NO: 94465, SEQ ID NO: 94477, SEQ ID NO: 94525, SEQ ID NO: 94587, SEQ ID NOs: 95593 to 113807, SEQ ID NO: 217120, SEQ ID NO: 247270, SEQ ID NO: 248009, SEQ ID NOs: 248159 to 248160, SEQ ID NOs: 248735 to 248738, SEQ ID NOs: 249358 to 249362, SEQ ID NOs: 249690 to 249691, SEQ ID NOs: 252562 to 252564, SEQ ID NOs: 252836 to 252837, SEQ ID NO: 256214, SEQ ID NO: 256221, SEQ ID NO: 256226, SEQ ID NO: 256229, SEQ ID NO: 256235, SEQ ID NO: 256705, SEQ ID NO: 257337, SEQ ID NO: 257341, SEQ ID NO: 257345, SEQ ID NO: 257995, SEQ ID NO: 258292, SEQ ID NO: 258295, SEQ ID NOs: 258614 to 258616, SEQ ID NO: 259467, SEQ ID NO: 259471, SEQ ID NO: 259474, SEQ ID NO: 260118, SEQ ID NO: 260122, SEQ ID NO: 260126, SEQ ID NO: 260131, SEQ ID NO: 260138, SEQ ID NO: 260145, SEQ ID NO: 260153, SEQ ID NOs: 260367 to 260384, SEQ ID NO: 260407, SEQ ID NO: 260412, SEQ ID NO: 261788, SEQ ID NO: 261790, SEQ ID NOs: 261792 to 261793, SEQ ID NO: 261795, SEQ ID NO: 261798, SEQ ID NO: 261800, SEQ ID NO: 261803, SEQ ID NO: 261805, SEQ ID NO: 261809, SEQ ID NO: 261811, SEQ ID NO: 261814, SEQ ID NO: 261816, SEQ ID NO: 261821, SEQ ID NO: 261823, SEQ ID NO: 261830, SEQ ID NO: 261832, SEQ ID NO: 261837, SEQ ID NO: 261839, SEQ ID NO: 262119, SEQ ID NO: 262122, SEQ ID NOs: 262261 to 262285, SEQ ID NO: 262313, SEQ ID NO: 262318, SEQ ID NOs: 263471 to 263474, SEQ ID NO: 263494, SEQ ID NO: 263498, SEQ ID NOs: 266653 to 266654, SEQ ID NO: 269139, SEQ ID NO: 269143, SEQ ID NO: 269149, SEQ ID NO: 269156, SEQ ID NO: 269169, SEQ ID NOs: 270516 to 270517, SEQ ID NOs: 270519 to 270520, SEQ ID NOs: 270523 to 270524, SEQ ID NOs: 270527 to 270528, SEQ ID NO: 272016, SEQ ID NO: 272020, SEQ ID NOs: 272214 to 272222, SEQ ID NO: 272243, SEQ ID NO: 272248, SEQ ID NO: 272896, SEQ ID NOs: 273018 to 273020, SEQ ID NOs: 278350 to 278351, SEQ ID NO: 278355, SEQ ID NOs: 278358 to 278359, SEQ ID NOs: 278361 to 278362, SEQ ID NO: 278364, SEQ ID NO: 278367, SEQ ID NO: 278369, SEQ ID NO: 278371, SEQ ID NO: 278373, SEQ ID NO: 278375, SEQ ID NO: 278377, SEQ ID NO: 278383, SEQ ID NO: 278385, SEQ ID NO: 278388, SEQ ID NO: 278390, SEQ ID NO: 278394, SEQ ID NO: 278396, SEQ ID NOs: 281013 to 281014, SEQ ID NO: 281018, SEQ ID NO: 281022, SEQ ID NO: 281026, SEQ ID NO: 281031, SEQ ID NOs: 281037 to 281038, SEQ ID NOs: 281044 to 281045, SEQ ID NOs: 281052 to 281053, SEQ ID NOs: 281151 to 281152, SEQ ID NO: 281155, SEQ ID NO: 281159, SEQ ID NOs: 281162 to 281163, SEQ ID NOs: 281165 to 281166, SEQ ID NO: 281169, SEQ ID NO: 281171, SEQ ID NO: 281174, SEQ ID NO: 281176, SEQ ID NO: 281179, SEQ ID NO: 281181, SEQ ID NO: 281184, SEQ ID NO: 281186, SEQ ID NO: 281190, SEQ ID NO: 281192, SEQ ID NO: 281197, SEQ ID NO: 281199, or SEQ ID NOs: 281350 to 305565.

In some embodiments, the amino acid sequence for a MHC class I and/or MHC class II peptides may be used to create a single target (individual) or combined peptide vaccine for the SSX2 protein having between about 2 and about 40 peptides. In some embodiments, any one of the peptides in the vaccine for the SSX2 protein comprises one or more of the SEQ ID NOs: 162383 to 166443 and SEQ ID NOs: 369027 to 373347. In some embodiments, any one of the peptides in the SSX2 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 162383 to 166443 or SEQ ID NOs: 369027 to 373347.

In some embodiments, the amino acid sequence for a MHC class I and/or MHC class II peptides may be used to create a single target (individual) or combined peptide vaccine for the PRAME protein having between about 2 and about 40 peptides. In some embodiments, any one of the peptides in the vaccine for the PRAME protein comprises one or more of the SEQ ID NOs: 144109 to 162382 and SEQ ID NOs: 342521 to 369026. In some embodiments, any one of the peptides in the PRAME vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 144109 to 162382 or SEQ ID NOs: 342521 to 369026.

In some embodiments, the amino acid sequence for a MHC class I and/or MHC class II peptides may be used to create a single target (individual) or combined peptide vaccine for the KKLC1 protein having between about 2 and about 40 peptides. In some embodiments, any one of the peptides in the vaccine for the KKLC1 protein comprises one or more of the SEQ ID NOs: 37110 to 41320 and SEQ ID NOs: 206663 to 211900. In some embodiments, any one of the peptides in the KKLC1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 37110 to 41320 or SEQ ID NOs: 206663 to 211900.

In some embodiments, the amino acid sequence for a MHC class I and/or MHC class II peptides may be used to create a single target (individual) or combined peptide vaccine for the PMEL protein having between about 2 and about 40 peptides. In some embodiments, any one of the peptides in the vaccine for the PMEL protein comprises one or more of the SEQ ID NOs: 125134 to 144108 and SEQ ID NOs: 317360 to 342520. In some embodiments, any one of the peptides in the PMEL vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 125134 to 144108 or SEQ ID NOs: 317360 to 342520.

In some embodiments, the amino acid sequence for a MHC class I and/or MHC class II peptides may be used to create a single target (individual) or combined peptide vaccine for the TYRP1 protein having between about 2 and about 40 peptides. In some embodiments, any one of the peptides in the vaccine for the TYRP1 protein comprises one or more of the SEQ ID NOs: 166444 to 182573 and SEQ ID NOs: 373348 to 392433. In some embodiments, any one of the peptides in the TYRP1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 166444 to 182573 or SEQ ID NOs: 373348 to 392433.

In some embodiments, the amino acid sequence for a MHC class I and/or MHC class II peptides may be used to create a single target (individual) or combined peptide vaccine for the TYRP2 protein having between about 2 and about 40 peptides. In some embodiments, any one of the peptides in the vaccine for the TYRP2 protein comprises one or more of the SEQ ID NOs: 166476 to 166477, SEQ ID NO: 166486, SEQ ID NO: 166513, SEQ ID NO: 166591, SEQ ID NO: 166606, SEQ ID NO: 166629, SEQ ID NO: 166641, SEQ ID NO: 166667, SEQ ID NOs: 166678 to 166679, SEQ ID NO: 166795, SEQ ID NO: 166799, SEQ ID NO: 166834, SEQ ID NO: 166854, SEQ ID NO: 166909, SEQ ID NO: 166912, SEQ ID NO: 166942, SEQ ID NOs: 166991 to 166992, SEQ ID NO: 167062, SEQ ID NO: 167067, SEQ ID NOs: 167073 to 167074, SEQ ID NO: 167106, SEQ ID NO: 167118, SEQ ID NO: 167151, SEQ ID NO: 167177, SEQ ID NO: 167241, SEQ ID NO: 167271, SEQ ID NO: 167395, SEQ ID NO: 167491, SEQ ID NO: 167505, SEQ ID NO: 167687, SEQ ID NO: 167736, SEQ ID NO: 167740, SEQ ID NO: 167743, SEQ ID NO: 167755, SEQ ID NO: 167810, SEQ ID NO: 167831, SEQ ID NO: 167837, SEQ ID NO: 167844, SEQ ID NOs: 167847 to 167848, SEQ ID NO: 167859, SEQ ID NO: 167880, SEQ ID NO: 167891, SEQ ID NO: 167897, SEQ ID NO: 167933, SEQ ID NO: 168094, SEQ ID NOs: 168111 to 168112, SEQ ID NO: 168132, SEQ ID NO: 168144, SEQ ID NO: 168167, SEQ ID NO: 168211, SEQ ID NO: 168252, SEQ ID NO: 168268, SEQ ID NO: 168343, SEQ ID NO: 168354, SEQ ID NO: 168376, SEQ ID NO: 168396, SEQ ID NO: 168410, SEQ ID NO: 168423, SEQ ID NO: 168460, SEQ ID NO: 168484, SEQ ID NO: 168496, SEQ ID NO: 168616, SEQ ID NO: 168626, SEQ ID NO: 168646, SEQ ID NO: 168660, SEQ ID NO: 168681, SEQ ID NO: 168703, SEQ ID NO: 168711, SEQ ID NO: 168725, SEQ ID NO: 168728, SEQ ID NO: 168760, SEQ ID NOs: 168792 to 168793, SEQ ID NO: 168815, SEQ ID NO: 168851, SEQ ID NO: 168863, SEQ ID NO: 168867, SEQ ID NO: 168871, SEQ ID NO: 168924, SEQ ID NO: 168927, SEQ ID NO: 168947, SEQ ID NO: 168974, SEQ ID NO: 169000, SEQ ID NO: 169024, SEQ ID NO: 169035, SEQ ID NO: 169112, SEQ ID NO: 169150, SEQ ID NO: 169187, SEQ ID NO: 169233, SEQ ID NO: 169240, SEQ ID NO: 169247, SEQ ID NO: 169275, SEQ ID NO: 169375, SEQ ID NO: 169403, SEQ ID NO: 169428, SEQ ID NO: 169460, SEQ ID NO: 169474, SEQ ID NO: 169500, SEQ ID NO: 169530, SEQ ID NO: 169542, SEQ ID NO: 169546, SEQ ID NO: 169548, SEQ ID NO: 169553, SEQ ID NO: 169555, SEQ ID NO: 169563, SEQ ID NO: 169565, SEQ ID NO: 169578, SEQ ID NO: 169584, SEQ ID NO: 169605, SEQ ID NO: 169641, SEQ ID NO: 169665, SEQ ID NO: 169673, SEQ ID NO: 169682, SEQ ID NO: 169700, SEQ ID NO: 169704, SEQ ID NO: 169740, SEQ ID NO: 169768, SEQ ID NO: 169850, SEQ ID NO: 169858, SEQ ID NO: 169867, SEQ ID NO: 169871, SEQ ID NO: 169886, SEQ ID NO: 169915, SEQ ID NO: 169966, SEQ ID NO: 170057, SEQ ID NO: 170061, SEQ ID NO: 170081, SEQ ID NOs: 170178 to 170179, SEQ ID NO: 170261, SEQ ID NO: 170268, SEQ ID NO: 170278, SEQ ID NO: 170290, SEQ ID NO: 170320, SEQ ID NO: 170329, SEQ ID NO: 170390, SEQ ID NO: 170443, SEQ ID NO: 170488, SEQ ID NO: 170543, SEQ ID NO: 170574, SEQ ID NO: 170679, SEQ ID NO: 170704, SEQ ID NOs: 170706 to 170707, SEQ ID NO: 170735, SEQ ID NO: 170754, SEQ ID NO: 170771, SEQ ID NOs: 170809 to 170810, SEQ ID NO: 170834, SEQ ID NO: 170847, SEQ ID NO: 170876, SEQ ID NOs: 170902 to 170903, SEQ ID NO: 170964, SEQ ID NO: 170968, SEQ ID NO: 170970, SEQ ID NO: 170976, SEQ ID NO: 170981, SEQ ID NO: 171011, SEQ ID NO: 171029, SEQ ID NO: 171080, SEQ ID NO: 171085, SEQ ID NO: 171091, SEQ ID NO: 171174, SEQ ID NO: 171182, SEQ ID NO: 171212, SEQ ID NO: 171229, SEQ ID NO: 171242, SEQ ID NO: 171256, SEQ ID NO: 171260, SEQ ID NO: 171263, SEQ ID NO: 171291, SEQ ID NO: 171329, SEQ ID NO: 171334, SEQ ID NO: 171340, SEQ ID NO: 171406, SEQ ID NO: 171412, SEQ ID NO: 171428, SEQ ID NO: 171462, SEQ ID NO: 171474, SEQ ID NO: 171485, SEQ ID NO: 171490, SEQ ID NO: 171526, SEQ ID NO: 171536, SEQ ID NO: 171550, SEQ ID NO: 171581, SEQ ID NO: 171608, SEQ ID NO: 171625, SEQ ID NO: 171655, SEQ ID NO: 171662, SEQ ID NO: 171709, SEQ ID NO: 171732, SEQ ID NO: 171746, SEQ ID NO: 171752, SEQ ID NO: 171768, SEQ ID NO: 171786, SEQ ID NO: 171788, SEQ ID NO: 171814, SEQ ID NO: 171855, SEQ ID NO: 171863, SEQ ID NO: 171980, SEQ ID NO: 172007, SEQ ID NO: 172010, SEQ ID NO: 172062, SEQ ID NO: 172161, SEQ ID NO: 172181, SEQ ID NO: 172203, SEQ ID NO: 172225, SEQ ID NO: 172231, SEQ ID NO: 172255, SEQ ID NO: 172272, SEQ ID NO: 172276, SEQ ID NO: 172294, SEQ ID NO: 172348, SEQ ID NO: 172372, SEQ ID NO: 172375, SEQ ID NO: 172378, SEQ ID NO: 172387, SEQ ID NO: 172389, SEQ ID NO: 172421, SEQ ID NOs: 172439 to 172440, SEQ ID NO: 172484, SEQ ID NO: 172495, SEQ ID NO: 172563, SEQ ID NO: 172594, SEQ ID NO: 172660, SEQ ID NO: 172693, SEQ ID NO: 172702, SEQ ID NO: 172704, SEQ ID NO: 172709, SEQ ID NO: 172717, SEQ ID NO: 172726, SEQ ID NO: 172742, SEQ ID NO: 172793, SEQ ID NO: 172801, SEQ ID NO: 172816, SEQ ID NO: 172849, SEQ ID NO: 172862, SEQ ID NO: 172900, SEQ ID NO: 172907, SEQ ID NO: 172919, SEQ ID NO: 172926, SEQ ID NO: 172990, SEQ ID NO: 172994, SEQ ID NO: 172999, SEQ ID NO: 173004, SEQ ID NO: 173007, SEQ ID NO: 173084, SEQ ID NO: 173202, SEQ ID NO: 173206, SEQ ID NO: 173284, SEQ ID NO: 173288, SEQ ID NO: 173318, SEQ ID NO: 173321, SEQ ID NO: 173412, SEQ ID NO: 173433, SEQ ID NO: 173452, SEQ ID NO: 173467, SEQ ID NOs: 173469 to 173470, SEQ ID NO: 173494, SEQ ID NO: 173497, SEQ ID NO: 173516, SEQ ID NO: 173611, SEQ ID NO: 173633, SEQ ID NO: 173713, SEQ ID NO: 173726, SEQ ID NO: 173762, SEQ ID NO: 173792, SEQ ID NO: 173837, SEQ ID NO: 173849, SEQ ID NO: 173858, SEQ ID NO: 173864, SEQ ID NO: 173884, SEQ ID NO: 173918, SEQ ID NO: 173923, SEQ ID NO: 173929, SEQ ID NO: 173958, SEQ ID NO: 173993, SEQ ID NO: 174020, SEQ ID NO: 174026, SEQ ID NO: 174044, SEQ ID NO: 174047, SEQ ID NO: 174110, SEQ ID NO: 174116, SEQ ID NO: 174161, SEQ ID NO: 174164, SEQ ID NO: 174168, SEQ ID NO: 174180, SEQ ID NO: 174190, SEQ ID NO: 174210, SEQ ID NO: 174228, SEQ ID NO: 174260, SEQ ID NO: 174265, SEQ ID NO: 174277, SEQ ID NO: 174283, SEQ ID NO: 174301, SEQ ID NO: 174311, SEQ ID NO: 174316, SEQ ID NO: 174356, SEQ ID NO: 174387, SEQ ID NO: 174424, SEQ ID NO: 174452, SEQ ID NO: 174486, SEQ ID NO: 174491, SEQ ID NO: 174507, SEQ ID NO: 174510, SEQ ID NO: 174595, SEQ ID NO: 174611, SEQ ID NO: 174633, SEQ ID NO: 174679, SEQ ID NO: 174702, SEQ ID NO: 174724, SEQ ID NO: 174747, SEQ ID NO: 174756, SEQ ID NO: 174779, SEQ ID NO: 174847, SEQ ID NO: 174880, SEQ ID NO: 174904, SEQ ID NO: 174956, SEQ ID NO: 174960, SEQ ID NO: 174978, SEQ ID NO: 175027, SEQ ID NO: 175063, SEQ ID NO: 175076, SEQ ID NO: 175129, SEQ ID NO: 175160, SEQ ID NO: 175175, SEQ ID NO: 175186, SEQ ID NO: 175191, SEQ ID NO: 175251, SEQ ID NO: 175269, SEQ ID NO: 175292, SEQ ID NO: 175295, SEQ ID NO: 175300, SEQ ID NO: 175416, SEQ ID NO: 175423, SEQ ID NO: 175506, SEQ ID NO: 175541, SEQ ID NO: 175557, SEQ ID NO: 175585, SEQ ID NO: 175625, SEQ ID NO: 175649, SEQ ID NO: 175671, SEQ ID NOs: 175721 to 175722, SEQ ID NO: 175820, SEQ ID NO: 175886, SEQ ID NO: 175902, SEQ ID NO: 175951, SEQ ID NOs: 175960 to 175961, SEQ ID NO: 175968, SEQ ID NO: 175975, SEQ ID NO: 175993, SEQ ID NO: 176018, SEQ ID NO: 176041, SEQ ID NO: 176051, SEQ ID NO: 176112, SEQ ID NO: 176118, SEQ ID NO: 176149, SEQ ID NO: 176179, SEQ ID NO: 176248, SEQ ID NO: 176306, SEQ ID NO: 176309, SEQ ID NO: 176312, SEQ ID NO: 176335, SEQ ID NO: 176338, SEQ ID NO: 176355, SEQ ID NO: 176369, SEQ ID NO: 176379, SEQ ID NO: 176452, SEQ ID NO: 176466, SEQ ID NO: 176503, SEQ ID NO: 176548, SEQ ID NO: 176560, SEQ ID NO: 176611, SEQ ID NO: 176621, SEQ ID NO: 176639, SEQ ID NO: 176693, SEQ ID NO: 176700, SEQ ID NO: 176713, SEQ ID NO: 176764, SEQ ID NOs: 176795 to 176796, SEQ ID NO: 176806, SEQ ID NO: 176815, SEQ ID NO: 176953, SEQ ID NO: 176958, SEQ ID NO: 176969, SEQ ID NO: 176980, SEQ ID NO: 176991, SEQ ID NO: 177016, SEQ ID NO: 177033, SEQ ID NO: 177044, SEQ ID NO: 177061, SEQ ID NO: 177065, SEQ ID NO: 177080, SEQ ID NO: 177088, SEQ ID NO: 177102, SEQ ID NO: 177119, SEQ ID NO: 177343, SEQ ID NO: 177358, SEQ ID NO: 177390, SEQ ID NO: 177430, SEQ ID NO: 177437, SEQ ID NO: 177465, SEQ ID NOs: 177482 to 177483, SEQ ID NO: 177492, SEQ ID NO: 177495, SEQ ID NO: 177522, SEQ ID NO: 177585, SEQ ID NO: 177604, SEQ ID NO: 177611, SEQ ID NO: 177664, SEQ ID NO: 177669, SEQ ID NO: 177701, SEQ ID NO: 177707, SEQ ID NO: 177710, SEQ ID NO: 177712, SEQ ID NO: 177714, SEQ ID NO: 177734, SEQ ID NO: 177808, SEQ ID NO: 177841, SEQ ID NO: 177848, SEQ ID NO: 177892, SEQ ID NO: 177918, SEQ ID NO: 177958, SEQ ID NOs: 177989 to 177990, SEQ ID NO: 178023, SEQ ID NO: 178032, SEQ ID NO: 178035, SEQ ID NO: 178039, SEQ ID NO: 178122, SEQ ID NO: 178161, SEQ ID NO: 178195, SEQ ID NO: 178208, SEQ ID NO: 178244, SEQ ID NO: 178272, SEQ ID NO: 178293, SEQ ID NO: 178310, SEQ ID NO: 178338, SEQ ID NO: 178353, SEQ ID NO: 178385, SEQ ID NO: 178399, SEQ ID NO: 178477, SEQ ID NO: 178519, SEQ ID NO: 178568, SEQ ID NO: 178587, SEQ ID NO: 178600, SEQ ID NO: 178612, SEQ ID NO: 178615, SEQ ID NO: 178651, SEQ ID NO: 178726, SEQ ID NO: 178740, SEQ ID NO: 178743, SEQ ID NO: 178750, SEQ ID NO: 178821, SEQ ID NO: 178886, SEQ ID NO: 178895, SEQ ID NO: 178911, SEQ ID NO: 178942, SEQ ID NO: 178946, SEQ ID NO: 178948, SEQ ID NO: 178966, SEQ ID NO: 179020, SEQ ID NO: 179031, SEQ ID NO: 179034, SEQ ID NO: 179130, SEQ ID NO: 179134, SEQ ID NO: 179151, SEQ ID NO: 179154, SEQ ID NO: 179224, SEQ ID NO: 179257, SEQ ID NO: 179387, SEQ ID NO: 179404, SEQ ID NO: 179444, SEQ ID NO: 179455, SEQ ID NO: 179462, SEQ ID NO: 179483, SEQ ID NO: 179544, SEQ ID NO: 179586, SEQ ID NO: 179600, SEQ ID NO: 179612, SEQ ID NO: 179619, SEQ ID NO: 179632, SEQ ID NO: 179677, SEQ ID NO: 179695, SEQ ID NO: 179697, SEQ ID NO: 179760, SEQ ID NO: 179863, SEQ ID NO: 179898, SEQ ID NO: 179904, SEQ ID NO: 179934, SEQ ID NO: 179957, SEQ ID NO: 179981, SEQ ID NO: 180013, SEQ ID NO: 180019, SEQ ID NO: 180036, SEQ ID NO: 180077, SEQ ID NO: 180086, SEQ ID NO: 180167, SEQ ID NO: 180257, SEQ ID NO: 180259, SEQ ID NO: 180271, SEQ ID NO: 180291, SEQ ID NO: 180327, SEQ ID NO: 180348, SEQ ID NO: 180378, SEQ ID NO: 180396, SEQ ID NO: 180430, SEQ ID NO: 180452, SEQ ID NO: 180458, SEQ ID NO: 180481, SEQ ID NO: 180489, SEQ ID NO: 180492, SEQ ID NO: 180528, SEQ ID NO: 180551, SEQ ID NO: 180567, SEQ ID NO: 180577, SEQ ID NO: 180597, SEQ ID NO: 180622, SEQ ID NO: 180683, SEQ ID NO: 180694, SEQ ID NOs: 180720 to 180721, SEQ ID NO: 180772, SEQ ID NO: 180799, SEQ ID NO: 180823, SEQ ID NO: 180843, SEQ ID NO: 180848, SEQ ID NO: 180858, SEQ ID NO: 180866, SEQ ID NO: 180879, SEQ ID NO: 180977, SEQ ID NOs: 181032 to 181033, SEQ ID NO: 181173, SEQ ID NO: 181204, SEQ ID NO: 181259, SEQ ID NO: 181406, SEQ ID NO: 181630, SEQ ID NO: 181685, SEQ ID NO: 181792, SEQ ID NO: 181963, SEQ ID NO: 181984, SEQ ID NOs: 182157 to 182159, SEQ ID NO: 182471, SEQ ID NOs: 182574 to 197896, SEQ ID NO: 379327, SEQ ID NO: 379329, SEQ ID NO: 379332, SEQ ID NO: 379334, SEQ ID NO: 379770, SEQ ID NO: 381531, SEQ ID NO: 382109, SEQ ID NO: 383301, SEQ ID NO: 383305, SEQ ID NO: 383310, SEQ ID NO: 386111, SEQ ID NO: 387057, SEQ ID NO: 387062, and SEQ ID NOs: 392434 to 410309. In some embodiments, any one of the peptides in the TYRP2 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 166476 to 166477, SEQ ID NO: 166486, SEQ ID NO: 166513, SEQ ID NO: 166591, SEQ ID NO: 166606, SEQ ID NO: 166629, SEQ ID NO: 166641, SEQ ID NO: 166667, SEQ ID NOs: 166678 to 166679, SEQ ID NO: 166795, SEQ ID NO: 166799, SEQ ID NO: 166834, SEQ ID NO: 166854, SEQ ID NO: 166909, SEQ ID NO: 166912, SEQ ID NO: 166942, SEQ ID NOs: 166991 to 166992, SEQ ID NO: 167062, SEQ ID NO: 167067, SEQ ID NOs: 167073 to 167074, SEQ ID NO: 167106, SEQ ID NO: 167118, SEQ ID NO: 167151, SEQ ID NO: 167177, SEQ ID NO: 167241, SEQ ID NO: 167271, SEQ ID NO: 167395, SEQ ID NO: 167491, SEQ ID NO: 167505, SEQ ID NO: 167687, SEQ ID NO: 167736, SEQ ID NO: 167740, SEQ ID NO: 167743, SEQ ID NO: 167755, SEQ ID NO: 167810, SEQ ID NO: 167831, SEQ ID NO: 167837, SEQ ID NO: 167844, SEQ ID NOs: 167847 to 167848, SEQ ID NO: 167859, SEQ ID NO: 167880, SEQ ID NO: 167891, SEQ ID NO: 167897, SEQ ID NO: 167933, SEQ ID NO: 168094, SEQ ID NOs: 168111 to 168112, SEQ ID NO: 168132, SEQ ID NO: 168144, SEQ ID NO: 168167, SEQ ID NO: 168211, SEQ ID NO: 168252, SEQ ID NO: 168268, SEQ ID NO: 168343, SEQ ID NO: 168354, SEQ ID NO: 168376, SEQ ID NO:

168396, SEQ ID NO: 168410, SEQ ID NO: 168423, SEQ ID NO: 168460, SEQ ID NO: 168484, SEQ ID NO: 168496, SEQ ID NO: 168616, SEQ ID NO: 168626, SEQ ID NO: 168646, SEQ ID NO: 168660, SEQ ID NO: 168681, SEQ ID NO: 168703, SEQ ID NO: 168711, SEQ ID NO: 168725, SEQ ID NO: 168728, SEQ ID NO: 168760, SEQ ID NOs: 168792 to 168793, SEQ ID NO: 168815, SEQ ID NO: 168851, SEQ ID NO: 168863, SEQ ID NO: 168867, SEQ ID NO: 168871, SEQ ID NO: 168924, SEQ ID NO: 168927, SEQ ID NO: 168947, SEQ ID NO: 168974, SEQ ID NO: 169000, SEQ ID NO: 169024, SEQ ID NO: 169035, SEQ ID NO: 169112, SEQ ID NO: 169150, SEQ ID NO: 169187, SEQ ID NO: 169233, SEQ ID NO: 169240, SEQ ID NO: 169247, SEQ ID NO: 169275, SEQ ID NO: 169375, SEQ ID NO: 169403, SEQ ID NO: 169428, SEQ ID NO: 169460, SEQ ID NO: 169474, SEQ ID NO: 169500, SEQ ID NO: 169530, SEQ ID NO: 169542, SEQ ID NO: 169546, SEQ ID NO: 169548, SEQ ID NO: 169553, SEQ ID NO: 169555, SEQ ID NO: 169563, SEQ ID NO: 169565, SEQ ID NO: 169578, SEQ ID NO: 169584, SEQ ID NO: 169605, SEQ ID NO: 169641, SEQ ID NO: 169665, SEQ ID NO: 169673, SEQ ID NO: 169682, SEQ ID NO: 169700, SEQ ID NO: 169704, SEQ ID NO: 169740, SEQ ID NO: 169768, SEQ ID NO: 169850, SEQ ID NO: 169858, SEQ ID NO: 169867, SEQ ID NO: 169871, SEQ ID NO: 169886, SEQ ID NO: 169915, SEQ ID NO: 169966, SEQ ID NO: 170057, SEQ ID NO: 170061, SEQ ID NO: 170081, SEQ ID NOs: 170178 to 170179, SEQ ID NO: 170261, SEQ ID NO: 170268, SEQ ID NO: 170278, SEQ ID NO: 170290, SEQ ID NO: 170320, SEQ ID NO: 170329, SEQ ID NO: 170390, SEQ ID NO: 170443, SEQ ID NO: 170488, SEQ ID NO: 170543, SEQ ID NO: 170574, SEQ ID NO: 170679, SEQ ID NO: 170704, SEQ ID NOs: 170706 to 170707, SEQ ID NO: 170735, SEQ ID NO: 170754, SEQ ID NO: 170771, SEQ ID NOs: 170809 to 170810, SEQ ID NO: 170834, SEQ ID NO: 170847, SEQ ID NO: 170876, SEQ ID NOs: 170902 to 170903, SEQ ID NO: 170964, SEQ ID NO: 170968, SEQ ID NO: 170970, SEQ ID NO: 170976, SEQ ID NO: 170981, SEQ ID NO: 171011, SEQ ID NO: 171029, SEQ ID NO: 171080, SEQ ID NO: 171085, SEQ ID NO: 171091, SEQ ID NO: 171174, SEQ ID NO: 171182, SEQ ID NO: 171212, SEQ ID NO: 171229, SEQ ID NO: 171242, SEQ ID NO: 171256, SEQ ID NO: 171260, SEQ ID NO: 171263, SEQ ID NO: 171291, SEQ ID NO: 171329, SEQ ID NO: 171334, SEQ ID NO: 171340, SEQ ID NO: 171406, SEQ ID NO: 171412, SEQ ID NO: 171428, SEQ ID NO: 171462, SEQ ID NO: 171474, SEQ ID NO: 171485, SEQ ID NO: 171490, SEQ ID NO: 171526, SEQ ID NO: 171536, SEQ ID NO: 171550, SEQ ID NO: 171581, SEQ ID NO: 171608, SEQ ID NO: 171625, SEQ ID NO: 171655, SEQ ID NO: 171662, SEQ ID NO: 171709, SEQ ID NO: 171732, SEQ ID NO: 171746, SEQ ID NO: 171752, SEQ ID NO: 171768, SEQ ID NO: 171786, SEQ ID NO: 171788, SEQ ID NO: 171814, SEQ ID NO: 171855, SEQ ID NO: 171863, SEQ ID NO: 171980, SEQ ID NO: 172007, SEQ ID NO: 172010, SEQ ID NO: 172062, SEQ ID NO: 172161, SEQ ID NO: 172181, SEQ ID NO: 172203, SEQ ID NO: 172225, SEQ ID NO: 172231, SEQ ID NO: 172255, SEQ ID NO: 172272, SEQ ID NO: 172276, SEQ ID NO: 172294, SEQ ID NO: 172348, SEQ ID NO: 172372, SEQ ID NO: 172375, SEQ ID NO: 172378, SEQ ID NO: 172387, SEQ ID NO: 172389, SEQ ID NO: 172421, SEQ ID NOs: 172439 to 172440, SEQ ID NO: 172484, SEQ ID NO: 172495, SEQ ID NO: 172563, SEQ ID NO: 172594, SEQ ID NO: 172660, SEQ ID NO: 172693, SEQ ID NO: 172702, SEQ ID NO: 172704, SEQ ID NO: 172709, SEQ ID NO: 172717, SEQ ID NO: 172726, SEQ ID NO: 172742, SEQ ID NO: 172793, SEQ ID NO: 172801, SEQ ID NO: 172816, SEQ ID NO: 172849, SEQ ID NO: 172862, SEQ ID NO: 172900, SEQ ID NO: 172907, SEQ ID NO: 172919, SEQ ID NO: 172926, SEQ ID NO: 172990, SEQ ID NO: 172994, SEQ ID NO: 172999, SEQ ID NO: 173004, SEQ ID NO: 173007, SEQ ID NO: 173084, SEQ ID NO: 173202, SEQ ID NO: 173206, SEQ ID NO: 173284, SEQ ID NO: 173288, SEQ ID NO: 173318, SEQ ID NO: 173321, SEQ ID NO: 173412, SEQ ID NO: 173433, SEQ ID NO: 173452, SEQ ID NO: 173467, SEQ ID NOs: 173469 to 173470, SEQ ID NO: 173494, SEQ ID NO: 173497, SEQ ID NO: 173516, SEQ ID NO: 173611, SEQ ID NO: 173633, SEQ ID NO: 173713, SEQ ID NO: 173726, SEQ ID NO: 173762, SEQ ID NO: 173792, SEQ ID NO: 173837, SEQ ID NO: 173849, SEQ ID NO: 173858, SEQ ID NO: 173864, SEQ ID NO: 173884, SEQ ID NO: 173918, SEQ ID NO: 173923, SEQ ID NO: 173929, SEQ ID NO: 173958, SEQ ID NO: 173993, SEQ ID NO: 174020, SEQ ID NO: 174026, SEQ ID NO: 174044, SEQ ID NO: 174047, SEQ ID NO: 174110, SEQ ID NO: 174116, SEQ ID NO: 174161, SEQ ID NO: 174164, SEQ ID NO: 174168, SEQ ID NO: 174180, SEQ ID NO: 174190, SEQ ID NO: 174210, SEQ ID NO: 174228, SEQ ID NO: 174260, SEQ ID NO: 174265, SEQ ID NO: 174277, SEQ ID NO: 174283, SEQ ID NO: 174301, SEQ ID NO: 174311, SEQ ID NO: 174316, SEQ ID NO: 174356, SEQ ID NO: 174387, SEQ ID NO: 174424, SEQ ID NO: 174452, SEQ ID NO: 174486, SEQ ID NO: 174491, SEQ ID NO: 174507, SEQ ID NO: 174510, SEQ ID NO: 174595, SEQ ID NO: 174611, SEQ ID NO: 174633, SEQ ID NO: 174679, SEQ ID NO: 174702, SEQ ID NO: 174724, SEQ ID NO: 174747, SEQ ID NO: 174756, SEQ ID NO: 174779, SEQ ID NO: 174847, SEQ ID NO: 174880, SEQ ID NO: 174904, SEQ ID NO: 174956, SEQ ID NO: 174960, SEQ ID NO: 174978, SEQ ID NO: 175027, SEQ ID NO: 175063, SEQ ID NO: 175076, SEQ ID NO: 175129, SEQ ID NO: 175160, SEQ ID NO: 175175, SEQ ID NO: 175186, SEQ ID NO: 175191, SEQ ID NO: 175251, SEQ ID NO: 175269, SEQ ID NO: 175292, SEQ ID NO: 175295, SEQ ID NO: 175300, SEQ ID NO: 175416, SEQ ID NO: 175423, SEQ ID NO: 175506, SEQ ID NO: 175541, SEQ ID NO: 175557, SEQ ID NO: 175585, SEQ ID NO: 175625, SEQ ID NO: 175649, SEQ ID NO: 175671, SEQ ID NOs: 175721 to 175722, SEQ ID NO: 175820, SEQ ID NO: 175886, SEQ ID NO: 175902, SEQ ID NO: 175951, SEQ ID NOs: 175960 to 175961, SEQ ID NO: 175968, SEQ ID NO: 175975, SEQ ID NO: 175993, SEQ ID NO: 176018, SEQ ID NO: 176041, SEQ ID NO: 176051, SEQ ID NO: 176112, SEQ ID NO: 176118, SEQ ID NO: 176149, SEQ ID NO: 176179, SEQ ID NO: 176248, SEQ ID NO: 176306, SEQ ID NO: 176309, SEQ ID NO: 176312, SEQ ID NO: 176335, SEQ ID NO: 176338, SEQ ID NO: 176355, SEQ ID NO: 176369, SEQ ID NO: 176379, SEQ ID NO: 176452, SEQ ID NO: 176466, SEQ ID NO: 176503, SEQ ID NO: 176548, SEQ ID NO: 176560, SEQ ID NO: 176611, SEQ ID NO: 176621, SEQ ID NO: 176639, SEQ ID NO: 176693, SEQ ID NO: 176700, SEQ ID NO: 176713, SEQ ID NO: 176764, SEQ ID NOs: 176795 to 176796, SEQ ID NO: 176806, SEQ ID NO: 176815, SEQ ID NO: 176953, SEQ ID NO: 176958, SEQ ID NO: 176969, SEQ ID NO: 176980, SEQ ID NO: 176991, SEQ ID NO: 177016, SEQ ID NO: 177033, SEQ ID NO: 177044, SEQ ID NO: 177061, SEQ ID NO: 177065, SEQ ID NO: 177080, SEQ ID NO: 177088, SEQ ID NO: 177102, SEQ ID NO: 177119, SEQ ID NO: 177343, SEQ ID NO: 177358, SEQ ID NO: 177390, SEQ ID NO: 177430, SEQ ID NO: 177437, SEQ ID NO: 177465, SEQ ID NOs: 177482 to 177483, SEQ ID NO: 177492, SEQ ID NO: 177495, SEQ ID NO: 177522, SEQ ID NO: 177585, SEQ ID NO: 177604, SEQ ID NO: 177611, SEQ ID NO: 177664, SEQ ID NO: 177669, SEQ ID

NO: 177701, SEQ ID NO: 177707, SEQ ID NO: 177710, SEQ ID NO: 177712, SEQ ID NO: 177714, SEQ ID NO: 177734, SEQ ID NO: 177808, SEQ ID NO: 177841, SEQ ID NO: 177848, SEQ ID NO: 177892, SEQ ID NO: 177918, SEQ ID NO: 177958, SEQ ID NOs: 177989 to 177990, SEQ ID NO: 178023, SEQ ID NO: 178032, SEQ ID NO: 178035, SEQ ID NO: 178039, SEQ ID NO: 178122, SEQ ID NO: 178161, SEQ ID NO: 178195, SEQ ID NO: 178208, SEQ ID NO: 178244, SEQ ID NO: 178272, SEQ ID NO: 178293, SEQ ID NO: 178310, SEQ ID NO: 178338, SEQ ID NO: 178353, SEQ ID NO: 178385, SEQ ID NO: 178399, SEQ ID NO: 178477, SEQ ID NO: 178519, SEQ ID NO: 178568, SEQ ID NO: 178587, SEQ ID NO: 178600, SEQ ID NO: 178612, SEQ ID NO: 178615, SEQ ID NO: 178651, SEQ ID NO: 178726, SEQ ID NO: 178740, SEQ ID NO: 178743, SEQ ID NO: 178750, SEQ ID NO: 178821, SEQ ID NO: 178886, SEQ ID NO: 178895, SEQ ID NO: 178911, SEQ ID NO: 178942, SEQ ID NO: 178946, SEQ ID NO: 178948, SEQ ID NO: 178966, SEQ ID NO: 179020, SEQ ID NO: 179031, SEQ ID NO: 179034, SEQ ID NO: 179130, SEQ ID NO: 179134, SEQ ID NO: 179151, SEQ ID NO: 179154, SEQ ID NO: 179224, SEQ ID NO: 179257, SEQ ID NO: 179387, SEQ ID NO: 179404, SEQ ID NO: 179444, SEQ ID NO: 179455, SEQ ID NO: 179462, SEQ ID NO: 179483, SEQ ID NO: 179544, SEQ ID NO: 179586, SEQ ID NO: 179600, SEQ ID NO: 179612, SEQ ID NO: 179619, SEQ ID NO: 179632, SEQ ID NO: 179677, SEQ ID NO: 179695, SEQ ID NO: 179697, SEQ ID NO: 179760, SEQ ID NO: 179863, SEQ ID NO: 179898, SEQ ID NO: 179904, SEQ ID NO: 179934, SEQ ID NO: 179957, SEQ ID NO: 179981, SEQ ID NO: 180013, SEQ ID NO: 180019, SEQ ID NO: 180036, SEQ ID NO: 180077, SEQ ID NO: 180086, SEQ ID NO: 180167, SEQ ID NO: 180257, SEQ ID NO: 180259, SEQ ID NO: 180271, SEQ ID NO: 180291, SEQ ID NO: 180327, SEQ ID NO: 180348, SEQ ID NO: 180378, SEQ ID NO: 180396, SEQ ID NO: 180430, SEQ ID NO: 180452, SEQ ID NO: 180458, SEQ ID NO: 180481, SEQ ID NO: 180489, SEQ ID NO: 180492, SEQ ID NO: 180528, SEQ ID NO: 180551, SEQ ID NO: 180567, SEQ ID NO: 180577, SEQ ID NO: 180597, SEQ ID NO: 180622, SEQ ID NO: 180683, SEQ ID NO: 180694, SEQ ID NOs: 180720 to 180721, SEQ ID NO: 180772, SEQ ID NO: 180799, SEQ ID NO: 180823, SEQ ID NO: 180843, SEQ ID NO: 180848, SEQ ID NO: 180858, SEQ ID NO: 180866, SEQ ID NO: 180879, SEQ ID NO: 180977, SEQ ID NOs: 181032 to 181033, SEQ ID NO: 181173, SEQ ID NO: 181204, SEQ ID NO: 181259, SEQ ID NO: 181406, SEQ ID NO: 181630, SEQ ID NO: 181685, SEQ ID NO: 181792, SEQ ID NO: 181963, SEQ ID NO: 181984, SEQ ID NOs: 182157 to 182159, SEQ ID NO: 182471, SEQ ID NOs: 182574 to 197896, SEQ ID NO: 379327, SEQ ID NO: 379329, SEQ ID NO: 379332, SEQ ID NO: 379334, SEQ ID NO: 379770, SEQ ID NO: 381531, SEQ ID NO: 382109, SEQ ID NO: 383301, SEQ ID NO: 383305, SEQ ID NO: 383310, SEQ ID NO: 386111, SEQ ID NO: 387057, SEQ ID NO: 387062, or SEQ ID NOs: 392434 to 410309.

In some embodiments, the amino acid sequence for a MHC class I and/or MHC class II peptides may be used to create a single target (individual) or combined peptide vaccine for the MAR1 protein having between about 2 and about 40 peptides. In some embodiments, any one of the peptides in the vaccine for the MAR1 protein comprises one or more of the SEQ ID NOs: 113808 to 116477 and SEQ ID NOs: 305566 to 307669. In some embodiments, any one of the peptides in the MAR1 vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 113808 to 116477 or SEQ ID NOs: 305566 to 307669.

In some embodiments, any combination of MHC class I and/or MHC class II peptides disclosed herein (SEQ ID NOs: 1 to 34168, 37110 to 116477, 125134 to 203516, 206663 to 307669, or 317360 to 410309) may be used to create a single target (individual) or combined peptide vaccine having between about 2 and about 40 peptides. In some embodiments, any one of the peptides (peptides 1 to 34168, 37110 to 116477, 125134 to 203516, 206663 to 307669, or 317360 to 410309; SEQ ID NOs: 1 to 34168, 37110 to 116477, 125134 to 203516, 206663 to 307669, or 317360 to 410309) in the combined vaccine comprises an amino acid sequence 80, 81, 82, 83, 84, 85, 86, 87, 88, 89, 90, 91, 92, 93, 94, 95, 96, 97, 98 or 99% identical to any of SEQ ID NOs: 1 to 34168, 37110 to 116477, 125134 to 203516, 206663 to 307669, or 317360 to 410309.

Vaccines for Autoimmune Diseases

MHC Class I Peptide Sequences

In some embodiments, the amino acid sequence for a MHC class I peptide vaccine for the INS protein comprises one or more of the SEQ ID NOs: 34169 to 34224. In some embodiments, any one of the peptides in the INS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 34169 to 34224.

In some embodiments, the amino acid sequence for a MHC class I peptide vaccine for the INS protein comprises one or more of the SEQ ID NOs: 34169 to 37109. In some embodiments, any one of the peptides in the INS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 34169 to 37109.

In some embodiments, the amino acid sequence for a MEW class I peptide vaccine for the INS protein comprises two or more of the SEQ ID NOs: 34169 to 34224. In some embodiments, any one of the peptides in the INS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 34169 to 34224.

In some embodiments, the amino acid sequence for a MEW class I peptide vaccine for the INS protein comprises two or more of the SEQ ID NOs: 34169 to 37109. In some embodiments, any one of the peptides in the INS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 34169 to 37109.

In some embodiments, the amino acid sequence for a MEW class I peptide vaccine for the MOG protein comprises one or more of the SEQ ID NOs: 116478 to 116563. In some embodiments, any one of the peptides in the MOG vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 116478 to 116563.

In some embodiments, the amino acid sequence for a MEW class I peptide vaccine for the MOG protein comprises one or more of the SEQ ID NOs: 116478 to 125133. In some embodiments, any one of the peptides in the MOG vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 116478 to 125133.

In some embodiments, the amino acid sequence for a MEW class I peptide vaccine for the MOG protein comprises two or more of the SEQ ID NOs: 116478 to 116563. In some embodiments, any one of the peptides in the MOG vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 116478 to 116563.

In some embodiments, the amino acid sequence for a MHC class I peptide vaccine for the MOG protein comprises two or more of the SEQ ID NOs: 116478 to 125133. In some embodiments, any one of the peptides in the MOG vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 116478 to 125133.

WIC Class II Peptide Sequences

In some embodiments, the amino acid sequence for a MHC class II peptide vaccine for the INS protein comprises one or more of the SEQ ID NOs: 203517 to 203524. In some embodiments, any one of the peptides in the INS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 203517 to 203524.

In some embodiments, the amino acid sequence for a MHC class II peptide vaccine for the INS protein comprises one or more of the SEQ ID NOs: 203517 to 206662. In some embodiments, any one of the peptides in the INS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 203517 to 206662.

In some embodiments, the amino acid sequence for a MHC class II peptide vaccine for the INS protein comprises two or more of the SEQ ID NOs: 203517 to 203524. In some embodiments, any one of the peptides in the INS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 203517 to 203524.

In some embodiments, the amino acid sequence for a MHC class II peptide vaccine for the INS protein comprises two or more of the SEQ ID NOs: 203517 to 206662. In some embodiments, any one of the peptides in the INS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 203517 to 206662.

In some embodiments, the amino acid sequence for a MHC class II peptide vaccine for the MOG protein comprises one or more of the SEQ ID NOs: 307670 to 307685. In some embodiments, any one of the peptides in the MOG vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 307670 to 307685.

In some embodiments, the amino acid sequence for a MHC class II peptide vaccine for the MOG protein comprises one or more of the SEQ ID NOs: 307670 to 317359. In some embodiments, any one of the peptides in the MOG vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 307670 to 317359.

In some embodiments, the amino acid sequence for a MHC class II peptide vaccine for the MOG protein comprises two or more of the SEQ ID NOs: 307670 to 307685. In some embodiments, any one of the peptides in the MOG vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 307670 to 307685.

In some embodiments, the amino acid sequence for a MHC class II peptide vaccine for the MOG protein comprises two or more of the SEQ ID NOs: 307670 to 317359. In some embodiments, any one of the peptides in the MOG vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 307670 to 317359.

In some embodiments, the amino acid sequence for a MHC class I and/or MHC class II peptides may be used to create a single target (individual) or combined peptide vaccine for the INS protein having between about 2 and about 40 peptides. In some embodiments, any one of the peptides in the vaccine for the INS protein comprises one or more of the SEQ ID NOs: 34169 to 37109 and SEQ ID NOs: 203517 to 206662. In some embodiments, any one of the peptides in the INS vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 34169 to 37109 or SEQ ID NOs: 203517 to 206662.

In some embodiments, the amino acid sequence for a MHC class I and/or MHC class II peptides may be used to create a single target (individual) or combined peptide vaccine for the MOG protein having between about 2 and about 40 peptides. In some embodiments, any one of the peptides in the vaccine for the MOG protein comprises one or more of the SEQ ID NOs: 116478 to 125133 and SEQ ID NOs: 307670 to 317359. In some embodiments, any one of the peptides in the MOG vaccine comprise an amino acid sequence 80, 81, 82, 83, 84, 85, 86, 87, 88, 89, 90, 91, 92, 93, 94, 95, 96, 97, 98 or 99% identical to SEQ ID NOs: 116478 to 125133 or SEQ ID NOs: 307670 to 317359.

TABLE 1

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 1 | KFIKTWRPRK | AKT1 E17K | KYIKTWRPRY | Y2F | Y10K | Individual AKT1_E17K Vaccine (5-peptide, NetMHCpan, Set 1); Individual AKT1_E17K Vaccine (5-peptide, NetMHCpan, Set 2) |
| SEQ ID NO: 2 | KVIKTWRPRY | AKT1 E17K | KYIKTWRPRY | Y2V | — | Individual AKT1_E17K Vaccine (5-peptide, NetMHCpan, Set 1) |
| SEQ ID NO: 3 | RVKYIKTWR | AKT1 E17K | RGKYIKTWR | G2V | — | Individual AKT1_E17K Vaccine (5-peptide, NetMHCpan, Set 1) |
| SEQ ID NO: 4 | WAHKRGKYL | AKT1 E17K | WLHKRGKYI | L2A | I9L | Individual AKT1_E17K Vaccine (5-peptide, NetMHCpan, Set 1) |
| SEQ ID NO: 5 | GTLHKRGKY | AKT1 E17K | GWLHKRGKY | W2T | — | Individual AKT1_E17K Vaccine (8-peptide, MHCflurry, Set 1) |
| SEQ ID NO: 6 | KRGYIKTF | AKT1 E17K | KRGKYIKTW | — | W9F | Individual AKT1_E17K Vaccine (8-peptide, MHCflurry, Set 1); Individual AKT1_E17K Vaccine (8-peptide, MHCflurry, Set 2) |
| SEQ ID NO: 7 | KRGYIKTY | AKT1 E17K | KRGKYIKTW | — | W9Y | Individual AKT1_E17K Vaccine (8-peptide, MHCflurry, Set 1) |
| SEQ ID NO: 8 | KTGKYIKTF | AKT1 E17K | KRGKYIKTW | R2T | W9F | Individual AKT1_E17K Vaccine (8-peptide, MHCflurry, Set 1) |
| SEQ ID NO: 9 | KYIKTWRPRF | AKT1 E17K | KYIKTWRPRY | — | Y10F | Individual AKT1_E17K Vaccine (8-peptide, MHCflurry, Set 1); Individual AKT1 E17K Vaccine (8-peptide, MHCflurry, Set 2) |
| SEQ ID NO: 10 | RTKYIKTWK | AKT1 E17K | RGKYIKTWR | G2T | R9K | Individual AKT1_E17K Vaccine (8-peptide, MHCflurry, Set 1); Individual AKT1_E17K Vaccine (8-peptide, MHCflurry, Set 2) |
| SEQ ID NO: 11 | RVKYIKTWK | AKT1 E17K | RGKYIKTWR | G2V | R9K | Individual AKT1_E17K Vaccine (8-peptide, MHCflurry, Set 2) |
| SEQ ID NO: 12 | WLHKRGKYV | AKT1 E17K | WLHKRGKYI | — | I9V | Individual AKT1_E17K Vaccine (5-peptide, MHCflurry, Set 1); Individual AKT1_E17K Vaccine (5-peptide, NetMHCpan, Set 2) |

TABLE 1-continued

| SEQ ID NO | Sequence corresponding to SEQ ID | Target | Seed | Example Vaccine Peptides (MHC class I) | | | Note |
|---|---|---|---|---|---|---|---|
| | | | | Heteroclitic Modification P2 | Heteroclitic Modification C-term | | |
| SEQ ID NO: 13 | KMIKTWRPRY | AKT1 E17K | KYIKTWRPRY | Y2M | — | | Individual AKT1_E17K Vaccine (5-peptide, NetMHCpan, Set 2); Individual AKT1_E17K Vaccine (8-peptide, MHCflurry, Set 2) |
| SEQ ID NO: 14 | RMKYIKTWR | AKT1 E17K | RGKYIKTWR | G2M | — | | Individual AKT1_E17K Vaccine (5-peptide, NetMHCpan, Set 2) |
| SEQ ID NO: 15 | GMLHKRGKY | AKT1 E17K | GWLHKRGKY | W2M | — | | Individual AKT1_E17K Vaccine (8-peptide, MHCflurry, Set 2) |
| SEQ ID NO: 16 | KRGKYIKTL | AKT1 E17K | KRGKYIKTW | — | W9L | | Individual AKT1_E17K Vaccine (8-peptide, MHCflurry, Set 2) |
| SEQ ID NO: 17 | RSKYIKTWK | AKT1 E17K | RGKYIKTWR | G2S | R9K | | Individual AKT1_E17K Vaccine (8-peptide, MHCflurry, Set 2) |
| SEQ ID NO: 18 | WMHKRGKYV | AKT1 E17K | WLHKRGKYI | L2M | I9V | | Individual AKT1_E17K Vaccine (8-peptide, MHCflurry, Set 2) |
| SEQ ID NO: 19 | FSLATEKSRW | BRAF V600E | FGLATEKSRW | G2S | — | | Individual BRAF_V600E Vaccine (5-peptide, NetMHCpan, Set 1); Skin Cancer Vaccine (20-peptide); Thyroid Cancer Vaccine (10-peptide); Individual BRAF_V600E Vaccine (4-peptide, NetMHCpan, Set 2); Individual BRAF_V600E Vaccine (8-peptide, MHCflurry, Set 2) |
| SEQ ID NO: 20 | FTLATEKSRW | BRAF V600E | FGLATEKSRW | G2T | — | | Individual BRAF_V600E Vaccine (5-peptide, NetMHCpan, Set 1); Colorectal Cancer Vaccine (20-peptide); Skin Cancer Vaccine (20-peptide); Thyroid Cancer Vaccine (10-peptide) |
| SEQ ID NO: 21 | KMGDFGLATEK | BRAF V600E | KIGDFGLATEK | I2M | — | | Individual BRAF_V600E Vaccine (5-peptide, NetMHCpan, Set 1); Colorectal Cancer Vaccine (20-peptide); Skin Cancer Vaccine (20-peptide); Thyroid Cancer Vaccine (10-peptide); Individual BRAF_V600E Vaccine (4-peptide, NetMHCpan, Set 2) |

TABLE 1-continued

Example Vaccine Peptides (MHC class I)

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 22 | KTGDFGLATEK | BRAF V600E | KIGDFGLATEK | I2T | — | Individual BRAF_V600E Vaccine (5-peptide, NetMHCpan, Set 1); Colorectal Cancer Vaccine (20-peptide); Skin Cancer Vaccine (20-peptide); Thyroid Cancer Vaccine (10-peptide); Individual BRAF_V600E Vaccine (4-peptide, NetMHCpan, Set 2) |
| SEQ ID NO: 23 | KVGDFGLATER | BRAF V600E | KIGDFGLATEK | I2V | K11R | Individual BRAF_V600E Vaccine (5-peptide, NetMHCpan, Set 1); Colorectal Cancer Vaccine (20-peptide); Skin Cancer Vaccine (20-peptide); Thyroid Cancer Vaccine (10-peptide); Individual BRAF_V600E Vaccine (8-peptide, MHCflurry, Set 1); Individual BRAF_V600E Vaccine (8-peptide, MHCflurry, Set 2) |
| SEQ ID NO: 24 | FTLATEKSR | BRAF V600E | FGLATEKSR | G2T | — | Individual BRAF_V600E Vaccine (8-peptide, MHCflurry, Set 1); Individual BRAF_V600E Vaccine (8-peptide, MHCflurry, Set 2) |
| SEQ ID NO: 25 | GAFGLATEL | BRAF V600E | GDFGLATEK | D2A | K9L | Individual BRAF_V600E Vaccine (8-peptide, MHCflurry, Set 1) |
| SEQ ID NO: 26 | GQATEKSRL | BRAF V600E | GLATEKSRW | L2Q | W9L | Individual BRAF_V600E Vaccine (8-peptide, MHCflurry, Set 1); Individual BRAF_V600E Vaccine (8-peptide, MHCflurry, Set 2) |
| SEQ ID NO: 27 | GSATEKSRW | BRAF V600E | GLATEKSRW | L2S | — | Individual BRAF_V600E Vaccine (8-peptide, MHCflurry, Set 1) |
| SEQ ID NO: 28 | ISDFGLATEY | BRAF V600E | IGDFGLATEK | G2S | K10Y | Individual BRAF_V600E Vaccine (8-peptide, MHCflurry, Set 1) |
| SEQ ID NO: 29 | KAGDFGLATEY | BRAF V600E | KIGDFGLATEK | I2A | K11Y | Individual BRAF_V600E Vaccine (8-peptide, MHCflurry, Set 1); Individual BRAF_V600E Vaccine (8-peptide, MHCflurry, Set 2) |
| SEQ ID NO: 30 | KVGDFGLATEK | BRAF V600E | KIGDFGLATEK | I2V | — | Individual BRAF_V600E Vaccine (8-peptide, MHCflurry, Set 1); Individual BRAF_V600E Vaccine (8-peptide, MHCflurry, Set 2) |

TABLE 1-continued

| SEQ ID NO | Sequence corresponding to SEQ ID | Target | Seed | Example Vaccine Peptides (MHC class I) | | | Note |
|---|---|---|---|---|---|---|---|
| | | | | Heteroclitic Modification P2 | Heteroclitic Modification C-term | | |
| SEQ ID NO: 31 | KMGDFGLATER | BRAF V600E | KIGDFGLATEK | I2M | K11R | | Individual BRAF_V600E Vaccine (4-peptide, NetMHCpan, Set 2) |
| SEQ ID NO: 32 | GAFGLATEF | BRAF V600E | GDFGLATEK | D2A | K9F | | Individual BRAF_V600E Vaccine (8-peptide, MHCflurry, Set 2) |
| SEQ ID NO: 33 | LADFGLATEY | BRAF V600E | IGDFGLATEK | G2A | K10Y | | Individual BRAF_V600E Vaccine (8-peptide, MHCflurry, Set 2) |
| SEQ ID NO: 34 | AYMKSRWSGK | BRAF V600M | ATMKSRWSGS | T2Y | S10K | | Individual BRAF_V600M Vaccine (5-peptide, NetMHCpan, Set 1); Skin Cancer Vaccine (20-peptide) |
| SEQ ID NO: 35 | FTLATMKSRW | BRAF V600M | FGLATMKSRW | G2T | — | | Individual BRAF_V600M Vaccine (5-peptide, NetMHCpan, Set 1); Skin Cancer Vaccine (20-peptide) |
| SEQ ID NO: 36 | KMGDFGLATMK | BRAF V600M | KIGDFGLATMK | I2M | — | | Individual BRAF_V600M Vaccine (5-peptide, NetMHCpan, Set 1); Skin Cancer Vaccine (20-peptide); Individual BRAF_V600M Vaccine (5-peptide, NetMHCpan, Set 2) |
| SEQ ID NO: 37 | KTGDFGLATMK | BRAF V600M | KIGDFGLATMK | I2T | — | | Individual BRAF_V600M Vaccine (5-peptide, NetMHCpan, Set 1); Skin Cancer Vaccine (20-peptide); Individual BRAF_V600M Vaccine (8-peptide, MHCflurry, Set 1); Individual BRAF_V600M Vaccine (5-peptide, NetMHCpan, Set 2) |
| SEQ ID NO: 38 | MMSRWSGSHQF | BRAF V600M | MKSRWSGSHQF | K2M | — | | Individual BRAF_V600M Vaccine (5-peptide, NetMHCpan, Set 1); Skin Cancer Vaccine (20-peptide) |
| SEQ ID NO: 39 | FTLATMKSR | BRAF V600M | FGLATMKSR | G2T | — | | Skin Cancer Vaccine (20-peptide); Individual BRAF_V600M Vaccine (8-peptide, MHCflurry, Set 1); Individual BRAF_V600M Vaccine (4-peptide, MHCflurry, Set 2) |
| SEQ ID NO: 40 | KYGDFGLATMR | BRAF V600M | KIGDFGLATMK | I2Y | K11R | | Skin Cancer Vaccine (20-peptide) |
| SEQ ID NO: 41 | FTLATMKSK | BRAF V600M | FGLATMKSR | G2T | R9K | | Individual BRAF_V600M Vaccine (8-peptide, MHCflurry, Set 1) |

TABLE 1-continued

| SEQ ID NO | Sequence corresponding to SEQ ID | Target | Seed | Example Vaccine Peptides (MHC class I) | | | Note |
|---|---|---|---|---|---|---|---|
| | | | | Heteroclitic Modification P2 | Heteroclitic Modification C-term | | |
| SEQ ID NO: 42 | FVLATMKSR | BRAF V600M | FGLATMKSR | G2V | — | | Individual BRAF_V600M Vaccine (8-peptide, MHCflurry, Set 1) |
| SEQ ID NO: 43 | GSATMKSRW | BRAF V600M | GLATMKSRW | L2S | — | | Individual BRAF_V600M Vaccine (8-peptide, MHCflurry, Set 1) |
| SEQ ID NO: 44 | GTATMKSRW | BRAF V600M | GLATMKSRW | L2T | — | | Individual BRAF_V600M Vaccine (8-peptide, MHCflurry, Set 1); Individual BRAF_V600M Vaccine (4-peptide, MHCflurry, Set 2) |
| SEQ ID NO: 45 | KTGDFGLATMR | BRAF V600M | KIGDFGLATMK | I2T | K11R | | Individual BRAF_V600M Vaccine (8-peptide, MHCflurry, Set 1) |
| SEQ ID NO: 46 | KVGDFGLATMK | BRAF V600M | KIGDFGLATMK | I2V | — | | Individual BRAF_V600M Vaccine (8-peptide, MHCflurry, Set 1); Individual BRAF_V600M Vaccine (4-peptide, MHCflurry, Set 2) |
| SEQ ID NO: 47 | ATMKSRWSK | BRAF V600M | ATMKSRWSG | — | G9K | | Individual BRAF_V600M Vaccine (5-peptide, NetMHCpan, Set 2) |
| SEQ ID NO: 48 | FSLATMKSRW | BRAF V600M | FGLATMKSRW | G2S | — | | Individual BRAF_V600M Vaccine (5-peptide, NetMHCpan, Set 2) |
| SEQ ID NO: 49 | MQSRWSGSHQF | BRAF V600M | MKSRWSGSHQF | K2Q | — | | Individual BRAF_V600M Vaccine (5-peptide, NetMHCpan, Set 2) |
| SEQ ID NO: 50 | ITDFGLATMY | BRAF V600M | IGDFGLATMK | G2T | K10Y | | Individual BRAF_V600M Vaccine (4-peptide, MHCflurry, Set 2) |
| SEQ ID NO: 51 | KMSFGVTCVK | EGFR A289V | KYSFGVTCVK | Y2M | — | | Individual EGFR_A289V Vaccine (5-peptide, NetMHCpan, Set 1); Brain Cancer Vaccine (25-peptide); Individual EGFR_A289V Vaccine (5-peptide, NetMHCpan, Set 2) |
| SEQ ID NO: 52 | KYSFGVTCL | EGFR A289V | KYSFGVTCV | — | V9L | | Individual EGFR_A289V Vaccine (5-peptide, NetMHCpan, Set 1); Brain Cancer Vaccine (25-peptide); Individual EGFR_A289V Vaccine (8-peptide, MHCflurry, Set 1); Individual EGFR_A289V Vaccine (8-peptide, MHCflurry, Set 2) |

TABLE 1-continued

| SEQ ID NO | Sequence corresponding to SEQ ID | Target | Seed | Example Vaccine Peptides (MHC class I) | | | Note |
|---|---|---|---|---|---|---|---|
| | | | | Heteroclitic Modification P2 | Heteroclitic Modification C-term | | |
| SEQ ID NO: 53 | YAFGVTCM | EGFR A289V | YSFGVTCV | S2A | V8M | | Individual EGFR_A289V Vaccine (5-peptide, NetMHCpan, Set 1); Brain Cancer Vaccine (25-peptide); Individual EGFR_A289V Vaccine (5-peptide, NetMHCpan, Set 2) |
| SEQ ID NO: 54 | YTFGVTCVR | EGFR A289V | YSFGVTCVK | S2T | K9R | | Individual EGFR_A289V Vaccine (5-peptide, NetMHCpan, Set 1); Brain Cancer Vaccine (25-peptide); Individual EGFR_A289V Vaccine (5-peptide, NetMHCpan, Set 2); Individual EGFR_A289V Vaccine (8-peptide, MHCflurry, Set 2) |
| SEQ ID NO: 55 | YVFGVTCVM | EGFR A289V | YSFGVTCVK | S2V | K9M | | Individual EGFR_A289V Vaccine (5-peptide, NetMHCpan, Set 1); Brain Cancer Vaccine (25-peptide) |
| SEQ ID NO: 56 | GRYSFGVTF | EGFR A289V | GKYSFGVTC | K2R | C9F | | Individual EGFR_A289V Vaccine (8-peptide, MHCflurry, Set 1) |
| SEQ ID NO: 57 | KYSFGVTCF | EGFR A289V | KYSFGVTCV | — | V9F | | Individual EGFR_A289V Vaccine (8-peptide, MHCflurry, Set 1); Individual EGFR_A289V Vaccine (5-peptide, NetMHCpan, Set 2); Individual EGFR_A289V Vaccine (8-peptide, MHCflurry, Set 2) |
| SEQ ID NO: 58 | YMFGVTCVK | EGFR A289V | YSFGVTCVK | S2M | — | | Individual EGFR_A289V Vaccine (8-peptide, MHCflurry, Set 1) |
| SEQ ID NO: 59 | YSFGVTCVM | EGFR A289V | YSFGVTCVK | — | K9M | | Individual EGFR_A289V Vaccine (8-peptide, MHCflurry, Set 1) |
| SEQ ID NO: 60 | YTFGVTCVK | EGFR A289V | YSFGVTCVK | S2T | — | | Individual EGFR_A289V Vaccine (8-peptide, MHCflurry, Set 1); Individual EGFR_A289V Vaccine (8-peptide, MHCflurry, Set 2) |
| SEQ ID NO: 61 | YTFGVTCVY | EGFR A289V | YSFGVTCVK | S2T | K9Y | | Individual EGFR_A289V Vaccine (8-peptide, MHCflurry, Set 1); Individual EGFR_A289V Vaccine (8-peptide, MHCflurry, Set 2) |
| SEQ ID NO: 62 | YVFGVTCVR | EGFR A289V | YSFGVTCVK | S2V | K9R | | Individual EGFR_A289V Vaccine (8-peptide, MHCflurry, Set 1) |

TABLE 1-continued

Example Vaccine Peptides (MHC class I)

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 63 | YMFGVTCVY | EGFR A289V | YSFGVTCVK | S2M | K9Y | Individual EGFR_A289V Vaccine (5-peptide, NetMHCpan, Set 2) |
| SEQ ID NO: 64 | GQYSFGVTL | EGFR A289V | GKYSFGVTC | K2Q | C9L | Individual EGFR_A289V Vaccine (8-peptide, MHCflurry, Set 2) |
| SEQ ID NO: 65 | YLFGVTCVK | EGFR A289V | YSFGVTCVK | S2L | — | Individual EGFR_A289V Vaccine (8-peptide, MHCflurry, Set 2) |
| SEQ ID NO: 66 | YTFGVTCVM | EGFR A289V | YSFGVTCVK | S2T | K9M | Individual EGFR_A289V Vaccine (8-peptide, MHCflurry, Set 2) |
| SEQ ID NO: 67 | VMMGENNTLV | EGFR G598V | VVMGENNTLV | V2M | — | Individual EGFR_G598V Vaccine (5-peptide, NetMHCpan, Set 1); Brain Cancer Vaccine (25-peptide); Individual EGFR_G598V Vaccine (5-peptide, NetMHCpan, Set 2) |
| SEQ ID NO: 68 | VMMGENNTV | EGFR G598V | VVMGENNTL | V2M | L9V | Individual EGFR_G598V Vaccine (5-peptide, NetMHCpan, Set 1); Brain Cancer Vaccine (25-peptide); Individual EGFR_G598V Vaccine (8-peptide, MHCflurry, Set 1); Individual EGFR_G598V Vaccine (5-peptide, NetMHCpan, Set 2); Individual EGFR_G598V Vaccine (8-peptide, MHCflurry, Set 2) |
| SEQ ID NO: 69 | VSMGENNTLVW | EGFR G598V | VVMGENNTLVW | V2S | — | Individual EGFR_G598V Vaccine (5-peptide, NetMHCpan, Set 1); Brain Cancer Vaccine (25-peptide); Individual EGFR_G598V Vaccine (5-peptide, NetMHCpan, Set 2) |
| SEQ ID NO: 70 | VSMGENNTM | EGFR G598V | VVMGENNTL | V2S | L9M | Individual EGFR_G598V Vaccine (5-peptide, NetMHCpan, Set 1); Brain Cancer Vaccine (25-peptide) |
| SEQ ID NO: 71 | VSTCPAVVF | EGFR G598V | VKTCPAVVM | K2S | M9F | Individual EGFR_G598V Vaccine (5-peptide, NetMHCpan, Set 1); Brain Cancer Vaccine (25-peptide) |
| SEQ ID NO: 72 | VAMGENNTM | EGFR G598V | VVMGENNTL | V2A | L9M | Brain Cancer Vaccine (25-peptide) |
| SEQ ID NO: 73 | VQTCPAVVL | EGFR G598V | VKTCPAVVM | K2Q | M9L | Brain Cancer Vaccine (25-peptide) |

TABLE 1-continued

| SEQ ID NO | Sequence corresponding to SEQ ID | Target | Seed | Example Vaccine Peptides (MHC class I) | | | Note |
|---|---|---|---|---|---|---|---|
| | | | | Heteroclitic Modification P2 | Heteroclitic Modification C-term | | |
| SEQ ID NO: 74 | VAMGENNTL | EGFR G598V | VVMGENNTL | V2A | — | | Individual EGFR_G598V Vaccine (8-peptide, MHCflurry, Set 1); Individual EGFR_G598V Vaccine (5-peptide, NetMHCpan, Set 2); Individual EGFR_G598V Vaccine (8-peptide, MHCflurry, Set 2) |
| SEQ ID NO: 75 | VLMGENNTW | EGFR G598V | VVMGENNTL | V2L | L9W | | Individual EGFR_G598V Vaccine (8-peptide, MHCflurry, Set 1); Individual EGFR_G598V Vaccine (8-peptide, MHCflurry, Set 2) |
| SEQ ID NO: 76 | VPMGENNTL | EGFR G598V | VVMGENNTL | V2P | — | | Individual EGFR_G598V Vaccine (8-peptide, MHCflurry, Set 1); Individual EGFR_G598V Vaccine (8-peptide, MHCflurry, Set 2) |
| SEQ ID NO: 77 | VPMGENNTLVW | EGFR G598V | VVMGENNTLVW | V2P | — | | Individual EGFR_G598V Vaccine (8-peptide, MHCflurry, Set 1); Individual EGFR_G598V Vaccine (8-peptide, MHCflurry, Set 2) |
| SEQ ID NO: 78 | VRMGENNTL | EGFR G598V | VVMGENNTL | V2R | — | | Individual EGFR_G598V Vaccine (8-peptide, MHCflurry, Set 1); Individual EGFR_G598V Vaccine (8-peptide, MHCflurry, Set 2) |
| SEQ ID NO: 79 | VTMGENNTLVW | EGFR G598V | VVMGENNTLVW | V2T | — | | Individual EGFR_G598V Vaccine (8-peptide, MHCflurry, Set 1); Individual EGFR_G598V Vaccine (8-peptide, MHCflurry, Set 2) |
| SEQ ID NO: 80 | VTMGENNTV | EGFR G598V | VVMGENNTL | V2T | L9V | | Individual EGFR_G598V Vaccine (8-peptide, MHCflurry, Set 1); Individual EGFR_G598V Vaccine (8-peptide, MHCflurry, Set 2) |
| SEQ ID NO: 81 | VQTCPAVVF | EGFR G598V | VKTCPAVVM | K2Q | M9F | | Individual EGFR_G598V Vaccine (5-peptide, NetMHCpan, Set 2) |
| SEQ ID NO: 82 | FQRAKLLGL | EGFR L858R | FGRAKLLGA | G2Q | A9L | | Individual EGFR_L858R Vaccine (5-peptide, NetMHCpan, Set 1); Bronchus And Lung Cancer Vaccine (30-peptide) |

TABLE 1-continued

| SEQ ID NO | Sequence corresponding to SEQ ID | Target | Seed | Example Vaccine Peptides (MHC class I) Heteroclitic Modification P2 | Heteroclitic Modification C-term | Note |
|---|---|---|---|---|---|---|
| SEQ ID NO: 83 | LADFGRAKM | EGFR L858R | ITDFGRAKL | T2A | L9M | Individual EGFR_L858R Vaccine (5-peptide, NetMHCpan, Set 1); Bronchus And Lung Cancer Vaccine (30-peptide); Individual EGFR_L858R Vaccine (5-peptide, NetMHCpan, Set 2) |
| SEQ ID NO: 84 | KMTDFGRAK | EGFR L858R | KITDFGRAK | I2M | — | Individual EGFR_L858R Vaccine (5-peptide, NetMHCpan, Set 1); Bronchus And Lung Cancer Vaccine (30-peptide); Individual EGFR_L858R Vaccine (5-peptide, NetMHCpan, Set 2) |
| SEQ ID NO: 85 | KTTDFGRAK | EGFR L858R | KITDFGRAK | I2T | — | Individual EGFR_L858R Vaccine (5-peptide, NetMHCpan, Set 1); Bronchus And Lung Cancer Vaccine (30-peptide); Individual EGFR_L858R Vaccine (8-peptide, MHCflurry, Set 1); Individual EGFR_L858R Vaccine (5-peptide, NetMHCpan, Set 2); Individual EGFR_L858R Vaccine (8-peptide, MHCflurry, Set 2) |
| SEQ ID NO: 86 | KVTDFGRAR | EGFR L858R | KITDFGRAK | I2V | K9R | Individual EGFR_L858R Vaccine (5-peptide, NetMHCpan, Set 1); Bronchus And Lung Cancer Vaccine (30-peptide) |
| SEQ ID NO: 87 | FPPRAKLLGL | EGFR L858R | FGRAKLLGA | G2P | A9L | Individual EGFR_L858R Vaccine (8-peptide, MHCflurry, Set 1); Individual EGFR_L858R Vaccine (8-peptide, MHCflurry, Set 2) |
| SEQ ID NO: 88 | IADFGRAKL | EGFR L858R | ITDFGRAKL | T2A | — | Individual EGFR_L858R Vaccine (8-peptide, MHCflurry, Set 1); Individual EGFR_L858R Vaccine (8-peptide, MHCflurry, Set 2) |
| SEQ ID NO: 89 | ITDFGRAKW | EGFR L858R | ITDFGRAKL | | L9W | Individual EGFR_L858R Vaccine (8-peptide, MHCflurry, Set 1) |
| SEQ ID NO: 90 | ITDFGRAKY | EGFR L858R | ITDFGRAKL | | L9Y | Individual EGFR_L858R Vaccine (8-peptide, MHCflurry, Set 1) |

TABLE 1-continued

Example Vaccine Peptides (MHC class I)

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 91 | KLTDFGRAKV | EGFR L858R | KITDFGRAKL | I2L | L10V | Individual EGFR_L858R Vaccine (8-peptide, MHCflurry, Set 1); Individual EGFR_L858R Vaccine (8-peptide, MHCflurry, Set 2) |
| SEQ ID NO: 92 | TEFGRAKLV | EGFR L858R | TDFGRAKLL | D2E | L9V | Individual EGFR_L858R Vaccine (8-peptide, MHCflurry, Set 1) |
| SEQ ID NO: 93 | TQFGRAKLL | EGFR L858R | TDFGRAKLL | D2Q | — | Individual EGFR_L858R Vaccine (8-peptide, MHCflurry, Set 1); Individual EGFR_L858R Vaccine (8-peptide, MHCflurry, Set 2) |
| SEQ ID NO: 94 | FMRAKLLGL | EGFR L858R | FGRAKLLGA | G2M | A9L | Individual EGFR_L858R Vaccine (5-peptide, NetMHCpan, Set 2) |
| SEQ ID NO: 95 | KMTDFGRAR | EGFR L858R | KITDFGRAK | I2M | K9R | Individual EGFR_L858R Vaccine (5-peptide, NetMHCpan, Set 2) |
| SEQ ID NO: 96 | ISDFGRAKW | EGFR L858R | ITDFGRAKL | T2S | L9W | Individual EGFR_L858R Vaccine (8-peptide, MHCflurry, Set 2) |
| SEQ ID NO: 97 | ISDFGRAKY | EGFR L858R | ITDFGRAKL | T2S | L9Y | Individual EGFR_L858R Vaccine (8-peptide, MHCflurry, Set 2) |
| SEQ ID NO: 98 | TEFGRAKLI | EGFR L858R | TDFGRAKLL | D2E | L9I | Individual EGFR_L858R Vaccine (8-peptide, MHCflurry, Set 2) |
| SEQ ID NO: 99 | HAKERIRFL | GTF2I L424H | HAKERIRFV | — | V9L | Individual GTF2I_L424H Vaccine (8-peptide, NetMHCpan, Set 1); Individual GTF2I_L424H Vaccine (10-peptide, MHCflurry, Set 1); Individual GTF2I_L424H Vaccine (5-peptide, NetMHCpan, Set 2); Individual GTF2I_L424H Vaccine (8-peptide, MHCflurry, Set 2) |
| SEQ ID NO: 100 | HAKERIRFM | GTF2I L424H | HAKERIRFV | — | V9M | Individual GTF2I_L424H Vaccine (8-peptide, NetMHCpan, Set 1) |
| SEQ ID NO: 101 | HRKERIRFV | GTF2I L424H | HAKERIRFV | A2R | — | Individual GTF2I_L424H Vaccine (8-peptide, NetMHCpan, Set 1) |
| SEQ ID NO: 102 | IPRLERILHM | GTF2I L424H | IPRLERILHA | — | A10M | Individual GTF2I_L424H Vaccine (8-peptide, NetMHCpan, Set 1) |

TABLE 1-continued

Example Vaccine Peptides (MHC class I)

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 103 | RMERILHAK | GTF2I L424H | RLERILHAK | L2M | — | Individual GTF2I_L424H Vaccine (8-peptide, NetMHCpan, Set 1); Individual GTF2I_L424H Vaccine (10-peptide, MHCflurry, Set 1); Individual GTF2I_L424H Vaccine (5-peptide, NetMHCpan, Set 2); Individual GTF2I_L424H Vaccine (8-peptide, MHCflurry, Set 2) |
| SEQ ID NO: 104 | RMLHAKERW | GTF2I L424H | RILHAKERI | I2M | I9W | Individual GTF2I_L424H Vaccine (8-peptide, NetMHCpan, Set 1) |
| SEQ ID NO: 105 | RTERILHAK | GTF2I L424H | RLERILHAK | L2T | — | Individual GTF2I_L424H Vaccine (8-peptide, NetMHCpan, Set 1); Individual GTF2I_L424H Vaccine (5-peptide, NetMHCpan, Set 2) |
| SEQ ID NO: 106 | RVERILHAK | GTF2I L424H | RLERILHAK | L2V | — | Individual GTF2I_L424H Vaccine (8-peptide, NetMHCpan, Set 1); Individual GTF2I_L424H Vaccine (10-peptide, MHCflurry, Set 1); Individual GTF2I_L424H Vaccine (8-peptide, MHCflurry, Set 2) |
| SEQ ID NO: 107 | HPKERIRFL | GTF2I L424H | HAKERIRFV | A2P | V9L | Individual GTF2I_L424H Vaccine (10-peptide, MHCflurry, Set 1); Individual GTF2I_L424H Vaccine (8-peptide, MHCflurry, Set 2) |
| SEQ ID NO: 108 | HQKERIRFL | GTF2I L424H | HAKERIRFV | A2Q | V9L | Individual GTF2I_L424H Vaccine (10-peptide, MHCflurry, Set 1) |
| SEQ ID NO: 109 | HYKERIRFM | GTF2I L424H | HAKERIRFV | A2Y | V9M | Individual GTF2I_L424H Vaccine (10-peptide, MHCflurry, Set 1) |
| SEQ ID NO: 110 | RQLHAKERV | GTF2I L424H | RILHAKERI | I2Q | I9V | Individual GTF2I_L424H Vaccine (10-peptide, MHCflurry, Set 1) |
| SEQ ID NO: 111 | RTERILHAR | GTF2I L424H | RLERILHAK | L2T | K9R | Individual GTF2I_L424H Vaccine (10-peptide, MHCflurry, Set 1); Individual GTF2I_L424H Vaccine (8-peptide, MHCflurry, Set 2) |
| SEQ ID NO: 112 | RTLHAKERY | GTF2I L424H | RILHAKERI | I2T | I9Y | Individual GTF2I_L424H Vaccine (10-peptide, MHCflurry, Set 1) |

TABLE 1-continued

Example Vaccine Peptides (MHC class I)

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 113 | RVLHAKERIRY | GTF2I L424H | RILHAKERIRF | I2V | F11Y | Individual GTF2I_L424H Vaccine (10-peptide, MHCflurry, Set 1) |
| SEQ ID NO: 114 | HRKERIRFM | GTF2I L424H | HAKERIRFV | A2R | V9M | Individual GTF2I_L424H Vaccine (5-peptide, NetMHCpan, Set 2) |
| SEQ ID NO: 115 | IPRLERILHA | GTF2I L424H | IPRLERILHA | – | A10L | Individual GTF2I_L424H Vaccine (5-peptide, NetMHCpan, Set 2) |
| SEQ ID NO: 116 | HFKERIRFL | GTF2I L424H | HAKERIRFV | A2F | V9L | Individual GTF2I_L424H Vaccine (8-peptide, MHCflurry, Set 2) |
| SEQ ID NO: 117 | RMLHAKERL | GTF2I L424H | RILHAKERI | I2M | I9L | Individual GTF2I_L424H Vaccine (8-peptide, MHCflurry, Set 2) |
| SEQ ID NO: 118 | RQLHAKERL | GTF2I L424H | RILHAKERI | I2Q | I9L | Individual GTF2I_L424H Vaccine (8-peptide, MHCflurry, Set 2) |
| SEQ ID NO: 119 | KMIIGCHAY | IDH1 R132C | KPIIGCHAY | P2M | – | Individual IDH1_R132C Vaccine (2-peptide, NetMHCpan, Set 1); Brain Cancer Vaccine (25-peptide); Individual IDH1_R132C Vaccine (2-peptide, NetMHCpan, Set 2) |
| SEQ ID NO: 120 | KPIIGCHL | IDH1 R132C | KPIIGCHA | – | A9L | Individual IDH1_R132C Vaccine (2-peptide, NetMHCpan, Set 1); Brain Cancer Vaccine (25-peptide); Individual IDH1_R132C Vaccine (2-peptide, NetMHCpan, Set 2) |
| SEQ ID NO: 121 | KPIIGCHAA | IDH1 R132C | KPIIGCHAY | – | Y10A | Individual IDH1_R132C Vaccine (5-peptide, MHCflurry, Set 1); Individual IDH1 R132C Vaccine (3-peptide, MHCflurry, Set 2) |
| SEQ ID NO: 122 | KPIIGCHAL | IDH1 R132C | KPIIGCHAY | – | Y10L | Individual IDH1_R132C Vaccine (5-peptide, MHCflurry, Set 1) |
| SEQ ID NO: 123 | KPIIGCHAM | IDH1 R132C | KPIIGCHAY | – | Y10M | Individual IDH1_R132C Vaccine (5-peptide, MHCflurry, Set 1); Individual IDH1_R132C Vaccine (3-peptide, MHCflurry, Set 2) |
| SEQ ID NO: 124 | KQIIGCHAY | IDH1 R132C | KPIIGCHAY | P2Q | – | Individual IDH1_R132C Vaccine (5-peptide, MHCflurry, Set 1) |

TABLE 1-continued

Example Vaccine Peptides (MHC class I)

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 125 | IMHHAYGDQY | IDH1 R132H | IGHHAYGDQY | G2M | — | Individual IDH1_R132H Vaccine (5-peptide, NetMHCpan, Set 1); Brain Cancer Vaccine (25-peptide); Individual IDH1_R132H Vaccine (5-peptide, NetMHCpan, Set 2) |
| SEQ ID NO: 126 | IMHHAYGDQYR | IDH1 R132H | IGHHAYGDQYR | G2M | — | Individual IDH1_R132H Vaccine (5-peptide, NetMHCpan, Set 1); Brain Cancer Vaccine (25-peptide); Individual IDH1_R132H Vaccine (5-peptide, NetMHCpan, Set 2) |
| SEQ ID NO: 127 | KMIIGHHAY | IDH1 R132H | KPIIGHHAY | P2M | — | Individual IDH1_R132H Vaccine (5-peptide, NetMHCpan, Set 1); Brain Cancer Vaccine (25-peptide); Individual IDH1_R132H Vaccine (5-peptide, NetMHCpan, Set 2) |
| SEQ ID NO: 128 | KPIIGHHM | IDH1 R132H | KPIIGHHA | — | A9M | Individual IDH1_R132H Vaccine (5-peptide, NetMHCpan, Set 1); Brain Cancer Vaccine (25-peptide) |
| SEQ ID NO: 129 | VMPIIGHHA | IDH1 R132H | VKPIIGHHA | K2M | — | Individual IDH1_R132H Vaccine (5-peptide, NetMHCpan, Set 1); Brain Cancer Vaccine (25-peptide); Individual IDH1_R132H Vaccine (5-peptide, NetMHCpan, Set 2) |
| SEQ ID NO: 130 | KQIIGHHAM | IDH1 R132H | KPIIGHHAY | P2Q | Y10M | Brain Cancer Vaccine (25-peptide) |
| SEQ ID NO: 131 | HHAYGDQL | IDH1 R132H | HHAYGDQY | — | Y8L | Individual IDH1_R132H Vaccine (8-peptide, MHCflurry, Set 1) |
| SEQ ID NO: 132 | HYAYGDQYR | IDH1 R132H | HHAYGDQYR | H2Y | — | Individual IDH1_R132H Vaccine (8-peptide, MHCflurry, Set 1) |
| SEQ ID NO: 133 | LAIGHHAL | IDH1 R132H | IIIGHHAY | I2A | Y8L | Individual IDH1_R132H Vaccine (8-peptide, MHCflurry, Set 1); Individual IDH1_R132H Vaccine (8-peptide, MHCflurry, Set 2) |
| SEQ ID NO: 134 | IQIGHHAY | IDH1 R132H | IIIGHHAY | I2Q | — | Individual IDH1_R132H Vaccine (8-peptide, MHCflurry, Set 1); Individual IDH1_R132H Vaccine (8-peptide, MHCflurry, Set 2) |

TABLE 1-continued

Example Vaccine Peptides (MHC class I)

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 135 | KHIIGHHA | IDH1 R132H | KPIIGHHA | P2H | — | Individual IDH1_R132H Vaccine (8-peptide, MHCflurry, Set 1); Individual IDH1_R132H Vaccine (8-peptide, MHCflurry, Set 2) |
| SEQ ID NO: 136 | KPIIIGHHL | IDH1 R132H | KPIIGHHA | — | A9L | Individual IDH1_R132H Vaccine (8-peptide, MHCflurry, Set 1); Individual IDH1_R132H Vaccine (5-peptide, NetMHCpan, Set 2); Individual IDH1_R132H Vaccine (8-peptide, MHCflurry, Set 2) |
| SEQ ID NO: 137 | PPIGHHAY | IDH1 R132H | PIIIGHHAY | I2P | — | Individual IDH1_R132H Vaccine (8-peptide, MHCflurry, Set 1) |
| SEQ ID NO: 138 | HHAYGDQF | IDH1 R132H | HHAYGDQY | — | Y8F | Individual IDH1_R132H Vaccine (8-peptide, MHCflurry, Set 2) |
| SEQ ID NO: 139 | HTAYGDQYR | IDH1 R132H | HHAYGDQYR | H2T | — | Individual IDH1_R132H Vaccine (8-peptide, MHCflurry, Set 2) |
| SEQ ID NO: 140 | PAIGHHAY | IDH1 R132H | PIIIGHHAY | I2A | — | Individual IDH1_R132H Vaccine (8-peptide, MHCflurry, Set 2) |
| SEQ ID NO: 141 | LMVGAAGV | KRAS G12A | LVVVGAAGV | V2M | — | Individual KRAS_G12A Vaccine (4-peptide, NetMHCpan, Set 1); Bronchus And Lung Cancer Vaccine (30-peptide); Individual KRAS_G12A Vaccine (8-peptide, MHCflurry, Set 1); Individual KRAS_G12A Vaccine (8-peptide, MHCflurry, Set 2) |
| SEQ ID NO: 142 | LQVGAAGV | KRAS G12A | LVVVGAAGV | V2Q | — | Individual KRAS_G12A Vaccine (4-peptide, NetMHCpan, Set 1); Bronchus And Lung Cancer Vaccine (30-peptide); Individual KRAS_G12A Vaccine (4-peptide, NetMHCpan, Set 2) |
| SEQ ID NO: 143 | LTVGAAGV | KRAS G12A | LVVVGAAGV | V2T | — | Individual KRAS_G12A Vaccine (4-peptide, NetMHCpan, Set 1); Bronchus And Lung Cancer Vaccine (30-peptide); Individual KRAS_G12A Vaccine (4-peptide, NetMHCpan, Set 2); Individual KRAS_G12A Vaccine (8-peptide, MHCflurry, Set 2) |

TABLE 1-continued

Example Vaccine Peptides (MHC class I)

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 144 | VTVGAAGVGR | KRAS G12A | VVVGAAGVGK | V2T | K10R | Individual KRAS_G12A Vaccine (4-peptide, NetMHCpan, Set 1); Bronchus And Lung Cancer Vaccine (30-peptide); Individual KRAS_G12A Vaccine (4-peptide, NetMHCpan, Set 2) |
| SEQ ID NO: 145 | GAAGVGKSL | KRAS G12A | GAAGVGKSA | — | A9L | Individual KRAS_G12A Vaccine (8-peptide, MHCflurry, Set 1); Individual KRAS_G12A Vaccine (8-peptide, MHCflurry, Set 2) |
| SEQ ID NO: 146 | GAAGVGKSM | KRAS G12A | GAAGVGKSA | — | A9M | Individual KRAS_G12A Vaccine (8-peptide, MHCflurry, Set 1); Individual KRAS_G12A Vaccine (8-peptide, MHCflurry, Set 2) |
| SEQ ID NO: 147 | GPAGVGKSA | KRAS G12A | GAAGVGKSA | A2P | — | Individual KRAS_G12A Vaccine (8-peptide, MHCflurry, Set 1) |
| SEQ ID NO: 148 | GPAGVGKSAL | KRAS G12A | GAAGVGKSAL | A2P | — | Individual KRAS_G12A Vaccine (8-peptide, MHCflurry, Set 1); Individual KRAS_G12A Vaccine (8-peptide, MHCflurry, Set 2) |
| SEQ ID NO: 149 | VTVGAAGVGK | KRAS G12A | VVVGAAGVGK | V2T | — | Individual KRAS_G12A Vaccine (8-peptide, MHCflurry, Set 1) |
| SEQ ID NO: 150 | VVVGAAGVGR | KRAS G12A | VVVGAAGVGK | — | K10R | Individual KRAS_G12A Vaccine (8-peptide, MHCflurry, Set 1); Individual KRAS_G12A Vaccine (8-peptide, MHCflurry, Set 2) |
| SEQ ID NO: 151 | LLVVGAAGV | KRAS G12A | LVVVGAAGV | V2L | — | Individual KRAS_G12A Vaccine (4-peptide, NetMHCpan, Set 2) |
| SEQ ID NO: 152 | GPAGVGKSV | KRAS G12A | GAAGVGKSA | A2P | A9V | Individual KRAS_G12A Vaccine (8-peptide, MHCflurry, Set 2) |
| SEQ ID NO: 153 | VMVGAAGVGK | KRAS G12A | VVVGAAGVGK | V2M | — | Individual KRAS_G12A Vaccine (8-peptide, MHCflurry, Set 2) |
| SEQ ID NO: 154 | LMVVGACGV | KRAS G12C | LVVVGACGV | V2M | — | Individual KRAS_G12C Vaccine (5-peptide, NetMHCpan, Set 1); Bronchus And Lung Cancer Vaccine (30-peptide); Individual KRAS_G12C |

TABLE 1-continued

| SEQ ID NO | Sequence corresponding to SEQ ID | Target | Seed | Heteroclitic Modification P2 | Heteroclitic Modification C-term | Note |
|---|---|---|---|---|---|---|
| | | | | | | Vaccine (8-peptide, MHCflurry, Set 1); Individual KRAS_G12C Vaccine (5-peptide, NetMHCpan, Set 2); Individual KRAS_G12C Vaccine (8-peptide, MHCflurry, Set 2) |
| SEQ ID NO: 155 | LQVVGACGV | KRAS G12C | LVVVGACGV | V2Q | — | Individual KRAS_G12C Vaccine (5-peptide, NetMHCpan, Set 1); Bronchus And Lung Cancer Vaccine (30-peptide); Individual KRAS_G12C Vaccine (8-peptide, MHCflurry, Set 1); Individual KRAS_G12C Vaccine (5-peptide, NetMHCpan, Set 2); Individual KRAS_G12C Vaccine (8-peptide, MHCflurry, Set 2) |
| SEQ ID NO: 156 | LTVVGACGV | KRAS G12C | LVVVGACGV | V2T | — | Individual KRAS_G12C Vaccine (5-peptide, NetMHCpan, Set 1); Bronchus And Lung Cancer Vaccine (30-peptide); Individual KRAS_G12C Vaccine (8-peptide, MHCflurry, Set 1); Individual KRAS_G12C Vaccine (5-peptide, NetMHCpan, Set 2); Individual KRAS_G12C Vaccine (8-peptide, MHCflurry, Set 2) |
| SEQ ID NO: 157 | VMGACGVGR | KRAS G12C | VVGACGVGK | V2M | K9R | Individual KRAS_G12C Vaccine (5-peptide, NetMHCpan, Set 1); Bronchus And Lung Cancer Vaccine (30-peptide) |
| SEQ ID NO: 158 | VVVGACGVGR | KRAS G12C | VVVGACGVGK | — | K10R | Individual KRAS_G12C Vaccine (5-peptide, NetMHCpan, Set 1); Bronchus And Lung Cancer Vaccine (30-peptide) |
| SEQ ID NO: 159 | VMGACGVGK | KRAS G12C | VVGACGVGK | V2M | — | Bronchus And Lung Cancer Vaccine (30-peptide) |
| SEQ ID NO: 160 | GACGVGKSL | KRAS G12C | GACGVGKSA | — | A9L | Individual KRAS_G12C Vaccine (8-peptide, MHCflurry, Set 1); Individual KRAS_G12C Vaccine (8-peptide, MHCflurry, Set 2) |
| SEQ ID NO: 161 | GPCGVGKSA | KRAS G12C | GACGVGKSA | A2P | — | Individual KRAS_G12C Vaccine (8-peptide, MHCflurry, Set 1); Individual KRAS_G12C Vaccine (8-peptide, MHCflurry, Set 2) |

TABLE 1-continued

| SEQ ID NO | Sequence corresponding to SEQ ID | Target | Seed | Example Vaccine Peptides (MHC class I) | | | Note |
|---|---|---|---|---|---|---|---|
| | | | | Heteroclitic Modification P2 | Heteroclitic Modification C-term | | |
| SEQ ID NO: 162 | GPCGVGKSAM | KRAS G12C | GACGVGKSAL | A2P | L10M | | Individual KRAS_G12C Vaccine (8-peptide, MHCflurry, Set 1) |
| SEQ ID NO: 163 | VMVGACGVGK | KRAS G12C | VVVGACGVGK | V2M | — | | Individual KRAS_G12C Vaccine (8-peptide, MHCflurry, Set 1); Individual KRAS_G12C Vaccine (8-peptide, MHCflurry, Set 2) |
| SEQ ID NO: 164 | VTVGACGVGR | KRAS G12C | VVVGACGVGK | V2T | K10R | | Individual KRAS_G12C Vaccine (8-peptide, MHCflurry, Set 1); Individual KRAS_G12C Vaccine (5-peptide, NetMHCpan, Set 2); Individual KRAS_G12C Vaccine (8-peptide, MHCflurry, Set 2) |
| SEQ ID NO: 165 | GPCGVGKSAL | KRAS G12C | GACGVGKSAL | A2P | — | | Individual KRAS_G12C Vaccine (8-peptide, MHCflurry, Set 2) |
| SEQ ID NO: 166 | VTVGACGVGK | KRAS G12C | VVVGACGVGK | V2T | — | | Individual KRAS_G12C Vaccine (8-peptide, MHCflurry, Set 2) |
| SEQ ID NO: 167 | LLVVGADGV | KRAS G12D | LVVVGADGV | V2L | — | | Individual KRAS_G12D Vaccine (5-peptide, NetMHCpan, Set 1); Colorectal Cancer Vaccine (20-peptide) |
| SEQ ID NO: 168 | LMVVGADGV | KRAS G12D | LVVVGADGV | V2M | — | | Individual KRAS_G12D Vaccine (5-peptide, NetMHCpan, Set 1); Pancreatic Cancer Vaccine (10-peptide); Bronchus And Lung Cancer Vaccine (30-peptide); Colorectal Cancer Vaccine (20-peptide); Individual KRAS_G12D Vaccine (8-peptide, MHCflurry, Set 1); Individual KRAS_G12D Vaccine (3-peptide, NetMHCpan, Set 2); Individual KRAS_G12D Vaccine (8-peptide, MHCflurry, Set 2) |

TABLE 1-continued

Example Vaccine Peptides (MHC class I)

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 169 | LTVVGADGV | KRAS G12D | LVVGADGV | V2T | — | Individual KRAS_G12D Vaccine (5-peptide, NetMHCpan, Set 1); Pancreatic Cancer Vaccine (10-peptide); Bronchus And Lung Cancer Vaccine (30-peptide); Colorectal Cancer Vaccine (20-peptide); Individual KRAS_G12D Vaccine (3-peptide, NetMHCpan, Set 2) |
| SEQ ID NO: 170 | VTVGADGVGR | KRAS G12D | VVVGADGVGK | V2T | K10R | Individual KRAS_G12D Vaccine (5-peptide, NetMHCpan, Set 1); Individual KRAS_G12D Vaccine (8-peptide, MHCflurry, Set 1); Individual KRAS_G12D Vaccine (3-peptide, NetMHCpan, Set 2); Individual KRAS_G12D Vaccine (8-peptide, MHCflurry, Set 2) |
| SEQ ID NO: 171 | VVVGADGVGR | KRAS G12D | VVVGADGVGK | — | K10R | Individual KRAS_G12D Vaccine (5-peptide, NetMHCpan, Set 1); Pancreatic Cancer Vaccine (10-peptide); Bronchus And Lung Cancer Vaccine (30-peptide); Colorectal Cancer Vaccine (20-peptide) |
| SEQ ID NO: 172 | GFDGVGKSL | KRAS G12D | GADGVGKSA | A2F | A9L | Individual KRAS_G12D Vaccine (8-peptide, MHCflurry, Set 1); Individual KRAS_G12D Vaccine (8-peptide, MHCflurry, Set 2) |
| SEQ ID NO: 173 | VAADGVGKSAF | KRAS G12D | VGADGVGKSAL | G2A | L11F | Individual KRAS_G12D Vaccine (8-peptide, MHCflurry, Set 1); Individual KRAS_G12D Vaccine (8-peptide, MHCflurry, Set 2) |
| SEQ ID NO: 174 | VAADGVGKSAL | KRAS G12D | VGADGVGKSAL | G2A | — | Individual KRAS_G12D Vaccine (8-peptide, MHCflurry, Set 1); Individual KRAS_G12D Vaccine (8-peptide, MHCflurry, Set 2) |
| SEQ ID NO: 175 | VRADGVGKSAF | KRAS G12D | VGADGVGKSAL | G2R | L11F | Individual KRAS_G12D Vaccine (8-peptide, MHCflurry, Set 1); Individual KRAS_G12D Vaccine (8-peptide, MHCflurry, Set 2) |
| SEQ ID NO: 176 | VTADGVGKSAF | KRAS G12D | VGADGVGKSAL | G2T | L11F | Individual KRAS_G12D Vaccine (8-peptide, MHCflurry, Set 1) |

TABLE 1-continued

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 177 | VSADGVGKSAF | KRAS G12D | VGADGVGKSAL | G2S | L11F | Individual KRAS_G12D Vaccine (8-peptide, MHCflurry, Set 2) |
| SEQ ID NO: 178 | VTVGADGVGK | KRAS G12D | VVVGADGVGK | V2T | — | Individual KRAS_G12D Vaccine (8-peptide, MHCflurry, Set 2) |
| SEQ ID NO: 179 | GPRGVGKSAV | KRAS G12R | GARGVGKSAL | A2P | L10V | Individual KRAS_G12R Vaccine (5-peptide, NetMHCpan, Set 1); Pancreatic Cancer Vaccine (10-peptide) |
| SEQ ID NO: 180 | LLVVGARGV | KRAS G12R | LVVVGARGV | V2L | — | Individual KRAS_G12R Vaccine (5-peptide, NetMHCpan, Set 1); Pancreatic Cancer Vaccine (10-peptide) |
| SEQ ID NO: 181 | LMVVGARGV | KRAS G12R | LVVVGARGV | V2M | — | Individual KRAS_G12R Vaccine (5-peptide, NetMHCpan, Set 1); Individual KRAS_G12R Vaccine (8-peptide, MHCflurry, Set 1); Individual KRAS_G12R Vaccine (4-peptide, NetMHCpan, Set 2); Individual KRAS_G12R Vaccine (8-peptide, MHCflurry, Set 2) |
| SEQ ID NO: 182 | VMGARGVGK | KRAS G12R | VVGARGVGK | V2M | — | Individual KRAS_G12R Vaccine (5-peptide, NetMHCpan, Set 1); Pancreatic Cancer Vaccine (10-peptide); Individual KRAS_G12R Vaccine (4-peptide, NetMHCpan, Set 2) |
| SEQ ID NO: 183 | VVVGARGVGR | KRAS G12R | VVVGARGVGK | — | K10R | Individual KRAS_G12R Vaccine (5-peptide, NetMHCpan, Set 1); Pancreatic Cancer Vaccine (10-peptide) |
| SEQ ID NO: 184 | GARGVGKSY | KRAS G12R | GARGVGKSA | — | A9Y | Individual KRAS_G12R Vaccine (8-peptide, MHCflurry, Set 1); Individual KRAS_G12R Vaccine (8-peptide, MHCflurry, Set 2) |
| SEQ ID NO: 185 | GPRGVGKSA | KRAS G12R | GARGVGKSA | A2P | — | Individual KRAS_G12R Vaccine (8-peptide, MHCflurry, Set 1); Individual KRAS_G12R Vaccine (8-peptide, MHCflurry, Set 2) |

TABLE 1-continued

Example Vaccine Peptides (MHC class I)

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 186 | GPRGVGKSAL | KRAS G12R | GARGVGKSAL | A2P | — | Individual KRAS_G12R Vaccine (8-peptide, MHCflurry, Set 1); Individual KRAS_G12R Vaccine (4-peptide, NetMHCpan, Set 2); Individual KRAS_G12R Vaccine (8-peptide, MHCflurry, Set 2) |
| SEQ ID NO: 187 | VAGARGVGM | KRAS G12R | VVGARGVGK | V2A | K9M | Individual KRAS_G12R Vaccine (8-peptide, MHCflurry, Set 1) |
| SEQ ID NO: 188 | VMVGARGVGK | KRAS G12R | VTVGARGVGK | V2M | — | Individual KRAS_G12R Vaccine (8-peptide, MHCflurry, Set 1); Individual KRAS_G12R Vaccine (8-peptide, MHCflurry, Set 2) |
| SEQ ID NO: 189 | VTVGARGVGR | KRAS G12R | VVVGARGVGK | V2T | K10R | Individual KRAS_G12R Vaccine (8-peptide, MHCflurry, Set 1); Individual KRAS_G12R Vaccine (4-peptide, NetMHCpan, Set 2); Individual KRAS_G12R Vaccine (8-peptide, MHCflurry, Set 2) |
| SEQ ID NO: 190 | VAGARGVGL | KRAS G12R | VVGARGVGK | V2A | K9L | Individual KRAS_G12R Vaccine (8-peptide, MHCflurry, Set 2) |
| SEQ ID NO: 191 | VTVGARGVGK | KRAS G12R | VVVGARGVGK | V2T | — | Individual KRAS_G12R Vaccine (8-peptide, MHCflurry, Set 2) |
| SEQ ID NO: 192 | LMVVGASGV | KRAS G12S | LVVVGASGV | V2M | — | Individual KRAS_G12S Vaccine (5-peptide, NetMHCpan, Set 1); Individual KRAS_G12S Vaccine (8-peptide, MHCflurry, Set 1); Individual KRAS_G12S Vaccine (5-peptide, NetMHCpan, Set 2); Individual KRAS_G12S Vaccine (8-peptide, MHCflurry, Set 2) |
| SEQ ID NO: 193 | LQVVGASGV | KRAS G12S | LVVVGASGV | V2Q | — | Individual KRAS_G12S Vaccine (5-peptide, NetMHCpan, Set 1); Individual KRAS_G12S Vaccine (5-peptide, NetMHCpan, Set 2) |
| SEQ ID NO: 194 | LTVVGASGV | KRAS G12S | LVVVGASGV | V2T | — | Individual KRAS_G12S Vaccine (5-peptide, NetMHCpan, Set 1); Individual KRAS_G12S Vaccine (8-peptide, MHCflurry, Set 1); Individual |

TABLE 1-continued

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 195 | VTVGASGVGK | KRAS G12S | VVVGASGVGK | V2T | — | KRAS_G12S Vaccine (5-peptide, NetMHCpan, Set 2); Individual KRAS_G12S Vaccine (8-peptide, MHCflurry, Set 2) |
| SEQ ID NO: 196 | VVVGASGVGR | KRAS G12S | VVVGASGVGK | — | K10R | Individual KRAS_G12S Vaccine (5-peptide, NetMHCpan, Set 1); Individual KRAS_G12S Vaccine (8-peptide, MHCflurry, Set 1); Individual KRAS_G12S Vaccine (5-peptide, NetMHCpan, Set 2); Individual KRAS_G12S Vaccine (8-peptide, MHCflurry, Set 2) |
| SEQ ID NO: 197 | GASGVGKSL | KRAS G12S | GASGVGKSA | — | A9L | Individual KRAS_G12S Vaccine (5-peptide, NetMHCpan, Set 1) |
| SEQ ID NO: 198 | GPSGVGKSAM | KRAS G12S | GASGVGKSAL | A2P | L10M | Individual KRAS_G12S Vaccine (8-peptide, MHCflurry, Set 1); Individual KRAS_G12S Vaccine (8-peptide, MHCflurry, Set 1) |
| SEQ ID NO: 199 | VAVGASGVGY | KRAS G12S | VVVGASGVGK | V2A | K10Y | Individual KRAS_G12S Vaccine (8-peptide, MHCflurry, Set 1) |
| SEQ ID NO: 200 | VTVGASGVGR | KRAS G12S | VVVGASGVGK | V2T | K10R | Individual KRAS_G12S Vaccine (8-peptide, MHCflurry, Set 1); Individual KRAS_G12S Vaccine (5-peptide, NetMHCpan, Set 2); Individual KRAS_G12S Vaccine (8-peptide, MHCflurry, Set 2) |
| SEQ ID NO: 201 | VTVGASGVGY | KRAS G12S | VVVGASGVGK | V2T | K10Y | Individual KRAS_G12S Vaccine (8-peptide, MHCflurry, Set 1); Individual KRAS_G12S Vaccine (8-peptide, MHCflurry, Set 2) |
| SEQ ID NO: 202 | GPSGVGKSAL | KRAS G12S | GASGVGKSAL | A2P | — | Individual KRAS_G12S Vaccine (8-peptide, MHCflurry, Set 2) |

TABLE 1-continued

| SEQ ID NO | Sequence corresponding to SEQ ID | Target | Seed | Example Vaccine Peptides (MHC class I) | | Note |
|---|---|---|---|---|---|---|
| | | | | Heteroclitic Modification P2 | Heteroclitic Modification C-term | |
| SEQ ID NO: 203 | LMVVGAVGV | KRAS G12V | LVVVGAVGV | V2M | — | Individual KRAS_G12V Vaccine (5-peptide, NetMHCpan, Set 1); Pancreatic Cancer Vaccine (10-peptide); Bronchus And Lung Cancer Vaccine (30-peptide); Colorectal Cancer Vaccine (20-peptide); Individual KRAS_G12V Vaccine (8-peptide, MHCflurry, Set 1); Individual KRAS_G12V Vaccine (5-peptide, NetMHCpan, Set 2); Individual KRAS_G12V Vaccine (8-peptide, MHCflurry, Set 2) |
| SEQ ID NO: 204 | LTVVGAVGV | KRAS G12V | LVVVGAVGV | V2T | — | Individual KRAS_G12V Vaccine (5-peptide, NetMHCpan, Set 1); Pancreatic Cancer Vaccine (10-peptide); Bronchus And Lung Cancer Vaccine (30-peptide); Colorectal Cancer Vaccine (20-peptide); Individual KRAS_G12V Vaccine (8-peptide, MHCflurry, Set 1); Individual KRAS_G12V Vaccine (5-peptide, NetMHCpan, Set 2); Individual KRAS_G12V Vaccine (8-peptide, MHCflurry, Set 2) |
| SEQ ID NO: 205 | VMGAVGVGK | KRAS G12V | VVGAVGVGK | V2M | — | Individual KRAS_G12V Vaccine (5-peptide, NetMHCpan, Set 1); Colorectal Cancer Vaccine (20-peptide); Individual KRAS_G12V Vaccine (5-peptide, NetMHCpan, Set 2) |
| SEQ ID NO: 206 | VMGAVGVGR | KRAS G12V | VVGAVGVGK | V2M | K9R | Individual KRAS_G12V Vaccine (5-peptide, NetMHCpan, Set 1); Colorectal Cancer Vaccine (20-peptide); Individual KRAS_G12V Vaccine (5-peptide, NetMHCpan, Set 2) |
| SEQ ID NO: 207 | VTVGAVGVGK | KRAS G12V | VVVGAVGVGK | V2T | — | Individual KRAS_G12V Vaccine (5-peptide, NetMHCpan, Set 1); Pancreatic Cancer Vaccine (10-peptide); Bronchus And Lung Cancer Vaccine (30-peptide); Colorectal Cancer Vaccine (20-peptide); Individual KRAS_G12V Vaccine (8-peptide, MHCflurry, Set 1); Individual KRAS_G12V Vaccine (5-peptide, |

TABLE 1-continued

Example Vaccine Peptides (MHC class I)

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 208 | GAVGVGKSL | KRAS G12V | GAVGVGKSA | — | A9L | NetMHCpan, Set 2); Individual KRAS_G12V Vaccine (8-peptide, MHCflurry, Set 2) |
| SEQ ID NO: 209 | GPVGVGKSA | KRAS G12V | GAVGVGKSA | A2P | — | Individual KRAS_G12V Vaccine (8-peptide, MHCflurry, Set 1); Individual KRAS_G12V Vaccine (8-peptide, MHCflurry, Set 2) |
| SEQ ID NO: 210 | GPVGVGKSAL | KRAS G12V | GAVGVGKSAL | A2P | — | Individual KRAS_G12V Vaccine (8-peptide, MHCflurry, Set 1) |
| SEQ ID NO: 211 | VMVGAVGVGR | KRAS G12V | VVVGAVGVGK | V2M | K10R | Individual KRAS_G12V Vaccine (8-peptide, MHCflurry, Set 1); Individual KRAS_G12V Vaccine (8-peptide, MHCflurry, Set 2) |
| SEQ ID NO: 212 | VVVGAVGVGR | KRAS G12V | VVVGAVGVGK | — | K10R | Individual KRAS_G12V Vaccine (8-peptide, MHCflurry, Set 1); Individual KRAS_G12V Vaccine (8-peptide, MHCflurry, Set 2) |
| SEQ ID NO: 213 | GPVGVGKSV | KRAS G12V | GAVGVGKSA | A2P | A9V | Individual KRAS_G12V Vaccine (8-peptide, MHCflurry, Set 2) |
| SEQ ID NO: 214 | ASDVGKSAL | KRAS G13D | AGDVGKSAL | G2S | — | Individual KRAS_G13D Vaccine (5-peptide, NetMHCpan, Set 1) |
| SEQ ID NO: 215 | ASDVGKSAM | KRAS G13D | AGDVGKSAL | G2S | L9M | Individual KRAS_G13D Vaccine (5-peptide, NetMHCpan, Set 1); Colorectal Cancer Vaccine (20-peptide) |
| SEQ ID NO: 216 | KMVVVGAGDV | KRAS G13D | KLVVVGAGDV | L2M | — | Individual KRAS_G13D Vaccine (5-peptide, NetMHCpan, Set 1); Colorectal Cancer Vaccine (20-peptide); Individual KRAS_G13D Vaccine (3-peptide, NetMHCpan, Set 2) |
| SEQ ID NO: 217 | VVVGAGDVGR | KRAS G13D | VVVGAGDVGK | — | K10R | Individual KRAS_G13D Vaccine (5-peptide, NetMHCpan, Set 1); |

TABLE 1-continued

Example Vaccine Peptides (MHC class I)

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 218 | AADVGKSAM | KRAS G13D | AGDVGKSAL | G2A | L9M | Colorectal Cancer Vaccine (20-peptide); Individual KRAS_G13D Vaccine (8-peptide, MHCflurry, Set 1); Individual KRAS_G13D Vaccine (8-peptide, MHCflurry, Set 2) |
| SEQ ID NO: 219 | AYDVGKSAM | KRAS G13D | AGDVGKSAL | G2Y | L9M | Individual KRAS_G13D Vaccine (8-peptide, MHCflurry, Set 1); Individual KRAS_G13D Vaccine (8-peptide, MHCflurry, Set 2) |
| SEQ ID NO: 220 | DAGKSALTV | KRAS G13D | DVGKSALTI | V2A | I9V | Individual KRAS_G13D Vaccine (8-peptide, MHCflurry, Set 1); Individual KRAS_G13D Vaccine (8-peptide, MHCflurry, Set 2) |
| SEQ ID NO: 221 | DVGKSALTY | KRAS G13D | DVGKSALTI | — | I9Y | Individual KRAS_G13D Vaccine (8-peptide, MHCflurry, Set 1) |
| SEQ ID NO: 222 | GAGDVGKSM | KRAS G13D | GAGDVGKSA | — | A9M | Individual KRAS_G13D Vaccine (8-peptide, MHCflurry, Set 1); Individual KRAS_G13D Vaccine (8-peptide, MHCflurry, Set 2) |
| SEQ ID NO: 223 | VTVGAGDVGK | KRAS G13D | VVVGAGDVGK | V2T | — | Individual KRAS_G13D Vaccine (8-peptide, MHCflurry, Set 1); Individual KRAS_G13D Vaccine (8-peptide, MHCflurry, Set 2) |
| SEQ ID NO: 224 | VVAGDVGKSAW | KRAS G13D | VGAGDVGKSAL | G2V | L11W | Individual KRAS_G13D Vaccine (8-peptide, MHCflurry, Set 1) |
| SEQ ID NO: 225 | AADVGKSAL | KRAS G13D | AGDVGKSAL | G2A | — | Individual KRAS_G13D Vaccine (3-peptide, NetMHCpan, Set 2) |
| SEQ ID NO: 226 | VTVGAGDVGR | KRAS G13D | VVVGAGDVGK | V2T | K10R | Individual KRAS_G13D Vaccine (3-peptide, NetMHCpan, Set 2) |
| SEQ ID NO: 227 | AYDVGKSAL | KRAS G13D | AGDVGKSAL | G2Y | — | Individual KRAS_G13D Vaccine (8-peptide, MHCflurry, Set 2) |
| SEQ ID NO: 228 | DVGKSALTF | KRAS G13D | DVGKSALTI | — | I9F | Individual KRAS_G13D Vaccine (8-peptide, MHCflurry, Set 2) |

TABLE 1-continued

| SEQ ID NO | Sequence corresponding to SEQ ID | Target | Seed | Example Vaccine Peptides (MHC class I) | | | Note |
|---|---|---|---|---|---|---|---|
| | | | | Heteroclitic Modification P2 | Heteroclitic Modification C-term | | |
| SEQ ID NO: 229 | VSAGDVGKSAF | KRAS G13D | VGAGDVGKSAL | G2S | L11F | | Individual KRAS_G13D Vaccine (8-peptide, MHCflurry, Set 2) |
| SEQ ID NO: 230 | ATKEEYSAMR | NRAS Q61K | AGKEEYSAMR | G2T | — | | Individual NRAS_Q61K Vaccine (2-peptide, NetMHCpan, Set 1); Skin Cancer Vaccine (20-peptide); Thyroid Cancer Vaccine (10-peptide); Individual NRAS_Q61K Vaccine (2-peptide, NetMHCpan, Set 2) |
| SEQ ID NO: 231 | ITDTAGKEEY | NRAS Q61K | ILDTAGKEEY | L2T | — | | Individual NRAS_Q61K Vaccine (2-peptide, NetMHCpan, Set 1); Skin Cancer Vaccine (20-peptide); Thyroid Cancer Vaccine (10-peptide); Individual NRAS_Q61K Vaccine (8-peptide, MHCflurry, Set 1); Individual NRAS_Q61K Vaccine (2-peptide, NetMHCpan, Set 2); Individual NRAS_Q61K Vaccine (8-peptide, MHCflurry, Set 2) |
| SEQ ID NO: 232 | AAKEEYSAL | NRAS Q61K | AGKEEYSAM | G2A | M9L | | Individual NRAS_Q61K Vaccine (8-peptide, MHCflurry, Set 1); Individual NRAS_Q61K Vaccine (8-peptide, MHCflurry, Set 2) |
| SEQ ID NO: 233 | AAKEEYSAY | NRAS Q61K | AGKEEYSAM | G2A | M9Y | | Individual NRAS_Q61K Vaccine (8-peptide, MHCflurry, Set 1); Individual NRAS_Q61K Vaccine (8-peptide, MHCflurry, Set 2) |
| SEQ ID NO: 234 | ARKEEYSAY | NRAS Q61K | AGKEEYSAM | G2R | M9Y | | Individual NRAS_Q61K Vaccine (8-peptide, MHCflurry, Set 1); Individual NRAS_Q61K Vaccine (8-peptide, MHCflurry, Set 2) |
| SEQ ID NO: 235 | ILDTAGKEEL | NRAS Q61K | ILDTAGKEEY | — | Y10L | | Individual NRAS_Q61K Vaccine (8-peptide, MHCflurry, Set 1); Individual NRAS_Q61K Vaccine (8-peptide, MHCflurry, Set 2) |
| SEQ ID NO: 236 | IMDTAGKEEL | NRAS Q61K | ILDTAGKEEY | L2M | Y10L | | Individual NRAS_Q61K Vaccine (8-peptide, MHCflurry, Set 1); Individual NRAS_Q61K Vaccine (8-peptide, MHCflurry, Set 2) |

TABLE 1-continued

| SEQ ID NO | Sequence corresponding to SEQ ID | Target | Seed | Example Vaccine Peptides (MHC class I) | | Note |
|---|---|---|---|---|---|---|
| | | | | Heteroclitic Modification P2 | Heteroclitic Modification C-term | |
| SEQ ID NO: 237 | LETAGKEEM | NRAS Q61K | LDTAGKEEY | D2E | Y9M | Individual NRAS_Q61K Vaccine (8-peptide, MHCflurry, Set 1); Individual NRAS_Q61K Vaccine (8-peptide, MHCflurry, Set 2) |
| SEQ ID NO: 238 | LETAGKEEW | NRAS Q61K | LDTAGKEEY | D2E | Y9W | Individual NRAS_Q61K Vaccine (8-peptide, MHCflurry, Set 1); Individual NRAS_Q61K Vaccine (8-peptide, MHCflurry, Set 2) |
| SEQ ID NO: 239 | ATLEEYSAF | NRAS Q61L | AGLEEYSAM | G2T | M9F | Individual NRAS_Q61L Vaccine (5-peptide, NetMHCpan, Set 1); Skin Cancer Vaccine (20-peptide) |
| SEQ ID NO: 240 | DTAGLEEYSV | NRAS Q61L | DTAGLEEYSA | — | A10V | Individual NRAS_Q61L Vaccine (5-peptide, NetMHCpan, Set 1); Individual NRAS_Q61L Vaccine (8-peptide, MHCflurry, Set 1); Individual NRAS_Q61L Vaccine (3-peptide, NetMHCpan, Set 2); Individual NRAS_Q61L Vaccine (8-peptide, MHCflurry, Set 2) |
| SEQ ID NO: 241 | DVAGLEEYSV | NRAS Q61L | DTAGLEEYSA | T2V | A10V | Individual NRAS_Q61L Vaccine (5-peptide, NetMHCpan, Set 1); Skin Cancer Vaccine (20-peptide) |
| SEQ ID NO: 242 | ISDTAGLEEY | NRAS Q61L | ILDTAGLEEY | L2S | — | Individual NRAS_Q61L Vaccine (5-peptide, NetMHCpan, Set 1); Skin Cancer Vaccine (20-peptide) |
| SEQ ID NO: 243 | ITDTAGLEEY | NRAS Q61L | ILDTAGLEEY | L2T | — | Individual NRAS_Q61L Vaccine (5-peptide, NetMHCpan, Set 1); Individual NRAS_Q61L Vaccine (3-peptide, NetMHCpan, Set 2) |
| SEQ ID NO: 244 | AALEEYSAL | NRAS Q61L | AGLEEYSAM | G2A | M9L | Individual NRAS_Q61L Vaccine (8-peptide, MHCflurry, Set 1); Individual NRAS_Q61L Vaccine (8-peptide, MHCflurry, Set 2) |
| SEQ ID NO: 245 | DVLDTAGLEER | NRAS Q61L | DILDTAGLEEY | I2V | Y11R | Individual NRAS_Q61L Vaccine (8-peptide, MHCflurry, Set 1) |
| SEQ ID NO: 246 | DVLDTAGLEEY | NRAS Q61L | DILDTAGLEEY | I2V | — | Individual NRAS_Q61L Vaccine (8-peptide, MHCflurry, Set 1) |

TABLE 1-continued

Example Vaccine Peptides (MHC class I)

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 247 | IMDTAGLEEM | NRAS_Q61L | ILDTAGLEEY | L2M | Y10M | Individual NRAS_Q61L Vaccine (8-peptide, MHCflurry, Set 1); Individual NRAS_Q61L Vaccine (8-peptide, MHCflurry, Set 2) |
| SEQ ID NO: 248 | IVDTAGLEEY | NRAS_Q61L | ILDTAGLEEY | L2V | — | Individual NRAS_Q61L Vaccine (8-peptide, MHCflurry, Set 1) |
| SEQ ID NO: 249 | LETAGLEEM | NRAS_Q61L | LDTAGLEEY | D2E | Y9M | Individual NRAS_Q61L Vaccine (8-peptide, MHCflurry, Set 1) |
| SEQ ID NO: 250 | LMTAGLEEY | NRAS_Q61L | LDTAGLEEY | D2M | — | Individual NRAS_Q61L Vaccine (8-peptide, MHCflurry, Set 1); Individual NRAS_Q61L Vaccine (8-peptide, MHCflurry, Set 2) |
| SEQ ID NO: 251 | AQLEEYSAF | NRAS_Q61L | AGLEEYSAM | G2Q | M9F | Individual NRAS_Q61L Vaccine (3-peptide, NetMHCpan, Set 2) |
| SEQ ID NO: 252 | DTLDTAGLEEY | NRAS_Q61L | DILDTAGLEEY | I2T | — | Individual NRAS_Q61L Vaccine (8-peptide, MHCflurry, Set 2) |
| SEQ ID NO: 253 | DVLDTAGLEEK | NRAS_Q61L | DILDTAGLEEY | I2V | Y11K | Individual NRAS_Q61L Vaccine (8-peptide, MHCflurry, Set 2) |
| SEQ ID NO: 254 | IMDTAGLEEY | NRAS_Q61L | ILDTAGLEEY | L2M | — | Individual NRAS_Q61L Vaccine (8-peptide, MHCflurry, Set 2) |
| SEQ ID NO: 255 | LETAGLEEF | NRAS_Q61L | LDTAGLEEY | D2E | Y9F | Individual NRAS_Q61L Vaccine (8-peptide, MHCflurry, Set 2) |
| SEQ ID NO: 256 | ASREEYSAF | NRAS_Q61R | AGREEYSAM | G2S | M9F | Individual NRAS_Q61R Vaccine (5-peptide, NetMHCpan, Set 1) |
| SEQ ID NO: 257 | ATREEYSAMR | NRAS_Q61R | AGREEYSAMR | G2T | — | Individual NRAS_Q61R Vaccine (5-peptide, NetMHCpan, Set 1) |
| SEQ ID NO: 258 | AVREEYSAM | NRAS_Q61R | AGREEYSAM | G2V | M9F | Individual NRAS_Q61R Vaccine (5-peptide, NetMHCpan, Set 1) |
| SEQ ID NO: 259 | ISDTAGREEY | NRAS_Q61R | ILDTAGREEY | L2S | — | Individual NRAS_Q61R Vaccine (5-peptide, NetMHCpan, Set 1) |
| SEQ ID NO: 260 | ITDTAGREEY | NRAS_Q61R | ILDTAGREEY | L2T | — | Individual NRAS_Q61R Vaccine (5-peptide, NetMHCpan, Set 1); Skin Cancer Vaccine (20-peptide); Thyroid Cancer Vaccine (10-peptide); |

TABLE 1-continued

Example Vaccine Peptides (MHC class I)

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 261 | AVREEYSAY | NRAS Q61R | AGREEYSAM | G2V | M9Y | Individual NRAS_Q61R Vaccine (8-peptide, MHCflurry, Set 1); Individual NRAS_Q61R Vaccine (3-peptide, NetMHCpan, Set 2); Individual NRAS_Q61R Vaccine (8-peptide, MHCflurry, Set 2) |
| SEQ ID NO: 262 | AYREEYSAMR | NRAS Q61R | AGREEYSAMR | G2Y | — | Skin Cancer Vaccine (20-peptide); Thyroid Cancer Vaccine (10-peptide) |
| SEQ ID NO: 263 | AAREEYSAL | NRAS Q61R | AGREEYSAM | G2A | M9L | Skin Cancer Vaccine (20-peptide); Thyroid Cancer Vaccine (10-peptide) |
| SEQ ID NO: 264 | AAREEYSAY | NRAS Q61R | AGREEYSAM | G2A | M9Y | Individual NRAS_Q61R Vaccine (8-peptide, MHCflurry, Set 1); Individual NRAS_Q61R Vaccine (8-peptide, MHCflurry, Set 2) |
| SEQ ID NO: 265 | ARREEYSAL | NRAS Q61R | AGREEYSAM | G2R | M9L | Individual NRAS_Q61R Vaccine (8-peptide, MHCflurry, Set 1) |
| SEQ ID NO: 266 | DVLDTAGREEW | NRAS Q61R | DILDTAGREEY | I2V | Y11W | Individual NRAS_Q61R Vaccine (8-peptide, MHCflurry, Set 1); Individual NRAS_Q61R Vaccine (8-peptide, MHCflurry, Set 2) |
| SEQ ID NO: 267 | IMDTAGREEL | NRAS Q61R | ILDTAGREEY | L2M | Y10L | Individual NRAS_Q61R Vaccine (8-peptide, MHCflurry, Set 1); Individual NRAS_Q61R Vaccine (8-peptide, MHCflurry, Set 2) |
| SEQ ID NO: 268 | LETAGREEM | NRAS Q61R | LDTAGREEY | D2E | Y9M | Individual NRAS_Q61R Vaccine (8-peptide, MHCflurry, Set 1); Individual NRAS_Q61R Vaccine (8-peptide, MHCflurry, Set 2) |
| SEQ ID NO: 269 | REEYSAMRDQW | NRAS Q61R | REEYSAMRDQY | — | Y11W | Individual NRAS_Q61R Vaccine (8-peptide, MHCflurry, Set 1); Individual NRAS_Q61R Vaccine (8-peptide, MHCflurry, Set 2) |

TABLE 1-continued

Example Vaccine Peptides (MHC class I)

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 270 | AMREEYSAMR | NRAS Q61R | AGREEYSAMR | G2M | — | Individual NRAS_Q61R Vaccine (3-peptide, NetMHCpan, Set 2) |
| SEQ ID NO: 271 | AQREEYSAF | NRAS Q61R | AGREEYSAM | G2Q | M9F | Individual NRAS_Q61R Vaccine (3-peptide, NetMHCpan, Set 2) |
| SEQ ID NO: 272 | ARREEYSAF | NRAS Q61R | AGREEYSAM | G2R | M9F | Individual NRAS_Q61R Vaccine (8-peptide, MHCflurry, Set 2) |
| SEQ ID NO: 273 | KSTEQEKDFLW | PIK3CA E542K | KITEQEKDFLW | I2S | — | Individual PIK3CA_E542K Vaccine (5-peptide, NetMHCpan, Set 1); Individual PIK3CA_E542K Vaccine (3-peptide, NetMHCpan, Set 2) |
| SEQ ID NO: 274 | KITEQEKDFLW | PIK3CA E542K | KITEQEKDFLW | I2T | — | Individual PIK3CA_E542K Vaccine (5-peptide, NetMHCpan, Set 1); Bronchus And Lung Cancer Vaccine (30-peptide); Individual PIK3CA_E542K Vaccine (8-peptide, MHCflurry, Set 1); Individual PIK3CA_E542K Vaccine (8-peptide, MHCflurry, Set 2) |
| SEQ ID NO: 275 | SARDPLSKF | PIK3CA E542K | STRDPLSKI | T2A | 19F | Individual PIK3CA_E542K Vaccine (5-peptide, NetMHCpan, Set 1); Bronchus And Lung Cancer Vaccine (30-peptide); Individual PIK3CA_E542K Vaccine (3-peptide, NetMHCpan, Set 2) |
| SEQ ID NO: 276 | STRDPLSKV | PIK3CA E542K | STRDPLSKI | — | I9V | Individual PIK3CA_E542K Vaccine (5-peptide, NetMHCpan, Set 1); Bronchus And Lung Cancer Vaccine (30-peptide) |
| SEQ ID NO: 277 | SVRDPLSKK | PIK3CA E542K | STRDPLSKI | T2V | I9K | Individual PIK3CA_E542K Vaccine (5-peptide, NetMHCpan, Set 1) |
| SEQ ID NO: 278 | SARDPLSKL | PIK3CA E542K | STRDPLSKI | T2A | I9L | Individual PIK3CA_E542K Vaccine (8-peptide, MHCflurry, Set 1); Individual PIK3CA_E542K Vaccine (8-peptide, MHCflurry, Set 2) |
| SEQ ID NO: 279 | SSRDPLSKL | PIK3CA E542K | STRDPLSKI | T2S | I9L | Individual PIK3CA_E542K Vaccine (8-peptide, MHCflurry, Set 1); Individual PIK3CA_E542K Vaccine (8-peptide, MHCflurry, Set 2) |

TABLE 1-continued

Example Vaccine Peptides (MHC class I)

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 280 | SSRDPLSKY | PIK3CA E542K | STRDPLSKI | T2S | I9Y | Individual PIK3CA_E542K Vaccine (8-peptide, MHCflurry, Set 1); Individual PIK3CA_E542K Vaccine (8-peptide, MHCflurry, Set 2) |
| SEQ ID NO: 281 | STRDPLSKR | PIK3CA E542K | STRDPLSKI | — | I9R | Individual PIK3CA_E542K Vaccine (8-peptide, MHCflurry, Set 1); Individual PIK3CA_E542K Vaccine (8-peptide, MHCflurry, Set 2) |
| SEQ ID NO: 282 | STRDPLSKW | PIK3CA E542K | STRDPLSKI | — | I9W | Individual PIK3CA_E542K Vaccine (8-peptide, MHCflurry, Set 1); Individual PIK3CA_E542K Vaccine (8-peptide, MHCflurry, Set 2) |
| SEQ ID NO: 283 | SVRDPLSKV | PIK3CA E542K | STRDPLSKI | T2V | I9V | Individual PIK3CA_E542K Vaccine (8-peptide, MHCflurry, Set 1); Individual PIK3CA_E542K Vaccine (8-peptide, MHCflurry, Set 2) |
| SEQ ID NO: 284 | TYDPLSKL | PIK3CA E542K | TRDPLSKI | R2Y | I8L | Individual PIK3CA_E542K Vaccine (8-peptide, MHCflurry, Set 1); Individual PIK3CA_E542K Vaccine (8-peptide, MHCflurry, Set 2) |
| SEQ ID NO: 285 | STRDPLSKIK | PIK3CA E542K | STRDPLSKIT | — | T10K | Individual PIK3CA_E542K Vaccine (3-peptide, NetMHCpan, Set 2) |
| SEQ ID NO: 286 | IAKQEKDFLW | PIK3CA E545K | ITKQEKDFLW | T2A | — | Individual PIK3CA_E545K Vaccine (4-peptide, NetMHCpan, Set 1); Individual PIK3CA_E545K Vaccine (8-peptide, MHCflurry, Set 1); Individual PIK3CA_E545K Vaccine (3-peptide, NetMHCpan, Set 2) |
| SEQ ID NO: 287 | ISKQEKDFLW | PIK3CA E545K | ITKQEKDFLW | T2S | — | Individual PIK3CA_E545K Vaccine (4-peptide, NetMHCpan, Set 1); Individual PIK3CA_E545K Vaccine (8-peptide, MHCflurry, Set 1); Individual PIK3CA_E545K Vaccine (3-peptide, NetMHCpan, Set 2) |
| SEQ ID NO: 288 | SEITKQEKDW | PIK3CA E545K | SEITKQEKDF | — | F10W | Individual PIK3CA_E545K Vaccine (4-peptide, NetMHCpan, Set 1); Bronchus And Lung Cancer Vaccine (30-peptide); Colorectal Cancer |

TABLE 1-continued

Example Vaccine Peptides (MHC class I)

| SEQ ID NO | Sequence corresponding to SEQ ID | Target | Seed | Heteroclitic Modification P2 | Heteroclitic Modification C-term | Note |
|---|---|---|---|---|---|---|
| | | | | | | Vaccine (20-peptide); Individual PIK3CA_E545K Vaccine (8-peptide, MHCflurry, Set 1); Individual PIK3CA_E545K Vaccine (3-peptide, NetMHCpan, Set 2) |
| SEQ ID NO: 289 | LSEITKQEY | PIK3CA E545K | LSEITKQEK | — | K9Y | Individual PIK3CA_E545K Vaccine (8-peptide, MHCflurry, Set 1) |
| SEQ ID NO: 290 | LTEITKQEY | PIK3CA E545K | LSEITKQEK | S2T | K9Y | Individual PIK3CA_E545K Vaccine (8-peptide, MHCflurry, Set 1); Individual PIK3CA_E545K Vaccine (4-peptide, MHCflurry, Set 2) |
| SEQ ID NO: 291 | SEITKQEKDFW | PIK3CA E545K | SEITKQEKDFL | — | L11W | Individual PIK3CA_E545K Vaccine (8-peptide, MHCflurry, Set 1); Individual PIK3CA_E545K Vaccine (4-peptide, MHCflurry, Set 2) |
| SEQ ID NO: 292 | SEITKQEKV | PIK3CA E545K | SEITKQEKD | — | D9V | Individual PIK3CA_E545K Vaccine (8-peptide, MHCflurry, Set 1) |
| SEQ ID NO: 293 | SEITKQEKA | PIK3CA E545K | SEITKQEKD | — | D9A | Individual PIK3CA_E545K Vaccine (4-peptide, MHCflurry, Set 2) |
| SEQ ID NO: 294 | DTRHGGWTTR | PIK3CA H1047R | DARHGGWTTK | A2T | K10R | Individual PIK3CA_H1047R Vaccine (5-peptide, NetMHCpan, Set 1); Individual PIK3CA_H1047R Vaccine (2-peptide, NetMHCpan, Set 2); Individual PIK3CA_H1047R Vaccine (8-peptide, MHCflurry, Set 2) |
| SEQ ID NO: 295 | KRMNDARHF | PIK3CA H1047R | KQMNDARHG | Q2R | G9F | Individual PIK3CA_H1047R Vaccine (5-peptide, NetMHCpan, Set 1) |
| SEQ ID NO: 296 | KVMNDARHY | PIK3CA H1047R | KQMNDARHG | Q2V | G9Y | Individual PIK3CA_H1047R Vaccine (5-peptide, NetMHCpan, Set 1) |
| SEQ ID NO: 297 | RMGGWTTKY | PIK3CA H1047R | RHGGWTTKM | H2M | M9Y | Individual PIK3CA_H1047R Vaccine (5-peptide, NetMHCpan, Set 1) |
| SEQ ID NO: 298 | RQGGWTTKM | PIK3CA H1047R | RHGGWTTKM | H2Q | — | Individual PIK3CA_H1047R Vaccine (5-peptide, NetMHCpan, Set 1) |
| SEQ ID NO: 299 | DVRHGGWTTK | PIK3CA H1047R | DARHGGWTTK | A2V | — | Individual PIK3CA_H1047R Vaccine (8-peptide, MHCflurry, Set 1) |

TABLE 1-continued

Example Vaccine Peptides (MHC class I)

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 300 | DVRHGGWTTR | PIK3CA H1047R | DARHGGWTTK | A2V | K10R | Individual PIK3CA_H1047R Vaccine (8-peptide, MHCflurry, Set 1) |
| SEQ ID NO: 301 | KEMNDARHGGW | PIK3CA H1047R | KQMNDARHGGW | Q2E | — | Individual PIK3CA_H1047R Vaccine (8-peptide, MHCflurry, Set 1); Individual PIK3CA_H1047R Vaccine (8-peptide, MHCflurry, Set 2) |
| SEQ ID NO: 302 | KQMNDARHGGF | PIK3CA H1047R | KQMNDARHGGW | — | W11F | Individual PIK3CA_H1047R Vaccine (8-peptide, MHCflurry, Set 1); Individual PIK3CA_H1047R Vaccine (8-peptide, MHCflurry, Set 2) |
| SEQ ID NO: 303 | KQMNDARHGGY | PIK3CA H1047R | KQMNDARHGGW | — | W11Y | Individual PIK3CA_H1047R Vaccine (8-peptide, MHCflurry, Set 1); Individual PIK3CA_H1047R Vaccine (8-peptide, MHCflurry, Set 2) |
| SEQ ID NO: 304 | KTMNDARHGGW | PIK3CA H1047R | KQMNDARHGGW | Q2T | — | Individual PIK3CA_H1047R Vaccine (8-peptide, MHCflurry, Set 1); Individual PIK3CA_H1047R Vaccine (8-peptide, MHCflurry, Set 2) |
| SEQ ID NO: 305 | RRGGWTTKF | PIK3CA H1047R | RHGGWTTKM | H2R | M9F | Individual PIK3CA_H1047R Vaccine (8-peptide, MHCflurry, Set 1); Individual PIK3CA_H1047R Vaccine (8-peptide, MHCflurry, Set 2) |
| SEQ ID NO: 306 | RRGGWTTKY | PIK3CA H1047R | RHGGWTTKM | H2R | M9Y | Individual PIK3CA_H1047R Vaccine (8-peptide, MHCflurry, Set 1) |
| SEQ ID NO: 307 | KQMNDARHF | PIK3CA H1047R | KQMNDARHG | — | G9F | Individual PIK3CA_H1047R Vaccine (2-peptide, NetMHCpan, Set 2) |
| SEQ ID NO: 308 | KAMNDARHGGW | PIK3CA H1047R | KQMNDARHGGW | Q2A | — | Individual PIK3CA_H1047R Vaccine (8-peptide, MHCflurry, Set 2) |
| SEQ ID NO: 309 | RRGGWTTKL | PIK3CA H1047R | RHGGWTTKM | H2R | M9L | Individual PIK3CA_H1047R Vaccine (8-peptide, MHCflurry, Set 2) |
| SEQ ID NO: 310 | EMRQLCDLR | PIK3CA R88Q | ETRQLCDLR | T2M | — | Individual PIK3CA_R88Q Vaccine (5-peptide, NetMHCpan, Set 1); Individual PIK3CA_R88Q Vaccine (5-peptide, NetMHCpan, Set 2) |

TABLE 1-continued

Example Vaccine Peptides (MHC class I)

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 311 | EVRQLCDLR | PIK3CA R88Q | ETRQLCDLR | T2V | — | Individual PIK3CA_R88Q Vaccine (5-peptide, NetMHCpan, Set 1); Individual PIK3CA_R88Q Vaccine (8-peptide, MHCflurry, Set 1); Individual PIK3CA_R88Q Vaccine (5-peptide, NetMHCpan, Set 2) |
| SEQ ID NO: 312 | FYDETRQL | PIK3CA R88Q | FFDETRQL | F2Y | — | Individual PIK3CA_R88Q Vaccine (5-peptide, NetMHCpan, Set 1) |
| SEQ ID NO: 313 | FYDETRQM | PIK3CA R88Q | FFDETRQL | F2Y | L8M | Individual PIK3CA_R88Q Vaccine (5-peptide, NetMHCpan, Set 1) |
| SEQ ID NO: 314 | EAFDETRQY | PIK3CA R88Q | EFFDETRQL | F2A | L9Y | Individual PIK3CA_R88Q Vaccine (8-peptide, MHCflurry, Set 1); Individual PIK3CA_R88Q Vaccine (8-peptide, MHCflurry, Set 2) |
| SEQ ID NO: 315 | EIRQLCDLR | PIK3CA R88Q | ETRQLCDLR | T2I | — | Individual PIK3CA_R88Q Vaccine (8-peptide, MHCflurry, Set 1); Individual PIK3CA_R88Q Vaccine (8-peptide, MHCflurry, Set 2) |
| SEQ ID NO: 316 | FADETROL | PIK3CA R88Q | FFDETRQL | F2A | — | Individual PIK3CA_R88Q Vaccine (8-peptide, MHCflurry, Set 1); Individual PIK3CA_R88Q Vaccine (8-peptide, MHCflurry, Set 2) |
| SEQ ID NO: 317 | FFDETRQLL | PIK3CA R88Q | FFDETRQLC | — | C9L | Individual PIK3CA_R88Q Vaccine (8-peptide, MHCflurry, Set 1); Individual PIK3CA_R88Q Vaccine (8-peptide, MHCflurry, Set 2) |
| SEQ ID NO: 318 | FFDETRQLM | PIK3CA R88Q | FFDETRQLC | — | C9M | Individual PIK3CA_R88Q Vaccine (8-peptide, MHCflurry, Set 1); Individual PIK3CA_R88Q Vaccine (8-peptide, MHCflurry, Set 2) |
| SEQ ID NO: 319 | FYDETRQLM | PIK3CA R88Q | FFDETRQLC | F2Y | C9M | Individual PIK3CA_R88Q Vaccine (8-peptide, MHCflurry, Set 1); Individual PIK3CA_R88Q Vaccine (8-peptide, MHCflurry, Set 2) |
| SEQ ID NO: 320 | DFTRQLCDLR | PIK3CA R88Q | DETRQLCDLR | E2F | — | Individual PIK3CA_R88Q Vaccine (5-peptide, NetMHCpan, Set 2) |

TABLE 1-continued

| SEQ ID NO | Sequence corresponding to SEQ ID | Target | Seed | Example Vaccine Peptides (MHC class I) | | | Note |
|---|---|---|---|---|---|---|---|
| | | | | Heteroclitic Modification P2 | Heteroclitic Modification C-term | | |
| SEQ ID NO: 321 | EYFDETRQM | PIK3CA R88Q | EFFDETRQL | F2Y | L9M | | Individual PIK3CA_R88Q Vaccine (5-peptide, NetMHCpan, Set 2) |
| SEQ ID NO: 322 | ESRQLCDLR | PIK3CA R88Q | ETRQLCDLR | T2S | — | | Individual PIK3CA_R88Q Vaccine (8-peptide, MHCflurry, Set 2) |
| SEQ ID NO: 323 | GLGVMICAYV | PTEN R130G | GTGVMICAYL | T2L | L10V | | Individual PTEN_R130G Vaccine (5-peptide, NetMHCpan, Set 1) |
| SEQ ID NO: 324 | GMGVMICAYL | PTEN R130G | GTGVMICAYL | T2M | — | | Individual PTEN_R130G Vaccine (5-peptide, NetMHCpan, Set 1) |
| SEQ ID NO: 325 | GMGVMICAYV | PTEN R130G | GTGVMICAYL | T2M | L10V | | Individual PTEN_R130G Vaccine (5-peptide, NetMHCpan, Set 1); Individual PTEN_R130G Vaccine (2-peptide, NetMHCpan, Set 2) |
| SEQ ID NO: 326 | GQGVMICAF | PTEN R130G | GTGVMICAY | T2Q | Y9F | | Individual PTEN_R130G Vaccine (5-peptide, NetMHCpan, Set 1) |
| SEQ ID NO: 327 | GQGVMICAY | PTEN R130G | GTGVMICAY | T2Q | — | | Individual PTEN_R130G Vaccine (5-peptide, NetMHCpan, Set 1); Individual PTEN_R130G Vaccine (8-peptide, MHCflurry, Set 1); Individual PTEN_R130G Vaccine (2-peptide, NetMHCpan, Set 2); Individual PTEN_R130G Vaccine (7-peptide, MHCflurry, Set 2) |
| SEQ ID NO: 328 | AAKGGTGVL | PTEN R130G | AGKGGTGVM | G2A | M9L | | Individual PTEN_R130G Vaccine (8-peptide, MHCflurry, Set 1); Individual PTEN_R130G Vaccine (7-peptide, MHCflurry, Set 2) |
| SEQ ID NO: 329 | AAKGGTGVY | PTEN R130G | AGKGGTGVM | G2A | M9Y | | Individual PTEN_R130G Vaccine (8-peptide, MHCflurry, Set 1); Individual PTEN_R130G Vaccine (7-peptide, MHCflurry, Set 2) |
| SEQ ID NO: 330 | APKGGTGVM | PTEN R130G | AGKGGTGVM | G2P | — | | Individual PTEN_R130G Vaccine (8-peptide, MHCflurry, Set 1) |
| SEQ ID NO: 331 | AYKGGTGVF | PTEN R130G | AGKGGTGVM | G2Y | M9F | | Individual PTEN_R130G Vaccine (8-peptide, MHCflurry, Set 1); Individual PTEN_R130G Vaccine (7-peptide, MHCflurry, Set 2) |

TABLE 1-continued

Example Vaccine Peptides (MHC class I)

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 332 | KMGKGGTGV | PTEN R130G | KAGKGGTGV | A2M | — | Individual PTEN_R130G Vaccine (8-peptide, MHCflurry, Set 1) |
| SEQ ID NO: 333 | KSGKGGTGVMW | PTEN R130G | KAGKGGTGVMI | A2S | I11W | Individual PTEN_R130G Vaccine (8-peptide, MHCflurry, Set 1) |
| SEQ ID NO: 334 | KTGKGGTGVMW | PTEN R130G | KAGKGGTGVMI | A2T | I11W | Individual PTEN_R130G Vaccine (8-peptide, MHCflurry, Set 1) |
| SEQ ID NO: 335 | APKGGTGVL | PTEN R130G | AGKGGTGVM | G2P | M9L | Individual PTEN_R130G Vaccine (8-peptide, MHCflurry, Set 1) |
| SEQ ID NO: 336 | KAGKGGTGVMW | PTEN R130G | KAGKGGTGVMI | — | I11W | Individual PTEN_R130G Vaccine (7-peptide, MHCflurry, Set 2) |
| SEQ ID NO: 337 | KVGKGGTGV | PTEN R130G | KAGKGGTGV | A2V | — | Individual PTEN_R130G Vaccine (7-peptide, MHCflurry, Set 2) |
| SEQ ID NO: 338 | QQGVMICAF | PTEN R130Q | QTGVMICAY | T2Q | Y9F | Individual PTEN_R130Q Vaccine (5-peptide, NetMHCpan, Set 1) |
| SEQ ID NO: 339 | QQGVMICAY | PTEN R130Q | QTGVMICAY | T2Q | — | Individual PTEN_R130Q Vaccine (5-peptide, NetMHCpan, Set 1) |
| SEQ ID NO: 340 | QSGVMICAYV | PTEN R130Q | QTGVMICAYL | T2S | L10V | Individual PTEN_R130Q Vaccine (5-peptide, NetMHCpan, Set 1) |
| SEQ ID NO: 341 | QTGVMICAYI | PTEN R130Q | QTGVMICAYL | — | L10I | Individual PTEN_R130Q Vaccine (5-peptide, NetMHCpan, Set 1) |
| SEQ ID NO: 342 | QTGVMICAYV | PTEN R130Q | QTGVMICAYL | — | L10V | Individual PTEN_R130Q Vaccine (5-peptide, NetMHCpan, Set 1); Individual PTEN_R130Q Vaccine (2-peptide, NetMHCpan, Set 2) |
| SEQ ID NO: 343 | AAKGQTGVF | PTEN R130Q | AGKGQTGVM | G2A | M9F | Individual PTEN_R130Q Vaccine (8-peptide, MHCflurry, Set 1) |
| SEQ ID NO: 344 | AAKGQTGVL | PTEN R130Q | AGKGQTGVM | G2A | M9L | Individual PTEN_R130Q Vaccine (8-peptide, MHCflurry, Set 1); Individual PTEN_R130Q Vaccine (6-peptide, MHCflurry, Set 2) |
| SEQ ID NO: 345 | AAKGQTGVY | PTEN R130Q | AGKGQTGVM | G2A | M9Y | Individual PTEN_R130Q Vaccine (8-peptide, MHCflurry, Set 1); Individual PTEN_R130Q Vaccine (6-peptide, MHCflurry, Set 2) |

TABLE 1-continued

Example Vaccine Peptides (MHC class I)

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 346 | AQKGQTGVY | PTEN R130Q | AGKGQTGVM | G2Q | M9Y | Individual PTEN_R130Q Vaccine (8-peptide, MHCflurry, Set 1) |
| SEQ ID NO: 347 | KQGKGQTGV | PTEN R130Q | KAGKGQTGV | A2Q | — | Individual PTEN_R130Q Vaccine (8-peptide, MHCflurry, Set 1); Individual PTEN_R130Q Vaccine (6-peptide, MHCflurry, Set 2) |
| SEQ ID NO: 348 | KVGKGQTGV | PTEN R130Q | KAGKGQTGV | A2V | — | Individual PTEN_R130Q Vaccine (8-peptide, MHCflurry, Set 1); Individual PTEN_R130Q Vaccine (6-peptide, MHCflurry, Set 2) |
| SEQ ID NO: 349 | QVGVMICAK | PTEN R130Q | QTGVMICAY | T2V | Y9K | Individual PTEN_R130Q Vaccine (8-peptide, MHCflurry, Set 1) |
| SEQ ID NO: 350 | QVGVMICAR | PTEN R130Q | QTGVMICAY | T2V | Y9R | Individual PTEN_R130Q Vaccine (8-peptide, MHCflurry, Set 1) |
| SEQ ID NO: 351 | QMGVMICAY | PTEN R130Q | QTGVMICAY | T2M | — | Individual PTEN_R130Q Vaccine (2-peptide, NetMHCpan, Set 2) |
| SEQ ID NO: 352 | QTGVMICAK | PTEN R130Q | QTGVMICAY | — | Y9K | Individual PTEN_R130Q Vaccine (6-peptide, MHCflurry, Set 2) |
| SEQ ID NO: 353 | QTGVMICAR | PTEN R130Q | QTGVMICAY | — | Y9R | Individual PTEN_R130Q Vaccine (6-peptide, MHCflurry, Set 2) |
| SEQ ID NO: 354 | VMRRCPHRER | TP53 H179R | VVRRCPHRER | V2M | — | Individual TP53_H179R Vaccine (2-peptide, NetMHCpan, Set 1); Individual TP53_H179R Vaccine (1-peptide, NetMHCpan, Set 2) |
| SEQ ID NO: 355 | EFVRRCPHRER | TP53 H179R | EVVRRCPHRER | V2F | — | Individual TP53_H179R Vaccine (2-peptide, NetMHCpan, Set 1) |
| SEQ ID NO: 356 | RQCPHRERL | TP53 H179R | RRCPHRERC | R2Q | C9L | Individual TP53_H179R Vaccine (2-peptide, MHCflurry, Set 1); Individual TP53_H179R Vaccine (2-peptide, MHCflurry, Set 2) |
| SEQ ID NO: 357 | RRCPHRERY | TP53 H179R | RRCPHRERC | — | C9Y | Individual TP53_H179R Vaccine (2-peptide, MHCflurry, Set 1) |
| SEQ ID NO: 358 | RRCPHRERF | TP53 H179R | RRCPHRERC | — | C9F | Individual TP53_H179R Vaccine (2-peptide, MHCflurry, Set 2) |

TABLE 1-continued

Example Vaccine Peptides (MHC class I)

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 359 | GQRVLAMAIY | TP53 R158L | GTRVLAMAIY | T2Q | — | Individual TP53_R158L Vaccine (5-peptide, NetMHCpan, Set 1); Bronchus And Lung Cancer Vaccine (30-peptide) |
| SEQ ID NO: 360 | GTR VLAMAY | TP53 R158L | GTRVLAMAI | — | I9Y | Individual TP53_R158L Vaccine (5-peptide, NetMHCpan, Set 1); Individual TP53_R158L Vaccine (5-peptide, NetMHCpan, Set 2) |
| SEQ ID NO: 361 | RMLAMAIF | TP53 R158L | RVLAMAIY | V2M | Y8F | Individual TP53_R158L Vaccine (5-peptide, NetMHCpan, Set 1) |
| SEQ ID NO: 362 | RMLAMAIYK | TP53 R158L | RVLAMAIYK | V2M | — | Individual TP53_R158L Vaccine (5-peptide, NetMHCpan, Set 1); Bronchus And Lung Cancer Vaccine (30-peptide); Individual TP53_R158L Vaccine (5-peptide, NetMHCpan, Set 2) |
| SEQ ID NO: 363 | TMVLAMAIYK | TP53 R158L | TRVLAMAIYK | R2M | — | Individual TP53_R158L Vaccine (5-peptide, NetMHCpan, Set 1); Bronchus And Lung Cancer Vaccine (30-peptide); Individual TP53_R158L Vaccine (5-peptide, NetMHCpan, Set 2) |
| SEQ ID NO: 364 | RQLAMAIY | TP53 R158L | RVLAMAIY | V2Q | — | Bronchus And Lung Cancer Vaccine (30-peptide) |
| SEQ ID NO: 365 | RTLAMAIYR | TP53 R158L | RVLAMAIYK | V2T | K9R | Individual TP53_R158L Vaccine (8-peptide, MHCflurry, Set 1); Individual TP53_R158L Vaccine (7-peptide, MHCflurry, Set 2) |
| SEQ ID NO: 366 | RYLAMAIYY | TP53 R158L | RVLAMAIYK | V2Y | K9Y | Individual TP53_R158L Vaccine (8-peptide, MHCflurry, Set 1) |
| SEQ ID NO: 367 | THVLAMAA | TP53 R158L | TRVLAMAI | R2H | I8A | Individual TP53_R158L Vaccine (8-peptide, MHCflurry, Set 1); Individual TP53_R158L Vaccine (7-peptide, MHCflurry, Set 2) |

TABLE 1-continued

| SEQ ID NO | Sequence corresponding to SEQ ID | Target | Seed | Example Vaccine Peptides (MHC class I) | | | Note |
|---|---|---|---|---|---|---|---|
| | | | | Heteroclitic Modification P2 | Heteroclitic Modification C-term | | |
| SEQ ID NO: 368 | TPPPGTRVLL | TP53 R158L | TPPPGTRVLA | — | A10L | | Individual TP53_R158L Vaccine (8-peptide, MHCflurry, Set 1); Individual TP53_R158L Vaccine (7-peptide, MHCflurry, Set 2) |
| SEQ ID NO: 369 | TQVLAMAIY | TP53 R158L | TRVLAMAIY | R2Q | — | | Individual TP53_R158L Vaccine (8-peptide, MHCflurry, Set 1); Individual TP53_R158L Vaccine (7-peptide, MHCflurry, Set 2) |
| SEQ ID NO: 370 | TVPPGTRVLAM | TP53 R158L | TPPPGTRVLAM | P2V | — | | Individual TP53_R158L Vaccine (8-peptide, MHCflurry, Set 1) |
| SEQ ID NO: 371 | GMRVLAMAIY | TP53 R158L | GTRVLAMAIY | T2M | — | | Individual TP53_R158L Vaccine (5-peptide, NetMHCpan, Set 2) |
| SEQ ID NO: 372 | TQVLAMAIF | TP53 R158L | TRVLAMAIY | R2Q | Y9F | | Individual TP53_R158L Vaccine (5-peptide, NetMHCpan, Set 2) |
| SEQ ID NO: 373 | RTLAMAIYY | TP53 R158L | RVLAMAIYK | V2T | K9Y | | Individual TP53_R158L Vaccine (7-peptide, MHCflurry, Set 2) |
| SEQ ID NO: 374 | TAPPGTRVLAL | TP53 R158L | TPPPGTRVLAM | P2A | M11L | | Individual TP53_R158L Vaccine (7-peptide, MHCflurry, Set 2) |
| SEQ ID NO: 375 | ETVRHCPHHER | TP53 R175H | EVVRHCPHHER | V2T | — | | Individual TP53_R175H Vaccine (5-peptide, NetMHCpan, Set 1); Brain Cancer Vaccine (25-peptide) |
| SEQ ID NO: 376 | VMRHCPHHER | TP53 R175H | VVRHCPHHER | V2M | — | | Individual TP53_R175H Vaccine (5-peptide, NetMHCpan, Set 1); Individual TP53_R175H Vaccine (2-peptide, NetMHCpan, Set 2) |
| SEQ ID NO: 377 | VTRHCPHHER | TP53 R175H | VVRHCPHHER | V2T | — | | Individual TP53_R175H Vaccine (5-peptide, NetMHCpan, Set 1) |
| SEQ ID NO: 378 | EVVRHCPHR | TP53 R175H | EVVRHCPHH | — | H9R | | Individual TP53_R175H Vaccine (8-peptide, MHCflurry, Set 1); Individual TP53_R175H Vaccine (5-peptide, MHCflurry, Set 2) |
| SEQ ID NO: 379 | HQTEVVRHL | TP53 R175H | HMTEVVRHC | M2Q | C9L | | Individual TP53_R175H Vaccine (8-peptide, MHCflurry, Set 1) |

TABLE 1-continued

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 380 | HQTEVVRHV | TP53 R175H | HMTEVVRHC | M2Q | C9V | Individual TP53_R175H Vaccine (8-peptide, MHCflurry, Set 1); Individual TP53_R175H Vaccine (5-peptide, MHCflurry, Set 2) |
| SEQ ID NO: 381 | QHMTEVVRHL | TP53 R175H | QHMTEVVRHC | — | C10L | Individual TP53_R175H Vaccine (8-peptide, MHCflurry, Set 1); Individual TP53_R175H Vaccine (5-peptide, MHCflurry, Set 2) |
| SEQ ID NO: 382 | VRHCPHHEM | TP53 R175H | VRHCPHHER | — | R9M | Individual TP53_R175H Vaccine (8-peptide, MHCflurry, Set 1) |
| SEQ ID NO: 383 | VRHCPHHEY | TP53 R175H | VRHCPHHER | — | R9Y | Individual TP53_R175H Vaccine (8-peptide, MHCflurry, Set 1) |
| SEQ ID NO: 384 | VTHCPHHER | TP53 R175H | VRHCPHHER | R2T | — | Individual TP53_R175H Vaccine (8-peptide, MHCflurry, Set 1); Individual TP53_R175H Vaccine (5-peptide, MHCflurry, Set 2) |
| SEQ ID NO: 385 | VVHCPHHER | TP53 R175H | VRHCPHHER | R2V | — | Individual TP53_R175H Vaccine (8-peptide, MHCflurry, Set 1) |
| SEQ ID NO: 386 | VRHCPHHEF | TP53 R175H | VRHCPHHER | — | R9F | Individual TP53_R175H Vaccine (5-peptide, MHCflurry, Set 2) |
| SEQ ID NO: 387 | GMNQRPILTV | TP53 R248Q | GMNQRPILTI | — | I10V | Individual TP53_R248Q Vaccine (5-peptide, NetMHCpan, Set 1); Individual TP53_R248Q Vaccine (8-peptide, MHCflurry, Set 1); Individual TP53_R248Q Vaccine (4-peptide, NetMHCpan, Set 2) |
| SEQ ID NO: 388 | MLQRPILTIY | TP53 R248Q | MNQRPILTII | N2L | I10Y | Individual TP53_R248Q Vaccine (5-peptide, NetMHCpan, Set 1) |
| SEQ ID NO: 389 | STCMGGMNQK | TP53 R248Q | SSCMGGMNQR | S2T | R10K | Individual TP53_R248Q Vaccine (5-peptide, NetMHCpan, Set 1); Individual TP53_R248Q Vaccine (8-peptide, MHCflurry, Set 2) |

TABLE 1-continued

Example Vaccine Peptides (MHC class I)

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 390 | STMGGMNQR | TP53 R248Q | SCMGGMNQR | C2T | — | Individual TP53_R248Q Vaccine (5-peptide, NetMHCpan, Set 1); Individual TP53_R248Q Vaccine (4-peptide, NetMHCpan, Set 2); Individual TP53_R248Q Vaccine (8-peptide, MHCflurry, Set 2) |
| SEQ ID NO: 391 | SVCMGGMNQK | TP53 R248Q | SSCMGGMNQR | S2V | R10K | Individual TP53_R248Q Vaccine (5-peptide, NetMHCpan, Set 1); Individual TP53_R248Q Vaccine (8-peptide, MHCflurry, Set 1); Individual TP53_R248Q Vaccine (4-peptide, NetMHCpan, Set 2) |
| SEQ ID NO: 392 | MAQRPILTL | TP53 R248Q | MNQRPILTI | N2A | I9L | Individual TP53_R248Q Vaccine (8-peptide, MHCflurry, Set 1); Individual TP53_R248Q Vaccine (8-peptide, MHCflurry, Set 2) |
| SEQ ID NO: 393 | MQQRPILTV | TP53 R248Q | MNQRPILTI | N2Q | I9V | Individual TP53_R248Q Vaccine (8-peptide, MHCflurry, Set 1) |
| SEQ ID NO: 394 | MRQRPILTL | TP53 R248Q | MNQRPILTI | N2R | I9L | Individual TP53_R248Q Vaccine (8-peptide, MHCflurry, Set 1); Individual TP53_R248Q Vaccine (8-peptide, MHCflurry, Set 2) |
| SEQ ID NO: 395 | STCMGGMNQY | TP53 R248Q | SSCMGGMNQR | S2T | R10Y | Individual TP53_R248Q Vaccine (8-peptide, MHCflurry, Set 1); Individual TP53_R248Q Vaccine (8-peptide, MHCflurry, Set 2) |
| SEQ ID NO: 396 | SVMGGMNQM | TP53 R248Q | SCMGGMNQR | C2V | R9M | Individual TP53_R248Q Vaccine (8-peptide, MHCflurry, Set 1) |
| SEQ ID NO: 397 | SVMGGMNQR | TP53 R248Q | SCMGGMNQR | C2V | — | Individual TP53_R248Q Vaccine (8-peptide, MHCflurry, Set 1) |
| SEQ ID NO: 398 | MMQRPILTIM | TP53 R248Q | MNQRPILTII | N2M | I10M | Individual TP53_R248Q Vaccine (4-peptide, NetMHCpan, Set 2) |
| SEQ ID NO: 399 | GLNQRPILTV | TP53 R248Q | GMNQRPILTI | M2L | I10V | Individual TP53_R248Q Vaccine (8-peptide, MHCflurry, Set 2) |
| SEQ ID NO: 400 | MQQRPILTL | TP53 R248Q | MNQRPILTI | N2Q | I9L | Individual TP53_R248Q Vaccine (8-peptide, MHCflurry, Set 2) |

TABLE 1-continued

| SEQ ID NO | Sequence corresponding to SEQ ID | Target | Seed | Example Vaccine Peptides (MHC class I) | | | Note |
|---|---|---|---|---|---|---|---|
| | | | | Heteroclitic Modification P2 | Heteroclitic Modification C-term | | |
| SEQ ID NO: 401 | STMGGMNQM | TP53 R248Q | SCMGGMNQR | C2T | R9M | | Individual TP53_R248Q Vaccine (8-peptide, MHCflurry, Set 2) |
| SEQ ID NO: 402 | GMNWRPILTV | TP53 R248W | GMNWRPILTI | — | I10V | | Individual TP53_R248W Vaccine (5-peptide, NetMHCpan, Set 1); Individual TP53_R248W Vaccine (5-peptide, NetMHCpan, Set 2) |
| SEQ ID NO: 403 | MSWRPILTV | TP53 R248W | MNWRPILTI | N2S | I9V | | Individual TP53_R248W Vaccine (5-peptide, NetMHCpan, Set 1) |
| SEQ ID NO: 404 | MVWRPILTY | TP53 R248W | MNWRPILTI | N2V | I9Y | | Individual TP53_R248W Vaccine (5-peptide, NetMHCpan, Set 1) |
| SEQ ID NO: 405 | SAMGGMNWR | TP53 R248W | SCMGGMNWR | C2A | — | | Individual TP53_R248W Vaccine (5-peptide, NetMHCpan, Set 1) |
| SEQ ID NO: 406 | SVCMGGMNWK | TP53 R248W | SSCMGGMNWR | S2V | R10K | | Individual TP53_R248W Vaccine (5-peptide, NetMHCpan, Set 1) |
| SEQ ID NO: 407 | MAWRPILTL | TP53 R248W | MNWRPILTI | N2A | I9L | | Individual TP53_R248W Vaccine (8-peptide, MHCflurry, Set 1) |
| SEQ ID NO: 408 | MQWRPILTL | TP53 R248W | MNWRPILTI | N2Q | I9L | | Individual TP53_R248W Vaccine (8-peptide, MHCflurry, Set 1); Individual TP53_R248W Vaccine (8-peptide, MHCflurry, Set 2) |
| SEQ ID NO: 409 | MQWRPILTV | TP53 R248W | MNWRPILTI | N2Q | I9V | | Individual TP53_R248W Vaccine (8-peptide, MHCflurry, Set 1) |
| SEQ ID NO: 410 | MRWRPILTM | TP53 R248W | MNWRPILTI | N2R | I9M | | Individual TP53_R248W Vaccine (8-peptide, MHCflurry, Set 1) |
| SEQ ID NO: 411 | MSWRPILTL | TP53 R248W | MNWRPILTI | N2S | I9L | | Individual TP53_R248W Vaccine (8-peptide, MHCflurry, Set 1); Individual TP53_R248W Vaccine (8-peptide, MHCflurry, Set 2) |
| SEQ ID NO: 412 | MTWRPILTL | TP53 R248W | MNWRPILTI | N2T | I9L | | Individual TP53_R248W Vaccine (8-peptide, MHCflurry, Set 1); Individual TP53_R248W Vaccine (8-peptide, MHCflurry, Set 2) |

TABLE 1-continued

Example Vaccine Peptides (MHC class I)

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 413 | STMGGMNWR | TP53 R248W | SCMGGMNWR | C2T | — | Individual TP53_R248W Vaccine (8-peptide, MHCflurry, Set 1); Individual TP53_R248W Vaccine (5-peptide, NetMHCpan, Set 2); Individual TP53_R248W Vaccine (8-peptide, MHCflurry, Set 2) |
| SEQ ID NO: 414 | SVMGGMNWR | TP53 R248W | SCMGGMNWR | C2V | — | Individual TP53_R248W Vaccine (8-peptide, MHCflurry, Set 1) |
| SEQ ID NO: 415 | MSWRPILTF | TP53 R248W | MNWRPILTI | N2S | I9F | Individual TP53_R248W Vaccine (5-peptide, NetMHCpan, Set 2) |
| SEQ ID NO: 416 | MTWRPILTV | TP53 R248W | MNWRPILTI | N2T | I9V | Individual TP53_R248W Vaccine (5-peptide, NetMHCpan, Set 2) |
| SEQ ID NO: 417 | STCMGGMNWK | TP53 R248W | SSCMGGMNWR | S2T | R10K | Individual TP53_R248W Vaccine (5-peptide, NetMHCpan, Set 2) |
| SEQ ID NO: 418 | MEWRPILTV | TP53 R248W | MNWRPILTI | N2E | I9V | Individual TP53_R248W Vaccine (8-peptide, MHCflurry, Set 2) |
| SEQ ID NO: 419 | MQWRPILTW | TP53 R248W | MNWRPILTI | N2Q | I9W | Individual TP53_R248W Vaccine (8-peptide, MHCflurry, Set 2) |
| SEQ ID NO: 420 | MRWRPILTY | TP53 R248W | MNWRPILTI | N2R | I9Y | Individual TP53_R248W Vaccine (8-peptide, MHCflurry, Set 2) |
| SEQ ID NO: 421 | SSMGGMNWR | TP53 R248W | SCMGGMNWR | C2S | — | Individual TP53_R248W Vaccine (8-peptide, MHCflurry, Set 2) |
| SEQ ID NO: 422 | ETCVCACPGR | TP53 R273C | EVCVCACPGR | V2T | — | Individual TP53_R273C Vaccine (5-peptide, NetMHCpan, Set 1); Individual TP53_R273C Vaccine (3-peptide, NetMHCpan, Set 2); Individual TP53_R273C Vaccine (6-peptide, MHCflurry, Set 2) |
| SEQ ID NO: 423 | NVFEVCVCI | TP53 R273C | NSFEVCVCA | S2V | A9I | Individual TP53_R273C Vaccine (5-peptide, NetMHCpan, Set 1); Brain Cancer Vaccine (25-peptide); Individual TP53_R273C Vaccine (8-peptide, MHCflurry, Set 1) |
| SEQ ID NO: 424 | NVFEVCVCV | TP53 R273C | NSFEVCVCA | S2V | A9V | Individual TP53_R273C Vaccine (5-peptide, NetMHCpan, Set 1) |

TABLE 1-continued

| SEQ ID NO | Sequence corresponding to SEQ ID | Target | Seed | Example Vaccine Peptides (MHC class I) | | | Note |
|---|---|---|---|---|---|---|---|
| | | | | Heteroclitic Modification P2 | Heteroclitic Modification C-term | | |
| SEQ ID NO: 425 | SEEVCVCACA | TP53 R273C | SFEVCVCACP | F2E | P10A | | Individual TP53_R273C Vaccine (5-peptide, NetMHCpan, Set 1); Brain Cancer Vaccine (25-peptide); Individual TP53_R273C Vaccine (3-peptide, NetMHCpan, Set 2) |
| SEQ ID NO: 426 | ETCVCACPGK | TP53 R273C | EVCVCACPGR | V2T | R10K | | Individual TP53_R273C Vaccine (8-peptide, MHCflurry, Set 1); Individual TP53_R273C Vaccine (6-peptide, MHCflurry, Set 2) |
| SEQ ID NO: 427 | EYCVCACPGR | TP53 R273C | EVCVCACPGR | V2Y | — | | Individual TP53_R273C Vaccine (8-peptide, MHCflurry, Set 1); Individual TP53_R273C Vaccine (6-peptide, MHCflurry, Set 2) |
| SEQ ID NO: 428 | GRNSFEVCL | TP53 R273C | GRNSFEVCV | — | V9L | | Individual TP53_R273C Vaccine (8-peptide, MHCflurry, Set 1); Individual TP53_R273C Vaccine (6-peptide, MHCflurry, Set 2) |
| SEQ ID NO: 429 | GRNSFEVCM | TP53 R273C | GRNSFEVCV | — | V9M | | Individual TP53_R273C Vaccine (8-peptide, MHCflurry, Set 1) |
| SEQ ID NO: 430 | NVFEVCVCL | TP53 R273C | NSFEVCVCA | S2V | A9L | | Individual TP53_R273C Vaccine (8-peptide, MHCflurry, Set 1) |
| SEQ ID NO: 431 | SFEVCVCAL | TP53 R273C | SFEVCVCAC | — | C9L | | Individual TP53_R273C Vaccine (8-peptide, MHCflurry, Set 1); Individual TP53_R273C Vaccine (6-peptide, MHCflurry, Set 2) |
| SEQ ID NO: 432 | NTFEVCVCV | TP53 R273C | NSFEVCVCA | S2T | A9V | | Individual TP53_R273C Vaccine (3-peptide, NetMHCpan, Set 2); Individual TP53_R273C Vaccine (6-peptide, MHCflurry, Set 2) |
| SEQ ID NO: 433 | EFHVCACPGR | TP53 R273H | EVHVCACPGR | V2F | — | | Individual TP53_R273H Vaccine (5-peptide, NetMHCpan, Set 1); Individual TP53_R273H Vaccine (5-peptide, NetMHCpan, Set 2) |
| SEQ ID NO: 434 | LMGRNSFEVHV | TP53 R273H | LLGRNSFEVHV | L2M | — | | Individual TP53_R273H Vaccine (5-peptide, NetMHCpan, Set 1); Individual TP53_R273H Vaccine (5-peptide, NetMHCpan, Set 2) |

TABLE 1-continued

Example Vaccine Peptides (MHC class I)

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 435 | NPFEVHVCV | TP53 R273H | NSFEVHVCA | S2P | A9V | Individual TP53_R273H Vaccine (5-peptide, NetMHCpan, Set 1); Individual TP53_R273H Vaccine (5-peptide, NetMHCpan, Set 2) |
| SEQ ID NO: 436 | NVFEVHVCV | TP53 R273H | NSFEVHVCA | S2V | A9V | Individual TP53_R273H Vaccine (5-peptide, NetMHCpan, Set 1); Individual TP53_R273H Vaccine (8-peptide, MHCflurry, Set 1) |
| SEQ ID NO: 437 | EVHVCACPGK | TP53 R273H | EVHVCACPGR | — | R10K | Individual TP53_R273H Vaccine (8-peptide, MHCflurry, Set 1) |
| SEQ ID NO: 438 | EYHVCACPGR | TP53 R273H | EVHVCACPGR | V2Y | — | Individual TP53_R273H Vaccine (8-peptide, MHCflurry, Set 1); Individual TP53_R273H Vaccine (7-peptide, MHCflurry, Set 2) |
| SEQ ID NO: 439 | GRNSFEVHF | TP53 R273H | GRNSFEVHV | — | V9F | Individual TP53_R273H Vaccine (8-peptide, MHCflurry, Set 1); Individual TP53_R273H Vaccine (7-peptide, MHCflurry, Set 2) |
| SEQ ID NO: 440 | GRNSFEVHY | TP53 R273H | GRNSFEVHV | — | V9Y | Individual TP53_R273H Vaccine (8-peptide, MHCflurry, Set 1) |
| SEQ ID NO: 441 | NPFEVHVCA | TP53 R273H | NSFEVHVCA | S2P | — | Individual TP53_R273H Vaccine (8-peptide, MHCflurry, Set 1); Individual TP53_R273H Vaccine (7-peptide, MHCflurry, Set 2) |
| SEQ ID NO: 442 | SYFVHVCAL | TP53 R273H | SFEVHVCAC | F2Y | C9L | Individual TP53_R273H Vaccine (8-peptide, MHCflurry, Set 1); Individual TP53_R273H Vaccine (7-peptide, MHCflurry, Set 2) |
| SEQ ID NO: 443 | ETHVCACPGR | TP53 R273H | EVHVCACPGR | V2T | — | Individual TP53_R273H Vaccine (7-peptide, MHCflurry, Set 2) |
| SEQ ID NO: 444 | NTFEVHVCV | TP53 R273H | NSFEVHVCA | S2T | A9V | Individual TP53_R273H Vaccine (5-peptide, NetMHCpan, Set 2) |
| SEQ ID NO: 445 | ETHVCACPGK | TP53 R273H | EVHVCACPGR | V2T | R10K | Individual TP53_R273H Vaccine (7-peptide, MHCflurry, Set 2) |

TABLE 1-continued

Example Vaccine Peptides (MHC class I)

| SEQ ID NO | Sequence corresponding to SEQ ID | Target | Seed | Heteroclitic Modification P2 | Heteroclitic Modification C-term | Note |
|---|---|---|---|---|---|---|
| SEQ ID NO: 446 | NAFEVHVCV | TP53 R273H | NSFEVHVCA | S2A | A9V | Individual TP53_R273H Vaccine (7-peptide, MHCflurry, Set 2) |
| SEQ ID NO: 447 | RMCACPGRDWR | TP53 R282W | RVCACPGRDWR | V2M | — | Individual TP53_R282W Vaccine (2-peptide, NetMHCpan, Set 1); Individual TP53_R282W Vaccine (1-peptide, NetMHCpan, Set 2) |
| SEQ ID NO: 448 | CTCPGRDWR | TP53 R282W | CACPGRDWR | A2T | — | Individual TP53_R282W Vaccine (2-peptide, NetMHCpan, Set 1) |
| SEQ ID NO: 449 | REWRTEEENL | TP53 R282W | RDWRTEEENL | D2E | — | Individual TP53_R282W Vaccine (1-peptide, MHCflurry, Set 1); Individual TP53_R282W Vaccine (1-peptide, MHCflurry, Set 2) |
| SEQ ID NO: 450 | VMPCEPPEV | TP53 Y220C | VVPCEPPEV | V2M | — | Individual TP53_Y220C Vaccine (1-peptide, NetMHCpan, Set 1); Individual TP53_Y220C Vaccine (8-peptide, MHCflurry, Set 1); Individual TP53_Y220C Vaccine (8-peptide, MHCflurry, Set 2) |
| SEQ ID NO: 451 | VAPCEPPEL | TP53 Y220C | VVPCEPPEV | V2A | V9L | Individual TP53_Y220C Vaccine (8-peptide, MHCflurry, Set 1); Individual TP53_Y220C Vaccine (8-peptide, MHCflurry, Set 2) |
| SEQ ID NO: 452 | VAPCEPPEM | TP53 Y220C | VVPCEPPEV | V2A | V9M | Individual TP53_Y220C Vaccine (8-peptide, MHCflurry, Set 1); Individual TP53_Y220C Vaccine (8-peptide, MHCflurry, Set 2) |
| SEQ ID NO: 453 | VFPCEPPEM | TP53 Y220C | VVPCEPPEV | V2F | V9M | Individual TP53_Y220C Vaccine (8-peptide, MHCflurry, Set 1); Individual TP53_Y220C Vaccine (8-peptide, MHCflurry, Set 2) |
| SEQ ID NO: 454 | VLPCEPPEV | TP53 Y220C | VVPCEPPEV | V2L | — | Individual TP53_Y220C Vaccine (8-peptide, MHCflurry, Set 1); Individual TP53_Y220C Vaccine (1-peptide, NetMHCpan, Set 2) |
| SEQ ID NO: 455 | VPCEPPEVA | TP53 Y220C | VPCEPPEVG | — | G9A | Individual TP53_Y220C Vaccine (8-peptide, MHCflurry, Set 1); Individual TP53_Y220C Vaccine (8-peptide, MHCflurry, Set 2) |

TABLE 1-continued

| SEQ ID NO | Sequence corresponding to SEQ ID | Target | Seed | Example Vaccine Peptides (MHC class I) | | | Note |
|---|---|---|---|---|---|---|---|
| | | | | Heteroclitic Modification P2 | Heteroclitic Modification C-term | | |
| SEQ ID NO: 456 | VPCEPPEVM | TP53 Y220C | VPCEPPEVG | — | G9M | | Individual TP53_Y220C Vaccine (8-peptide, MHCflurry, Set 1); Individual TP53_Y220C Vaccine (8-peptide, MHCflurry, Set 2) |
| SEQ ID NO: 457 | VYPCEPPEL | TP53 Y220C | VVPCEPPEV | V2Y | V9L | | Individual TP53_Y220C Vaccine (8-peptide, MHCflurry, Set 1); Individual TP53_Y220C Vaccine (8-peptide, MHCflurry, Set 2) |
| SEQ ID NO: 458 | VLPCEPPEL | TP53 Y220C | VVPCEPPEV | V2L | V9L | | Individual TP53_Y220C Vaccine (8-peptide, MHCflurry, Set 2) |
| SEQ ID NO: 459 | KYIKTWRPRYF | AKT1 E17K | KYIKTWRPRYF | — | — | | Individual AKT1_E17K Vaccine (5-peptide, NetMHCpan, Set 1); Individual AKT1_E17K Vaccine (5-peptide, NetMHCpan, Set 2) |
| SEQ ID NO: 460 | KPIIIGCHA | IDH1 R132C | KPIIIGCHA | — | — | | Individual IDH1_R132C Vaccine (5-peptide, NetMHCpan, Set 1) |
| SEQ ID NO: 461 | KPIIIGHHA | IDH1 R132H | KPIIIGHHA | — | — | | Individual IDH1_R132H Vaccine (8-peptide, MHCflurry, Set 1); Individual IDH1_R132H Vaccine (8-peptide, MHCflurry, Set 2) |
| SEQ ID NO: 462 | LVVVGAAGV | KRAS G12A | LVVVGAAGV | — | — | | Individual KRAS_G12A Vaccine (8-peptide, MHCflurry, Set 1) |
| SEQ ID NO: 463 | VVVGACGVGK | KRAS G12C | VVVGACGVGK | — | — | | Individual KRAS_G12C Vaccine (8-peptide, MHCflurry, Set 1) |
| SEQ ID NO: 464 | VVVGADGVGK | KRAS G12D | VVVGADGVGK | — | — | | Individual KRAS_G12D Vaccine (8-peptide, MHCflurry, Set 1) |
| SEQ ID NO: 465 | VVVGARGVGK | KRAS G12R | VVVGARGVGK | — | — | | Individual KRAS_G12R Vaccine (8-peptide, MHCflurry, Set 1) |
| SEQ ID NO: 466 | KLVVVGAGDV | KRAS G13D | KLVVVGAGDV | — | — | | Individual KRAS_G13D Vaccine (5-peptide, NetMHCpan, Set 1) |
| SEQ ID NO: 467 | ITKQEKDFLW | PIK3CA E545K | ITKQEKDFLW | — | — | | Individual PIK3CA_E545K Vaccine (4-peptide, NetMHCpan, Set 1); Bronchus And Lung Cancer Vaccine (30-peptide); Colorectal Cancer Vaccine (20-peptide); Individual |

TABLE 1-continued

Example Vaccine Peptides (MHC class I)

| SEQ ID NO | Sequence corresponding to SEQ ID | Target | Seed | Heteroclitic Modification P2 | Heteroclitic Modification C-term | Note |
|---|---|---|---|---|---|---|
| | | | | | | PIK3CA_E545K Vaccine (8-peptide, MHCflurry, Set 1); Individual PIK3CA_E545K Vaccine (4-peptide, MHCflurry, Set 2) |
| SEQ ID NO: 468 | ETRQLCDLR | PIK3CA R88Q | ETRQLCDLR | — | — | Individual PIK3CA_R88Q Vaccine (5-peptide, NetMHCpan, Set 1); Individual PIK3CA_R88Q Vaccine (8-peptide, MHCflurry, Set 1); Individual PIK3CA_R88Q Vaccine (5-peptide, NetMHCpan, Set 2); Individual PIK3CA_R88Q Vaccine (8-peptide, MHCflurry, Set 2) |
| SEQ ID NO: 469 | RVLAMAIYK | TP53 R158L | RVLAMAIYK | — | — | Individual TP53_R158L Vaccine (8-peptide, MHCflurry, Set 1) |
| SEQ ID NO: 470 | TPPPGTRVLA | TP53 R158L | TPPPGTRVLA | — | — | Individual TP53_R158L Vaccine (8-peptide, MHCflurry, Set 1); Individual TP53_R158L Vaccine (7-peptide, MHCflurry, Set 2) |
| SEQ ID NO: 471 | EVRHCPHHER | TP53 R175H | EVRHCPHHER | — | — | Individual TP53_R175H Vaccine (5-peptide, NetMHCpan, Set 1); Colorectal Cancer Vaccine (20-peptide); Brain Cancer Vaccine (25-peptide); Individual TP53_R175H Vaccine (2-peptide, NetMHCpan, Set 2) |
| SEQ ID NO: 472 | VVRHCPHHER | TP53 R175H | VVRHCPHHER | — | — | Individual TP53_R175H Vaccine (5-peptide, NetMHCpan, Set 1); Colorectal Cancer Vaccine (20-peptide); Brain Cancer Vaccine (25-peptide) |
| SEQ ID NO: 473 | EVCVCACPGR | TP53 R273C | EVCVCACPGR | — | — | Individual TP53_R273C Vaccine (5-peptide, NetMHCpan, Set 1); Brain Cancer Vaccine (25-peptide); Individual TP53_R273C Vaccine (8-peptide, MHCflurry, Set 1) |
| SEQ ID NO: 474 | EVHVCACPGR | TP53 R273H | EVHVCACPGR | — | — | Individual TP53_R273H Vaccine (5-peptide, NetMHCpan, Set 1); Individual TP53_R273H Vaccine (8-peptide, MHCflurry, Set 1) |

TABLE 2

Example Vaccine Peptides (MHC class II)

| SEQ ID NO | Sequence corresponding to SEQ ID | Core | Target | Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|---|
| SEQ ID NO: 475 | AIVKEGFLH ARAKYVKT WRPRYFLL | FLHA RAKY V | AKT1 E17K | AIVKEGWLHKR GKYIKTWRPRY FLL | WLHKRG KYI | W1F | K4A | G6A | I9V | Individual AKT1_E17K Vaccine (5-peptide) |
| SEQ ID NO: 476 | AIVKEGFLH TRFKYIKT WRPRYFLL | FLHT RFKYI | AKT1 E17K | AIVKEGWLHKR GKYIKTWRPRY FLL | WLHKRG KYI | W1F | K4T | G6F | — | Individual AKT1_E17K Vaccine (5-peptide); Individual AKT1_E17K Vaccine (5-peptide, Set 2) |
| SEQ ID NO: 477 | DVAIVKEG FLHERFKY MKTWRPR YF | FLHE RFKY M | AKT1 E17K | DVAIVKEGWLH KRGKYIKTWRP RYF | WLHKRG KYI | W1F | K4E | G6F | I9M | Individual AKT1_E17K Vaccine (5-peptide) |
| SEQ ID NO: 478 | DVAIVKEG LLHNRNKY IKTWRPRY F | LLHN RNKY I | AKT1 E17K | DVAIVKEGWLH KRGKYIKTWRP RYF | WLHKRG KYI | W1L | K4N | G6N | — | Individual AKT1_E17K Vaccine (5-peptide) |
| SEQ ID NO: 479 | VKEGFLHM RSKYIKTW RPRY | FLHM RSKYI | AKT1 E17K | VKEGWLHKRG KYIKTWRPRY | WLHKRG KYI | W1F | K4M | G6S | — | Individual AKT1_E17K Vaccine (5-peptide) |
| SEQ ID NO: 480 | AIVKEGILH ARAKYIKT WRPRYFLL | ILHAR AKYI | AKT1 E17K | AIVKEGWLHKR GKYIKTWRPRY FLL | WLHKRG KYI | W1I | K4A | G6A | — | Individual AKT1_E17K Vaccine (5-peptide, Set 2) |
| SEQ ID NO: 481 | DVAIVKEG FLHTRFKY LKTWRPRY F | FLHT RFKY L | AKT1 E17K | DVAIVKEGWLH KRGKYIKTWRP RYF | WLHKRG KYI | W1F | K4T | G6F | I9L | Individual AKT1_E17K Vaccine (5-peptide, Set 2) |
| SEQ ID NO: 482 | DVAIVKEGI LHNRFKYI KTWRPRYF | ILHNR FKYI | AKT1 E17K | DVAIVKEGWLH KRGKYIKTWRP RYF | WLHKRG KYI | W1I | K4N | G6F | — | Individual AKT1_E17K Vaccine (5-peptide, Set 2) |
| SEQ ID NO: 483 | VKEGFLHIR SKYVKTWR PRY | FLHIR SKYV | AKT1 E17K | VKEGWLHKRG KYIKTWRPRY | WLHKRG KYI | W1F | K4I | G6S | I9V | Individual AKT1_E17K Vaccine (5-peptide, Set 2) |

TABLE 2-continued

Example Vaccine Peptides (MHC class II)

| SEQ ID NO | Sequence corresponding to SEQ ID Core | Target Seed | Seed Core | Heteroclitic Modification P1 | Heteroclitic Modification P4 | Heteroclitic Modification P6 | Heteroclitic Modification P9 | Note |
|---|---|---|---|---|---|---|---|---|
| SEQ ID NO: 484 | FGLLTEWS RWSRSHQ | LTEW SRWS R | BRAF V600E | FGLATEKSRWS GSHQ | ATEKSR WSG | A1L | K4W | — | G9R | Individual BRAF_V600E Vaccine (5-peptide); Colorectal Cancer Vaccine (30-peptide); Skin Cancer Vaccine (20-peptide); Thyroid Cancer Vaccine (10-peptide) |
| SEQ ID NO: 485 | KIGLFGFAV EKARWS | LFGF AVEK A | BRAF V600E | KIGDFGLATEKS RWS | DFGLAT EKS | D1L | L4F | T6V | S9A | Individual BRAF_V600E Vaccine (5-peptide); Colorectal Cancer Vaccine (30-peptide); Skin Cancer Vaccine (20-peptide); Thyroid Cancer Vaccine (10-peptide) |
| SEQ ID NO: 486 | KIGLFGWA VEKVRWS | LFGW AVEK V | BRAF V600E | KIGDFGLATEKS RWS | DFGLAT EKS | D1L | L4W | T6V | S9V | Individual BRAF_V600E Vaccine (5-peptide) |
| SEQ ID NO: 487 | VKIGLFGIA IEKLRW | LFGIA IEKL | BRAF V600E | VKIGDFGLATE KSRW | DFGLAT EKS | D1L | L4I | T6I | S9L | Individual BRAF_V600E Vaccine (5-peptide) |
| SEQ ID NO: 488 | VKIGYFGW AAEKARW | YFGW AAEK A | BRAF V600E | VKIGDFGLATE KSRW | DFGLAT EKS | D1Y | L4W | T6A | S9A | Individual BRAF_V600E Vaccine (5-peptide); Colorectal Cancer Vaccine (30-peptide); Skin Cancer Vaccine (20-peptide); Thyroid Cancer Vaccine (10-peptide) |
| SEQ ID NO: 489 | VKIGLFGLA IEKMRW | LFGL AIEK M | BRAF V600E | VKIGDFGLATE KSRW | DFGLAT EKS | D1L | — | T6I | S9M | Colorectal Cancer Vaccine (30-peptide); Skin Cancer Vaccine (20-peptide); Thyroid Cancer Vaccine (10-peptide) |
| SEQ ID NO: 490 | FGLITEMSR WSKSHQ | ITEMS RWSK | BRAF V600E | FGLATEKSRWS GSHQ | ATEKSR WSG | A1I | K4M | — | G9K | Individual BRAF_V600E Vaccine (5-peptide, Set 2) |
| SEQ ID NO: 491 | KIGFFGIAIE KARWS | FFGIA IEKA | BRAF V600E | KIGDFGLATEKS RWS | DFGLAT EKS | D1F | L4I | T6I | S9A | Individual BRAF_V600E Vaccine (5-peptide, Set 2) |
| SEQ ID NO: 492 | KIGIFGYAI EKARWS | IFGYA IEKA | BRAF V600E | KIGDFGLATEKS RWS | DFGLAT EKS | D1I | L4Y | T6I | S9A | Individual BRAF_V600E Vaccine (5-peptide, Set 2) |

TABLE 2-continued

Example Vaccine Peptides (MHC class II)

| SEQ ID NO | Sequence corresponding to SEQ ID | Core | Target | Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|---|
| SEQ ID NO: 493 | VKIGFFGLA SEKVRW | FFGL ASEK V | BRAF V600E | VKIGDFGLATE KSRW | DFGLAT EKS | D1F | — | T6S | S9V | Individual BRAF V600E Vaccine (5-peptide, Set 2) |
| SEQ ID NO: 494 | VKIGVFGL AGEKLRW | VFGL AGEK L | BRAF V600E | VKIGDFGLATE KSRW | DFGLAT EKS | D1V | — | T6G | S9L | Individual BRAF V600E Vaccine (5-peptide, Set 2) |
| SEQ ID NO: 495 | GLLTMHSR WSKSHQF | LTMH SRWS K | BRAF V600M | GLATMKSRWSG SHQF | ATMKSR WSG | A1L | K4H | — | G9K | Individual BRAF V600M Vaccine (5-peptide); Skin Cancer Vaccine (20-peptide) |
| SEQ ID NO: 496 | KIGFFGAA VMKARWS | FFGA AVMK A | BRAF V600M | KIGDFGLATMK SRWS | DFGLAT MKS | D1F | L4A | T6V | S9A | Individual BRAF V600M Vaccine (5-peptide); Skin Cancer Vaccine (20-peptide) |
| SEQ ID NO: 497 | KIGIFGAAS MKARWS | IFGAA SMKA | BRAF V600M | KIGDFGLATMK SRWS | DFGLAT MKS | D1I | L4A | T6S | S9A | Individual BRAF V600M Vaccine (5-peptide); Skin Cancer Vaccine (20-peptide) |
| SEQ ID NO: 498 | KIGMFGIAN MKDRWS | MFGI ANMK D | BRAF V600M | KIGDFGLATMK SRWS | DFGLAT MKS | D1M | L4I | T6N | S9D | Individual BRAF V600M Vaccine (5-peptide); Skin Cancer Vaccine (20-peptide) |
| SEQ ID NO: 499 | TVKIGIFGI ATMKHRW S | IFGIA TMKH | BRAF V600M | TVKIGDFGLAT MKSRWS | DFGLAT MKS | D1I | L4I | — | S9H | Individual BRAF V600M Vaccine (5-peptide); Skin Cancer Vaccine (20-peptide); Individual BRAF V600M Vaccine (5-peptide, Set 2) |
| SEQ ID NO: 500 | GLITMISRW SRSHQF | ITMIS RWSR | BRAF V600M | GLATMKSRWSG SHQF | ATMKSR WSG | A1I | K4I | — | G9R | Individual BRAF V600M Vaccine (5-peptide, Set 2) |
| SEQ ID NO: 501 | KIGFFGAA AMKARWS | FFGA AAMK A | BRAF V600M | KIGDFGLATMK SRWS | DFGLAT MKS | D1F | L4A | T6A | S9A | Individual BRAF V600M Vaccine (5-peptide, Set 2) |
| SEQ ID NO: 502 | KIGMFGIAT MKDRWS | MFGI ATMK D | BRAF V600M | KIGDFGLATMK SRWS | DFGLAT MKS | D1M | L4I | — | S9D | Individual BRAF V600M Vaccine (5-peptide, Set 2) |
| SEQ ID NO: 503 | PEGKWSFQ VACVMKC | WSFQ VACV M | EGFR A289V | PEGKYSFGVTC VKKC | YSFGVT CVK | Y1W | G4Q | T6A | K9M | Individual EGFR_A289V Vaccine (5-peptide) |

TABLE 2-continued

Example Vaccine Peptides (MHC class II)

| SEQ ID NO | Sequence corresponding to SEQ ID Core | Target Seed | Seed Core | Heteroclitic Modification P1 | Heteroclitic Modification P4 | Heteroclitic Modification P6 | Heteroclitic Modification P9 | Note |
|---|---|---|---|---|---|---|---|---|
| SEQ ID NO: 504 | PEGKYSFL VGCVNKC | YSFL VGCV N | EGFR A289V | PEGKYSFGVTC VKKC | YSFGVT CVK | — | G4L | T6G | K9N | Individual EGFR_A289V Vaccine (5-peptide) |
| SEQ ID NO: 505 | PEGKYSFL VPCVMKC | YSFL VPCV M | EGFR A289V | PEGKYSFGVTC VKKC | YSFGVT CVK | — | G4L | T6P | K9M | Individual EGFR_A289V Vaccine (5-peptide) |
| SEQ ID NO: 506 | PEGKYSFM VSCVRKC | YSFM VSCV R | EGFR A289V | PEGKYSFGVTC VKKC | YSFGVT CVK | — | G4M | T6S | K9R | Individual EGFR_A289V Vaccine (5-peptide) |
| SEQ ID NO: 507 | PEGKYSYG VMCVKKLP RNYV | YGVM CVKK L | EGFR A289V | PEGKYSFGVTC VKKCPRNYV | FGVTCV KKC | F1Y | T4M | — | C9L | Individual EGFR_A289V Vaccine (5-peptide) |
| SEQ ID NO: 508 | PEGKYSYG VMCVKKVP RNYV | YGVM CVKK V | EGFR A289V | PEGKYSFGVTC VKKCPRNYV | FGVTCV KKC | F1Y | T4M | — | C9V | Brain Cancer Vaccine (20-peptide) |
| SEQ ID NO: 509 | PEGKFSFM VPCVAKC | FSFM VPCV A | EGFR A289V | PEGKYSFGVTC VKKC | YSFGVT CVK | Y1F | G4M | T6P | K9A | Individual EGFR_A289V Vaccine (1-peptide, Set 2) |
| SEQ ID NO: 510 | GPHCYKTL PAVVAGE | YKTL PAVV A | EGFR G598V | GPHCVKTCPAV VMGE | VKTCPA VVM | V1Y | C4L | — | M9A | Individual EGFR_G598V Vaccine (5-peptide); Brain Cancer Vaccine (20-peptide) |
| SEQ ID NO: 511 | PHCFKTSPA VVVGENNT LVW | FKTSP AVVV | EGFR G598V | PHCVKTCPAVV MGENNTLVW | VKTCPA VVM | V1F | C4S | — | M9V | Individual EGFR_G598V Vaccine (5-peptide) |
| SEQ ID NO: 512 | PHCYKTSP AVVIGENN TLVW | YKTS PAVVI | EGFR G598V | PHCVKTCPAVV MGENNTLVW | VKTCPA VVM | V1Y | C4S | — | M9I | Individual EGFR_G598V Vaccine (5-peptide); Brain Cancer Vaccine (20-peptide) |
| SEQ ID NO: 513 | YIDGPHCIK TNPVVVLG ENNTLV | IKTNP VVVL | EGFR G598V | YIDGPHCVKTCP AVVMGENNTL V | VKTCPA VVM | V1I | C4N | A6V | M9L | Individual EGFR_G598V Vaccine (5-peptide) |
| SEQ ID NO: 514 | YIDGPHCV KTNPSVVIG ENNTLV | VKTN PSVVI | EGFR G598V | YIDGPHCVKTCP AVVMGENNTL V | VKTCPA VVM | — | C4N | A6S | M9I | Individual EGFR_G598V Vaccine (5-peptide); Brain Cancer Vaccine (20-peptide) |

TABLE 2-continued

Example Vaccine Peptides (MHC class II)

| SEQ ID NO | Sequence corresponding to SEQ ID | Core | Target | Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|---|
| SEQ ID NO: 515 | GPHCFKTM PAVVAGE | FKTM PAVV A | EGFR G598V | GPHCVKTCPAV VMGE | VKTCPA VVM | V1F | C4M | — | M9A | Individual EGFR_G598V Vaccine (5-peptide, Set 2) |
| SEQ ID NO: 516 | GPHCMKTL PSVVAGE | MKTL PSVV A | EGFR G598V | GPHCVKTCPAV VMGE | VKTCPA VVM | V1M | C4L | A6S | M9A | Individual EGFR_G598V Vaccine (5-peptide, Set 2) |
| SEQ ID NO: 517 | GPHFVKTC SAVIMGE | FVKT CSAVI | EGFR G598V | GPHCVKTCPAV VMGE | CVKTCP AVV | C1F | — | P6S | V9I | Individual EGFR_G598V Vaccine (5-peptide, Set 2) |
| SEQ ID NO: 518 | PHCFKTAP AVVIGENN TLVW | FKTA PAVVI | EGFR G598V | PHCVKTCPAVV MGENNTLVW | VKTCPA VVM | V1F | C4A | — | M9I | Individual EGFR_G598V Vaccine (5-peptide, Set 2) |
| SEQ ID NO: 519 | YIDGPHCFK TNPAVVIGE NNTLV | FKTN PAVVI | EGFR G598V | YIDGPHCVKTCP AVVMGENNTL V | VKTCPA VVM | V1F | C4N | — | M9I | Individual EGFR_G598V Vaccine (5-peptide, Set 2) |
| SEQ ID NO: 520 | KTPQHFKIT DFGRVKLL GAE | FKITD FGRV | EGFR L858R | KTPQHVKITDFG RAKLLGAE | VKITDFG RA | V1F | — | — | A9V | Individual EGFR_L858R Vaccine (5-peptide); Bronchus And Lung Cancer Vaccine (30-peptide); Individual EGFR_L858R Vaccine (5-peptide, Set 2) |
| SEQ ID NO: 521 | KTPQHYKI ADSGRIKLL GAE | YKIA DSGRI | EGFR L858R | KTPQHVKITDFG RAKLLGAE | VKITDFG RA | V1Y | T4A | P6S | A9I | Individual EGFR_L858R Vaccine (5-peptide); Bronchus And Lung Cancer Vaccine (30-peptide); Individual EGFR_L858R Vaccine (5-peptide, Set 2) |
| SEQ ID NO: 522 | QHVKITDY GRIKRLGIE EKE | YGRI KRLGI | EGFR L858R | QHVKITDFGRA KLLGAEEKE | FGRAKL LGA | F1Y | A4I | L6R | A9I | Individual EGFR_L858R Vaccine (5-peptide) |
| SEQ ID NO: 523 | VKIMDFMR GKLSGAE | MDFM RGKL S | EGFR L858R | VKITDFGRAKLL GAE | TDFGRA KLL | T1M | G4M | A6G | L9S | Individual EGFR_L858R Vaccine (5-peptide); Bronchus And Lung Cancer Vaccine (30-peptide) |
| SEQ ID NO: 524 | VKITDFGR AKALGVE | FGRA KALG V | EGFR L858R | VKITDFGRAKLL GAE | FGRAKL LGA | — | — | L6A | A9V | Individual EGFR_L858R Vaccine (5-peptide); Bronchus And Lung Cancer Vaccine (30-peptide); Individual EGFR_L858R Vaccine (5-peptide, Set 2) |

TABLE 2-continued

Example Vaccine Peptides (MHC class II)

| SEQ ID NO | Sequence corresponding to SEQ ID | Core | Target | Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|---|
| SEQ ID NO: 525 | KTPQHFKIT DIGRLKLLG AE | FKITD IGRL | EGFR L858R | KTPQHVKITDFG RAKLLGAE | VKITDFG RA | V1F | — | F6I | A9L | Individual EGFR_L858R Vaccine (5-peptide, Set 2) |
| SEQ ID NO: 526 | QHVKITDF GRIKRLGV EEKE | FGRIK RLGV | EGFR L858R | QHVKITDFGRA KLLGAEEKE | FGRAKL LGA | — | A4I | L6R | A9V | Individual EGFR_L858R Vaccine (5-peptide, Set 2) |
| SEQ ID NO: 527 | VKIIDFMRA RAKL LGAE | IDFM RAKL L | EGFR L858R | VKITDFGRAKLL GAE | TDFGRA KLL | T1I | G4M | — | — | Individual EGFR_L858R Vaccine (5-peptide, Set 2) |
| SEQ ID NO: 528 | LERFLHMK SRIVFVI | FLHM KSRIV | GTF2I L424H | LERILHAKERIR FVI | ILHAKER IR | I1F | A4M | E6S | R9V | Individual GTF2I_L424H Vaccine (5-peptide); Individual GTF2I_L424H Vaccine (5-peptide, Set 2) |
| SEQ ID NO: 529 | LERFLHTKF KFRIL FVI | FLHT KFRIL | GTF2I L424H | LERILHAKERIR FVI | ILHAKER IR | I1F | A4T | E6F | R9L | Individual GTF2I_L424H Vaccine (5-peptide); Individual GTF2I_L424H Vaccine (5-peptide, Set 2) |
| SEQ ID NO: 530 | LERIHASE RIRVVI | IHASE RIRV | GTF2I L424H | LERILHAKERIR FVI | LHAKERI RF | L1I | K4S | — | F9L | Individual GTF2I_L424H Vaccine (5-peptide) |
| SEQ ID NO: 531 | PRLERIFHA NEFIR VVIK KH | FHAN EFIRV | GTF2I L424H | PRLERILHAKER IRFVIKKH | LHAKERI RF | L1F | K4N | R6F | F9V | Individual GTF2I_L424H Vaccine (5-peptide) |
| SEQ ID NO: 532 | YGIFRLVRL LHTKER | FRLV RLLH T | GTF2I L424H | YGIPRLERILHA KER | PRLERIL HA | P1F | E4V | I6L | A9T | Individual GTF2I_L424H Vaccine (5-peptide); Individual GTF2I_L424H Vaccine (5-peptide, Set 2) |
| SEQ ID NO: 533 | LERIHASE RIRLVI | IHASE RIRL | GTF2I L424H | LERILHAKERIR FVI | LHAKERI RF | L1I | K4S | — | F9L | Individual GTF2I_L424H Vaccine (5-peptide, Set 2) |
| SEQ ID NO: 534 | PRLERILHA AEFIR VVIK KH | LHAA EFIRV | GTF2I L424H | PRLERILHAKER IRFVIKKH | LHAKERI RF | — | K4A | R6F | F9V | Individual GTF2I_L424H Vaccine (5-peptide, Set 2) |

TABLE 2-continued

Example Vaccine Peptides (MHC class II)

| SEQ ID NO | Sequence corresponding to SEQ ID Core | Target Seed | Seed Core | Heteroclitic Modification P1 | Heteroclitic TABLE 2-continued Example Vaccine Peptides (MHC class II)

| SEQ ID NO | Sequence corresponding to SEQ ID | Core | Target | Seed Core | Heteroclitic Modification P1 | Heteroclitic Modification P4 | Heteroclitic Modification P6 | Heteroclitic Modification P9 | Note |
|---|---|---|---|---|---|---|---|---|---|
| SEQ ID NO: 545 | PRLVSGWV KPFIINHSA YID | FIINH SAYI | IDH1 R132H | PRLVSGWVKPII IGHHAYGD | I1F | G4N | H6S | G9I | Individual IDH1_R132H Vaccine (5-peptide); Brain Cancer Vaccine (20-peptide) |
| SEQ ID NO: 546 | RLVSGWVK PFIIAHPAY NDQ | FILAH FAYN | IDH1 R132H | RLVSGWVKPIII GHHAYGDQ | I1F | G4A | H6F | G9N | Individual IDH1_R132H Vaccine (5-peptide); Brain Cancer Vaccine (20-peptide) |
| SEQ ID NO: 547 | RLVSGWVK PFIIAHPAY VDQ | FILAH PAYV | IDH1 R132H | RLVSGWVKPIII GHHAYGDQ | I1F | G4A | H6P | G9V | Individual IDH1_R132H Vaccine (5-peptide); Brain Cancer Vaccine (20-peptide); Individual IDH1_R132H Vaccine (5-peptide, Set 2) |
| SEQ ID NO: 548 | GWVKPIIIM HSAYRD | IIIMH SAYR | IDH1 R132H | GWVKPIIIGHHA YGD | — | G4M | H6S | G9R | Brain Cancer Vaccine (20-peptide) |
| SEQ ID NO: 549 | PRLVSGWI KPAIVGHA AYGD | IKPAI VGHA | IDH1 R132H | VKPIIIG HH | V1I | I4A | I6V | H9A | Brain Cancer Vaccine (20-peptide) |
| SEQ ID NO: 550 | PRLVSGWV KPFIINHFA YYD | FIINH FAYY | IDH1 R132H | PRLVSGWVKPII IGHHAYGD | I1F | G4N | H6F | G9Y | Brain Cancer Vaccine (20-peptide) |
| SEQ ID NO: 551 | RLVSGWVK PFIIAHPAY ADQ | FILAH PAYA | IDH1 R132H | RLVSGWVKPIII GHHAYGDQ | I1F | G4A | H6P | G9A | Brain Cancer Vaccine (20-peptide) |
| SEQ ID NO: 552 | PRLVSGWV KPFIINHAA YID | FIINH AAYI | IDH1 R132H | PRLVSGWVKPII IGHHAYGD | I1F | G4N | H6A | G9I | Individual IDH1_R132H Vaccine (5-peptide, Set 2) |
| SEQ ID NO: 553 | RLVSGWVK PFIINHFAY VDQ | FIINH FAYV | IDH1 R132H | RLVSGWVKPIII GHHAYGDQ | I1F | G4N | H6F | G9V | Individual IDH1_R132H Vaccine (5-peptide, Set 2) |
| SEQ ID NO: 554 | EYKFVVIG NAGAGKSA | FVVIG NAGA | KRAS G12A | EYKLVVVGAAG AGVGKSA | L1F | V4I | A6N | V9A | Individual KRAS_G12A Vaccine (5-peptide); Bronchus And Lung Cancer Vaccine (30-peptide); Individual KRAS_G12A Vaccine (5-peptide, Set 2) |

TABLE 2-continued

| SEQ ID NO | Sequence corresponding to SEQ ID | Core | Target | Seed | Seed Core | Example Vaccine Peptides (MHC class II) | | | | Note |
|---|---|---|---|---|---|---|---|---|---|---|
| | | | | | | Heteroclitic Modification P1 | Heteroclitic Modification P4 | Heteroclitic Modification P6 | Heteroclitic Modification P9 | |
| SEQ ID NO: 555 | TEYKFVVIG NAGVGK | FVVIG NAGV | KRAS G12A | TEYKLVVVGAA GVGK | LVVVGA AGV | L1F | V4I | A6N | — | Individual KRAS_G12A Vaccine (5-peptide); Bronchus And Lung Cancer Vaccine (30-peptide); Individual KRAS_G12A Vaccine (5-peptide, Set 2) |
| SEQ ID NO: 556 | TEYKIVVIG RAGHGK | IVVIG RAGH | KRAS G12A | TEYKLVVVGAA GVGK | LVVVGA AGV | L1I | V4I | A6R | V9H | Individual KRAS_G12A Vaccine (5-peptide); Bronchus And Lung Cancer Vaccine (30-peptide); Individual KRAS_G12A Vaccine (5-peptide, Set 2) |
| SEQ ID NO: 557 | TEYKLVVVL GNAGYGK | LVVL GNAG Y | KRAS G12A | TEYKLVVVGAA GVGK | LVVVGA AGV | — | V4L | A6N | V9Y | Individual KRAS_G12A Vaccine (5-peptide) |
| SEQ ID NO: 558 | TEYKMVVY GNAGLGK | MVVY GNAG L | KRAS G12A | TEYKLVVVGAA GVGK | LVVVGA AGV | L1M | V4Y | A6N | V9L | Individual KRAS_G12A Vaccine (5-peptide); Bronchus And Lung Cancer Vaccine (30-peptide) |
| SEQ ID NO: 559 | TEYKIVVVL GNAGYGK | IVVL GNAG Y | KRAS G12A | TEYKLVVVGAA GVGK | LVVVGA AGV | L1I | V4L | A6N | V9Y | Individual KRAS_G12A Vaccine (5-peptide, Set 2) |
| SEQ ID NO: 560 | TEYKIVVVW GNAGVGK | IVVW GNAG V | KRAS G12A | TEYKLVVVGAA GVGK | LVVVGA AGV | L1I | V4W | A6N | | Individual KRAS_G12A Vaccine (5-peptide, Set 2) |
| SEQ ID NO: 561 | EYKFVVFPG NCGAGKS | FVVF GNCG A | KRAS G12C | EYKLVVVGACG VGKS | LVVVGA CGV | L1F | V4F | A6N | V9A | Individual KRAS_G12C Vaccine (5-peptide); Bronchus And Lung Cancer Vaccine (30-peptide); Individual KRAS_G12C Vaccine (5-peptide, Set 2) |
| SEQ ID NO: 562 | EYKFVVSG ACGVGKS | FVVS GACG V | KRAS G12C | EYKLVVVGACG VGKS | LVVVGA CGV | L1F | V4S | — | — | Individual KRAS_G12C Vaccine (5-peptide) |

TABLE 2-continued

| SEQ ID NO | Sequence corresponding to SEQ ID | Core | Target | Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|---|
| SEQ ID NO: 563 | EYKFVVSG NCGLGKS | FVVS GNCG L | KRAS G12C | EYKLVVVGACG VGKS | LVVVGA CGV | L1F | V4S | A6N | V9L | Individual KRAS_G12C Vaccine (5-peptide); Bronchus And Lung Cancer Vaccine (30-peptide); Individual KRAS_G12C Vaccine (5-peptide, Set 2) |
| SEQ ID NO: 564 | EYKLVVMG PCGAGKS | LVVM GPCG A | KRAS G12C | EYKLVVVGACG VGKS | LVVVGA CGV | — | V4M | A6P | V9A | Individual KRAS_G12C Vaccine (5-peptide); Bronchus And Lung Cancer Vaccine (30-peptide) |
| SEQ ID NO: 565 | KLIVIGMC RVGHSAL | IVGM CRVG H | KRAS G12C | KLVVVGACGV GKSAL | VVGACG VGK | V1I | A4M | G6R | K9H | Individual KRAS_G12C Vaccine (5-peptide); Bronchus And Lung Cancer Vaccine (30-peptide) |
| SEQ ID NO: 566 | EYKFVVSG ACGIGKS | FVVS GACG I | KRAS G12C | EYKLVVVGACG VGKS | LVVVGA CGV | L1F | V4S | — | V9I | Individual KRAS_G12C Vaccine (5-peptide, Set 2) |
| SEQ ID NO: 567 | EYKLVVLG SCGAGKS | LVVL GSCG A | KRAS G12C | EYKLVVVGACG VGKS | LVVVGA CGV | — | V4L | A6S | V9A | Individual KRAS_G12C Vaccine (5-peptide, Set 2) |
| SEQ ID NO: 568 | KLIVIGICR VGHSAL | IVGIC RVGH | KRAS G12C | KLVVVGACGV GKSAL | VVGACG VGK | V1I | A4I | G6R | K9H | Individual KRAS_G12C Vaccine (5-peptide, Set 2) |
| SEQ ID NO: 569 | EYKFVVPG SDGAGKS | FVVP GSDG A | KRAS G12D | EYKLVVVGADG VGKS | LVVVGA DGV | L1F | V4F | A6S | V9A | Individual KRAS_G12D Vaccine (5-peptide); Pancreatic Cancer Vaccine (20-peptide); Bronchus And Lung Cancer Vaccine (30-peptide); Colorectal Cancer Vaccine (30-peptide); Individual KRAS_G12D Vaccine (5-peptide, Set 2) |

TABLE 2-continued

Example Vaccine Peptides (MHC class II)

| SEQ ID NO | Sequence corresponding to SEQ ID | Core | Target | Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|---|
| SEQ ID NO: 570 | EYKFVVIG NDGAGKSA LTIQLIQN | FVVIG NDGA | KRAS G12D | EYKFVVIG NDGAGKSA LTIQLIQN | LVVVGA DGV | L1F | V4I | A6N | V9A | Individual KRAS_G12D Vaccine (5-peptide); Pancreatic Cancer Vaccine (20-peptide); Bronchus And Lung Cancer Vaccine (30-peptide); Colorectal Cancer Vaccine (30-peptide); Individual KRAS_G12D Vaccine (5-peptide, Set 2) |
| SEQ ID NO: 571 | EYKFVVLG ADGAGKS | FVVL GADG A | KRAS G12D | EYKLVVVGADG VGKS | LVVVGA DGV | L1F | V4L | — | V9A | Individual KRAS_G12D Vaccine (5-peptide); Pancreatic Cancer Vaccine (20-peptide); Bronchus And Lung Cancer Vaccine (30-peptide); Colorectal Cancer Vaccine (30-peptide) |
| SEQ ID NO: 572 | MTEYKFVV SGADGIGK SALT | FVVS GADG I | KRAS G12D | MTEYKLVVVG ADGVGKSALT | LVVVGA DGV | L1F | V4S | — | V9I | Individual KRAS_G12D Vaccine (5-peptide); Pancreatic Cancer Vaccine (20-peptide); Bronchus And Lung Cancer Vaccine (30-peptide); Colorectal Cancer Vaccine (30-peptide); Individual KRAS_G12D Vaccine (5-peptide, Set 2) |
| SEQ ID NO: 573 | YGSDGIGK SALT | GSDGI | G12D | ADGVGKSALT | DGV | — | — | — | — | Vaccine (5-peptide); Pancreatic Cancer Vaccine (20-peptide); Bronchus And Lung Cancer Vaccine (30-peptide); Colorectal Cancer Vaccine (30-peptide) |
| SEQ ID NO: 574 | MTEYKIVV MGIDGAGK SALT | IVVM GIDG A | KRAS G12D | MTEYKLVVVG ADGVGKSALT | LVVVGA DGV | L1I | V4M | A6I | V9A | Pancreatic Cancer Vaccine (20-peptide); Colorectal Cancer Vaccine (30-peptide) |
| SEQ ID NO: 575 | EYKFVVSG ADGIGKS | FVVS GADG I | KRAS G12D | EYKLVVVGADG VGKS | LVVVGA DGV | L1F | V4S | — | V9I | Colorectal Cancer Vaccine (30-peptide) |
| SEQ ID NO: 576 | EYKIVVMG ADGLGKS | IVVM GADG L | KRAS G12D | EYKLVVVGADG VGKS | LVVVGA DGV | L1I | V4M | — | V9L | Individual KRAS_G12D Vaccine (5-peptide, Set 2) |

TABLE 2-continued

Example Vaccine Peptides (MHC class II)

| SEQ ID NO | Sequence corresponding to SEQ ID | Core | Target | Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|---|
| SEQ ID NO: 577 | MTEYKFVV YGNDGVG KSALT | FVVY GNDG V | KRAS G12D | MTEYKLVVVG ADGVGKSALT | LVVVGA DGV | L1F | V4Y | A6N | — | Individual KRAS_G12D Vaccine (5-peptide, Set 2) |
| SEQ ID NO: 578 | TEYKFVVIG NRGLGK | FVVIG NRGL | KRAS G12R | TEYKLVVVGAR GVGK | LVVVGA RGV | L1F | V4I | A6N | V9L | Individual KRAS_G12R Vaccine (5-peptide); Pancreatic Cancer Vaccine (20-peptide); Individual KRAS_G12R Vaccine (5-peptide, Set 2) |
| SEQ ID NO: 579 | TEYKFVVT GFRGLGKS ALTI | FVVT GFRG L | KRAS G12R | TEYKLVVVGAR GVGKSALTI | LVVVGA RGV | L1F | V4T | A6F | V9L | Individual KRAS_G12R Vaccine (5-peptide); Pancreatic Cancer Vaccine (20-peptide); Individual KRAS_G12R Vaccine (5-peptide, Set 2) |
| SEQ ID NO: 580 | TEYKIVVA GARGSGK | IVVA GARG S | KRAS G12R | TEYKLVVVGAR GVGK | LVVVGA RGV | L1I | V4A | — | V9S | Individual KRAS_G12R Vaccine (5-peptide); Pancreatic Cancer Vaccine (20-peptide) |
| SEQ ID NO: 581 | TEYKLVVI GTRGAGKS ALTI | LVVI GTRG A | KRAS G12R | TEYKLVVVGAR GVGKSALTI | LVVVGA RGV | — | V4I | A6T | V9A | Individual KRAS_G12R Vaccine (5-peptide); Pancreatic Cancer Vaccine (20-peptide) |
| SEQ ID NO: 582 | TEYRLVSV FARSVGKS ALTI | RLVS VFAR S | KRAS G12R | TEYKLVVVGAR GVGKSALTI | KLVVVG ARG | K1R | V4S | G6F | G9S | Individual KRAS_G12R Vaccine (5-peptide); Pancreatic Cancer Vaccine (20-peptide) |
| SEQ ID NO: 583 | TEYKFVVIG RRGSGK | FVVIG RRGS | KRAS G12R | TEYKLVVVGAR GVGK | LVVVGA RGV | L1F | V4I | A6R | V9S | Pancreatic Cancer Vaccine (20-peptide) |
| SEQ ID NO: 584 | TEYKLVVL GMRGYGK | LVVL GMRG Y | KRAS G12R | TEYKLVVVGAR GVGK | LVVVGA RGV | — | V4L | A6M | V9Y | Pancreatic Cancer Vaccine (20-peptide) |
| SEQ ID NO: 585 | TEYKFVVIG TRGAGKSA LTI | FVVIG TRGA | KRAS G12R | TEYKLVVVGAR GVGKSALTI | LVVVGA RGV | L1F | V4I | A6T | V9A | Individual KRAS_G12R Vaccine (5-peptide, Set 2) |
| SEQ ID NO: 586 | TEYKIVVA GARGAGK | IVVA GARG A | KRAS G12R | TEYKLVVVGAR GVGK | LVVVGA RGV | L1I | V4A | — | V9A | Individual KRAS_G12R Vaccine (5-peptide, Set 2) |
| SEQ ID NO: 587 | TEYRLVSV LAREVGKS ALTI | RLVS VLAR E | KRAS G12R | TEYKLVVVGAR GVGKSALTI | KLVVVG ARG | K1R | V4S | G6L | G9E | Individual KRAS_G12R Vaccine (5-peptide, Set 2) |

TABLE 2-continued

Example Vaccine Peptides (MHC class II)

| SEQ ID NO | Sequence corresponding to SEQ ID | Core | Target Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|
| SEQ ID NO: 588 | EYKFVVIGS SGLGKS | FVVIG SSGL | KRAS G12S | EYKFVVIGASG VGKS | LVVVGA SGV | L1F | V4I | A6S | V9L | Individual KRAS_G12S Vaccine (5-peptide); Individual KRAS_G12S Vaccine (5-peptide, Set 2) |
| SEQ ID NO: 589 | EYKFVVMG ASGIGKS | FVVM GASGI | KRAS G12S | EYKLVVVGASG VGKS | LVVVGA SGV | L1F | V4M | — | V9I | Individual KRAS_G12S Vaccine (5-peptide); Individual KRAS_G12S Vaccine (5-peptide, Set 2) |
| SEQ ID NO: 590 | EYKIVVFG NSGAGKS | IVVFG NSGA | KRAS G12S | EYKLVVVGASG VGKS | LVVVGA SGV | L1I | V4F | A6N | V9A | Individual KRAS_G12S Vaccine (5-peptide) |
| SEQ ID NO: 591 | EYKIVVMG RSGMGKS | IVVM GRSG M | KRAS G12S | EYKLVVVGASG VGKS | LVVVGA SGV | L1I | V4M | A6R | V9M | Individual KRAS_G12S Vaccine (5-peptide) |
| SEQ ID NO: 592 | YKIVVLGA SGYGKSA | IVVL GASG Y | KRAS G12S | YKLVVVGASGV GKSA | LVVVGA SGV | L1I | V4L | — | V9Y | Individual KRAS_G12S Vaccine (5-peptide) |
| SEQ ID NO: 593 | EYKIVVFGS SGAGKS | IVVFG SSGA | KRAS G12S | EYKLVVVGASG VGKS | LVVVGA SGV | L1I | V4F | A6S | V9A | Individual KRAS_G12S Vaccine (5-peptide, Set 2) |
| SEQ ID NO: 594 | EYKIVVMG RSGLGKS | IVVM GRSG L | KRAS G12S | EYKLVVVGASG VGKS | LVVVGA SGV | L1I | V4M | A6R | V9L | Individual KRAS_G12S Vaccine (5-peptide, Set 2) |
| SEQ ID NO: 595 | YKIVVLGA SGFGKSA | IVVL GASG F | KRAS G12S | YKLVVVGASGV GKSA | LVVVGA SGV | L1I | V4L | — | V9F | Individual KRAS_G12S Vaccine (5-peptide, Set 2) |
| SEQ ID NO: 596 | EYKFVVIG RVGHGKS | FVVIG RVGH | KRAS G12V | EYKLVVVGAVG VGKS | LVVVGA VGV | L1F | V4I | A6R | V9H | Individual KRAS_G12V Vaccine (5-peptide); Pancreatic Cancer Vaccine (20-peptide); Bronchus And Lung Cancer Vaccine (30-peptide); Colorectal Cancer Vaccine (30-peptide); Individual KRAS_G12V Vaccine (5-peptide, Set 2) |

TABLE 2-continued

Example Vaccine Peptides (MHC class II)

| SEQ ID NO | Sequence corresponding to SEQ ID | Core | Target | Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|---|
| SEQ ID NO: 597 | EYKFVVLG NVGHGKS | FVVL GTVG H | KRAS G12V | EYKFVVGAVG VGKS | LVVVGA VGV | L1F | V4L | A6T | V9H | Individual KRAS_G12V Vaccine (5-peptide); Pancreatic Cancer Vaccine (20-peptide); Bronchus And Lung Cancer Vaccine (30-peptide); Colorectal Cancer Vaccine (30-peptide); Individual KRAS_G12V Vaccine (5-peptide, Set 2) |
| SEQ ID NO: 598 | EYKFVVYG NVGVGKS | FVVY GNVG V | KRAS G12V | EYKLVVVGAVG VGKS | LVVVGA VGV | L1F | V4Y | A6N | — | Individual KRAS_G12V Vaccine (5-peptide); Pancreatic Cancer Vaccine (20-peptide); Bronchus And Lung Cancer Vaccine (30-peptide); Colorectal Cancer Vaccine (30-peptide) |
| SEQ ID NO: 599 | EYKIVAG NVGIGKS | IVVA GNVG I | KRAS G12V | EYKLVVVGAVG VGKS | LVVVGA VGV | L1I | V4A | A6N | V9I | Individual KRAS_G12V Vaccine (5-peptide); Pancreatic Cancer Vaccine (20-peptide); Bronchus And Lung Cancer Vaccine (30-peptide); Colorectal Cancer Vaccine (30-peptide); Individual KRAS_G12V Vaccine (5-peptide, Set 2) |
| SEQ ID NO: 600 | TEYKIVVM GNVGYGK | IVVM GNVG Y | KRAS G12V | TEYKLVVVGAV GVGK | LVVVGA VGV | L1I | V4M | A6N | V9Y | Individual KRAS_G12V Vaccine (5-peptide); Bronchus And Lung Cancer Vaccine (30-peptide); Individual KRAS_G12V Vaccine (5-peptide, Set 2) |
| SEQ ID NO: 601 | EYKFVVNG AVGVGKS | FVVN GAVG V | KRAS G12V | EYKLVVVGAVG VGKS | LVVVGA VGV | L1F | V4N | — | — | Pancreatic Cancer Vaccine (20-peptide); Colorectal Cancer Vaccine (30-peptide) |
| SEQ ID NO: 602 | EYKIVMG NVGYGKS | IVVM GNVG Y | KRAS G12V | EYKLVVVGAVG VGKS | LVVVGA VGV | L1I | V4M | A6N | V9Y | Pancreatic Cancer Vaccine (20-peptide); Colorectal Cancer Vaccine (30-peptide) |
| SEQ ID NO: 603 | EYKLVLG RVGHGKS | LVVL GRVG H | KRAS G12V | EYKLVVVGAVG VGKS | LVVVGA VGV | L1 | V4L | A6R | V9H | Pancreatic Cancer Vaccine (20-peptide); Colorectal Cancer Vaccine (30-peptide) |

TABLE 2-continued

| SEQ ID NO | Sequence corresponding to SEQ ID | Core | Target Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|
| SEQ ID NO: 604 | EYKFVVIGS VGAGKS | FVVIG SVGA | KRAS G12V | EYKLVVVGAVG VGKS | LVVVGA VGV | L1F | V4I | A6S | V9A | Colorectal Cancer Vaccine (30-peptide) |
| SEQ ID NO: 605 | EYKFVVWMG NVGLGKS | FVVW GNVG L | KRAS G12V | EYKLVVVGAVG VGKS | LVVVGA VGV | L1F | V4W | A6N | V9L | Individual KRAS_G12V Vaccine (5-peptide, Set 2) |
| SEQ ID NO: 606 | EYKFVVMG NGDSGKS | FVVM GNGD S | KRAS G13D | EYKLVVVGAGD VGKS | LVVVGA GDV | L1F | V4M | A6N | V9S | Individual KRAS_G13D Vaccine (5-peptide); Colorectal Cancer Vaccine (30-peptide); Individual KRAS_G13D Vaccine (5-peptide, Set 2) |
| SEQ ID NO: 607 | EYKFVVSG SGDVGKS | FVVS GSGD V | KRAS G13D | EYKLVVVGAGD VGKS | LVVVGA GDV | L1F | V4S | A6S | — | Individual KRAS_G13D Vaccine (5-peptide); Colorectal Cancer Vaccine (30-peptide) |
| SEQ ID NO: 608 | EYKFVVYG SGDLGKS | FVVY GSGD L | KRAS G13D | EYKLVVVGAGD VGKS | LVVVGA GDV | L1F | V4Y | A6S | V9L | Individual KRAS_G13D Vaccine (5-peptide); Colorectal Cancer Vaccine (30-peptide) |
| SEQ ID NO: 609 | EYKIVVMG RGDMGKS | IVVM GRGD M | KRAS G13D | EYKLVVVGAGD VGKS | LVVVGA GDV | L1I | V4M | A6R | V9M | Individual KRAS_G13D Vaccine (5-peptide); Colorectal Cancer Vaccine (30-peptide) |
| SEQ ID NO: 610 | EYKLIVVSA NDVAKS | IVVSA NDVA | KRAS G13D | EYKLVVVGAGD VGKS | VVVGAG DVG | V1I | G4S | G6N | G9A | Colorectal Cancer Vaccine (30-peptide) |
| SEQ ID NO: 611 | EYKLVLLG AGDAGKS | LVVL GAGD A | KRAS G13D | EYKLVVVGAGD VGKS | LVVVGA GDV | L1F | V4L | — | V9A | Colorectal Cancer Vaccine (30-peptide) |
| SEQ ID NO: 612 | TEYKFVVV GFGDLGKS ALTIQLIQN | FVVV GFGD L | KRAS G13D | TEYKLVVVGAG DVGKSALTIQLI QN | LVVVGA GDV | — | — | A6F | V9L | Colorectal Cancer Vaccine (30-peptide) |
| SEQ ID NO: 613 | EYKFVVAG NGDIGKS | FVVA GNGD I | KRAS G13D | EYKLVVVGAGD VGKS | LVVVGA GDV | L1F | V4A | A6N | V9I | Individual KRAS_G13D Vaccine (5-peptide, Set 2) |
| SEQ ID NO: 614 | EYKFVVFG NGDVGKS | FVVF GNGD V | KRAS G13D | EYKLVVVGAGD VGKS | LVVVGA GDV | L1F | V4F | A6N | — | Individual KRAS_G13D Vaccine (5-peptide, Set 2) |

TABLE 2-continued

Example Vaccine Peptides (MHC class II)

| SEQ ID NO | Sequence corresponding to SEQ ID | Core | Target | Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|---|
| SEQ ID NO: 615 | EYKIVVIGR GDMGKS | IVVIG RGDM | KRAS G13D | EYKLVVVGAGD VGKS | LVVVGA GDV | L1I | V4I | A6R | V9M | Individual KRAS_G13D Vaccine (5-peptide, Set 2) |
| SEQ ID NO: 616 | LDILNTAG KVEYAAM RDQYM | NTAG KVEY A | NRAS Q61K | LDILDTAGKEEY SAMRDQYM | DTAGKE EYS | D1N | — | E6V | S9A | Individual NRAS_Q61K Vaccine (5-peptide); Skin Cancer Vaccine (20-peptide); Thyroid Cancer Vaccine (10-peptide) |
| SEQ ID NO: 617 | LDILNTASK IEYAAMRD QYM | NTAS KIEY A | NRAS Q61K | LDILDTAGKEEY SAMRDQYM | DTAGKE EYS | D1N | G4S | E6I | S9A | Individual NRAS_Q61K Vaccine (5-peptide) |
| SEQ ID NO: 618 | LLDFLDIAG KEVYSA | FLDIA GKEV | NRAS Q61K | LLDILDTAGKEE YSA | ILDTAG KEE | I1F | T4I | — | E9V | Individual NRAS_Q61K Vaccine (5-peptide) |
| SEQ ID NO: 619 | LLDYLDMA TKELYSA | YLDM ATKE L | NRAS Q61K | LLDILDTAGKEE YSA | ILDTAG KEE | I1Y | T4M | G6T | E9L | Individual NRAS_Q61K Vaccine (5-peptide); Skin Cancer Vaccine (20-peptide); Thyroid Cancer Vaccine (10-peptide) |
| SEQ ID NO: 620 | QVVIDGET CLLDFLDT AFKELYSA M | FLDT AFKE L | NRAS Q61K | QVVIDGETCLL DILDTAGKEEYS AM | ILDTAG KEE | I1F | — | G6F | E9L | Individual NRAS_Q61K Vaccine (5-peptide); Skin Cancer Vaccine (20-peptide); Thyroid Cancer Vaccine (10-peptide); Individual NRAS_Q61K Vaccine (5-peptide, Set 2) |
| SEQ ID NO: 621 | LDILNTAA KIEYAAMR DQYM | NTAA KIEY A | NRAS Q61K | LDILDTAGKEEY SAMRDQYM | DTAGKE EYS | D1N | G4A | E6I | S9A | Individual NRAS_Q61K Vaccine (5-peptide, Set 2) |
| SEQ ID NO: 622 | LLDFLDAA AKELYSA | FLDA AAKE L | NRAS Q61K | LLDILDTAGKEE YSA | ILDTAG KEE | I1F | T4A | G6A | E9L | Individual NRAS_Q61K Vaccine (5-peptide, Set 2) |
| SEQ ID NO: 623 | QVVIDGET CLLDFLDS AFKELYSA M | FLDS AFKE L | NRAS Q61K | QVVIDGETCLL DILDTAGKEEYS AM | ILDTAG KEE | I1F | T4S | G6F | E9L | Individual NRAS_Q61K Vaccine (5-peptide, Set 2) |

TABLE 2-continued

Example Vaccine Peptides (MHC class II)

| SEQ ID NO | Sequence corresponding to SEQ ID | Core | Target Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|
| SEQ ID NO: 624 | QVVIDGET CLLDFLDT AFKEIYSA M | FLDT AFKEI | NRAS Q61K | QVVIDGETCLL DILDTAGKEEYS AM | ILDTAG KEE | I1F | — | G6F | E9I | Individual NRAS_Q61K Vaccine (5-peptide, Set 2) |
| SEQ ID NO: 625 | GETCLLDFL DTAFLEY | FLDT AFLE Y | NRAS Q61L | GETCLLDILDTA GLEE | ILDTAGL EE | I1F | — | G6F | E9Y | Individual NRAS_Q61L Vaccine (5-peptide); Skin Cancer Vaccine (20-peptide) |
| SEQ ID NO: 626 | LLDFLDVA TLEDYSA | FLDV ATLE D | NRAS Q61L | LLDILDTAGLEE YSA | ILDTAGL EE | I1F | T4V | G6T | E9D | Individual NRAS_Q61L Vaccine (5-peptide); Skin Cancer Vaccine (20-peptide) |
| SEQ ID NO: 627 | LLDLLDMA NLEAYSA | LLDM ANLE A | NRAS Q61L | LLDILDTAGLEE YSA | ILDTAGL EE | I1L | T4M | G6N | E9A | Individual NRAS_Q61L Vaccine (5-peptide); Skin Cancer Vaccine (20-peptide) |
| SEQ ID NO: 628 | TCLLDILNT AALAEYAA MRD | NTAA LAEY A | NRAS Q61L | TCLLDILDTAGL EEYSAMRD | DTAGLE EYS | D1N | G4A | E6A | S9A | Individual NRAS_Q61L Vaccine (5-peptide); Skin Cancer Vaccine (20-peptide); Individual NRAS_Q61L Vaccine (5-peptide, Set 2) |
| SEQ ID NO: 629 | TCLLDILNT AALAEYSA MRD | NTAA LAEY S | NRAS Q61L | TCLLDILDTAGL EEYSAMRD | DTAGLE EYS | D1N | G4A | E6A | — | Individual NRAS_Q61L Vaccine (5-peptide) |
| SEQ ID NO: 630 | GETCLLDFL DHAFLEL | FLDH AFLE L | NRAS Q61L | GETCLLDILDTA GLEE | ILDTAGL EE | I1F | T4H | G6F | E9L | Individual NRAS_Q61L Vaccine (5-peptide, Set 2) |
| SEQ ID NO: 631 | LLDFLDIAN LEDYSA | FLDIA NLED | NRAS Q61L | LLDILDTAGLEE YSA | ILDTAGL EE | I1F | T4I | G6N | E9D | Individual NRAS_Q61L Vaccine (5-peptide, Set 2) |
| SEQ ID NO: 632 | LLDILDIAN LESYSA | ILDIA NLES | NRAS Q61L | LLDILDTAGLEE YSA | ILDTAGL EE | — | T4I | G6N | E9S | Individual NRAS_Q61L Vaccine (5-peptide, Set 2) |
| SEQ ID NO: 633 | TCLLDILNT AALVEYAA MRD | NTAA LVEY A | NRAS Q61L | TCLLDILDTAGL EEYSAMRD | DTAGLE EYS | D1N | G4A | E6V | S9A | Individual NRAS_Q61L Vaccine (5-peptide, Set 2) |

TABLE 2-continued

Example Vaccine Peptides (MHC class II)

| SEQ ID NO | Sequence corresponding to SEQ ID | Core | Target | Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|---|
| SEQ ID NO: 634 | LDILVTAAR IEYAAMRD QYM | VTAA RIEYA | NRAS Q61R | LDILDTAGREEY SAMRDQYM | DTAGRE EYS | D1V | G4A | E6I | S9A | Individual NRAS_Q61R Vaccine (5-peptide); Skin Cancer Vaccine (20-peptide); Thyroid Cancer Vaccine (10-peptide) |
| SEQ ID NO: 635 | LDILVTASR IEYAAMRD QYM | VTAS RIEYA | NRAS Q61R | LDILDTAGREEY SAMRDQYM | DTAGRE EYS | D1V | G4S | E6I | S9A | Individual NRAS_Q61R Vaccine (5-peptide) |
| SEQ ID NO: 636 | LLDFLDAA VREVYSA | FLDA AVRE V | NRAS Q61R | LLDILDTAGREE YSA | ILDTAGR EE | I1F | T4A | G6V | E9V | Individual NRAS_Q61R Vaccine (5-peptide) |
| SEQ ID NO: 637 | LLDFLDFA AREVYSA | FLDF AARE V | NRAS Q61R | LLDILDTAGREE YSA | ILDTAGR EE | I1F | T4F | G6A | E9V | Individual NRAS_Q61R Vaccine (5-peptide); Skin Cancer Vaccine (20-peptide); Thyroid Cancer Vaccine (10-peptide) |
| SEQ ID NO: 638 | TCLLDFLDE AFREIYSA MRD | FLDE AFREI | NRAS Q61R | TCLLDILDTAGR EEYSAMRD | ILDTAGR EE | I1F | T4E | G6F | E9I | Individual NRAS_Q61R Vaccine (5-peptide) |
| SEQ ID NO: 639 | LLDFLDFA AREIYSA | FLDF AAREI | NRAS Q61R | LLDILDTAGREE YSA | ILDTAGR EE | I1F | T4F | G6A | E9I | Skin Cancer Vaccine (20-peptide) |
| SEQ ID NO: 640 | TCLLDFLDT AFREVYSA MRD | FLDT AFRE V | NRAS Q61R | TCLLDILDTAGR EEYSAMRD | ILDTAGR EE | I1F | — | G6F | E9V | Skin Cancer Vaccine (20-peptide); Thyroid Cancer Vaccine (10-peptide) |
| SEQ ID NO: 641 | LDILNTAAR IEYAAMRD QYM | NTAA RIEYA | NRAS Q61R | LDILDTAGREEY SAMRDQYM | DTAGRE EYS | D1N | G4A | E6I | S9A | Individual NRAS_Q61R Vaccine (5-peptide, Set 2) |
| SEQ ID NO: 642 | LLDFLDAAI REIYSA | FLDA AIREI | NRAS Q61R | LLDILDTAGREE YSA | ILDTAGR EE | I1F | T4A | G6I | E9I | Individual NRAS_Q61R Vaccine (5-peptide, Set 2) |
| SEQ ID NO: 643 | LLDFLDFA ARELYSA | FLDF AARE L | NRAS Q61R | LLDILDTAGREE YSA | ILDTAGR EE | I1F | T4F | G6A | E9L | Individual NRAS_Q61R Vaccine (5-peptide, Set 2) |
| SEQ ID NO: 644 | LLDYLDAA GRELYSA | YLDA AGRE L | NRAS Q61R | LLDILDTAGREE YSA | ILDTAGR EE | I1Y | T4A | — | E9L | Individual NRAS_Q61R Vaccine (5-peptide, Set 2) |

TABLE 2-continued

Example Vaccine Peptides (MHC class II)

| SEQ ID NO | Sequence corresponding to SEQ ID Core | Target Seed | Seed Core | Heteroclitic Modification P1 | Heteroclitic Modification P4 | Heteroclitic Modification P6 | Heteroclitic Modification P9 | Note |
|---|---|---|---|---|---|---|---|---|
| SEQ ID NO: 645 | TCLLDFLDT AFRELYSA MRD / FLDTAFRELYSAL | NRAS Q61R | TCLLDILDTAGR EEYSAMRD | ILDTAGR EE | I1F | — | G6F | E9L | Individual NRAS_Q61R Vaccine (5-peptide, Set 2) |
| SEQ ID NO: 646 | RDPFSKSTF QEVDFLWS HRHYCV / FSKSTFQEV | PIK3C A E542K | RDPLSKITEQEK DFLWSHRHYCV TI | LSKITEQ EK | L1F | I4S | E6F | K9V | Individual PIK3CA_E542K Vaccine (5-peptide) |
| SEQ ID NO: 647 | RDPFSKTTF QEIDFLWS HRHYCV / FSKTTFQEI | PIK3C A E542K | RDPLSKITEQEK DFLWSHRHYCV TI | LSKITEQ EK | L1F | I4T | E6F | K9I | Individual PIK3CA_E542K Vaccine (5-peptide); Individual PIK3CA_E542K Vaccine (1-peptide, Set 2) |
| SEQ ID NO: 648 | RDPFSKTTF QELDFLWS HRHYCV / FSKTTFQEL | PIK3C A E542K | RDPLSKITEQEK DFLWSHRHYCV TI | LSKITEQ EK | L1F | I4T | E6F | K9L | Individual PIK3CA_E542K Vaccine (5-peptide) |
| SEQ ID NO: 649 | RDPFSKTTF QETDFLWS HRHYCV / FSKTTFQET | PIK3C A E542K | RDPLSKITEQEK DFLWSHRHYCV TI | LSKITEQ EK | L1F | I4T | E6F | K9T | Individual PIK3CA_E542K Vaccine (5-peptide) |
| SEQ ID NO: 650 | RDPFSKTTF QEVDFLWS HRHYCV / FSKTTFQEV | PIK3C A E542K | RDPLSKITEQEK DFLWSHRHYCV TI | LSKITEQ EK | L1F | I4T | E6F | K9V | Individual PIK3CA_E542K Vaccine (5-peptide); Bronchus And Lung Cancer Vaccine (30-peptide) |
| SEQ ID NO: 651 | LSEIIKQWK AFLVSHRH YCV / IKQW KAFL V | PIK3C A E545K | LSEITKQEKDFL WSHRHYCV | TKQEKD FLW | T1I | E4W | D6A | W9V | Individual PIK3CA_E545K Vaccine (5-peptide) |
| SEQ ID NO: 652 | LSEIIKQYKI FLASHRHY CV | PIK3C A E545K | LSEITKQEKDFL WSHRHYCV | TKQEKD FLW | T1I | E4Y | D6I | W9A | Individual PIK3CA_E545K Vaccine (5-peptide) |
| SEQ ID NO: 653 | LSEIILKQM KAFLISHRH YCV / LKQM KAFLI | PIK3C A E545K | LSEITKQEKDFL WSHRHYCV | TKQEKD FLW | T1L | E4M | D6A | W9I | Individual PIK3CA_E545K Vaccine (5-peptide) |
| SEQ ID NO: 654 | LSEIVKQFK DFLASHRH YCV / VKQF KDFL A | PIK3C A E545K | LSEITKQEKDFL WSHRHYCV | TKQEKD FLW | T1V | E4F | — | W9A | Individual PIK3CA_E545K Vaccine (5-peptide) |
| SEQ ID NO: 655 | LSEIVKQFK DFLLSHRH YCV / VKQF KDFL L | PIK3C A E545K | LSEITKQEKDFL WSHRHYCV | TKQEKD FLW | T1V | E4F | — | W9L | Individual PIK3CA_E545K Vaccine (5-peptide) |

TABLE 2-continued

| SEQ ID NO | Sequence corresponding to SEQ ID | Core | Target Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|
| SEQ ID NO: 656 | LSEIVKQM KAFLISHRH YCV | VKQM KAFLI | PIK3C A E545K | LSEITKQEKDFL WSHRHYCV | TKQEKD FLW | T1V | E4M | D6A | W9I | Bronchus And Lung Cancer Vaccine (30-peptide); Colorectal Cancer Vaccine (30-peptide) |
| SEQ ID NO: 657 | LSEIIKQFK DFLISHRHY CV | IKQFK DFLI | PIK3C A E545K | LSEITKQEKDFL WSHRHYCV | TKQEKD FLW | T1I | E4F | — | W9I | Individual PIK3CA_E545K Vaccine (1-peptide, Set 2) |
| SEQ ID NO: 658 | ALEYFFKQ MNTARAG | FKQM NTAR A | PIK3C A H1047 R | ALEYFMKQMN DARHG | MKQMN DARH | M1F | — | D6T | H9A | Individual PIK3CA_H1047R Vaccine (5-peptide) |
| SEQ ID NO: 659 | ALEYFIKQ MNRARLGG WTTK | IKQM NRAR L | PIK3C A H1047 R | ALEYFMKQMN DARHGGWTTK | MKQMN DARH | M1I | — | D6R | H9L | Individual PIK3CA_H1047R Vaccine (5-peptide) |
| SEQ ID NO: 660 | ALEYFLKQ ANRARSG | LKQA NRAR S | PIK3C A H1047 R | ALEYFMKQMN DARHG | MKQMN DARH | M1L | M4A | D6R | H9S | Individual PIK3CA_H1047R Vaccine (5-peptide) |
| SEQ ID NO: 661 | ALEYFLKQ MNIARVGG WTTK | LKQM NIAR V | PIK3C A H1047 R | ALEYFMKQMN DARHGGWTTK | MKQMN DARH | M1L | — | D6I | H9V | Individual PIK3CA_H1047R Vaccine (5-peptide) |
| SEQ ID NO: 662 | YFFKQMNN ARDGGWT | FKQM NNAR D | PIK3C A H1047 R | YFMKQMNDAR HGGWT | MKQMN DARH | M1F | — | D6N | H9D | Individual PIK3CA_H1047R Vaccine (5-peptide) |
| SEQ ID NO: 663 | ALEYFFKQI NTARAG | FKQIN TARA | PIK3C A H1047 R | ALEYFMKQMN DARHG | MKQMN DARH | M1F | M4I | D6T | H9A | Individual PIK3CA_H1047R Vaccine (5-peptide, Set 2) |
| SEQ ID NO: 664 | ALEYFIKQA NRARHG | IKQA NRAR H | PIK3C A H1047 R | ALEYFMKQMN DARHG | MKQMN DARH | M1I | M4A | D6R | — | Individual PIK3CA_H1047R Vaccine (5-peptide, Set 2) |

TABLE 2-continued

Example Vaccine Peptides (MHC class II)

| SEQ ID NO | Sequence corresponding to SEQ ID | Core | Target Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|
| SEQ ID NO: 665 | ALEYFIKQI NRARVGG WTTK | IKQIN RARV | PIK3C A H1047 R | ALEYFMKQMN DARHGGWTTK | MKQMN DARH | M1I | M4I | D6R | H9V | Individual PIK3CA_H1047R Vaccine (5-peptide, Set 2) |
| SEQ ID NO: 666 | ALEYFIKQ MNAARVG GWTTK | IKQM NAAR V | PIK3C A H1047 R | ALEYFMKQMN DARHGGWTTK | MKQMN DARH | M1I | | D6A | H9V | Individual PIK3CA_H1047R Vaccine (5-peptide, Set 2) |
| SEQ ID NO: 667 | YFFKQMNS ARDGGWT | FKQM NSAR D | PIK3C A H1047 R | YFMKQMNDAR HGGWT | MKQMN DARH | M1F | | D6S | H9D | Individual PIK3CA_H1047R Vaccine (5-peptide, Set 2) |
| SEQ ID NO: 668 | AEREEFFD HTFQLVDL RLFQPFLKV | FFDH TFQL V | PIK3C A R88Q | AEREEFFDETRQ LCDLRLFQPFLK V | FFDETR QLC | | E4H | D6R | H9V | Individual PIK3CA_R88Q Vaccine (5-peptide) |
| SEQ ID NO: 669 | AEREEYFD LTPQLIDLR LFQPFLKV | YFDL TPQLI | PIK3C A R88Q | AEREEFFDETRQ LCDLRLFQPFLK V | FFDETR QLC | F1Y | E4L | D6A | H9V | Individual PIK3CA_R88Q Vaccine (5-peptide) |
| SEQ ID NO: 670 | EFFDEFRQF CALRIFQPF LK | FRQF CALRI | PIK3C A R88Q | EFFDETRQLCD LRLFQPFLK | TRQLCD LRL | T1F | L4F | D6A | L9I | Individual PIK3CA_R88Q Vaccine (5-peptide); Individual PIK3CA_R88Q Vaccine (5-peptide, Set 2) |
| SEQ ID NO: 671 | EFFDETFQL TDFRLVQPF LK | FQLT DFRL V | PIK3C A R88Q | EFFDETRQLCDL RLFQPFLK | RQLCDL RLF | R1F | C4T | L6F | C9V | Individual PIK3CA_R88Q Vaccine (5-peptide); Individual PIK3CA_R88Q Vaccine (5-peptide, Set 2) |
| SEQ ID NO: 672 | FFDETFQLT DFRLLQPFL KV | FQLT DFRL L | PIK3C A R88Q | FFDETRQLCDLR LFQPFLKV | RQLCDL RLF | R1F | C4T | L6F | F9L | Individual PIK3CA_R88Q Vaccine (5-peptide) |
| SEQ ID NO: 673 | AEREEFFDL TPQLIDLRL FQPFLKV | FFDLT PQLI | PIK3C A R88Q | AEREEFFDETRQ LCDLRLFQPFLK V | FFDETR QLC | | E4L | R6P | C9I | Individual PIK3CA_R88Q Vaccine (5-peptide, Set 2) |
| SEQ ID NO: 674 | AEREEFFDS TFQLVDLR LFQPFLKV | FFDST FQLV | PIK3C A R88Q | AEREEFFDETRQ LCDLRLFQPFLK V | FFDETR QLC | | E4S | R6F | C9V | Individual PIK3CA_R88Q Vaccine (5-peptide, Set 2) |

TABLE 2-continued

Example Vaccine Peptides (MHC class II)

| SEQ ID NO | Sequence corresponding to SEQ ID | Core | Target Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|
| SEQ ID NO: 675 | FFDETFQLT DFRLVQPFL KV | FQLT DFRL V | PIK3C A R88Q | FFDETRQLCDLR LFQPFLKV | RQLCDL RLF | R1F | C4T | L6F | F9V | Individual PIK3CA_R88Q Vaccine (5-peptide, Set 2) |
| SEQ ID NO: 676 | KAGIGGAG AMIAAYL | IGGA GAMI A | PTEN R130G | KAGKGGTGVMI CAYL | KGGTGV MIC | K1I | T4A | V6A | C9A | Individual PTEN_R130G Vaccine (5-peptide); Individual PTEN_R130G Vaccine (1-peptide, Set 2) |
| SEQ ID NO: 677 | KAGIGGAG AMISAYL | IGGA GAMI S | PTEN R130G | KAGKGGTGVMI CAYL | KGGTGV MIC | K1I | T4A | V6A | C9S | Individual PTEN_R130G Vaccine (5-peptide) |
| SEQ ID NO: 678 | KAGMGGA GAMIAAYL | MGGA GAMI A | PTEN R130G | KAGKGGTGVMI CAYL | KGGTGV MIC | K1M | T4A | V6A | C9A | Individual PTEN_R130G Vaccine (5-peptide) |
| SEQ ID NO: 679 | KAGMGGA GAMISAYL | MGGA GAMI S | PTEN R130G | KAGKGGTGVMI CAYL | KGGTGV MIC | K1M | T4A | V6A | C9S | Individual PTEN_R130G Vaccine (5-peptide) |
| SEQ ID NO: 680 | KAGVGGA GAMIAAYL | VGGA GAMI A | PTEN R130G | KAGKGGTGVMI CAYL | KGGTGV MIC | K1V | T4A | V6A | C9A | Individual PTEN_R130G Vaccine (5-peptide) |
| SEQ ID NO: 681 | AAIHWKAAK KPQTAVMI CAYLLHR | WKA AKPQ TA | PTEN R130Q | AAIHCKAGKGQ TGVMICAYLLH R | CKAGKG QTG | C1W | G4A | G6P | G9A | Individual PTEN_R130Q Vaccine (5-peptide) |
| SEQ ID NO: 682 | AAIHYKAG KAQTIVMIC AYLLHR | YKAG KAQT I | PTEN R130Q | AAIHCKAGKGQ TGVMICAYLLH R | CKAGKG QTG | C1Y | — | G6A | G9I | Individual PTEN_R130Q Vaccine (5-peptide) |
| SEQ ID NO: 683 | AIHLKAAK PQTAVMIC AYLL | LKAA KPQT A | PTEN R130Q | AIHCKAGKGQT GVMICAYLL | CKAGKG QTG | C1L | G4A | G6P | G9A | Individual PTEN_R130Q Vaccine (5-peptide) |
| SEQ ID NO: 684 | AIHVKAAK AQTAVMIC AYLL | VKAA KAQT A | PTEN R130Q | AIHCKAGKGQT GVMICAYLL | CKAGKG QTG | C1V | G4A | G6A | G9A | Individual PTEN_R 130Q Vaccine (5-peptide) |
| SEQ ID NO: 685 | AIHVKAAK PQTAVMIC AYLL | VKAA KPQT A | PTEN R130Q | AIHCKAGKGQT GVMICAYLL | CKAGKG QTG | C1V | G4A | G6P | G9A | Individual PTEN_R130Q Vaccine (5-peptide) |

TABLE 2-continued

Example Vaccine Peptides (MHC class II)

| SEQ ID NO | Sequence corresponding to SEQ ID | Core | Target Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|
| SEQ ID NO: 686 | AAIHIKAAK AQTAVMIC AYLLHR | IKAA KAQT A | PTEN R130Q | AAIHCKAGKGQ TGVMICAYLLH R | CKAGKG QTG | C1I | G4A | G6A | G9A | Individual PTEN_R130Q Vaccine (5-peptide, Set 2) |
| SEQ ID NO: 687 | AAIHIKAAK PQTAVMIC AYLLHR | IKAA KPQT A | PTEN R130Q | AAIHCKAGKGQ TGVMICAYLLH R | CKAGKG QTG | C1I | G4A | G6P | G9A | Individual PTEN_R130Q Vaccine (5-peptide, Set 2) |
| SEQ ID NO: 688 | AAIHNKAA KIQTVVMIC AYLLHR | NKAA KIQT V | PTEN R130Q | AAIHCKAGKGQ TGVMICAYLLH R | CKAGKG QTG | C1N | G4A | G6I | G9V | Individual PTEN_R130Q Vaccine (5-peptide, Set 2) |
| SEQ ID NO: 689 | AIHIKAAKA QTAVMI | IKAA KAQT A | PTEN R130Q | AIHCKAGKGQT GVMI | CKAGKG QTG | C1I | G4A | G6A | G9A | Individual PTEN_R130Q Vaccine (5-peptide, Set 2) |
| SEQ ID NO: 690 | AIHIKAAKA QTAVMICA YLL | IKAA KAQT A | PTEN R130Q | AIHCKAGKGQT GVMICAYLL | CKAGKG QTG | C1I | G4A | G6A | G9A | Individual PTEN_R130Q Vaccine (5-peptide, Set 2) |
| SEQ ID NO: 691 | KQSQHMTE VIRRIPRRE RCS | IRRIP RRER | TP53 H179R | KQSQHMTEVVR RCPHRER | VRRCPH RER | V1I | C4I | H6R | — | Individual TP53_H179R Vaccine (5-peptide) |
| SEQ ID NO: 692 | KQSQHMTE VIRRMPRR ERCS | IRRM PRRE R | TP53 H179R | KQSQHMTEVVR RCPHRER | VRRCPH RER | V1I | C4M | H6R | — | Individual TP53_H179R Vaccine (5-peptide); Individual TP53_H179R Vaccine (5-peptide, Set 2) |
| SEQ ID NO: 693 | MAIYKQSQ HMTEVIRR MPRREVCS D | IRRM PRRE V | TP53 H179R | MAIYKQSQHMT EVVRRCPHRER CSD | VRRCPH RER | V1I | C4M | H6R | R9V | Individual TP53_H179R Vaccine (5-peptide) |
| SEQ ID NO: 694 | QHMTELVR ICKHRAR | LVRIC KHRA | TP53 H179R | QHMTEVVRRCP HRE | VVRRCP HRE | V1L | R4I | P6K | E9A | Individual TP53_H179R Vaccine (5-peptide) |
| SEQ ID NO: 695 | QHMTEMV RLCRHRAR | MVRL CRHR A | TP53 H179R | QHMTEVVRRCP HRE | VVRRCP HRE | V1M | R4L | P6R | E9A | Individual TP53_H179R Vaccine (5-peptide) |
| SEQ ID NO: 696 | KQSQHMTE VIRRFPRRE ICS | IRRFP RREI | TP53 H179R | KQSQHMTEVVR RCPHRERCS | VRRCPH RER | V1I | C4F | H6R | R9I | Individual TP53_H179R Vaccine (5-peptide, Set 2) |

TABLE 2-continued

Example Vaccine Peptides (MHC class II)

| SEQ ID NO | Sequence corresponding to SEQ ID | Core | Target Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|
| SEQ ID NO: 697 | KQSQHMTE VIRRMPRR EVCS | IRRM PRRE V | TP53 H179R | KQSQHMTEVR RCPHRERCS | VRRCPH RER | V1I | C4M | H6R | R9V | Individual TP53_H179R Vaccine (5-peptide, Set 2) |
| SEQ ID NO: 698 | QHMTEIVRI CRHRAR | IVRIC RHRA | TP53 H179R | QHMTEVRRCP HRER | VVRRCP HRE | V1I | R4I | P6R | E9A | Individual TP53_H179R Vaccine (5-peptide, Set 2) |
| SEQ ID NO: 699 | QHMTELVR LCSHRSR | LVRL CSHR S | TP53 H179R | QHMTEVRRCP HRER | VVRRCP HRE | V1L | R4L | P6S | E9S | Individual TP53_H179R Vaccine (5-peptide, Set 2) |
| SEQ ID NO: 700 | PGTFVLSM SIYEQSQ | FVLS MSIY E | TP53 R158L | PGTRVLAMAIY KQSQ | RVLAMA IYK | R1F | A4S | A6S | K9E | Individual TP53_R158L Vaccine (5-peptide); Bronchus And Lung Cancer Vaccine (30-peptide) |
| SEQ ID NO: 701 | PGTRFLAIA SYKVSQ | FLAIA SYKV | TP53 R158L | PGTRVLAMAIY KQSQ | VLAMAI YKQ | V1F | M4I | I6S | Q9V | Individual TP53_R158L Vaccine (5-peptide); Bronchus And Lung Cancer Vaccine (30-peptide); Individual TP53_R158L Vaccine (5-peptide, Set 2) |
| SEQ ID NO: 702 | PGTRFLAT AFYKLSQH | FLAT AFYK L | TP53 R158L | PGTRVLAMAIY KQSQH | VLAMAI YKQ | V1F | M4T | I6F | Q9L | Individual TP53_R158L Vaccine (5-peptide); Bronchus And Lung Cancer Vaccine (30-peptide); Individual TP53_R158L Vaccine (5-peptide, Set 2) |
| SEQ ID NO: 703 | PGTRILALA KYKFSQ | ILALA KYKF | TP53 R158L | PGTRVLAMAIY KQSQ | VLAMAI YKQ | V1I | M4L | I6K | Q9F | Individual TP53_R158L Vaccine (5-peptide); Bronchus And Lung Cancer Vaccine (30-peptide); Individual TP53_R158L Vaccine (5-peptide, Set 2) |
| SEQ ID NO: 704 | PGTRILATA FYKLS | ILATA FYKL | TP53 R158L | PGTRVLAMAIY KQS | VLAMAI YKQ | V1I | M4T | I6F | Q9L | Individual TP53_R158L Vaccine (5-peptide); Bronchus And Lung Cancer Vaccine (30-peptide); Individual TP53_R158L Vaccine (5-peptide, Set 2) |
| SEQ ID NO: 705 | PGTRILAAA TYKASQ | ILAA ATYK A | TP53 R158L | PGTRVLAMAIY KQSQ | VLAMAI YKQ | V1I | M4A | I6T | Q9A | Bronchus And Lung Cancer Vaccine (30-peptide) |

TABLE 2-continued

Example Vaccine Peptides (MHC class II)

| SEQ ID NO | Sequence corresponding to SEQ ID | Core | Target | Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|---|
| SEQ ID NO: 706 | PGTFVLAM PIYNQSQ | FVLA MPIY N | TP53 R158L | PGTRVLAMAIY KQSQ | RVLAMA IYK | R1F | — | A6P | K9N | Individual TP53_R158L Vaccine (5-peptide, Set 2) |
| SEQ ID NO: 707 | PGTRFLAA AFYKFS | FLAA AFYK F | TP53 R158L | PGTRVLAMAIY KQS | VLAMAI YKQ | V1F | M4A | I6F | Q9F | Individual TP53_R158L Vaccine (5-peptide, Set 2) |
| SEQ ID NO: 708 | AIYKQSQY MTLVVRHV PHHE | YMTL VVRH V | TP53 R175H | AIYKQSQHMTE VVRHCPHHE | HMTEVV RHC | H1Y | E4L | — | C9V | Individual TP53_R175H Vaccine (5-peptide); Colorectal Cancer Vaccine (30-peptide); Brain Cancer Vaccine (20-peptide) |
| SEQ ID NO: 709 | AIYKQSQY MTVVLRHA PHHE | YMTV VLRH A | TP53 R175H | AIYKQSQHMTE VVRHCPHHE | HMTEVV RHC | H1Y | E4V | V6L | C9A | Individual TP53_R175H Vaccine (5-peptide) |
| SEQ ID NO: 710 | MAIYKQSQ FMTAVMR HIPHH | FMTA VMRH I | TP53 R175H | MAIYKQSQHMT EVVRHCPHH | HMTEVV RHC | H1F | E4A | V6M | C9I | Individual TP53_R175H Vaccine (5-peptide) |
| SEQ ID NO: 711 | MAIYKQSQ FMTTVRH VPHH | FMTT VVRH V | TP53 R175H | MAIYKQSQHMT EVVRHCPHH | HMTEVV RHC | H1F | E4T | — | C9V | Individual TP53_R175H Vaccine (5-peptide) |
| SEQ ID NO: 712 | MAIYKQSQ YMTLVMR HVPHH | YMTL VMRH V | TP53 R175H | MAIYKQSQHMT EVVRHCPHH | HMTEVV RHC | H1Y | E4L | V6M | C9V | Individual TP53_R175H Vaccine (5-peptide); Colorectal Cancer Vaccine (30-peptide); Brain Cancer Vaccine (20-peptide) |
| SEQ ID NO: 713 | AIYKQSQF MTLVARHA PHHE | FMTL VARH A | TP53 R175H | AIYKQSQHMTE VVRHCPHHE | HMTEVV RHC | H1F | E4L | V6A | C9A | Individual TP53_R175H Vaccine (5-peptide, Set 2) |
| SEQ ID NO: 714 | AIYKQSQF MTMVARH NPHHE | FMTM VARH N | TP53 R175H | AIYKQSQHMTE VVRHCPHHE | HMTEVV RHC | H1F | E4M | V6A | C9N | Individual TP53_R175H Vaccine (5-peptide, Set 2) |
| SEQ ID NO: 715 | MAIYKQSQ FMTIVARH VPHH | FMTI VARH V | TP53 R175H | MAIYKQSQHMT EVVRHCPHH | HMTEVV RHC | H1F | E4I | V6A | C9V | Individual TP53_R175H Vaccine (5-peptide, Set 2) |
| SEQ ID NO: 716 | MAIYKQSQ FMTLVARH VPHH | FMTL VARH V | TP53 R175H | MAIYKQSQHMT EVVRHCPHH | HMTEVV RHC | H1F | E4L | V6A | C9V | Individual TP53_R175H Vaccine (5-peptide, Set 2) |

TABLE 2-continued

Example Vaccine Peptides (MHC class II)

| SEQ ID NO | Sequence corresponding to SEQ ID | Core | Target Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|
| SEQ ID NO: 717 | MAIYKQSQ FMTMVIRH LPHH | FMTM VIRHL | TP53 R175H | MAIYKQSQHMT EVVRHCPHH | HMTEVV RHC | H1F | E4M | V6I | C9L | Individual TP53_R175H Vaccine (5-peptide, Set 2) |
| SEQ ID NO: 718 | MGGINQPP DLTIITL | INQFP DLTI | TP53 R248Q | MGGMNQRPILT IITL | MNQRPI LTI | M1I | R4F | I6D | — | Individual TP53_R248Q Vaccine (5-peptide); Individual TP53_R248Q Vaccine (5-peptide, Set 2) |
| SEQ ID NO: 719 | MGGINQIPA LTRITL | INQIP ALTR | TP53 R248Q | MGGMNQRPILT IITL | MNQRPI LTI | M1I | R4I | I6A | I9R | Individual TP53_R248Q Vaccine (5-peptide); Individual TP53_R248Q Vaccine (5-peptide, Set 2) |
| SEQ ID NO: 720 | MGGINQLP RLTSITL | INQLP RLTS | TP53 R248Q | MGGMNQRPILT IITL | MNQRPI LTI | M1I | R4L | I6R | I9S | Individual TP53_R248Q Vaccine (5-peptide); Individual TP53_R248Q Vaccine (5-peptide, Set 2) |
| SEQ ID NO: 721 | YMCNSSCM GGFNQTPF LTVITLEDS | FNQT PFLTV | TP53 R248Q | YMCNSSCMGG MNQRPILTITLE DS | MNQRPI LTI | M1F | R4T | I6F | I9V | Individual TP53_R248Q Vaccine (5-peptide); Individual TP53_R248Q Vaccine (5-peptide, Set 2) |
| SEQ ID NO: 722 | YMCNSSNM GSMAQRSI LTII | NMGS MAQR S | TP53 R248Q | YMCNSSCMGG MNQRPILTII | CMGGM NQRP | C1N | G4S | N6A | P9S | Individual TP53_R248Q Vaccine (5-peptide) |
| SEQ ID NO: 723 | YMCNSSNM GAMVQRAI LTII | NMGA MVQR A | TP53 R248Q | YMCNSSCMGG MNQRPILTII | CMGGM NQRP | C1N | G4A | N6V | P9A | Individual TP53_R248Q Vaccine (5-peptide, Set 2) |
| SEQ ID NO: 724 | CMGGFNW TPFLTVIT | FNWT PFLTV | TP53 R248 W | CMGGMNWRPIL TIIT | MNWRPI LTI | M1F | R4T | I6F | I9V | Individual TP53_R248W Vaccine (5-peptide); Individual TP53_R248W Vaccine (5-peptide, Set 2) |
| SEQ ID NO: 725 | MGGINWHP SLTIITL | INWH PSLTI | TP53 R248 W | MGGMNWRPILT IITL | MNWRPI LTI | M1I | R4H | I6S | — | Individual TP53_R248W Vaccine (5-peptide) |
| SEQ ID NO: 726 | MGGINWVP KLTVITL | INWV PKLT V | TP53 R248 W | MGGMNWRPILT IITL | MNWRPI LTI | M1I | R4V | I6K | I9V | Individual TP53_R248W Vaccine (5-peptide) |

TABLE 2-continued

Example Vaccine Peptides (MHC class II)

| SEQ ID NO | Sequence corresponding to SEQ ID | Core | Target Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|
| SEQ ID NO: 727 | MGGLNWFPPALTRITL | LNWFPALTR | TP53 R248W | MGGMNWRPIILTL | MNWRPILTI | M1L | R4F | I6A | I9R | Individual TP53_R248W Vaccine (5-peptide) |
| SEQ ID NO: 728 | SCMGGFNWMPALTII | FNWMPALTII | TP53 R248W | SCMGGMNWRPILTII | MNWRPILTI | M1F | R4M | I6A | — | Individual TP53_R248W Vaccine (5-peptide) |
| SEQ ID NO: 729 | MGGINWFPPALTRITL | INWFPALTR | TP53 R248W | MGGMNWRPIILTL | MNWRPILTI | M1I | R4F | I6A | I9R | Individual TP53_R248W Vaccine (5-peptide, Set 2) |
| SEQ ID NO: 730 | MGGINWHPPALTLITL | INWHPALTL | TP53 R248W | MGGMNWRPITL | MNWRPILTI | M1I | R4H | I6A | I9L | Individual TP53_R248W Vaccine (5-peptide, Set 2) |
| SEQ ID NO: 731 | MGGINWIPKLTLITL | INWIPKLTL | TP53 R248W | MGGMNWRPIILTL | MNWRPILTI | M1I | R4I | I6K | I9L | Individual TP53_R248W Vaccine (5-peptide, Set 2) |
| SEQ ID NO: 732 | SCMGGINWLPALTII | INWLPALTI | TP53 R248W | SCMGGMNWRPILTII | MNWRPILTI | M1I | R4L | I6A | — | Individual TP53_R248W Vaccine (5-peptide, Set 2) |
| SEQ ID NO: 733 | SFFVCVCACPTRDRR | FVCVCACPT | TP53 R273C | SFEVCVCACPGRDRR | EVCVCACPG | E1F | — | — | G9T | Individual TP53_R273C Vaccine (5-peptide) |
| SEQ ID NO: 734 | SFFVCVCSCPLRDRR | FVCVCSCPL | TP53 R273C | SFEVCVCACPGRDRR | EVCVCACPG | E1F | — | A6S | G9L | Individual TP53_R273C Vaccine (5-peptide) |
| SEQ ID NO: 735 | SFYVCFCACPMRDRR | YVCFCACPM | TP53 R273C | SFEVCVCACPGRDRR | EVCVCACPG | E1Y | V4F | — | G9M | Individual TP53_R273C Vaccine (5-peptide) |
| SEQ ID NO: 736 | SFYVCICTCPVRDRR | YVCICTCPV | TP53 R273C | SFEVCVCACPGRDRR | EVCVCACPG | E1Y | V4I | A6T | G9V | Individual TP53_R273C Vaccine (5-peptide) |
| SEQ ID NO: 737 | SFYVCVCTCPARDRR | YVCVCTCPA | TP53 R273C | SFEVCVCACPGRDRR | EVCVCACPG | E1Y | — | A6T | G9A | Individual TP53_R273C Vaccine (5-peptide) |
| SEQ ID NO: 738 | SFYVCVCTCPLRDRR | YVCVCTCPL | TP53 R273C | SFEVCVCACPGRDRR | EVCVCACPG | E1Y | — | A6T | G9L | Brain Cancer Vaccine (20-peptide) |

TABLE 2-continued

Example Vaccine Peptides (MHC class II)

| SEQ ID NO | Sequence corresponding to SEQ ID | Core | Target | Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|---|
| SEQ ID NO: 739 | SFFVCLCAC PARDRR | FVCL CACP A | TP53 R273C | SFEVCVCACPG RDRR | EVCVCA CPG | E1F | V4L | — | G9A | Individual TP53_R273C Vaccine (1-peptide, Set 2) |
| SEQ ID NO: 740 | LLGFNSLEI HVLACP | FNSLE IHVL | TP53 R273H | LLGRNSFEVHV CACP | RNSFEV HVC | R1F | F4L | V6I | C9L | Individual TP53_R273H Vaccine (5-peptide) |
| SEQ ID NO: 741 | LLGINSFED HVAACP | INSFE DHVA | TP53 R273H | LLGRNSFEVHV CACP | RNSFEV HVC | R1I | — | V6D | C9A | Individual TP53_R273H Vaccine (5-peptide) |
| SEQ ID NO: 742 | SGNLLGFN SLEFHVVA CPGR | FNSLE FHVV | TP53 R273H | SGNLLGRNSFE VHVCACPGR | RNSFEV HVC | R1F | F4L | V6F | C9V | Individual TP53_R273H Vaccine (5-peptide); Individual TP53_R273H Vaccine (5-peptide, Set 2) |
| SEQ ID NO: 743 | SGNLLGRN SFYVHLCP CPARDRRT E | YVHL CPCP A | TP53 R273H | SGNLLGRNSFE VHVCACPGRDR RTE | EVHVCA CPG | E1Y | V4L | A6P | G9A | Individual TP53_R273H Vaccine (5-peptide) |
| SEQ ID NO: 744 | SGNLLGRN SFYVHVCT CPVRDRRT E | YVHV CTCP V | TP53 R273H | SGNLLGRNSFE VHVCACPGRDR RTE | EVHVCA CPG | E1Y | — | A6T | G9V | Individual TP53_R273H Vaccine (5-peptide) |
| SEQ ID NO: 745 | LLGFNSFEA HVLACP | FNSFE AHVL | TP53 R273H | LLGRNSFEVHV CACP | RNSFEV HVC | R1F | — | V6A | C9L | Individual TP53_R273H Vaccine (5-peptide, Set 2) |
| SEQ ID NO: 746 | LLGFNSLEI HVIACP | FNSLE IHVI | TP53 R273H | LLGRNSFEVHV CACP | RNSFEV HVC | R1F | F4L | V6I | C9I | Individual TP53_R273H Vaccine (5-peptide, Set 2) |
| SEQ ID NO: 747 | LLGINSFEA HVLACP | INSFE AHVL | TP53 R273H | LLGRNSFEVHV CACP | RNSFEV HVC | R1I | — | V6A | C9L | Individual TP53_R273H Vaccine (5-peptide, Set 2) |
| SEQ ID NO: 748 | SGNLLGRN SFFVHMCA CPVRDRRT E | FVHM CACP V | TP53 R273H | SGNLLGRNSFE VHVCACPGRDR RTE | EVHVCA CPG | E1F | V4M | — | G9V | Individual TP53_R273H Vaccine (5-peptide, Set 2) |

TABLE 2-continued

Example Vaccine Peptides (MHC class II)

| SEQ ID NO | Sequence corresponding to SEQ ID | Core | Target Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|
| SEQ ID NO: 749 | FEVRVCICP ARIWRAEE | ICPAR IWRA | TP53 R282W | FEVRVCACPGR DWRTEE | ACPGRD WRT | A1I | G4A | D6I | T9A | Individual TP53_R282W Vaccine (2-peptide); Individual TP53_R282W Vaccine (1-peptide, Set 2) |
| SEQ ID NO: 750 | FEVRVCICP ARVWRAEE | ICPAR VWRA | TP53 R282W | FEVRVCACPGR DWRTEE | ACPGRD WRT | A1I | G4A | D6V | T9A | Individual TP53_R282W Vaccine (2-peptide) |
| SEQ ID NO: 751 | RNTFFHSLV FPCLPPE | FHSL VFPC L | TP53 Y220C | RNTFRHSVVVP CEPPE | RHSVVV PCE | R1F | V4L | V6F | E9L | Individual TP53_Y220C Vaccine (5-peptide); Individual TP53_Y220C Vaccine (5-peptide, Set 2) |
| SEQ ID NO: 752 | RNTFRHSIV APCAPPE | RHSIV APCA | TP53 Y220C | RNTFRHSVVVP CEPPE | RHSVVV PCE | — | V4I | V6A | E9A | Individual TP53_Y220C Vaccine (5-peptide) |
| SEQ ID NO: 753 | RNTFRHSIV APCVPPE | RHSIV APCV | TP53 Y220C | RNTFRHSVVVP CEPPE | RHSVVV PCE | — | V4I | V6A | E9V | Individual TP53_Y220C Vaccine (5-peptide); Individual TP53_Y220C Vaccine (5-peptide, Set 2) |
| SEQ ID NO: 754 | TFFHSSVFP CIPPEVG | FHSS VFPCI | TP53 Y220C | TFRHSVVVPCEP PEVG | RHSVVV PCE | R1F | V4S | V6F | E9I | Individual TP53_Y220C Vaccine (5-peptide) |
| SEQ ID NO: 755 | TFFHSTVFP CIPPEVG | FHST VFPCI | TP53 Y220C | TFRHSVVVPCEP PEVG | RHSVVV PCE | R1F | V4T | V6F | E9I | Individual TP53_Y220C Vaccine (5-peptide) |
| SEQ ID NO: 756 | RNTFRHSL VAPCVPPE | RHSL VAPC V | TP53 Y220C | RNTFRHSVVVP CEPPE | RHSVVV PCE | — | V4L | V6A | E9V | Individual TP53_Y220C Vaccine (5-peptide, Set 2) |
| SEQ ID NO: 757 | TFFHSLVFP CLPPEVG | FHSL VFPC L | TP53 Y220C | TFRHSVVVPCEP PEVG | RHSVVV PCE | R1F | V4L | V6F | E9L | Individual TP53_Y220C Vaccine (5-peptide, Set 2) |

TABLE 2-continued

Example Vaccine Peptides (MHC class II)

| SEQ ID NO | Sequence corresponding to SEQ ID | Core | Target | Seed | Seed Core | Heteroclitic Modification P1 | Heteroclitic Modification P4 | Heteroclitic Modification P6 | Heteroclitic Modification P9 | Note |
|---|---|---|---|---|---|---|---|---|---|---|
| SEQ ID NO: 758 | TFFHSTVFP CLPPEVG | FHST VFPC L | TP53 Y220C | TFRHSVVVPCEP PEVG | RHSVVV PCE | R1F | V4T | V6F | E9L | Individual TP53_Y220C Vaccine (5-peptide, Set 2) |
| SEQ ID NO: 759 | YKLVVVGA GDVGKSA | — | KRAS G13D | — | — | — | — | — | — | Individual KRAS_G13D Vaccine (5-peptide); Colorectal Cancer Vaccine (30-peptide); Individual KRAS_G13D Vaccine (5-peptide, Set 2) | mRNA and DNA Vaccines

In some embodiments, vaccine peptides are encoded as mRNA or DNA molecules and are administered for expression in vivo as is known in the art. One example of the delivery of vaccines by mRNA is found in Kranz et al., (2016), incorporated herein by reference. In some embodiments, vaccine peptides are encoded in more than one mRNA or DNA molecule as is found in Sahin et. al. (2017), incorporated in its entirety herein. In one embodiment, a construct comprises 30 peptides, including a ten-peptide MEW class I combined pancreatic cancer vaccine (targets: KRAS G12D, KRAS G12V, KRAS G12R) and a twenty-peptide MEW class II combined pancreatic cancer vaccine (targets: KRAS G12D, KRAS G12V, KRAS G12R), as optimized by the procedure described herein. Peptides are prepended with a secretion signal sequence at the N-terminus and followed by an MEW class I trafficking signal (MITD) (Kreiter et al., 2008; Sahin et al., 2017). The MITD has been shown to route antigens to pathways for HLA class I and class II presentation (Kreiter et al., 2008). Here we combine all peptides of each MEW class into a single construct using non-immunogenic glycine/serine linkers from Sahin et al., (2017), though it is also plausible to construct individual constructs containing single peptides with the same secretion and MITD signals as demonstrated by Kreiter et al., (2008).

In some embodiments, the amino acid sequence encoded by the mRNA vaccine comprises SEQ ID NO: 410310. Underlined amino acids correspond to the signal peptide (or leader) sequence. Bolded amino acids correspond to MEW class I (8-11 amino acids in length; 10 peptides) and MEW class II (13-25 amino acids in length; 20 peptides) peptide sequences. Italicized amino acids correspond to the trafficking signal.

(SEQ ID NO: 410310)
MRVTAPRTLILLLSGALALTETWAGSGGSGGGGSGGLMVVGADGVGGSG

GGGSGGLTVVGADGVGGSGGGGSGGVVVGADGVGRGGSGGGGSGGGPRG

VGKSAVGGSGGGGSGGLLVVGARGVGGSGGGGSGGVMGARGVGKGGSGG

GGSGGVVVGARGVGRGGSGGGGSGGLMVVGAVGVGGSGGGGSGGLTVVG

AVGVGGSGGGGSGGVTVGAVGVGKGGSGGGGSGGEYKFVVFGSDGAGKS

GGSGGGGSGGEYKFVVIGNDGAGKSALTIQLIQNGGSGGGGSGGEYKFV

VLGADGAGKSGGSGGGGSGGMTEYKFVVSGADGIGKSALTGGSGGGGSG

GMTEYKFVVYGSDGIGKSALTGGSGGGGSGGMTEYKIVVMGIDGAGKSA

LTGGSGGGGSGGTEYKFVVIGNRGLGKGGSGGGGSGGTEYKFVVTGFRG

LGKSALTIGGSGGGGSGGTEYKIVVAGARGSGKGGSGGGGSGGTEYKLV

VIGTRGAGKSALTIGGSGGGGSGGTEYRLVSVFARSVGKSALTIGGSGG

GGSGGTEYKFVVIGRRGSGKGGSGGGGSGGTEYKLVVLGMRGYGKGGSG

GGGSGGEYKFVVIGRVGHGKGGSGGGGSGGEYKFVVLGTVGHGKSGGS

GGGGSGGEYKFVVYGNVGVGKSGGSGGGGSGGEYKIVVAGNVGIGKSGG

SGGGGSGGEYKFVVNGAVGVGKSGGSGGGGSGGEYKIVVMGNVGYGKSG

GSGGGGSGGEYKLVVLGRVGHGKSGGSLGGGGSG*IVGIVAGLAVLAVVV*

*IGAVVATVMCRRKSSGGKGGSYSQAASSDSAQGSDVSLTA*.

In some embodiments, the vaccine is an mRNA vaccine comprising a nucleic acids sequence encoding the amino acid sequence consisting of SEQ ID NO: 410310. In some embodiments, the nucleic acid sequence of the mRNA vaccine encodes for an amino acid sequence 80, 81, 82, 83, 84, 85, 86, 87, 88, 89, 90, 91, 92, 93, 94, 95, 96, 97, 98 or 99% identical to SEQ ID NO: 410310.

In some embodiments, the vaccine is a DNA vaccine comprising a nucleic acids sequence encoding the amino acid sequence consisting of SEQ ID NO: 410310. In some embodiments, the nucleic acid sequence of the DNA vaccine encodes for an amino acid sequence 80, 81, 82, 83, 84, 85, 86, 87, 88, 89, 90, 91, 92, 93, 94, 95, 96, 97, 98 or 99% identical to SEQ ID NO: 410310.

In some embodiments, one or more MHC class I and/or MHC class II peptides disclosed herein (SEQ ID NO: 1 to 410310) can be encoded in one or more mRNA or DNA molecules and administered for expression in vivo. In some embodiments, between about 2 and about 40 peptide sequences are encoded in one or more mRNA constructs. In some embodiments, between about 2 and about 40 peptide sequences are encoded in one or more DNA constructs (i.e., nucleic acids encoding the amino acids sequences comprising on or more of SEQ ID NOs: 1 to 410310). In some embodiments, the amino acid sequence of the mRNA vaccine or the nucleic acid sequence of the DNA vaccine encodes for an amino acid sequence 80, 81, 82, 83, 84, 85, 86, 87, 88, 89, 90, 91, 92, 93, 94, 95, 96, 97, 98 or 99% identical to any of SEQ ID NOs: 1 to 410310.

Non-Limiting Embodiments of the Subject Matter

In one aspect, the invention provides for nucleic acid sequences encoding one or more amino acid sequences selected from the group consisting of SEQ ID NOs: 1 to 474.

In some embodiments, the nucleic acid sequences encode two or more amino acid sequences selected from the group consisting of SEQ ID NOs: 1 to 474.

In another aspect, the invention provides for an immunogenic composition comprising nucleic acid sequences encoding one or more amino acid sequences selected from the group consisting of SEQ ID NOs: 1 to 474.

In some embodiments, the immunogenic composition is administered to a subject. In some embodiments, the immunogenic composition comprises nucleic acid sequences encoding two or more amino acid sequences selected from the group consisting of SEQ ID NOs: 1 to 474. In some embodiments, the nucleic acid sequences are administered in a construct for expression in vivo. In some embodiments, the in vivo administration of the nucleic acid sequences is configured to produce one or more peptides that is displayed by an HLA class I molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic composition is administered in an effective amount to a subject to prevent cancer. In some embodiments, the immunogenic composition is administered in an effective amount to a subject to treat cancer. In some embodiments, the cancer is selected from the group consisting of pancreatic cancer, skin cancer, thyroid cancer, brain cancer, colorectal cancer, bronchus and lung cancer, breast cancer, and ovarian cancer. In some embodiments, the immunogenic composition comprises nucleic acid sequences encoding at least three amino acid sequences selected from the group consisting of SEQ ID NOs: 1 to 474.

In another aspect, the invention provides for an immunogenic peptide composition comprising one or more peptides selected from the group consisting of SEQ ID NOs: 1 to 474.

In some embodiments, the immunogenic peptide composition comprises two or more peptides selected from the group consisting of SEQ ID NOs: 1 to 474.

In another aspect, the invention provides for an immunogenic composition comprising nucleic acid sequences encoding one or more amino acid sequences selected from the group consisting of SEQ ID NOs: 1 to 18.

In some embodiments, the immunogenic composition comprises nucleic acid sequences encoding one or more amino acid sequences derived from a AKT1 protein mutation. In some embodiments, the immunogenic composition comprises nucleic acid sequences encoding two or more amino acid sequences selected from the group consisting of SEQ ID NOs: 1 to 18.

In another aspect, the invention provides for an immunogenic peptide composition comprising one or more peptides selected from the group consisting of SEQ ID NOs: 1 to 18.

In some embodiments, the immunogenic peptide composition comprises two or more peptides selected from the group consisting of SEQ ID NOs: 1 to 18. In some embodiments, the one or more peptides is a modified or unmodified fragment of a mutated AKT1 protein.

In another aspect, the invention provides for an immunogenic composition comprising nucleic acid sequences encoding one or more amino acid sequences selected from the group consisting of SEQ ID NOs: 19 to 50.

In some embodiments, the immunogenic composition comprises nucleic acid sequences encoding one or more amino acid sequences derived from a BRAF protein mutation. In some embodiments, the immunogenic composition comprises nucleic acid sequences encoding two or more amino acid sequences selected from the group consisting of SEQ ID NOs: 19 to 50.

In another aspect, the invention provides for an immunogenic peptide composition comprising one or more peptides selected from the group consisting of SEQ ID NOs: 19 to 50.

In some embodiments, the immunogenic peptide composition comprises two or more peptides selected from the group consisting of SEQ ID NOs: 19 to 50. In some embodiments, the one or more peptides is a modified or unmodified fragment of a mutated BRAF protein.

In another aspect, the invention provides for an immunogenic composition comprising nucleic acid sequences encoding one or more amino acid sequences selected from the group consisting of SEQ ID NOs: 51 to 98.

In some embodiments, the immunogenic composition comprises nucleic acid sequences encoding one or more amino acid sequences derived from a EGFR protein mutation. In some embodiments, the immunogenic composition comprises nucleic acid sequences encoding two or more amino acid sequences selected from the group consisting of SEQ ID NOs: 51 to 98.

In another aspect, the invention provides for an immunogenic peptide composition comprising one or more peptides selected from the group consisting of SEQ ID NOs: 51 to 98.

In some embodiments, the immunogenic peptide composition comprises two or more peptides selected from the group consisting of SEQ ID NOs: 51 to 98. In some embodiments, the one or more peptides is a modified or unmodified fragment of a mutated EGFR protein.

In another aspect, the invention provides for an immunogenic composition comprising nucleic acid sequences encoding one or more amino acid sequences selected from the group consisting of SEQ ID NOs: 99 to 118.

In some embodiments, the immunogenic composition comprises nucleic acid sequences encoding one or more amino acid sequences derived from a GTF2I protein mutation. In some embodiments, the immunogenic composition comprises nucleic acid sequences encoding two or more amino acid sequences selected from the group consisting of SEQ ID NOs: 99 to 118.

In another aspect, the invention provides for an immunogenic peptide composition comprising one or more peptides selected from the group consisting of SEQ ID NOs: 99 to 118.

In some embodiments, the immunogenic peptide composition comprises two or more peptides selected from the group consisting of SEQ ID NOs: 99 to 118. In some embodiments, the one or more peptides is a modified or unmodified fragment of a mutated GTF2I protein.

In another aspect, the invention provides for an immunogenic composition comprising nucleic acid sequences encoding one or more amino acid sequences selected from the group consisting of SEQ ID NOs: 119 to 140.

In some embodiments, the immunogenic composition comprises nucleic acid sequences encoding one or more amino acid sequences derived from a IDH1 protein mutation. In some embodiments, the immunogenic composition comprises nucleic acid sequences encoding two or more amino acid sequences selected from the group consisting of SEQ ID NOs: 119 to 140.

In another aspect, the invention provides for an immunogenic peptide composition comprising one or more peptides selected from the group consisting of SEQ ID NOs: 119 to 140.

In some embodiments, the immunogenic peptide composition comprises two or more peptides selected from the group consisting of SEQ ID NOs: 119 to 140. In some embodiments, the one or more peptides is a modified or unmodified fragment of a mutated IDH1 protein.

In another aspect, the invention provides for an immunogenic composition comprising nucleic acid sequences encoding one or more amino acid sequences selected from the group consisting of SEQ ID NOs: 141 to 229.

In some embodiments, the immunogenic composition comprises nucleic acid sequences encoding one or more amino acid sequences derived from a KRAS protein mutation. In some embodiments, the immunogenic composition comprises nucleic acid sequences encoding two or more amino acid sequences selected from the group consisting of SEQ ID NOs: 141 to 229.

In another aspect, the invention provides for an immunogenic peptide composition comprising one or more peptides selected from the group consisting of SEQ ID NOs: 141 to 229.

In some embodiments, the immunogenic peptide composition comprises two or more peptides selected from the group consisting of SEQ ID NOs: 141 to 229. In some embodiments, the one or more peptides is a modified or unmodified fragment of a mutated KRAS protein.

In another aspect, the invention provides for an immunogenic composition comprising nucleic acid sequences encoding one or more amino acid sequences selected from the group consisting of SEQ ID NOs: 230 to 272.

In some embodiments, the immunogenic composition comprises nucleic acid sequences encoding one or more amino acid sequences derived from a NRAS protein mutation. In some embodiments, the immunogenic composition comprises nucleic acid sequences encoding two or more amino acid sequences selected from the group consisting of SEQ ID NOs: 230 to 272.

In another aspect, the invention provides for an immunogenic peptide composition comprising one or more peptides selected from the group consisting of SEQ ID NOs: 230 to 272.

In some embodiments, the immunogenic peptide composition comprises two or more peptides selected from the group consisting of SEQ ID NOs: 230 to 272. In some embodiments, the one or more peptides is a modified or unmodified fragment of a mutated NRAS protein.

In another aspect, the invention provides for an immunogenic composition comprising nucleic acid sequences encoding one or more amino acid sequences selected from the group consisting of SEQ ID NOs: 273 to 322.

In some embodiments, the immunogenic composition comprises nucleic acid sequences encoding one or more amino acid sequences derived from a PIK3CA protein mutation. In some embodiments, the immunogenic composition comprises nucleic acid sequences encoding two or more amino acid sequences selected from the group consisting of SEQ ID NOs: 273 to 322.

In another aspect, the invention provides for an immunogenic peptide composition comprising one or more peptides selected from the group consisting of SEQ ID NOs: 273 to 322.

In some embodiments, the immunogenic peptide composition comprises two or more peptides selected from the group consisting of SEQ ID NOs: 273 to 322. In some embodiments, the one or more peptides is a modified or unmodified fragment of a mutated PIK3CA protein.

In another aspect, the invention provides for an immunogenic composition comprising nucleic acid sequences encoding one or more amino acid sequences selected from the group consisting of SEQ ID NOs: 323 to 353.

In some embodiments, the immunogenic composition comprises nucleic acid sequences encoding one or more amino acid sequences derived from a PTEN protein mutation. In some embodiments, the immunogenic composition comprises nucleic acid sequences encoding two or more amino acid sequences selected from the group consisting of SEQ ID NOs: 323 to 353.

In another aspect, the invention provides for an immunogenic peptide composition comprising one or more peptides selected from the group consisting of SEQ ID NOs: 323 to 353.

In some embodiments, the immunogenic peptide composition comprises two or more peptides selected from the group consisting of SEQ ID NOs: 323 to 353. In some embodiments, the one or more peptides is a modified or unmodified fragment of a mutated PTEN protein.

In another aspect, the invention provides for an immunogenic composition comprising nucleic acid sequences encoding one or more amino acid sequences selected from the group consisting of SEQ ID NOs: 354 to 458.

In some embodiments, the immunogenic composition comprises nucleic acid sequences encoding one or more amino acid sequences derived from a TP53 protein mutation. In some embodiments, the immunogenic composition comprises nucleic acid sequences encoding two or more amino acid sequences selected from the group consisting of SEQ ID NOs: 354 to 458.

In another aspect, the invention provides for an immunogenic peptide composition comprising one or more peptides selected from the group consisting of SEQ ID NOs: 354 to 458.

In some embodiments, the immunogenic peptide composition comprises two or more peptides selected from the group consisting of SEQ ID NOs: 354 to 458. In some embodiments, the one or more peptides is a modified or unmodified fragment of a mutated TP53 protein.

In another aspect, the invention provides for an immunogenic composition comprising nucleic acid sequences encoding one or more amino acid sequences selected from the group consisting of SEQ ID NOs: 141 to 272.

In some embodiments, the immunogenic composition comprises nucleic acid sequences encoding one or more amino acid sequences derived from a RAS protein mutation. In some embodiments, the immunogenic composition comprises nucleic acid sequences encoding two or more amino acid sequences selected from the group consisting of SEQ ID NOs: 141 to 272.

In another aspect, the invention provides for an immunogenic peptide composition comprising one or more peptides selected from the group consisting of SEQ ID NOs: 141 to 272.

In some embodiments, the immunogenic peptide composition comprises two or more peptides selected from the group consisting of SEQ ID NOs: 141 to 272. In some embodiments, the one or more peptides is a modified or unmodified fragment of a mutated RAS protein.

In another aspect, the invention provides for an immunogenic composition comprising nucleic acid sequences encoding one or more amino acid sequences selected from the group consisting of SEQ ID NOs: 19 to 33.

In some embodiments, the immunogenic composition comprises nucleic acid sequences encoding one or more amino acid sequences derived from a BRAF V600 protein mutation. In some embodiments, the immunogenic composition comprises nucleic acid sequences encoding two or more amino acid sequences selected from the group consisting of SEQ ID NOs: 19 to 33.

In another aspect, the invention provides for an immunogenic peptide composition comprising one or more peptides selected from the group consisting of SEQ ID NOs: 19 to 33.

In some embodiments, the immunogenic peptide composition comprises two or more peptides selected from the group consisting of SEQ ID NOs: 19 to 33. In some embodiments, the immunogenic peptide composition comprises a peptide derived from a BRAF V600 protein mutation.

In another aspect, the invention provides for an immunogenic composition comprising nucleic acid sequences encoding one or more amino acid sequences selected from the group consisting of SEQ ID NOs: 34 to 50.

In some embodiments, the immunogenic composition comprises nucleic acid sequences encoding one or more amino acid sequences derived from a BRAF V600M protein mutation. In some embodiments, the immunogenic composition comprises nucleic acid sequences encoding two or more amino acid sequences selected from the group consisting of SEQ ID NOs: 34 to 50.

In another aspect, the invention provides for an immunogenic peptide composition comprising one or more peptides selected from the group consisting of SEQ ID NOs: 34 to 50.

In some embodiments, the immunogenic peptide composition comprises two or more peptides selected from the group consisting of SEQ ID NOs: 34 to 50. In some embodiments, the immunogenic peptide composition comprises a peptide derived from a BRAF V600M protein mutation.

In another aspect, the invention provides for an immunogenic composition comprising nucleic acid sequences encoding one or more amino acid sequences selected from the group consisting of SEQ ID NOs: 51 to 66.

In some embodiments, the immunogenic composition comprises nucleic acid sequences encoding one or more amino acid sequences derived from a EGFR A289V protein mutation. In some embodiments, the immunogenic composition comprises nucleic acid sequences encoding two or more amino acid sequences selected from the group consisting of SEQ ID NOs: 51 to 66.

In another aspect, the invention provides for an immunogenic peptide composition comprising one or more peptides selected from the group consisting of SEQ ID NOs: 51 to 66.

In some embodiments, the immunogenic peptide composition comprises two or more peptides selected from the group consisting of SEQ ID NOs: 51 to 66. In some embodiments, the immunogenic peptide composition comprises a peptide derived from a EGFR A289V protein mutation.

In another aspect, the invention provides for an immunogenic composition comprising nucleic acid sequences encoding one or more amino acid sequences selected from the group consisting of SEQ ID NOs: 67 to 81.

In some embodiments, the immunogenic composition comprises nucleic acid sequences encoding one or more amino acid sequences derived from a EGFR G598V protein mutation. In some embodiments, the immunogenic composition comprises nucleic acid sequences encoding two or more amino acid sequences selected from the group consisting of SEQ ID NOs: 67 to 81.

In another aspect, the invention provides for an immunogenic peptide composition comprising one or more peptides selected from the group consisting of SEQ ID NOs: 67 to 81.

In some embodiments, the immunogenic peptide composition comprises two or more peptides selected from the group consisting of SEQ ID NOs: 67 to 81. In some embodiments, the immunogenic peptide composition comprises a peptide derived from a EGFR G598V protein mutation.

In another aspect, the invention provides for an immunogenic composition comprising nucleic acid sequences encoding one or more amino acid sequences selected from the group consisting of SEQ ID NOs: 82 to 98.

In some embodiments, the immunogenic composition comprises nucleic acid sequences encoding one or more amino acid sequences derived from a EGFR L858R protein mutation. In some embodiments, the immunogenic composition comprises nucleic acid sequences encoding two or more amino acid sequences selected from the group consisting of SEQ ID NOs: 82 to 98.

In another aspect, the invention provides for an immunogenic peptide composition comprising one or more peptides selected from the group consisting of SEQ ID NOs: 82 to 98.

In some embodiments, the immunogenic peptide composition comprises two or more peptides selected from the group consisting of SEQ ID NOs: 82 to 98. In some embodiments, the immunogenic peptide composition comprises a peptide derived from a EGFR L858R protein mutation.

In another aspect, the invention provides for an immunogenic composition comprising nucleic acid sequences encoding one or more amino acid sequences selected from the group consisting of SEQ ID NOs: 125 to 140.

In some embodiments, the immunogenic composition comprises nucleic acid sequences encoding one or more amino acid sequences derived from a IDH1 R132H protein mutation. In some embodiments, the immunogenic composition comprises nucleic acid sequences encoding two or more amino acid sequences selected from the group consisting of SEQ ID NOs: 125 to 140.

In another aspect, the invention provides for an immunogenic peptide composition comprising one or more peptides selected from the group consisting of SEQ ID NOs: 125 to 140.

In some embodiments, the immunogenic peptide composition comprises two or more peptides selected from the group consisting of SEQ ID NOs: 125 to 140. In some embodiments, the immunogenic peptide composition comprises a peptide derived from a IDH1 R132H protein mutation.

In another aspect, the invention provides for an immunogenic composition comprising nucleic acid sequences encoding one or more amino acid sequences selected from the group consisting of SEQ ID NOs: 119 to 124.

In some embodiments, the immunogenic composition comprises nucleic acid sequences encoding one or more amino acid sequences derived from a IDH1 R132C protein mutation. In some embodiments, the immunogenic composition comprises nucleic acid sequences encoding two or more amino acid sequences selected from the group consisting of SEQ ID NOs: 119 to 124.

In another aspect, the invention provides for an immunogenic peptide composition comprising one or more peptides selected from the group consisting of SEQ ID NOs: 119 to 124.

In some embodiments, the immunogenic peptide composition comprises two or more peptides selected from the group consisting of SEQ ID NOs: 119 to 124. In some embodiments, the immunogenic peptide composition comprises a peptide derived from a IDH1 R132C protein mutation.

In another aspect, the invention provides for an immunogenic composition comprising nucleic acid sequences encoding one or more amino acid sequences selected from the group consisting of SEQ ID NOs: 167 to 178.

In some embodiments, the immunogenic composition comprises nucleic acid sequences encoding one or more amino acid sequences derived from a KRAS G12D protein mutation. In some embodiments, the immunogenic composition comprises nucleic acid sequences encoding two or more amino acid sequences selected from the group consisting of SEQ ID NOs: 167 to 178.

In another aspect, the invention provides for an immunogenic peptide composition comprising one or more peptides selected from the group consisting of SEQ ID NOs: 167 to 178.

In some embodiments, the immunogenic peptide composition comprises two or more peptides selected from the group consisting of SEQ ID NOs: 167 to 178. In some embodiments, the immunogenic peptide composition comprises a peptide derived from a KRAS G12D protein mutation.

In another aspect, the invention provides for an immunogenic composition comprising nucleic acid sequences encoding one or more amino acid sequences selected from the group consisting of SEQ ID NOs: 203 to 213.

In some embodiments, the immunogenic composition comprises nucleic acid sequences encoding one or more amino acid sequences derived from a KRAS G12V protein mutation. In some embodiments, the immunogenic composition comprises nucleic acid sequences encoding two or more amino acid sequences selected from the group consisting of SEQ ID NOs: 203 to 213.

In another aspect, the invention provides for an immunogenic peptide composition comprising one or more peptides selected from the group consisting of SEQ ID NOs: 203 to 213.

In some embodiments, the immunogenic peptide composition comprises two or more peptides selected from the group consisting of SEQ ID NOs: 203 to 213. In some embodiments, the immunogenic peptide composition comprises a peptide derived from a KRAS G12V protein mutation.

In another aspect, the invention provides for an immunogenic composition comprising nucleic acid sequences encoding one or more amino acid sequences selected from the group consisting of SEQ ID NOs: 179 to 191.

In some embodiments, the immunogenic composition comprises nucleic acid sequences encoding one or more amino acid sequences derived from a KRAS G12R protein mutation. In some embodiments, the immunogenic composition comprises nucleic acid sequences encoding two or more amino acid sequences selected from the group consisting of SEQ ID NOs: 179 to 191.

In another aspect, the invention provides for an immunogenic peptide composition comprising one or more peptides selected from the group consisting of SEQ ID NOs: 179 to 191.

In some embodiments, the immunogenic peptide composition comprises two or more peptides selected from the group consisting of SEQ ID NOs: 179 to 191. In some embodiments, the immunogenic peptide composition comprises a peptide derived from a KRAS G12R protein mutation.

In another aspect, the invention provides for an immunogenic composition comprising nucleic acid sequences encoding one or more amino acid sequences selected from the group consisting of SEQ ID NOs: 154 to 166.

In some embodiments, the immunogenic composition comprises nucleic acid sequences encoding one or more amino acid sequences derived from a KRAS G12C protein mutation. In some embodiments, the immunogenic composition comprises nucleic acid sequences encoding two or more amino acid sequences selected from the group consisting of SEQ ID NOs: 154 to 166.

In another aspect, the invention provides for an immunogenic peptide composition comprising one or more peptides selected from the group consisting of SEQ ID NOs: 154 to 166.

In some embodiments, the immunogenic peptide composition comprises two or more peptides selected from the group consisting of SEQ ID NOs: 154 to 166. In some embodiments, the immunogenic peptide composition comprises a peptide derived from a KRAS G12C protein mutation.

In another aspect, the invention provides for an immunogenic composition comprising nucleic acid sequences encoding one or more amino acid sequences selected from the group consisting of SEQ ID NOs: 214 to 229.

In some embodiments, the immunogenic composition comprises nucleic acid sequences encoding one or more amino acid sequences derived from a KRAS G13D protein mutation. In some embodiments, the immunogenic composition comprises nucleic acid sequences encoding two or more amino acid sequences selected from the group consisting of SEQ ID NOs: 214 to 229.

In another aspect, the invention provides for an immunogenic peptide composition comprising one or more peptides selected from the group consisting of SEQ ID NOs: 214 to 229.

In some embodiments, the immunogenic peptide composition comprises two or more peptides selected from the group consisting of SEQ ID NOs: 214 to 229. In some embodiments, the immunogenic peptide composition comprises a peptide derived from a KRAS G13D protein mutation.

In another aspect, the invention provides for an immunogenic composition comprising nucleic acid sequences encoding one or more amino acid sequences selected from the group consisting of SEQ ID NOs: 141 to 153.

In some embodiments, the immunogenic composition comprises nucleic acid sequences encoding one or more amino acid sequences derived from a KRAS G12A protein mutation. In some embodiments, the immunogenic composition comprises nucleic acid sequences encoding two or more amino acid sequences selected from the group consisting of SEQ ID NOs: 141 to 153.

In another aspect, the invention provides for an immunogenic peptide composition comprising one or more peptides selected from the group consisting of SEQ ID NOs: 141 to 153.

In some embodiments, the immunogenic peptide composition comprises two or more peptides selected from the group consisting of SEQ ID NOs: 141 to 153. In some embodiments, the immunogenic peptide composition comprises a peptide derived from a KRAS G12A protein mutation.

In another aspect, the invention provides for an immunogenic composition comprising nucleic acid sequences encoding one or more amino acid sequences selected from the group consisting of SEQ ID NOs: 192 to 202.

In some embodiments, the immunogenic composition comprises nucleic acid sequences encoding one or more amino acid sequences derived from a KRAS G12S protein mutation. In some embodiments, the immunogenic composition comprises nucleic acid sequences encoding two or more amino acid sequences selected from the group consisting of SEQ ID NOs: 192 to 202.

In another aspect, the invention provides for an immunogenic peptide composition comprising one or more peptides selected from the group consisting of SEQ ID NOs: 192 to 202.

In some embodiments, the immunogenic peptide composition comprises two or more peptides selected from the group consisting of SEQ ID NOs: 192 to 202. In some embodiments, the immunogenic peptide composition comprises a peptide derived from a KRAS G12S protein mutation.

In another aspect, the invention provides for an immunogenic composition comprising nucleic acid sequences encoding one or more amino acid sequences selected from the group consisting of SEQ ID NOs: 256 to 272.

In some embodiments, the immunogenic composition comprises nucleic acid sequences encoding one or more amino acid sequences derived from a NRAS Q61R protein mutation. In some embodiments, the immunogenic composition comprises nucleic acid sequences encoding two or more amino acid sequences selected from the group consisting of SEQ ID NOs: 256 to 272.

In another aspect, the invention provides for an immunogenic peptide composition comprising one or more peptides selected from the group consisting of SEQ ID NOs: 256 to 272.

In some embodiments, the immunogenic peptide composition comprises two or more peptides selected from the group consisting of SEQ ID NOs: 256 to 272. In some embodiments, the immunogenic peptide composition comprises a peptide derived from a NRAS Q61R protein mutation.

In another aspect, the invention provides for an immunogenic composition comprising nucleic acid sequences encoding one or more amino acid sequences selected from the group consisting of SEQ ID NOs: 230 to 238.

In some embodiments, the immunogenic composition comprises nucleic acid sequences encoding one or more amino acid sequences derived from a NRAS Q61K protein mutation. In some embodiments, the immunogenic composition comprises nucleic acid sequences encoding two or more amino acid sequences selected from the group consisting of SEQ ID NOs: 230 to 238.

In another aspect, the invention provides for an immunogenic peptide composition comprising one or more peptides selected from the group consisting of SEQ ID NOs: 230 to 238.

In some embodiments, the immunogenic peptide composition comprises two or more peptides selected from the group consisting of SEQ ID NOs: 230 to 238. In some embodiments, the immunogenic peptide composition comprises a peptide derived from a NRAS Q61K protein mutation.

In another aspect, the invention provides for an immunogenic composition comprising nucleic acid sequences encoding one or more amino acid sequences selected from the group consisting of SEQ ID NOs: 239 to 255.

In some embodiments, the immunogenic composition comprises nucleic acid sequences encoding one or more amino acid sequences derived from a NRAS Q61L protein mutation. In some embodiments, the immunogenic composition comprises nucleic acid sequences encoding two or more amino acid sequences selected from the group consisting of SEQ ID NOs: 239 to 255.

In another aspect, the invention provides for an immunogenic peptide composition comprising one or more peptides selected from the group consisting of SEQ ID NOs: 239 to 255.

In some embodiments, the immunogenic peptide composition comprises two or more peptides selected from the group consisting of SEQ ID NOs: 239 to 255. In some embodiments, the immunogenic peptide composition comprises a peptide derived from a NRAS Q61L protein mutation.

In another aspect, the invention provides for an immunogenic composition comprising nucleic acid sequences encoding one or more amino acid sequences selected from the group consisting of SEQ ID NOs: 273 to 285.

In some embodiments, the immunogenic composition comprises nucleic acid sequences encoding one or more amino acid sequences derived from a PIK3CA E542K protein mutation. In some embodiments, the immunogenic composition comprises nucleic acid sequences encoding two or more amino acid sequences selected from the group consisting of SEQ ID NOs: 273 to 285.

In another aspect, the invention provides for an immunogenic peptide composition comprising one or more peptides selected from the group consisting of SEQ ID NOs: 273 to 285.

In some embodiments, the immunogenic peptide composition comprises two or more peptides selected from the group consisting of SEQ ID NOs: 273 to 285. In some embodiments, the immunogenic peptide composition comprises a peptide derived from a PIK3CA E542K protein mutation.

In another aspect, the invention provides for an immunogenic composition comprising nucleic acid sequences encoding one or more amino acid sequences selected from the group consisting of SEQ ID NOs: 286 to 293.

In some embodiments, the immunogenic composition comprises nucleic acid sequences encoding one or more amino acid sequences derived from a PIK3CA E545K protein mutation. In some embodiments, the immunogenic composition comprises nucleic acid sequences encoding two or more amino acid sequences selected from the group consisting of SEQ ID NOs: 286 to 293.

In another aspect, the invention provides for an immunogenic peptide composition comprising one or more peptides selected from the group consisting of SEQ ID NOs: 286 to 293.

In some embodiments, the immunogenic peptide composition comprises two or more peptides selected from the group consisting of SEQ ID NOs: 286 to 293. In some embodiments, the immunogenic peptide composition comprises a peptide derived from a PIK3CA E545K protein mutation.

In another aspect, the invention provides for an immunogenic composition comprising nucleic acid sequences encoding one or more amino acid sequences selected from the group consisting of SEQ ID NOs: 294 to 309.

In some embodiments, the immunogenic composition comprises nucleic acid sequences encoding one or more amino acid sequences derived from a PIK3CA H1047R protein mutation. In some embodiments, the immunogenic composition comprises nucleic acid sequences encoding two or more amino acid sequences selected from the group consisting of SEQ ID NOs: 294 to 309.

In another aspect, the invention provides for an immunogenic peptide composition comprising one or more peptides selected from the group consisting of SEQ ID NOs: 294 to 309.

In some embodiments, the immunogenic peptide composition comprises two or more peptides selected from the group consisting of SEQ ID NOs: 294 to 309. In some embodiments, the immunogenic peptide composition comprises a peptide derived from a PIK3CA H1047R protein mutation.

In another aspect, the invention provides for an immunogenic composition comprising nucleic acid sequences encoding one or more amino acid sequences selected from the group consisting of SEQ ID NOs: 359 to 374.

In some embodiments, the immunogenic composition comprises nucleic acid sequences encoding one or more amino acid sequences derived from a TP53 R158L protein mutation. In some embodiments, the immunogenic composition comprises nucleic acid sequences encoding two or more amino acid sequences selected from the group consisting of SEQ ID NOs: 359 to 374.

In another aspect, the invention provides for an immunogenic peptide composition comprising one or more peptides selected from the group consisting of SEQ ID NOs: 359 to 374.

In some embodiments, the immunogenic peptide composition comprises two or more peptides selected from the group consisting of SEQ ID NOs: 359 to 374. In some embodiments, the immunogenic peptide composition comprises a peptide derived from a TP53 R158L protein mutation.

In another aspect, the invention provides for an immunogenic composition comprising nucleic acid sequences encoding one or more amino acid sequences selected from the group consisting of SEQ ID NOs: 375 to 386.

In some embodiments, the immunogenic composition comprises nucleic acid sequences encoding one or more amino acid sequences derived from a TP53 R175H protein mutation. In some embodiments, the immunogenic composition comprises nucleic acid sequences encoding two or more amino acid sequences selected from the group consisting of SEQ ID NOs: 375 to 386.

In another aspect, the invention provides for an immunogenic peptide composition comprising one or more peptides selected from the group consisting of SEQ ID NOs: 375 to 386.

In some embodiments, the immunogenic peptide composition comprises two or more peptides selected from the group consisting of SEQ ID NOs: 375 to 386. In some embodiments, the immunogenic peptide composition comprises a peptide derived from a TP53 R175H protein mutation.

In another aspect, the invention provides for an immunogenic composition comprising nucleic acid sequences encoding one or more amino acid sequences selected from the group consisting of SEQ ID NOs: 387 to 401.

In some embodiments, the immunogenic composition comprises nucleic acid sequences encoding one or more amino acid sequences derived from a TP53 R248Q protein mutation. In some embodiments, the immunogenic composition comprises nucleic acid sequences encoding two or more amino acid sequences selected from the group consisting of SEQ ID NOs: 387 to 401.

In another aspect, the invention provides for an immunogenic peptide composition comprising one or more peptides selected from the group consisting of SEQ ID NOs: 387 to 401.

In some embodiments, the immunogenic peptide composition comprises two or more peptides selected from the group consisting of SEQ ID NOs: 387 to 401. In some embodiments, the immunogenic peptide composition comprises a peptide derived from a TP53 R248Q protein mutation.

In another aspect, the invention provides for an immunogenic composition comprising nucleic acid sequences encoding one or more amino acid sequences selected from the group consisting of SEQ ID NOs: 422 to 432.

In some embodiments, the immunogenic composition comprises nucleic acid sequences encoding one or more amino acid sequences derived from a TP53 R273C protein mutation. In some embodiments, the immunogenic composition comprises nucleic acid sequences encoding two or more amino acid sequences selected from the group consisting of SEQ ID NOs: 422 to 432.

In another aspect, the invention provides for an immunogenic peptide composition comprising one or more peptides selected from the group consisting of SEQ ID NOs: 422 to 432.

In some embodiments, the immunogenic peptide composition comprises two or more peptides selected from the group consisting of SEQ ID NOs: 422 to 432. In some embodiments, the immunogenic peptide composition comprises a peptide derived from a TP53 R273C protein mutation.

In another aspect, the invention provides for an immunogenic composition comprising nucleic acid sequences encoding one or more amino acid sequences selected from the group consisting of SEQ ID NOs: 433 to 446.

In some embodiments, the immunogenic composition comprises nucleic acid sequences encoding one or more amino acid sequences derived from a TP53 R273H protein mutation. In some embodiments, the immunogenic composition comprises nucleic acid sequences encoding two or more amino acid sequences selected from the group consisting of SEQ ID NOs: 433 to 446.

In another aspect, the invention provides for an immunogenic peptide composition comprising one or more peptides selected from the group consisting of SEQ ID NOs: 433 to 446.

In some embodiments, the immunogenic peptide composition comprises two or more peptides selected from the group consisting of SEQ ID NOs: 433 to 446. In some embodiments, the immunogenic peptide composition comprises a peptide derived from a TP53 R273H protein mutation.

In another aspect, the invention provides for an immunogenic composition comprising nucleic acid sequences encoding one or more amino acid sequences selected from the group consisting of SEQ ID NOs: 402 to 421.

In some embodiments, the immunogenic composition comprises nucleic acid sequences encoding one or more amino acid sequences derived from a TP53 R248W protein mutation. In some embodiments, the immunogenic composition comprises nucleic acid sequences encoding two or more amino acid sequences selected from the group consisting of SEQ ID NOs: 402 to 421.

In another aspect, the invention provides for an immunogenic peptide composition comprising one or more peptides selected from the group consisting of SEQ ID NOs: 402 to 421.

In some embodiments, the immunogenic peptide composition comprises two or more peptides selected from the group consisting of SEQ ID NOs: 402 to 421. In some embodiments, the immunogenic peptide composition comprises a peptide derived from a TP53 R248W protein mutation.

In another aspect, the invention provides for an immunogenic composition comprising nucleic acid sequences encoding one or more amino acid sequences selected from the group consisting of SEQ ID NOs: 447 to 449.

In some embodiments, the immunogenic composition comprises nucleic acid sequences encoding one or more amino acid sequences derived from a TP53 R282W protein mutation. In some embodiments, the immunogenic composition comprises nucleic acid sequences encoding two or more amino acid sequences selected from the group consisting of SEQ ID NOs: 447 to 449.

In another aspect, the invention provides for an immunogenic peptide composition comprising one or more peptides selected from the group consisting of SEQ ID NOs: 447 to 449.

In some embodiments, the immunogenic peptide composition comprises two or more peptides selected from the group consisting of SEQ ID NOs: 447 to 449. In some embodiments, the immunogenic peptide composition comprises a peptide derived from a TP53 R282W protein mutation.

In another aspect, the invention provides for an immunogenic composition comprising nucleic acid sequences encoding one or more amino acid sequences selected from the group consisting of SEQ ID NOs: 450 to 458.

In some embodiments, the immunogenic composition comprises nucleic acid sequences encoding one or more amino acid sequences derived from a TP53 Y220C protein mutation. In some embodiments, the immunogenic composition comprises nucleic acid sequences encoding two or more amino acid sequences selected from the group consisting of SEQ ID NOs: 450 to 458.

In another aspect, the invention provides for an immunogenic peptide composition comprising one or more peptides selected from the group consisting of SEQ ID NOs: 450 to 458.

In some embodiments, the immunogenic peptide composition comprises two or more peptides selected from the group consisting of SEQ ID NOs: 450 to 458. In some embodiments, the immunogenic peptide composition comprises a peptide derived from a TP53 Y220C protein mutation.

In another aspect, the invention provides for an immunogenic composition comprising nucleic acid sequences encoding one or more amino acid sequences selected from the group consisting of SEQ ID NOs: 310 to 322.

In some embodiments, the immunogenic composition comprises nucleic acid sequences encoding one or more amino acid sequences derived from a PIK3CA R88Q protein mutation. In some embodiments, the immunogenic composition comprises nucleic acid sequences encoding two or more amino acid sequences selected from the group consisting of SEQ ID NOs: 310 to 322.

In another aspect, the invention provides for an immunogenic peptide composition comprising one or more peptides selected from the group consisting of SEQ ID NOs: 310 to 322.

In some embodiments, the immunogenic peptide composition comprises two or more peptides selected from the group consisting of SEQ ID NOs: 310 to 322. In some embodiments, the immunogenic peptide composition comprises a peptide derived from a PIK3CA R88Q protein mutation.

In another aspect, the invention provides for an immunogenic composition comprising nucleic acid sequences encoding one or more amino acid sequences selected from the group consisting of SEQ ID NOs: 99 to 118.

In some embodiments, the immunogenic composition comprises nucleic acid sequences encoding one or more amino acid sequences derived from a GTF2I L424H protein mutation. In some embodiments, the immunogenic composition comprises nucleic acid sequences encoding two or more amino acid sequences selected from the group consisting of SEQ ID NOs: 99 to 118.

In another aspect, the invention provides for an immunogenic peptide composition comprising one or more peptides selected from the group consisting of SEQ ID NOs: 99 to 118.

In some embodiments, the immunogenic peptide composition comprises two or more peptides selected from the group consisting of SEQ ID NOs: 99 to 118. In some embodiments, the immunogenic peptide composition comprises a peptide derived from a GTF2I L424H protein mutation.

In another aspect, the invention provides for an immunogenic composition comprising nucleic acid sequences encoding one or more amino acid sequences selected from the group consisting of SEQ ID NOs: 338 to 353.

In some embodiments, the immunogenic composition comprises nucleic acid sequences encoding one or more amino acid sequences derived from a PTEN R130Q protein mutation. In some embodiments, the immunogenic composition comprises nucleic acid sequences encoding two or more amino acid sequences selected from the group consisting of SEQ ID NOs: 338 to 353.

In another aspect, the invention provides for an immunogenic peptide composition comprising one or more peptides selected from the group consisting of SEQ ID NOs: 338 to 353.

In some embodiments, the immunogenic peptide composition comprises two or more peptides selected from the group consisting of SEQ ID NOs: 338 to 353. In some embodiments, the immunogenic peptide composition comprises a peptide derived from a PTEN R130Q protein mutation.

In another aspect, the invention provides for an immunogenic composition comprising nucleic acid sequences encoding one or more amino acid sequences selected from the group consisting of SEQ ID NOs: 1 to 18.

In some embodiments, the immunogenic composition comprises nucleic acid sequences encoding one or more amino acid sequences derived from a AKT1 E17K protein mutation. In some embodiments, the immunogenic composition comprises nucleic acid sequences encoding two or more amino acid sequences selected from the group consisting of SEQ ID NOs: 1 to 18.

In another aspect, the invention provides for an immunogenic peptide composition comprising one or more peptides selected from the group consisting of SEQ ID NOs: 1 to 18.

In some embodiments, the immunogenic peptide composition comprises two or more peptides selected from the group consisting of SEQ ID NOs: 1 to 18. In some embodiments, the immunogenic peptide composition comprises a peptide derived from a AKT1 E17K protein mutation.

In another aspect, the invention provides for an immunogenic composition comprising nucleic acid sequences encoding one or more amino acid sequences selected from the group consisting of SEQ ID NOs: 323 to 337.

In some embodiments, the immunogenic composition comprises nucleic acid sequences encoding one or more amino acid sequences derived from a PTEN R130G protein mutation. In some embodiments, the immunogenic composition comprises nucleic acid sequences encoding two or more amino acid sequences selected from the group consisting of SEQ ID NOs: 323 to 337.

In another aspect, the invention provides for an immunogenic peptide composition comprising one or more peptides selected from the group consisting of SEQ ID NOs: 323 to 337.

In some embodiments, the immunogenic peptide composition comprises two or more peptides selected from the group consisting of SEQ ID NOs: 323 to 337. In some embodiments, the immunogenic peptide composition comprises a peptide derived from a PTEN R130G protein mutation.

In another aspect, the invention provides for an immunogenic composition comprising nucleic acid sequences encoding one or more amino acid sequences selected from the group consisting of SEQ ID NOs: 354 to 358.

In some embodiments, the immunogenic composition comprises nucleic acid sequences encoding one or more amino acid sequences derived from a TP53 H179R protein mutation. In some embodiments, the immunogenic composition comprises nucleic acid sequences encoding two or more amino acid sequences selected from the group consisting of SEQ ID NOs: 354 to 358.

In another aspect, the invention provides for an immunogenic peptide composition comprising one or more peptides selected from the group consisting of SEQ ID NOs: 354 to 358.

In some embodiments, the immunogenic peptide composition comprises two or more peptides selected from the group consisting of SEQ ID NOs: 354 to 358. In some embodiments, the immunogenic peptide composition comprises a peptide derived from a TP53 H179R protein mutation.

In another aspect, the invention provides for an immunogenic composition comprising nucleic acid sequences encoding one or more amino acid sequences selected from the group consisting of SEQ ID NOs: 168 to 169, SEQ ID NO: 171, SEQ ID NOs: 179 to 180, SEQ ID NOs: 182 to 183, SEQ ID NOs: 203 to 204, and SEQ ID NO: 207.

In some embodiments, the immunogenic composition comprises nucleic acid sequences encoding two or more amino acid sequences selected from the group consisting of SEQ ID NOs: 168 to 169, SEQ ID NO: 171, SEQ ID NOs: 179 to 180, SEQ ID NOs: 182 to 183, SEQ ID NOs: 203 to 204, and SEQ ID NO: 207. In some embodiments, the nucleic acid sequences are administered in a construct for expression in vivo. In some embodiments, the in vivo administration of the nucleic acid sequences is configured to produce one or more peptides that is displayed by an HLA class I molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is pancreatic cancer.

In another aspect, the invention provides for a method of treating or preventing pancreatic cancer by administering to a subject an immunogenic composition comprising nucleic acid sequences encoding one or more amino acid sequences selected from the group consisting of SEQ ID NOs: 168 to 169, SEQ ID NO: 171, SEQ ID NOs: 179 to 180, SEQ ID NOs: 182 to 183, SEQ ID NOs: 203 to 204, and SEQ ID NO: 207.

In some embodiments, the immunogenic composition comprises nucleic acid sequences encoding two or more amino acid sequences selected from the group consisting of SEQ ID NOs: 168 to 169, SEQ ID NO: 171, SEQ ID NOs: 179 to 180, SEQ ID NOs: 182 to 183, SEQ ID NOs: 203 to 204, and SEQ ID NO: 207.

In another aspect, the invention provides for an immunogenic peptide composition comprising one or more peptides selected from the group consisting of SEQ ID NOs: 168 to 169, SEQ ID NO: 171, SEQ ID NOs: 179 to 180, SEQ ID NOs: 182 to 183, SEQ ID NOs: 203 to 204, and SEQ ID NO: 207.

In some embodiments, the immunogenic peptide composition comprises two or more peptides selected from the group consisting of SEQ ID NOs: 168 to 169, SEQ ID NO: 171, SEQ ID NOs: 179 to 180, SEQ ID NOs: 182 to 183, SEQ ID NOs: 203 to 204, and SEQ ID NO: 207. In some embodiments, a peptide in the immunogenic peptide composition is displayed by an HLA class I molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is pancreatic cancer.

In another aspect, the invention provides for a method of treating or preventing pancreatic cancer in a subject comprising administering to the subject an immunogenic peptide composition comprising one or more peptides selected from the group consisting of SEQ ID NOs: 168 to 169, SEQ ID NO: 171, SEQ ID NOs: 179 to 180, SEQ ID NOs: 182 to 183, SEQ ID NOs: 203 to 204, and SEQ ID NO: 207.

In some embodiments, the immunogenic peptide composition comprises two or more peptides selected from the group consisting of SEQ ID NOs: 168 to 169, SEQ ID NO: 171, SEQ ID NOs: 179 to 180, SEQ ID NOs: 182 to 183, SEQ ID NOs: 203 to 204, and SEQ ID NO: 207.

In another aspect, the invention provides for an immunogenic composition comprising nucleic acid sequences encoding one or more amino acid sequences selected from the group consisting of SEQ ID NOs: 19 to 23, SEQ ID NOs: 34 to 40, SEQ ID NOs: 230 to 231, SEQ ID NO: 239, SEQ ID NOs: 241 to 242, and SEQ ID NOs: 260 to 262.

In some embodiments, the immunogenic composition comprises nucleic acid sequences encoding two or more amino acid sequences selected from the group consisting of SEQ ID NOs: 19 to 23, SEQ ID NOs: 34 to 40, SEQ ID NOs: 230 to 231, SEQ ID NO: 239, SEQ ID NOs: 241 to 242, and SEQ ID NOs: 260 to 262. In some embodiments, the nucleic acid sequences are administered in a construct for expression in vivo. In some embodiments, the in vivo administration of the nucleic acid sequences is configured to produce one or more peptides that is displayed by an HLA class I molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1

R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is skin cancer.

In another aspect, the invention provides for a method of treating or preventing skin cancer by administering to a subject an immunogenic composition comprising nucleic acid sequences encoding one or more amino acid sequences selected from the group consisting of SEQ ID NOs: 19 to 23, SEQ ID NOs: 34 to 40, SEQ ID NOs: 230 to 231, SEQ ID NO: 239, SEQ ID NOs: 241 to 242, and SEQ ID NOs: 260 to 262.

In some embodiments, the immunogenic composition comprises nucleic acid sequences encoding two or more amino acid sequences selected from the group consisting of SEQ ID NOs: 19 to 23, SEQ ID NOs: 34 to 40, SEQ ID NOs: 230 to 231, SEQ ID NO: 239, SEQ ID NOs: 241 to 242, and SEQ ID NOs: 260 to 262.

In another aspect, the invention provides for an immunogenic peptide composition comprising one or more peptides selected from the group consisting of SEQ ID NOs: 19 to 23, SEQ ID NOs: 34 to 40, SEQ ID NOs: 230 to 231, SEQ ID NO: 239, SEQ ID NOs: 241 to 242, and SEQ ID NOs: 260 to 262.

In some embodiments, the immunogenic peptide composition comprises two or more peptides selected from the group consisting of SEQ ID NOs: 19 to 23, SEQ ID NOs: 34 to 40, SEQ ID NOs: 230 to 231, SEQ ID NO: 239, SEQ ID NOs: 241 to 242, and SEQ ID NOs: 260 to 262. In some embodiments, a peptide in the immunogenic peptide composition is displayed by an HLA class I molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is skin cancer.

In another aspect, the invention provides for a method of treating or preventing skin cancer in a subject comprising administering to the subject an immunogenic peptide composition comprising one or more peptides selected from the group consisting of SEQ ID NOs: 19 to 23, SEQ ID NOs: 34 to 40, SEQ ID NOs: 230 to 231, SEQ ID NO: 239, SEQ ID NOs: 241 to 242, and SEQ ID NOs: 260 to 262.

In some embodiments, the immunogenic peptide composition comprises two or more peptides selected from the group consisting of SEQ ID NOs: 19 to 23, SEQ ID NOs: 34 to 40, SEQ ID NOs: 230 to 231, SEQ ID NO: 239, SEQ ID NOs: 241 to 242, and SEQ ID NOs: 260 to 262.

In another aspect, the invention provides for an immunogenic composition comprising nucleic acid sequences encoding one or more amino acid sequences selected from the group consisting of SEQ ID NOs: 19 to 23, SEQ ID NOs: 230 to 231, and SEQ ID NOs: 260 to 262.

In some embodiments, the immunogenic composition comprises nucleic acid sequences encoding two or more amino acid sequences selected from the group consisting of SEQ ID NOs: 19 to 23, SEQ ID NOs: 230 to 231, and SEQ ID NOs: 260 to 262. In some embodiments, the nucleic acid sequences are administered in a construct for expression in vivo. In some embodiments, the in vivo administration of the nucleic acid sequences is configured to produce one or more peptides that is displayed by an HLA class I molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is thyroid cancer.

In another aspect, the invention provides for a method of treating or preventing thyroid cancer by administering to a subject an immunogenic composition comprising nucleic acid sequences encoding one or more amino acid sequences selected from the group consisting of SEQ ID NOs: 19 to 23, SEQ ID NOs: 230 to 231, and SEQ ID NOs: 260 to 262.

In some embodiments, the immunogenic composition comprises nucleic acid sequences encoding two or more amino acid sequences selected from the group consisting of SEQ ID NOs: 19 to 23, SEQ ID NOs: 230 to 231, and SEQ ID NOs: 260 to 262.

In another aspect, the invention provides for an immunogenic peptide composition comprising one or more peptides selected from the group consisting of SEQ ID NOs: 19 to 23, SEQ ID NOs: 230 to 231, and SEQ ID NOs: 260 to 262.

In some embodiments, the immunogenic peptide composition comprises two or more peptides selected from the group consisting of SEQ ID NOs: 19 to 23, SEQ ID NOs: 230 to 231, and SEQ ID NOs: 260 to 262. In some embodiments, a peptide in the immunogenic peptide composition is displayed by an HLA class I molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is thyroid cancer.

In another aspect, the invention provides for a method of treating or preventing thyroid cancer in a subject comprising administering to the subject an immunogenic peptide composition comprising one or more peptides selected from the group consisting of SEQ ID NOs: 19 to 23, SEQ ID NOs: 230 to 231, and SEQ ID NOs: 260 to 262.

In some embodiments, the immunogenic peptide composition comprises two or more peptides selected from the group consisting of SEQ ID NOs: 19 to 23, SEQ ID NOs: 230 to 231, and SEQ ID NOs: 260 to 262.

In another aspect, the invention provides for an immunogenic composition comprising nucleic acid sequences encoding one or more amino acid sequences selected from the group consisting of SEQ ID NOs: 51 to 55, SEQ ID NOs: 67 to 70, SEQ ID NOs: 72 to 73, SEQ ID NOs: 119 to 120, SEQ ID NOs: 125 to 130, SEQ ID NO: 375, SEQ ID NO: 423, and SEQ ID NO: 425.

In some embodiments, the immunogenic composition comprises nucleic acid sequences encoding two or more amino acid sequences selected from the group consisting of SEQ ID NOs: 51 to 55, SEQ ID NOs: 67 to 70, SEQ ID NOs: 72 to 73, SEQ ID NOs: 119 to 120, SEQ ID NOs: 125 to 130, SEQ ID NO: 375, SEQ ID NO: 423, and SEQ ID NO: 425. In some embodiments, the nucleic acid sequences are administered in a construct for expression in vivo. In some embodiments, the in vivo administration of the nucleic acid sequences is configured to produce one or more peptides that is displayed by an HLA class I molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is brain cancer.

In another aspect, the invention provides for a method of treating or preventing brain cancer by administering to a subject an immunogenic composition comprising nucleic acid sequences encoding one or more amino acid sequences selected from the group consisting of SEQ ID NOs: 51 to 55, SEQ ID NOs: 67 to 70, SEQ ID NOs: 72 to 73, SEQ ID NOs: 119 to 120, SEQ ID NOs: 125 to 130, SEQ ID NO: 375, SEQ ID NO: 423, and SEQ ID NO: 425.

In some embodiments, the immunogenic composition comprises nucleic acid sequences encoding two or more amino acid sequences selected from the group consisting of SEQ ID NOs: 51 to 55, SEQ ID NOs: 67 to 70, SEQ ID NOs: 72 to 73, SEQ ID NOs: 119 to 120, SEQ ID NOs: 125 to 130, SEQ ID NO: 375, SEQ ID NO: 423, and SEQ ID NO: 425.

In another aspect, the invention provides for an immunogenic peptide composition comprising one or more peptides selected from the group consisting of SEQ ID NOs: 51 to 55, SEQ ID NOs: 67 to 70, SEQ ID NOs: 72 to 73, SEQ ID NOs: 119 to 120, SEQ ID NOs: 125 to 130, SEQ ID NO: 375, SEQ ID NO: 423, and SEQ ID NO: 425.

In some embodiments, the immunogenic peptide composition comprises two or more peptides selected from the group consisting of SEQ ID NOs: 51 to 55, SEQ ID NOs: 67 to 70, SEQ ID NOs: 72 to 73, SEQ ID NOs: 119 to 120, SEQ ID NOs: 125 to 130, SEQ ID NO: 375, SEQ ID NO: 423, and SEQ ID NO: 425. In some embodiments, a peptide in the immunogenic peptide composition is displayed by an HLA class I molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is brain cancer.

In another aspect, the invention provides for a method of treating or preventing brain cancer in a subject comprising administering to the subject an immunogenic peptide composition comprising one or more peptides selected from the group consisting of SEQ ID NOs: 51 to 55, SEQ ID NOs: 67 to 70, SEQ ID NOs: 72 to 73, SEQ ID NOs: 119 to 120, SEQ ID NOs: 125 to 130, SEQ ID NO: 375, SEQ ID NO: 423, and SEQ ID NO: 425.

In some embodiments, the immunogenic peptide composition comprises two or more peptides selected from the group consisting of SEQ ID NOs: 51 to 55, SEQ ID NOs: 67 to 70, SEQ ID NOs: 72 to 73, SEQ ID NOs: 119 to 120, SEQ ID NOs: 125 to 130, SEQ ID NO: 375, SEQ ID NO: 423, and SEQ ID NO: 425.

In another aspect, the invention provides for an immunogenic composition comprising nucleic acid sequences encoding one or more amino acid sequences selected from the group consisting of SEQ ID NOs: 20 to 23, SEQ ID NOs: 167 to 169, SEQ ID NO: 171, SEQ ID NOs: 203 to 207, SEQ ID NOs: 215 to 217, and SEQ ID NO: 288.

In some embodiments, the immunogenic composition comprises nucleic acid sequences encoding two or more amino acid sequences selected from the group consisting of SEQ ID NOs: 20 to 23, SEQ ID NOs: 167 to 169, SEQ ID NO: 171, SEQ ID NOs: 203 to 207, SEQ ID NOs: 215 to 217, and SEQ ID NO: 288. In some embodiments, the nucleic acid sequences are administered in a construct for expression in vivo. In some embodiments, the in vivo administration of the nucleic acid sequences is configured to produce one or more peptides that is displayed by an HLA class I molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is colorectal cancer.

In another aspect, the invention provides for a method of treating or preventing colorectal cancer by administering to a subject an immunogenic composition comprising nucleic acid sequences encoding one or more amino acid sequences selected from the group consisting of SEQ ID NOs: 20 to 23, SEQ ID NOs: 167 to 169, SEQ ID NO: 171, SEQ ID NOs: 203 to 207, SEQ ID NOs: 215 to 217, and SEQ ID NO: 288.

In some embodiments, the immunogenic composition comprises nucleic acid sequences encoding two or more amino acid sequences selected from the group consisting of SEQ ID NOs: 20 to 23, SEQ ID NOs: 167 to 169, SEQ ID NO: 171, SEQ ID NOs: 203 to 207, SEQ ID NOs: 215 to 217, and SEQ ID NO: 288.

In another aspect, the invention provides for an immunogenic peptide composition comprising one or more peptides selected from the group consisting of SEQ ID NOs: 20 to 23, SEQ ID NOs: 167 to 169, SEQ ID NO: 171, SEQ ID NOs: 203 to 207, SEQ ID NOs: 215 to 217, and SEQ ID NO: 288.

In some embodiments, the immunogenic peptide composition comprises two or more peptides selected from the group consisting of SEQ ID NOs: 20 to 23, SEQ ID NOs: 167 to 169, SEQ ID NO: 171, SEQ ID NOs: 203 to 207, SEQ ID NOs: 215 to 217, and SEQ ID NO: 288. In some embodiments, a peptide in the immunogenic peptide composition is displayed by an HLA class I molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is colorectal cancer.

In another aspect, the invention provides for a method of treating or preventing colorectal cancer in a subject comprising administering to the subject an immunogenic peptide composition comprising one or more peptides selected from the group consisting of SEQ ID NOs: 20 to 23, SEQ ID NOs: 167 to 169, SEQ ID NO: 171, SEQ ID NOs: 203 to 207, SEQ ID NOs: 215 to 217, and SEQ ID NO: 288.

In some embodiments, the immunogenic peptide composition comprises two or more peptides selected from the group consisting of SEQ ID NOs: 20 to 23, SEQ ID NOs: 167 to 169, SEQ ID NO: 171, SEQ ID NOs: 203 to 207, SEQ ID NOs: 215 to 217, and SEQ ID NO: 288.

In another aspect, the invention provides for an immunogenic composition comprising nucleic acid sequences encoding one or more amino acid sequences selected from the group consisting of SEQ ID NOs: 82 to 86, SEQ ID NOs: 141 to 144, SEQ ID NOs: 154 to 159, SEQ ID NOs: 168 to 169, SEQ ID NO: 171, SEQ ID NOs: 203 to 204, SEQ ID NO: 207, SEQ ID NOs: 274 to 276, SEQ ID NO: 288, SEQ ID NO: 359, and SEQ ID NOs: 362 to 364.

In some embodiments, the immunogenic composition comprises nucleic acid sequences encoding two or more amino acid sequences selected from the group consisting of SEQ ID NOs: 82 to 86, SEQ ID NOs: 141 to 144, SEQ ID NOs: 154 to 159, SEQ ID NOs: 168 to 169, SEQ ID NO: 171, SEQ ID NOs: 203 to 204, SEQ ID NO: 207, SEQ ID NOs: 274 to 276, SEQ ID NO: 288, SEQ ID NO: 359, and SEQ ID NOs: 362 to 364. In some embodiments, the nucleic acid sequences are administered in a construct for expression in vivo. In some embodiments, the in vivo administration of the nucleic acid sequences is configured to produce one or more peptides that is displayed by an HLA class I molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is bronchus and lung cancer.

In another aspect, the invention provides for a method of treating or preventing bronchus and lung cancer by administering to a subject an immunogenic composition comprising nucleic acid sequences encoding one or more amino acid sequences selected from the group consisting of SEQ ID NOs: 82 to 86, SEQ ID NOs: 141 to 144, SEQ ID NOs: 154 to 159, SEQ ID NOs: 168 to 169, SEQ ID NO: 171, SEQ ID NOs: 203 to 204, SEQ ID NO: 207, SEQ ID NOs: 274 to 276, SEQ ID NO: 288, SEQ ID NO: 359, and SEQ ID NOs: 362 to 364.

In some embodiments, the immunogenic composition comprises nucleic acid sequences encoding two or more amino acid sequences selected from the group consisting of SEQ ID NOs: 82 to 86, SEQ ID NOs: 141 to 144, SEQ ID NOs: 154 to 159, SEQ ID NOs: 168 to 169, SEQ ID NO: 171, SEQ ID NOs: 203 to 204, SEQ ID NO: 207, SEQ ID NOs: 274 to 276, SEQ ID NO: 288, SEQ ID NO: 359, and SEQ ID NOs: 362 to 364.

In another aspect, the invention provides for an immunogenic peptide composition comprising one or more peptides selected from the group consisting of SEQ ID NOs: 82 to 86, SEQ ID NOs: 141 to 144, SEQ ID NOs: 154 to 159, SEQ ID NOs: 168 to 169, SEQ ID NO: 171, SEQ ID NOs: 203 to 204, SEQ ID NO: 207, SEQ ID NOs: 274 to 276, SEQ ID NO: 288, SEQ ID NO: 359, and SEQ ID NOs: 362 to 364.

In some embodiments, the immunogenic peptide composition comprises two or more peptides selected from the group consisting of SEQ ID NOs: 82 to 86, SEQ ID NOs: 141 to 144, SEQ ID NOs: 154 to 159, SEQ ID NOs: 168 to 169, SEQ ID NO: 171, SEQ ID NOs: 203 to 204, SEQ ID NO: 207, SEQ ID NOs: 274 to 276, SEQ ID NO: 288, SEQ ID NO: 359, and SEQ ID NOs: 362 to 364. In some embodiments, a peptide in the immunogenic peptide composition is displayed by an HLA class I molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is bronchus and lung cancer.

In another aspect, the invention provides for a method of treating or preventing bronchus and lung cancer in a subject comprising administering to the subject an immunogenic peptide composition comprising one or more peptides selected from the group consisting of SEQ ID NOs: 82 to 86, SEQ ID NOs: 141 to 144, SEQ ID NOs: 154 to 159, SEQ ID NOs: 168 to 169, SEQ ID NO: 171, SEQ ID NOs: 203 to 204, SEQ ID NO: 207, SEQ ID NOs: 274 to 276, SEQ ID NO: 288, SEQ ID NO: 359, and SEQ ID NOs: 362 to 364.

In some embodiments, the immunogenic peptide composition comprises two or more peptides selected from the group consisting of SEQ ID NOs: 82 to 86, SEQ ID NOs: 141 to 144, SEQ ID NOs: 154 to 159, SEQ ID NOs: 168 to 169, SEQ ID NO: 171, SEQ ID NOs: 203 to 204, SEQ ID NO: 207, SEQ ID NOs: 274 to 276, SEQ ID NO: 288, SEQ ID NO: 359, and SEQ ID NOs: 362 to 364.

In another aspect, the invention provides for an immunogenic composition comprising nucleic acid sequences encoding one or more amino acid sequences selected from the group consisting of SEQ ID NOs: 273 to 309, SEQ ID NOs: 375 to 386, and SEQ ID NOs: 422 to 446.

In some embodiments, the immunogenic composition comprises nucleic acid sequences encoding two or more amino acid sequences selected from the group consisting of SEQ ID NOs: 273 to 309, SEQ ID NOs: 375 to 386, and SEQ ID NOs: 422 to 446. In some embodiments, the nucleic acid sequences are administered in a construct for expression in vivo. In some embodiments, the in vivo administration of the nucleic acid sequences is configured to produce one or more peptides that is displayed by an HLA class I molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is breast cancer.

In another aspect, the invention provides for a method of treating or preventing breast cancer by administering to a subject an immunogenic composition comprising nucleic acid sequences encoding one or more amino acid sequences selected from the group consisting of SEQ ID NOs: 273 to 309, SEQ ID NOs: 375 to 386, and SEQ ID NOs: 422 to 446.

In some embodiments, the immunogenic composition comprises nucleic acid sequences encoding two or more amino acid sequences selected from the group consisting of SEQ ID NOs: 273 to 309, SEQ ID NOs: 375 to 386, and SEQ ID NOs: 422 to 446.

In another aspect, the invention provides for an immunogenic peptide composition comprising one or more peptides selected from the group consisting of SEQ ID NOs: 273 to 309, SEQ ID NOs: 375 to 386, and SEQ ID NOs: 422 to 446.

In some embodiments, the immunogenic peptide composition comprises two or more peptides selected from the group consisting of SEQ ID NOs: 273 to 309, SEQ ID NOs: 375 to 386, and SEQ ID NOs: 422 to 446. In some embodiments, a peptide in the immunogenic peptide composition is displayed by an HLA class I molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is breast cancer.

In another aspect, the invention provides for a method of treating or preventing breast cancer in a subject comprising administering to the subject an immunogenic peptide composition comprising one or more peptides selected from the group consisting of SEQ ID NOs: 273 to 309, SEQ ID NOs: 375 to 386, and SEQ ID NOs: 422 to 446.

In some embodiments, the immunogenic peptide composition comprises two or more peptides selected from the group consisting of SEQ ID NOs: 273 to 309, SEQ ID NOs: 375 to 386, and SEQ ID NOs: 422 to 446.

In another aspect, the invention provides for an immunogenic composition comprising nucleic acid sequences encoding one or more amino acid sequences selected from the group consisting of SEQ ID NOs: 273 to 309, SEQ ID NOs: 375 to 386, and SEQ ID NOs: 422 to 446.

In some embodiments, the immunogenic composition comprises nucleic acid sequences encoding two or more amino acid sequences selected from the group consisting of SEQ ID NOs: 273 to 309, SEQ ID NOs: 375 to 386, and SEQ ID NOs: 422 to 446. In some embodiments, the nucleic acid sequences are administered in a construct for expression in vivo. In some embodiments, the in vivo administration of the nucleic acid sequences is configured to produce one or more peptides that is displayed by an HLA class I molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is ovarian cancer.

In another aspect, the invention provides for a method of treating or preventing ovarian cancer by administering to a subject an immunogenic composition comprising nucleic acid sequences encoding one or more amino acid sequences selected from the group consisting of SEQ ID NOs: 273 to 309, SEQ ID NOs: 375 to 386, and SEQ ID NOs: 422 to 446.

In some embodiments, the immunogenic composition comprises nucleic acid sequences encoding two or more amino acid sequences selected from the group consisting of SEQ ID NOs: 273 to 309, SEQ ID NOs: 375 to 386, and SEQ ID NOs: 422 to 446.

In another aspect, the invention provides for an immunogenic peptide composition comprising one or more peptides selected from the group consisting of SEQ ID NOs: 273 to 309, SEQ ID NOs: 375 to 386, and SEQ ID NOs: 422 to 446.

In some embodiments, the immunogenic peptide composition comprises two or more peptides selected from the group consisting of SEQ ID NOs: 273 to 309, SEQ ID NOs: 375 to 386, and SEQ ID NOs: 422 to 446. In some embodiments, a peptide in the immunogenic peptide composition is displayed by an HLA class I molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is ovarian cancer.

In another aspect, the invention provides for a method of treating or preventing ovarian cancer in a subject comprising administering to the subject an immunogenic peptide composition comprising one or more peptides selected from the group consisting of SEQ ID NOs: 273 to 309, SEQ ID NOs: 375 to 386, and SEQ ID NOs: 422 to 446.

In some embodiments, the immunogenic peptide composition comprises two or more peptides selected from the group consisting of SEQ ID NOs: 273 to 309, SEQ ID NOs: 375 to 386, and SEQ ID NOs: 422 to 446.

In one aspect, the invention provides for nucleic acid sequences encoding one or more amino acid sequences selected from the group consisting of SEQ ID NOs: 475 to 759.

In some embodiments, the nucleic acid sequences encode two or more amino acid sequences selected from the group consisting of SEQ ID NOs: 475 to 759.

In another aspect, the invention provides for an immunogenic composition comprising nucleic acid sequences encoding one or more amino acid sequences selected from the group consisting of SEQ ID NOs: 475 to 759.

In some embodiments, the immunogenic composition is administered to a subject. In some embodiments, the immunogenic composition comprises nucleic acid sequences encoding two or more amino acid sequences selected from the group consisting of SEQ ID NOs: 475 to 759. In some embodiments, the nucleic acid sequences are administered in a construct for expression in vivo. In some embodiments, the in vivo administration of the nucleic acid sequences is configured to produce one or more peptides that is displayed by an HLA class II molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic composition is administered in an effective amount to a subject to prevent cancer. In some embodiments, the immunogenic composition is administered in an effective amount to a subject to treat cancer. In some embodiments, the cancer is selected from the group consisting of pancreatic cancer, skin cancer, thyroid cancer, brain cancer, colorectal cancer, bronchus and lung cancer, breast cancer, and ovarian cancer. In some embodiments, the immunogenic composition comprises nucleic acid sequences encoding at least three amino acid sequences selected from the group consisting of SEQ ID NOs: 475 to 759.

In another aspect, the invention provides for an immunogenic peptide composition comprising one or more peptides selected from the group consisting of SEQ ID NOs: 475 to 759.

In some embodiments, the immunogenic peptide composition comprises two or more peptides selected from the group consisting of SEQ ID NOs: 475 to 759.

In another aspect, the invention provides for an immunogenic composition comprising nucleic acid sequences encoding one or more amino acid sequences selected from the group consisting of SEQ ID NOs: 475 to 483.

In some embodiments, the immunogenic composition comprises nucleic acid sequences encoding one or more amino acid sequences derived from a AKT1 protein mutation. In some embodiments, the immunogenic composition comprises nucleic acid sequences encoding two or more amino acid sequences selected from the group consisting of SEQ ID NOs: 475 to 483.

In another aspect, the invention provides for an immunogenic peptide composition comprising one or more peptides selected from the group consisting of SEQ ID NOs: 475 to 483.

In some embodiments, the immunogenic peptide composition comprises two or more peptides selected from the group consisting of SEQ ID NOs: 475 to 483. In some embodiments, the one or more peptides is a modified or unmodified fragment of a mutated AKT1 protein.

In another aspect, the invention provides for an immunogenic composition comprising nucleic acid sequences encoding one or more amino acid sequences selected from the group consisting of SEQ ID NOs: 484 to 502.

In some embodiments, the immunogenic composition comprises nucleic acid sequences encoding one or more amino acid sequences derived from a BRAF protein mutation. In some embodiments, the immunogenic composition comprises nucleic acid sequences encoding two or more amino acid sequences selected from the group consisting of SEQ ID NOs: 484 to 502.

In another aspect, the invention provides for an immunogenic peptide composition comprising one or more peptides selected from the group consisting of SEQ ID NOs: 484 to 502.

In some embodiments, the immunogenic peptide composition comprises two or more peptides selected from the group consisting of SEQ ID NOs: 484 to 502. In some embodiments, the one or more peptides is a modified or unmodified fragment of a mutated BRAF protein.

In another aspect, the invention provides for an immunogenic composition comprising nucleic acid sequences encoding one or more amino acid sequences selected from the group consisting of SEQ ID NOs: 503 to 527.

In some embodiments, the immunogenic composition comprises nucleic acid sequences encoding one or more amino acid sequences derived from a EGFR protein mutation. In some embodiments, the immunogenic composition comprises nucleic acid sequences encoding two or more amino acid sequences selected from the group consisting of SEQ ID NOs: 503 to 527.

In another aspect, the invention provides for an immunogenic peptide composition comprising one or more peptides selected from the group consisting of SEQ ID NOs: 503 to 527.

In some embodiments, the immunogenic peptide composition comprises two or more peptides selected from the group consisting of SEQ ID NOs: 503 to 527. In some embodiments, the one or more peptides is a modified or unmodified fragment of a mutated EGFR protein.

In another aspect, the invention provides for an immunogenic composition comprising nucleic acid sequences encoding one or more amino acid sequences selected from the group consisting of SEQ ID NOs: 528 to 534.

In some embodiments, the immunogenic composition comprises nucleic acid sequences encoding one or more amino acid sequences derived from a GTF2I protein mutation. In some embodiments, the immunogenic composition comprises nucleic acid sequences encoding two or more amino acid sequences selected from the group consisting of SEQ ID NOs: 528 to 534.

In another aspect, the invention provides for an immunogenic peptide composition comprising one or more peptides selected from the group consisting of SEQ ID NOs: 528 to 534.

In some embodiments, the immunogenic peptide composition comprises two or more peptides selected from the group consisting of SEQ ID NOs: 528 to 534. In some embodiments, the one or more peptides is a modified or unmodified fragment of a mutated GTF2I protein.

In another aspect, the invention provides for an immunogenic composition comprising nucleic acid sequences encoding one or more amino acid sequences selected from the group consisting of SEQ ID NOs: 535 to 553.

In some embodiments, the immunogenic composition comprises nucleic acid sequences encoding one or more amino acid sequences derived from a IDH1 protein mutation. In some embodiments, the immunogenic composition comprises nucleic acid sequences encoding two or more amino acid sequences selected from the group consisting of SEQ ID NOs: 535 to 553.

In another aspect, the invention provides for an immunogenic peptide composition comprising one or more peptides selected from the group consisting of SEQ ID NOs: 535 to 553.

In some embodiments, the immunogenic peptide composition comprises two or more peptides selected from the group consisting of SEQ ID NOs: 535 to 553. In some embodiments, the one or more peptides is a modified or unmodified fragment of a mutated IDH1 protein.

In another aspect, the invention provides for an immunogenic composition comprising nucleic acid sequences encoding one or more amino acid sequences selected from the group consisting of SEQ ID NOs: 554 to 615.

In some embodiments, the immunogenic composition comprises nucleic acid sequences encoding one or more amino acid sequences derived from a KRAS protein mutation. In some embodiments, the immunogenic composition comprises nucleic acid sequences encoding two or more amino acid sequences selected from the group consisting of SEQ ID NOs: 554 to 615.

In another aspect, the invention provides for an immunogenic peptide composition comprising one or more peptides selected from the group consisting of SEQ ID NOs: 554 to 615.

In some embodiments, the immunogenic peptide composition comprises two or more peptides selected from the group consisting of SEQ ID NOs: 554 to 615. In some embodiments, the one or more peptides is a modified or unmodified fragment of a mutated KRAS protein.

In another aspect, the invention provides for an immunogenic composition comprising nucleic acid sequences encoding one or more amino acid sequences selected from the group consisting of SEQ ID NOs: 616 to 645.

In some embodiments, the immunogenic composition comprises nucleic acid sequences encoding one or more amino acid sequences derived from a NRAS protein mutation. In some embodiments, the immunogenic composition comprises nucleic acid sequences encoding two or more amino acid sequences selected from the group consisting of SEQ ID NOs: 616 to 645.

In another aspect, the invention provides for an immunogenic peptide composition comprising one or more peptides selected from the group consisting of SEQ ID NOs: 616 to 645.

In some embodiments, the immunogenic peptide composition comprises two or more peptides selected from the group consisting of SEQ ID NOs: 616 to 645. In some embodiments, the one or more peptides is a modified or unmodified fragment of a mutated NRAS protein.

In another aspect, the invention provides for an immunogenic composition comprising nucleic acid sequences encoding one or more amino acid sequences selected from the group consisting of SEQ ID NOs: 646 to 675.

In some embodiments, the immunogenic composition comprises nucleic acid sequences encoding one or more amino acid sequences derived from a PIK3CA protein mutation. In some embodiments, the immunogenic composition comprises nucleic acid sequences encoding two or more amino acid sequences selected from the group consisting of SEQ ID NOs: 646 to 675.

In another aspect, the invention provides for an immunogenic peptide composition comprising one or more peptides selected from the group consisting of SEQ ID NOs: 646 to 675.

In some embodiments, the immunogenic peptide composition comprises two or more peptides selected from the group consisting of SEQ ID NOs: 646 to 675. In some embodiments, the one or more peptides is a modified or unmodified fragment of a mutated PIK3CA protein.

In another aspect, the invention provides for an immunogenic composition comprising nucleic acid sequences encoding one or more amino acid sequences selected from the group consisting of SEQ ID NOs: 676 to 690.

In some embodiments, the immunogenic composition comprises nucleic acid sequences encoding one or more amino acid sequences derived from a PTEN protein mutation. In some embodiments, the immunogenic composition comprises nucleic acid sequences encoding two or more amino acid sequences selected from the group consisting of SEQ ID NOs: 676 to 690.

In another aspect, the invention provides for an immunogenic peptide composition comprising one or more peptides selected from the group consisting of SEQ ID NOs: 676 to 690.

In some embodiments, the immunogenic peptide composition comprises two or more peptides selected from the group consisting of SEQ ID NOs: 676 to 690. In some embodiments, the one or more peptides is a modified or unmodified fragment of a mutated PTEN protein.

In another aspect, the invention provides for an immunogenic composition comprising nucleic acid sequences encoding one or more amino acid sequences selected from the group consisting of SEQ ID NOs: 691 to 758.

In some embodiments, the immunogenic composition comprises nucleic acid sequences encoding one or more amino acid sequences derived from a TP53 protein mutation. In some embodiments, the immunogenic composition comprises nucleic acid sequences encoding two or more amino acid sequences selected from the group consisting of SEQ ID NOs: 691 to 758.

In another aspect, the invention provides for an immunogenic peptide composition comprising one or more peptides selected from the group consisting of SEQ ID NOs: 691 to 758.

In some embodiments, the immunogenic peptide composition comprises two or more peptides selected from the group consisting of SEQ ID NOs: 691 to 758. In some embodiments, the one or more peptides is a modified or unmodified fragment of a mutated TP53 protein.

In another aspect, the invention provides for an immunogenic composition comprising nucleic acid sequences encoding one or more amino acid sequences selected from the group consisting of SEQ ID NOs: 554 to 645.

In some embodiments, the immunogenic composition comprises nucleic acid sequences encoding one or more amino acid sequences derived from a RAS protein mutation. In some embodiments, the immunogenic composition comprises nucleic acid sequences encoding two or more amino acid sequences selected from the group consisting of SEQ ID NOs: 554 to 645.

In another aspect, the invention provides for an immunogenic peptide composition comprising one or more peptides selected from the group consisting of SEQ ID NOs: 554 to 645.

In some embodiments, the immunogenic peptide composition comprises two or more peptides selected from the group consisting of SEQ ID NOs: 554 to 645. In some embodiments, the one or more peptides is a modified or unmodified fragment of a mutated RAS protein.

In another aspect, the invention provides for an immunogenic composition comprising nucleic acid sequences encoding one or more amino acid sequences selected from the group consisting of SEQ ID NOs: 484 to 494.

In some embodiments, the immunogenic composition comprises nucleic acid sequences encoding one or more amino acid sequences derived from a BRAF V600 protein mutation. In some embodiments, the immunogenic composition comprises nucleic acid sequences encoding two or more amino acid sequences selected from the group consisting of SEQ ID NOs: 484 to 494.

In another aspect, the invention provides for an immunogenic peptide composition comprising one or more peptides selected from the group consisting of SEQ ID NOs: 484 to 494.

In some embodiments, the immunogenic peptide composition comprises two or more peptides selected from the group consisting of SEQ ID NOs: 484 to 494. In some embodiments, the immunogenic peptide composition comprises a peptide derived from a BRAF V600 protein mutation.

In another aspect, the invention provides for an immunogenic composition comprising nucleic acid sequences encoding one or more amino acid sequences selected from the group consisting of SEQ ID NOs: 495 to 502.

In some embodiments, the immunogenic composition comprises nucleic acid sequences encoding one or more amino acid sequences derived from a BRAF V600M protein mutation. In some embodiments, the immunogenic composition comprises nucleic acid sequences encoding two or more amino acid sequences selected from the group consisting of SEQ ID NOs: 495 to 502.

In another aspect, the invention provides for an immunogenic peptide composition comprising one or more peptides selected from the group consisting of SEQ ID NOs: 495 to 502.

In some embodiments, the immunogenic peptide composition comprises two or more peptides selected from the group consisting of SEQ ID NOs: 495 to 502. In some embodiments, the immunogenic peptide composition comprises a peptide derived from a BRAF V600M protein mutation.

In another aspect, the invention provides for an immunogenic composition comprising nucleic acid sequences encoding one or more amino acid sequences selected from the group consisting of SEQ ID NOs: 503 to 509.

In some embodiments, the immunogenic composition comprises nucleic acid sequences encoding one or more amino acid sequences derived from a EGFR A289V protein mutation. In some embodiments, the immunogenic composition comprises nucleic acid sequences encoding two or more amino acid sequences selected from the group consisting of SEQ ID NOs: 503 to 509.

In another aspect, the invention provides for an immunogenic peptide composition comprising one or more peptides selected from the group consisting of SEQ ID NOs: 503 to 509.

In some embodiments, the immunogenic peptide composition comprises two or more peptides selected from the group consisting of SEQ ID NOs: 503 to 509. In some embodiments, the immunogenic peptide composition comprises a peptide derived from a EGFR A289V protein mutation.

In another aspect, the invention provides for an immunogenic composition comprising nucleic acid sequences encoding one or more amino acid sequences selected from the group consisting of SEQ ID NOs: 510 to 519.

In some embodiments, the immunogenic composition comprises nucleic acid sequences encoding one or more amino acid sequences derived from a EGFR G598V protein mutation. In some embodiments, the immunogenic composition comprises nucleic acid sequences encoding two or more amino acid sequences selected from the group consisting of SEQ ID NOs: 510 to 519.

In another aspect, the invention provides for an immunogenic peptide composition comprising one or more peptides selected from the group consisting of SEQ ID NOs: 510 to 519.

In some embodiments, the immunogenic peptide composition comprises two or more peptides selected from the group consisting of SEQ ID NOs: 510 to 519. In some embodiments, the immunogenic peptide composition comprises a peptide derived from a EGFR G598V protein mutation.

In another aspect, the invention provides for an immunogenic composition comprising nucleic acid sequences encoding one or more amino acid sequences selected from the group consisting of SEQ ID NOs: 520 to 527.

In some embodiments, the immunogenic composition comprises nucleic acid sequences encoding one or more amino acid sequences derived from a EGFR L858R protein mutation. In some embodiments, the immunogenic composition comprises nucleic acid sequences encoding two or more amino acid sequences selected from the group consisting of SEQ ID NOs: 520 to 527.

In another aspect, the invention provides for an immunogenic peptide composition comprising one or more peptides selected from the group consisting of SEQ ID NOs: 520 to 527.

In some embodiments, the immunogenic peptide composition comprises two or more peptides selected from the group consisting of SEQ ID NOs: 520 to 527. In some embodiments, the immunogenic peptide composition comprises a peptide derived from a EGFR L858R protein mutation.

In another aspect, the invention provides for an immunogenic composition comprising nucleic acid sequences encoding one or more amino acid sequences selected from the group consisting of SEQ ID NOs: 543 to 553.

In some embodiments, the immunogenic composition comprises nucleic acid sequences encoding one or more amino acid sequences derived from a IDH1 R132H protein mutation. In some embodiments, the immunogenic composition comprises nucleic acid sequences encoding two or more amino acid sequences selected from the group consisting of SEQ ID NOs: 543 to 553.

In another aspect, the invention provides for an immunogenic peptide composition comprising one or more peptides selected from the group consisting of SEQ ID NOs: 543 to 553.

In some embodiments, the immunogenic peptide composition comprises two or more peptides selected from the group consisting of SEQ ID NOs: 543 to 553. In some embodiments, the immunogenic peptide composition comprises a peptide derived from a IDH1 R132H protein mutation.

In another aspect, the invention provides for an immunogenic composition comprising nucleic acid sequences encoding one or more amino acid sequences selected from the group consisting of SEQ ID NOs: 535 to 542.

In some embodiments, the immunogenic composition comprises nucleic acid sequences encoding one or more amino acid sequences derived from a IDH1 R132C protein mutation. In some embodiments, the immunogenic composition comprises nucleic acid sequences encoding two or more amino acid sequences selected from the group consisting of SEQ ID NOs: 535 to 542.

In another aspect, the invention provides for an immunogenic peptide composition comprising one or more peptides selected from the group consisting of SEQ ID NOs: 535 to 542.

In some embodiments, the immunogenic peptide composition comprises two or more peptides selected from the group consisting of SEQ ID NOs: 535 to 542. In some embodiments, the immunogenic peptide composition comprises a peptide derived from a IDH1 R132C protein mutation.

In another aspect, the invention provides for an immunogenic composition comprising nucleic acid sequences encoding one or more amino acid sequences selected from the group consisting of SEQ ID NOs: 569 to 577.

In some embodiments, the immunogenic composition comprises nucleic acid sequences encoding one or more amino acid sequences derived from a KRAS G12D protein mutation. In some embodiments, the immunogenic composition comprises nucleic acid sequences encoding two or more amino acid sequences selected from the group consisting of SEQ ID NOs: 569 to 577.

In another aspect, the invention provides for an immunogenic peptide composition comprising one or more peptides selected from the group consisting of SEQ ID NOs: 569 to 577.

In some embodiments, the immunogenic peptide composition comprises two or more peptides selected from the group consisting of SEQ ID NOs: 569 to 577. In some embodiments, the immunogenic peptide composition comprises a peptide derived from a KRAS G12D protein mutation.

In another aspect, the invention provides for an immunogenic composition comprising nucleic acid sequences encoding one or more amino acid sequences selected from the group consisting of SEQ ID NOs: 596 to 605.

In some embodiments, the immunogenic composition comprises nucleic acid sequences encoding one or more amino acid sequences derived from a KRAS G12V protein mutation. In some embodiments, the immunogenic composition comprises nucleic acid sequences encoding two or more amino acid sequences selected from the group consisting of SEQ ID NOs: 596 to 605.

In another aspect, the invention provides for an immunogenic peptide composition comprising one or more peptides selected from the group consisting of SEQ ID NOs: 596 to 605.

In some embodiments, the immunogenic peptide composition comprises two or more peptides selected from the group consisting of SEQ ID NOs: 596 to 605. In some embodiments, the immunogenic peptide composition comprises a peptide derived from a KRAS G12V protein mutation.

In another aspect, the invention provides for an immunogenic composition comprising nucleic acid sequences encoding one or more amino acid sequences selected from the group consisting of SEQ ID NOs: 578 to 587.

In some embodiments, the immunogenic composition comprises nucleic acid sequences encoding one or more amino acid sequences derived from a KRAS G12R protein mutation. In some embodiments, the immunogenic composition comprises nucleic acid sequences encoding two or more amino acid sequences selected from the group consisting of SEQ ID NOs: 578 to 587.

In another aspect, the invention provides for an immunogenic peptide composition comprising one or more peptides selected from the group consisting of SEQ ID NOs: 578 to 587.

In some embodiments, the immunogenic peptide composition comprises two or more peptides selected from the group consisting of SEQ ID NOs: 578 to 587. In some embodiments, the immunogenic peptide composition comprises a peptide derived from a KRAS G12R protein mutation.

In another aspect, the invention provides for an immunogenic composition comprising nucleic acid sequences encoding one or more amino acid sequences selected from the group consisting of SEQ ID NOs: 561 to 568.

In some embodiments, the immunogenic composition comprises nucleic acid sequences encoding one or more amino acid sequences derived from a KRAS G12C protein mutation. In some embodiments, the immunogenic composition comprises nucleic acid sequences encoding two or more amino acid sequences selected from the group consisting of SEQ ID NOs: 561 to 568.

In another aspect, the invention provides for an immunogenic peptide composition comprising one or more peptides selected from the group consisting of SEQ ID NOs: 561 to 568.

In some embodiments, the immunogenic peptide composition comprises two or more peptides selected from the group consisting of SEQ ID NOs: 561 to 568. In some embodiments, the immunogenic peptide composition comprises a peptide derived from a KRAS G12C protein mutation.

In another aspect, the invention provides for an immunogenic composition comprising nucleic acid sequences encoding one or more amino acid sequences selected from the group consisting of SEQ ID NOs: 606 to 615.

In some embodiments, the immunogenic composition comprises nucleic acid sequences encoding one or more amino acid sequences derived from a KRAS G13D protein mutation. In some embodiments, the immunogenic composition comprises nucleic acid sequences encoding two or more amino acid sequences selected from the group consisting of SEQ ID NOs: 606 to 615.

In another aspect, the invention provides for an immunogenic peptide composition comprising one or more peptides selected from the group consisting of SEQ ID NOs: 606 to 615.

In some embodiments, the immunogenic peptide composition comprises two or more peptides selected from the group consisting of SEQ ID NOs: 606 to 615. In some embodiments, the immunogenic peptide composition comprises a peptide derived from a KRAS G13D protein mutation.

In another aspect, the invention provides for an immunogenic composition comprising nucleic acid sequences encoding one or more amino acid sequences selected from the group consisting of SEQ ID NOs: 554 to 560.

In some embodiments, the immunogenic composition comprises nucleic acid sequences encoding one or more amino acid sequences derived from a KRAS G12A protein mutation. In some embodiments, the immunogenic composition comprises nucleic acid sequences encoding two or more amino acid sequences selected from the group consisting of SEQ ID NOs: 554 to 560.

In another aspect, the invention provides for an immunogenic peptide composition comprising one or more peptides selected from the group consisting of SEQ ID NOs: 554 to 560.

In some embodiments, the immunogenic peptide composition comprises two or more peptides selected from the group consisting of SEQ ID NOs: 554 to 560. In some embodiments, the immunogenic peptide composition comprises a peptide derived from a KRAS G12A protein mutation.

In another aspect, the invention provides for an immunogenic composition comprising nucleic acid sequences encoding one or more amino acid sequences selected from the group consisting of SEQ ID NOs: 588 to 595.

In some embodiments, the immunogenic composition comprises nucleic acid sequences encoding one or more amino acid sequences derived from a KRAS G12S protein mutation. In some embodiments, the immunogenic composition comprises nucleic acid sequences encoding two or more amino acid sequences selected from the group consisting of SEQ ID NOs: 588 to 595.

In another aspect, the invention provides for an immunogenic peptide composition comprising one or more peptides selected from the group consisting of SEQ ID NOs: 588 to 595.

In some embodiments, the immunogenic peptide composition comprises two or more peptides selected from the group consisting of SEQ ID NOs: 588 to 595. In some embodiments, the immunogenic peptide composition comprises a peptide derived from a KRAS G12S protein mutation.

In another aspect, the invention provides for an immunogenic composition comprising nucleic acid sequences encoding one or more amino acid sequences selected from the group consisting of SEQ ID NOs: 634 to 645.

In some embodiments, the immunogenic composition comprises nucleic acid sequences encoding one or more amino acid sequences derived from a NRAS Q61R protein mutation. In some embodiments, the immunogenic composition comprises nucleic acid sequences encoding two or more amino acid sequences selected from the group consisting of SEQ ID NOs: 634 to 645.

In another aspect, the invention provides for an immunogenic peptide composition comprising one or more peptides selected from the group consisting of SEQ ID NOs: 634 to 645.

In some embodiments, the immunogenic peptide composition comprises two or more peptides selected from the group consisting of SEQ ID NOs: 634 to 645. In some embodiments, the immunogenic peptide composition comprises a peptide derived from a NRAS Q61R protein mutation.

In another aspect, the invention provides for an immunogenic composition comprising nucleic acid sequences encoding one or more amino acid sequences selected from the group consisting of SEQ ID NOs: 616 to 624.

In some embodiments, the immunogenic composition comprises nucleic acid sequences encoding one or more amino acid sequences derived from a NRAS Q61K protein mutation. In some embodiments, the immunogenic composition comprises nucleic acid sequences encoding two or more amino acid sequences selected from the group consisting of SEQ ID NOs: 616 to 624.

In another aspect, the invention provides for an immunogenic peptide composition comprising one or more peptides selected from the group consisting of SEQ ID NOs: 616 to 624.

In some embodiments, the immunogenic peptide composition comprises two or more peptides selected from the group consisting of SEQ ID NOs: 616 to 624. In some embodiments, the immunogenic peptide composition comprises a peptide derived from a NRAS Q61K protein mutation.

In another aspect, the invention provides for an immunogenic composition comprising nucleic acid sequences encoding one or more amino acid sequences selected from the group consisting of SEQ ID NOs: 625 to 633.

In some embodiments, the immunogenic composition comprises nucleic acid sequences encoding one or more amino acid sequences derived from a NRAS Q61L protein mutation. In some embodiments, the immunogenic composition comprises nucleic acid sequences encoding two or more amino acid sequences selected from the group consisting of SEQ ID NOs: 625 to 633.

In another aspect, the invention provides for an immunogenic peptide composition comprising one or more peptides selected from the group consisting of SEQ ID NOs: 625 to 633.

In some embodiments, the immunogenic peptide composition comprises two or more peptides selected from the group consisting of SEQ ID NOs: 625 to 633. In some embodiments, the immunogenic peptide composition comprises a peptide derived from a NRAS Q61L protein mutation.

In another aspect, the invention provides for an immunogenic composition comprising nucleic acid sequences encoding one or more amino acid sequences selected from the group consisting of SEQ ID NOs: 646 to 650.

In some embodiments, the immunogenic composition comprises nucleic acid sequences encoding one or more amino acid sequences derived from a PIK3CA E542K protein mutation. In some embodiments, the immunogenic composition comprises nucleic acid sequences encoding two or more amino acid sequences selected from the group consisting of SEQ ID NOs: 646 to 650.

In another aspect, the invention provides for an immunogenic peptide composition comprising one or more peptides selected from the group consisting of SEQ ID NOs: 646 to 650.

In some embodiments, the immunogenic peptide composition comprises two or more peptides selected from the group consisting of SEQ ID NOs: 646 to 650. In some embodiments, the immunogenic peptide composition comprises a peptide derived from a PIK3CA E542K protein mutation.

In another aspect, the invention provides for an immunogenic composition comprising nucleic acid sequences encoding one or more amino acid sequences selected from the group consisting of SEQ ID NOs: 651 to 657.

In some embodiments, the immunogenic composition comprises nucleic acid sequences encoding one or more amino acid sequences derived from a PIK3CA E545K protein mutation. In some embodiments, the immunogenic composition comprises nucleic acid sequences encoding two or more amino acid sequences selected from the group consisting of SEQ ID NOs: 651 to 657.

In another aspect, the invention provides for an immunogenic peptide composition comprising one or more peptides selected from the group consisting of SEQ ID NOs: 651 to 657.

In some embodiments, the immunogenic peptide composition comprises two or more peptides selected from the group consisting of SEQ ID NOs: 651 to 657. In some embodiments, the immunogenic peptide composition comprises a peptide derived from a PIK3CA E545K protein mutation.

In another aspect, the invention provides for an immunogenic composition comprising nucleic acid sequences encoding one or more amino acid sequences selected from the group consisting of SEQ ID NOs: 658 to 667.

In some embodiments, the immunogenic composition comprises nucleic acid sequences encoding one or more amino acid sequences derived from a PIK3CA H1047R protein mutation. In some embodiments, the immunogenic composition comprises nucleic acid sequences encoding two or more amino acid sequences selected from the group consisting of SEQ ID NOs: 658 to 667.

In another aspect, the invention provides for an immunogenic peptide composition comprising one or more peptides selected from the group consisting of SEQ ID NOs: 658 to 667.

In some embodiments, the immunogenic peptide composition comprises two or more peptides selected from the group consisting of SEQ ID NOs: 658 to 667. In some embodiments, the immunogenic peptide composition comprises a peptide derived from a PIK3CA H1047R protein mutation.

In another aspect, the invention provides for an immunogenic composition comprising nucleic acid sequences encoding one or more amino acid sequences selected from the group consisting of SEQ ID NOs: 700 to 707.

In some embodiments, the immunogenic composition comprises nucleic acid sequences encoding one or more amino acid sequences derived from a TP53 R158L protein mutation. In some embodiments, the immunogenic composition comprises nucleic acid sequences encoding two or more amino acid sequences selected from the group consisting of SEQ ID NOs: 700 to 707.

In another aspect, the invention provides for an immunogenic peptide composition comprising one or more peptides selected from the group consisting of SEQ ID NOs: 700 to 707.

In some embodiments, the immunogenic peptide composition comprises two or more peptides selected from the group consisting of SEQ ID NOs: 700 to 707. In some embodiments, the immunogenic peptide composition comprises a peptide derived from a TP53 R158L protein mutation.

In another aspect, the invention provides for an immunogenic composition comprising nucleic acid sequences encoding one or more amino acid sequences selected from the group consisting of SEQ ID NOs: 708 to 717.

In some embodiments, the immunogenic composition comprises nucleic acid sequences encoding one or more amino acid sequences derived from a TP53 R175H protein mutation. In some embodiments, the immunogenic composition comprises nucleic acid sequences encoding two or more amino acid sequences selected from the group consisting of SEQ ID NOs: 708 to 717.

In another aspect, the invention provides for an immunogenic peptide composition comprising one or more peptides selected from the group consisting of SEQ ID NOs: 708 to 717.

In some embodiments, the immunogenic peptide composition comprises two or more peptides selected from the group consisting of SEQ ID NOs: 708 to 717. In some embodiments, the immunogenic peptide composition comprises a peptide derived from a TP53 R175H protein mutation.

In another aspect, the invention provides for an immunogenic composition comprising nucleic acid sequences encoding one or more amino acid sequences selected from the group consisting of SEQ ID NOs: 718 to 723.

In some embodiments, the immunogenic composition comprises nucleic acid sequences encoding one or more amino acid sequences derived from a TP53 R248Q protein mutation. In some embodiments, the immunogenic composition comprises nucleic acid sequences encoding two or more amino acid sequences selected from the group consisting of SEQ ID NOs: 718 to 723.

In another aspect, the invention provides for an immunogenic peptide composition comprising one or more peptides selected from the group consisting of SEQ ID NOs: 718 to 723.

In some embodiments, the immunogenic peptide composition comprises two or more peptides selected from the group consisting of SEQ ID NOs: 718 to 723. In some embodiments, the immunogenic peptide composition comprises a peptide derived from a TP53 R248Q protein mutation.

In another aspect, the invention provides for an immunogenic composition comprising nucleic acid sequences encoding one or more amino acid sequences selected from the group consisting of SEQ ID NOs: 733 to 739.

In some embodiments, the immunogenic composition comprises nucleic acid sequences encoding one or more amino acid sequences derived from a TP53 R273C protein mutation. In some embodiments, the immunogenic composition comprises nucleic acid sequences encoding two or more amino acid sequences selected from the group consisting of SEQ ID NOs: 733 to 739.

In another aspect, the invention provides for an immunogenic peptide composition comprising one or more peptides selected from the group consisting of SEQ ID NOs: 733 to 739.

In some embodiments, the immunogenic peptide composition comprises two or more peptides selected from the group consisting of SEQ ID NOs: 733 to 739. In some embodiments, the immunogenic peptide composition comprises a peptide derived from a TP53 R273C protein mutation.

In another aspect, the invention provides for an immunogenic composition comprising nucleic acid sequences encoding one or more amino acid sequences selected from the group consisting of SEQ ID NOs: 740 to 748.

In some embodiments, the immunogenic composition comprises nucleic acid sequences encoding one or more amino acid sequences derived from a TP53 R273H protein mutation. In some embodiments, the immunogenic composition comprises nucleic acid sequences encoding two or more amino acid sequences selected from the group consisting of SEQ ID NOs: 740 to 748.

In another aspect, the invention provides for an immunogenic peptide composition comprising one or more peptides selected from the group consisting of SEQ ID NOs: 740 to 748.

In some embodiments, the immunogenic peptide composition comprises two or more peptides selected from the group consisting of SEQ ID NOs: 740 to 748. In some embodiments, the immunogenic peptide composition comprises a peptide derived from a TP53 R273H protein mutation.

In another aspect, the invention provides for an immunogenic composition comprising nucleic acid sequences encoding one or more amino acid sequences selected from the group consisting of SEQ ID NOs: 724 to 732.

In some embodiments, the immunogenic composition comprises nucleic acid sequences encoding one or more amino acid sequences derived from a TP53 R248W protein mutation. In some embodiments, the immunogenic composition comprises nucleic acid sequences encoding two or more amino acid sequences selected from the group consisting of SEQ ID NOs: 724 to 732.

In another aspect, the invention provides for an immunogenic peptide composition comprising one or more peptides selected from the group consisting of SEQ ID NOs: 724 to 732.

In some embodiments, the immunogenic peptide composition comprises two or more peptides selected from the group consisting of SEQ ID NOs: 724 to 732. In some embodiments, the immunogenic peptide composition comprises a peptide derived from a TP53 R248W protein mutation.

In another aspect, the invention provides for an immunogenic composition comprising nucleic acid sequences encoding one or more amino acid sequences selected from the group consisting of SEQ ID NOs: 749 to 750.

In some embodiments, the immunogenic composition comprises nucleic acid sequences encoding one or more amino acid sequences derived from a TP53 R282W protein mutation. In some embodiments, the immunogenic composition comprises nucleic acid sequences encoding two or more amino acid sequences selected from the group consisting of SEQ ID NOs: 749 to 750.

In another aspect, the invention provides for an immunogenic peptide composition comprising one or more peptides selected from the group consisting of SEQ ID NOs: 749 to 750.

In some embodiments, the immunogenic peptide composition comprises two or more peptides selected from the group consisting of SEQ ID NOs: 749 to 750. In some embodiments, the immunogenic peptide composition comprises a peptide derived from a TP53 R282W protein mutation.

In another aspect, the invention provides for an immunogenic composition comprising nucleic acid sequences encoding one or more amino acid sequences selected from the group consisting of SEQ ID NOs: 751 to 758.

In some embodiments, the immunogenic composition comprises nucleic acid sequences encoding one or more amino acid sequences derived from a TP53 Y220C protein mutation. In some embodiments, the immunogenic composition comprises nucleic acid sequences encoding two or more amino acid sequences selected from the group consisting of SEQ ID NOs: 751 to 758.

In another aspect, the invention provides for an immunogenic peptide composition comprising one or more peptides selected from the group consisting of SEQ ID NOs: 751 to 758.

In some embodiments, the immunogenic peptide composition comprises two or more peptides selected from the group consisting of SEQ ID NOs: 751 to 758. In some embodiments, the immunogenic peptide composition comprises a peptide derived from a TP53 Y220C protein mutation.

In another aspect, the invention provides for an immunogenic composition comprising nucleic acid sequences encoding one or more amino acid sequences selected from the group consisting of SEQ ID NOs: 668 to 675.

In some embodiments, the immunogenic composition comprises nucleic acid sequences encoding one or more amino acid sequences derived from a PIK3CA R88Q protein mutation. In some embodiments, the immunogenic composition comprises nucleic acid sequences encoding two or more amino acid sequences selected from the group consisting of SEQ ID NOs: 668 to 675.

In another aspect, the invention provides for an immunogenic peptide composition comprising one or more peptides selected from the group consisting of SEQ ID NOs: 668 to 675.

In some embodiments, the immunogenic peptide composition comprises two or more peptides selected from the group consisting of SEQ ID NOs: 668 to 675. In some embodiments, the immunogenic peptide composition comprises a peptide derived from a PIK3CA R88Q protein mutation.

In another aspect, the invention provides for an immunogenic composition comprising nucleic acid sequences encoding one or more amino acid sequences selected from the group consisting of SEQ ID NOs: 528 to 534.

In some embodiments, the immunogenic composition comprises nucleic acid sequences encoding one or more amino acid sequences derived from a GTF2I L424H protein mutation. In some embodiments, the immunogenic composition comprises nucleic acid sequences encoding two or more amino acid sequences selected from the group consisting of SEQ ID NOs: 528 to 534.

In another aspect, the invention provides for an immunogenic peptide composition comprising one or more peptides selected from the group consisting of SEQ ID NOs: 528 to 534.

In some embodiments, the immunogenic peptide composition comprises two or more peptides selected from the group consisting of SEQ ID NOs: 528 to 534. In some embodiments, the immunogenic peptide composition comprises a peptide derived from a GTF2I L424H protein mutation.

In another aspect, the invention provides for an immunogenic composition comprising nucleic acid sequences encoding one or more amino acid sequences selected from the group consisting of SEQ ID NOs: 681 to 690.

In some embodiments, the immunogenic composition comprises nucleic acid sequences encoding one or more amino acid sequences derived from a PTEN R130Q protein mutation. In some embodiments, the immunogenic composition comprises nucleic acid sequences encoding two or more amino acid sequences selected from the group consisting of SEQ ID NOs: 681 to 690.

In another aspect, the invention provides for an immunogenic peptide composition comprising one or more peptides selected from the group consisting of SEQ ID NOs: 681 to 690.

In some embodiments, the immunogenic peptide composition comprises two or more peptides selected from the group consisting of SEQ ID NOs: 681 to 690. In some embodiments, the immunogenic peptide composition comprises a peptide derived from a PTEN R130Q protein mutation.

In another aspect, the invention provides for an immunogenic composition comprising nucleic acid sequences encoding one or more amino acid sequences selected from the group consisting of SEQ ID NOs: 475 to 483.

In some embodiments, the immunogenic composition comprises nucleic acid sequences encoding one or more amino acid sequences derived from a AKT1 E17K protein mutation. In some embodiments, the immunogenic composition comprises nucleic acid sequences encoding two or more amino acid sequences selected from the group consisting of SEQ ID NOs: 475 to 483.

In another aspect, the invention provides for an immunogenic peptide composition comprising one or more peptides selected from the group consisting of SEQ ID NOs: 475 to 483.

In some embodiments, the immunogenic peptide composition comprises two or more peptides selected from the group consisting of SEQ ID NOs: 475 to 483. In some embodiments, the immunogenic peptide composition comprises a peptide derived from a AKT1 E17K protein mutation.

In another aspect, the invention provides for an immunogenic composition comprising nucleic acid sequences encoding one or more amino acid sequences selected from the group consisting of SEQ ID NOs: 676 to 680.

In some embodiments, the immunogenic composition comprises nucleic acid sequences encoding one or more amino acid sequences derived from a PTEN R130G protein mutation. In some embodiments, the immunogenic composition comprises nucleic acid sequences encoding two or more amino acid sequences selected from the group consisting of SEQ ID NOs: 676 to 680.

In another aspect, the invention provides for an immunogenic peptide composition comprising one or more peptides selected from the group consisting of SEQ ID NOs: 676 to 680.

In some embodiments, the immunogenic peptide composition comprises two or more peptides selected from the group consisting of SEQ ID NOs: 676 to 680. In some embodiments, the immunogenic peptide composition comprises a peptide derived from a PTEN R130G protein mutation.

In another aspect, the invention provides for an immunogenic composition comprising nucleic acid sequences encoding one or more amino acid sequences selected from the group consisting of SEQ ID NOs: 691 to 699.

In some embodiments, the immunogenic composition comprises nucleic acid sequences encoding one or more amino acid sequences derived from a TP53 H179R protein mutation. In some embodiments, the immunogenic composition comprises nucleic acid sequences encoding two or more amino acid sequences selected from the group consisting of SEQ ID NOs: 691 to 699.

In another aspect, the invention provides for an immunogenic peptide composition comprising one or more peptides selected from the group consisting of SEQ ID NOs: 691 to 699.

In some embodiments, the immunogenic peptide composition comprises two or more peptides selected from the group consisting of SEQ ID NOs: 691 to 699. In some embodiments, the immunogenic peptide composition comprises a peptide derived from a TP53 H179R protein mutation.

In another aspect, the invention provides for an immunogenic composition comprising nucleic acid sequences encoding one or more amino acid sequences selected from the group consisting of SEQ ID NOs: 569 to 574, SEQ ID NOs: 578 to 584, SEQ ID NOs: 596 to 599, and SEQ ID NOs: 601 to 603.

In some embodiments, the immunogenic composition comprises nucleic acid sequences encoding two or more amino acid sequences selected from the group consisting of SEQ ID NOs: 569 to 574, SEQ ID NOs: 578 to 584, SEQ ID NOs: 596 to 599, and SEQ ID NOs: 601 to 603. In some embodiments, the nucleic acid sequences are administered in a construct for expression in vivo. In some embodiments, the in vivo administration of the nucleic acid sequences is configured to produce one or more peptides that is displayed by an HLA class II molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is pancreatic cancer.

In another aspect, the invention provides for a method of treating or preventing pancreatic cancer by administering to a subject an immunogenic composition comprising nucleic acid sequences encoding one or more amino acid sequences selected from the group consisting of SEQ ID NOs: 569 to 574, SEQ ID NOs: 578 to 584, SEQ ID NOs: 596 to 599, and SEQ ID NOs: 601 to 603.

In some embodiments, the immunogenic composition comprises nucleic acid sequences encoding two or more amino acid sequences selected from the group consisting of SEQ ID NOs: 569 to 574, SEQ ID NOs: 578 to 584, SEQ ID NOs: 596 to 599, and SEQ ID NOs: 601 to 603.

In another aspect, the invention provides for an immunogenic peptide composition comprising one or more peptides selected from the group consisting of SEQ ID NOs: 569 to 574, SEQ ID NOs: 578 to 584, SEQ ID NOs: 596 to 599, and SEQ ID NOs: 601 to 603.

In some embodiments, the immunogenic peptide composition comprises two or more peptides selected from the group consisting of SEQ ID NOs: 569 to 574, SEQ ID NOs: 578 to 584, SEQ ID NOs: 596 to 599, and SEQ ID NOs: 601 to 603. In some embodiments, a peptide in the immunogenic peptide composition is displayed by an HLA class II molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is pancreatic cancer.

In another aspect, the invention provides for a method of treating or preventing pancreatic cancer in a subject comprising administering to the subject an immunogenic peptide composition comprising one or more peptides selected from the group consisting of SEQ ID NOs: 569 to 574, SEQ ID NOs: 578 to 584, SEQ ID NOs: 596 to 599, and SEQ ID NOs: 601 to 603.

In some embodiments, the immunogenic peptide composition comprises two or more peptides selected from the group consisting of SEQ ID NOs: 569 to 574, SEQ ID NOs: 578 to 584, SEQ ID NOs: 596 to 599, and SEQ ID NOs: 601 to 603.

In another aspect, the invention provides for an immunogenic composition comprising nucleic acid sequences encoding one or more amino acid sequences selected from the group consisting of SEQ ID NOs: 484 to 485, SEQ ID NOs: 488 to 489, SEQ ID NOs: 495 to 499, SEQ ID NO: 616, SEQ ID NOs: 619 to 620, SEQ ID NOs: 625 to 628, SEQ ID NO: 634, SEQ ID NO: 637, and SEQ ID NOs: 639 to 640.

In some embodiments, the immunogenic composition comprises nucleic acid sequences encoding two or more amino acid sequences selected from the group consisting of SEQ ID NOs: 484 to 485, SEQ ID NOs: 488 to 489, SEQ ID NOs: 495 to 499, SEQ ID NO: 616, SEQ ID NOs: 619 to 620, SEQ ID NOs: 625 to 628, SEQ ID NO: 634, SEQ ID NO: 637, and SEQ ID NOs: 639 to 640. In some embodiments, the nucleic acid sequences are administered in a construct for expression in vivo. In some embodiments, the in vivo administration of the nucleic acid sequences is configured to produce one or more peptides that is displayed by an HLA class II molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is skin cancer.

In another aspect, the invention provides for a method of treating or preventing skin cancer by administering to a subject an immunogenic composition comprising nucleic acid sequences encoding one or more amino acid sequences selected from the group consisting of SEQ ID NOs: 484 to 485, SEQ ID NOs: 488 to 489, SEQ ID NOs: 495 to 499, SEQ ID NO: 616, SEQ ID NOs: 619 to 620, SEQ ID NOs: 625 to 628, SEQ ID NO: 634, SEQ ID NO: 637, and SEQ ID NOs: 639 to 640.

In some embodiments, the immunogenic composition comprises nucleic acid sequences encoding two or more amino acid sequences selected from the group consisting of SEQ ID NOs: 484 to 485, SEQ ID NOs: 488 to 489, SEQ ID NOs: 495 to 499, SEQ ID NO: 616, SEQ ID NOs: 619 to 620, SEQ ID NOs: 625 to 628, SEQ ID NO: 634, SEQ ID NOs: 639 to 640.

In another aspect, the invention provides for an immunogenic peptide composition comprising one or more peptides selected from the group consisting of SEQ ID NOs: 484 to 485, SEQ ID NOs: 488 to 489, SEQ ID NOs: 495 to 499, SEQ ID NO: 616, SEQ ID NOs: 619 to 620, SEQ ID NOs: 625 to 628, SEQ ID NO: 634, SEQ ID NO: 637, and SEQ ID NOs: 639 to 640.

In some embodiments, the immunogenic peptide composition comprises two or more peptides selected from the group consisting of SEQ ID NOs: 484 to 485, SEQ ID NOs: 488 to 489, SEQ ID NOs: 495 to 499, SEQ ID NO: 616, SEQ ID NOs: 619 to 620, SEQ ID NOs: 625 to 628, SEQ ID NO: 634, SEQ ID NO: 637, and SEQ ID NOs: 639 to 640. In some embodiments, a peptide in the immunogenic peptide composition is displayed by an HLA class II molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is skin cancer.

In another aspect, the invention provides for a method of treating or preventing skin cancer in a subject comprising administering to the subject an immunogenic peptide composition comprising one or more peptides selected from the group consisting of SEQ ID NOs: 484 to 485, SEQ ID NOs: 488 to 489, SEQ ID NOs: 495 to 499, SEQ ID NO: 616, SEQ ID NOs: 619 to 620, SEQ ID NOs: 625 to 628, SEQ ID NO: 634, SEQ ID NO: 637, and SEQ ID NOs: 639 to 640.

In some embodiments, the immunogenic peptide composition comprises two or more peptides selected from the group consisting of SEQ ID NOs: 484 to 485, SEQ ID NOs: 488 to 489, SEQ ID NOs: 495 to 499, SEQ ID NO: 616, SEQ ID NOs: 619 to 620, SEQ ID NOs: 625 to 628, SEQ ID NO: 634, SEQ ID NO: 637, and SEQ ID NOs: 639 to 640.

In another aspect, the invention provides for an immunogenic composition comprising nucleic acid sequences encoding one or more amino acid sequences selected from the group consisting of SEQ ID NOs: 484 to 485, SEQ ID NOs: 488 to 489, SEQ ID NO: 616, SEQ ID NOs: 619 to 620, SEQ ID NO: 634, SEQ ID NO: 637, and SEQ ID NO: 640.

In some embodiments, the immunogenic composition comprises nucleic acid sequences encoding two or more amino acid sequences selected from the group consisting of SEQ ID NOs: 484 to 485, SEQ ID NOs: 488 to 489, SEQ ID NO: 616, SEQ ID NOs: 619 to 620, SEQ ID NO: 634, SEQ ID NO: 637, and SEQ ID NO: 640. In some embodiments, the nucleic acid sequences are administered in a construct for expression in vivo. In some embodiments, the in vivo administration of the nucleic acid sequences is configured to produce one or more peptides that is displayed by an HLA class II molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is thyroid cancer.

In another aspect, the invention provides for a method of treating or preventing thyroid cancer by administering to a subject an immunogenic composition comprising nucleic acid sequences encoding one or more amino acid sequences selected from the group consisting of SEQ ID NOs: 484 to 485, SEQ ID NOs: 488 to 489, SEQ ID NO: 616, SEQ ID NOs: 619 to 620, SEQ ID NO: 634, SEQ ID NO: 637, and SEQ ID NO: 640.

In some embodiments, the immunogenic composition comprises nucleic acid sequences encoding two or more amino acid sequences selected from the group consisting of SEQ ID NOs: 484 to 485, SEQ ID NOs: 488 to 489, SEQ ID NO: 616, SEQ ID NOs: 619 to 620, SEQ ID NO: 634, SEQ ID NO: 637, and SEQ ID NO: 640.

In another aspect, the invention provides for an immunogenic peptide composition comprising one or more peptides selected from the group consisting of SEQ ID NOs: 484 to 485, SEQ ID NOs: 488 to 489, SEQ ID NO: 616, SEQ ID NOs: 619 to 620, SEQ ID NO: 634, SEQ ID NO: 637, and SEQ ID NO: 640.

In some embodiments, the immunogenic peptide composition comprises two or more peptides selected from the group consisting of SEQ ID NOs: 484 to 485, SEQ ID NOs: 488 to 489, SEQ ID NO: 616, SEQ ID NOs: 619 to 620, SEQ ID NO: 634, SEQ ID NO: 637, and SEQ ID NO: 640. In some embodiments, a peptide in the immunogenic peptide composition is displayed by an HLA class II molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is thyroid cancer.

In another aspect, the invention provides for a method of treating or preventing thyroid cancer in a subject comprising administering to the subject an immunogenic peptide composition comprising one or more peptides selected from the group consisting of SEQ ID NOs: 484 to 485, SEQ ID NOs: 488 to 489, SEQ ID NO: 616, SEQ ID NOs: 619 to 620, SEQ ID NO: 634, SEQ ID NO: 637, and SEQ ID NO: 640.

In some embodiments, the immunogenic peptide composition comprises two or more peptides selected from the group consisting of SEQ ID NOs: 484 to 485, SEQ ID NOs: 488 to 489, SEQ ID NO: 616, SEQ ID NOs: 619 to 620, SEQ ID NO: 634, SEQ ID NO: 637, and SEQ ID NO: 640.

In another aspect, the invention provides for an immunogenic composition comprising nucleic acid sequences encoding one or more amino acid sequences selected from the group consisting of SEQ ID NO: 508, SEQ ID NO: 510, SEQ ID NO: 512, SEQ ID NO: 514, SEQ ID NOs: 535 to 537, SEQ ID NO: 539, SEQ ID NOs: 543 to 551, SEQ ID NO: 708, SEQ ID NO: 712, and SEQ ID NO: 738.

In some embodiments, the immunogenic composition comprises nucleic acid sequences encoding two or more amino acid sequences selected from the group consisting of SEQ ID NO: 508, SEQ ID NO: 510, SEQ ID NO: 512, SEQ ID NO: 514, SEQ ID NOs: 535 to 537, SEQ ID NO: 539, SEQ ID NOs: 543 to 551, SEQ ID NO: 708, SEQ ID NO: 712, and SEQ ID NO: 738. In some embodiments, the nucleic acid sequences are administered in a construct for expression in vivo. In some embodiments, the in vivo administration of the nucleic acid sequences is configured to produce one or more peptides that is displayed by an HLA class II molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is brain cancer.

In another aspect, the invention provides for a method of treating or preventing brain cancer by administering to a subject an immunogenic composition comprising nucleic acid sequences encoding one or more amino acid sequences selected from the group consisting of SEQ ID NO: 508, SEQ ID NO: 510, SEQ ID NO: 512, SEQ ID NO: 514, SEQ ID NOs: 535 to 537, SEQ ID NO: 539, SEQ ID NOs: 543 to 551, SEQ ID NO: 708, SEQ ID NO: 712, and SEQ ID NO: 738.

In some embodiments, the immunogenic composition comprises nucleic acid sequences encoding two or more amino acid sequences selected from the group consisting of SEQ ID NO: 508, SEQ ID NO: 510, SEQ ID NO: 512, SEQ ID NO: 514, SEQ ID NOs: 535 to 537, SEQ ID NO: 539, SEQ ID NOs: 543 to 551, SEQ ID NO: 708, SEQ ID NO: 712, and SEQ ID NO: 738.

In another aspect, the invention provides for an immunogenic peptide composition comprising one or more peptides selected from the group consisting of SEQ ID NO: 508, SEQ ID NO: 510, SEQ ID NO: 512, SEQ ID NO: 514, SEQ ID NOs: 535 to 537, SEQ ID NO: 539, SEQ ID NOs: 543 to 551, SEQ ID NO: 708, SEQ ID NO: 712, and SEQ ID NO: 738.

In some embodiments, the immunogenic peptide composition comprises two or more peptides selected from the group consisting of SEQ ID NO: 508, SEQ ID NO: 510, SEQ ID NO: 512, SEQ ID NO: 514, SEQ ID NOs: 535 to 537, SEQ ID NO: 539, SEQ ID NOs: 543 to 551, SEQ ID NO: 708, SEQ ID NO: 712, and SEQ ID NO: 738. In some embodiments, a peptide in the immunogenic peptide composition is displayed by an HLA class II molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is brain cancer.

In another aspect, the invention provides for a method of treating or preventing brain cancer in a subject comprising administering to the subject an immunogenic peptide composition comprising one or more peptides selected from the group consisting of SEQ ID NO: 508, SEQ ID NO: 510, SEQ ID NO: 512, SEQ ID NO: 514, SEQ ID NOs: 535 to 537, SEQ ID NO: 539, SEQ ID NOs: 543 to 551, SEQ ID NO: 708, SEQ ID NO: 712, and SEQ ID NO: 738.

In some embodiments, the immunogenic peptide composition comprises two or more peptides selected from the group consisting of SEQ ID NO: 508, SEQ ID NO: 510, SEQ ID NO: 512, SEQ ID NO: 514, SEQ ID NOs: 535 to 537, SEQ ID NO: 539, SEQ ID NOs: 543 to 551, SEQ ID NO: 708, SEQ ID NO: 712, and SEQ ID NO: 738.

In another aspect, the invention provides for an immunogenic composition comprising nucleic acid sequences encoding one or more amino acid sequences selected from the group consisting of SEQ ID NOs: 484 to 485, SEQ ID NOs: 488 to 489, SEQ ID NOs: 569 to 575, SEQ ID NOs: 596 to 599, SEQ ID NOs: 601 to 604, SEQ ID NOs: 606 to 612, SEQ ID NO: 656, SEQ ID NO: 708, and SEQ ID NO: 712.

In some embodiments, the immunogenic composition comprises nucleic acid sequences encoding two or more amino acid sequences selected from the group consisting of SEQ ID NOs: 484 to 485, SEQ ID NOs: 488 to 489, SEQ ID NOs: 569 to 575, SEQ ID NOs: 596 to 599, SEQ ID NOs: 601 to 604, SEQ ID NOs: 606 to 612, SEQ ID NO: 656, SEQ ID NO: 708, and SEQ ID NO: 712. In some embodiments, the nucleic acid sequences are administered in a construct for expression in vivo. In some embodiments, the in vivo administration of the nucleic acid sequences is configured to produce one or more peptides that is displayed by an HLA class II molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is colorectal cancer.

In another aspect, the invention provides for a method of treating or preventing colorectal cancer by administering to a subject an immunogenic composition comprising nucleic acid sequences encoding one or more amino acid sequences selected from the group consisting of SEQ ID NOs: 484 to 485, SEQ ID NOs: 488 to 489, SEQ ID NOs: 569 to 575, SEQ ID NOs: 596 to 599, SEQ ID NOs: 601 to 604, SEQ ID NOs: 606 to 612, SEQ ID NO: 656, SEQ ID NO: 708, and SEQ ID NO: 712.

In some embodiments, the immunogenic composition comprises nucleic acid sequences encoding two or more amino acid sequences selected from the group consisting of SEQ ID NOs: 484 to 485, SEQ ID NOs: 488 to 489, SEQ ID NOs: 569 to 575, SEQ ID NOs: 596 to 599, SEQ ID NOs: 601 to 604, SEQ ID NOs: 606 to 612, SEQ ID NO: 656, SEQ ID NO: 708, and SEQ ID NO: 712.

In another aspect, the invention provides for an immunogenic peptide composition comprising one or more peptides selected from the group consisting of SEQ ID NOs: 484 to 485, SEQ ID NOs: 488 to 489, SEQ ID NOs: 569 to 575, SEQ ID NOs: 596 to 599, SEQ ID NOs: 601 to 604, SEQ ID NOs: 606 to 612, SEQ ID NO: 656, SEQ ID NO: 708, and SEQ ID NO: 712.

In some embodiments, the immunogenic peptide composition comprises two or more peptides selected from the group consisting of SEQ ID NOs: 484 to 485, SEQ ID NOs: 488 to 489, SEQ ID NOs: 569 to 575, SEQ ID NOs: 596 to 599, SEQ ID NOs: 601 to 604, SEQ ID NOs: 606 to 612, SEQ ID NO: 656, SEQ ID NO: 708, and SEQ ID NO: 712. In some embodiments, a peptide in the immunogenic peptide composition is displayed by an HLA class II molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is colorectal cancer.

In another aspect, the invention provides for a method of treating or preventing colorectal cancer in a subject comprising administering to the subject an immunogenic peptide composition comprising one or more peptides selected from the group consisting of SEQ ID NOs: 484 to 485, SEQ ID NOs: 488 to 489, SEQ ID NOs: 569 to 575, SEQ ID NOs: 596 to 599, SEQ ID NOs: 601 to 604, SEQ ID NOs: 606 to 612, SEQ ID NO: 656, SEQ ID NO: 708, and SEQ ID NO: 712.

In some embodiments, the immunogenic peptide composition comprises two or more peptides selected from the group consisting of SEQ ID NOs: 484 to 485, SEQ ID NOs: 488 to 489, SEQ ID NOs: 569 to 575, SEQ ID NOs: 596 to 599, SEQ ID NOs: 601 to 604, SEQ ID NOs: 606 to 612, SEQ ID NO: 656, SEQ ID NO: 708, and SEQ ID NO: 712.

In another aspect, the invention provides for an immunogenic composition comprising nucleic acid sequences encoding one or more amino acid sequences selected from the group consisting of SEQ ID NOs: 520 to 521, SEQ ID NOs: 523 to 524, SEQ ID NOs: 554 to 556, SEQ ID NO: 558, SEQ ID NO: 561, SEQ ID NOs: 563 to 565, SEQ ID NOs: 569 to 573, SEQ ID NOs: 596 to 600, SEQ ID NO: 650, SEQ ID NO: 656, and SEQ ID NOs: 700 to 705.

In some embodiments, the immunogenic composition comprises nucleic acid sequences encoding two or more amino acid sequences selected from the group consisting of SEQ ID NOs: 520 to 521, SEQ ID NOs: 523 to 524, SEQ ID NOs: 554 to 556, SEQ ID NO: 558, SEQ ID NO: 561, SEQ ID NOs: 563 to 565, SEQ ID NOs: 569 to 573, SEQ ID NOs: 596 to 600, SEQ ID NO: 650, SEQ ID NO: 656, and SEQ ID NOs: 700 to 705. In some embodiments, the nucleic acid sequences are administered in a construct for expression in vivo. In some embodiments, the in vivo administration of the nucleic acid sequences is configured to produce one or more peptides that is displayed by an HLA class II molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is bronchus and lung cancer.

In another aspect, the invention provides for a method of treating or preventing bronchus and lung cancer by administering to a subject an immunogenic composition comprising nucleic acid sequences encoding one or more amino acid sequences selected from the group consisting of SEQ ID NOs: 520 to 521, SEQ ID NOs: 523 to 524, SEQ ID NOs: 554 to 556, SEQ ID NO: 558, SEQ ID NO: 561, SEQ ID NOs: 563 to 565, SEQ ID NOs: 569 to 573, SEQ ID NOs: 596 to 600, SEQ ID NO: 650, SEQ ID NO: 656, and SEQ ID NOs: 700 to 705.

In some embodiments, the immunogenic composition comprises nucleic acid sequences encoding two or more amino acid sequences selected from the group consisting of SEQ ID NOs: 520 to 521, SEQ ID NOs: 523 to 524, SEQ ID NOs: 554 to 556, SEQ ID NO: 558, SEQ ID NO: 561, SEQ ID NOs: 563 to 565, SEQ ID NOs: 569 to 573, SEQ ID NOs: 596 to 600, SEQ ID NO: 650, SEQ ID NO: 656, and SEQ ID NOs: 700 to 705.

In another aspect, the invention provides for an immunogenic peptide composition comprising one or more peptides selected from the group consisting of SEQ ID NOs: 520 to 521, SEQ ID NOs: 523 to 524, SEQ ID NOs: 554 to 556, SEQ ID NO: 558, SEQ ID NO: 561, SEQ ID NOs: 563 to 565, SEQ ID NOs: 569 to 573, SEQ ID NOs: 596 to 600, SEQ ID NO: 650, SEQ ID NO: 656, and SEQ ID NOs: 700 to 705.

In some embodiments, the immunogenic peptide composition comprises two or more peptides selected from the group consisting of SEQ ID NOs: 520 to 521, SEQ ID NOs: 523 to 524, SEQ ID NOs: 554 to 556, SEQ ID NO: 558, SEQ ID NO: 561, SEQ ID NOs: 563 to 565, SEQ ID NOs: 569 to 573, SEQ ID NOs: 596 to 600, SEQ ID NO: 650, SEQ ID NO: 656, and SEQ ID NOs: 700 to 705. In some embodiments, a peptide in the immunogenic peptide composition is displayed by an HLA class II molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is bronchus and lung cancer.

In another aspect, the invention provides for a method of treating or preventing bronchus and lung cancer in a subject comprising administering to the subject an immunogenic peptide composition comprising one or more peptides selected from the group consisting of SEQ ID NOs: 520 to 521, SEQ ID NOs: 523 to 524, SEQ ID NOs: 554 to 556, SEQ ID NO: 558, SEQ ID NO: 561, SEQ ID NOs: 563 to 565, SEQ ID NOs: 569 to 573, SEQ ID NOs: 596 to 600, SEQ ID NO: 650, SEQ ID NO: 656, and SEQ ID NOs: 700 to 705.

In some embodiments, the immunogenic peptide composition comprises two or more peptides selected from the group consisting of SEQ ID NOs: 520 to 521, SEQ ID NOs: 523 to 524, SEQ ID NOs: 554 to 556, SEQ ID NO: 558, SEQ ID NO: 561, SEQ ID NOs: 563 to 565, SEQ ID NOs: 569 to 573, SEQ ID NOs: 596 to 600, SEQ ID NO: 650, SEQ ID NO: 656, and SEQ ID NOs: 700 to 705.

In another aspect, the invention provides for an immunogenic composition comprising nucleic acid sequences encoding one or more amino acid sequences selected from the group consisting of SEQ ID NOs: 646 to 667, SEQ ID NOs: 708 to 717, and SEQ ID NOs: 733 to 748.

In some embodiments, the immunogenic composition comprises nucleic acid sequences encoding two or more amino acid sequences selected from the group consisting of SEQ ID NOs: 646 to 667, SEQ ID NOs: 708 to 717, and SEQ ID NOs: 733 to 748. In some embodiments, the nucleic acid sequences are administered in a construct for expression in vivo. In some embodiments, the in vivo administration of the nucleic acid sequences is configured to produce one or more peptides that is displayed by an HLA class II molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is breast cancer.

In another aspect, the invention provides for a method of treating or preventing breast cancer by administering to a subject an immunogenic composition comprising nucleic acid sequences encoding one or more amino acid sequences selected from the group consisting of SEQ ID NOs: 646 to 667, SEQ ID NOs: 708 to 717, and SEQ ID NOs: 733 to 748.

In some embodiments, the immunogenic composition comprises nucleic acid sequences encoding two or more amino acid sequences selected from the group consisting of SEQ ID NOs: 646 to 667, SEQ ID NOs: 708 to 717, and SEQ ID NOs: 733 to 748.

In another aspect, the invention provides for an immunogenic peptide composition comprising one or more peptides selected from the group consisting of SEQ ID NOs: 646 to 667, SEQ ID NOs: 708 to 717, and SEQ ID NOs: 733 to 748.

In some embodiments, the immunogenic peptide composition comprises two or more peptides selected from the group consisting of SEQ ID NOs: 646 to 667, SEQ ID NOs: 708 to 717, and SEQ ID NOs: 733 to 748. In some embodiments, a peptide in the immunogenic peptide composition is displayed by an HLA class II molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is breast cancer.

In another aspect, the invention provides for a method of treating or preventing breast cancer in a subject comprising administering to the subject an immunogenic peptide composition comprising one or more peptides selected from the group consisting of SEQ ID NOs: 646 to 667, SEQ ID NOs: 708 to 717, and SEQ ID NOs: 733 to 748.

In some embodiments, the immunogenic peptide composition comprises two or more peptides selected from the group consisting of SEQ ID NOs: 646 to 667, SEQ ID NOs: 708 to 717, and SEQ ID NOs: 733 to 748.

In another aspect, the invention provides for an immunogenic composition comprising nucleic acid sequences encoding one or more amino acid sequences selected from the group consisting of SEQ ID NOs: 646 to 667, SEQ ID NOs: 708 to 717, and SEQ ID NOs: 733 to 748.

In some embodiments, the immunogenic composition comprises nucleic acid sequences encoding two or more amino acid sequences selected from the group consisting of SEQ ID NOs: 646 to 667, SEQ ID NOs: 708 to 717, and SEQ ID NOs: 733 to 748. In some embodiments, the nucleic acid sequences are administered in a construct for expression in vivo. In some embodiments, the in vivo administration of the nucleic acid sequences is configured to produce one or more peptides that is displayed by an HLA class II molecule. In some embodiments, the one or more peptides is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, the one or more peptides is a modified or unmodified fragment of a protein with a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, TP53 H179R, TP53 R158L, TP53

R175H, TP53 R248Q, TP53 R248W, TP53 R273C, TP53 R273H, TP53 R282W, and TP53 Y220C. In some embodiments, the nucleic acid sequences are administered in an effective amount to a subject to prevent cancer. In some embodiments, the nucleic acid sequences are administered in an effective amount to a subject to treat cancer. In some embodiments, the cancer is ovarian cancer.

In another aspect, the invention provides for a method of treating or preventing ovarian cancer by administering to a subject an immunogenic composition comprising nucleic acid sequences encoding one or more amino acid sequences selected from the group consisting of SEQ ID NOs: 646 to 667, SEQ ID NOs: 708 to 717, and SEQ ID NOs: 733 to 748.

In some embodiments, the immunogenic composition comprises nucleic acid sequences encoding two or more amino acid sequences selected from the group consisting of SEQ ID NOs: 646 to 667, SEQ ID NOs: 708 to 717, and SEQ ID NOs: 733 to 748.

In another aspect, the invention provides for an immunogenic peptide composition comprising one or more peptides selected from the group consisting of SEQ ID NOs: 646 to 667, SEQ ID NOs: 708 to 717, and SEQ ID NOs: 733 to 748.

In some embodiments, the immunogenic peptide composition comprises two or more peptides selected from the group consisting of SEQ ID NOs: 646 to 667, SEQ ID NOs: 708 to 717, and SEQ ID NOs: 733 to 748. In some embodiments, a peptide in the immunogenic peptide composition is displayed by an HLA class II molecule. In some embodiments, a peptide in the immunogenic peptide composition is a modified or unmodified fragment of a mutated protein selected from the group consisting of AKT1, BRAF, EGFR, GTF2I, HRAS, IDH1, KRAS, NRAS, PIK3CA, PTEN, and TP53. In some embodiments, a peptide in the immunogenic peptide composition is a modified or unmodified fragment of a protein, wherein the protein comprises a mutation selected from the group consisting of AKT1 E17K, BRAF V600E, BRAF V600M, EGFR A289V, EGFR G598V, EGFR L858R, GTF2I L424H, IDH1 R132C, IDH1 R132H, KRAS G12A, KRAS G12C, KRAS G12D, KRAS G12R, KRAS G12S, KRAS G12V, KRAS G13D, NRAS Q61K, NRAS Q61L, NRAS Q61R, PIK3CA E542K, PIK3CA E545K, PIK3CA H1047R, PIK3CA R88Q, PTEN R130G, PTEN R130Q, PTEN R179R, TP53 R158L, TP53 R175H, TP53 R248Q, TP53 R248W, TP53 R273C, TP53 R273H, TP53 R282W, and TP53 Y220C. In some embodiments, the immunogenic peptide composition is administered in an effective amount to a subject to prevent cancer. In some embodiments, the immunogenic peptide composition is administered in an effective amount to a subject to treat cancer. In some embodiments, the cancer is ovarian cancer.

In another aspect, the invention provides for a method of treating or preventing ovarian cancer in a subject comprising administering to the subject an immunogenic peptide composition comprising one or more peptides selected from the group consisting of SEQ ID NOs: 646 to 667, SEQ ID NOs: 708 to 717, and SEQ ID NOs: 733 to 748.

In some embodiments, the immunogenic peptide composition comprises two or more peptides selected from the group consisting of SEQ ID NOs: 646 to 667, SEQ ID NOs: 708 to 717, and SEQ ID NOs: 733 to 748.

Vaccines for CT Antigens

In one aspect, the invention provides for nucleic acid sequences encoding one or more amino acid sequences selected from the group consisting of SEQ ID NOs: 28796 to 28864, SEQ ID NOs: 37110 to 37174, SEQ ID NOs: 41321 to 41397, SEQ ID NO: 41770, SEQ ID NO: 49004, SEQ ID NO: 49071, SEQ ID NO: 49395, SEQ ID NO: 50632, SEQ ID NO: 50729, SEQ ID NOs: 51434 to 51510, SEQ ID NO: 55758, SEQ ID NOs: 60456 to 60527, SEQ ID NOs: 68238 to 68321, SEQ ID NO: 77091, SEQ ID NO: 77210, SEQ ID NO: 84188, SEQ ID NO: 87951, SEQ ID NO: 88144, SEQ ID NOs: 95593 to 95664, SEQ ID NOs: 113808 to 113869, SEQ ID NOs: 125134 to 125218, SEQ ID NOs: 144109 to 144188, SEQ ID NOs: 162383 to 162453, SEQ ID NOs: 166444 to 166531, SEQ ID NO: 167118, SEQ ID NO: 169740, SEQ ID NO: 173412, SEQ ID NO: 179404, and SEQ ID NOs: 182574 to 182654.

In some embodiments, the nucleic acid sequences encode two or more amino acid sequences selected from the group consisting of SEQ ID NOs: 28796 to 28864, SEQ ID NOs: 37110 to 37174, SEQ ID NOs: 41321 to 41397, SEQ ID NO: 41770, SEQ ID NO: 49004, SEQ ID NO: 49071, SEQ ID NO: 49395, SEQ ID NO: 50632, SEQ ID NO: 50729, SEQ ID NOs: 51434 to 51510, SEQ ID NO: 55758, SEQ ID NOs: 60456 to 60527, SEQ ID NOs: 68238 to 68321, SEQ ID NO: 77091, SEQ ID NO: 77210, SEQ ID NO: 84188, SEQ ID NO: 87951, SEQ ID NO: 88144, SEQ ID NOs: 95593 to 95664, SEQ ID NOs: 113808 to 113869, SEQ ID NOs: 125134 to 125218, SEQ ID NOs: 144109 to 144188, SEQ ID NOs: 162383 to 162453, SEQ ID NOs: 166444 to 166531, SEQ ID NO: 167118, SEQ ID NO: 169740, SEQ ID NO: 173412, SEQ ID NO: 179404, and SEQ ID NOs: 182574 to 182654.

In another aspect, the invention provides for an immunogenic composition comprising nucleic acid sequences encoding one or more amino acid sequences selected from the group consisting of SEQ ID NOs: 28796 to 28864, SEQ ID NOs: 37110 to 37174, SEQ ID NOs: 41321 to 41397, SEQ ID NO: 41770, SEQ ID NO: 49004, SEQ ID NO: 49071, SEQ ID NO: 49395, SEQ ID NO: 50632, SEQ ID NO: 50729, SEQ ID NOs: 51434 to 51510, SEQ ID NO: 55758, SEQ ID NOs: 60456 to 60527, SEQ ID NOs: 68238 to 68321, SEQ ID NO: 77091, SEQ ID NO: 77210, SEQ ID NO: 84188, SEQ ID NO: 87951, SEQ ID NO: 88144, SEQ ID NOs: 95593 to 95664, SEQ ID NOs: 113808 to 113869, SEQ ID NOs: 125134 to 125218, SEQ ID NOs: 144109 to 144188, SEQ ID NOs: 162383 to 162453, SEQ ID NOs: 166444 to 166531, SEQ ID NO: 167118, SEQ ID NO: 169740, SEQ ID NO: 173412, SEQ ID NO: 179404, and SEQ ID NOs: 182574 to 182654.

In some embodiments, the immunogenic composition is administered to a subject. In some embodiments, the immunogenic composition comprises nucleic acid sequences encoding two or more amino acid sequences selected from the group consisting of SEQ ID NOs: 28796 to 28864, SEQ ID NOs: 37110 to 37174, SEQ ID NOs: 41321 to 41397, SEQ ID NO: 41770, SEQ ID NO: 49004, SEQ ID NO: 49071, SEQ ID NO: 49395, SEQ ID NO: 50632, SEQ ID NO: 50729, SEQ ID NOs: 51434 to 51510, SEQ ID NO: 55758, SEQ ID NOs: 60456 to 60527, SEQ ID NOs: 68238 to 68321, SEQ ID NO: 77091, SEQ ID NO: 77210, SEQ ID NO: 84188, SEQ ID NO: 87951, SEQ ID NO: 88144, SEQ ID NOs: 95593 to 95664, SEQ ID NOs: 113808 to 113869, SEQ ID NOs: 125134 to 125218, SEQ ID NOs: 144109 to 144188, SEQ ID NOs: 162383 to 162453, SEQ ID NOs: 166444 to 166531, SEQ ID NO: 167118, SEQ ID NO: 169740, SEQ ID NO: 173412, SEQ ID NO: 179404, and SEQ ID NOs: 182574 to 182654. In some embodiments, the nucleic acid sequences are administered in a construct for expression in vivo. In some embodiments, the in vivo administration of the nucleic acid sequences is configured to produce one or more peptides that is displayed by an HLA class I molecule. In some embodiments, the one or more peptides is a modified or unmodified fragment of a protein selected from the group consisting of CTG1B, KKLC1, MAGA1, MAGA3, MAGA4, MAGC1, MAGC3, MAR1, PMEL, PRAME, SSX2, TYRP1, and TYRP2. In some embodiments, the immunogenic composition is administered in an effective amount to a subject to prevent cancer. In some embodiments, the immunogenic composition is administered in an effective amount to a subject to treat cancer. In some embodiments, the cancer is selected from the group consisting of pancreatic cancer, skin cancer, thyroid cancer, brain cancer, colorectal cancer, bronchus and lung cancer, breast cancer, and ovarian cancer. In some embodiments, the immunogenic composition comprises nucleic acid sequences encoding at least three amino acid sequences selected from the group consisting of SEQ ID NOs: 28796 to 28864, SEQ ID NOs: 37110 to 37174, SEQ ID NOs: 41321 to 41397, SEQ ID NO: 41770, SEQ ID NO: 49004, SEQ ID NO: 49071, SEQ ID NO: 49395, SEQ ID NO: 50632, SEQ ID NO: 50729, SEQ ID NOs: 51434 to 51510, SEQ ID NO: 55758, SEQ ID NOs: 60456 to 60527, SEQ ID NOs: 68238 to 68321, SEQ ID NO: 77091, SEQ ID NO: 77210, SEQ ID NO: 84188, SEQ ID NO: 87951, SEQ ID NO: 88144, SEQ ID NOs: 95593 to 95664, SEQ ID NOs: 113808 to 113869, SEQ ID NOs: 125134 to 125218, SEQ ID NOs: 144109 to 144188, SEQ ID NOs: 162383 to 162453, SEQ ID NOs: 166444 to 166531, SEQ ID NO: 167118, SEQ ID NO: 169740, SEQ ID NO: 173412, SEQ ID NO: 179404, and SEQ ID NOs: 182574 to 182654.

In another aspect, the invention provides for an immunogenic peptide composition comprising one or more peptides selected from the group consisting of SEQ ID NOs: 28796 to 28864, SEQ ID NOs: 37110 to 37174, SEQ ID NOs: 41321 to 41397, SEQ ID NO: 41770, SEQ ID NO: 49004, SEQ ID NO: 49071, SEQ ID NO: 49395, SEQ ID NO: 50632, SEQ ID NO: 50729, SEQ ID NOs: 51434 to 51510, SEQ ID NO: 55758, SEQ ID NOs: 60456 to 60527, SEQ ID NOs: 68238 to 68321, SEQ ID NO: 77091, SEQ ID NO: 77210, SEQ ID NO: 84188, SEQ ID NO: 87951, SEQ ID NO: 88144, SEQ ID NOs: 95593 to 95664, SEQ ID NOs: 113808 to 113869, SEQ ID NOs: 125134 to 125218, SEQ ID NOs: 144109 to 144188, SEQ ID NOs: 162383 to 162453, SEQ ID NOs: 166444 to 166531, SEQ ID NO: 167118, SEQ ID NO: 169740, SEQ ID NO: 173412, SEQ ID NO: 179404, and SEQ ID NOs: 182574 to 182654.

In some embodiments, the immunogenic peptide composition comprises two or more peptides selected from the group consisting of SEQ ID NOs: 28796 to 28864, SEQ ID NOs: 37110 to 37174, SEQ ID NOs: 41321 to 41397, SEQ ID NO: 41770, SEQ ID NO: 49004, SEQ ID NO: 49071, SEQ ID NO: 49395, SEQ ID NO: 50632, SEQ ID NO: 50729, SEQ ID NOs: 51434 to 51510, SEQ ID NO: 55758, SEQ ID NOs: 60456 to 60527, SEQ ID NOs: 68238 to 68321, SEQ ID NO: 77091, SEQ ID NO: 77210, SEQ ID NO: 84188, SEQ ID NO: 87951, SEQ ID NO: 88144, SEQ ID NOs: 95593 to 95664, SEQ ID NOs: 113808 to 113869, SEQ ID NOs: 125134 to 125218, SEQ ID NOs: 144109 to 144188, SEQ ID NOs: 162383 to 162453, SEQ ID NOs: 166444 to 166531, SEQ ID NO: 167118, SEQ ID NO: 169740, SEQ ID NO: 173412, SEQ ID NO: 179404, and SEQ ID NOs: 182574 to 182654.

In another aspect, the invention provides for an immunogenic composition comprising nucleic acid sequences encoding one or more amino acid sequences selected from the group consisting of SEQ ID NOs: 28796 to 28830.

In some embodiments, the immunogenic composition comprises nucleic acid sequences encoding one or more amino acid sequences derived from a CTG1B protein. In some embodiments, the immunogenic composition comprises nucleic acid sequences encoding two or more amino acid sequences selected from the group consisting of SEQ ID NOs: 28796 to 28830.

In another aspect, the invention provides for an immunogenic peptide composition comprising one or more peptides selected from the group consisting of SEQ ID NOs: 28796 to 28830.

In some embodiments, the immunogenic peptide composition comprises two or more peptides selected from the group consisting of SEQ ID NOs: 28796 to 28830. In some embodiments, the one or more peptides is a modified or unmodified fragment of a CTG1B protein.

In another aspect, the invention provides for an immunogenic composition comprising nucleic acid sequences encoding one or more amino acid sequences selected from the group consisting of SEQ ID NOs: 41321 to 41354.

In some embodiments, the immunogenic composition comprises nucleic acid sequences encoding one or more amino acid sequences derived from a MAGA1 protein. In some embodiments, the immunogenic composition comprises nucleic acid sequences encoding two or more amino acid sequences selected from the group consisting of SEQ ID NOs: 41321 to 41354.

In another aspect, the invention provides for an immunogenic peptide composition comprising one or more peptides selected from the group consisting of SEQ ID NOs: 41321 to 41354.

In some embodiments, the immunogenic peptide composition comprises two or more peptides selected from the group consisting of SEQ ID NOs: 41321 to 41354. In some embodiments, the one or more peptides is a modified or unmodified fragment of a MAGA1 protein.

In another aspect, the invention provides for an immunogenic composition comprising nucleic acid sequences encoding one or more amino acid sequences selected from the group consisting of SEQ ID NO: 41770, SEQ ID NO: 49004, and SEQ ID NOs: 51434 to 51468.

In some embodiments, the immunogenic composition comprises nucleic acid sequences encoding one or more amino acid sequences derived from a MAGA3 protein. In some embodiments, the immunogenic composition comprises nucleic acid sequences encoding two or more amino acid sequences selected from the group consisting of SEQ ID NO: 41770, SEQ ID NO: 49004, and SEQ ID NOs: 51434 to 51468.

In another aspect, the invention provides for an immunogenic peptide composition comprising one or more peptides selected from the group consisting of SEQ ID NO: 41770, SEQ ID NO: 49004, and SEQ ID NOs: 51434 to 51468.

In some embodiments, the immunogenic peptide composition comprises two or more peptides selected from the group consisting of SEQ ID NO: 41770, SEQ ID NO: 49004, and SEQ ID NOs: 51434 to 51468. In some embodiments, the one or more peptides is a modified or unmodified fragment of a MAGA3 protein.

In another aspect, the invention provides for an immunogenic composition comprising nucleic acid sequences encoding one or more amino acid sequences selected from the group consisting of SEQ ID NO: 41352, SEQ ID NO: 41770, and SEQ ID NOs: 60456 to 60487.

In some embodiments, the immunogenic composition comprises nucleic acid sequences encoding one or more amino acid sequences derived from a MAGA4 protein. In some embodiments, the immunogenic composition comprises nucleic acid sequences encoding two or more amino acid sequences selected from the group consisting of SEQ ID NO: 41352, SEQ ID NO: 41770, and SEQ ID NOs: 60456 to 60487.

In another aspect, the invention provides for an immunogenic peptide composition comprising one or more peptides selected from the group consisting of SEQ ID NO: 41352, SEQ ID NO: 41770, and SEQ ID NOs: 60456 to 60487.

In some embodiments, the immunogenic peptide composition comprises two or more peptides selected from the group consisting of SEQ ID NO: 41352, SEQ ID NO: 41770, and SEQ ID NOs: 60456 to 60487. In some embodiments, the one or more peptides is a modified or unmodified fragment of a MAGA4 protein.

In another aspect, the invention provides for an immunogenic composition comprising nucleic acid sequences encoding one or more amino acid sequences selected from the group consisting of SEQ ID NO: 49395 and SEQ ID NOs: 68238 to 68272.

In some embodiments, the immunogenic composition comprises nucleic acid sequences encoding one or more amino acid sequences derived from a MAGC1 protein. In some embodiments, the immunogenic composition comprises nucleic acid sequences encoding two or more amino acid sequences selected from the group consisting of SEQ ID NO: 49395 and SEQ ID NOs: 68238 to 68272.

In another aspect, the invention provides for an immunogenic peptide composition comprising one or more peptides selected from the group consisting of SEQ ID NO: 49395 and SEQ ID NOs: 68238 to 68272.

In some embodiments, the immunogenic peptide composition comprises two or more peptides selected from the group consisting of SEQ ID NO: 49395 and SEQ ID NOs: 68238 to 68272. In some embodiments, the one or more peptides is a modified or unmodified fragment of a MAGC1 protein.

In another aspect, the invention provides for an immunogenic composition comprising nucleic acid sequences encoding one or more amino acid sequences selected from the group consisting of SEQ ID NO: 77091, SEQ ID NO: 77210, SEQ ID NO: 84188, SEQ ID NO: 88144, and SEQ ID NOs: 95593 to 95624.

In some embodiments, the immunogenic composition comprises nucleic acid sequences encoding one or more amino acid sequences derived from a MAGC3 protein. In some embodiments, the immunogenic composition comprises nucleic acid sequences encoding two or more amino acid sequences selected from the group consisting of SEQ ID NO: 77091, SEQ ID NO: 77210, SEQ ID NO: 84188, SEQ ID NO: 88144, and SEQ ID NOs: 95593 to 95624.

In another aspect, the invention provides for an immunogenic peptide composition comprising one or more peptides selected from the group consisting of SEQ ID NO: 77091, SEQ ID NO: 77210, SEQ ID NO: 84188, SEQ ID NO: 88144, and SEQ ID NOs: 95593 to 95624.

In some embodiments, the immunogenic peptide composition comprises two or more peptides selected from the group consisting of SEQ ID NO: 77091, SEQ ID NO: 77210, SEQ ID NO: 84188, SEQ ID NO: 88144, and SEQ ID NOs: 95593 to 95624. In some embodiments, the one or more peptides is a modified or unmodified fragment of a MAGC3 protein.

In another aspect, the invention provides for an immunogenic composition comprising nucleic acid sequences encoding one or more amino acid sequences selected from the group consisting of SEQ ID NOs: 162383 to 162420.

In some embodiments, the immunogenic composition comprises nucleic acid sequences encoding one or more amino acid sequences derived from a SSX2 protein. In some embodiments, the immunogenic composition comprises nucleic acid sequences encoding two or more amino acid sequences selected from the group consisting of SEQ ID NOs: 162383 to 162420.

In another aspect, the invention provides for an immunogenic peptide composition comprising one or more peptides selected from the group consisting of SEQ ID NOs: 162383 to 162420.

In some embodiments, the immunogenic peptide composition comprises two or more peptides selected from the group consisting of SEQ ID NOs: 162383 to 162420. In some embodiments, the one or more peptides is a modified or unmodified fragment of a SSX2 protein.

In another aspect, the invention provides for an immunogenic composition comprising nucleic acid sequences encoding one or more amino acid sequences selected from the group consisting of SEQ ID NOs: 144109 to 144142.

In some embodiments, the immunogenic composition comprises nucleic acid sequences encoding one or more amino acid sequences derived from a PRAME protein. In some embodiments, the immunogenic composition comprises nucleic acid sequences encoding two or more amino acid sequences selected from the group consisting of SEQ ID NOs: 144109 to 144142.

In another aspect, the invention provides for an immunogenic peptide composition comprising one or more peptides selected from the group consisting of SEQ ID NOs: 144109 to 144142.

In some embodiments, the immunogenic peptide composition comprises two or more peptides selected from the group consisting of SEQ ID NOs: 144109 to 144142. In some embodiments, the one or more peptides is a modified or unmodified fragment of a PRAME protein.

In another aspect, the invention provides for an immunogenic composition comprising nucleic acid sequences encoding one or more amino acid sequences selected from the group consisting of SEQ ID NOs: 37110 to 37145.

In some embodiments, the immunogenic composition comprises nucleic acid sequences encoding one or more amino acid sequences derived from a KKLC1 protein. In some embodiments, the immunogenic composition comprises nucleic acid sequences encoding two or more amino acid sequences selected from the group consisting of SEQ ID NOs: 37110 to 37145.

In another aspect, the invention provides for an immunogenic peptide composition comprising one or more peptides selected from the group consisting of SEQ ID NOs: 37110 to 37145.

In some embodiments, the immunogenic peptide composition comprises two or more peptides selected from the group consisting of SEQ ID NOs: 37110 to 37145. In some embodiments, the one or more peptides is a modified or unmodified fragment of a KKLC1 protein.

In another aspect, the invention provides for an immunogenic composition comprising nucleic acid sequences encoding one or more amino acid sequences selected from the group consisting of SEQ ID NOs: 125134 to 125167.

In some embodiments, the immunogenic composition comprises nucleic acid sequences encoding one or more amino acid sequences derived from a PMEL protein. In some embodiments, the immunogenic composition comprises nucleic acid sequences encoding two or more amino acid sequences selected from the group consisting of SEQ ID NOs: 125134 to 125167.

In another aspect, the invention provides for an immunogenic peptide composition comprising one or more peptides selected from the group consisting of SEQ ID NOs: 125134 to 125167.

In some embodiments, the immunogenic peptide composition comprises two or more peptides selected from the group consisting of SEQ ID NOs: 125134 to 125167. In some embodiments, the one or more peptides is a modified or unmodified fragment of a PMEL protein.

In another aspect, the invention provides for an immunogenic composition comprising nucleic acid sequences encoding one or more amino acid sequences selected from the group consisting of SEQ ID NOs: 166444 to 166480.

In some embodiments, the immunogenic composition comprises nucleic acid sequences encoding one or more amino acid sequences derived from a TYRP1 protein. In some embodiments, the immunogenic composition comprises nucleic acid sequences encoding two or more amino acid sequences selected from the group consisting of SEQ ID NOs: 166444 to 166480.

In another aspect, the invention provides for an immunogenic peptide composition comprising one or more peptides selected from the group consisting of SEQ ID NOs: 166444 to 166480.

In some embodiments, the immunogenic peptide composition comprises two or more peptides selected from the group consisting of SEQ ID NOs: 166444 to 166480. In some embodiments, the one or more peptides is a modified or unmodified fragment of a TYRP1 protein.

In another aspect, the invention provides for an immunogenic composition comprising nucleic acid sequences encoding one or more amino acid sequences selected from the group consisting of SEQ ID NO: 169740, SEQ ID NO: 173412, SEQ ID NO: 179404, and SEQ ID NOs: 182574 to 182606.

In some embodiments, the immunogenic composition comprises nucleic acid sequences encoding one or more amino acid sequences derived from a TYRP2 protein. In some embodiments, the immunogenic composition comprises nucleic acid sequences encoding two or more amino acid sequences selected from the group consisting of SEQ ID NO: 169740, SEQ ID NO: 173412, SEQ ID NO: 179404, and SEQ ID NOs: 182574 to 182606.

In another aspect, the invention provides for an immunogenic peptide composition comprising one or more peptides selected from the group consisting of SEQ ID NO: 169740, SEQ ID NO: 173412, SEQ ID NO: 179404, and SEQ ID NOs: 182574 to 182606.

In some embodiments, the immunogenic peptide composition comprises two or more peptides selected from the group consisting of SEQ ID NO: 169740, SEQ ID NO: 173412, SEQ ID NO: 179404, and SEQ ID NOs: 182574 to 182606. In some embodiments, the one or more peptides is a modified or unmodified fragment of a TYRP2 protein.

In another aspect, the invention provides for an immunogenic composition comprising nucleic acid sequences encoding one or more amino acid sequences selected from the group consisting of SEQ ID NOs: 113808 to 113843.

In some embodiments, the immunogenic composition comprises nucleic acid sequences encoding one or more amino acid sequences derived from a MAR1 protein. In some embodiments, the immunogenic composition comprises nucleic acid sequences encoding two or more amino acid sequences selected from the group consisting of SEQ ID NOs: 113808 to 113843.

In another aspect, the invention provides for an immunogenic peptide composition comprising one or more peptides selected from the group consisting of SEQ ID NOs: 113808 to 113843.

In some embodiments, the immunogenic peptide composition comprises two or more peptides selected from the group consisting of SEQ ID NOs: 113808 to 113843. In some embodiments, the one or more peptides is a modified or unmodified fragment of a MAR1 protein.

In one aspect, the invention provides for nucleic acid sequences encoding one or more amino acid sequences selected from the group consisting of SEQ ID NOs: 28796 to 28864, SEQ ID NOs: 37110 to 37174, SEQ ID NOs: 41321 to 41397, SEQ ID NO: 41770, SEQ ID NO: 49004, SEQ ID NO: 49071, SEQ ID NO: 49395, SEQ ID NO: 50632, SEQ ID NO: 50729, SEQ ID NOs: 51434 to 51510, SEQ ID NO: 55758, SEQ ID NOs: 60456 to 60527, SEQ ID NOs: 68238 to 68321, SEQ ID NO: 77091, SEQ ID NO: 77210, SEQ ID NO: 84188, SEQ ID NO: 87951, SEQ ID NO: 88144, SEQ ID NOs: 95593 to 95664, SEQ ID NOs: 113808 to 113869, SEQ ID NOs: 125134 to 125218, SEQ ID NOs: 144109 to 144188, SEQ ID NOs: 162383 to 162453, SEQ ID NOs: 166444 to 166531, SEQ ID NO: 167118, SEQ ID NO: 169740, SEQ ID NO: 173412, SEQ ID NO: 179404, and SEQ ID NOs: 182574 to 182654.

In some embodiments, the nucleic acid sequences encode two or more amino acid sequences selected from the group consisting of SEQ ID NOs: 28796 to 28864, SEQ ID NOs: 37110 to 37174, SEQ ID NOs: 41321 to 41397, SEQ ID NO: 41770, SEQ ID NO: 49004, SEQ ID NO: 49071, SEQ ID NO: 49395, SEQ ID NO: 50632, SEQ ID NO: 50729, SEQ ID NOs: 51434 to 51510, SEQ ID NO: 55758, SEQ ID NOs: 60456 to 60527, SEQ ID NOs: 68238 to 68321, SEQ ID NO: 77091, SEQ ID NO: 77210, SEQ ID NO: 84188, SEQ ID NO: 87951, SEQ ID NO: 88144, SEQ ID NOs: 95593 to 95664, SEQ ID NOs: 113808 to 113869, SEQ ID NOs: 125134 to 125218, SEQ ID NOs: 144109 to 144188, SEQ ID NOs: 162383 to 162453, SEQ ID NOs: 166444 to 166531, SEQ ID NO: 167118, SEQ ID NO: 169740, SEQ ID NO: 173412, SEQ ID NO: 179404, and SEQ ID NOs: 182574 to 182654.

In another aspect, the invention provides for an immunogenic composition comprising nucleic acid sequences encoding one or more amino acid sequences selected from the group consisting of SEQ ID NOs: 28796 to 28864, SEQ ID NOs: 37110 to 37174, SEQ ID NOs: 41321 to 41397, SEQ ID NO: 41770, SEQ ID NO: 49004, SEQ ID NO: 49071, SEQ ID NO: 49395, SEQ ID NO: 50632, SEQ ID NO: 50729, SEQ ID NOs: 51434 to 51510, SEQ ID NO: 55758, SEQ ID NOs: 60456 to 60527, SEQ ID NOs: 68238 to 68321, SEQ ID NO: 77091, SEQ ID NO: 77210, SEQ ID NO: 84188, SEQ ID NO: 87951, SEQ ID NO: 88144, SEQ ID NOs: 95593 to 95664, SEQ ID NOs: 113808 to 113869, SEQ ID NOs: 125134 to 125218, SEQ ID NOs: 144109 to 144188, SEQ ID NOs: 162383 to 162453, SEQ ID NOs: 166444 to 166531, SEQ ID NO: 167118, SEQ ID NO: 169740, SEQ ID NO: 173412, SEQ ID NO: 179404, and SEQ ID NOs: 182574 to 182654.

In some embodiments, the immunogenic composition is administered to a subject. In some embodiments, the immunogenic composition comprises nucleic acid sequences encoding two or more amino acid sequences selected from the group consisting of SEQ ID NOs: 28796 to 28864, SEQ ID NOs: 37110 to 37174, SEQ ID NOs: 41321 to 41397, SEQ ID NO: 41770, SEQ ID NO: 49004, SEQ ID NO: 49071, SEQ ID NO: 49395, SEQ ID NO: 50632, SEQ ID NO: 50729, SEQ ID NOs: 51434 to 51510, SEQ ID NO:

55758, SEQ ID NOs: 60456 to 60527, SEQ ID NOs: 68238 to 68321, SEQ ID NO: 77091, SEQ ID NO: 77210, SEQ ID NO: 84188, SEQ ID NO: 87951, SEQ ID NO: 88144, SEQ ID NOs: 95593 to 95664, SEQ ID NOs: 113808 to 113869, SEQ ID NOs: 125134 to 125218, SEQ ID NOs: 144109 to 144188, SEQ ID NOs: 162383 to 162453, SEQ ID NOs: 166444 to 166531, SEQ ID NO: 167118, SEQ ID NO: 169740, SEQ ID NO: 173412, SEQ ID NO: 179404, and SEQ ID NOs: 182574 to 182654. In some embodiments, the nucleic acid sequences are administered in a construct for expression in vivo. In some embodiments, the in vivo administration of the nucleic acid sequences is configured to produce one or more peptides that is displayed by an HLA class II molecule. In some embodiments, the one or more peptides is a modified or unmodified fragment of a protein selected from the group consisting of CTG1B, KKLC1, MAGA1, MAGA3, MAGA4, MAGC1, MAGC3, MAR1, PMEL, PRAME, SSX2, TYRP1, and TYRP2. In some embodiments, the immunogenic composition is administered in an effective amount to a subject to prevent cancer. In some embodiments, the immunogenic composition is administered in an effective amount to a subject to treat cancer. In some embodiments, the cancer is selected from the group consisting of pancreatic cancer, skin cancer, thyroid cancer, brain cancer, colorectal cancer, bronchus and lung cancer, breast cancer, and ovarian cancer. In some embodiments, the immunogenic composition comprises nucleic acid sequences encoding at least three amino acid sequences selected from the group consisting of SEQ ID NOs: 28796 to 28864, SEQ ID NOs: 37110 to 37174, SEQ ID NOs: 41321 to 41397, SEQ ID NO: 41770, SEQ ID NO: 49004, SEQ ID NO: 49071, SEQ ID NO: 49395, SEQ ID NO: 50632, SEQ ID NO: 50729, SEQ ID NOs: 51434 to 51510, SEQ ID NO: 55758, SEQ ID NOs: 60456 to 60527, SEQ ID NOs: 68238 to 68321, SEQ ID NO: 77091, SEQ ID NO: 77210, SEQ ID NO: 84188, SEQ ID NO: 87951, SEQ ID NO: 88144, SEQ ID NOs: 95593 to 95664, SEQ ID NOs: 113808 to 113869, SEQ ID NOs: 125134 to 125218, SEQ ID NOs: 144109 to 144188, SEQ ID NOs: 162383 to 162453, SEQ ID NOs: 166444 to 166531, SEQ ID NO: 167118, SEQ ID NO: 169740, SEQ ID NO: 173412, SEQ ID NO: 179404, and SEQ ID NOs: 182574 to 182654.

In another aspect, the invention provides for an immunogenic peptide composition comprising one or more peptides selected from the group consisting of SEQ ID NOs: 28796 to 28864, SEQ ID NOs: 37110 to 37174, SEQ ID NOs: 41321 to 41397, SEQ ID NO: 41770, SEQ ID NO: 49004, SEQ ID NO: 49071, SEQ ID NO: 49395, SEQ ID NO: 50632, SEQ ID NO: 50729, SEQ ID NOs: 51434 to 51510, SEQ ID NO: 55758, SEQ ID NOs: 60456 to 60527, SEQ ID NOs: 68238 to 68321, SEQ ID NO: 77091, SEQ ID NO: 77210, SEQ ID NO: 84188, SEQ ID NO: 87951, SEQ ID NO: 88144, SEQ ID NOs: 95593 to 95664, SEQ ID NOs: 113808 to 113869, SEQ ID NOs: 125134 to 125218, SEQ ID NOs: 144109 to 144188, SEQ ID NOs: 162383 to 162453, SEQ ID NOs: 166444 to 166531, SEQ ID NO: 167118, SEQ ID NO: 169740, SEQ ID NO: 173412, SEQ ID NO: 179404, and SEQ ID NOs: 182574 to 182654.

In some embodiments, the immunogenic peptide composition comprises two or more peptides selected from the group consisting of SEQ ID NOs: 28796 to 28864, SEQ ID NOs: 37110 to 37174, SEQ ID NOs: 41321 to 41397, SEQ ID NO: 41770, SEQ ID NO: 49004, SEQ ID NO: 49071, SEQ ID NO: 49395, SEQ ID NO: 50632, SEQ ID NO: 50729, SEQ ID NOs: 51434 to 51510, SEQ ID NO: 55758, SEQ ID NOs: 60456 to 60527, SEQ ID NOs: 68238 to 68321, SEQ ID NO: 77091, SEQ ID NO: 77210, SEQ ID NO: 84188, SEQ ID NO: 87951, SEQ ID NO: 88144, SEQ ID NOs: 95593 to 95664, SEQ ID NOs: 113808 to 113869, SEQ ID NOs: 125134 to 125218, SEQ ID NOs: 144109 to 144188, SEQ ID NOs: 162383 to 162453, SEQ ID NOs: 166444 to 166531, SEQ ID NO: 167118, SEQ ID NO: 169740, SEQ ID NO: 173412, SEQ ID NO: 179404, and SEQ ID NOs: 182574 to 182654.

In another aspect, the invention provides for an immunogenic composition comprising nucleic acid sequences encoding one or more amino acid sequences selected from the group consisting of SEQ ID NOs: 197897 to 197901.

In some embodiments, the immunogenic composition comprises nucleic acid sequences encoding one or more amino acid sequences derived from a CTG1B protein. In some embodiments, the immunogenic composition comprises nucleic acid sequences encoding two or more amino acid sequences selected from the group consisting of SEQ ID NOs: 197897 to 197901.

In another aspect, the invention provides for an immunogenic peptide composition comprising one or more peptides selected from the group consisting of SEQ ID NOs: 197897 to 197901.

In some embodiments, the immunogenic peptide composition comprises two or more peptides selected from the group consisting of SEQ ID NOs: 197897 to 197901. In some embodiments, the one or more peptides is a modified or unmodified fragment of a CTG1B protein.

In another aspect, the invention provides for an immunogenic composition comprising nucleic acid sequences encoding one or more amino acid sequences selected from the group consisting of SEQ ID NOs: 211901 to 211904.

In some embodiments, the immunogenic composition comprises nucleic acid sequences encoding one or more amino acid sequences derived from a MAGA1 protein. In some embodiments, the immunogenic composition comprises nucleic acid sequences encoding two or more amino acid sequences selected from the group consisting of SEQ ID NOs: 211901 to 211904.

In another aspect, the invention provides for an immunogenic peptide composition comprising one or more peptides selected from the group consisting of SEQ ID NOs: 211901 to 211904.

In some embodiments, the immunogenic peptide composition comprises two or more peptides selected from the group consisting of SEQ ID NOs: 211901 to 211904. In some embodiments, the one or more peptides is a modified or unmodified fragment of a MAGA1 protein.

In another aspect, the invention provides for an immunogenic composition comprising nucleic acid sequences encoding one or more amino acid sequences selected from the group consisting of SEQ ID NOs: 223623 to 223627.

In some embodiments, the immunogenic composition comprises nucleic acid sequences encoding one or more amino acid sequences derived from a MAGA3 protein. In some embodiments, the immunogenic composition comprises nucleic acid sequences encoding two or more amino acid sequences selected from the group consisting of SEQ ID NOs: 223623 to 223627.

In another aspect, the invention provides for an immunogenic peptide composition comprising one or more peptides selected from the group consisting of SEQ ID NOs: 223623 to 223627.

In some embodiments, the immunogenic peptide composition comprises two or more peptides selected from the group consisting of SEQ ID NOs: 223623 to 223627. In some embodiments, the one or more peptides is a modified or unmodified fragment of a MAGA3 protein.

In another aspect, the invention provides for an immunogenic composition comprising nucleic acid sequences encoding one or more amino acid sequences selected from the group consisting of SEQ ID NOs: 236016 to 236020.

In some embodiments, the immunogenic composition comprises nucleic acid sequences encoding one or more amino acid sequences derived from a MAGA4 protein. In some embodiments, the immunogenic composition comprises nucleic acid sequences encoding two or more amino acid sequences selected from the group consisting of SEQ ID NOs: 236016 to 236020.

In another aspect, the invention provides for an immunogenic peptide composition comprising one or more peptides selected from the group consisting of SEQ ID NOs: 236016 to 236020.

In some embodiments, the immunogenic peptide composition comprises two or more peptides selected from the group consisting of SEQ ID NOs: 236016 to 236020. In some embodiments, the one or more peptides is a modified or unmodified fragment of a MAGA4 protein.

In another aspect, the invention provides for an immunogenic composition comprising nucleic acid sequences encoding one or more amino acid sequences selected from the group consisting of SEQ ID NOs: 247059 to 247063.

In some embodiments, the immunogenic composition comprises nucleic acid sequences encoding one or more amino acid sequences derived from a MAGC1 protein. In some embodiments, the immunogenic composition comprises nucleic acid sequences encoding two or more amino acid sequences selected from the group consisting of SEQ ID NOs: 247059 to 247063.

In another aspect, the invention provides for an immunogenic peptide composition comprising one or more peptides selected from the group consisting of SEQ ID NOs: 247059 to 247063.

In some embodiments, the immunogenic peptide composition comprises two or more peptides selected from the group consisting of SEQ ID NOs: 247059 to 247063. In some embodiments, the one or more peptides is a modified or unmodified fragment of a MAGC1 protein.

In another aspect, the invention provides for an immunogenic composition comprising nucleic acid sequences encoding one or more amino acid sequences selected from the group consisting of SEQ ID NOs: 281350 to 281353.

In some embodiments, the immunogenic composition comprises nucleic acid sequences encoding one or more amino acid sequences derived from a MAGC3 protein. In some embodiments, the immunogenic composition comprises nucleic acid sequences encoding two or more amino acid sequences selected from the group consisting of SEQ ID NOs: 281350 to 281353.

In another aspect, the invention provides for an immunogenic peptide composition comprising one or more peptides selected from the group consisting of SEQ ID NOs: 281350 to 281353.

In some embodiments, the immunogenic peptide composition comprises two or more peptides selected from the group consisting of SEQ ID NOs: 281350 to 281353. In some embodiments, the one or more peptides is a modified or unmodified fragment of a MAGC3 protein.

In another aspect, the invention provides for an immunogenic composition comprising nucleic acid sequences encoding one or more amino acid sequences selected from the group consisting of SEQ ID NOs: 369027 to 369031.

In some embodiments, the immunogenic composition comprises nucleic acid sequences encoding one or more amino acid sequences derived from a SSX2 protein. In some embodiments, the immunogenic composition comprises nucleic acid sequences encoding two or more amino acid sequences selected from the group consisting of SEQ ID NOs: 369027 to 369031.

In another aspect, the invention provides for an immunogenic peptide composition comprising one or more peptides selected from the group consisting of SEQ ID NOs: 369027 to 369031.

In some embodiments, the immunogenic peptide composition comprises two or more peptides selected from the group consisting of SEQ ID NOs: 369027 to 369031. In some embodiments, the one or more peptides is a modified or unmodified fragment of a SSX2 protein.

In another aspect, the invention provides for an immunogenic composition comprising nucleic acid sequences encoding one or more amino acid sequences selected from the group consisting of SEQ ID NOs: 342521 to 342525.

In some embodiments, the immunogenic composition comprises nucleic acid sequences encoding one or more amino acid sequences derived from a PRAME protein. In some embodiments, the immunogenic composition comprises nucleic acid sequences encoding two or more amino acid sequences selected from the group consisting of SEQ ID NOs: 342521 to 342525.

In another aspect, the invention provides for an immunogenic peptide composition comprising one or more peptides selected from the group consisting of SEQ ID NOs: 342521 to 342525.

In some embodiments, the immunogenic peptide composition comprises two or more peptides selected from the group consisting of SEQ ID NOs: 342521 to 342525. In some embodiments, the one or more peptides is a modified or unmodified fragment of a PRAME protein.

In another aspect, the invention provides for an immunogenic composition comprising nucleic acid sequences encoding one or more amino acid sequences selected from the group consisting of SEQ ID NOs: 206663 to 206665.

In some embodiments, the immunogenic composition comprises nucleic acid sequences encoding one or more amino acid sequences derived from a KKLC1 protein. In some embodiments, the immunogenic composition comprises nucleic acid sequences encoding two or more amino acid sequences selected from the group consisting of SEQ ID NOs: 206663 to 206665.

In another aspect, the invention provides for an immunogenic peptide composition comprising one or more peptides selected from the group consisting of SEQ ID NOs: 206663 to 206665.

In some embodiments, the immunogenic peptide composition comprises two or more peptides selected from the group consisting of SEQ ID NOs: 206663 to 206665. In some embodiments, the one or more peptides is a modified or unmodified fragment of a KKLC1 protein.

In another aspect, the invention provides for an immunogenic composition comprising nucleic acid sequences encoding one or more amino acid sequences selected from the group consisting of SEQ ID NOs: 317360 to 317363.

In some embodiments, the immunogenic composition comprises nucleic acid sequences encoding one or more amino acid sequences derived from a PMEL protein. In some embodiments, the immunogenic composition comprises nucleic acid sequences encoding two or more amino acid sequences selected from the group consisting of SEQ ID NOs: 317360 to 317363.

In another aspect, the invention provides for an immunogenic peptide composition comprising one or more peptides selected from the group consisting of SEQ ID NOs: 317360 to 317363.

In some embodiments, the immunogenic peptide composition comprises two or more peptides selected from the group consisting of SEQ ID NOs: 317360 to 317363. In some embodiments, the one or more peptides is a modified or unmodified fragment of a PMEL protein.

In another aspect, the invention provides for an immunogenic composition comprising nucleic acid sequences encoding one or more amino acid sequences selected from the group consisting of SEQ ID NOs: 373348 to 373350.

In some embodiments, the immunogenic composition comprises nucleic acid sequences encoding one or more amino acid sequences derived from a TYRP1 protein. In some embodiments, the immunogenic composition comprises nucleic acid sequences encoding two or more amino acid sequences selected from the group consisting of SEQ ID NOs: 373348 to 373350.

In another aspect, the invention provides for an immunogenic peptide composition comprising one or more peptides selected from the group consisting of SEQ ID NOs: 373348 to 373350.

In some embodiments, the immunogenic peptide composition comprises two or more peptides selected from the group consisting of SEQ ID NOs: 373348 to 373350. In some embodiments, the one or more peptides is a modified or unmodified fragment of a TYRP1 protein.

In another aspect, the invention provides for an immunogenic composition comprising nucleic acid sequences encoding one or more amino acid sequences selected from the group consisting of SEQ ID NOs: 392434 to 392437.

In some embodiments, the immunogenic composition comprises nucleic acid sequences encoding one or more amino acid sequences derived from a TYRP2 protein. In some embodiments, the immunogenic composition comprises nucleic acid sequences encoding two or more amino acid sequences selected from the group consisting of SEQ ID NOs: 392434 to 392437.

In another aspect, the invention provides for an immunogenic peptide composition comprising one or more peptides selected from the group consisting of SEQ ID NOs: 392434 to 392437.

In some embodiments, the immunogenic peptide composition comprises two or more peptides selected from the group consisting of SEQ ID NOs: 392434 to 392437. In some embodiments, the one or more peptides is a modified or unmodified fragment of a TYRP2 protein.

In another aspect, the invention provides for an immunogenic composition comprising nucleic acid sequences encoding one or more amino acid sequences selected from the group consisting of SEQ ID NOs: 305566 to 305570.

In some embodiments, the immunogenic composition comprises nucleic acid sequences encoding one or more amino acid sequences derived from a MAR1 protein. In some embodiments, the immunogenic composition comprises nucleic acid sequences encoding two or more amino acid sequences selected from the group consisting of SEQ ID NOs: 305566 to 305570.

In another aspect, the invention provides for an immunogenic peptide composition comprising one or more peptides selected from the group consisting of SEQ ID NOs: 305566 to 305570.

In some embodiments, the immunogenic peptide composition comprises two or more peptides selected from the group consisting of SEQ ID NOs: 305566 to 305570. In some embodiments, the one or more peptides is a modified or unmodified fragment of a MAR1 protein.

Vaccines for Autoimmune Diseases

In another aspect, the invention provides for an immunogenic composition comprising nucleic acid sequences encoding one or more amino acid sequences selected from the group consisting of SEQ ID NOs: 34169 to 34204.

In some embodiments, the immunogenic composition comprises nucleic acid sequences encoding one or more amino acid sequences derived from a INS protein. In some embodiments, the immunogenic composition comprises nucleic acid sequences encoding two or more amino acid sequences selected from the group consisting of SEQ ID NOs: 34169 to 34204.

In another aspect, the invention provides for an immunogenic peptide composition comprising one or more peptides selected from the group consisting of SEQ ID NOs: 34169 to 34204.

In some embodiments, the immunogenic peptide composition comprises two or more peptides selected from the group consisting of SEQ ID NOs: 34169 to 34204. In some embodiments, the one or more peptides is a modified or unmodified fragment of a INS protein.

In another aspect, the invention provides for an immunogenic composition comprising nucleic acid sequences encoding one or more amino acid sequences selected from the group consisting of SEQ ID NOs: 116478 to 116515.

In some embodiments, the immunogenic composition comprises nucleic acid sequences encoding one or more amino acid sequences derived from a MOG protein. In some embodiments, the immunogenic composition comprises nucleic acid sequences encoding two or more amino acid sequences selected from the group consisting of SEQ ID NOs: 116478 to 116515.

In another aspect, the invention provides for an immunogenic peptide composition comprising one or more peptides selected from the group consisting of SEQ ID NOs: 116478 to 116515.

In some embodiments, the immunogenic peptide composition comprises two or more peptides selected from the group consisting of SEQ ID NOs: 116478 to 116515. In some embodiments, the one or more peptides is a modified or unmodified fragment of a MOG protein.

In another aspect, the invention provides for an immunogenic composition comprising nucleic acid sequences encoding one or more amino acid sequences selected from the group consisting of SEQ ID NOs: 203517 to 203521.

In some embodiments, the immunogenic composition comprises nucleic acid sequences encoding one or more amino acid sequences derived from a INS protein. In some embodiments, the immunogenic composition comprises nucleic acid sequences encoding two or more amino acid sequences selected from the group consisting of SEQ ID NOs: 203517 to 203521.

In another aspect, the invention provides for an immunogenic peptide composition comprising one or more peptides selected from the group consisting of SEQ ID NOs: 203517 to 203521.

In some embodiments, the immunogenic peptide composition comprises two or more peptides selected from the group consisting of SEQ ID NOs: 203517 to 203521. In some embodiments, the one or more peptides is a modified or unmodified fragment of a INS protein.

In another aspect, the invention provides for an immunogenic composition comprising nucleic acid sequences encoding one or more amino acid sequences selected from the group consisting of SEQ ID NOs: 307670 to 307674.

In some embodiments, the immunogenic composition comprises nucleic acid sequences encoding one or more amino acid sequences derived from a MOG protein. In some embodiments, the immunogenic composition comprises nucleic acid sequences encoding two or more amino acid sequences selected from the group consisting of SEQ ID NOs: 307670 to 307674.

In another aspect, the invention provides for an immunogenic peptide composition comprising one or more peptides selected from the group consisting of SEQ ID NOs: 307670 to 307674.

In some embodiments, the immunogenic peptide composition comprises two or more peptides selected from the group consisting of SEQ ID NOs: 307670 to 307674. In some embodiments, the one or more peptides is a modified or unmodified fragment of a MOG protein.

Compositions

In some embodiments, a peptide vaccine comprises one or more peptides of this disclosure and is administered in a pharmaceutical composition that includes a pharmaceutically acceptable carrier. In some embodiments, the peptide vaccine is comprised of the third peptide set, as described in this disclosure. In some embodiments, the pharmaceutical composition is in the form of a spray, aerosol, gel, solution, emulsion, lipid nanoparticle, nanoparticle, or suspension.

The composition is preferably administered to a subject with a pharmaceutically acceptable carrier. Typically, in some embodiments, an appropriate amount of a pharmaceutically acceptable salt is used in the formulation, which in some embodiments can render the formulation isotonic.

In certain embodiments, the peptides are provided as an immunogenic composition comprising any one of the peptides described herein and a pharmaceutically acceptable carrier. In certain embodiments, the immunogenic composition further comprises an adjuvant. In certain embodiments, the peptides are conjugated with other molecules to increase their effectiveness as is known by those practiced in the art. For example, peptides can be coupled to antibodies that recognize cell surface proteins on antigen presenting cells to enhance vaccine effectiveness. One such method for increasing the effectiveness of peptide delivery is described in Woodham, et al., (2018). In certain embodiments for the treatment of autoimmune disorders, the peptides are delivered with a composition and protocol designed to induce tolerance as is known in the art. Example methods for using peptides for immune tolerization are described in Alhadj Ali, et al., (2017) and Gibson, et al., (2015).

In some embodiments, the pharmaceutically acceptable carrier is selected from the group consisting of saline, Ringer's solution, dextrose solution, and a combination thereof. Other suitable pharmaceutically acceptable carriers known in the art are contemplated. Suitable carriers and their formulations are described in Remington's Pharmaceutical Sciences, 2005, Mack Publishing Co. The pH of the solution is preferably from about 5 to about 8, and more preferably from about 7 to about 7.5. The formulation may also comprise a lyophilized powder. Further carriers include sustained release preparations such as semipermeable matrices of solid hydrophobic polymers, which matrices are in the form of shaped articles, e.g., films, liposomes or microparticles. It will be apparent to those persons skilled in the art that certain carriers may be more preferable depending upon, for instance, the route of administration and concentration of peptides being administered.

The phrase pharmaceutically acceptable carrier as used herein means a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier is acceptable in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as butylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. The term carrier denotes an organic or inorganic ingredient, natural or synthetic, with which the active ingredient is combined to facilitate the application. The components of the pharmaceutical compositions also are capable of being comingled with the compounds of the present invention, and with each other, in a manner such that there is no interaction which would substantially impair the desired pharmaceutical efficiency. The composition may also include additional agents such as an isotonicity agent, a preservative, a surfactant, and, a divalent cation, preferably, zinc.

The composition can also include an excipient, or an agent for stabilization of a peptide composition, such as a buffer, a reducing agent, a bulk protein, amino acids (such as e.g., glycine or praline) or a carbohydrate. Bulk proteins useful in formulating peptide compositions include albumin. Typical carbohydrates useful in formulating peptides include but are not limited to sucrose, mannitol, lactose, trehalose, or glucose.

Surfactants may also be used to prevent soluble and insoluble aggregation and/or precipitation of peptides or proteins included in the composition. Suitable surfactants include but are not limited to sorbitan trioleate, soya lecithin, and oleic acid. In certain cases, solution aerosols are preferred using solvents such as ethanol. Thus, formulations including peptides can also include a surfactant that can reduce or prevent surface-induced aggregation of peptides by atomization of the solution in forming an aerosol. Various conventional surfactants can be employed, such as polyoxyethylene fatty acid esters and alcohols, and polyoxyethylene sorbitol fatty acid esters. Amounts will generally range between 0.001% and 4% by weight of the formulation. In some embodiments, surfactants used with the present disclosure are polyoxyethylene sorbitan mono-oleate, polysorbate 80, polysorbate 20. Additional agents known in the art can also be included in the composition.

In some embodiments, the pharmaceutical compositions and dosage forms further comprise one or more compounds that reduce the rate by which an active ingredient will decay, or the composition will change in character. So called stabilizers or preservatives may include, but are not limited to, amino acids, antioxidants, pH buffers, or salt buffers. Nonlimiting examples of antioxidants include butylated hydroxy anisole (BHA), ascorbic acid and derivatives thereof, tocopherol and derivatives thereof, butylated hydroxy anisole and cysteine. Nonlimiting examples of preservatives include parabens, such as methyl or propyl p-hydroxybenzoate and benzalkonium chloride. Additional nonlimiting examples of amino acids include glycine or proline.

The present invention also teaches the stabilization (preventing or minimizing thermally or mechanically induced soluble or insoluble aggregation and/or precipitation of an inhibitor protein) of liquid solutions containing peptides at neutral pH or less than neutral pH by the use of amino acids including proline or glycine, with or without divalent cations resulting in clear or nearly clear solutions that are stable at room temperature or preferred for pharmaceutical administration.

In one embodiment, the composition is a pharmaceutical composition of single unit or multiple unit dosage forms. Pharmaceutical compositions of single unit or multiple unit dosage forms of the invention comprise a prophylactically or therapeutically effective amount of one or more compositions (e.g., a compound of the invention, or other prophylactic or therapeutic agent), typically, one or more vehicles, carriers, or excipients, stabilizing agents, and/or preservatives. Preferably, the vehicles, carriers, excipients, stabilizing agents and preservatives are pharmaceutically acceptable.

In some embodiments, the pharmaceutical compositions and dosage forms comprise anhydrous pharmaceutical compositions and dosage forms. Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprise a primary or secondary amine are preferably anhydrous if substantial contact with moisture and/or humidity during manufacturing, packaging, and/or storage is expected. An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Suitable vehicles are well known to those skilled in the art of pharmacy, and non-limiting examples of suitable vehicles include glucose, sucrose, starch, lactose, gelatin, rice, silica gel, glycerol, talc, sodium chloride, dried skim milk, propylene glycol, water, sodium stearate, ethanol, and similar substances well known in the art. Saline solutions and aqueous dextrose and glycerol solutions can also be employed as liquid vehicles. Whether a particular vehicle is suitable for incorporation into a pharmaceutical composition or dosage form depends on a variety of factors well known in the art including, but not limited to, the way in which the dosage form will be administered to a patient and the specific active ingredients in the dosage form. Pharmaceutical vehicles can be sterile liquids, such as water and oils, including those of petroleum, animal, vegetable or synthetic origin, such as peanut oil, soybean oil, mineral oil, sesame oil and the like.

The invention also provides that a pharmaceutical composition can be packaged in a hermetically sealed container such as an ampoule or sachet indicating the quantity. In one embodiment, the pharmaceutical composition can be supplied as a dry sterilized lyophilized powder in a delivery device suitable for administration to the lower airways of a patient. The pharmaceutical compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for administration may be in the form of powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes and the like, each containing a predetermined amount of a compound of the present invention (e.g., peptides) as an active ingredient.

A liquid composition herein can be used as such with a delivery device, or they can be used for the preparation of pharmaceutically acceptable formulations comprising peptides that are prepared for example by the method of spray drying. The methods of spray freeze-drying peptides/proteins for pharmaceutical administration disclosed in Maa et al., Curr. Pharm. Biotechnol., 2001, 1, 283-302, are incorporated herein. In another embodiment, the liquid solutions herein are freeze spray dried and the spray-dried product is collected as a dispersible peptide-containing powder that is therapeutically effective when administered to an individual.

The compounds and pharmaceutical compositions of the present invention can be employed in combination therapies, that is, the compounds and pharmaceutical compositions can be administered concurrently with, prior to, or subsequent to, one or more other desired therapeutics or medical procedures (e.g., peptide vaccine can be used in combination therapy with another treatment such as chemotherapy, radiation, pharmaceutical agents, and/or another treatment). The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, the compound of the present invention may be administered concurrently with another therapeutic or prophylactic).

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The current invention provides for dosage forms comprising peptides suitable for treating cancer or other diseases. The dosage forms can be formulated, e.g., as sprays, aerosols, nanoparticles, liposomes, or other forms known to one of skill in the art. See, e.g., Remington's Pharmaceutical Sciences; Remington: The Science and Practice of Pharmacy supra; Pharmaceutical Dosage Forms and Drug Delivery Systems by Howard C., Ansel et al., Lippincott Williams & Wilkins; 7th edition (Oct. 1, 1999).

Generally, a dosage form used in the acute treatment of a disease may contain larger amounts of one or more of the active ingredients it comprises than a dosage form used in the chronic treatment of the same disease. In addition, the prophylactically and therapeutically effective dosage form may vary among different conditions. For example, a therapeutically effective dosage form may contain peptides that has an appropriate immunogenic action when intending to treat cancer or other disease. On the other hand, a different effective dosage may contain peptides that has an appropriate immunogenic action when intending to use the peptides of the invention as a prophylactic (e.g., vaccine) against cancer or another disease/condition. These and other ways in which specific dosage forms encompassed by this invention will vary from one another and will be readily apparent to those skilled in the art. See, e.g., Remington's Pharmaceutical Sciences, 2005, Mack Publishing Co.; Remington: The Science and Practice of Pharmacy by Gennaro, Lippincott Williams & Wilkins; 20th edition (2003); Pharmaceutical Dosage Forms and Drug Delivery Systems by Howard C. Ansel et al., Lippincott Williams & Wilkins; 7th edition (Oct. 1, 1999); and Encyclopedia of Pharmaceutical Technology, edited by Swarbrick, J. & J. C. Boylan, Marcel Dekker, Inc., New York, 1988, which are incorporated herein by reference in their entirety.

The pH of a pharmaceutical composition or dosage form may also be adjusted to improve delivery and/or stability of one or more active ingredients. Similarly, the polarity of a solvent carrier, its ionic strength, or tonicity can be adjusted to improve delivery. Compounds such as stearates can also be added to pharmaceutical compositions or dosage forms to alter advantageously the hydrophilicity or lipophilicity of one or more active ingredients to improve delivery. In this regard, stearates can also serve as a lipid vehicle for the formulation, as an emulsifying agent or surfactant, and as a delivery enhancing or penetration-enhancing agent. Different salts, hydrates, or solvates of the active ingredients can be used to adjust further the properties of the resulting composition.

Compositions can be formulated with appropriate carriers and adjuvants using techniques to yield compositions suitable for immunization. The compositions can include an adjuvant, such as, for example but not limited to, alum, poly IC, MF-59, squalene-based adjuvants, or liposomal based adjuvants suitable for immunization.

In some embodiments, the compositions and methods comprise any suitable agent or immune modulation which could modulate mechanisms of host immune tolerance and release of the induced antibodies. In certain embodiments, an immunomodulatory agent is administered in at time and in an amount sufficient for transient modulation of the subject's immune response so as to induce an immune response which comprises antibodies against for example tumor neoantigens (i.e., tumor-specific antigens (TSA)).

Expression Systems

In certain aspects, the invention provides culturing a cell line that expresses any one of the peptides of the invention in a culture medium comprising any of the peptides described herein.

Various expression systems for producing recombinant proteins/peptides are known in the art, and include, prokaryotic (e.g., bacteria), plant, insect, yeast, and mammalian expression systems. Suitable cell lines, can be transformed, transduced, or transfected with nucleic acids containing coding sequences for the peptides of the invention in order to produce the molecule of interest. Expression vectors containing such a nucleic acid sequence, which can be linked to at least one regulatory sequence in a manner that allows expression of the nucleotide sequence in a host cell, can be introduced via methods known in the art. Practitioners in the art understand that designing an expression vector can depend on factors, such as the choice of host cell to be transfected and/or the type and/or amount of desired protein to be expressed. Enhancer regions, which are those sequences found upstream or downstream of the promoter region in non-coding DNA regions, are also known in the art to be important in optimizing expression. If needed, origins of replication from viral sources can be employed, such as if a prokaryotic host is utilized for introduction of plasmid DNA. However, in eukaryotic organisms, chromosome integration is a common mechanism for DNA replication. For stable transfection of mammalian cells, a small fraction of cells can integrate introduced DNA into their genomes. The expression vector and transfection method utilized can be factors that contribute to a successful integration event. For stable amplification and expression of a desired protein, a vector containing DNA encoding a protein of interest is stably integrated into the genome of eukaryotic cells (for example mammalian cells), resulting in the stable expression of transfected genes. A gene that encodes a selectable marker (for example, resistance to antibiotics or drugs) can be introduced into host cells along with the gene of interest in order to identify and select clones that stably express a gene encoding a protein of interest. Cells containing the gene of interest can be identified by drug selection wherein cells that have incorporated the selectable marker gene will survive in the presence of the drug. Cells that have not incorporated the gene for the selectable marker die. Surviving cells can then be screened for the production of the desired protein molecule.

A host cell strain, which modulates the expression of the inserted sequences, or modifies and processes the nucleic acid in a specific fashion desired also may be chosen. Such modifications (for example, glycosylation and other post-translational modifications) and processing (for example, cleavage) of peptide/protein products may be important for the function of the peptide/protein. Different host cell strains have characteristic and specific mechanisms for the post-translational processing and modification of proteins and gene products. As such, appropriate host systems or cell lines can be chosen to ensure the correct modification and processing of the target protein expressed. Thus, eukaryotic host cells possessing the cellular machinery for proper processing of the primary transcript, glycosylation, and phosphorylation of the gene product may be used.

Various culturing parameters can be used with respect to the host cell being cultured. Appropriate culture conditions for mammalian cells are well known in the art (Cleveland W L, et al., J Immunol Methods, 1983, 56(2): 221-234) or can be determined by the skilled artisan (see, for example, Animal Cell Culture: A Practical Approach 2nd Ed., Rickwood, D. and Hames, B. D., eds. (Oxford University Press: New York, 1992)). Cell culturing conditions can vary according to the type of host cell selected. Commercially available medium can be utilized.

Peptides of the invention can be purified from any human or non-human cell which expresses the polypeptide, including those which have been transfected with expression constructs that express peptides of the invention. For protein recovery, isolation and/or purification, the cell culture medium or cell lysate is centrifuged to remove particulate cells and cell debris. The desired polypeptide molecule is isolated or purified away from contaminating soluble proteins and polypeptides by suitable purification techniques.

Non-limiting purification methods for proteins include: size exclusion chromatography; affinity chromatography; ion exchange chromatography; ethanol precipitation; reverse phase HPLC; chromatography on a resin, such as silica, or cation exchange resin, e.g., DEAE; chromatofocusing; SDS-PAGE; ammonium sulfate precipitation; gel filtration using, e.g., Sephadex G-75, Sepharose; protein A sepharose chromatography for removal of immunoglobulin contaminants; and the like. Other additives, such as protease inhibitors (e.g., PMSF or proteinase K) can be used to inhibit proteolytic degradation during purification. Purification procedures that can select for carbohydrates can also be used, e.g., ion-exchange soft gel chromatography, or HPLC using cation- or anionexchange resins, in which the more acidic fraction(s) is/are collected.

Methods of Treatment

In one embodiment, the subject matter disclosed herein relates to a preventive medical treatment started after following diagnosis of cancer in order to prevent the disease from worsening or curing the disease. In one embodiment, the subject matter disclosed herein relates to prophylaxis of subjects who are believed to be at risk for cancer or have previously been diagnosed with cancer (or another disease). In one embodiment, said subjects can be administered the peptide vaccine described herein or pharmaceutical compositions thereof. The invention contemplates using any of the peptides produced by the systems and methods described herein. In one embodiment, the peptide vaccines described herein can be administered subcutaneously via syringe or any other suitable method know in the art.

The compound(s) or combination of compounds disclosed herein, or pharmaceutical compositions may be administered to a cell, mammal, or human by any suitable means. Non-limiting examples of methods of administration include, among others, (a) administration though oral pathways, which includes administration in capsule, tablet, granule, spray, syrup, or other such forms; (b) administration through non-oral pathways such as intraocular, intranasal, intraauricular, rectal, vaginal, intraurethral, transmucosal, buccal, or transdermal, which includes administration as an aqueous suspension, an oily preparation or the like or as a drip, spray, suppository, salve, ointment or the like; (c) administration via injection, including subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; (e) administration topically; as deemed appropriate by those of skill in the art for bringing the compound or combination of compounds disclosed herein into contact with living tissue; (f) administration via inhalation, including through aerosolized, nebulized, and powdered formulations; and (g) administration through implantation.

As will be readily apparent to one skilled in the art, the effective in vivo dose to be administered and the particular mode of administration will vary depending upon the age, weight and species treated, and the specific use for which the compound or combination of compounds disclosed herein are employed. The determination of effective dose levels, that is the dose levels necessary to achieve the desired result, can be accomplished by one skilled in the art using routine pharmacological methods. Typically, human clinical applications of products are commenced at lower dose levels, with dose level being increased until the desired effect is achieved. Alternatively, acceptable in vitro studies can be used to establish useful doses and routes of administration of the compositions identified by the present methods using established pharmacological methods. Effective animal doses from in vivo studies can be converted to appropriate human doses using conversion methods known in the art (e.g., see Nair A B, Jacob S. A simple practice guide for dose conversion between animals and human. Journal of basic and clinical pharmacy. 2016 March; 7(2):27.)

Methods of Prevention

In some embodiments, the peptides prepared using methods of the invention can be used as a vaccine to promote an immune response against cancer (e.g., against tumor neoantigens). In some embodiments, the invention provides compositions and methods for induction of immune response, for example induction of antibodies to tumor neoantigens. In some embodiments, the antibodies are broadly neutralizing antibodies. In some embodiments, the peptides prepared using methods of the invention can be used as a vaccine to promote an immune response against a pathogen. In some embodiments, the peptides prepared using methods of the invention can be used to promote immune tolerance as an autoimmune disease therapeutic.

The compositions, systems, and methods disclosed herein are not to be limited in scope to the specific embodiments described herein. Indeed, various modifications of the compositions, systems, and methods in addition to those described will become apparent to those of skill in the art from the foregoing description.

SEQUENCE LISTING

The patent contains a lengthy sequence listing. A copy of the sequence listing is available in electronic form from the USPTO web site (https://seqdata.uspto.gov/?pageRequest=docDetail&DocID=US12064475B2). An electronic copy of the sequence listing will also be available from the USPTO upon request and payment of the fee set forth in 37 CFR 1.19(b)(3).

What is claimed is:

1. An immunogenic composition comprising nucleic acid sequences encoding at least one amino acid sequence selected from the group consisting of SEQ ID NO: 163, SEQ ID NO: 164, SEQ ID NO: 7882, SEQ ID NO: 7884, SEQ ID NO: 7887, SEQ ID NO: 7888, SEQ ID NO: 7894, SEQ ID NO: 7920, SEQ ID NO: 7921, SEQ ID NO: 7933, SEQ ID NO: 7934, SEQ ID NO: 7950, SEQ ID NO: 7970, SEQ ID NO: 7972, SEQ ID NO: 7976, SEQ ID NO: 7982, SEQ ID NO: 8269, SEQ ID NO: 8277, SEQ ID NO: 8296, and SEQ ID NO: 8422.

2. The immunogenic composition of claim 1, wherein the nucleic acid sequences are contained in a construct for in vivo expression of one or more peptides encoded by the nucleic acid sequences.

3. The immunogenic composition of claim 2, wherein an administration of the nucleic acid sequences causes the one or more peptides encoded by the nucleic acid sequences to be displayed by an HLA class I allele in a subject.

4. The immunogenic composition of claim 2, wherein the nucleic acid sequences are contained in a construct for the in vivo expression of at least two peptides encoded by the nucleic acid sequences, wherein an administration of the nucleic acid sequences causes:
 a first peptide of the at least two peptides to be displayed by a first plurality of HLA class I alleles in a subject; and
 a second peptide of the at least two peptides to be displayed by a second plurality of HLA class I alleles in the subject,
 wherein the first plurality of HLA class I alleles and the second plurality of HLA class I alleles differ by at least one HLA class I allele.

5. The immunogenic composition of claim 3, wherein the at least one amino acid sequence comprises two heteroclitic modifications of a fragment of a KRAS protein containing a KRAS G12C mutation.

6. The immunogenic composition of claim 1, wherein the at least one amino acid sequence is selected based on a HLA class I allele that is expressed in a subject.

7. The immunogenic composition of claim 1, wherein the nucleic acid sequences encode at least one amino acid sequence selected from the group consisting of SEQ ID NO: 163, SEQ ID NO: 164, SEQ ID NO: 7921, SEQ ID NO: 7933, SEQ ID NO: 7950, SEQ ID NO: 8296, and SEQ ID NO: 8422.

8. An immunogenic composition comprising nucleic acid sequences encoding at least one amino acid sequence selected from the group consisting of SEQ ID NO: 11053, SEQ ID NO: 11064, SEQ ID NO: 11073, SEQ ID NO: 11079, SEQ ID NO: 11080, SEQ ID NO: 11094, SEQ ID NO: 11102, SEQ ID NO: 11106, SEQ ID NO: 11116, SEQ ID NO: 11122, SEQ ID NO: 11193, SEQ ID NO: 11203, SEQ ID NO: 11206, SEQ ID NO: 11212, SEQ ID NO: 11220, SEQ ID NO: 11227, SEQ ID NO: 11283, SEQ ID NO: 11305, SEQ ID NO: 11342, SEQ ID NO: 11343, SEQ ID NO: 11352, SEQ ID NO: 11469, SEQ ID NO: 11474, SEQ ID NO: 11585, SEQ ID NO: 11617, SEQ ID NO: 11701, and SEQ ID NO: 11734.

9. The immunogenic composition of claim 8, wherein the nucleic acid sequences are contained in a construct for in vivo expression of one or more peptides encoded by the nucleic acid sequences.

10. The immunogenic composition of claim 9, wherein an administration of the nucleic acid sequences causes the one or more peptides encoded by the nucleic acid sequences to be displayed by an HLA class I allele in a subject.

11. The immunogenic composition of claim 9, wherein the nucleic acid sequences are contained in a construct for the in vivo expression of at least two peptides encoded by the nucleic acid sequences, wherein an administration of the nucleic acid sequences causes:
 a first peptide of the at least two peptides to be displayed by a first plurality of HLA class I alleles in a subject; and
 a second peptide of the at least two peptides to be displayed by a second plurality of HLA class I alleles in the subject,
 wherein the first plurality of HLA class I alleles and the second plurality of HLA class I alleles differ by at least one HLA class I allele.

12. The immunogenic composition of claim 10, wherein the at least one amino acid sequence comprises two heteroclitic modifications of a fragment of a KRAS protein containing a KRAS G12V mutation.

13. The immunogenic composition of claim 8, wherein the at least one amino acid sequence is selected based on a HLA class I allele that is expressed in a subject.

14. The immunogenic composition of claim 8, wherein the nucleic acid sequences encode at least one amino acid sequence selected from the group consisting of SEQ ID NO: 11080, SEQ ID NO: 11122, SEQ ID NO: 11469, and SEQ ID NO: 11474.

15. The immunogenic composition of claim 11, wherein the nucleic acid sequences encode at least two amino acid sequences selected from the group consisting of SEQ ID NO: 11080, SEQ ID NO: 11122, SEQ ID NO: 11469, and SEQ ID NO: 11474.

16. An immunogenic composition comprising nucleic acid sequences encoding at least one amino acid sequence selected from the group consisting of SEQ ID NO: 188, SEQ ID NO: 189, SEQ ID NO: 9760, SEQ ID NO: 9772, SEQ ID NO: 9776, SEQ ID NO: 9780, SEQ ID NO: 9784, SEQ ID NO: 9785, SEQ ID NO: 9927, SEQ ID NO: 9933, SEQ ID NO: 10072, SEQ ID NO: 10076, SEQ ID NO: 10079, SEQ ID NO: 10103, SEQ ID NO: 10192, and SEQ ID NO: 10227.

17. The immunogenic composition of claim 16, wherein the nucleic acid sequences are contained in a construct for in vivo expression of one or more peptides encoded by the nucleic acid sequences.

18. The immunogenic composition of claim 17, wherein an administration of the nucleic acid sequences causes the one or more peptides encoded by the nucleic acid sequences to be displayed by an HLA class I allele in a subject.

19. The immunogenic composition of claim 17, wherein the nucleic acid sequences are contained in a construct for the in vivo expression of at least two peptides encoded by the nucleic acid sequences, wherein an administration of the nucleic acid sequences causes:
 a first peptide of the at least two peptides to be displayed by a first plurality of HLA class I alleles in a subject; and
 a second peptide of the at least two peptides to be displayed by a second plurality of HLA class I alleles in the subject, wherein the first plurality of HLA class I alleles and the second plurality of HLA class I alleles differ by at least one HLA class I allele.

20. The immunogenic composition of claim 18, wherein the at least one amino acid sequence comprises two heteroclitic modifications of a fragment of a KRAS protein containing a KRAS G12R mutation.

21. The immunogenic composition of claim 20, wherein the at least one amino acid sequence is selected based on a HLA class I allele that is expressed in a subject.

22. The immunogenic composition of claim 16, wherein the nucleic acid sequences encode at least one amino acid sequence selected from the group consisting of SEQ ID NO: 188, SEQ ID NO: 189, SEQ ID NO: 9760, SEQ ID NO: 9772, SEQ ID NO: 9785, SEQ ID NO: 10076, SEQ ID NO: 10103, and SEQ ID NO: 10227.

23. An immunogenic composition comprising nucleic acid sequences encoding at least one amino acid sequence selected from the group consisting of SEQ ID NO: 173, SEQ ID NO: 174, SEQ ID NO: 175, SEQ ID NO: 176, SEQ ID NO: 177, SEQ ID NO: 8439, SEQ ID NO: 8464, SEQ ID NO: 8465, SEQ ID NO: 8467, SEQ ID NO: 8468, SEQ ID NO: 8472, SEQ ID NO: 8510, SEQ ID NO: 8513, SEQ ID NO: 8514, SEQ ID NO: 8518, SEQ ID NO: 8554, SEQ ID NO: 8605, SEQ ID NO: 8667, SEQ ID NO: 8672, SEQ ID NO: 8708, SEQ ID NO: 8731, SEQ ID NO: 8734, SEQ ID NO: 8736, SEQ ID NO: 8828, SEQ ID NO: 8841, SEQ ID NO: 8849, SEQ ID NO: 8852, SEQ ID NO: 8880, SEQ ID NO: 8898, SEQ ID NO: 8958, SEQ ID NO: 9059, SEQ ID NO: 9066, SEQ ID NO: 9067, SEQ ID NO: 9070, SEQ ID NO: 9072, SEQ ID NO: 9073, SEQ ID NO: 9075, SEQ ID NO: 9076, SEQ ID NO: 9083, SEQ ID NO: 9085, SEQ ID NO: 9103, SEQ ID NO: 9107, SEQ ID NO: 9112, SEQ ID NO: 9221, SEQ ID NO: 9222, SEQ ID NO: 9279, SEQ ID NO: 9280, SEQ ID NO: 9286, SEQ ID NO: 9287, SEQ ID NO: 9336, SEQ ID NO: 9341, SEQ ID NO: 9345, SEQ ID NO: 9368, SEQ ID NO: 9371, SEQ ID NO: 9375, SEQ ID NO: 9376, SEQ ID NO: 9381, SEQ ID NO: 9393, SEQ ID NO: 9412, SEQ ID NO: 9425, SEQ ID NO: 9458, SEQ ID NO: 9486, SEQ ID NO: 9491, SEQ ID NO: 9538, SEQ ID NO: 9543, SEQ ID NO: 9544, SEQ ID NO: 9546, SEQ ID NO: 9551, SEQ ID NO: 9558, SEQ ID NO: 9587, SEQ ID NO: 9591, SEQ ID NO: 9592, SEQ ID NO: 9594, SEQ ID NO: 9598, SEQ ID NO: 9599, SEQ ID NO: 9633, SEQ ID NO: 9637, SEQ ID NO: 9642, SEQ ID NO: 9643, SEQ ID NO: 9649, SEQ ID NO: 9650, SEQ ID NO: 9657, SEQ ID NO: 9698, and SEQ ID NO: 9721.

24. The immunogenic composition of claim 23, wherein the nucleic acid sequences are contained in a construct for in vivo expression of one or more peptides encoded by the nucleic acid sequences.

25. The immunogenic composition of claim 24, wherein an administration of the nucleic acid sequences causes the one or more peptides encoded by the nucleic acid sequences to be displayed by an HLA class I allele in a subject.

26. The immunogenic composition of claim 24, wherein the nucleic acid sequences are contained in a construct for the in vivo expression of at least two peptides encoded by the nucleic acid sequences, wherein an administration of the nucleic acid sequences causes:
  a first peptide of the at least two peptides to be displayed by a first plurality of HLA class I alleles in a subject; and
  a second peptide of the at least two peptides to be displayed by a second plurality of HLA class I alleles in the subject,
  wherein the first plurality of HLA class I alleles and the second plurality of HLA class I alleles differ by at least one HLA class I allele.

27. The immunogenic composition of claim 23, wherein the at least one amino acid sequence comprises two heteroclitic modifications of a fragment of a KRAS protein containing a KRAS G12D mutation.

28. The immunogenic composition of claim 23, wherein the at least one amino acid sequence is selected based on a HLA class I allele that is expressed in a subject.

29. The immunogenic composition of claim 23, wherein the nucleic acid sequences encode at least one amino acid sequence selected from the group consisting of SEQ ID NO: 173, SEQ ID NO: 174, SEQ ID NO: 175, SEQ ID NO: 176, SEQ ID NO: 8439, SEQ ID NO: 8465, SEQ ID NO: 9059, SEQ ID NO: 9067, SEQ ID NO: 9642, SEQ ID NO: 9698, and SEQ ID NO: 9721.

30. The immunogenic composition of claim 26, wherein the nucleic acid sequences encode at least two amino acid sequences selected from the group consisting of SEQ ID NO: 173, SEQ ID NO: 174, SEQ ID NO: 175, SEQ ID NO: 176, SEQ ID NO: 8439, SEQ ID NO: 8465, SEQ ID NO: 9059, SEQ ID NO: 9067, SEQ ID NO: 9642, SEQ ID NO: 9698, and SEQ ID NO: 9721.

* * * * *